(12) United States Patent
Phillips et al.

(10) Patent No.: US 12,048,747 B2
(45) Date of Patent: Jul. 30, 2024

(54) SUBSTITUTED PIPERIDINE DEGRONIMERS FOR TARGET PROTEIN DEGRADATION

(71) Applicant: C4 Therapeutics, Inc., Watertown, MA (US)

(72) Inventors: Andrew J. Phillips, Arlington, VA (US); Christopher G. Nasveschuk, Stoneham, MA (US); James A. Henderson, Weston, MA (US); Yanke Liang, Belmont, MA (US); Chi-Li Chen, Newton, MA (US); Martin Duplessis, Somerville, MA (US); Minsheng He, Andover, MA (US); Kiel Lazarski, Boston, MA (US)

(73) Assignee: C4 Therapeutics, Inc., Watertown, MA (US)

( * ) Notice: Subject to any disclaimer, the term of this patent is extended or adjusted under 35 U.S.C. 154(b) by 164 days.

(21) Appl. No.: 17/121,389

(22) Filed: Dec. 14, 2020

(65) Prior Publication Data

US 2022/0313827 A1 Oct. 6, 2022

Related U.S. Application Data

(63) Continuation of application No. 16/186,333, filed on Nov. 9, 2018, now abandoned, which is a
(Continued)

(51) Int. Cl.
| | |
|---|---|
| *C07D 401/14* | (2006.01) |
| *A61K 31/45* | (2006.01) |
| *A61K 31/454* | (2006.01) |
| *A61K 31/4545* | (2006.01) |
| *A61K 31/4709* | (2006.01) |
| *A61K 31/513* | (2006.01) |
| *A61K 47/54* | (2017.01) |
| *C07D 211/88* | (2006.01) |
| *C07D 401/04* | (2006.01) |
| *C07D 401/12* | (2006.01) |
| *C07D 405/14* | (2006.01) |
| *C07D 413/04* | (2006.01) |
| *C07D 413/12* | (2006.01) |
| *C07D 471/04* | (2006.01) |
| *C07D 487/04* | (2006.01) |
| *C07D 495/14* | (2006.01) |

(52) U.S. Cl.
CPC ............ *A61K 47/545* (2017.08); *A61K 31/45* (2013.01); *A61K 31/454* (2013.01); *A61K 31/4545* (2013.01); *A61K 31/4709* (2013.01); *A61K 31/513* (2013.01); *A61K 47/554* (2017.08); *C07D 211/88* (2013.01); *C07D 401/04* (2013.01); *C07D 401/12* (2013.01); *C07D 401/14* (2013.01); *C07D 405/14* (2013.01); *C07D 413/04* (2013.01); *C07D 413/12* (2013.01); *C07D 471/04* (2013.01); *C07D 487/04* (2013.01); *C07D 495/14* (2013.01)

(58) Field of Classification Search
CPC ..................................................... C07D 401/04
USPC ........................................................... 546/208
See application file for complete search history.

(56) References Cited

U.S. PATENT DOCUMENTS

| | | | |
|---|---|---|---|
| 5,635,517 A | 6/1997 | Muller et al. | |
| 6,306,663 B1 | 10/2001 | Kenten et al. | |

(Continued)

FOREIGN PATENT DOCUMENTS

| | | |
|---|---|---|
| BR | PI1100318 A2 | 5/2013 |
| CN | 103421061 A | 12/2013 |

(Continued)

OTHER PUBLICATIONS

European Examination Search Report for EP17796812 mailed on Sep. 28, 2020.
(Continued)

*Primary Examiner* — Douglas M Willis
(74) *Attorney, Agent, or Firm* — Knowles Intellectual Property Strategies, LLC

(57) ABSTRACT

This invention provides amine-linked $C^3$-glutarimide Degronimers for therapeutic applications as described further herein, and methods of use and compositions thereof as well as methods for their preparation, wherein the $C^3$-glutarimide Degronimers have the formula:

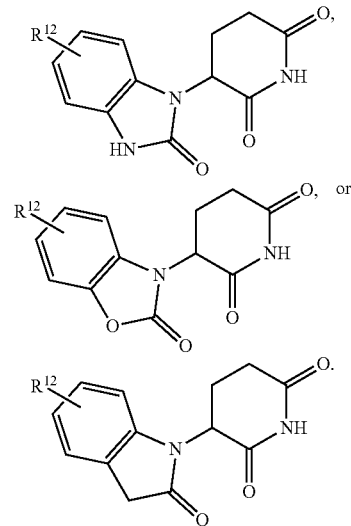

22 Claims, 389 Drawing Sheets

Related U.S. Application Data continuation of application No. PCT/US2017/032046, filed on May 10, 2017.

(60) Provisional application No. 62/334,338, filed on May 10, 2016.

(56) References Cited

U.S. PATENT DOCUMENTS

| | | | |
|---|---|---|---|
| 7,041,298 | B2 | 5/2006 | Deshaies et al. |
| 7,208,157 | B2 | 4/2007 | Deshaies et al. |
| 9,125,915 | B2 | 9/2015 | Miyoshi et al. |
| 9,249,161 | B2 | 2/2016 | Albrecht et al. |
| 10,351,568 | B2 | 7/2019 | Finley et al. |
| 2006/0069067 | A1 | 3/2006 | Bhatnagar et al. |
| 2013/0190340 | A1 | 7/2013 | Hedstrom et al. |
| 2014/0302523 | A1 | 10/2014 | Crews et al. |
| 2014/0356322 | A1 | 12/2014 | Crews et al. |
| 2015/0119435 | A1 | 4/2015 | Crews et al. |
| 2015/0274738 | A1 | 10/2015 | Gray et al. |
| 2015/0291562 | A1 | 10/2015 | Crew et al. |
| 2016/0016966 | A1 | 1/2016 | Amans et al. |
| 2016/0022642 | A1 | 1/2016 | Crews et al. |
| 2016/0045607 | A1 | 2/2016 | Crew et al. |
| 2016/0046661 | A1 | 2/2016 | Gray et al. |
| 2016/0058872 | A1 | 3/2016 | Crew et al. |
| 2016/0176916 | A1 | 6/2016 | Bradner et al. |
| 2016/0214972 | A1 | 7/2016 | Jin et al. |
| 2016/0272639 | A1 | 9/2016 | Crew et al. |
| 2017/0008904 | A1 | 1/2017 | Crew et al. |
| 2017/0037004 | A1 | 2/2017 | Crew et al. |
| 2017/0065719 | A1 | 3/2017 | Qian et al. |
| 2018/0015087 | A1 | 1/2018 | Liu et al. |
| 2018/0085465 | A1 | 3/2018 | Bradner et al. |

FOREIGN PATENT DOCUMENTS

| | | |
|---|---|---|
| WO | WO 1998/011111 A1 | 3/1998 |
| WO | WO 2002/059106 A1 | 8/2002 |
| WO | WO 2006/102557 A2 | 9/2006 |
| WO | WO 2007/031791 A1 | 3/2007 |
| WO | WO 2008/027542 A2 | 3/2008 |
| WO | WO 2008/033567 A1 | 3/2008 |
| WO | WO 2008/039489 A2 | 4/2008 |
| WO | WO 2008/115516 A2 | 9/2008 |
| WO | WO 2008/122038 A1 | 10/2008 |
| WO | WO 2009/042177 A1 | 4/2009 |
| WO | WO 2009/139880 A1 | 11/2009 |
| WO | WO 2009/145899 A1 | 12/2009 |
| WO | WO 2010/053732 A1 | 5/2010 |
| WO | WO 2010/107485 A1 | 9/2010 |
| WO | WO 2011/097218 A1 | 8/2011 |
| WO | WO 2011/143669 A2 | 11/2011 |
| WO | WO 2012/079022 A1 | 6/2012 |
| WO | WO 2012/178208 A2 | 12/2012 |
| WO | WO 2013/059215 A1 | 4/2013 |
| WO | WO 2013/106646 A2 | 7/2013 |
| WO | WO 2013/170147 A1 | 11/2013 |
| WO | WO 2014/145887 A1 | 9/2014 |
| WO | WO 2015/173764 A1 | 11/2015 |
| WO | WO 2016/065139 A1 | 4/2016 |
| WO | WO 2016/105518 A1 | 6/2016 |
| WO | WO 2016/146985 A1 | 9/2016 |
| WO | WO 2016/169989 A1 | 10/2016 |
| WO | WO 2016/191178 A1 | 12/2016 |
| WO | WO 2016/197032 A1 | 12/2016 |
| WO | WO 2016/197114 A1 | 12/2016 |
| WO | WO 2017/007612 A1 | 1/2017 |
| WO | WO 2017/024317 A2 | 2/2017 |
| WO | WO 2017/024318 A1 | 2/2017 |
| WO | WO 2017/024319 A1 | 2/2017 |
| WO | WO 2017/079267 A1 | 5/2017 |
| WO | WO 2017/161119 A1 | 9/2017 |
| WO | WO 2017/176708 A1 | 10/2017 |
| WO | WO 2017/176957 A1 | 10/2017 |
| WO | WO 2017/176958 A1 | 10/2017 |
| WO | WO 2017/180417 A1 | 10/2017 |
| WO | WO 2017/197240 A1 | 11/2017 |
| WO | WO 2017/201069 A1 | 11/2017 |
| WO | WO 2017/201449 A1 | 11/2017 |
| WO | WO 2018/023029 A1 | 2/2018 |
| WO | WO 2018/051107 A1 | 3/2018 |
| WO | WO 2018/052945 A1 | 3/2018 |
| WO | WO 2018/052949 A1 | 3/2018 |
| WO | WO 2018/053354 A1 | 3/2018 |
| WO | WO 2018/071606 A1 | 4/2018 |
| WO | WO 2018/085247 A1 | 5/2018 |
| WO | WO 2018/102067 A2 | 6/2018 |
| WO | WO 2018/102725 A1 | 6/2018 |
| WO | WO 2018/118598 A1 | 6/2018 |
| WO | WO 2018/118947 A1 | 6/2018 |
| WO | WO 2018/119357 A1 | 6/2018 |
| WO | WO 2018/119441 A1 | 6/2018 |
| WO | WO 2018/119448 A1 | 6/2018 |
| WO | WO 2018/140809 A1 | 8/2018 |
| WO | WO 2018/144649 A1 | 8/2018 |
| WO | WO 2018/169777 A1 | 9/2018 |
| WO | WO 2018/183411 A1 | 10/2018 |
| WO | WO 2018/189554 A1 | 10/2018 |
| WO | WO 2018/191199 A1 | 10/2018 |

OTHER PUBLICATIONS

Bartlett, et al. "The evolution of thalidomide and its IMiD derivatives as anticancer agents." Nat Rev Cancer 2004, 4(4):312-322.

Berndsen et al. "New insights into ubiquitin E3 ligase mechanism" Nat. Struct. Mol. Biol. 2014, 21:301-307.

Buckley et al. "HaloPROTACS: Use of Small Molecule PROTACS to Induce Degradation of HaloTag Fusion Proteins" ACS Chemical Biology 2015, 10:1831-1837.

Buckley et al. "Small-Molecule Control of Intracellular Protein Levels through Modulation of the Ubiquitin Proteasome System" Angewandte Reviews, 2014, 53:2312-2330.

Buckley et al. "Targeting the Von Hippel-Lindau E3 Ubiquitin Ligase Using Small Molecules to Disrupt the Vhl/Hif-1alpha Interaction" J. Am. Chem. Soc. 2012, 134:4465-4468.

Bondeson et al. "Catalytic in vivo protein knockdown by small-molecule PROTACs" Nature Chemical Biology 2015, 11:611-617.

Burkhard et al. "Synthesis and Stability of Oxetane Analogs of Thalidomide and Lenalidomide" Organic Letters 2013, 15(7):4312-4315.

Chamberlain et al. "Structure of the human cereblon-DDB1-lenalidomide complex reveals basis for responsiveness to thalidomide analogs" Nature Structural and Molecule Biology, 2014, 21(9):803-809.

Chang, X. and Stewart, K. A. "What is the functional role of the thalidomide binding protein cereblon?" Int J Biochem Mol Bio. 2011, 2(3):287-294.

Contino-Pepin, et al., "Preliminary biological evaluations of new thalidomide analogues for multiple sclerosis application", Bioorganic & Medicinal Chemistry Letters, 2009, 19, 878-881.

Corson et al. "Design and applications of bifunctional small molecules: Why two heads are better than one" ACS Chemical Biology 2008, 3(11): 677-692.

Crew, C. M. "Targeting the undruggable proteome: the small molecules of my dreams" Chemistry and Biology 2010, 17(6):551-555.

Deshaies et al. "Ring domain E3 ubiquitin ligases." Ann. Rev. Biochem. 2009, 78:399-434.

Faden et al. "Generic tools for conditionally altering protein abundance and phenotypes on demain" Biol. Chem. 2014, 395(7-8):737-762.

Fischer et al. "Structure of the DDB1-CRBN E3 ubiquitin ligase in complex with thalidomide" Nature 2014, 512:49-53.

Fischer et al. "The Molecular Basis of CRL4DDB2/CSA Ubiquitin Ligase Architecture, Targeting, and Activation," Cell 2011, 147:1024-1039.

Gosink et al. "Redirecting the Specificity of Ubiquitination by Modifying Ubiquitin-Conjugating Enzymes" Proc. Natl. Acad. Sci. USA 1995, 92:9117-9121.

(56) References Cited

OTHER PUBLICATIONS

Gustafson et al. "Small-Molecule-Mediated Degradation of the Androgen Receptor through Hydrophobic Tagging" Angewandte Chemie 2015, 54:9659-9662.
Hines et al. "Posttranslational protein knockdown couple to receptor tyrosine kinase activation with phosphoPROTACs" PNAS 2013, 110(22):8942-8947.
International Search Report and Written Opinion for PCT/US17/32046 mailed Aug. 4, 2017.
Ito et al. "Identification of a Primary Target of Thalidomide Teratogenicity" Science 2010, 327(5971):1345-1350.
Itoh et al. "Protein knockdown using methyl bestatin-ligand hybrid molecules: design and synthesis of inducers of ubiquitination-mediated degradation of cellular retinoic acid-binding proteins" Journal of the American Chemical Society 2010, 132(16):5820-5826.
Jacques et al. "Differentiation of anti-inflammatory and antitumorigenic properties of stabilized enantiomers of thalidomide analogs" PNAS 2015, 112:E1471-E1479.
Kronke et al. "Lenalidomide induces ubiquitination and degradation of CDK1[alpha] in del(5q) MDS" Nature 2015, 523(7559):183-188.
Kronke et al. "Lenalidomide Causes Selective Degradation of IKZF1 and IKZF3 in Multiple Myeloma Cells" Science 2014, 343(6168):301-305.
Lai et al. "Modular PROTAC Design for the Degradation of Oncogenic BCR-ABL" Angewandte Chemie International Edition 2016, 55:807-810.
Lee et al. "Targeted Degradation of the Aryl Hydrocarbon Receptor by the PROTAC Approach: A Useful Chemical Genetic Tool" ChemBioChem 2007, 8:2058-2062.
Li et al. "Genome-wide and functional annotation of human E3 ubiquitin ligases identifies MULAN, a mitochondrial E3 that regulates the organelle's dynamics and signaling" PLOS One 2008, 3:1487.
Liu et al. "Design and biological characterization of hybrid compounds of curcumin and thalidomide for multiple myeloma" Organic and Biomolecular Chemistry 2013, 11:4757.
Lu et al. "The myeloma drug lenalidomide promotes the cereblon-dependent destruction of Ikaros proteins" Science 2014, 343:305-309.
Lu et al. "Hijacking the E3 Ubiquitin Ligase Cereblon to Efficiently Target BRD4" Chemistry and Biology 2015, 22(6):755-763.
Nawaz et al. "Proteasome-Dependent Degradation of the Human Estrogen Receptor" Proc. Natl. Acad. Sci. USA 1999, 96:1858-1862.
Neklesa et al. "Small-molecule hydrophobic tagging-induced degradation of HaloTag fusion proteins." Nat Chem Biol 2011, 7(8):538-543.
Raina et al. "Chemical Inducers of Targeted Protein Degradation" Journal of Biological Chemistry 2010, 285:11057-11060.
Rodriguez-Gonzalez et al. "Targeting steroid hormone receptors for ubiquitination and degradation in breast and prostate cancer" Oncogene 2008, 27:7201-7211.
Ruchelman et al. "Isosteric analogs of lenalidomide and pomalidomide: Synthesis and biological activity" Bioorganic and Medicinal Chemistry Letters 2012, 23:360-365.
Sakamoto et al. "Protacs: chimeric molecules that target proteins to the Skp1-Cullin-F box complex for ubiquitination and degradation" PNAS 2001, 98(15):8554-8559.
Sakamoto et al. "Development of Protacs to Target Cancer-Promoting Proteins for Ubiquitination and Degradation" Molecular and Cellular Proteomics 2003, 2(12):1350-1357.
Schneekloth et al. "Targeted Intracellular Protein Degradation Induced by a Small Molecule: En Route to Chemical Proteomics" Bioorganic and Medicinal Chemistry Letters 2008, 18:5904-5908.
Schneekloth et al. "Chemical approaches to controlling intracellular protein degradation" Chembiochem 2005, 6(1):40-46.
Schneekloth et al. "Chemical Genetic Control of Protein Levels: Selective in Vivo Targeted Degradation" Journal of the American Chemical Society 2004, 126(12):3748-3754.
Shoji, et al., "Modified DNA Aptamer That Binds the (R)-Isomer of a Thalidomide Derivative with High Enantioselectivity", J. Am. Chem. Soc., 2007, 129, 1456-1464.
Smith et al. "Targeted Intracellular Protein Degradation Induced by a Small Molecule: En Route to Chemical Proteomics" Bioorg. Med. Chem. Lett. 2008, 18(22):5904-5908.
Spratt et al. "RBR E3 ubiquitin ligases: new structures, new insights, new questions." Biochem. 2014, 458:421-437.
Toure et al. "Small-Molecule PROTACs: New Approaches to Protein Degradation" Angewandte Chemie International Edition 2016, 55:1966-1973.
Vassilev et al. "In Vivo Activation of the P53 Pathway by Small-Molecule Antagonists of MDM2" Science 2004, 303:844-848.
Wang et al. "Roles of F-box proteins in cancer." Nat. Rev. Cancer 2014, 14:233-347.
Winter et al. "Phthalimide conjugation as a strategy for in vivo target protein degradation" Science 2015, 348(6241):1376-1381.
Zengerle et al. "Selective Small Molecule Induced Degradation of the BET Bromodomain Protein BRD4" ACS Chem. Biol. 2015, 10:1770-1777.
Zhou et al. "Harnessing the Ubiquitination Machinery to Target the Degradation of Specific Cellular Proteins" Molecular Cell 2000, 6:751-756.
U.S. Pat. No. 10,646,575, B2, U.S. Appl. No. 16/186,339, Phillips et al., May 12, 2020.
U.S. Pat. No. 10,660,968, B2, U.S. Appl. No. 16/186,334, Phillips et al., May 26, 2020.
U.S. Pat. No. 10,849,982, B2, U.S. Appl. No. 16/186,341, Phillips et al., Dec. 1, 2020.
U.S. Pat. No. 10,905,768, B2, U.S. Appl. No. 16/872,225, Phillips et al., Feb. 2, 2021.
US, 2020/0140456, A1, U.S. Appl. No. 16/721,650, Phillips et al., May 7, 2020.
US, 2020/0207764, A1, U.S. Appl. No. 16/809,325, Norcross et al., Jul. 2, 2020.
US, 2020/0207783, A1, U.S. Appl. No. 16/809,336, Norcross et al., Jul. 2, 2020.
US, 2020/0207733, A1, U.S. Appl. No. 16/809,345, Norcross et al., Jul. 2, 2020.
US, 2020/0308171, A1, U.S. Appl. No. 16/903,237, Jaeschke et al., Oct. 1, 2020.
US, 2020/0361930, A1, U.S. Appl. No. 16/984,987, Duplessis et al., Nov. 19, 2020.
US, 2021/0009559, A1, U.S. Appl. No. 17/031,550, Henderson et al., Jan. 14, 2021.
US, 2021/0032245, A1, U.S. Appl. No. 17/072,896, Nasveschuk et al., Feb. 4, 2021.
U.S. Appl. No. 16/874,475, Phillips et al., filed May 15, 2020,
U.S. Appl. No. 16/882,236, Phillips et al., filed May 22, 2020.
U.S. Appl. No. 17/103,621, Nasveschuk et al., filed Nov. 24, 2020.
U.S. Appl. No. 17/107,781, Phillips et al., filed Nov. 30, 2020.
U.S. Appl. No. 17/164,446, Phillips et al., filed Feb. 1, 2021

FIG. 1Q
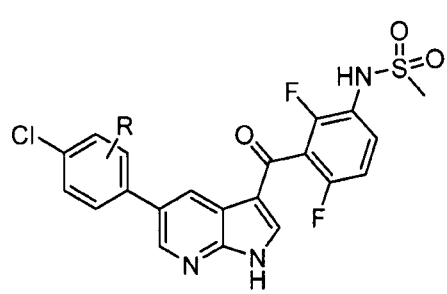
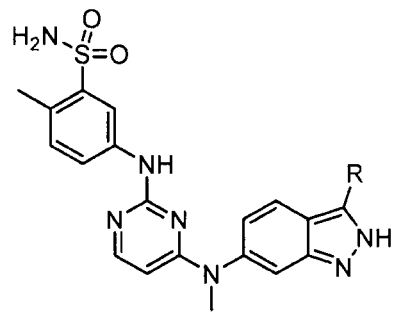
FIG. 1R
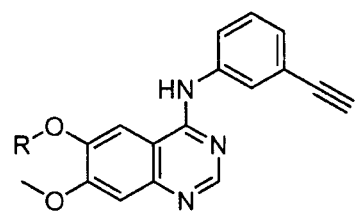
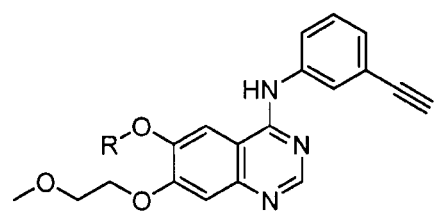
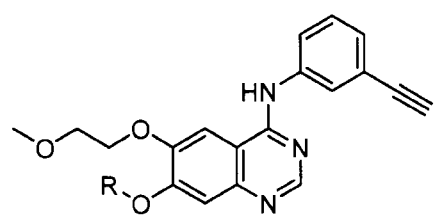
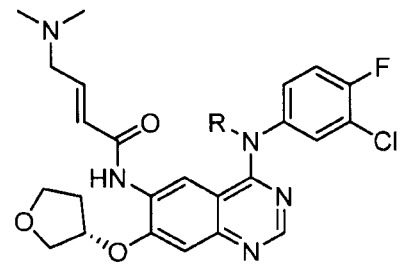
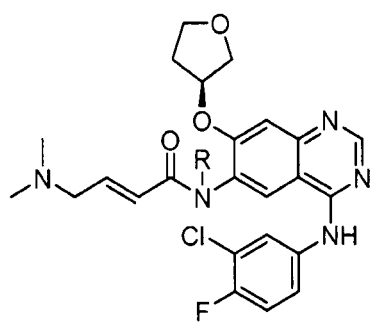
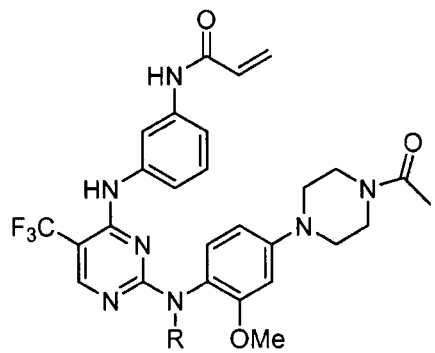

FIG. 1AA
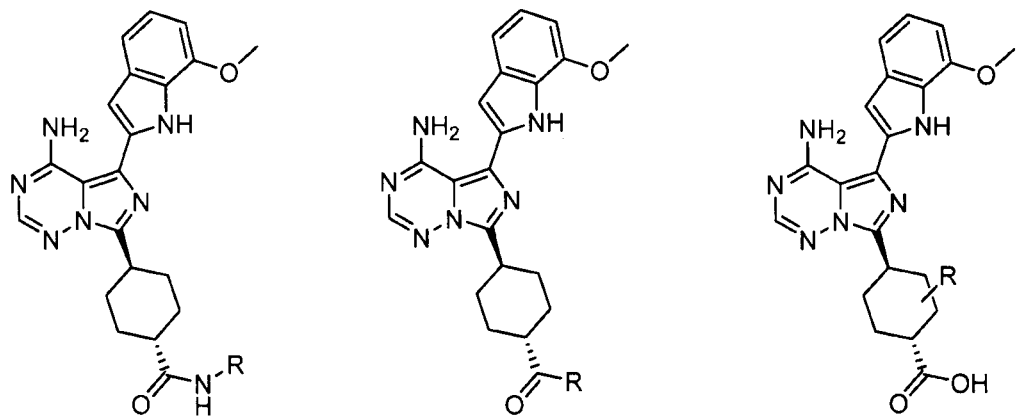
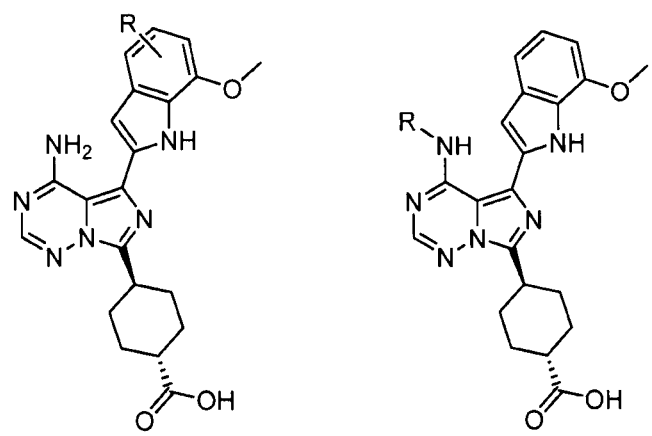
FIG. 1BB
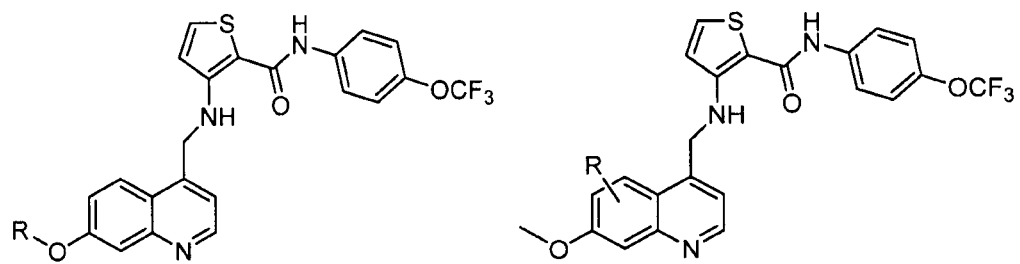

FIG. 1EE
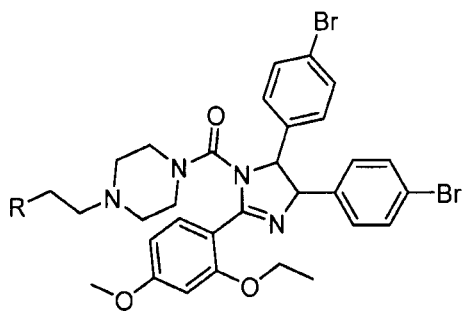
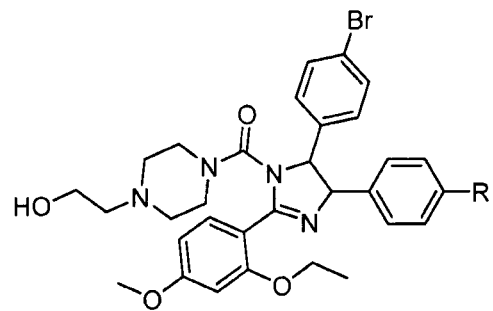
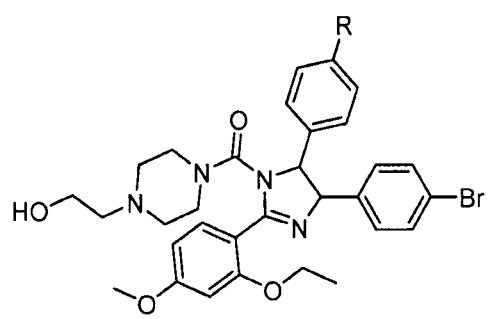
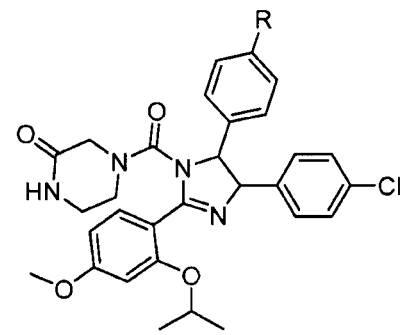
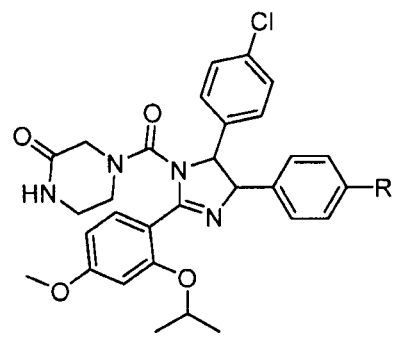
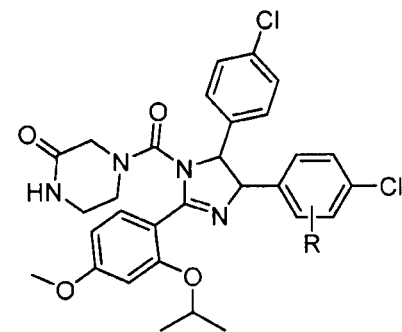
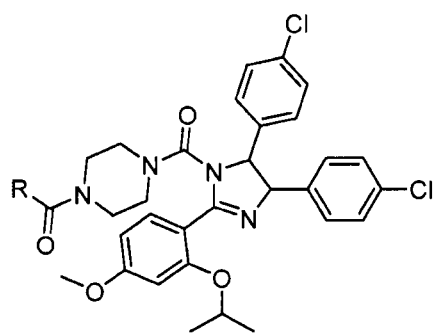
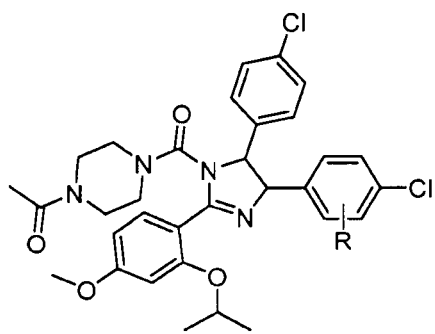

FIG. 1LL
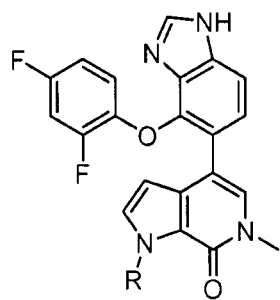
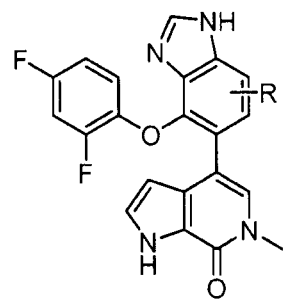
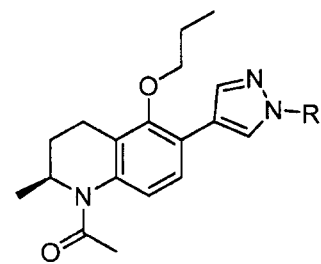
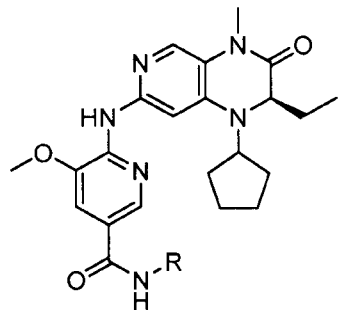
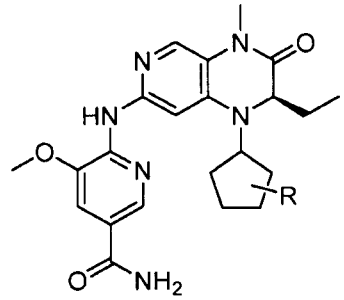
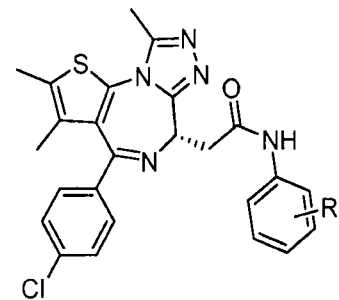
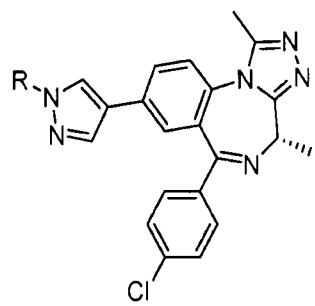
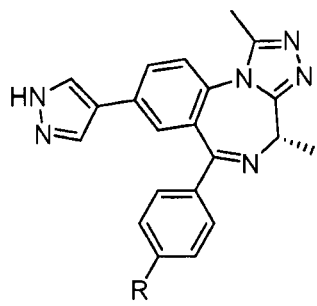
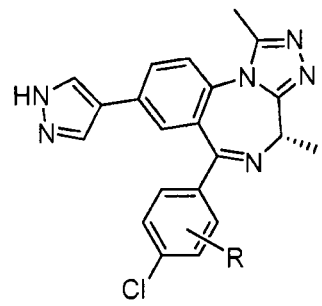
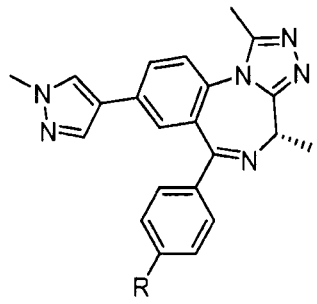
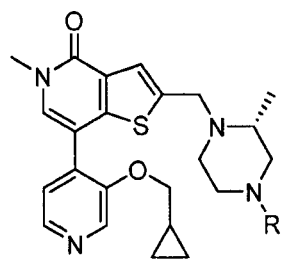
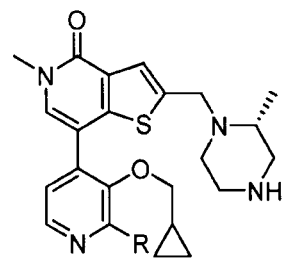

FIG. 1PP
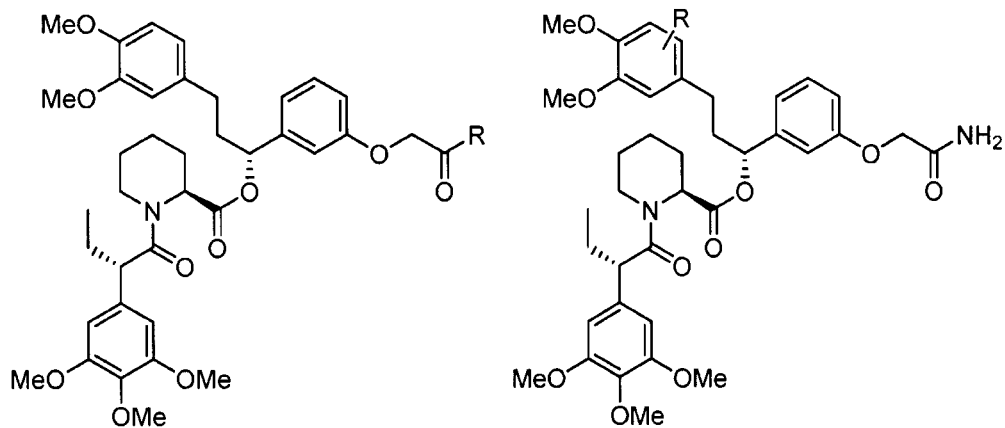
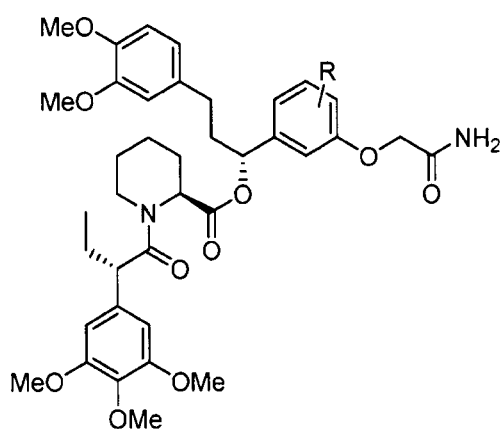
FIG. 1QQ
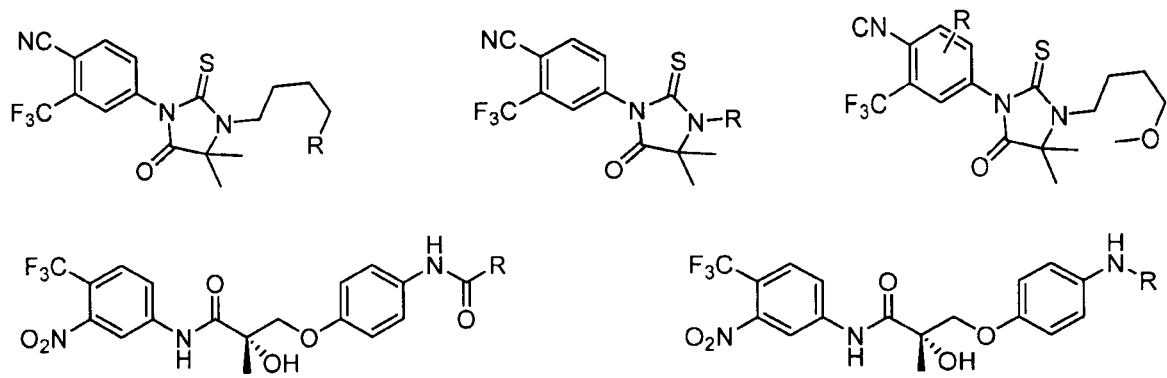

FIG. 1RR
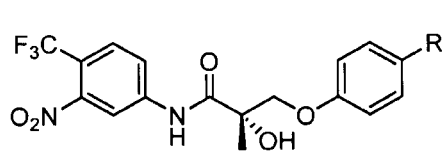
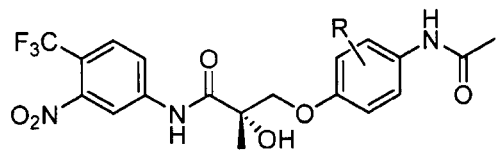
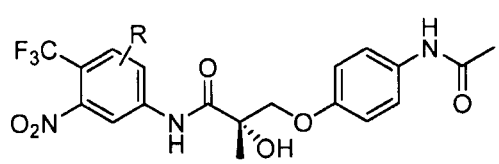
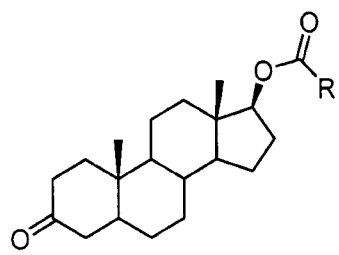
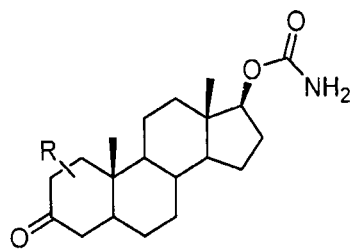
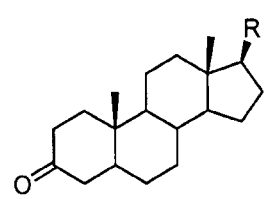
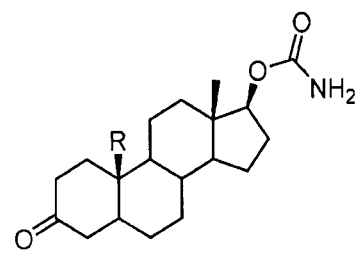
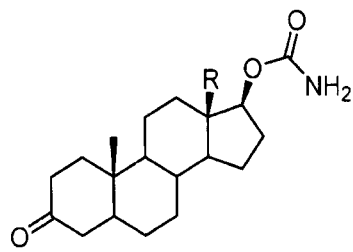
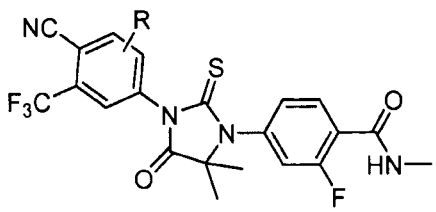
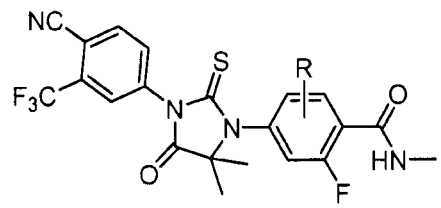
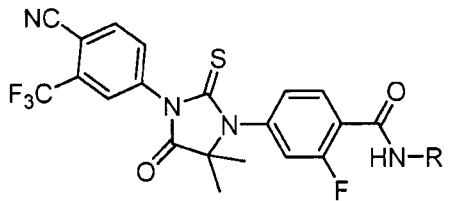
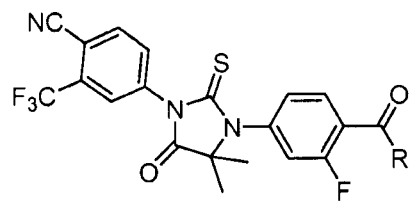
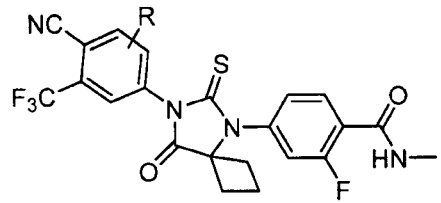

FIG. 1TT
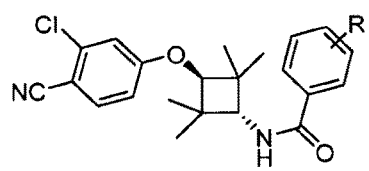
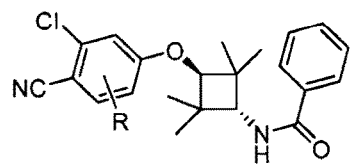
FIG. 1UU
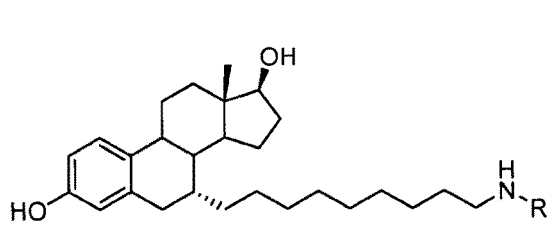
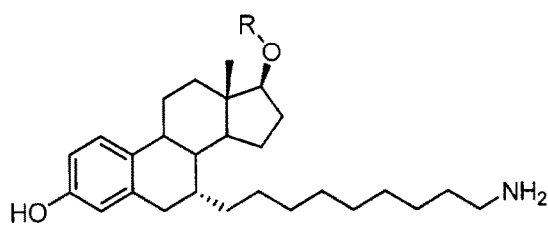
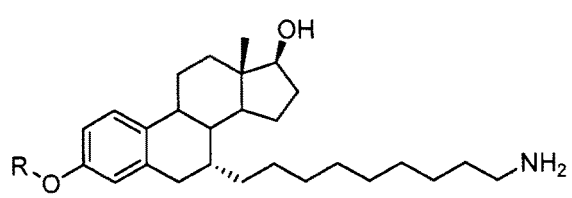
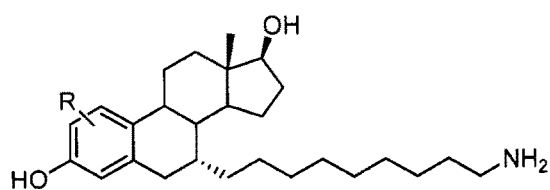
FIG. 1VV
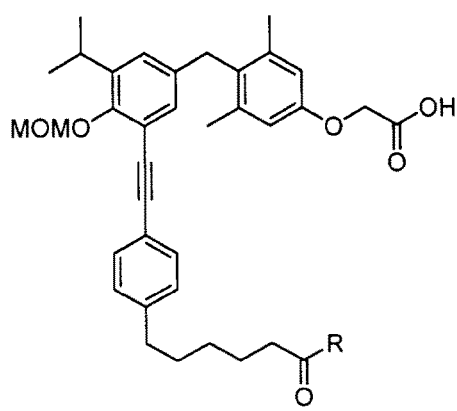
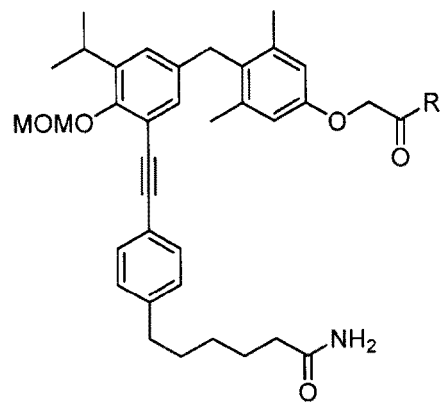

FIG. 1WW
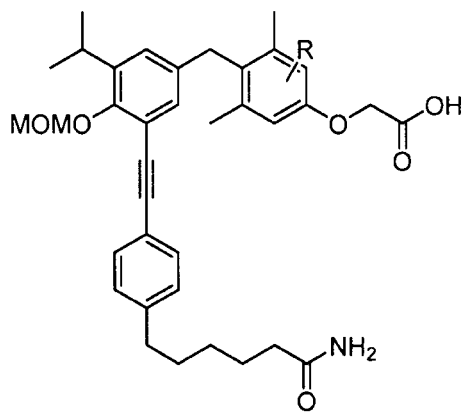
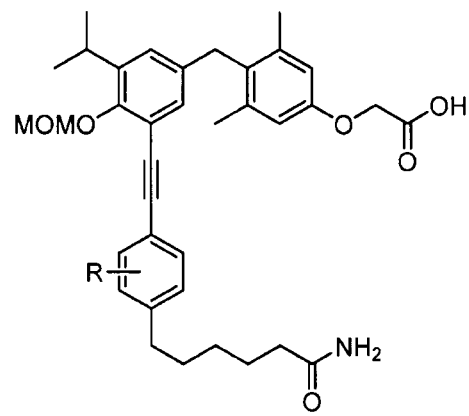
FIG. 1XX
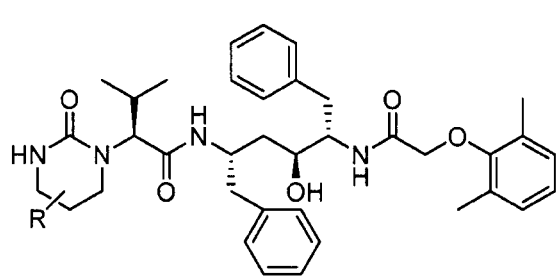
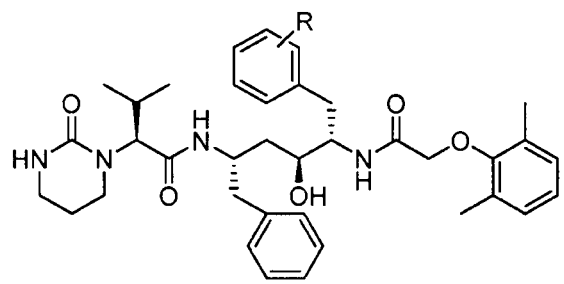
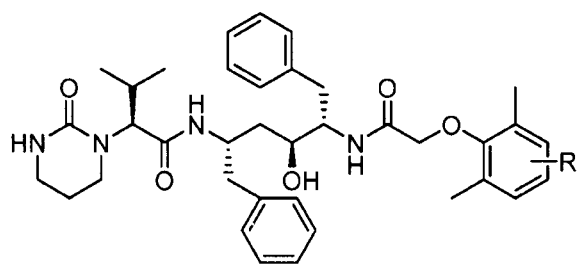
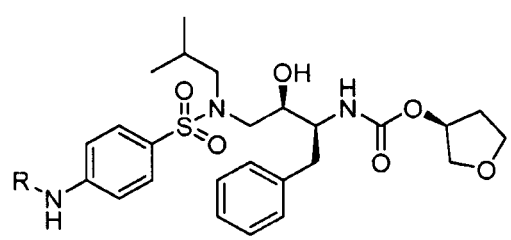
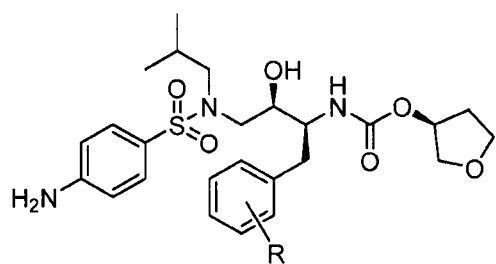
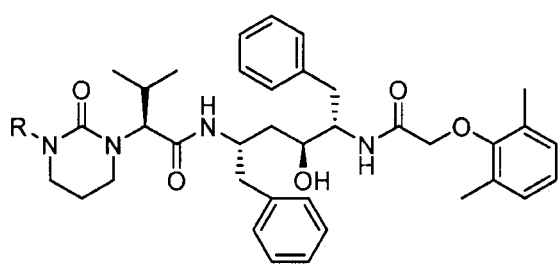

FIG. 1AAA
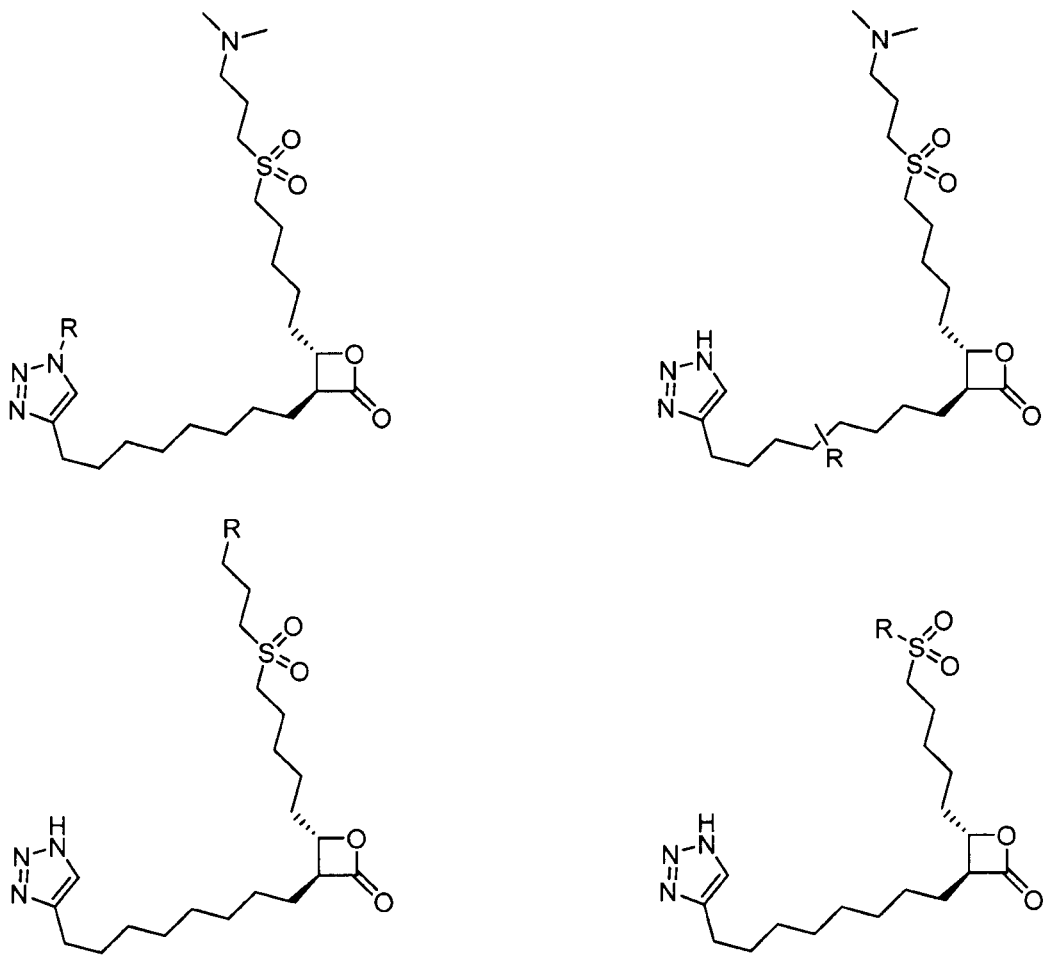
FIG. 1BBB
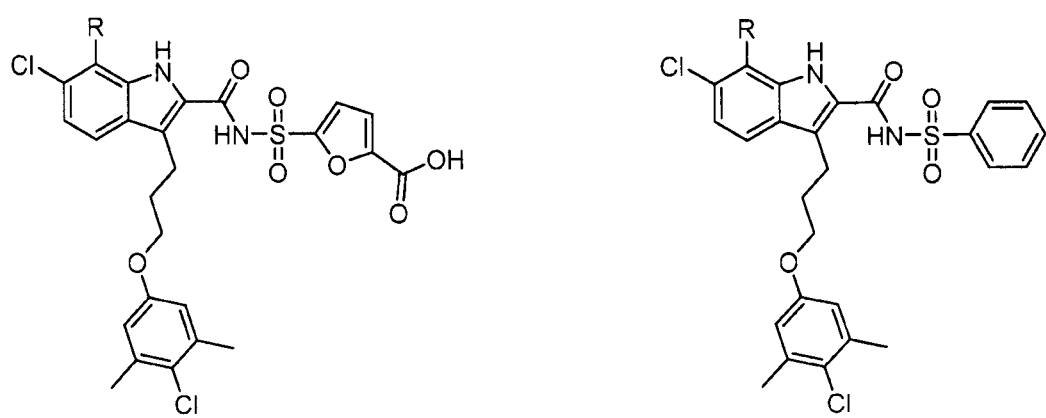

FIG. 1CCC
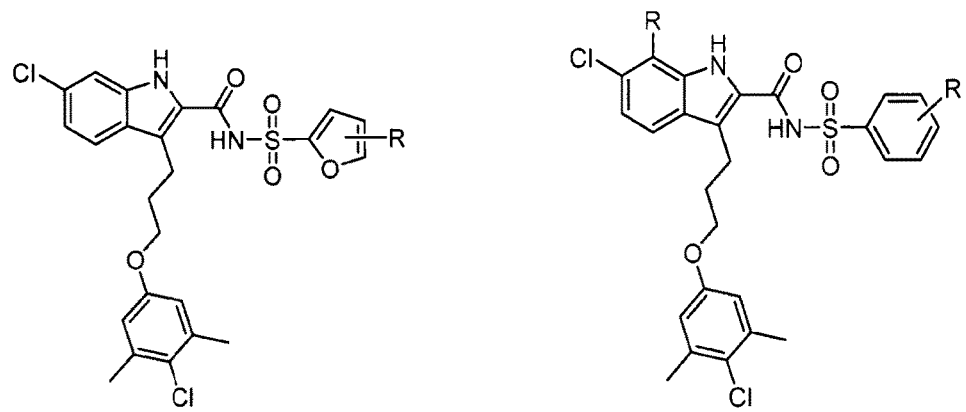
FIG. 1DDD
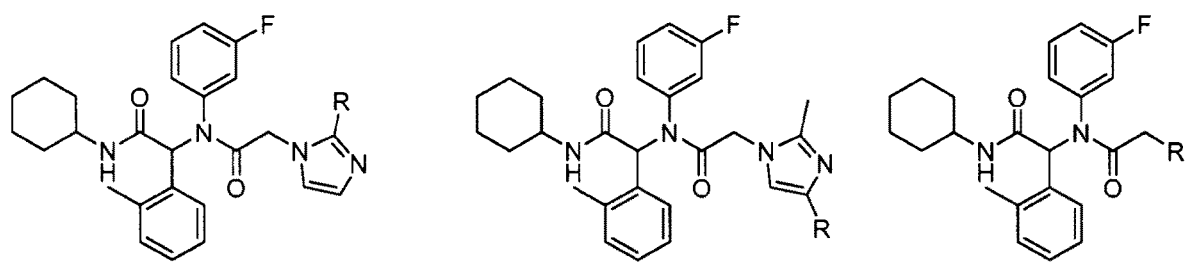
FIG. 1EEE
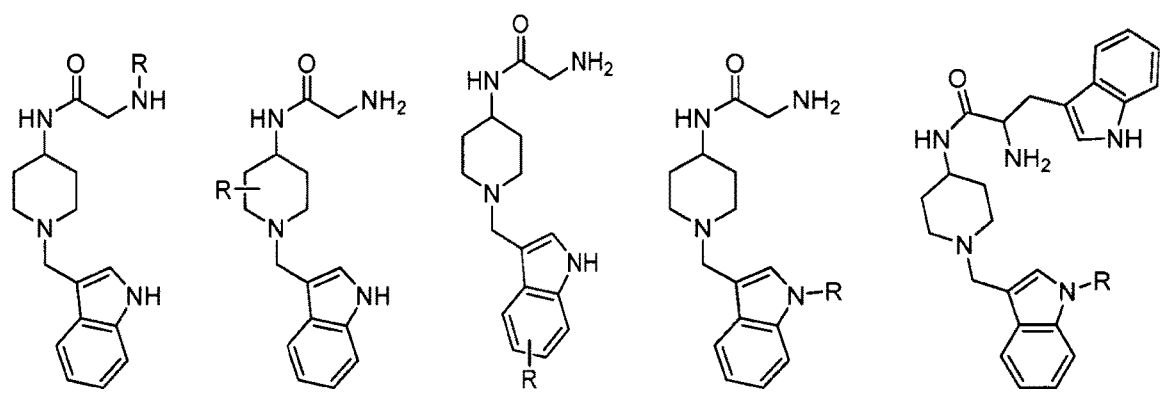

FIG. 1FFF
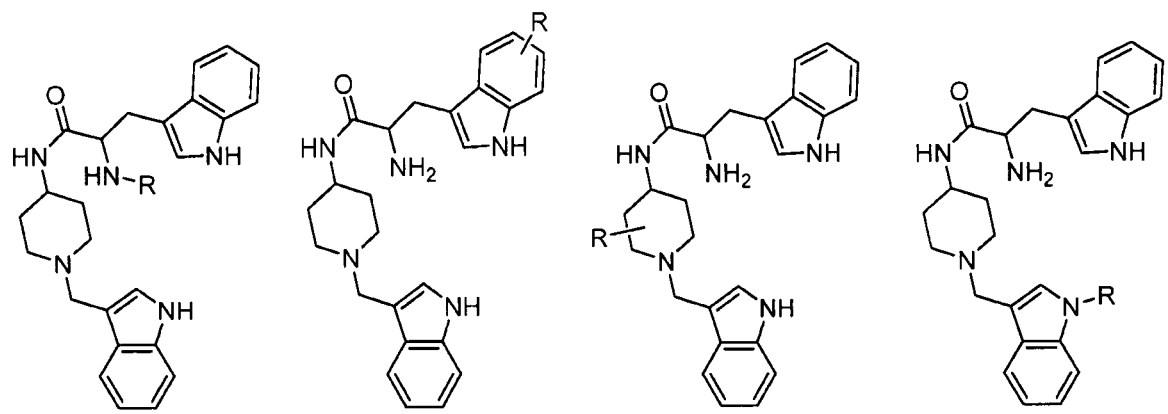
FIG. 1GGG
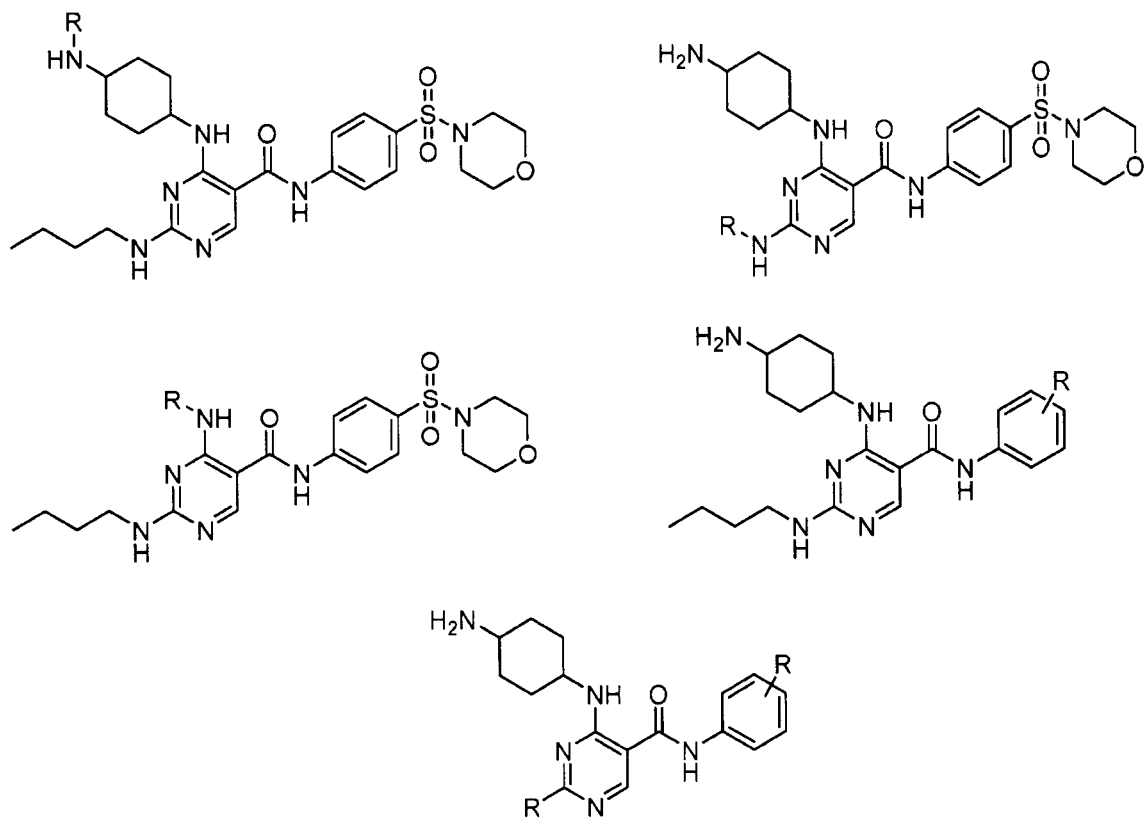

FIG. 1HHH
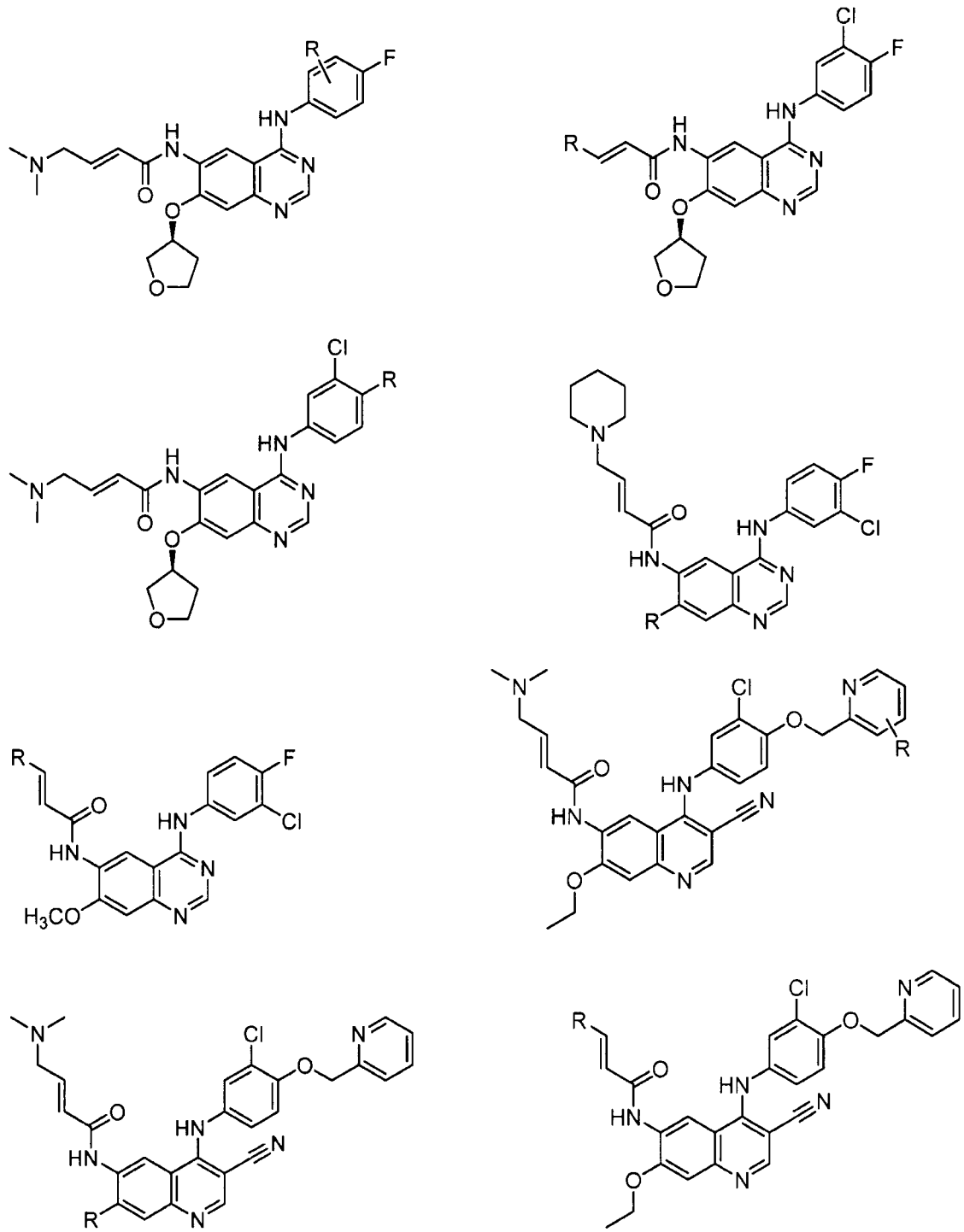

FIG. 1III
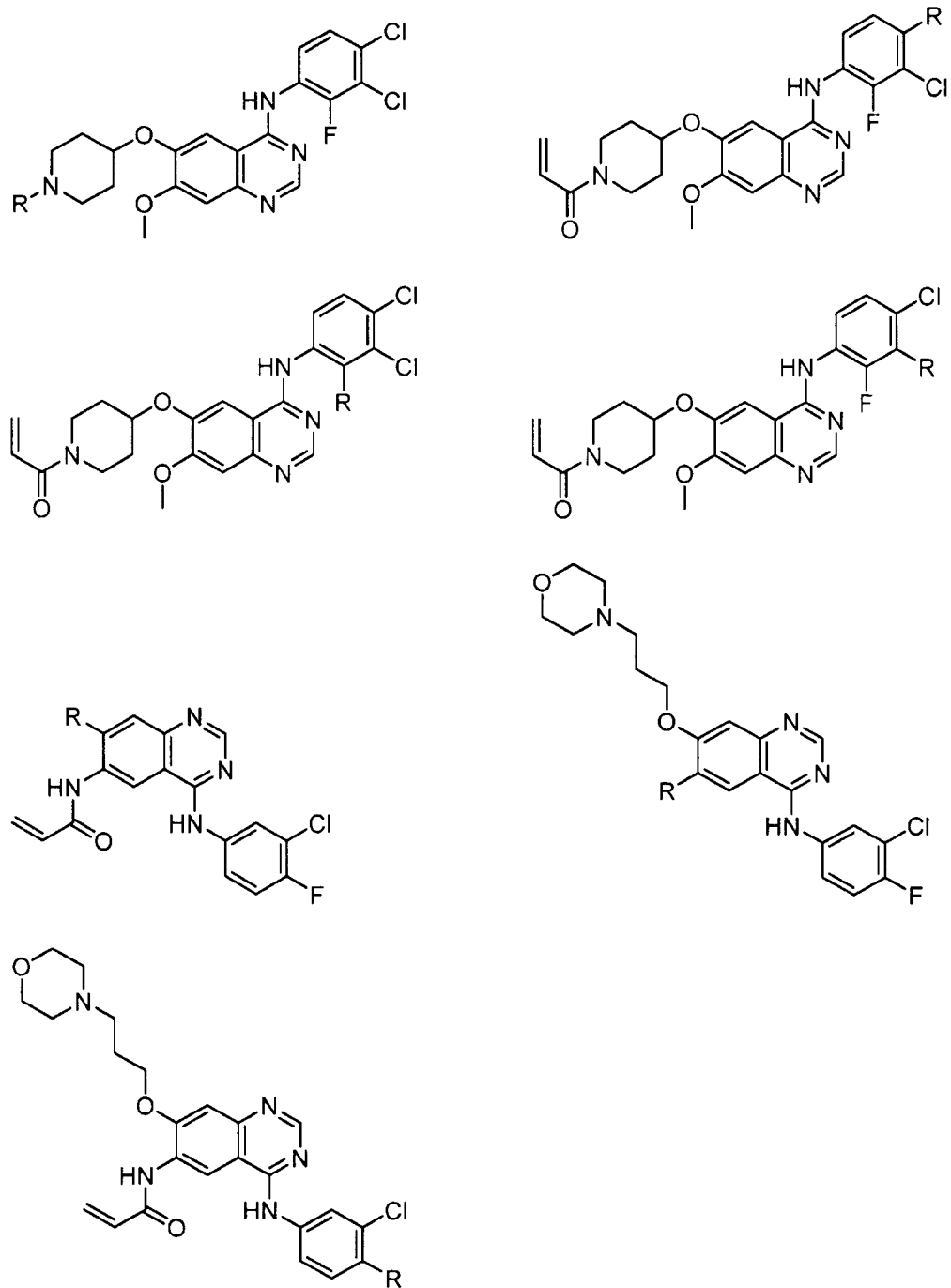

FIG. 1JJJ
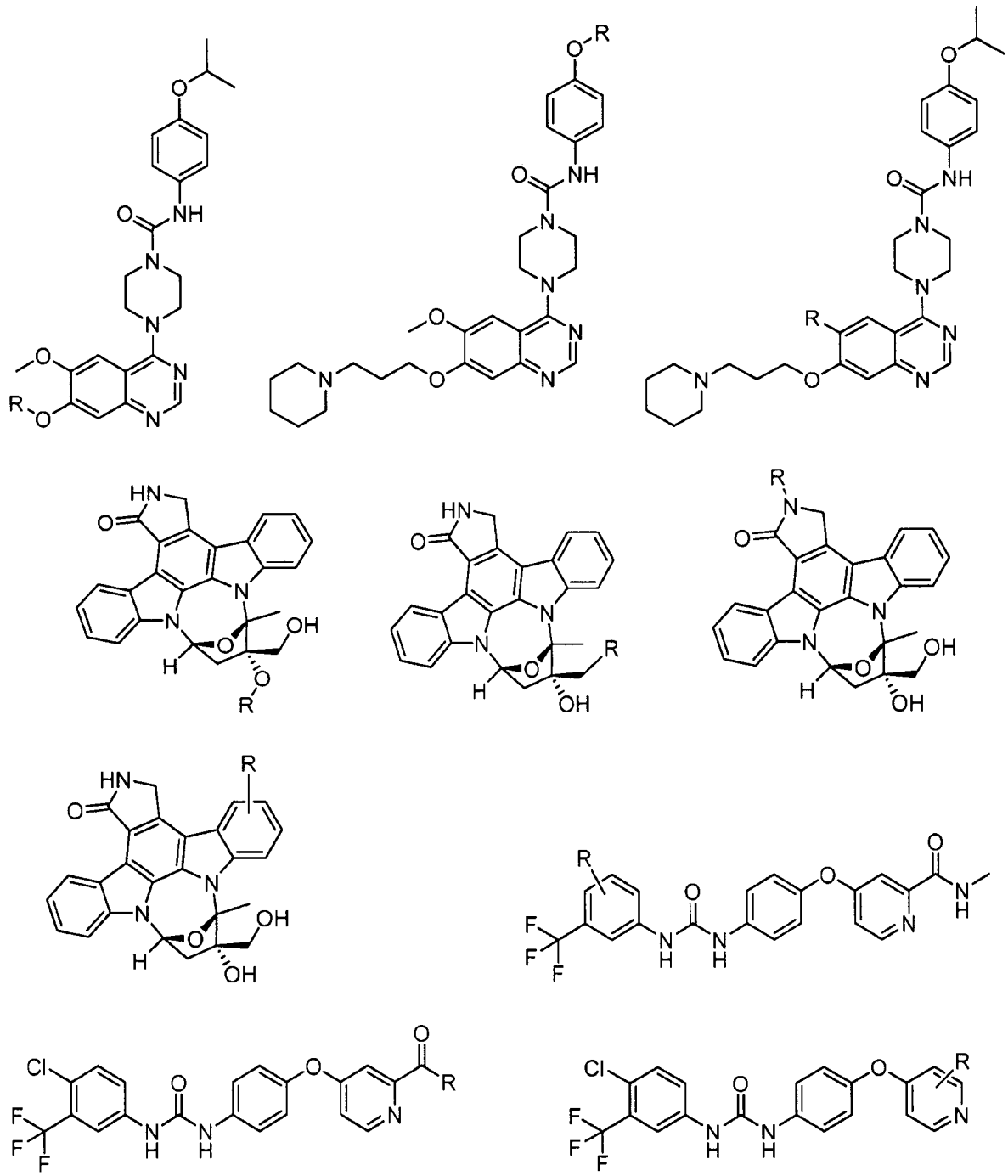

FIG. 1KKK
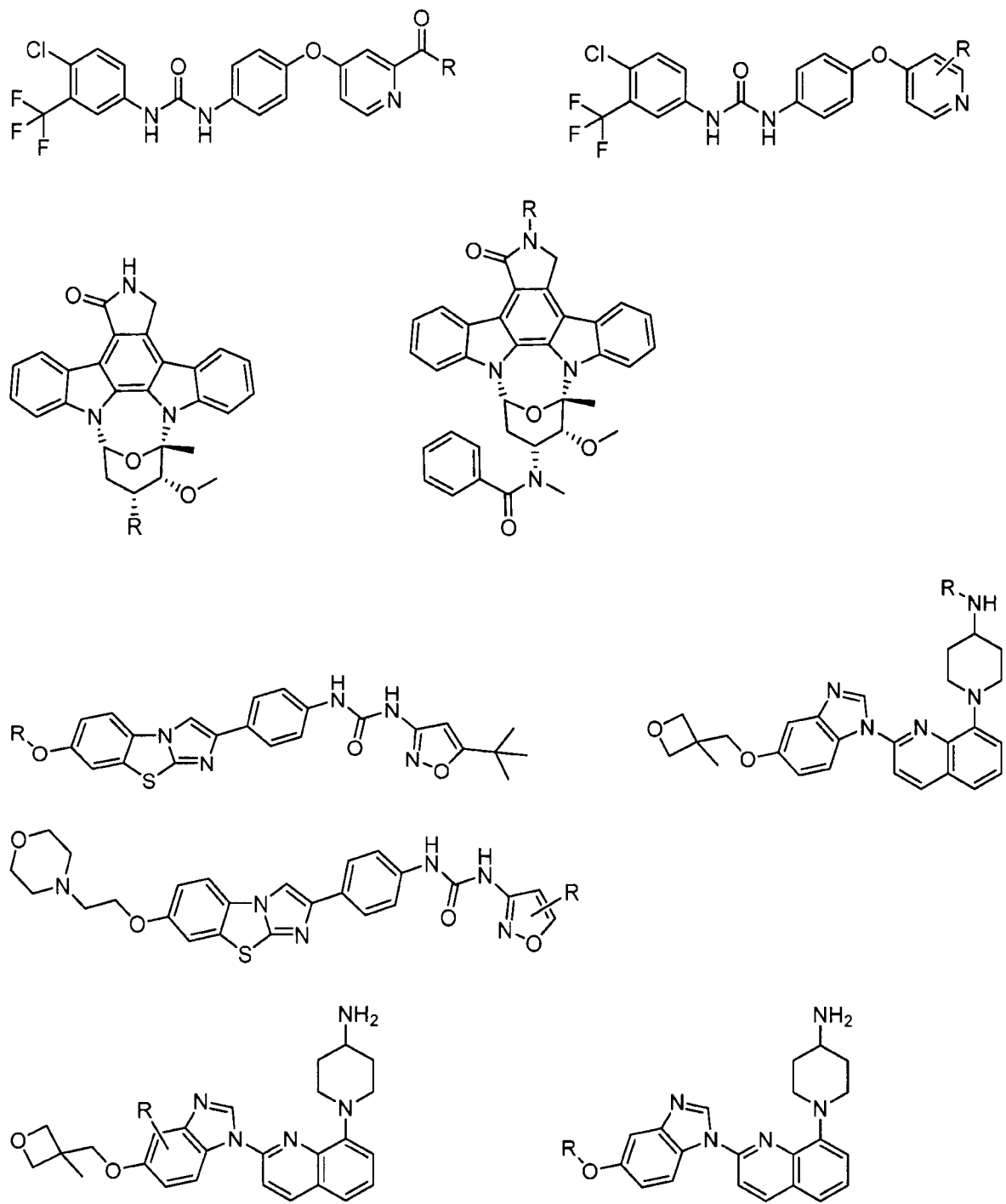

FIG. 1LLL
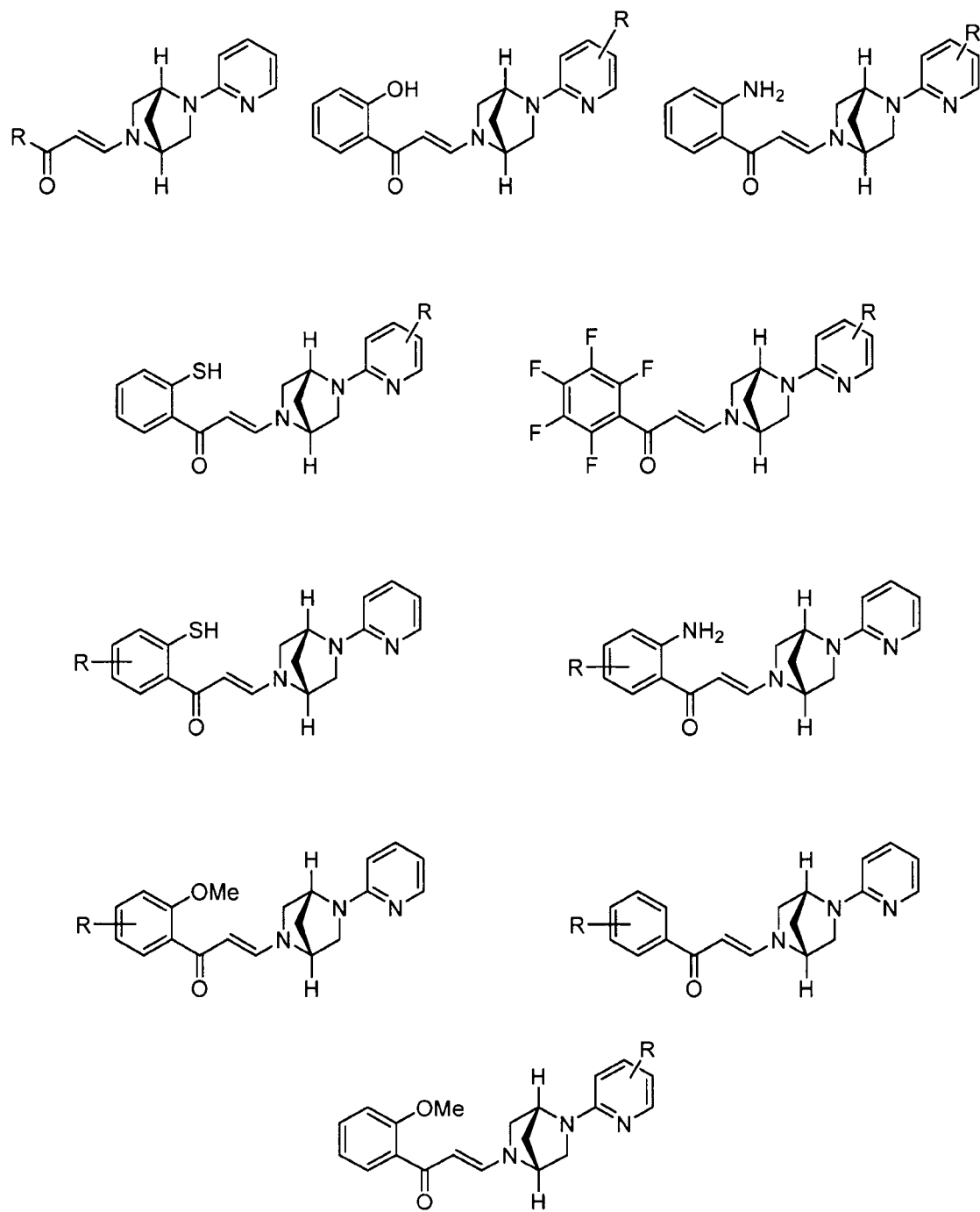

FIG. 2D
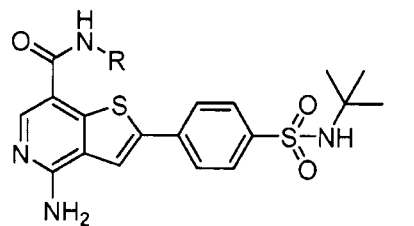
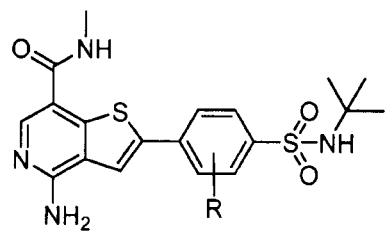
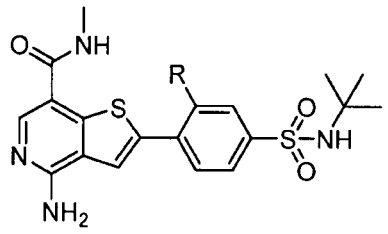
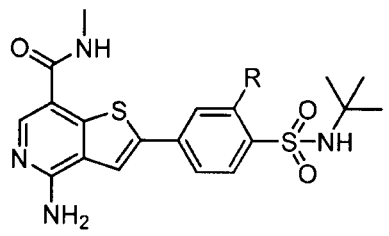
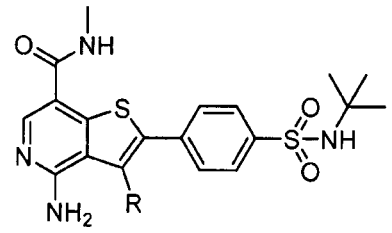
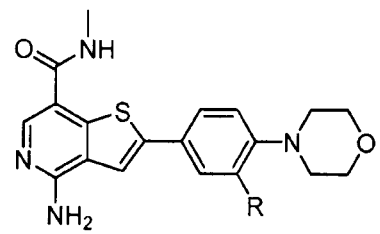
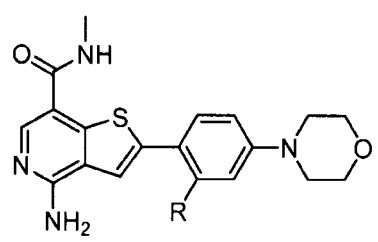
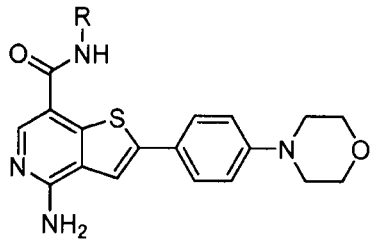
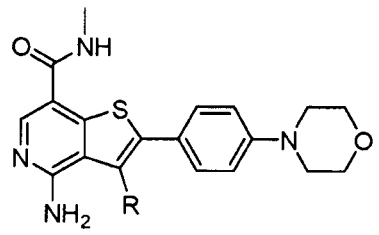
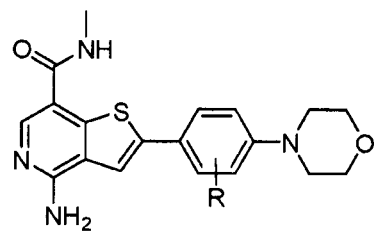

FIG. 2F
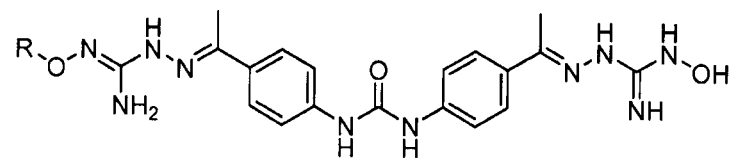
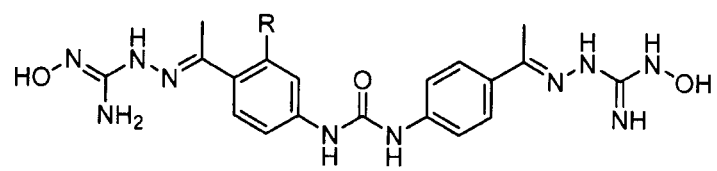
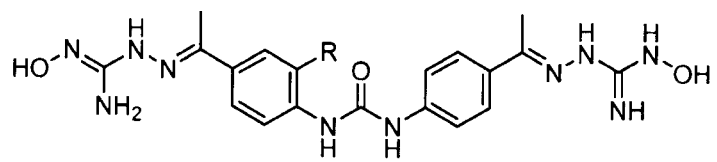
FIG. 2G
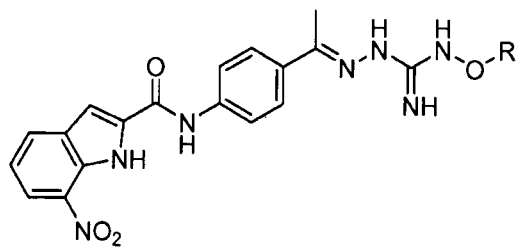
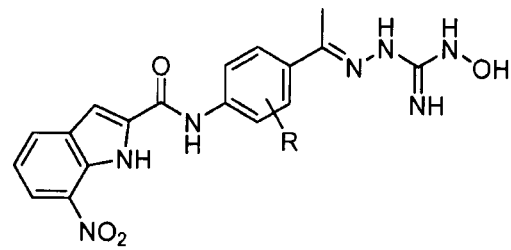
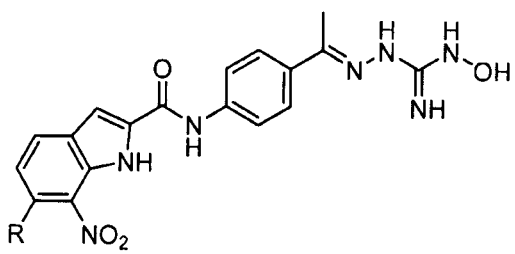
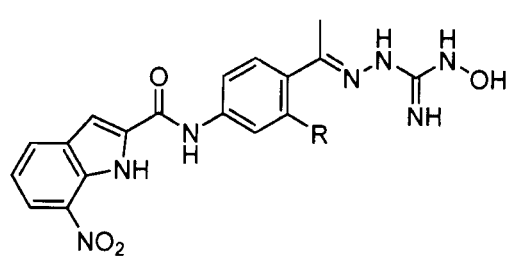
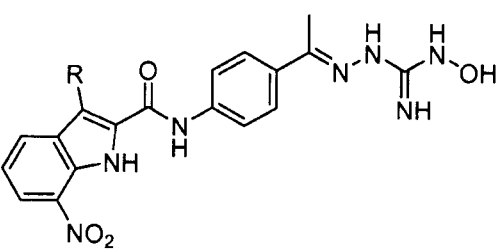
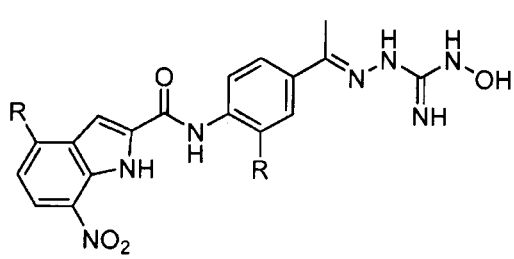

FIG. 21
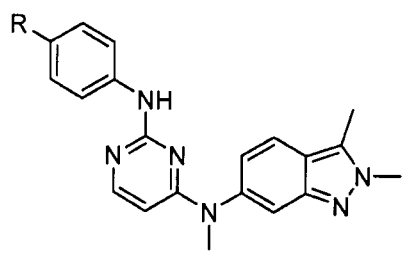
derivatized pazopanib
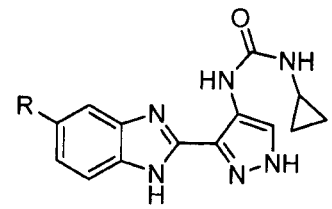
derivatized AT-9283
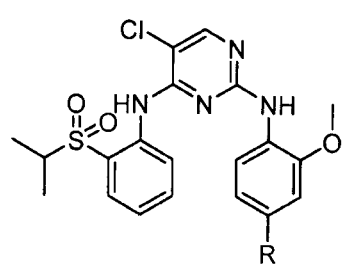
derivatized TAE684
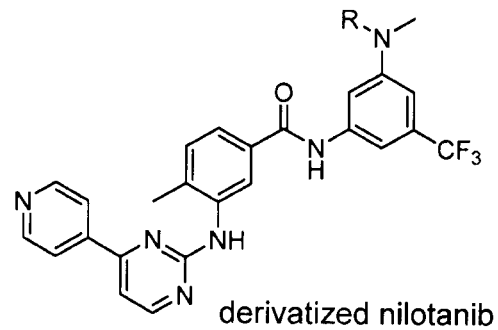
derivatized nilotanib
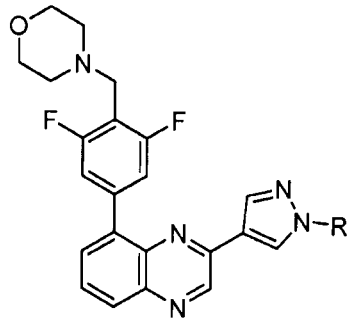
derivatized NVP-BSK805
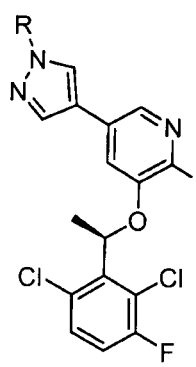
derivatized Crizotinib
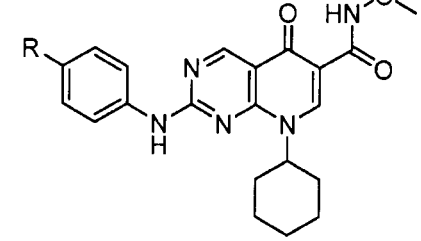
derivatized JNJ FMS
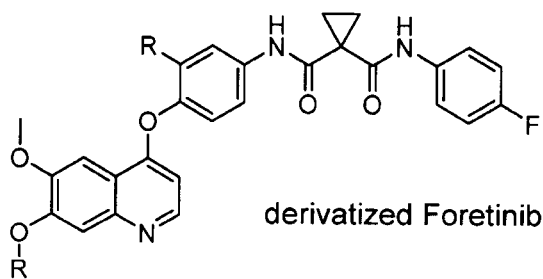
derivatized Foretinib
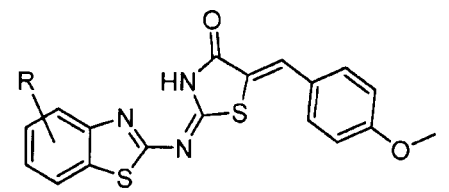
derivatized inhibitor of SHP-2 Domain of Tyrosine Phospatase derivatized PTP1B derivatized inhibitor of BRAF (BRAFV600E)/MEK derivatized mTORC1/2 kinase inhibitor OSI-027 derivatized c-Kit/KDR kinase inhibitor OSI-930 derivatized IGF1R/IR kinase inhibitor OSI-906

FIG. 2W
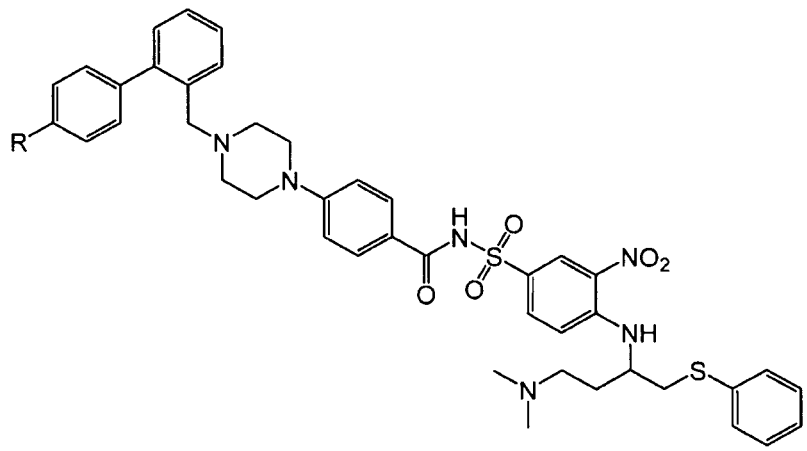
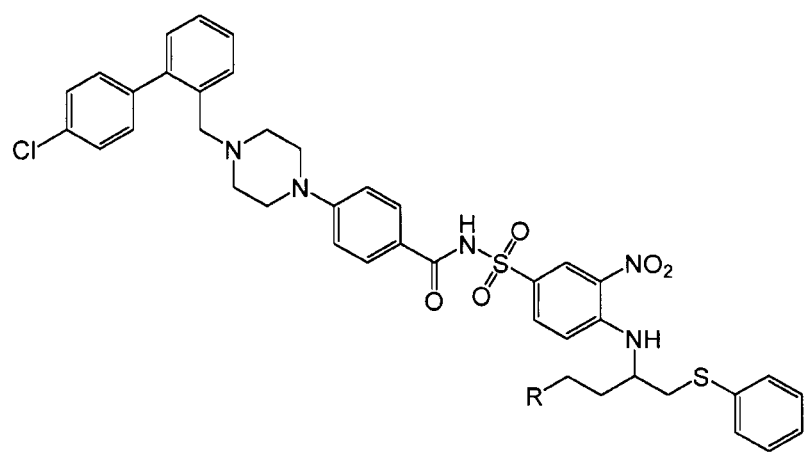
FIG. 2X
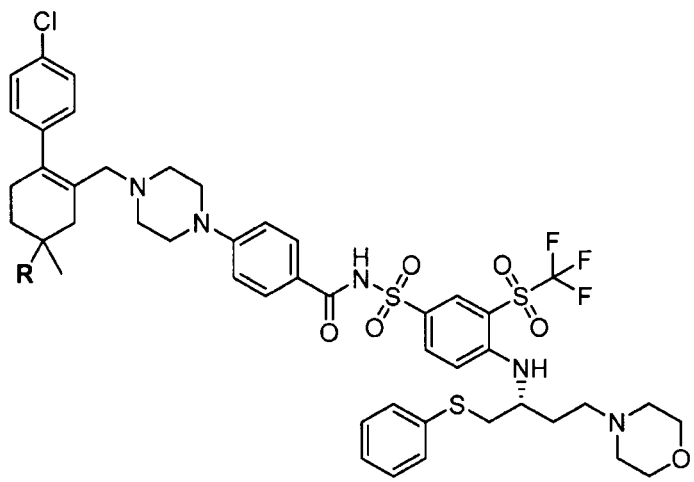
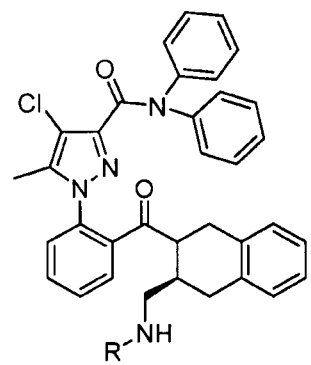

FIG. 2Y
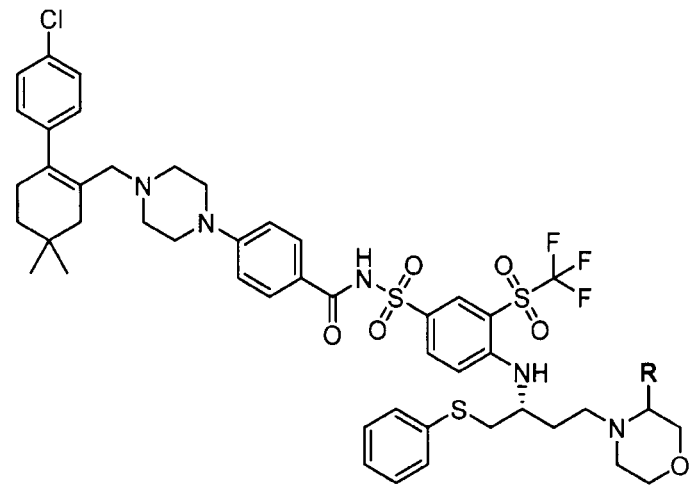
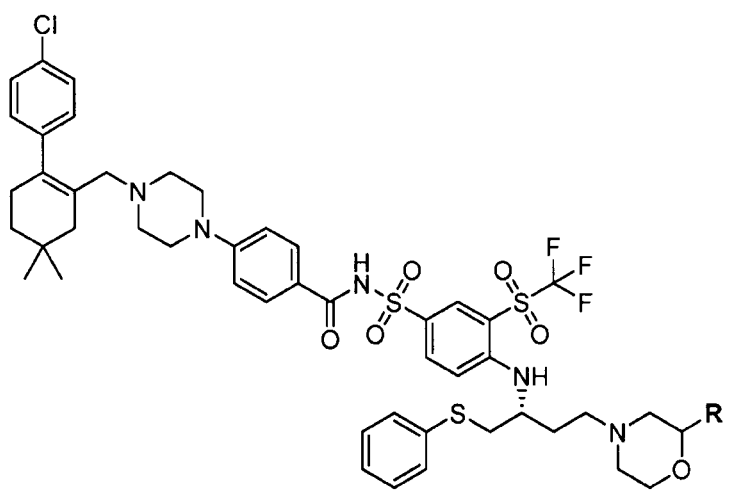
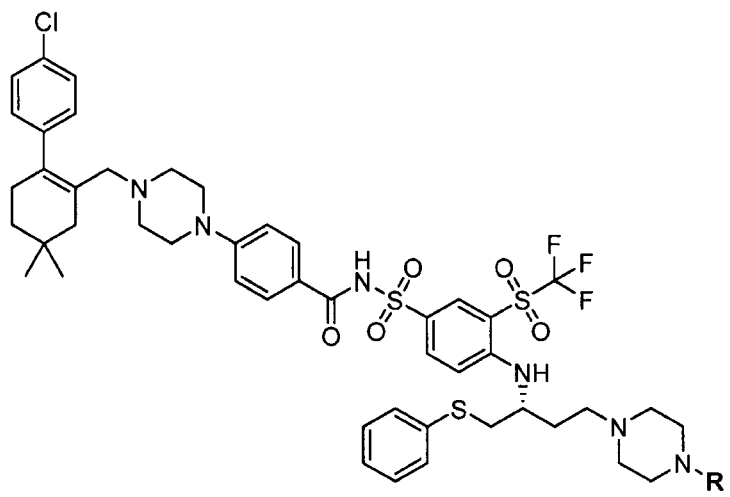

FIG. 2RR
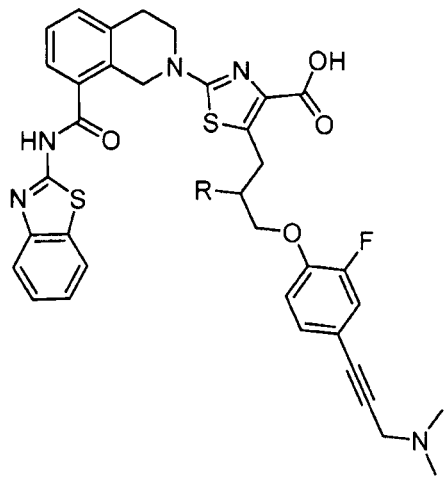
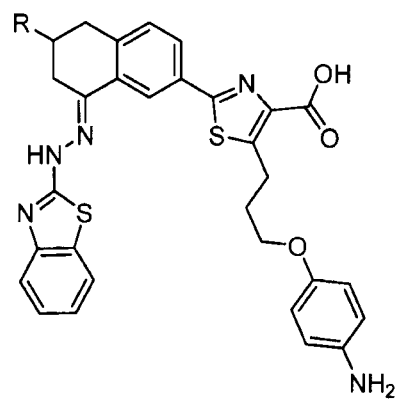
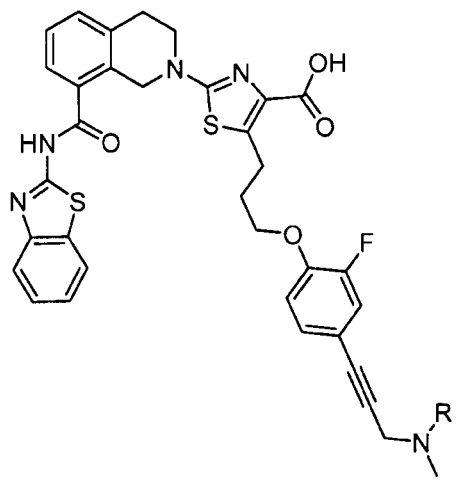
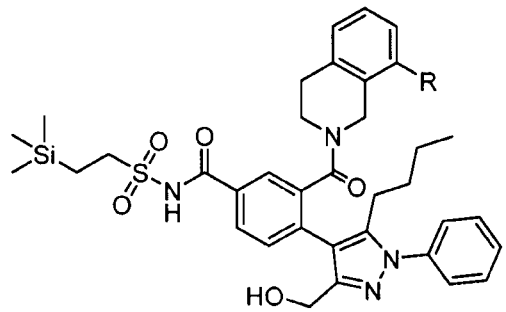
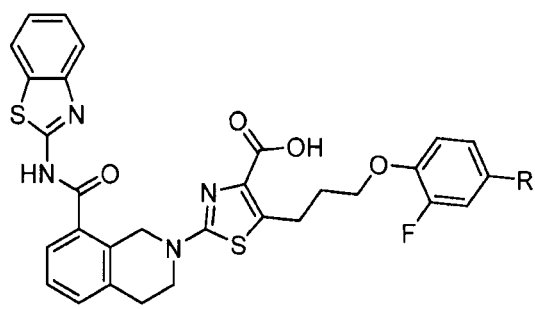
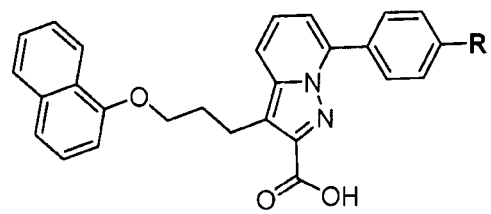

FIG. 2AAA
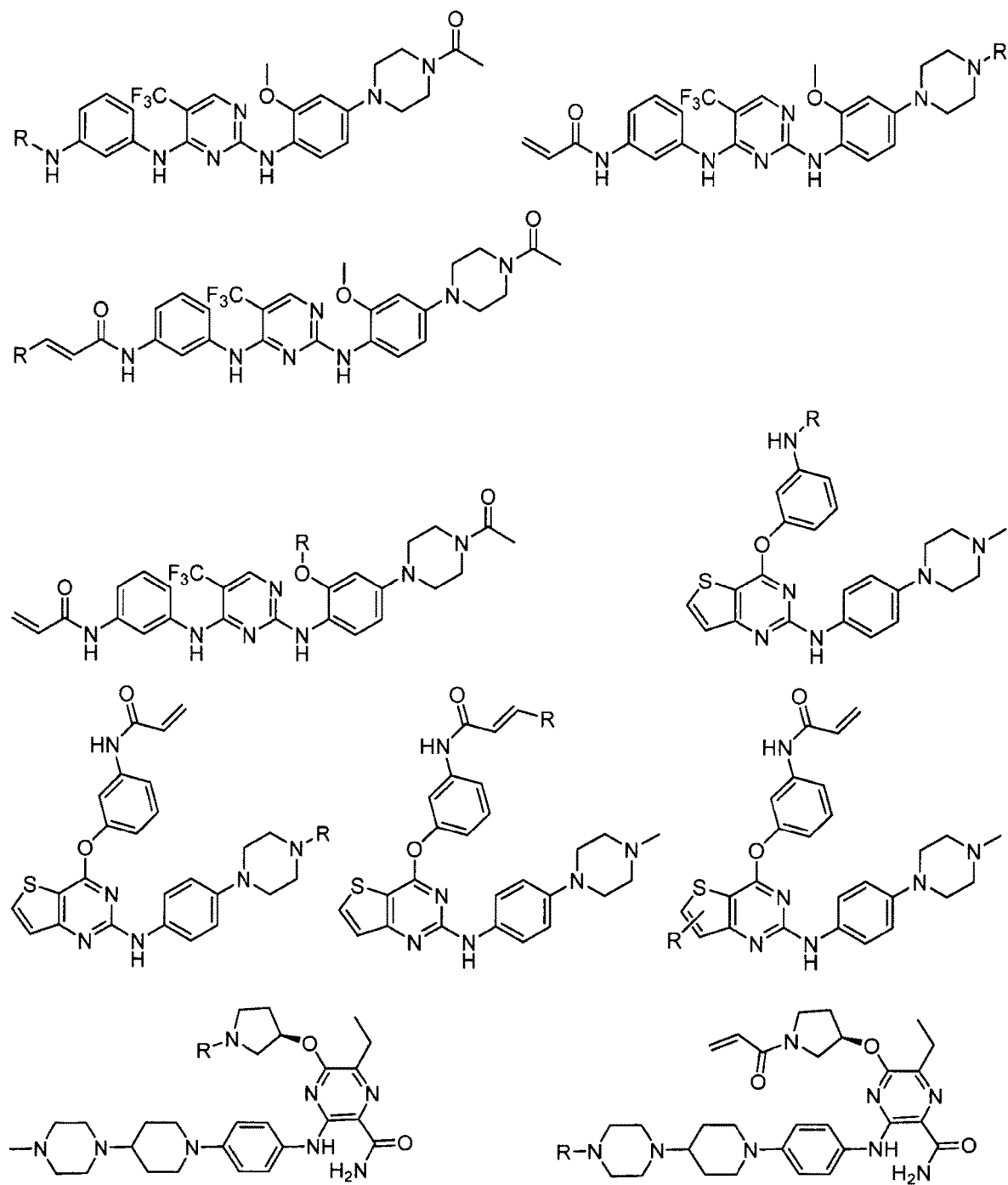

FIG. 2BBB
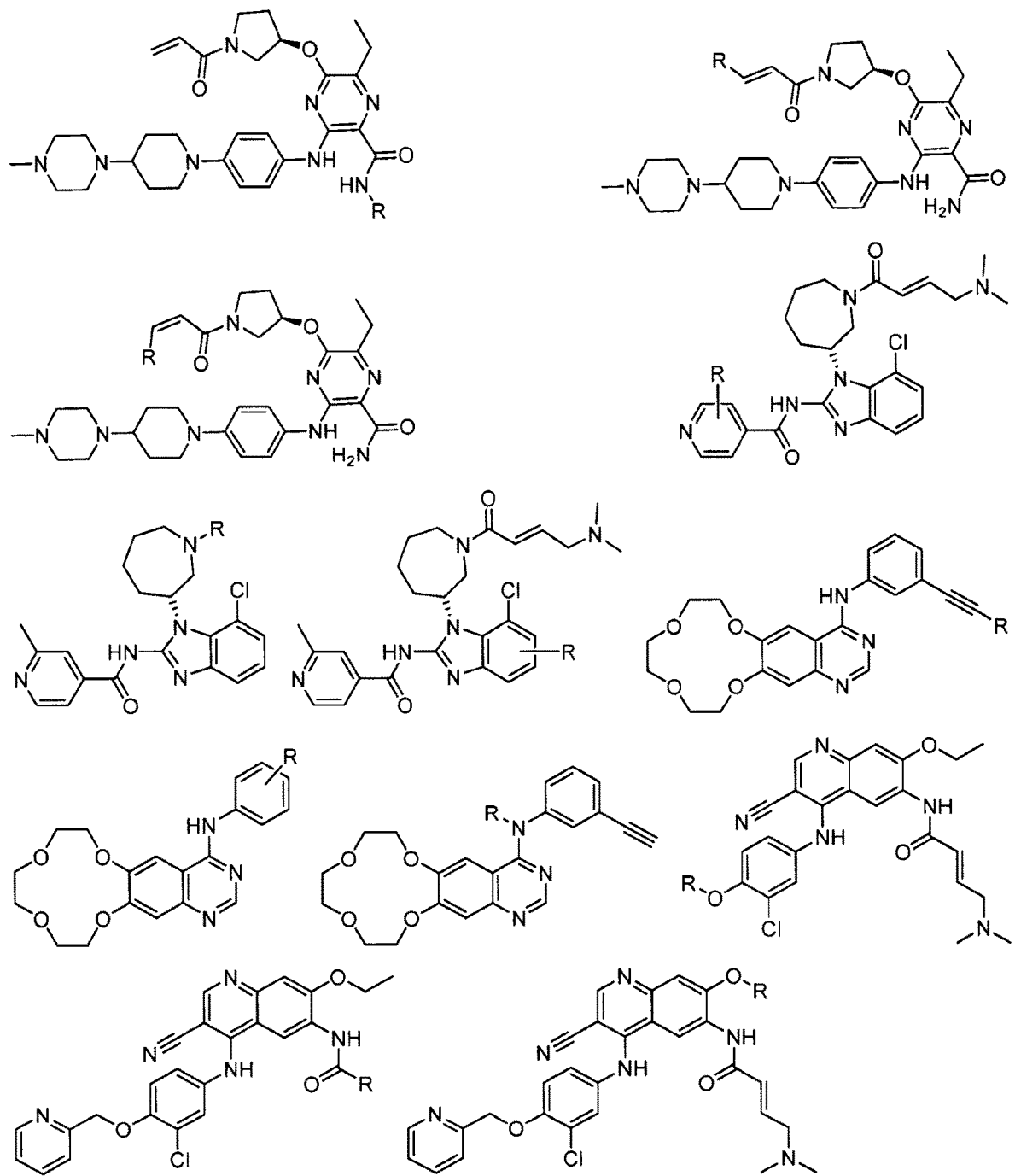

FIG. 2CCC
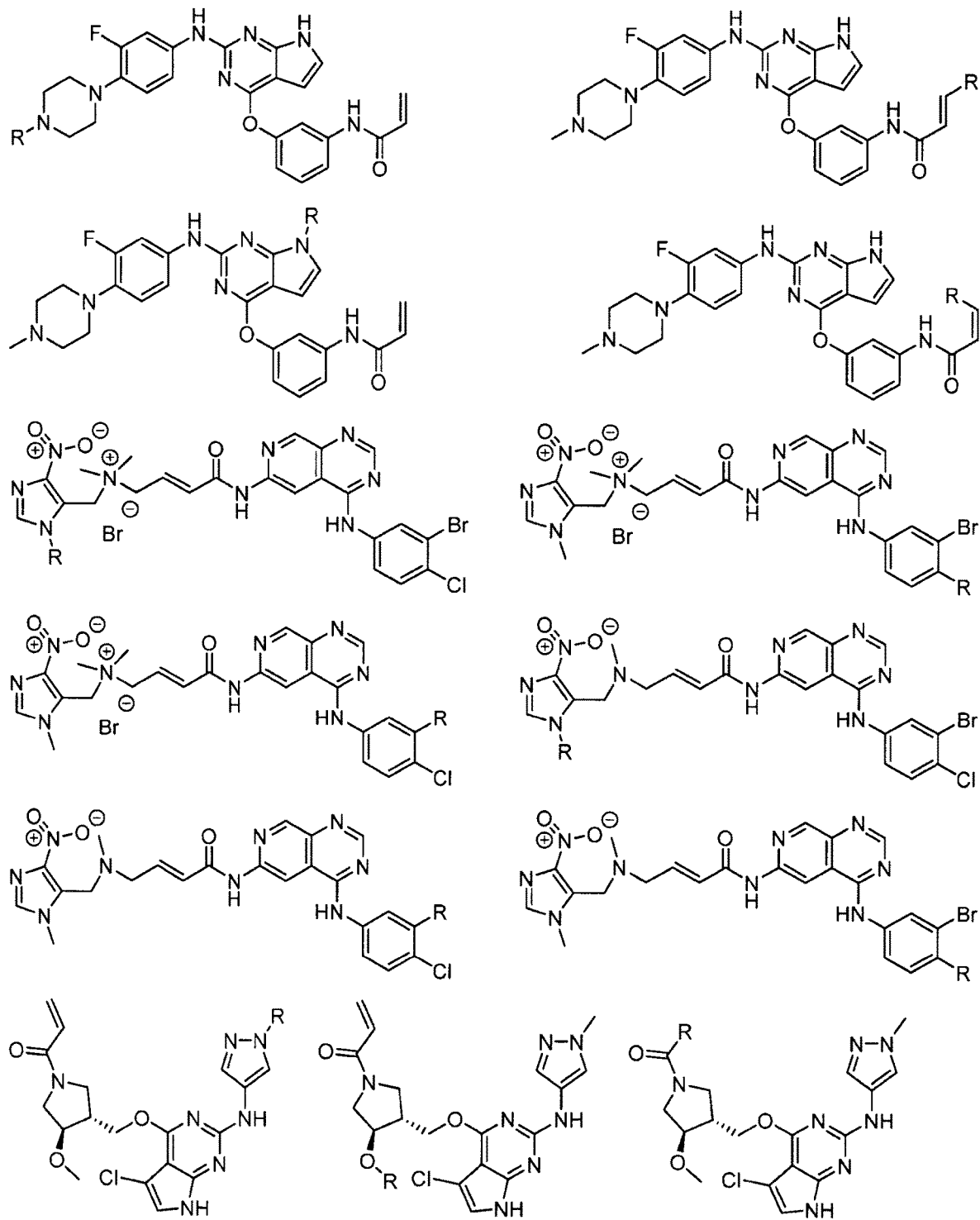

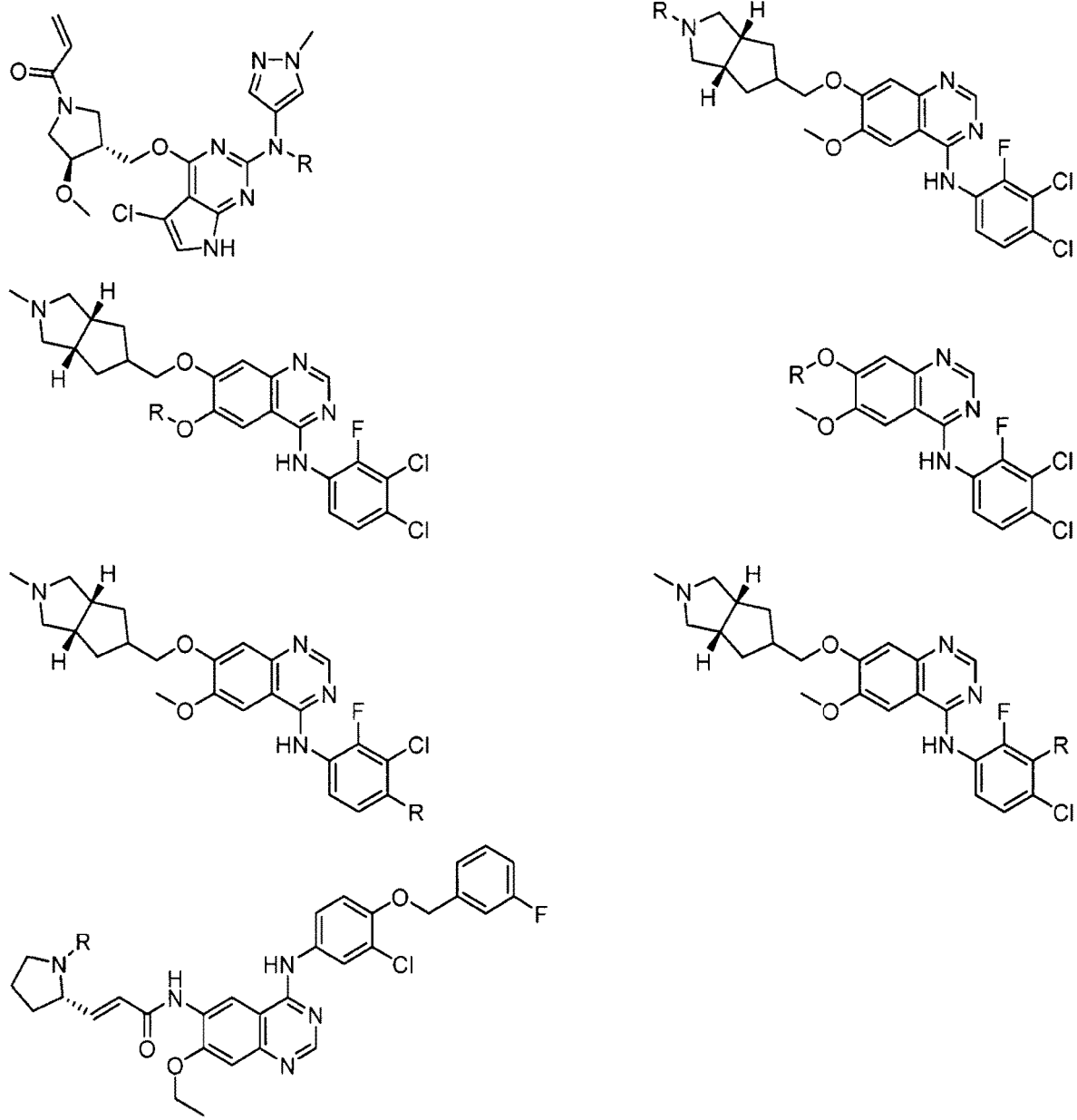
FIG. 2DDD

FIG. 2EEE
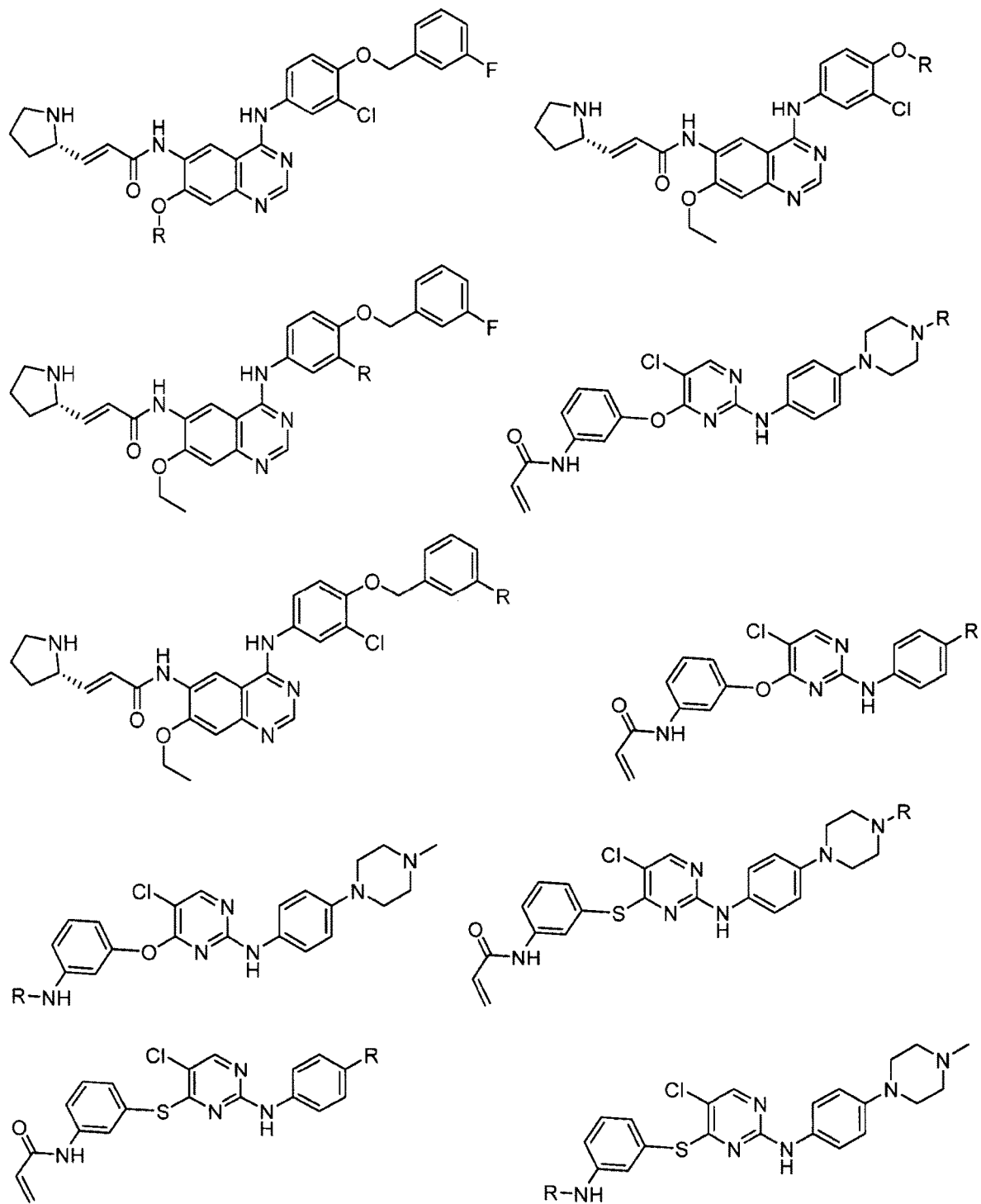

FIG. 2FFF
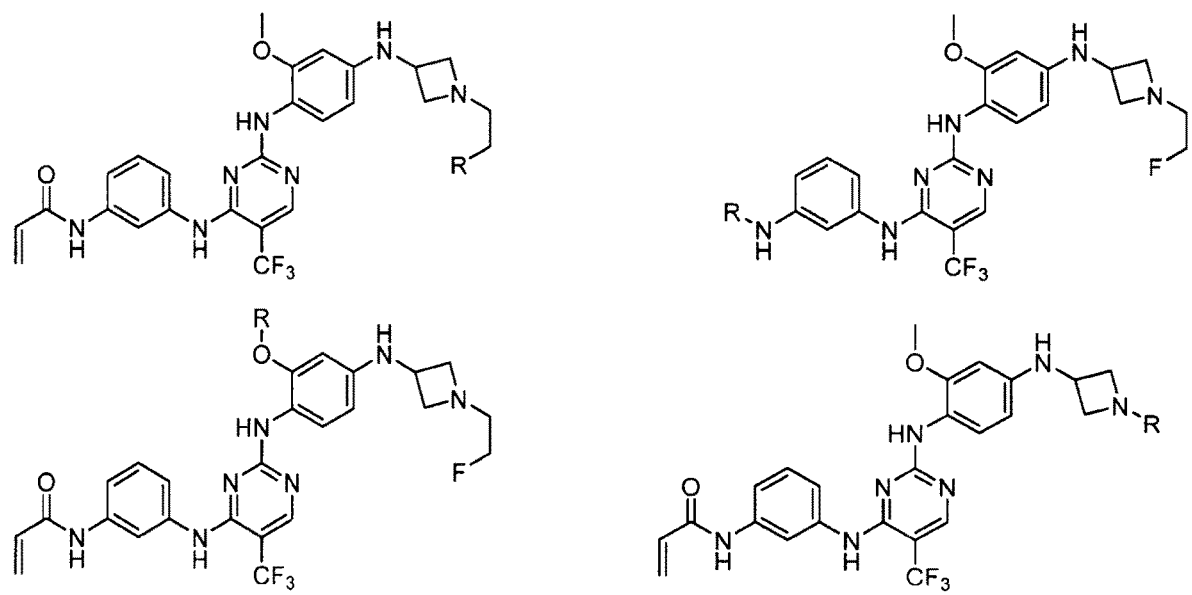
FIG. 2GGG
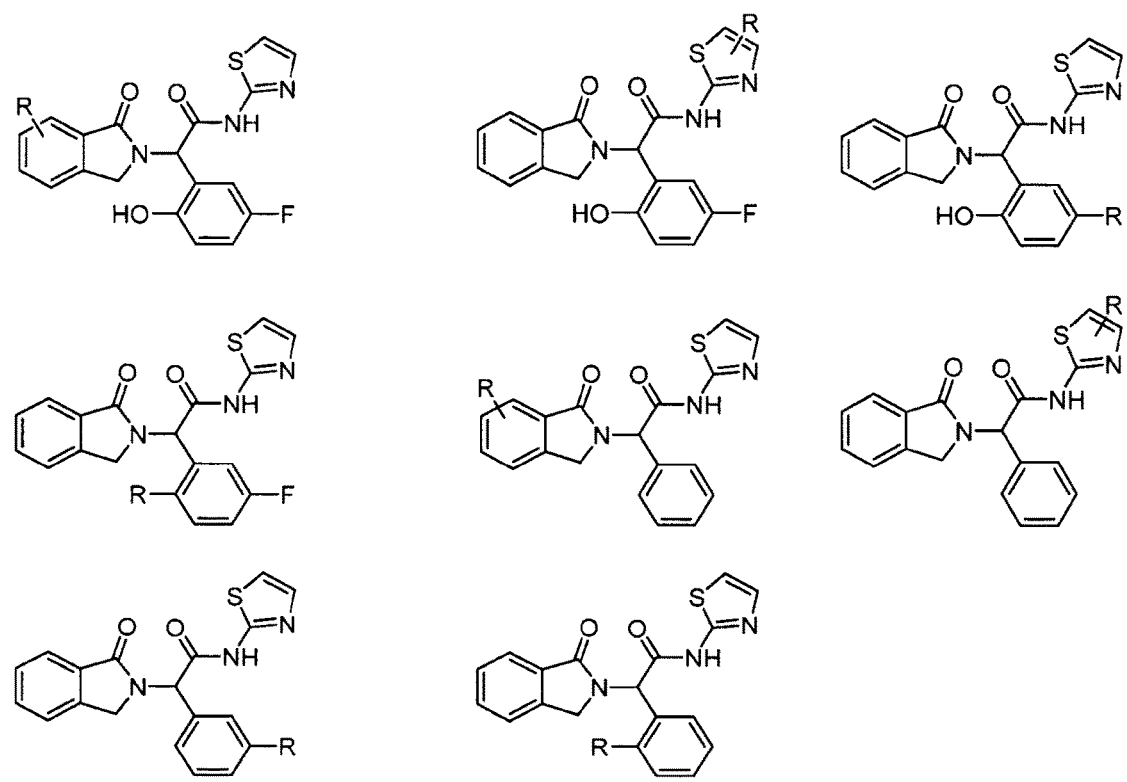

FIG. 2HHH
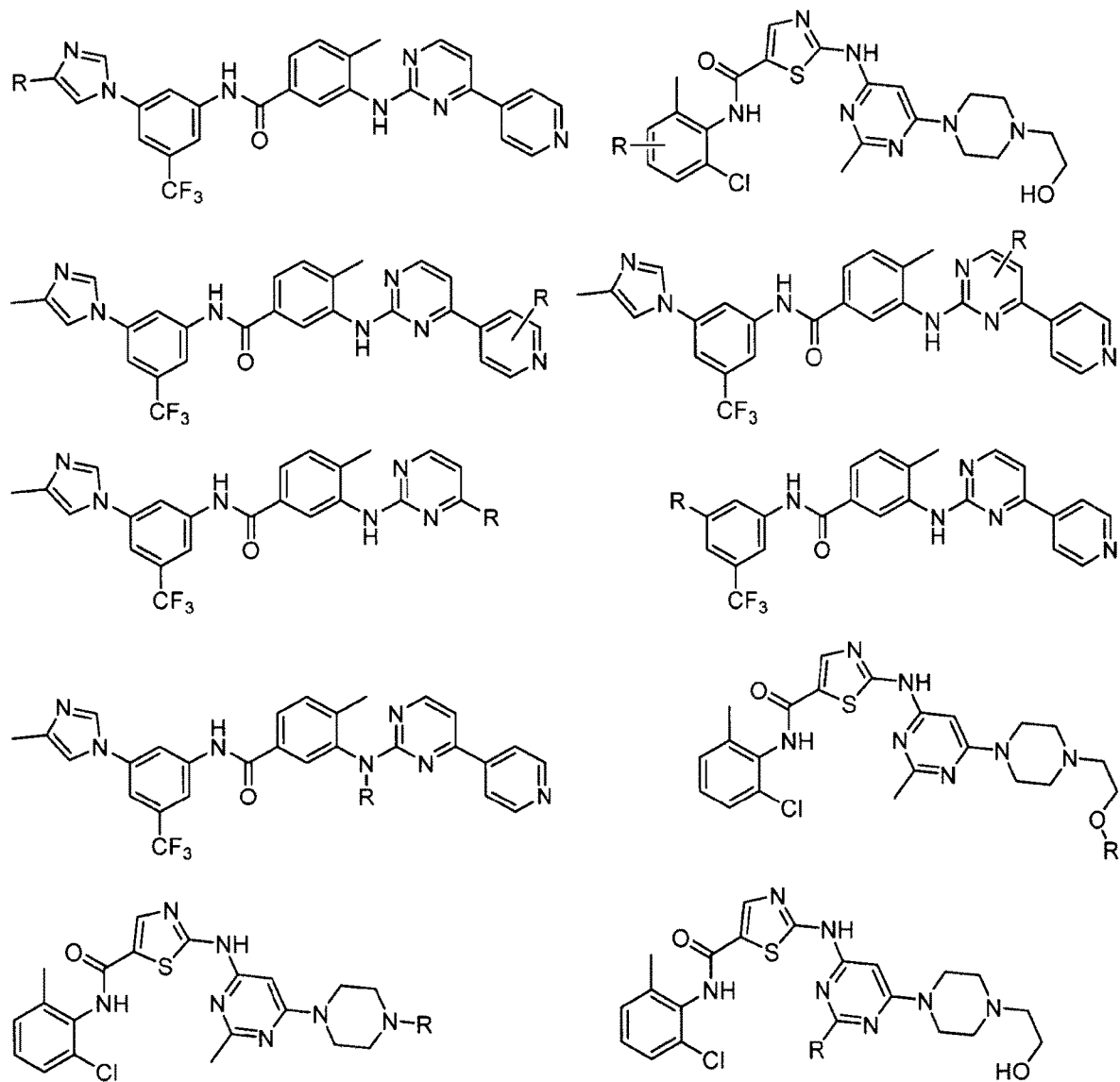

FIG. 2III
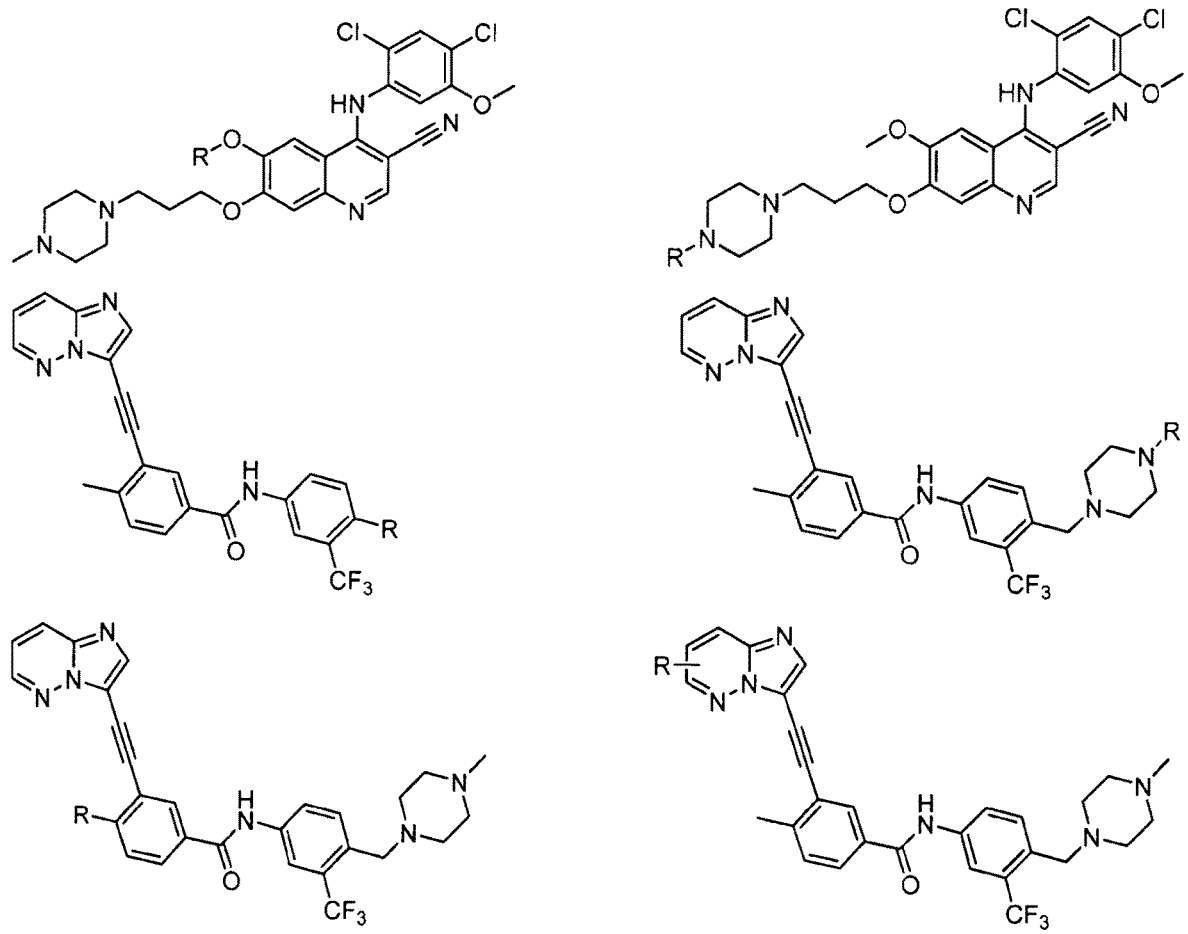
FIG. 2JJJ
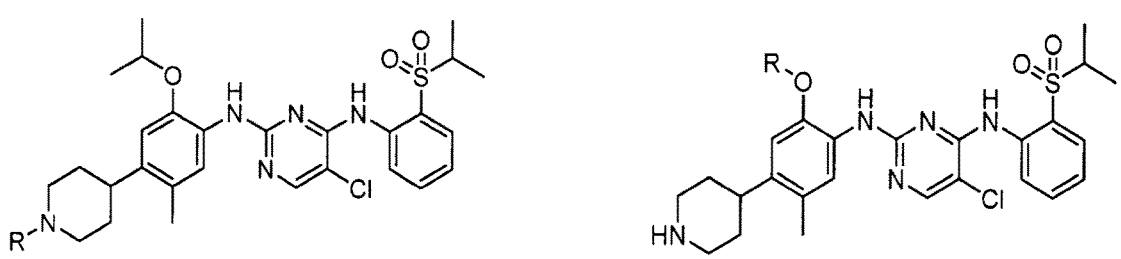

FIG. 2KKK
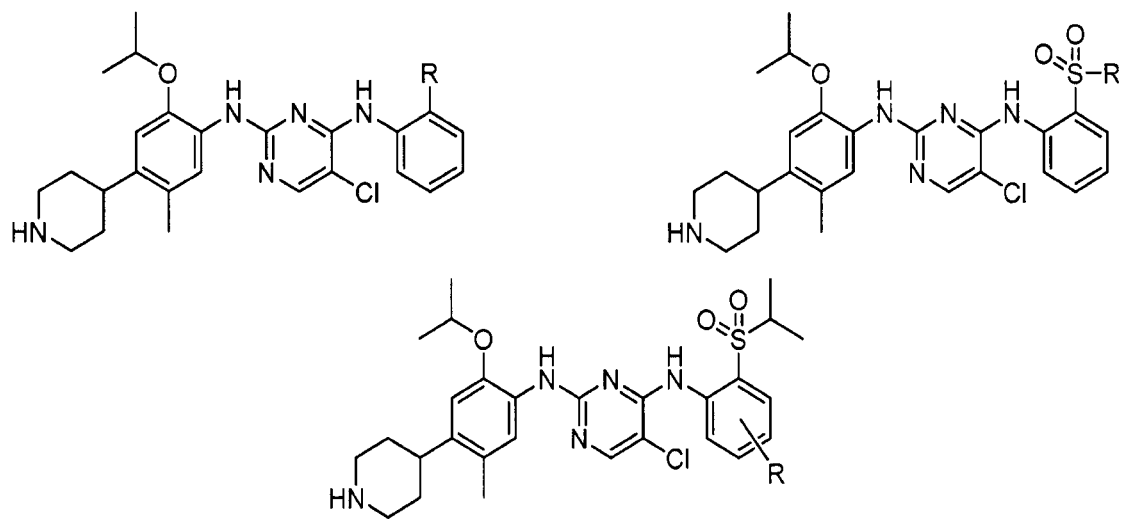
FIG. 2LLL
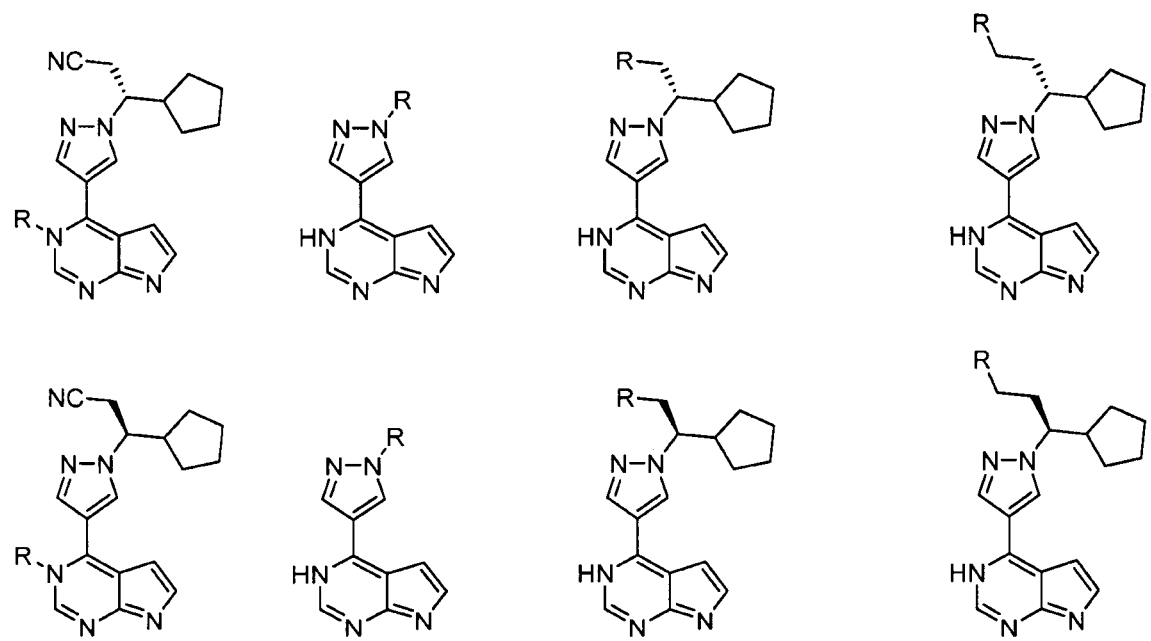

FIG. 2MMM
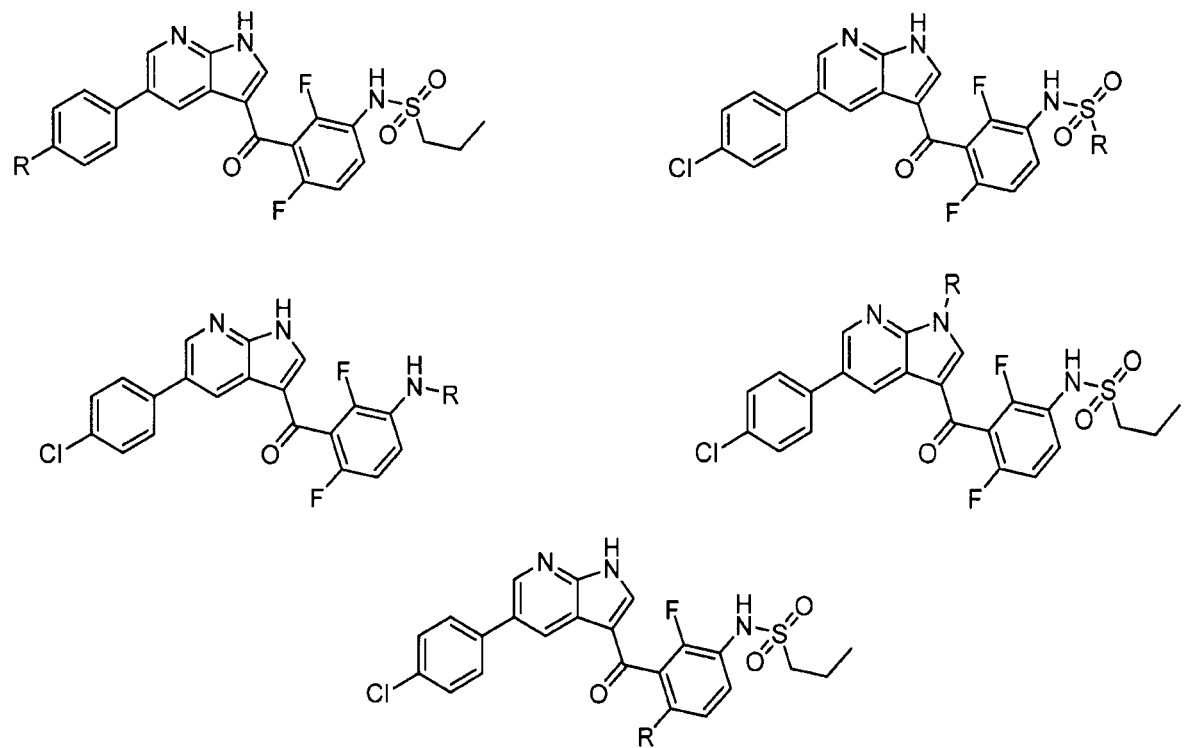
FIG. 2NNN
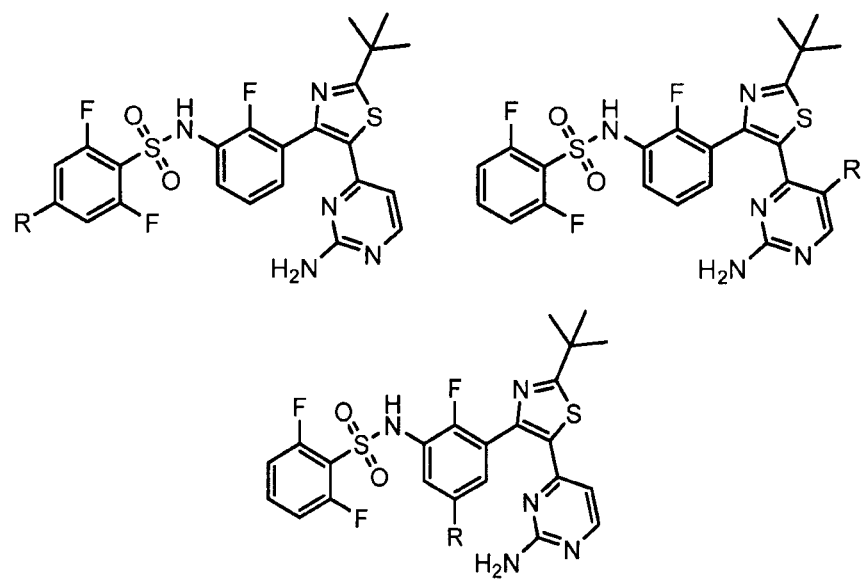

FIG. 2OOO
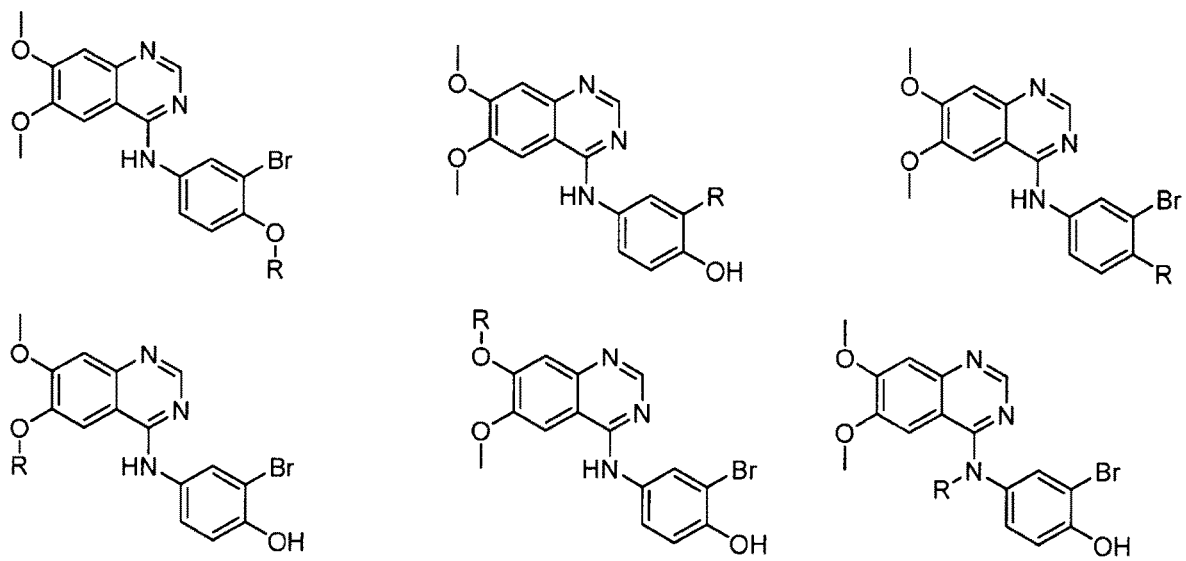
FIG. 2PPP
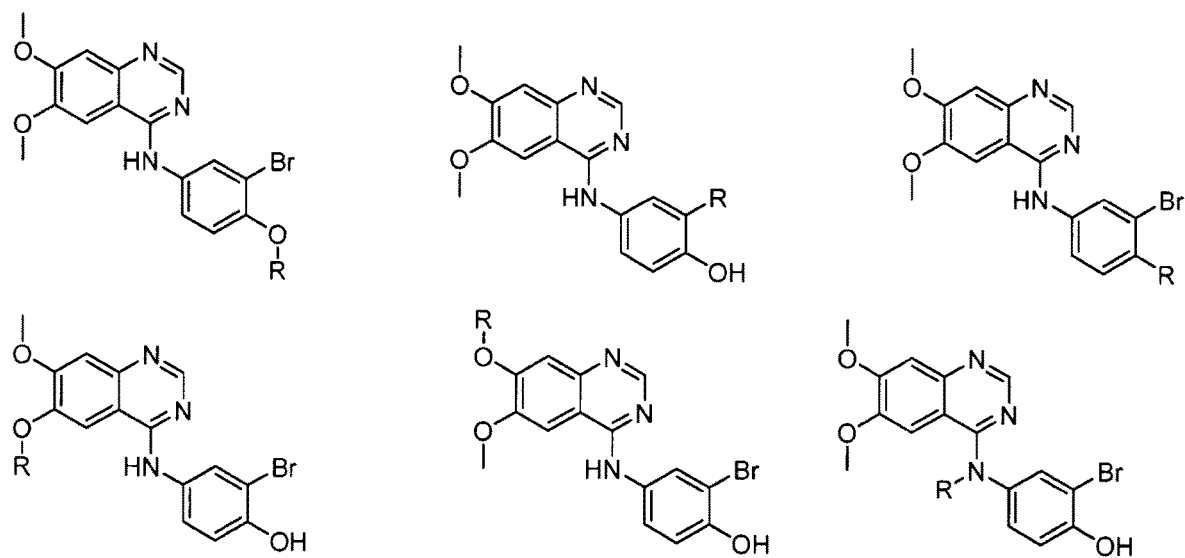

FIG. 2QQQ
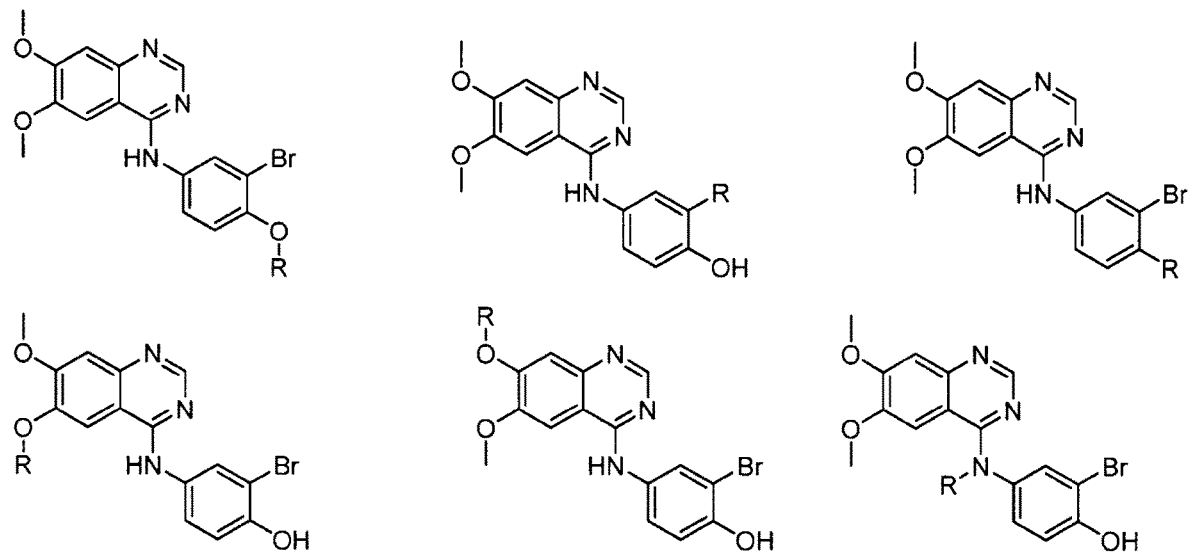
FIG. 2RRR
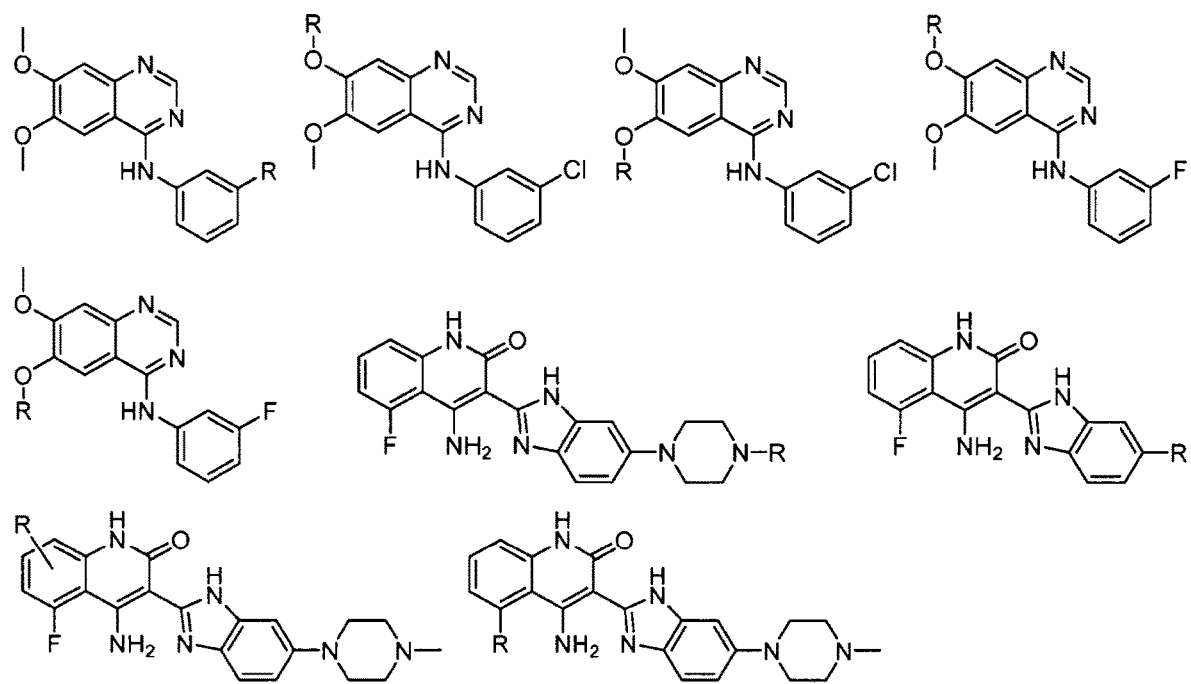

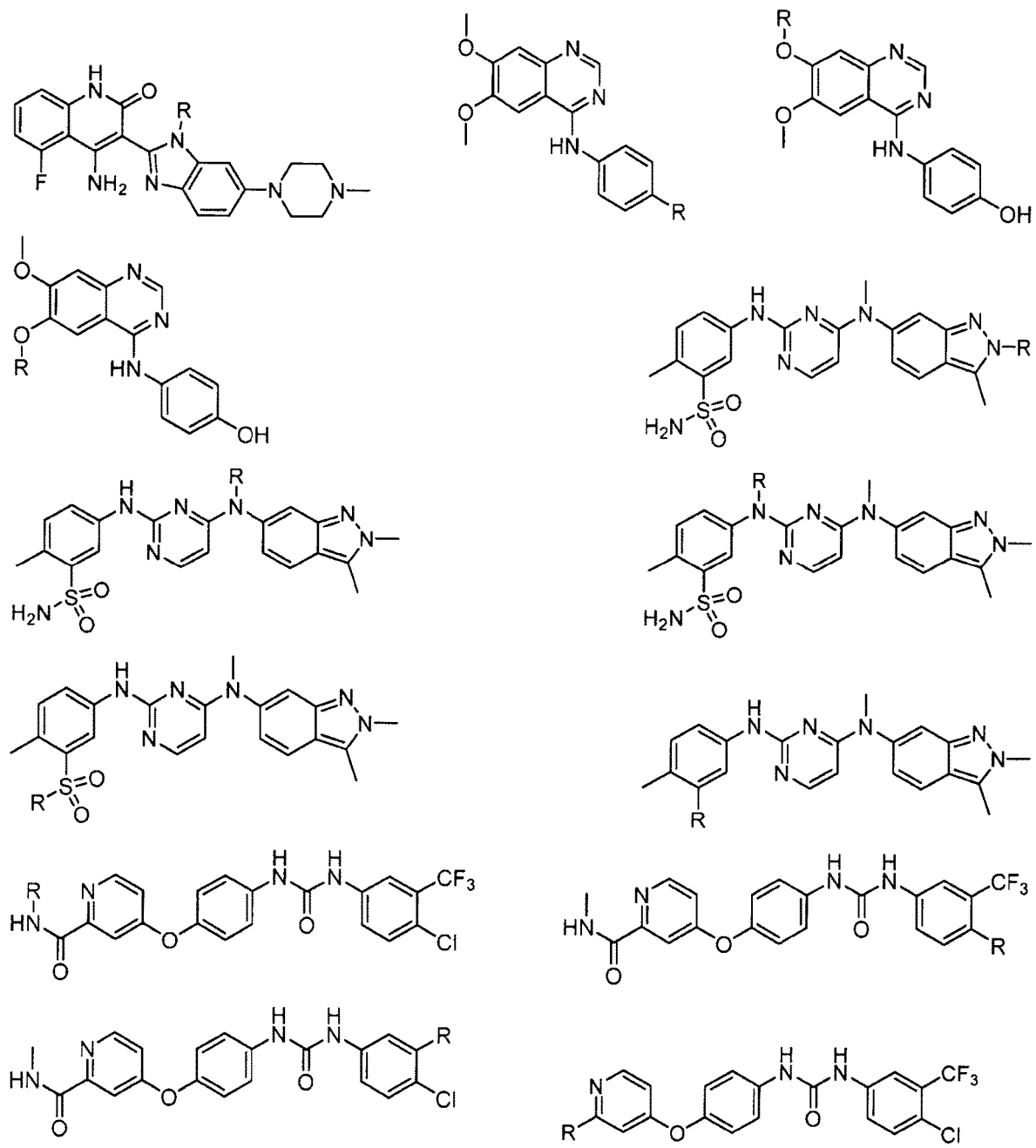
FIG. 2SSS

FIG. 2TTT
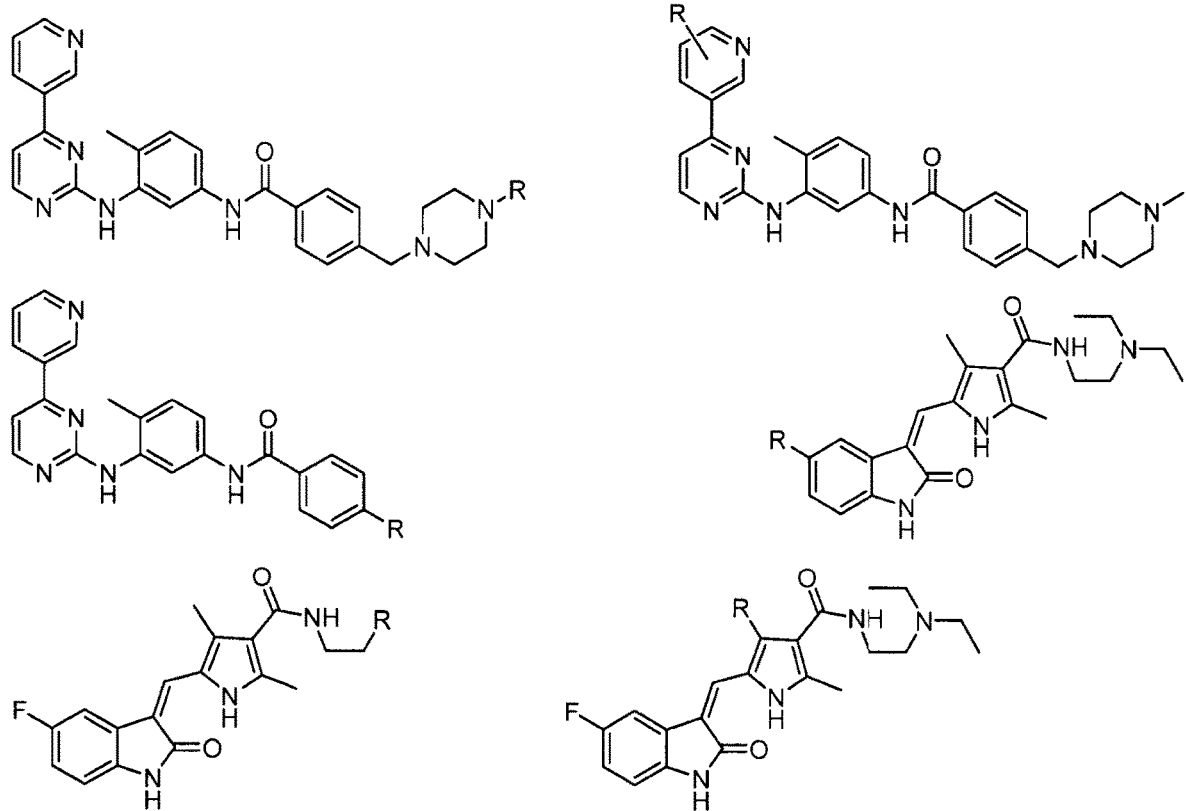
FIG. 2UUU
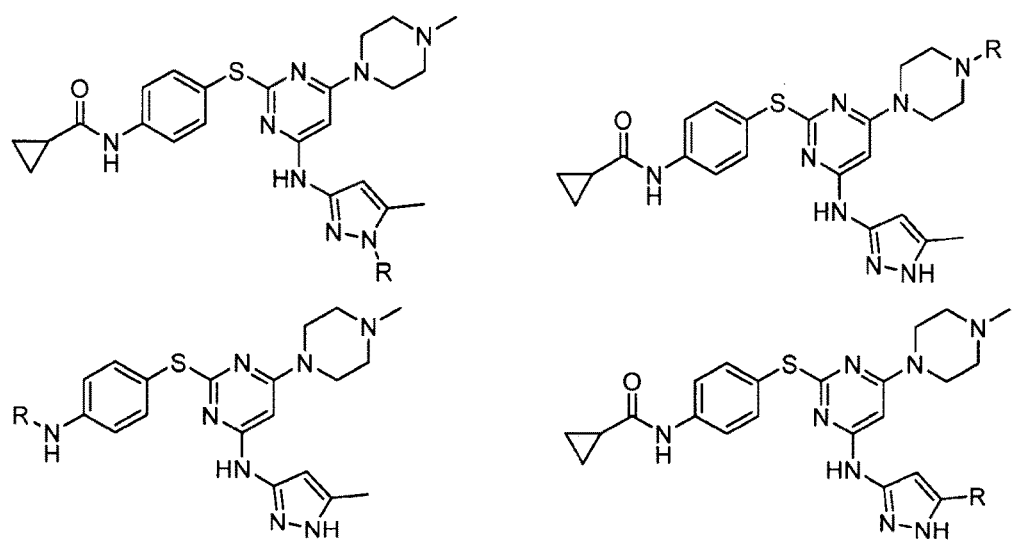

FIG. 2VVV
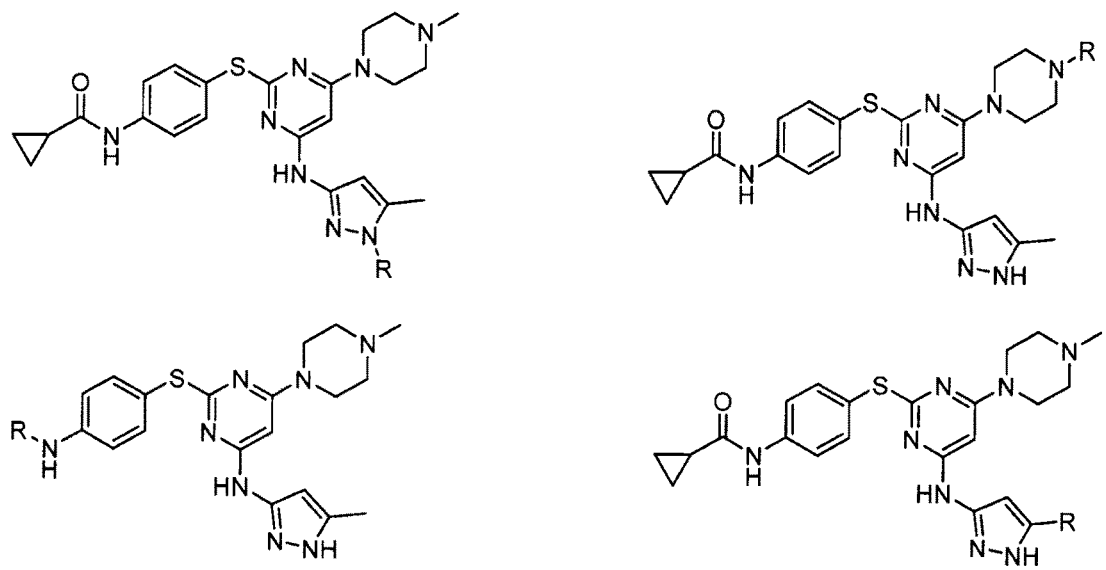
FIG. 2WWW
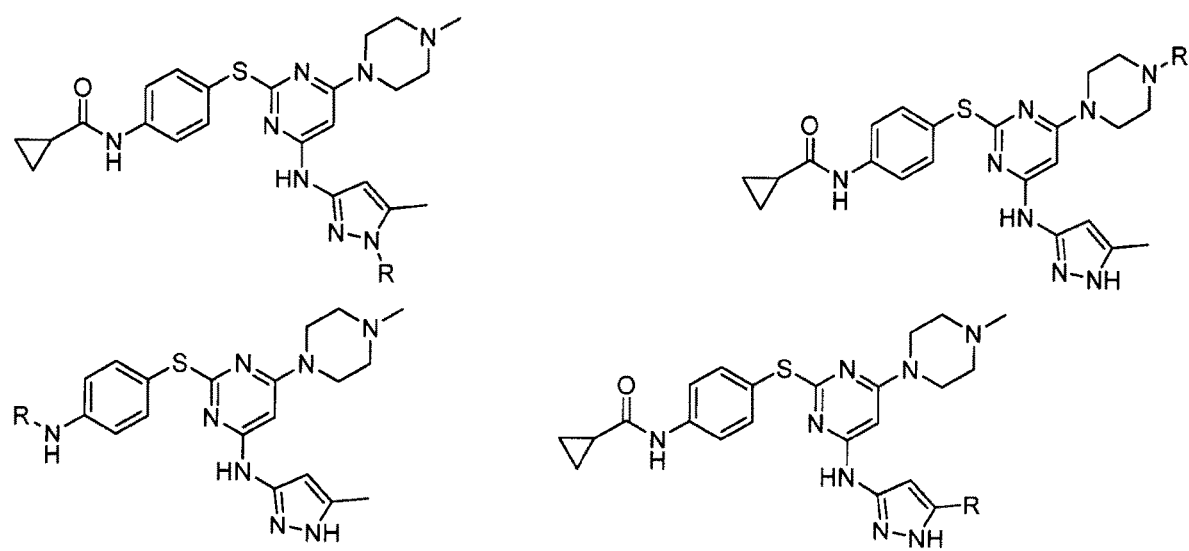

FIG. 2XXX
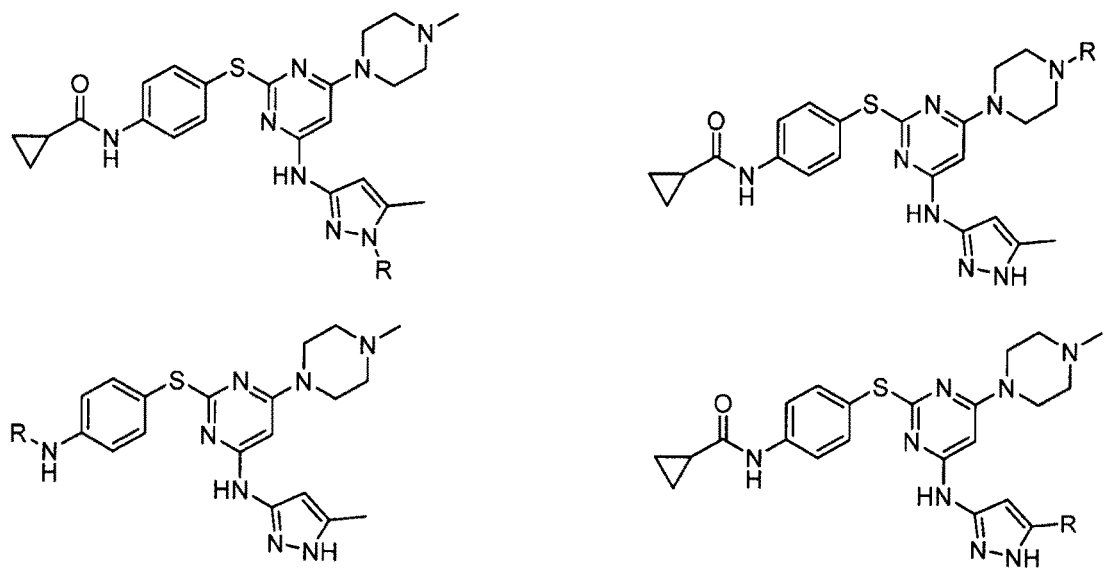
FIG. 2YYY
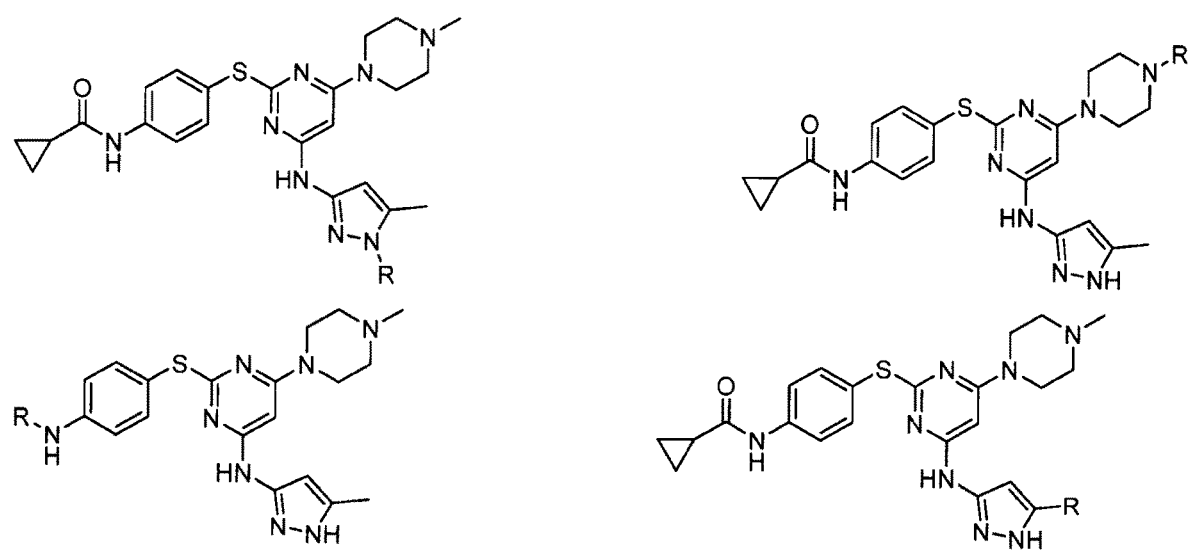

FIG. 2ZZZ
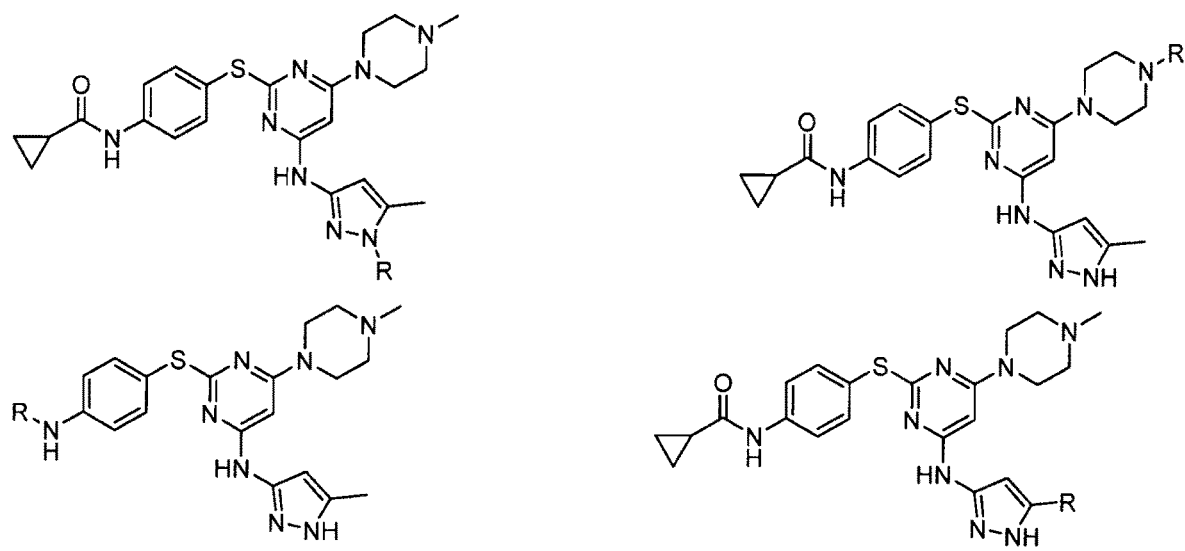
FIG. 2AAAA
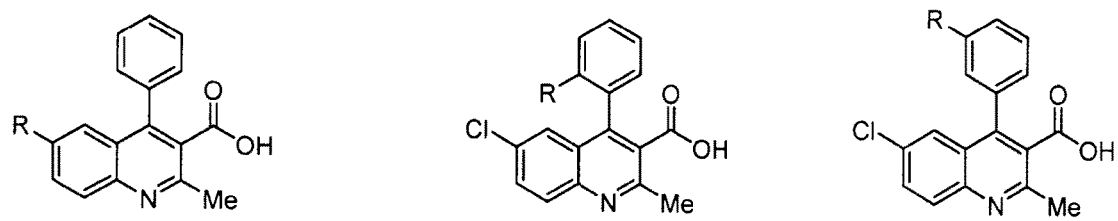
FIG. 2BBBB
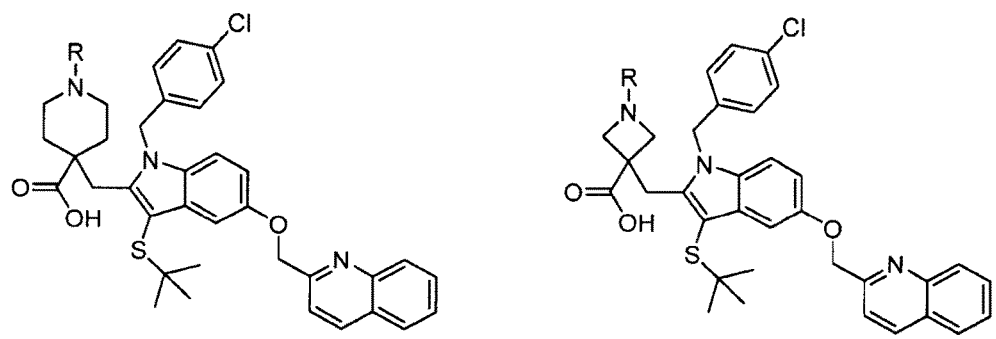

FIG. 2CCCC
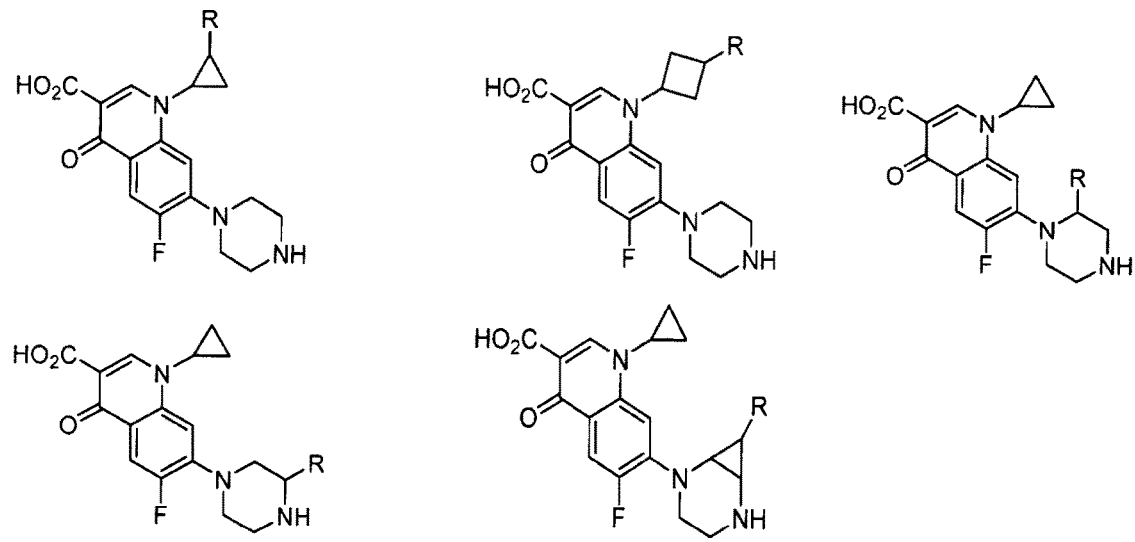
FIG. 2DDDD
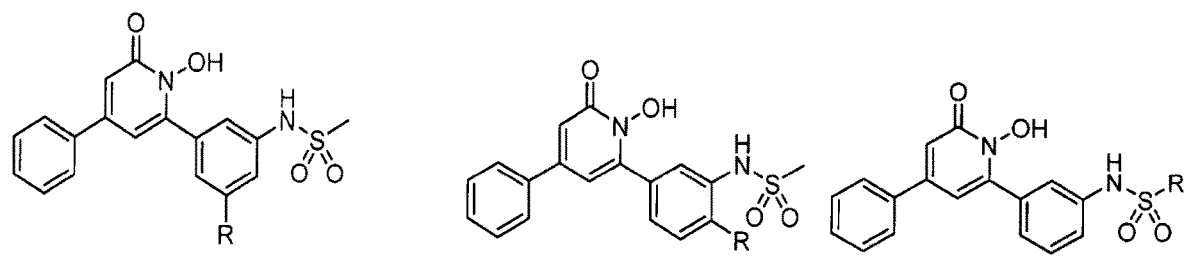
FIG. 2EEEE
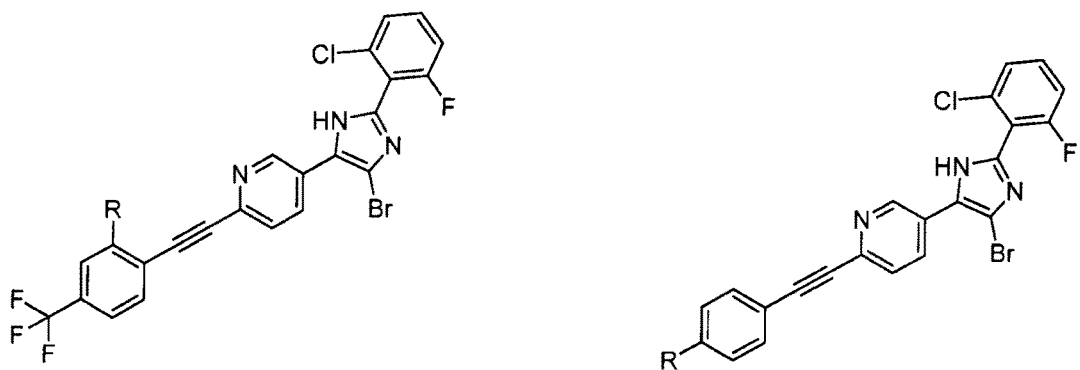

FIG. 2FFFF
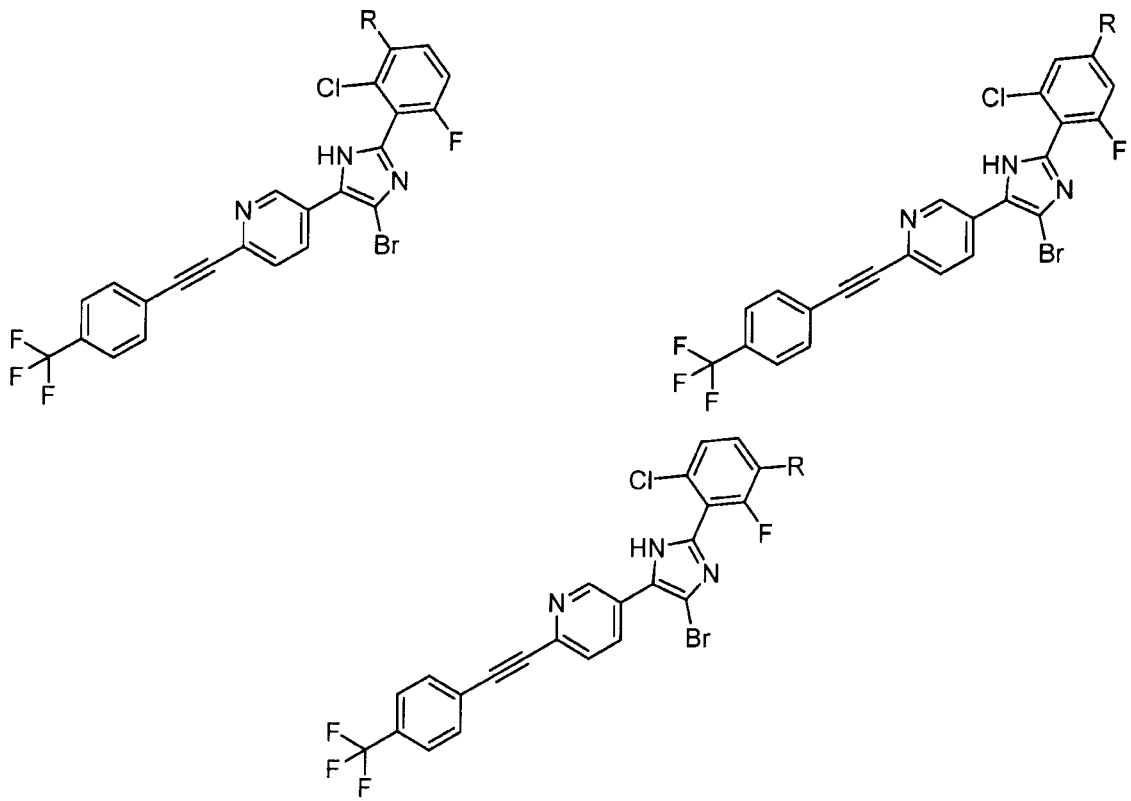
FIG. 2GGGG
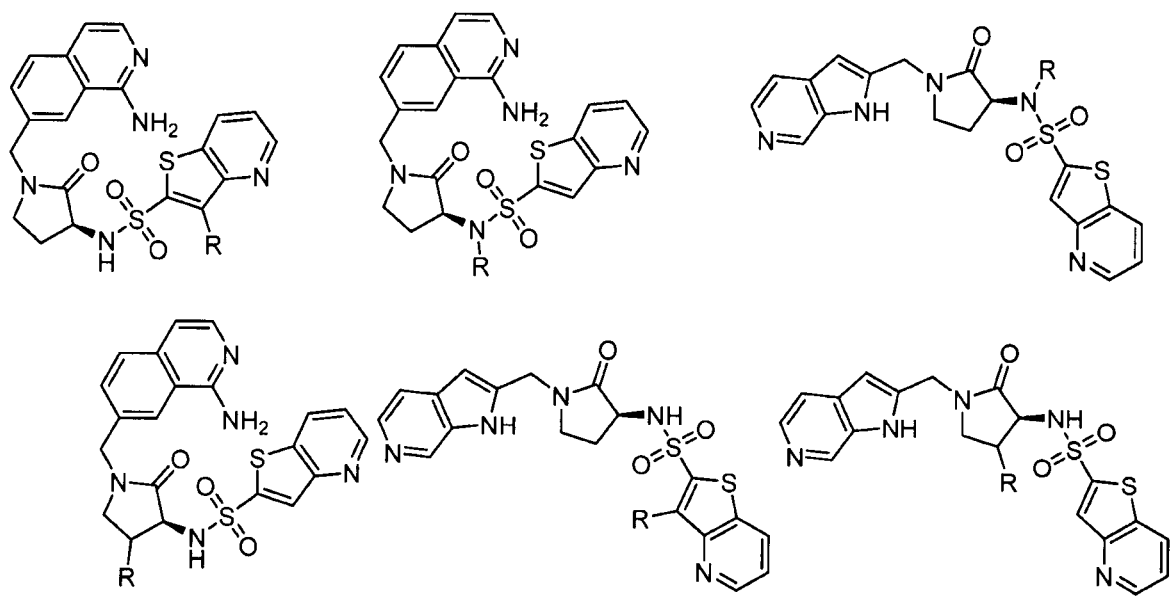

FIG. 2HHHH
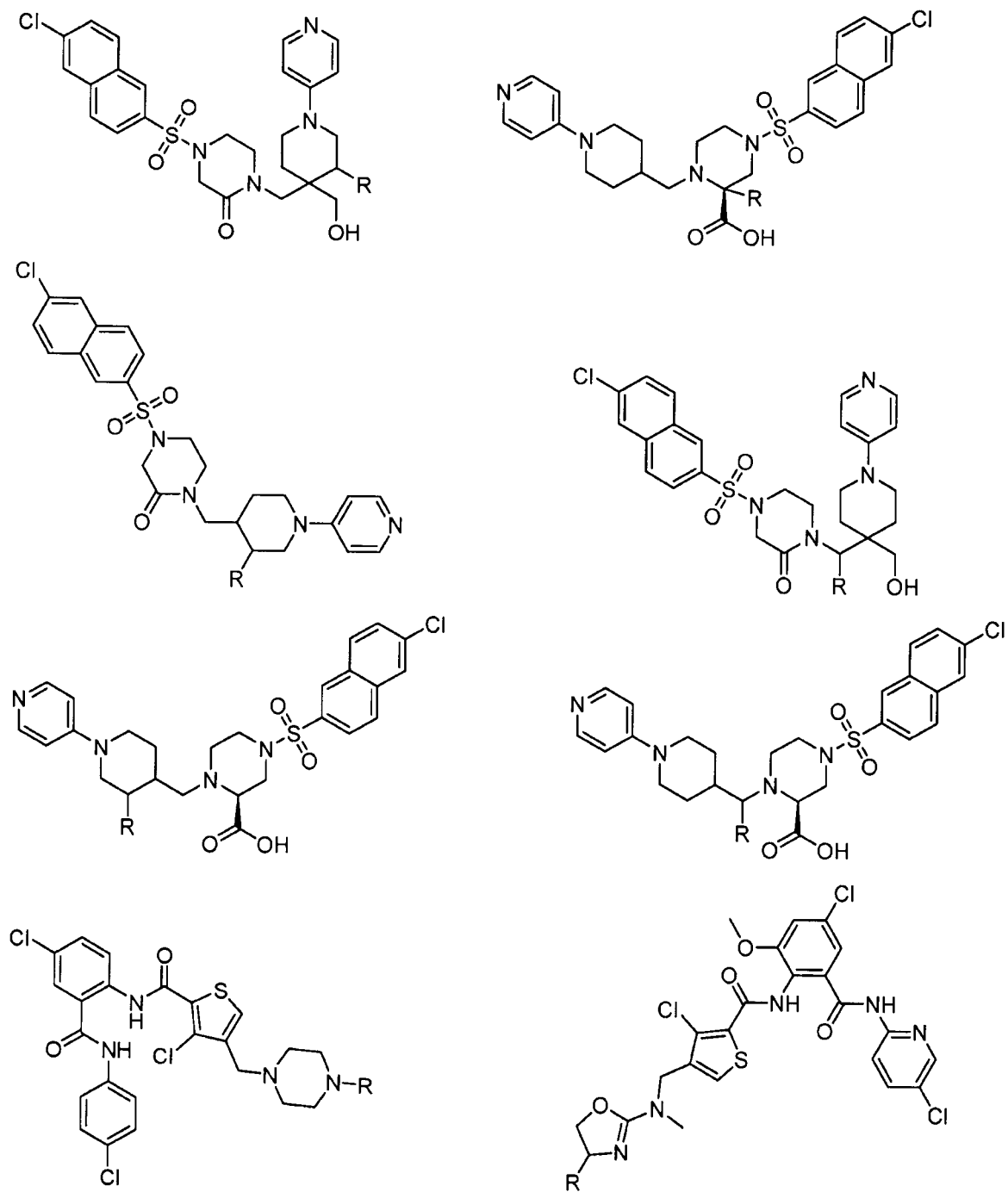

FIG. 2IIII
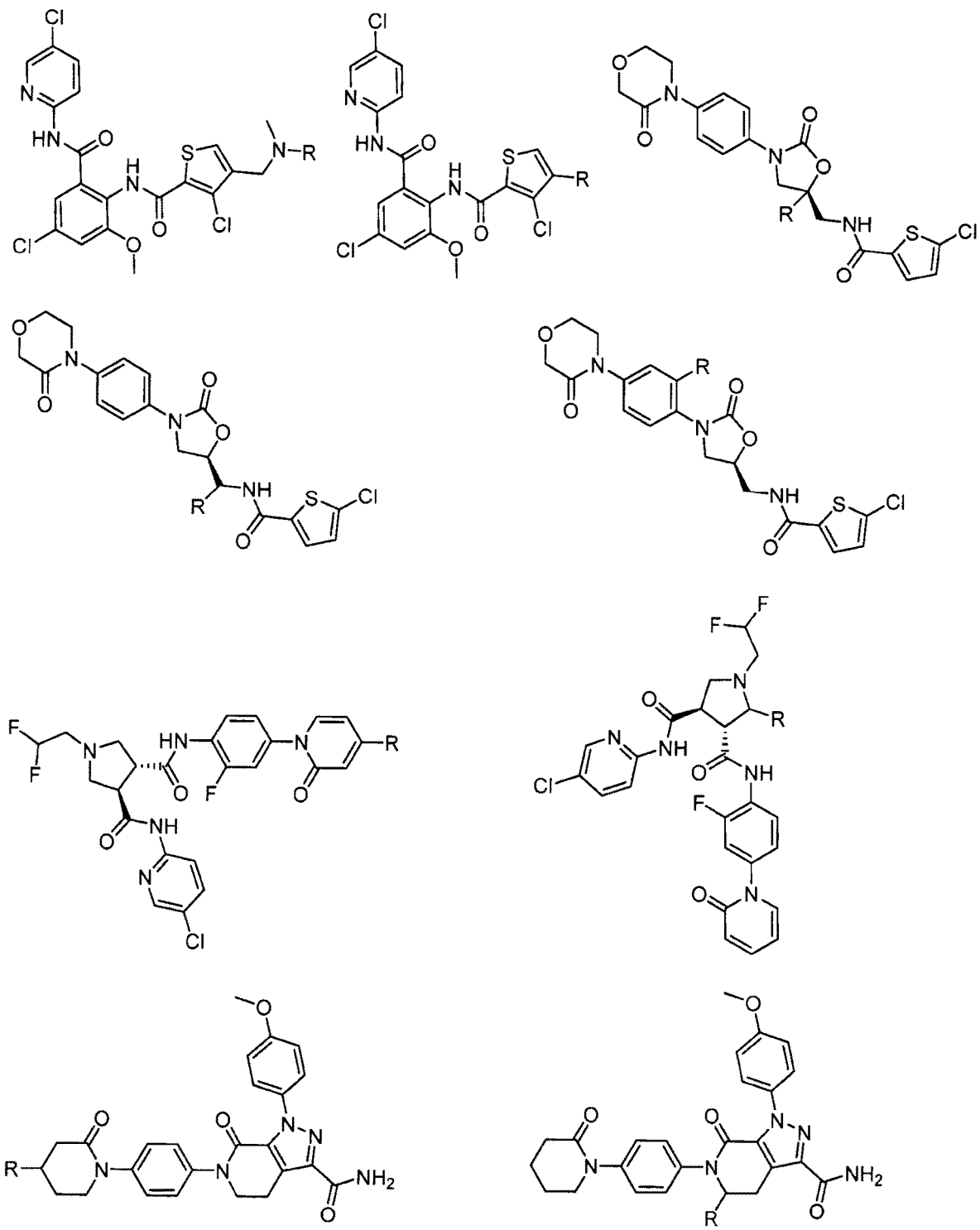

FIG. 2JJJJ
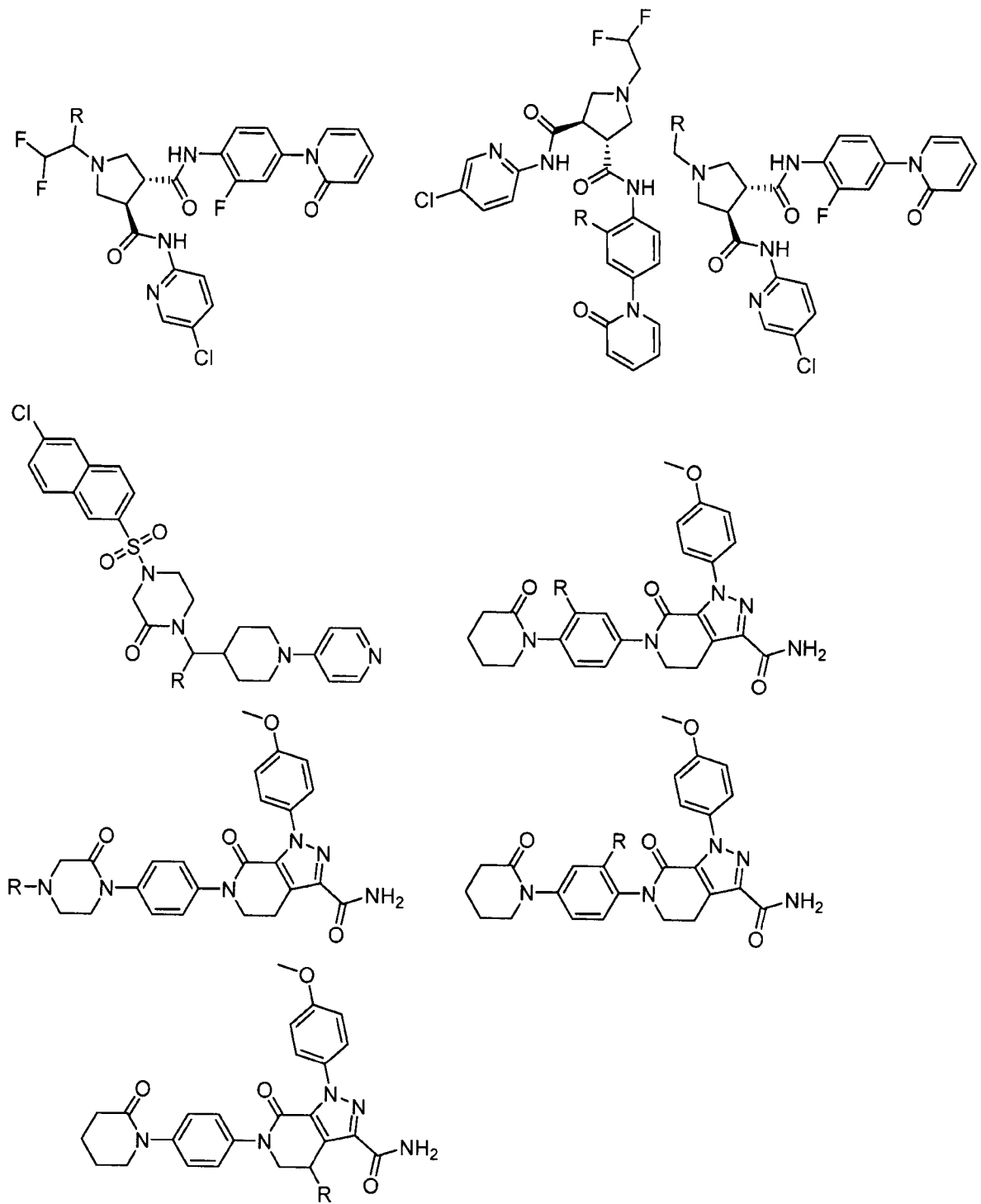

FIG. 2KKKK
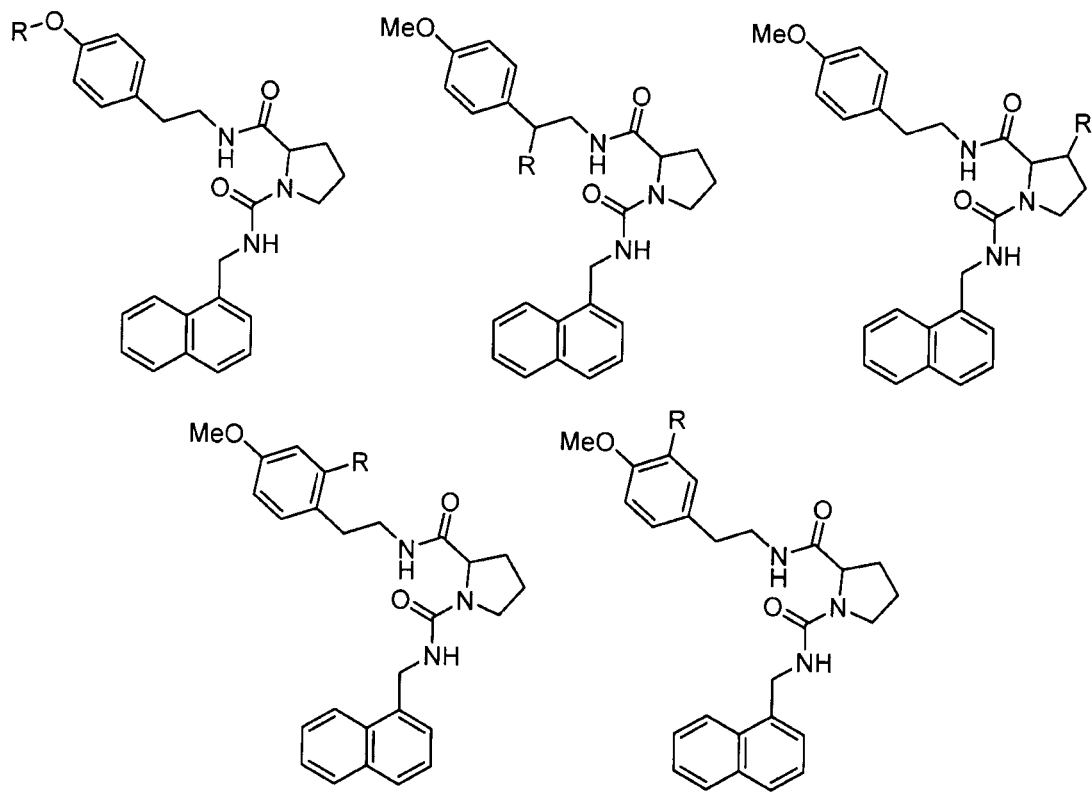
FIG. 2LLLL
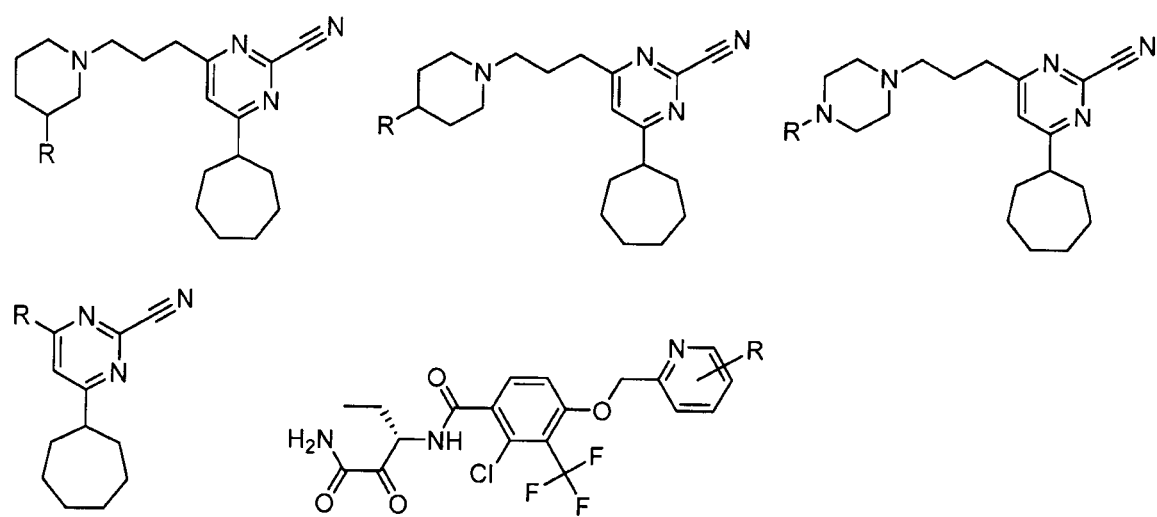

FIG. 2MMMM
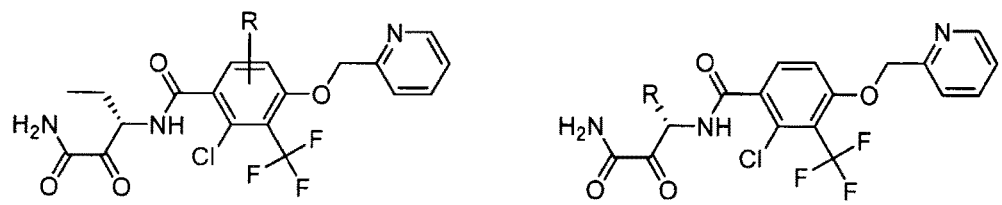
FIG. 2NNNN
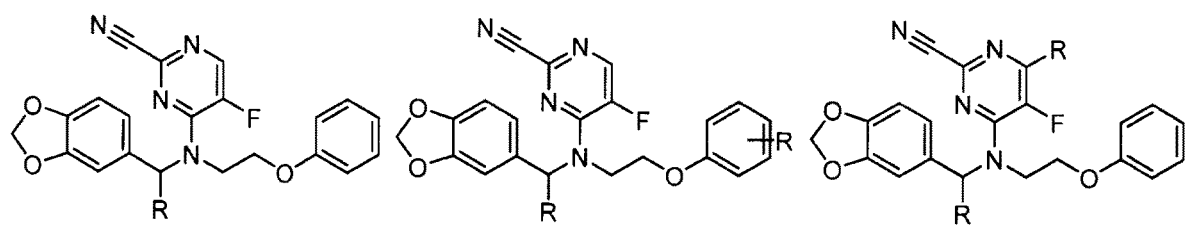
FIG. 2OOOO
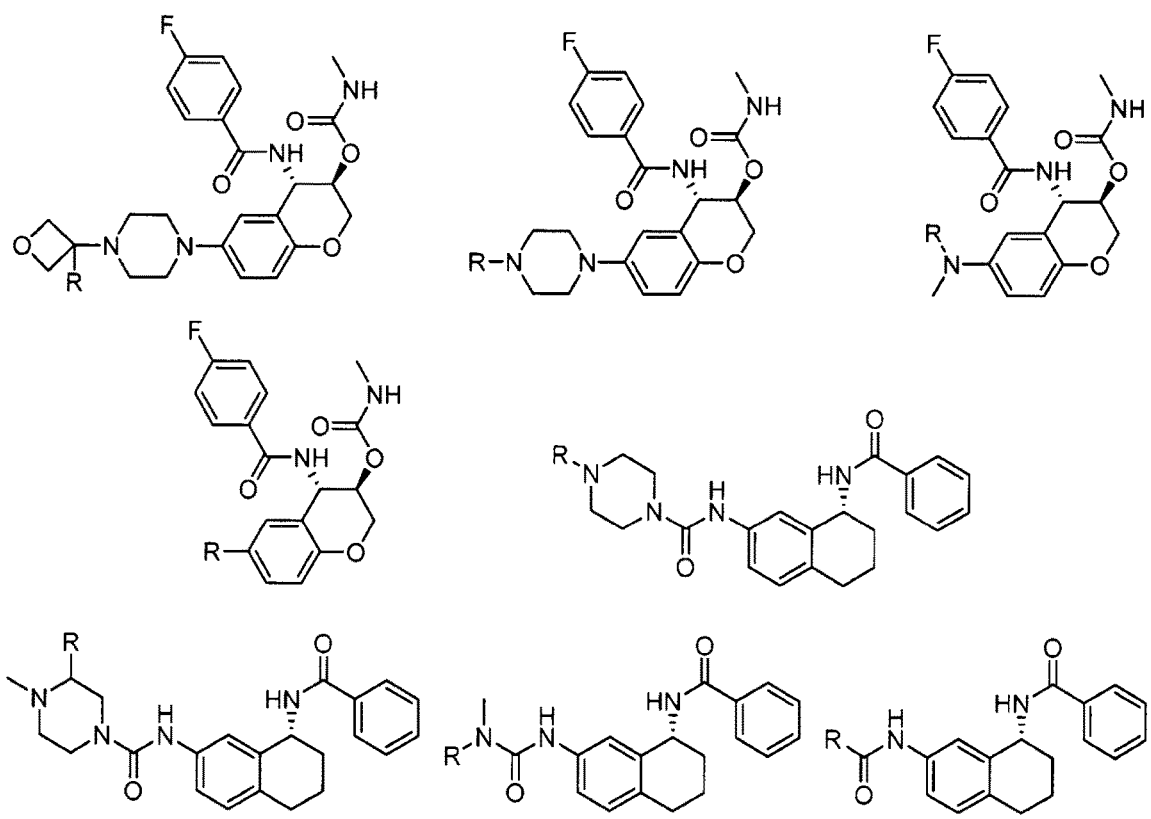

FIG. 2PPPP
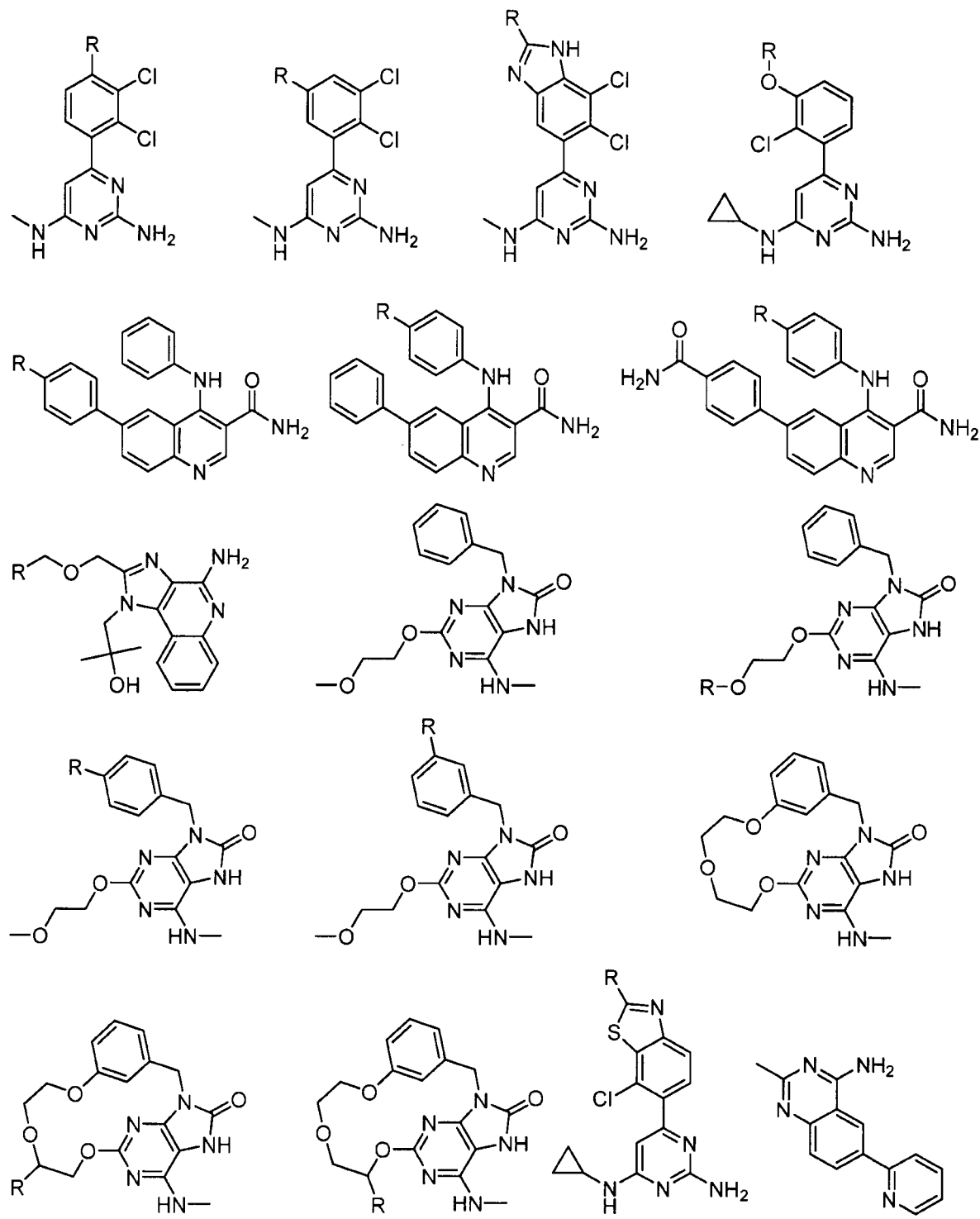

FIG. 2QQQQ
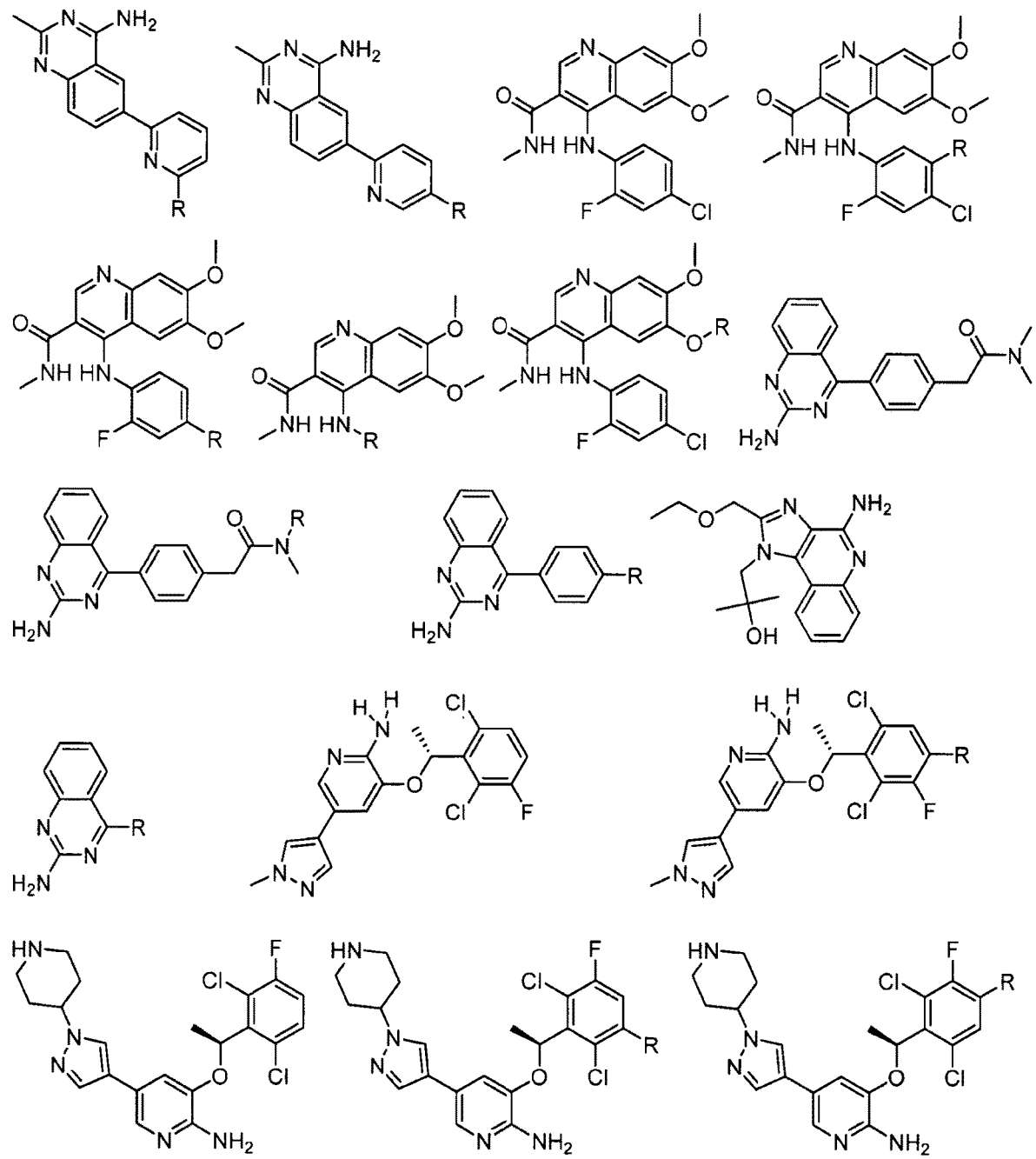

FIG. 2RRRR
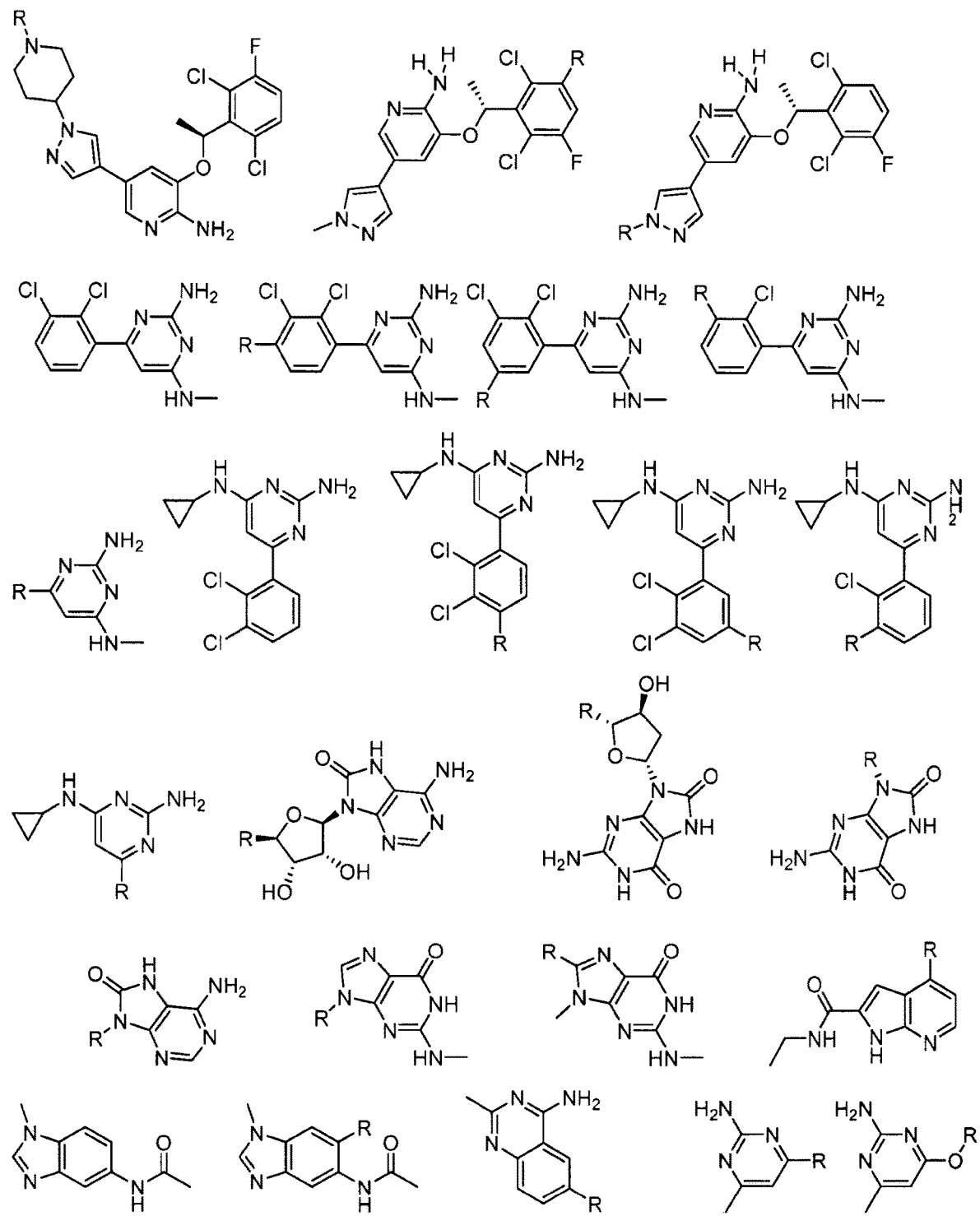

FIG. 2SSSS
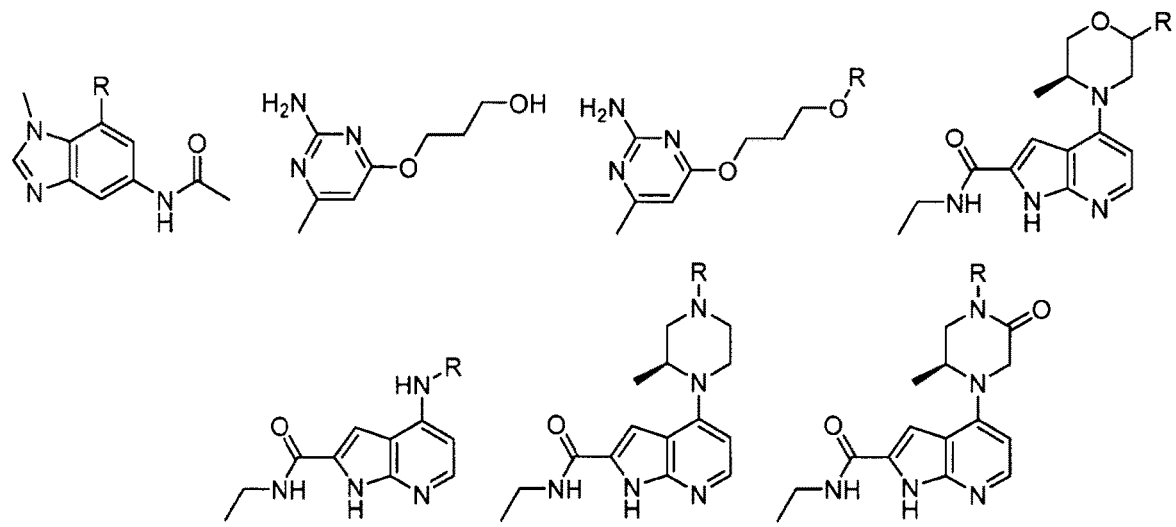
FIG. 2TTTT
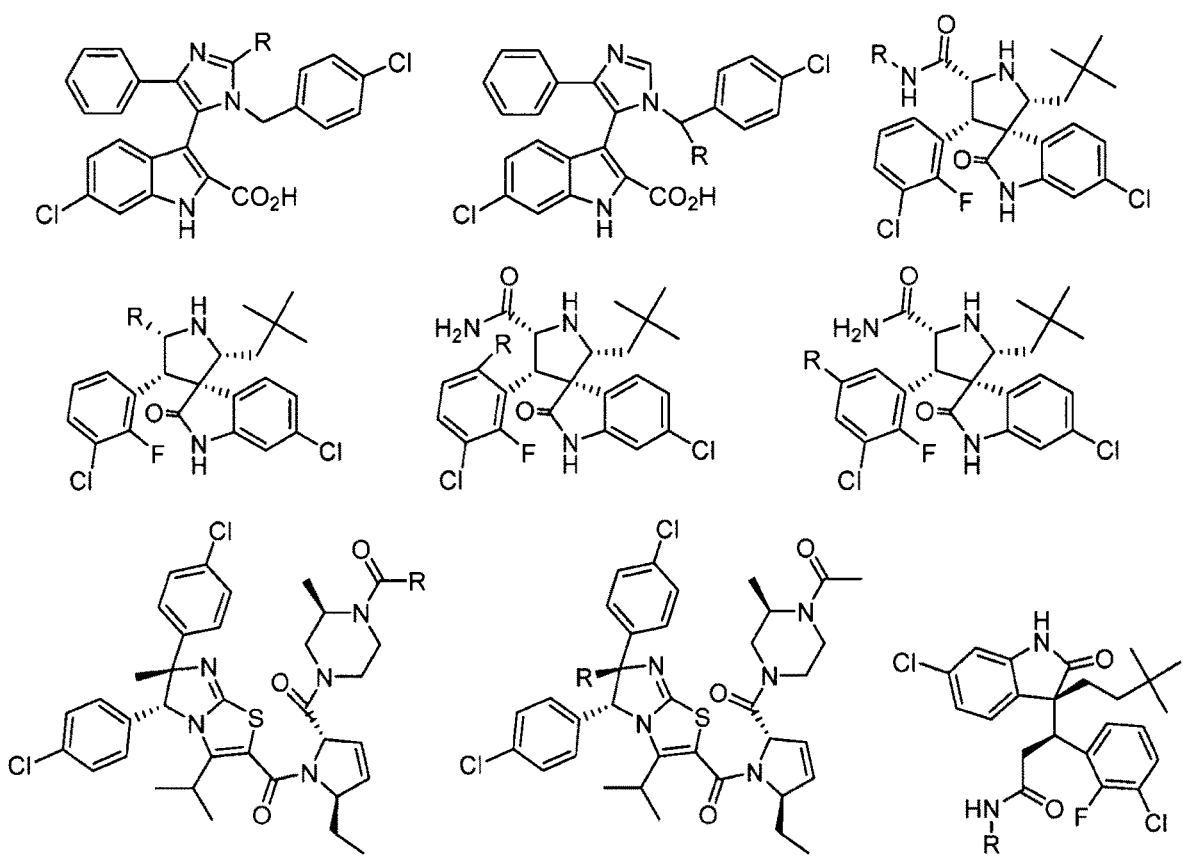

FIG. 2UUUU
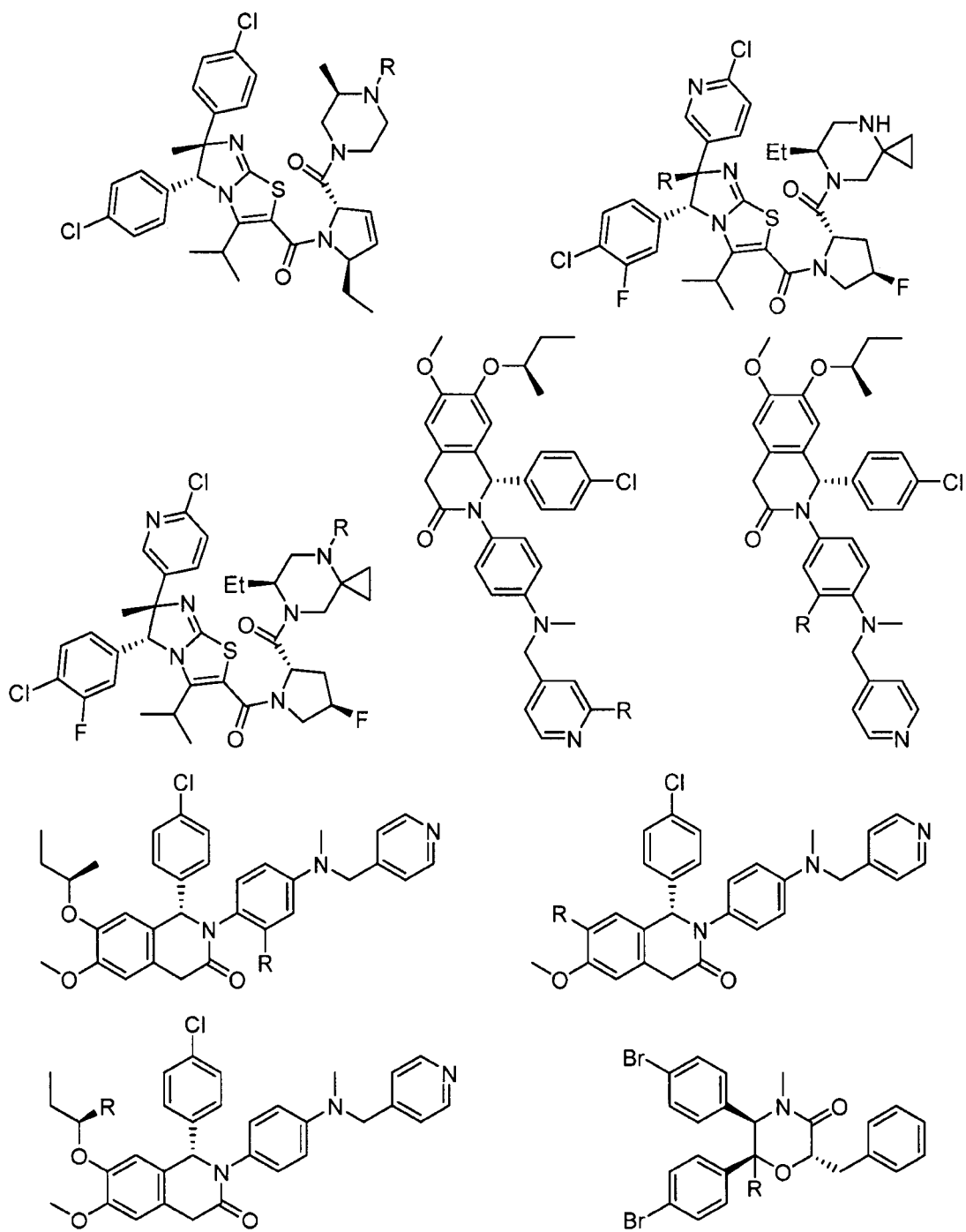

FIG. 2VVVV
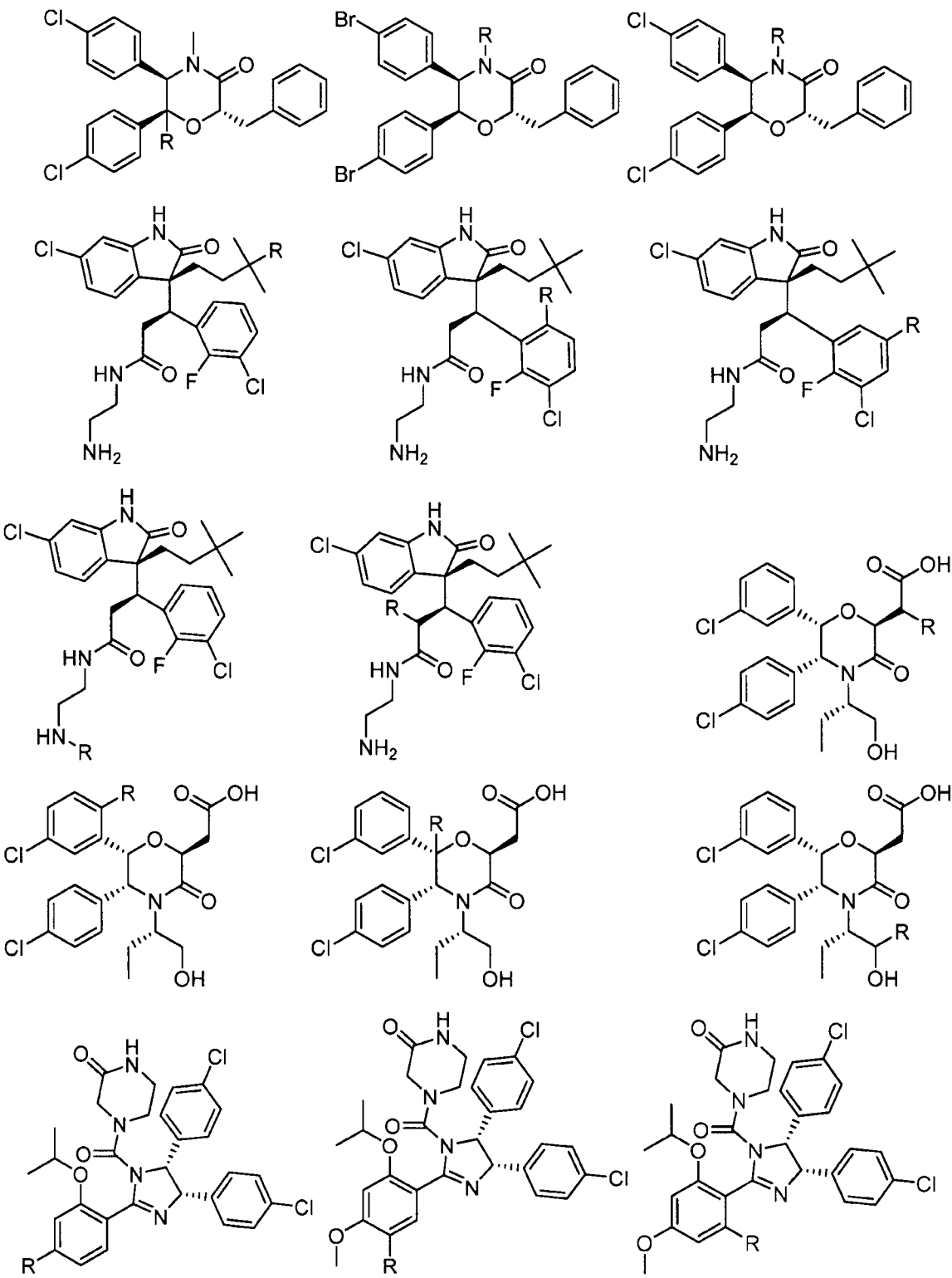

FIG. 2WWWW
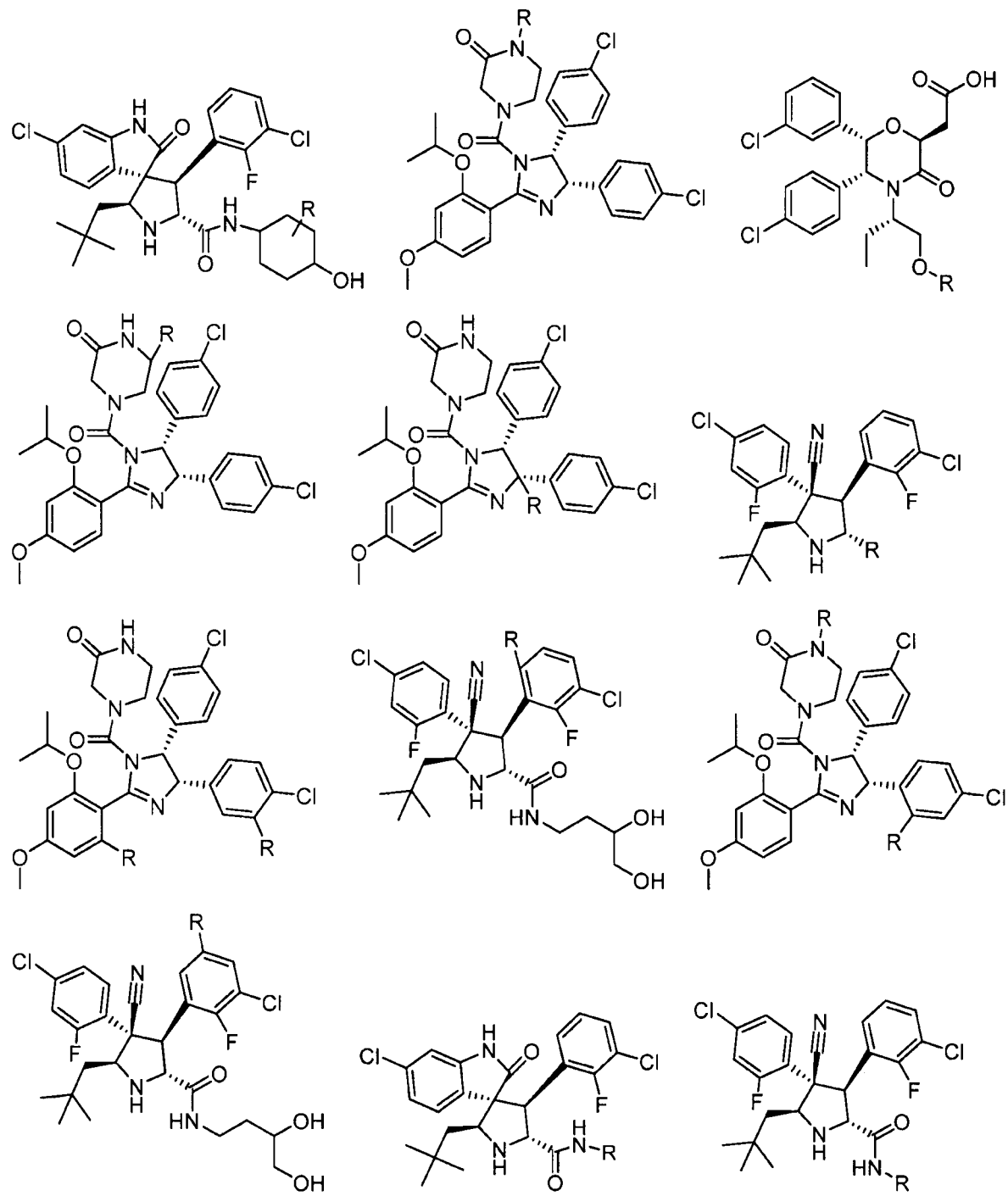

FIG. 2XXXX
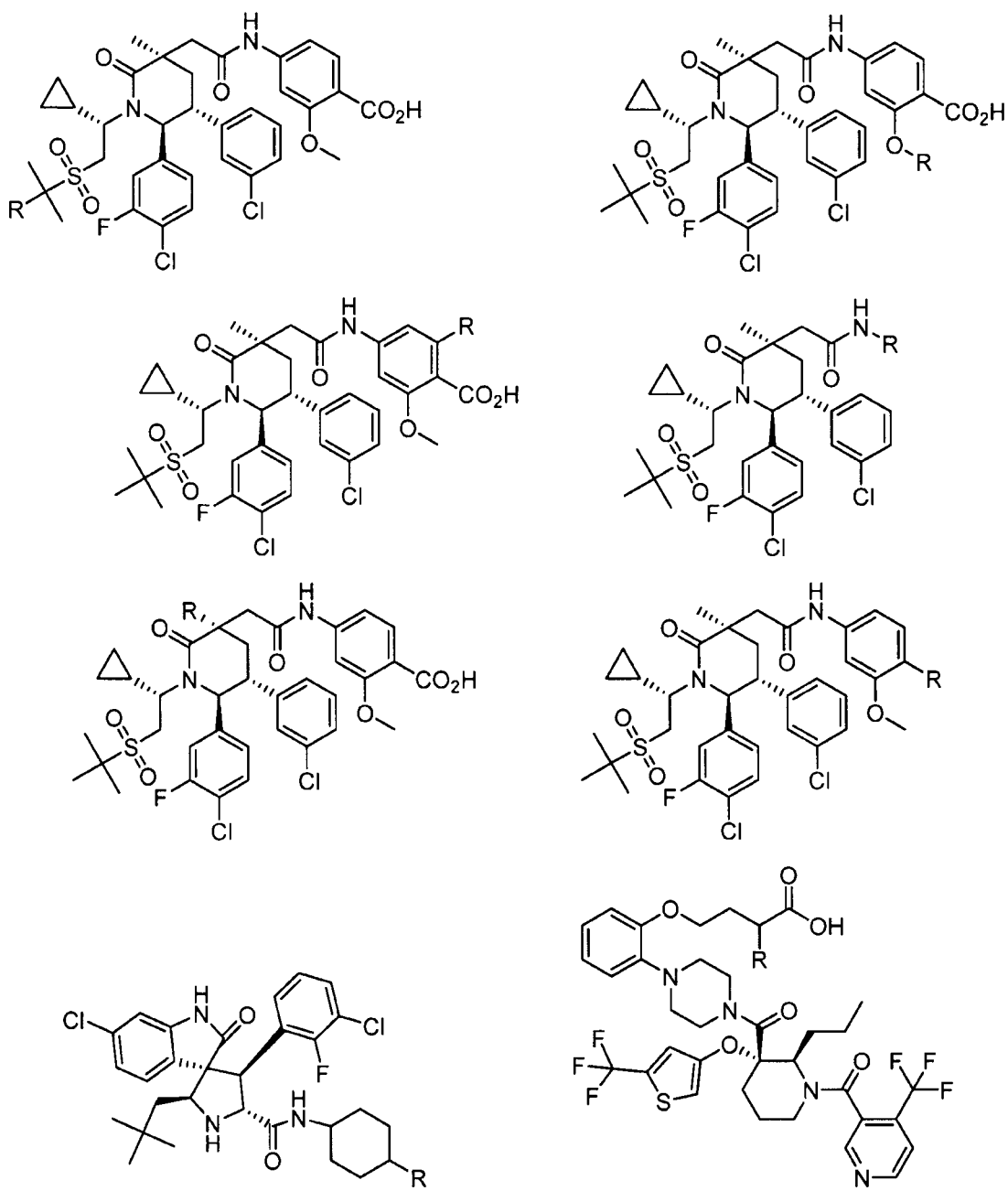

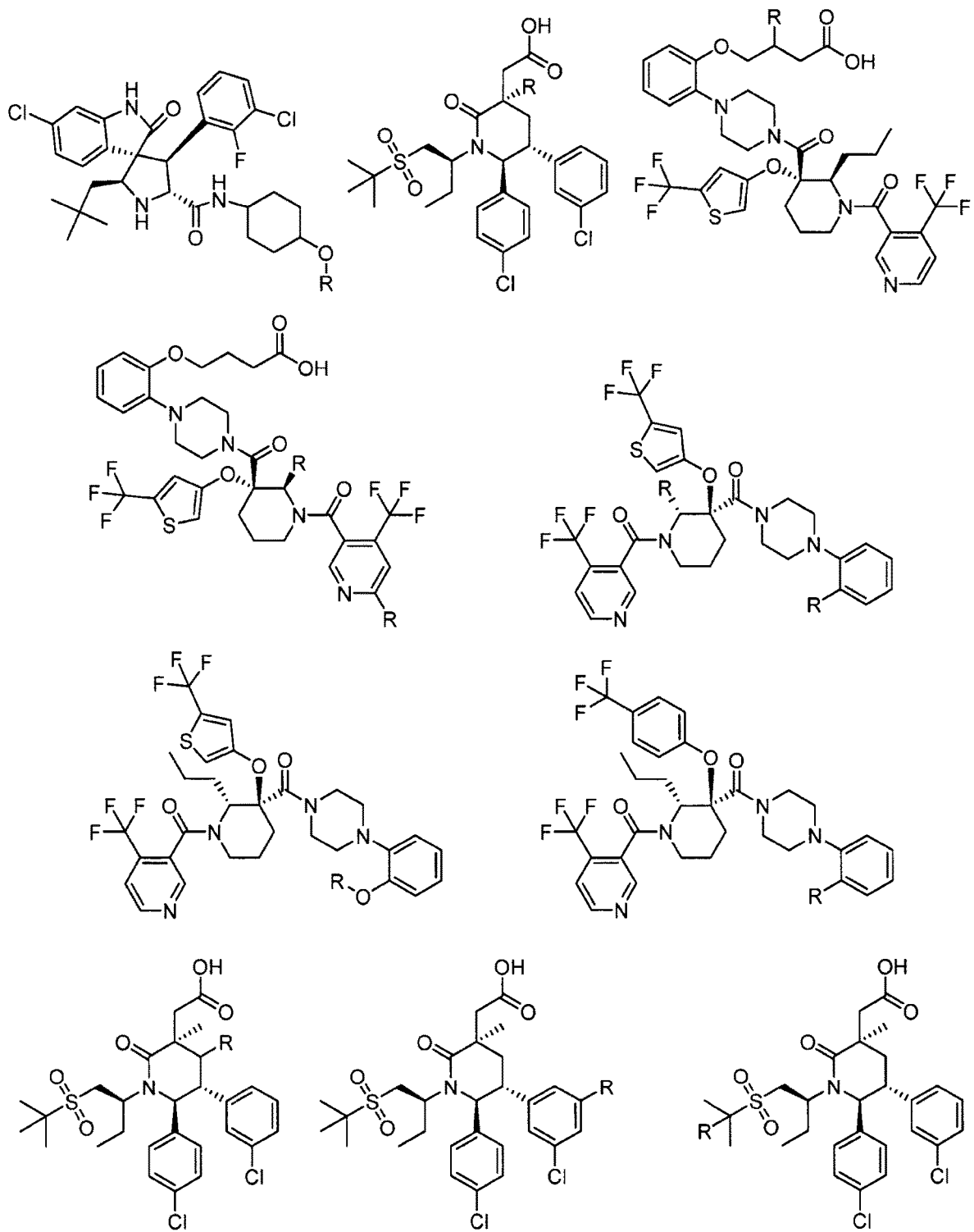
FIG. 2YYYY

FIG. 2ZZZZ
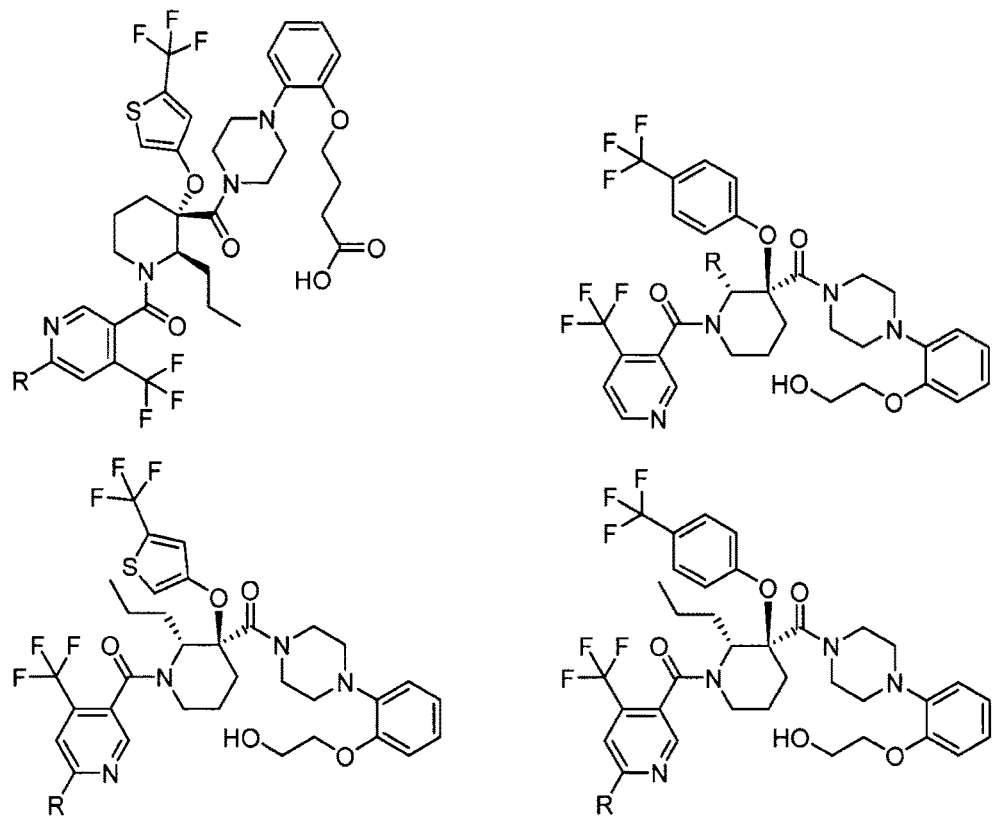
FIG. 2AAAAA
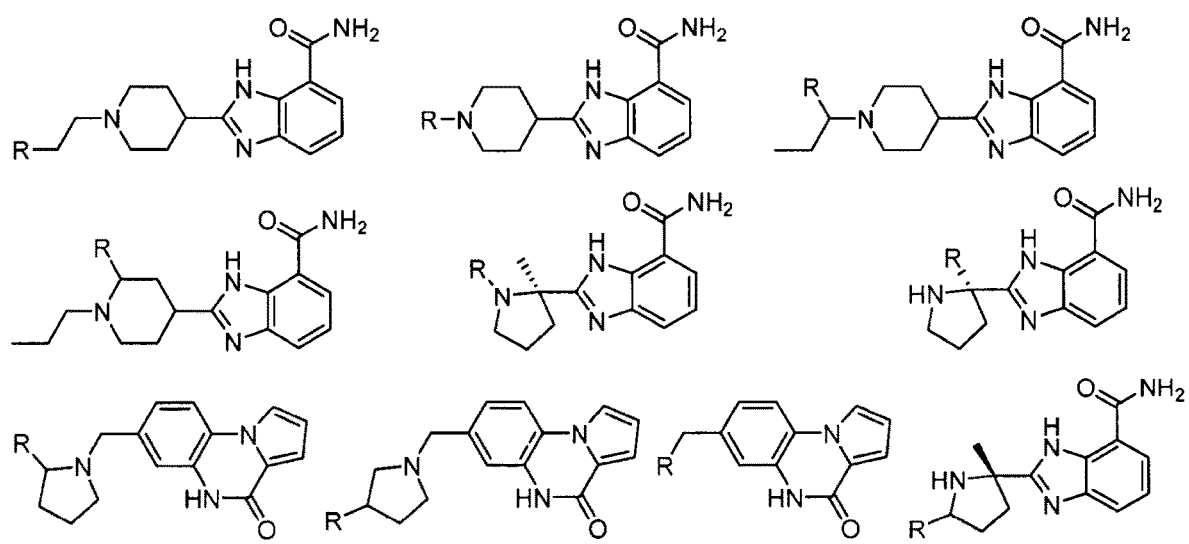

FIG. 2BBBBB
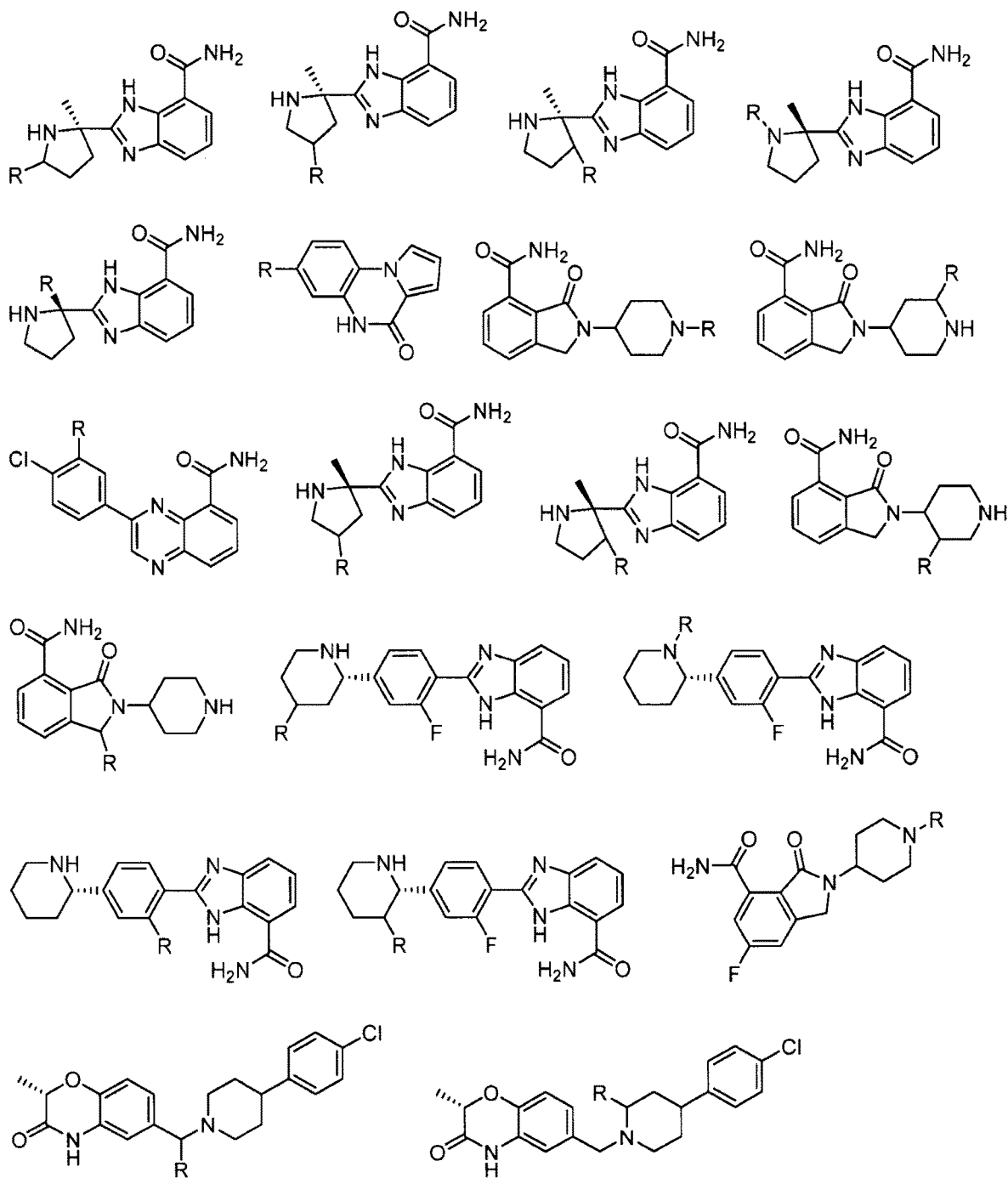

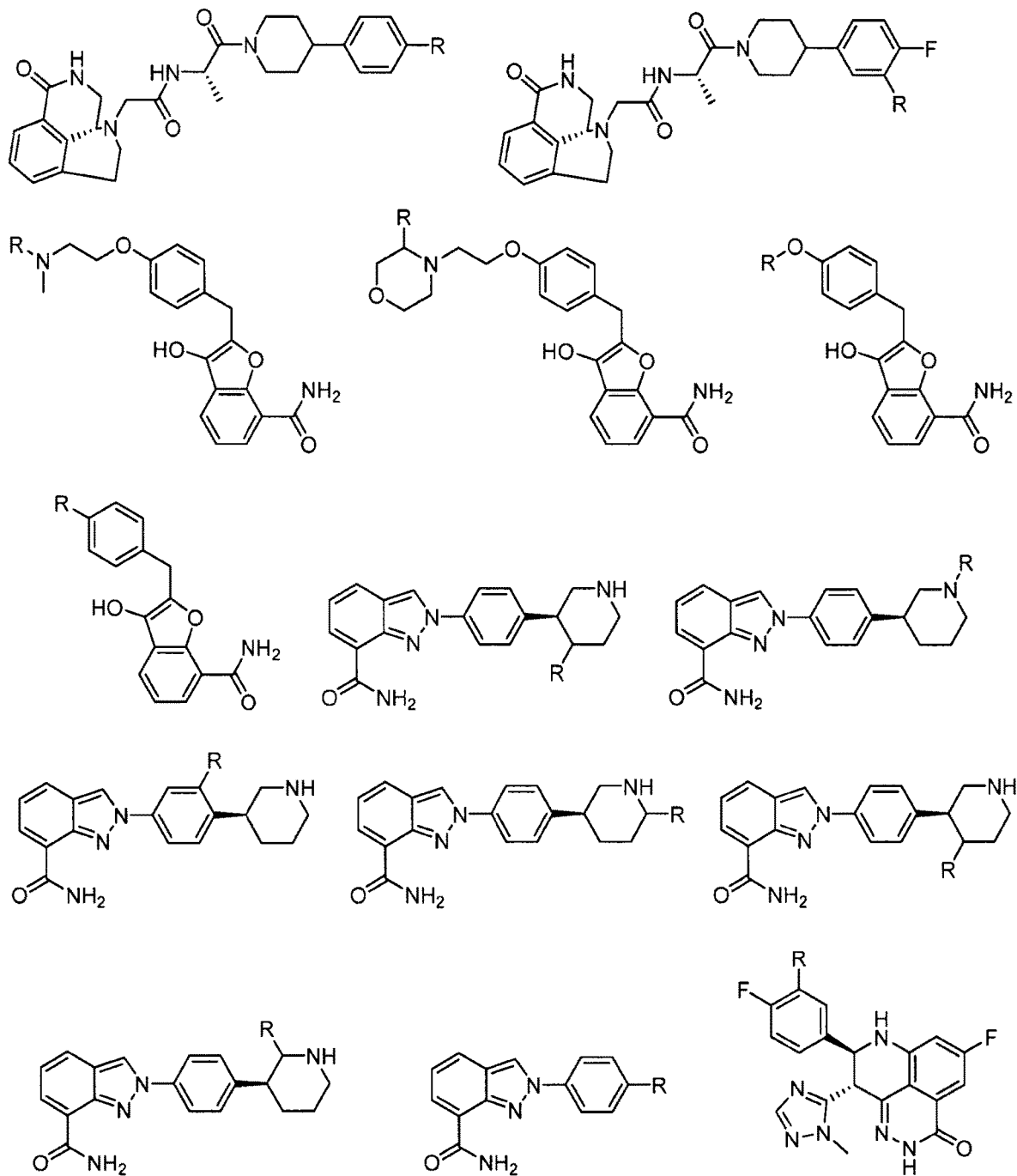
FIG. 2CCCCC

FIG. 2DDDDD
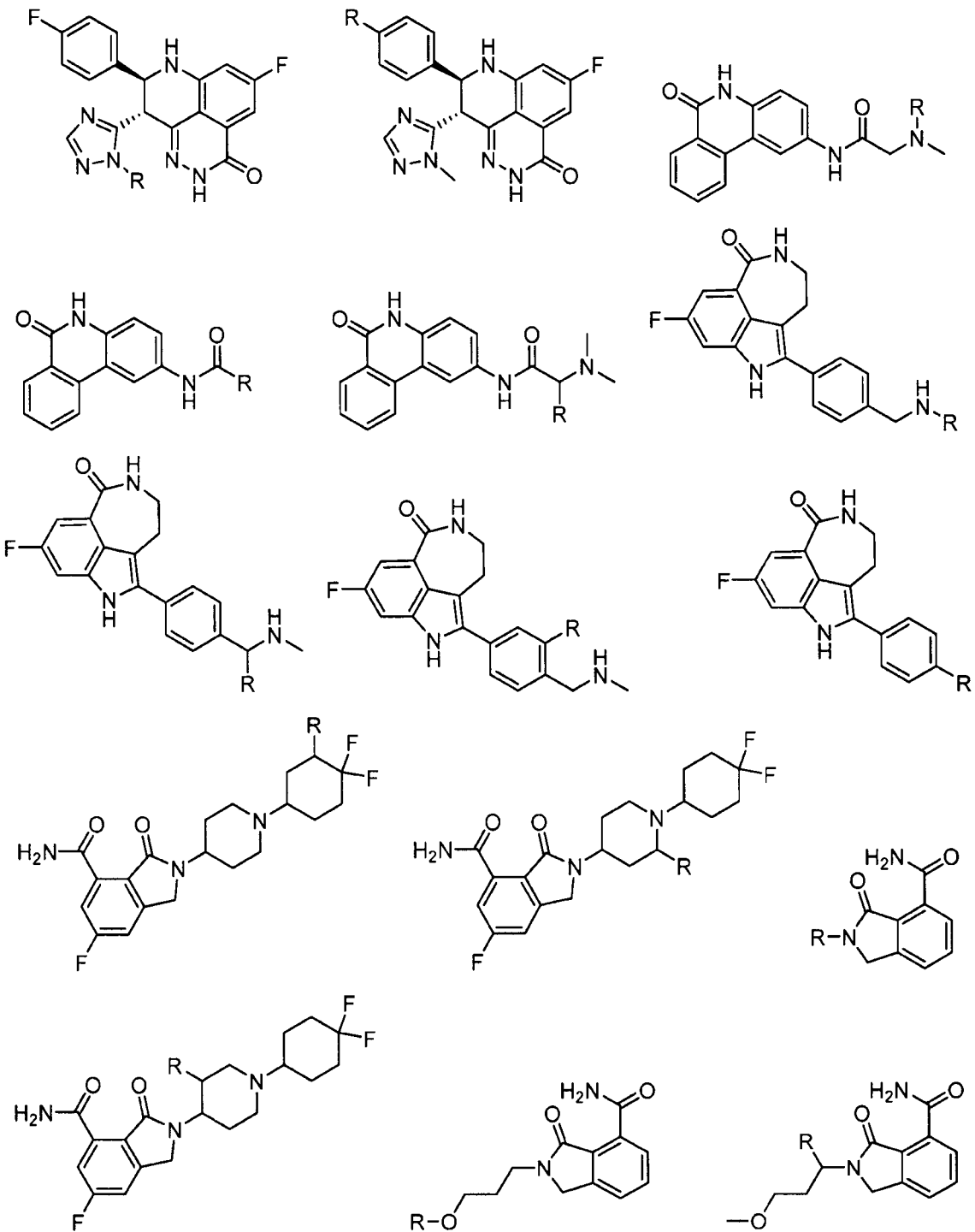

FIG. 2EEEEE
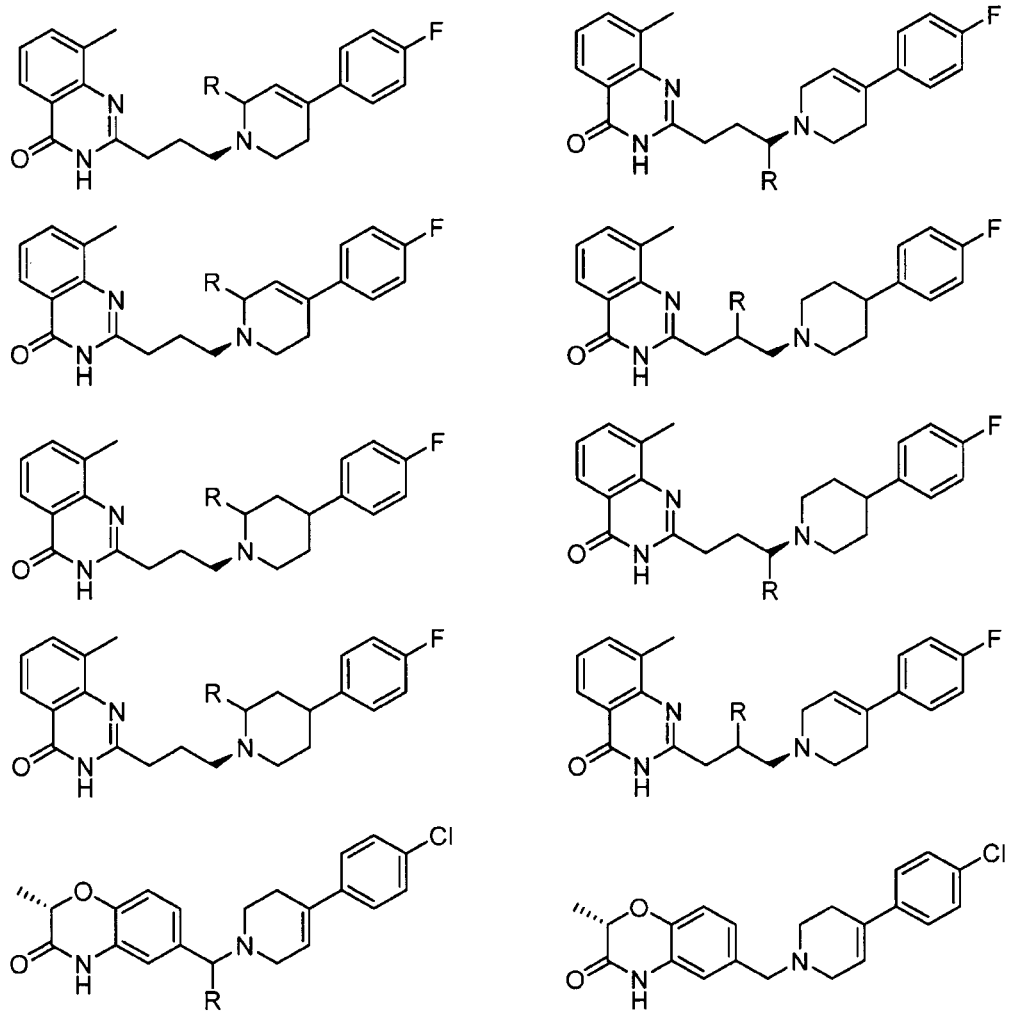
FIG. 2FFFFF
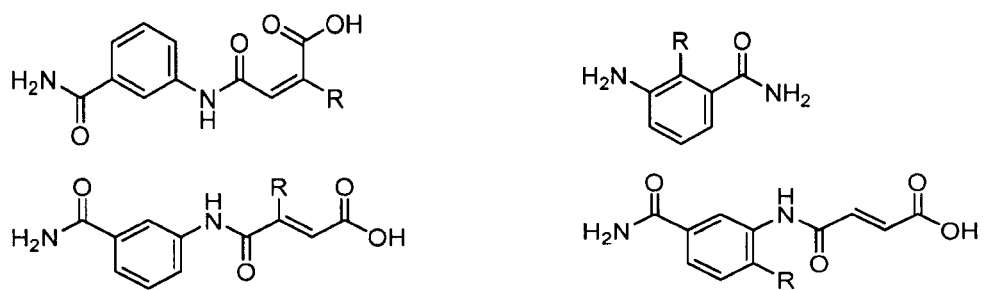

FIG. 2GGGGG
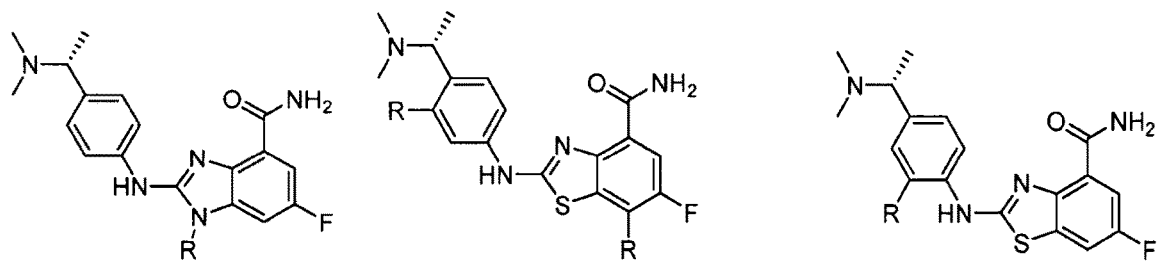
FIG. 2HHHHH
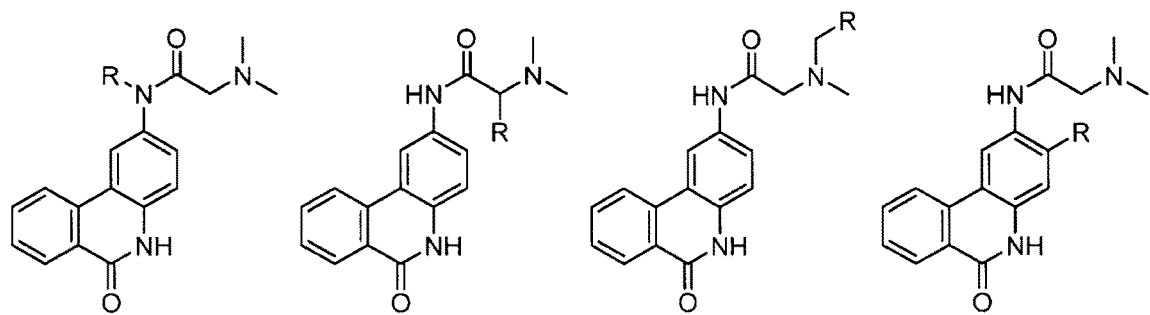
FIG. 2IIIII
FIG. 2JJJJJ
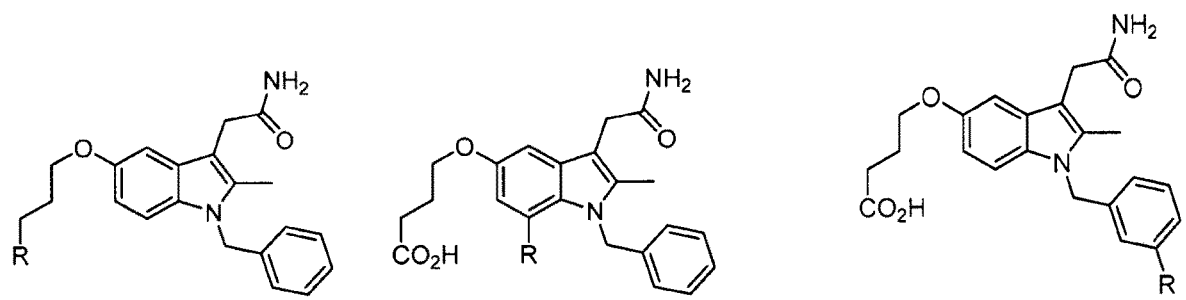

FIG. 2KKKKK
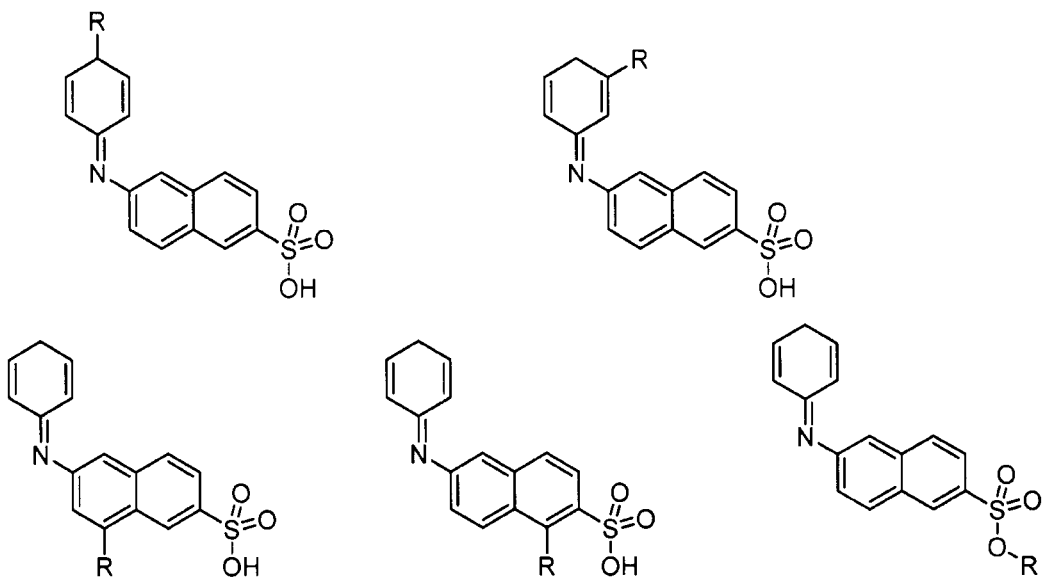
FIG. 2LLLLL
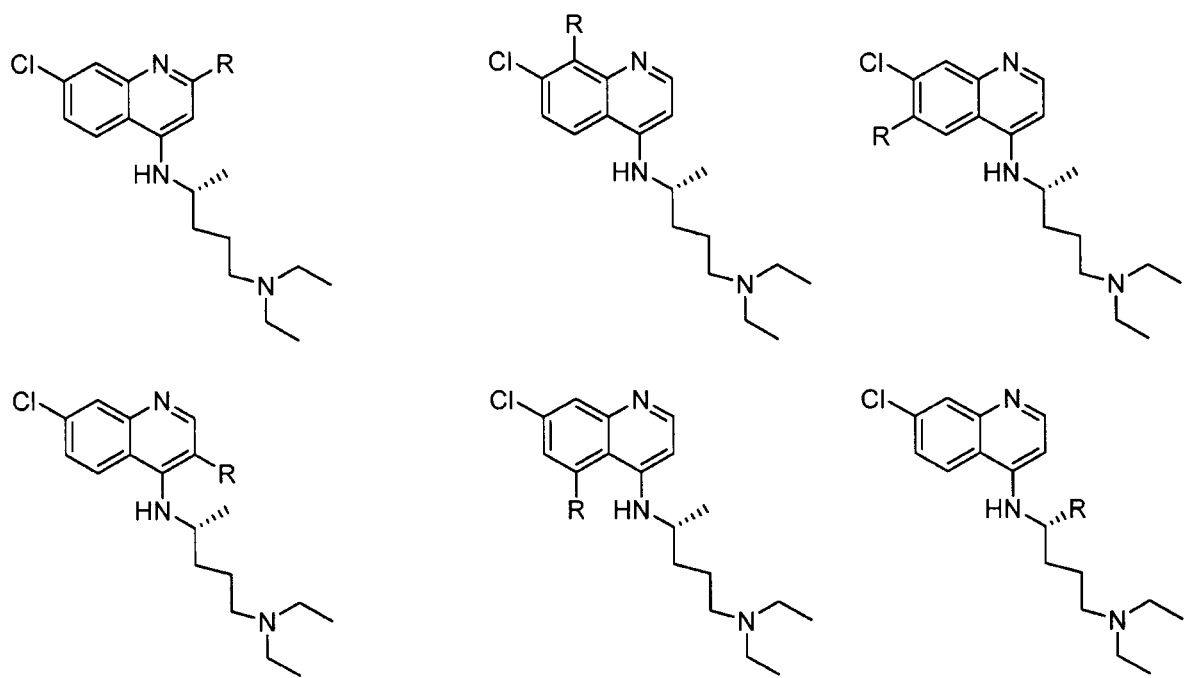

FIG. 2MMMMM
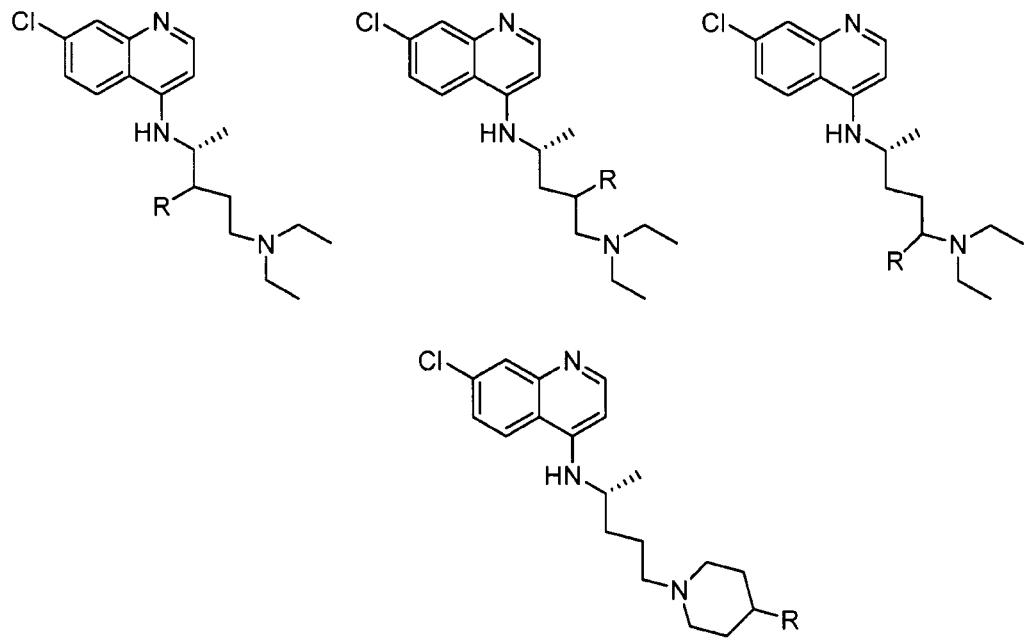
FIG. 2NNNNN
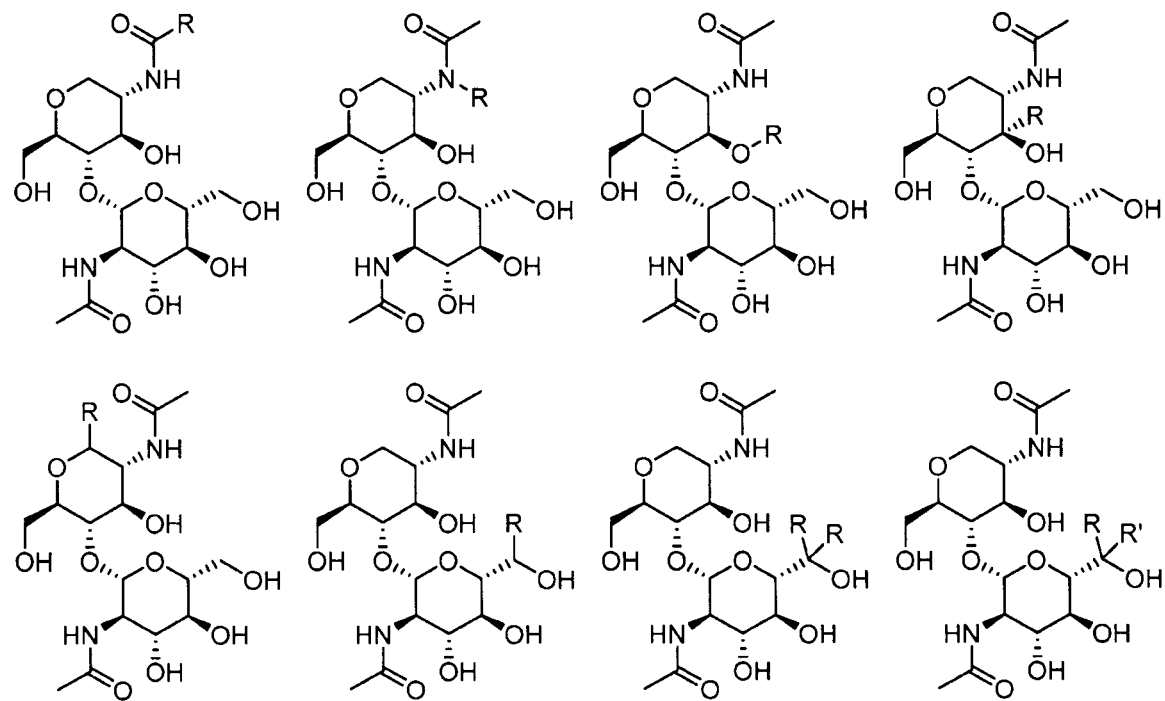

FIG. 2OOOOO
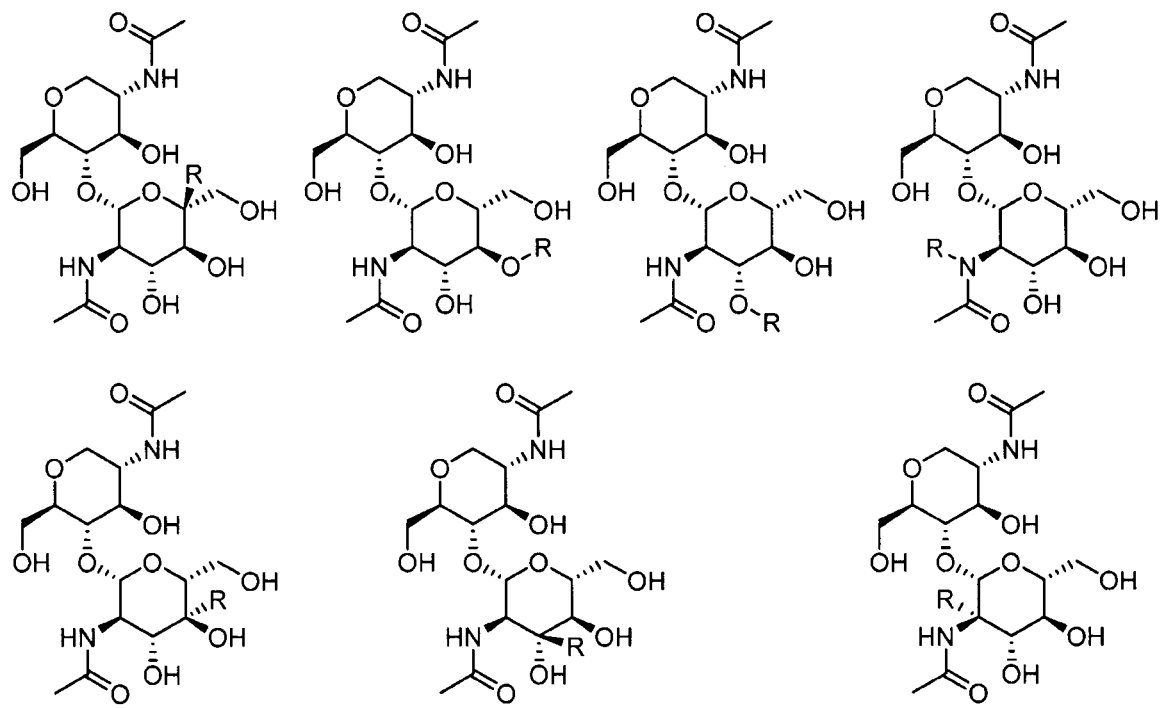
FIG. 2PPPPP
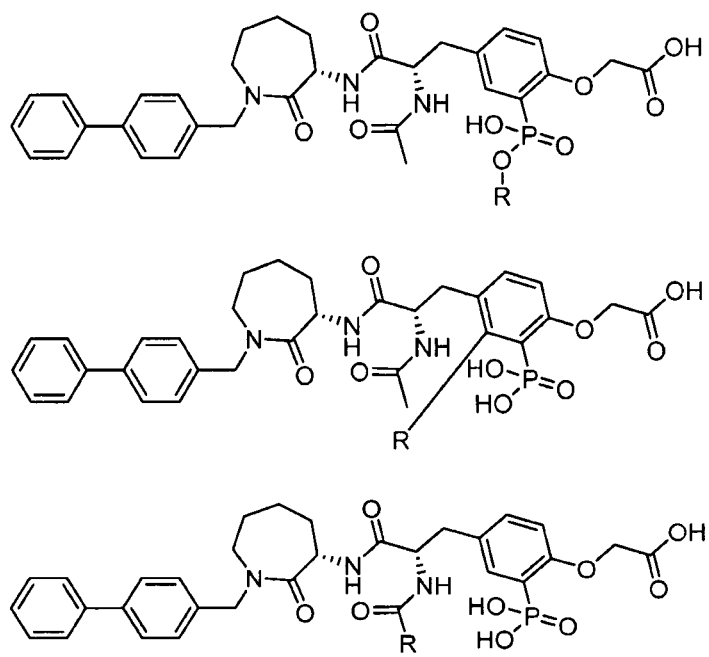

FIG. 2QQQQQ
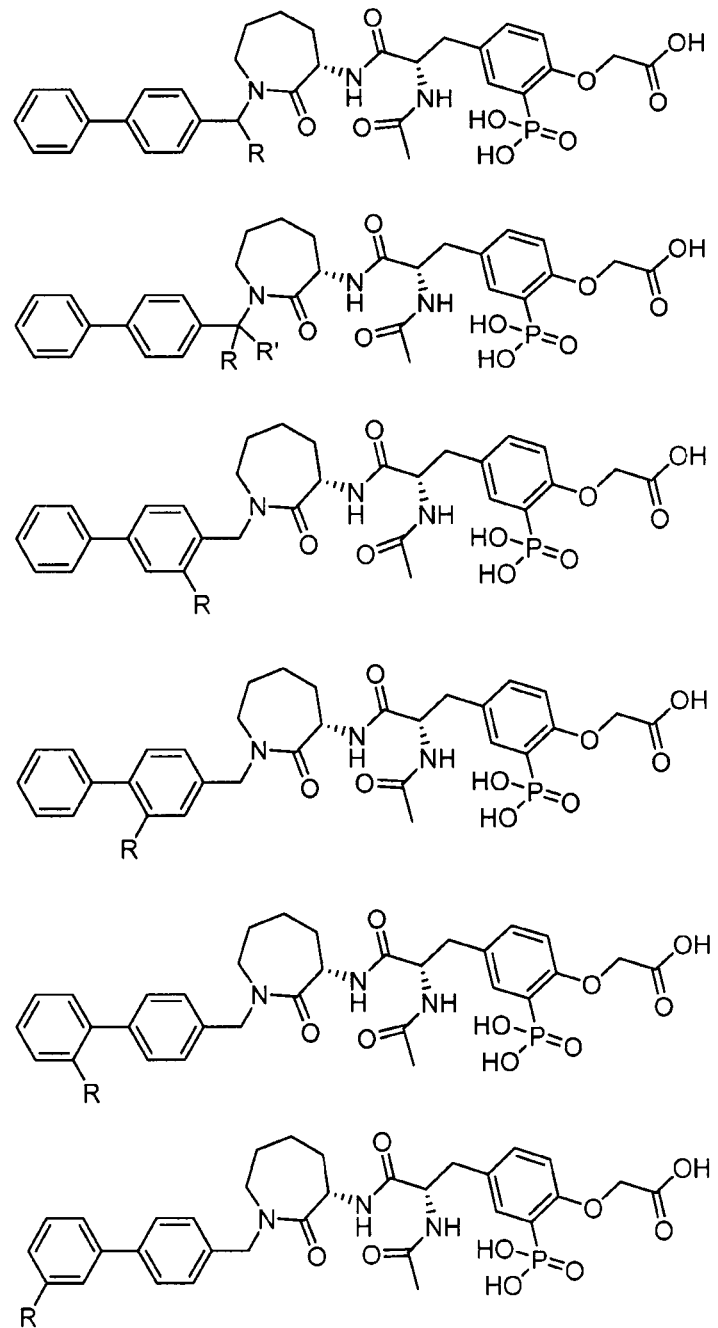

FIG. 2RRRRR
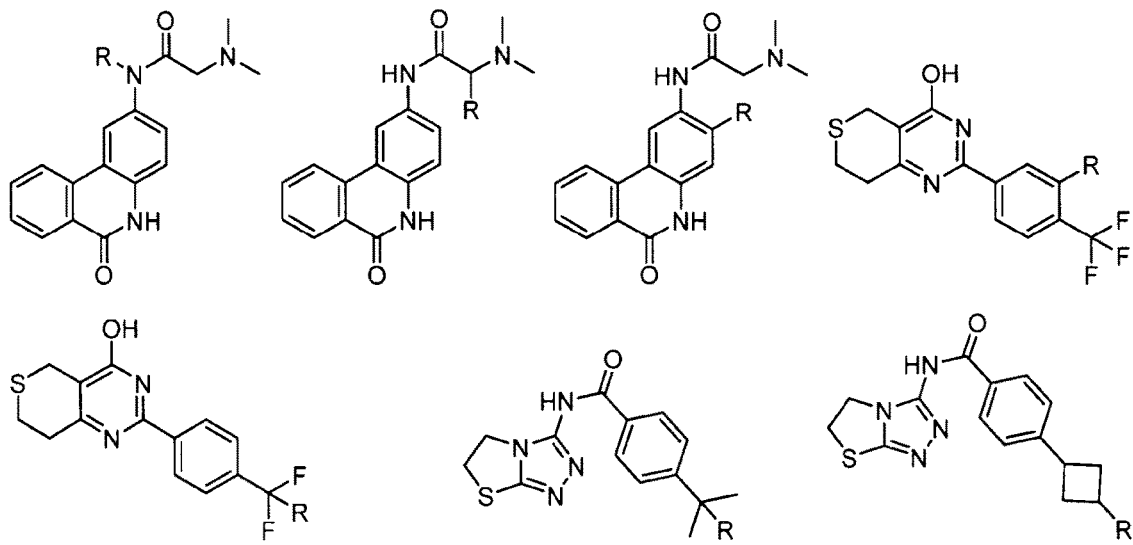
FIG. 2SSSSS
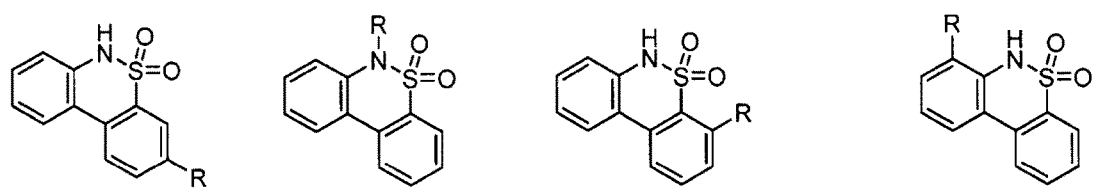
FIG. 2TTTTT
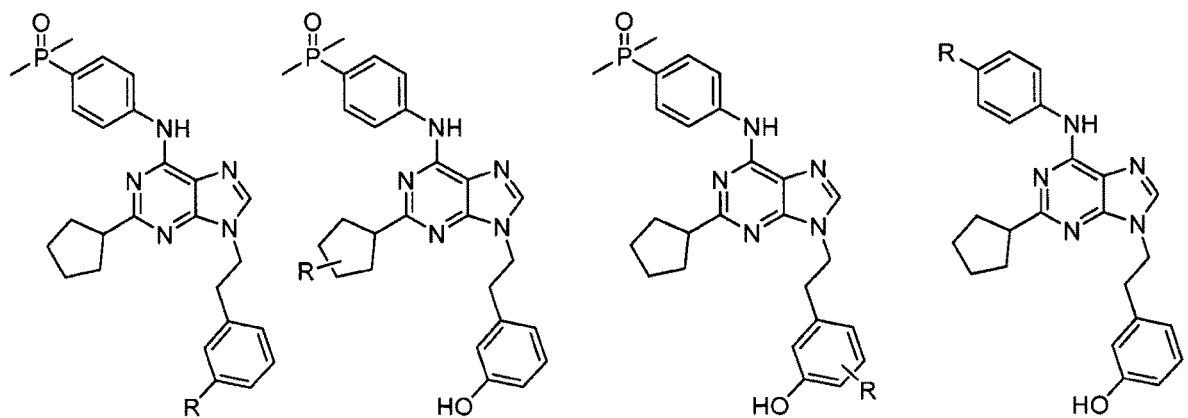

FIG. 2UUUUU
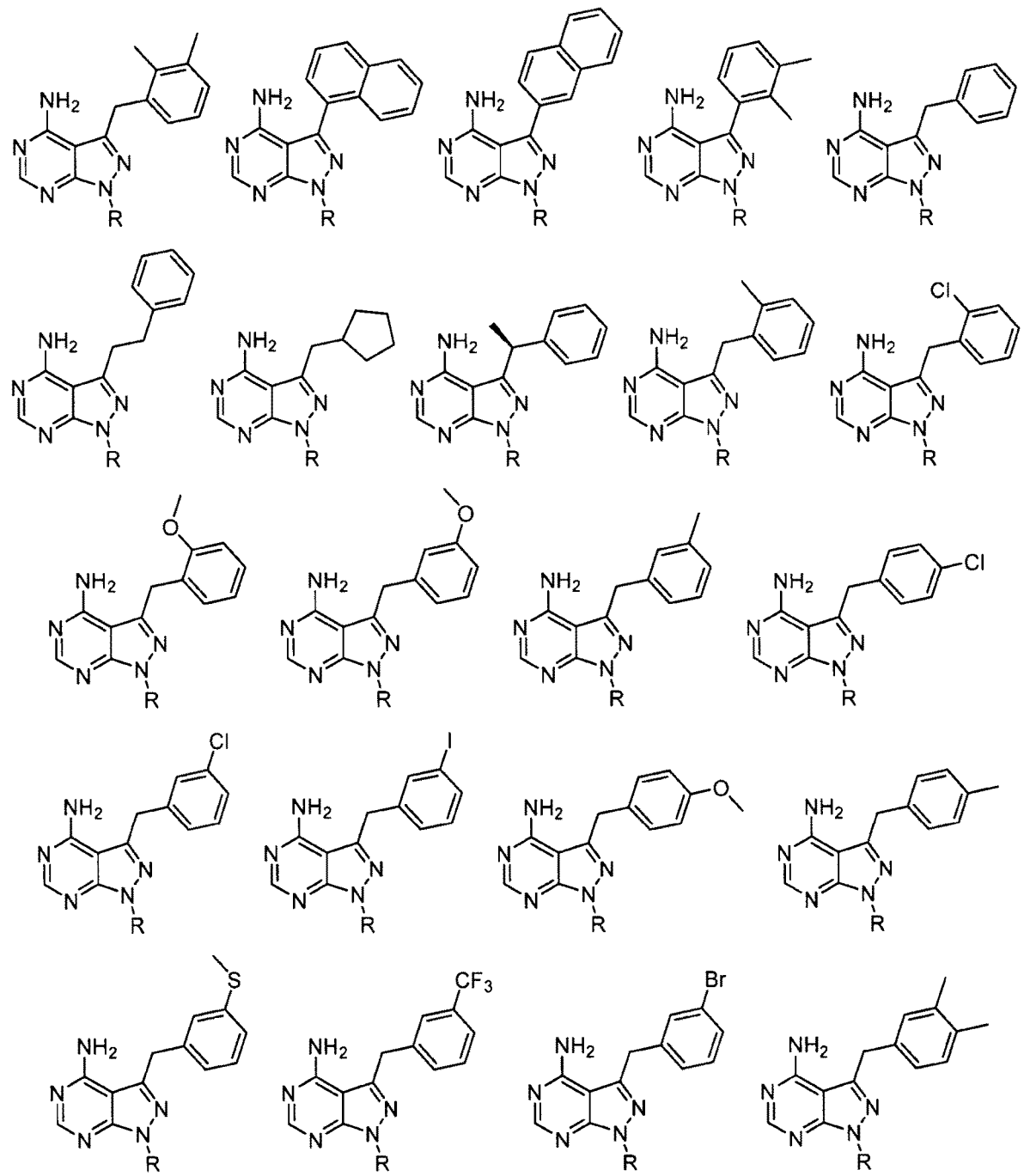

FIG. 2VVVVV
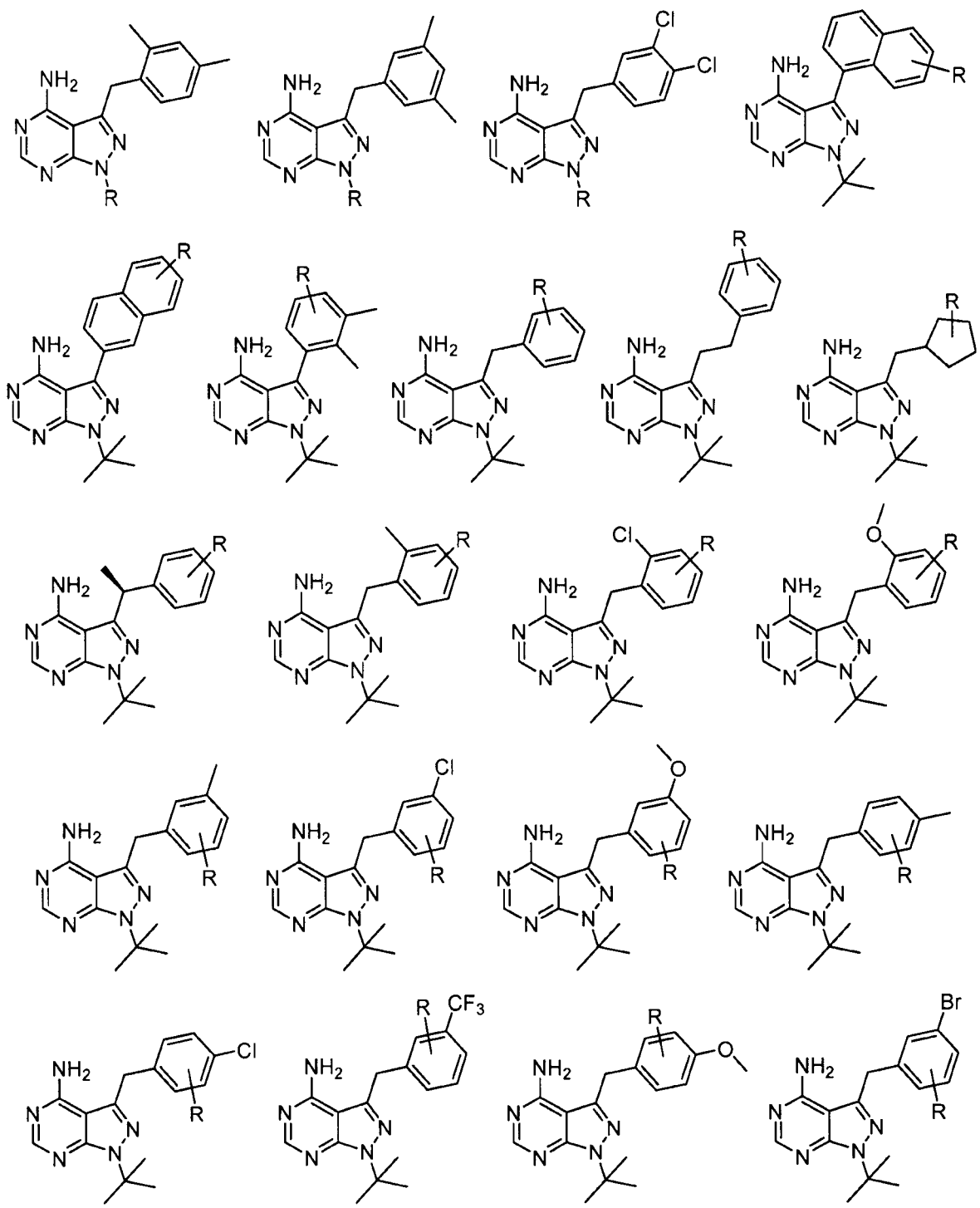

FIG. 2WWWWW
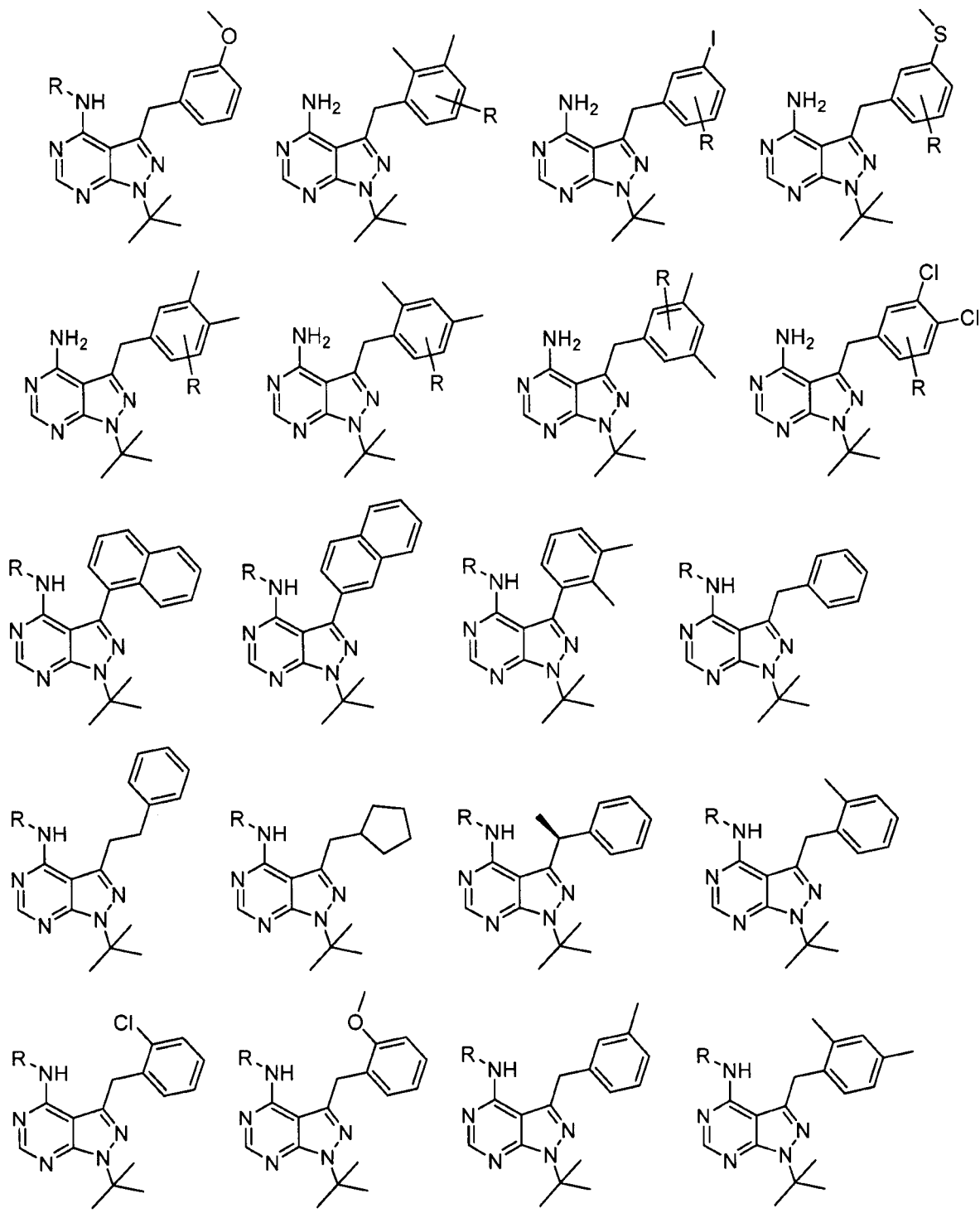

FIG. 2XXXXX
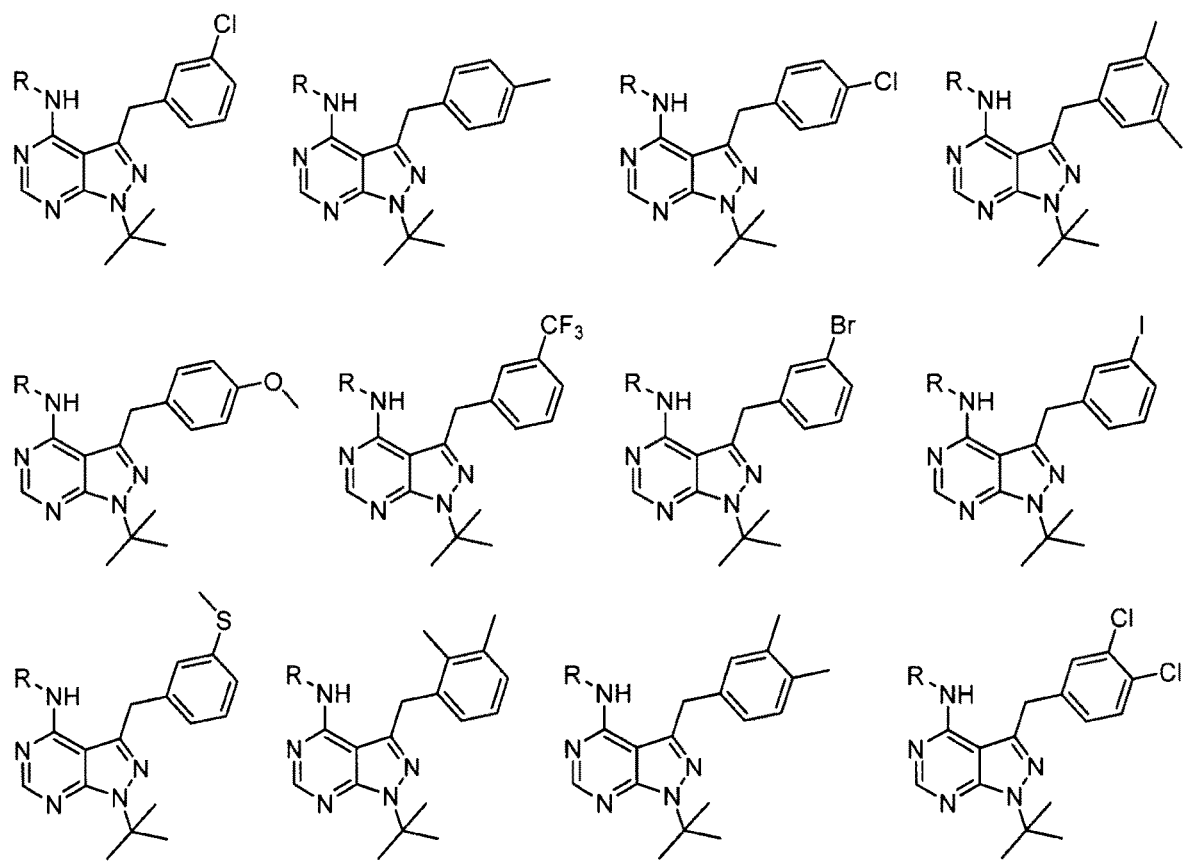
FIG. 2YYYYY
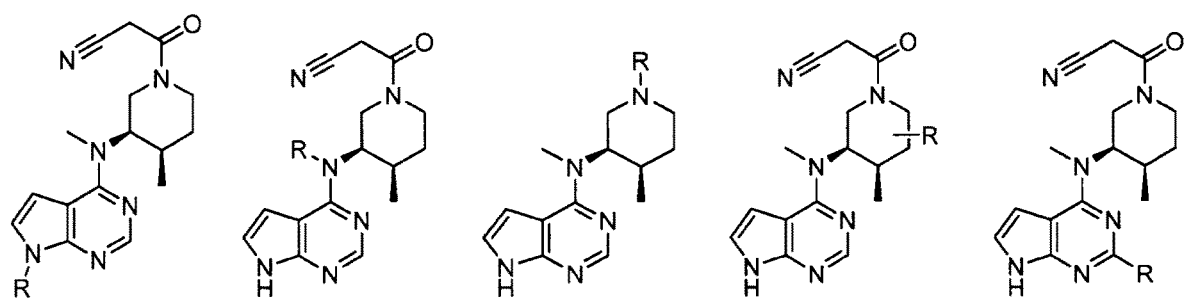

FIG. 2ZZZZZ
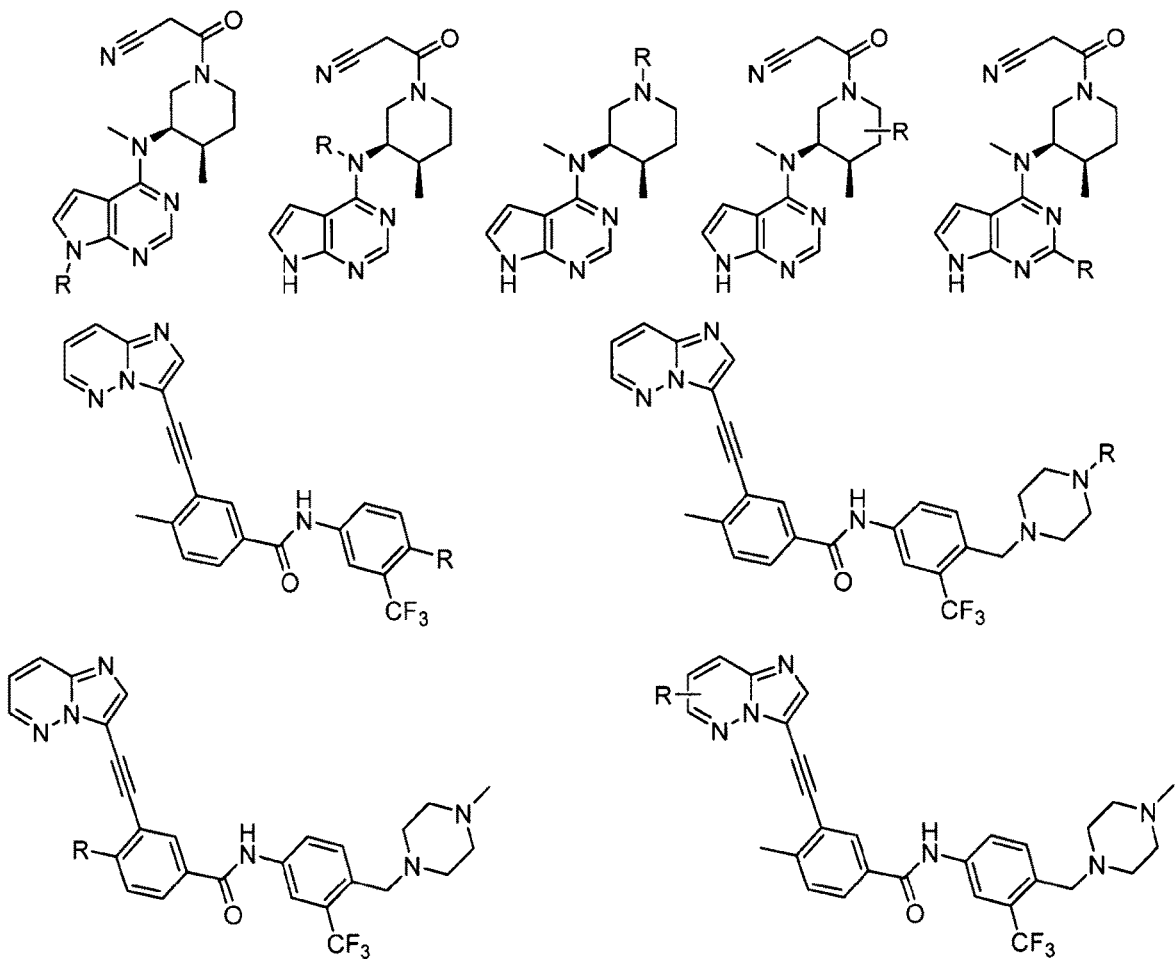
FIG. 3A
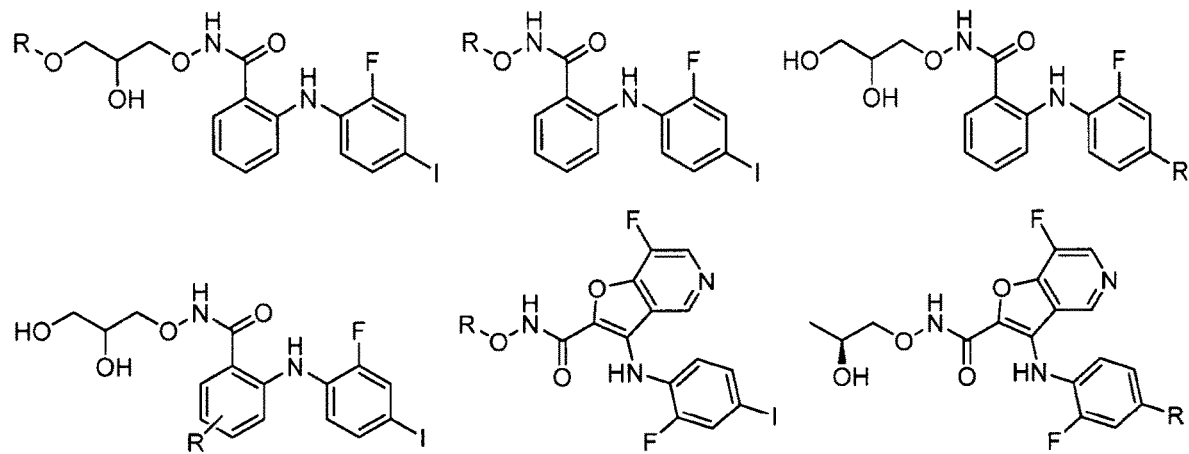

FIG. 3I
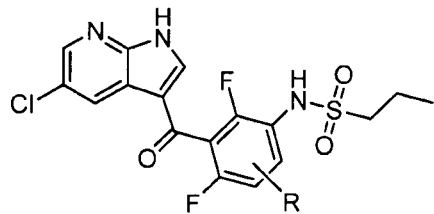 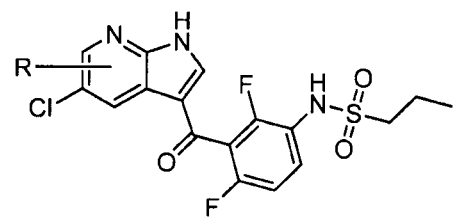
FIG. 3J
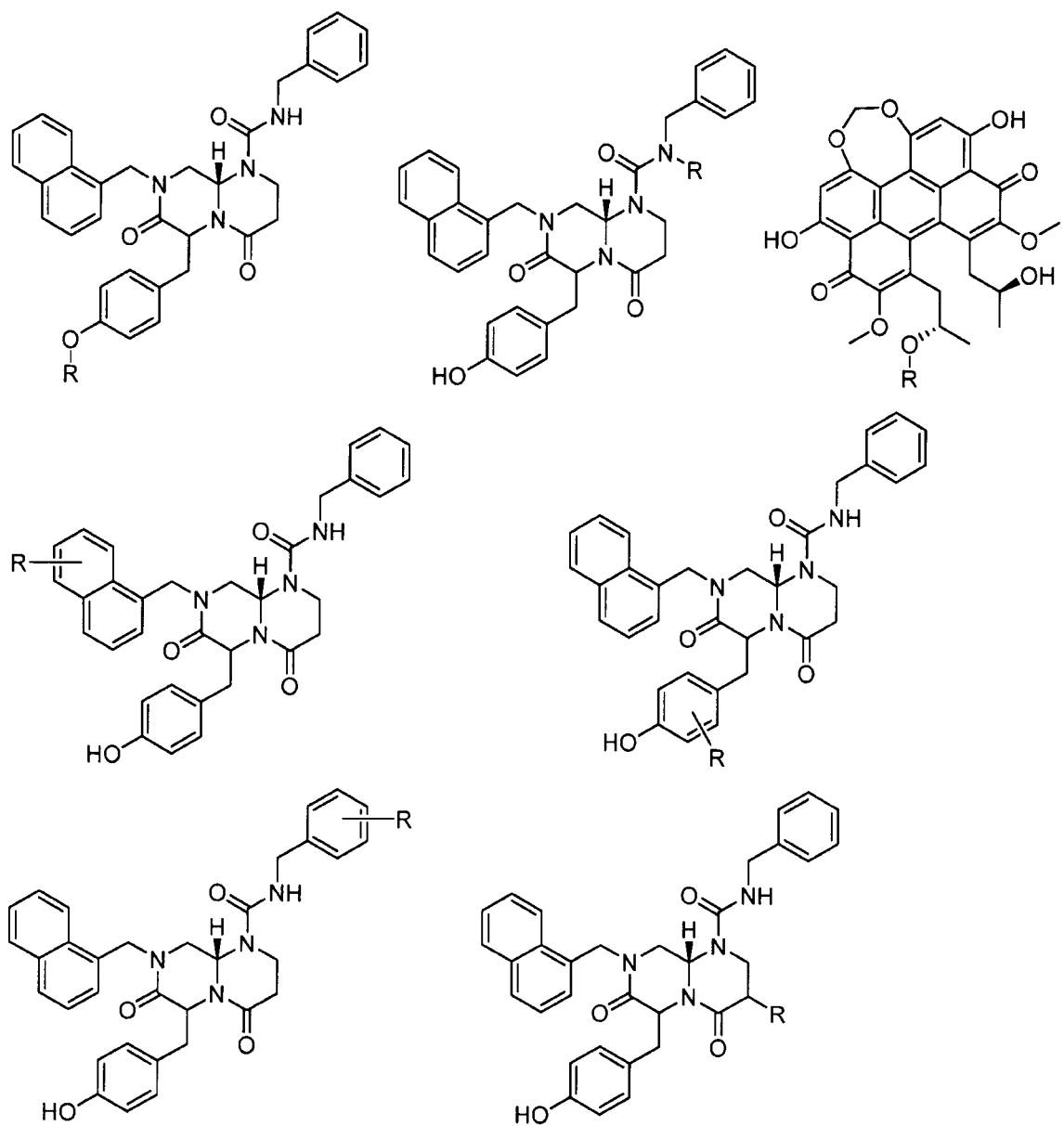

FIG. 3AA
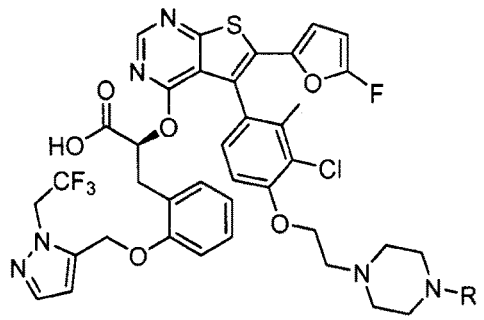
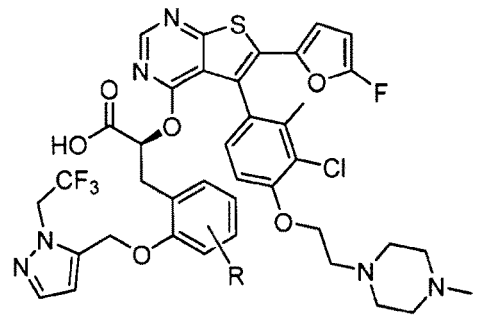
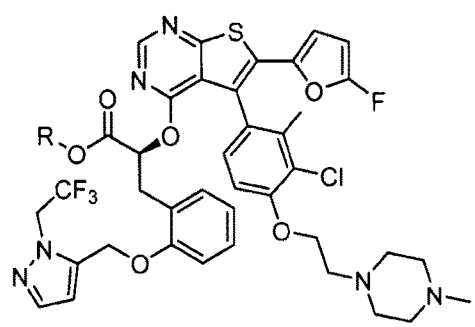
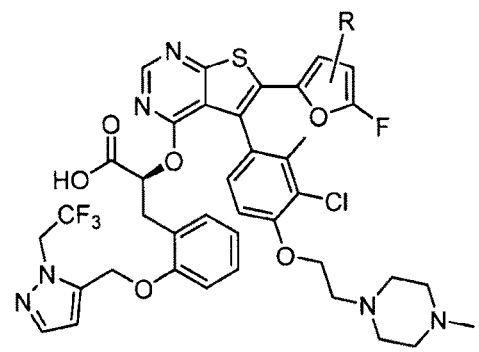
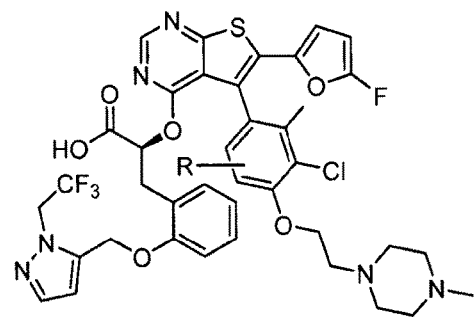
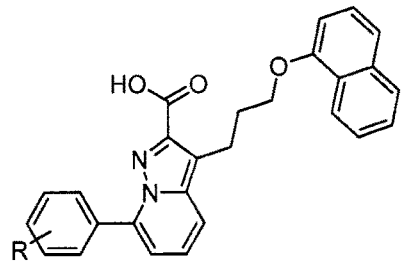
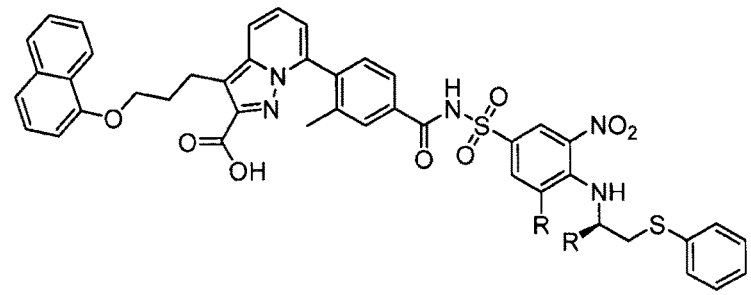
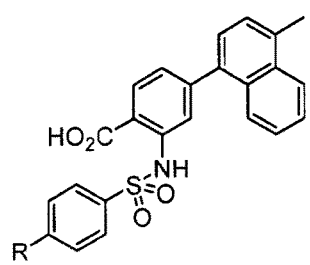

FIG. 3FF
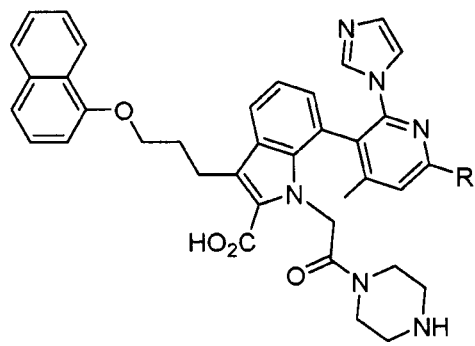
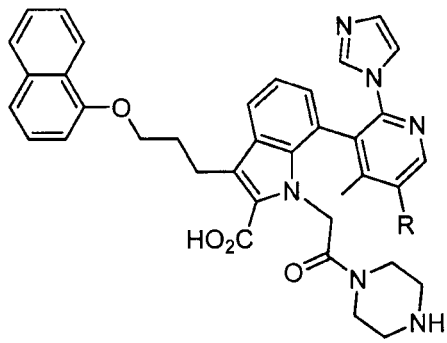
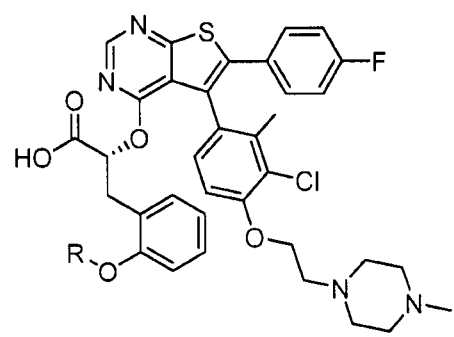
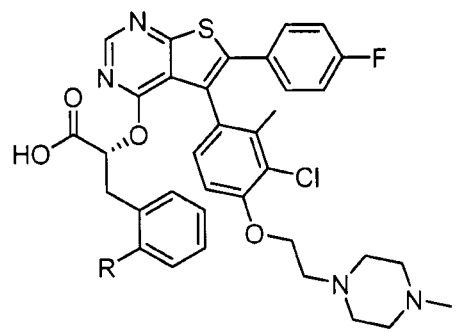
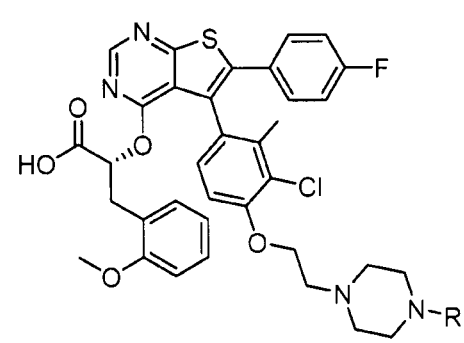
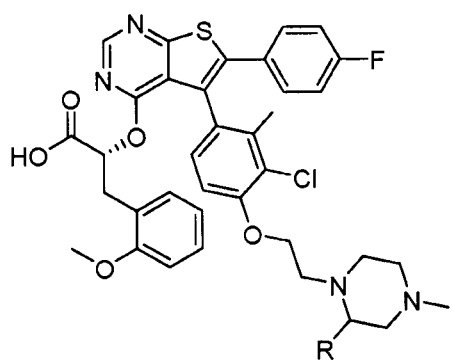
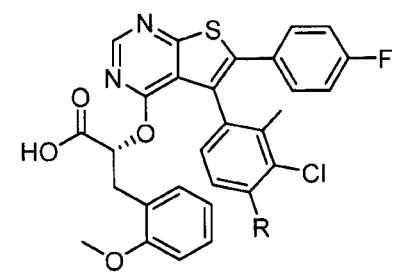
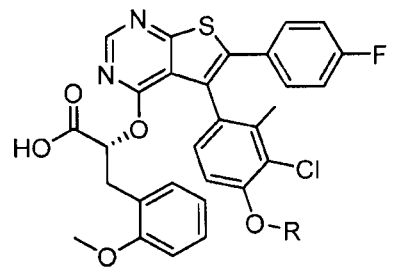

FIG. 3GG
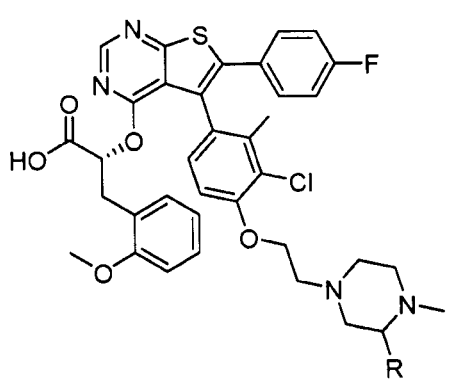
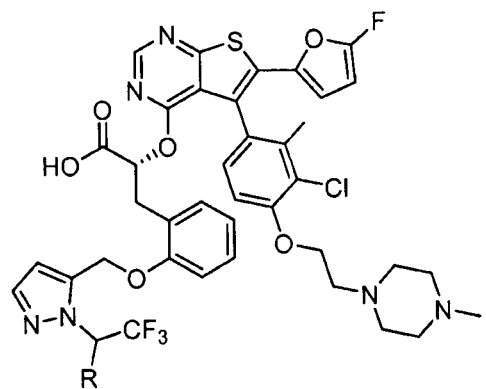
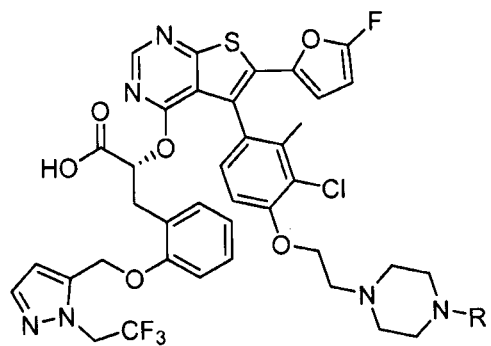
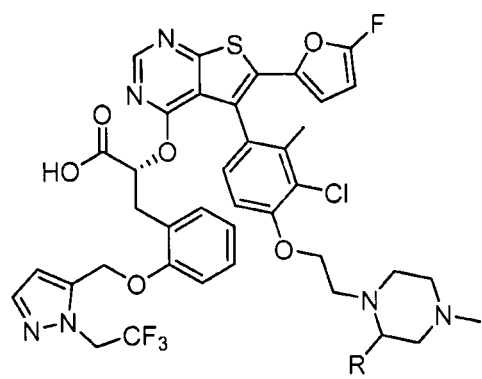
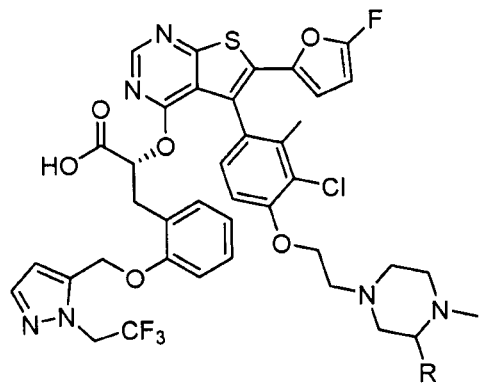
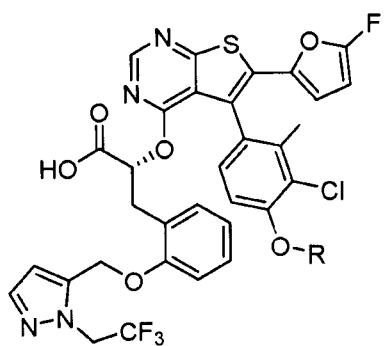

FIG. 3JJ
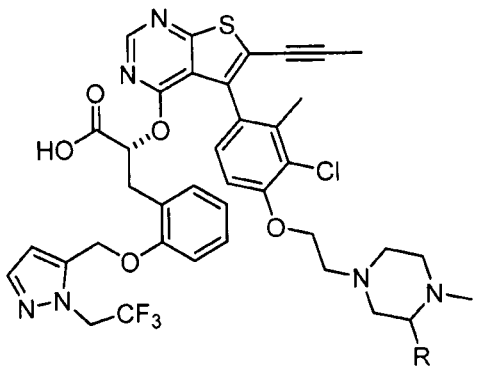
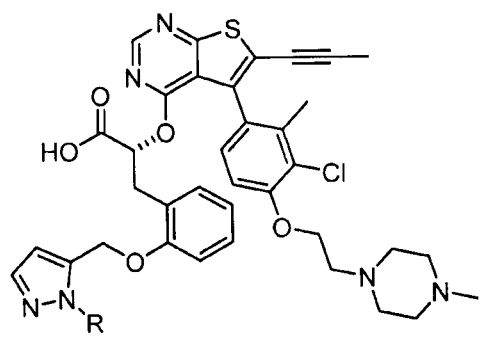
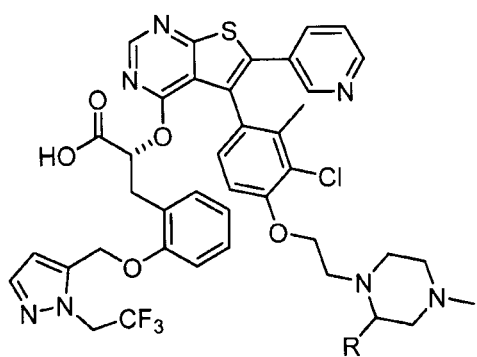
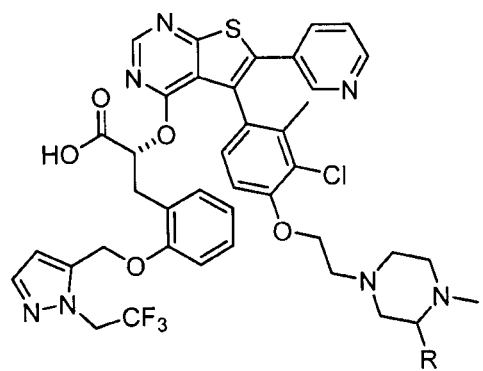
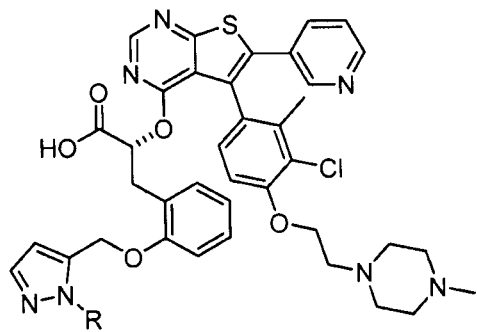
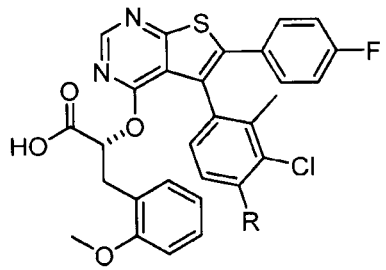
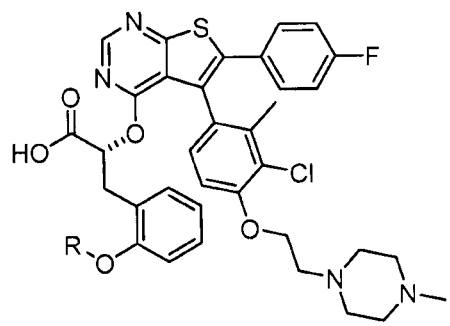
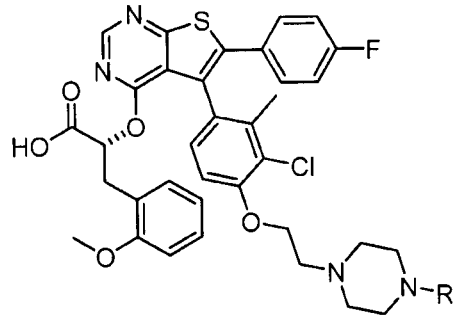

FIG. 3NN
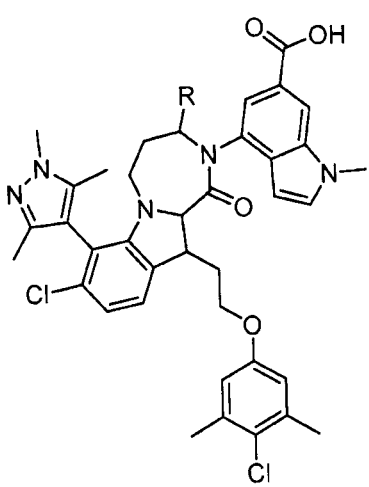
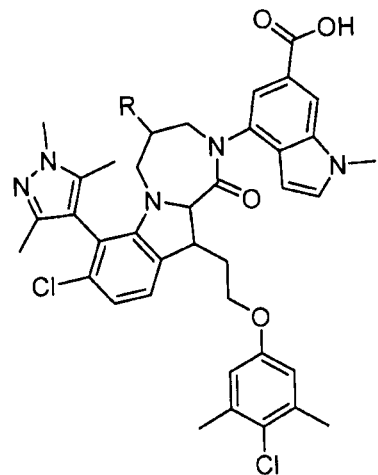
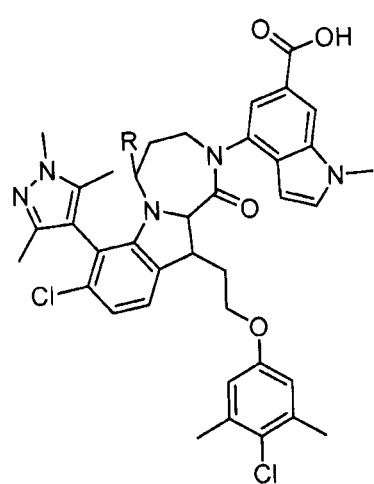
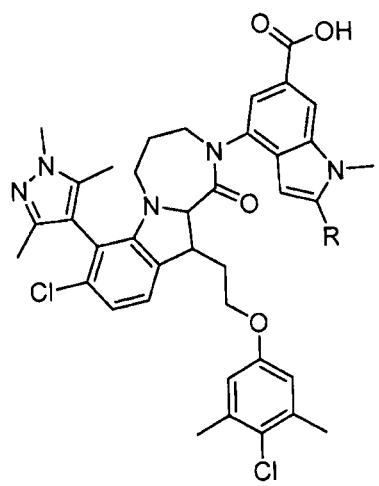
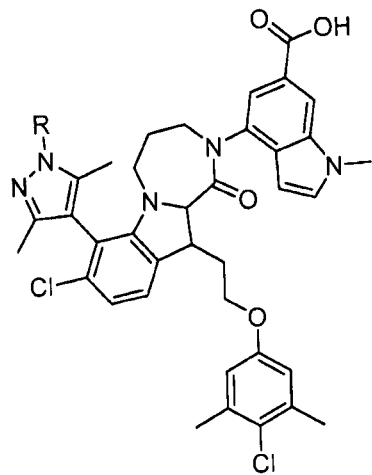
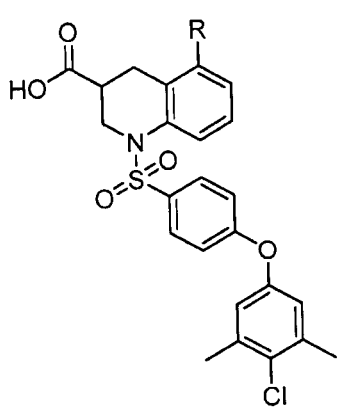

FIG. 3AAA
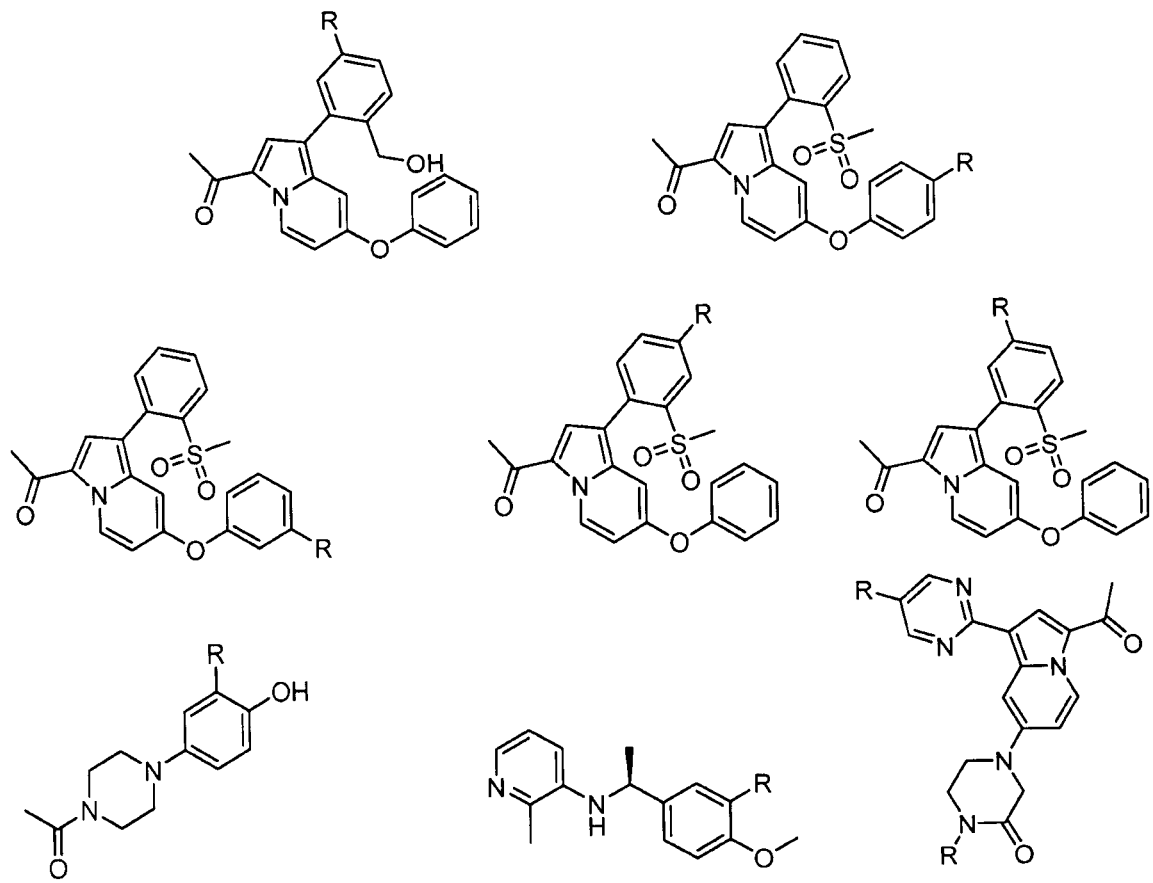
FIG. 3BBB
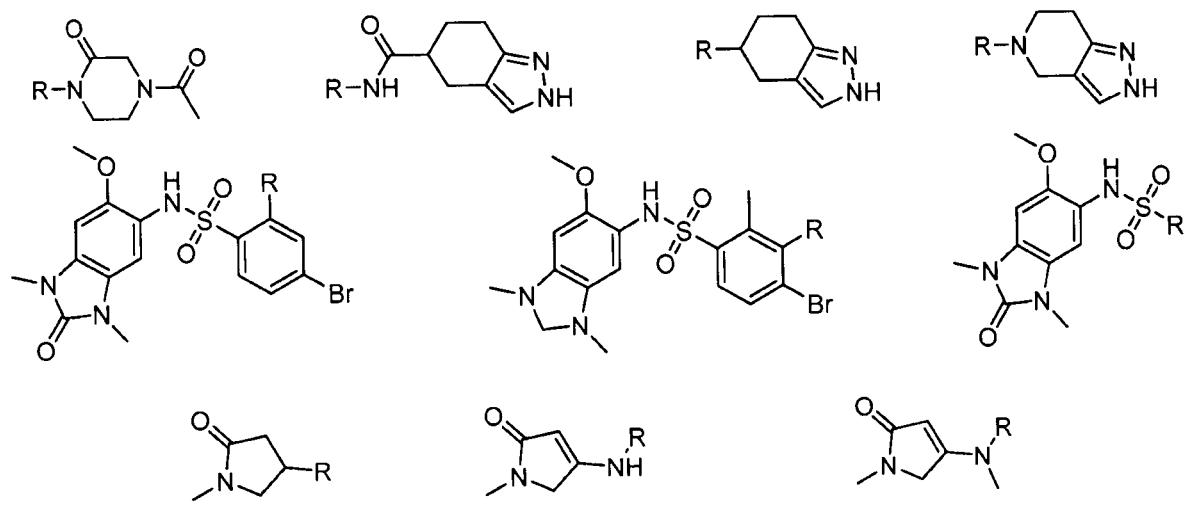

FIG. 3CCC
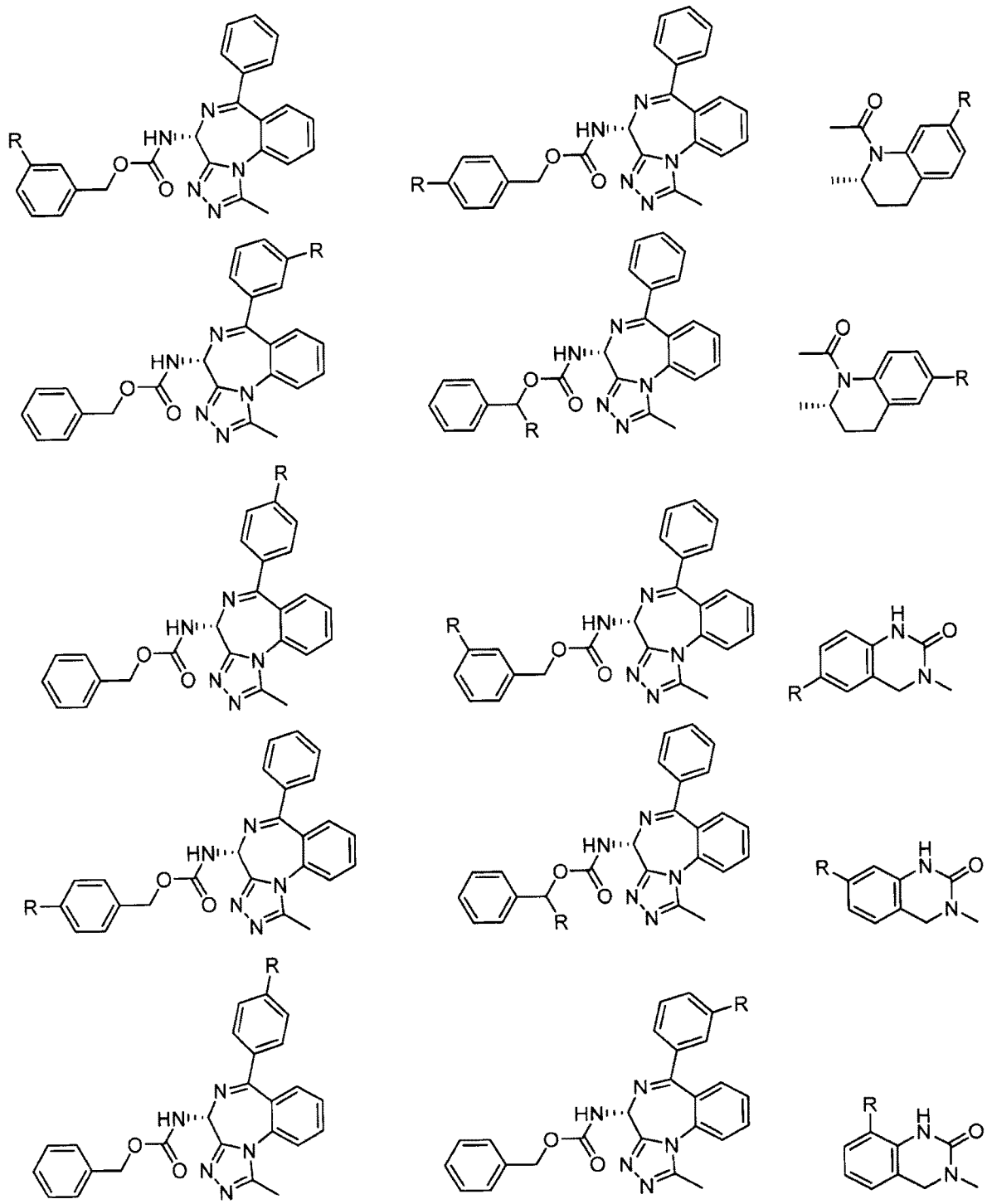

FIG. 3DDD
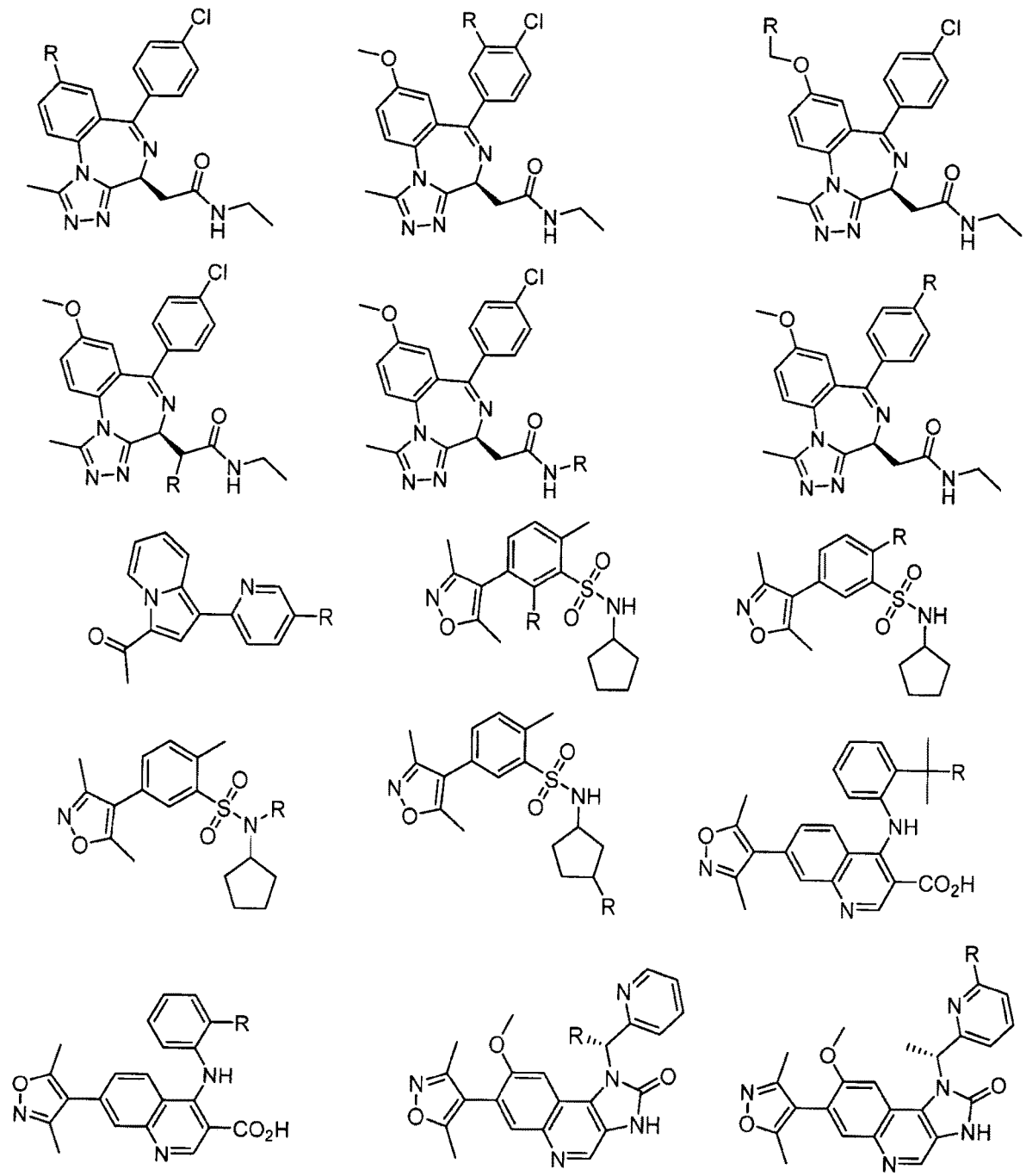

FIG. 3EEE
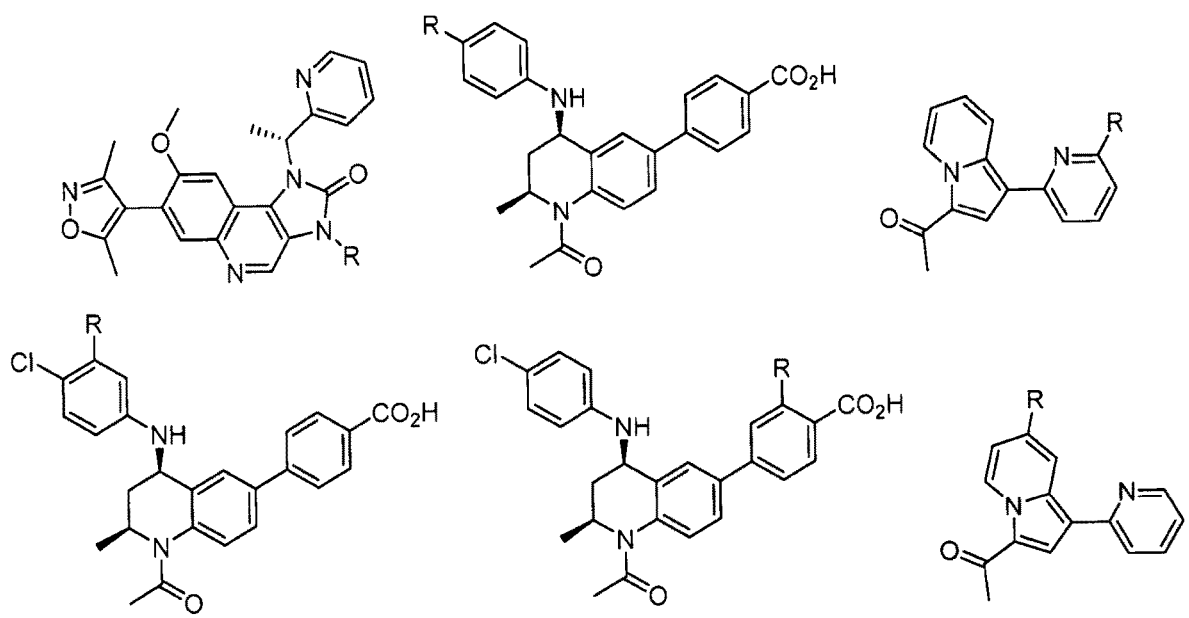
FIG. 3FFF
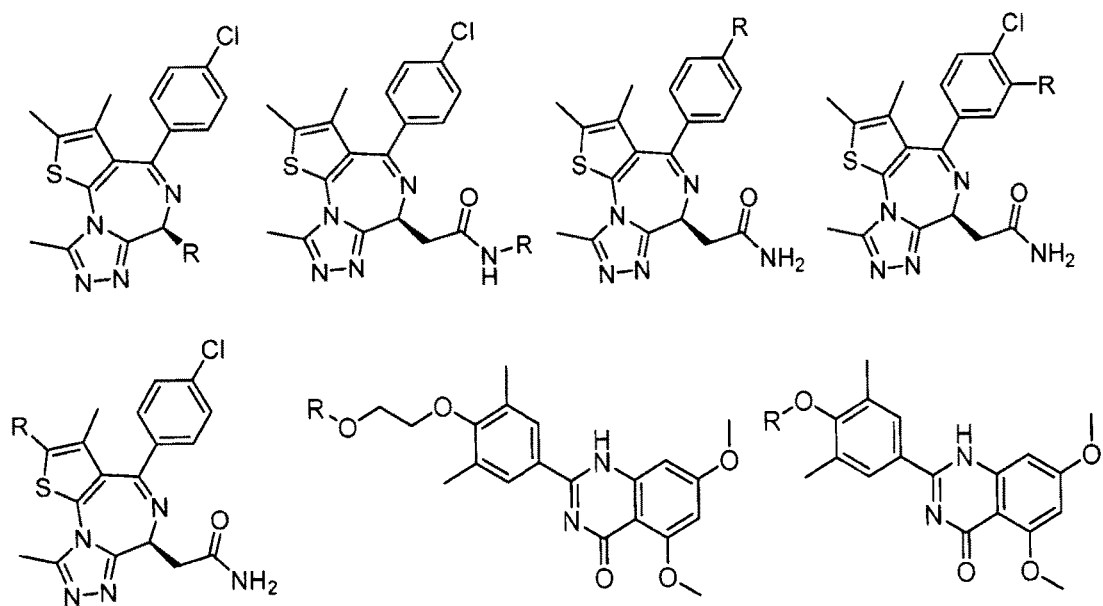

FIG. 3GGG
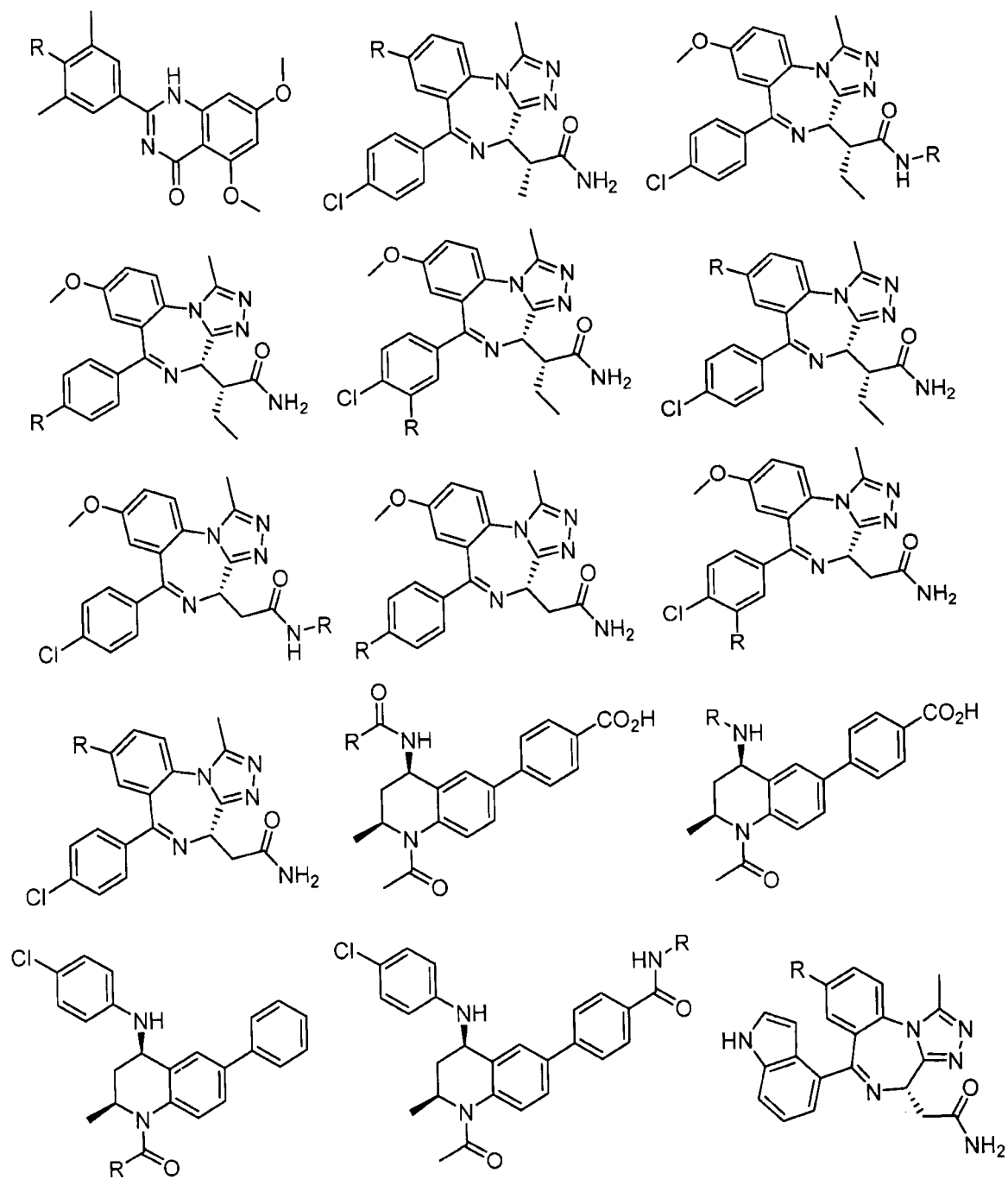

FIG. 3HHH
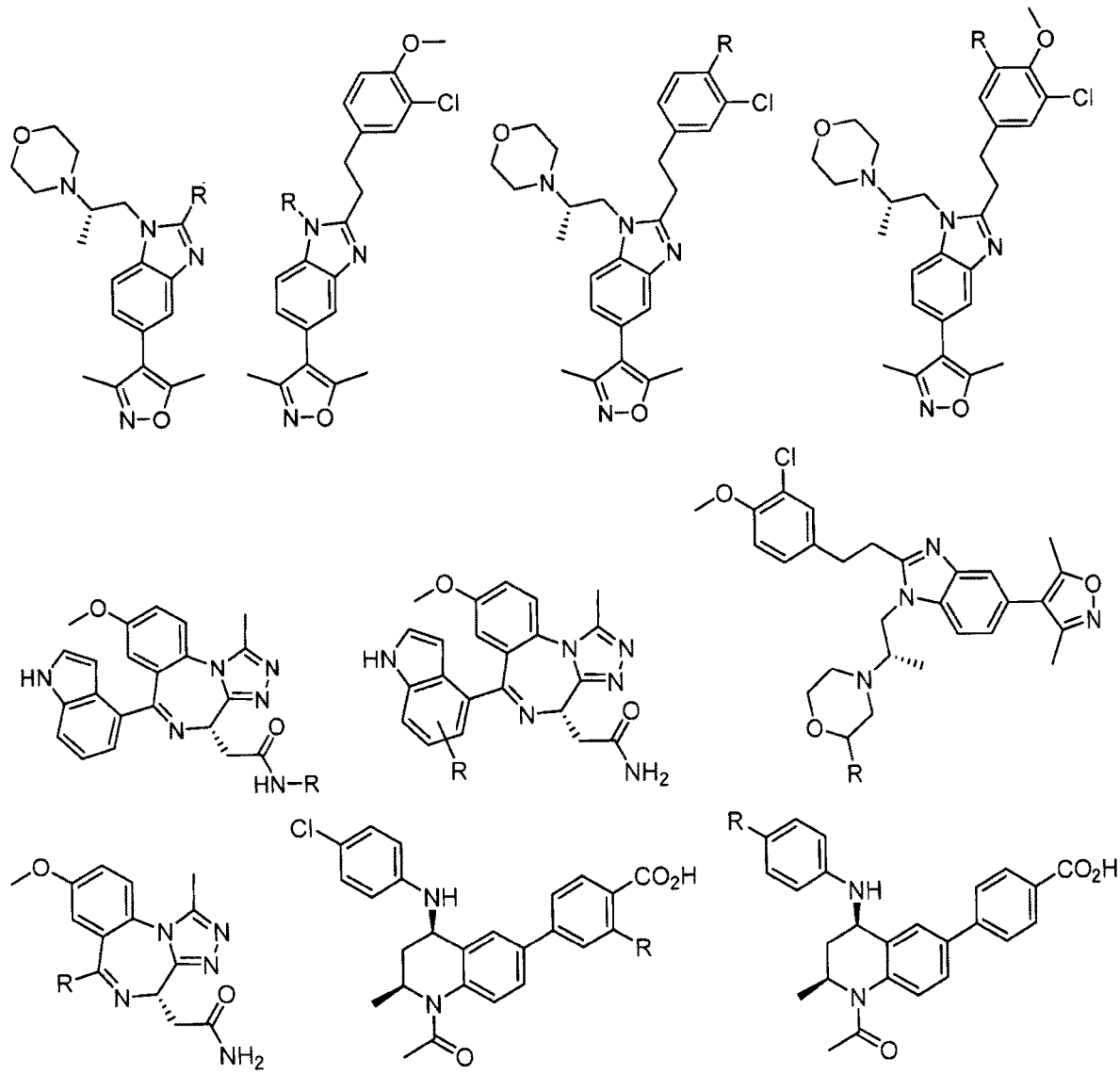
FIG. 3III
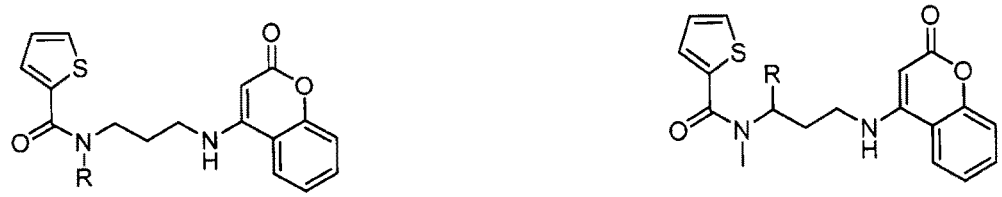

FIG. 3JJJ
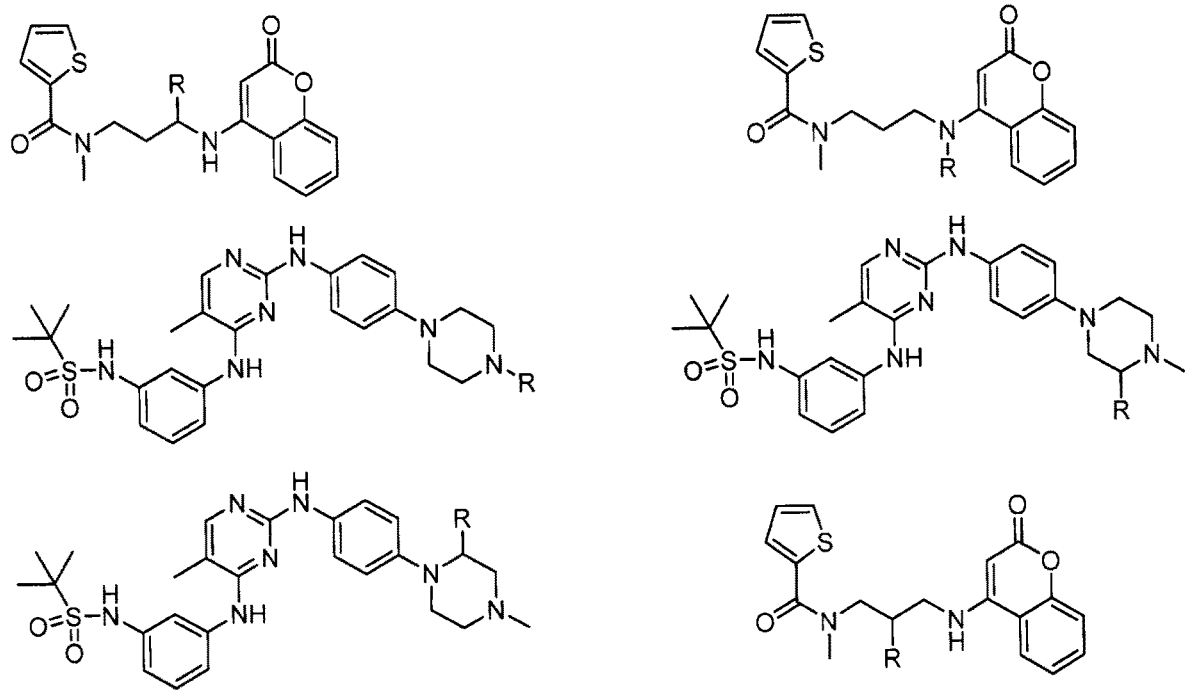
FIG. 3KKK
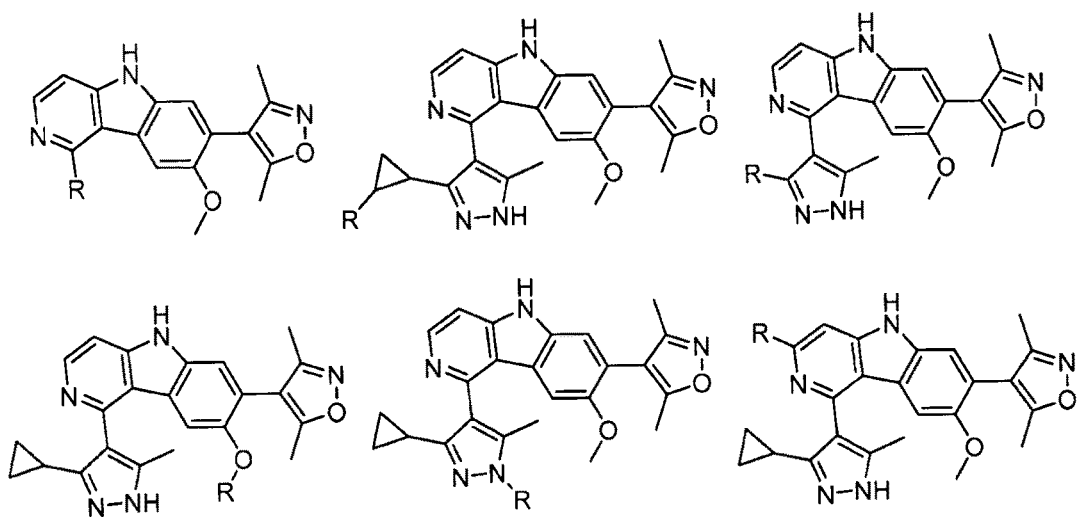

FIG. 3LLL
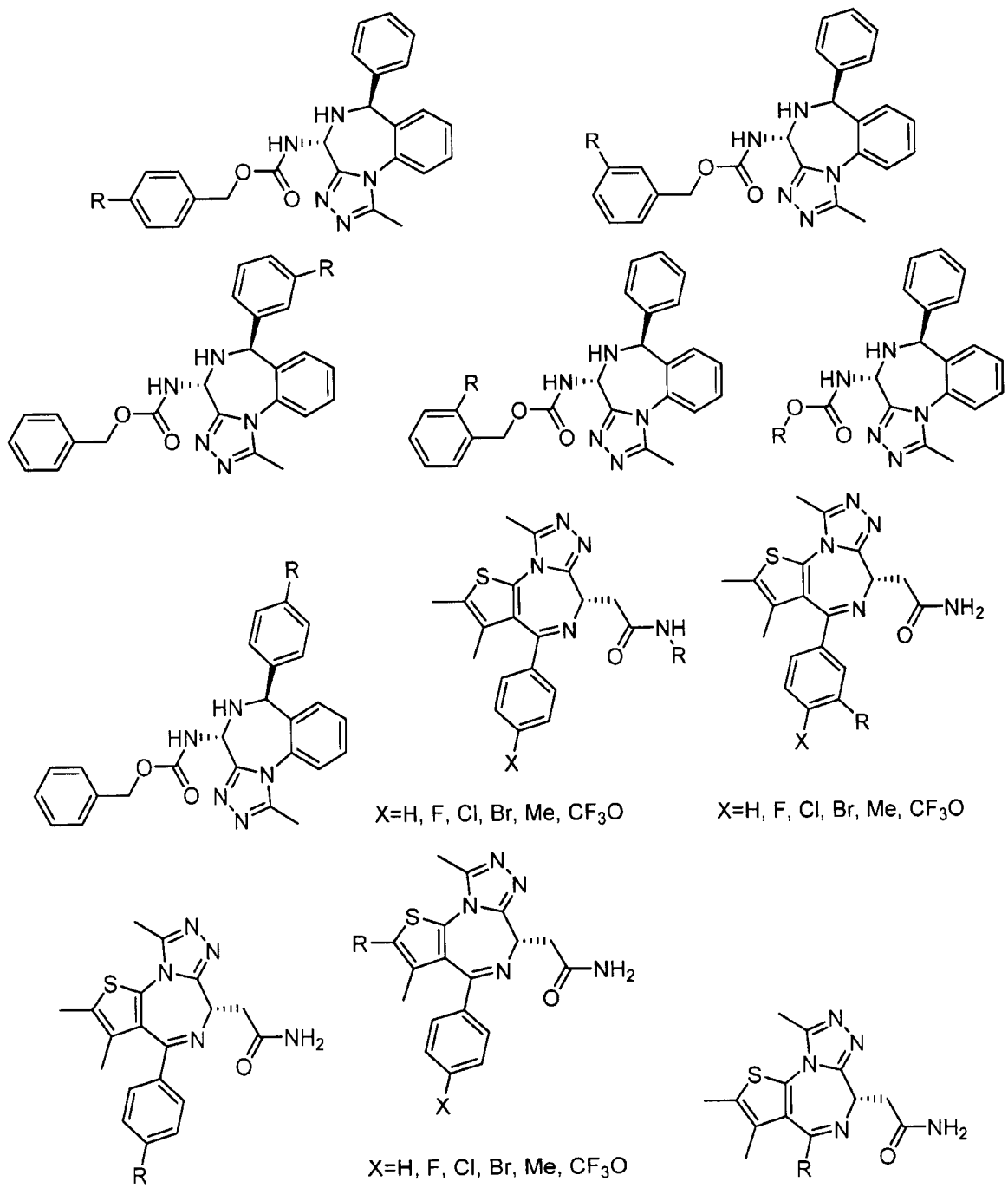

FIG. 3MMM
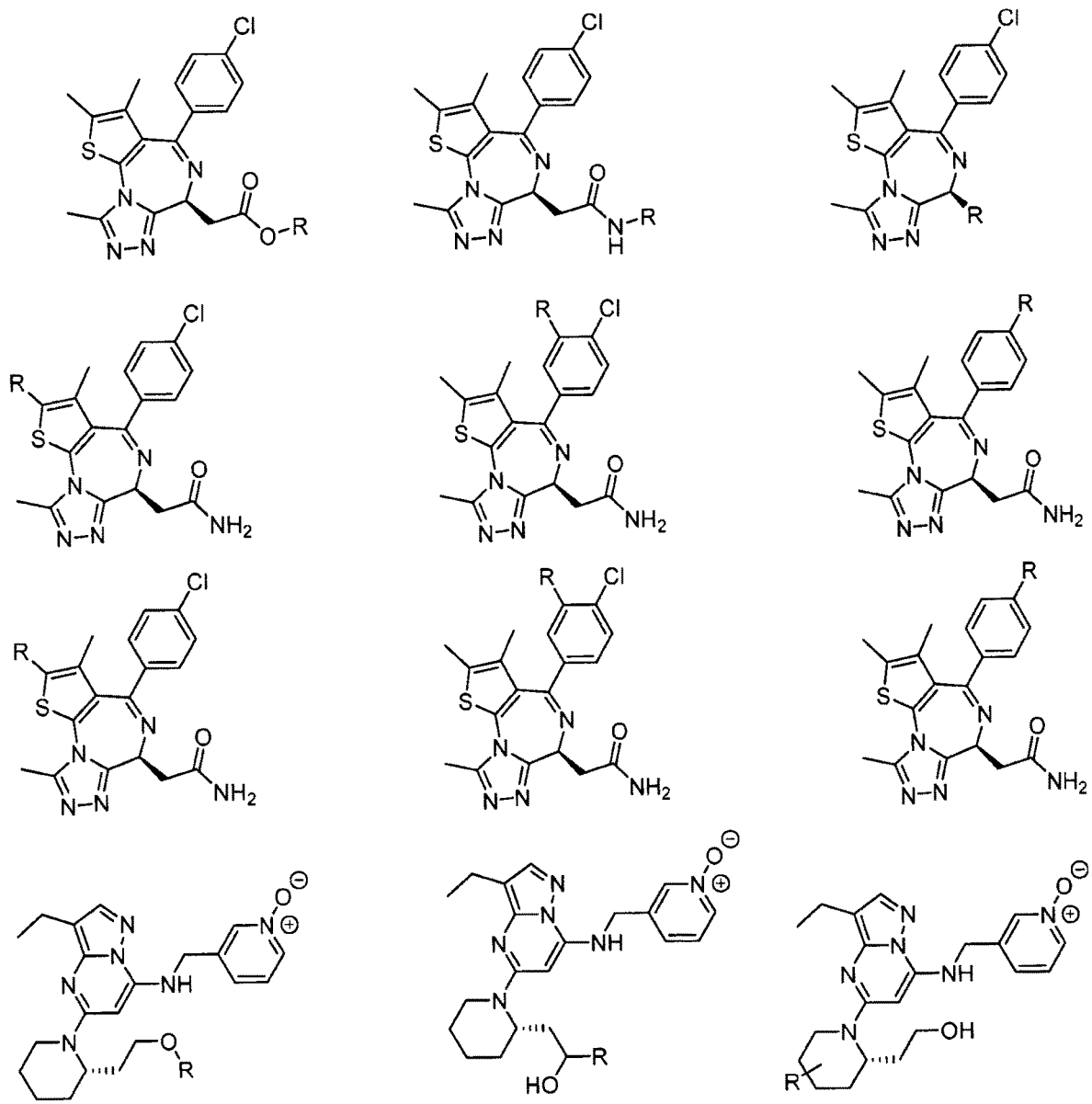
FIG. 3NNN
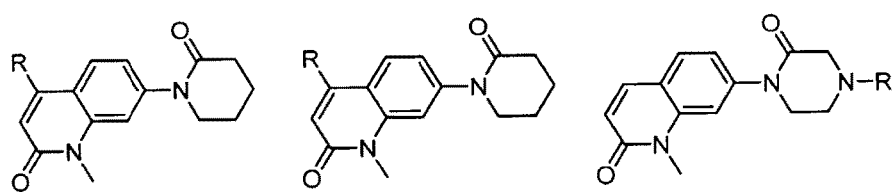

FIG. 3OOO
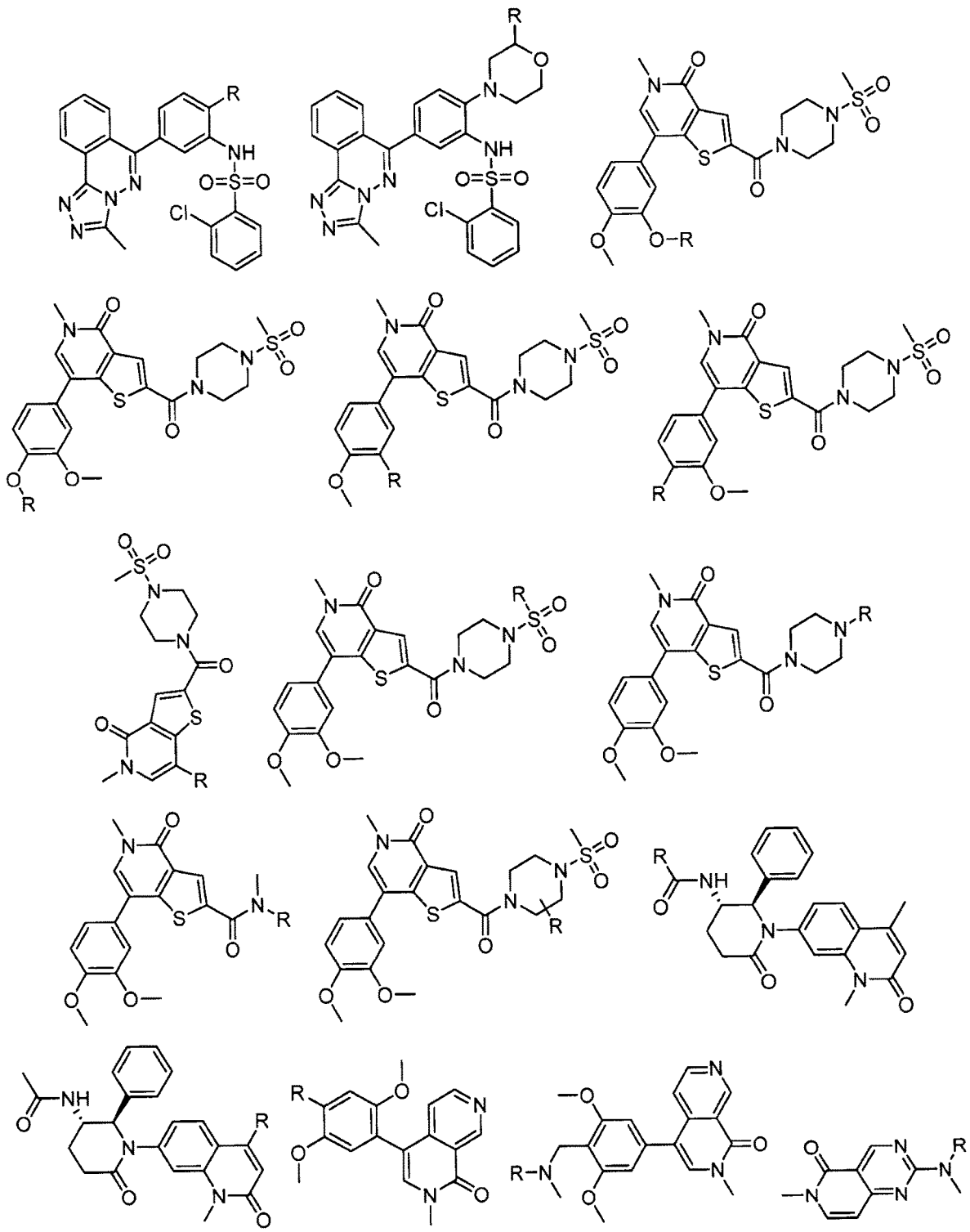

FIG. 3PPP
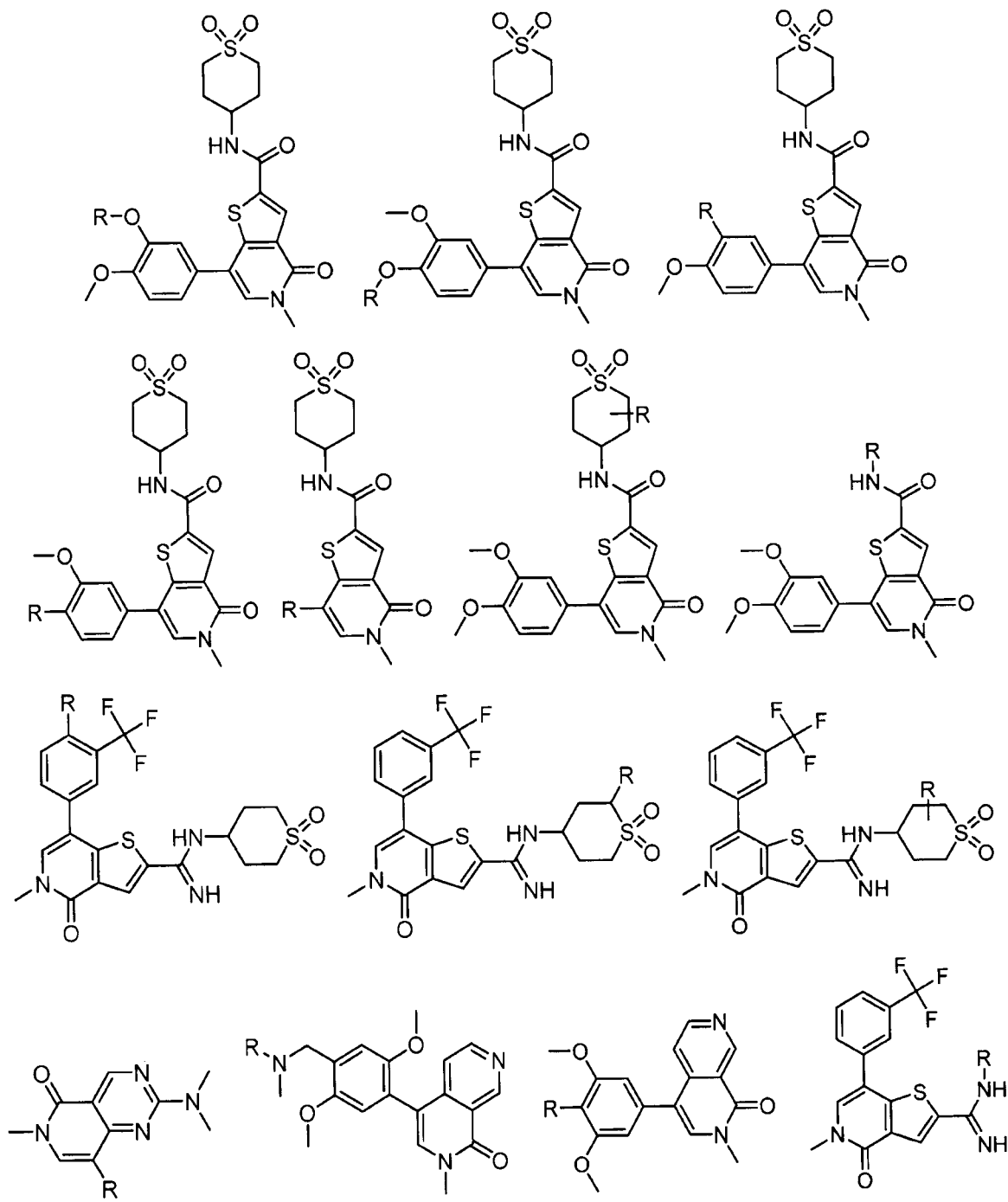

FIG. 3QQQ
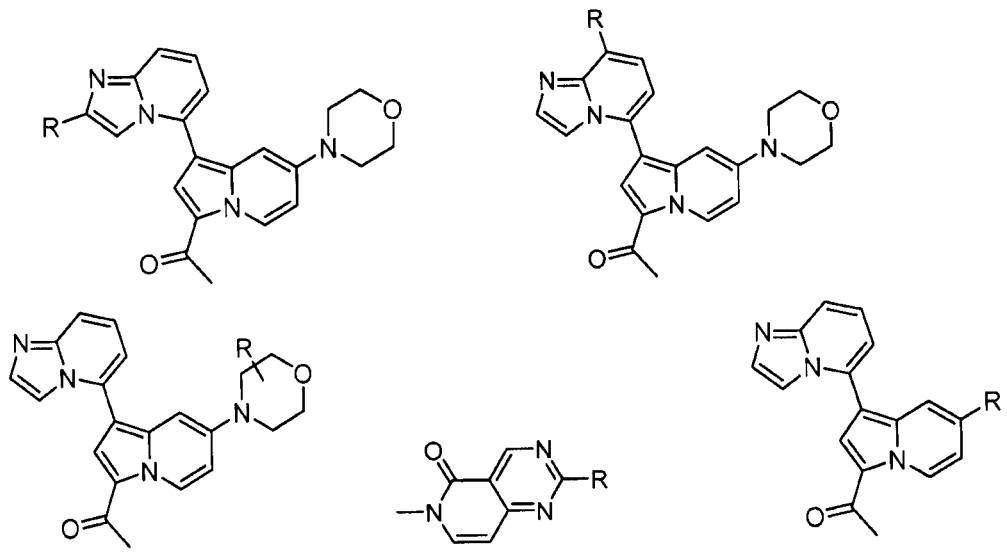
FIG. 3RRR
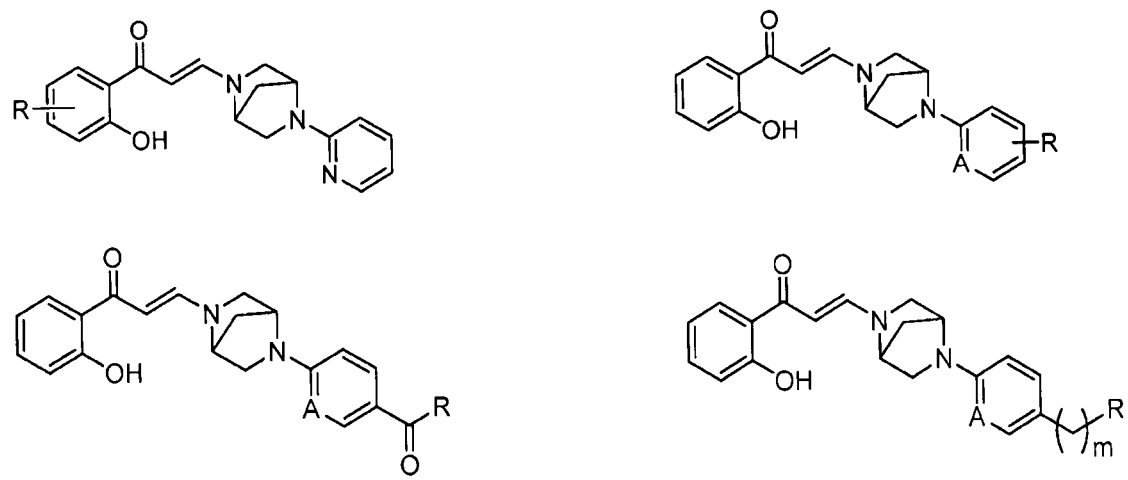
FIG. 3SSS

FIG. 3TTT
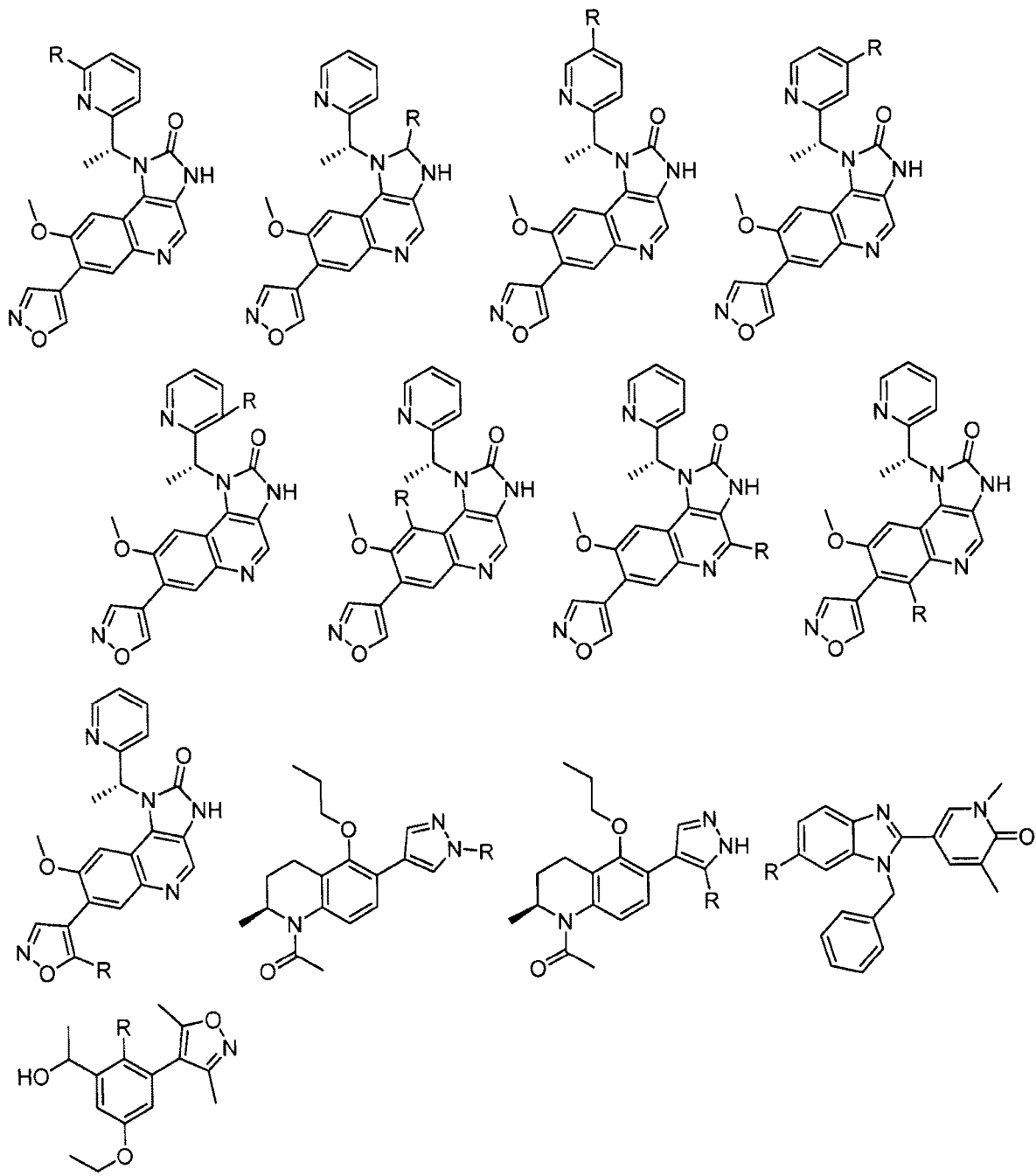

FIG. 3UUU
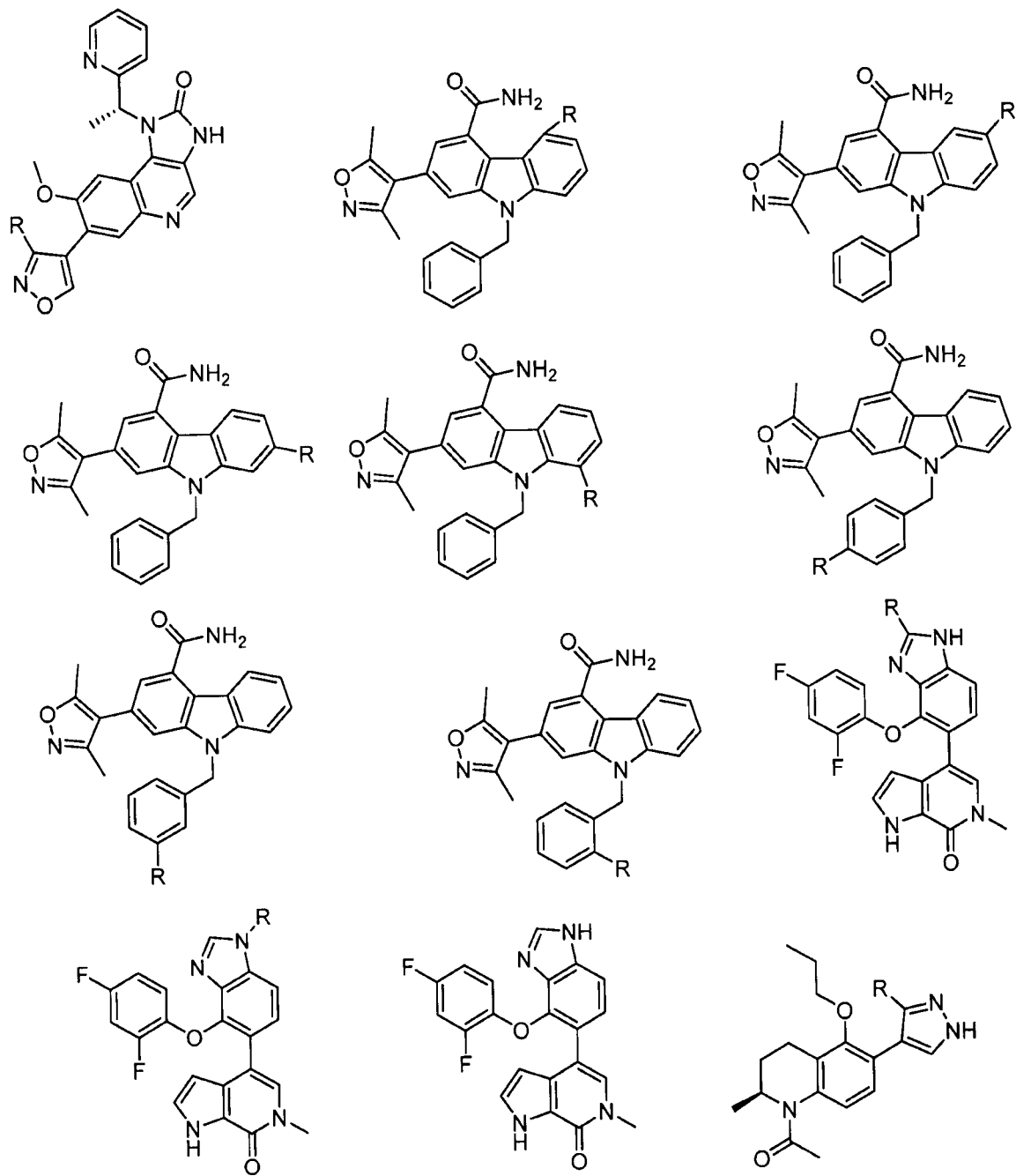

FIG. 3VVV
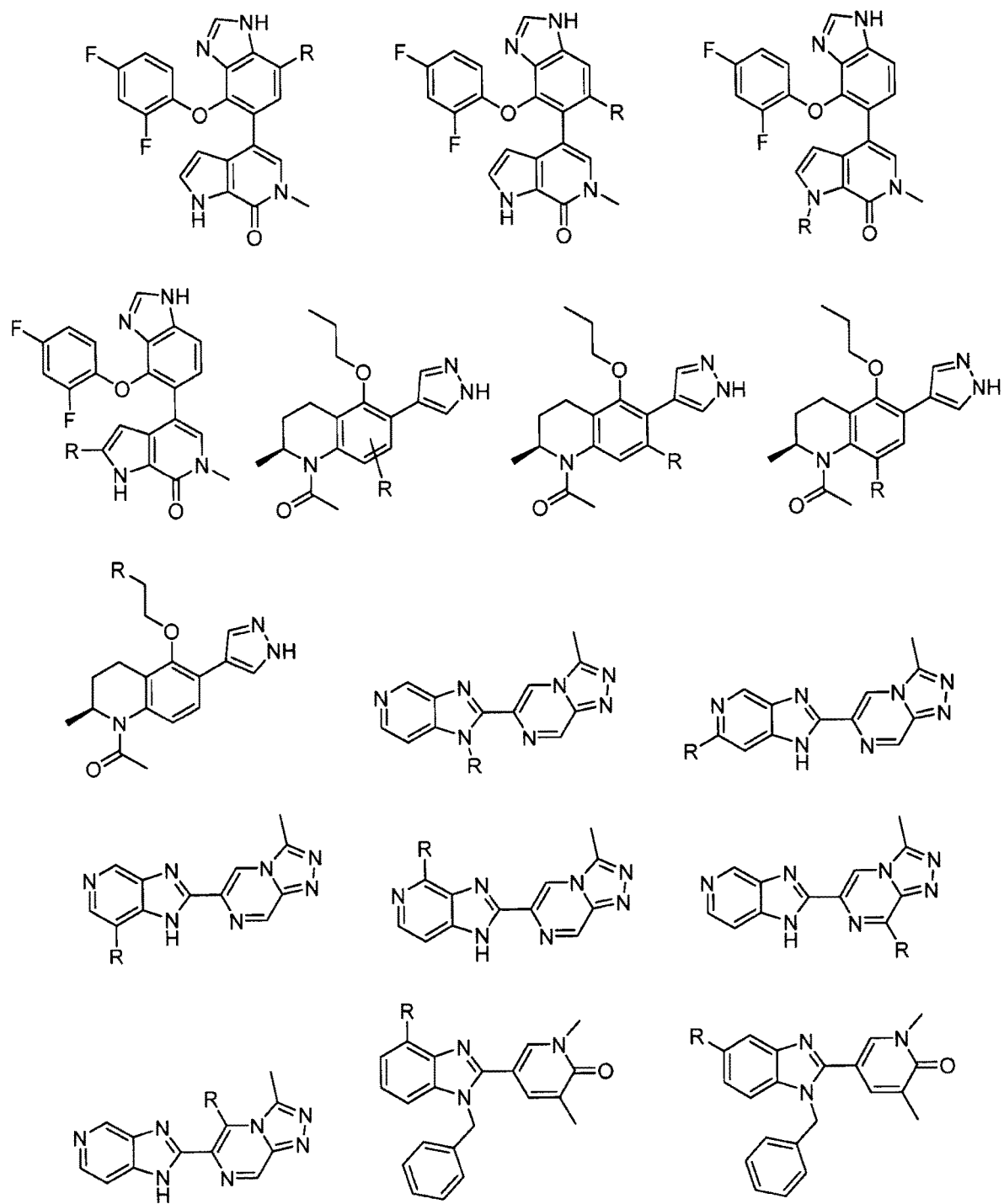

FIG. 3WWW
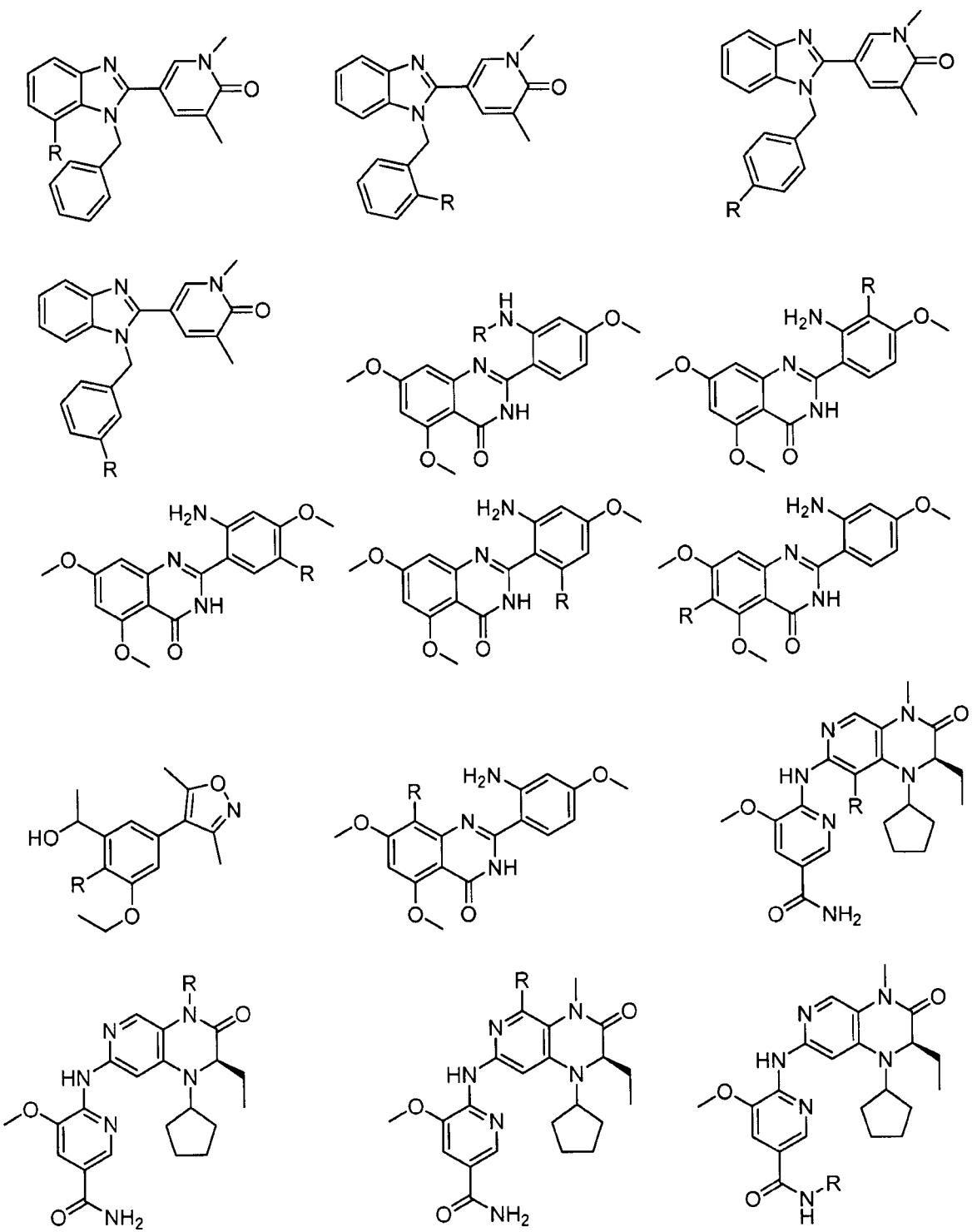

FIG. 3XXX
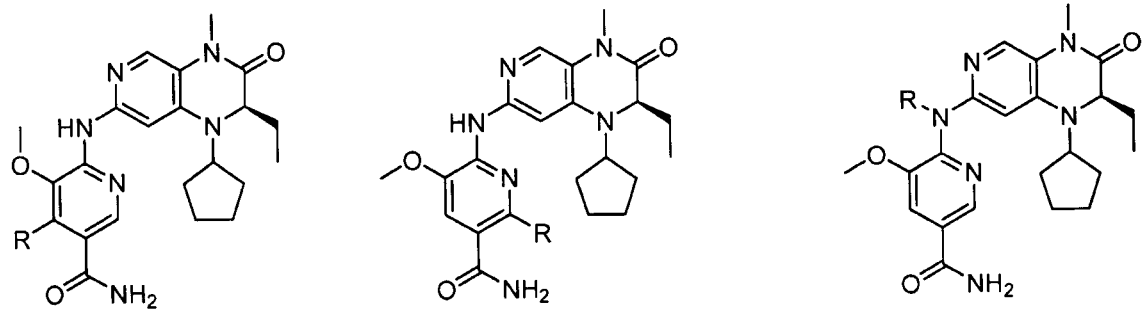
FIG. 3YYY
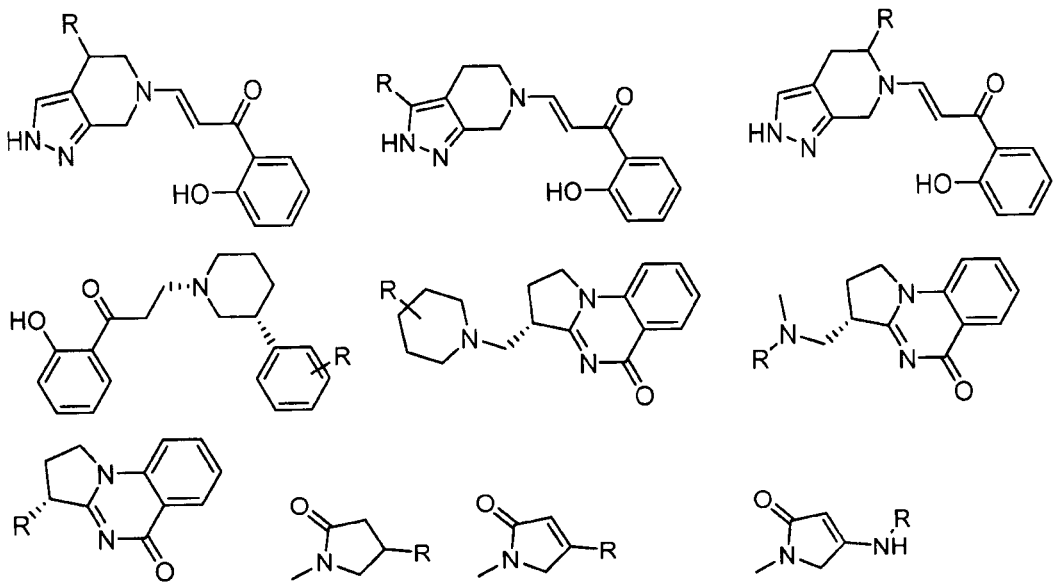
FIG. 3ZZZ
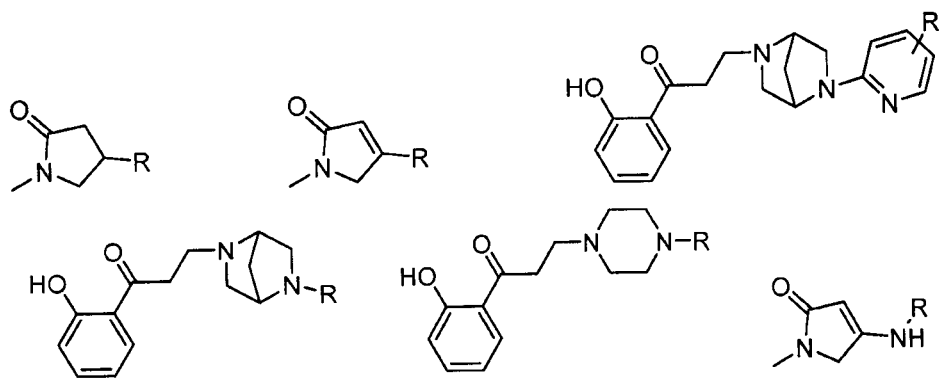

FIG. 3AAAA
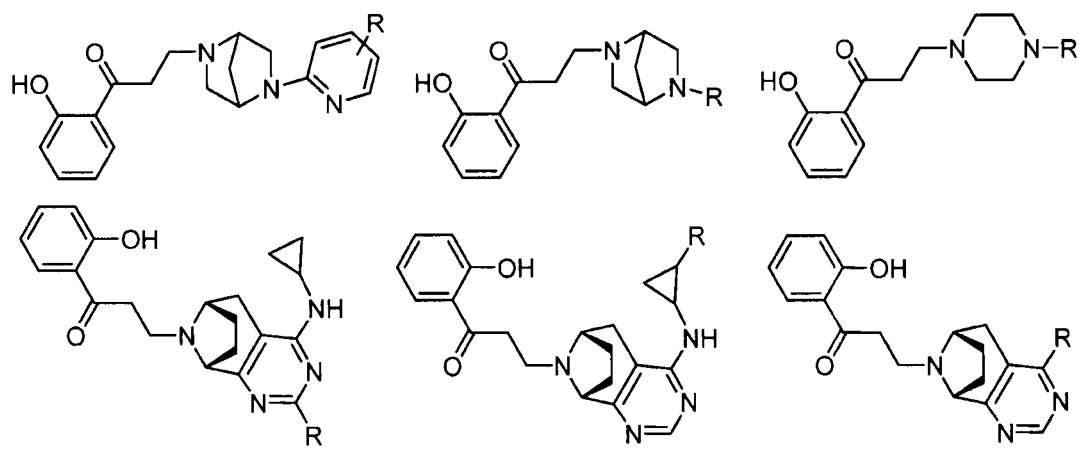
FIG. 3BBBB
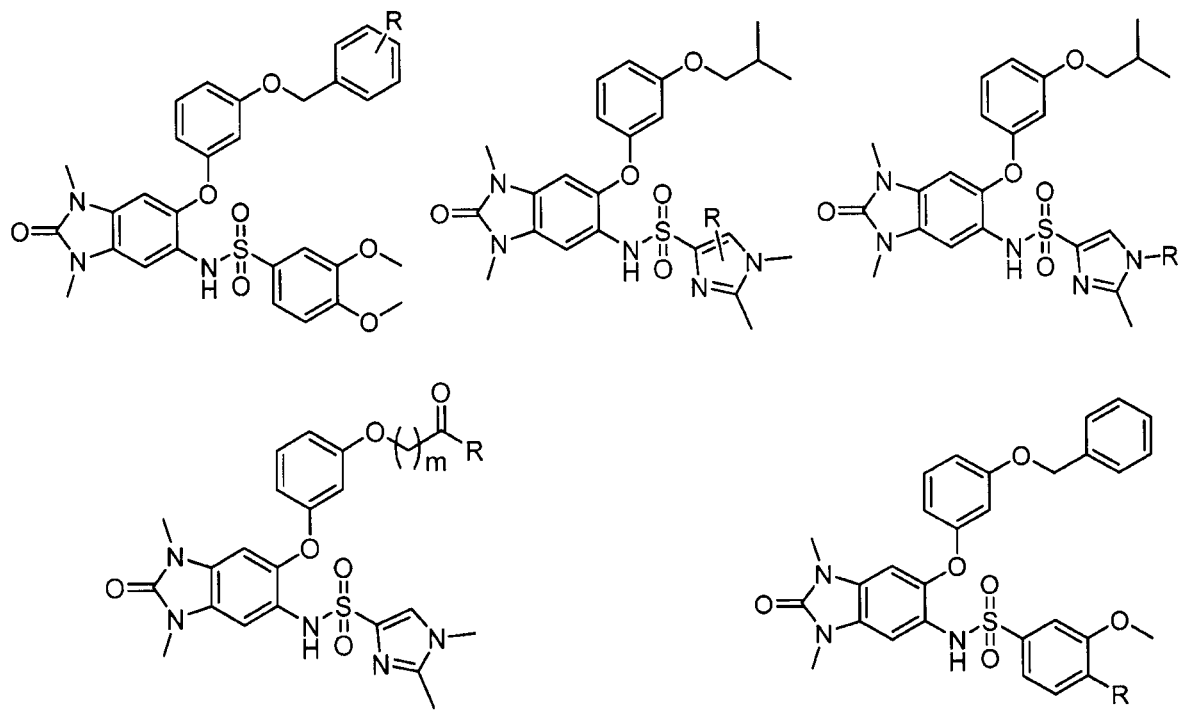

FIG. 3CCCC
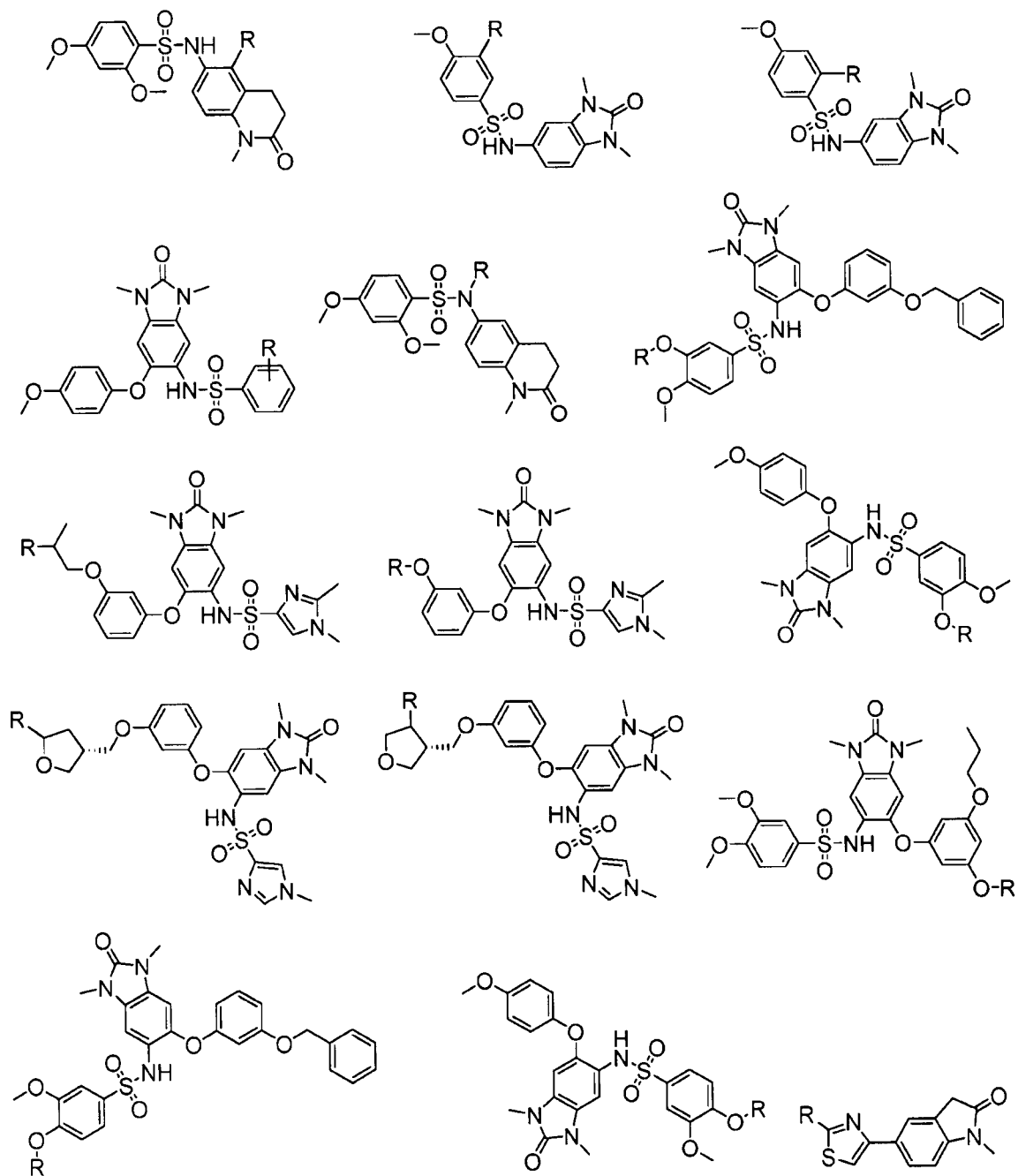

FIG. 3DDDD
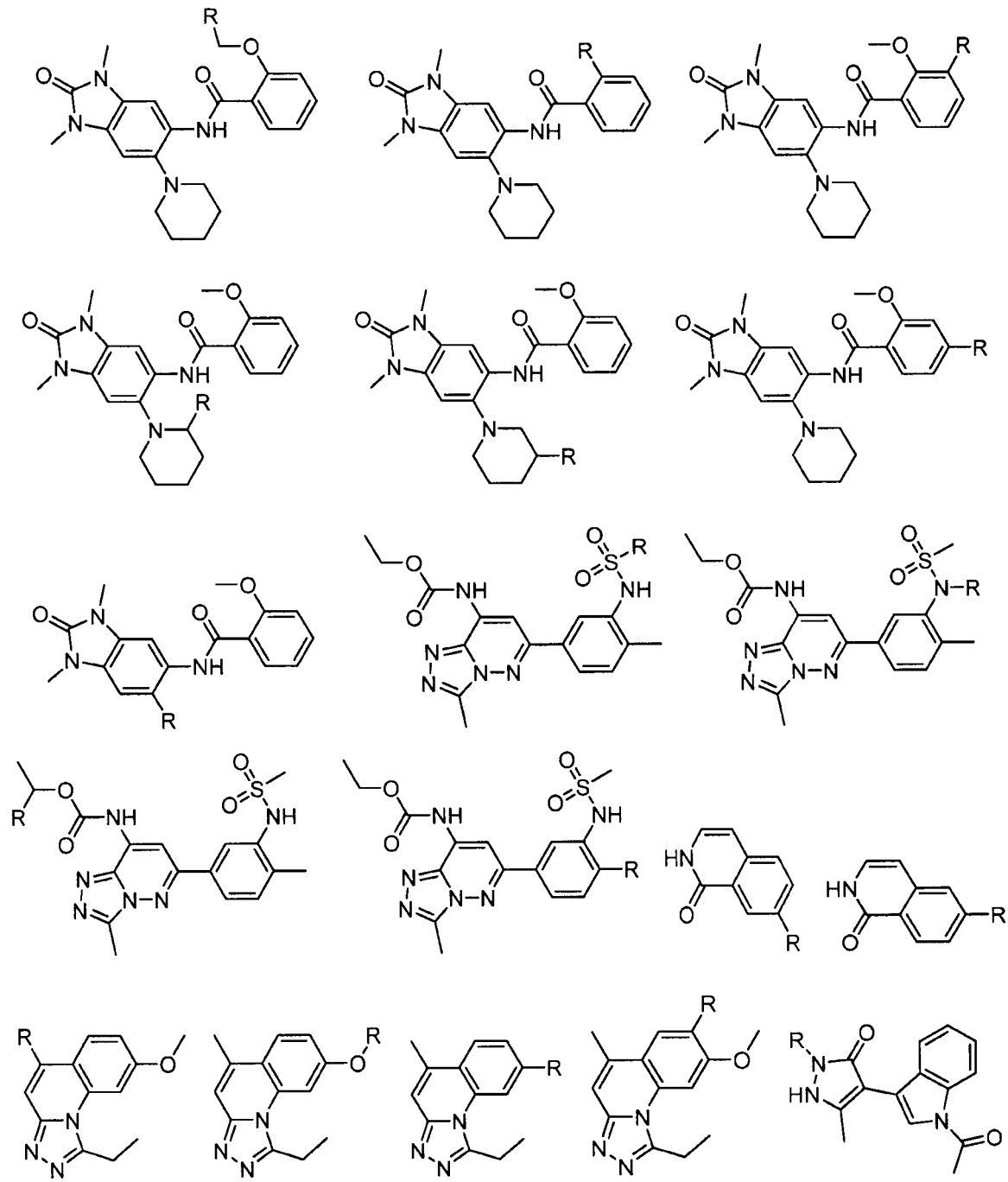

FIG. 3EEEE
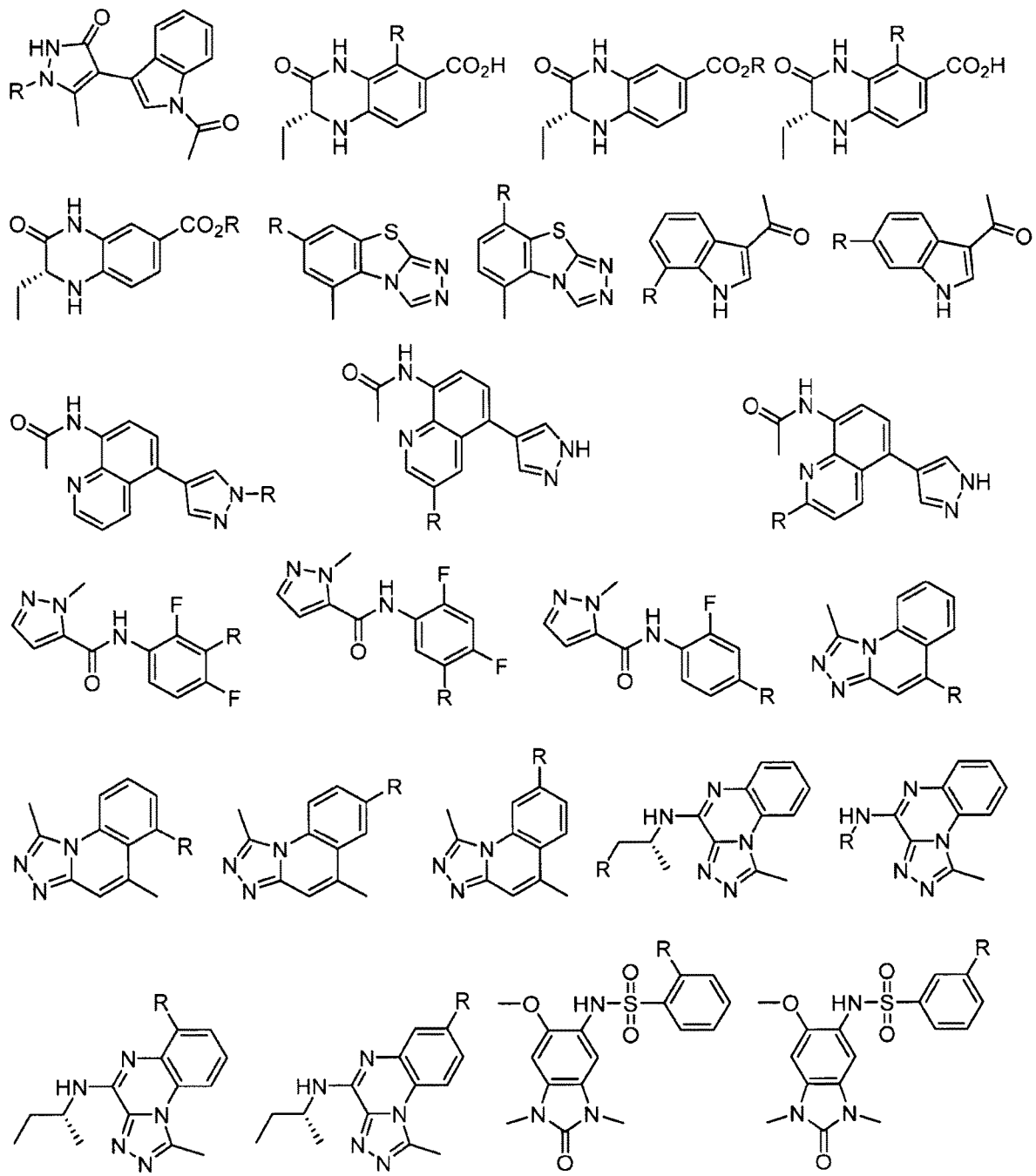

FIG. 3FFFF
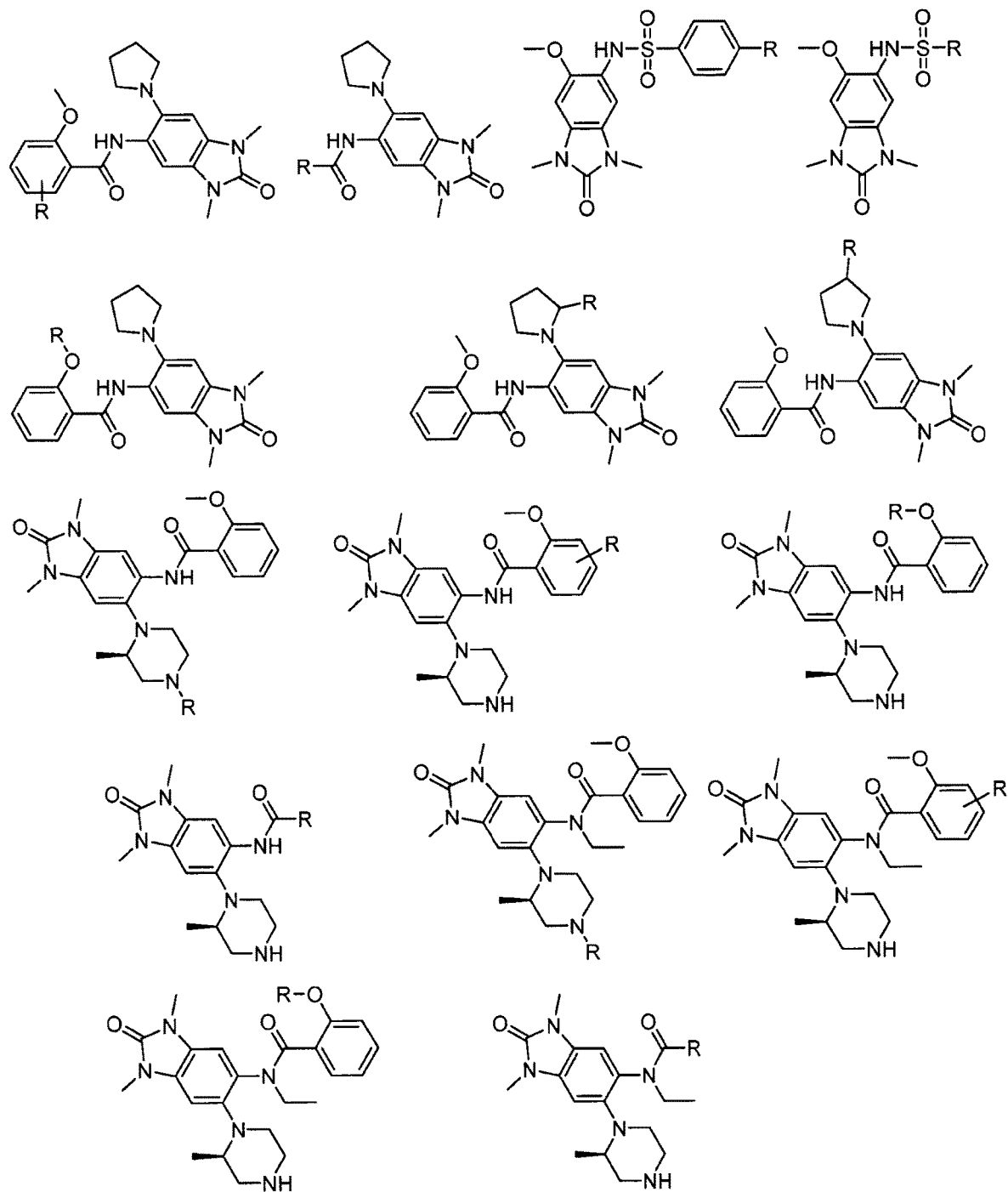

FIG. 3GGGG
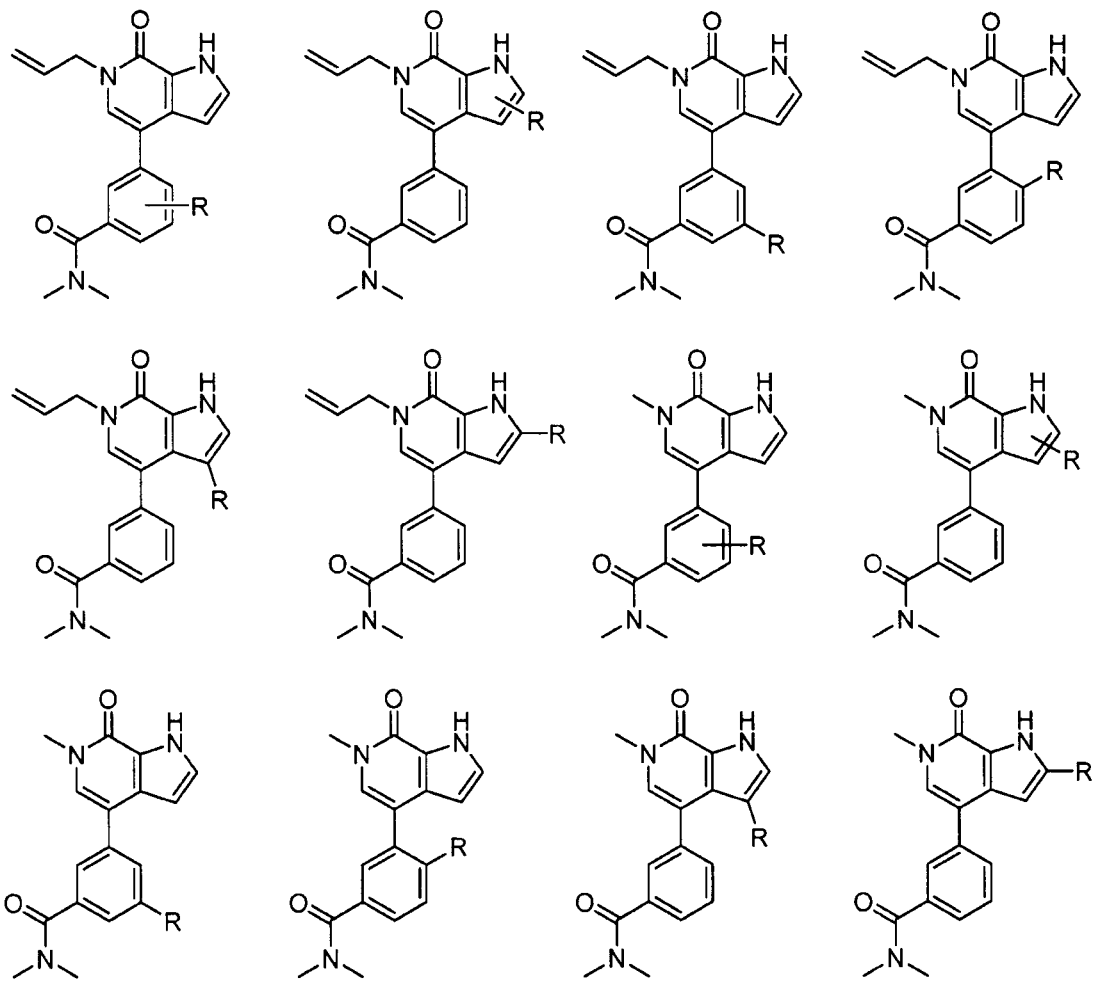
FIG. 3HHHH
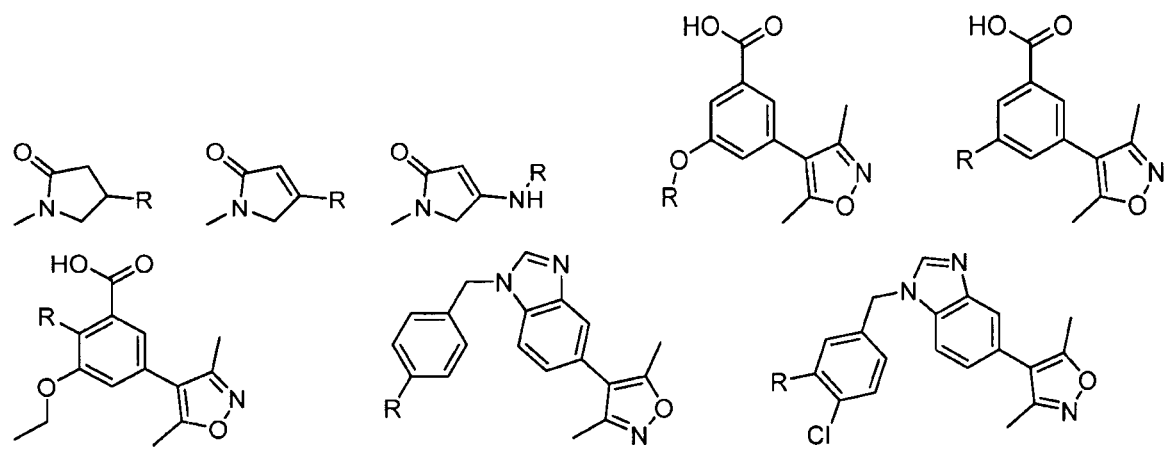

FIG. 3IIII
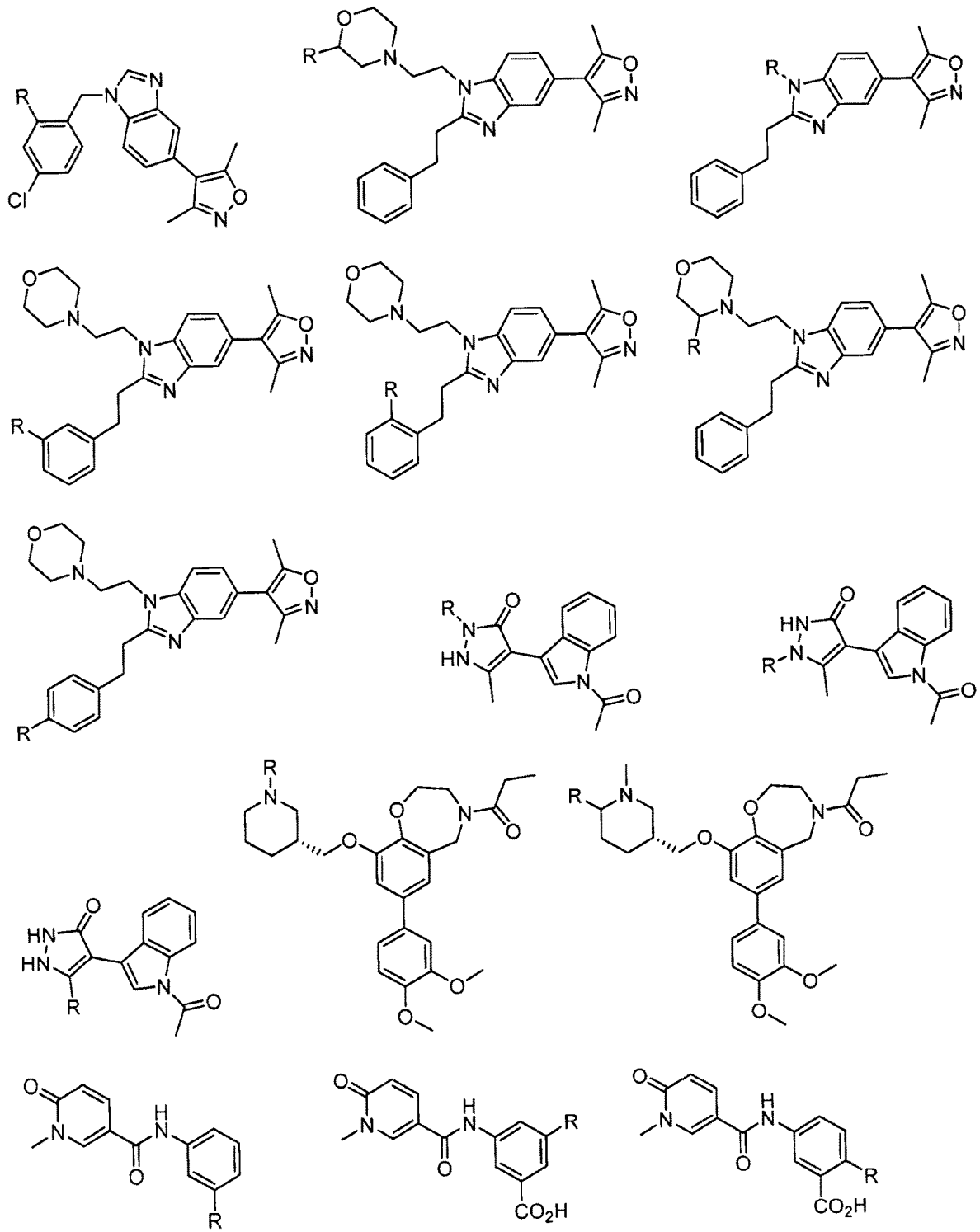

FIG. 3JJJJ
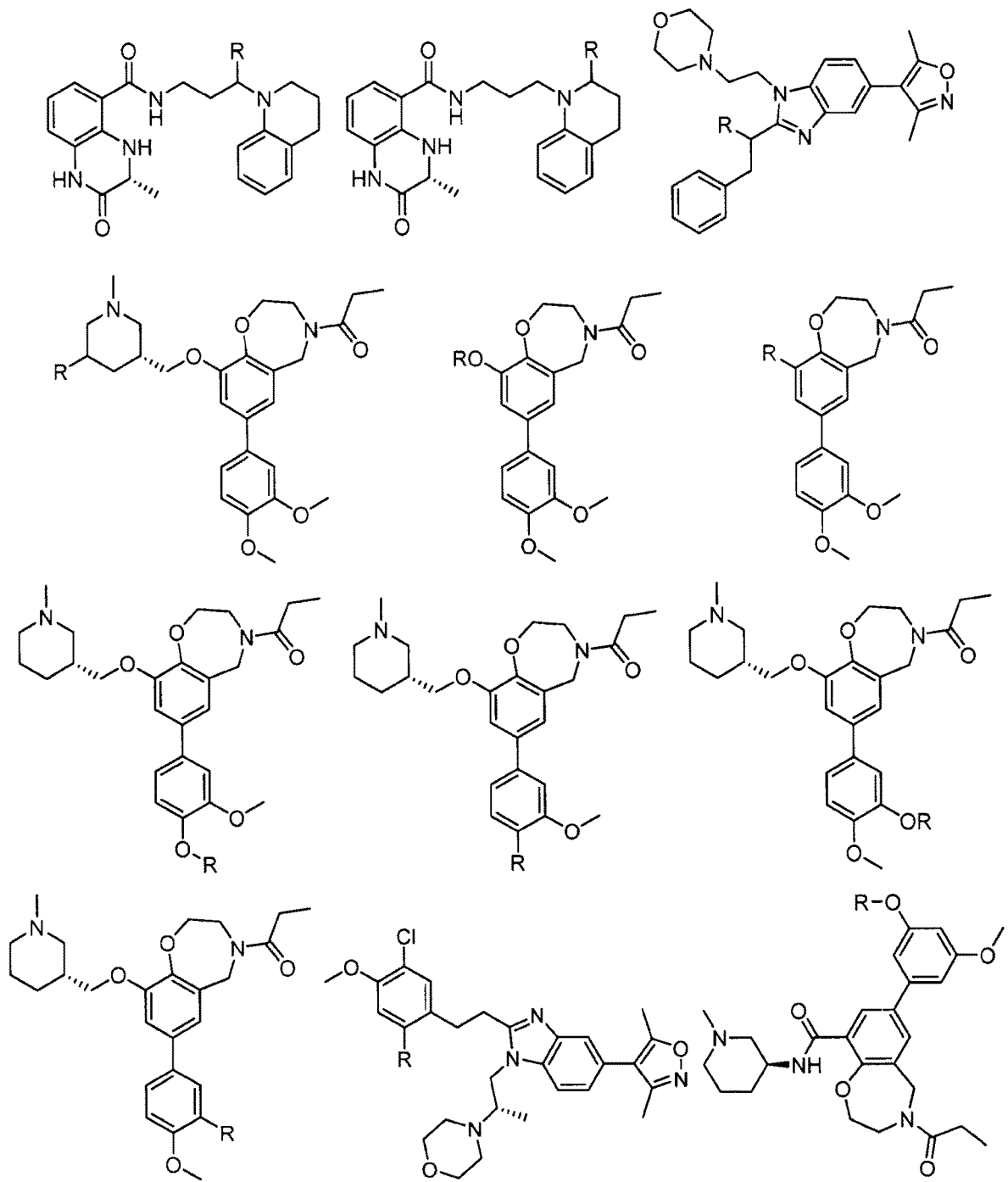

FIG. 3KKKK
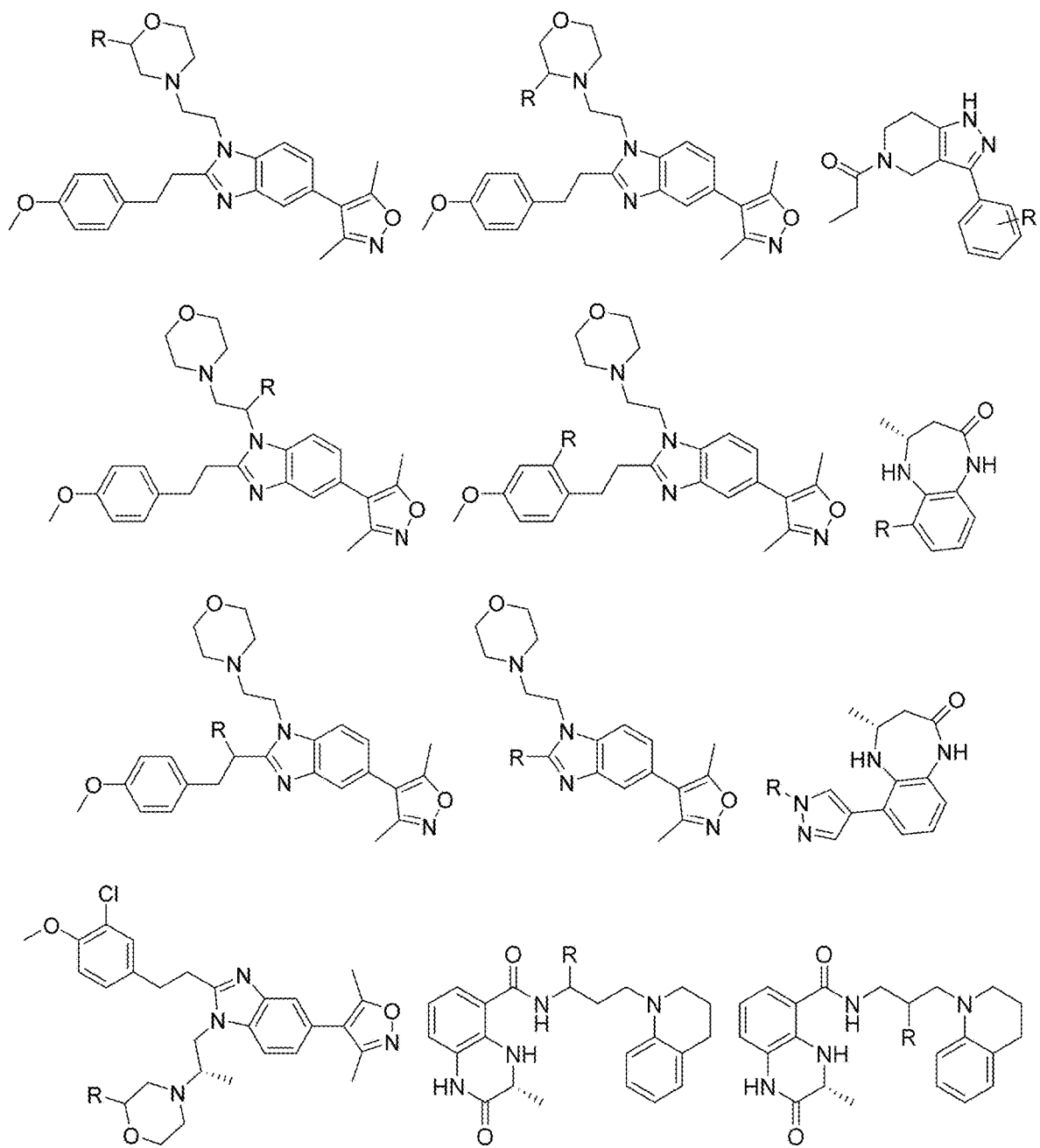

FIG. 3MMMM
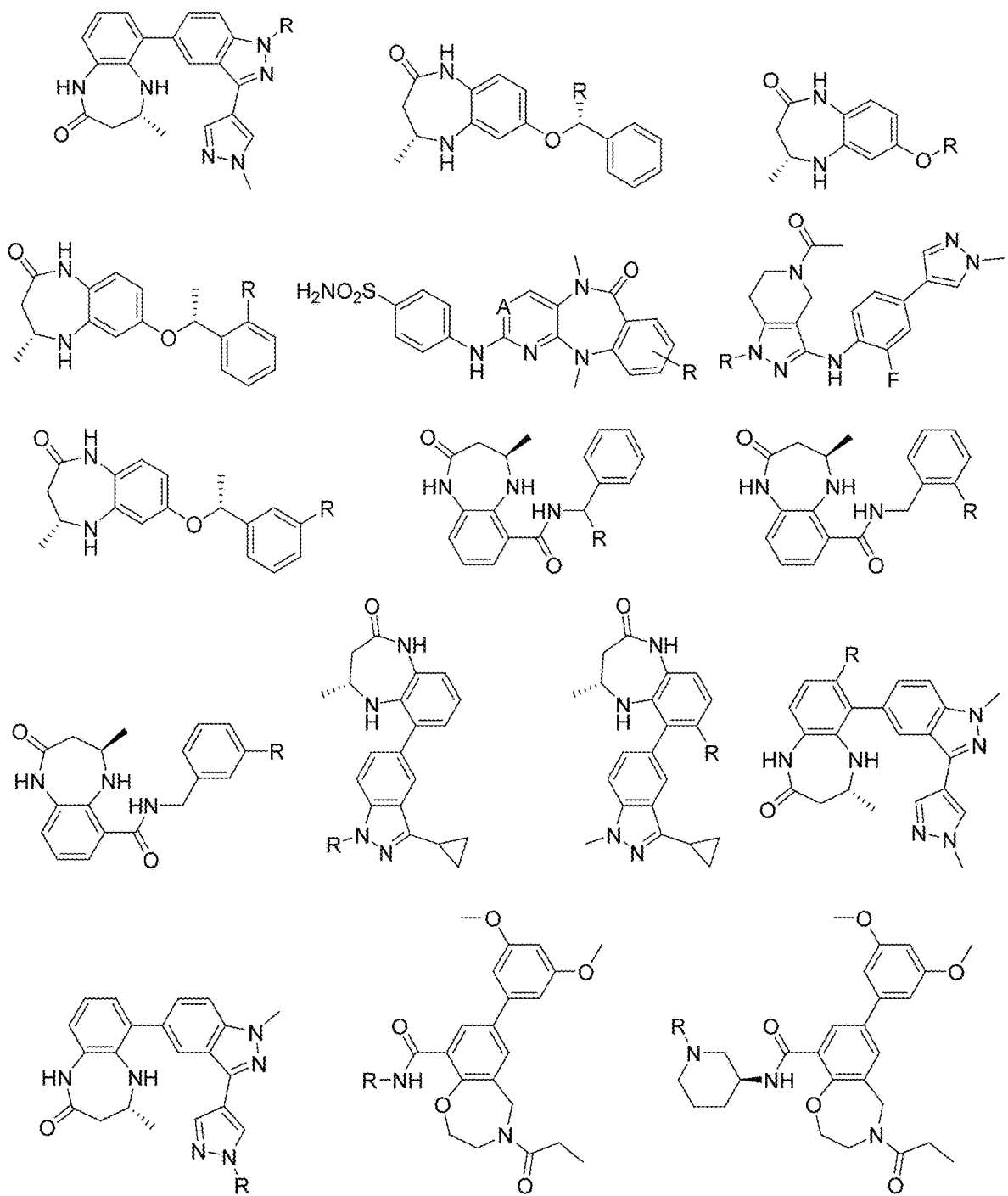

FIG. 3LLLL
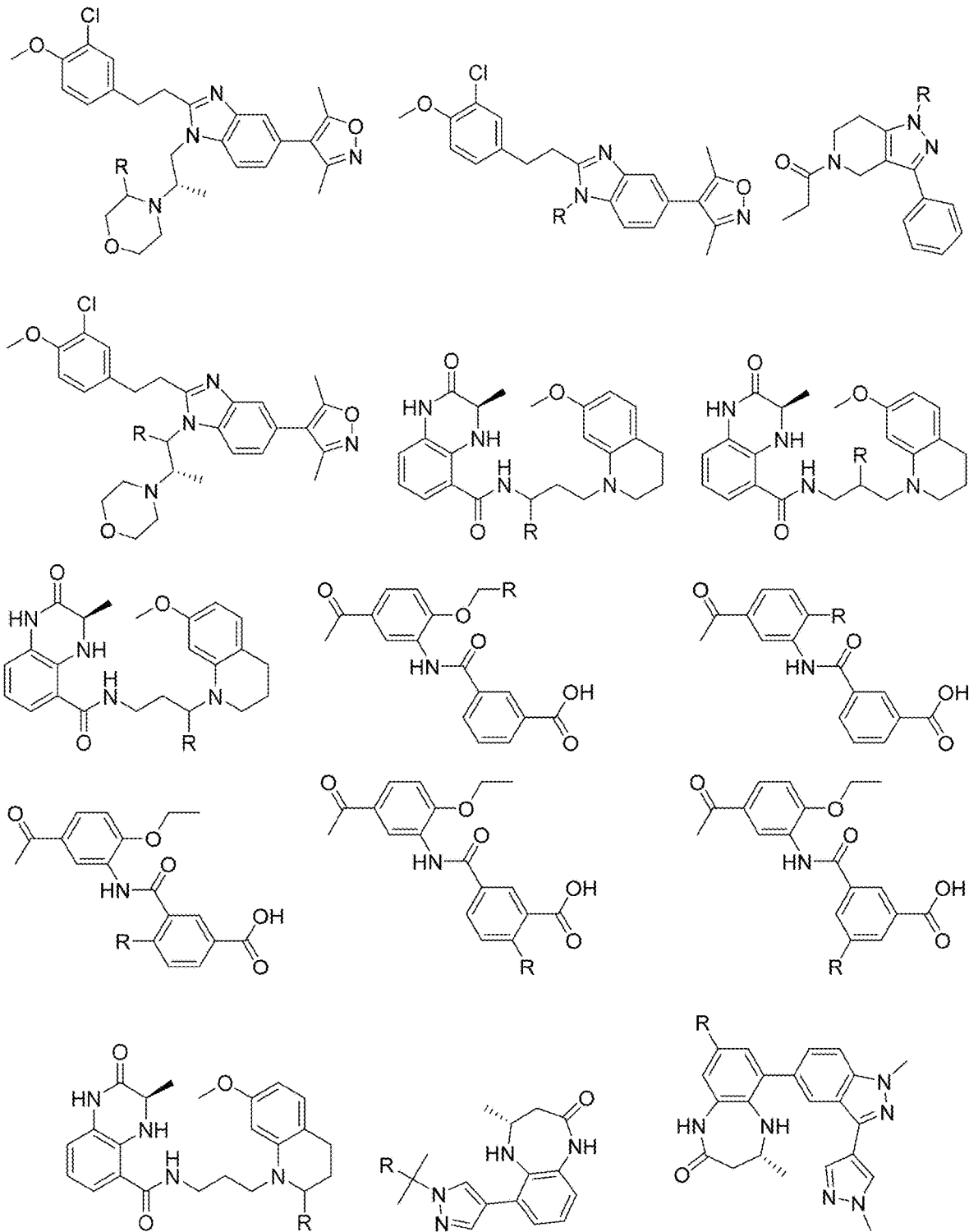

FIG. 3NNNN
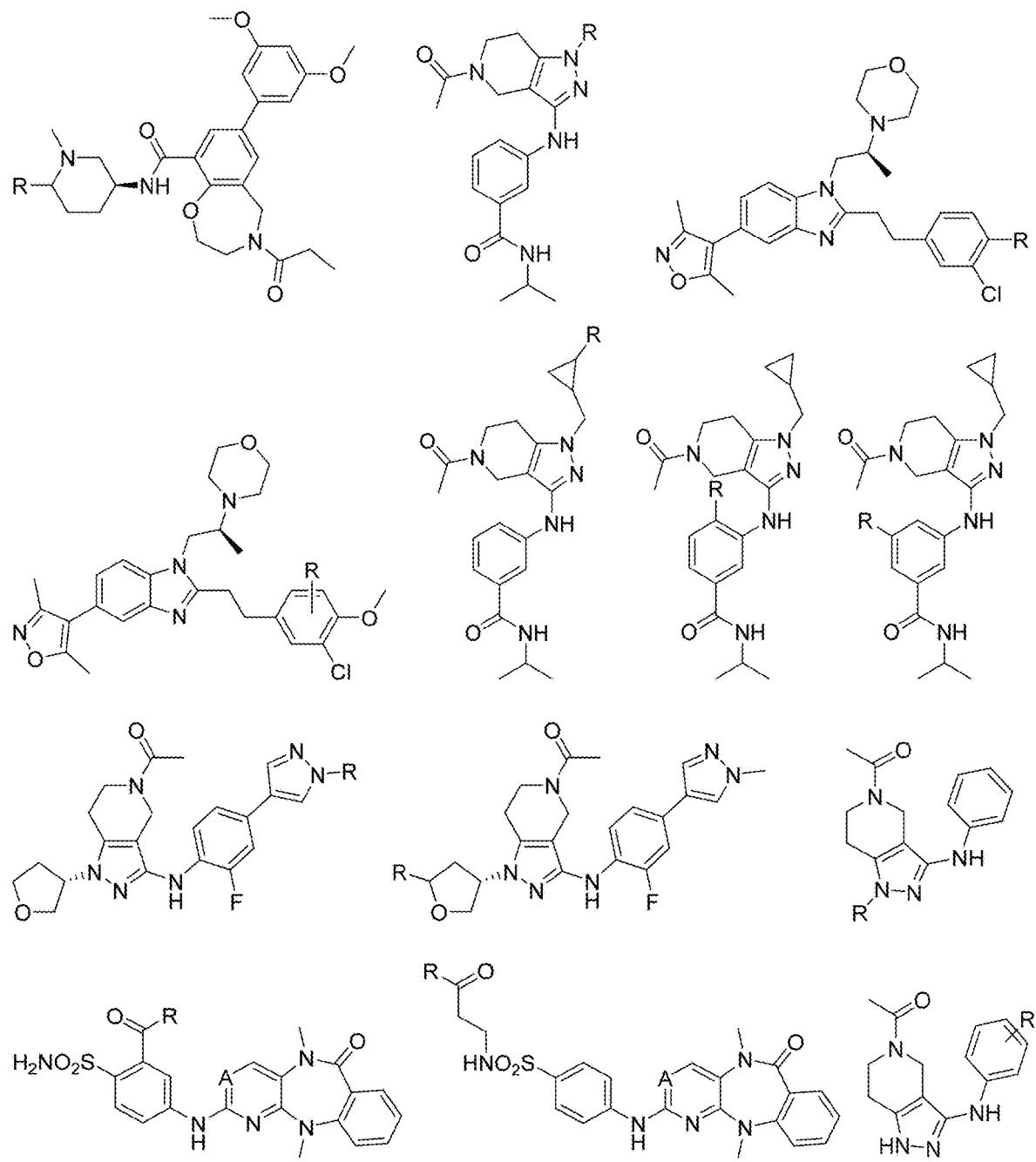

FIG. 3OOOO
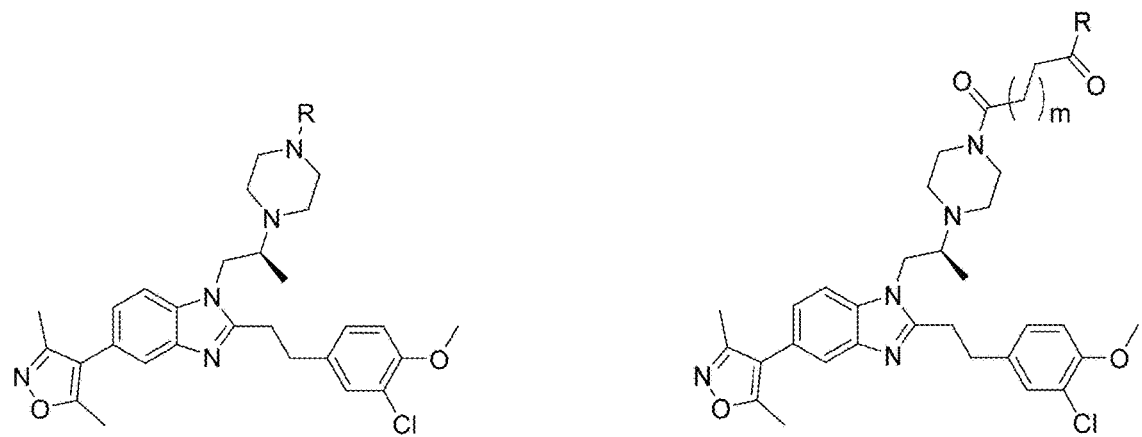
FIG. 3PPPP
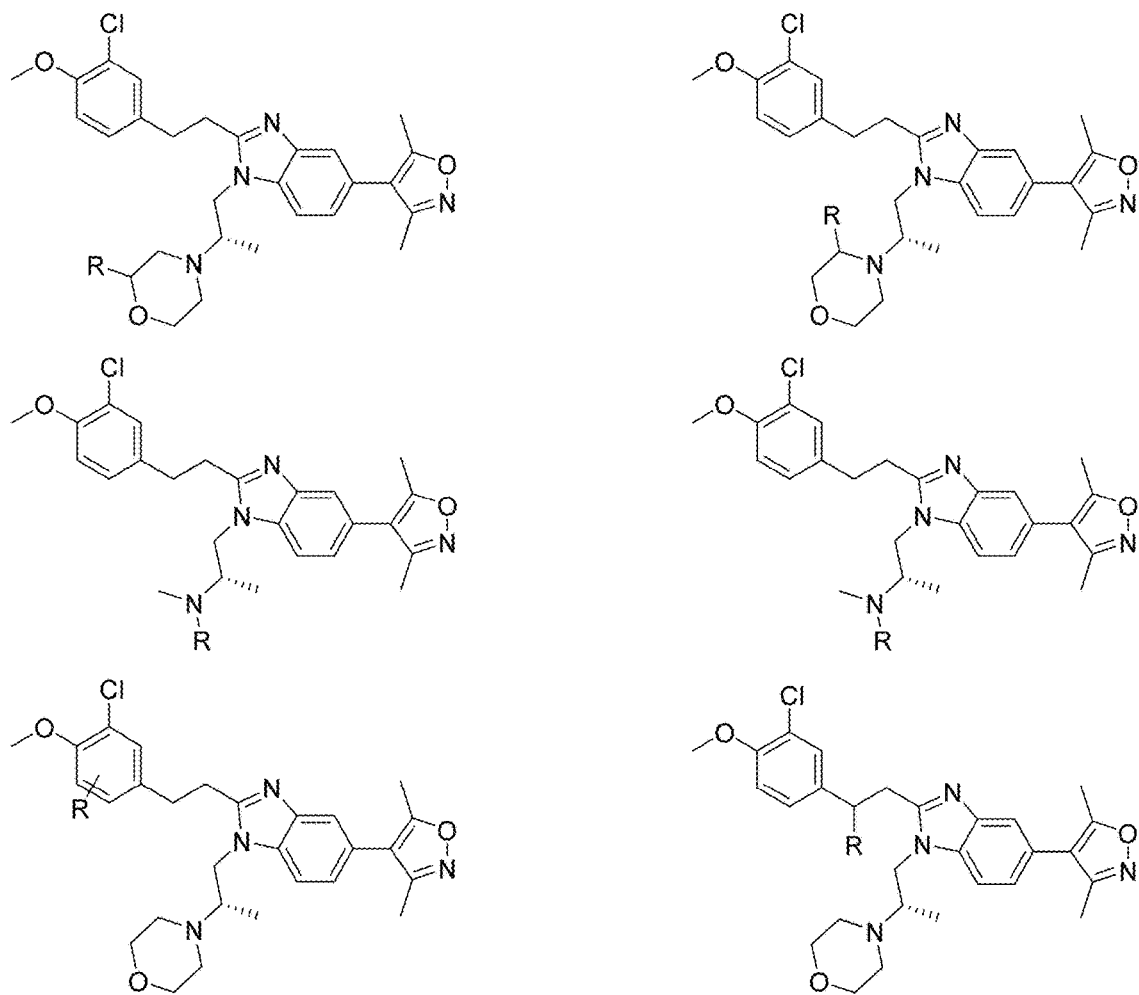

FIG. 3QQQQ
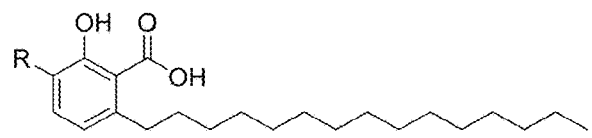
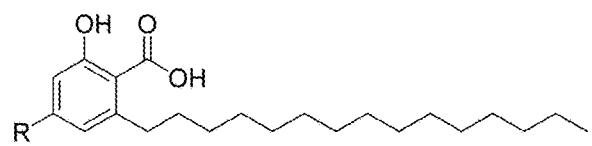
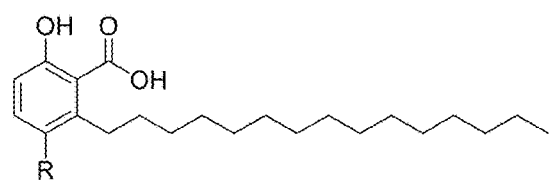
FIG. 3RRRR
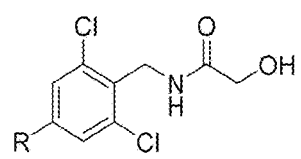
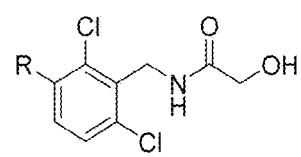
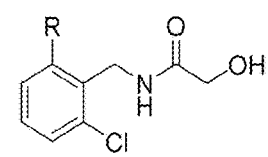
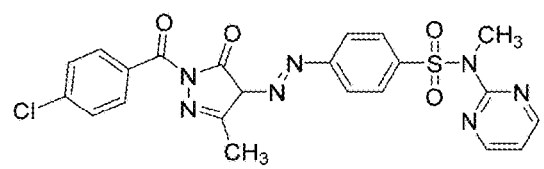
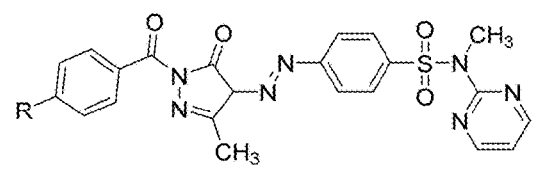
FIG. 3SSSS
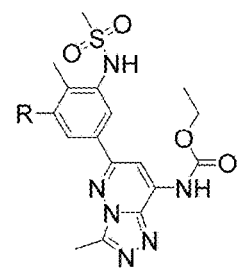
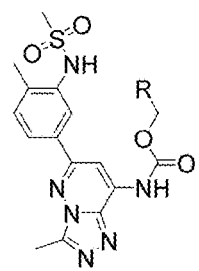
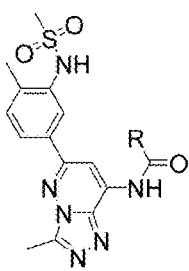
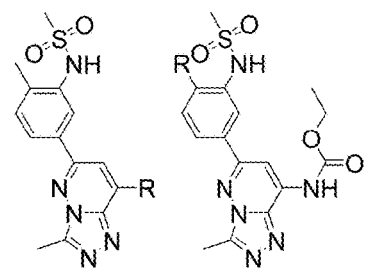

FIG. 3TTTT
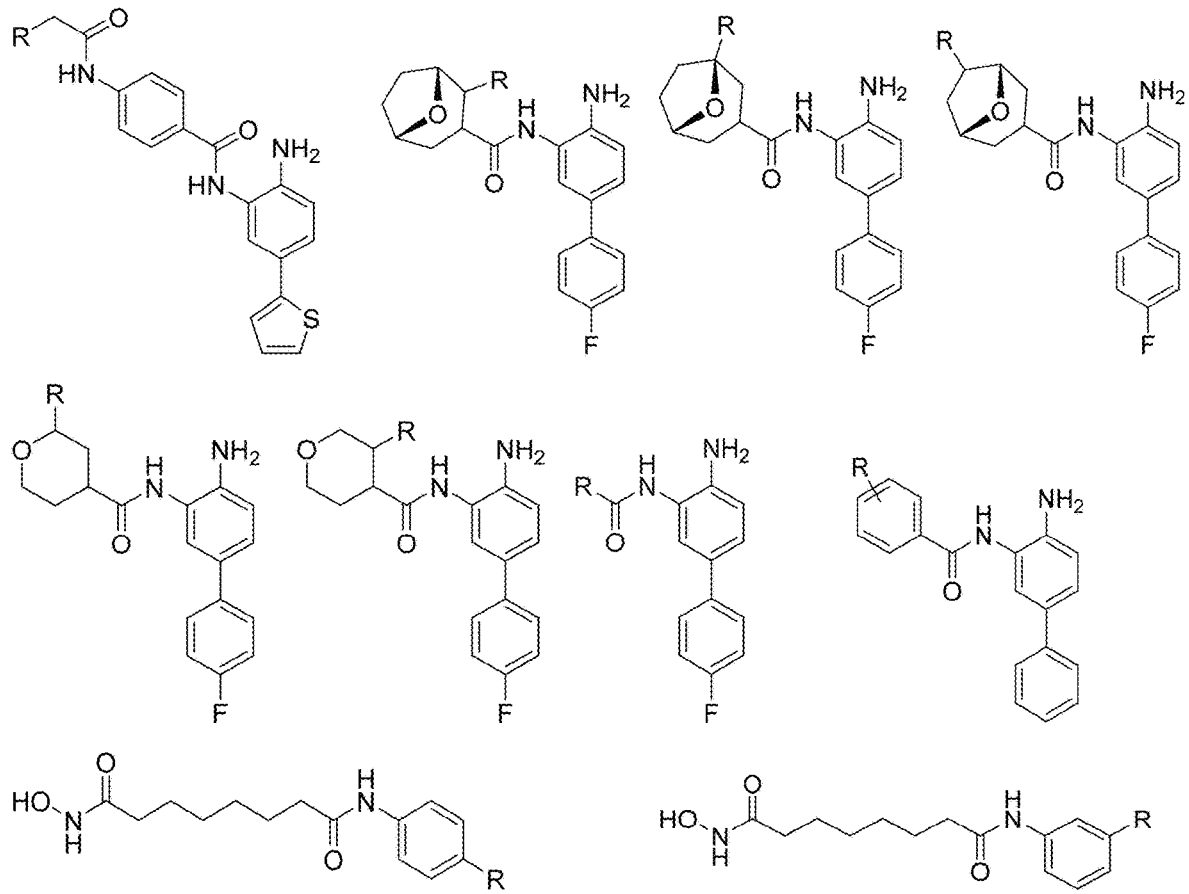
FIG. 3UUUU
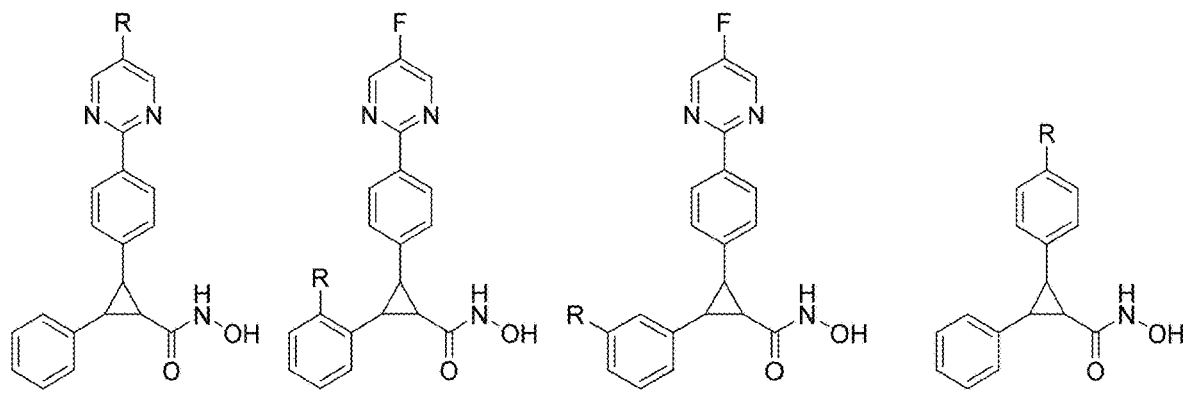

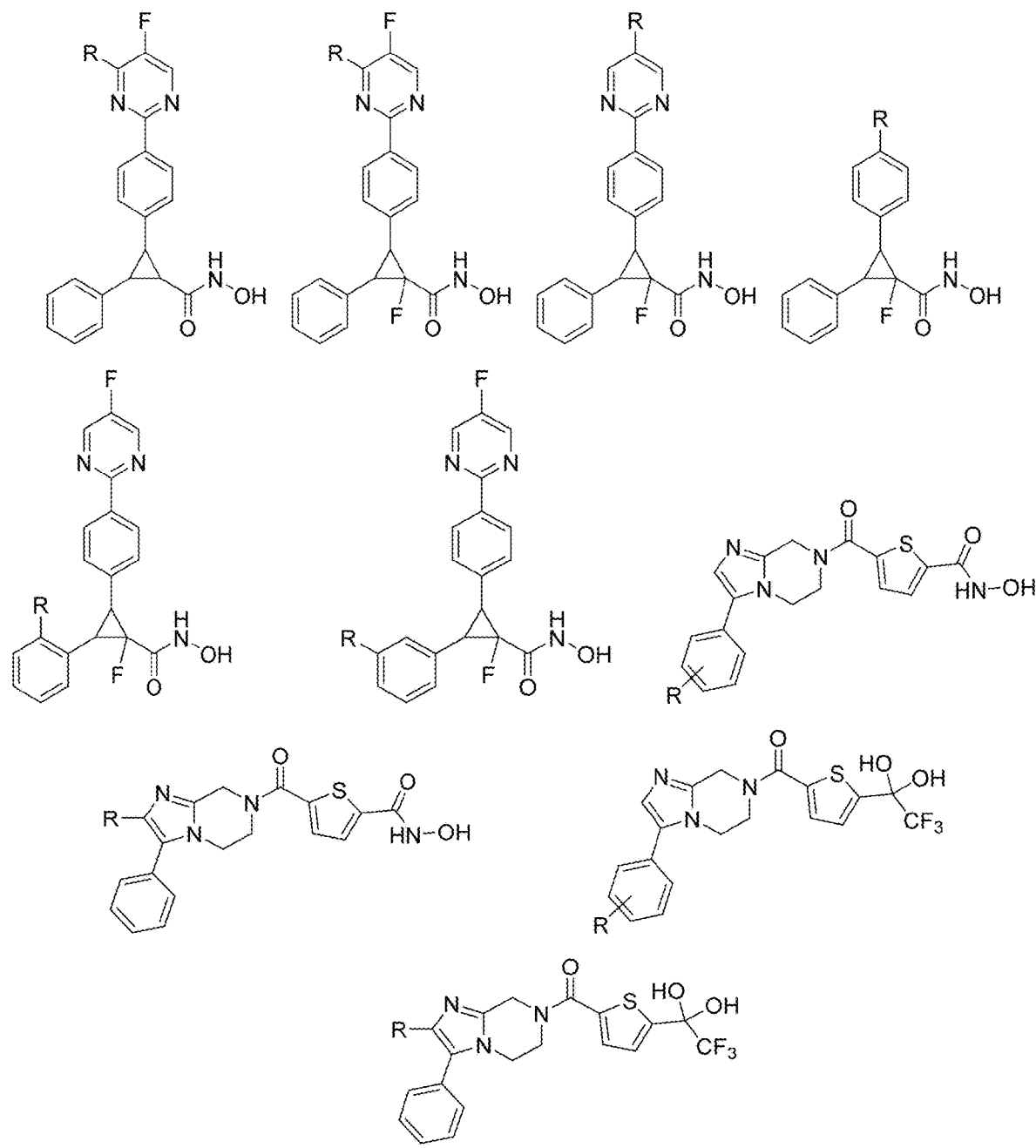
FIG. 3VVVV

FIG. 3WWWW
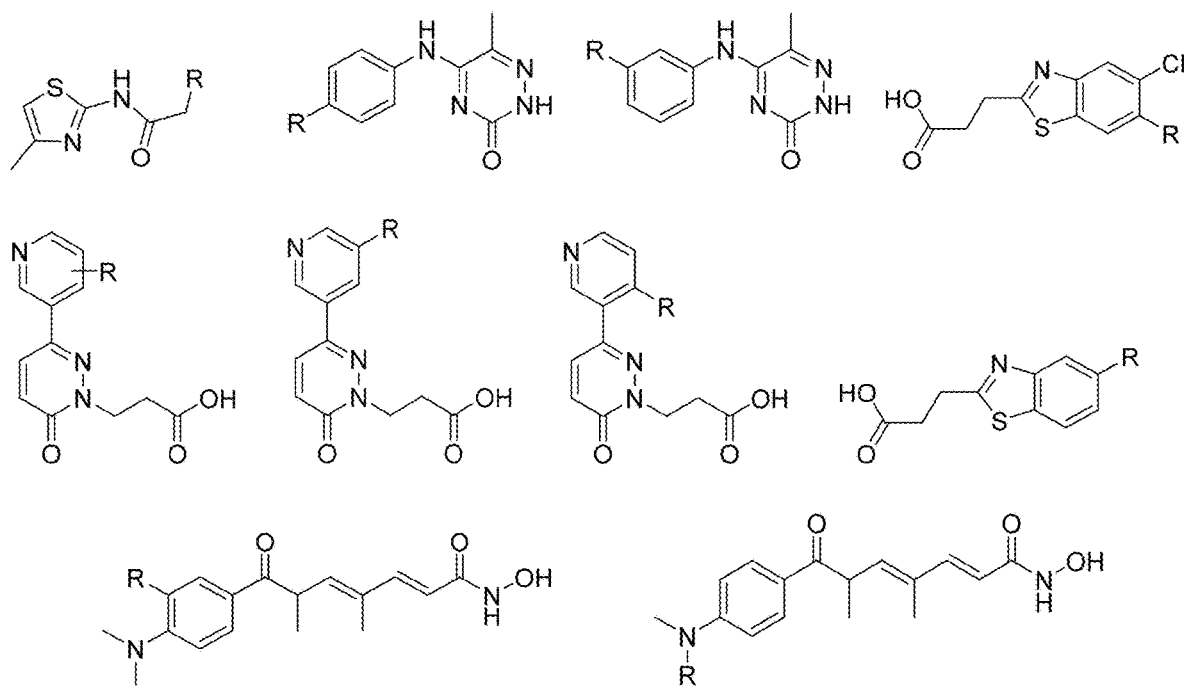
FIG. 3XXXX
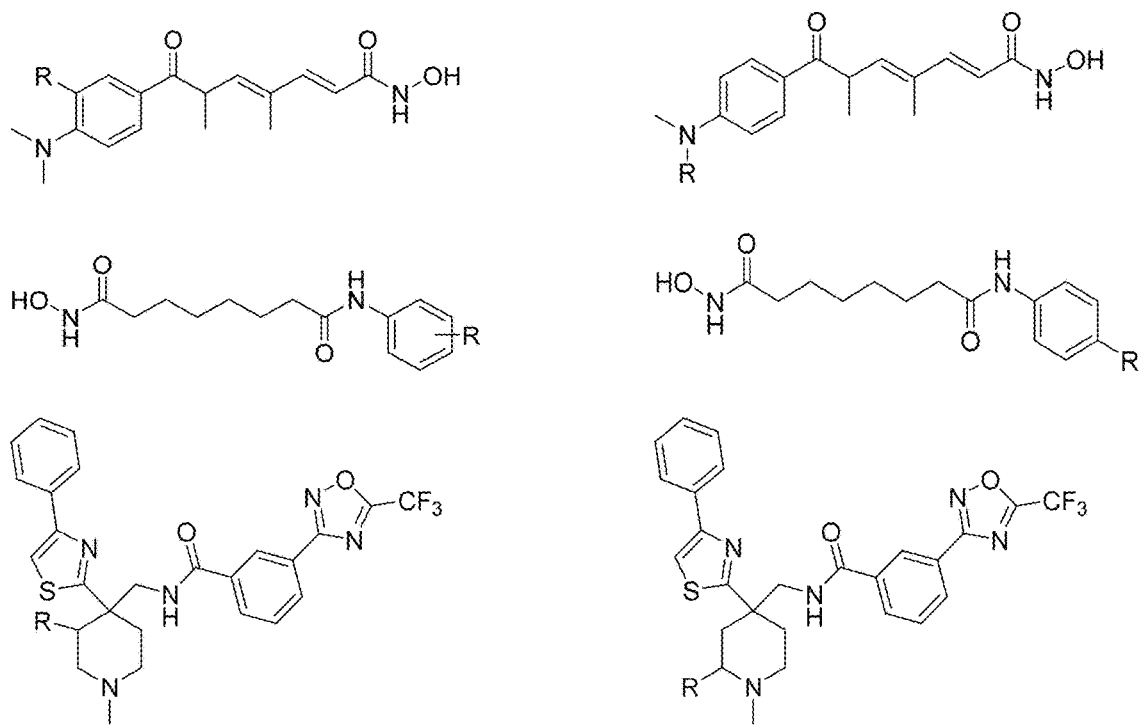

FIG. 3YYYY
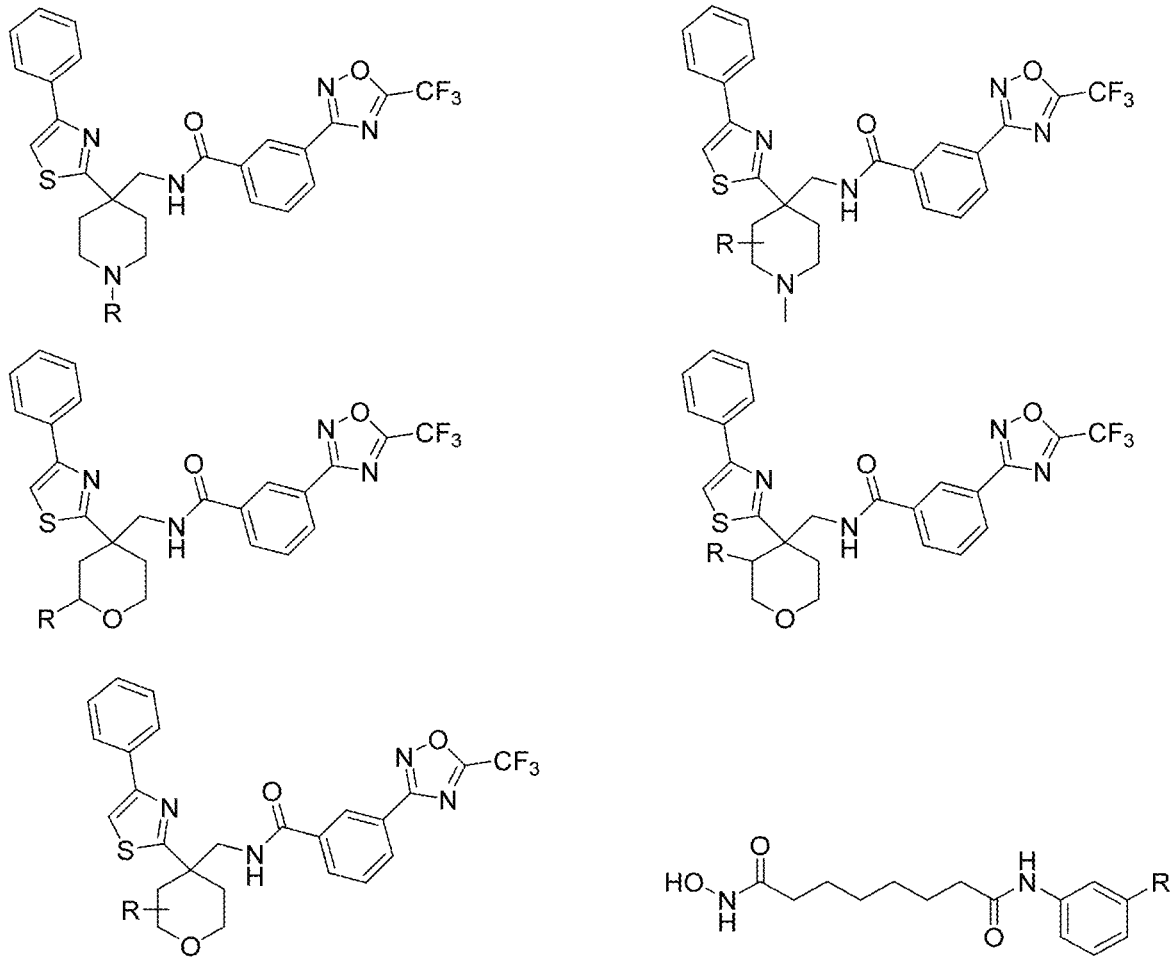
FIG. 3ZZZZ
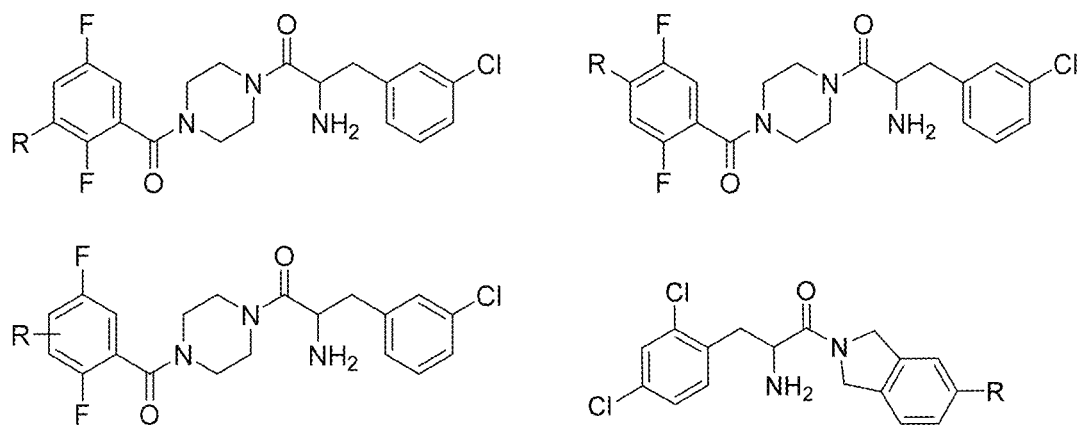

FIG. 3AAAAA
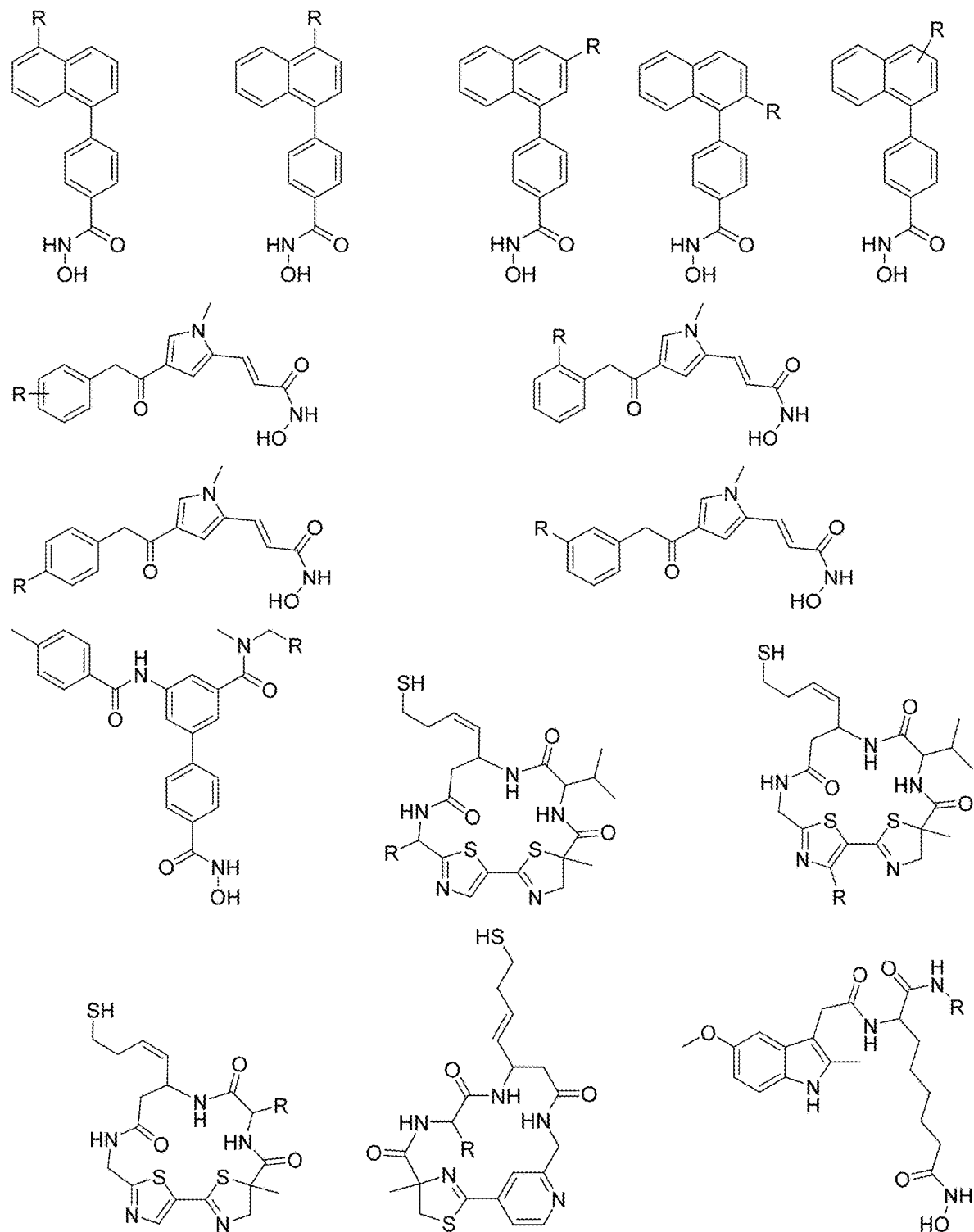

FIG. 3BBBBB
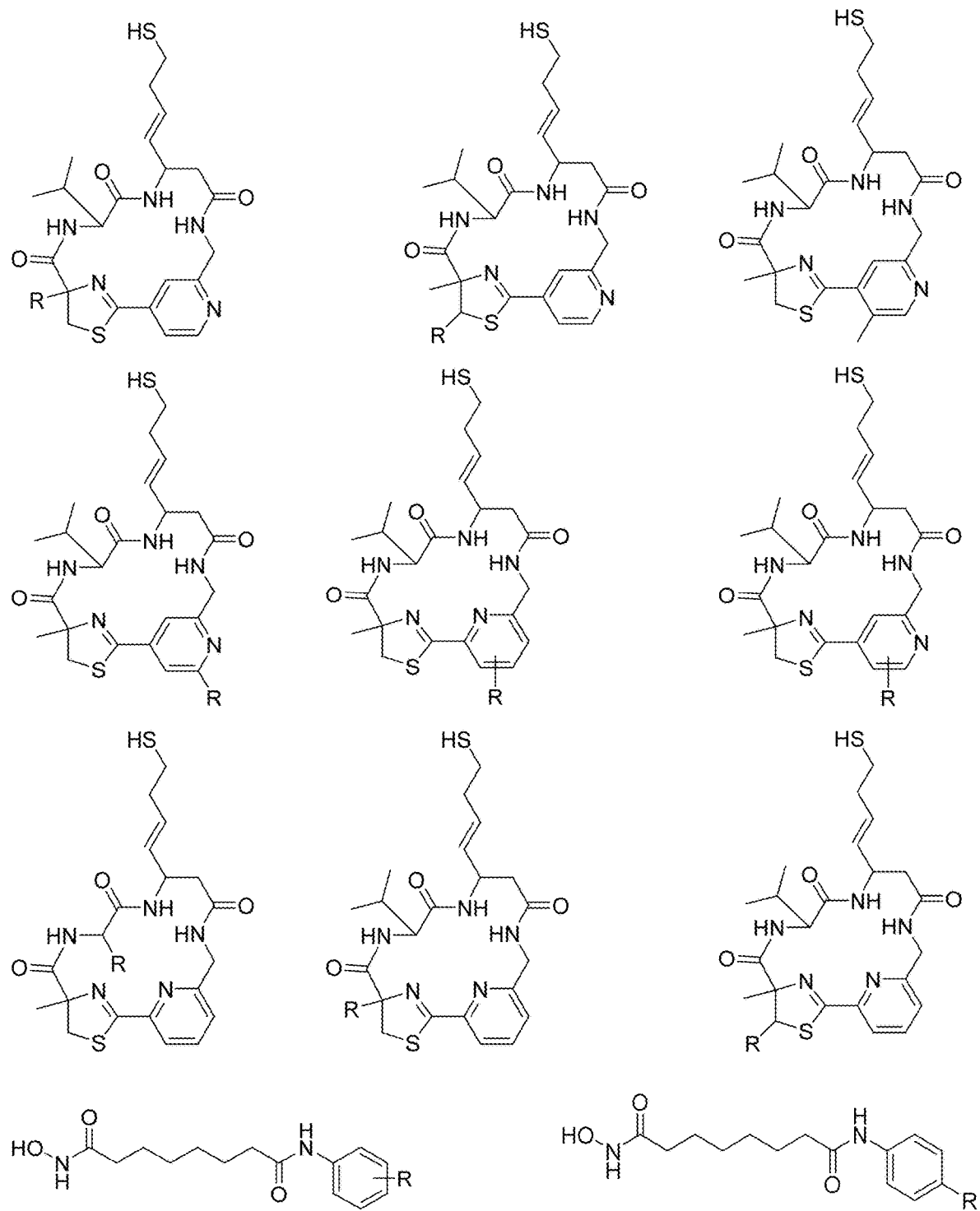

FIG. 3CCCCC
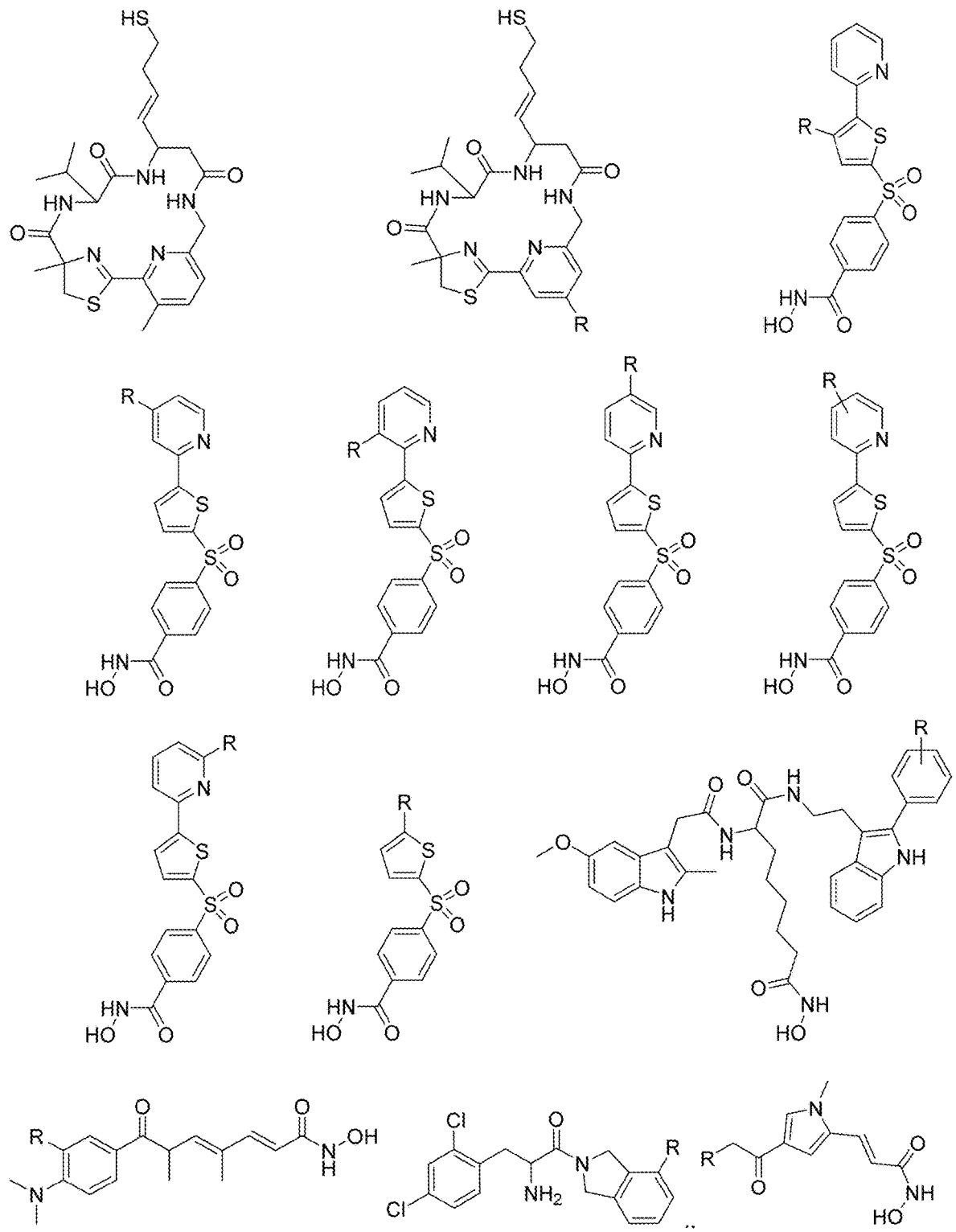

FIG. 3DDDDD
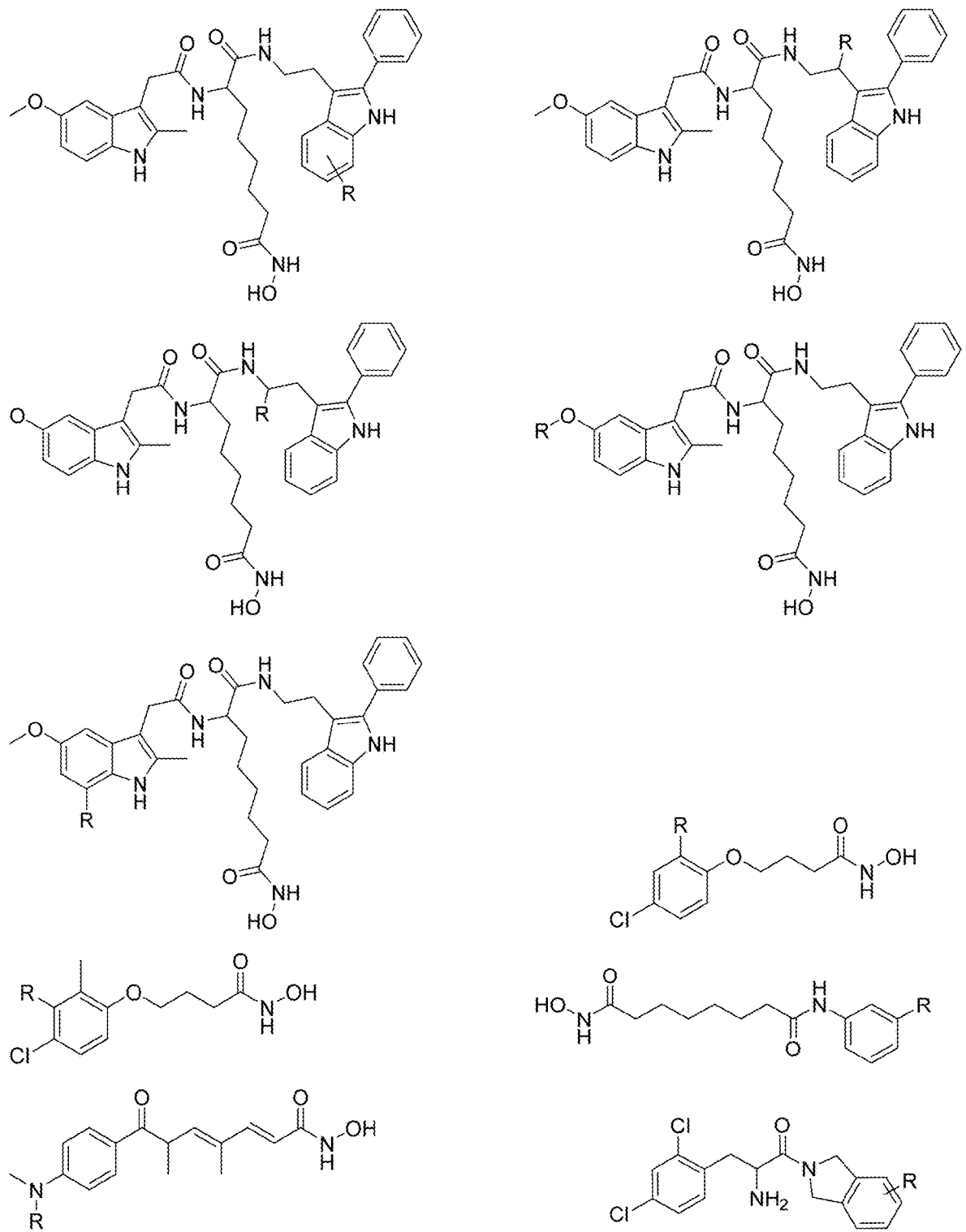

FIG. 3EEEEE
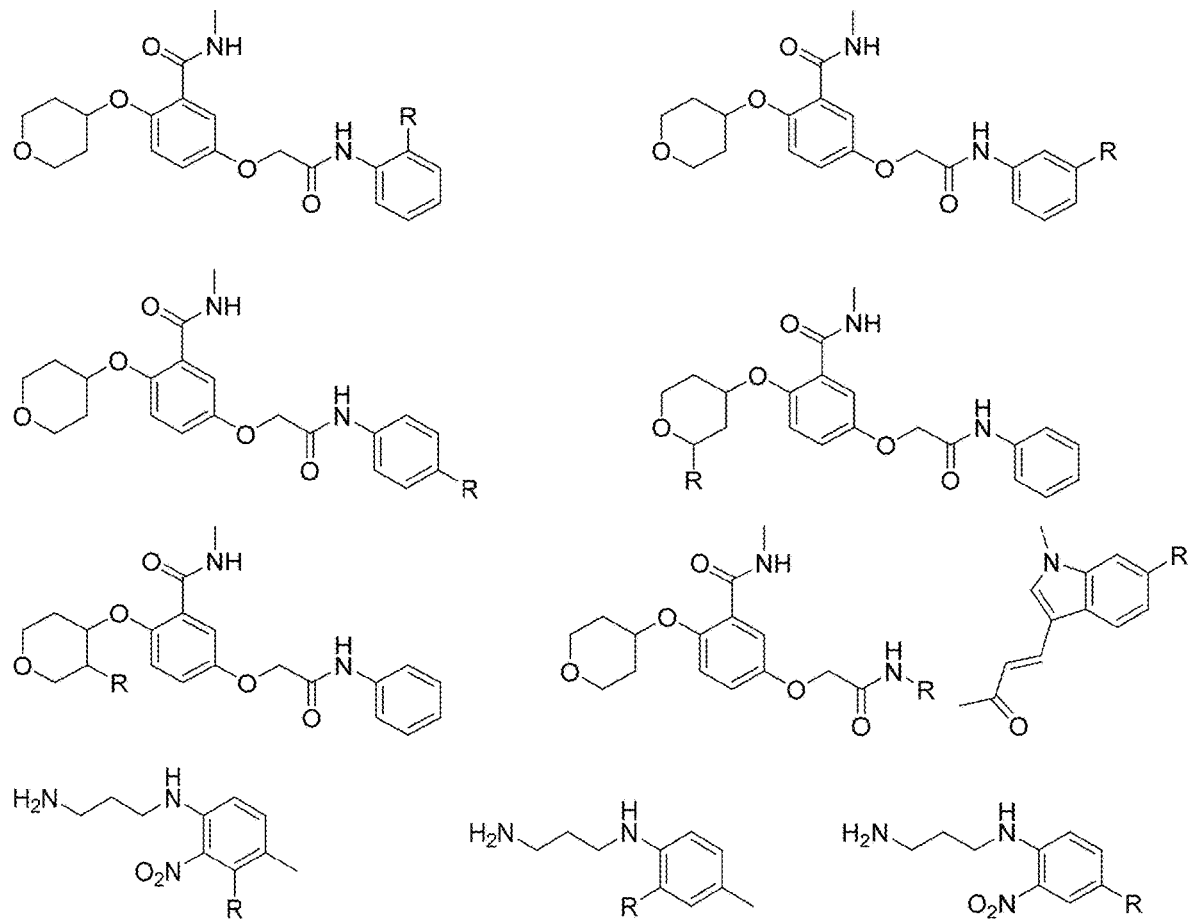
FIG. 3FFFFF
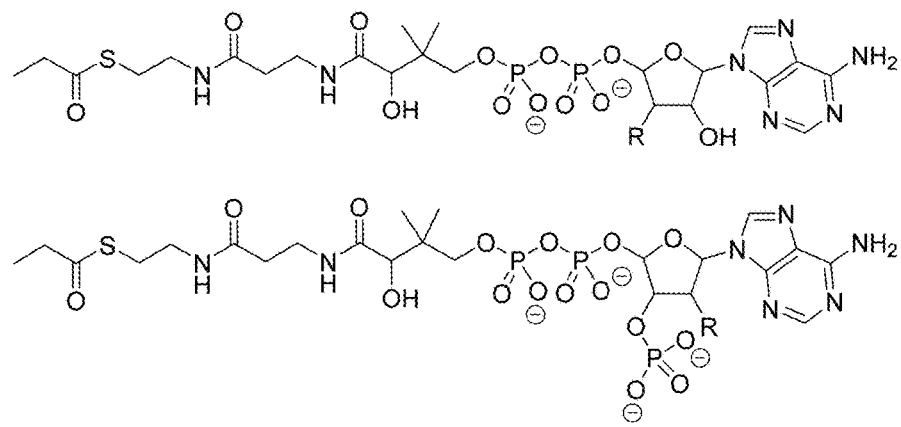

FIG. 3GGGGG
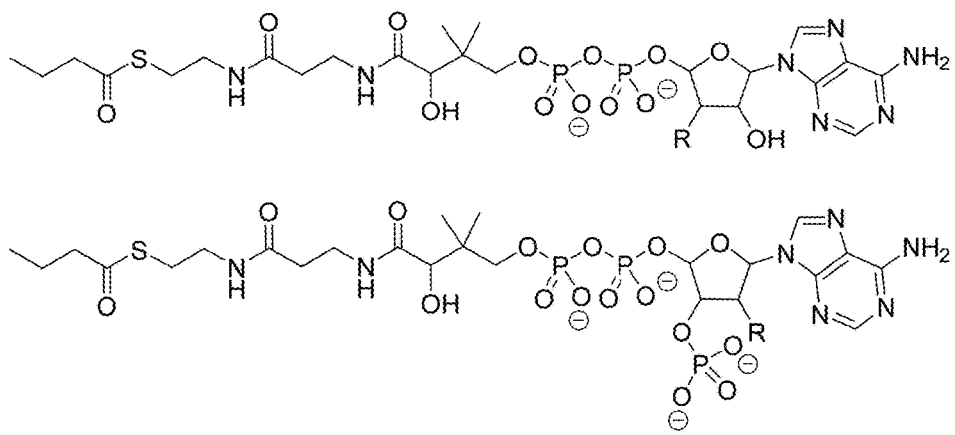
FIG. 3HHHHH
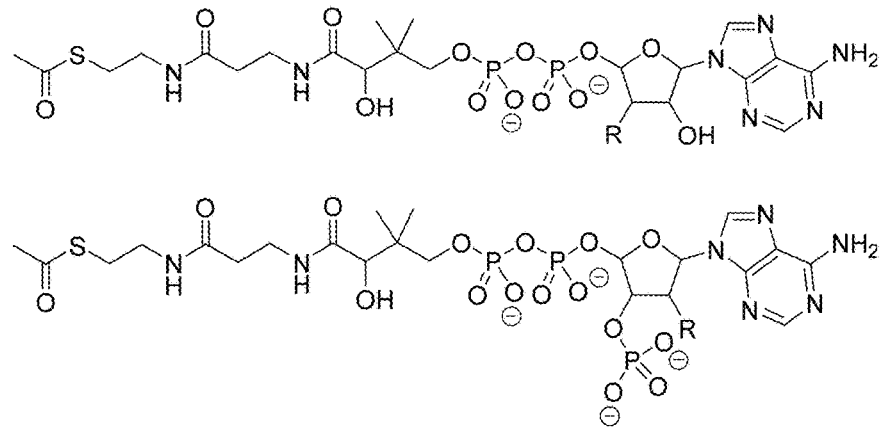
FIG. 3IIIII
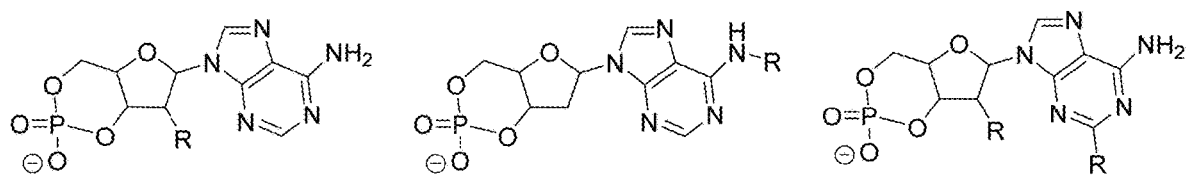

FIG. 3JJJJJ
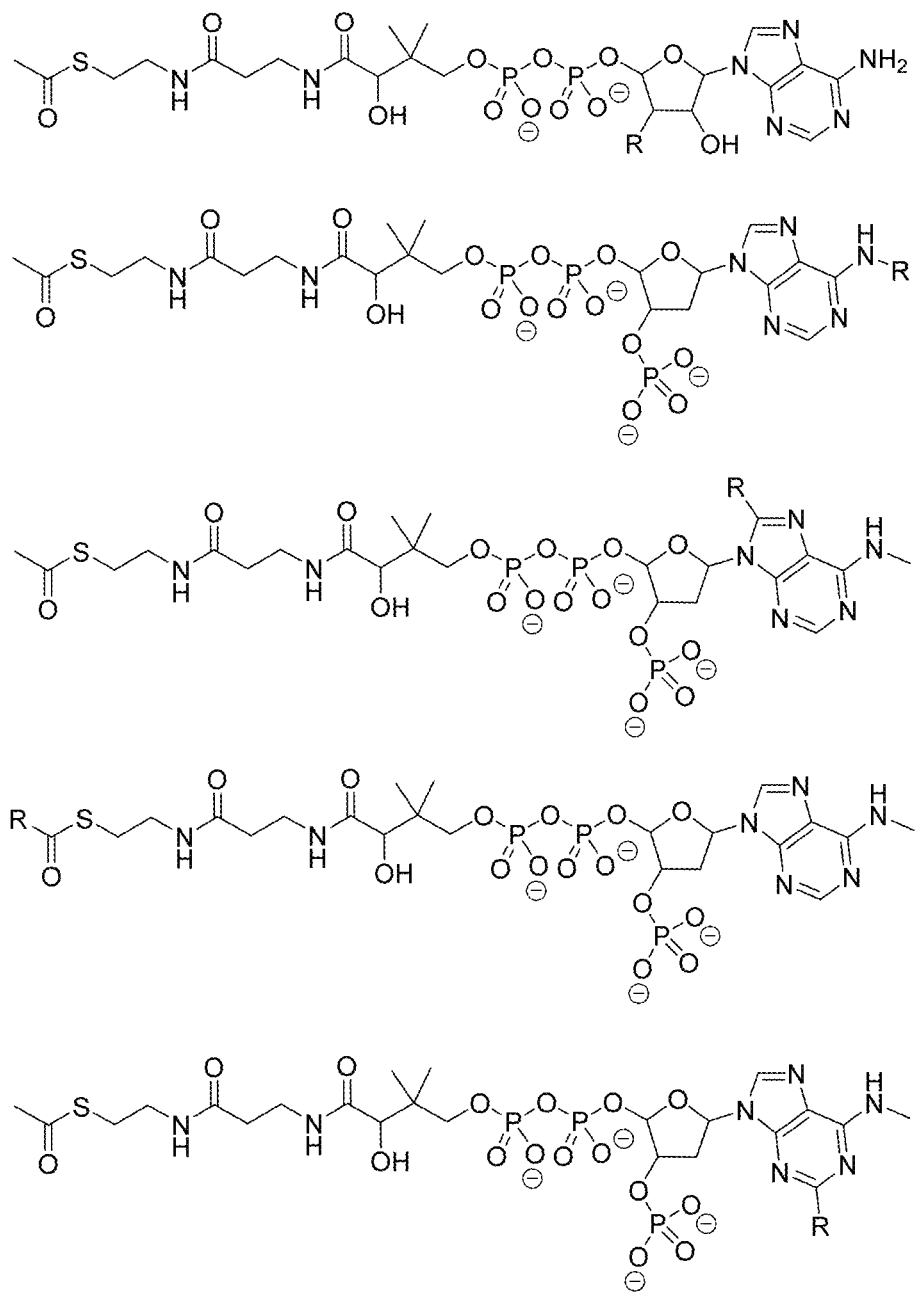

FIG. 3KKKKK
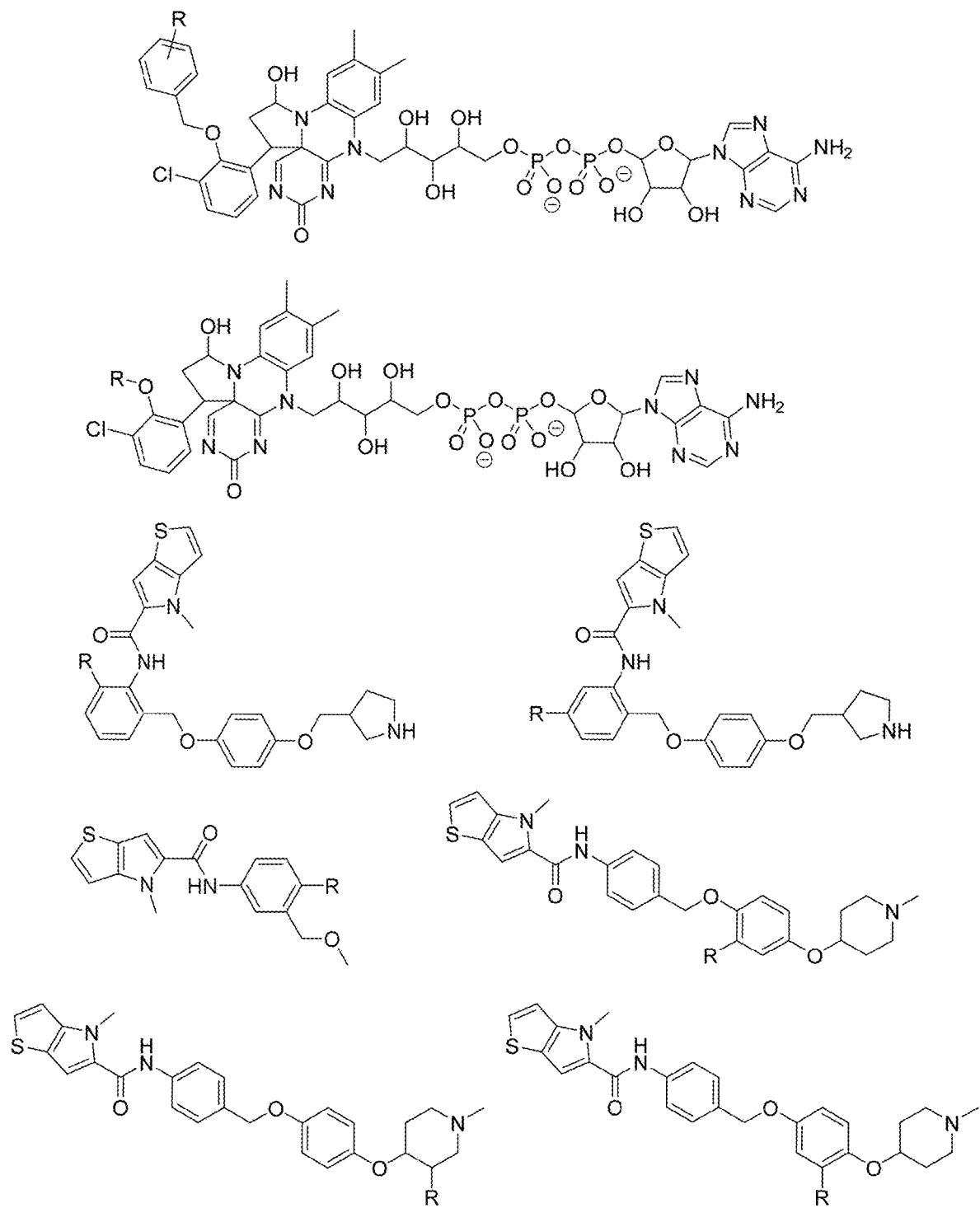

FIG. 3LLLLL
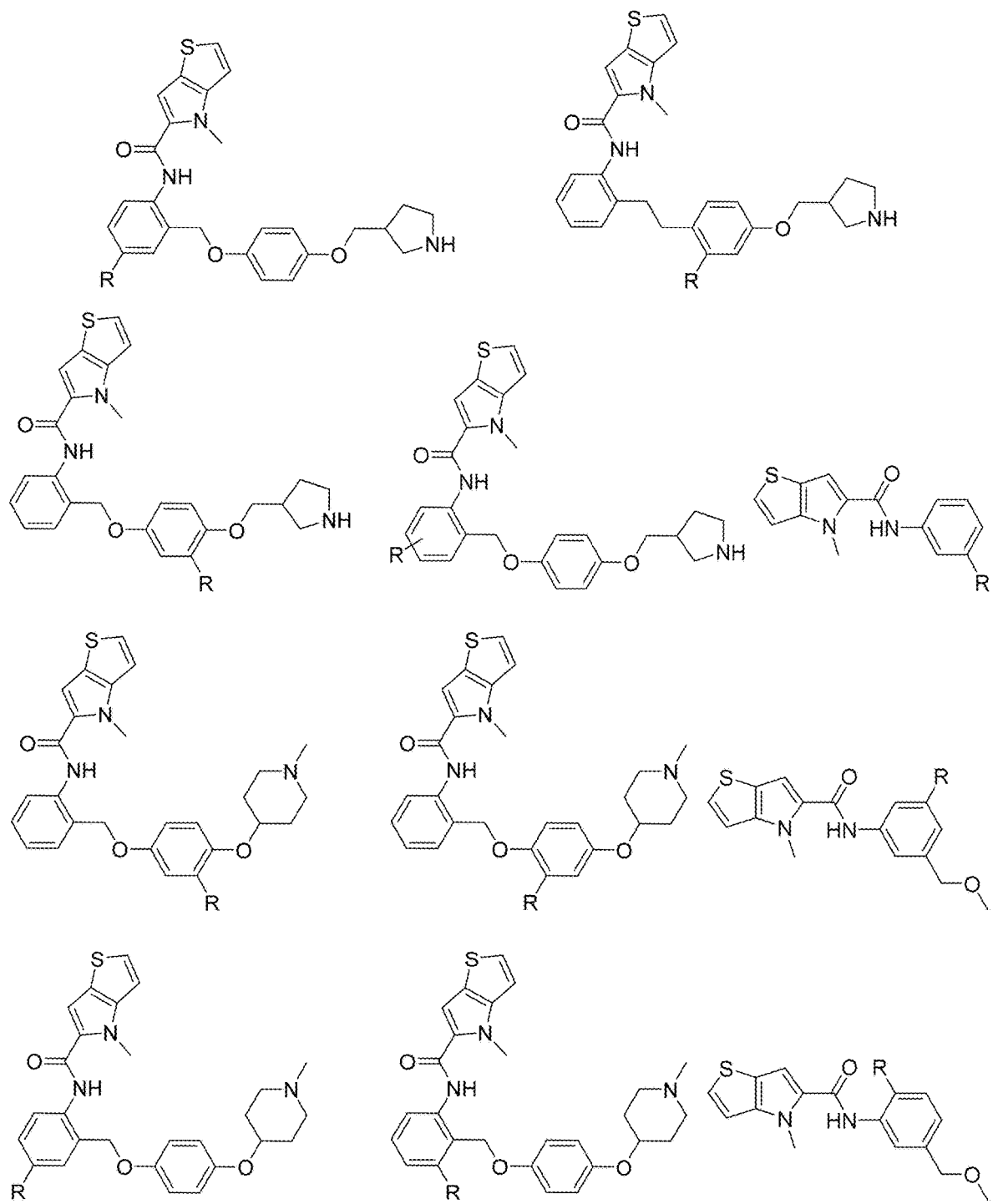

FIG. 3MMMMM
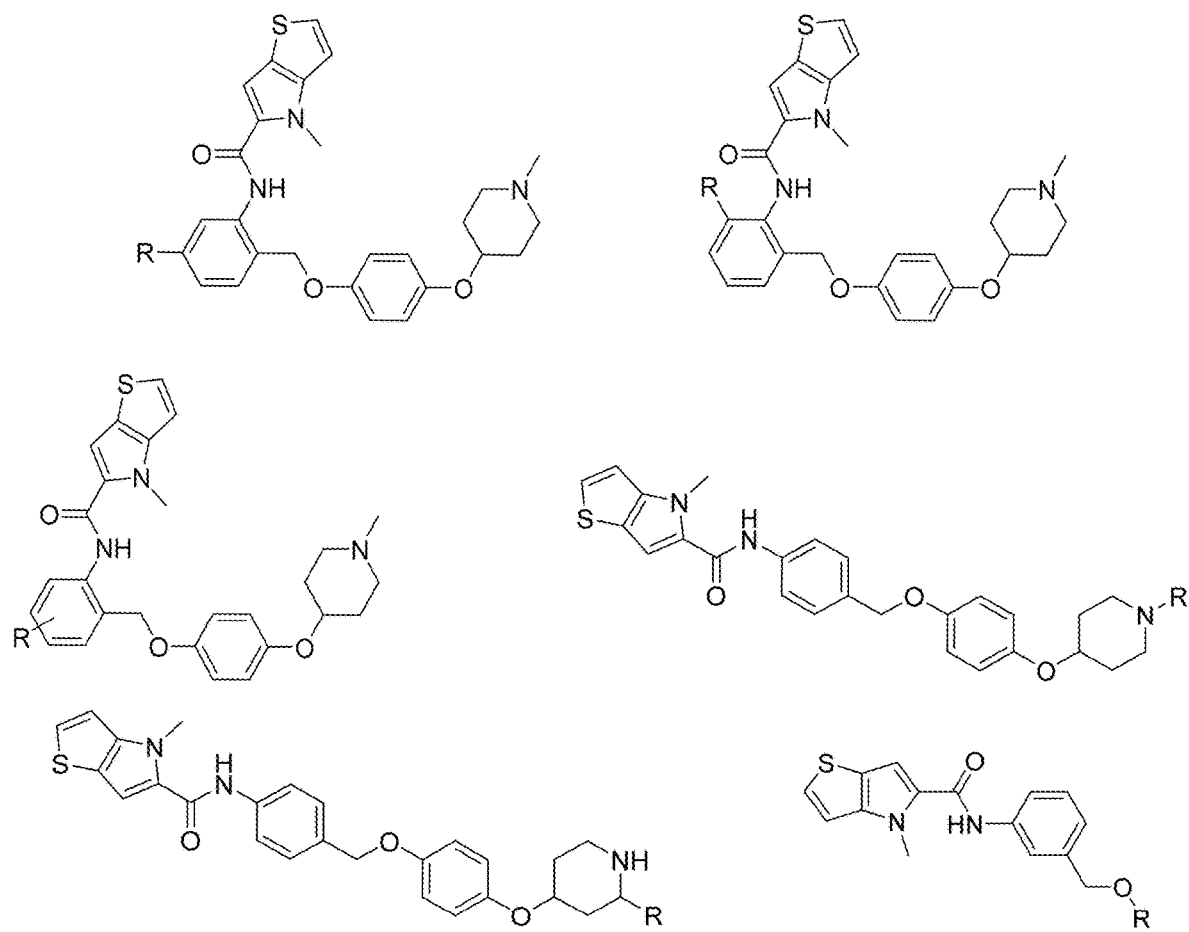
FIG. 3NNNNN
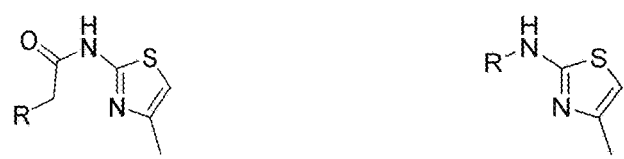

FIG. 300000
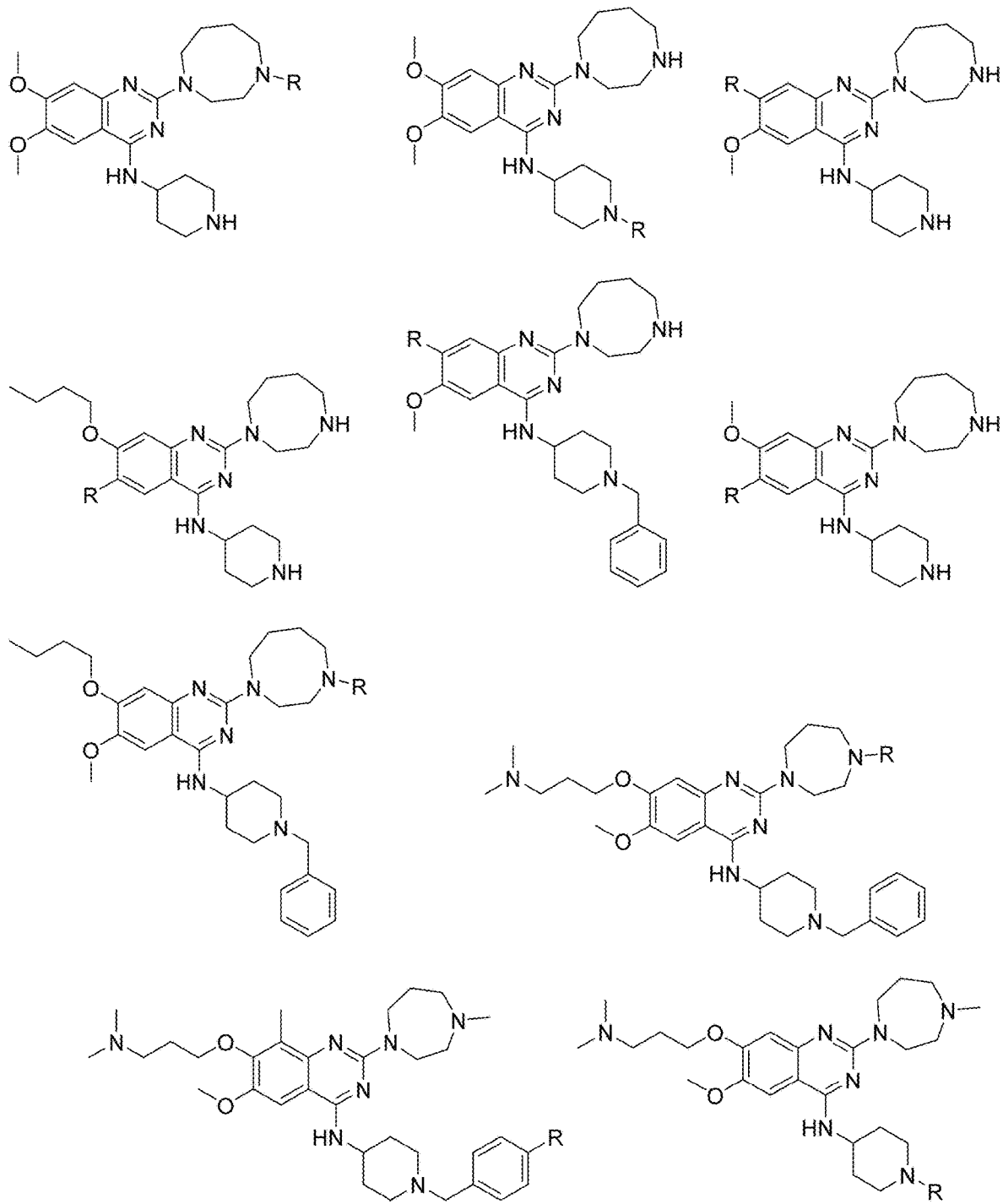

FIG. 3PPPPP
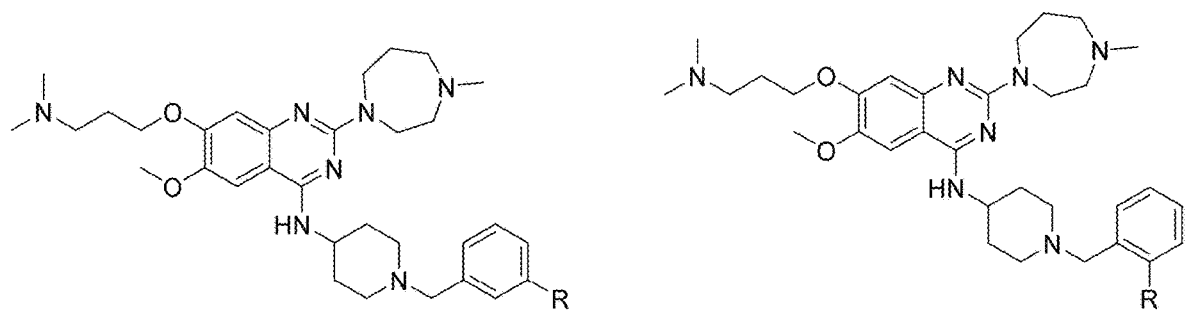
FIG. 3QQQQQ
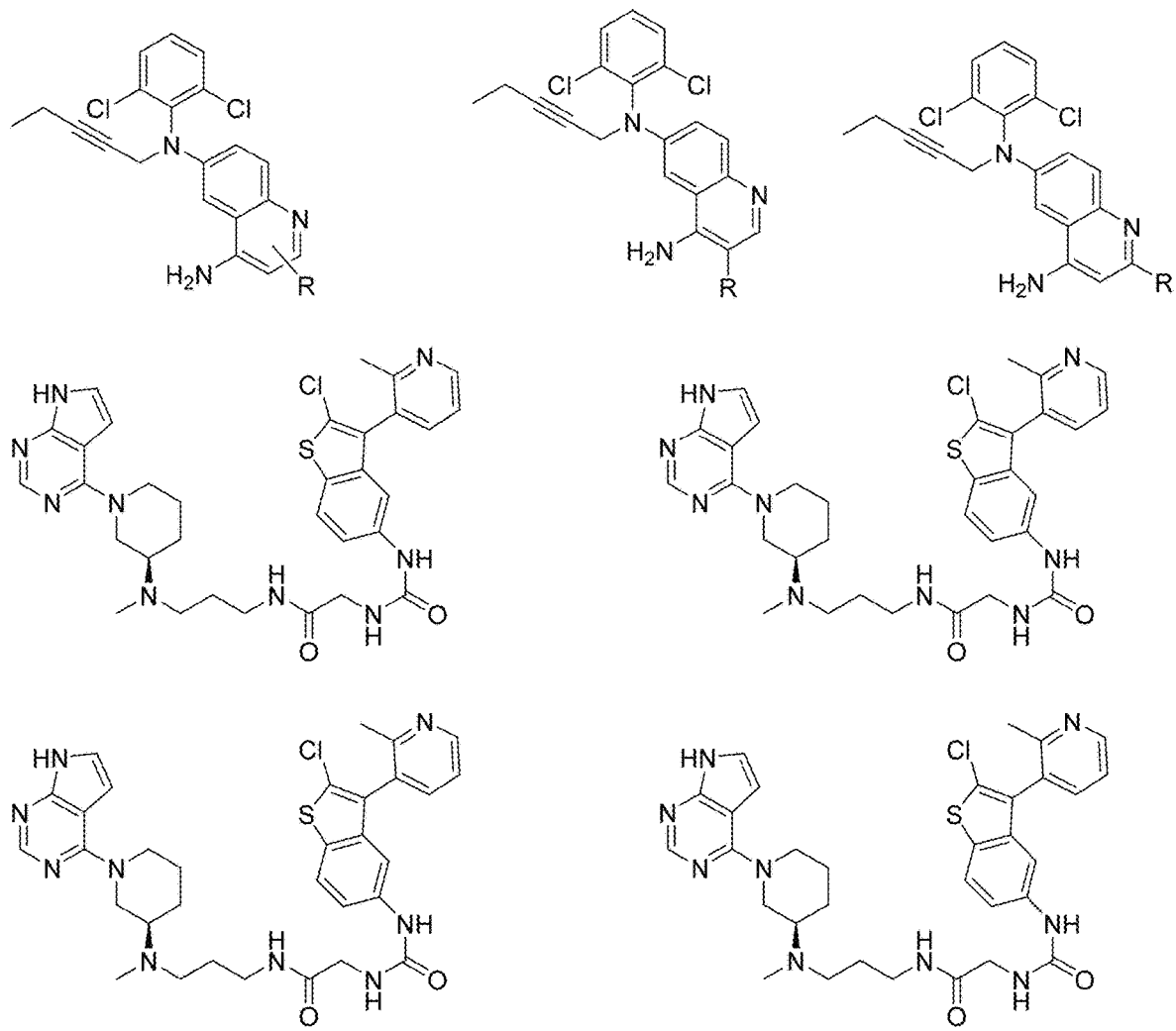

FIG. 3RRRRR
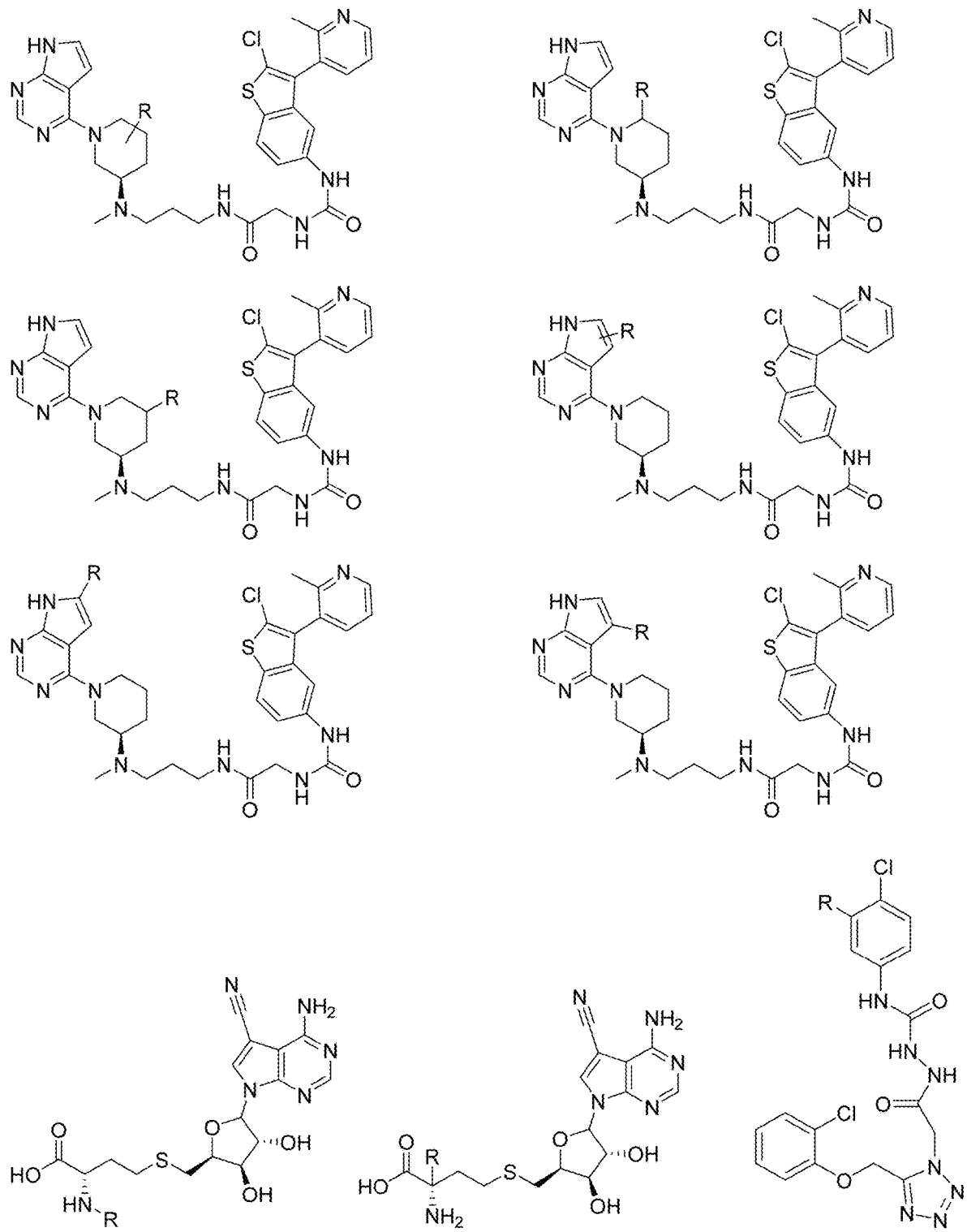

FIG. 3SSSSS
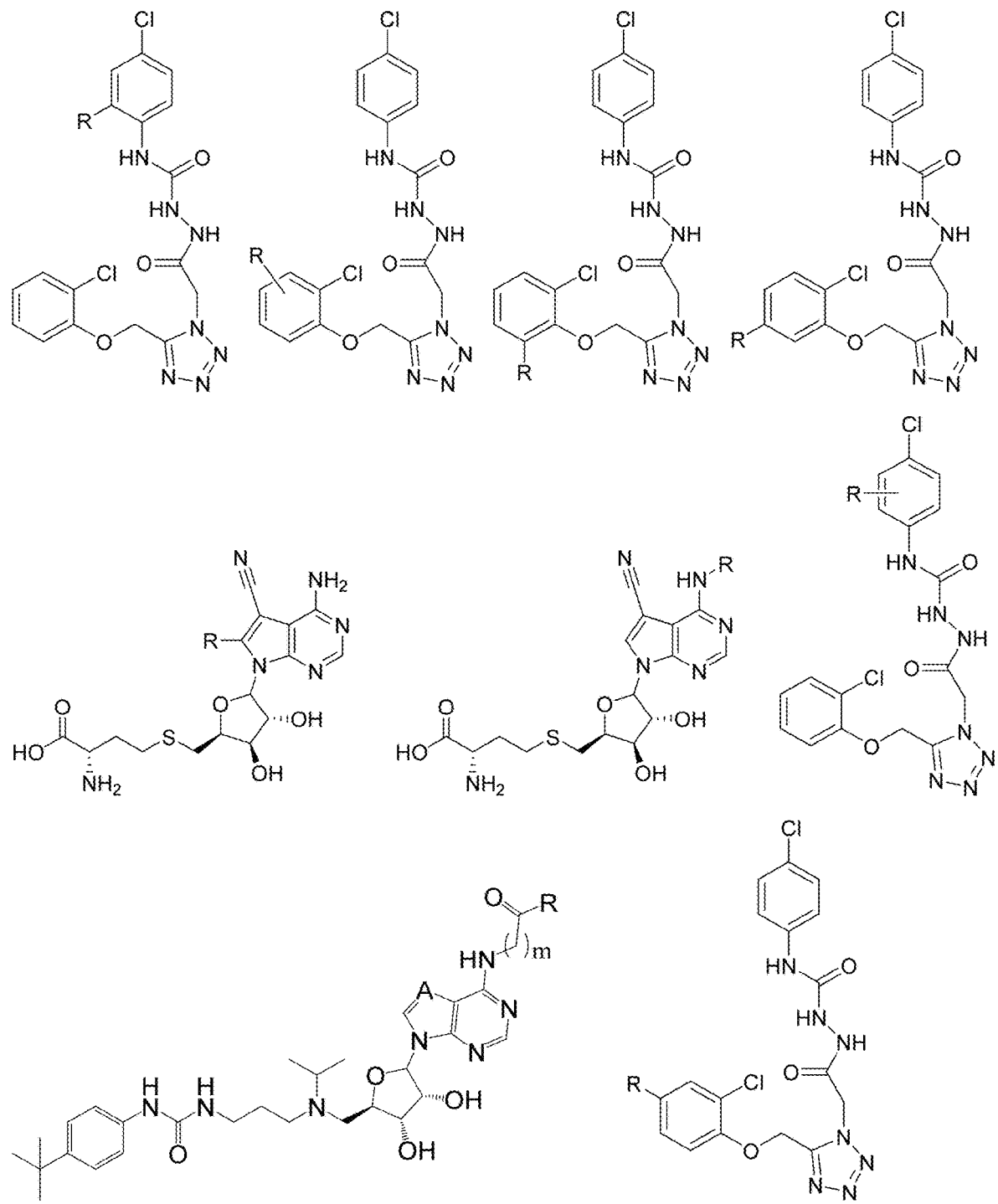

FIG. 3TTTTT
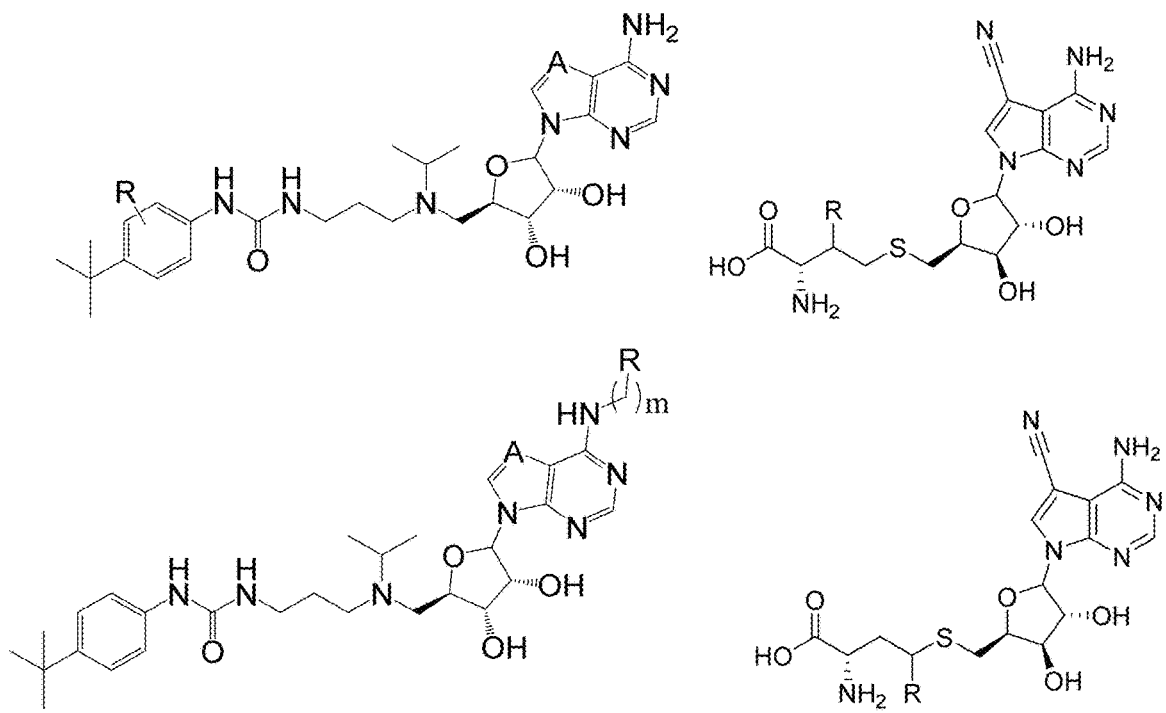
FIG. 3UUUUU
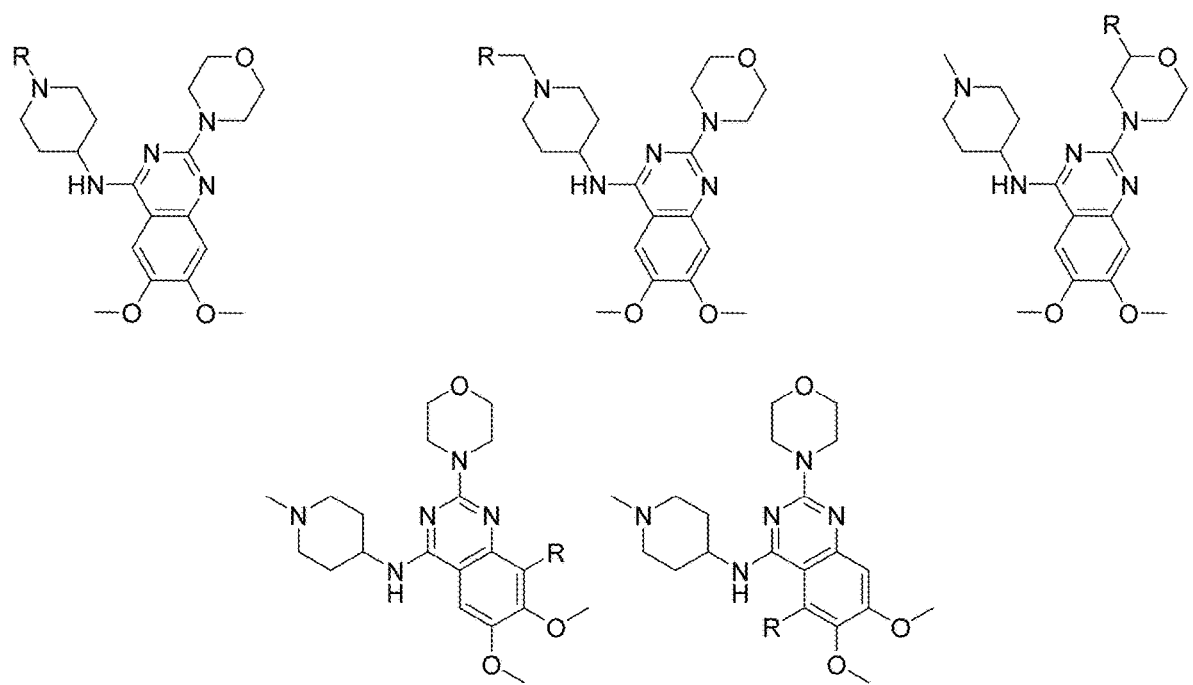

FIG. 3VVVVV
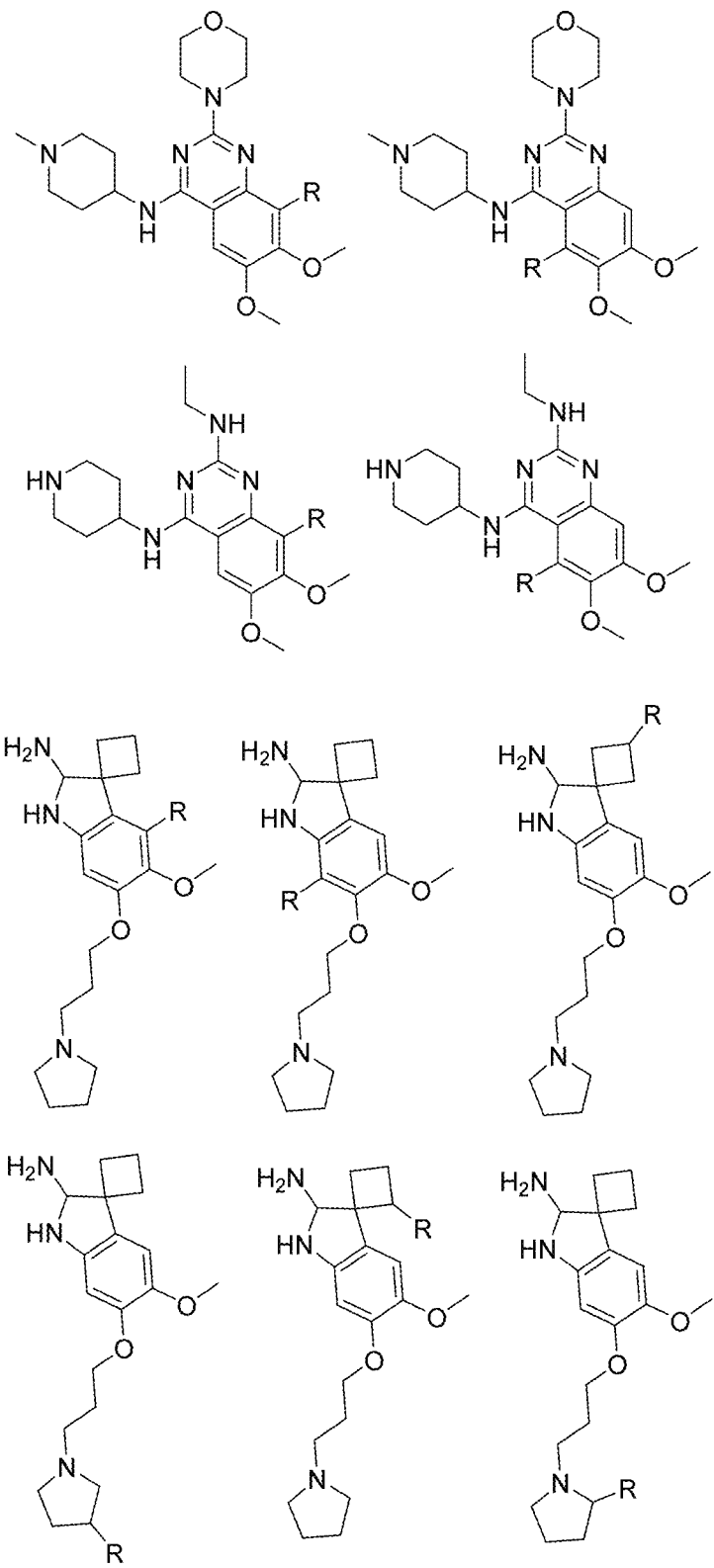

FIG. 3WWWWW
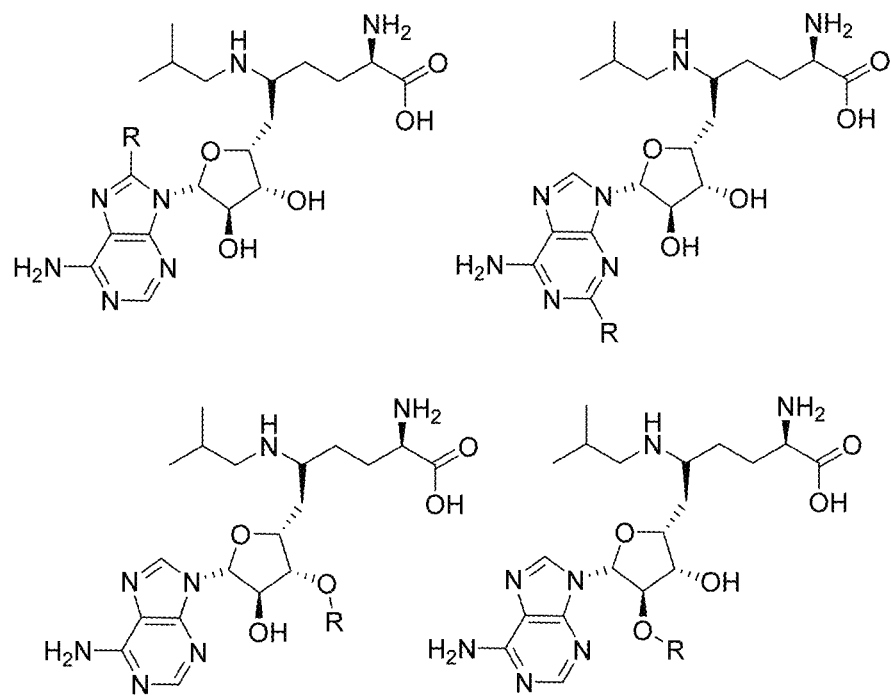
FIG. 3XXXXX
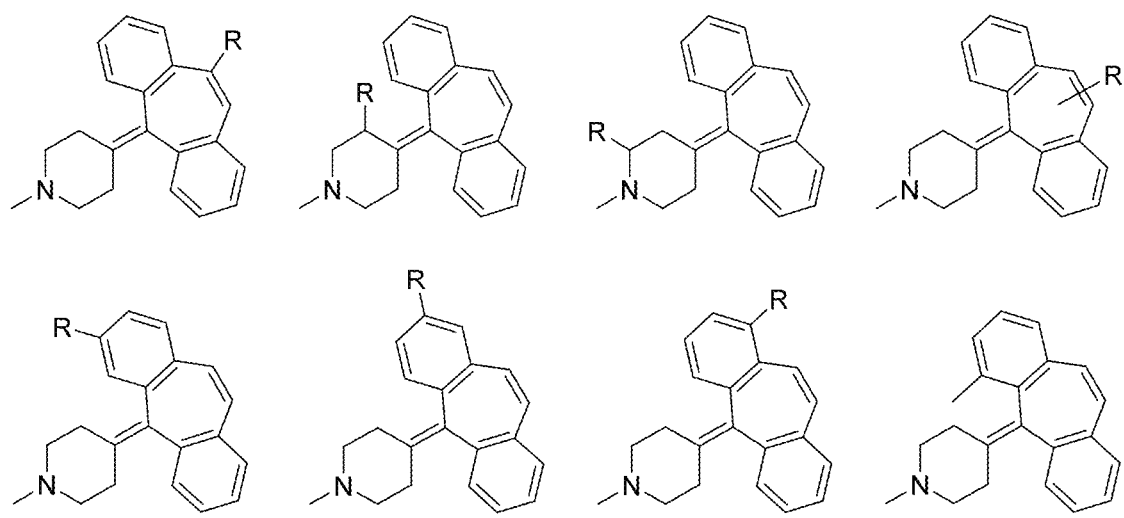

FIG. 3YYYYY
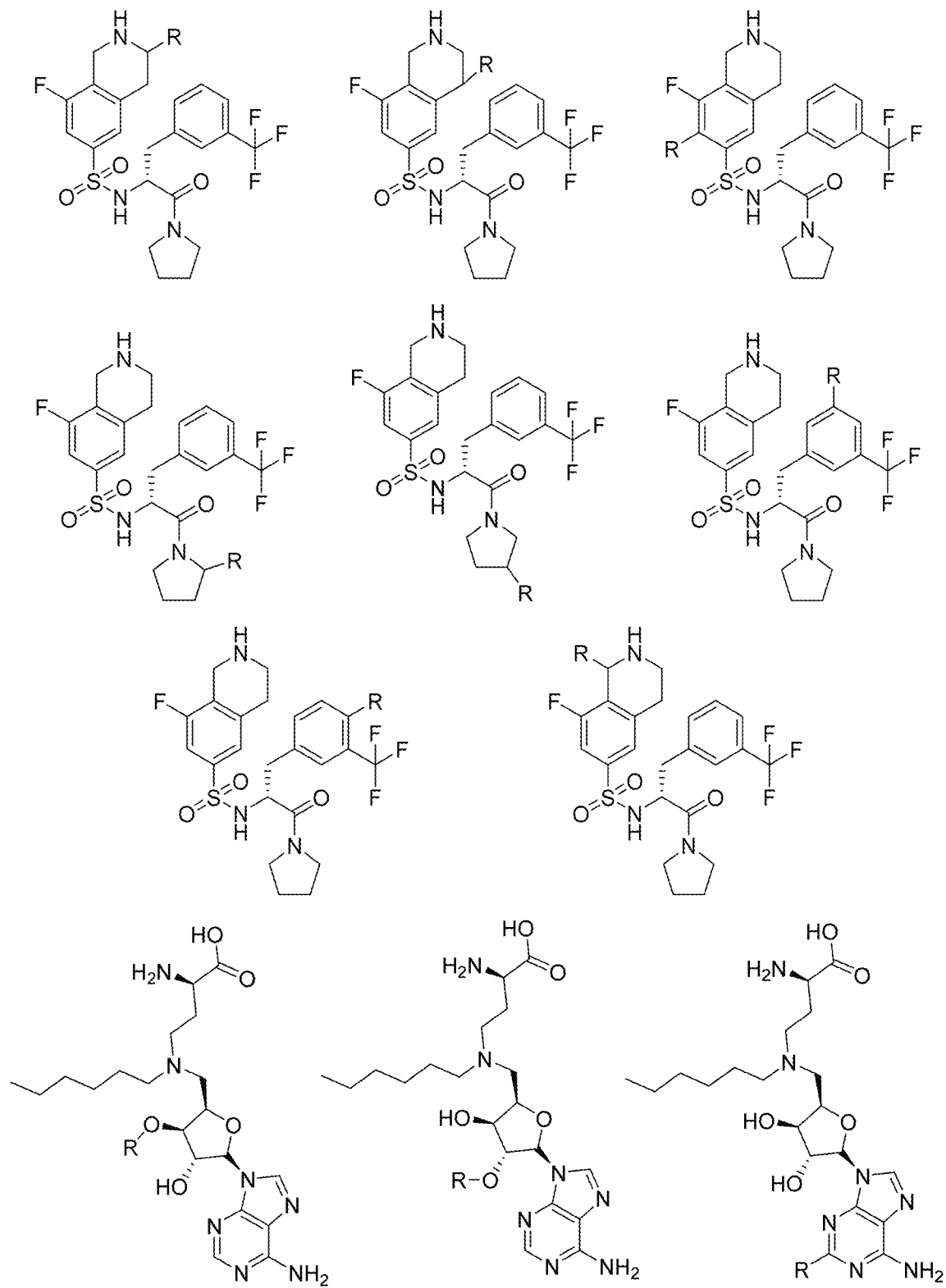

FIG. 3ZZZZZ
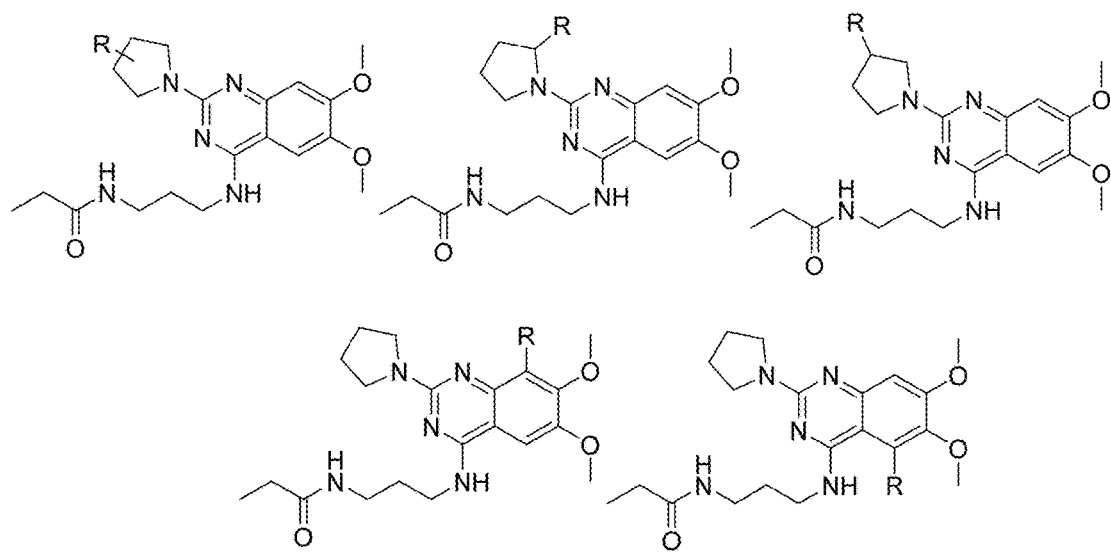
FIG. 4A
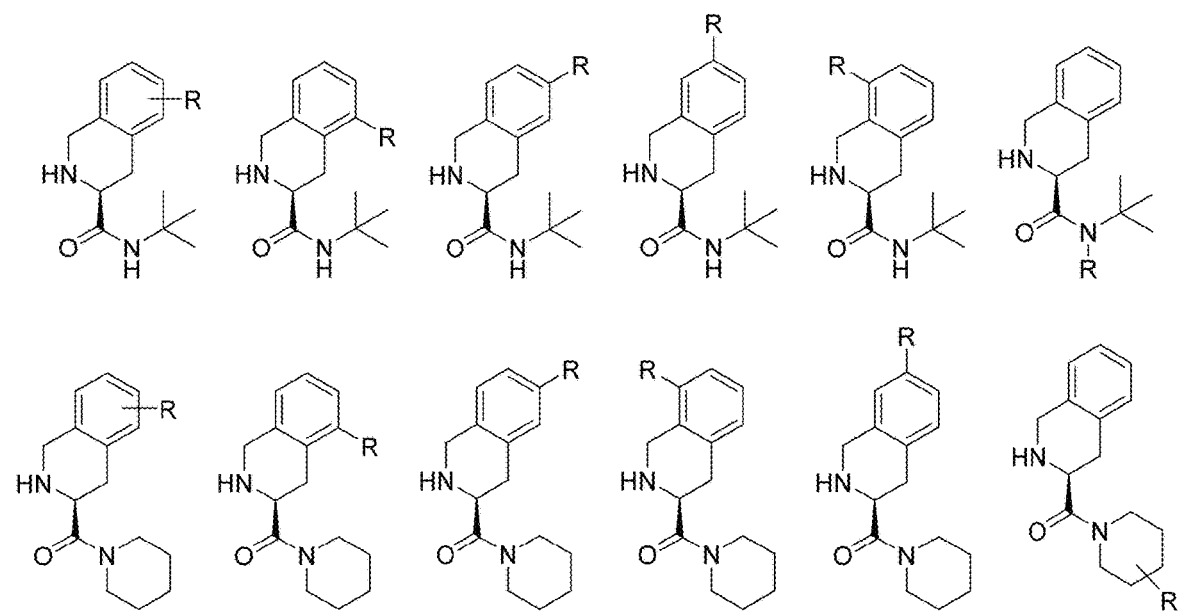

FIG. 5L
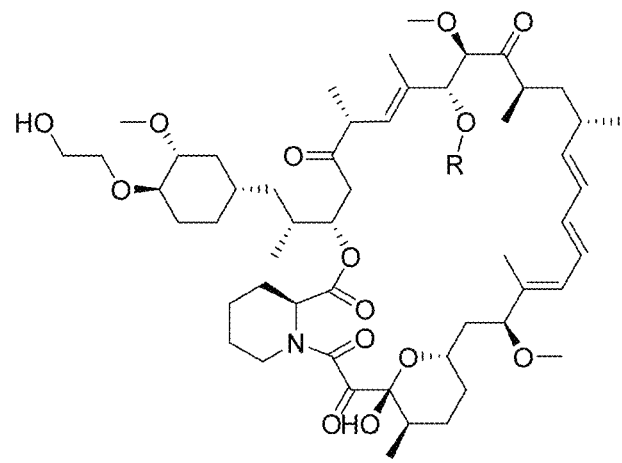
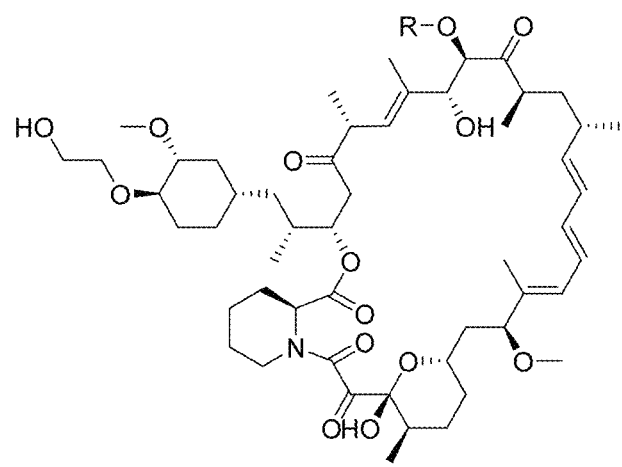
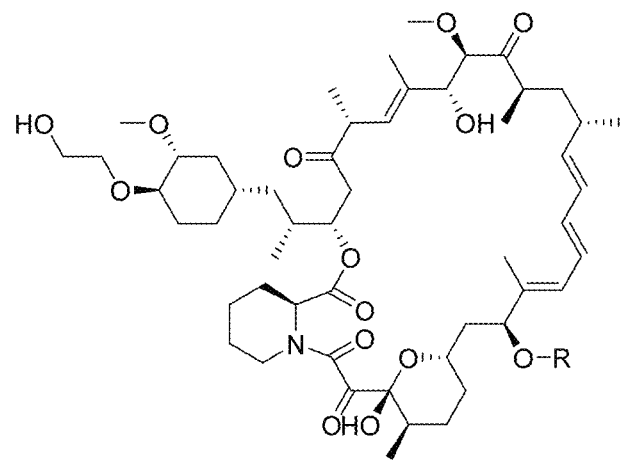

FIG. 5M
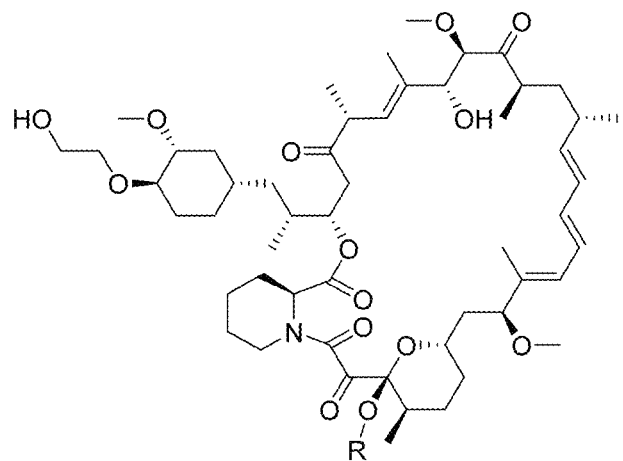
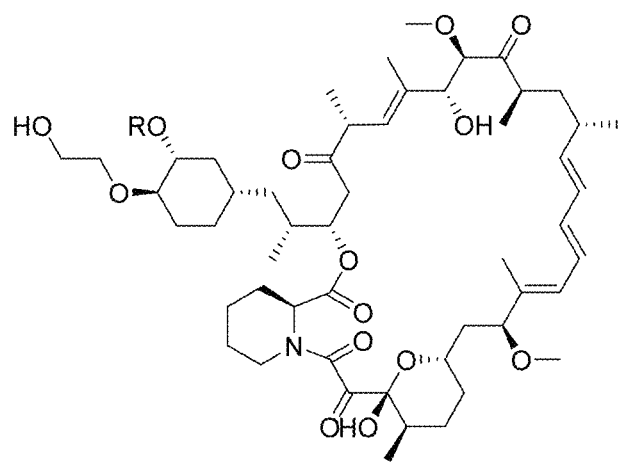
FIG. 5N
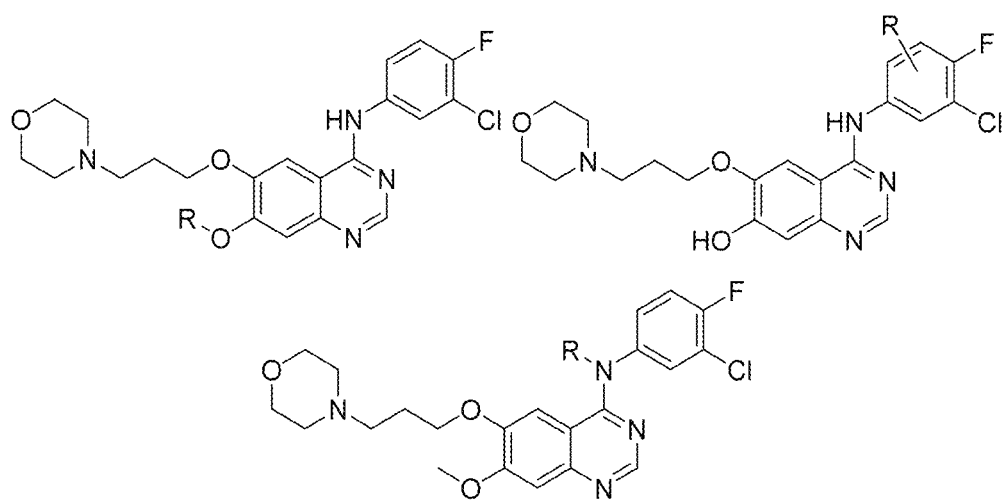

FIG. 5JJ
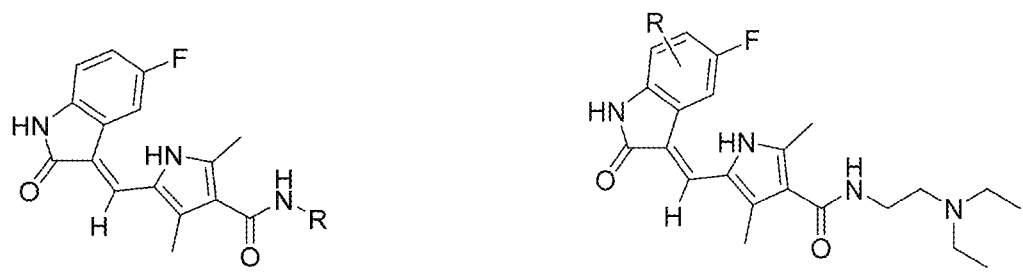
FIG. 5KK
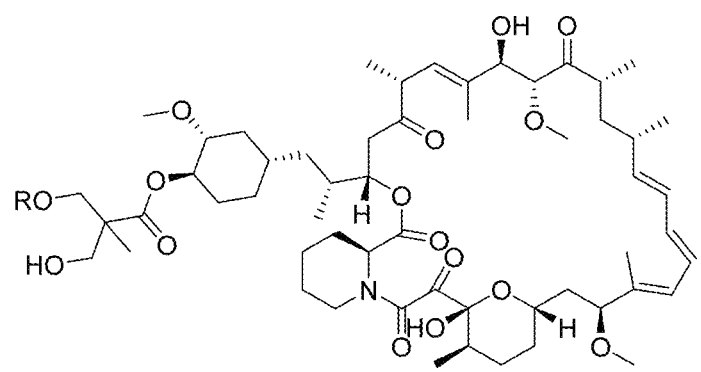
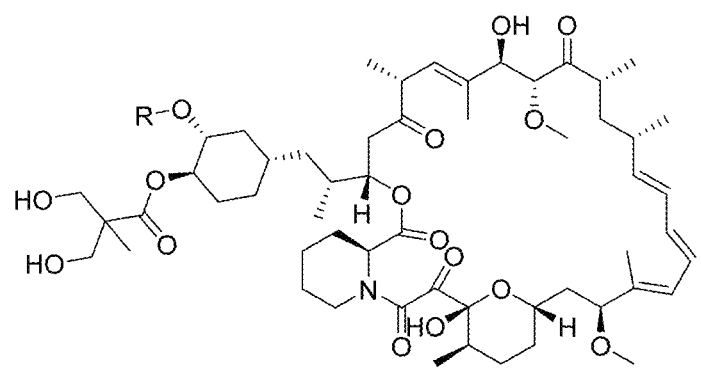

FIG. 6N
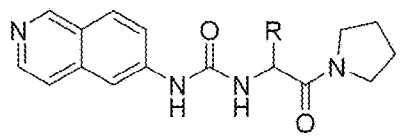
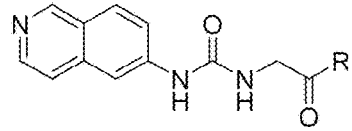
FIG. 6O
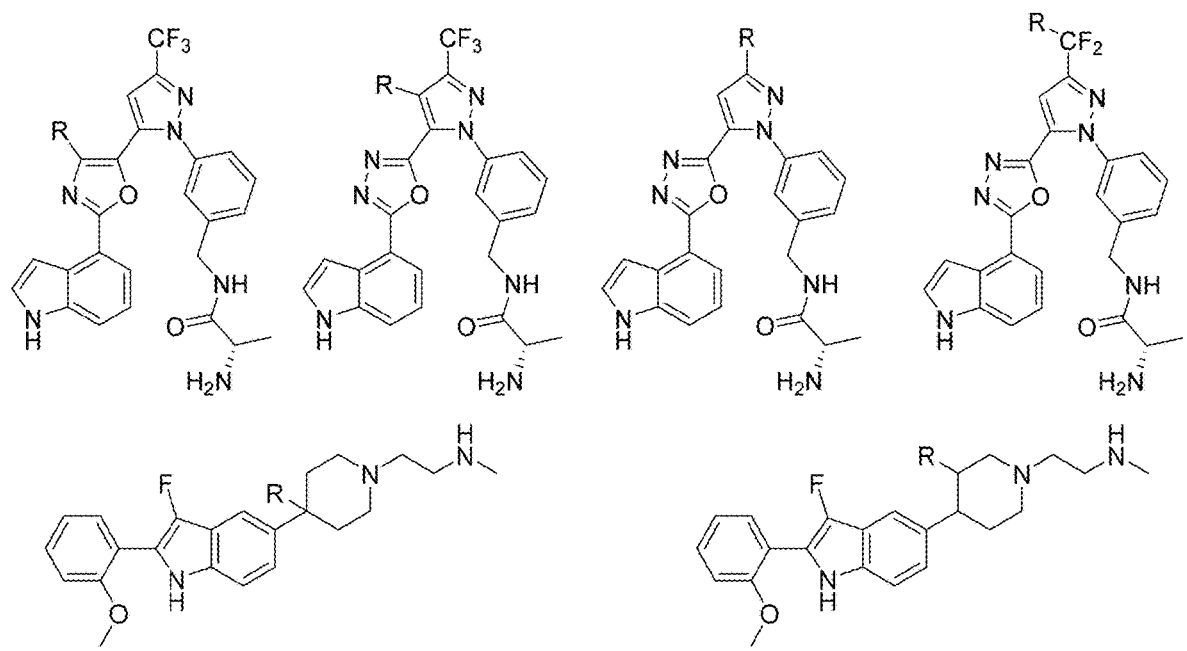
FIG. 6P
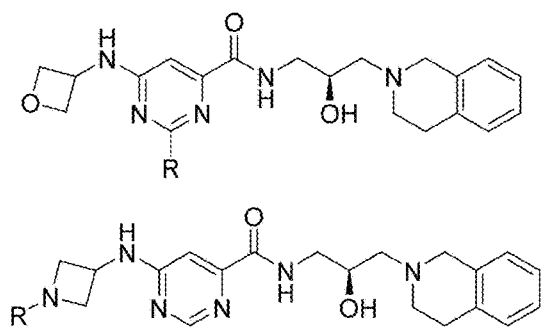
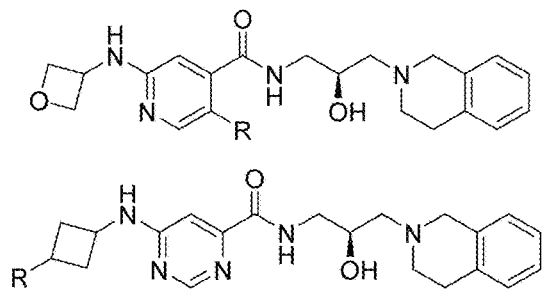

X=H, F, Cl, Br, Me, CF₃O

FIG. 8S
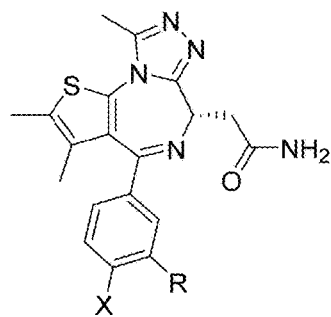
X=H, F, Cl, Br, Me, CF₃O
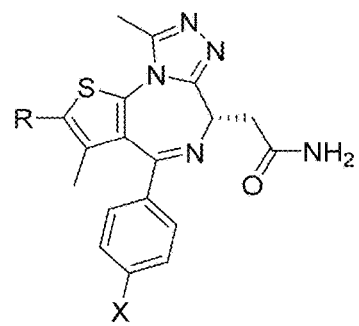
X=H, F, Cl, Br, Me, CF₃O
FIG. 8T
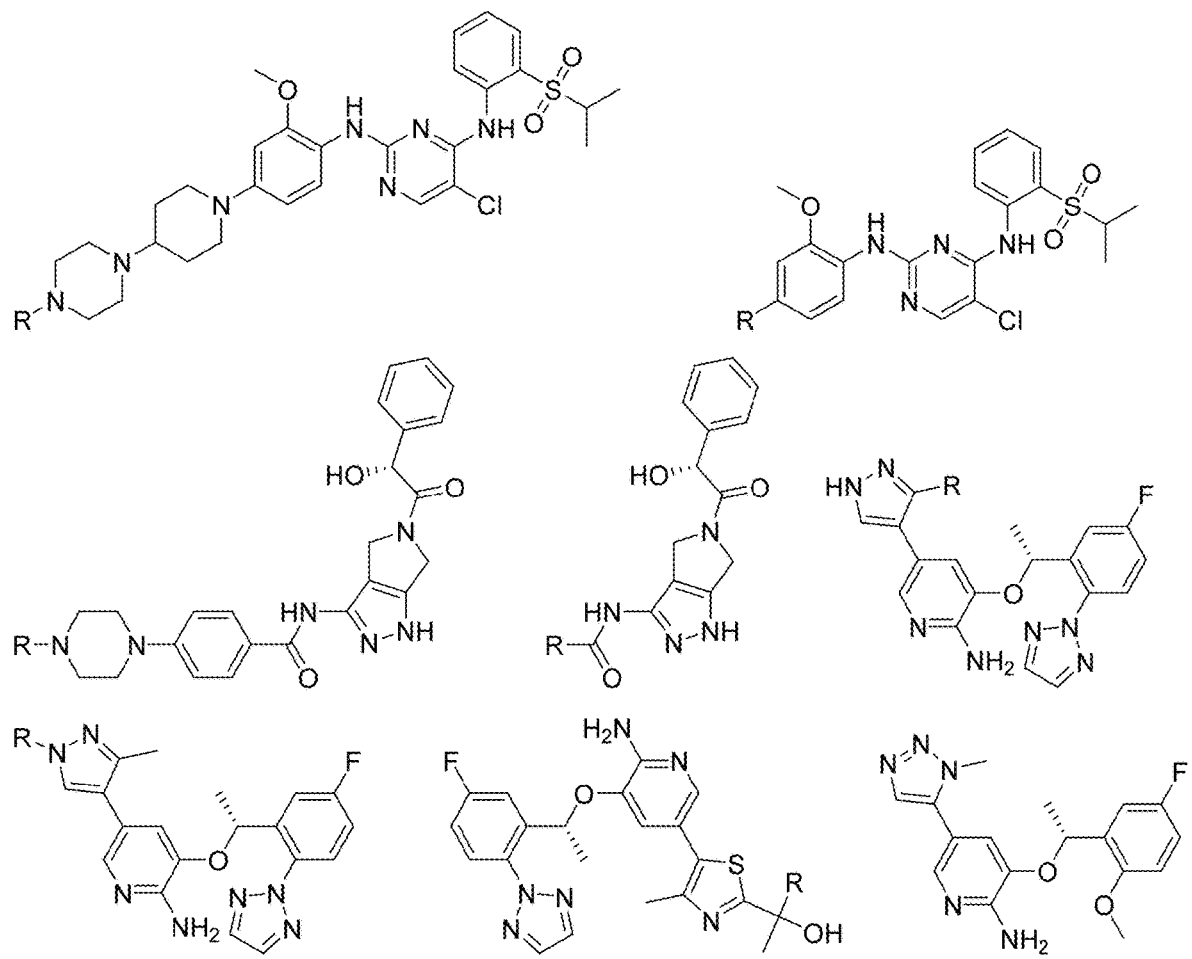

FIG. 8AAA
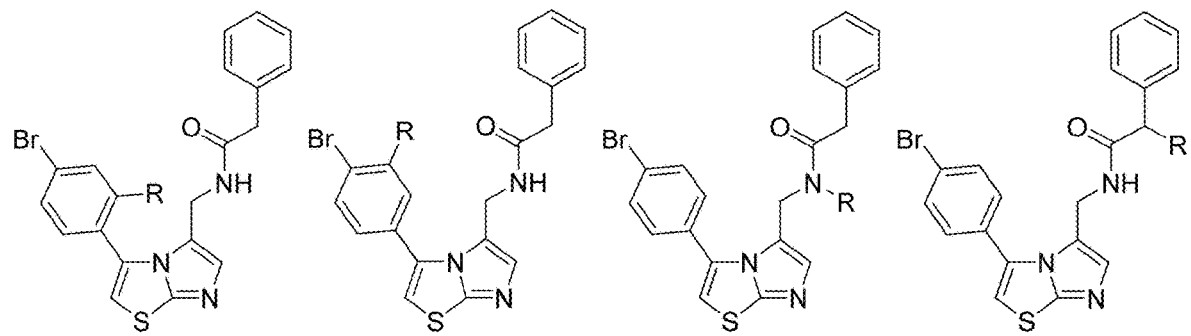
FIG. 8BBB
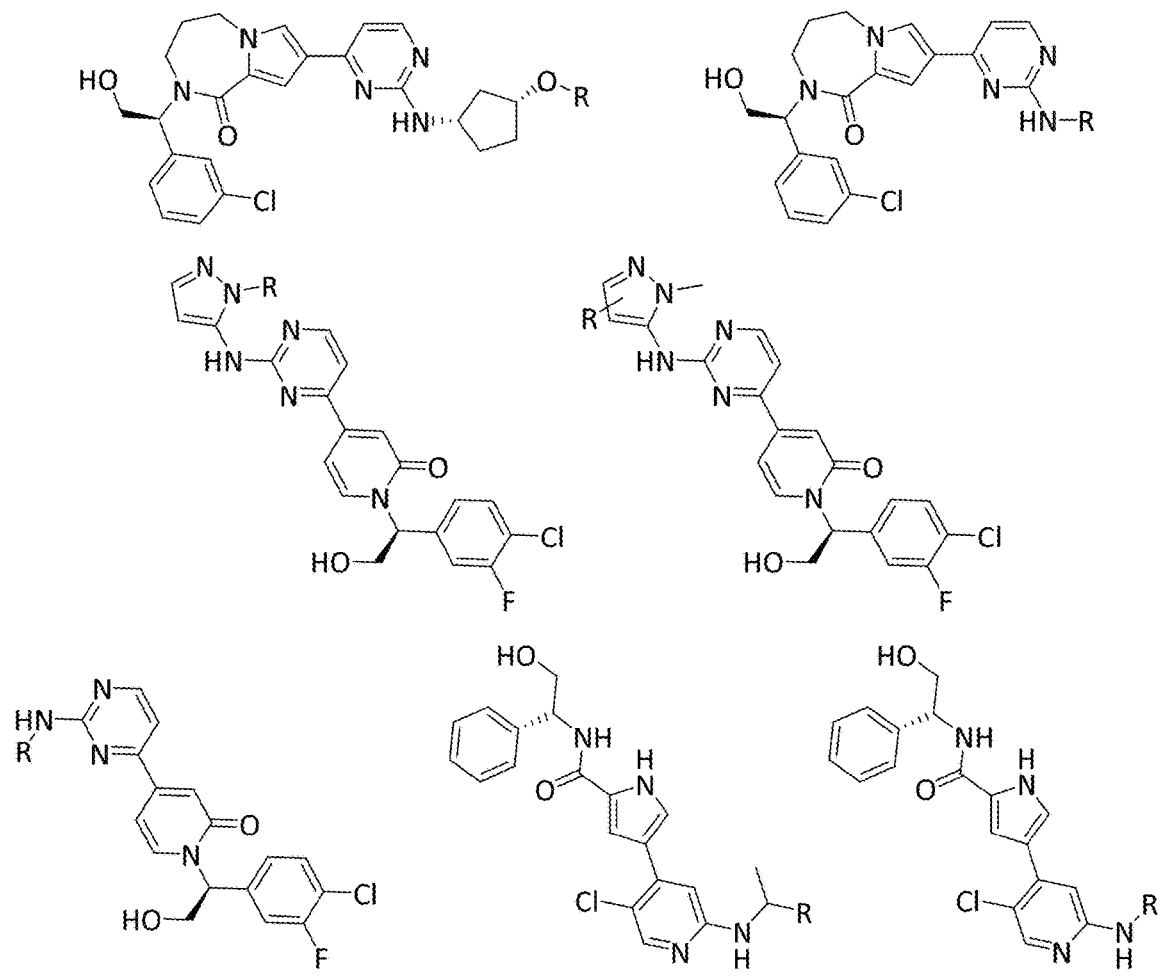

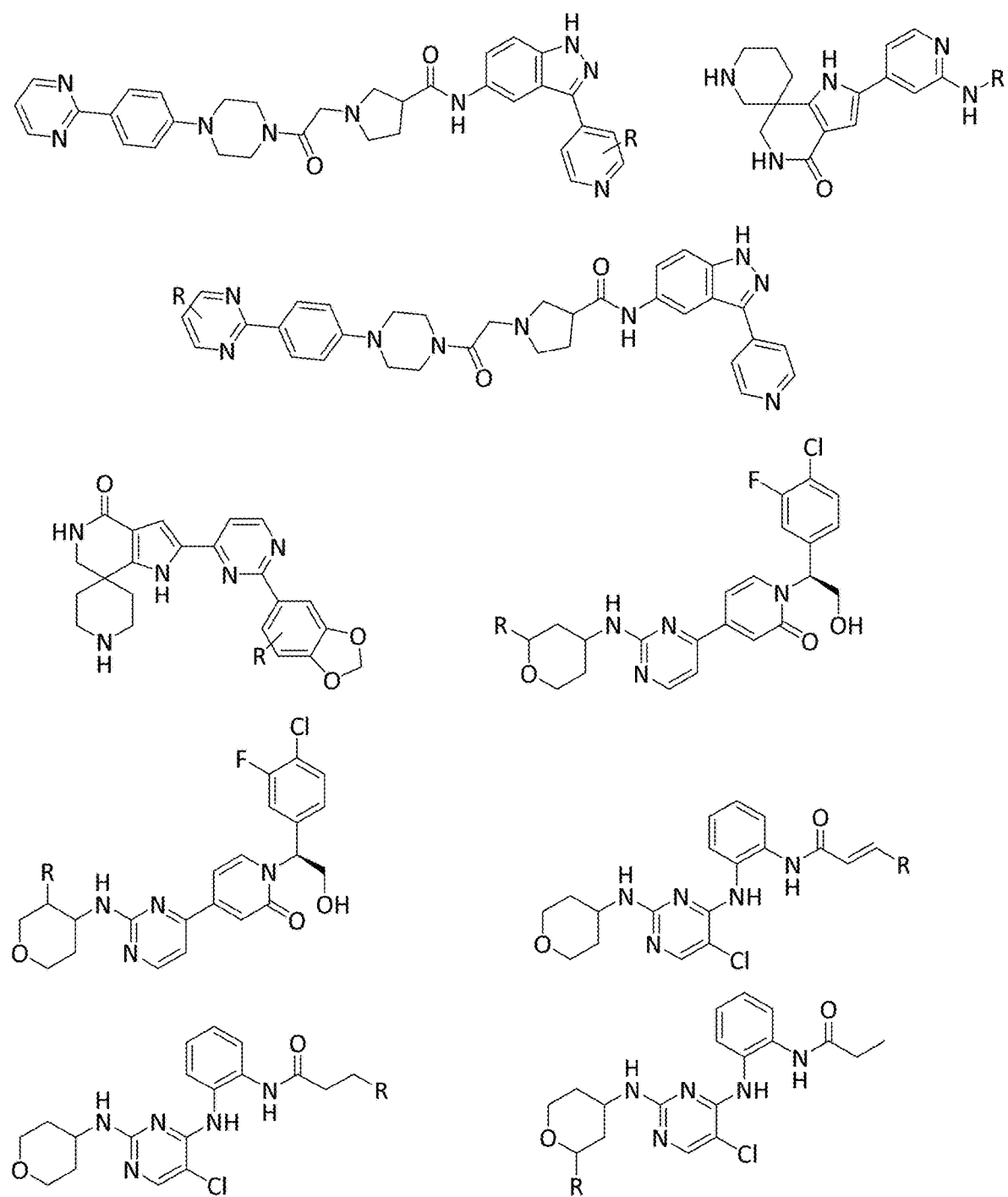
FIG. 8CCC

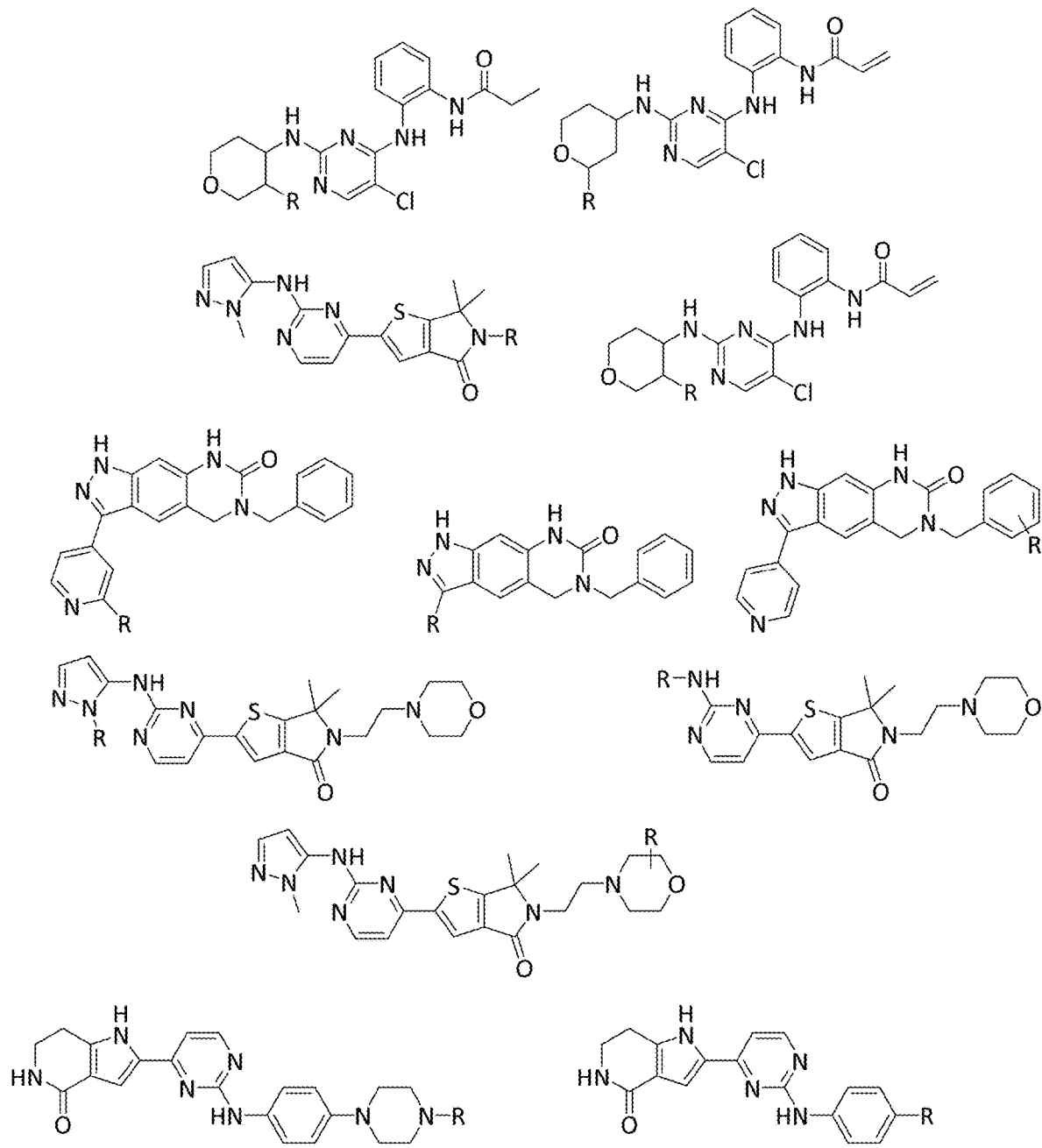
FIG. 8DDD

FIG. 8EEE
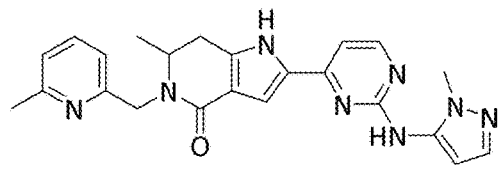
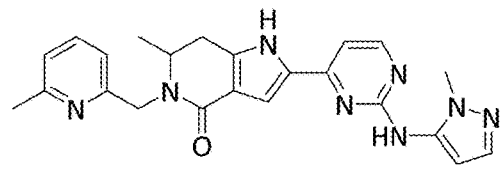
FIG. 8FFF
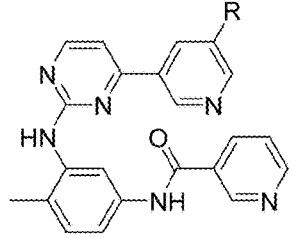
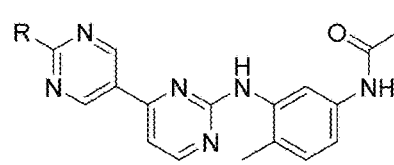
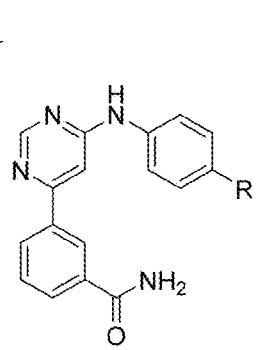
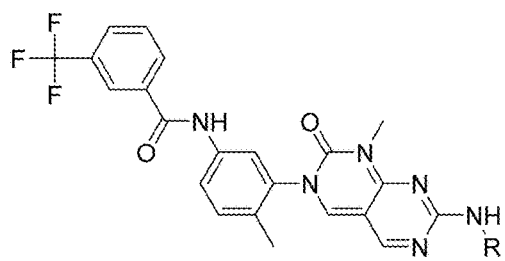
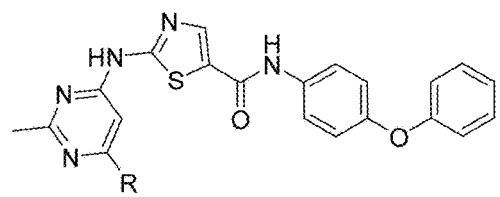
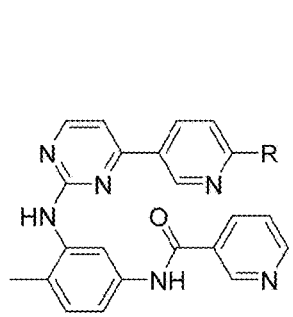
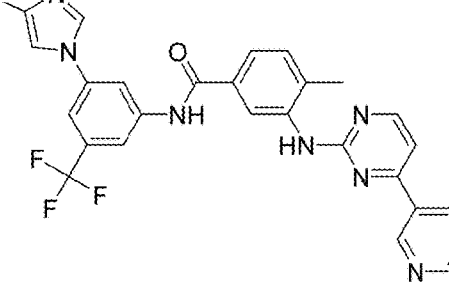
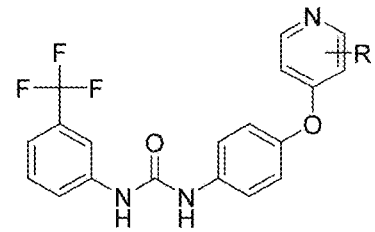
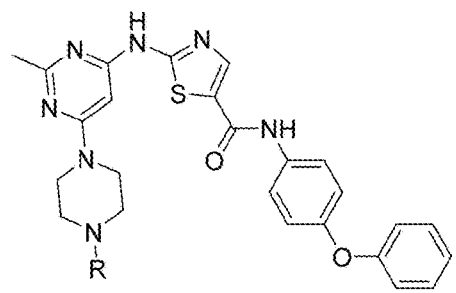
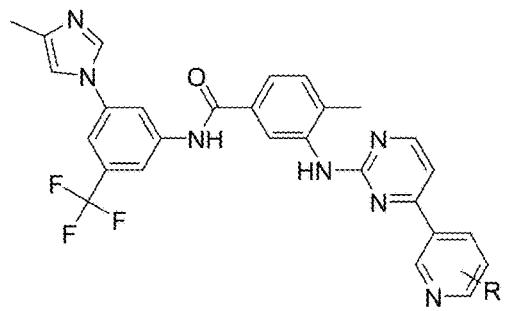

FIG. 8GGG
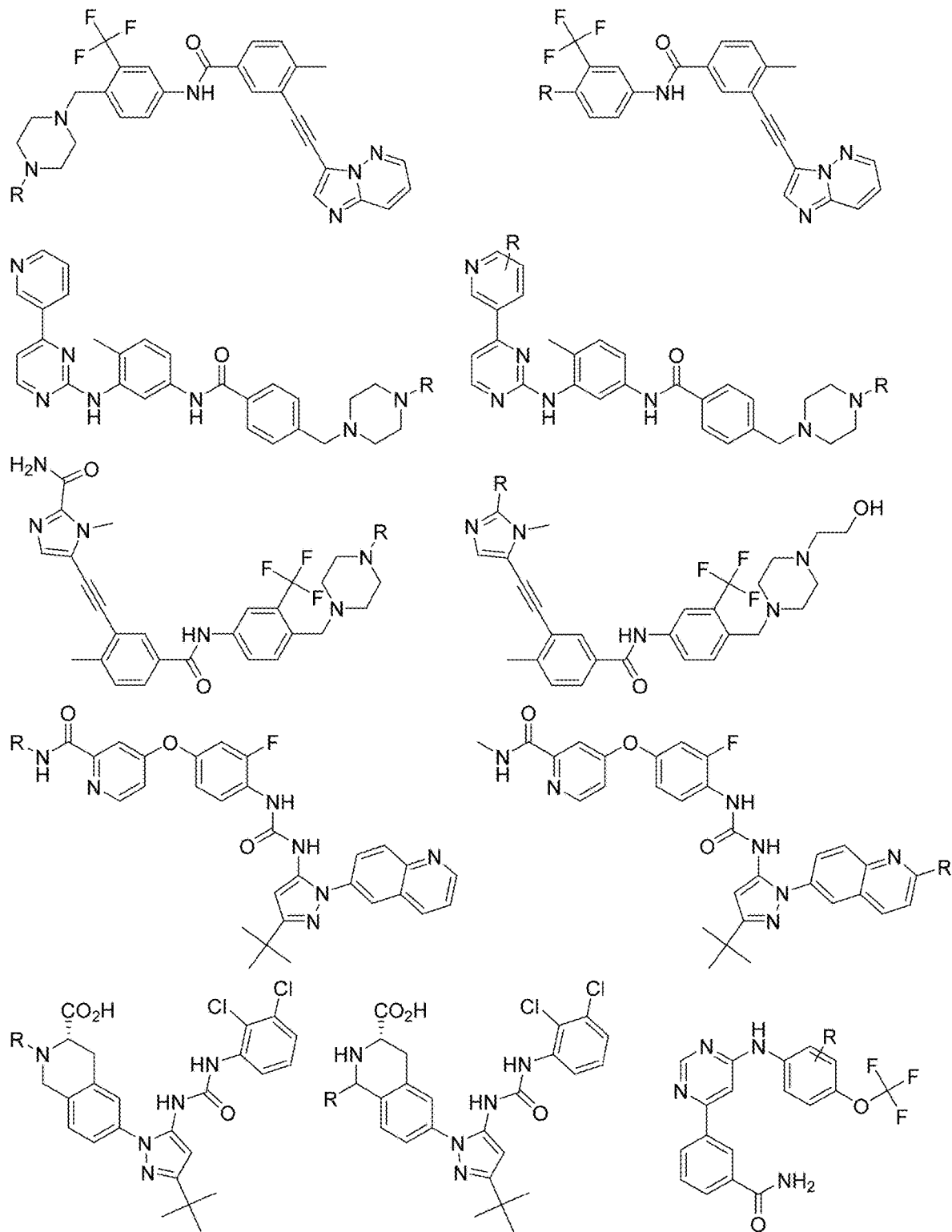

FIG. 8HHH
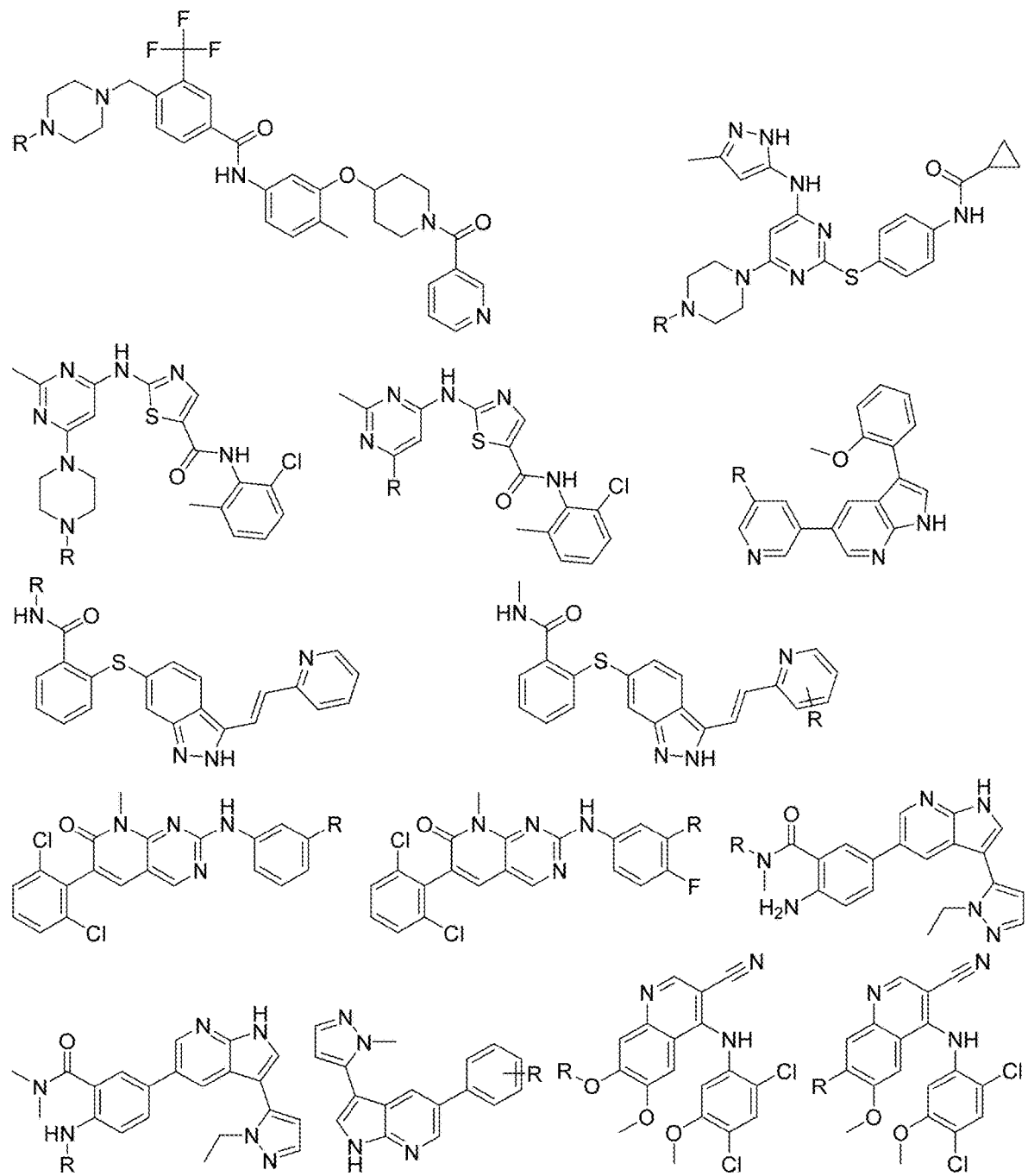

FIG. 8III
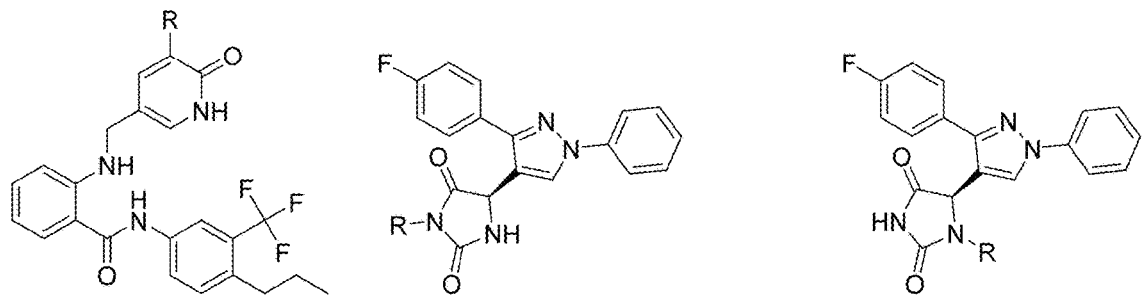
FIG. 8JJJ
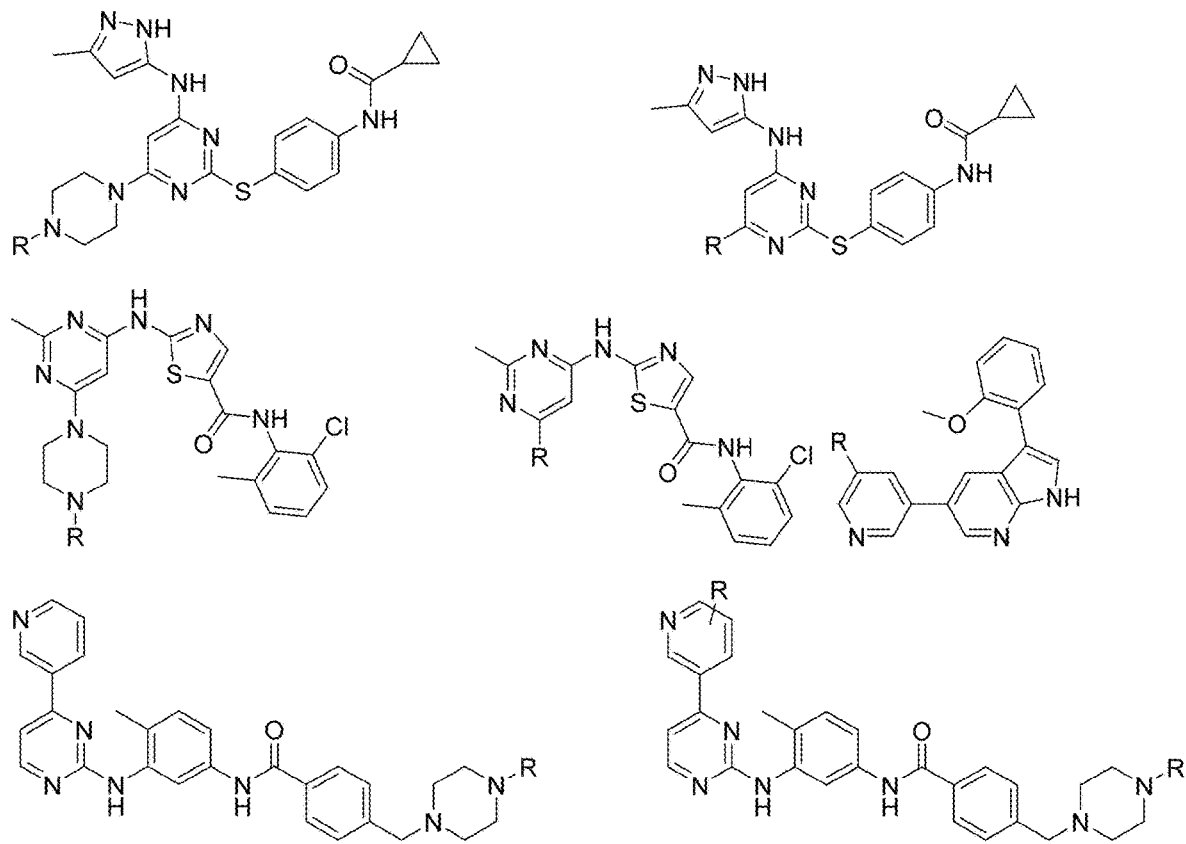

FIG. 8KKK
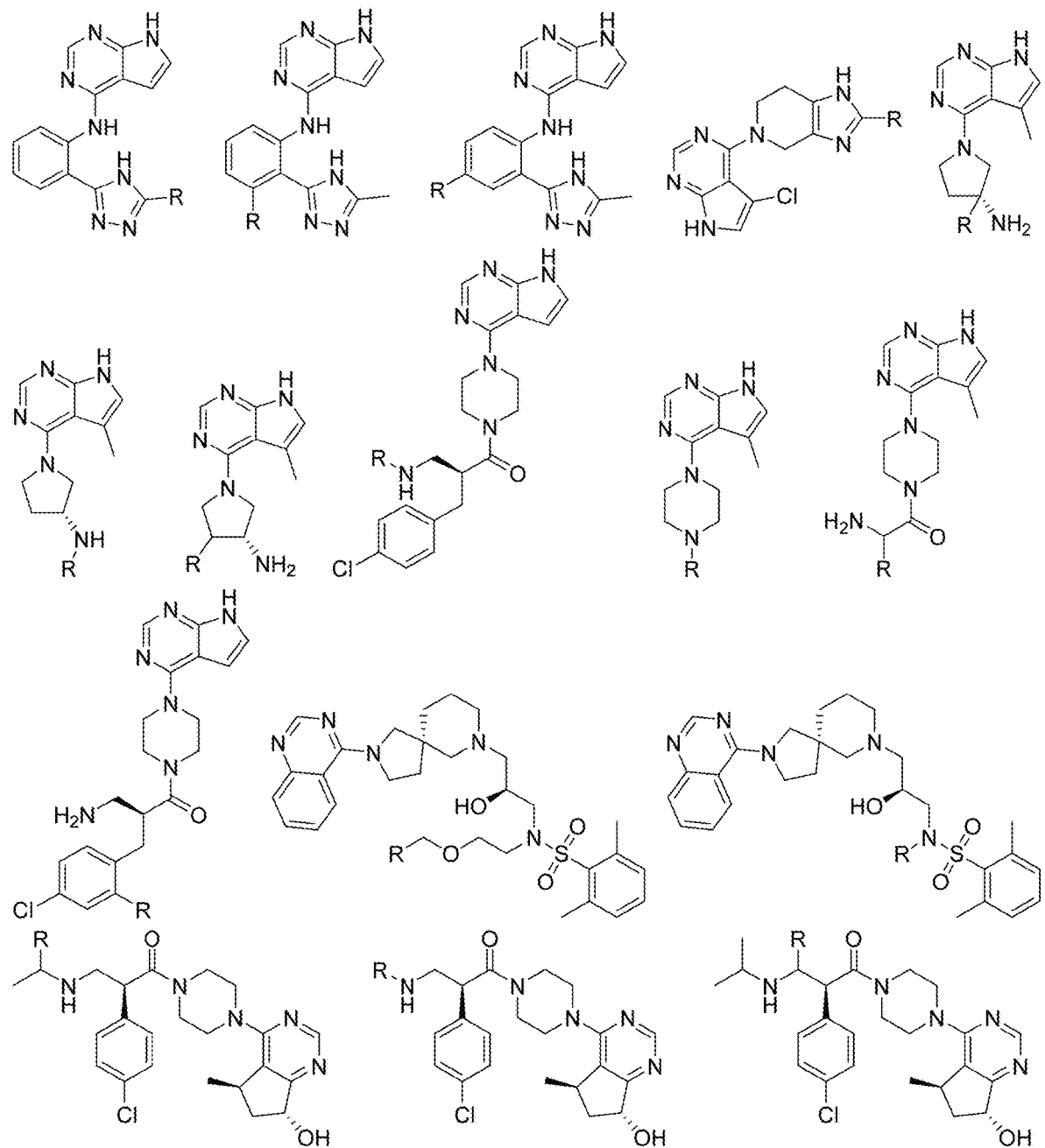

FIG. 8LLL
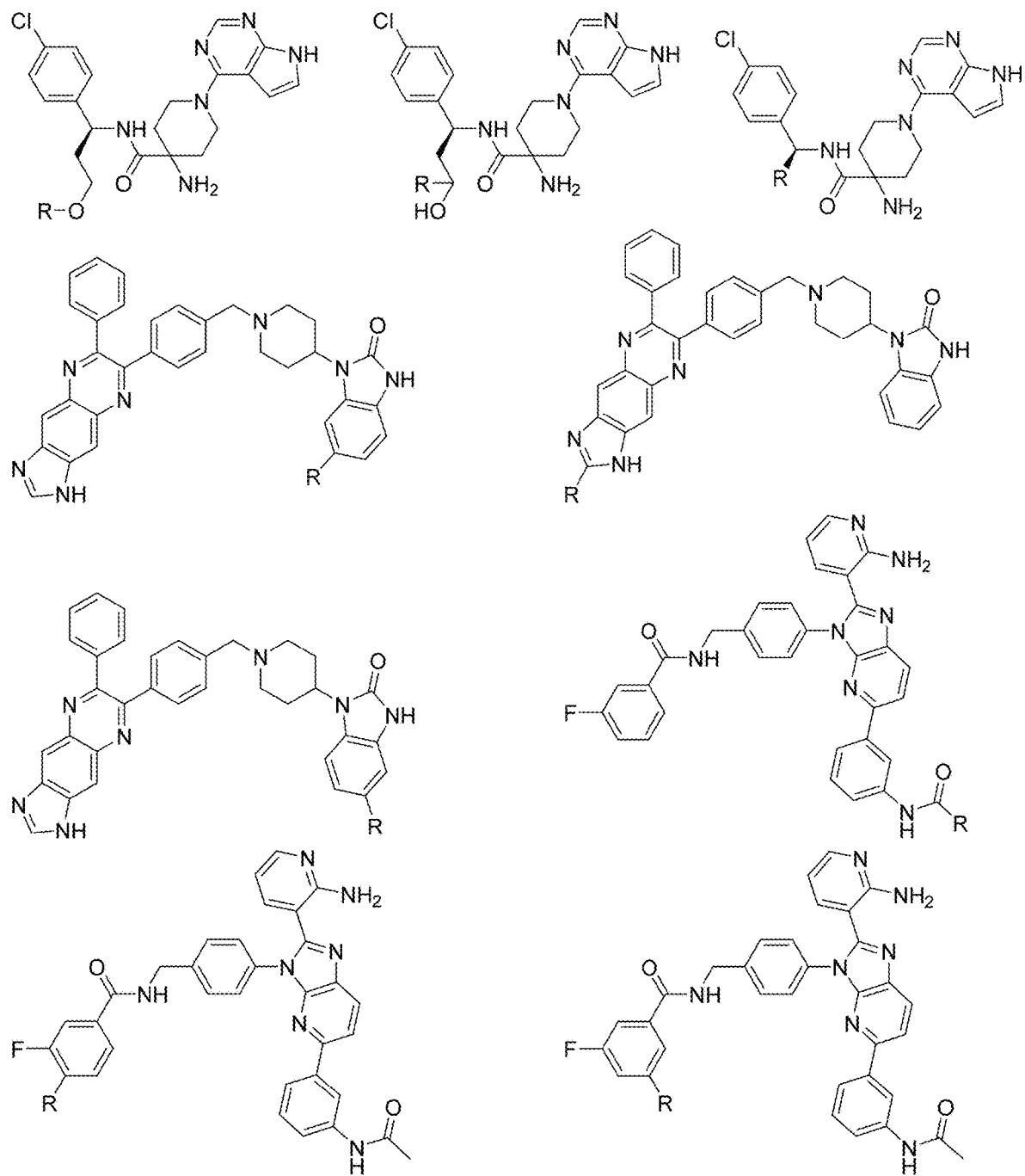

FIG. 8MMM
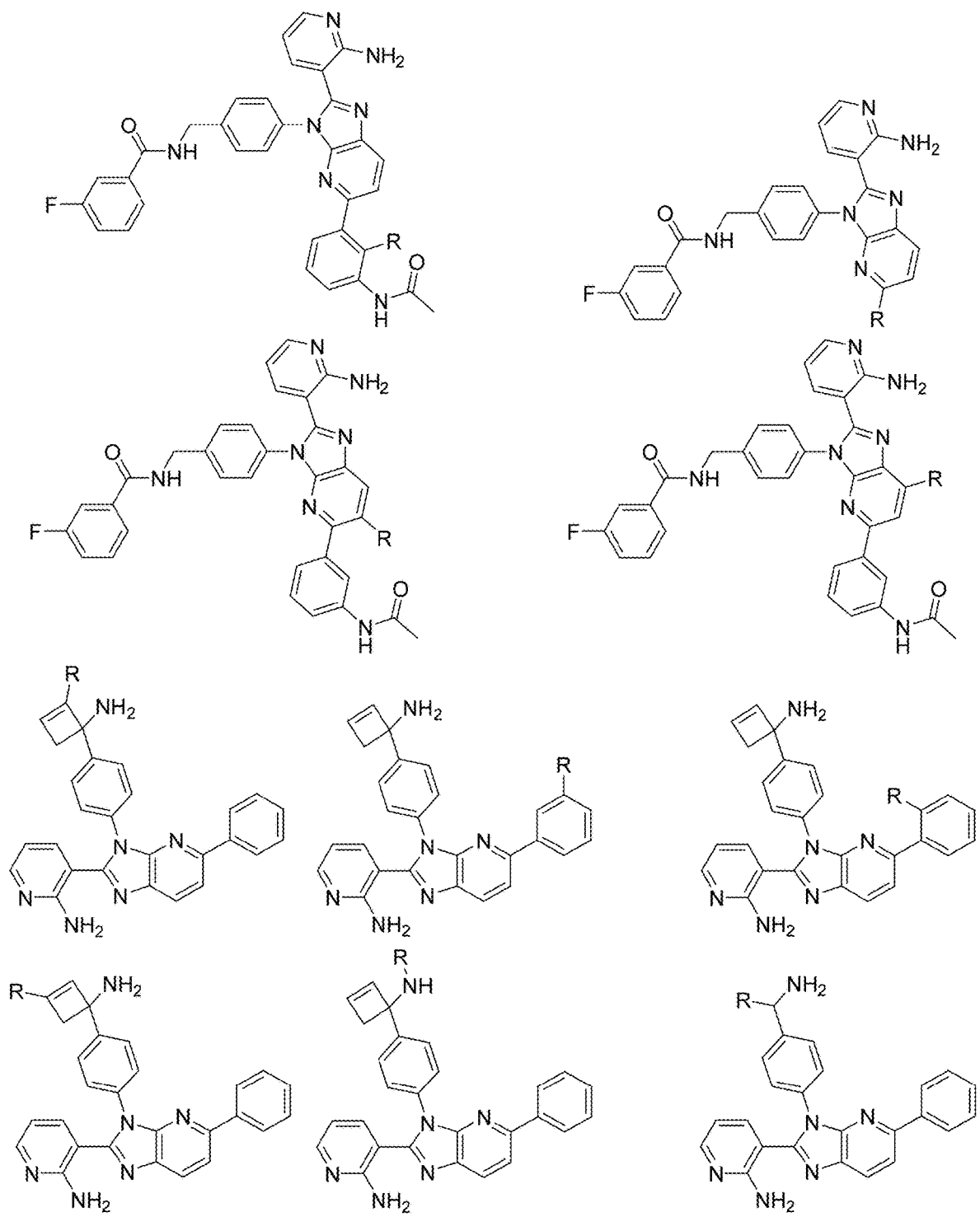

FIG. 8NNN
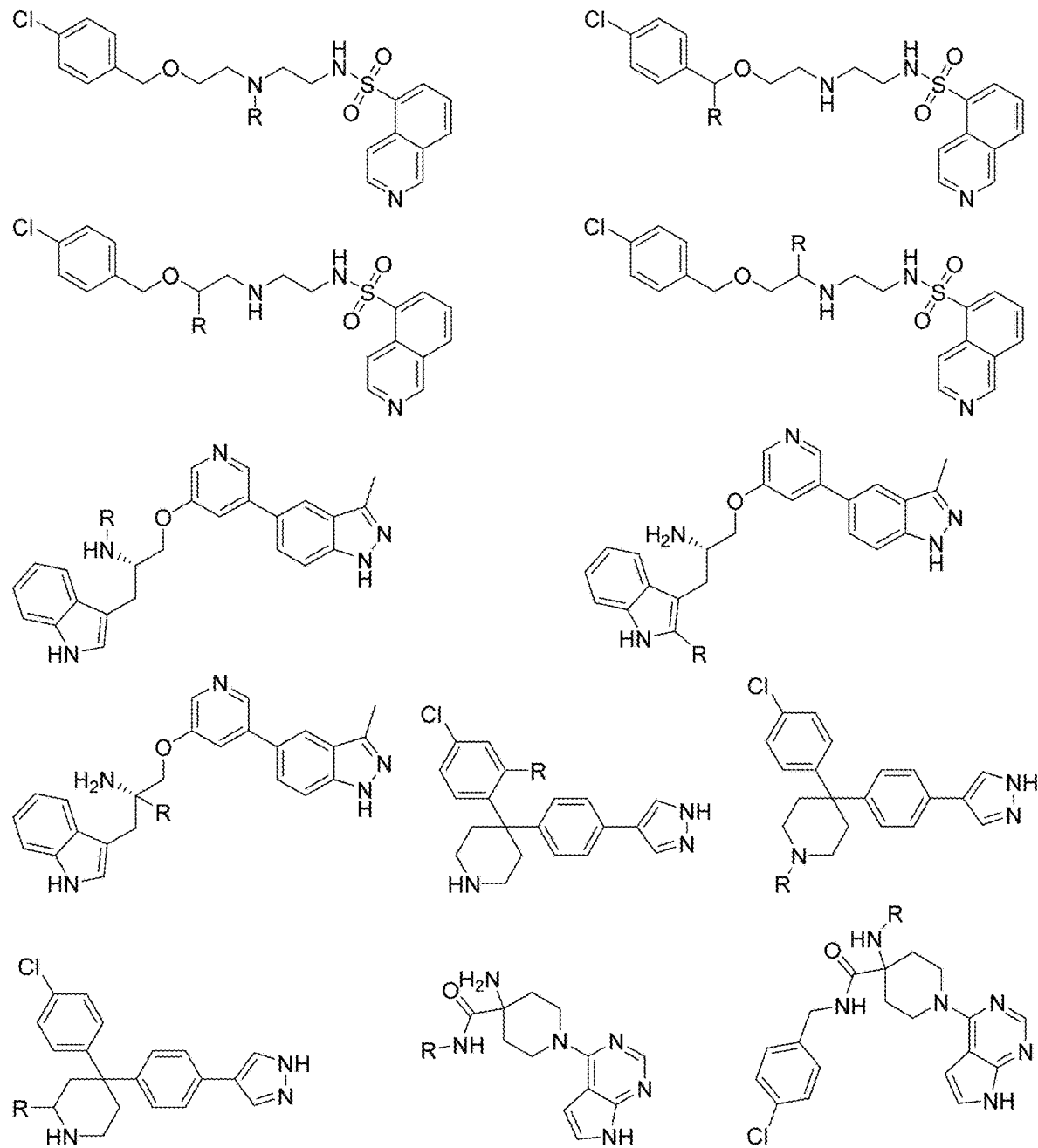

FIG. 8OOO
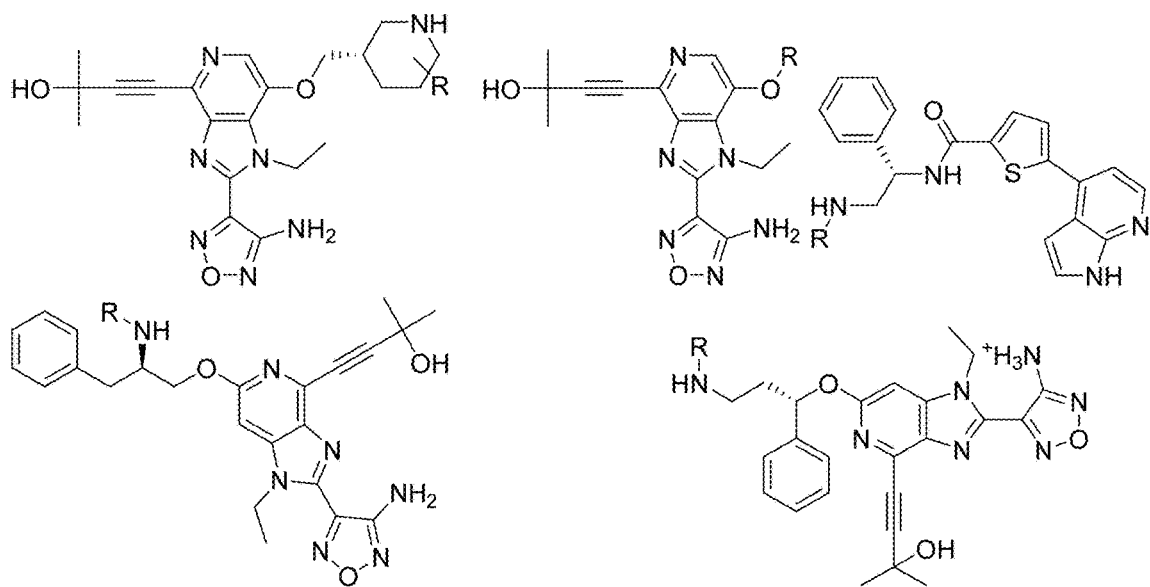
FIG. 8PPP
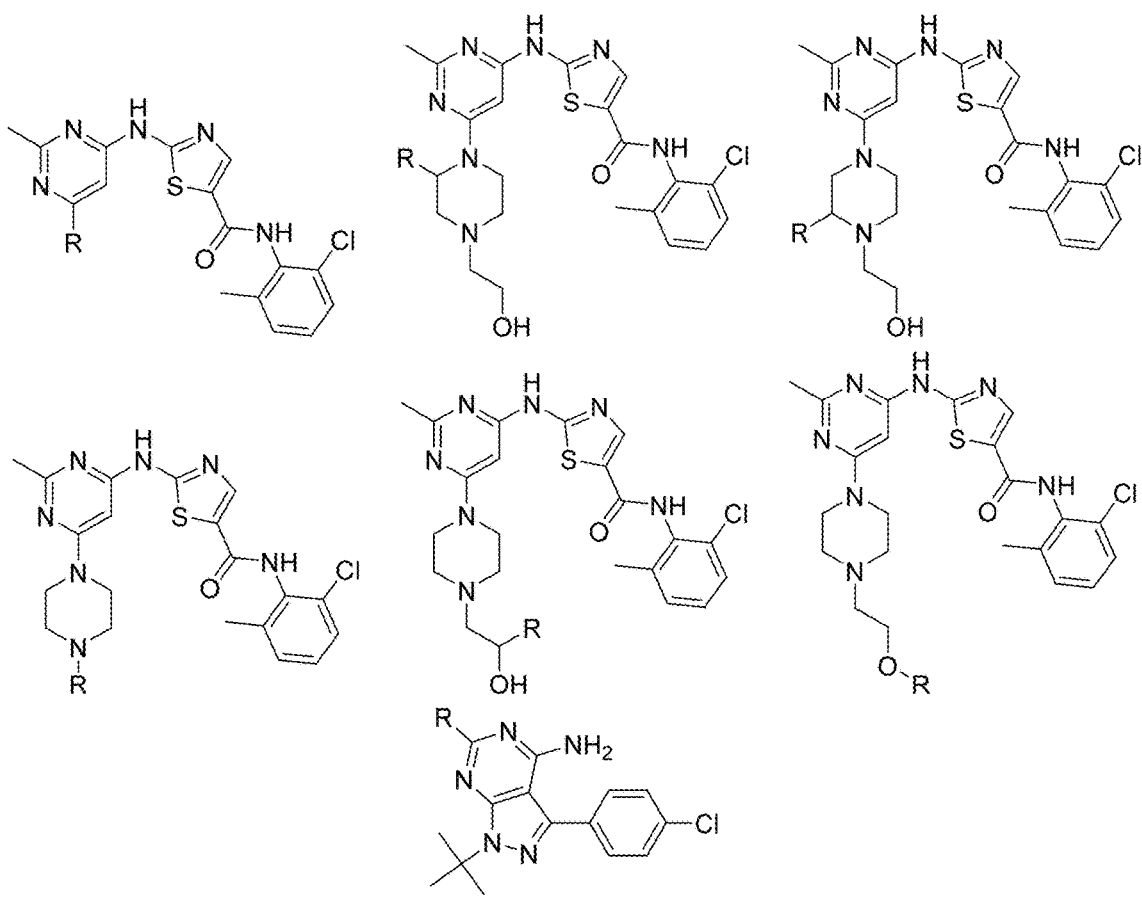

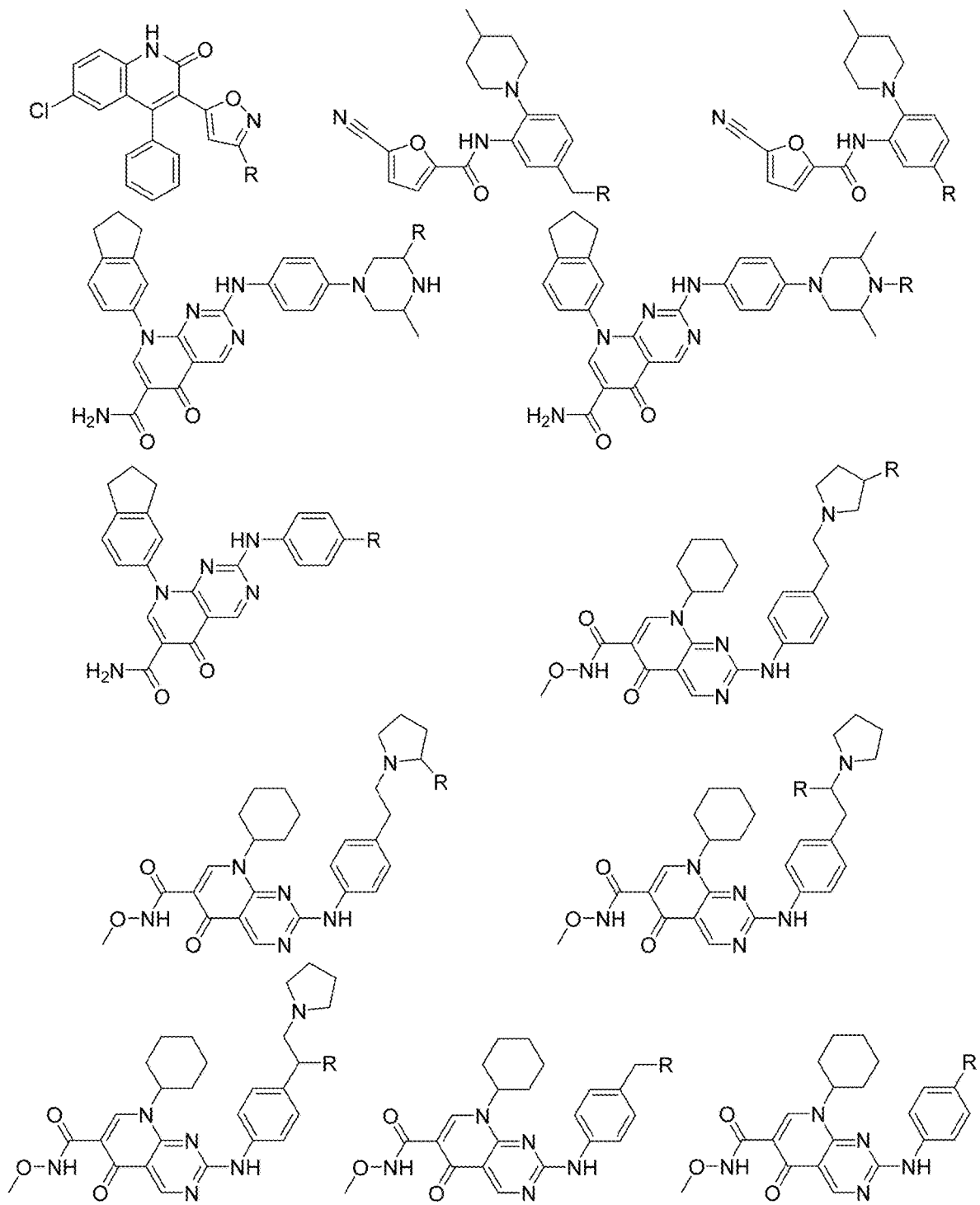
FIG. 8QQQ

FIG. 8RRR
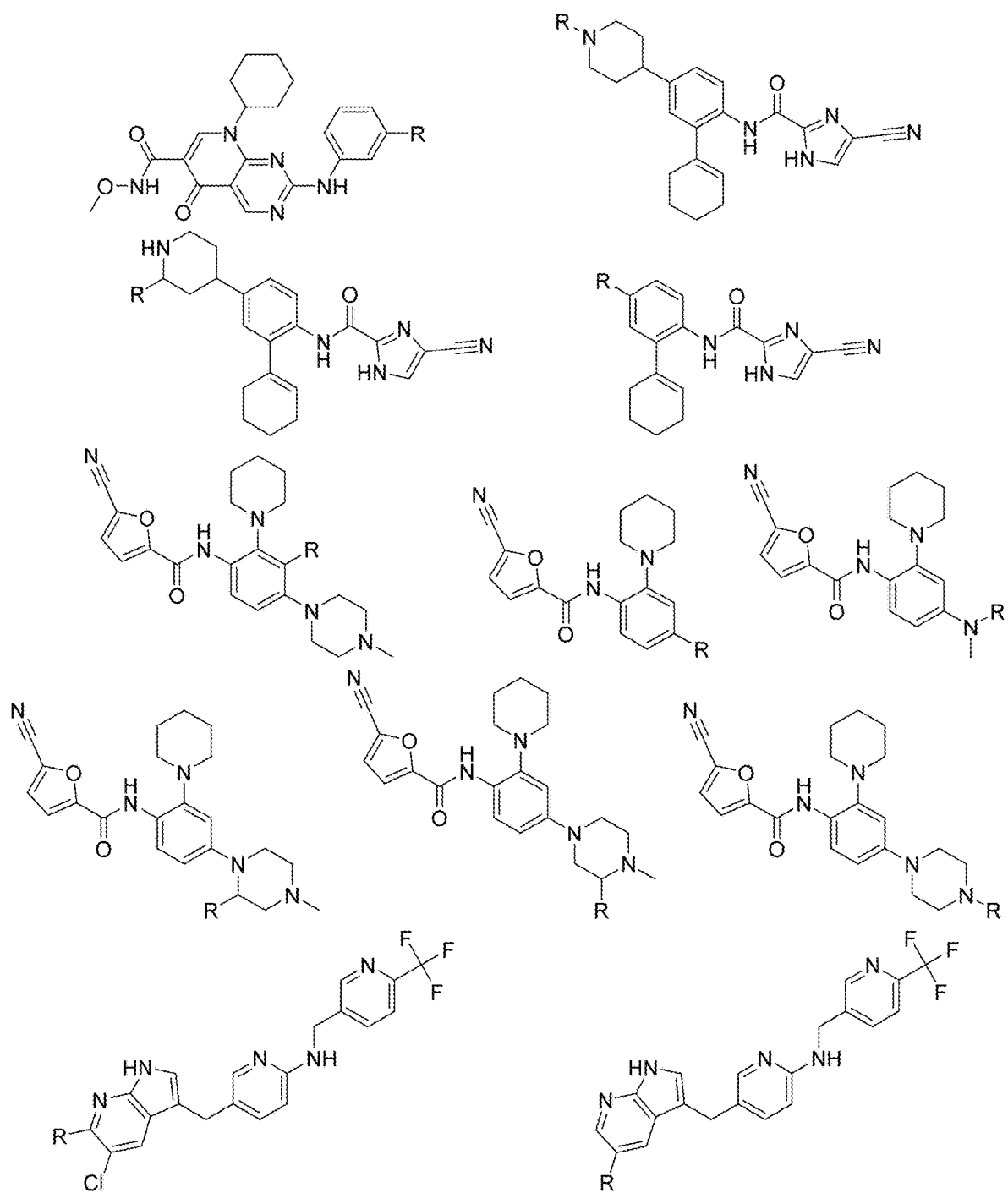

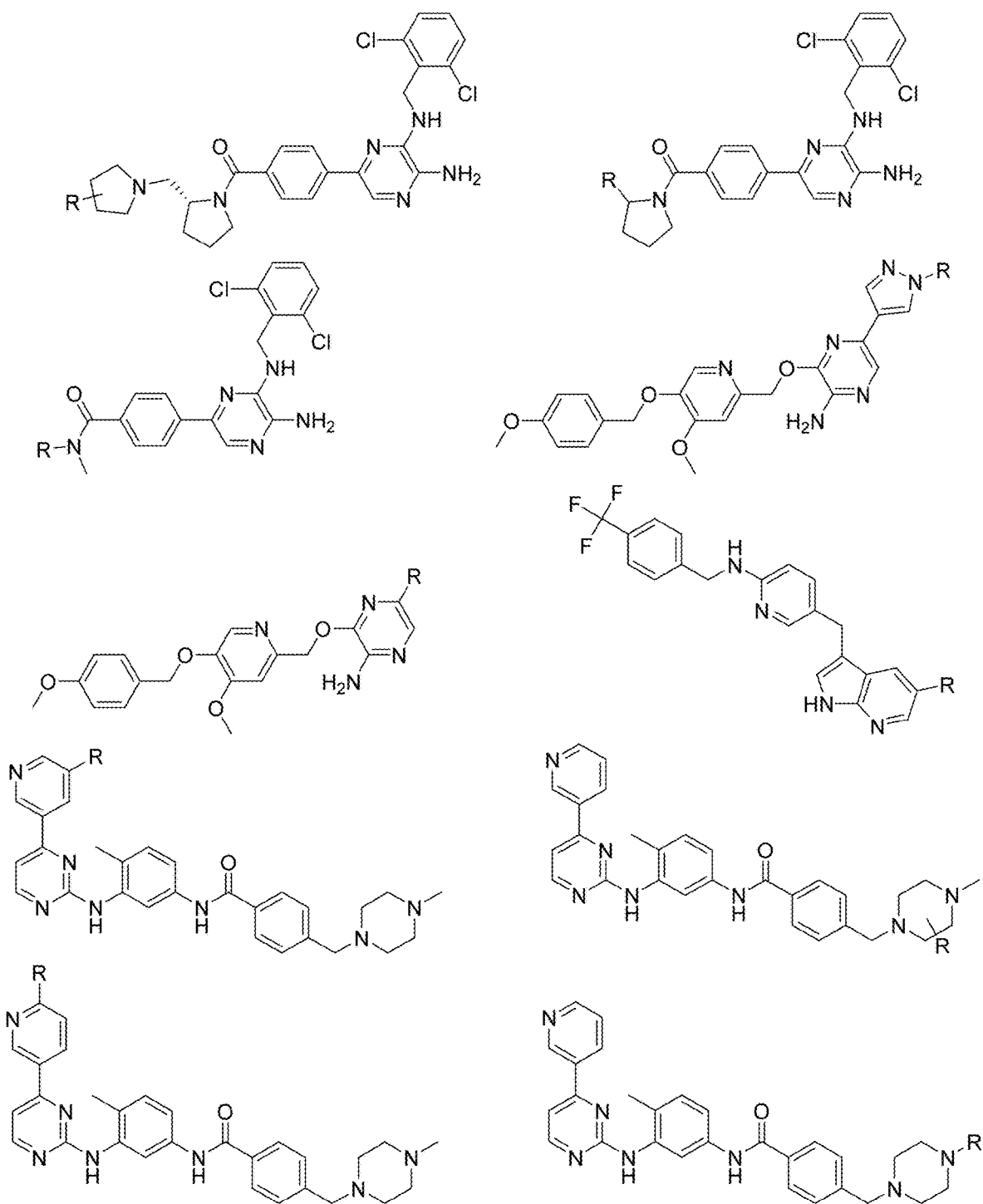
FIG. 8SSS

FIG. 8TTT
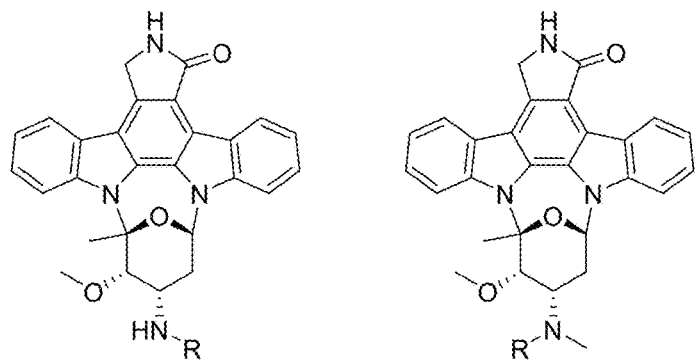
FIG. 8UUU
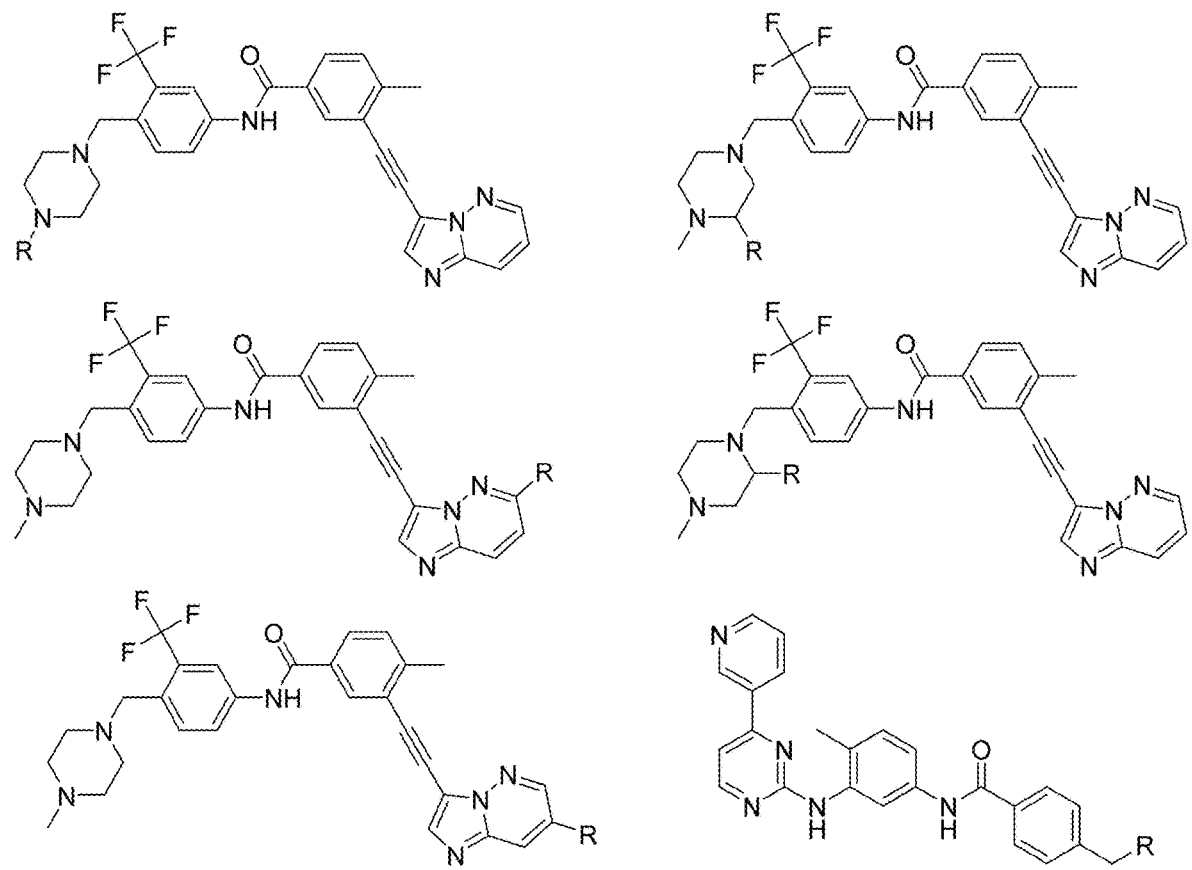

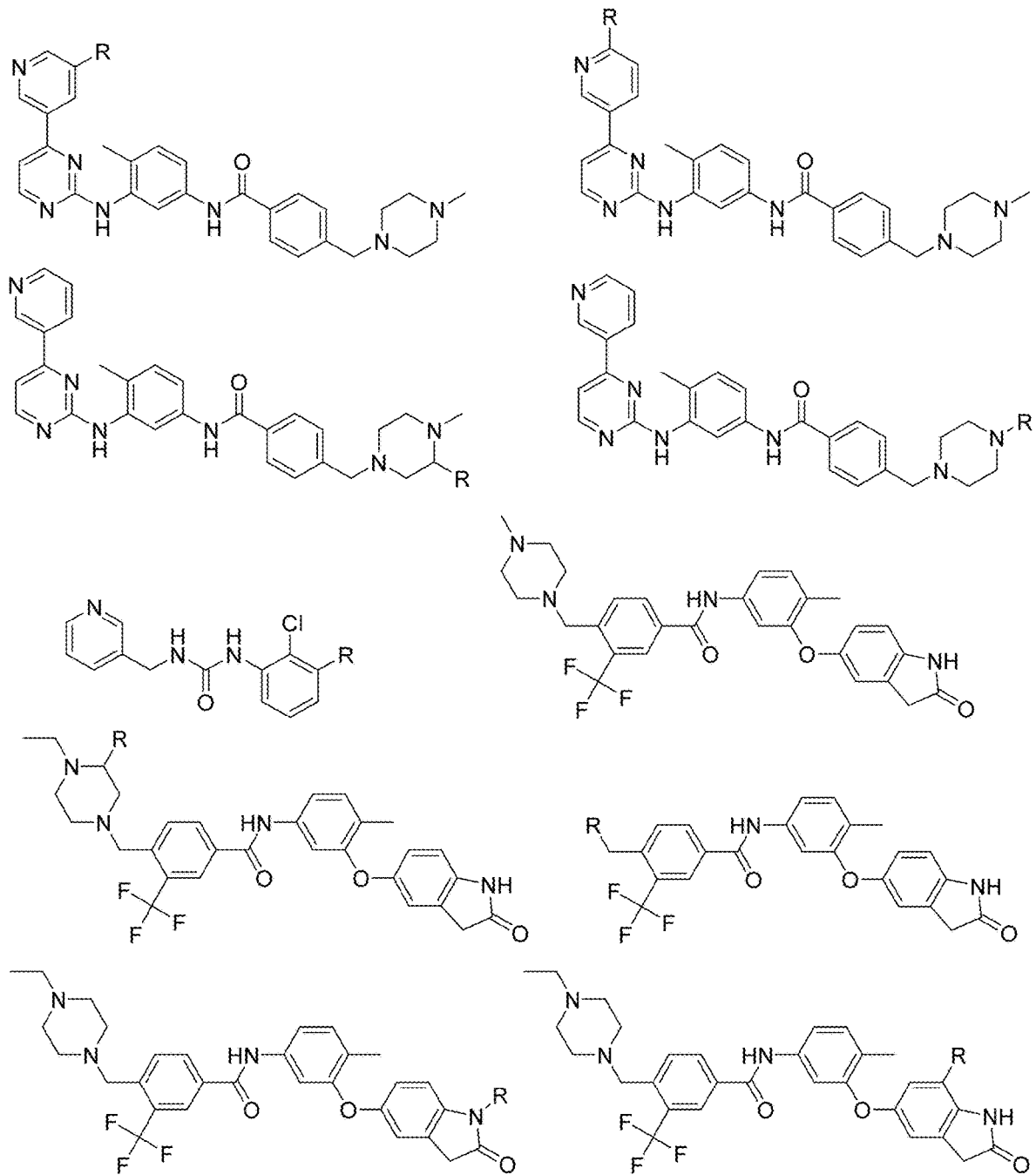
FIG. 8VVV

FIG. 8WWW
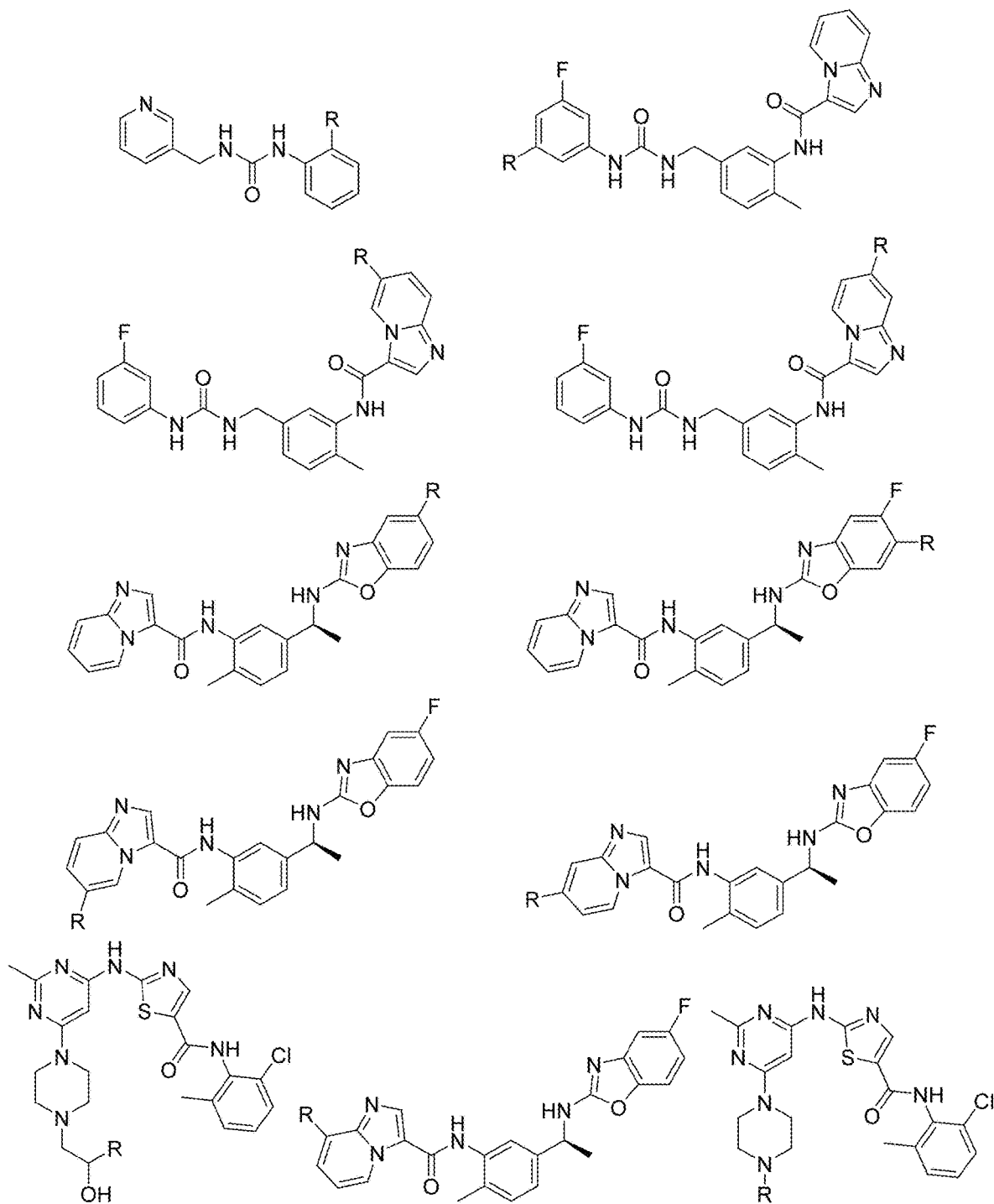

FIG. 8XXX
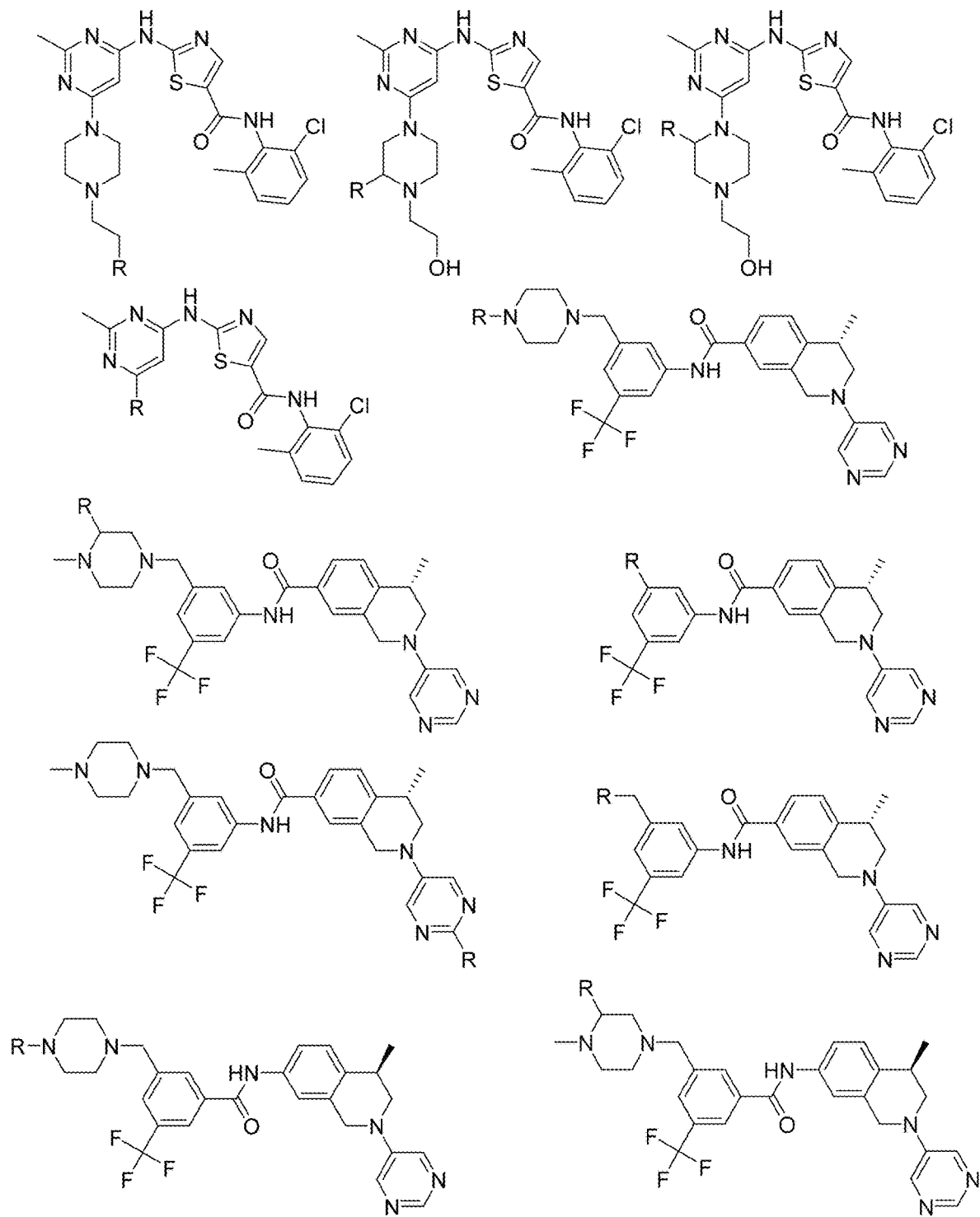

FIG. 8YYY
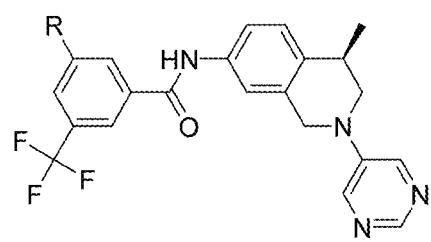
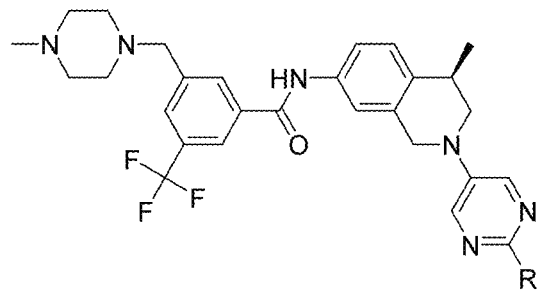
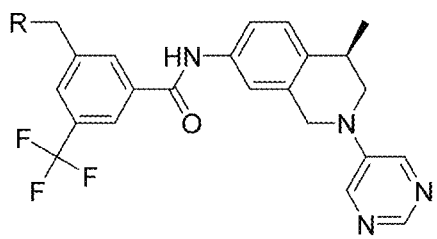
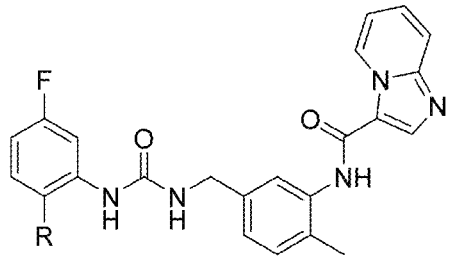
FIG. 8ZZZ
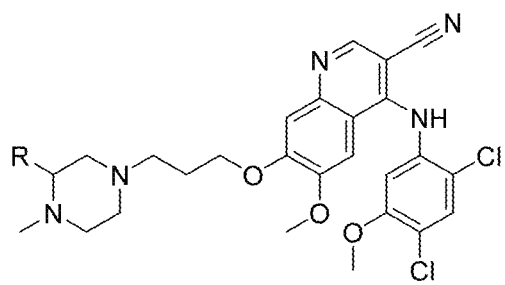
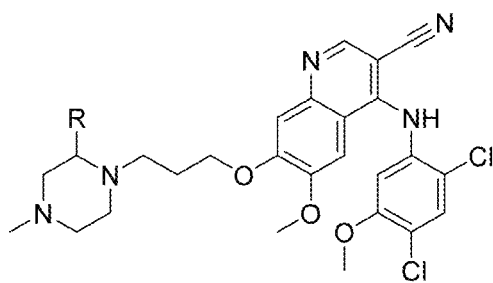
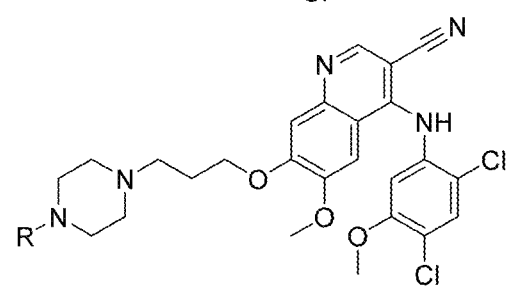
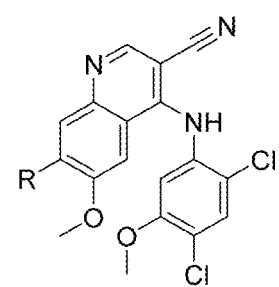
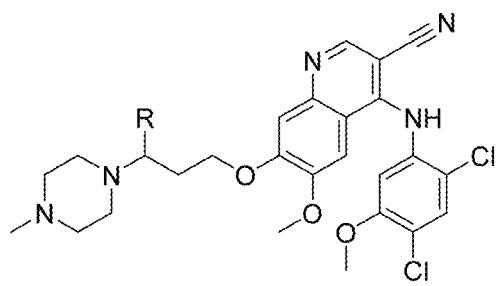
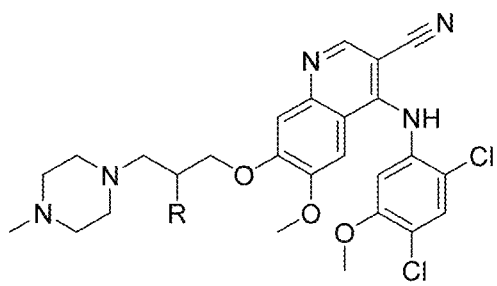

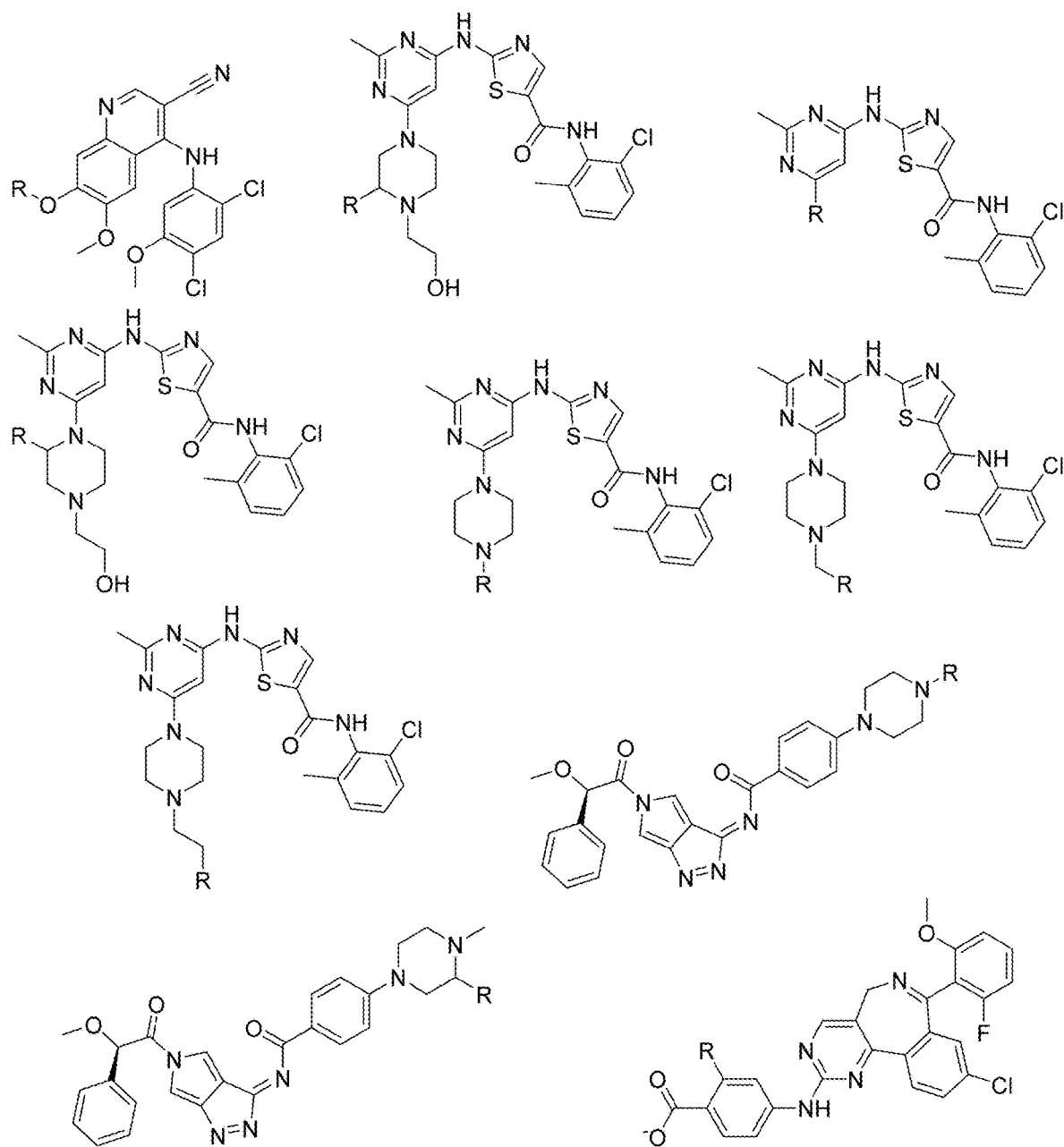
FIG. 8AAAA

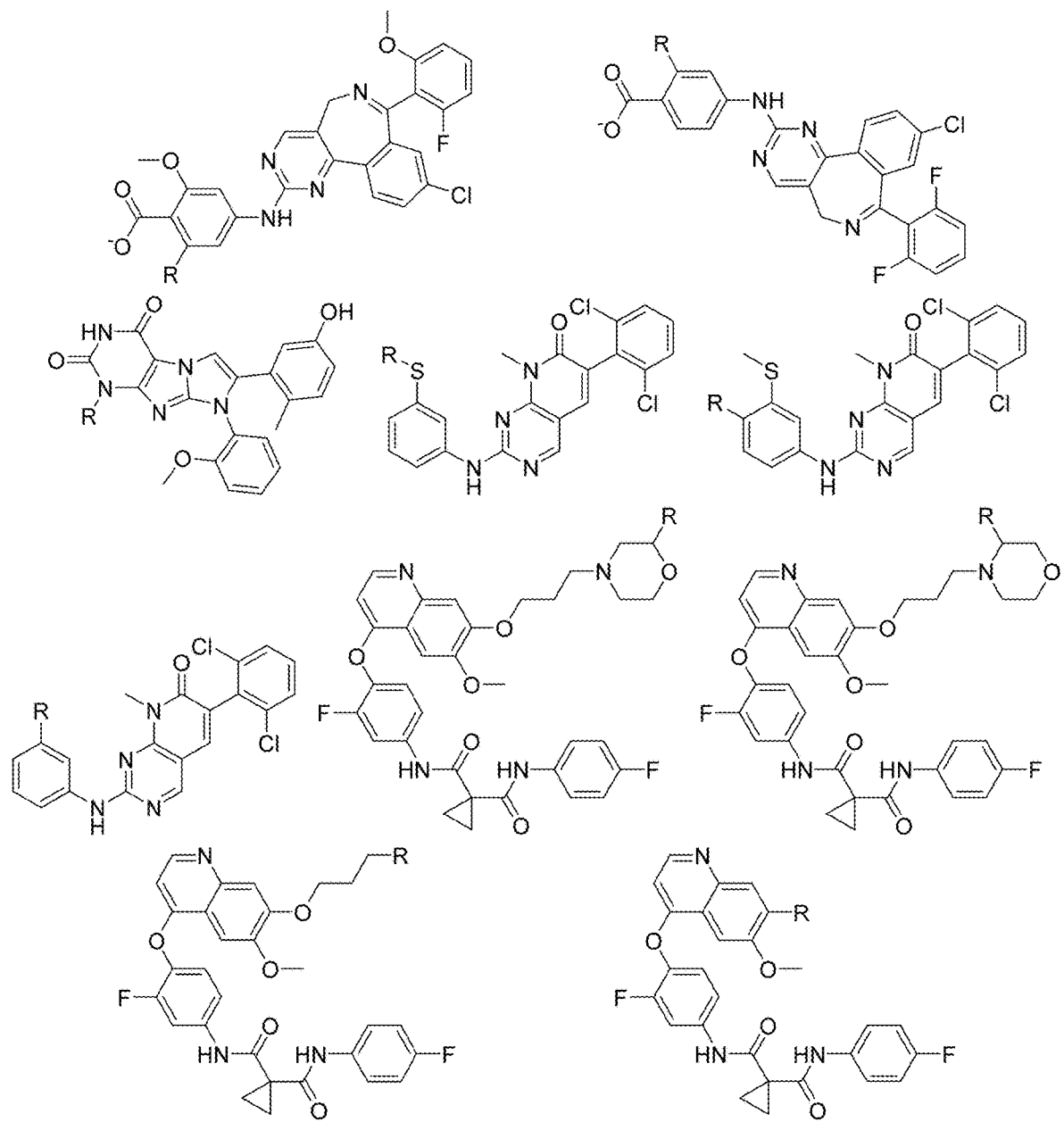
FIG. 8BBBB

FIG. 8CCCC
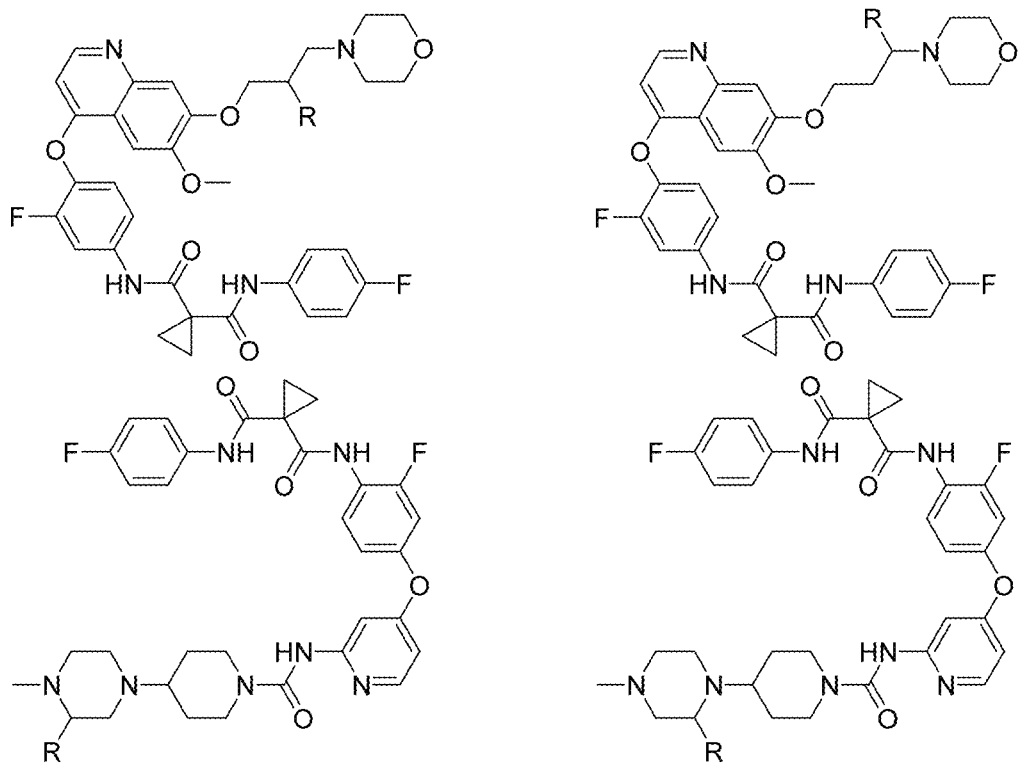
FIG. 8DDDD
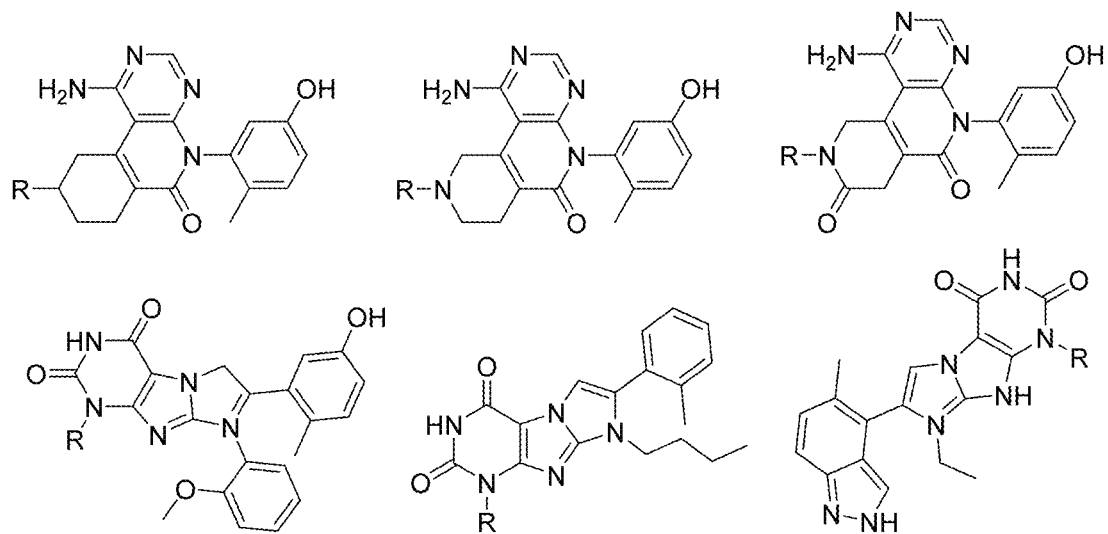

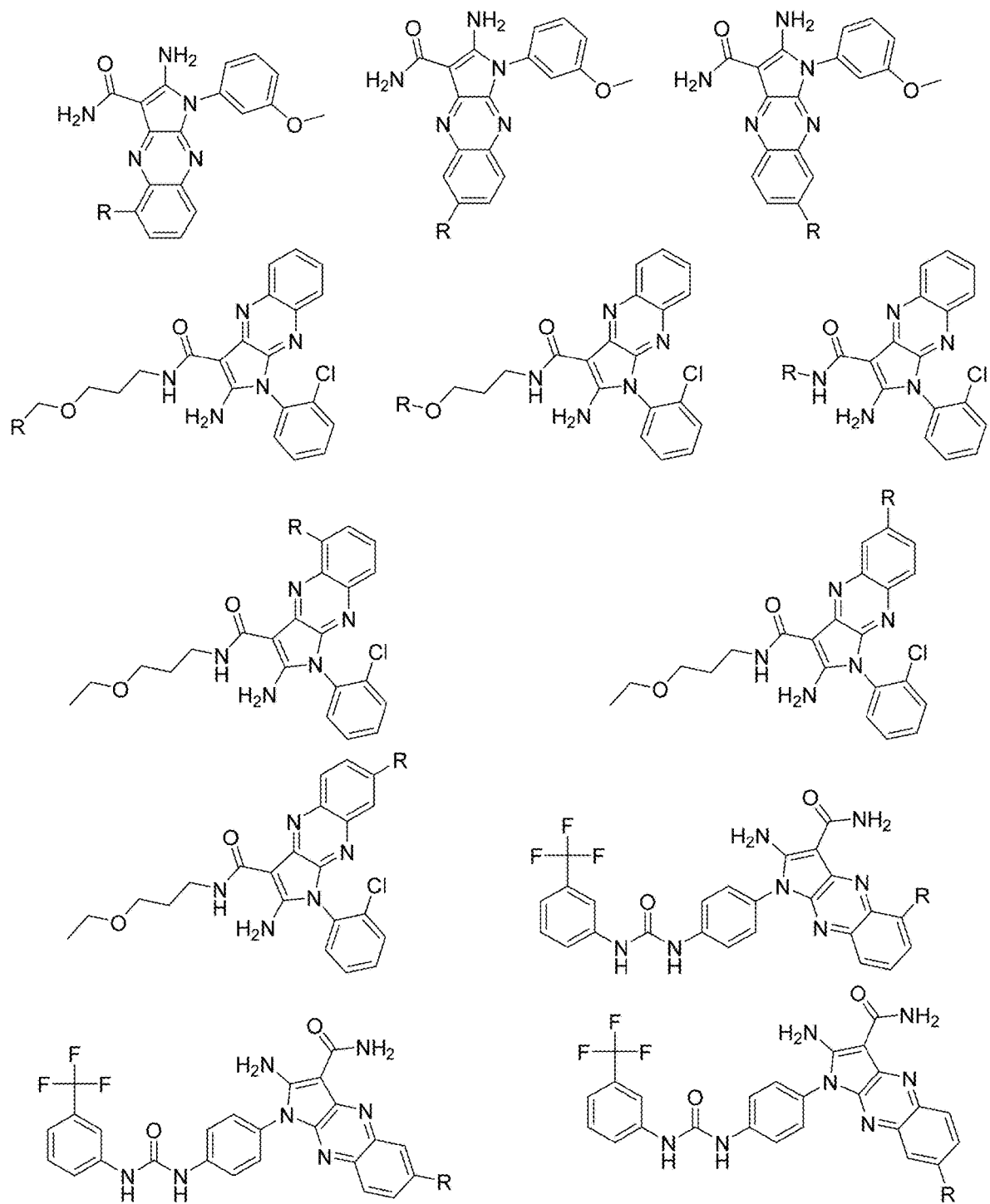
FIG. 8EEEE

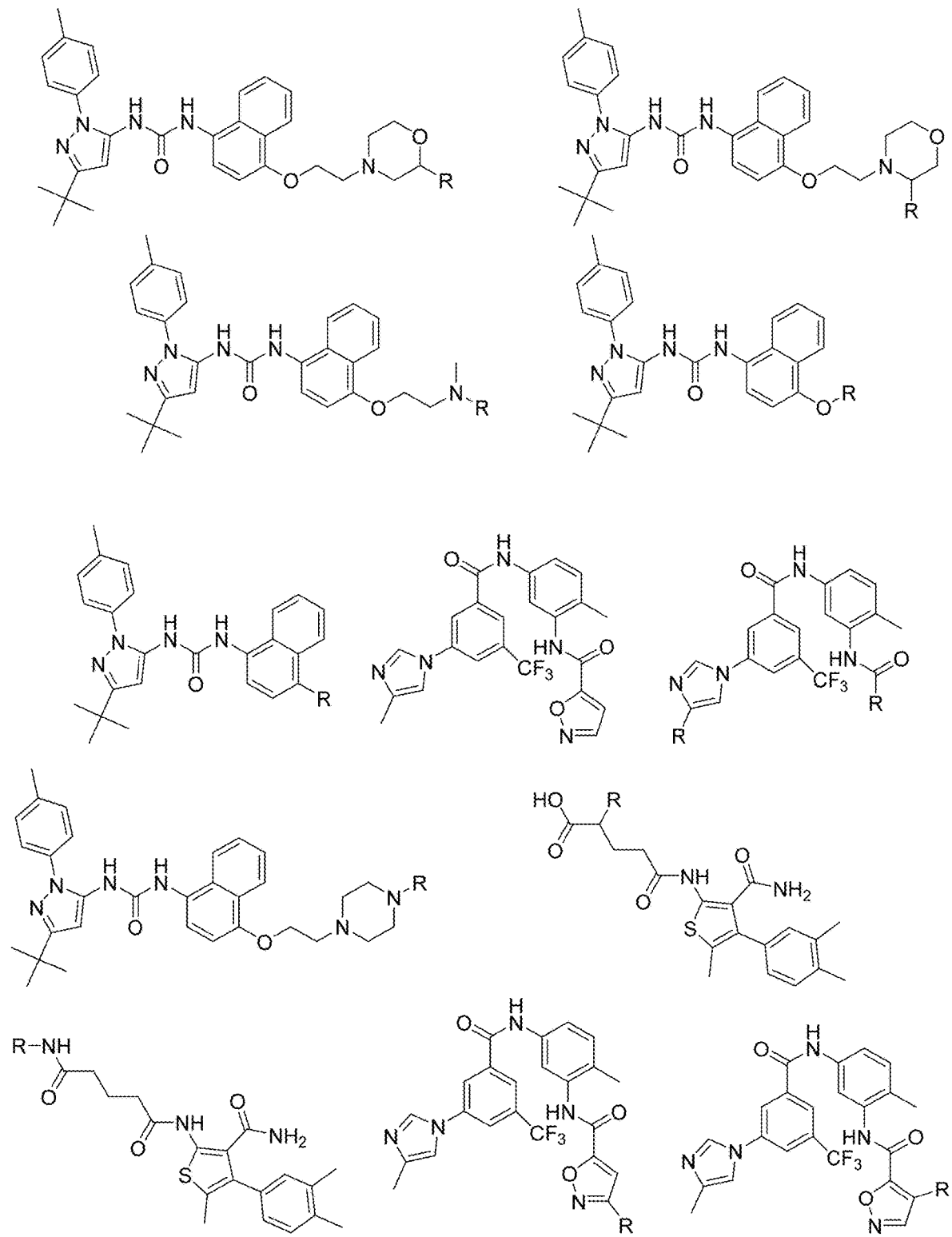
FIG. 8FFFF

FIG. 8GGGG
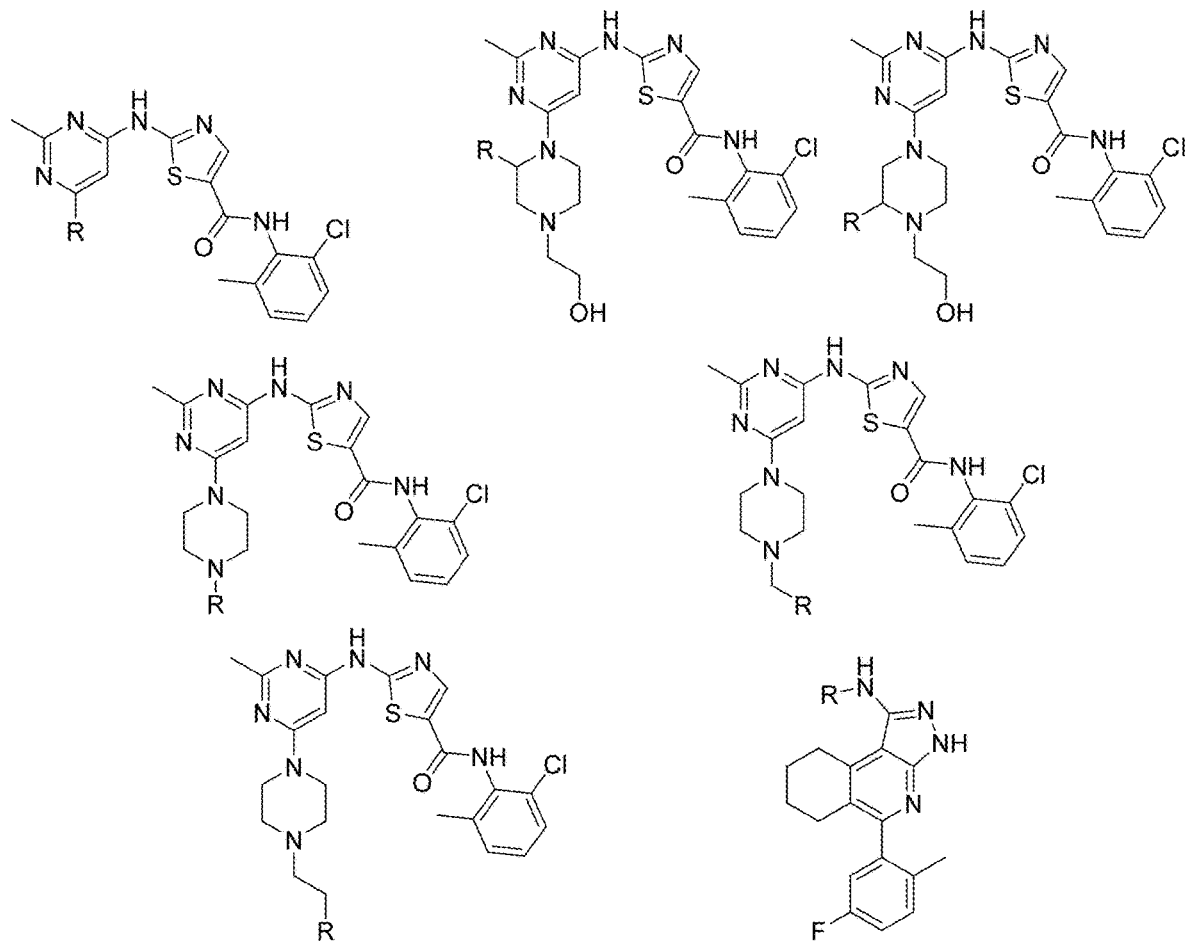
FIG. 8HHHH
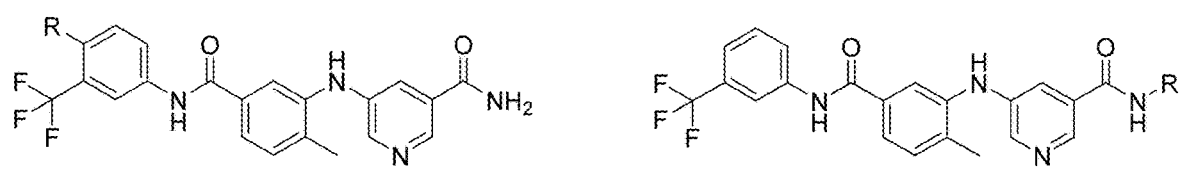
FIG. 8IIII
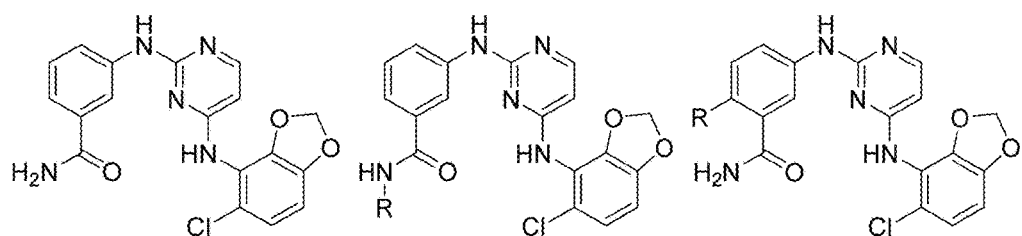

FIG. 8JJJJ
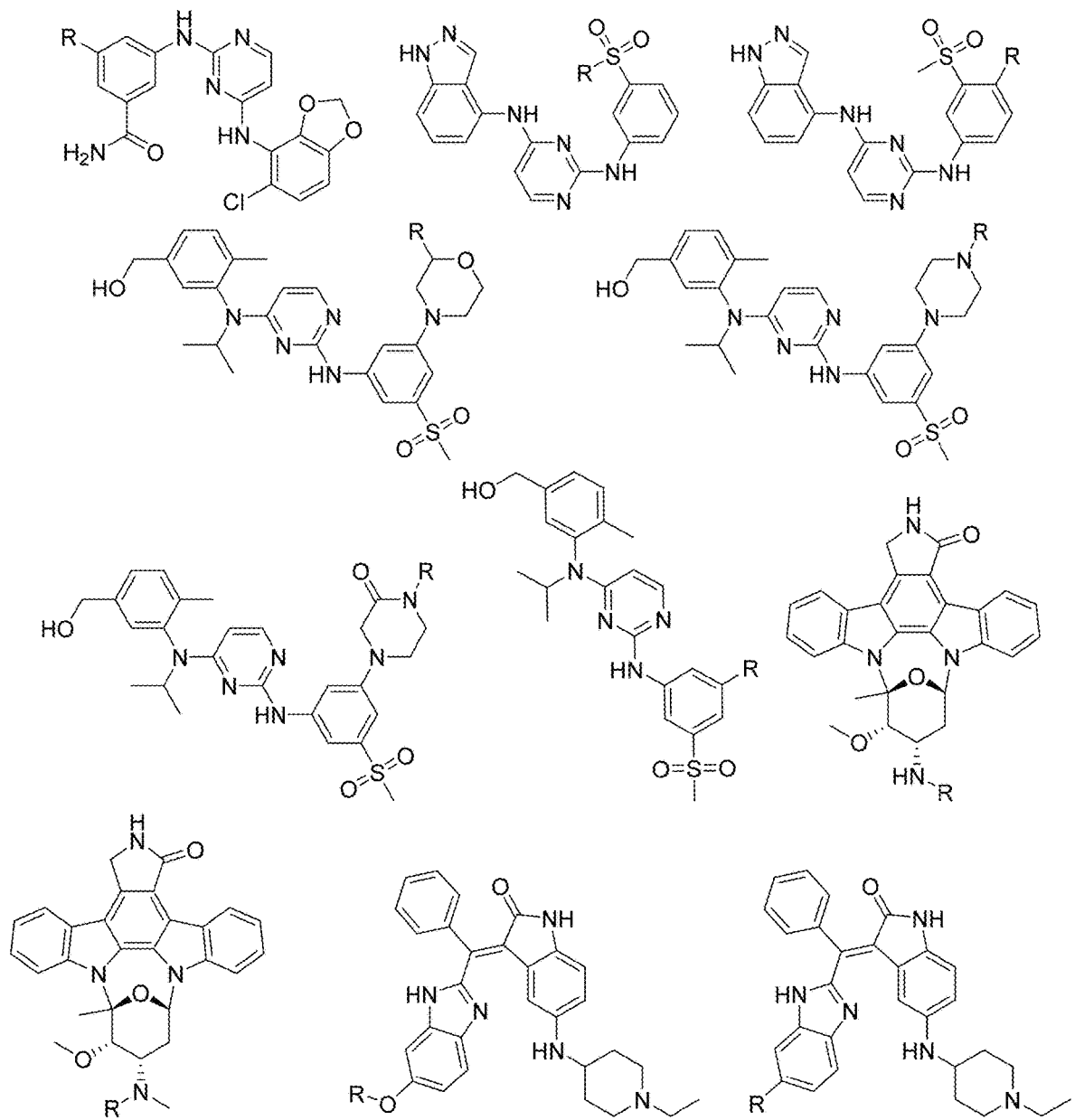

FIG. 8KKKK
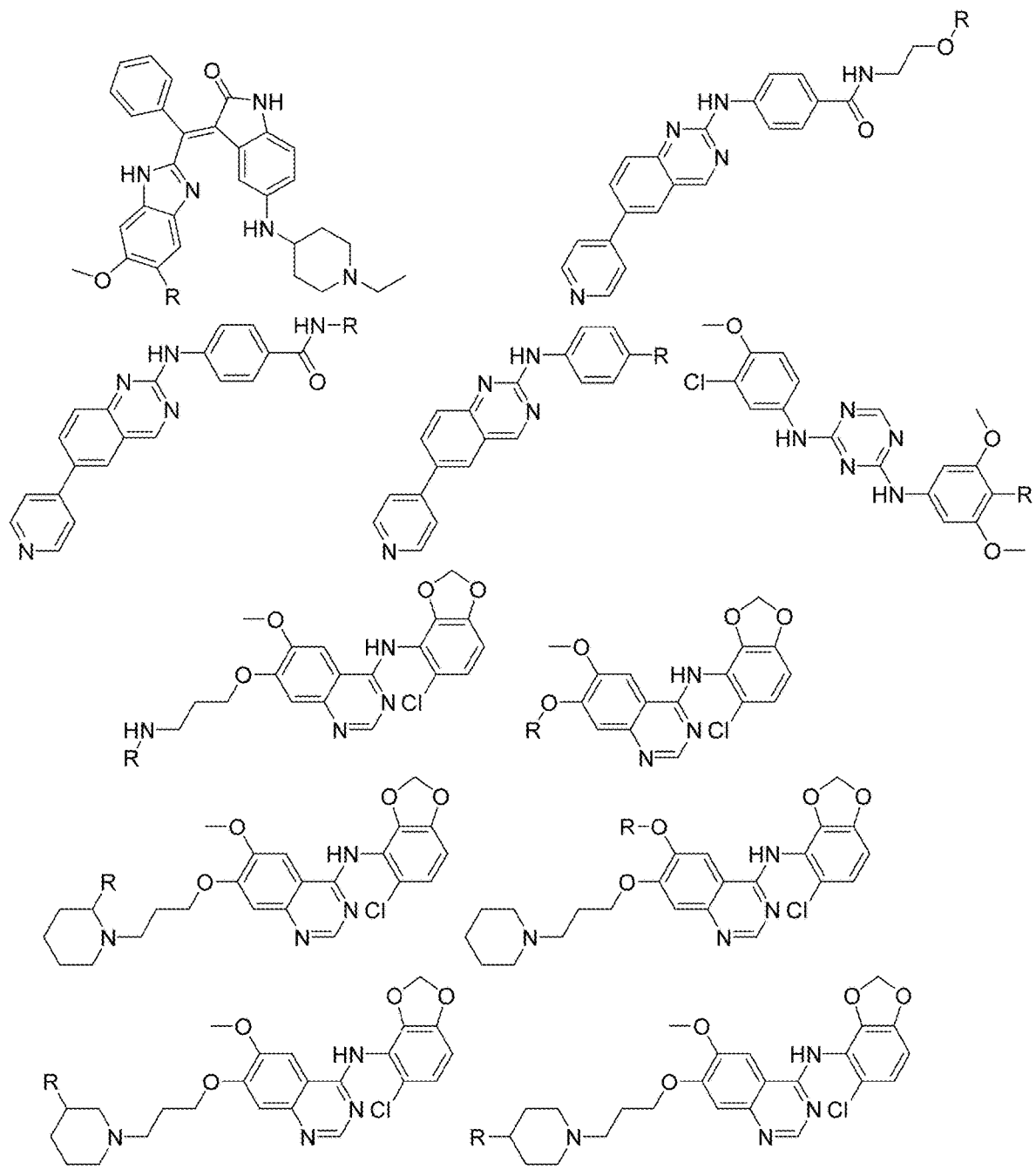

FIG. 8LLLL
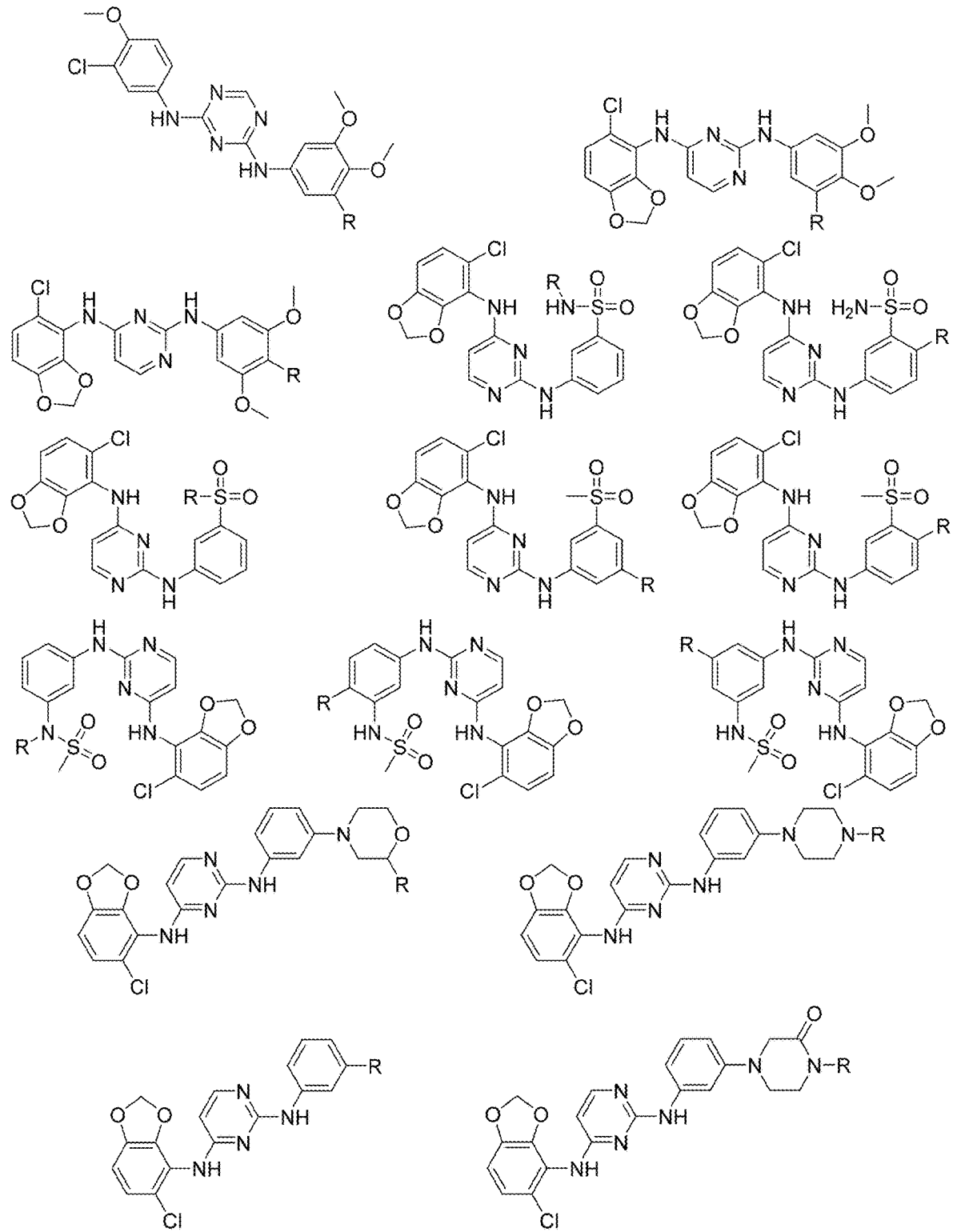

FIG. 8MMMM
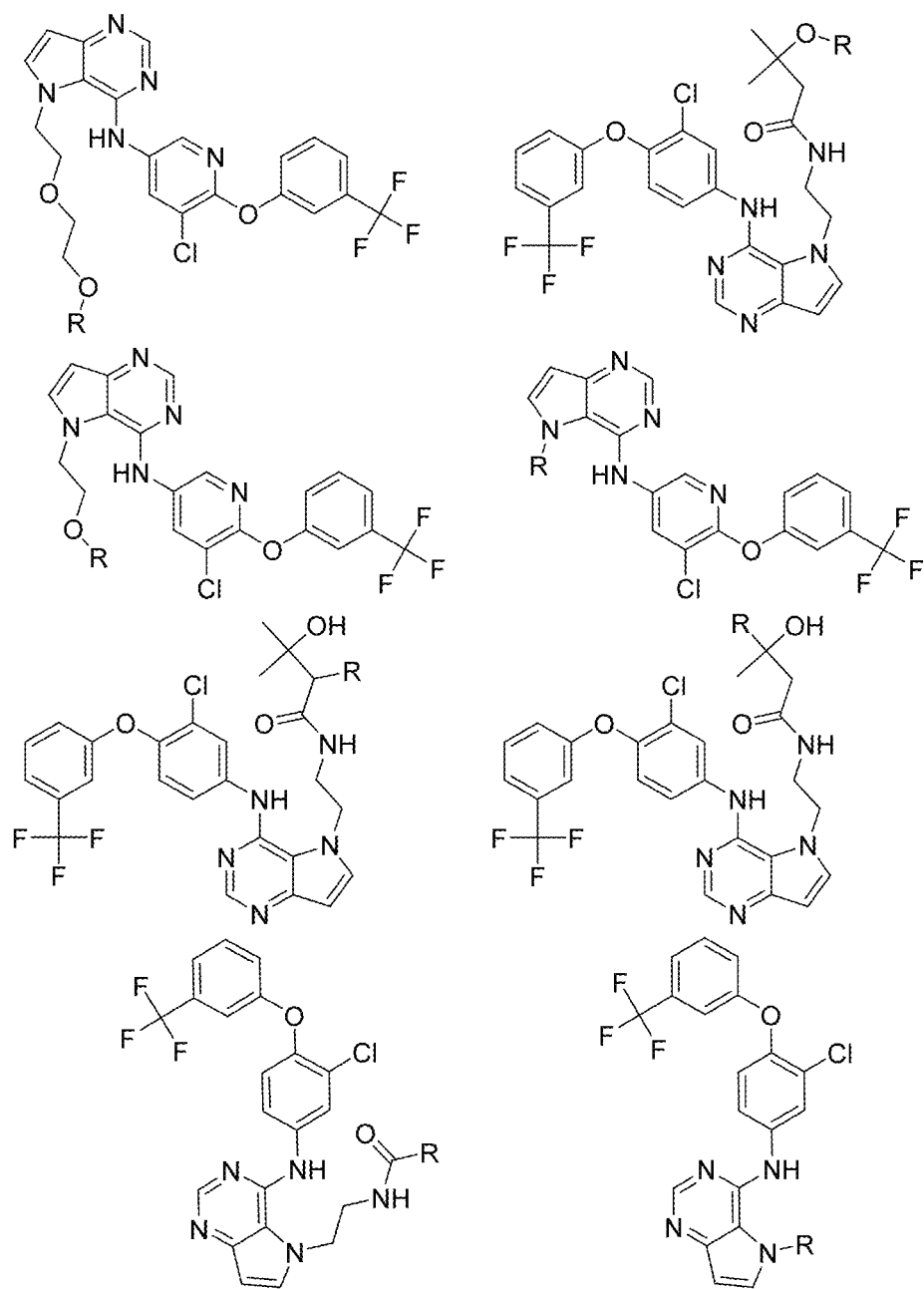

FIG. 8NNNN
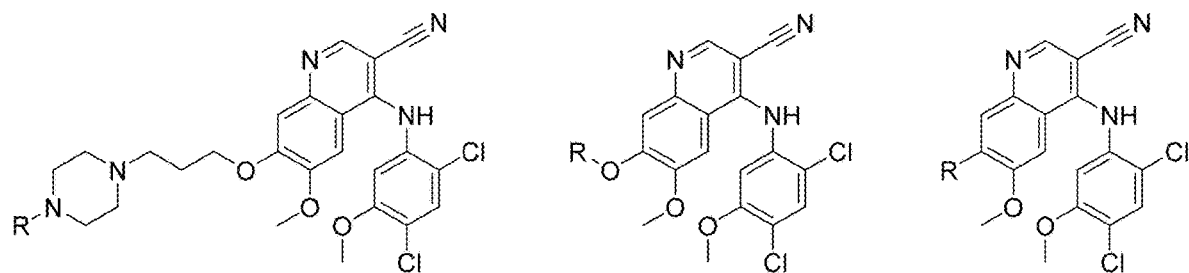
FIG. 8OOOO
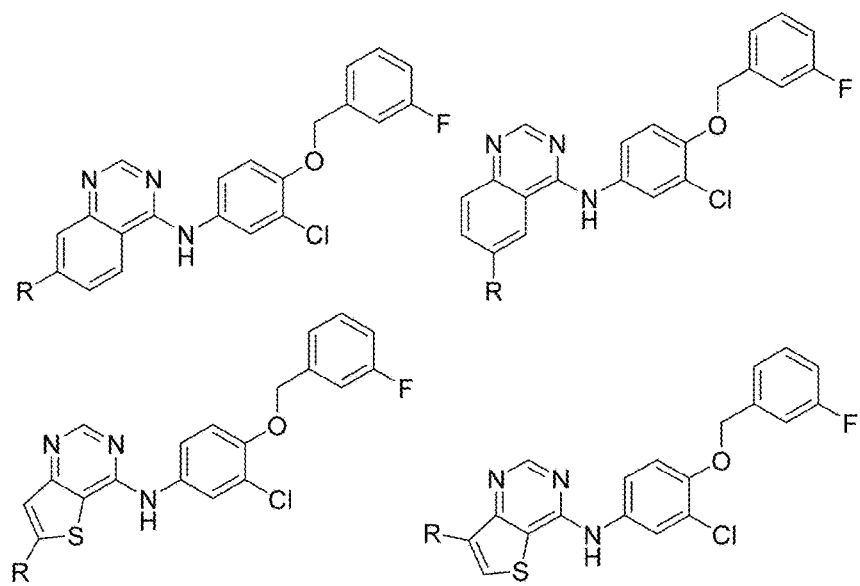
FIG. 8PPPP
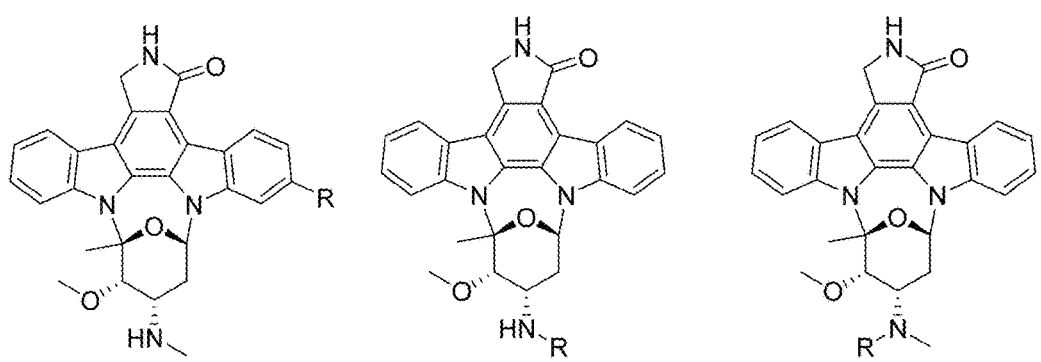

FIG. 8QQQQ
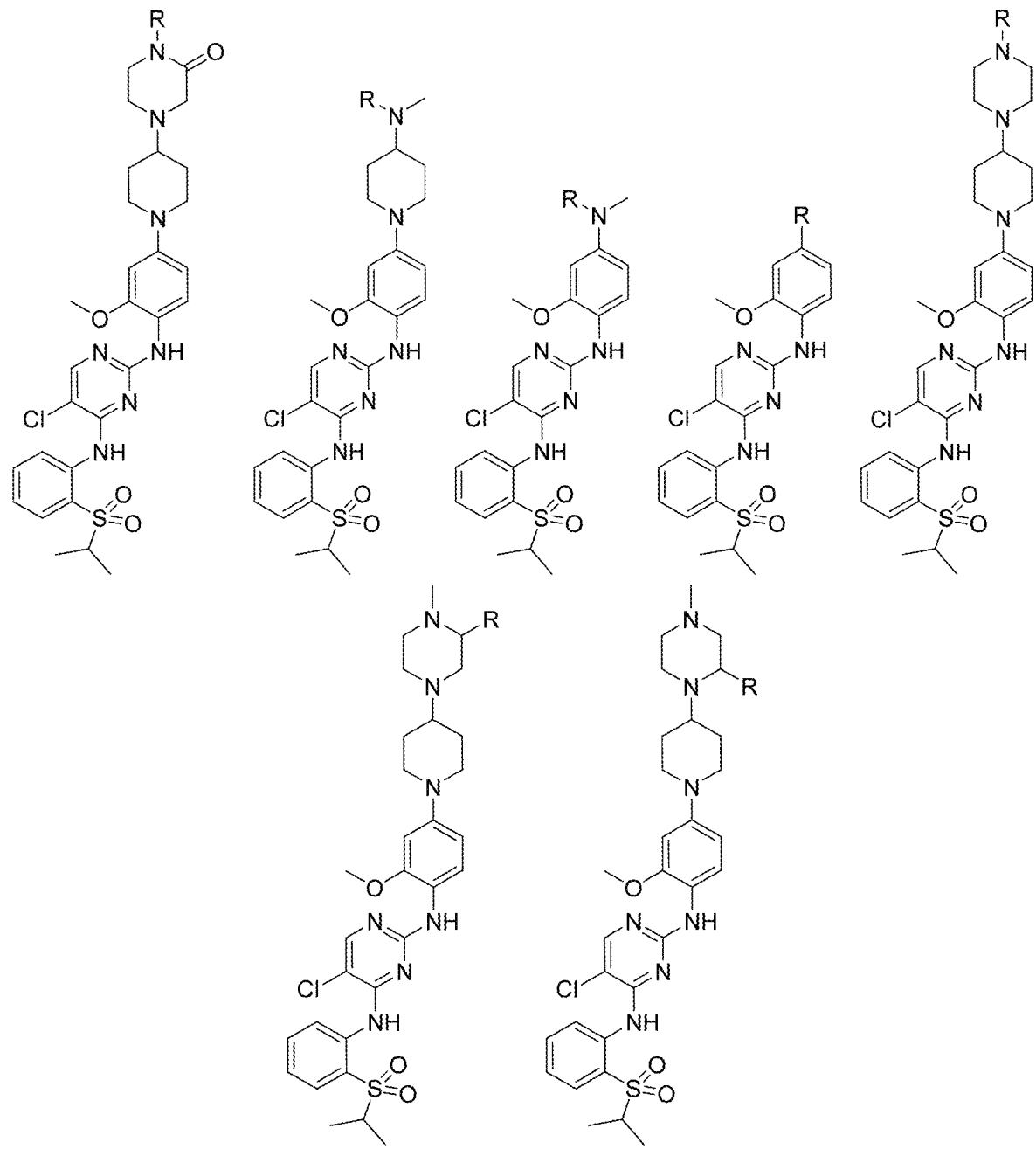

FIG. 8RRRR
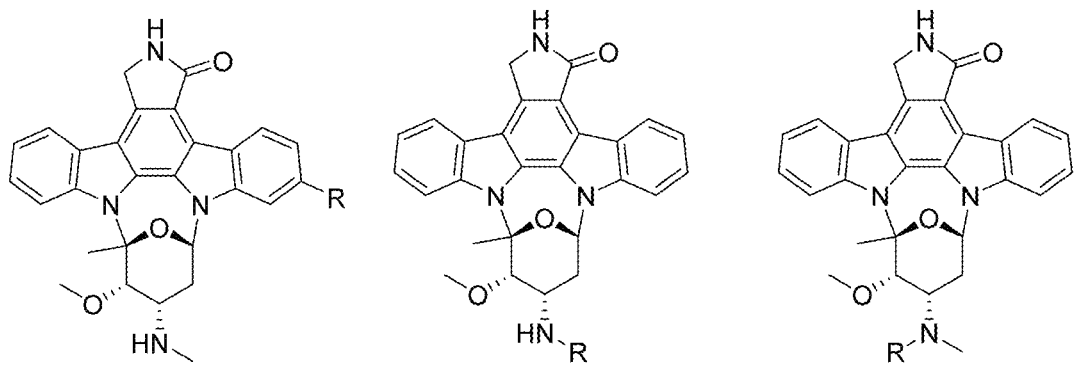
FIG. 8SSSS
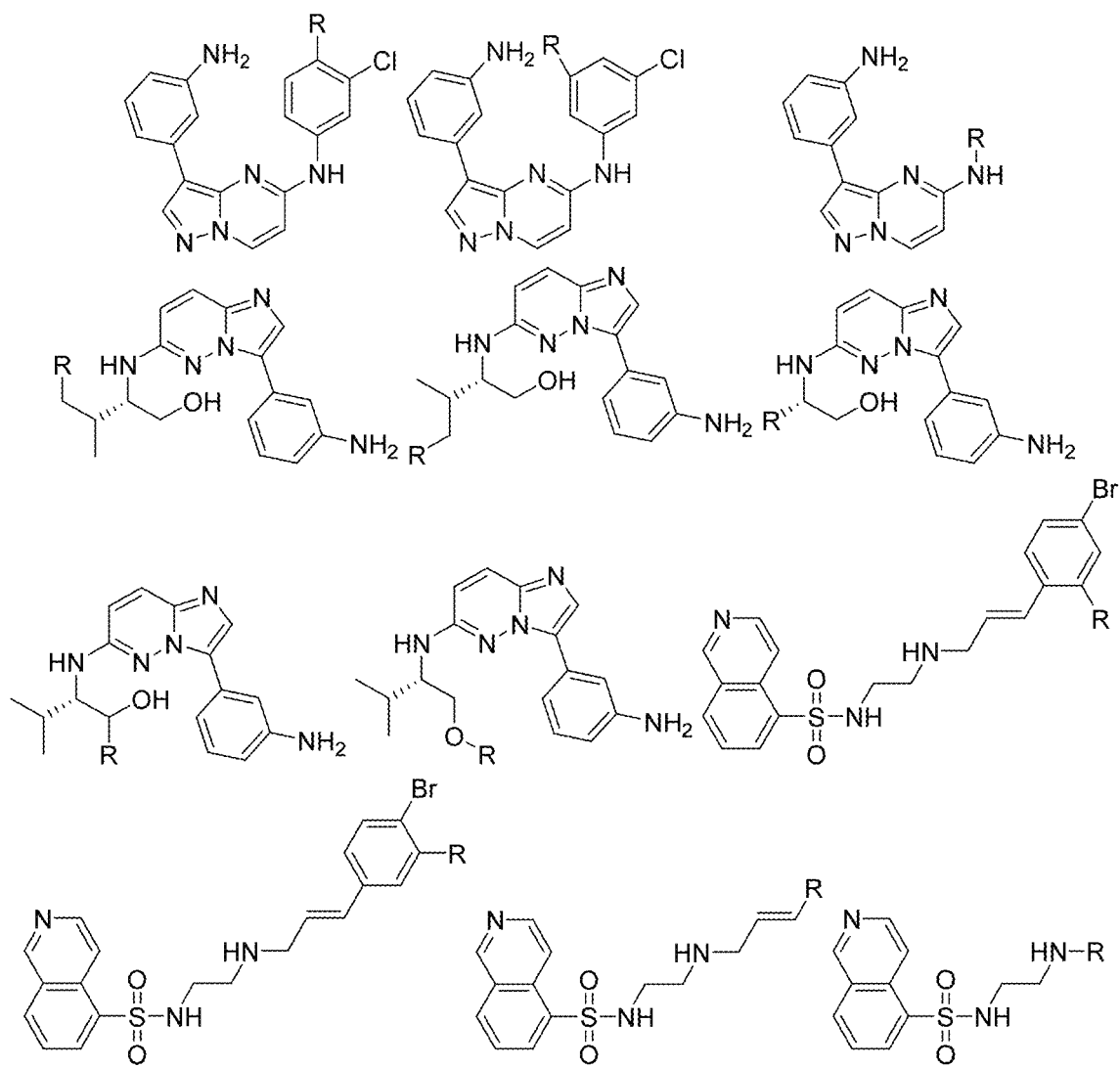

FIG. 8TTTT
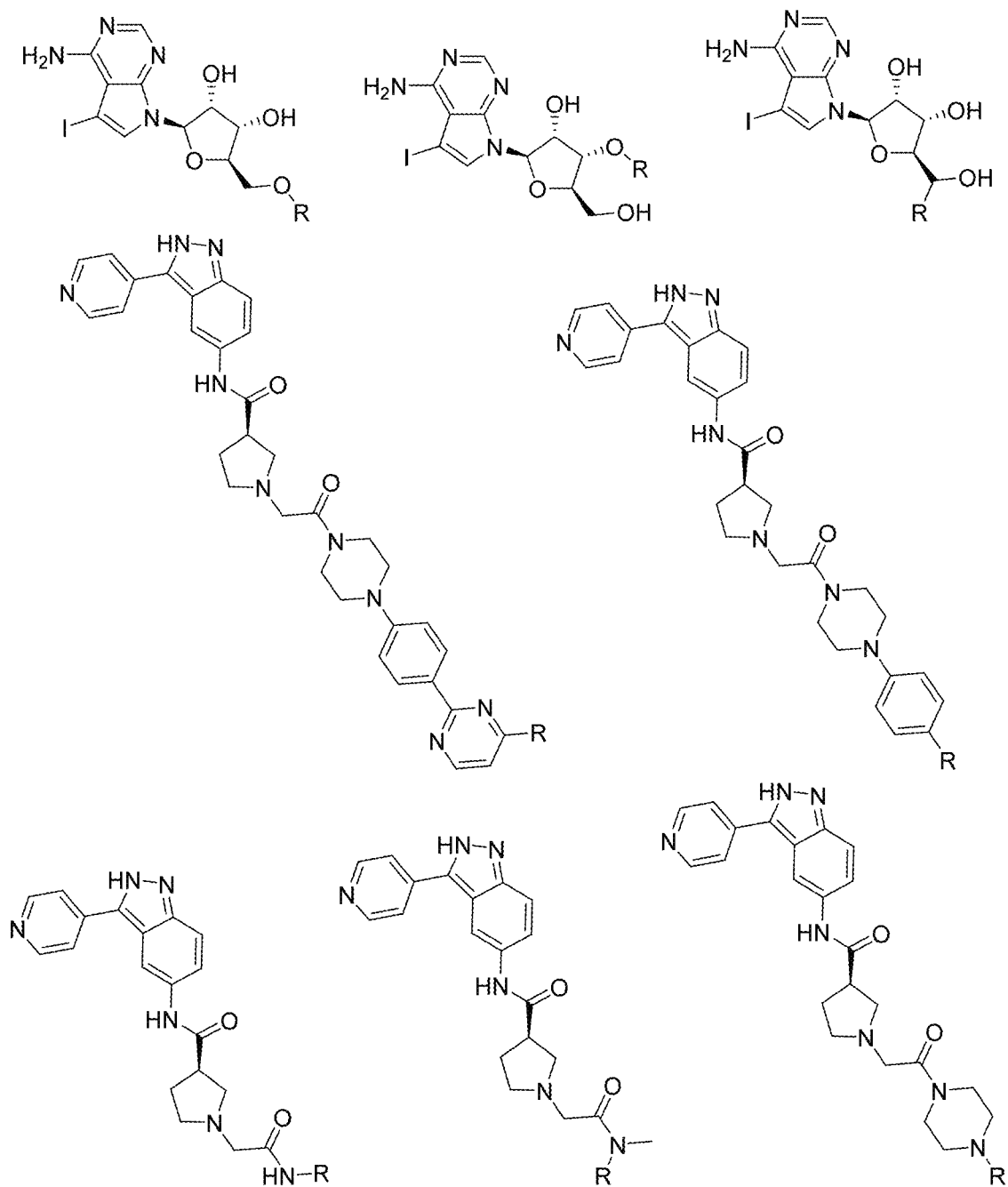

FIG. 8UUUU
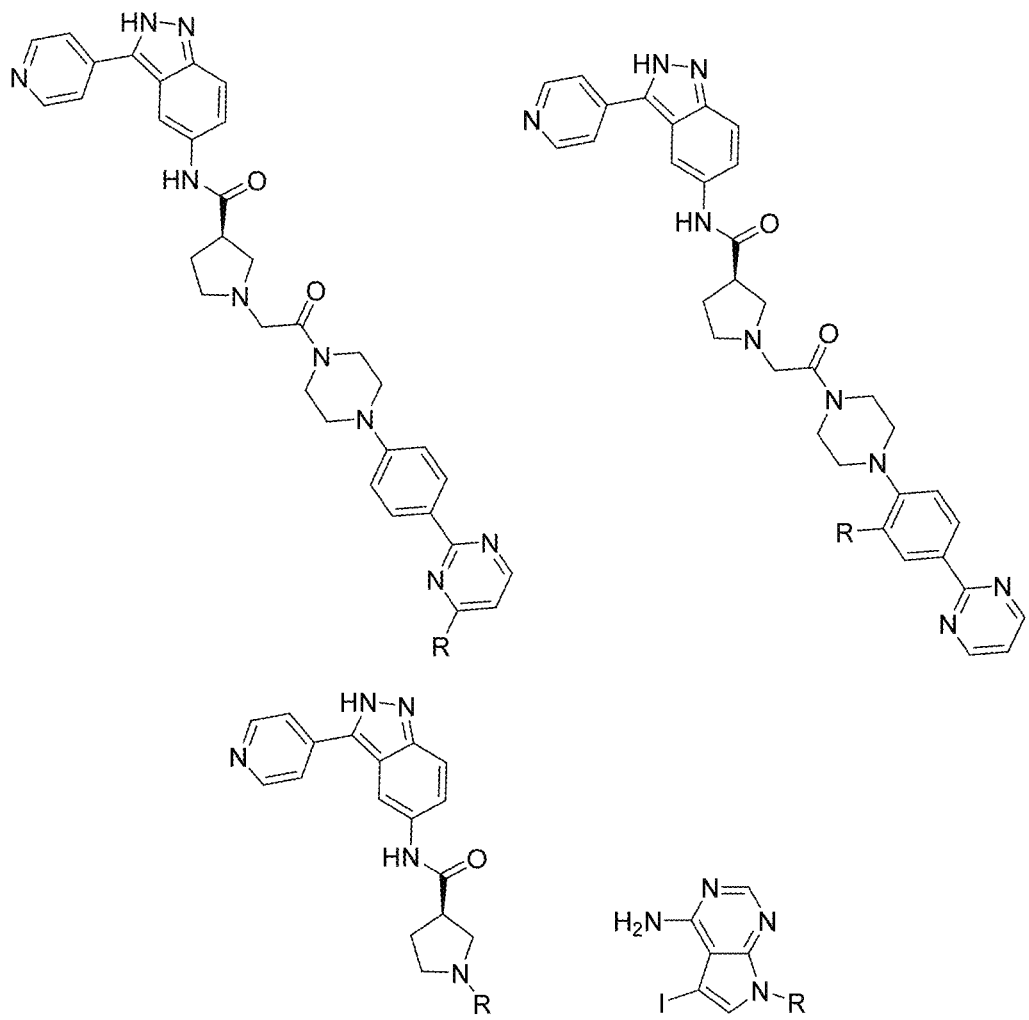

FIG. 8VVVV
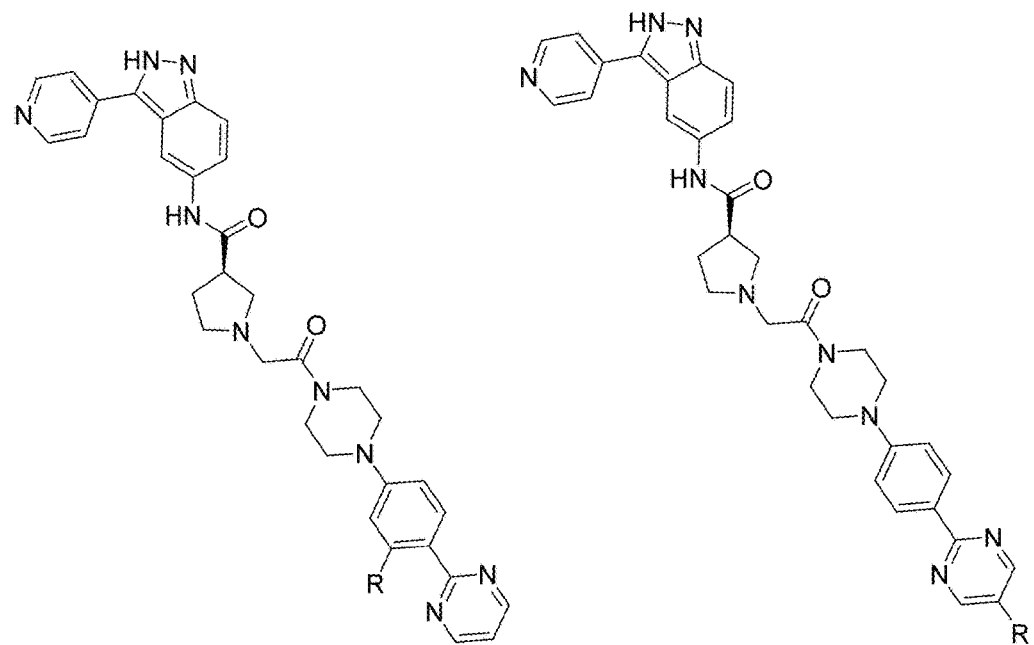
FIG. 8WWWW
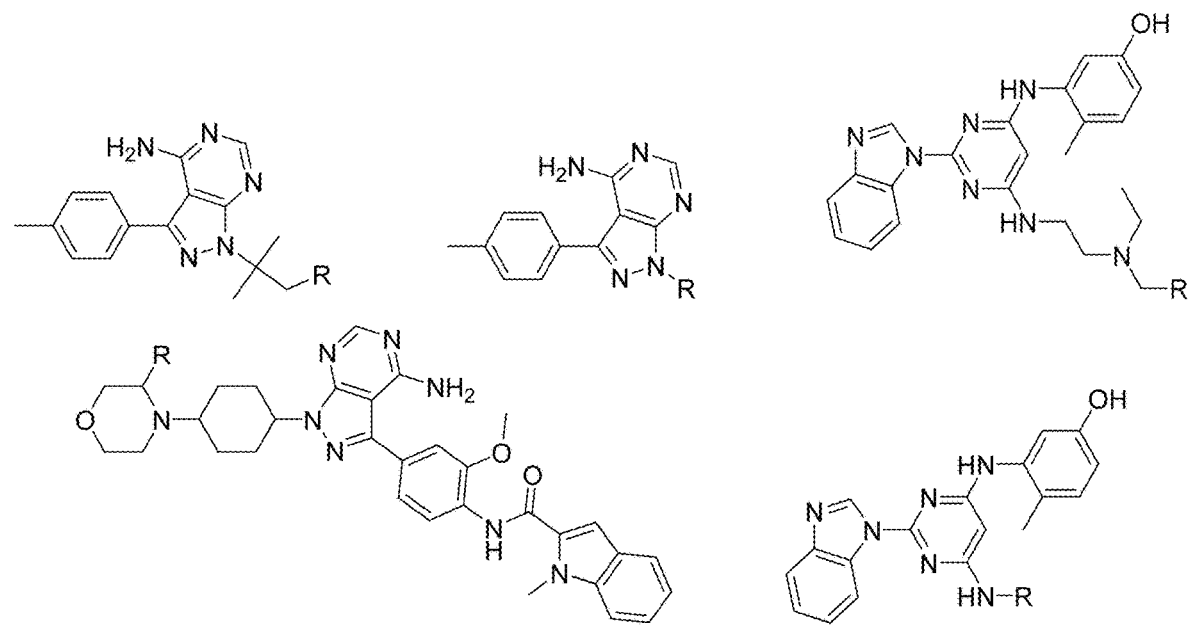

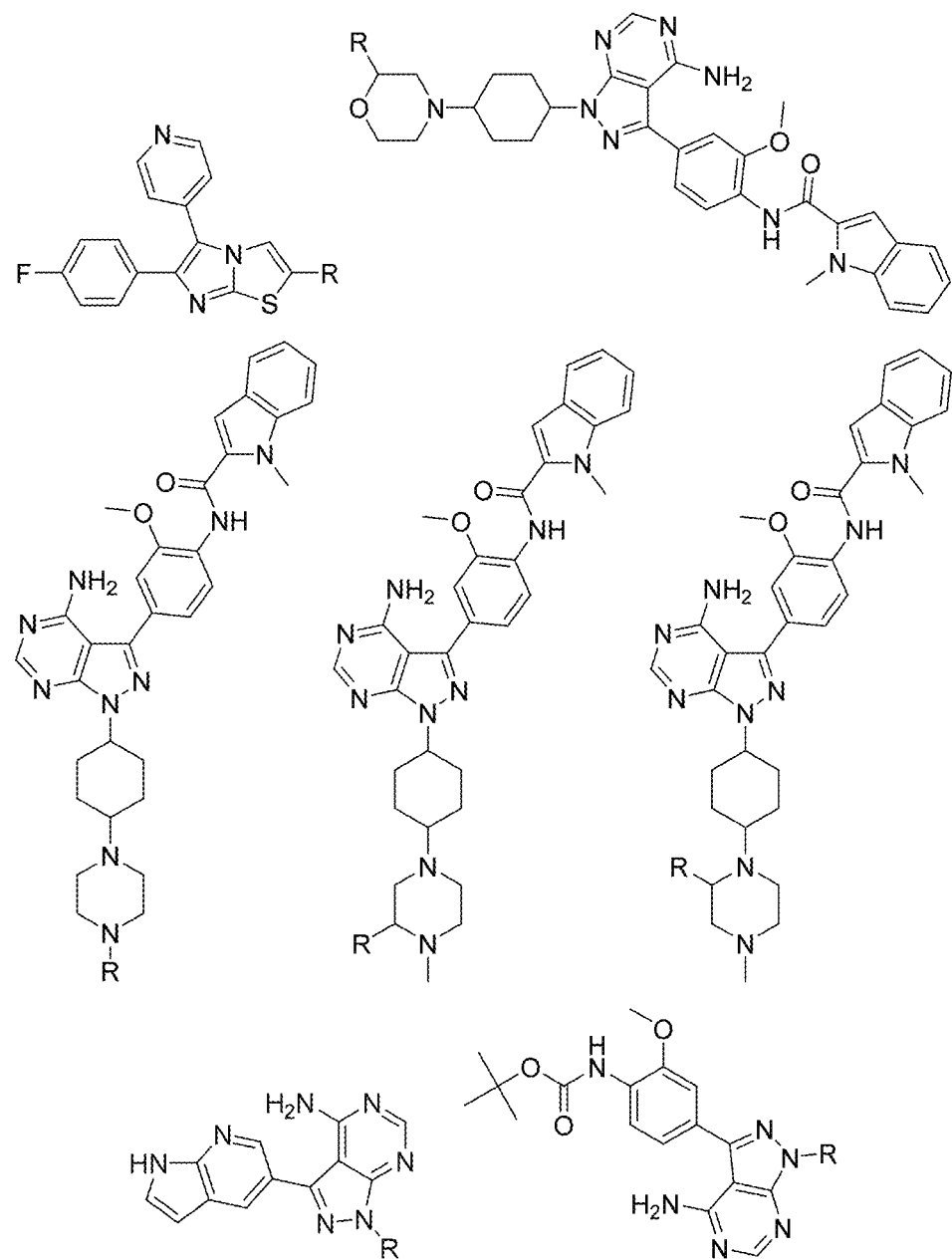
FIG. 8XXXX

FIG. 8YYYY
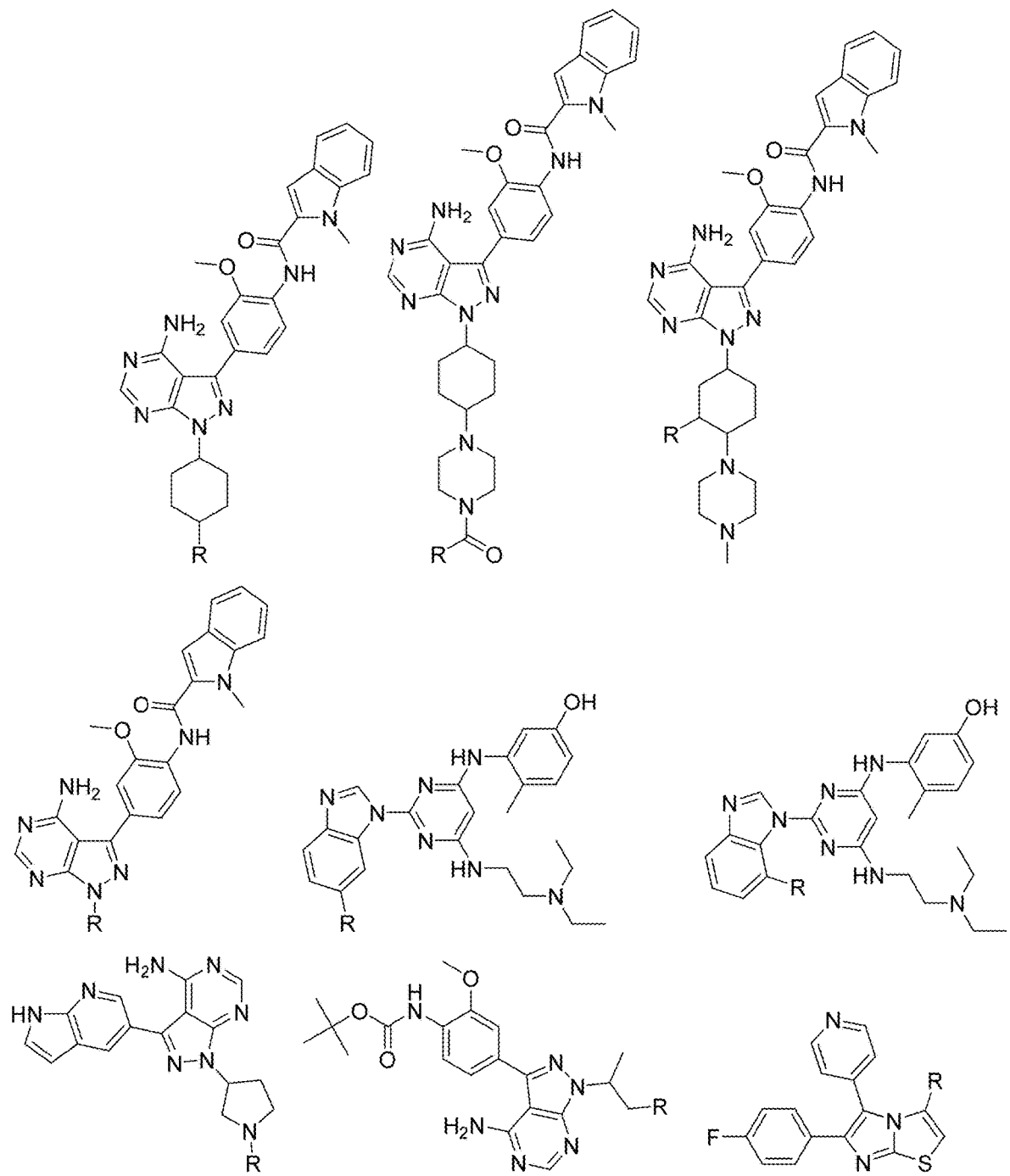

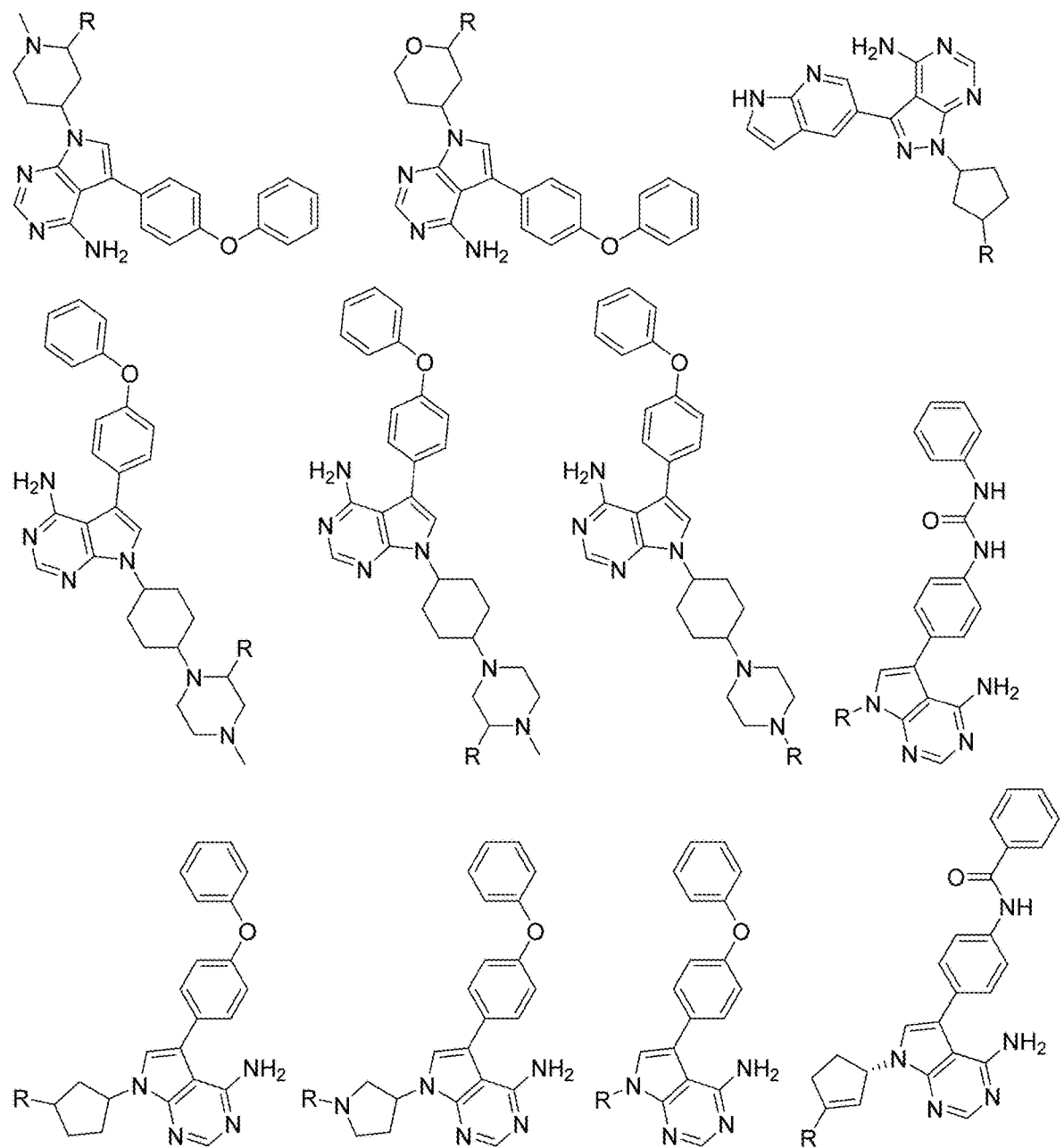
FIG. 8ZZZZ

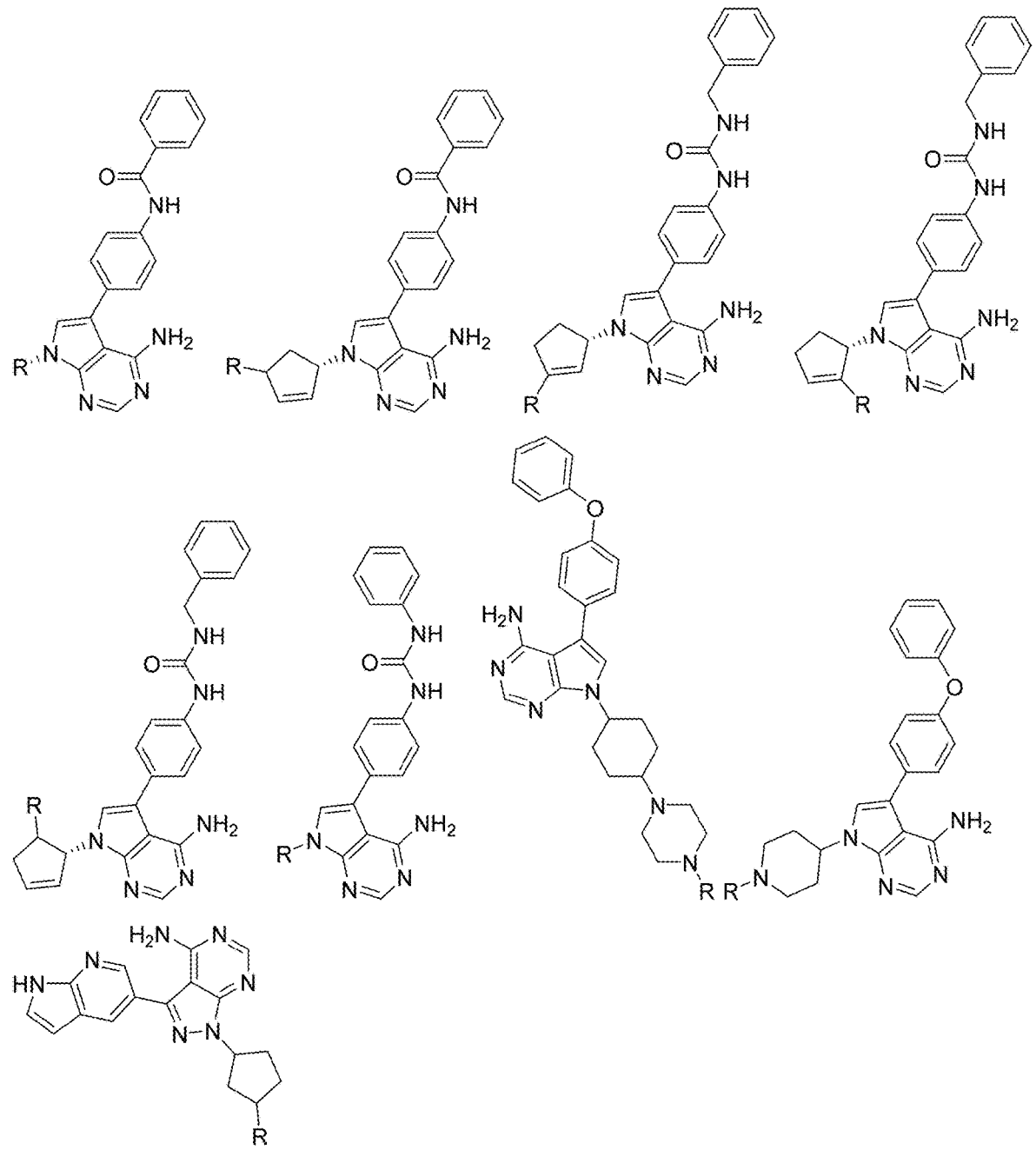
FIG. 8AAAAA

FIG. 8BBBBB
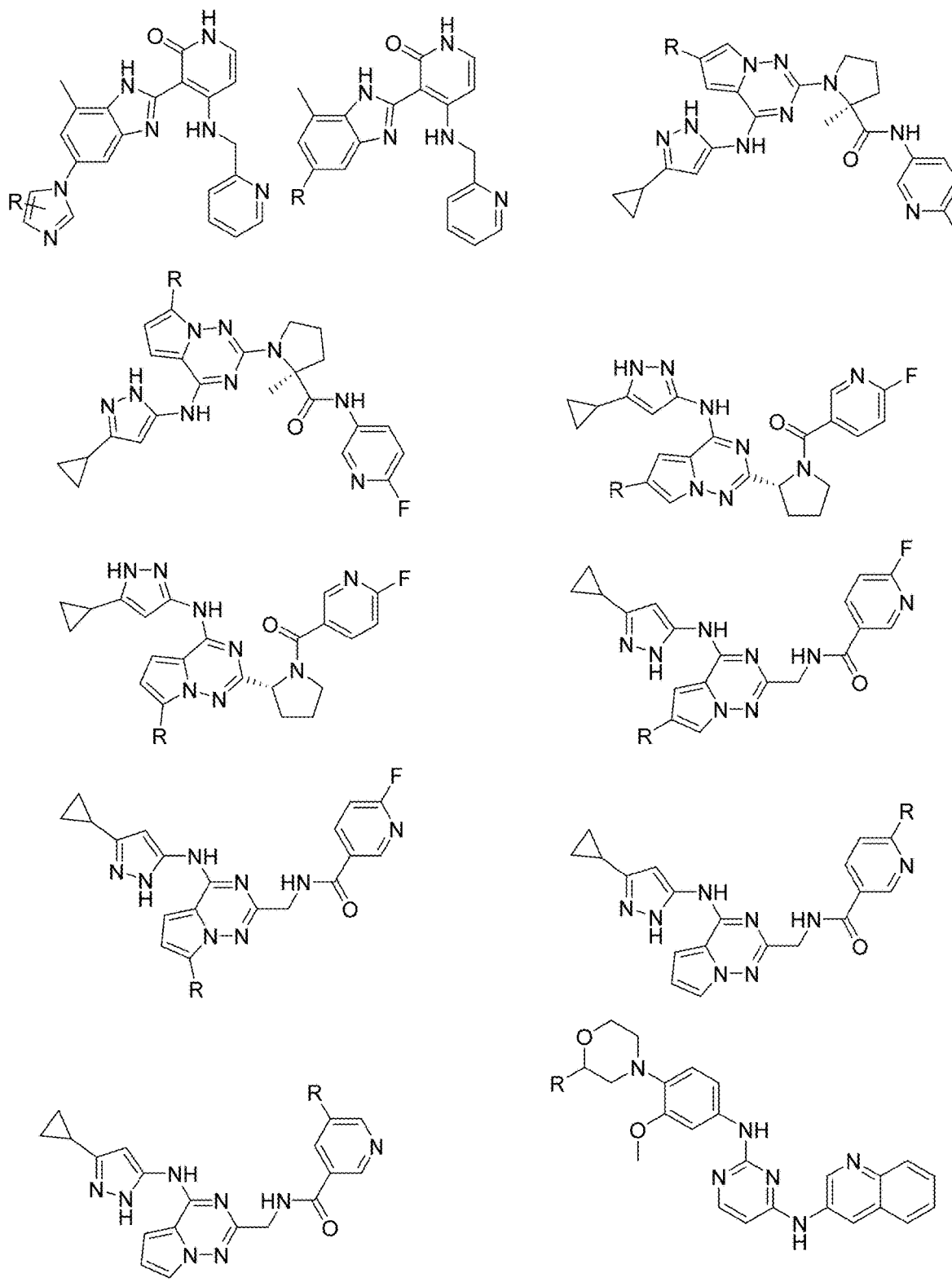

FIG. 8CCCCC
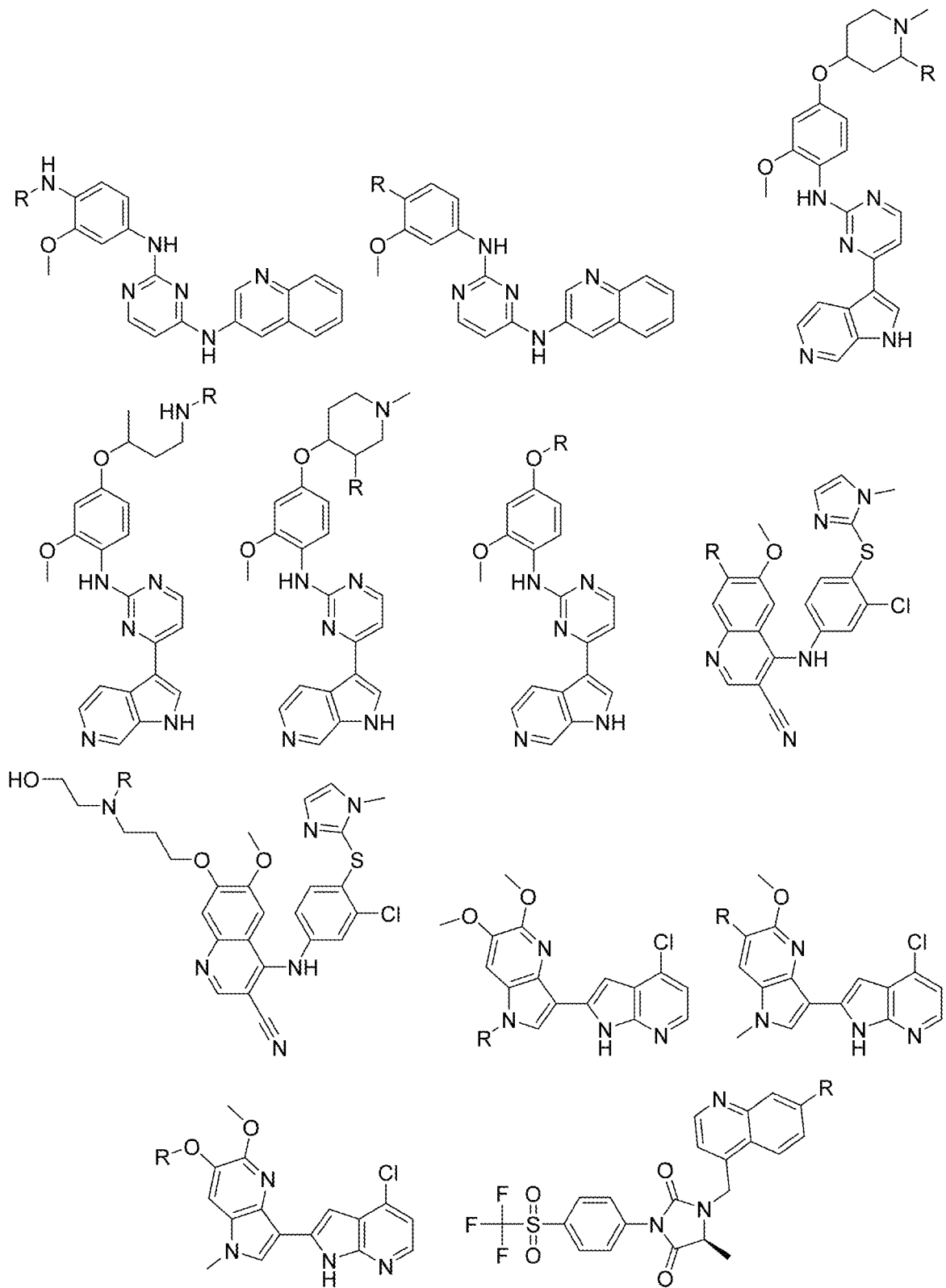

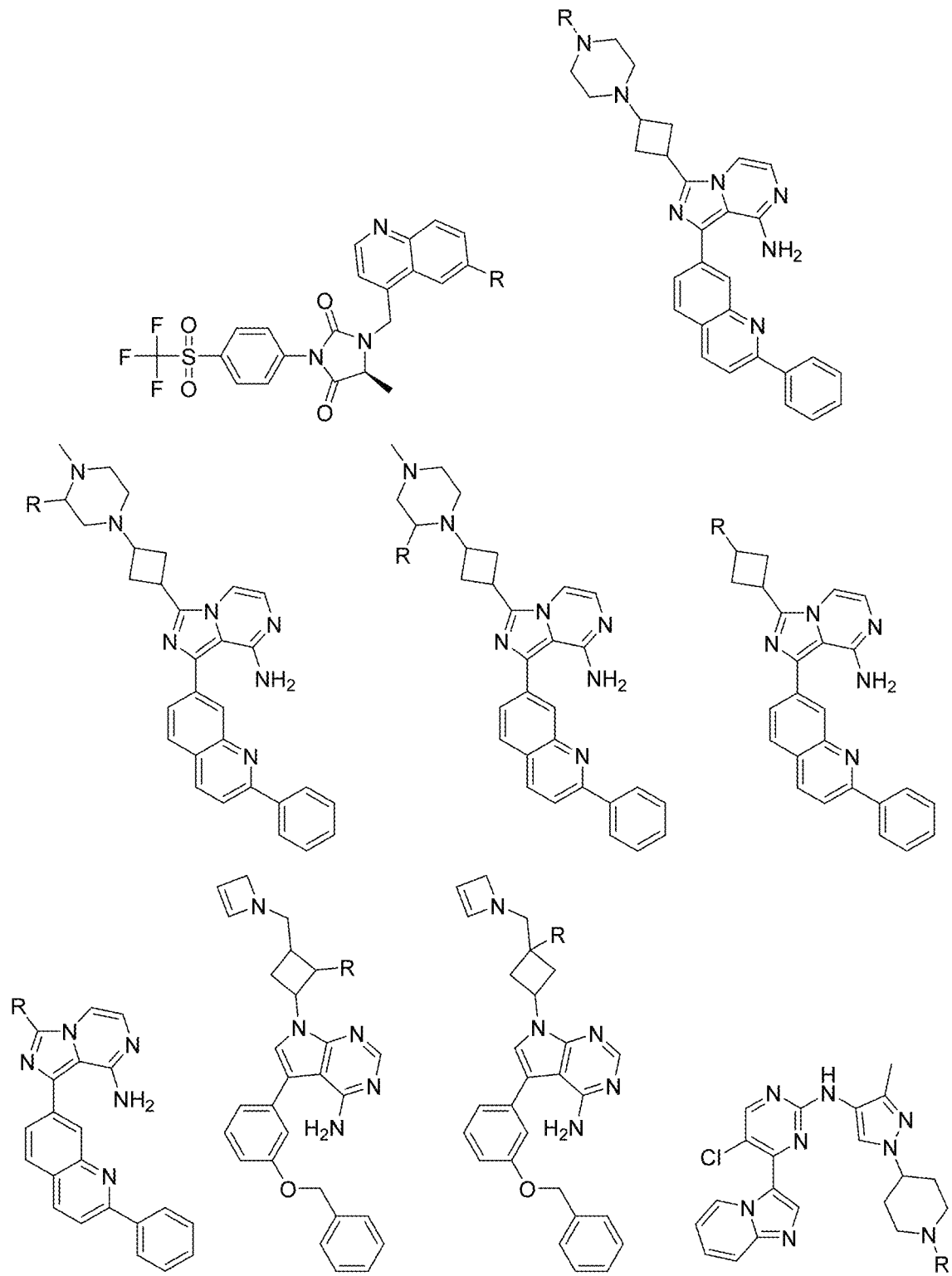
FIG. 8DDDDD

FIG. 8EEEEE
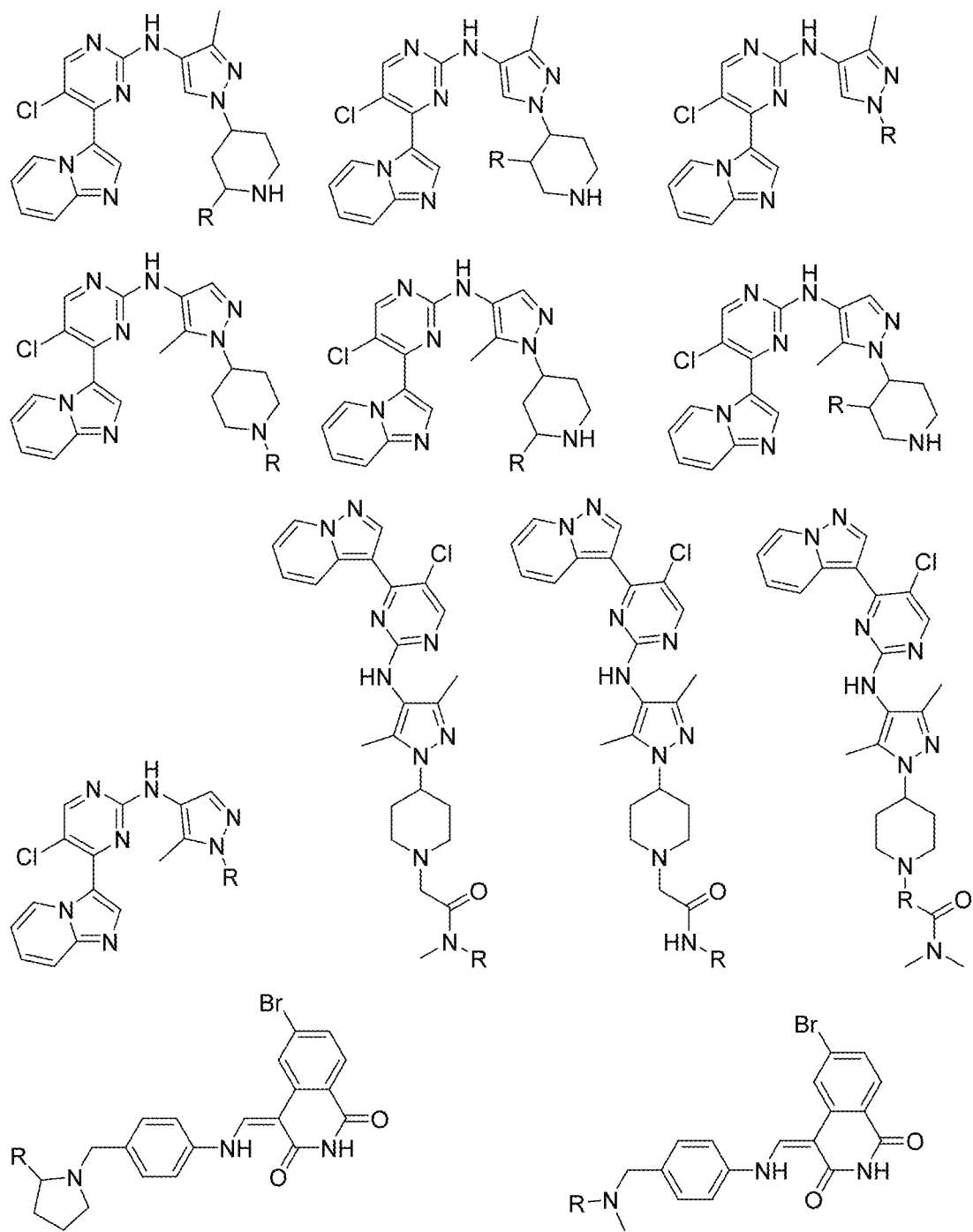

FIG. 8FFFFF
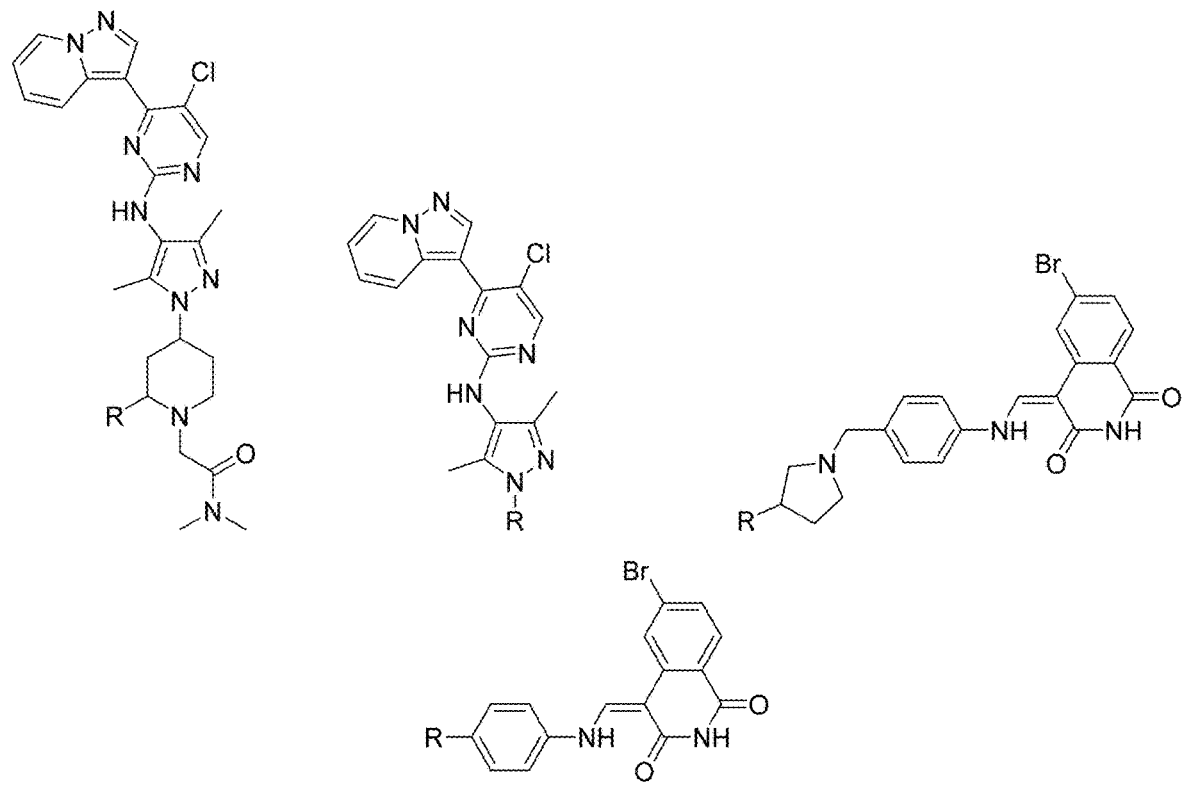
FIG. 8GGGGG
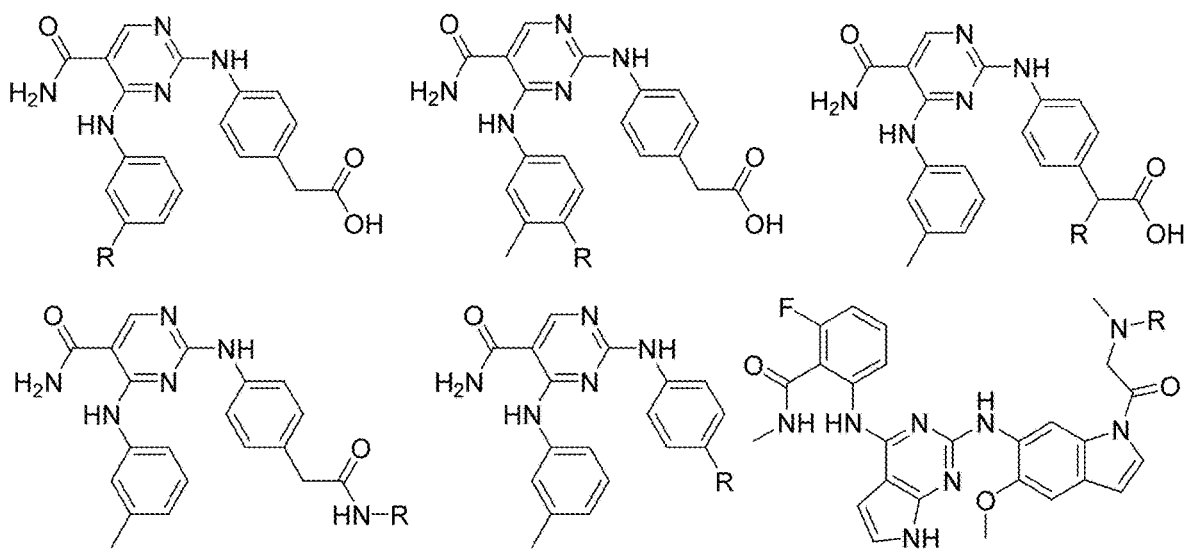

FIG. 8HHHHH
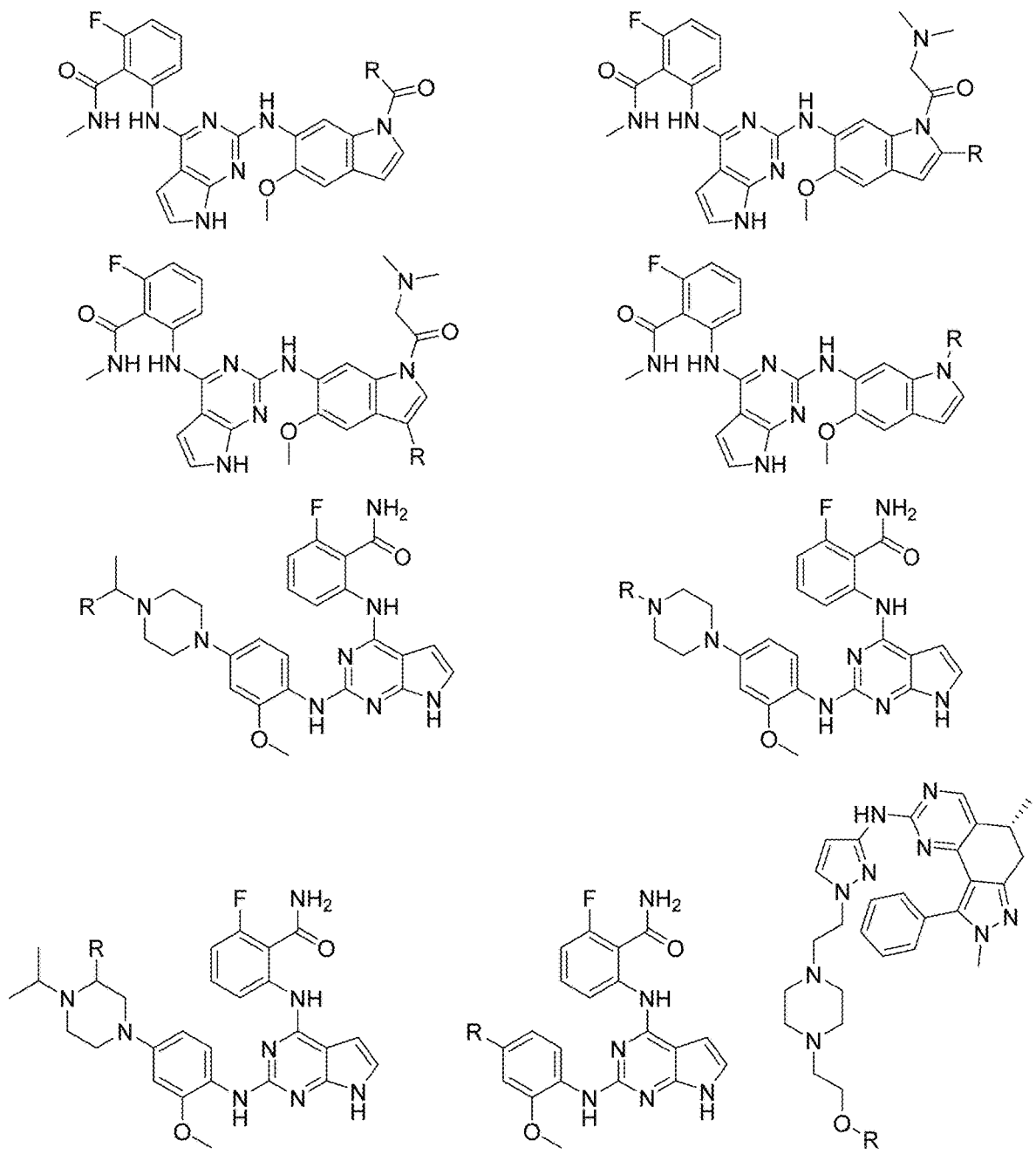

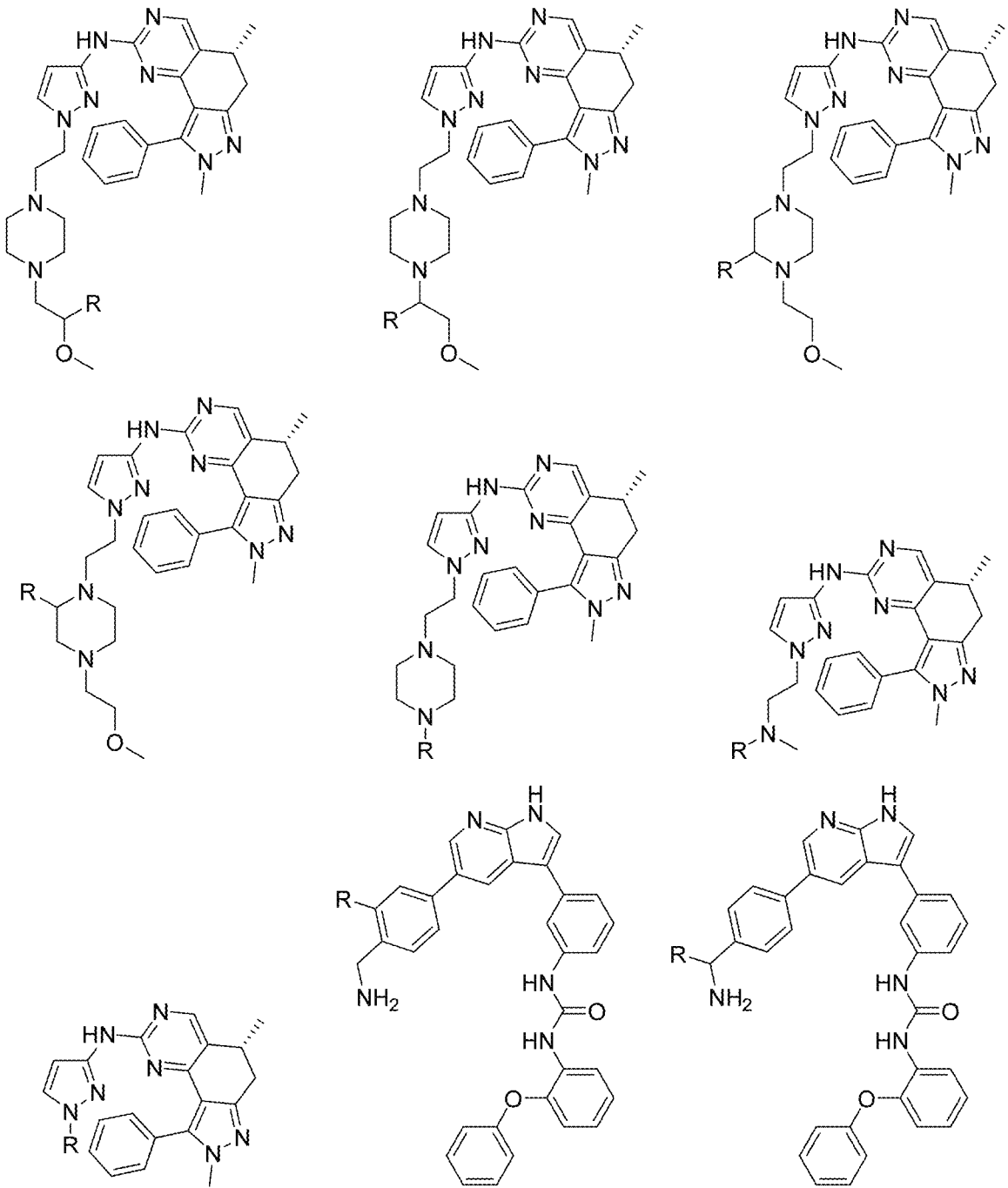
FIG. 8IIII

FIG. 8JJJJJ
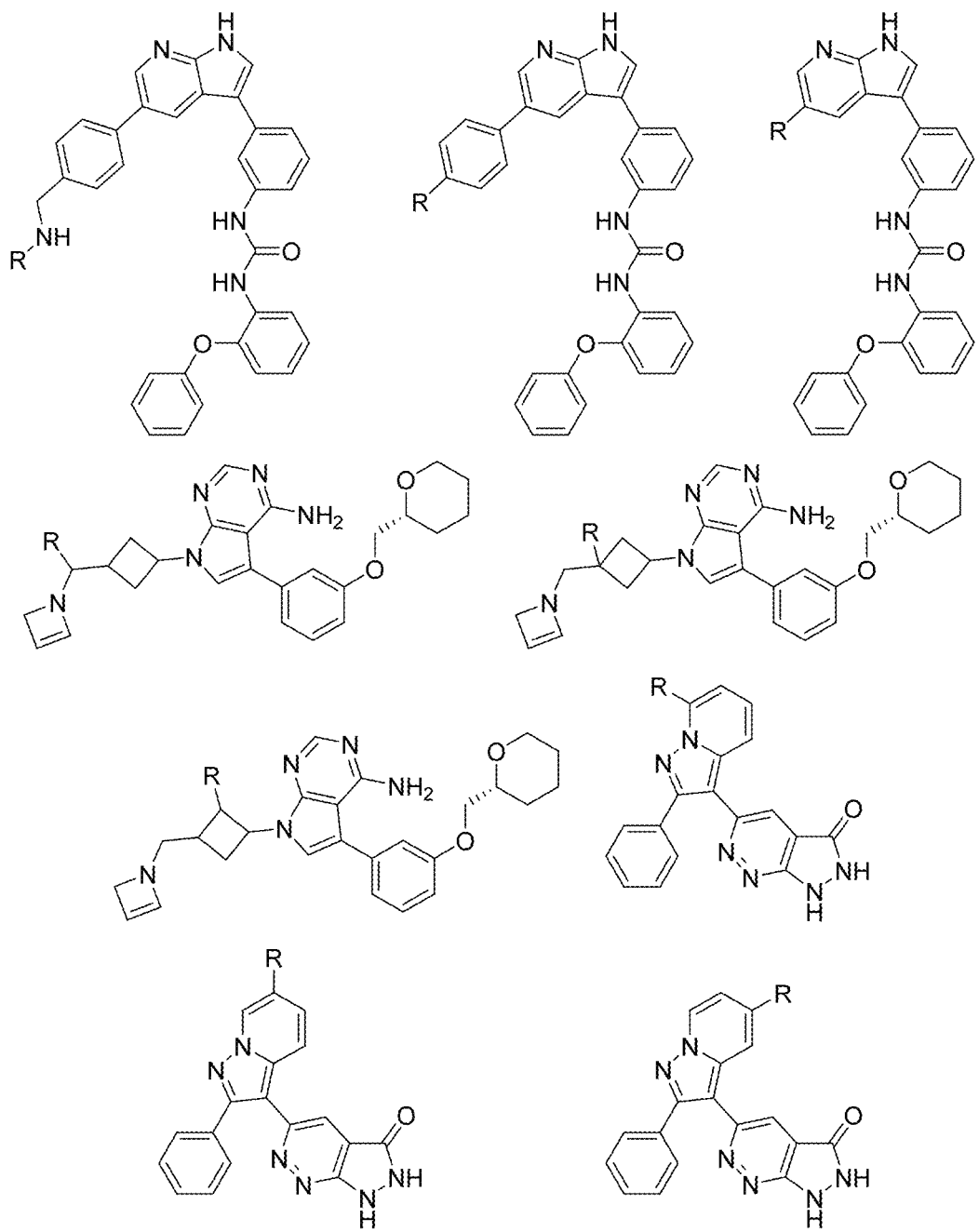

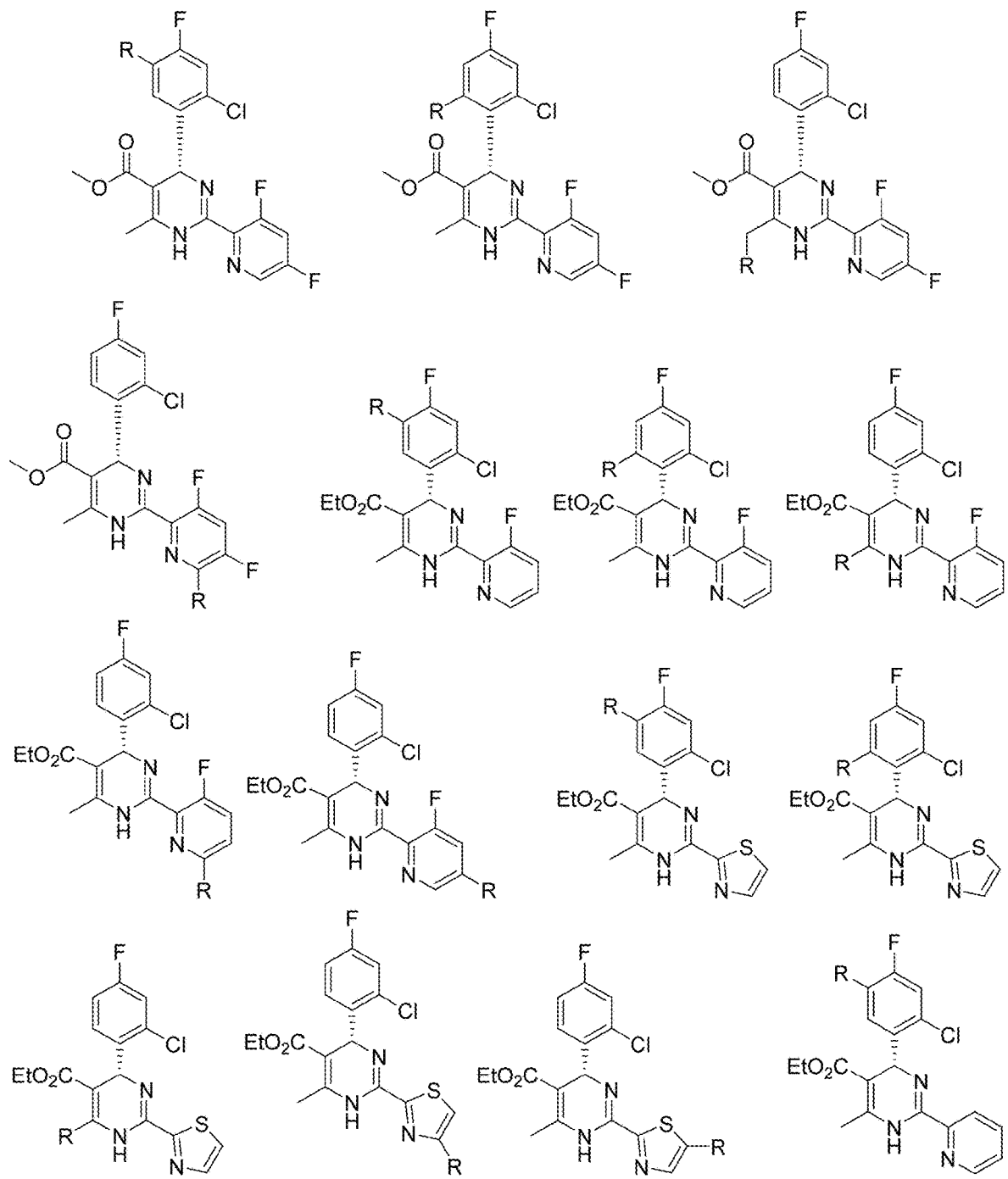
FIG. 8KKKKK

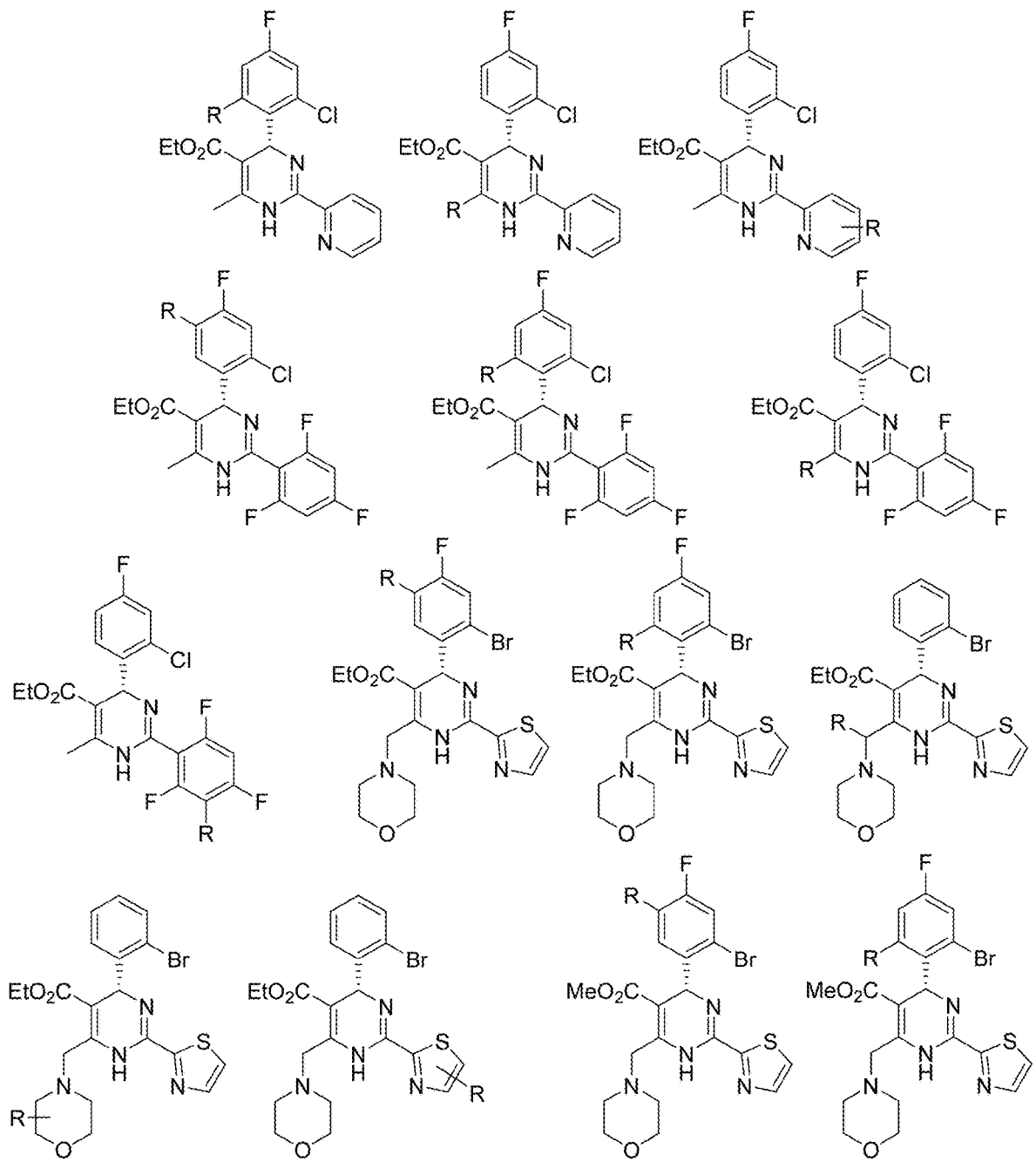
FIG. 8LLLLL

FIG. 8MMMMM
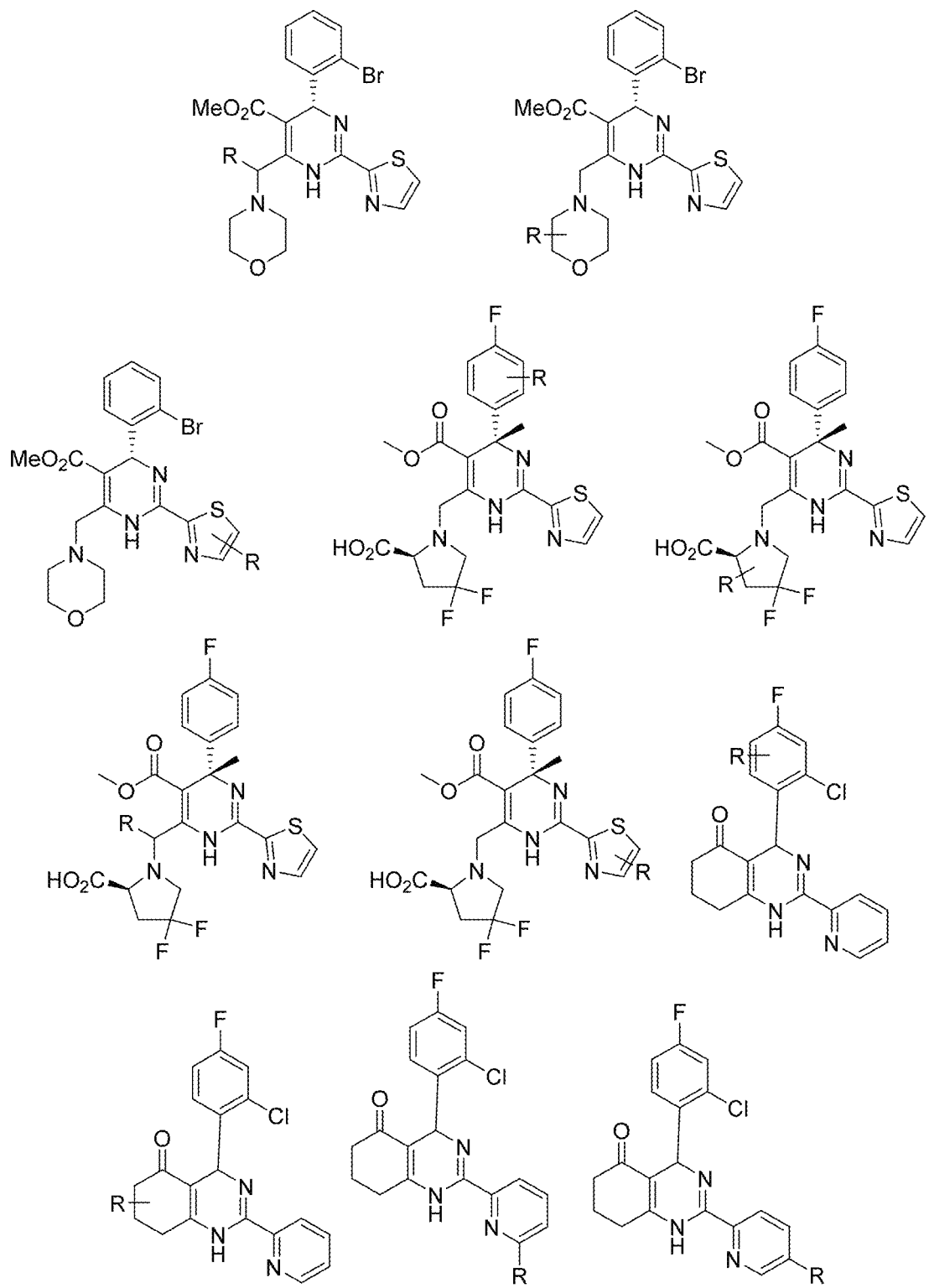

FIG. 8NNNNN
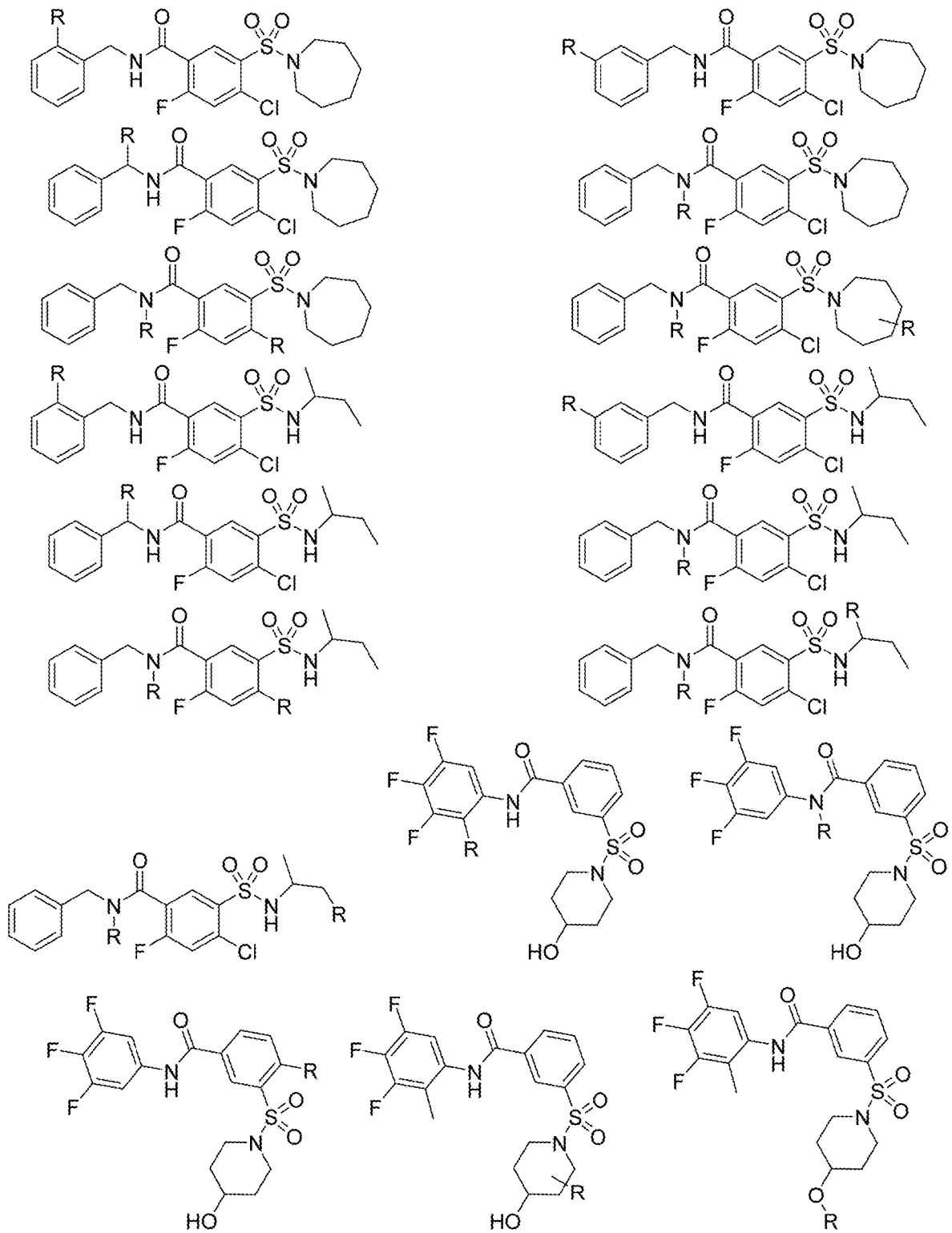

FIG. 800000
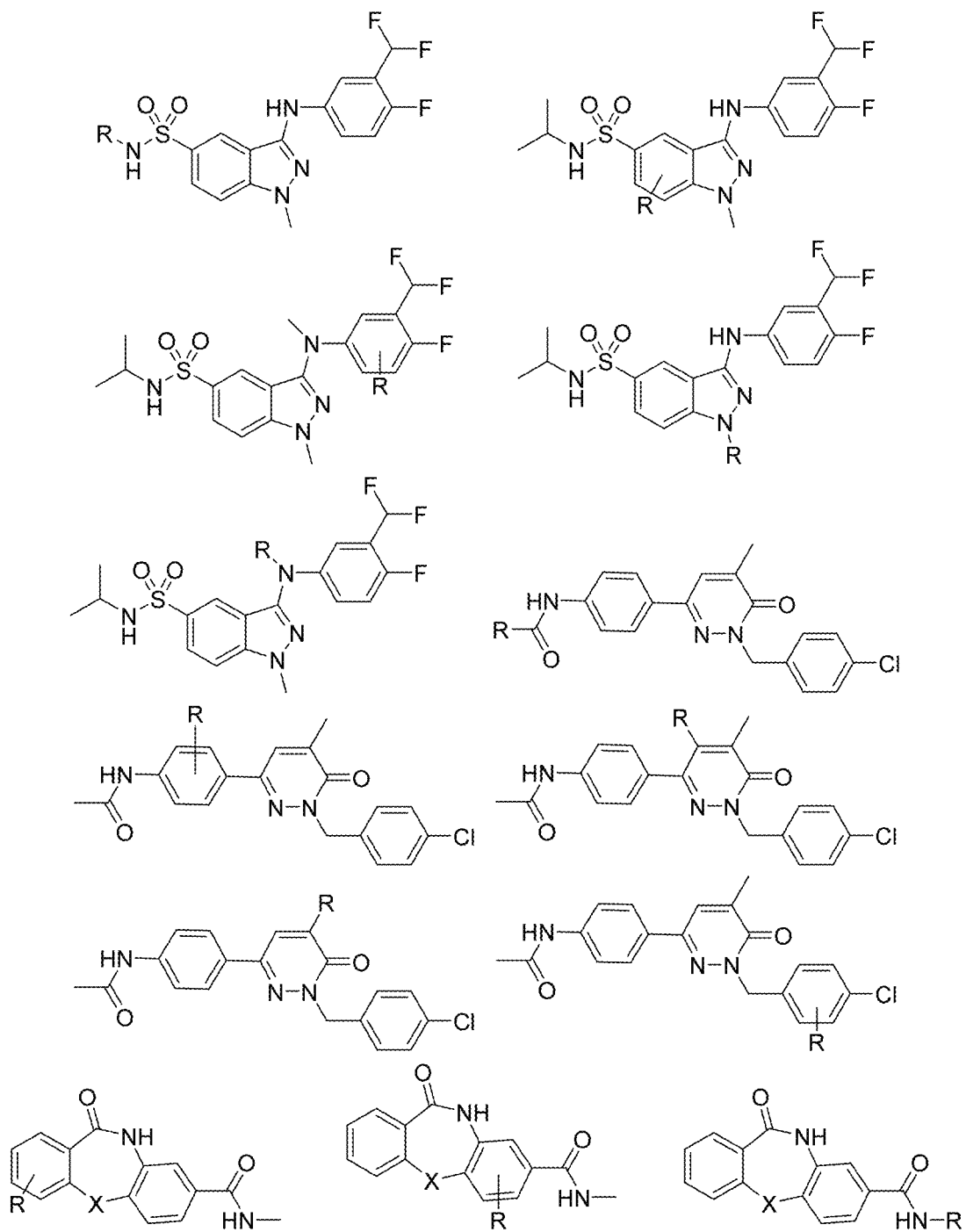

FIG. 8PPPPP
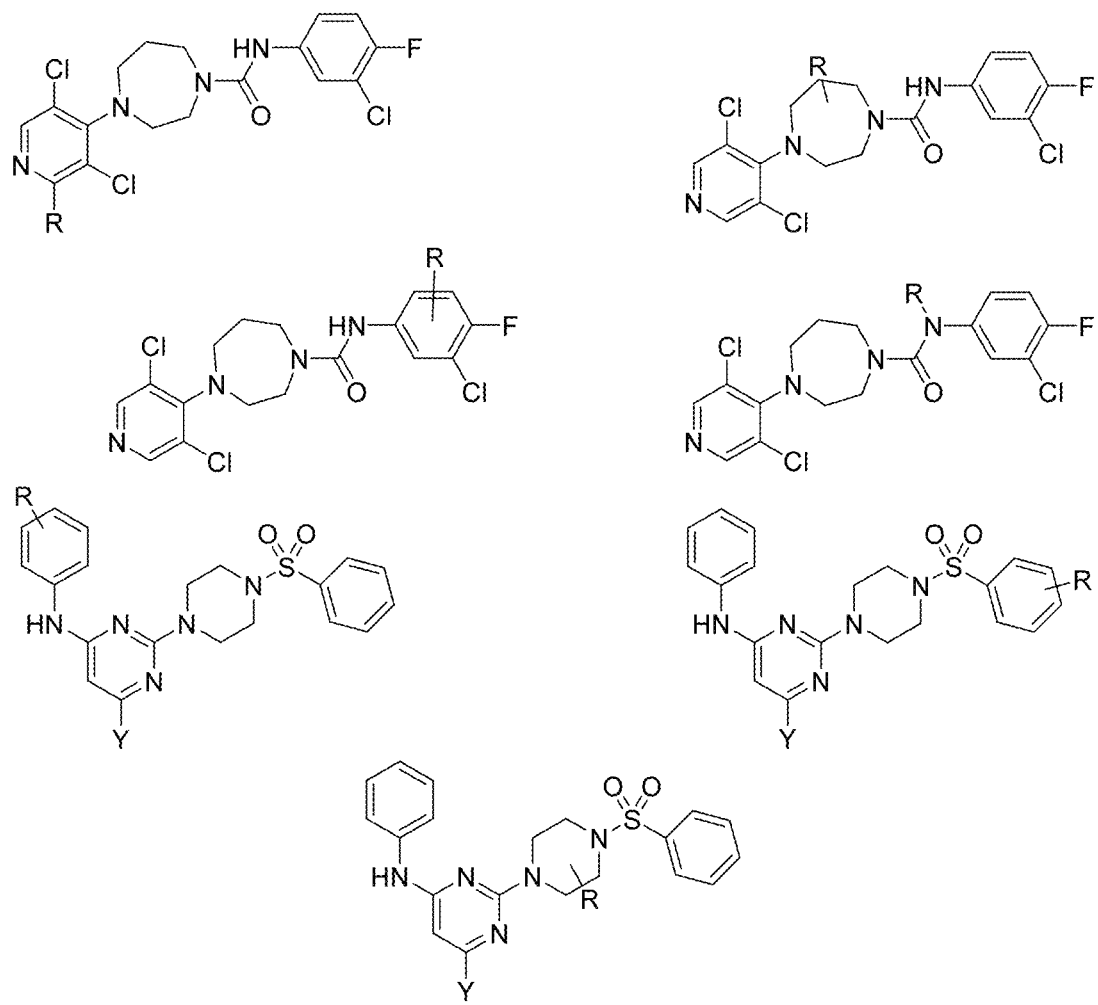

SUBSTITUTED PIPERIDINE DEGRONIMERS FOR TARGET PROTEIN DEGRADATION

CROSS-REFERENCE TO RELATED APPLICATIONS

This application is a continuation of U.S. patent application Ser. No. 16/186,333, filed on Nov. 9, 2018, which is a continuation of International Application No. PCT/US2017/032046, filed in the Patent Cooperation Treaty, U.S. Receiving Office on May 10, 2017, which claims the benefit of U.S. Provisional Application 62/334,338 filed May 10, 2016. The entirety of these applications are hereby incorporated by reference herein for all purposes.

FIELD OF THE INVENTION

This invention provides amine-linked $C^3$-glutarimide Degronimers and Degrons for therapeutic applications as described further herein, and methods of use and compositions thereof as well as methods for their preparation.

BACKGROUND

Protein degradation is a highly regulated and essential process that maintains cellular homeostasis. The selective identification and removal of damaged, misfolded, or excess proteins is achieved via the ubiquitin-proteasome pathway (UPP). The UPP is central to the regulation of almost all cellular processes, including antigen processing, apoptosis, biogenesis of organelles, cell cycling, DNA transcription and repair, differentiation and development, immune response and inflammation, neural and muscular degeneration, morphogenesis of neural networks, modulation of cell surface receptors, ion channels and the secretory pathway, the response to stress and extracellular modulators, ribosome biogenesis and viral infection.

Covalent attachment of multiple ubiquitin molecules by an E3 ubiquitin ligase to a terminal lysine residue marks the protein for proteasome degradation, where the protein is digested into small peptides and eventually into its constituent amino acids that serve as building blocks for new proteins. Defective proteasomal degradation has been linked to a variety of clinical disorders including Alzheimer's disease, Parkinson's disease, Huntington's disease, muscular dystrophies, cardiovascular disease, and cancer among others.

There are over 600 E3 ubiquitin ligases which facilitate the ubiquitination of different proteins in vivo, which can be divided into four families: HECT-domain E3s, U-box E3s, monomeric RING E3s and multi-subunit E3s. See generally Li et al. (*PLOS One*, 2008, 3, 1487) titled "Genome-wide and functional annotation of human E3 ubiquitin ligases identifies MULAN, a mitochondrial E3 that regulates the organelle's dynamics and signaling."; Berndsen et al. (*Nat. Struct. Mol. Biol.*, 2014, 21, 301-307) titled "New insights into ubiquitin E3 ligase mechanism"; Deshaies et al. (*Ann. Rev. Biochem.*, 2009, 78, 399-434) titled "RING domain E3 ubiquitin ligases."; Spratt et al. (*Biochem.* 2014, 458, 421-437) titled "RBR E3 ubiquitin ligases: new structures, new insights, new questions."; and Wang et al. (*Nat. Rev. Cancer.*, 2014, 14, 233-347) titled "Roles of F-box proteins in cancer.".

In 1995, Gosink et al. (*Proc. Natl. Acad. Sci. USA* 1995, 92, 9117-9121) in a publication titled "Redirecting the Specificity of Ubiquitination by Modifying Ubiquitin-Conjugating Enzymes", provided proof of concept in vitro that engineered peptides can selectively direct ubiquitination of intracellular proteins. The publication by Nawaz et al. (*Proc. Natl. Acad. Sci. USA.* 1999, 96, 1858-1862) titled "Proteasome-Dependent Degradation of the Human Estrogen Receptor" describes ER degradation which takes advantage of the ubiquitin-proteasome pathway.

Proteinex, Inc. filed a patent application in February 1999 that issued as U.S. Pat. No. 6,306,663 claiming a method of generating a compound for activating the ubiquitination of a Target Protein which comprises covalently linking a Target Protein binding element able to bind specifically to the Target Protein via a ubiquitination recognition element. Proteinex described that the invention can be used to control protein levels in eukaryotes. While the '663 patent may have been based on the first patent application to describe the high level concept of how to manipulate the UPP system to degrade selected proteins in vivo, the patent did not provide sufficient detail to allow persons of skill to easily construct the range of proposed compounds. For example, for the ubiquitination recognition elements, the skilled person was told among other things to use standard methods for drug discovery and screen for appropriate small molecules that would bind to the ligase. Proteinex also emphasized the use of peptides as ubiquitination recognition elements, which can pose significant difficulties for oral drug administration.

Since then, harnessing the ubiquitin-proteasome pathway for therapeutic intervention has received significant interest from the scientific community. The publication by Zhou et al. from Harvard Medical School (*Mol. Cell* 2000, 6, 751-756) titled "Harnessing the Ubiquitination Machinery to Target the Degradation of Specific Cellular Proteins" described an engineered receptor capable of directing ubiquitination in mammalian and yeast cells.

Following from these early publications and others in the mid to late 1990s, the work of Proteinex was confirmed by Craig Crews and coworkers (Yale University) that a molecule that is capable of binding a Target Protein and a ubiquitin ligase may cause the Target Protein to be degraded. Their first description of such compounds was provided in U.S. Pat. No. 7,041,298 filed in September 2000 by Deshaies et al. and granted in May 2006 titled "Proteolysis Targeting Chimeric Pharmaceutical", which described a "PROTAC" consisting of a small molecule binder of MAP-AP-2 linked to a peptide capable of binding the F-box protein β-TRCP. Information in the '298 patent is also presented in the corresponding publication by Sakamoto et al. (*Proc. Natl. Acad. Sci. USA* 2001, 98, 8554-8559) titled "Protacs: Chimeric Molecules That Target Proteins to the Skp1-Cullin-F Box Complex for Ubiquitination and Degradation". The publication by Sakamoto et al. (*Mol. Cell. Proteomics* 2003, 2, 1350-1358) titled "Development of Protacs to Target Cancer-Promoting Proteins for Ubiquitination and Degradation" describes an analogous PROTAC (PROTAC2) that instead of degrading MAP-AP-2 degrades estrogen and androgen receptors.

The first E3 ligase successfully targeted with a small molecule was MDM2, which ubiquitinates the tumor suppressor p53. The targeting ligand was an HDM2/MDM2 inhibitor identified in Vassilev et al. (*Science* 2004, 303, 844-848) titled "In Vivo Activation of the P53 Pathway by Small-Molecule Antagonists of MDM2".

Other examples of direct small molecule-induced recruitment of Target Proteins to the proteasome for degradation on addition to cultured cells were described in 2004 (Schneekloth et al. (*J. Am. Chem. Soc.* 2004, 126, 3748-3754) titled "Chemical Genetic Control of Protein Levels: Selective in Vivo Targeted Degradation"). Schneekloth et al. describe a degradation agent (PROTAC3) that targets the FK506 binding protein (FKBP12) and shows that both PROTAC2 and PROTAC3 hit their respective targets with green fluorescent protein (GFP) imaging. The publication by Schneekloth et al. (*ChemBioChem* 2005, 6, 40-46) titled "Chemical Approaches to Controlling Intracellular Protein Degradation" described the state of the field at the time.

The publication by Schneekloth et al. (*Bioorg. Med. Chem. Lett.* 2008, 18, 5904-5908) titled "Targeted Intracellular Protein Degradation Induced by a Small Molecule: En Route to Chemical Proteomics" describes a degradation agent that consists of two small molecules linked by PEG that in vivo degrades the androgen receptor by concurrently binding the androgen receptor and ubiquitin E3 ligase.

WO 2013/170147 filed by Crews et al. titled "Compounds Useful for Promoting Protein Degradation and Methods of Using Same" describes compounds comprising a protein degradation moiety covalently bound to a linker, wherein the ClogP of the compound is equal to or higher than 1.5. In particular, the specification discloses protein degrading compounds that incorporate certain small molecules that can bind to an E3 ubiquitin ligase.

In unrelated parallel research, scientists were investigating thalidomide toxicity. Ito et al. (*Science* 2010, 327, 1345-1350) titled "Identification of a Primary Target of Thalidomide Teratogenicity", described that cereblon is a thalidomide binding protein. Cereblon forms part of an E3 ubiquitin ligase protein complex which interacts with damaged DNA binding protein 1, forming an E3 ubiquitin ligase complex with Cullin 4 and the E2-binding protein ROC1 (also known as RBX1) where it functions as a substrate receptor to select proteins for ubiquitination. The study revealed that thalidomide-cereblon binding in vivo may be responsible for thalidomide teratogenicity. After the discovery that thalidomide causes teratogenicity in the mid-1960's, the compound and related structures were notwithstanding found to be useful as anti-inflammatory, anti-angiogenic and anti-cancer agents (see Bartlett et al. (*Nat. Rev. Cancer* 2004, 4, 314-322) titled "The Evolution of Thalidomide and Its Imid Derivatives as Anticancer Agents").

The disclosure that thalidomide binds to the cereblon E3 ubiquitin ligase led to research to investigate incorporating thalidomide and certain derivatives into compounds for the targeted destruction of proteins. Two seminal papers were published in Science in 2014: G. Lu et al., The Myeloma Drug Lenalidomide Promotes the Cereblon-Dependent Destruction of Ikaros Proteins, *Science*, 343, 305-309 (2014); and J. Kronke et al., Lenalidomide Causes Selective Degradation of IKZF1 and IKZF3 in Multiple Myeloma Cells, *Science*, 343, 301-305 (2014).

U.S. 2014/0356322 assigned to Yale University, GlaxoSmithKline, and Cambridge Enterprise Limited University of Cambridge titled "Compounds and Methods for the Enhanced Degradation of Target Proteins & Other Polypeptides by an E3 Ubiquitin Ligase" describes protein degrading compounds that bind to the VHL E3 Ubiquitin Ligase. See also Buckley et al. (*J. Am. Chem. Soc.* 2012, 134, 4465-4468) titled "Targeting the Von Hippel-Lindau E3 Ubiquitin Ligase Using Small Molecules to Disrupt the Vhl/Hif-1alpha Interaction".

Additional publications in this area include the following: Lu et al. (*Chem. Biol.* 2015, 22, 755-763) titled "Hijacking the E3 Ubiquitin Ligase Cereblon to Efficiently Target Brd4"; Bondeson et al. (*Nat. Chem. Biol.* 2015, 11, 611-617) titled "Catalytic in Vivo Protein Knockdown by Small-Molecule Protacs"; Gustafson et al. (*Angewandte Chemie, International Edition in English* 2015, 54, 9659-9662) titled "Small-Molecule-Mediated Degradation of the Androgen Receptor through Hydrophobic Tagging"; Lai et al. (*Angewandte Chemie, International Edition* in English 2016, 55, 807-810) titled "Modular Protac Design for the Degradation of Oncogenic Bcr-Abl"; Toure et al. (*Angew. Chem. Int. Ed.* 2016, 55, 1966-1973) titled "Small-Molecule Protacs: New Approaches to Protein Degradation"; and Winter et al. (*Science* 2015, 348, 1376-1381) titled "Drug Development. Phthalimide Conjugation as a Strategy for in Vivo Target Protein Degradation" describes thalidomide based Target Protein degradation technology.

WO 2015/160845 assigned to Arvinas Inc. titled "Imide Based Modulators of Proteolysis and Associated Methods of Use" describes protein degradation compounds that incorporate thalidomide and certain derivatives which bind to a cereblon E3 ligase. Additional patent applications filed by Arvinas Inc. directed to the degradation of a Target Protein using known E3 ligase ligands to direct the Target Protein to the proteasome for degradation include U.S. 2016/0058872 titled "Imide Based Modulators of Proteolysis and Associated Methods of Use"; U.S. 2016/0045607 titled "Estrogen-related Receptor Alpha Based PROTAC Compounds and Associated Methods of Use"; U.S. 2016/0214972 titled "Compounds and Methods for the Targeted Degradation of Androgen Receptor"; U.S. 2016/0272639 titled "Compounds and Methods for the Enhanced Degradation of Target Proteins"; U.S. 2017/0008904 titled "MDM2-Based Modulators of Proteolysis and Associated Methods of Use"; U.S. 2017/0037004 titled "Alanine-Based Modulators of Proteolysis and Associated Methods of Use"; U.S. 2017/0065719 titled "Compounds and Methods for the Targeted Degradation of Bromodomain containing proteins"; WO 2016/036036 titled "Tank Binding Kinase-1 PROTACS and Associated Methods of Use"; and WO 2016/197032 "Imide-Based Modulators and Proteolysis and Associated Methods of Use".

Dana-Farber Cancer Institute has also filed several patent applications directed to the degradation of a Target Protein using known E3 ligase ligands to direct the Target Protein to the proteasome for degradation. These filings include US 2016/0176916 titled "Methods to Induce Target Protein Degradation through Bifunctional Molecules; WO 2017/024318 titled "Target Protein Degradation to Attenuate Adoptive T-Cell Therapy Associated Adverse Inflammatory Responses"; WO 2017/024317 titled "Methods to Induce Target Protein Degradation through Bifunctional Molecules"; and WO 2017/024319 titled "Tunable Endogenous Protein Degradation".

While progress has been made in the area of modulation of the UPP for in vivo protein degradation, it would be useful to have additional compounds and approaches to more fully harness the UPP for therapeutic treatments.

It is an object of the present invention to provide new compounds, methods, compositions, and methods of manufacture that are useful to degrade selected proteins in vivo.

SUMMARY

Compounds and their uses and manufacture are provided that cause degradation of a selected protein via the ubiquitin proteasome pathway (UPP). N(substituted)$_2$-C$^3$-glutarimides (wherein one substitutent can be hydrogen) and analogues thereof are described (Degrons) that bind an E3 ligase (typically the cereblon subunit). Degronimers are disclosed of Formulas I, II and V that include a "Targeting Ligand" that binds (typically non-covalently) to a selected Target Protein, a "Degron" which binds (typically non-covalently) to an E3 Ligase (typically via cereblon) and optionally a Linker that covalently links the Targeting Ligand to the Degron.

A Degronimer provided herein or its pharmaceutically acceptable salt and/or its pharmaceutically acceptable composition can be used to treat a disorder which is mediated by the selected Target Protein that binds to the Targeting Ligand. Therefore, in some embodiments a method to treat a host with a disorder mediated by the Target Protein is provided that includes administering an effective amount of the Degronimer or its pharmaceutically acceptable salt described herein to the host, typically a human, optionally in a pharmaceutically acceptable composition.

In one embodiment, the selected Target Protein is derived from a gene that has undergone an amplification, translocation, deletion, or inversion event which causes or is caused by a medical disorder. In certain aspects, the selected Target Protein has been post-translationally modified by one, or combinations, of phosphorylation, acetylation, acylation including propionylation and crotylation, N-linked glycosylation, amidation, hydroxylation, methylation, poly-methylation, 0-linked glycosylation, pyroglutamoylation, myristoylation, farnesylation, geranylation, ubiquitination, sumoylation, or sulfation which causes or is caused by a medical disorder. In an alternative embodiment, the Target Protein can be covalently modified by a Targeting Ligand that has been functionalized to create a covalent bond with the Target Protein, and the covalently bond can be irreversible or reversible.

In one aspect of the present invention a Degronimer of Formula I, Formula II, or Formula V is provided:

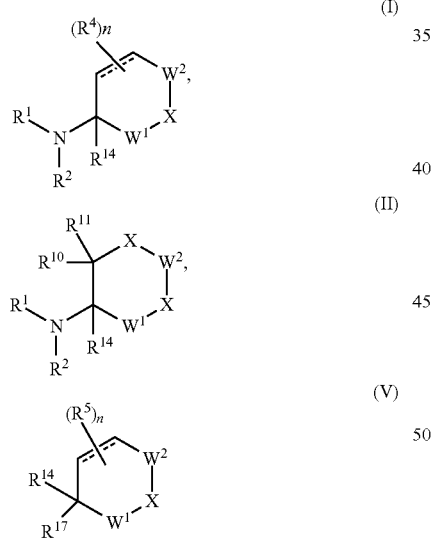

or a pharmaceutically acceptable salt, N-oxide, isotopic derivative, or prodrug thereof, optionally in a pharmaceutically acceptable carrier to form a composition;
wherein:
  $W^1$ is $CR^6R^7$, C=O, C=S, C=$CH_2$, $SO_2$, S(O), P(O) Oalkyl, P(O)NHalkyl, P(O)N(alkyl)$_2$, P(O)alkyl, P(O)OH, or P(O)NH$_2$;
  $W^2$ is $CR^8R^9$, C=O, C=S, C=$CH_2$, $SO_2$, S(O), P(O) Oalkyl, P(O)NHalkyl, P(O)N(alkyl)$_2$, P(O)alkyl, P(O)OH, or P(O)NH$_2$;
  in a typical embodiment $W^1$ is C=O;
  in another typical embodiment $W^2$ is C=O;

X is independently selected from NH, $NR^3$, $CH_2$, $CHR_3$, $C(R^3)_2$, O, and S;

n is 0, 1, or 3;

=== is a single or double bond;

wherein when === represents a single bond, n is 0, 1, 2, or 3;

wherein when === represents a double bond, n is 0, 1, or 2;

$R^1$ is selected from:

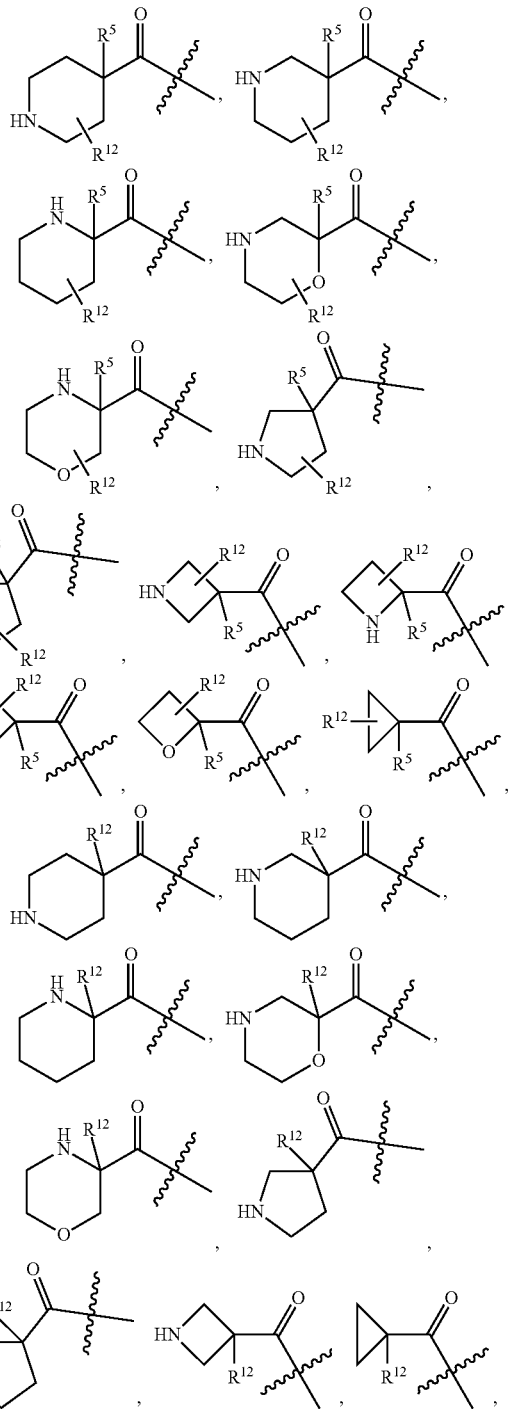

-continued and R¹*;

or R¹ is selected from:

-continued

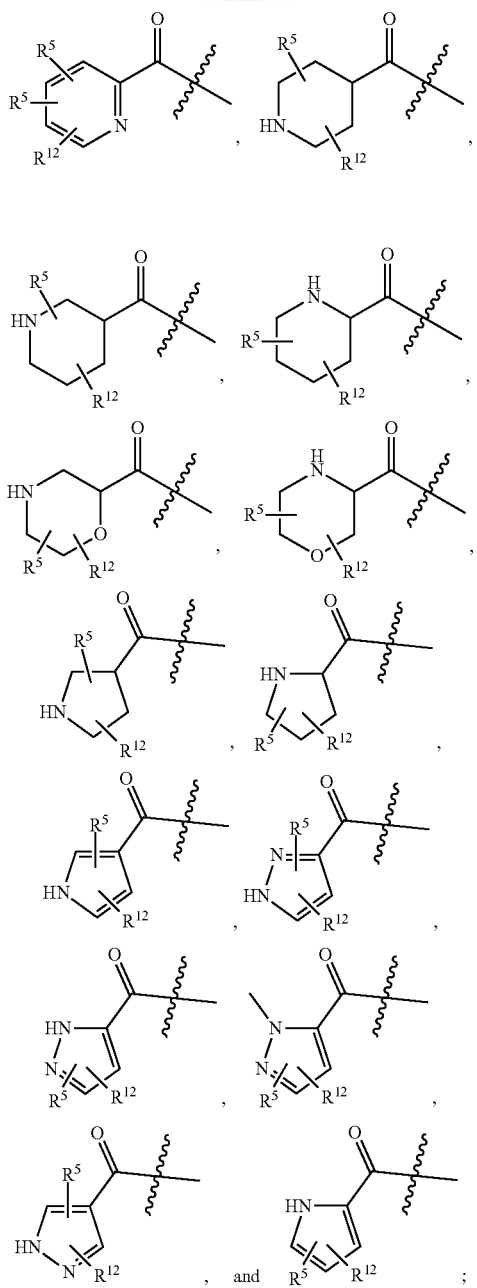

$R^{1*}$ is selected from:

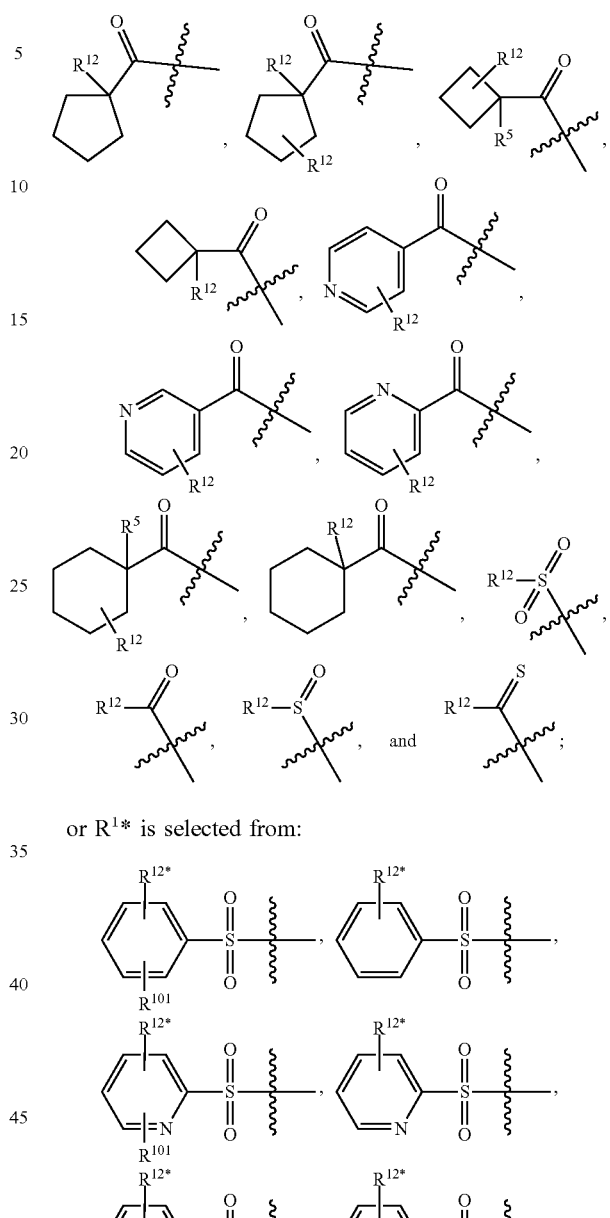

or $R^{1*}$ is selected from:

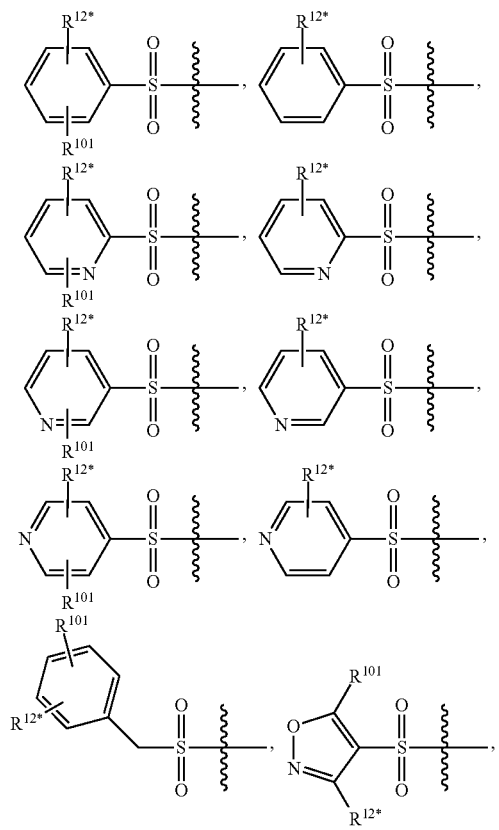

$R^2$ is alkyl, hydrogen, aliphatic, heteroaliphatic, aryl, heteroaryl or heterocyclic;

in some embodiments alkyl is $C_1$-$C_6$, $C_1$-$C_5$, $C_1$-$C_4$, $C_1$-$C_3$, $C_1$-$C_2$, or methyl;

or $R^1$ and $R^2$ are combined to form a 4, 5, 6, 7, 8, 9, or 10 membered heterocyclo or heteroaryl species, wherein the heterocyclo or heteroaryl species is substituted with $R^{12}$ at any desired position, wherein the heterocyclo or heteroaryl species is optionally further substituted with one or more substituents selected from $R^5$;

and in an additional alternative embodiment the heterocyclo or heteroaryl species is optionally further substituted with one or more =O(oxo) at a position allowed by valence;

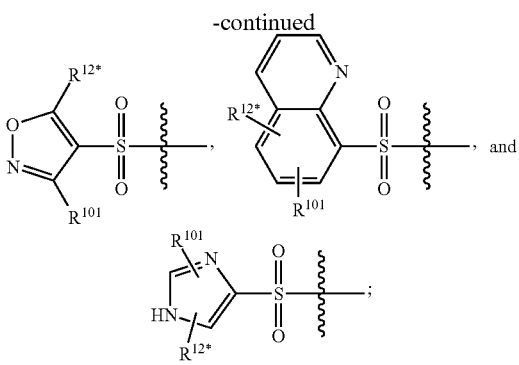

R³ is selected at each instance from: alkyl, —C(O)H, —C(O)OH, —C(O)alkyl, —C(O)Oalkyl, alkene, and alkyne, and in addition to these can also be selected from aliphatic, heteroaliphatic, aryl, heteroaryl, and heteroalkyl;

R⁴ is selected at each instance from: alkyl, alkene, alkyne, halogen, hydroxyl, alkoxy, azide, amino, cyano, —NH(aliphatic, including alkyl), —N(aliphatic, including alkyl)₂, —NHSO₂(aliphatic, including alkyl), —N(aliphatic, including alkyl)SO₂alkyl, —NHSO₂(aryl, heteroaryl or heterocyclic), —N(alkyl)SO₂(aryl, heteroaryl or heterocyclic) —NHSO₂alkenyl, —N(alkyl)SO₂alkenyl, —NHSO₂alkynyl, —N(alkyl)SO₂alkynyl, and haloalkyl; and in addition to these can also be selected from aliphatic, heteroaliphatic, aryl, heteroaryl, heteroalkyl and carbocyclic;

or two R⁴ substituents together with the carbon atom(s) to which they are bound can form a 3, 4, 5 or 6 membered ring;

R⁵ and R¹⁴ are selected at each instance from: hydrogen, alkyl, alkene, alkyne, halogen, hydroxyl, alkoxy, azide, amino, cyano, —NH(aliphatic, including alkyl), —N(aliphatic, including alkyl)₂, —NHSO₂(aliphatic, including alkyl), —N(aliphatic, including alkyl)SO₂alkyl, —NHSO₂(aryl, heteroaryl or heterocyclic), —N(alkyl)SO₂(aryl, heteroaryl or heterocyclic) —NHSO₂alkenyl, —N(alkyl)SO₂alkenyl, —NHSO₂alkynyl, —N(alkyl)SO₂alkynyl, and haloalkyl; and in addition to these can also be selected from aliphatic, heteroaliphatic, aryl, heteroaryl, heteroalkyl and carbocyclic;

or in the alternative, R⁵ is independently selected from C(O)R⁴, cyano, aryl, aryloxy, heterocyclo, heteroaryl, arylalkyl, alkoxy, hydroxyl, O-arylalkyl, and cycloalkyl;

each of which R⁵ can be optionally substituted, for example, with one or more substituents selected from alkyl, alkene, alkyne, halogen, hydroxyl, alkoxy, azide, amino, —NHalkyl, —N(alkyl)₂, aryl, heterocyclo, heteroaryl, haloalkyl, and cycloalkyl, or as otherwise described herein;

R⁶, R⁷, R⁸, R⁹, R¹⁰, and R¹¹, are independently selected from hydrogen, alkyl, aliphatic, heteroaliphatic, hydroxyl, alkoxy, amine, —NH(aliphatic, including alkyl), and —N(aliphatic, including alkyl)₂;

or R⁶ and R⁷ together with the carbon to which they are bound form a 3-, 4-, 5-, or 6-membered spirocarbocycle, or a 4-, 5-, or 6-membered spiroheterocycle comprising 1 or 2 heteroatoms selected from N and O;

or R⁸ and R⁹ together with the carbon to which they are bound form a 3-, 4-, 5-, or 6-membered spirocarbocycle, or a 4-, 5-, or 6-membered spiroheterocycle comprising 1 or 2 heteroatoms selected from N and O;

or R¹⁰ and R¹¹ together with the carbon to which they are bound form a 3-, 4-, 5-, or 6-membered spirocarbocycle, or a 4-, 5-, or 6-membered spiroheterocycle comprising 1 or 2 heteroatoms selected from N and O;

or R⁶ and R⁸ form a 1 or 2 carbon bridged ring;
or R⁶ and R¹⁰ form a 1 or 2 carbon bridged ring;
or R⁸ and R¹⁰ form a 1 or 2 carbon bridged ring;
or R¹⁴ and R⁶ form a 3, 4, 5, or 6 carbon fused ring;
or R¹⁴ and R¹⁰ form a 3, 4, 5, or 6 carbon fused ring;
or R¹⁴ and R⁸ form a 1 or 2 carbon bridged ring;
or R¹⁴ and R⁴ form a 3, 4, 5, or 6 carbon fused ring wherein R⁵ is on the carbon alpha to R¹⁴ or a 1, 2, 3, or 4 carbon bridged ring wherein R⁵ is not on the carbon alpha to R¹⁴;

R¹² is Linker-Targeting Ligand;

R¹²* is

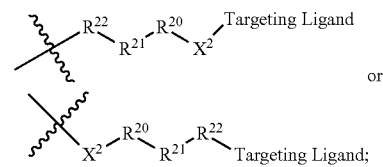

X¹ is selected from bond, NH, NR²⁵, CH₂, CHR²⁵, C(R²⁵)₂, O, and S;

R²⁰, R²¹, and R²² are independently selected from bond, alkyl (typically C₁-C₁₂, and more typically C₁, C₂, C₃, C₄, C₅ or C₆), —C(O)—, —C(O)O—, —OC(O)—, —C(O)alkyl, —C(O)Oalkyl, —C(S)—, —SO₂—, —S(O)—, —C(S)—, —C(O)NH—, —NHC(O)—, —N(alkyl)C(O)—, —C(O)N(alkyl)-, —O—, —S—, —NH—, —N(alkyl)-, —CH(—O—R²⁶)—, —CH(—NHR²⁵)—, —CH(—NH₂)—, —CH(—NR²⁵₂)—, —C(—O—R²⁶)alkyl-, —C(—NHR²⁵)alkyl-, —C(—NH₂)alkyl-, —C(—NR²⁵₂)alkyl-, —C(R⁴R⁴)—, -alkyl(R²⁷)-alkyl(R²⁸)—, —C(R²⁷R²⁸)—, —P(O)(OR²⁶)O—, —P(O)(OR²⁶)—, —NHC(O)NH—, —N(R²⁵)C(O)N(R²⁵)₋, —N(H)C(O)N(R²⁵)—, polyethylene glycol, poly(lactic-co-glycolic acid), alkene, haloalkyl, alkoxy, and alkyne;

or R²⁰, R²¹, and R²² in addition to these can also be selected from heteroarylalkyl, aryl, arylalkyl, heterocycle, heteroaliphatic, heteroaryl, aliphatic and carbocycle in addition to the substituents named above;

each of which R²⁰, R²¹, and R²², is optionally substituted with one or more substituents selected from R¹⁰¹ and in addition to these substituents can also be selected from those in the definition of optional substituent in the Definitions section below.

R²⁵ is selected at each instance from: alkyl, —C(O)H, —C(O)OH, —C(O)alkyl, —C(O)Oalkyl, alkenyl, and alkynyl; or alternatively can be aliphatic, heteroaliphatic, aryl, heteroaryl or heterocyclic;

R²⁶ is hydrogen, alkyl, silane, arylalkyl, heteroarylalkyl, alkene, and alkyne; or in addition to these can also be selected from aryl, heteroaryl, heterocyclic, aliphatic and heteroaliphatic;

R²⁷ and R²⁸ are independently selected from hydrogen, alkyl, and amine; or together with the carbon atom to which they are attached, form C( ), C(S), C=CH₂, a C₃-C₆ spirocarbocycle, or a 4-, 5-, or 6-membered spiroheterocycle comprising 1 or 2 heteroatoms selected from N and O, or form a 1 or 2 carbon bridged ring;

$R^{101}$ is independently selected at each occurrence from hydrogen, alkyl, alkene, alkyne, haloalkyl, alkoxy, hydroxyl, aryl, heteroaryl, heterocycle, arylalkyl, heteroarylalkyl, heterocycloalkyl, aryloxy, heteroaryloxy, CN, —COOalkyl, COOH, NO$_2$, F, Cl, Br, I, CF$_3$, NH$_2$, NHalkyl, N(alkyl)$_2$, aliphatic, and heteroaliphatic;

$R^{17}$ is selected from:

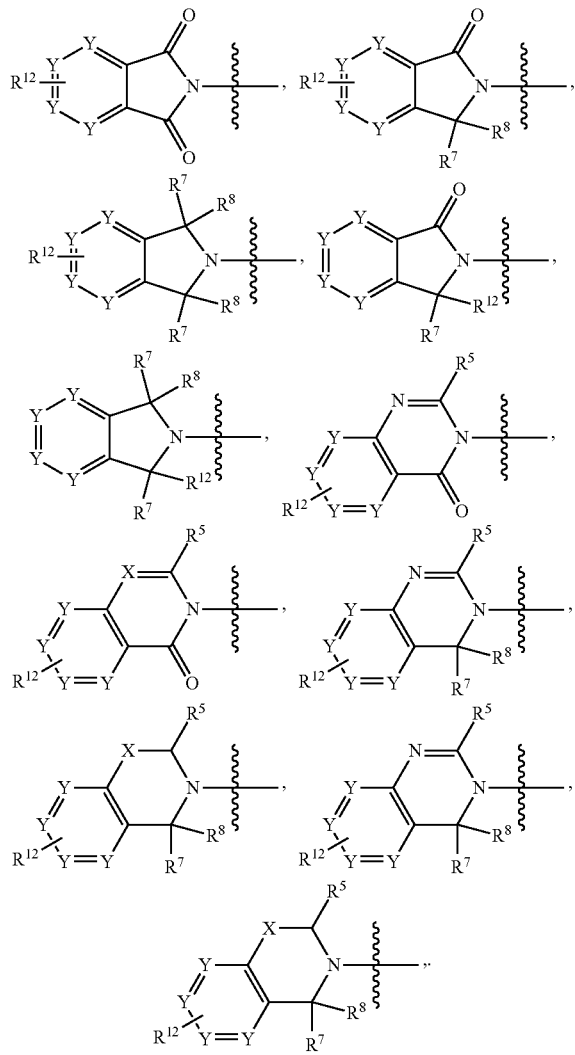

Y is independently selected from N, CH, or CR$^{101}$, wherein 0, 1, 2, or 3 instances of Y are selected to be N; and wherein in certain embodiments the number of nitrogen atoms is 0, 1, 2, 3, or 4 per ring (as allowed by context), and more typically, 1 or 2, and is selected to produce a stable ring and a pharmaceutically acceptable Degronimer. When Y's are in a six-membered ring (unfused or fused), the ring can be, in non-limiting embodiments as allowed by context, a pyridine, diazine, triazine, pyrimidine, pyridazine, pyrazine, triazine or tetrazine.

and when $R^{12}$ is bonded to a Y that is carbon, then Y is CR$^{12}$;

for example

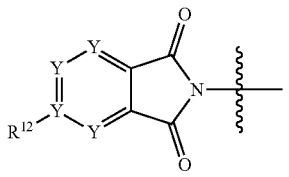

is typically

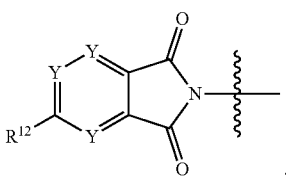

The structure of the Degronimer is typically selected such that it is sufficiently stable to sustain a shelf life of at least two, three, four, or five months under ambient conditions. To accomplish this, each of the R groups described herein must be sufficiently stable to sustain the corresponding desired shelf life of at least two, three, four or five months under ambient conditions. One of ordinary skill in the art is well aware of the stability of chemical moieties and can avoid those that are not stable or are too reactive under the appropriate conditions.

The Degronimer (Degron, Linker and Targeting Ligand), including any of the "R" groups defined herein, may be optionally substituted as described below in Section I. Definitions, if desired to achieve the target effect, results in a stable R moiety and final compound that makes chemical sense to the routineer, and if a final compound for therapy, is pharmaceutically acceptable. Also, all R groups, with or without optional substituents, should be interpreted in a manner that does not include redundancy (i.e., as known in the art, alkyl substituted with alkyl is redundant; however for examples, alkoxy substituted with alkoxy is not redundant).

Linker is a chemical group that attaches the Degron to a Targeting Ligand.

Targeting Ligand is a small molecule that binds to a Target Protein, and wherein the Target Protein is a mediator of disease in a host.

Degronimers of Formula I, Formula II, and Formula V are bifunctional compounds with an amine E3 Ubiquitin Ligase targeting moiety (Degron) linked to protein Targeting Ligand (described in more detail below), which function to recruit Target Proteins, typically via a cereblon-containing E3 Ubiquitin Ligase for degradation. One non-limiting example of a disorder treatable by such compounds is abnormal cellular proliferation, such as a tumor or cancer, wherein the Target Protein is an oncogenic protein or a signaling mediator of an abnormal cellular proliferative pathway and its degradation decreases abnormal cell growth.

Based on this discovery, compounds and methods are presented for the treatment of a patient with a disorder mediated by a protein that is targeted for selective degradation that includes administering an effective amount of one or a combination of the Degronimers of Formula I, Formula II, or Formula V described herein to a patient (typically a human) in need thereof, optionally in a pharmaceutically acceptable carrier (composition). In certain embodiments the disorder is selected from a benign growth, neoplasm, tumor, cancer, abnormal cellular proliferation, immune disorder, autoimmune disorder, inflammatory disorder, graft-versus-host rejection, viral infection, bacterial infection, an amyloid-based proteinopathy, a proteinopathy, or fibrotic disorder. In a typical embodiment the patient is a human.

In one embodiment, the present invention provides N(substituted)$_2$-C$^3$-glutarimides and defined analogue Degrons thereof which are covalently linked to a Targeting Ligand through a Linker which can be of varying length and functionality. In one embodiment, the N(substituted)$_2$-C$^3$-glutarimides and defined analogue Degron is linked directly to the Targeting Ligand (i.e., the Linker is a bond). In certain embodiments, the Linker can be any chemically stable group that attaches the amine Degron to the Targeting Ligand. In a typical embodiment the Linker has a chain of 2 to 14, 15, 16, 17, 18 or 20 or more carbon atoms of which one or more carbons can be replaced by a heteroatom such as O, N, S, P, as long as the resulting molecule has a stable shelf life for at least 2 months, 3 months, 6 months or 1 year as part of a pharmaceutically acceptable dosage form, and itself is pharmaceutically acceptable. In certain embodiments the chain has 2, 3, 4, 5, 6, 7, 8, 9, 10, 11, 12, 13, or 14 contiguous atoms in the chain. For example, the chain may include 1 or more ethylene glycol units, and in some embodiments, may have at least 2, 3, 4, 5, 6, 7, 8, 9, or 10 or more contiguous, partially contiguous or non-contiguous ethylene glycol units in the Linker. In certain embodiments the chain has at least 1, 2, 3, 4, 5, 6, 7, or 8 branches which can be independently alkyl, heteroalkyl, aryl, heteroaryl, alkenyl, or alkynyl substituents, which in one embodiment, each branch has 10, 8, 6, 4, 3, 2 carbons or one carbon.

In one embodiment, the Target Protein is a protein that is not drugable in the classic sense in that it does not have a binding pocket or an active site that can be inhibited or otherwise bound, and cannot be easily allosterically controlled. In another embodiment, the Target Protein is a protein that is drugable in the classic sense. Examples of Target Proteins are provided below.

In an alternative embodiment, an N(substituted)$_2$-C$^3$-glutarimide as described herein can be used alone (i.e., not as part of a Degronimer) as an in vivo binder of cereblon, which can be administered to a host, for example, a human, in need thereof, in an effective amount, optionally as a pharmaceutically acceptable salt, and optionally in a pharmaceutically acceptable composition, for any therapeutic indication which can be treated by modulating the function and or activity of the cereblon-containing E3 Ubiquitin Ligase Protein Complex, including but not limited to uses known for the cereblon binders thalidomide, pomalidomide or lenalidomide. In certain alternative embodiments, the compound of Formula III or IV can activate, decrease or change the natural activity of cereblon. Nonlimiting examples of uses for cereblon binders are multiple myeloma, a hematological disorder such as myelodysplastic syndrome, cancer, tumors, abnormal cellular proliferation, HIV/AIDS, Crohn's disease, sarcoidosis, graft-versus-host disease, rheumatoid arthritis, Behcet's disease, tuberculosis, and myelofibrosis.

Thus in another aspect of the present invention a compound of Formula III or Formula IV is provided:

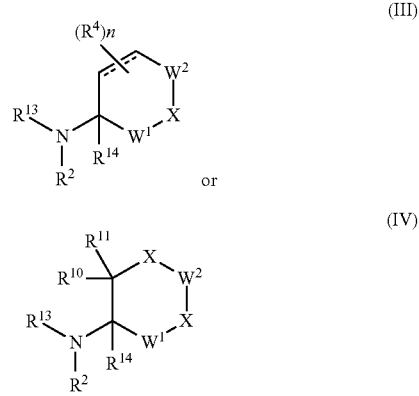

or a pharmaceutically acceptable salt, N-oxide, isotopic derivative, or prodrug thereof, optionally in a pharmaceutically acceptable carrier to form a composition;

wherein:

R$^{13}$ is selected from:

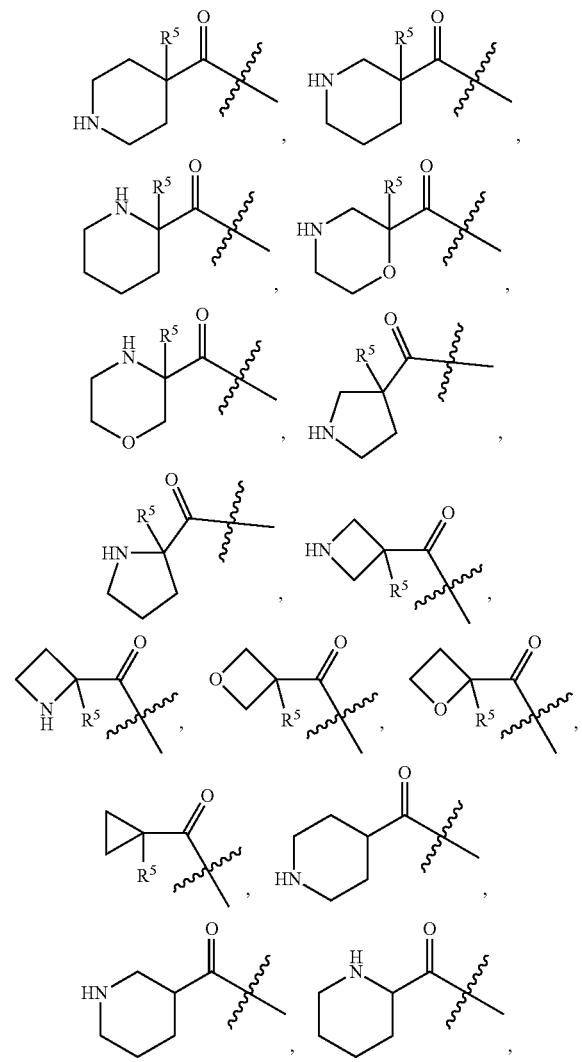

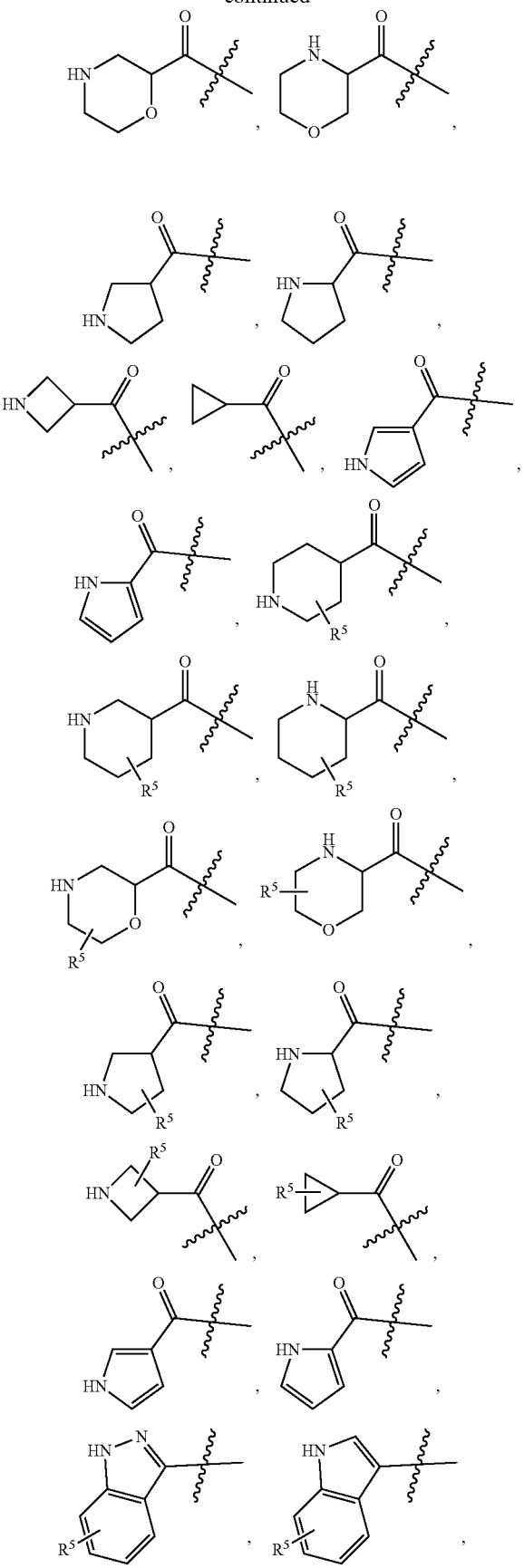

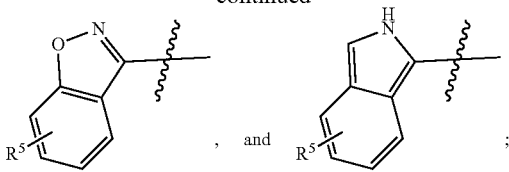

A is independently selected from C($R^{11}$), and N wherein in certain embodiments the number of nitrogen atoms is 0, 1, 2, 3, or 4 per ring (as allowed by context) and is selected to produce a stable ring and a pharmaceutically acceptable Degronimer. When A's are in a six-membered ring (unfused or fused), the ring can be, in non-limiting embodiments as allowed by context, a pyridine, diazine, triazine, pyrimidine, pyridazine, pyrazine, triazine or tetrazine.

or $R^{13}$ and $R^2$ are combined to form a 4 to 10 membered heterocyclo or heteroaryl species, wherein the heterocyclo or heteroaryl species is optionally further substituted with one or more substituents selected from $R^5$, and wherein the heterocyclo or heteroaryl species is optionally further substituted with one or more =O (oxo) at a position allowed by valence.

The compounds of Formulas III and IV do not include a Linker or a Targeting Ligand. In certain alternative embodiments, the compound of Formula III, IV or VI can activate, decrease or change the natural activity of cereblon. These Formula III and IV compounds are useful as therapeutic agents when administered in an effective amount to a host, including a human, for the treatment of a medical disorder that can be treated with thalidomide, pomalidomide or lenalidomide, and/or including, but not limited to, abnormal cellular proliferation, including a tumor or cancer, or a myelo- or lymphoproliferative disorder such as B- or T-cell lymphomas, multiple myeloma, Waldenstrom's macroglobulinemia, Wiskott-Aldrich syndrome, or a post-transplant lymphoproliferative disorder; an immune disorder, including autoimmune disorders such as Addison disease, Celiac disease, dermatomyositis, Graves disease, thyroiditis, multiple sclerosis, pernicious anemia, reactive arthritis, lupus, or type I diabetes; a disease of cardiologic malfunction, including hypercholesterolemia; an infectious disease, including viral and/or bacterial infections; an inflammatory condition, including asthma, chronic peptic ulcers, tuberculosis, rheumatoid arthritis, periodontitis, ulcerative colitis, Crohn's disease, or hepatitis.

In certain embodiments, the compound of Formula I, Formula II, Formula III, Formula IV, or Formula V has at least one desired isotopic substitution of an atom, at an amount above the natural abundance of the isotope, i.e., enriched. In one embodiment, the compound of Formula I, Formula II, Formula III, Formula IV, or Formula V includes a deuterium or multiple deuterium atoms.

Unless otherwise defined, all technical and scientific terms used herein have the same meaning as commonly understood by one of ordinary skill in the art to which this application belongs. In the specification, the singular forms also include the plural unless the context clearly dictates otherwise. Although methods and materials similar or equivalent to those described herein can be used in the practice or testing of the present application, suitable methods and materials are described below. All publications, patent applications, patents, and other references mentioned herein are incorporated by reference. The references cited herein are not admitted to be prior art to the claimed application. In the case of conflict, the present specification, including definitions, will control. In addition, the materials, methods, and examples are illustrative only and are not intended to be limiting.

Other features and advantages of the present application will be apparent from the following detailed description and claims.

The present invention thus includes at least the following features:

(a) A Degronimer containing an N(substituted)$_2$-C$^3$-glutarimide Degron or defined analogue thereof of Formula I, Formula II, or Formula V and pharmaceutically acceptable salts, isotopic derivative (including a deuterated derivative) and prodrugs thereof;

(b) An N(substituted)$_2$-C$^3$-glutarimide Degron or defined analogue thereof of Formula III or Formula IV as described herein, and pharmaceutically acceptable salts, isotopic derivative (including a deuterated derivative) and prodrugs thereof;

(c) A Degronimer containing an N(substituted)$_2$-C$^3$-glutarimide Degron or defined analogue thereof of Formula I, Formula II, or Formula V, and pharmaceutically acceptable salts, isotopic derivative (including a deuterated derivative) and prodrugs thereof for the treatment of a disorder that is mediated by a Target Protein, wherein the compound includes a Targeting Ligand for the Target Protein, and wherein the Degron is optionally linked to the Targeting Ligand through a Linker;

(d) Use of a Degronimer containing an N(substituted)$_2$-C-glutarimide Degron or defined analogue thereof of Formula I, Formula II, or Formula V in an effective amount in the treatment of a patient, including a human, with any of the disorders described herein mediated by a Target Protein, including abnormal cellular proliferation such as a tumor or cancer, an immune or autoimmune disorder or inflammatory disorder, a cardiologic disorder, an infectious disease, or other disorder that responds to such treatment;

(e) Use of a compound of Formula III or Formula IV in an effective amount, in the treatment of a patient, including a human, with a disorder that responds to such treatment, including by decreasing the cereblon-based ubiquitination of a protein, such as for example, abnormal cellular proliferation such as a tumor or cancer, an immune or autoimmune disorder or inflammatory disorder, a cardiac disorder, an infectious disease, or other disorder that responds to such treatment;

(f) Use of a compound of Formula I, Formula II, Formula III, Formula IV, or Formula V and pharmaceutically acceptable salts, isotopic derivatives and prodrugs thereof in the manufacture of a medicament for the treatment of a medical disorder, as further described herein;

(g) A method for manufacturing a medicament intended for the therapeutic treatment of a disorder in a host characterized in that a compound of Formula I, Formula II, Formula III, Formula IV, or Formula V as described herein is used in the manufacture;

(h) A compound of Formula I, Formula II, Formula III, Formula IV, or Formula V as described herein, and pharmaceutically acceptable salts, isotopic derivatives and prodrugs thereof that are useful in the treatment of an abnormal cellular proliferation such as cancer, including any of the cancers described herein;

(i) Use of a compound of Formula I, Formula II, Formula III, Formula IV, or Formula V and pharmaceutically acceptable salts, isotopic derivatives and prodrugs thereof in the manufacture of a medicament for the treatment of an abnormal cellular proliferation such as cancer, including any of the cancers described herein;

(j) A method for manufacturing a medicament intended for the therapeutic use of treating an abnormal cellular proliferation such as cancer, including any of the cancers in a host described herein, characterized in that a compound of Formula I, Formula II, Formula III, Formula IV, or Formula V as described herein is used in the manufacture;

(k) A compound of Formula I, Formula II, Formula III, Formula IV, or Formula V as described herein, and pharmaceutically acceptable salts, isotopic derivatives and prodrugs thereof that are useful in the treatment of a tumor in a host, including any of the tumors described herein;

(l) Use of a compound of Formula I, Formula II, Formula III, Formula IV or Formula V and pharmaceutically acceptable salts and prodrugs thereof in the manufacture of a medicament for the treatment of a tumor, including any of the tumors described herein;

(m) A method for manufacturing a medicament intended for the therapeutic treatment of a tumor in a host, including any of the tumors described herein, characterized in that a compound of Formula I, Formula II, Formula III, Formula IV, or Formula V as described herein is used in the manufacture;

(n) A compound of Formula I, Formula II, Formula III, Formula IV, or Formula V as described herein, and pharmaceutically acceptable salts and prodrugs thereof that are useful in the treatment of an immune, autoimmune or inflammatory disorder in a host;

(o) Use of a compound of Formula I, Formula II, Formula III, Formula IV or Formula V and pharmaceutically acceptable salts, isotopic derivatives and prodrugs thereof in the manufacture of a medicament for the treatment of an immune, autoimmune or inflammatory disorder in a host;

(p) A method for manufacturing a medicament intended for the therapeutic treatment of an immune, autoimmune or inflammatory disorder in a host, characterized in that a compound of Formula I, Formula II, Formula III, Formula IV or Formula V as described herein is used in the manufacture;

(q) A compound of Formula I, Formula II, Formula III, Formula IV or Formula V as described herein, and pharmaceutically acceptable salts, isotopic derivatives and prodrugs thereof that are useful in the treatment of an infection, including a viral infection in a host, for example HIV, HBV, HCV and RSV;

(r) Use of a compound of Formula I-V and pharmaceutically acceptable salts, isotopic derivatives and prodrugs thereof in the manufacture of a medicament for the treatment of an infection in a host, for example. HIV, HBV, HCV and RSV;

(s) A method for manufacturing a medicament intended for the therapeutic treatment of an infection, including a viral infection in a host, for example. HIV, HBV, HCV and RSV, characterized in that a compound of Formula I-V as described herein is used in the manufacture;

(t) A pharmaceutical formulation comprising an effective host-treating amount of the compound of Formula I, Formula II, Formula III, Formula IV, or Formula V or a pharmaceutically acceptable salt, isotopic derivative or prodrug thereof together with a pharmaceutically acceptable carrier or diluent;

(u) A compound of Formula I, Formula II, Formula III, Formula IV, or Formula V as described herein as a mixture of enantiomers or diastereomers (as relevant), including as a racemate;
(v) A compound of Formula I, Formula II, Formula III, Formula IV, or Formula V as described herein in enantiomerically or diastereomerically (as relevant) enriched form, including as an isolated enantiomer or diastereomer (i.e., greater than 85, 90, 95, 97 or 99% pure); and
(w) A process for the preparation of therapeutic products that contain an effective amount of a compound of Formula I, Formula II, Formula III, Formula IV, or Formula V, as described herein.

BRIEF DESCRIPTION OF THE FIGURES

FIG. 1K-1Q present examples of General Kinase and Phosphatase Targeting Ligands wherein R is the point at which the Linker is attached.

FIG. 1R-1S present examples of Tyrosine Kinase Targeting Ligands wherein R is the point at which the Linker is attached.

FIG. 1AA presents examples of mTORC1 and/or mTORC2 Targeting Ligands wherein R is the point at which the Linker is attached.

FIG. 1BB-1CC present examples of Mast/stem cell growth factor receptor (SCFR), also known as c-KIT receptor, Targeting Ligands wherein R is the point at which the Linker is attached.

FIG. 1DD presents examples of IGF1R and/or IR Targeting Ligands wherein R is the point at which the Linker is attached.

FIG. 1EE-1FF present examples of HDM2 and/or MDM2 Targeting Ligands wherein R is the point at which the Linker is attached.

FIG. 1GG-1MM present examples of BET Bromodomain-Containing Protein Targeting Ligands wherein R is the point at which the Linker is attached.

FIG. 1NN presents examples of HDAC Targeting Ligands wherein R is the point at which the Linker is attached.

FIG. 1OO presents examples of RAF Receptor Targeting Ligands wherein R is the point at which the Linker is attached.

FIG. 1PP presents examples of FKBP Receptor Targeting Ligands wherein R is the point at which the Linker is attached.

FIG. 1QQ-1TT present examples of Androgen Receptor Targeting Ligands wherein R is the point at which the Linker is attached.

FIG. 1UU presents examples of Estrogen Receptor Targeting Ligands wherein R is the point at which the Linker is attached.

FIG. 1VV-1WW present examples of Thyroid Hormone Receptor Targeting Ligands wherein R is the point at which the Linker is attached.

FIG. 1XX presents examples of HIV Protease Targeting Ligands wherein R is the point at which the Linker is attached.

FIG. 1YY presents examples of HIV Integrase Targeting Ligands wherein R is the point at which the Linker is attached.

FIG. 1ZZ presents examples of HCV Protease Targeting Ligands wherein R is the point at which the Linker is attached.

FIG. 1AAA presents examples of AP1 and/or AP2 Targeting Ligands wherein R is the point at which the Linker is attached.

FIG. 1BBB-1CCC present examples of MCL-1 Targeting Ligands wherein R is the point at which the Linker is attached.

FIG. 1DDD presents examples of IDH1 Targeting Ligands wherein R is the point at which the Linker is attached.

FIG. 1EEE-1FFF present examples of RAS or RASK Targeting Ligands wherein R is the point at which the Linker is attached.

FIG. 1GGG presents examples of MERTK or MER Targeting Ligands wherein R is the point at which the linker is attached.

FIG. 1HHH-1III present examples of EGFR Targeting Ligands wherein R is the point at which the Linker is attached.

FIG. 1JJJ-1KKK present examples of FLT3 Targeting Ligands wherein R is the point at which the Linker is attached.

FIG. 1LLL presents examples of SMRCA2 Targeting Ligands wherein R is the point at which the Linker is attached.

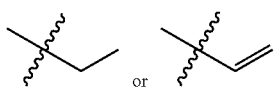

Figure 1A:
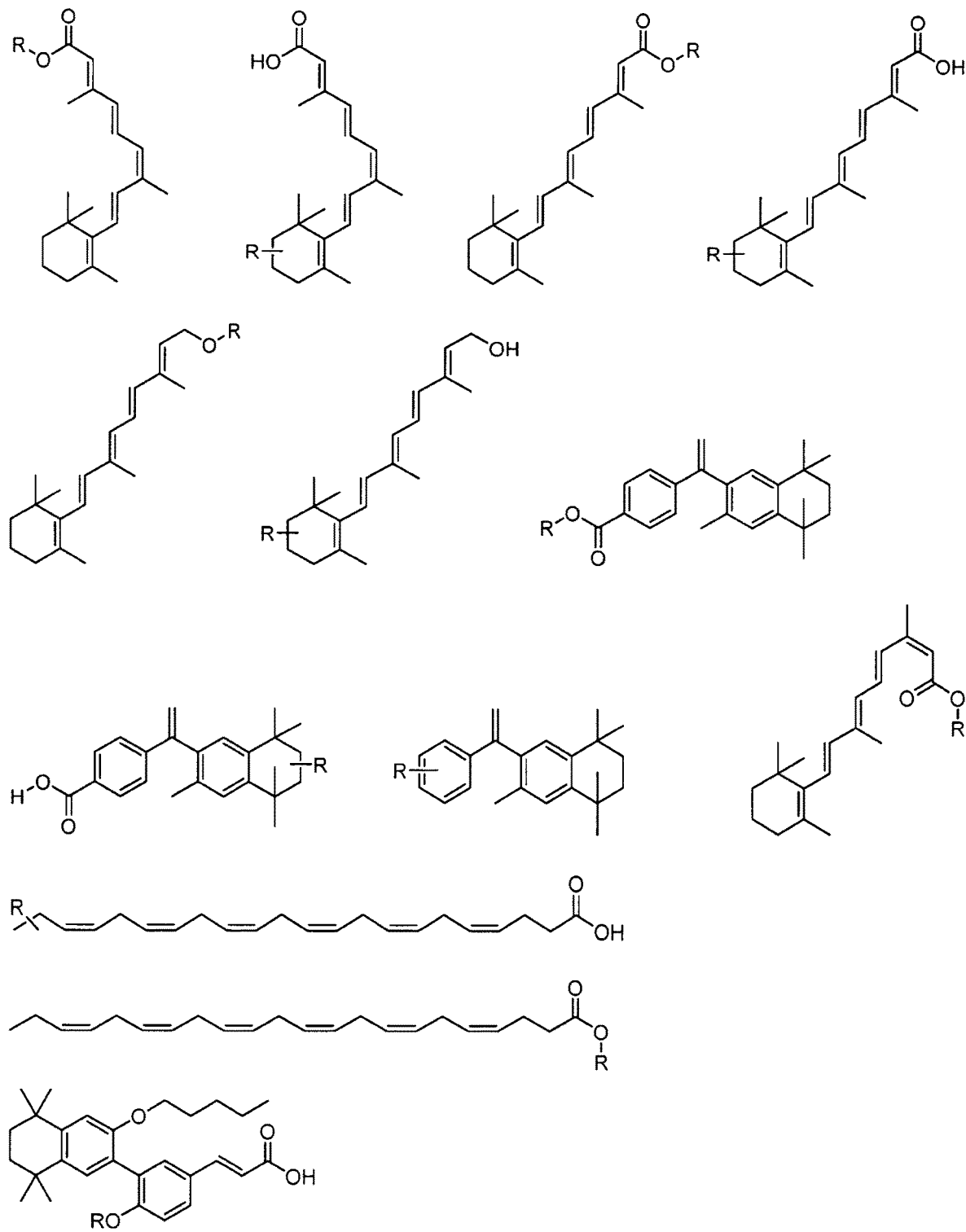
FIG. 1A-1C present examples of Retenoid X Receptor (RXR) Targeting Ligands wherein R is the point at which the Linker is attached.
Figure 1B:
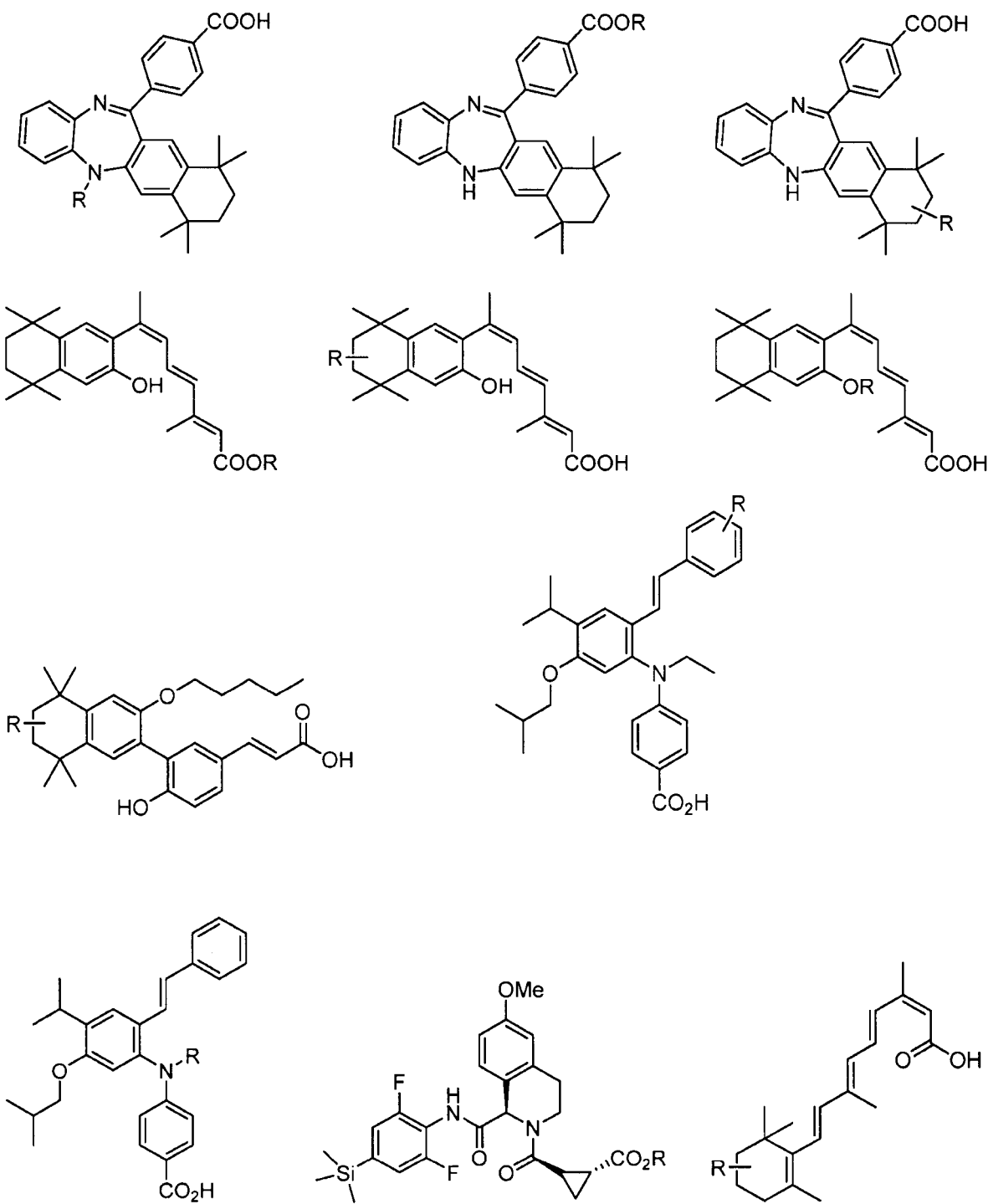
Figure 1C:
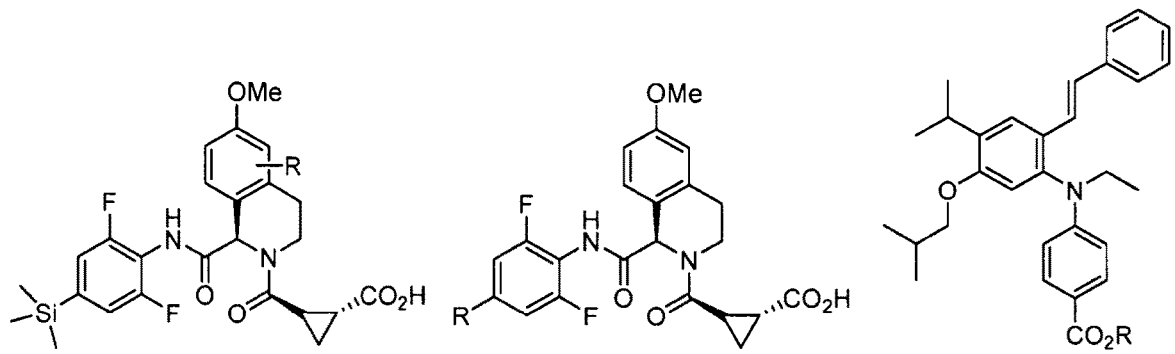
Figure 1D:
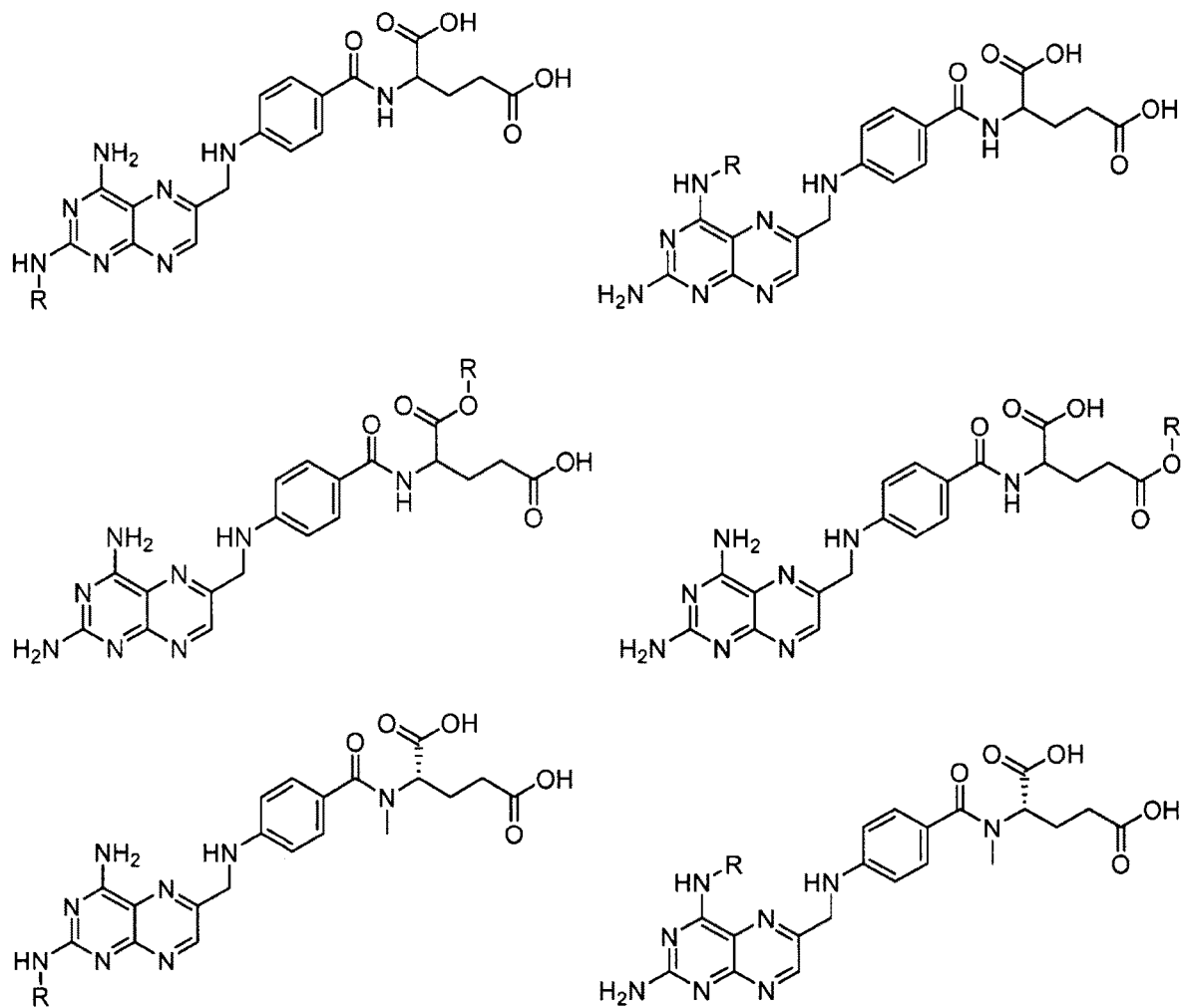
FIG. 1D-1F present examples of general Dihydrofolate reductase (DHFR) Targeting Ligands wherein R is the point at which the Linker is attached.
Figure 1E:
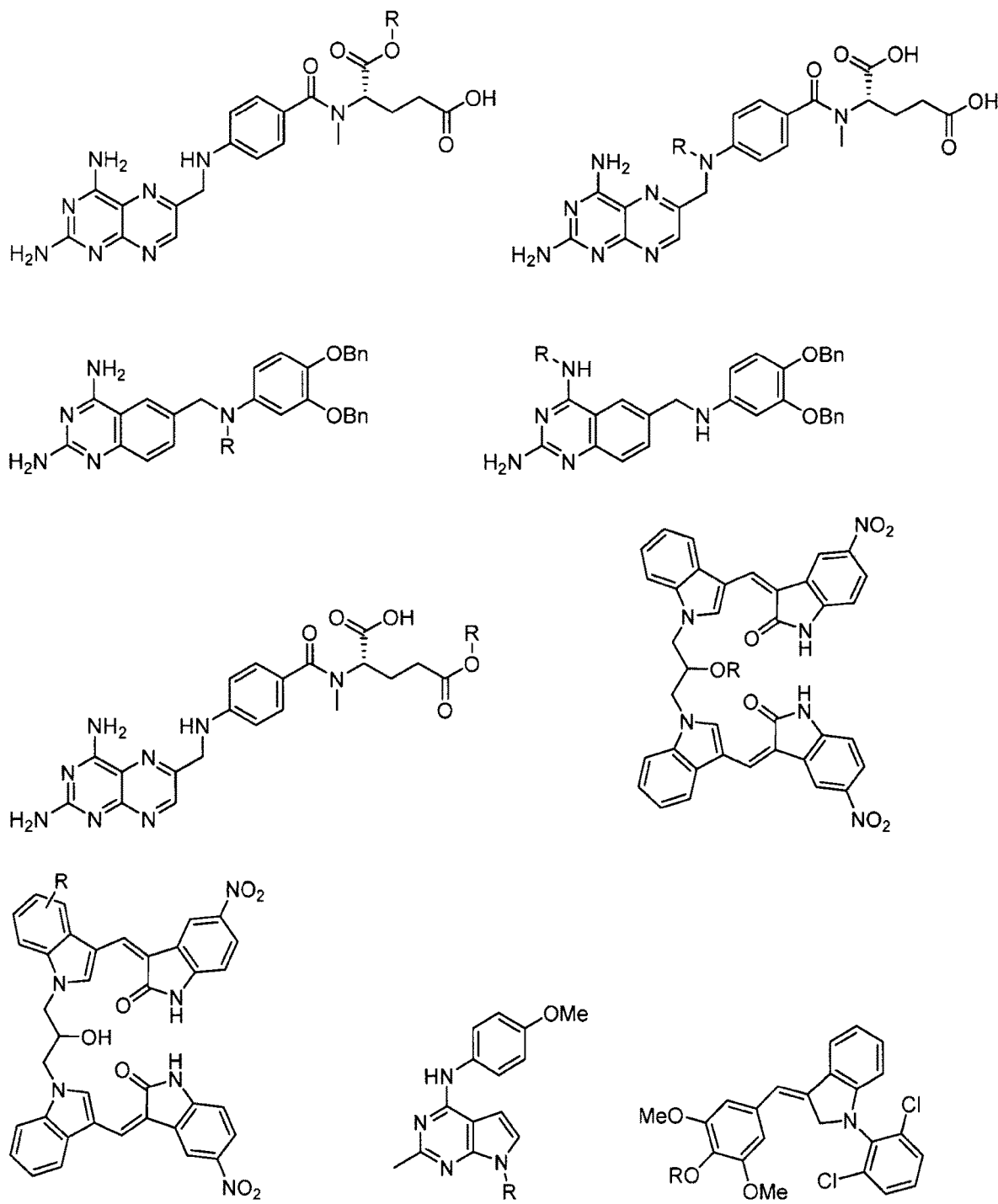
Figure 1F:
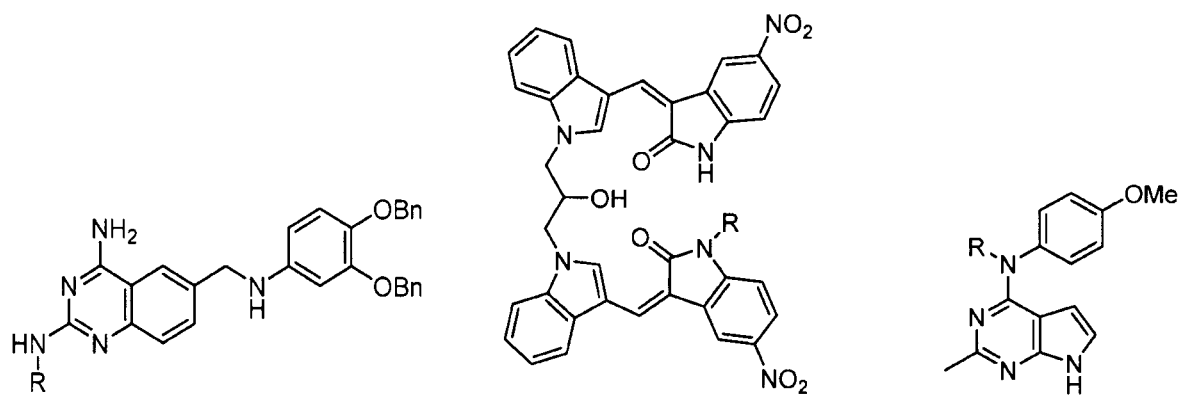
Figure 1G:
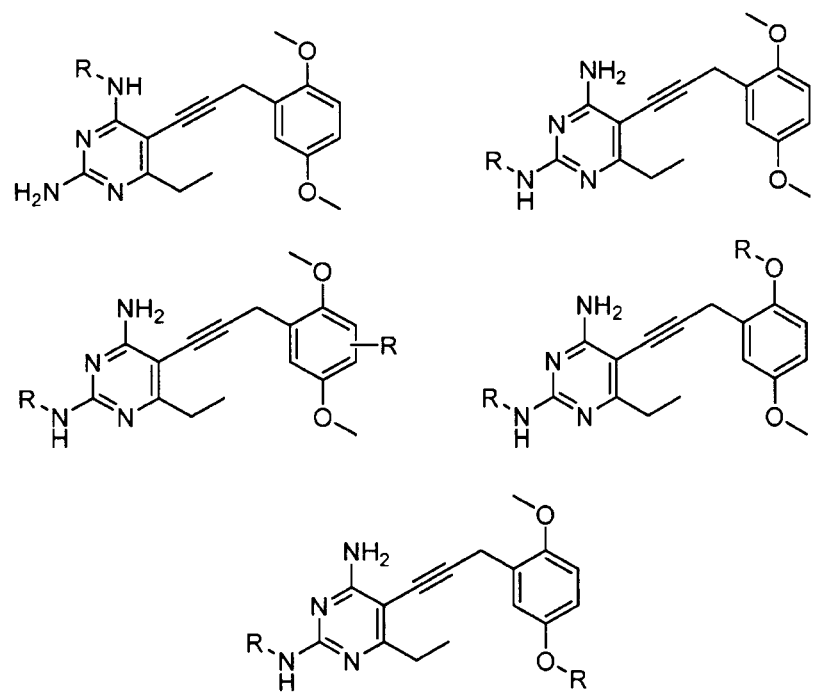
FIG. 1G presents examples of *Bacillus anthracis* Dihydrofolate reductase (BaDHFR) Targeting Ligands wherein R is the point at which the Linker is attached.
Figure 1H:
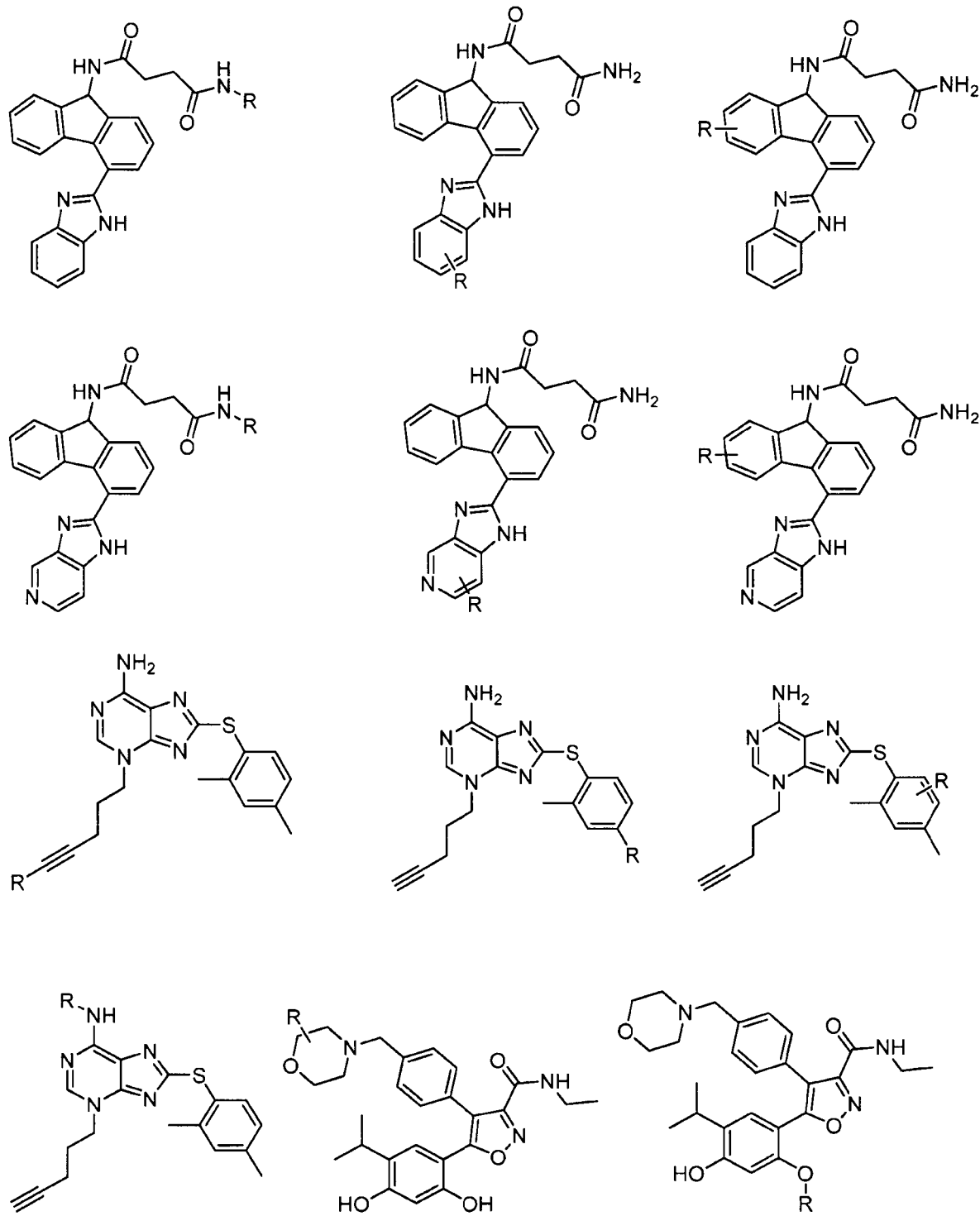
FIG. 1H-1J present examples of Heat Shock Protein 90 (HSP90) Targeting Ligands wherein R is the point at which the Linker is attached.
Figure 1I:
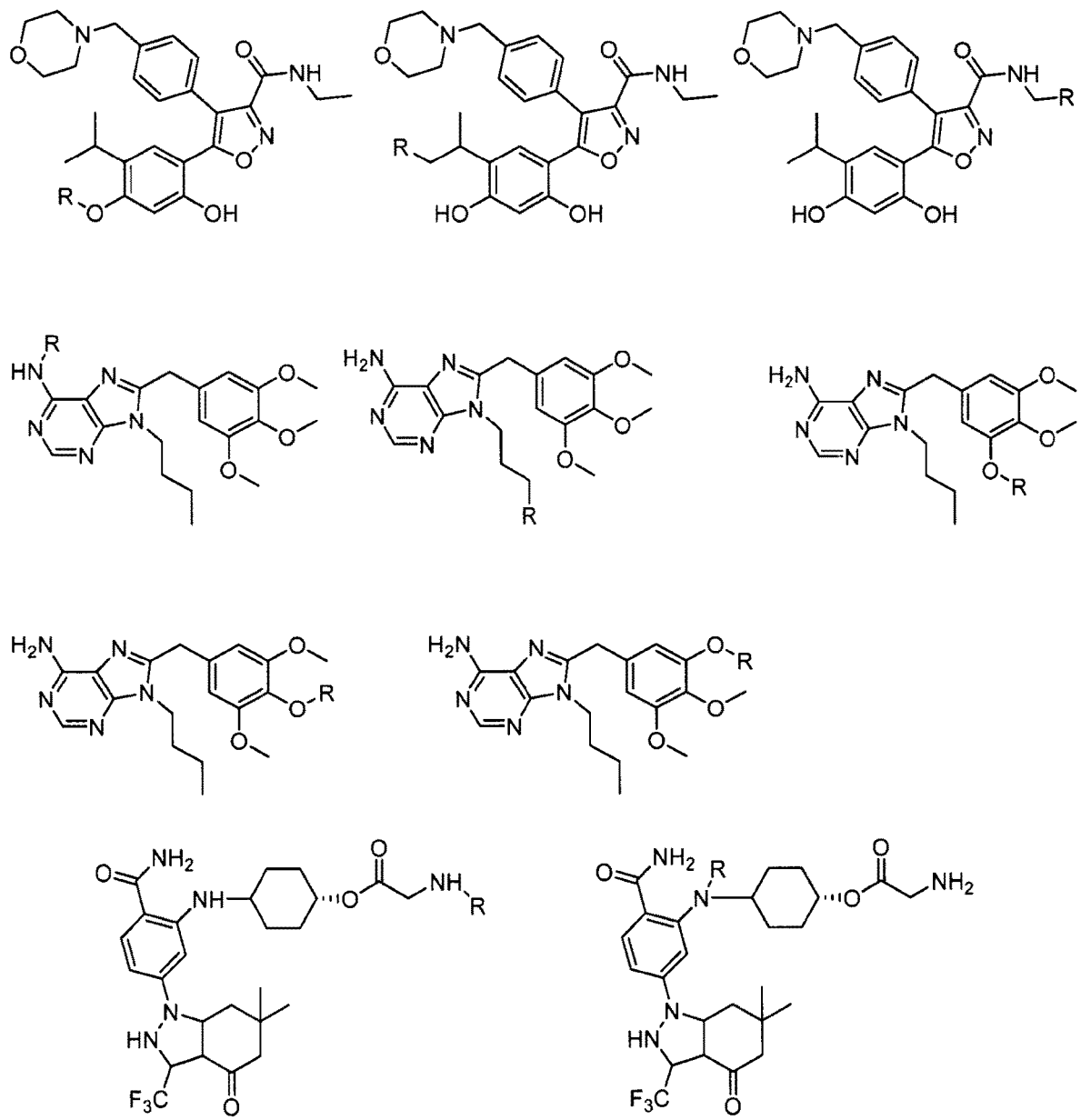
Figure 1J:
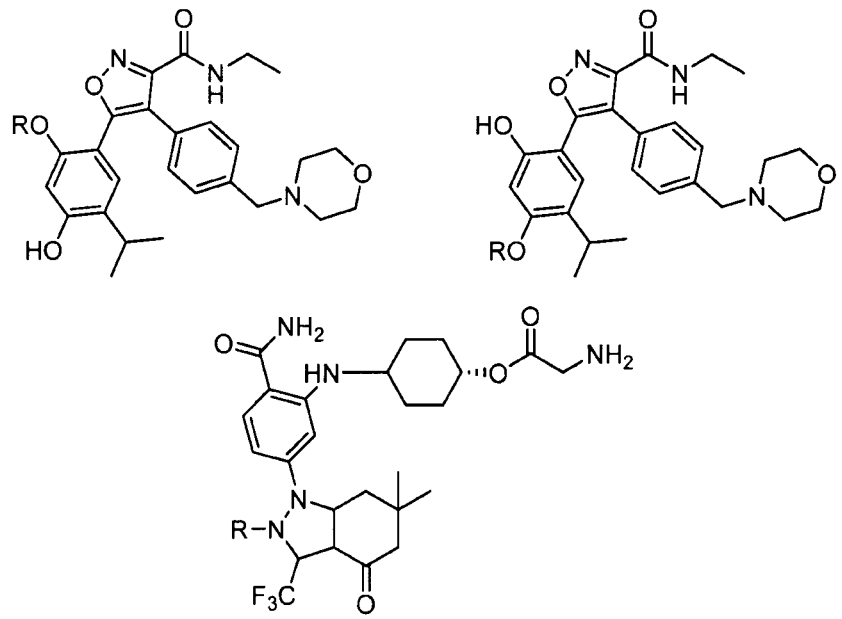
Figure 1K:
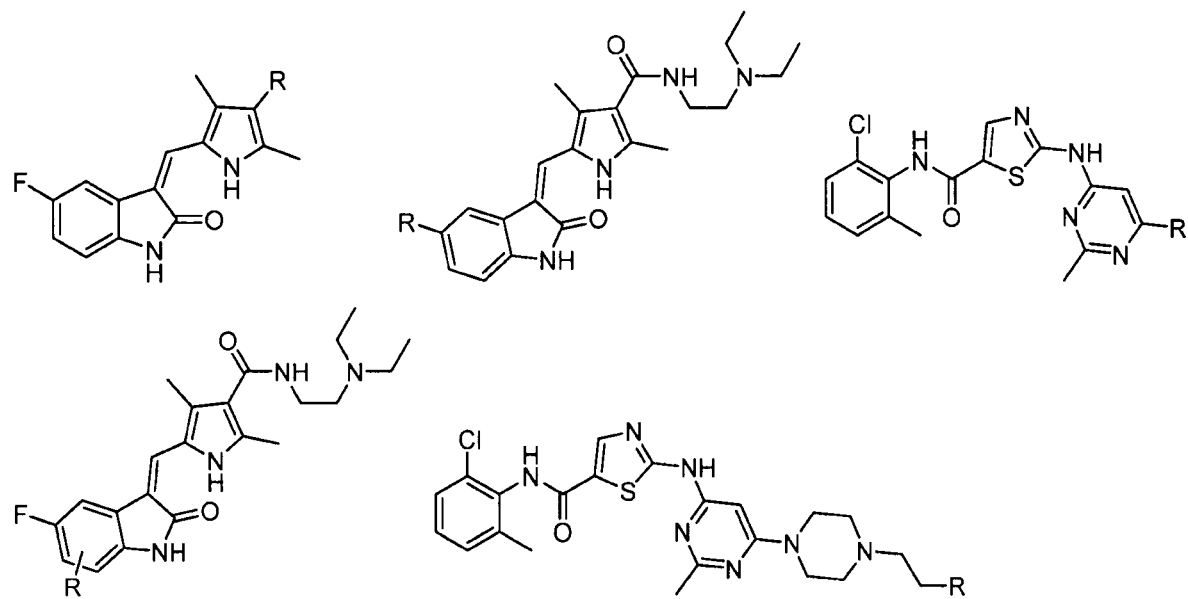
Figure 1L:
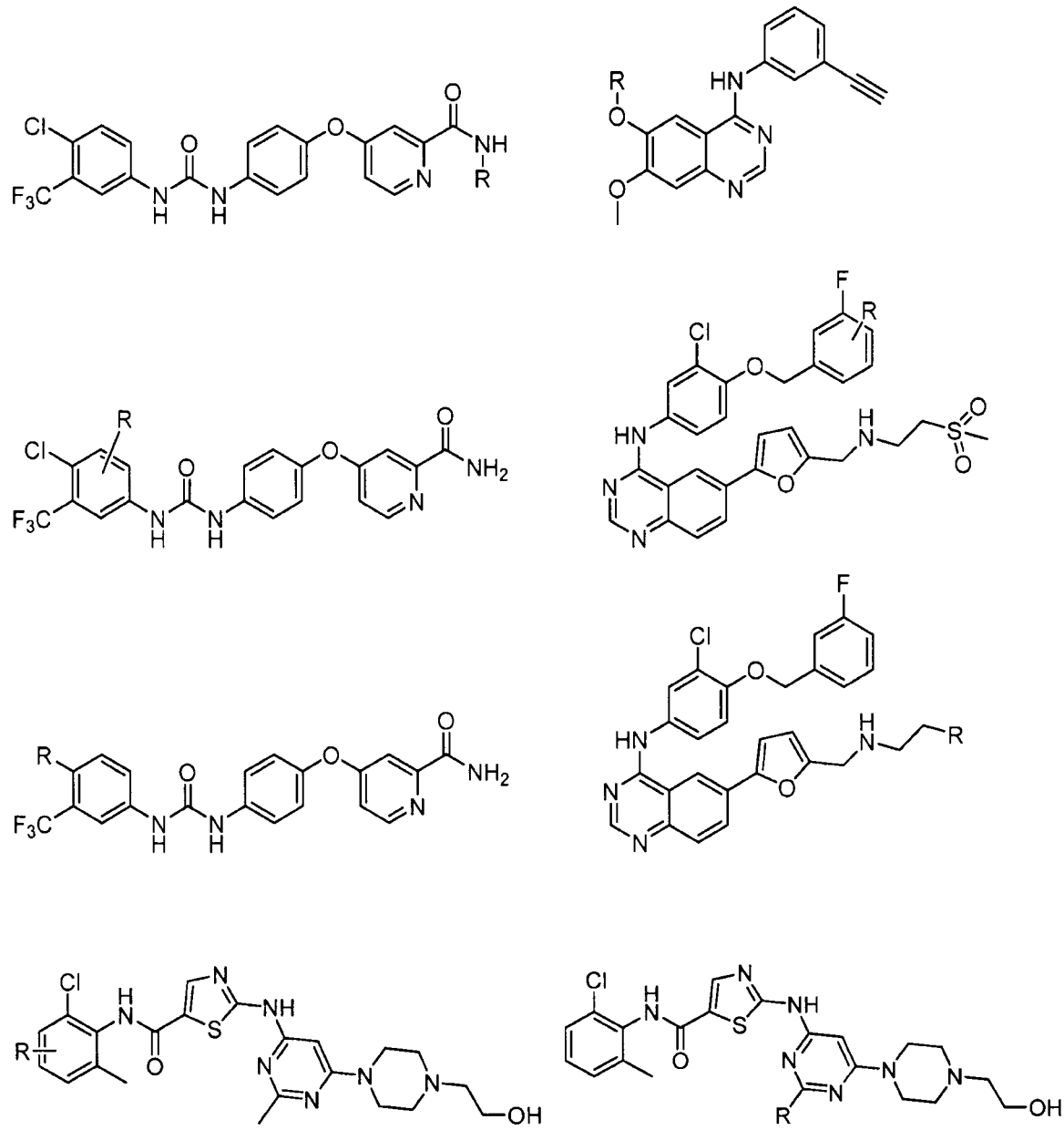
Figure 1M:
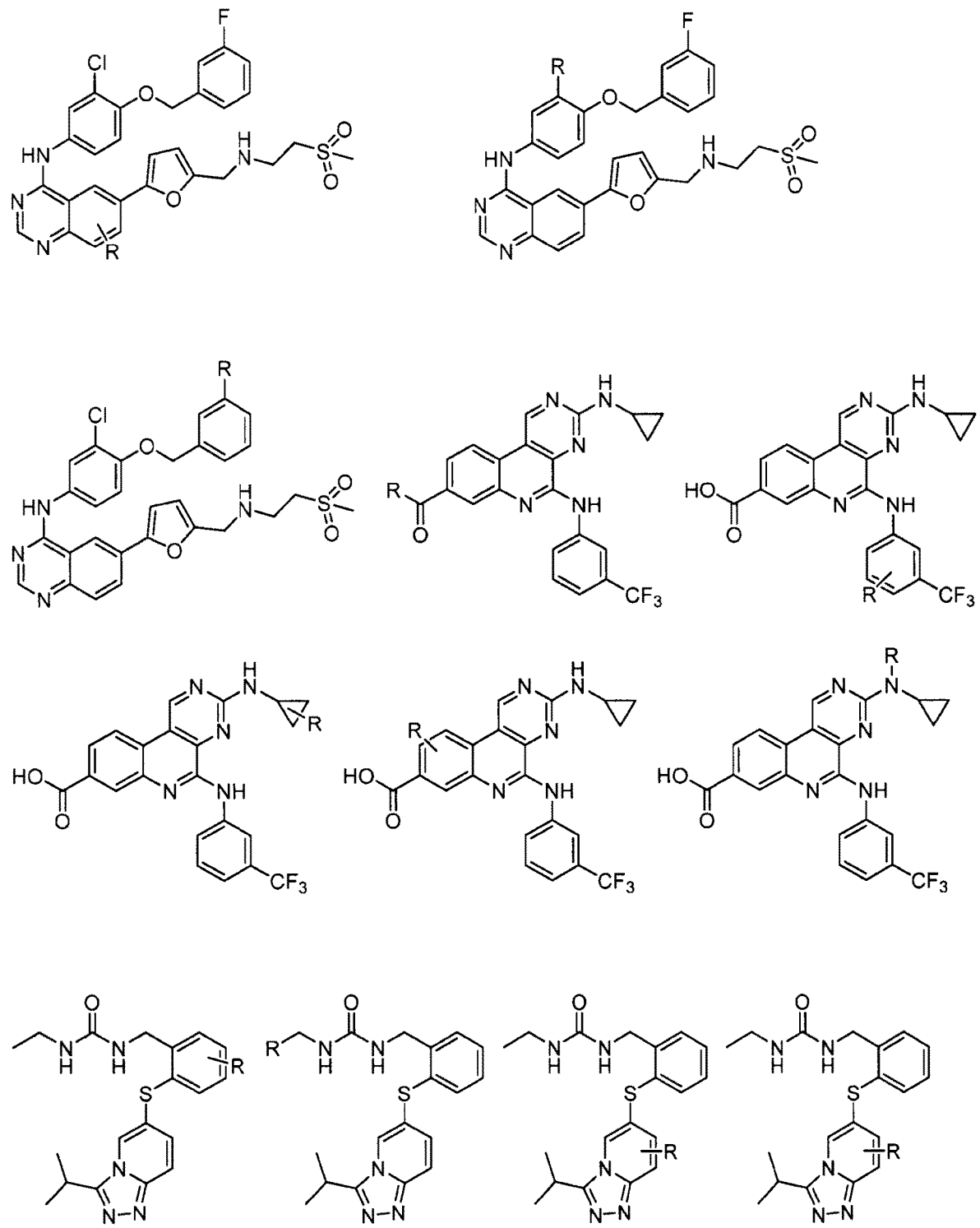
Figure 1N:
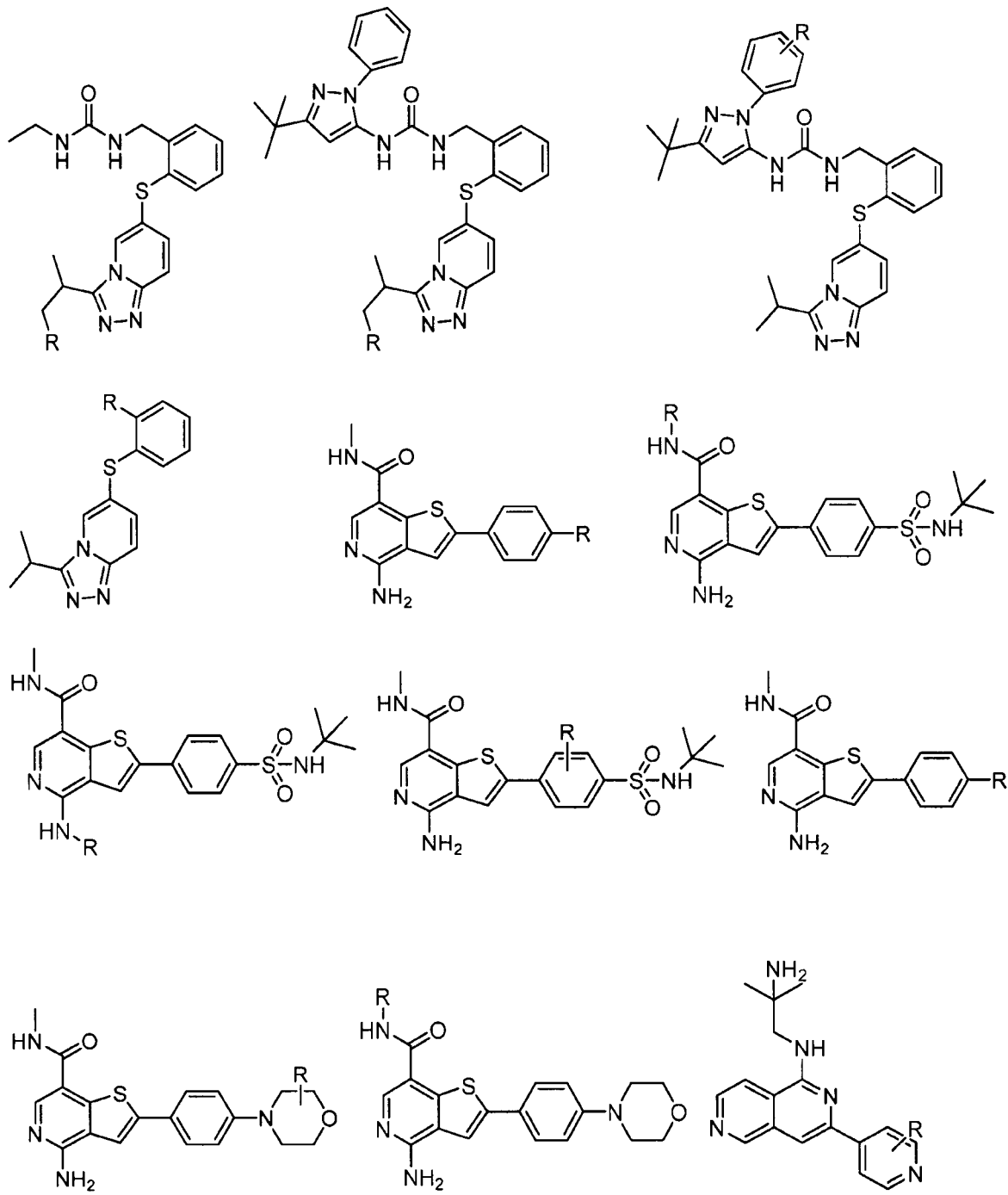
Figure 10:
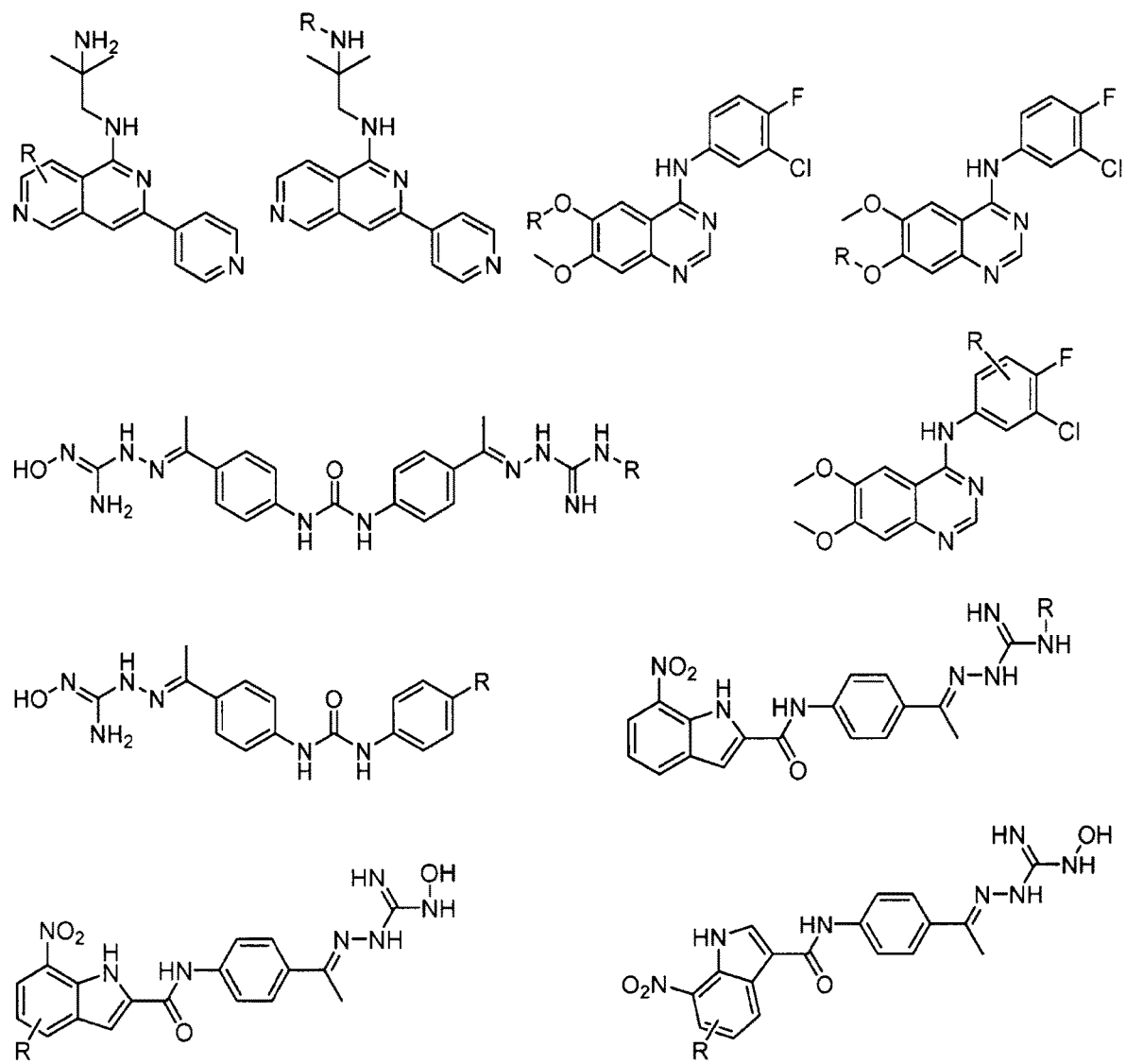
Figure 1P:
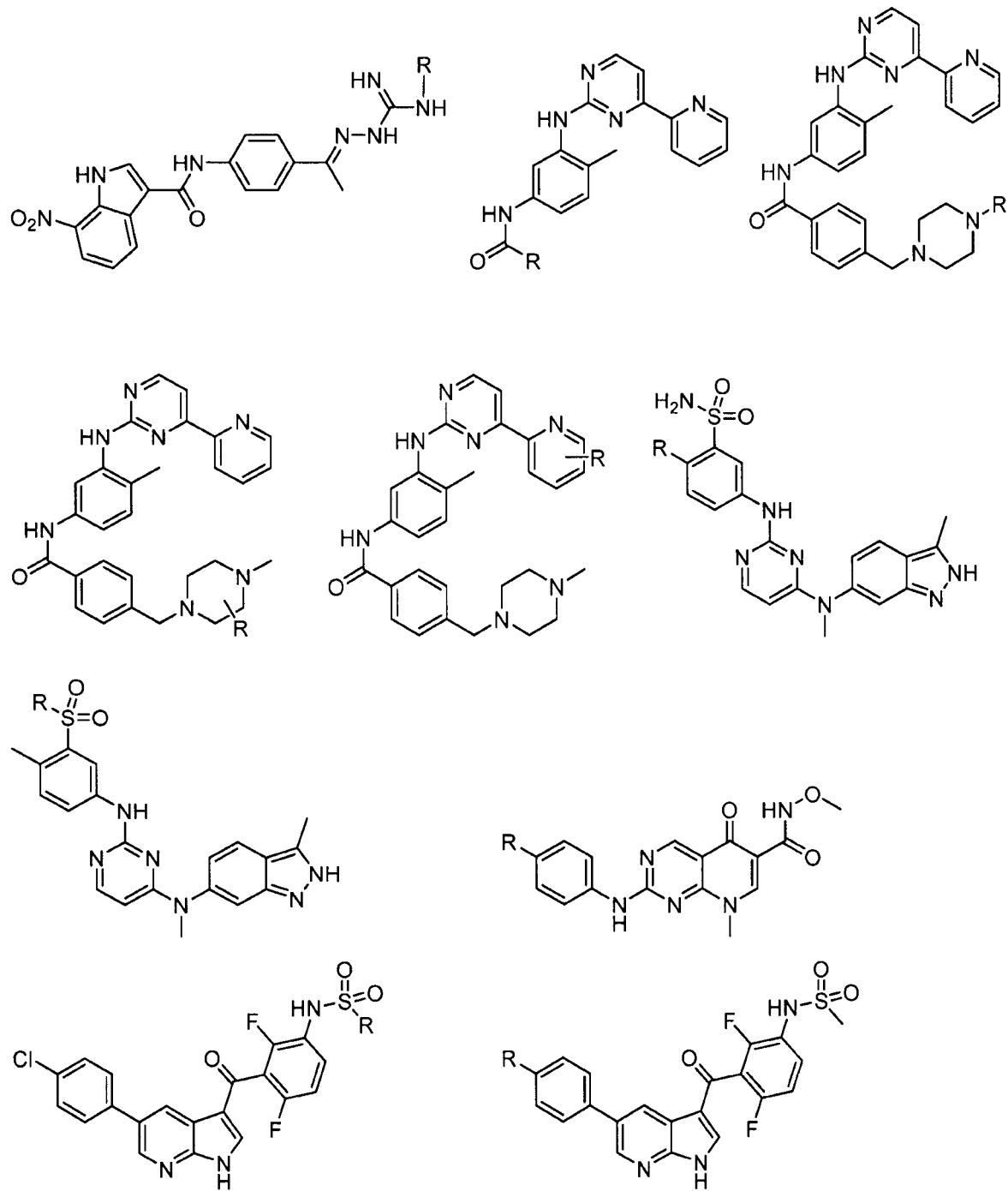
Figure 1S:
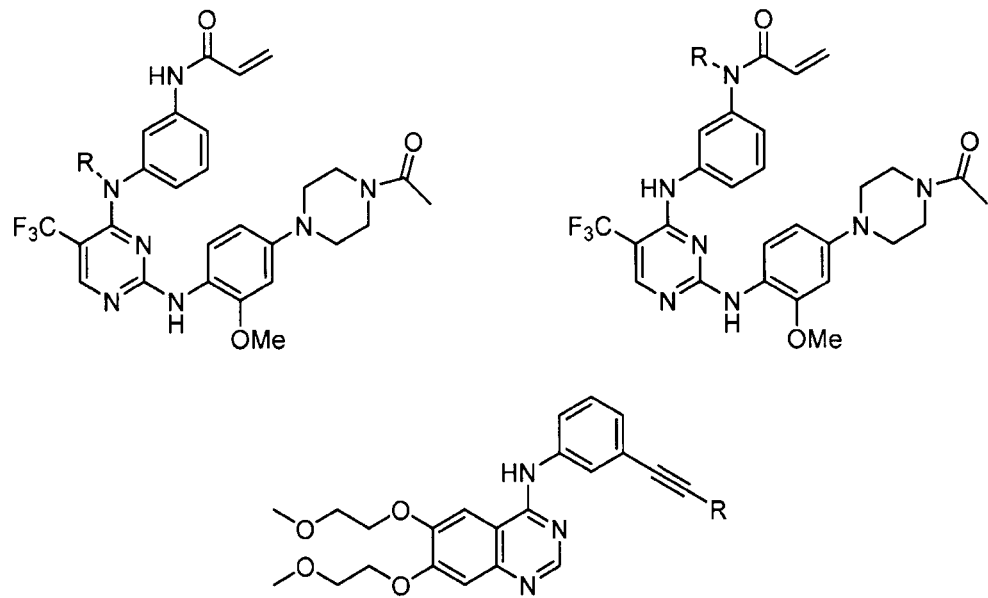
Figure 1T:
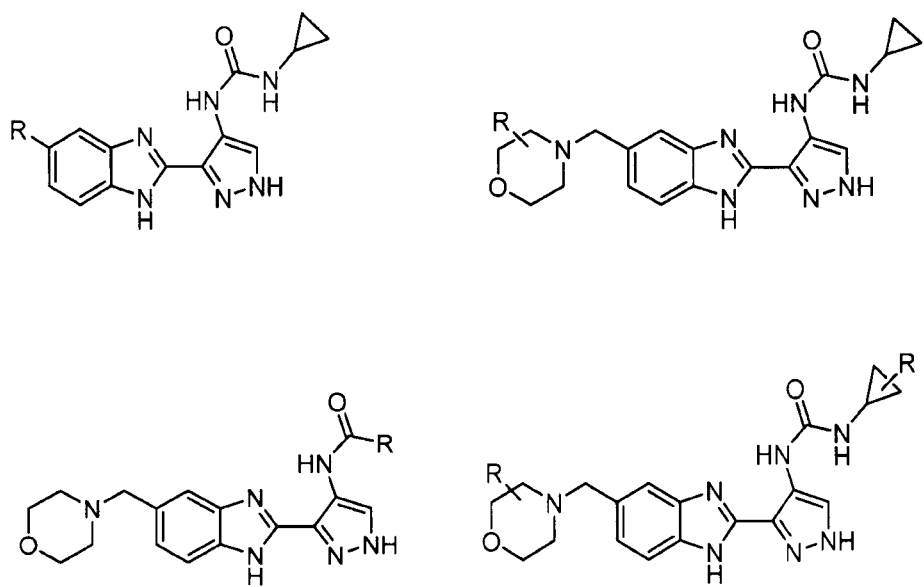
FIG. 1T presents examples of Aurora Kinase Targeting Ligands wherein R is the point at which the Linker is attached.
Figure 1U:
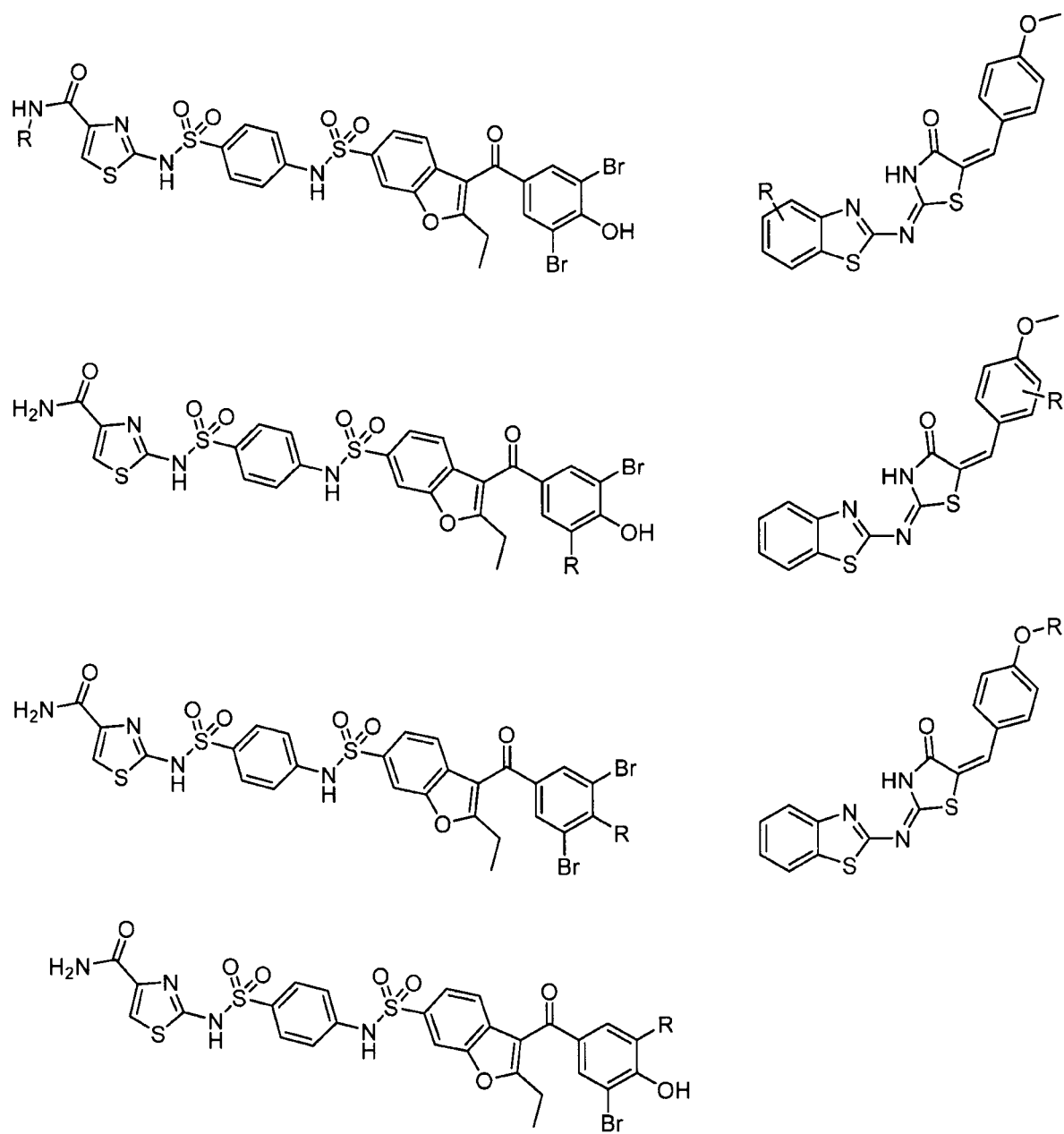
FIG. 1U presents examples of Protein Tyrosine Phosphatase Targeting Ligands wherein R is the point at which the Linker is attached.
Figure 1V:
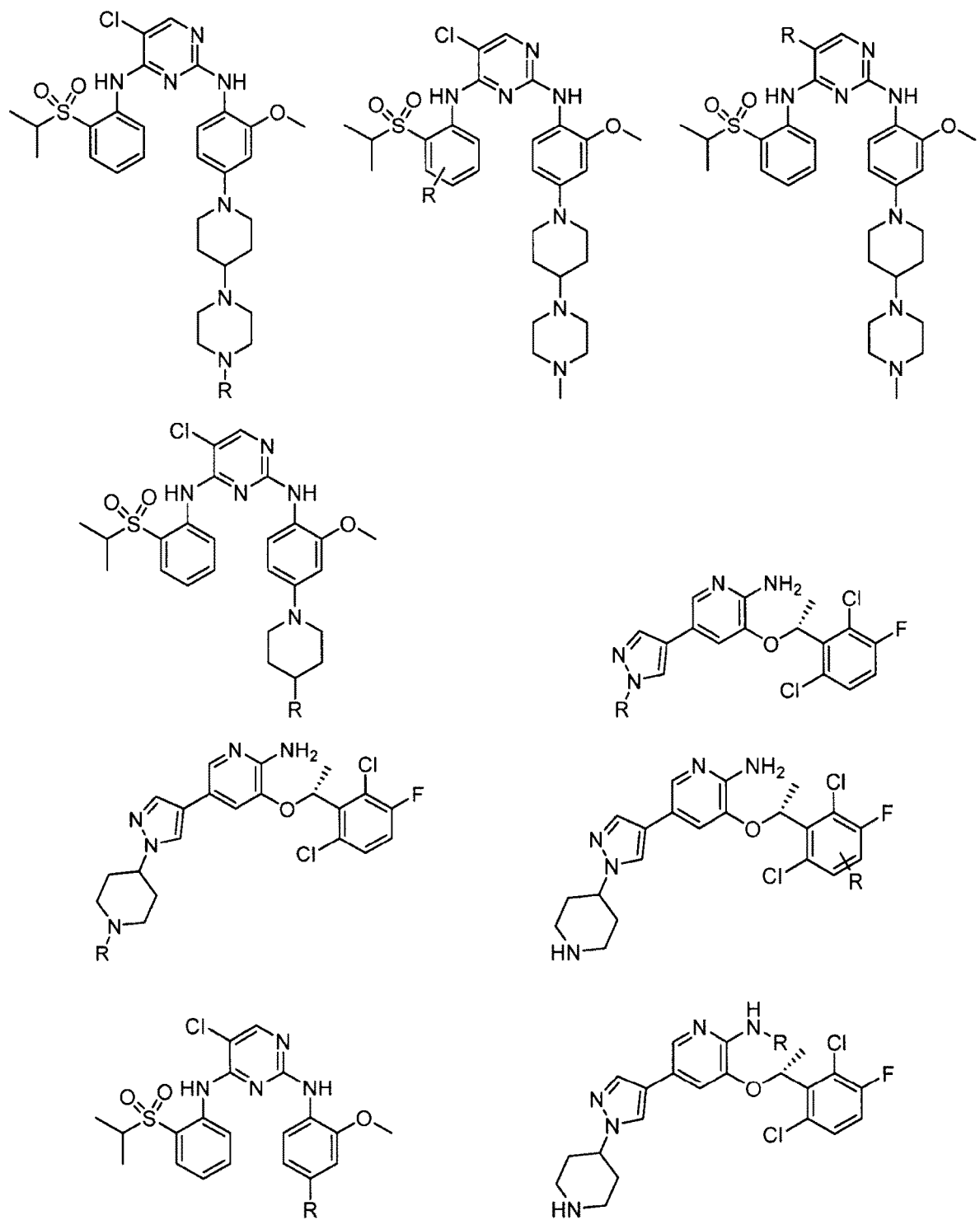
FIG. 1V presents examples of ALK Targeting Ligands wherein R is the point at which the Linker is attached.
Figure 1W:
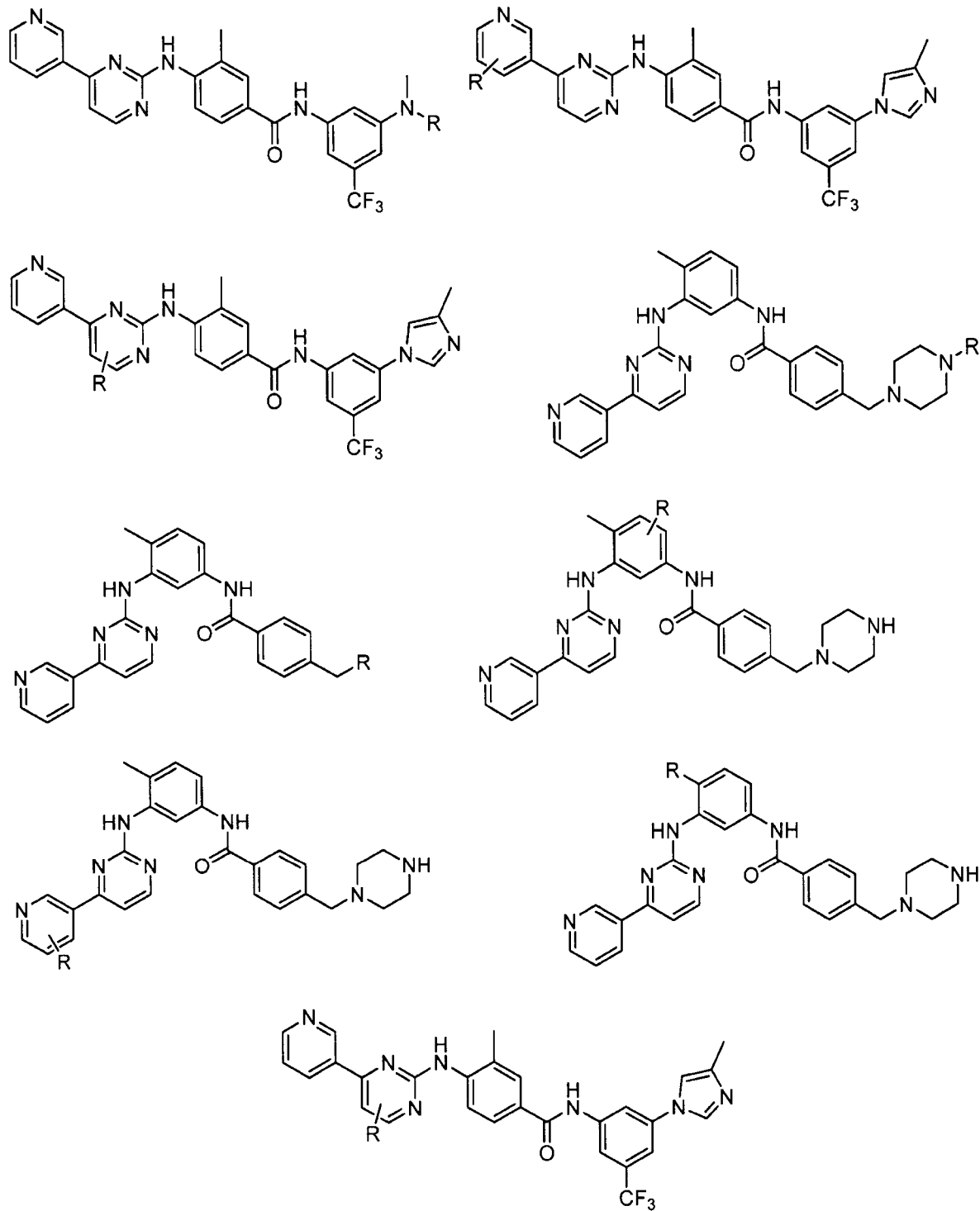
FIG. 1W presents examples of ABL Targeting Ligands wherein R is the point at which the Linker is attached.
Figure 1X:
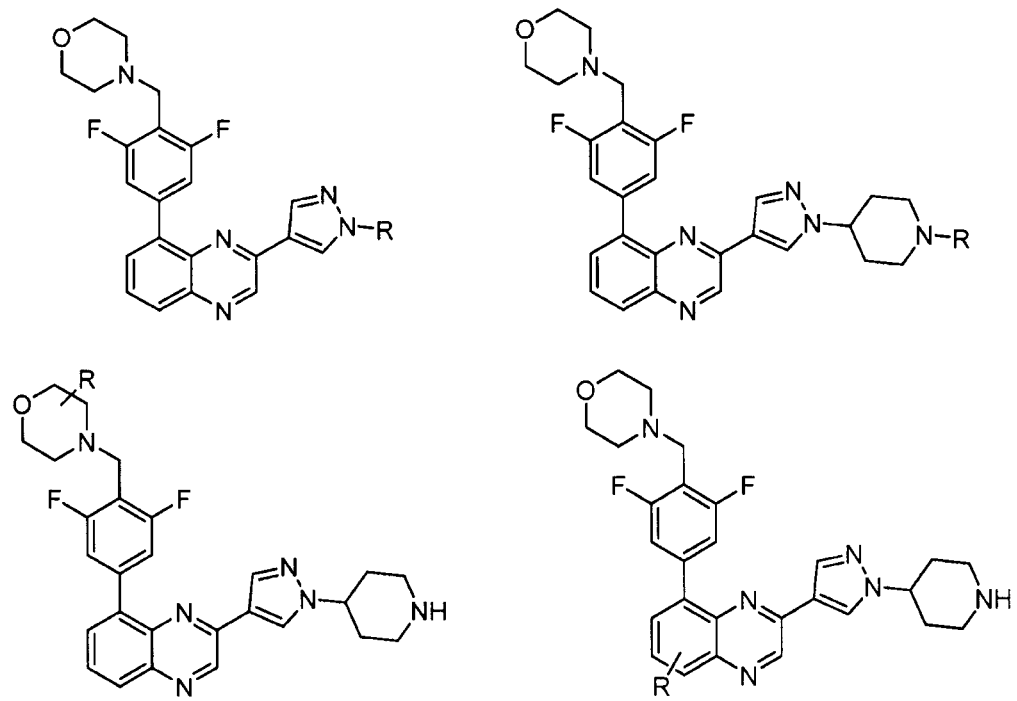
FIG. 1X presents examples of JAK2 Targeting Ligands wherein R is the point at which the Linker is attached.
Figure 1Y:
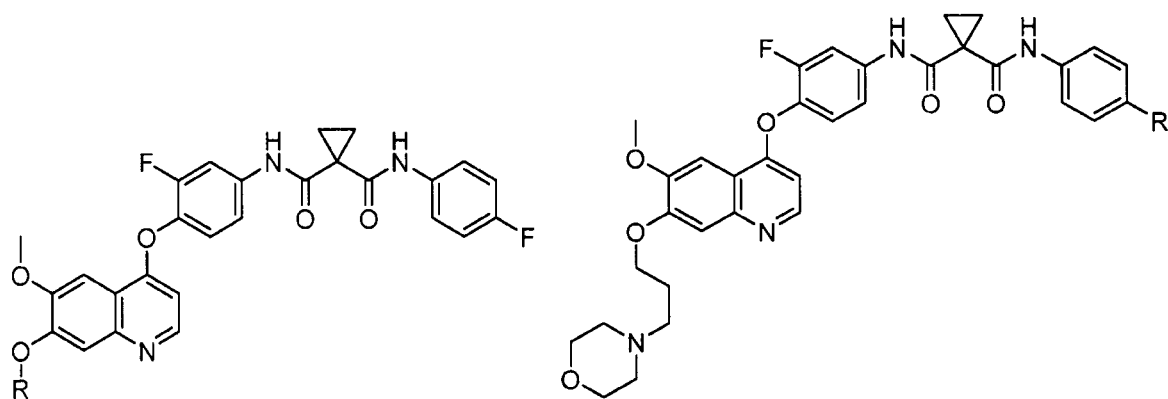
FIG. 1Y-1Z present examples of MET Targeting Ligands wherein R is the point at which the Linker is attached.
Figure 1Z:
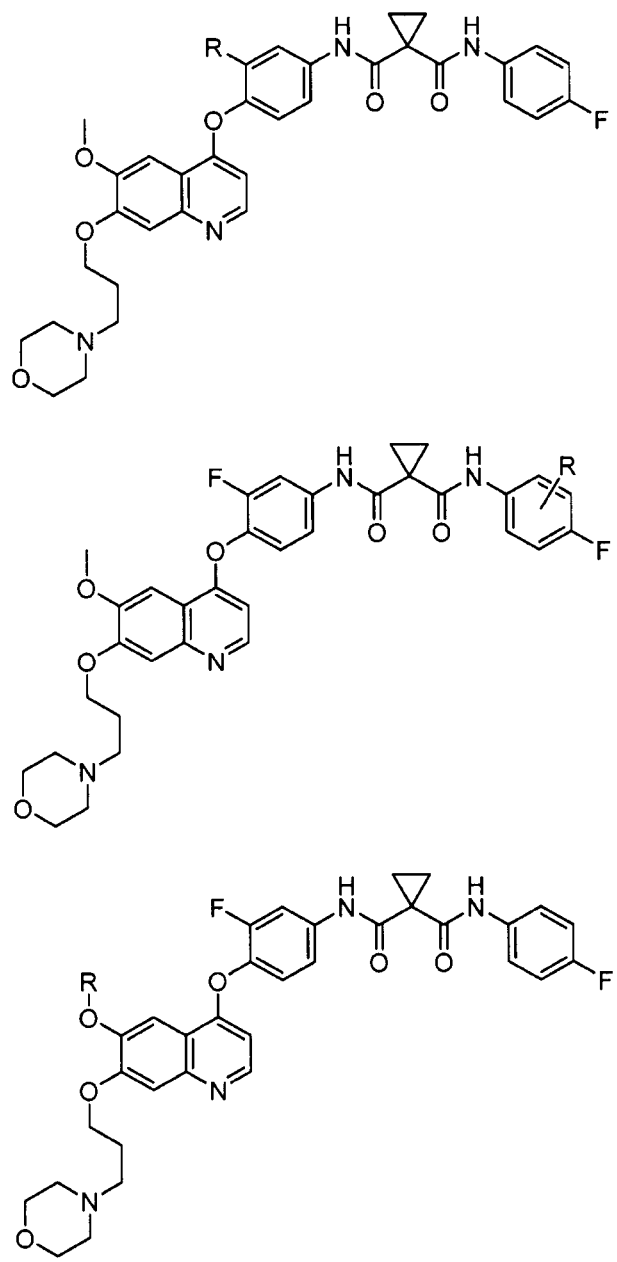
Figure 1C:
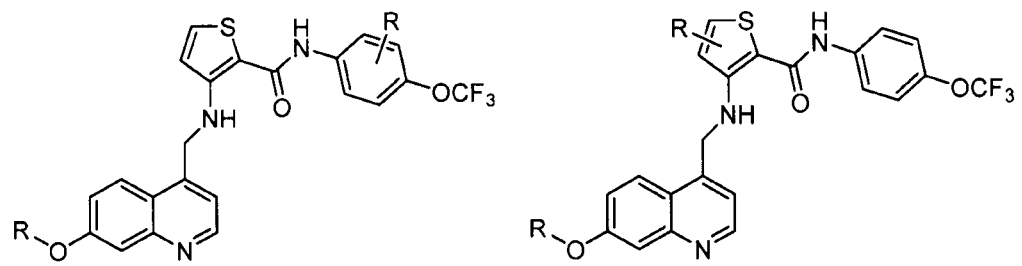
Figure 1D:
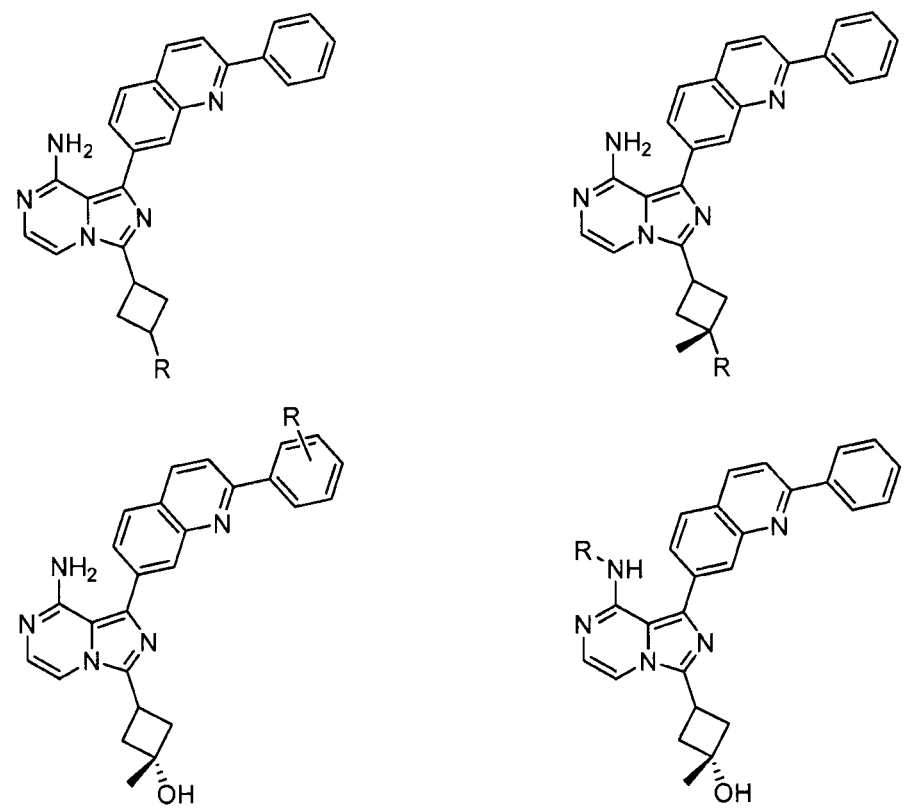
Figure 1F:
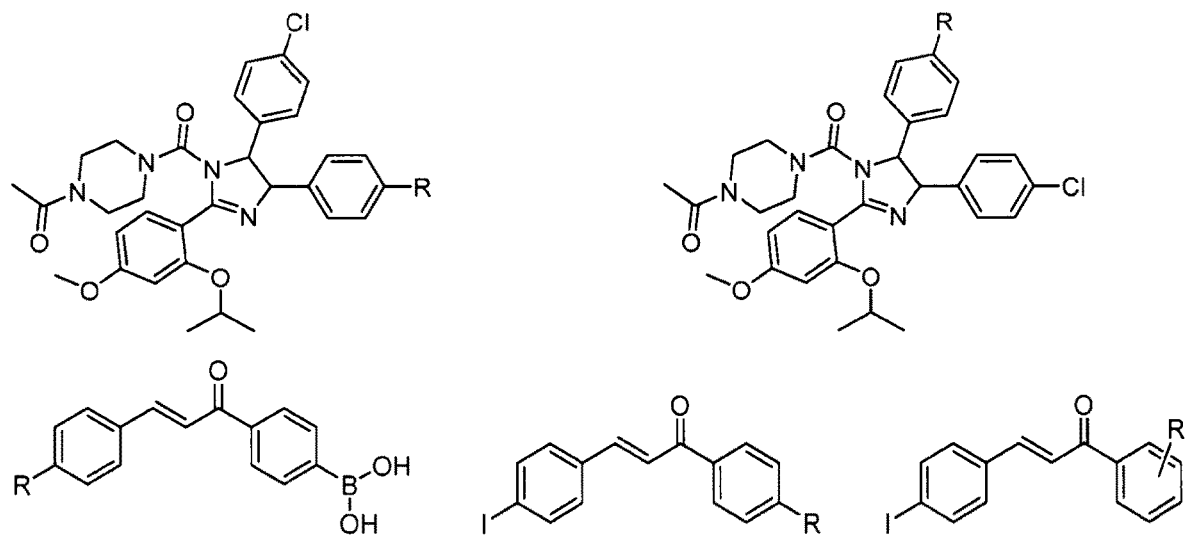
Figure 1G:
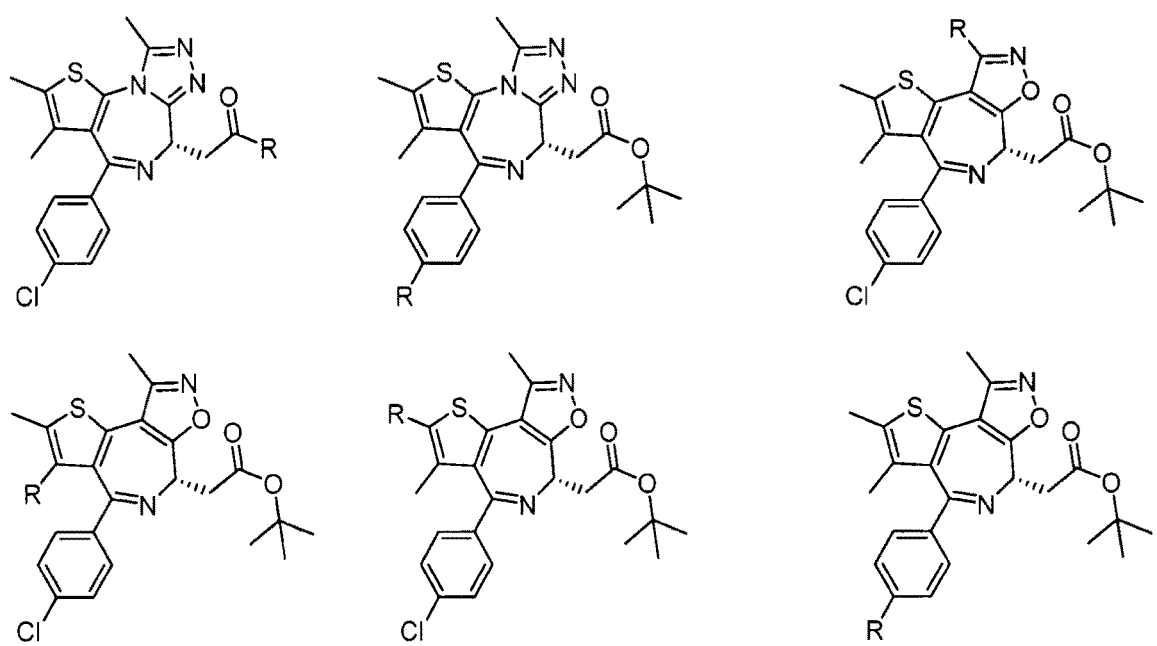
Figure 1H:
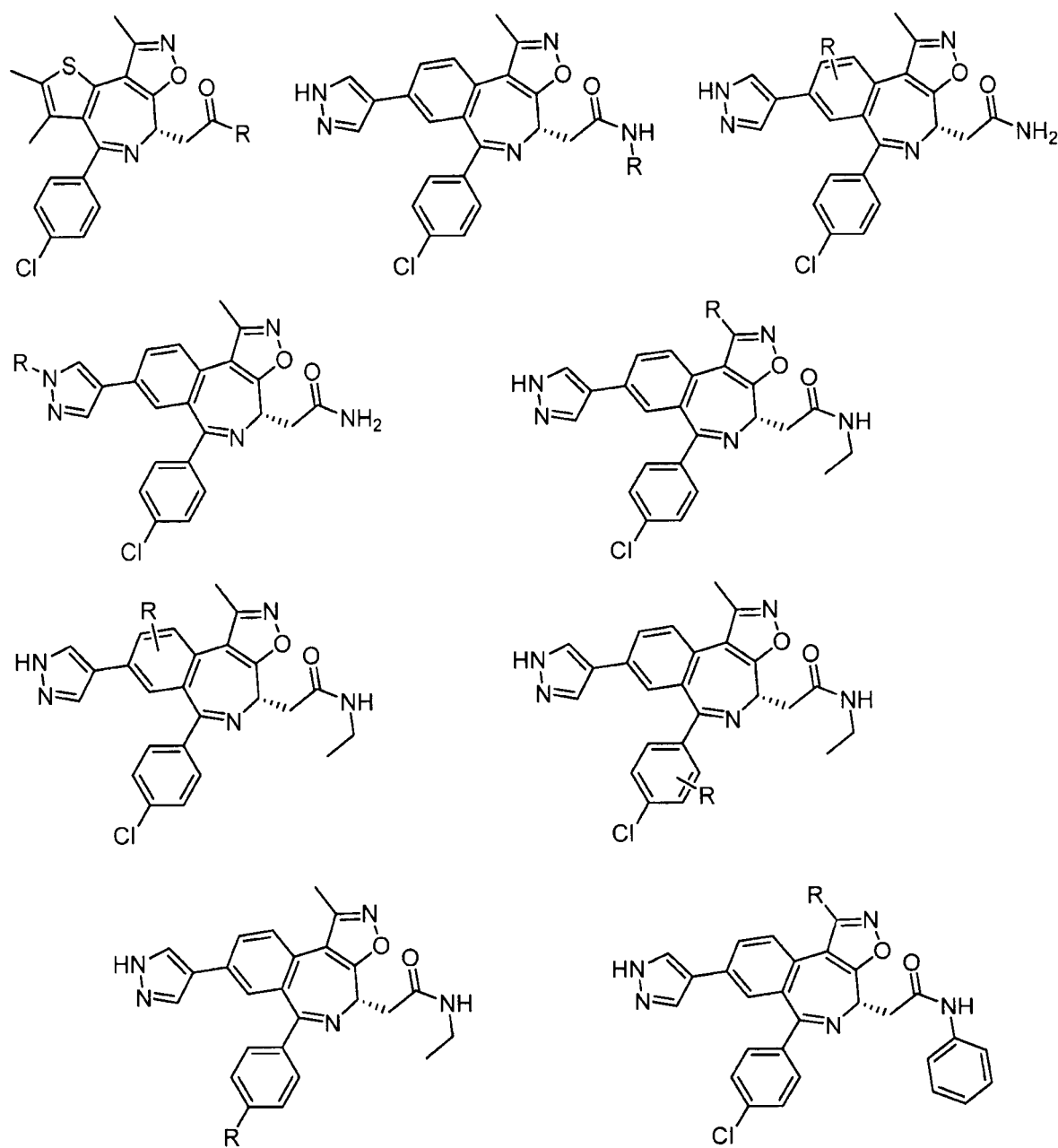
Figure 1I:
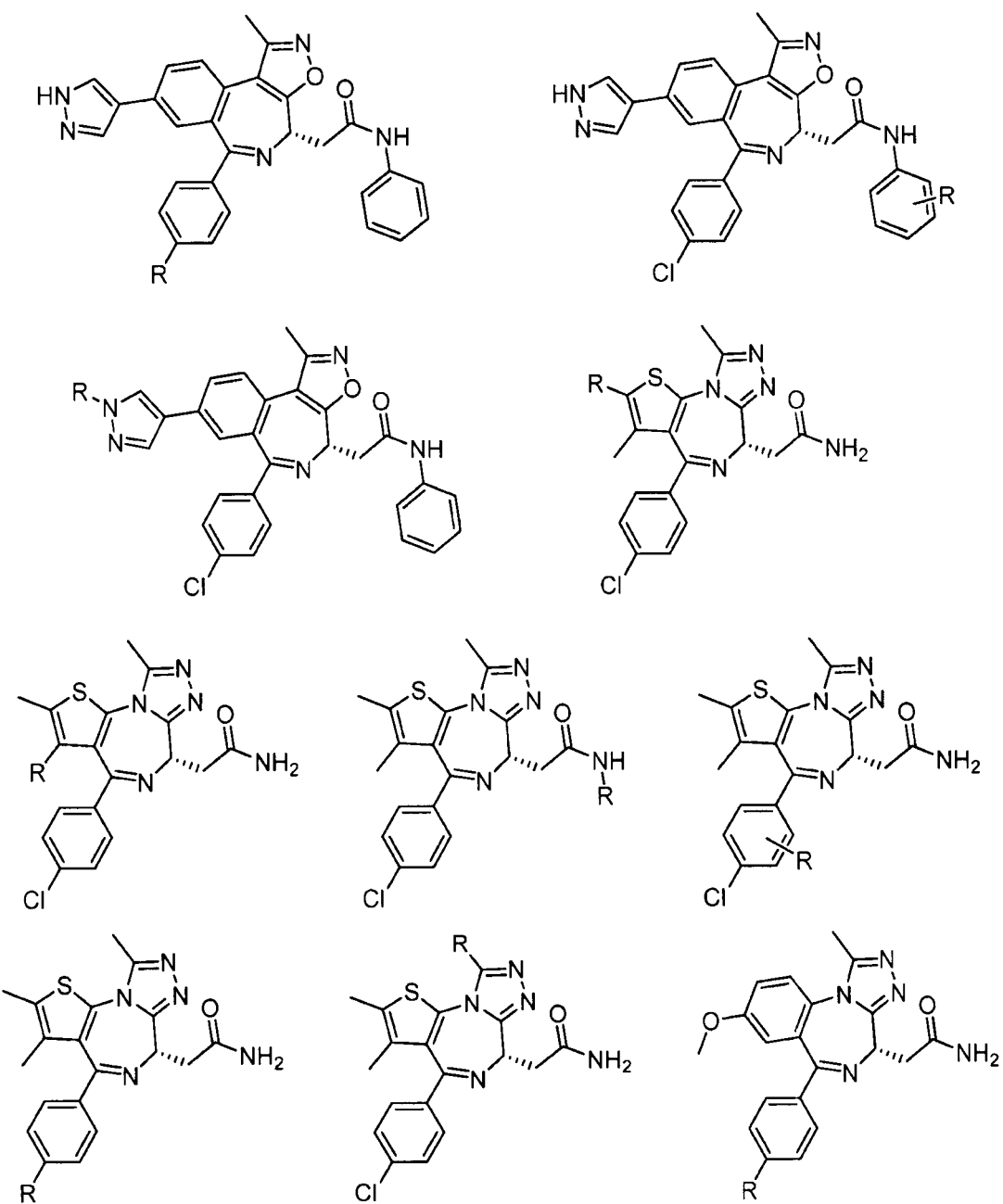
Figure 1J:
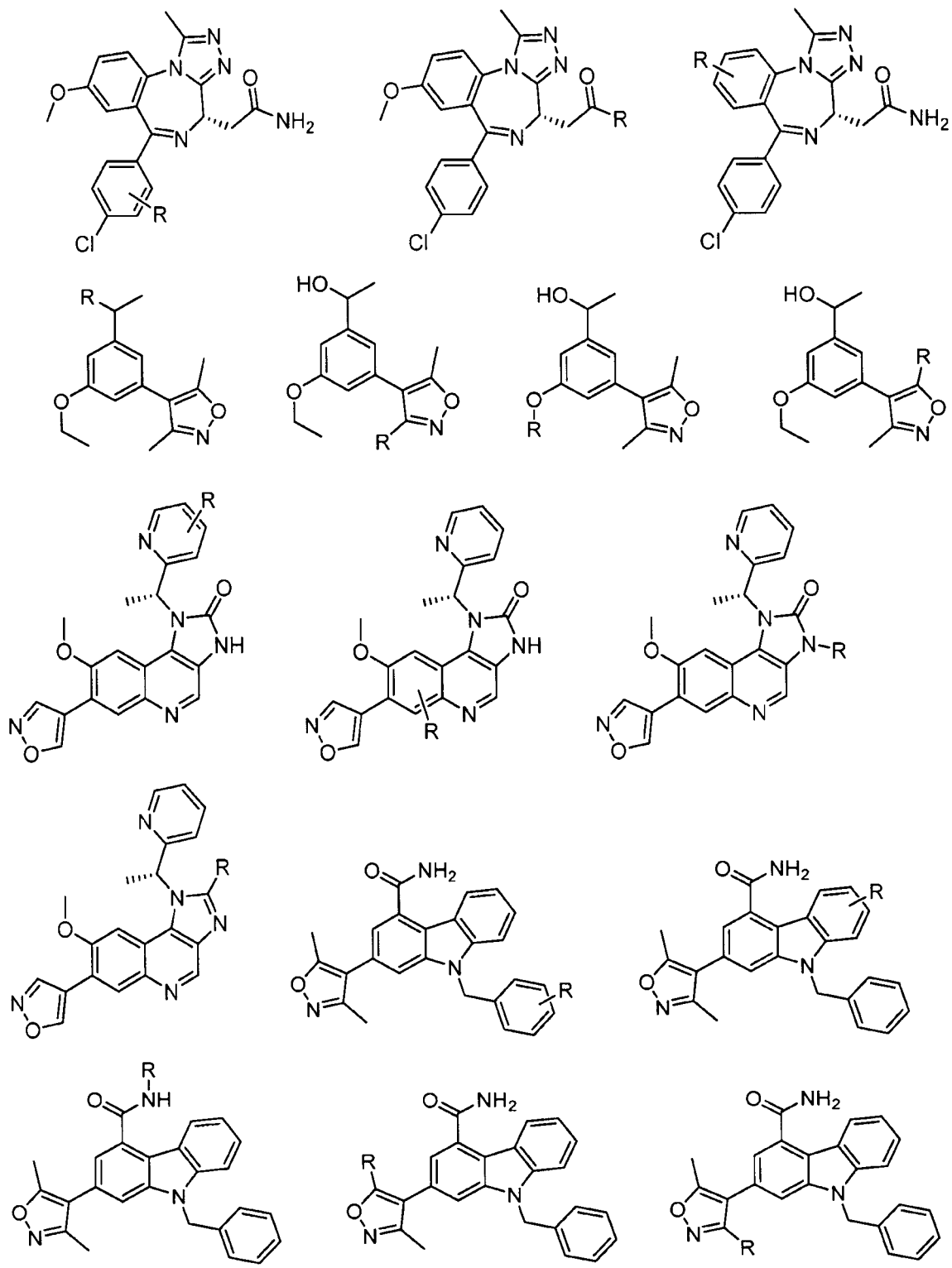
Figure 1K:
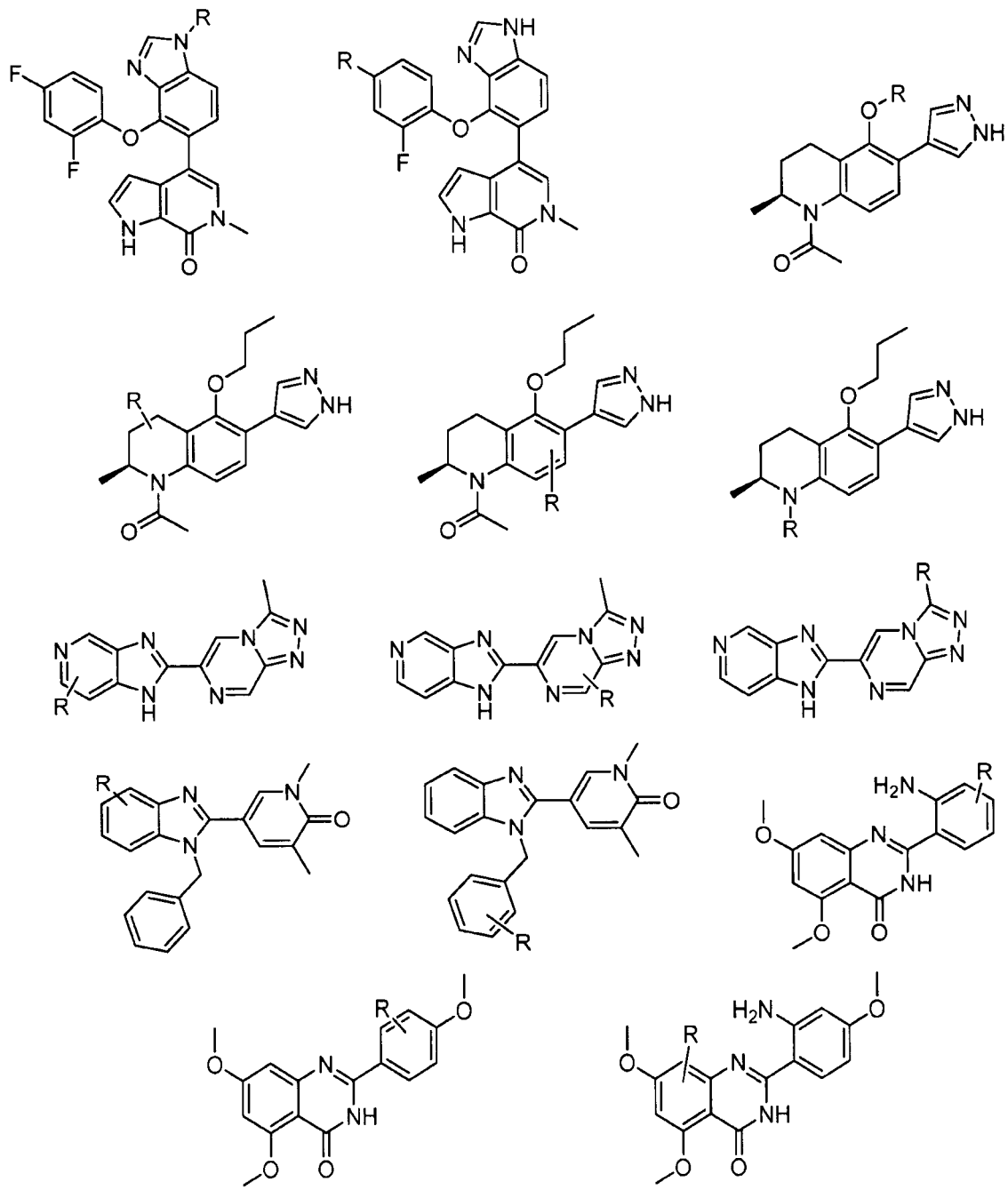
Figure 1M:
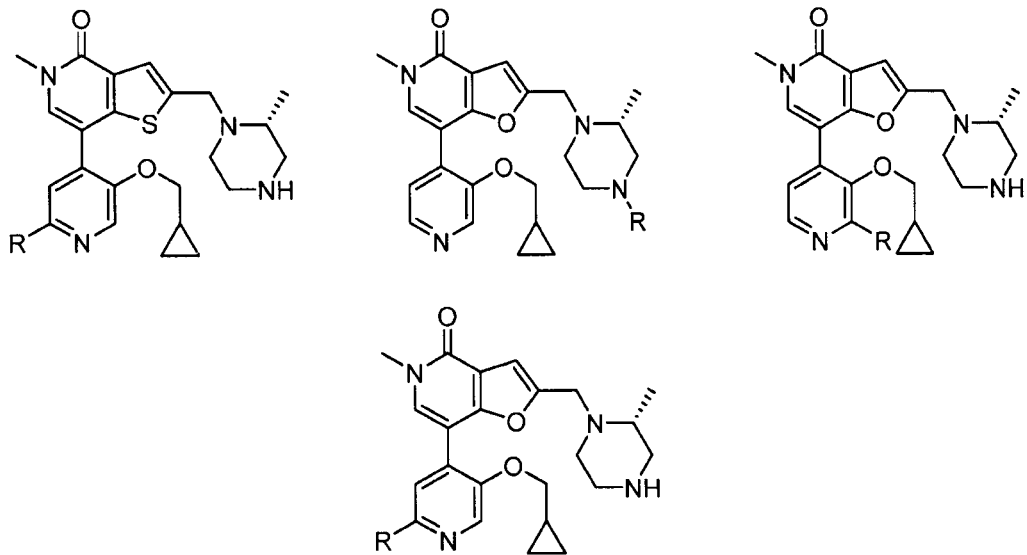
Figure 1N:
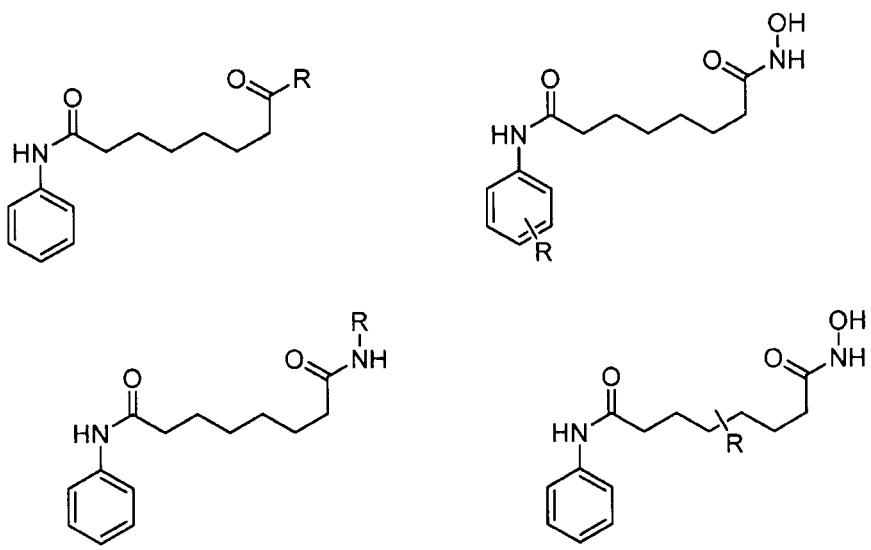
Figure 1O:
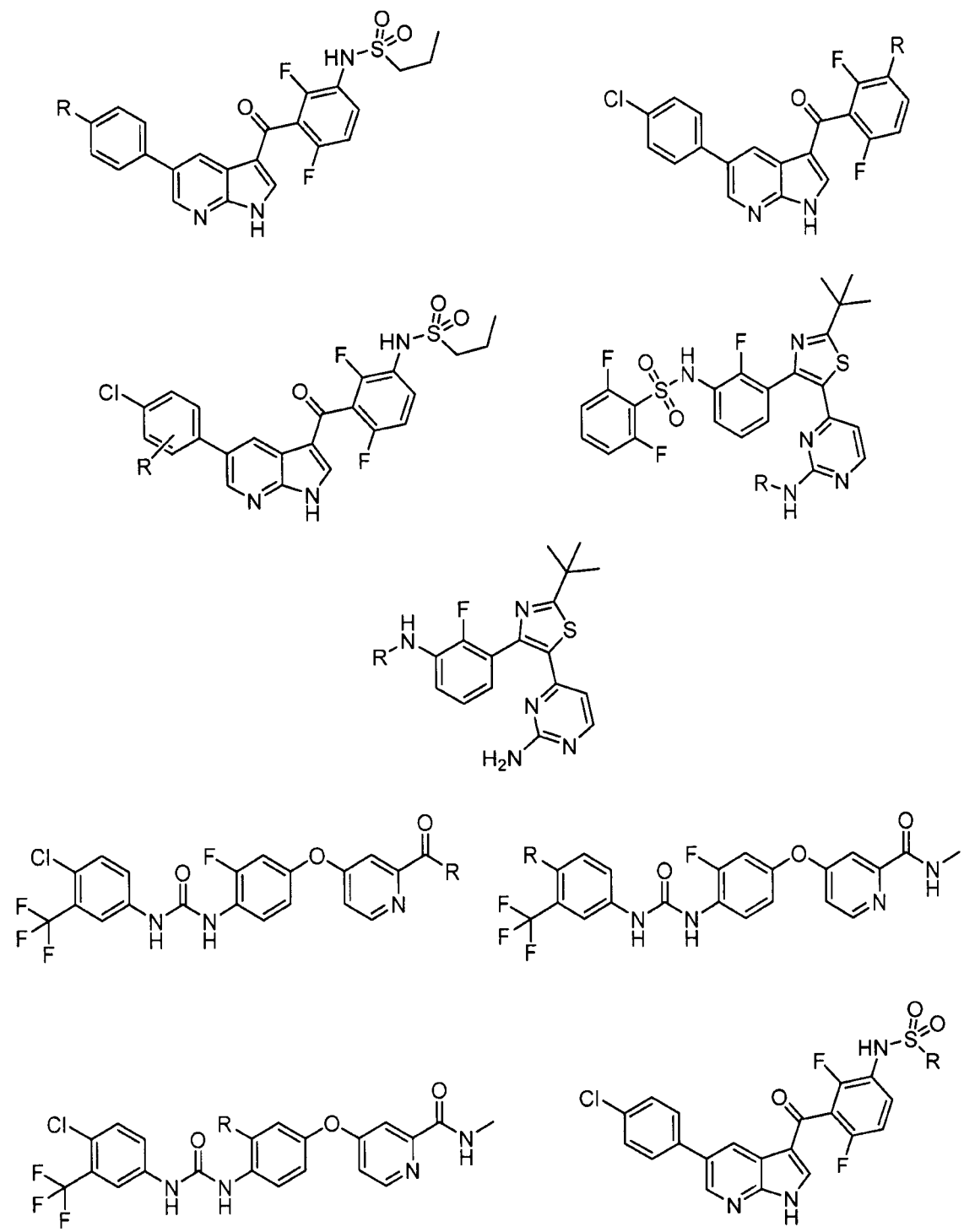
Figure 1S:
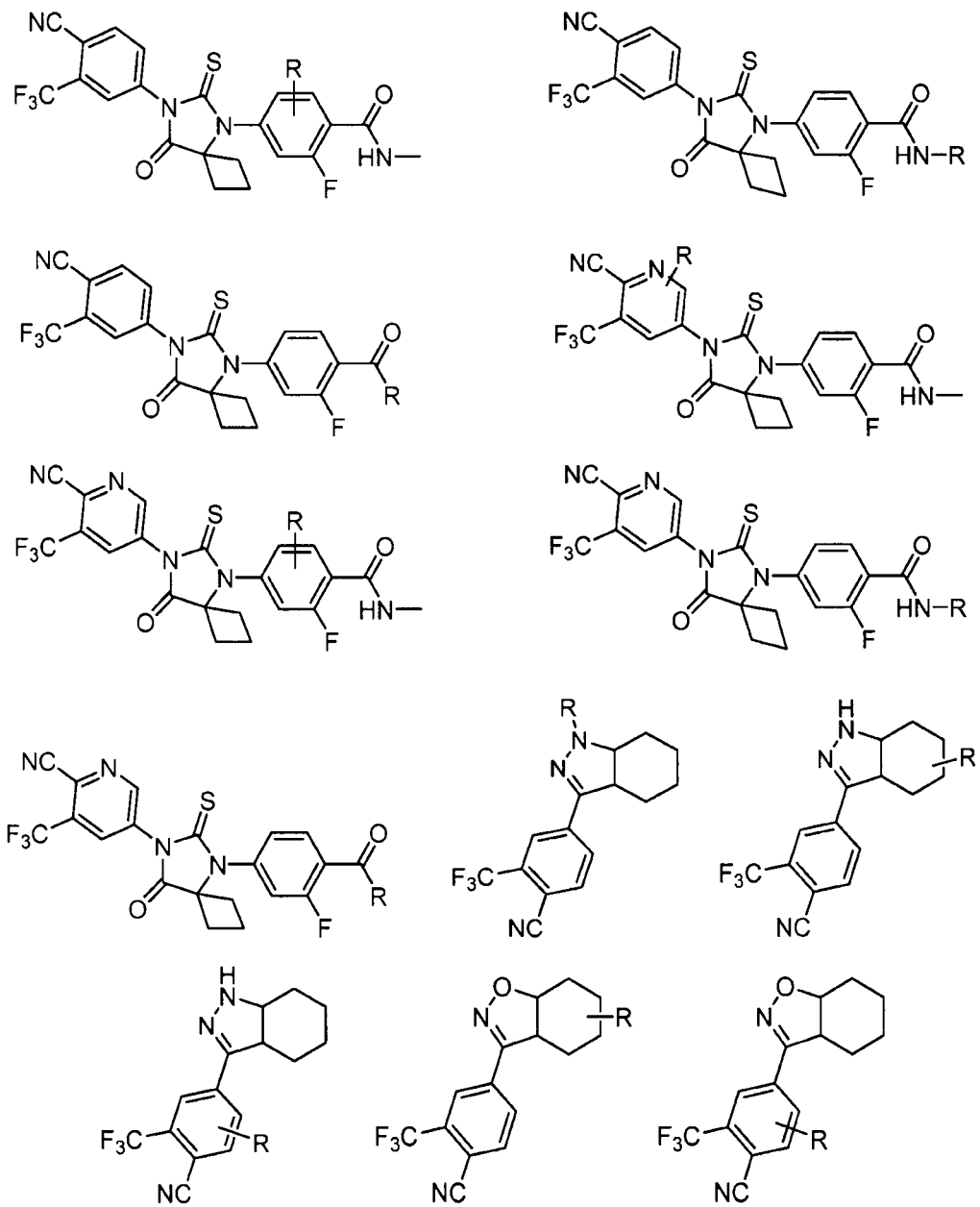
Figure 1Y:
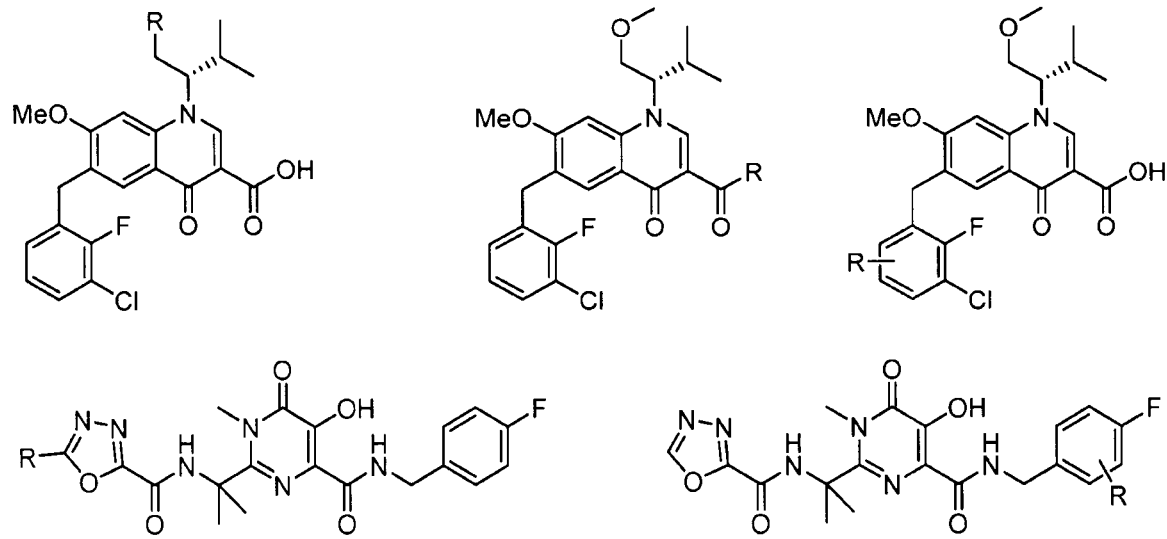
Figure 1Z:
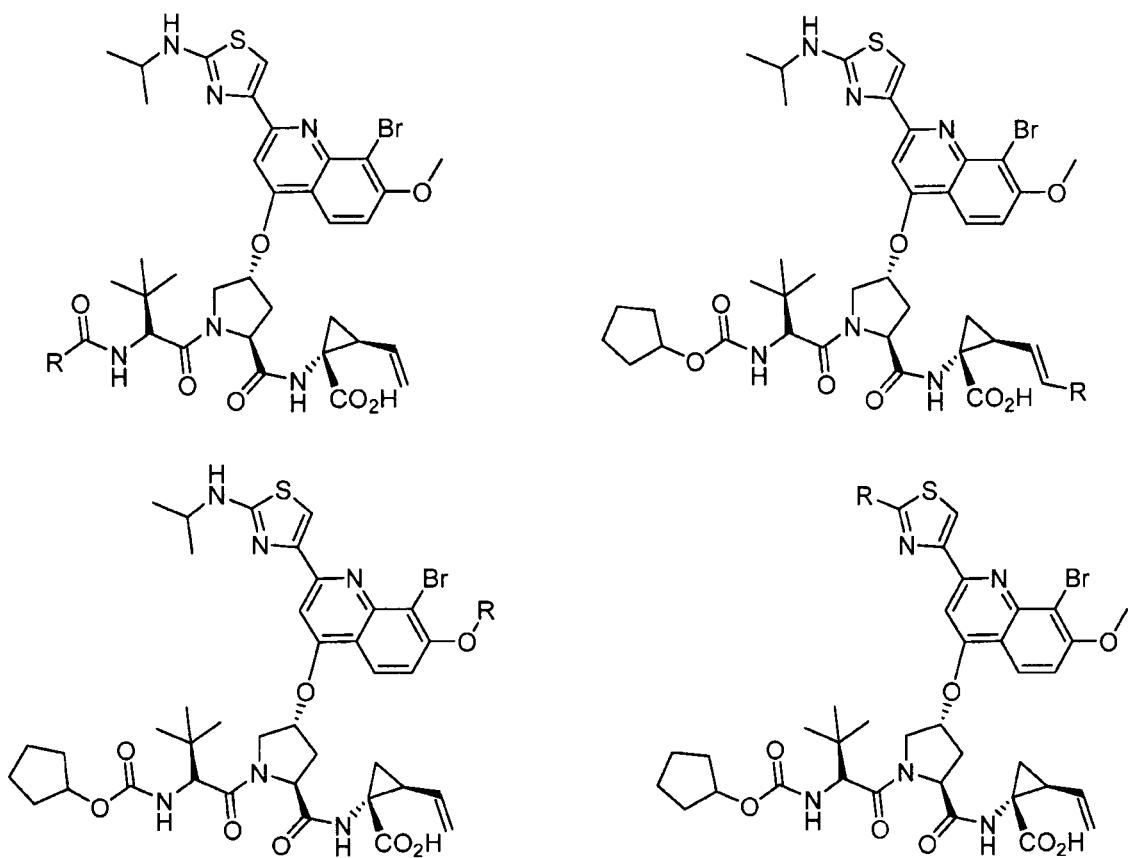
Figure 2A:
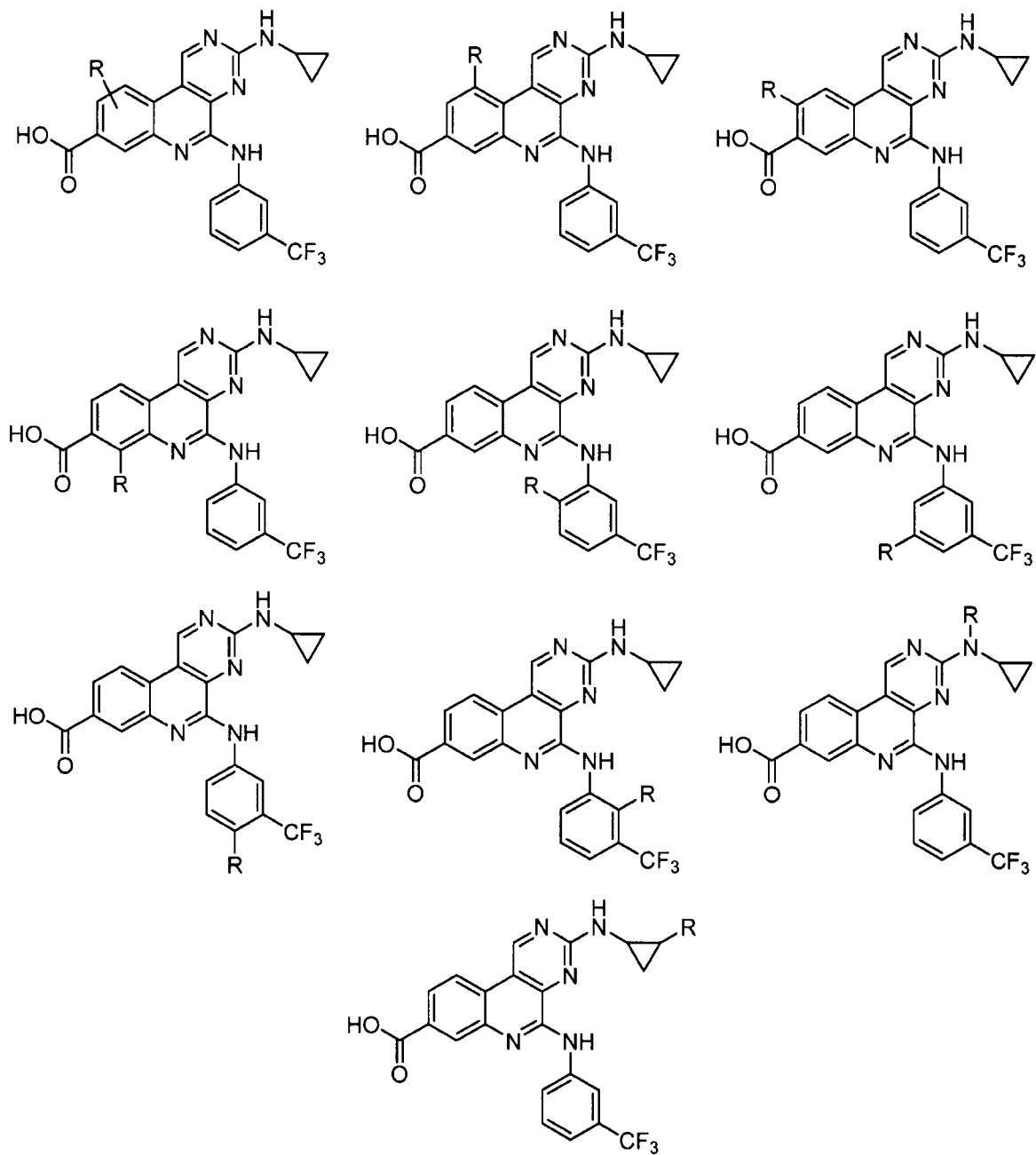
FIG. 2A presents examples of the kinase inhibitor Targeting Ligands U09-CX-5279 (derivatized) wherein R is the point at which the Linker is attached.
Figure 2B:
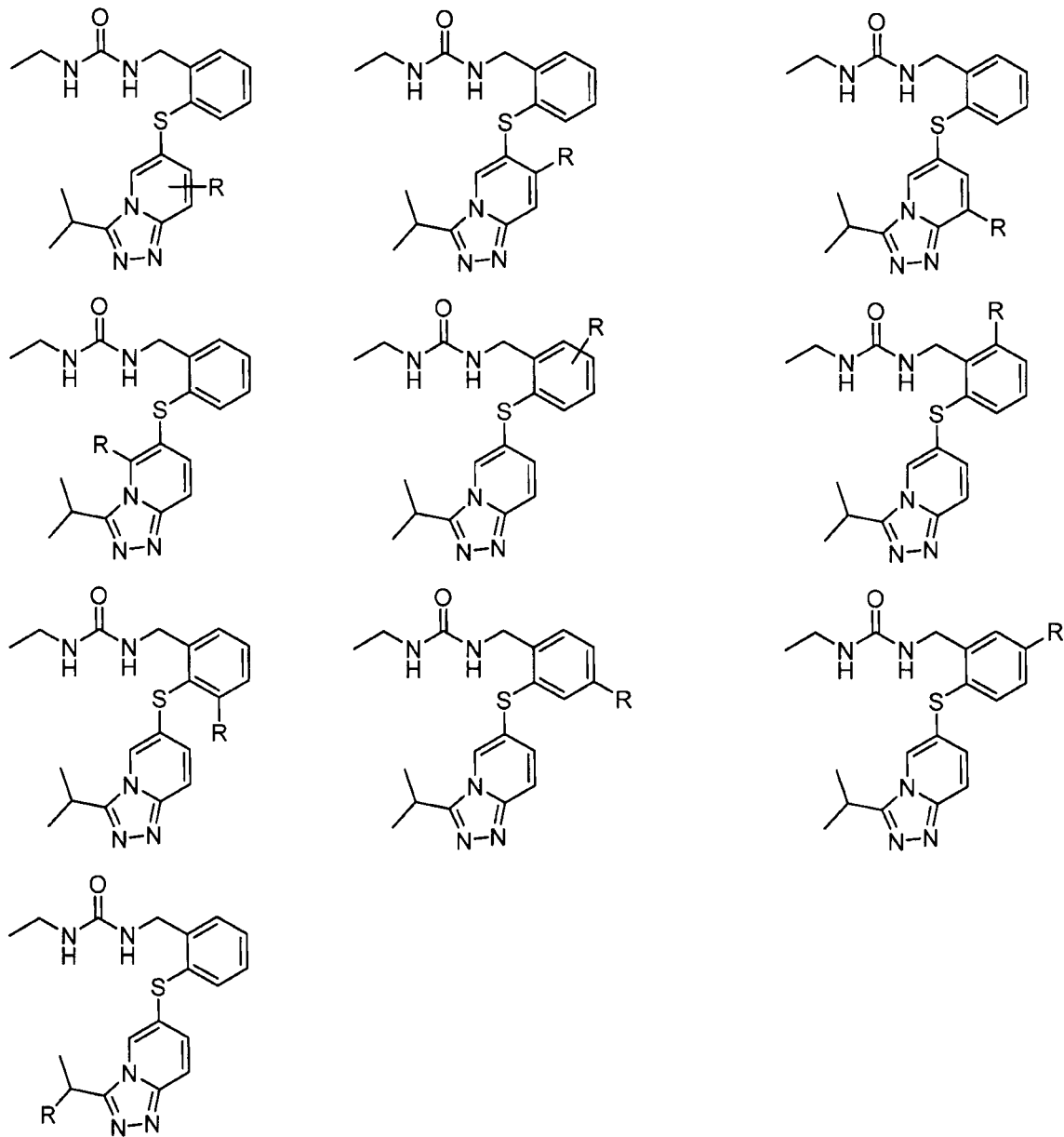
FIG. 2B-2C present examples of kinase inhibitor Targeting Ligands, including the kinase inhibitor compounds Y1W and Y1X (derivatized) wherein R is the point at which the Linker is attached. For additional examples and related ligands, see, the kinase inhibitors identified in Millan et al. "Design and Synthesis of Inhaled P38 Inhibitors for the Treatment of Chronic Obstructive Pulmonary Disease" *J. Med. Chem.*, 54: 7797 (2011).
Figure 2C:
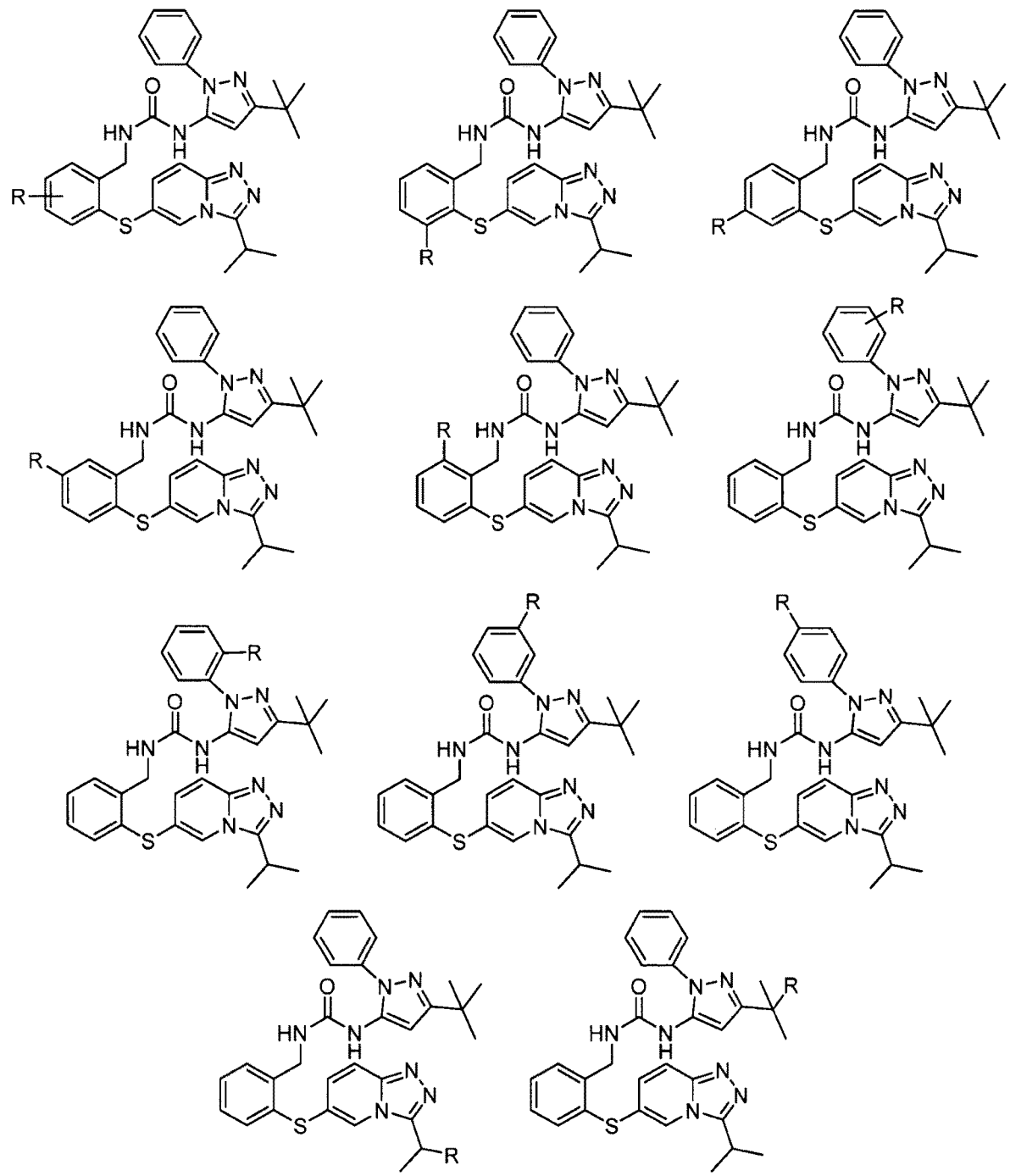
Figure 2E:
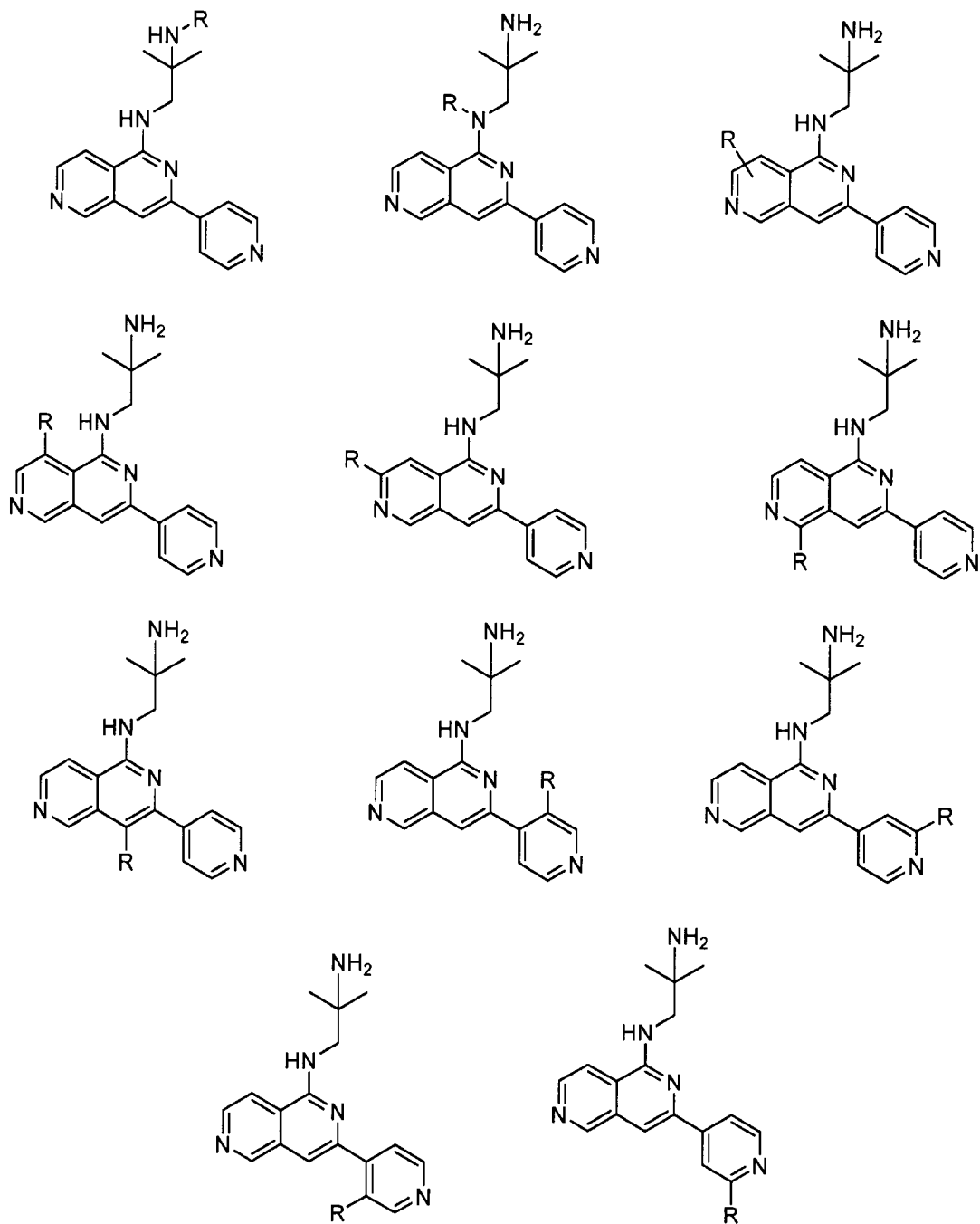
FIG. 2E presents examples of kinase inhibitor Targeting Ligands, including the kinase inhibitor compound 07U wherein R is the point at which the Linker is attached. For additional examples and related ligands, see, the kinase inhibitors identified in Van Eis et al. "2 6-Naphthyridines as potent and selective inhibitors of the novel protein kinase C isozymes" *Biorg. Med. Chem. Lett.,* 21(24): 7367-72 (2011).
Figure 2H:
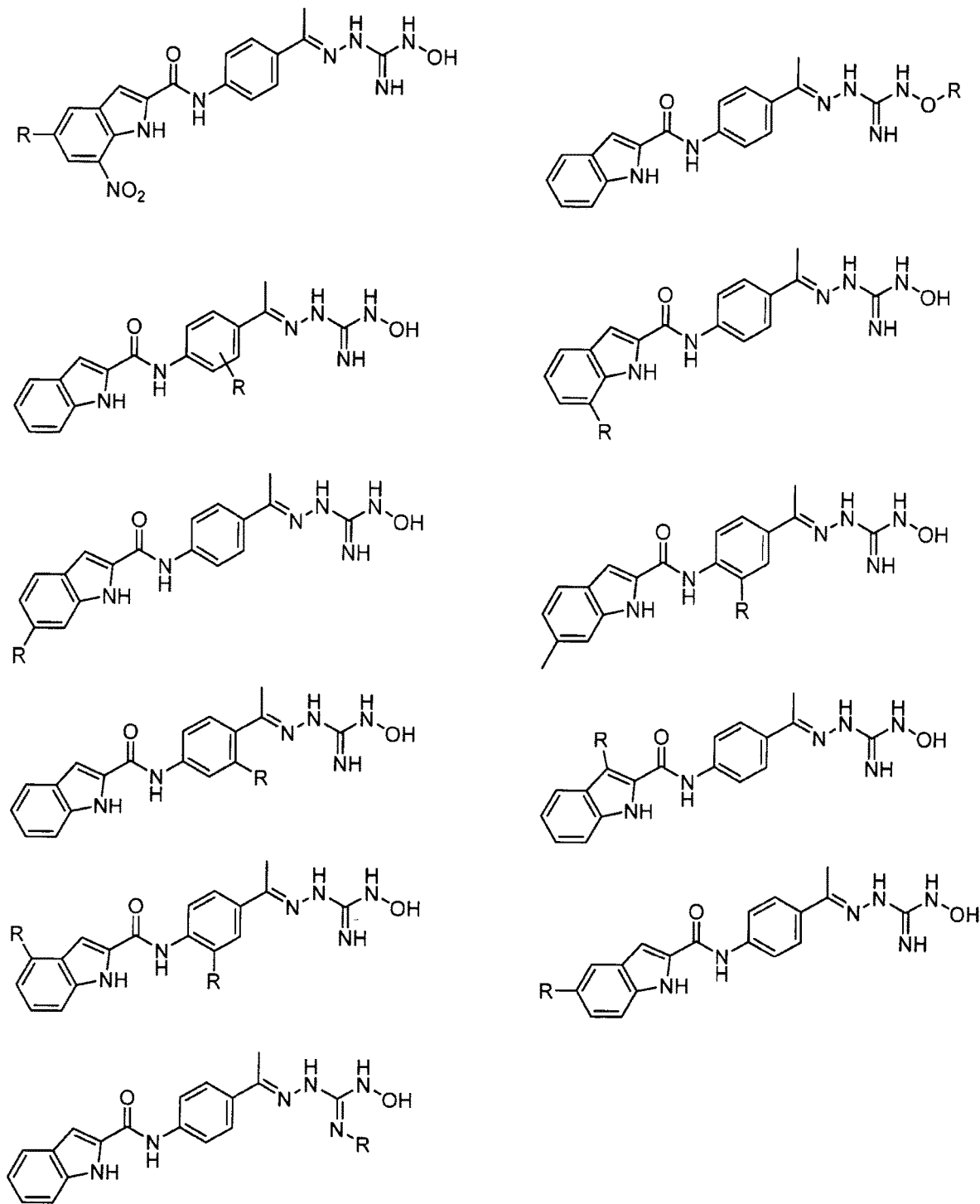
FIG. 2G-2H present examples of kinase inhibitor Targeting Ligands, including the kinase inhibitors XK9 and NXP (derivatized) wherein R is the point at which the Linker is attached. For additional examples and related ligands, see, the kinase inhibitors identified in Lountos et al. "Structural Characterization of Inhibitor Complexes with Checkpoint Kinase 2 (Chk2) a Drug Target for Cancer Therapy" *J. Struct. Biol.,* 176: 292 (2011).
Figure 2J:
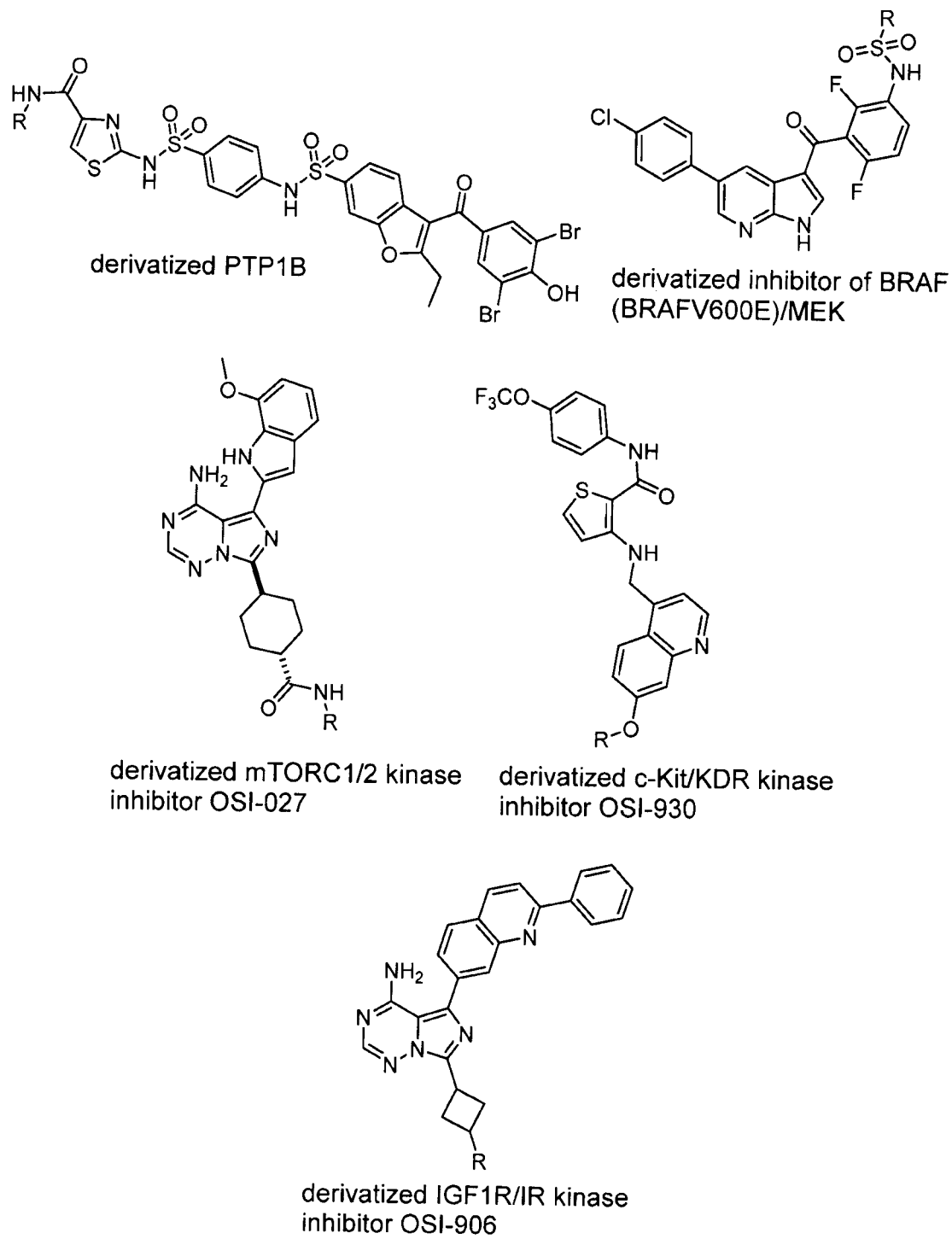
FIG. 2I-2J present examples of kinase inhibitor Targeting Ligands wherein R is the point at which the Linker r is attached.
Figure 2K:
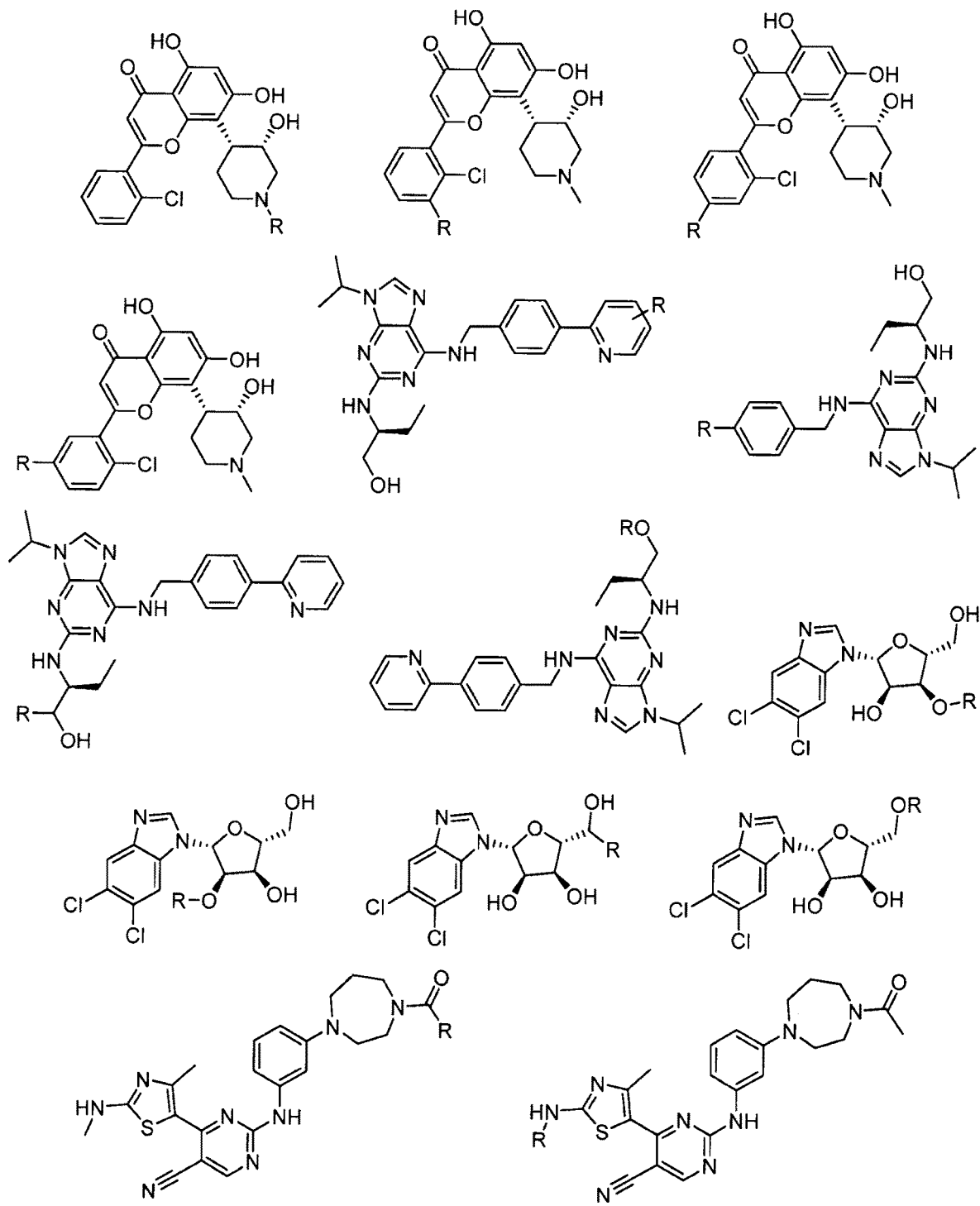
FIG. 2K-2M present examples of Cyclin Dependent Kinase 9 (CDK9) Targeting Ligands wherein R is the point at which the Linker is attached. For additional examples and related ligands, see, Baumli et al. "The structure of P-TEFb (CDK9/cyclin T1) its complex with flavopiridol and regulation by phosphorylation." *Embo J.,* 27: 1907-1918 (2008); Bettayeb et al. "CDK Inhibitors Roscovitine and CR8 Trigger Mcl-1 Down-Regulation and Apoptotic Cell Death in Neuroblastoma Cells." *Genes Cancer,* 1: 369-380 (2010); Baumli et al. "Halogen bonds form the basis for selective P-TEFb inhibition by DRB." *Chem. Biol.* 17: 931-936 (2010); Hole et al. "Comparative Structural and Functional Studies of 4-(Thiazol-5-Yl)-2-(Phenylamino)Pyrimidine-5-Carbonitrile Cdk9 Inhibitors Suggest the Basis for Isotype Selectivity." *J. Med. Chem.* 56: 660 (2013); Lücking et al. "Identification of the potent and highly selective PTEFb inhibitor BAY 1251152 for the treatment of cancer—From p.o. to i.v. application via scaffold hops." Lucking et al. U. AACR Annual Meeting, Apr. 1-5, 2017 Washington, D.C. USA.
Figure 2L:
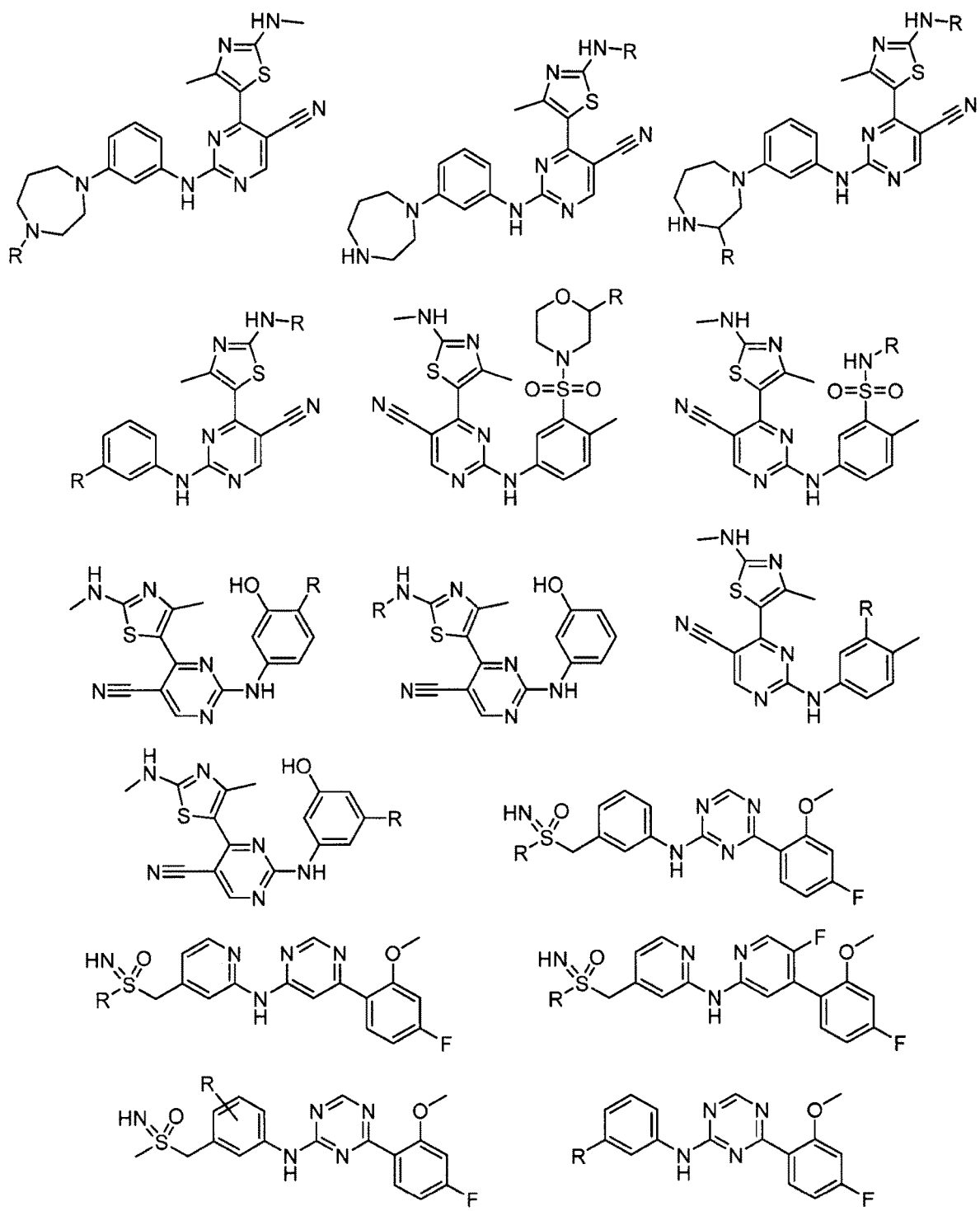
Figure 2M:
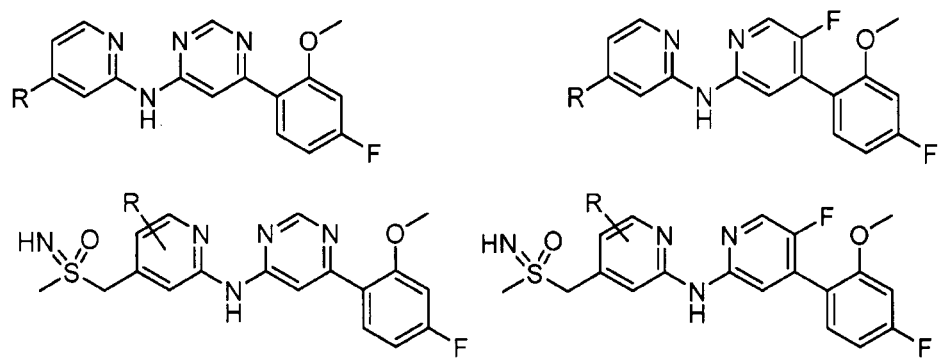
Figure 2N:
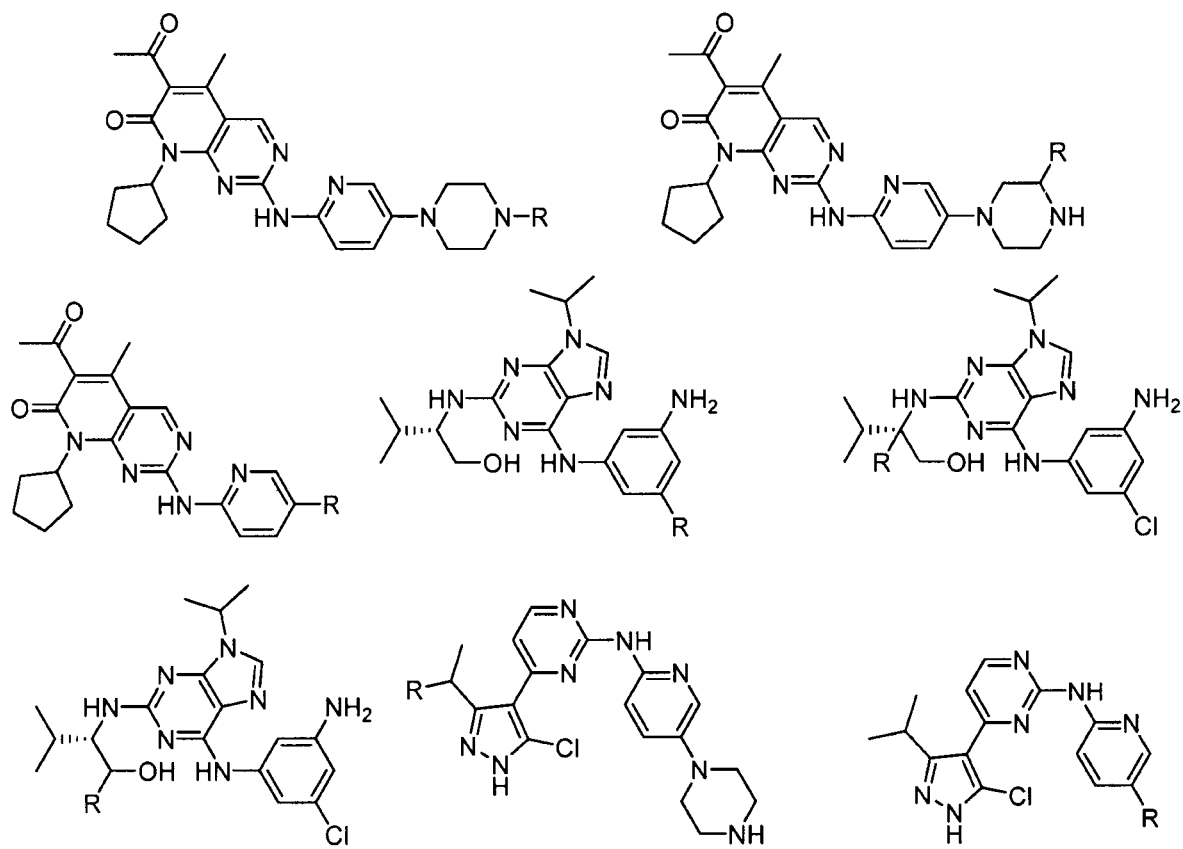
FIG. 2N-2P present examples of Cyclin Dependent Kinase 4/6 (CDK4/6) Targeting Ligands wherein R is the point at which the Linker is attached. For additional examples and related ligands, see, Lu H.; Schulze-Gahmen U.; "Toward understanding the structural basis of cyclin-dependent kinase 6 specific inhibition." *J. Med. Chem.,* 49: 3826-3831 (2006); 4-(Pyrazol-4-yl)-pyrimidines as selective inhibitors of cyclin-dependent kinase 4/6. Cho et al. (2010) J. Med. Chem. 53: 7938-7957; Cho Y. S. et al. "Fragment-Based Discovery of 7-Azabenzimidazoles as Potent Highly Selective and Orally Active CDK4/6 Inhibitors." *ACS Med Chem Lett* 3: 445-449 (2012); Li Z. et al. "Discovery of AMG 925 a FLT3 and CDK4 dual kinase inhibitor with preferential affinity for the activated state of FLT3." *J. Med. Chem.* 57: 3430-3449 (2014); Chen P. et al. "Spectrum and Degree of CDK Drug Interactions Predicts Clinical Performance." *Mol. Cancer Ther.* 15: 2273-2281 (2016).
Figure 2O:
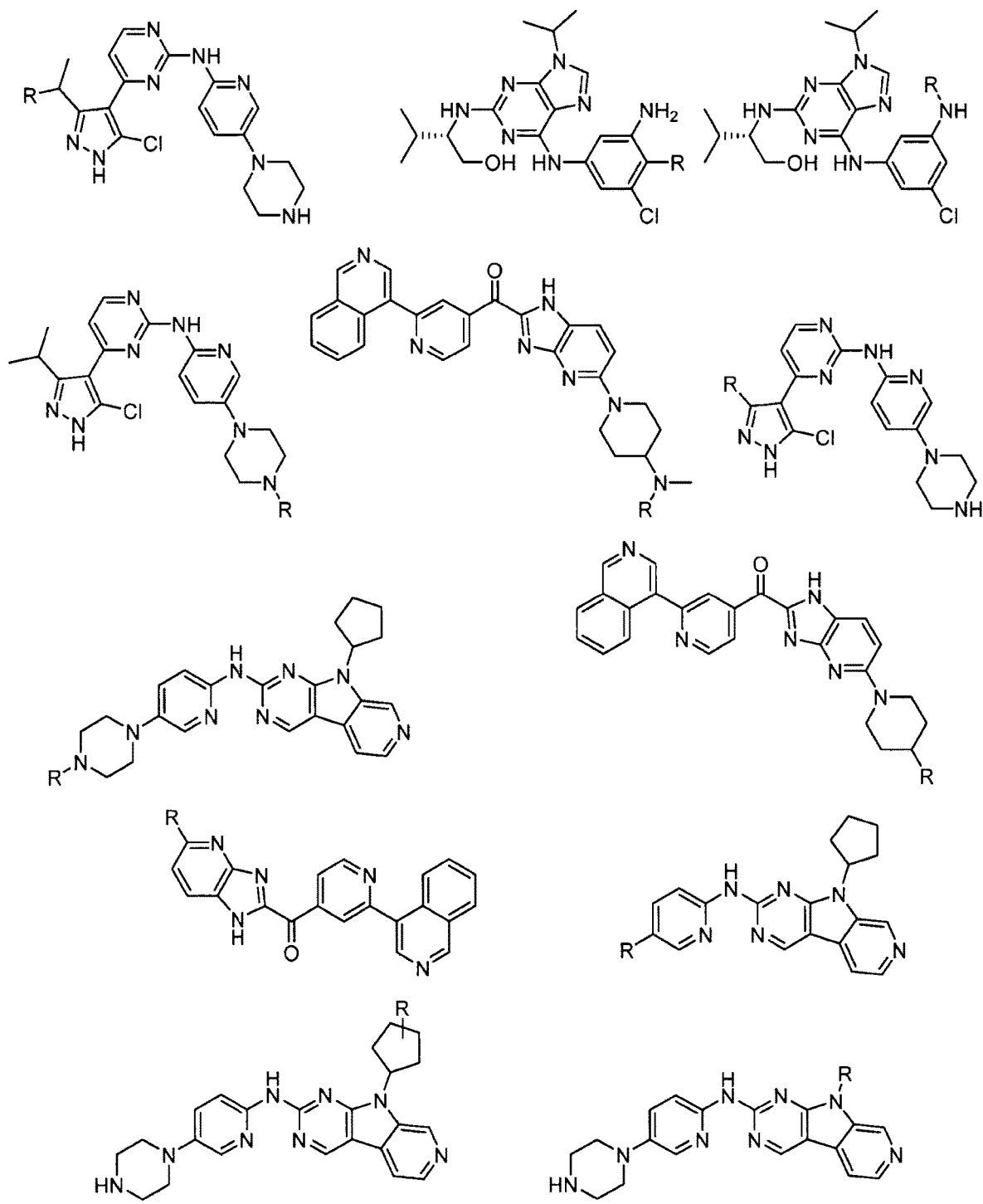
Figure 2P:
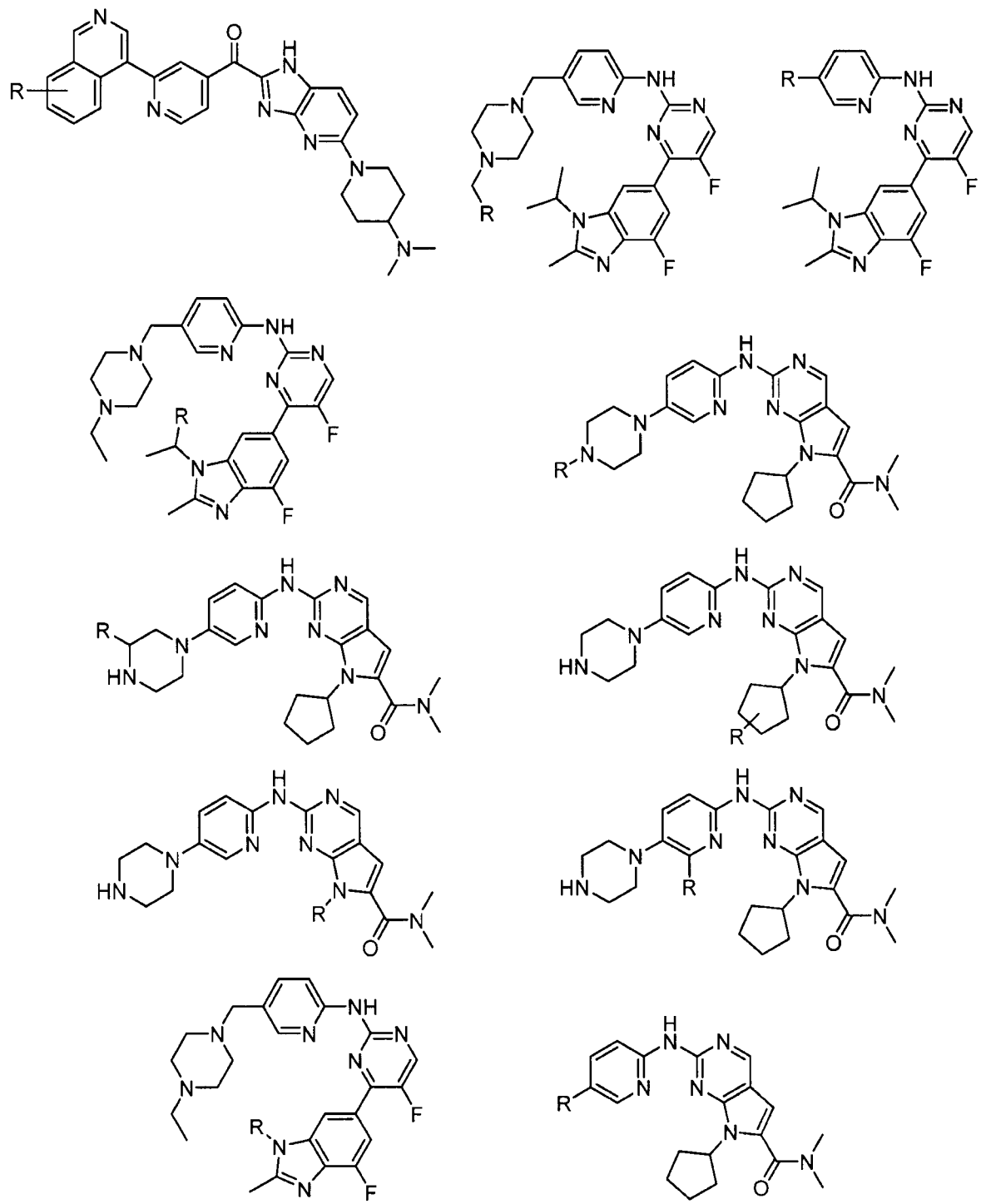
Figure 2Q:
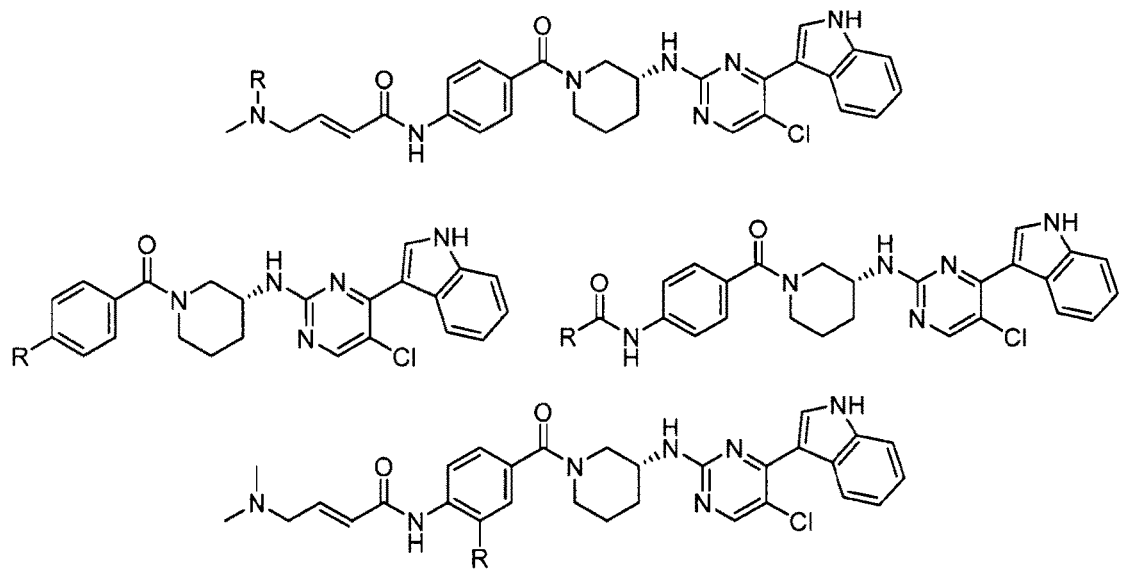
FIG. 2Q presents examples of Cyclin Dependent Kinase 12 and/or Cyclin Dependent Kinase 13 Targeting Ligands wherein R is the point at which the Linker is attached. For additional examples and related ligands, see, Zhang T. et al. "Covalent Targeting of Remote Cysteine Residues to Develop Cdk12 and Cdk13 Inhibitors." *Nat. Chem. Biol.* 12: 876 (2016).
Figure 2R:
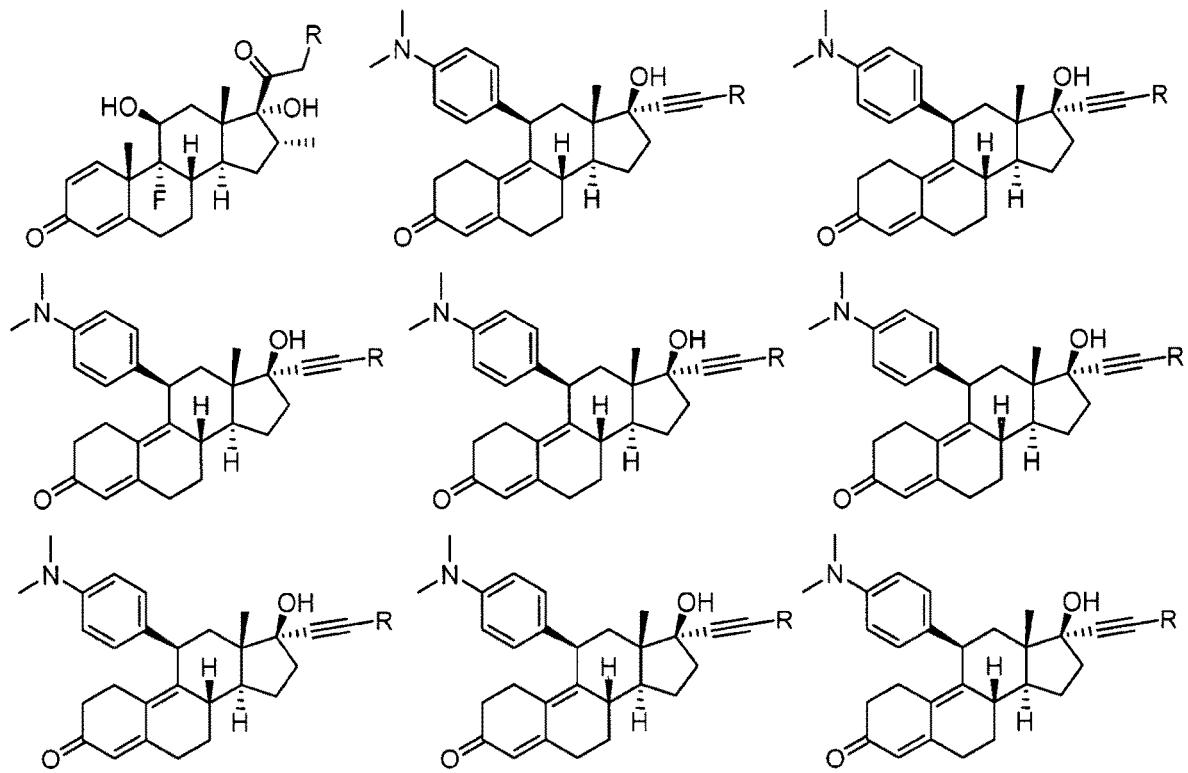
FIG. 2R-2S present examples of Glucocorticoid Receptor Targeting Ligands wherein R is the point at which the Linker is attached.
Figure 2S:
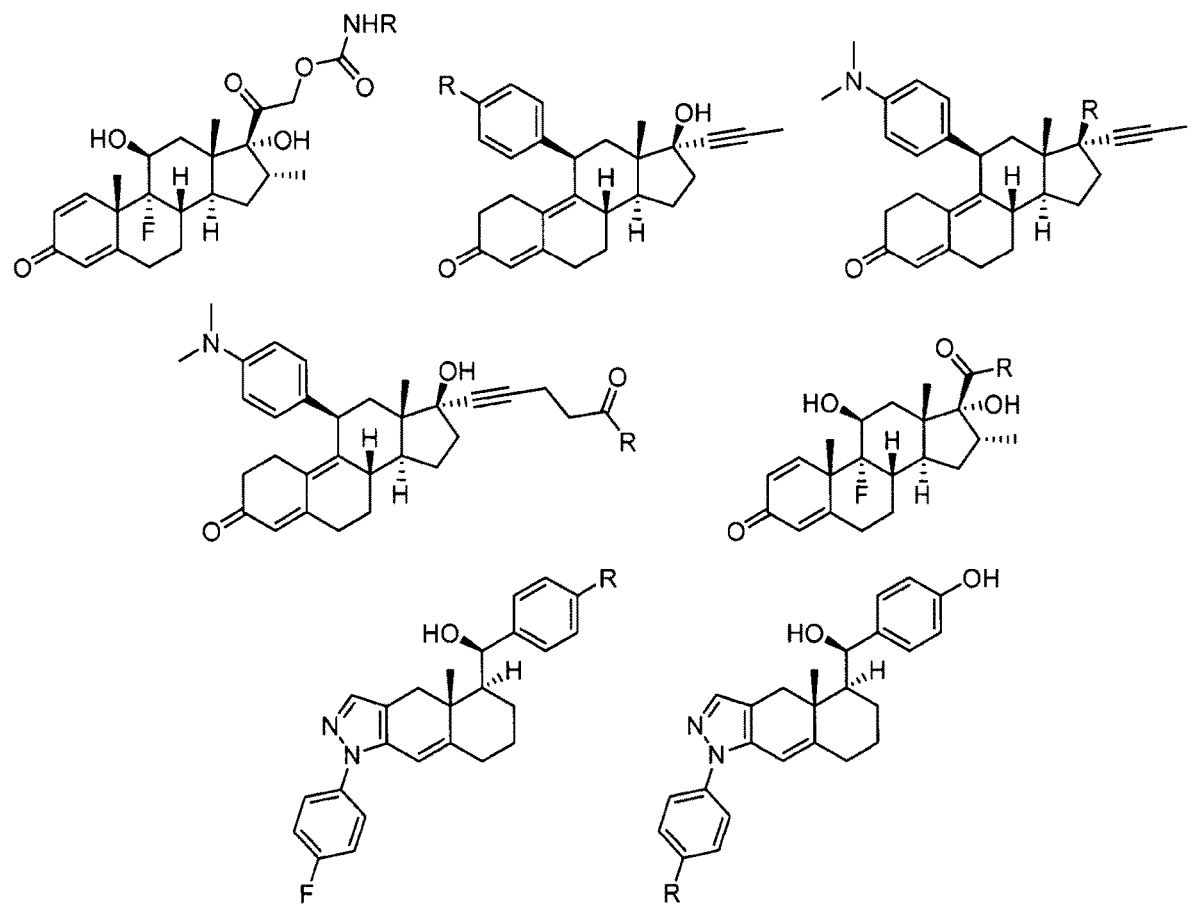
Figure 2T:
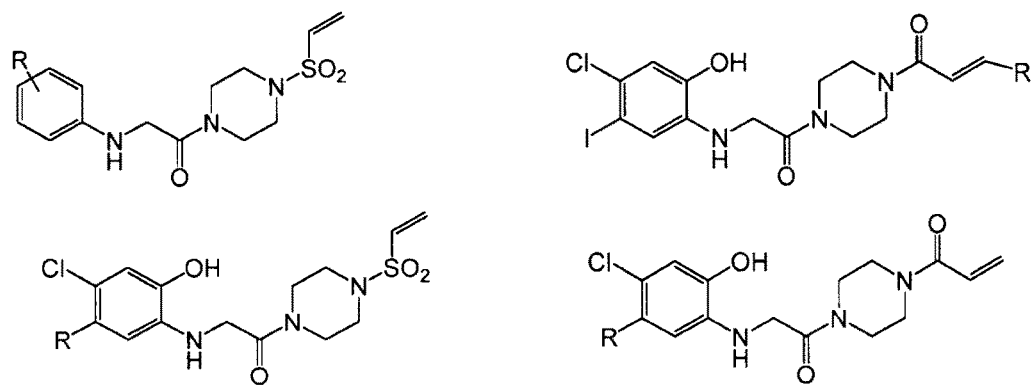
FIG. 2T-2U present examples of RasG12C Targeting Ligands wherein R is the point at which the Linker is attached.
Figure 2U:
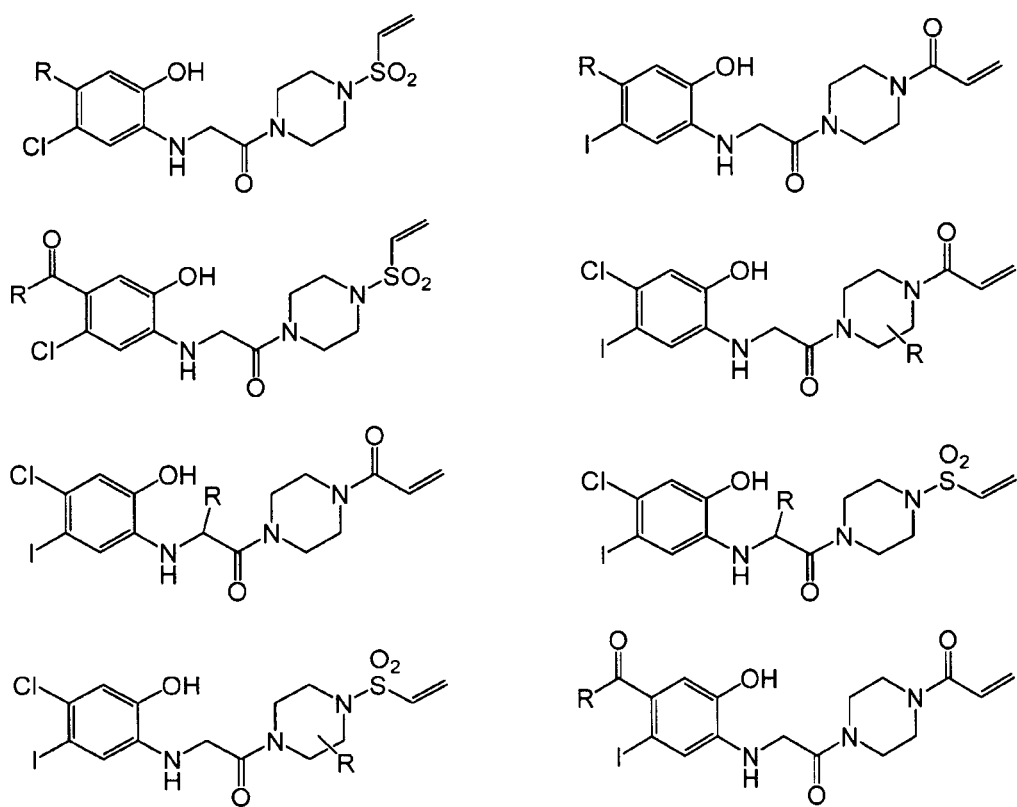
Figure 2V:
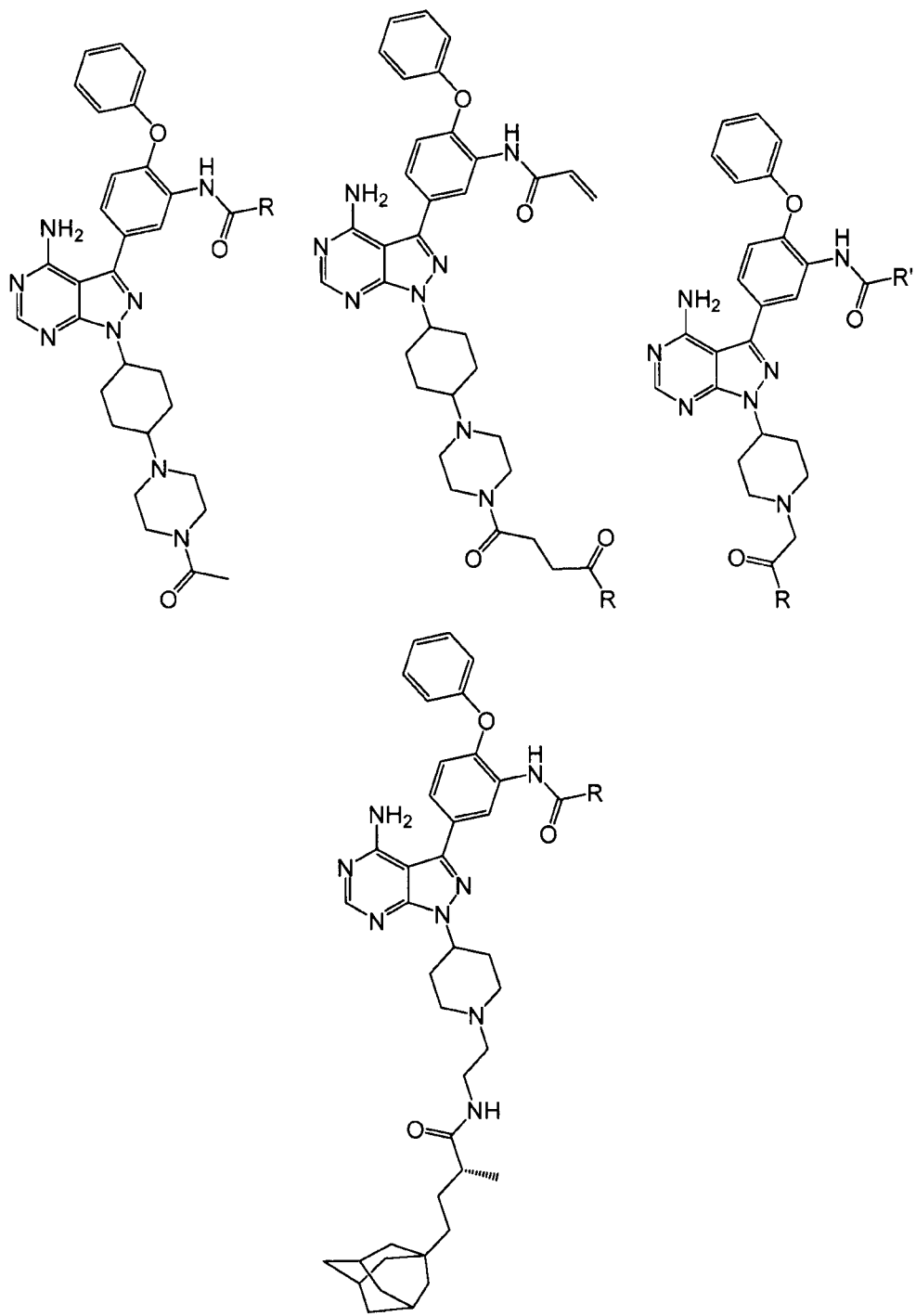
FIG. 2V presents examples of Her3 Targeting Ligands wherein R is the point at which the Linker is attached and R' is
Figure 2Z:
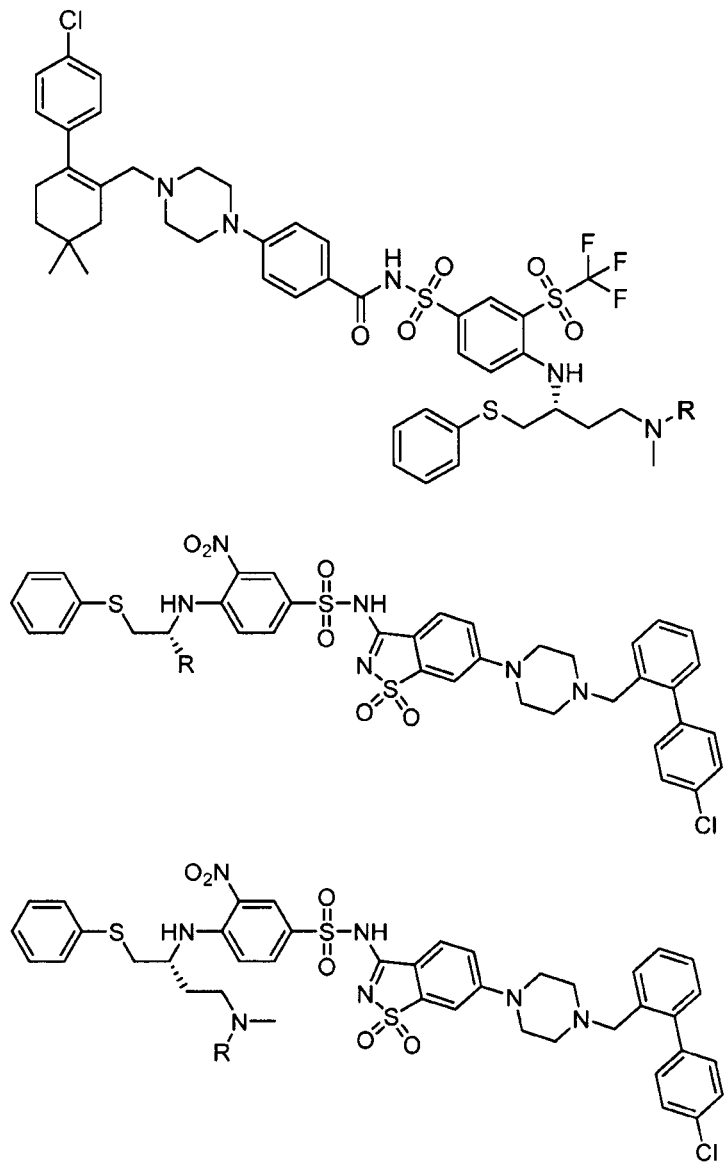
FIG. 2D presents examples of kinase inhibitor Targeting Ligands, including the kinase inhibitor compounds 6TP and 0TP (derivatized) wherein R is the point at which the Linker is attached. For additional examples and related ligands, see, the kinase inhibitors identified in Schenkel et al. "Discovery of Potent and Highly Selective Thienopyridine Janus Kinase 2 Inhibitors" *J. Med. Chem.*, 54 (24): 8440-8450 (2011).
FIG. 2F presents examples of kinase inhibitor Targeting Ligands, including the kinase inhibitor compound YCF, wherein R is the point at which the Linker is attached. For additional examples and related ligands, see, the kinase inhibitors identified in Lountos et al. "Structural Characterization of Inhibitor Complexes with Checkpoint Kinase 2 (Chk2) a Drug Target for Cancer Therapy" *J. Struct. Biol.,* 176: 292 (2011).
Figure 2A:
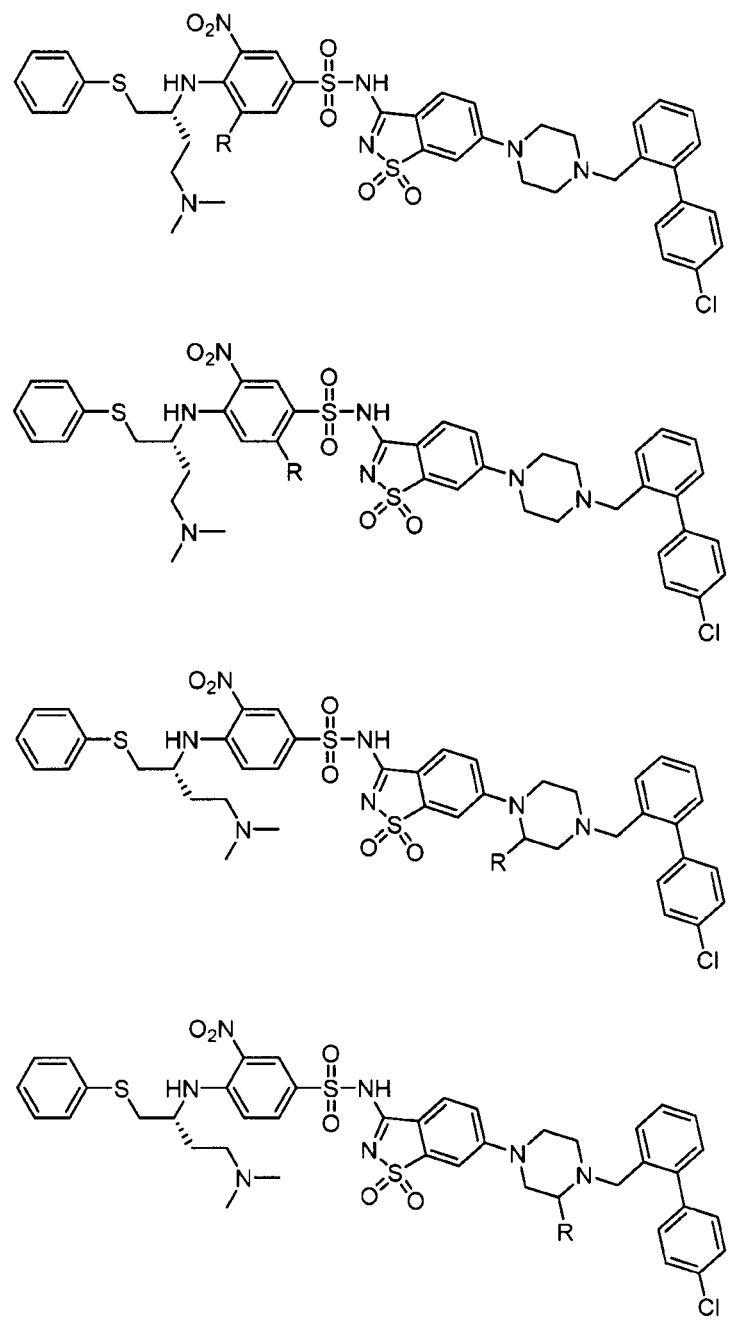
Figure 2B:
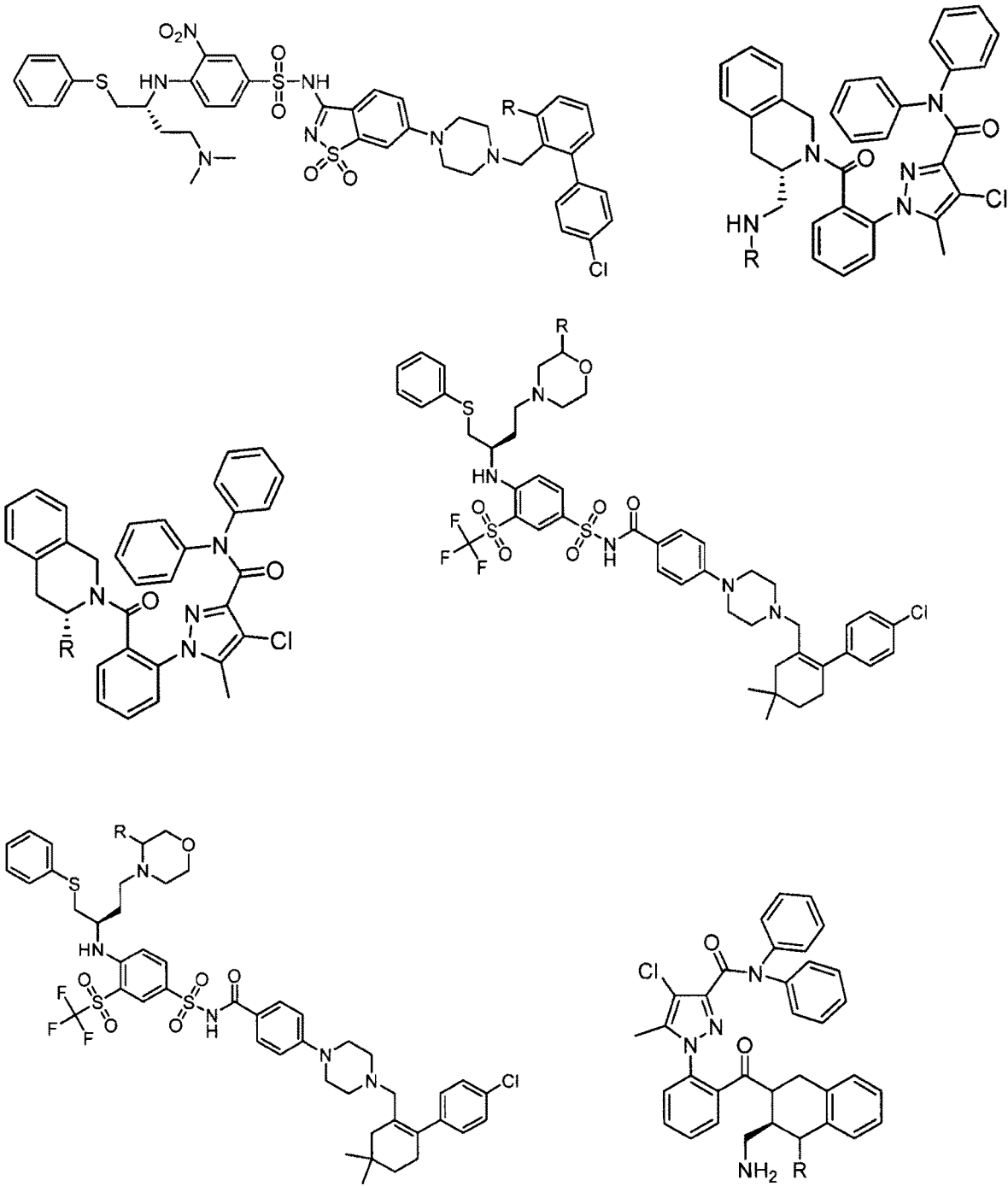
Figure 2C:
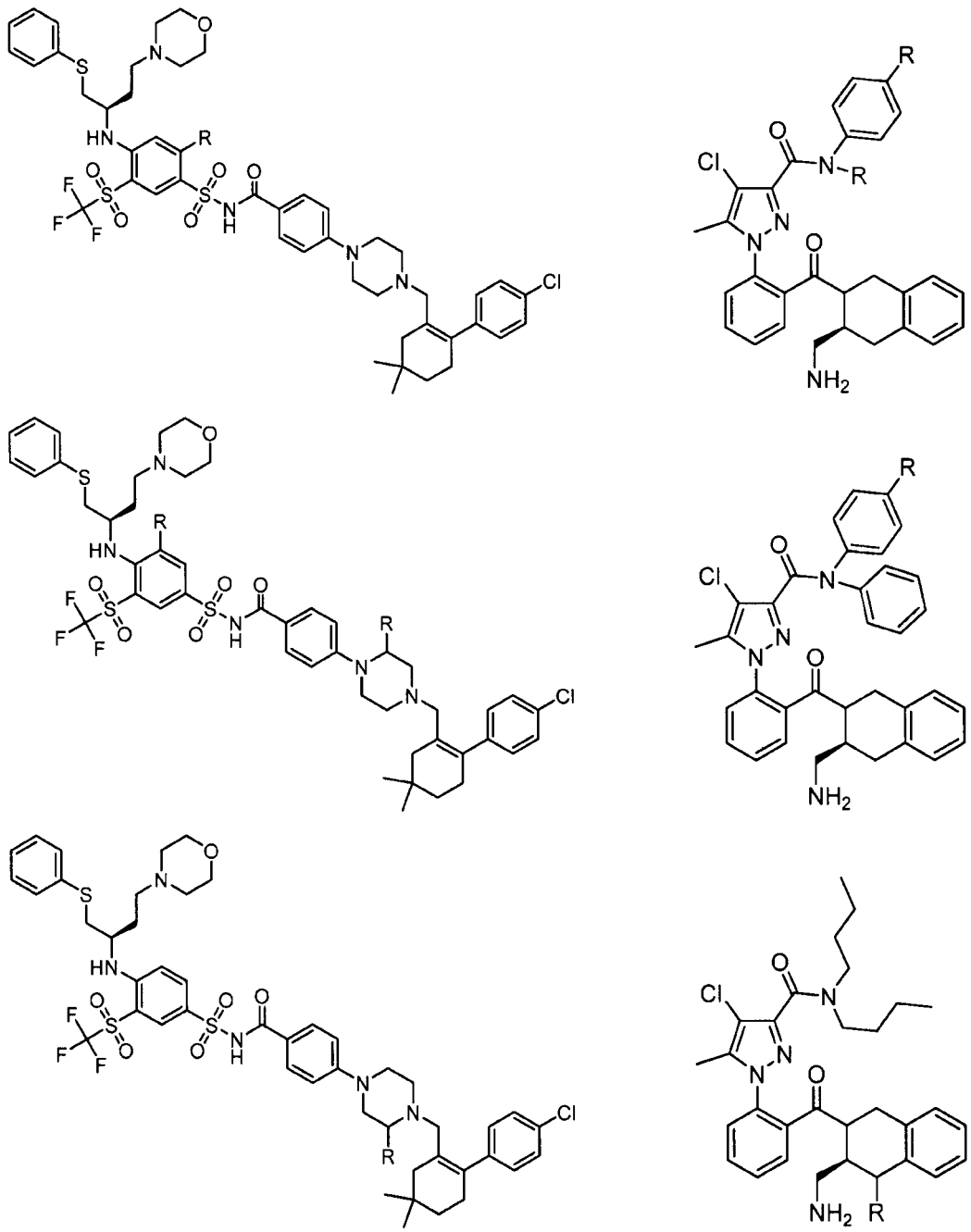
Figure 2D:
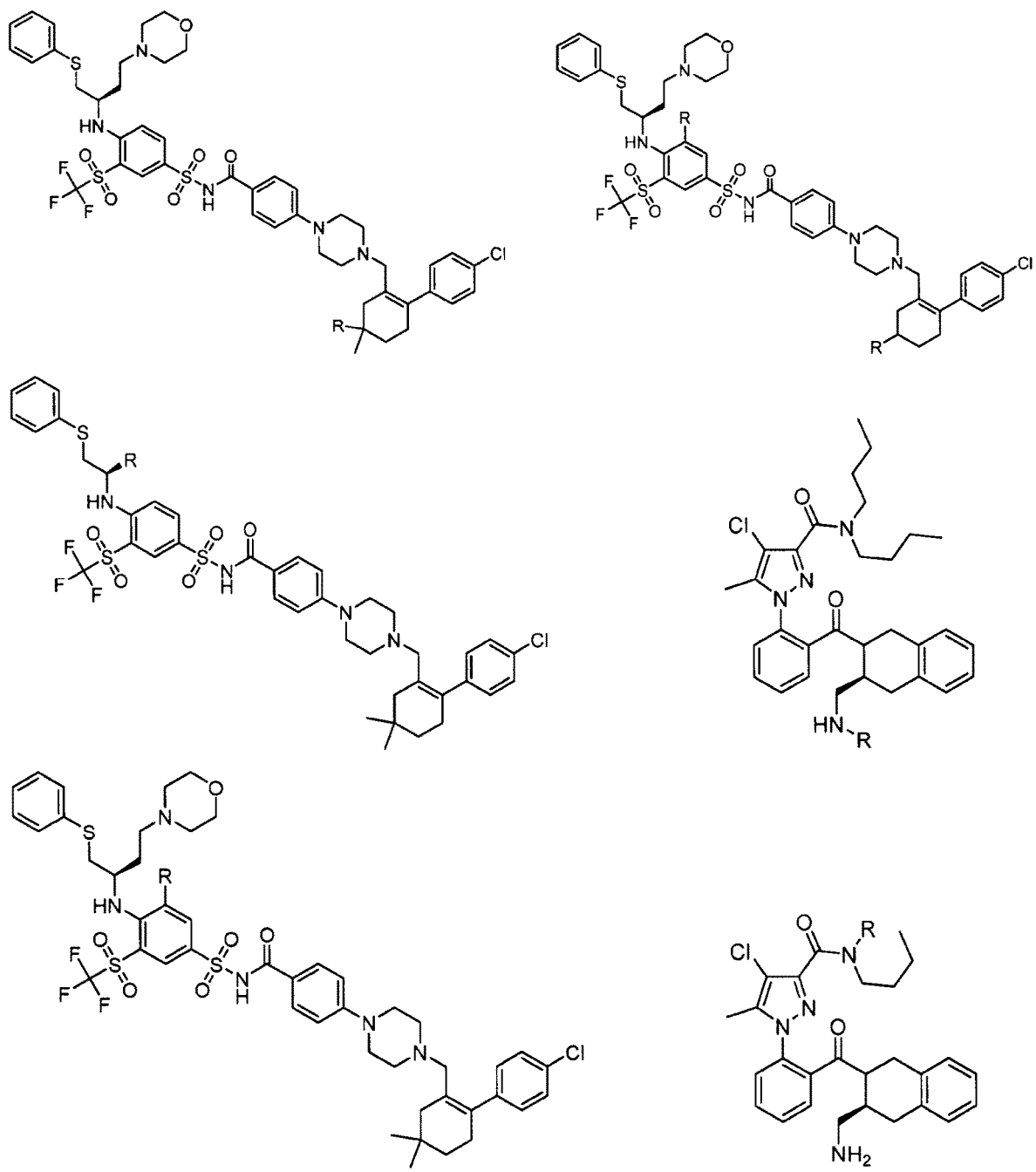
Figure 2E:
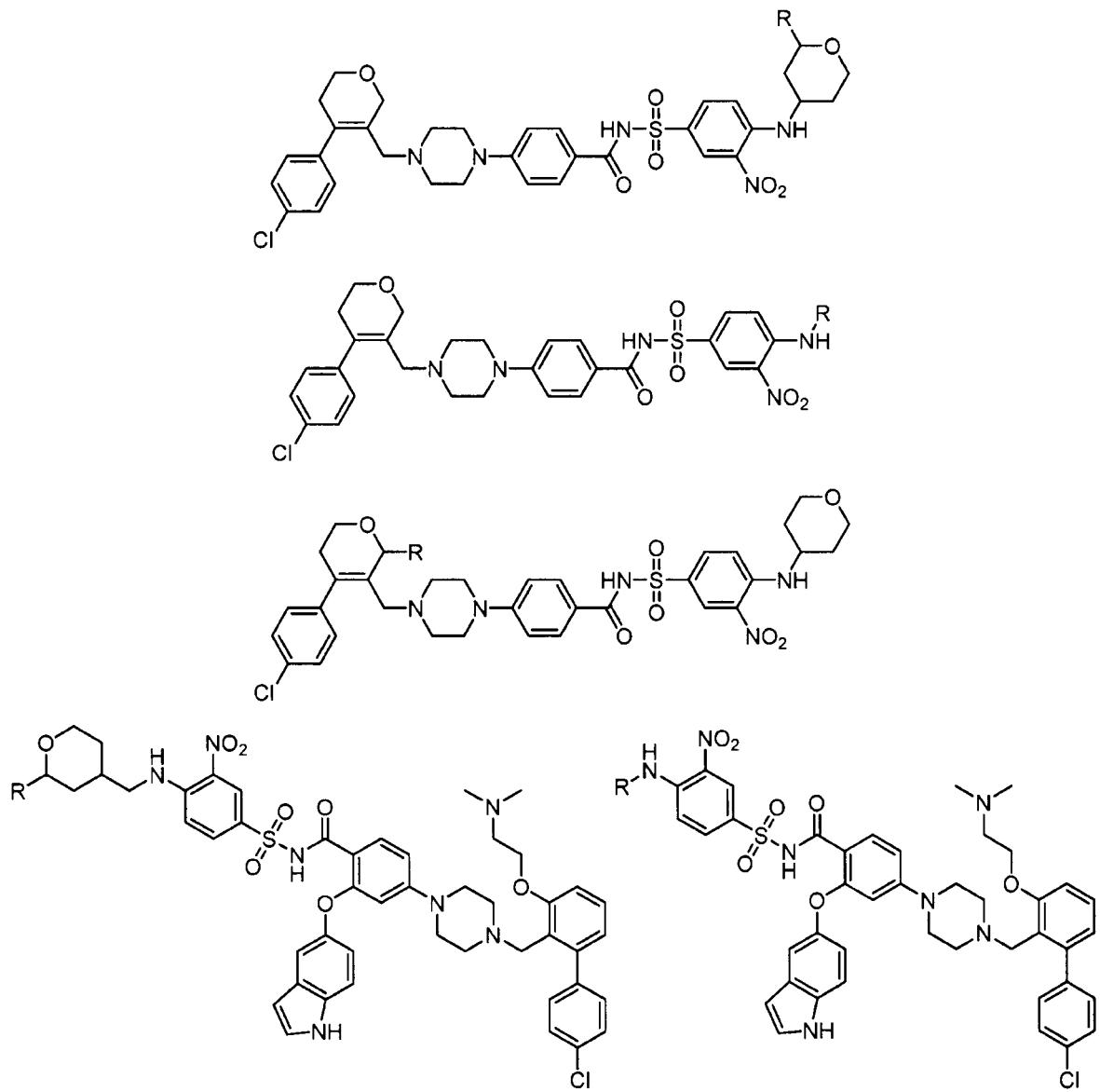
Figure 2F:
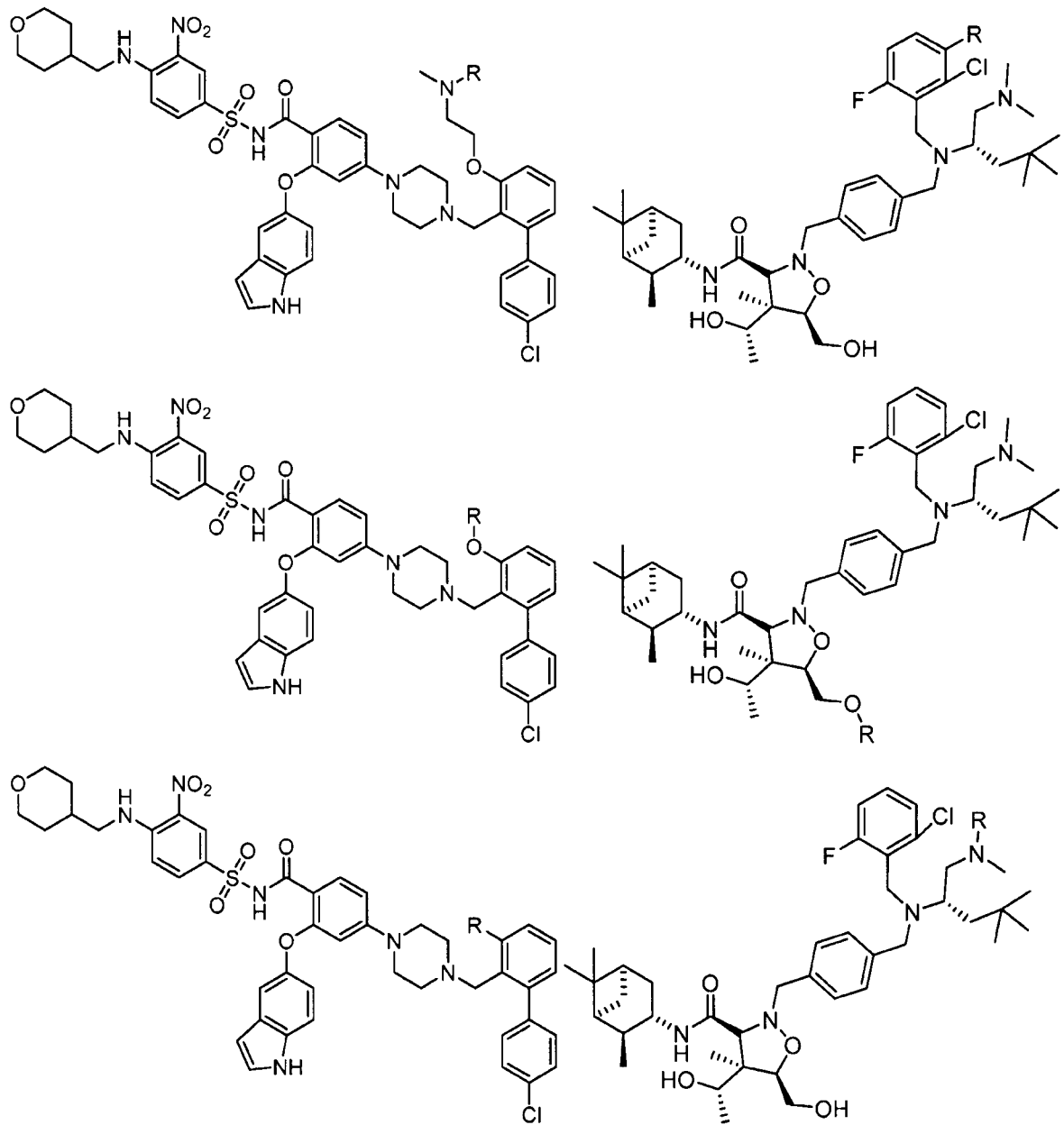
Figure 2G:
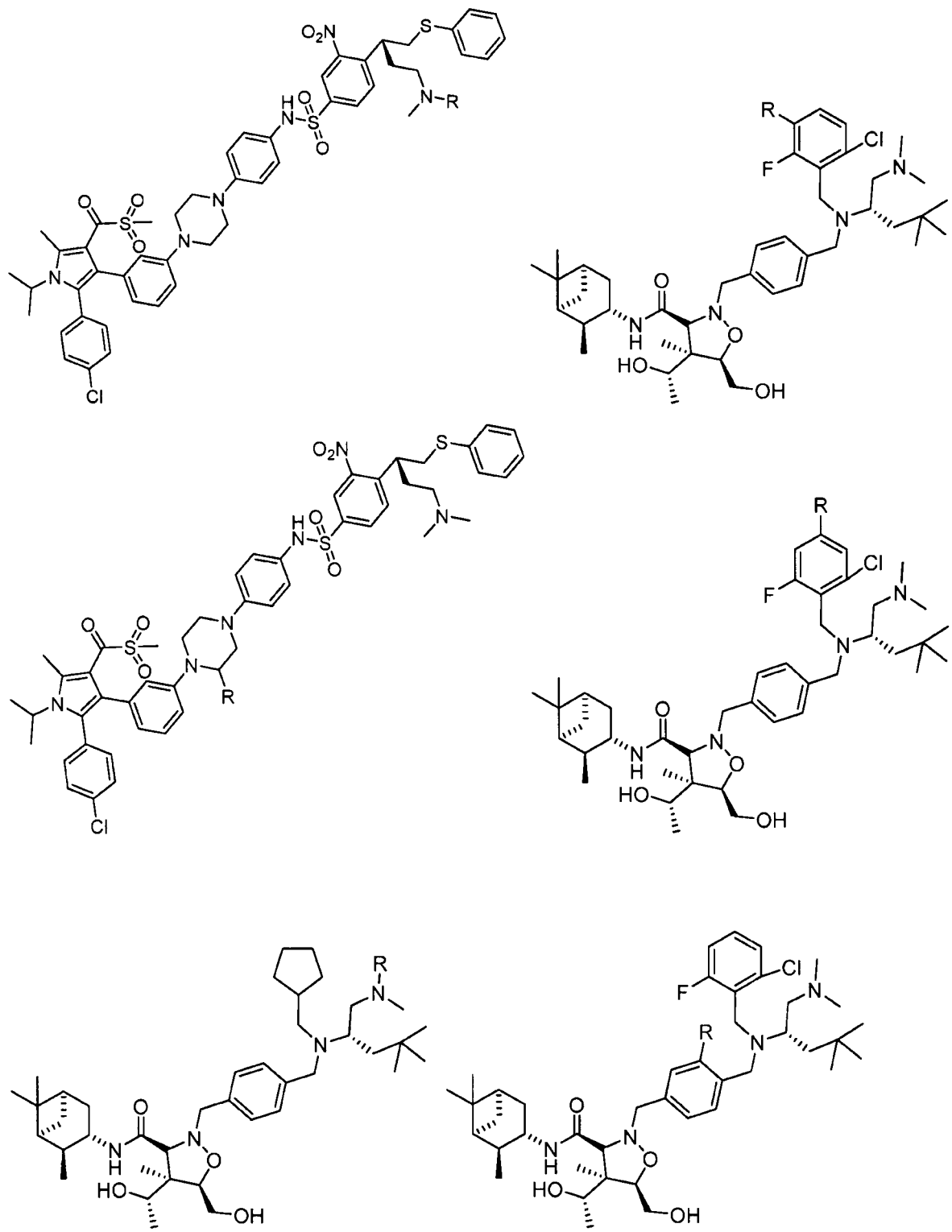
Figure 2H:
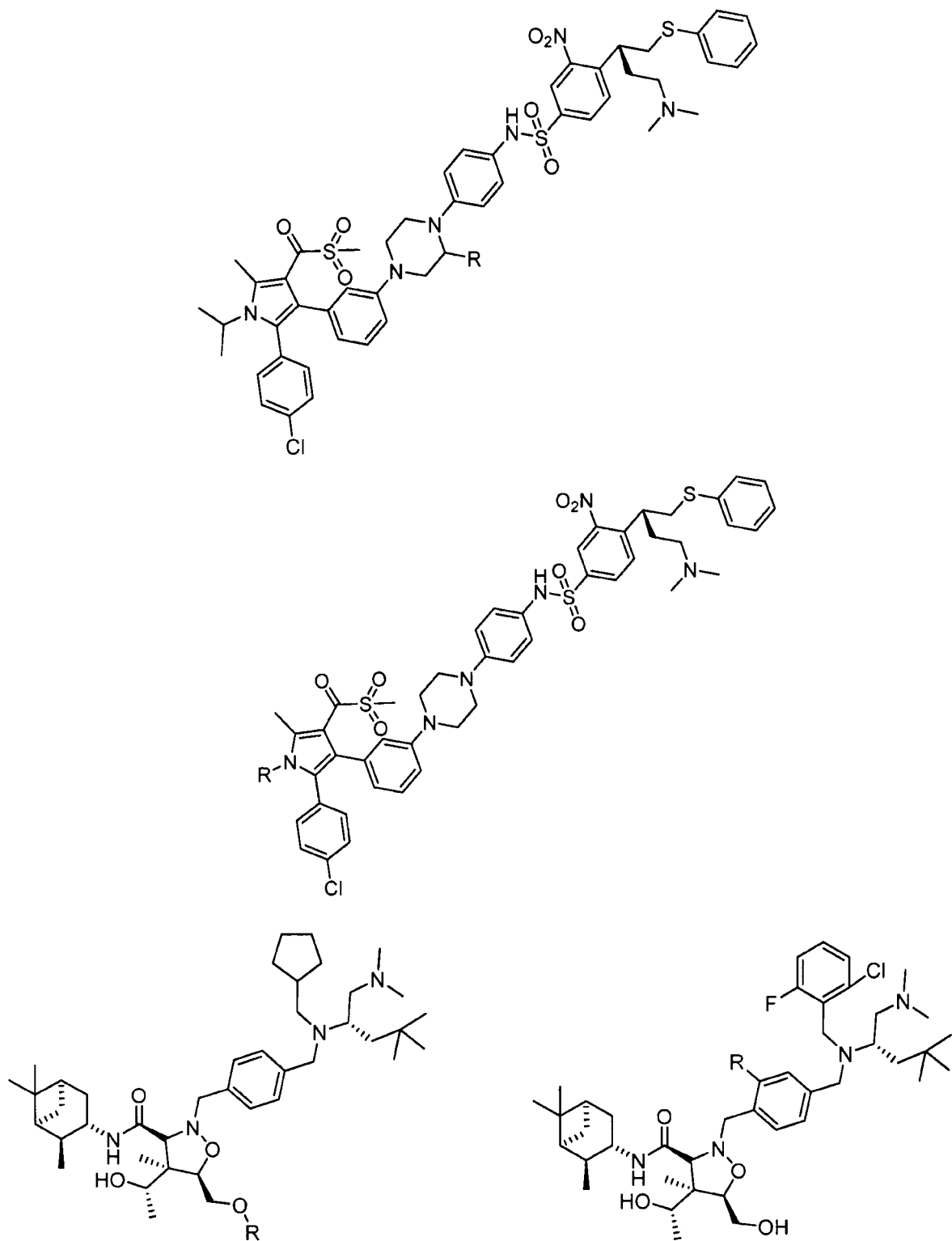
Figure 2I:
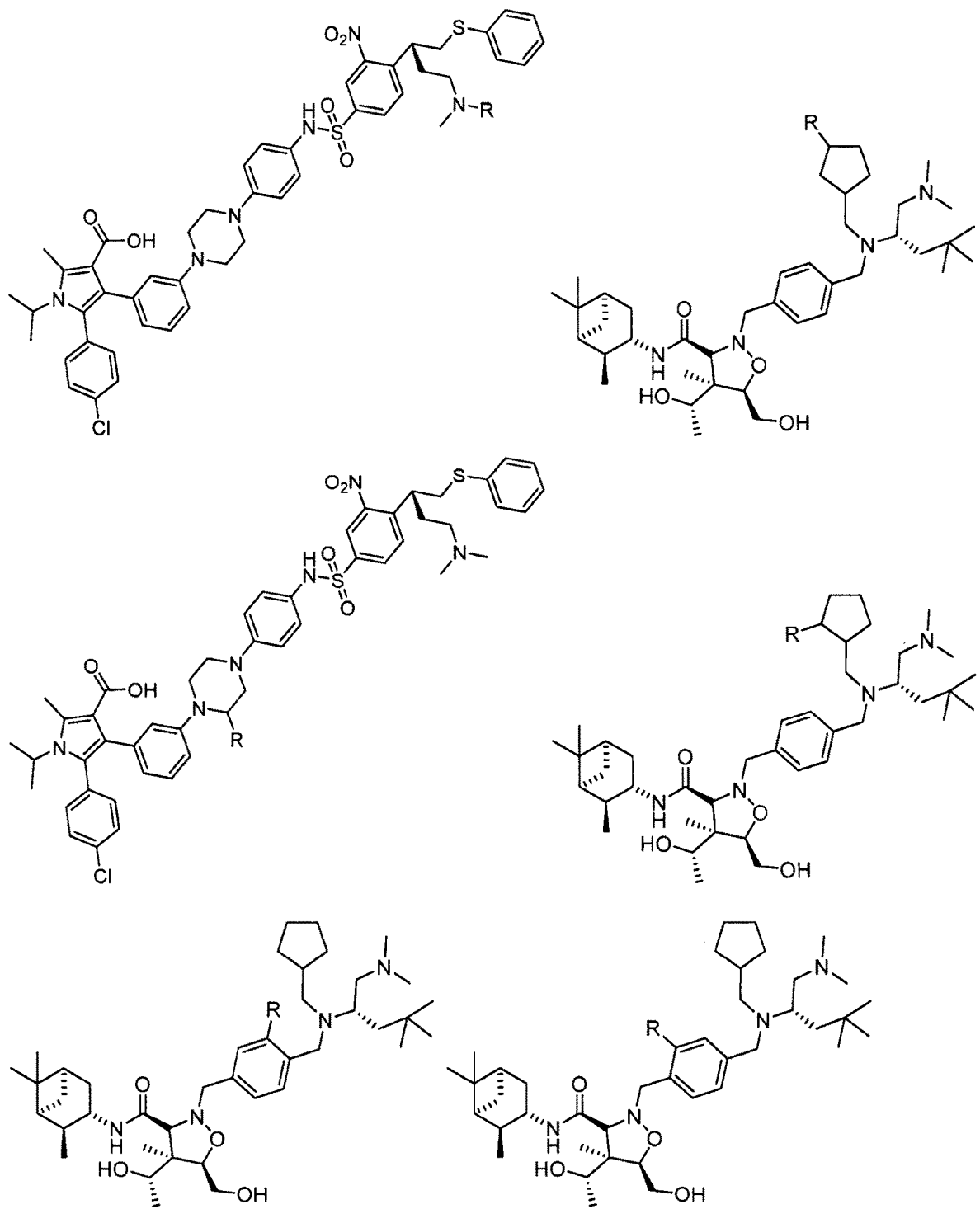
Figure 2J:
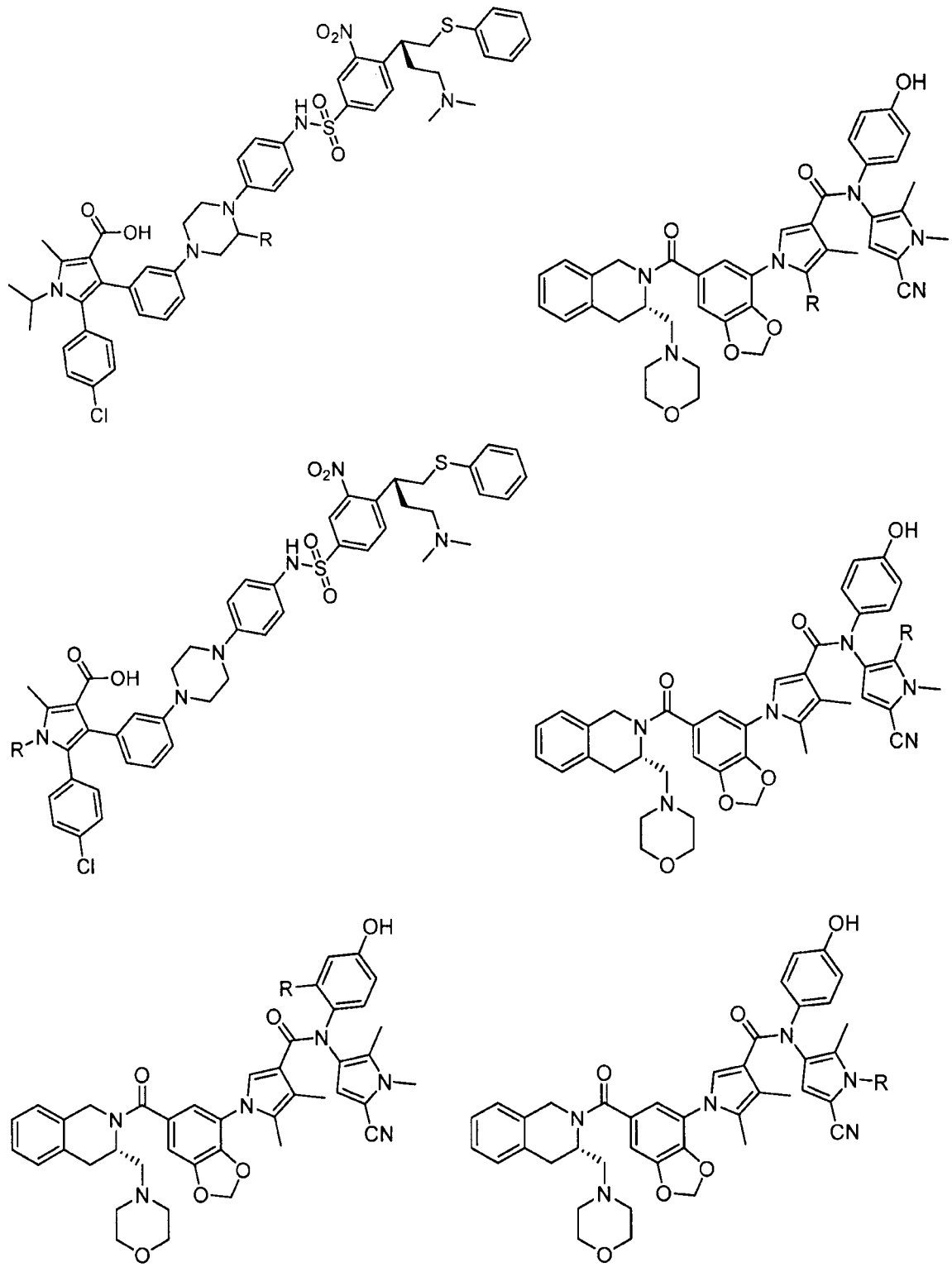
Figure 2K:
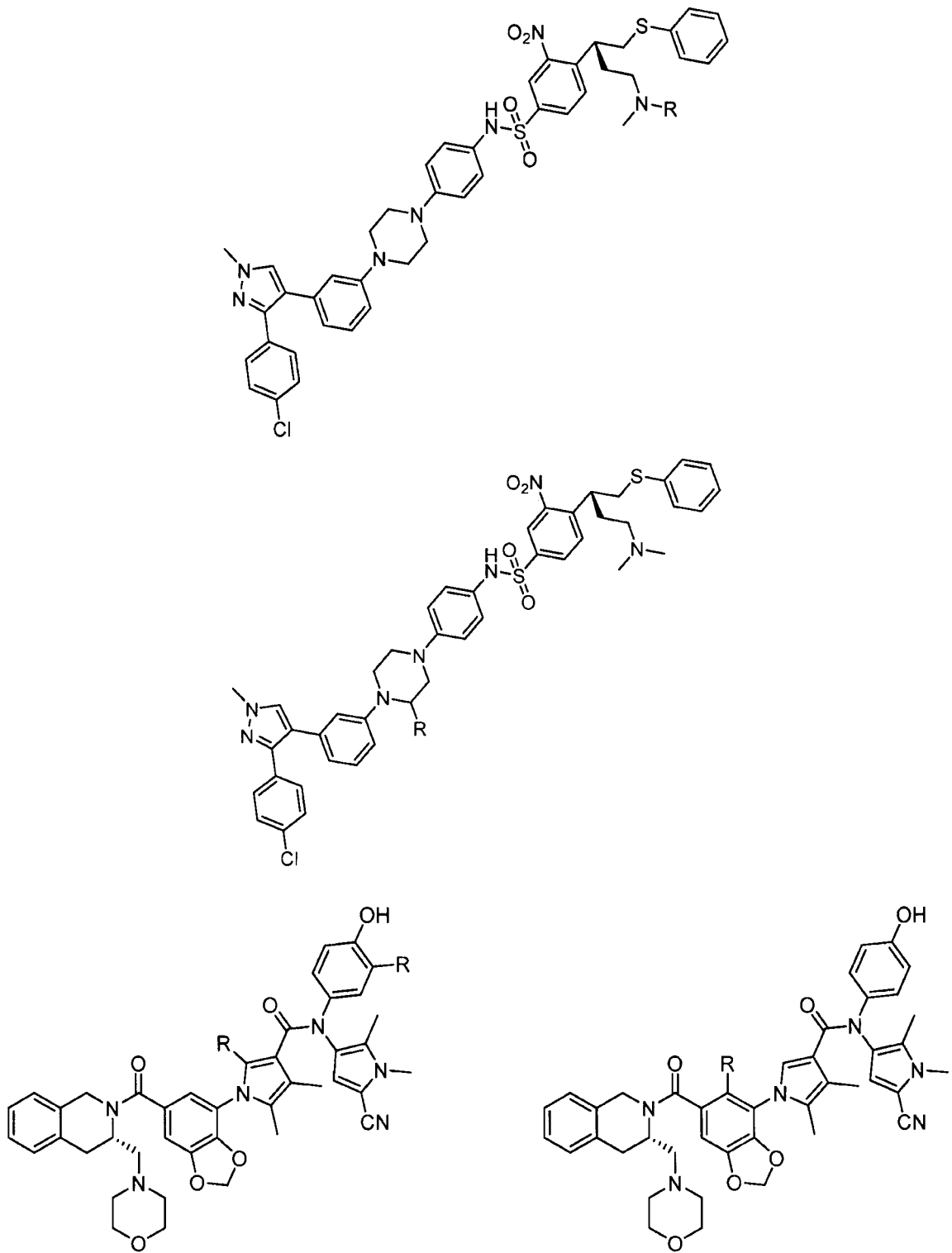
Figure 2L:
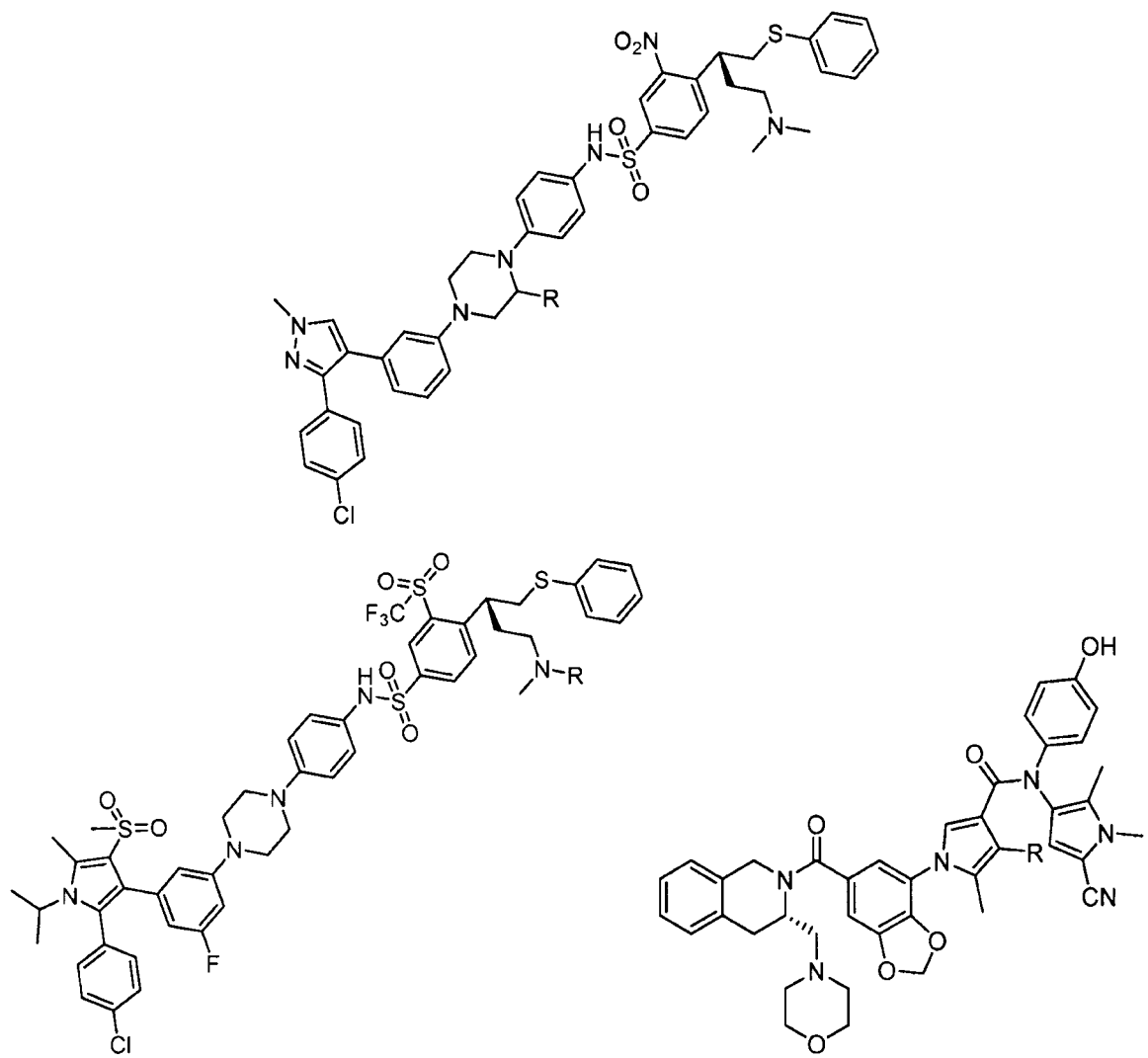
Figure 2M:
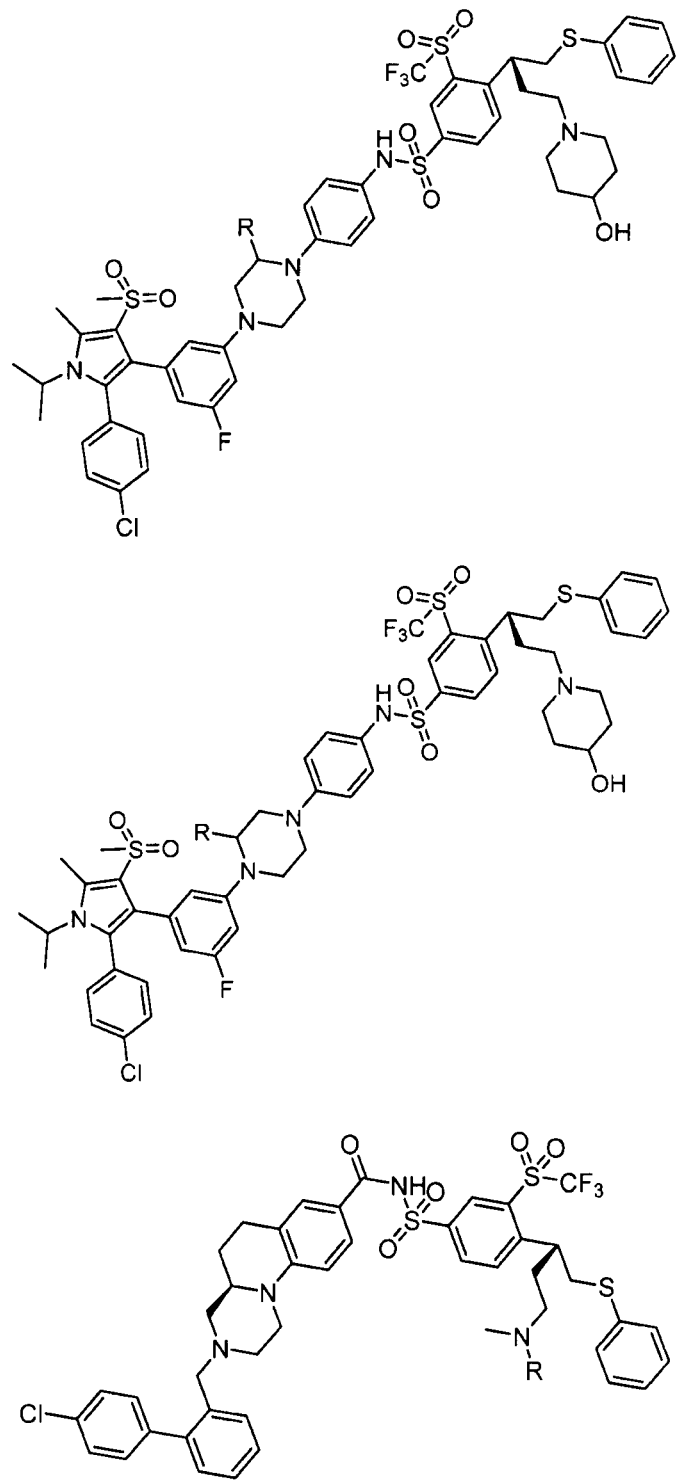
Figure 2N:
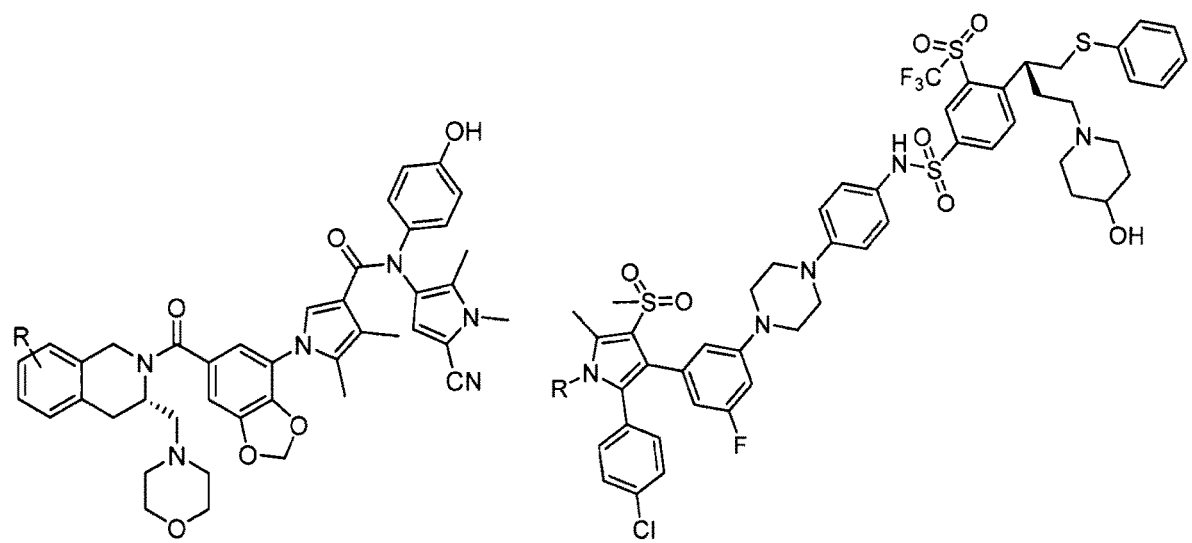
Figure 2O:
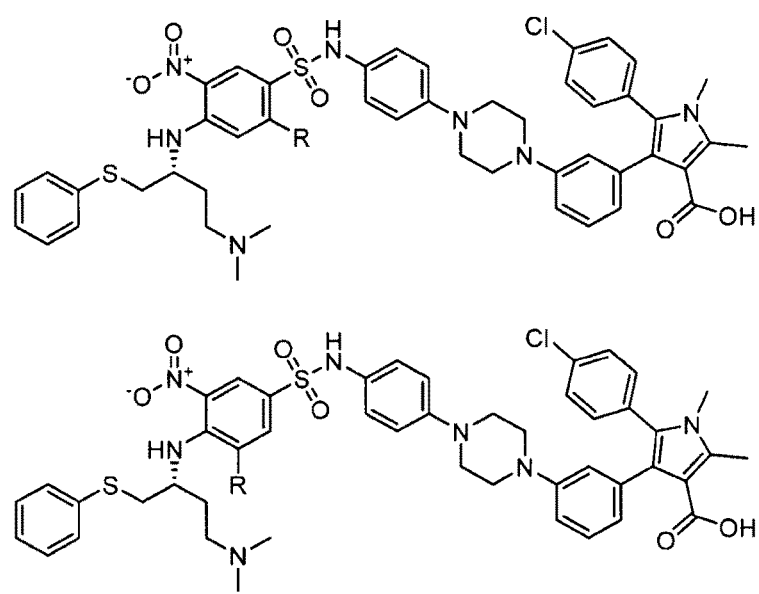
Figure 2P:
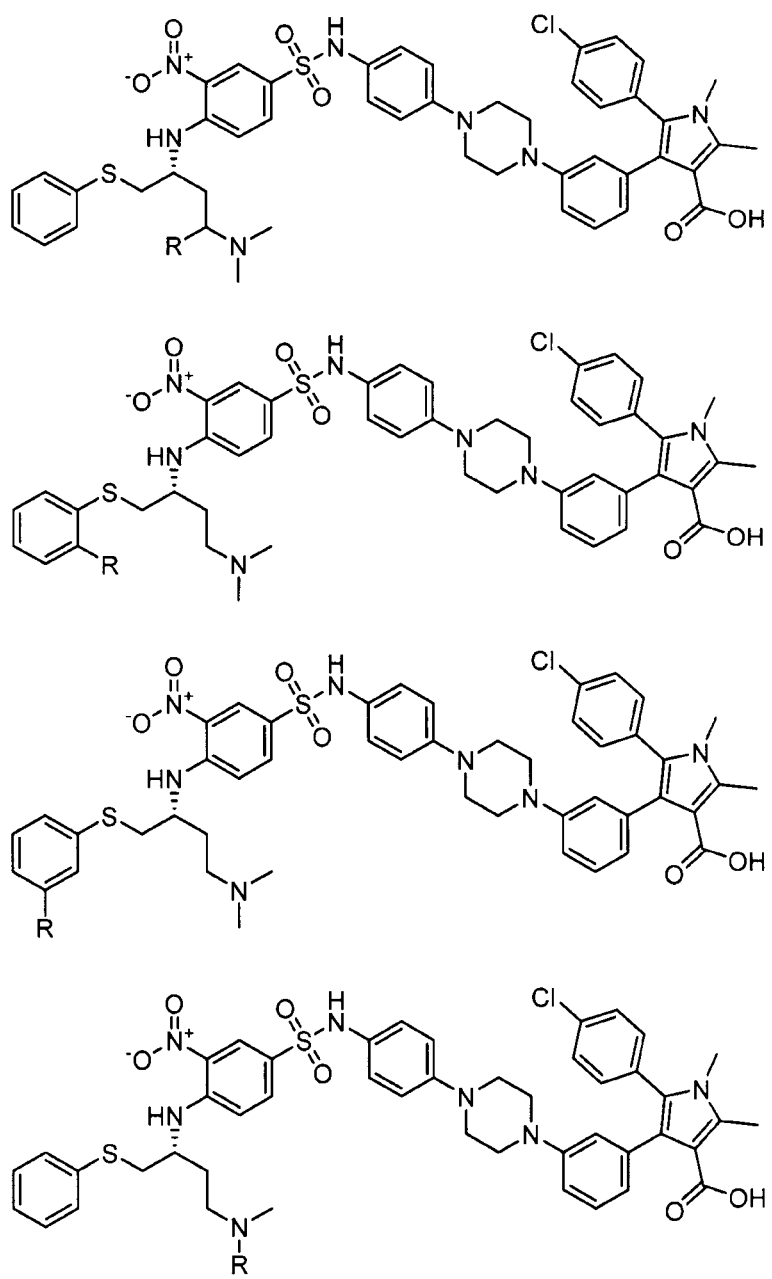
Figure 2Q:
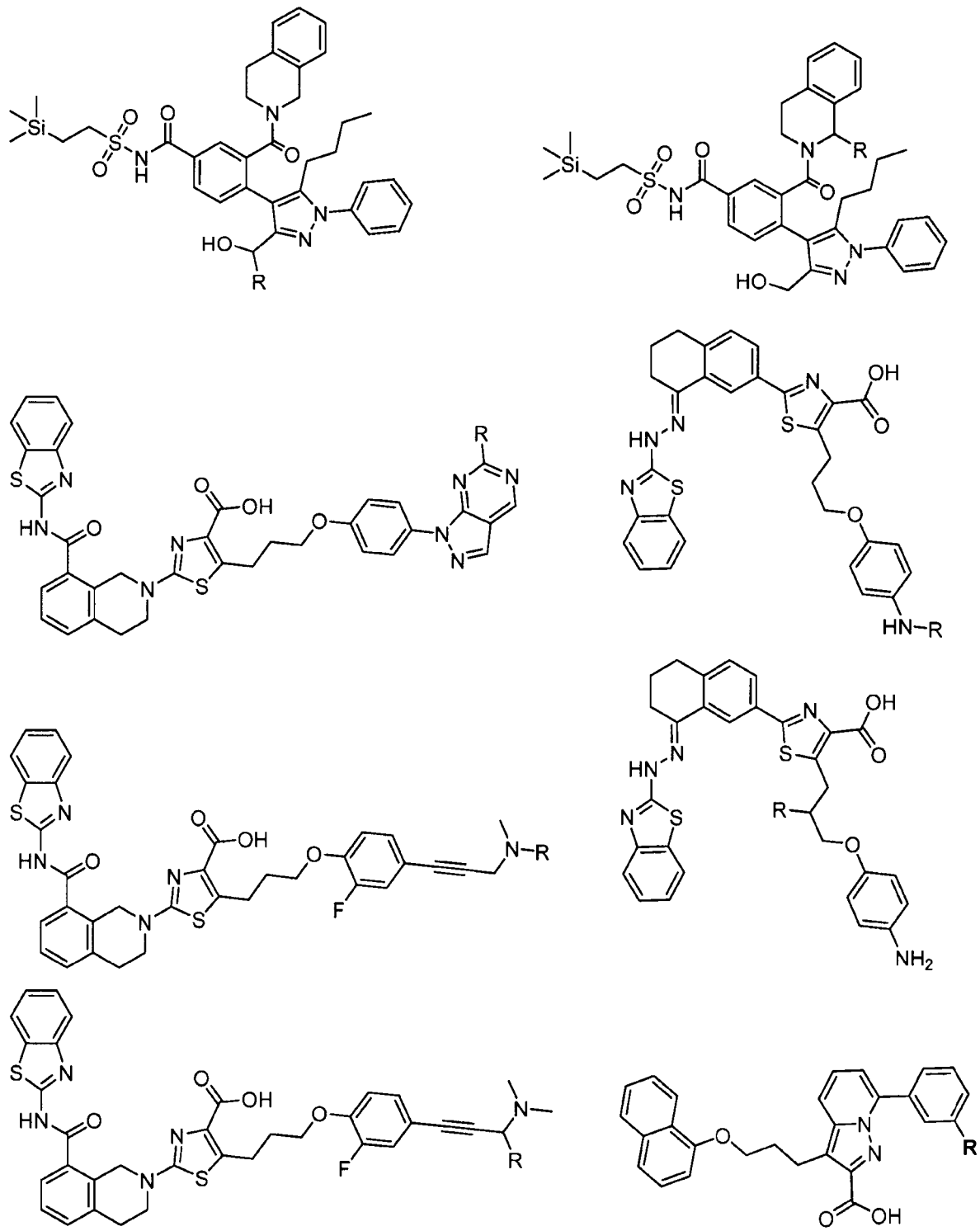
Figure 2S:
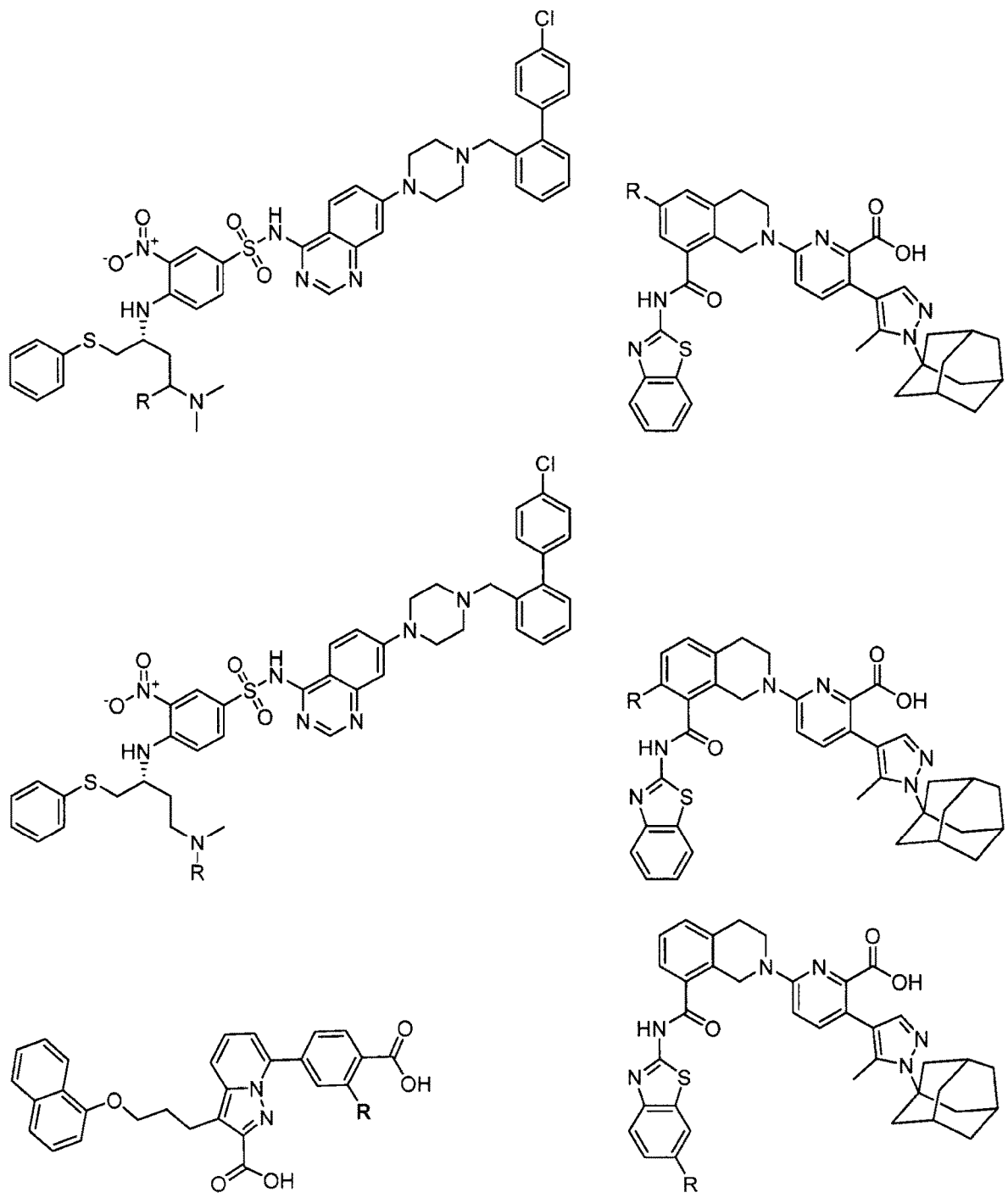
Figure 2T:
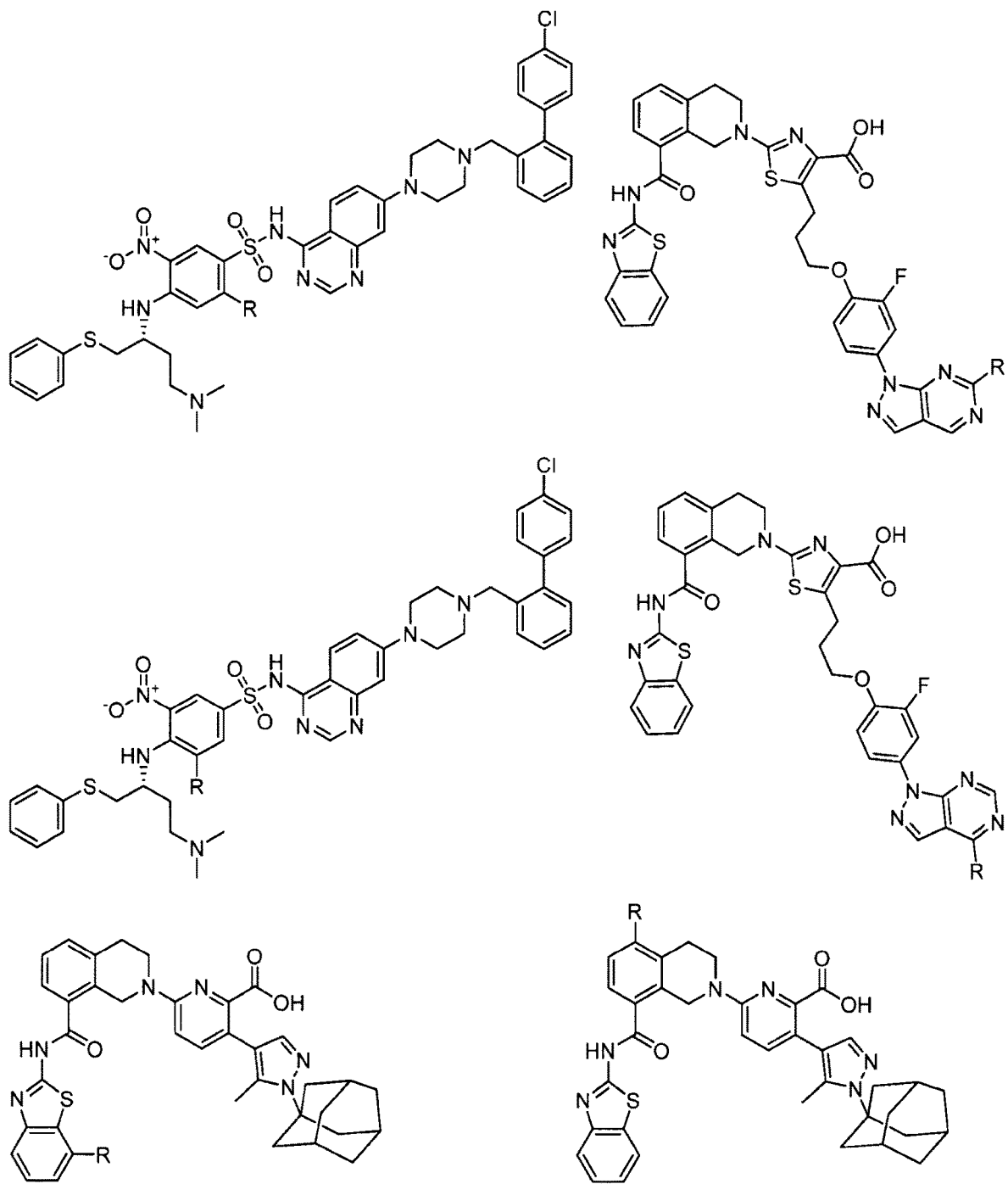
Figure 2U:
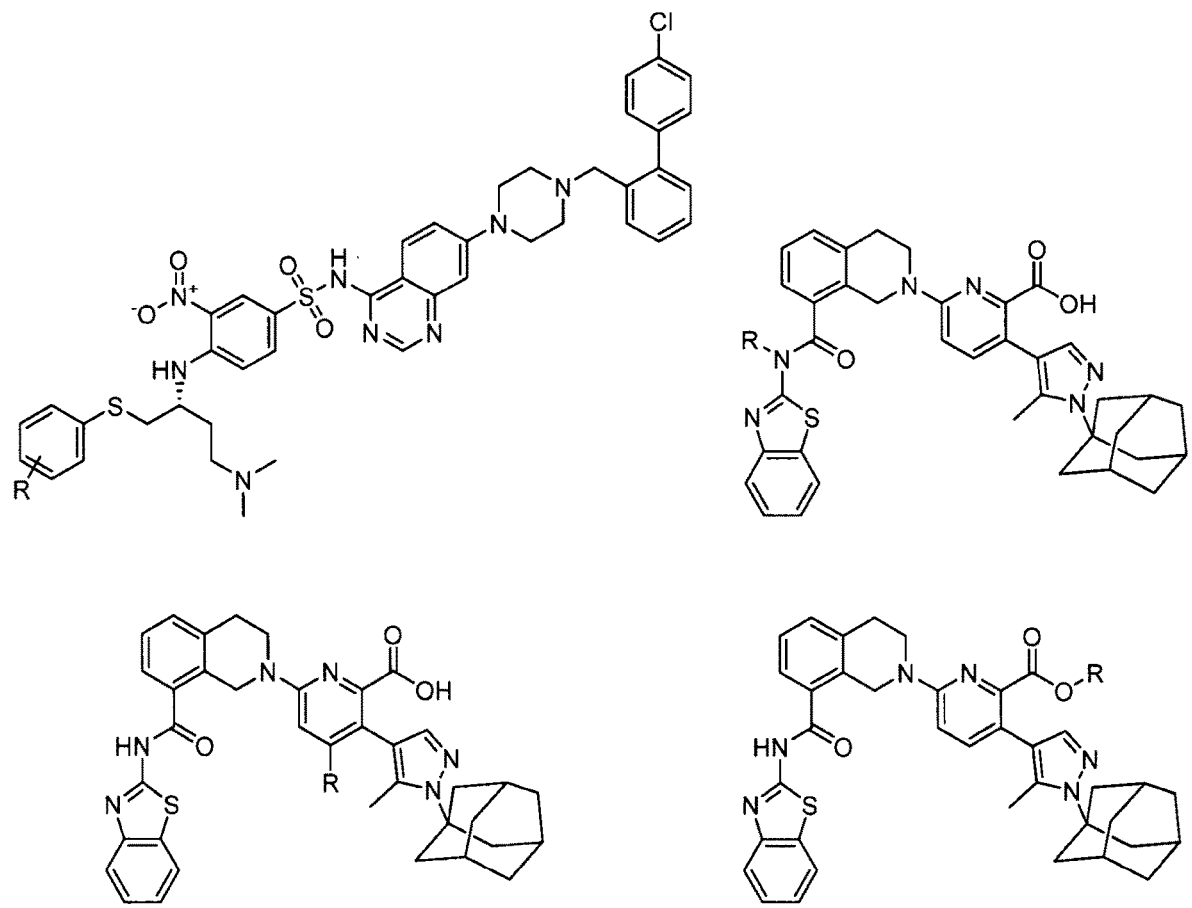
Figure 2V:
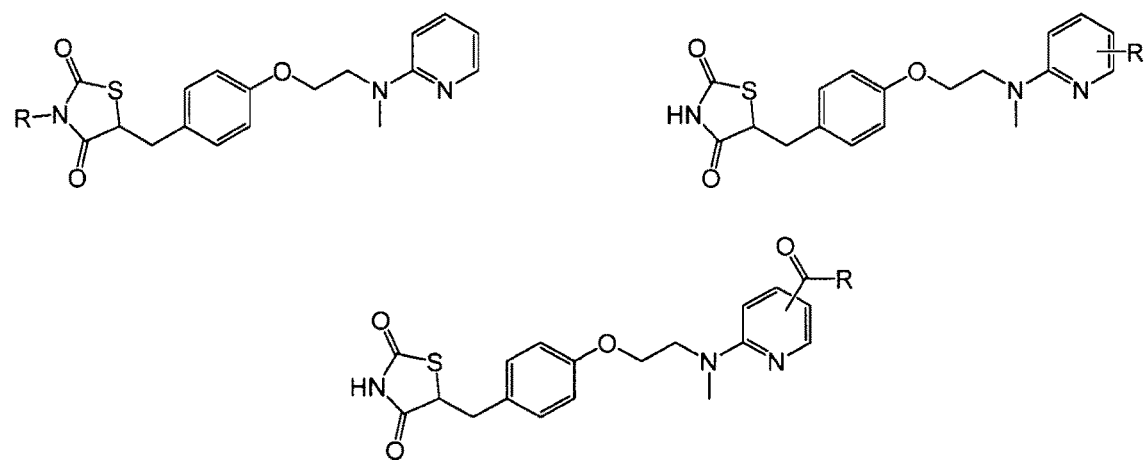
Figure 2W:
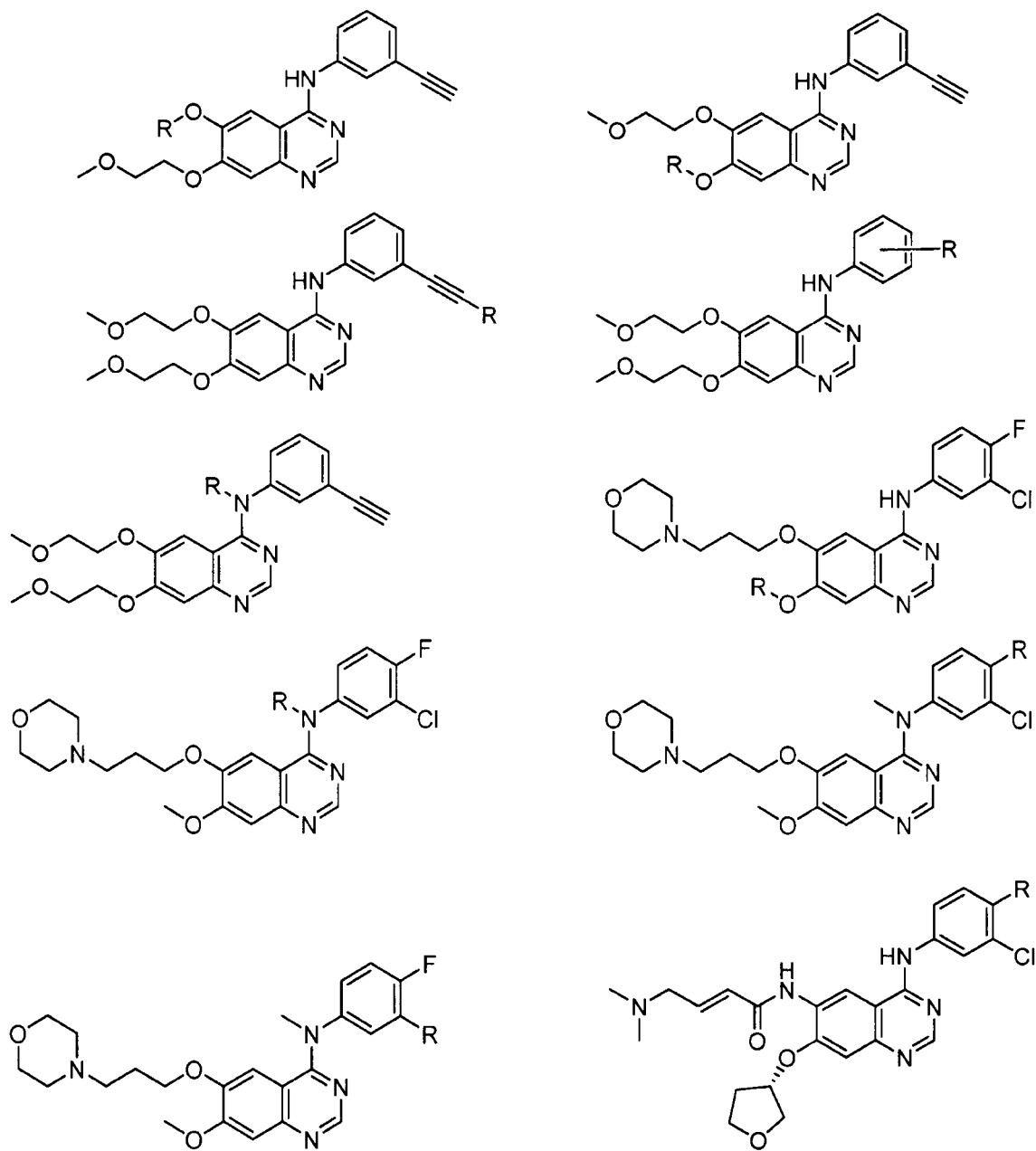

FIG. 2W presents examples of Bcl-2 or Bcl-XL Targeting Ligands wherein R is the point at which the Linker is attached.

Figure 2X:
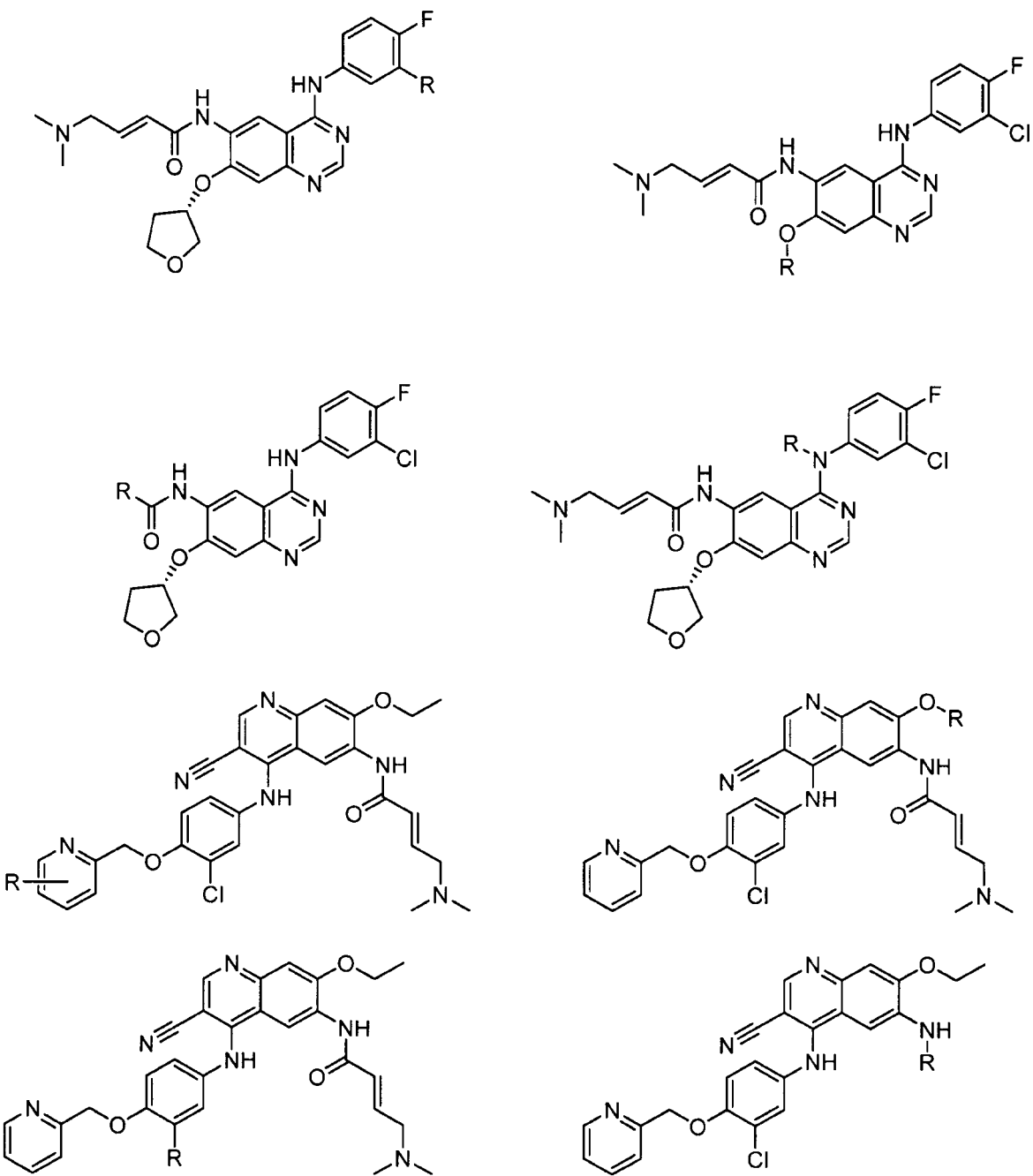

FIG. 2X-2NN present examples of BCL2 Targeting Ligands wherein R is the point at which the Linker is attached. For additional examples and related ligands, see, Toure B. B. et al. "The role of the acidity of N-heteroaryl sulfonamides as inhibitors of bcl-2 family protein-protein interactions." *ACS Med Chem Lett,* 4: 186-190 (2013); Porter J. e.t al. "Tetrahydroisoquinoline Amide Substituted Phenyl Pyrazoles as Selective Bcl-2 Inhibitors" *Bioorg. Med. Chem. Lett.* 19: 230 (2009); Souers A. J. et al. "ABT-199 a potent and selective BCL-2 inhibitor achieves antitumor activity while sparing platelets." *Nature Med.* 19: 202-208 (2013); Angelo Aguilar et al. "A Potent and Highly Efficacious Bcl-2/Bcl-xL Inhibitor" *J Med Chem.* 56(7): 3048-3067 (2013); Longchuan Bai et al. "BM-1197: A Novel and Specific Bcl-2/Bcl-xL Inhibitor Inducing Complete and Long-Lasting Tumor Regression In Vivo" *PLoS ONE* 9(6): e99404; Fariba Ne'matil et al. "Targeting Bcl-2/Bcl-XL Induces Antitumor Activity in Uveal Melanoma Patient-Derived Xenografts" *PLoS ONE* 9(1): e80836; WO2015011396 titled "Novel derivatives of indole and pyrrole method for the production thereof and pharmaceutical compositions containing same"; WO2008060569A1 titled "Compounds and methods for inhibiting the interaction of Bcl proteins with binding partners"; "Inhibitors of the anti-apoptotic Bcl-2 proteins: a patent review" *Expert Opin. Ther. Patents* 22(1):2008 (2012); and, Porter et al. "Tetrahydroisoquinoline amide substituted phenyl pyrazoles as selective Bcl-2 inhibitors" *Bioorg Med Chem Lett.,* 19(1): 230-3 (2009).

FIG. 2OO-2UU present examples of BCL-XL Targeting Ligands wherein R is the point at which the Linker is attached. For additional examples and related ligands, see, Zhi-Fu Tao et al. "Discovery of a Potent and Selective BCL-XL Inhibitor with in Vivo Activity" *ACS Med. Chem. Lett.,* 5: 1088-1093 (2014); Joel D. Leverson et al. "Exploiting selective BCL-2 family inhibitors to dissect cell survival dependencies and define improved strategies for cancer therapy" *Science Translational Medicine,* 7:279ra40 (2015); and, the crystal structure PDB 3ZK6 (Guillaume Lessene et al. "Structure-guided design of a selective BCL-XL inhibitor" *Nature Chemical Biology* 9: 390-397 (2013))

FIG. 2VV presents examples of PPAR-gamma Targeting Ligands wherein R is the point at which the Linker is attached.

FIG. 2WW-2YY present examples of EGFR Targeting Ligands that target the EGFR L858R mutant, including erlotinib, gefitnib, afatinib, neratinib, and dacomitinib, wherein R is the point at which the Linker is attached.

FIG. 2ZZ-2FFF present examples of EGFR Targeting Ligands that target the EGFR T790M mutant, including osimertinib, rociletinib, olmutinib, naquotinib, nazartinib, PF-06747775, Icotinib, Neratinib Avitinib, Tarloxotinib, PF-0645998, Tesevatinib, Transtinib, WZ-3146, WZ8040, and CNX-2006, wherein R is the point at which the Linker is attached.

FIG. 2GGG presents examples of EGFR Targeting Ligands that target the EGFR C797S mutant, including EAI045, wherein R is the point at which the Linker is attached.

FIG. 2HHH presents examples of BCR-ABL Targeting Ligands that target the BCR-ABL T315I mutantm including Nilotinib and Dasatinib, wherein R is the point at which the Linker is attached. See for example, the crystal structure PDB 3CS9.

FIG. 2III presents examples of Targeting Ligands that target BCR-ABL, including Nilotinib, Dasatinib Ponatinib and Bosutinib, wherein R is the point at which the Linker is attached.

FIG. 2JJJ-2KKK present examples of ALK Targeting Ligands that target the ALK L1196M mutant including Ceritinib, wherein R is the point at which the Linker is attached. See for example, the crystal structure PDB 4MKC.

FIG. 2LLL presents examples of JAK2 Targeting Ligands that target the JAK2V617F mutant, including Ruxolitinib, wherein R is the point at which the Linker is attached.

FIG. 2MMM presents examples of BRAF Targeting Ligands that target the BRAF V600E mutant including Vemurafenib, wherein R is the point at which the Linker is attached. For additional examples and related ligands, see, the crystal structure PBD 3OG7.

FIG. 2NNN presents examples of BRAF Targeting Ligands, including Dabrafenib, wherein R is the point at which the Linker is attached.

FIG. 2OOO presents examples of LRRK2 Targeting Ligands that target the LRRK2 R1441C mutant wherein R is the point at which the Linker is attached.

FIG. 2PPP presents examples of LRRK2 Targeting Ligands that target the LRRK2 G2019S mutant wherein R is the point at which the Linker is attached.

FIG. 2QQQ presents examples of LRRK2 Targeting Ligands that target the LRRK2 I2020T mutant wherein R is the point at which the Linker is attached.

FIG. 2RRR-2TTT present examples of PDGFRα Targeting Ligands that target the PDGFRα T674I mutant, including AG-1478, CHEMBL94431, Dovitinib, erlotinib, gefitinib, imatinib, Janex 1, Pazopanib, PD153035, Sorafenib, Sunitinib, and WHI-P180, wherein R is the point at which the Linker is attached.

FIG. 2UUU presents examples of RET Targeting Ligands that target the RET G691S mutant, including tozasertib, wherein R is the point at which the Linker is attached.

FIG. 2VVV presents examples of RET Targeting Ligands that target the RET R749T mutant, including tozasertib, wherein R is the point at which the Linker is attached.

FIG. 2WWW presents examples of RET Targeting Ligands that target the RET E762Q mutant, including tozasertib, wherein R is the point at which the Linker is attached.

FIG. 2XXX presents examples of RET Targeting Ligands that target the RET Y791F mutant, including tozasertib, wherein R is the point at which the Linker is attached.

Figure 2Y:
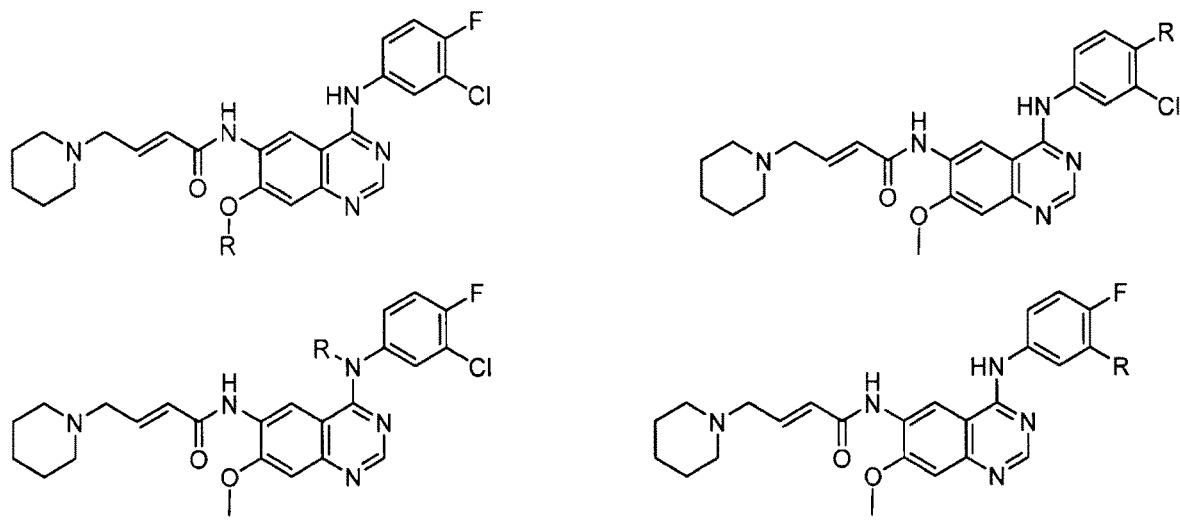
Figure 2Z:
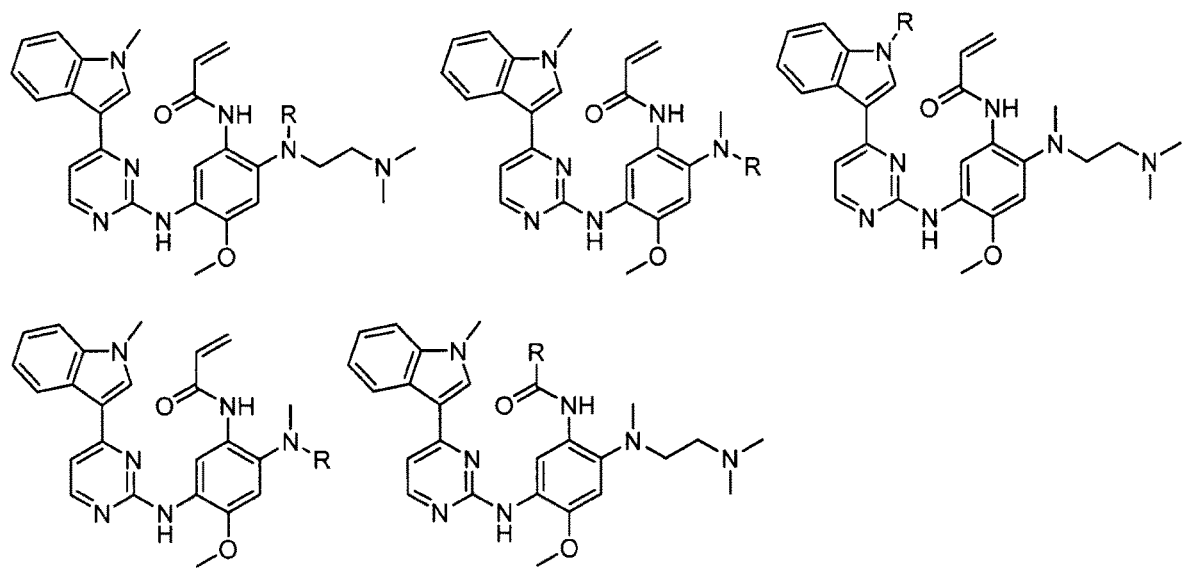

FIG. 2YYY presents examples of RET Targeting Ligands that target the RET V804M mutant, including tozasertib, wherein R is the point at which the Linker is attached.

FIG. 2ZZZ presents examples of RET Targeting Ligands that target the RET M918T mutant, including tozasertib, wherein R is the point at which the Linker is attached.

FIG. 2AAAA presents examples of Fatty Acid Binding Protein Targeting Ligands wherein R is the point at which the Linker is attached.

FIG. 2BBBB presents examples of 5-Lipoxygenase Activating Protein (FLAP) Targeting Ligands wherein R is the point at which the Linker is attached.

FIG. 2CCC presents examples of Kringle Domain V 4BVV Targeting Ligands wherein R is the point at which the Linker is attached.

FIG. 2DDDD presents examples of Lactoylglutathione Lyase Targeting Ligands wherein R is the point at which the Linker is attached.

FIG. 2EEEE-2FFFF present examples of mPGES-1 Targeting Ligands wherein R is the point at which the Linker is attached.

FIG. 2GGGG-2JJJJ present examples of Factor Xa Targeting Ligands wherein R is the point at which the Linker is attached. For additional examples and related ligands, see, Maignan S. et al. "Crystal structures of human factor Xa complexed with potent inhibitors." *J. Med. Chem.* 43: 3226-3232 (2000); Matsusue T. et al. "Factor Xa Specific Inhibitor that Induces the Novel Binding Model in Complex with Human Fxa." (to be published); the crystal structures PDB 1iqh, 1iqi, 1iqk, and 1igm; Adler M. et al. "Crystal Structures of Two Potent Nonamidine Inhibitors Bound to Factor Xa." *Biochemistry* 41: 15514-15523 (2002); Roehrig S. et al. "Discovery of the Novel Antithrombotic Agent 5-Chloro-N-({(5S)-2-Oxo-3-[4-(3-Oxomorpholin-4-Yl)Phenyl]-13-Oxazolidin-5-Yl}Methyl)Thiophene-2-Carboxamide(Bay 59-7939): An Oral Direct Factor Xa Inhibitor." *J. Med Chem.* 48: 5900 (2005); Anselm L. et al. "Discovery of a Factor Xa Inhibitor (3R 4R)-1-(2 2-Difluoro-Ethyl)-Pyrrolidine-3 4-Dicarboxylic Acid 3-[(5-Chloro-Pyridin-2-Yl)-Amide] 4-{[2-Fluoro-4-(2-Oxo-2H-Pyridin-1-Yl)-Phenyl]-Amide} as a Clinical Candidate." *Bioorg. Med Chem.* 20: 5313 (2010); and, Pinto D. J. et al. "Discovery of 1-(4-Methoxyphenyl)-7-oxo-6-(4-(2-oxopiperidin-1-yl)phenyl)-4 5 6 7-tetrahydro-1H-pyrazolo[3 4-c]pyridine-3-carboxamide (Apixaban BMS-562247) a Highly Potent Selective Efficacious and Orally Bioavailable Inhibitor of Blood Coagulation Factor Xa." *J. Med Chem.* 50: 5339-5356 (2007).

FIG. 2KKKK presents examples of Kallikrein 7 Targeting Ligands wherein R is the point at which the Linker is attached. For additional examples and related ligands, see, Maibaum J. et al. "Small-molecule factor D inhibitors targeting the alternative complement pathway." *Nat. Chem. Biol.* 12: 1105-1110 (2016).

FIG. 2LLLL-2MMMM present examples of Cathepsin K Targeting Ligands wherein R is the point at which the Linker is attached. For additional examples and related ligands, see, Rankovic Z. et al. "Design and optimization of a series of novel 2-cyano-pyrimidines as cathepsin K inhibitors" *Bioorg. Med Chem. Lett.* 20: 1524-1527 (2010); and, Cai J. et al. "Trifluoromethylphenyl as P2 for ketoamide-based cathepsin S inhibitors." *Bioorg. Med Chem. Lett.* 20: 6890-6894 (2010).

FIG. 2NNNN presents examples of Cathepsin L Targeting Ligands wherein R is the point at which the Linker is attached. For additional examples and related ligands, see, Kuhn B. et al. "Prospective Evaluation of Free Energy Calculations for the Prioritization of Cathepsin L Inhibitors." *J. Med Chem.* 60: 2485-2497 (2017).

FIG. 2OOOO presents examples of Cathepsin S Targeting Ligands wherein R is the point at which the Linker is attached. For additional examples and related ligands, see, Jadhav P. K. et al. "Discovery of Cathepsin S Inhibitor LY3000328 for the Treatment of Abdominal Aortic Aneurysm" *ACS Med Chem. Lett.* 5: 1138-1142." (2014).

FIG. 2PPPP-2SSSS present examples of MTH1 Targeting Ligands wherein R is the point at which the Linker is attached. For additional examples and related ligands, see, Kettle J. G. et al. "Potent and Selective Inhibitors of Mth1 Probe its Role in Cancer Cell Survival." *J. Med Chem.* 59: 2346 (2016); Huber K. V. M. et al. "Stereospecific Targeting of Mth1 by (S)-Crizotinib as an Anticancer Strategy." *Nature* 508: 222 (2014); Gad H. et al. "MTH1 inhibition eradicates cancer by preventing sanitation of the dNTP pool." *Nature* 508: 215-221 (2014); Nissink J. W. M. et al. "Mth1 Substrate Recognition—an Example of Specific Promiscuity." *Plos One* 11: 51154 (2016); and, Manuel Ellermann et al. "Novel class of potent and selective inhibitors efface MTH1 as broad-spectrum cancer target." AACR National Meeting Abstract 5226, 2017.

FIG. 2TTTT-2ZZZZ present examples of MDM2 and/or MDM4 Targeting Ligands wherein R is the point at which the Linker is attached. For additional examples and related ligands, see, Popowicz G. M. et al. "Structures of low molecular weight inhibitors bound to MDMX and MDM2 reveal new approaches for p53-MDMX/MDM2 antagonist drug discovery." Cell Cycle, 9 (2010); Miyazaki M. et al. "Synthesis and evaluation of novel orally active p53-MDM2 interaction inhibitors." *Bioorg. Med Chem.* 21: 4319-4331 (2013); Miyazaki M. et al. "Discovery of DS-5272 as a promising candidate: A potent and orally active p53-MDM2 interaction inhibitor." *Bioorg Med Chem.* 23: 2360-7 (2015); Holzer P. et al. "Discovery of a Dihydroisoquinolinone Derivative (NVP-CGM097): A Highly Potent and Selective MDM2 Inhibitor Undergoing Phase 1 Clinical Trials in p53wt Tumors." *J. Med Chem.* 58: 6348-6358 (2015); Gonzalez-Lopez de Turiso F. et al. "Rational Design and Binding Mode Duality of MDM2-p53 Inhibitors." *J. Med. Chem.* 56: 4053-4070 (2013); Gessier F. et al. "Discovery of dihydroisoquinolinone derivatives as novel inhibitors of the p53-MDM2 interaction with a distinct binding mode." *Bioorg. Med Chem. Lett.* 25: 3621-3625 (2015); Fry D. C. et al. "Deconstruction of a nutlin: dissecting the binding determinants of a potent protein-protein interaction inhibitor." *ACS Med Chem Lett* 4: 660-665 (2013); Ding Q. et al. "Discovery of RG7388 a Potent and Selective p53-MDM2 Inhibitor in Clinical Development." *J. Med Chem.* 56: 5979-5983 (2013); Wang S. et al. "SAR405838: an optimized inhibitor of MDM2-p53 interaction that induces complete and durable tumor regression." *Cancer Res.* 74: 5855-5865 (2014); Rew Y. et al. "Discovery of AM-7209 a Potent and Selective 4-Amidobenzoic Acid Inhibitor of the MDM2-p53 Interaction." *J. Med Chem.* 57: 10499-10511 (2014); Bogen S. L. et al. "Discovery of Novel 3 3-Disubstituted Piperidines as Orally Bioavailable Potent and Efficacious HDM2-p53 Inhibitors." *ACS Med Chem. Lett.* 7: 324-329 (2016); and, Sun D. et al. "Discovery of AMG 232 a Potent Selective and Orally Bioavailable MDM2-p53 Inhibitor in Clinical Development." *J. Med Chem.* 57: 1454-1472 (2014).

FIG. 2AAAAA-2EEEEE present examples of PARP1, PARP2, and/or PARP3 Targeting Ligands wherein R is the point at which the Linker is attached. For additional examples and related ligands, see, Iwashita A. et al. "Discovery of quinazolinone and quinoxaline derivatives as potent and selective poly(ADP-ribose) polymerase-1/2 inhibitors." *Febs Lett.* 579: 1389-1393 (2005); the crystal structure PDB 2RCW (PARP complexed with A861695, Park C. H.); the crystal structure PDB 2RD6 (PARP complexed with A861696, Park C. H.); the crystal structure PDB 3GN7; Miyashiro J. et al. "Synthesis and SAR of novel tricyclic quinoxalinone inhibitors of poly(ADP-ribose)polymerase-1 (PARP-1)" *Bioorg. Med Chem. Lett.* 19: 4050-4054 (2009); Gandhi V. B. et al. "Discovery and SAR of substituted 3-oxoisoindoline-4-carboxamides as potent inhibitors of poly(ADP-ribose) polymerase (PARP) for the treatment of cancer." *Bioorg. Med Chem. Lett.* 20: 1023-1026 (2010); Penning T. D. et al. "Optimization of phenyl-substituted benzimidazole carboxamide poly(ADP-ribose) polymerase inhibitors: identification of (S)-2-(2-fluoro-4-(pyrrolidin-2-yl)phenyl)-1H-benzimidazole-4-carboxamide (A-966492) a highly potent and efficacious inhibitor." *J. Med Chem.* 53: 3142-3153 (2010); Ye N. et al. "Design, Synthesis, and Biological Evaluation of a Series of Benzo [de][1 7]naphthyridin-7(8H)-ones Bearing a Functionalized Longer Chain Appendage as Novel PARP1 Inhibitors." *J. Med Chem.* 56: 2885-2903 (2013); Patel M. R. et al. "Discovery and Structure-Activity Relationship of Novel 2 3-Dihydrobenzofuran-7-carboxamide and 2 3-Dihydrobenzofuran-3(2H)-one-7-carboxamide Derivatives as Poly (ADP-ribose)polymerase-1 Inhibitors." *J. Med Chem.* 57: 5579-5601 (2014); Thorsell A. G. et al. "Structural Basis for Potency and Promiscuity in Poly(ADP-ribose) Polymerase (PARP) and Tankyrase Inhibitors." *J. Med Chem.* 60:1262-1271 (2012); the crystal structure PDB 4RV6 ("Human ARTD1 (PARP1) catalytic domain in complex with inhibitor Rucaparib", Karlberg T. et al.); Papeo G. M. E. et al. "Discovery of 2-[1-(4 4-Difluorocyclohexyl)Piperidin-4-Yl]-6-Fluoro-3-Oxo-2 3-Dihydro-1H-Isoindole-4-Carboxamide (Nms-P118): A Potent Orally Available and Highly Selective Parp-1 Inhibitor for Cancer Therapy." *J. Med Chem.* 58: 6875 (2015); Kinoshita T. et al. "Inhibitor-induced structural change of the active site of human poly (ADP-ribose) polymerase." *Febs Lett.* 556: 43-46 (2004); and, Gangloff A. R. et al. "Discovery of novel benzo[b][1 4]oxazin-3(4H)-ones as poly(ADP-ribose)polymerase inhibitors." *Bioorg. Med Chem. Lett.* 23: 4501-4505 (2013).

FIG. 2FFFFF-2GGGGG present examples of PARP14 Targeting Ligands wherein R is the point at which the Linker is attached.

FIG. 2HHHHH presents examples of PARP15 Targeting Ligands wherein R is the point at which the Linker is attached.

FIG. 2IIIII presents examples of PDZ domain Targeting Ligands wherein R is the point at which the Linker(s) are attached.

FIG. 2JJJJJ presents examples of Phospholipase A2 domain Targeting Ligands wherein R is the point at which the Linker is attached.

FIG. 2KKKKK presents examples of Protein S100-A7 2WOS Targeting Ligands wherein R is the point at which the Linker is attached.

FIG. 2LLLLL-2MMMMM present examples of Saposin-B Targeting Ligands wherein R is the point at which the Linker is attached.

FIG. 2NNNNN-2OOOOO present examples of Sec7 Targeting Ligands wherein R is the point at which the Linker is attached.

FIG. 2PPPPP-2QQQQQ present examples of SH2 domain of pp60 Src Targeting Ligands wherein R is the point at which the Linker is attached.

FIG. 2RRRRR presents examples of Tank1 Targeting Ligands wherein R is the point at which the Linker is attached.

FIG. 2SSSSS presents examples of Ubc9 SUMO E2 ligase SF6D Targeting Ligands wherein R is the point at which the Linker is attached.

FIG. 2TTTTT presents examples of Src Targeting Ligands, including AP23464, wherein R is the point at which the Linker is attached.

FIG. 2UUUUU-2XXXXX present examples of Src-AS1 and/or Src AS2 Targeting Ligands wherein R is the point at which the Linker is attached.

FIG. 2YYYYY presents examples of JAK3 Targeting Ligands, including Tofacitinib, wherein R is the point at which the Linker is attached.

FIG. 2ZZZZZ presents examples of ABL Targeting Ligands, including Tofacitinib and Ponatinib, wherein R is the point at which the Linker is attached.

Figure 3B:
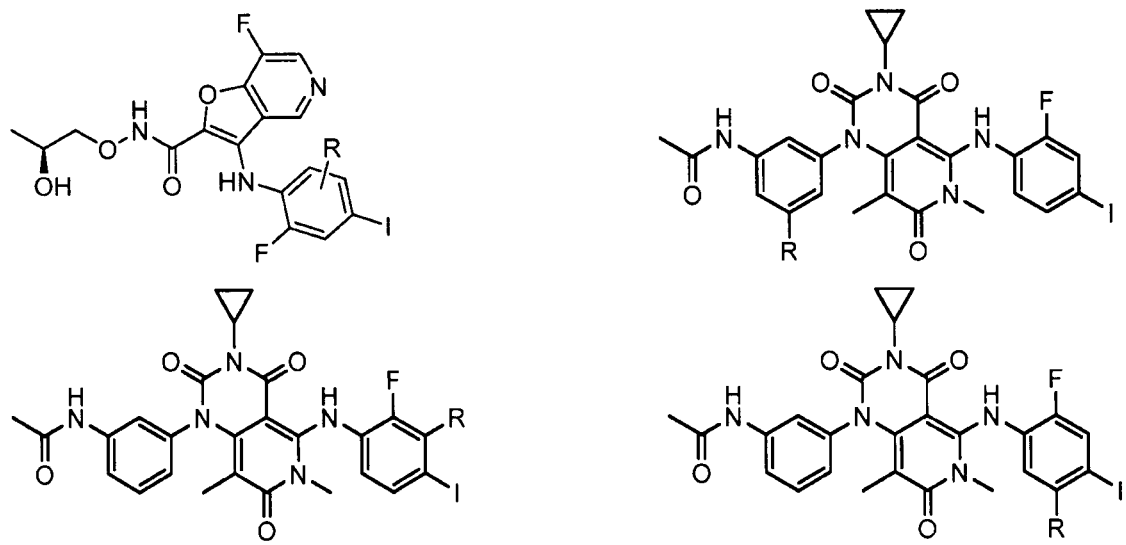

FIG. 3A-3B present examples of MEK1 Targeting Ligands, including PD318088, Trametinib and G-573, wherein R is the point at which the Linker is attached.

Figure 3C:
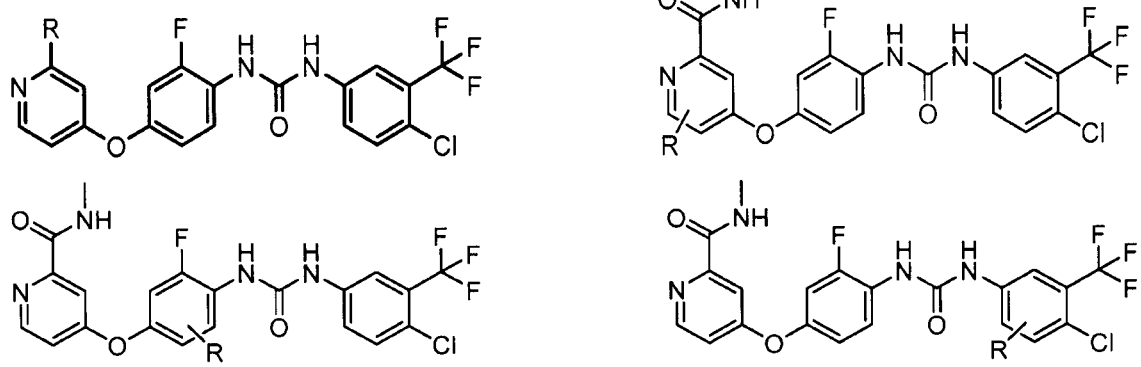

FIG. 3C presents examples of KIT Targeting Ligands, including Regorafenib, wherein R is the point at which the Linker is attached.

Figure 3D:
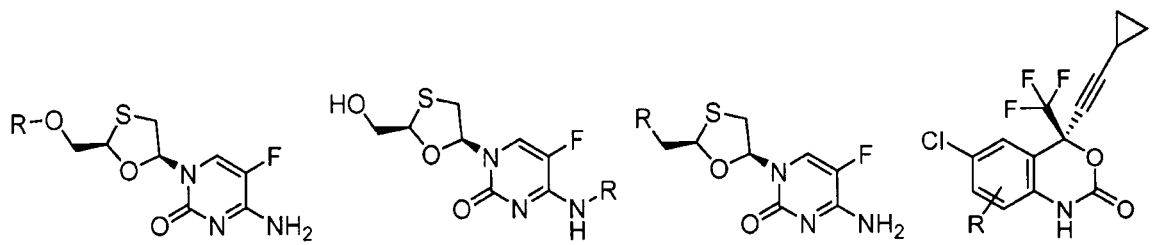
Figure 3E:
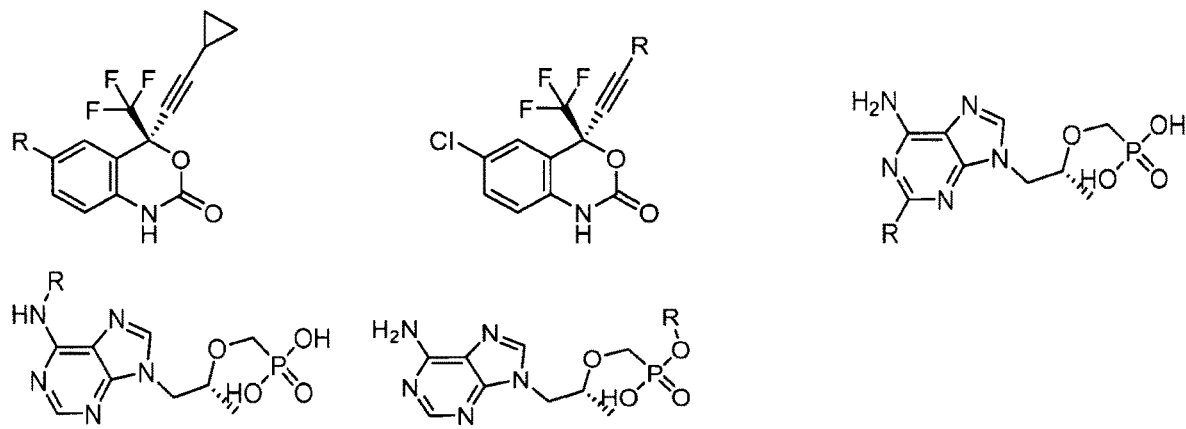

FIG. 3D-3E present examples of HIV Reverse Transcriptase Targeting Ligands, including Efavirenz, Tenofovir, Emtricitabine, Ritonavir, Raltegravir, and Atazanavir, wherein R is the point at which the Linker is attached.

Figure 3F:
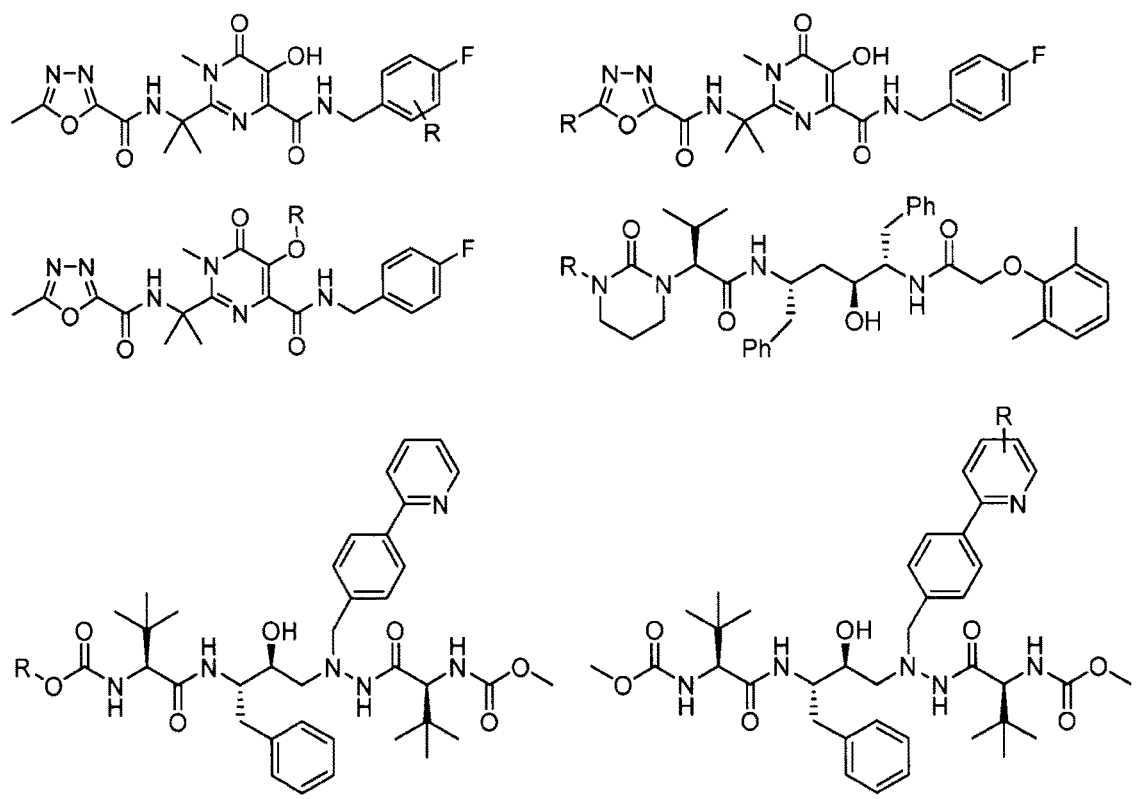
Figure 3G:
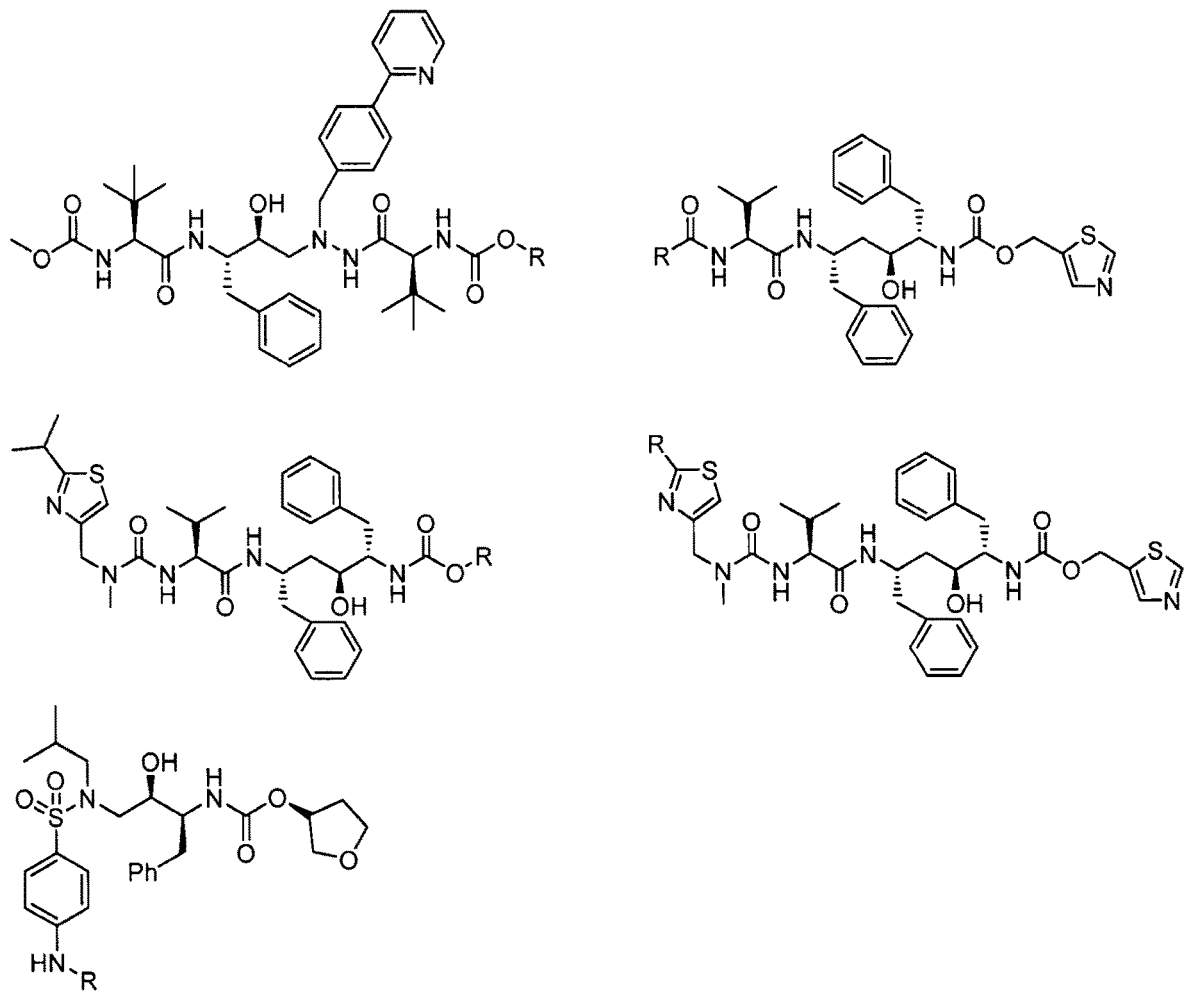

FIG. 3F-3G present examples of HIV Protease Targeting Ligands, including Ritonavir, Raltegravir, and Atazanavir, wherein R is the point at which the Linker is attached.

Figure 3H:
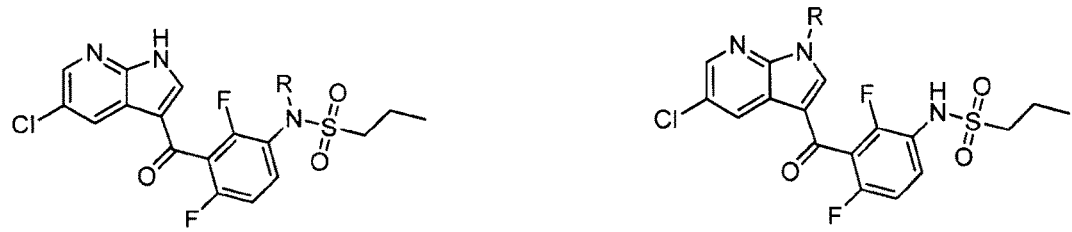
Figure 3K:
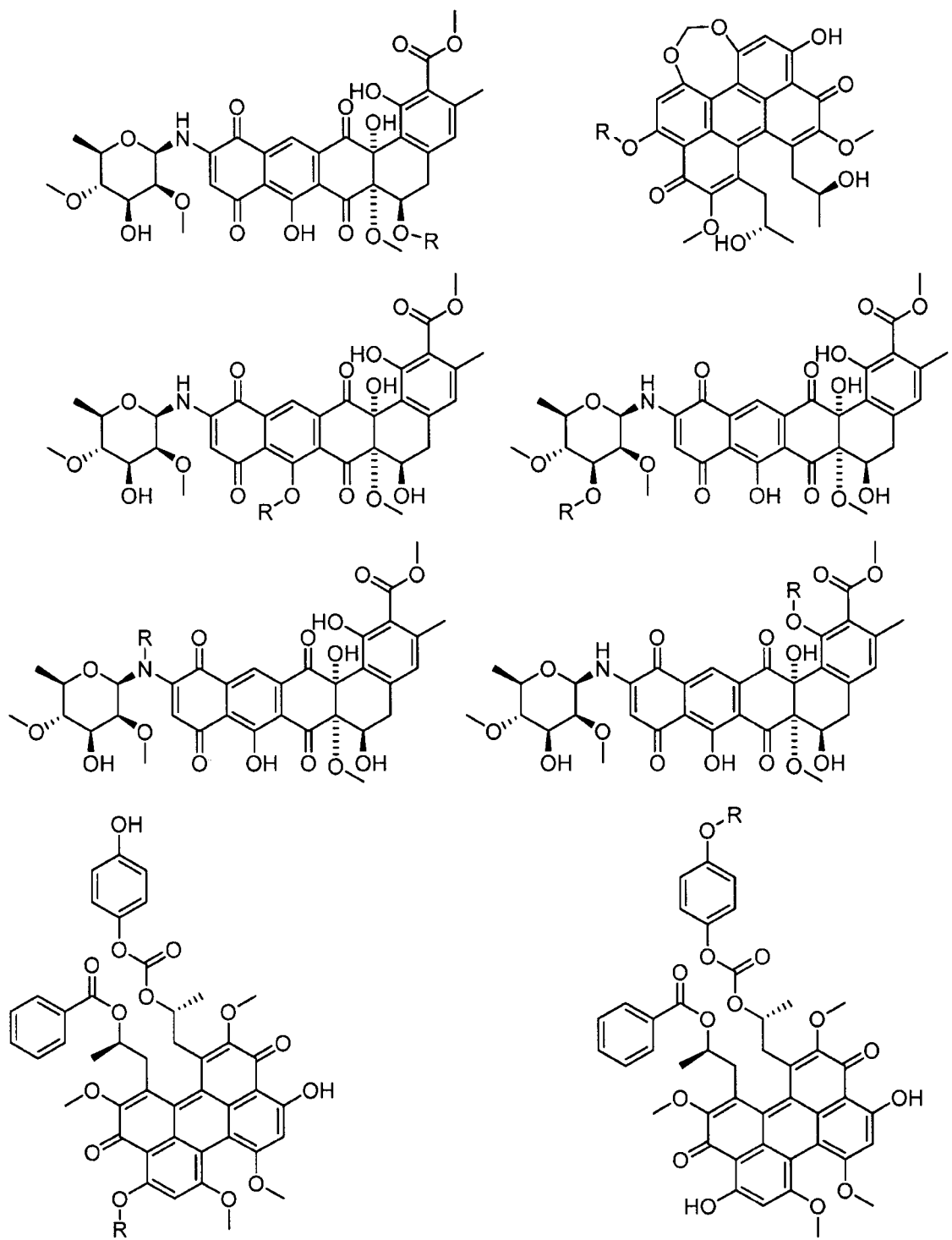
Figure 3L:
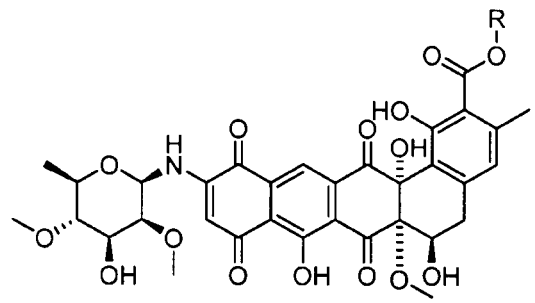
Figure 3M:
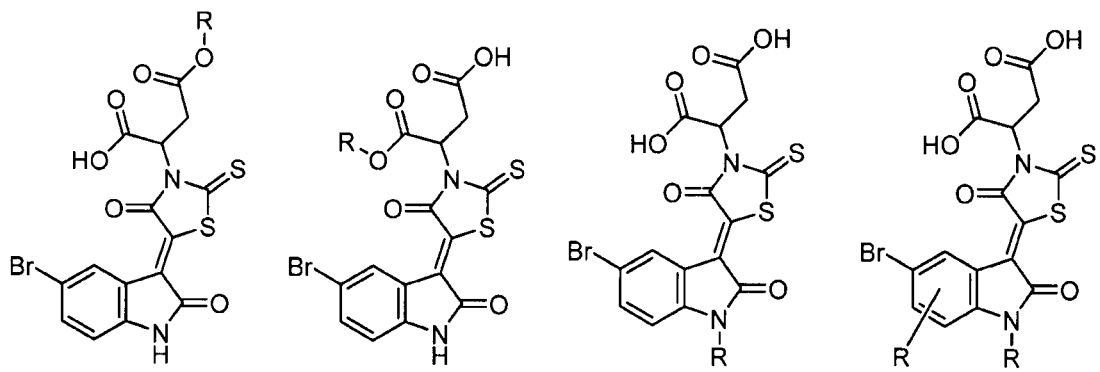
Figure 3N:
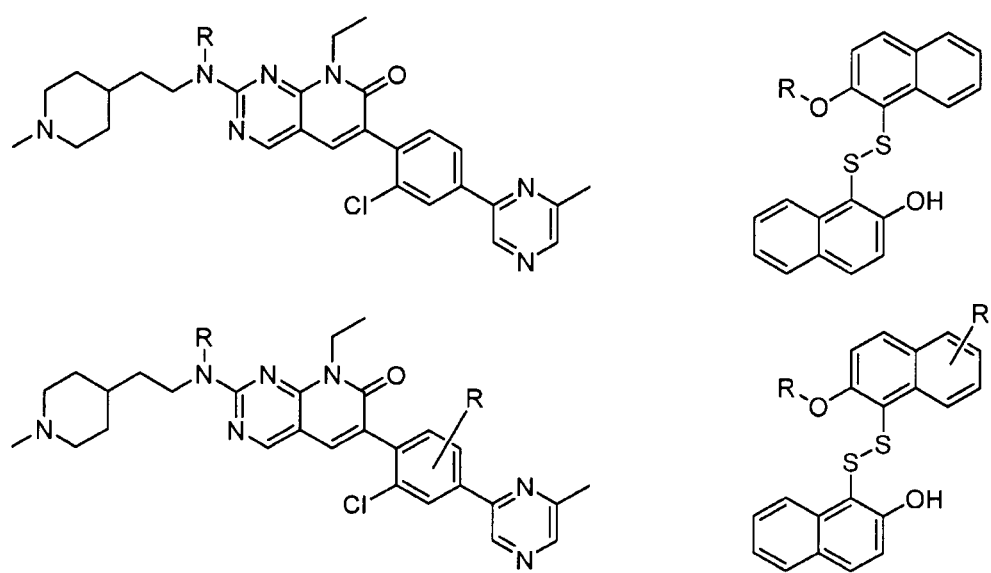
Figure 3O:
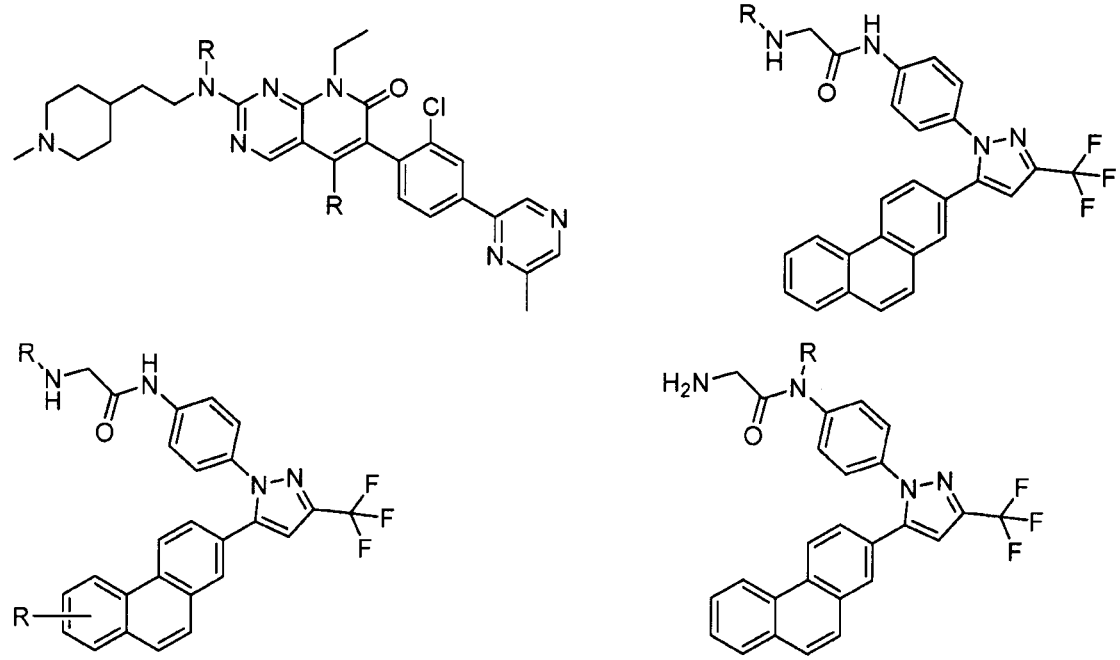
Figure 3P:
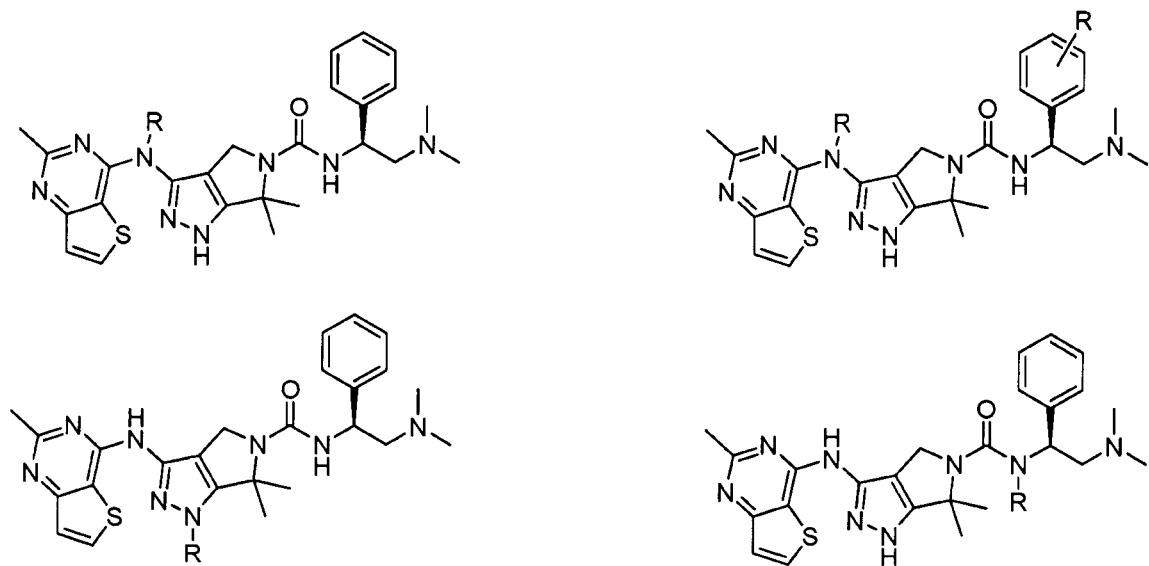
Figure 3Q:
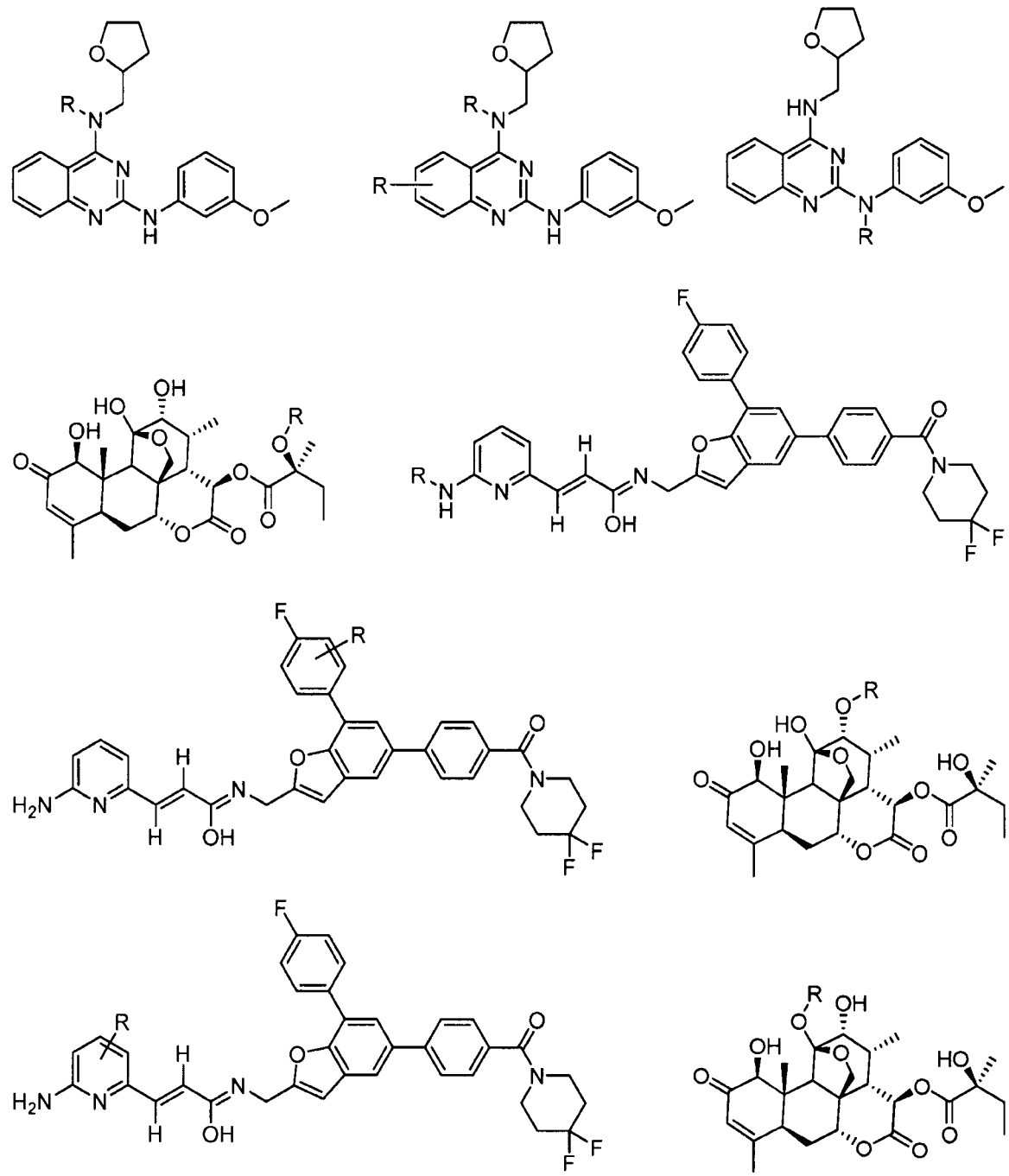
Figure 3R:
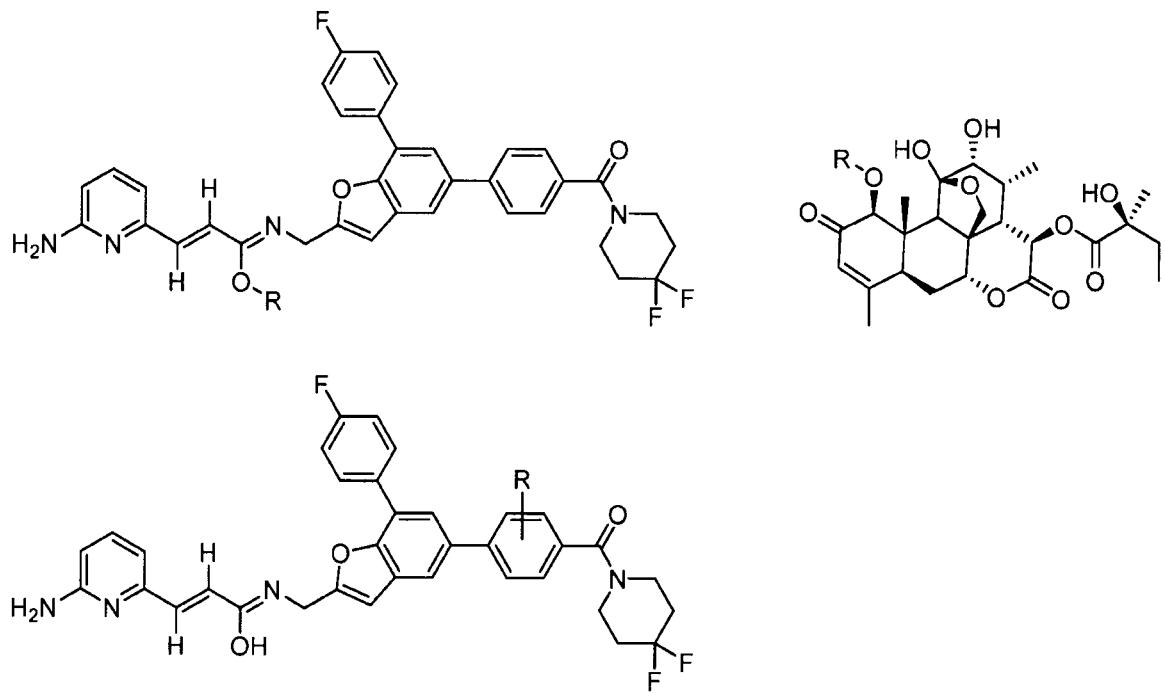
Figure 3S:
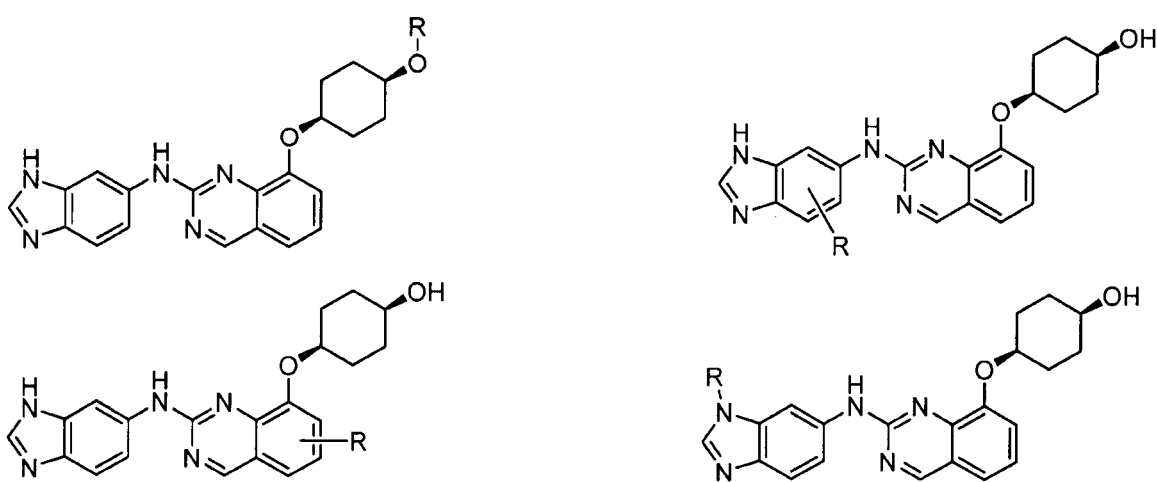
Figure 3T:
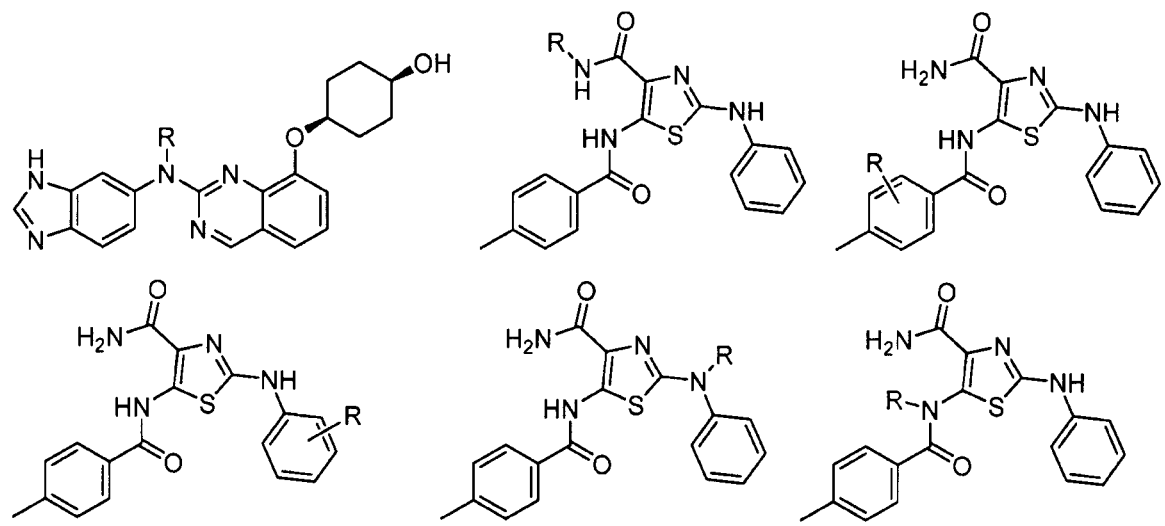
Figure 3U:
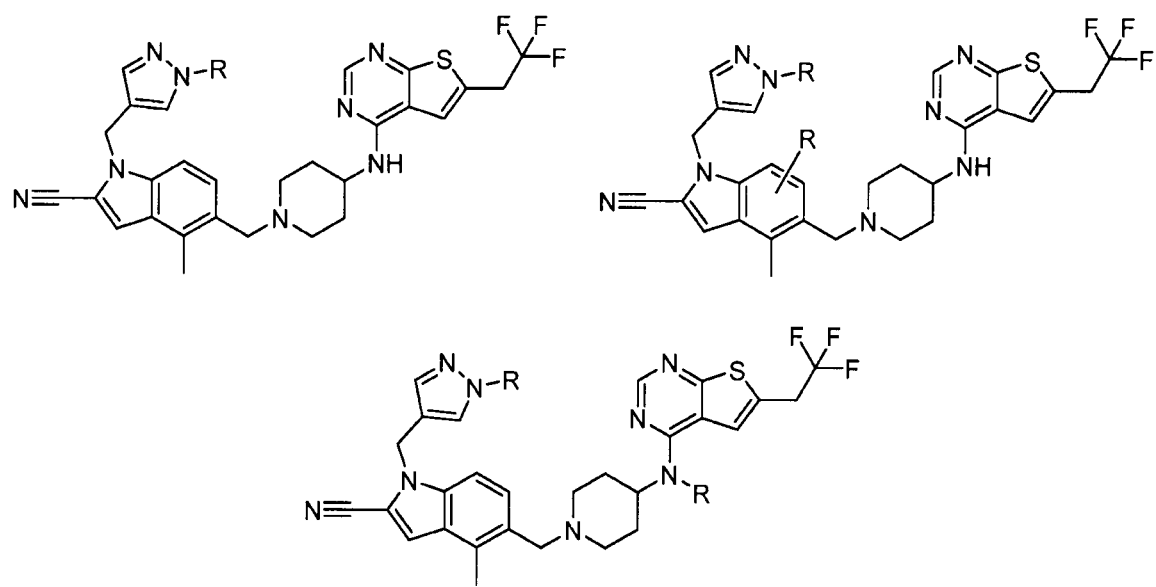
Figure 3V:
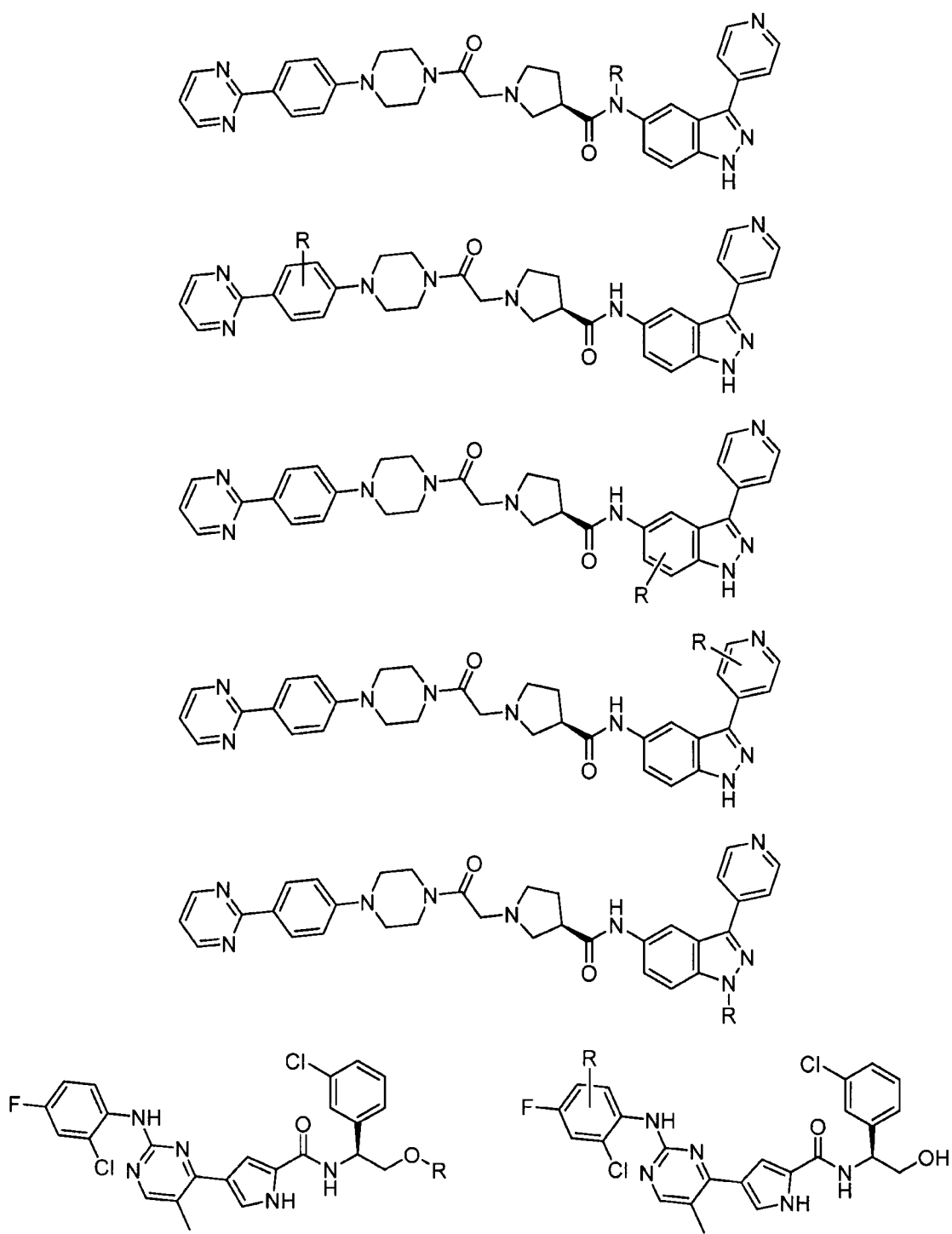
Figure 3W:
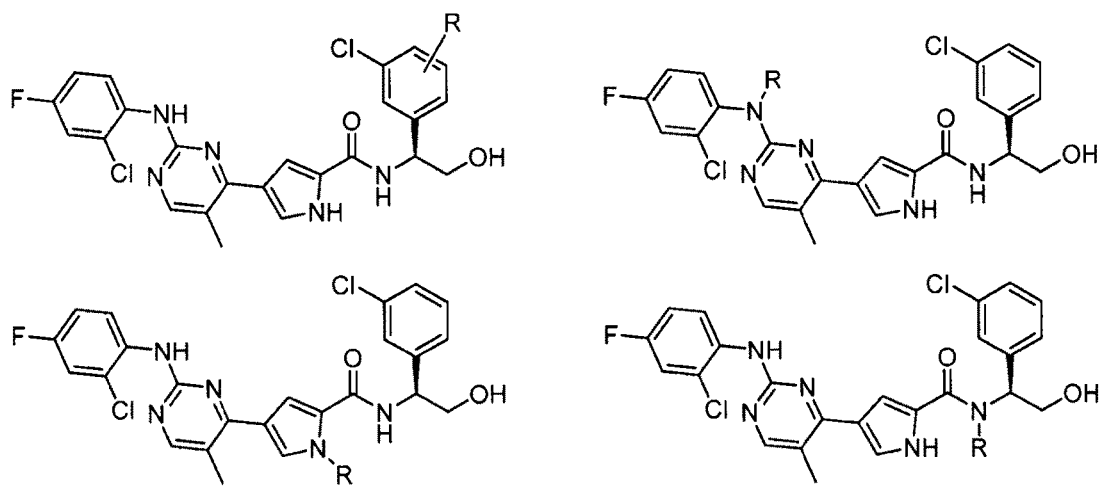
Figure 3X:
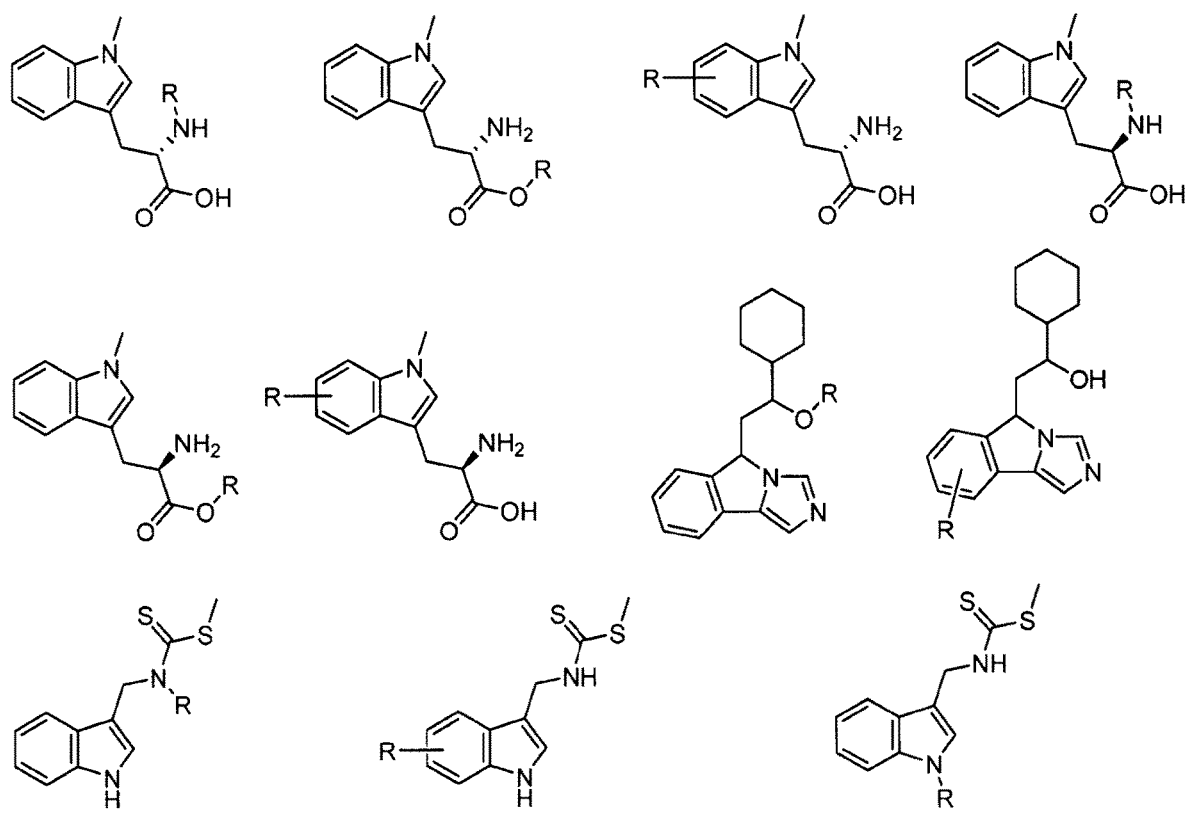
Figure 3Y:
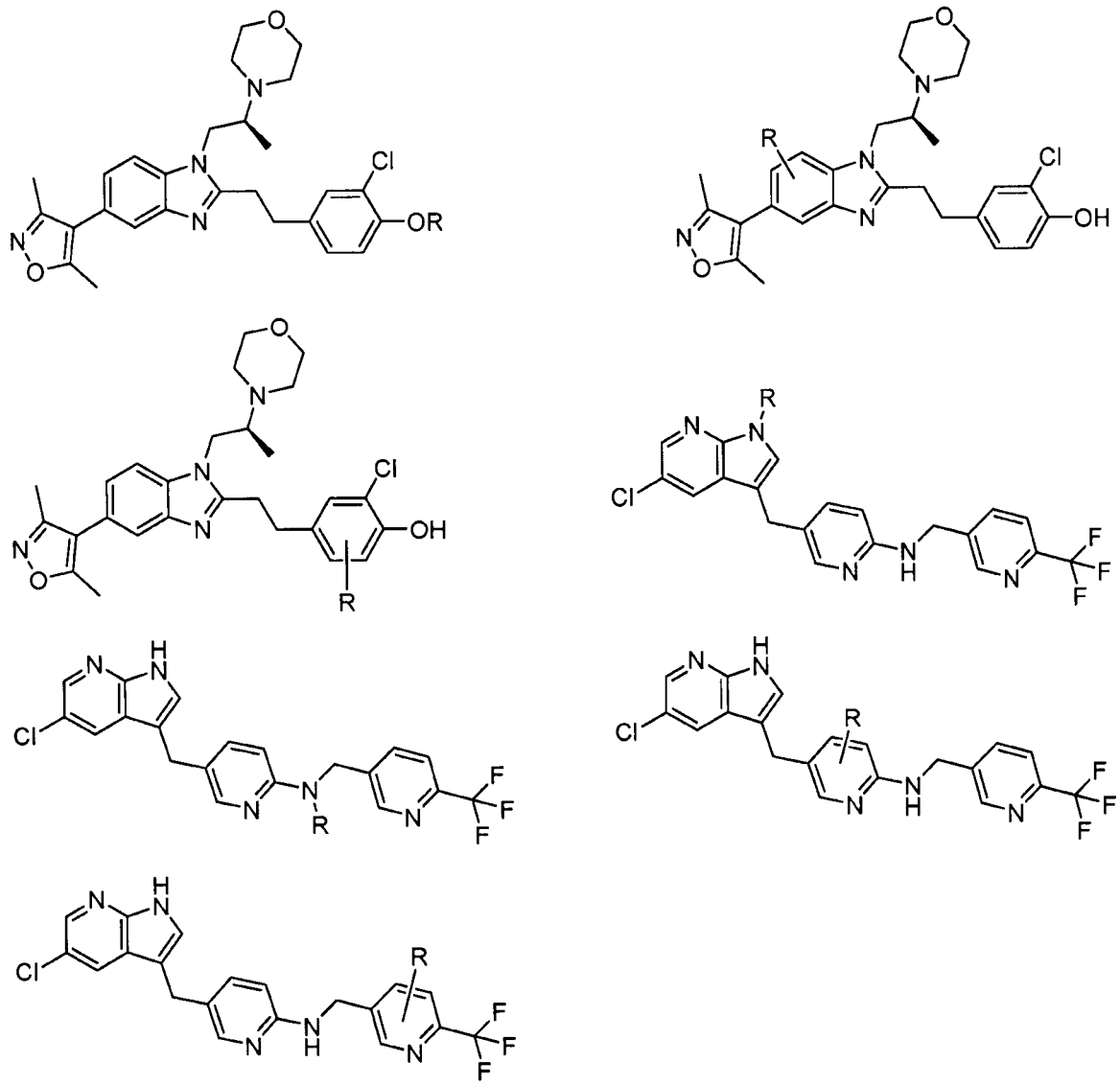
Figure 3Z:
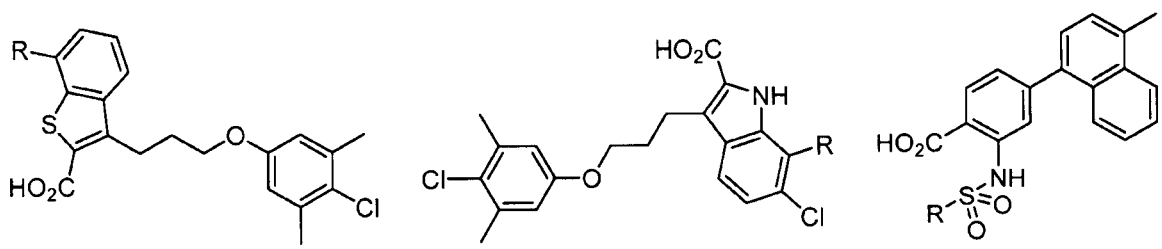
Figure 3B:
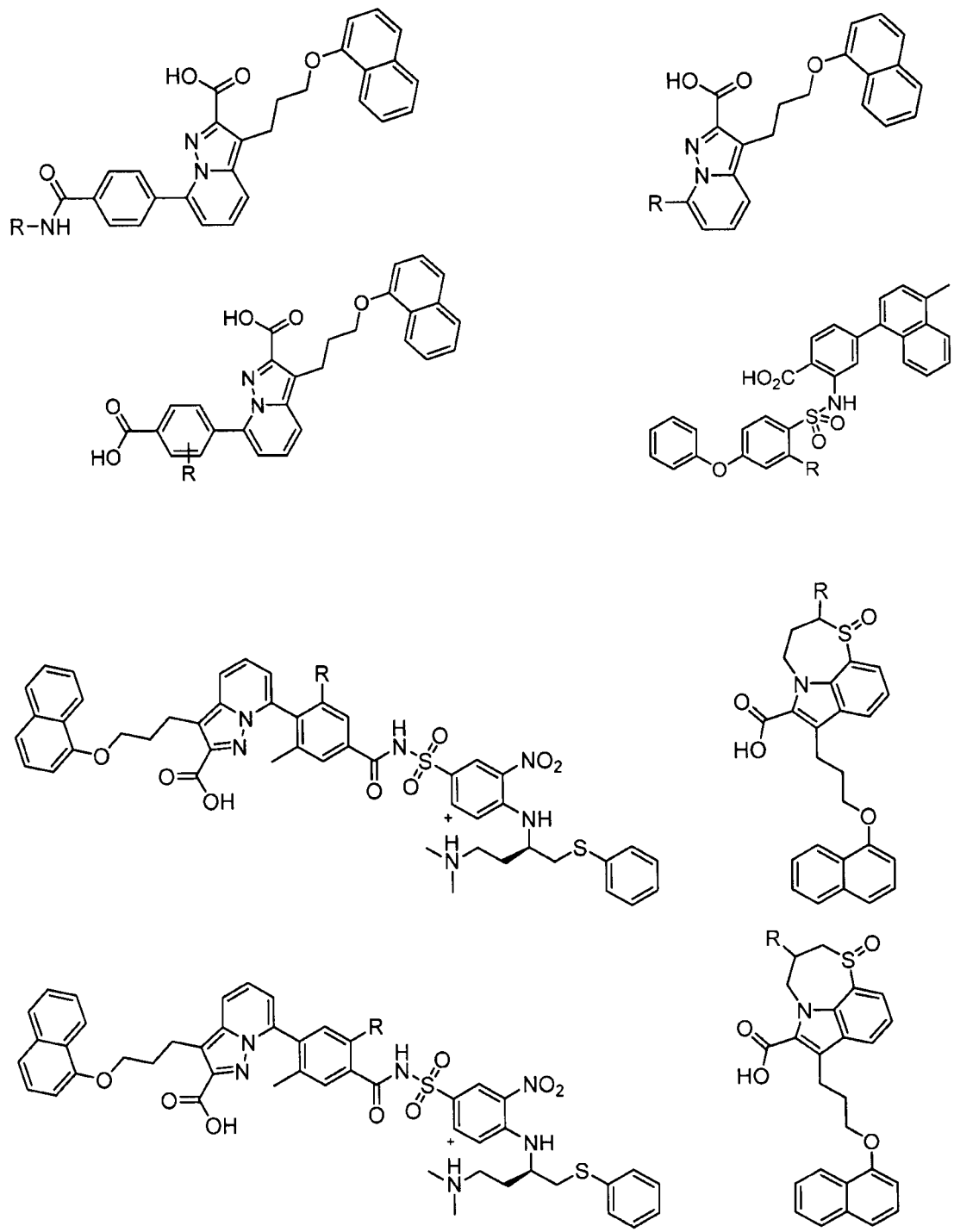
Figure 3C:
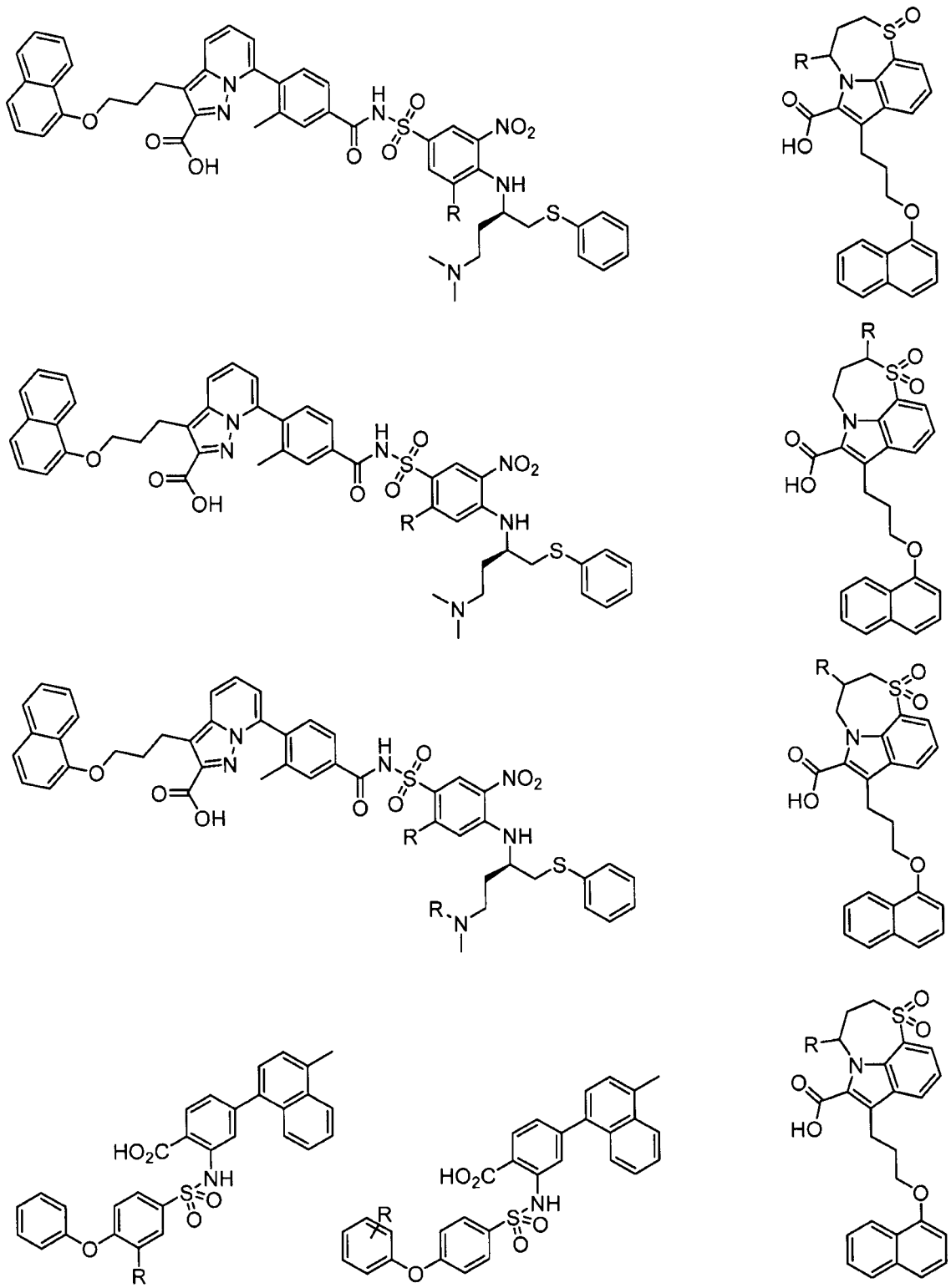
Figure 3D:
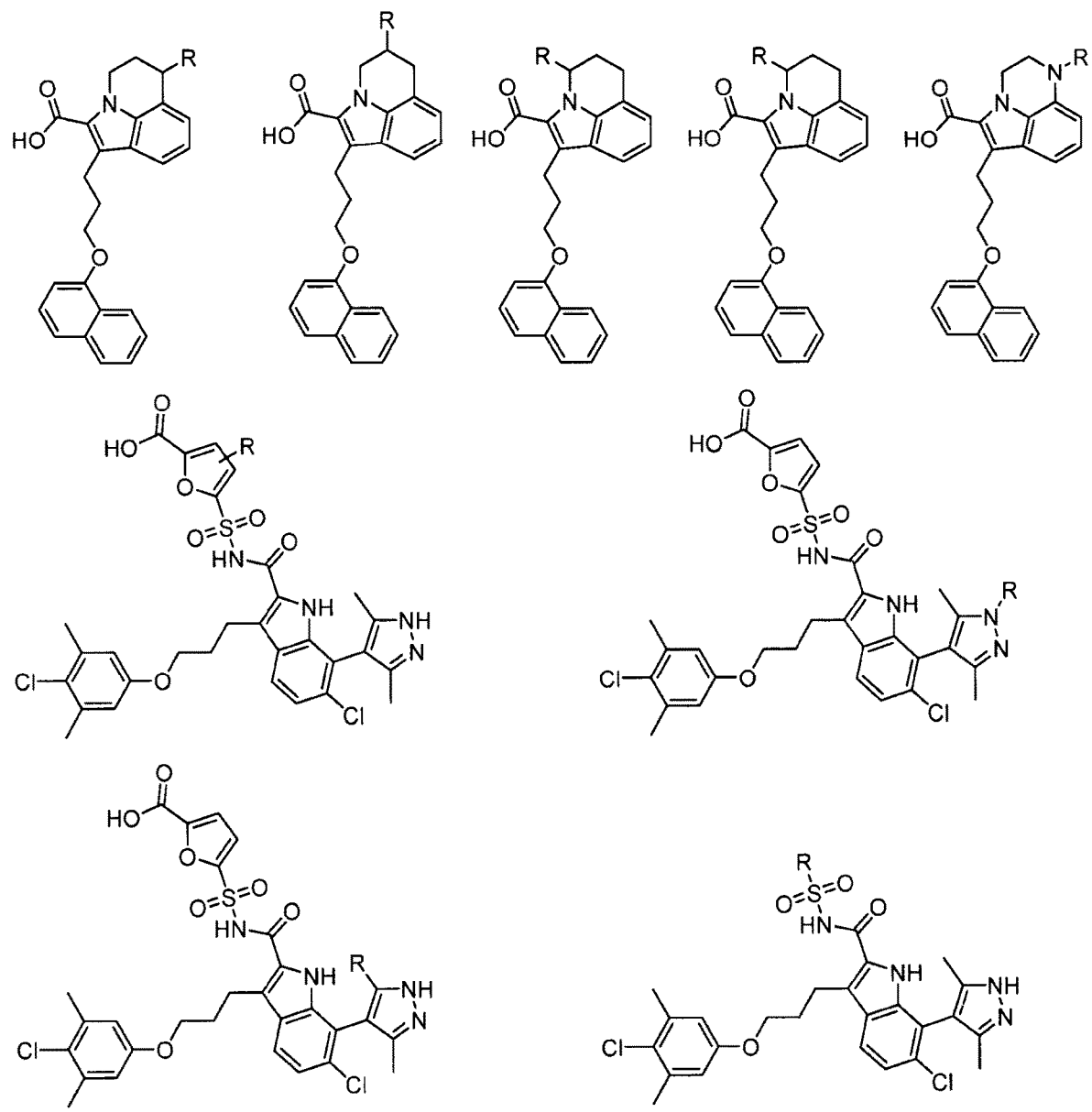
Figure 3E:
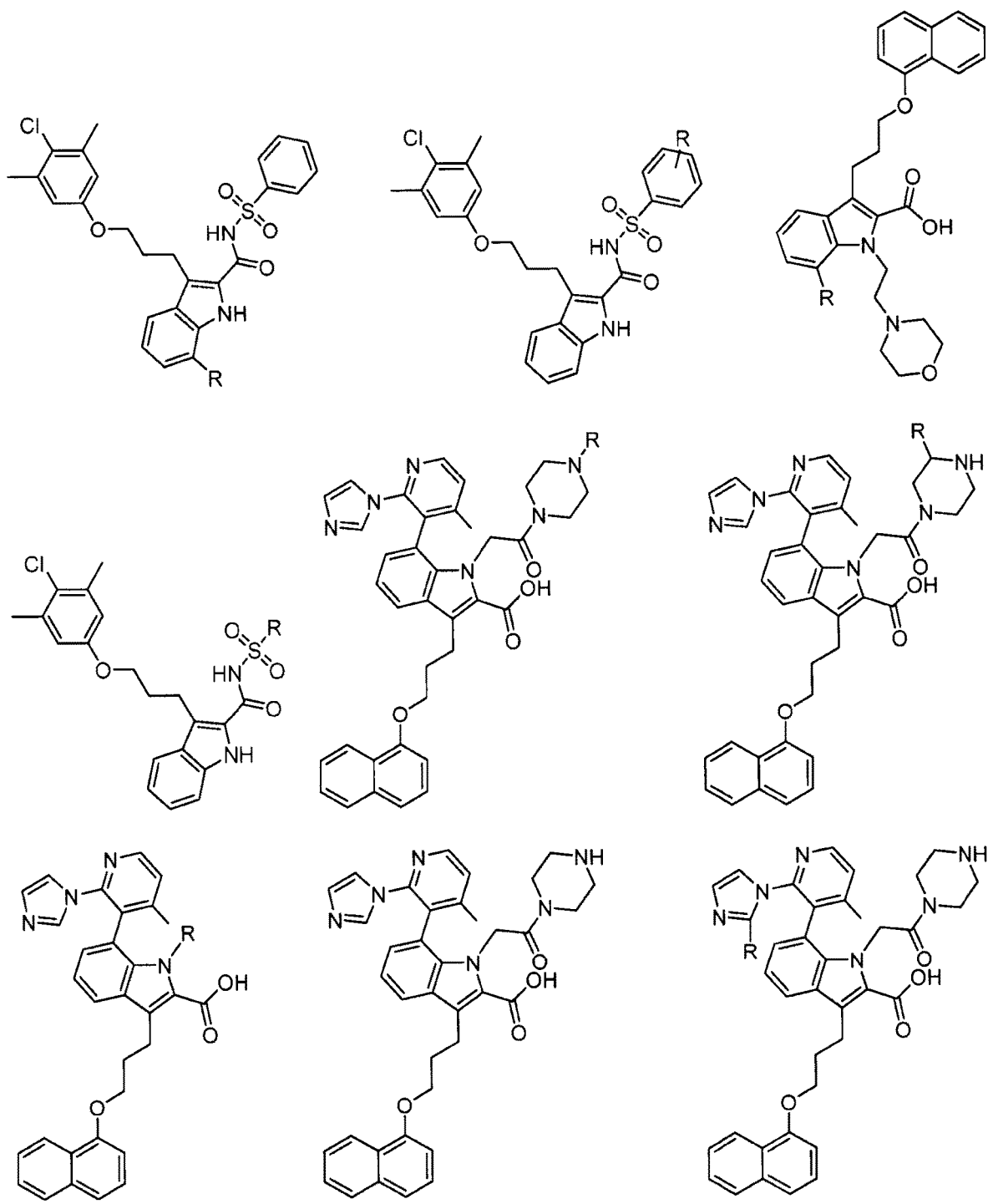
Figure 3H:
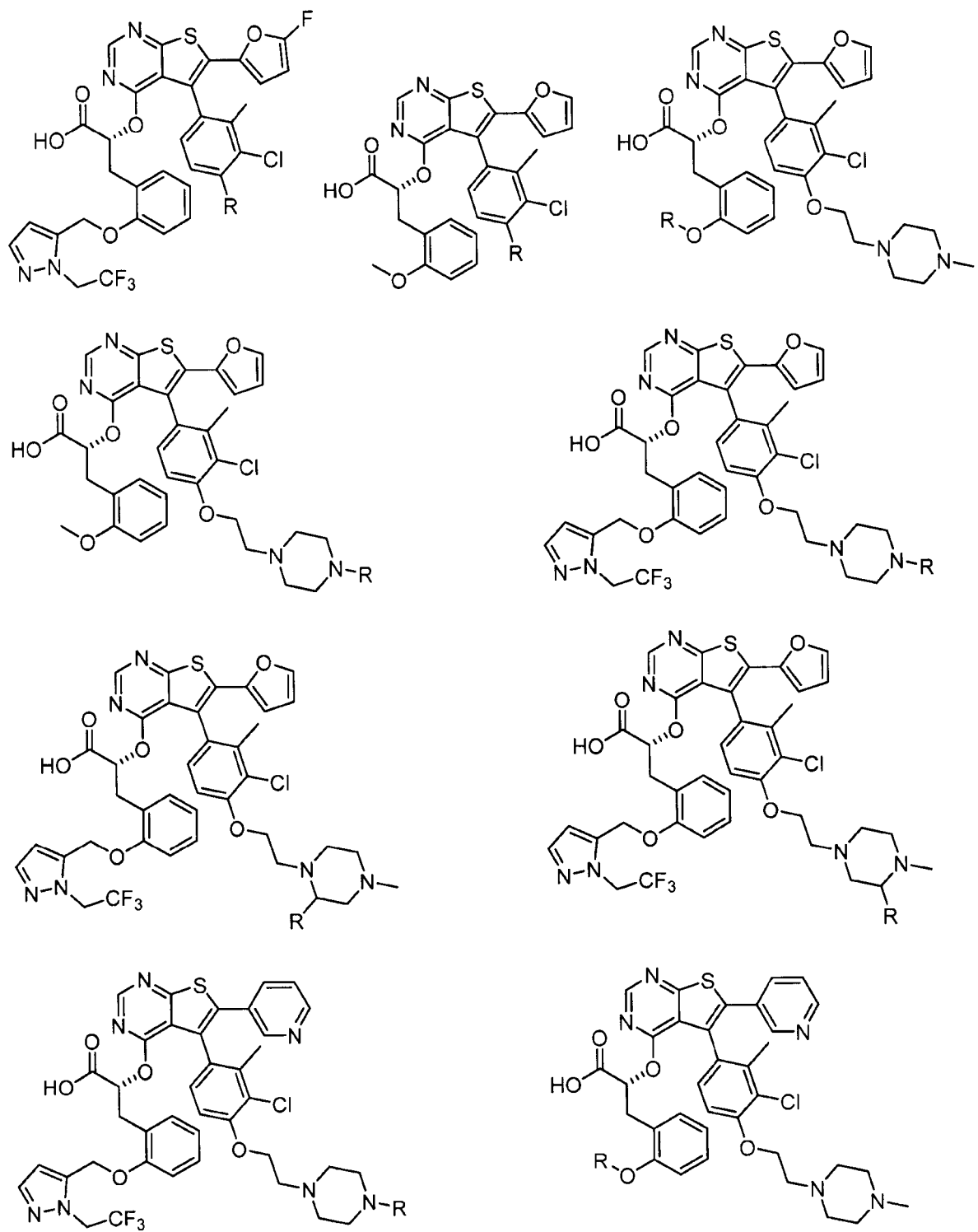
Figure 3I:
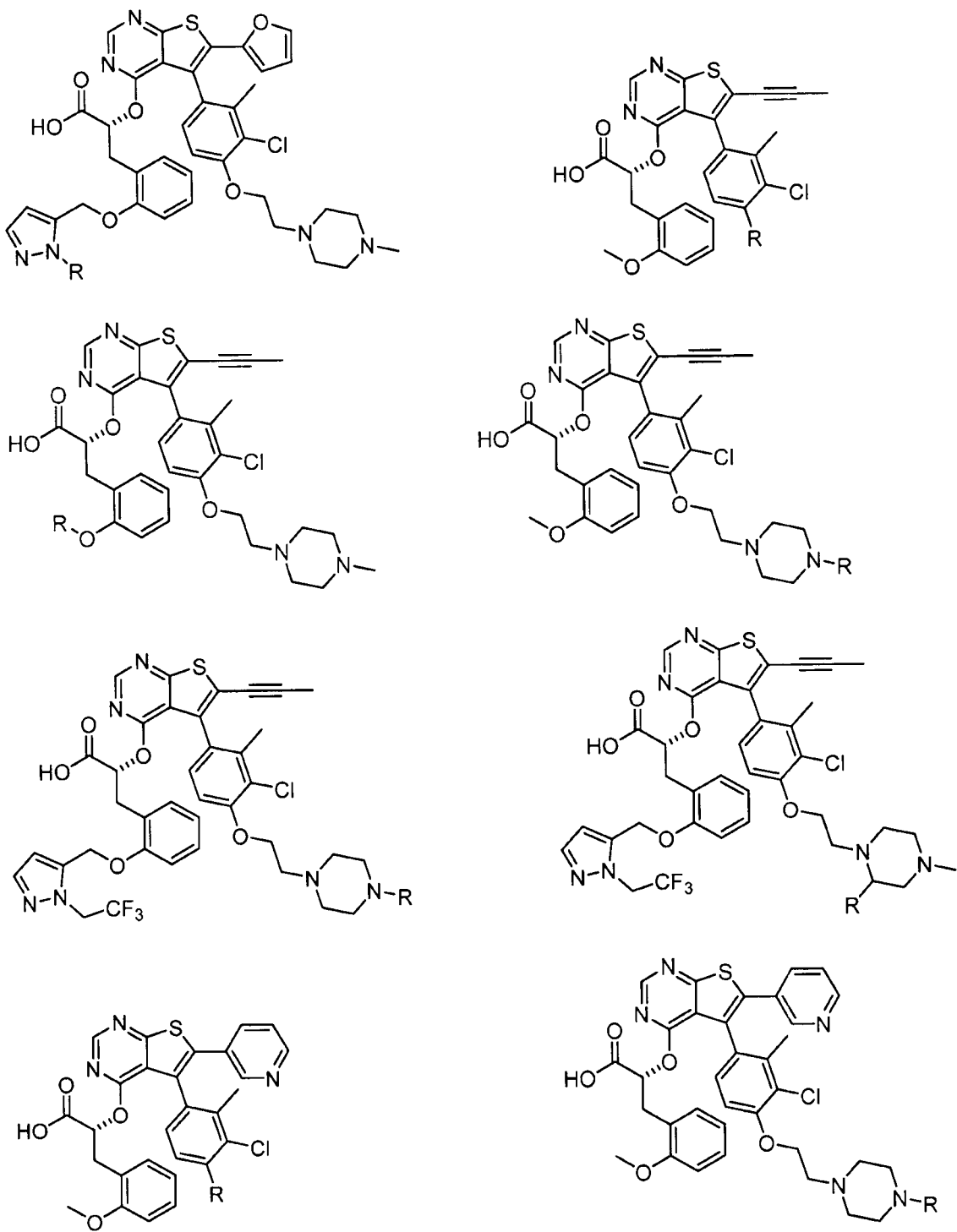
Figure 3K:
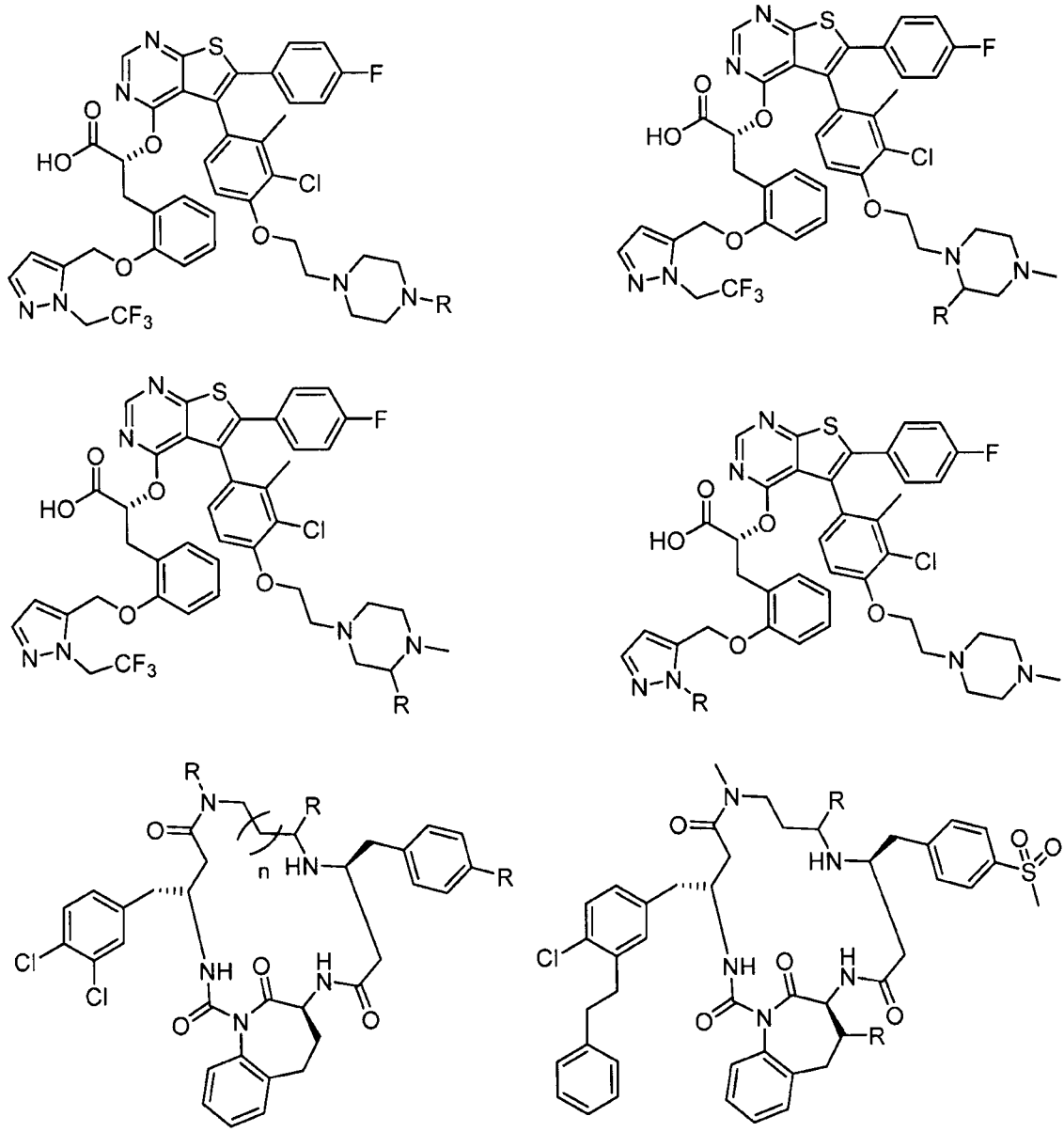
Figure 3L:
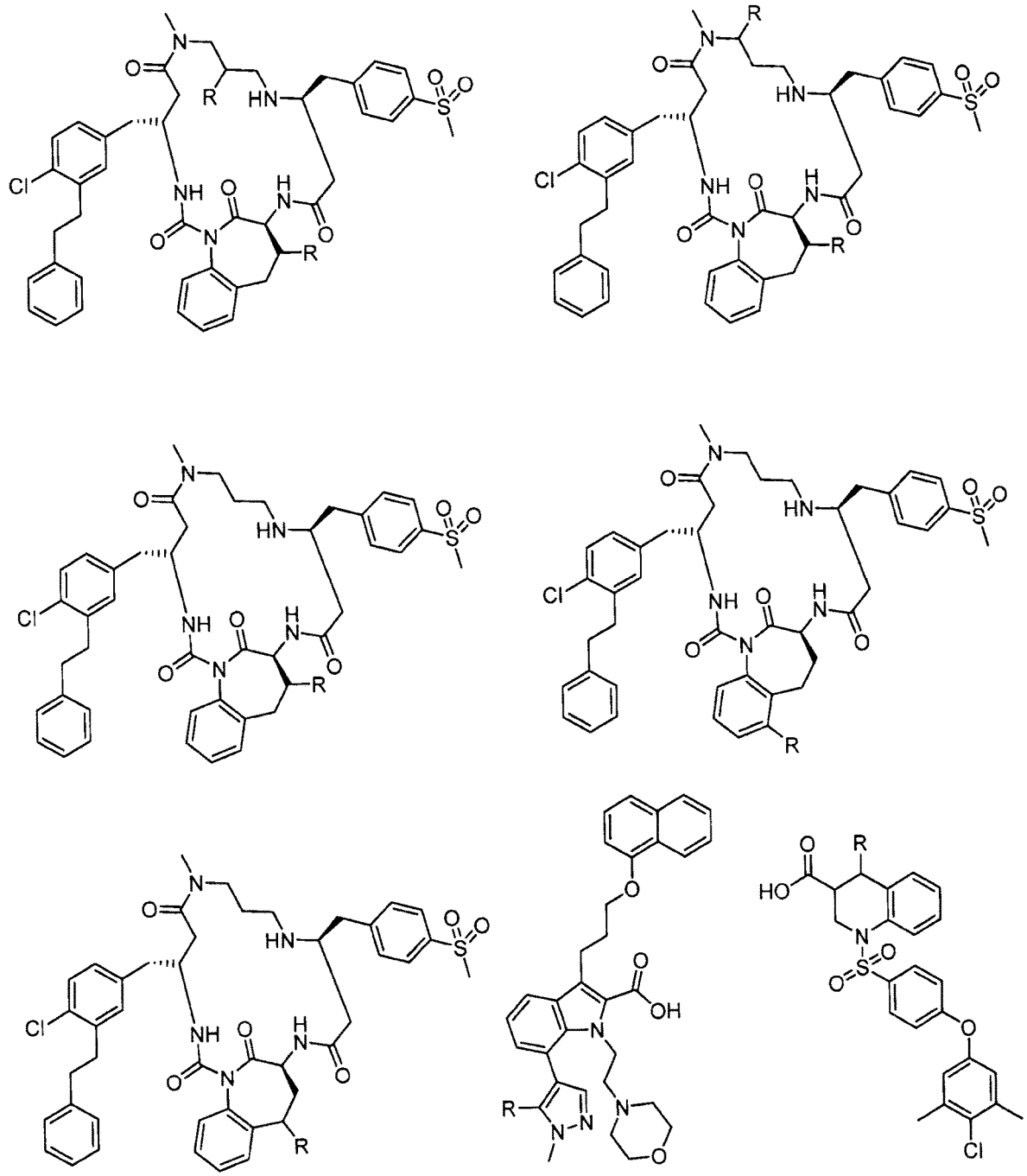
Figure 3M:
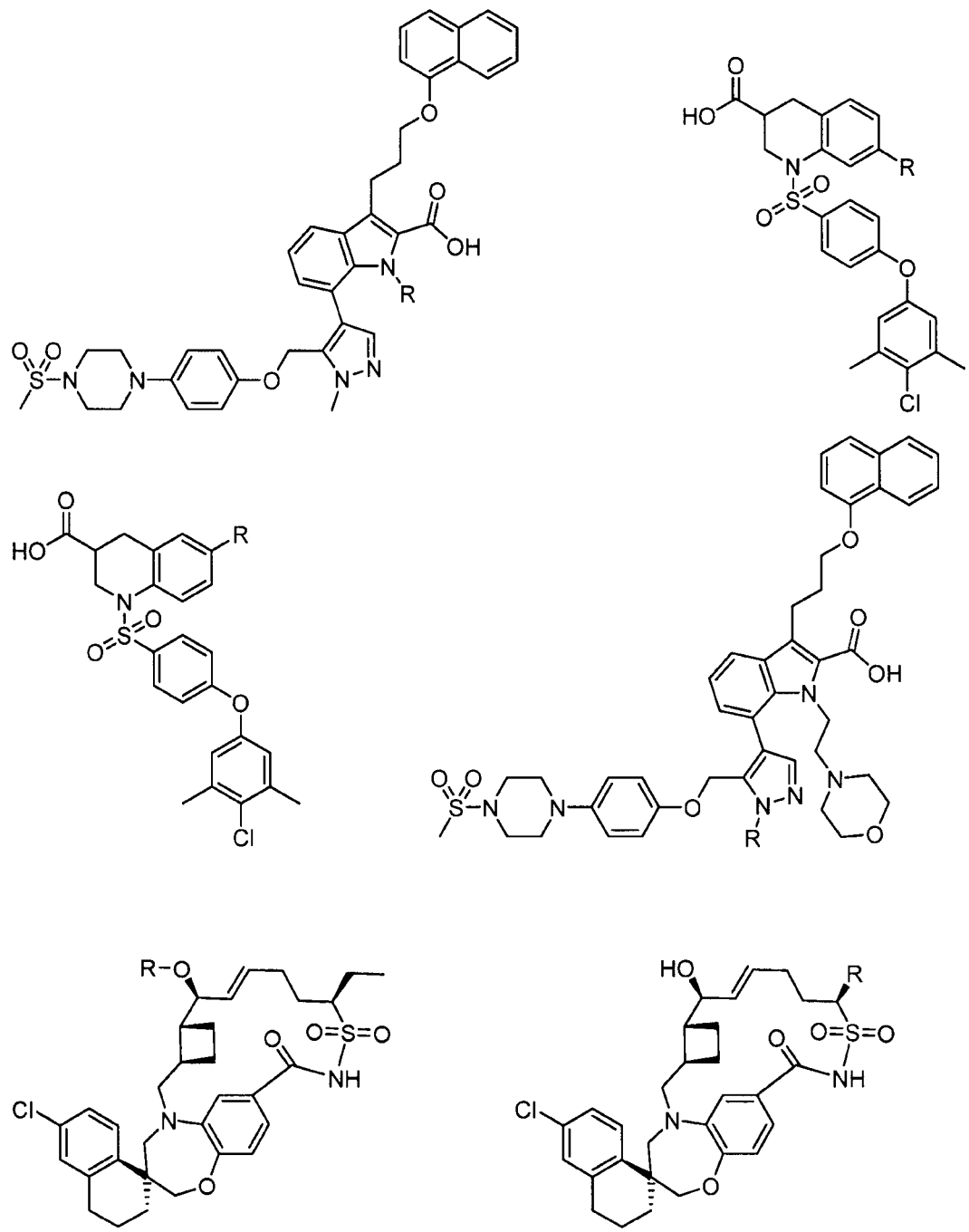
Figure 3O:
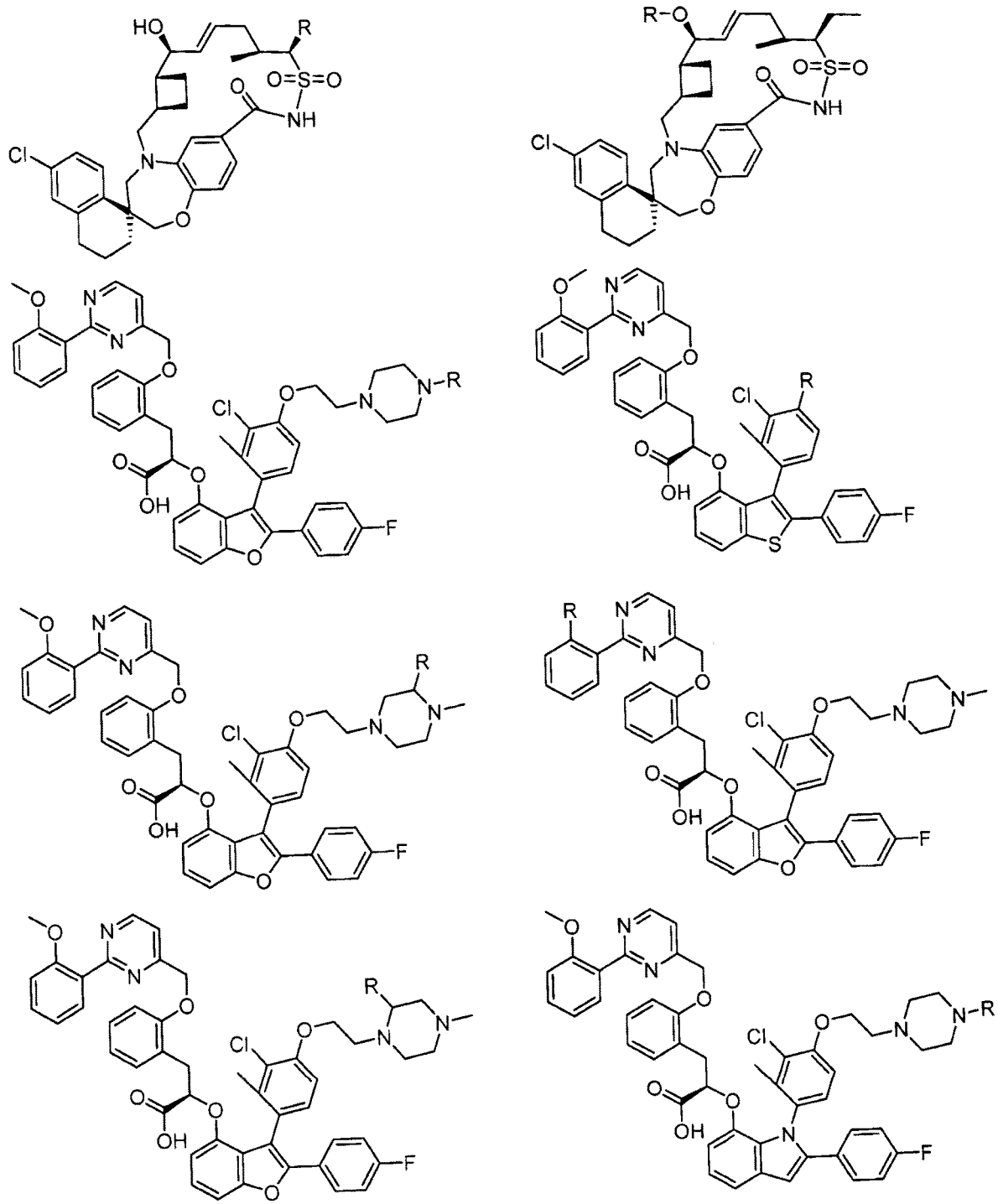
Figure 3P:
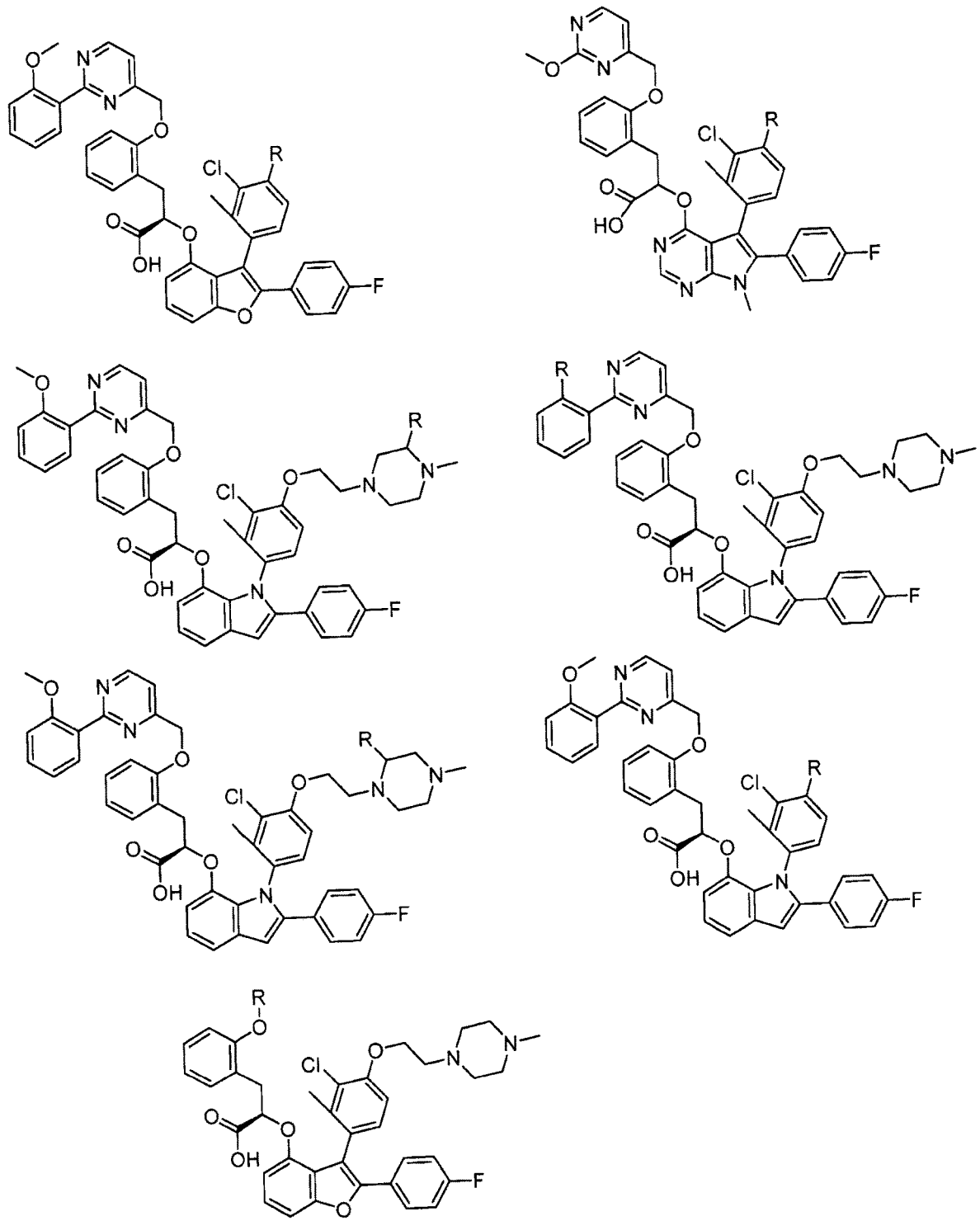
Figure 3Q:
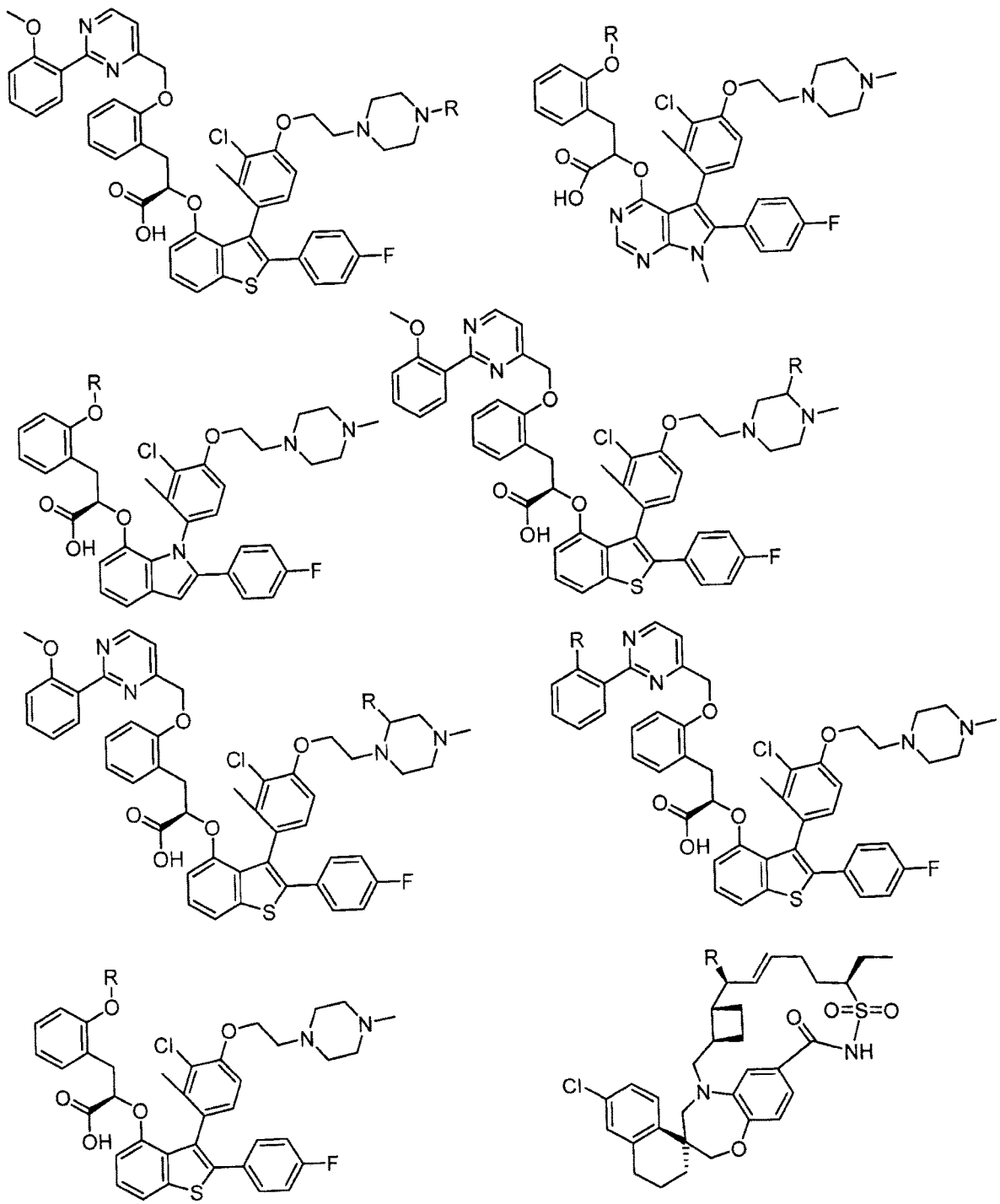
Figure 3R:
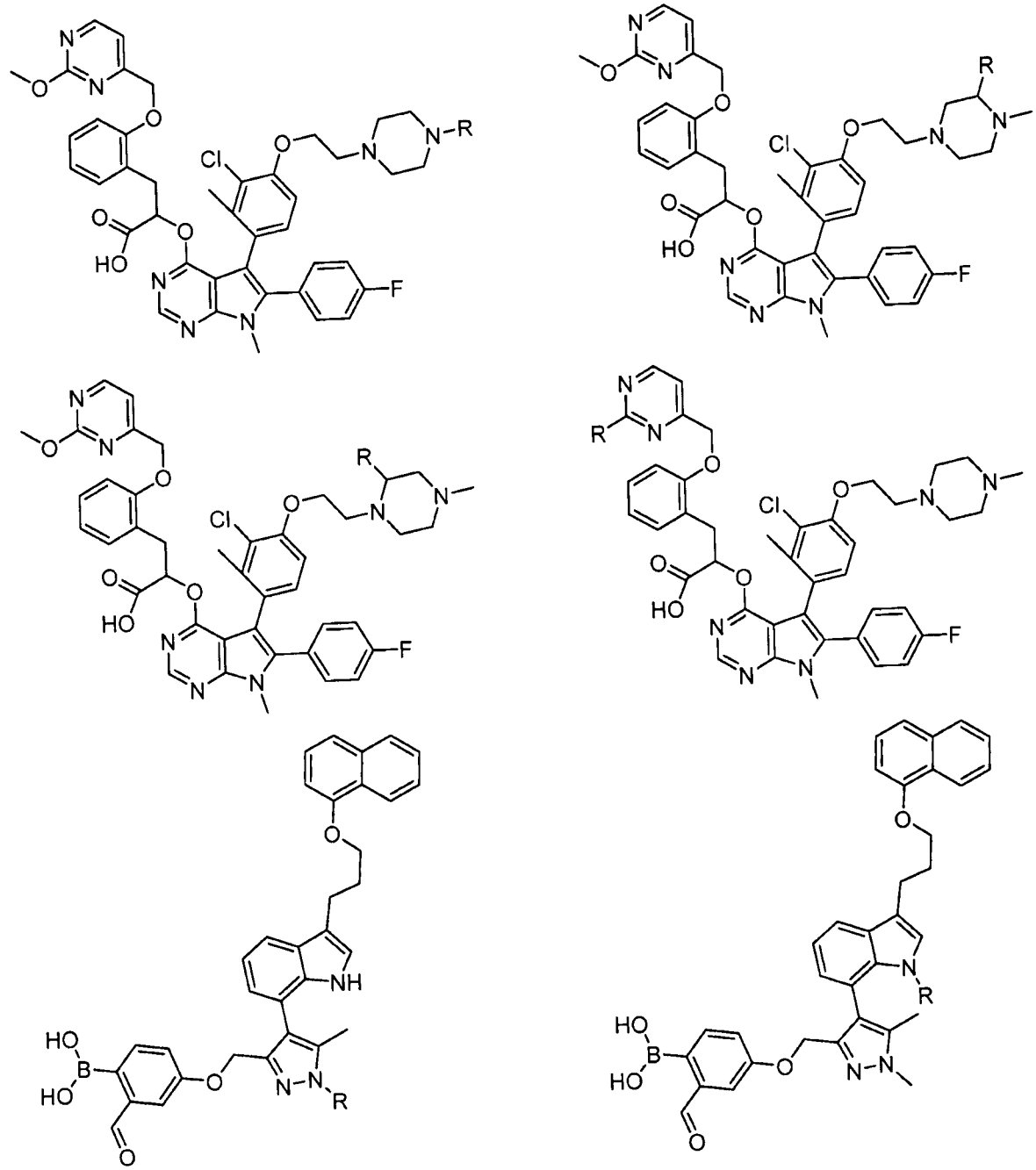
Figure 3S:
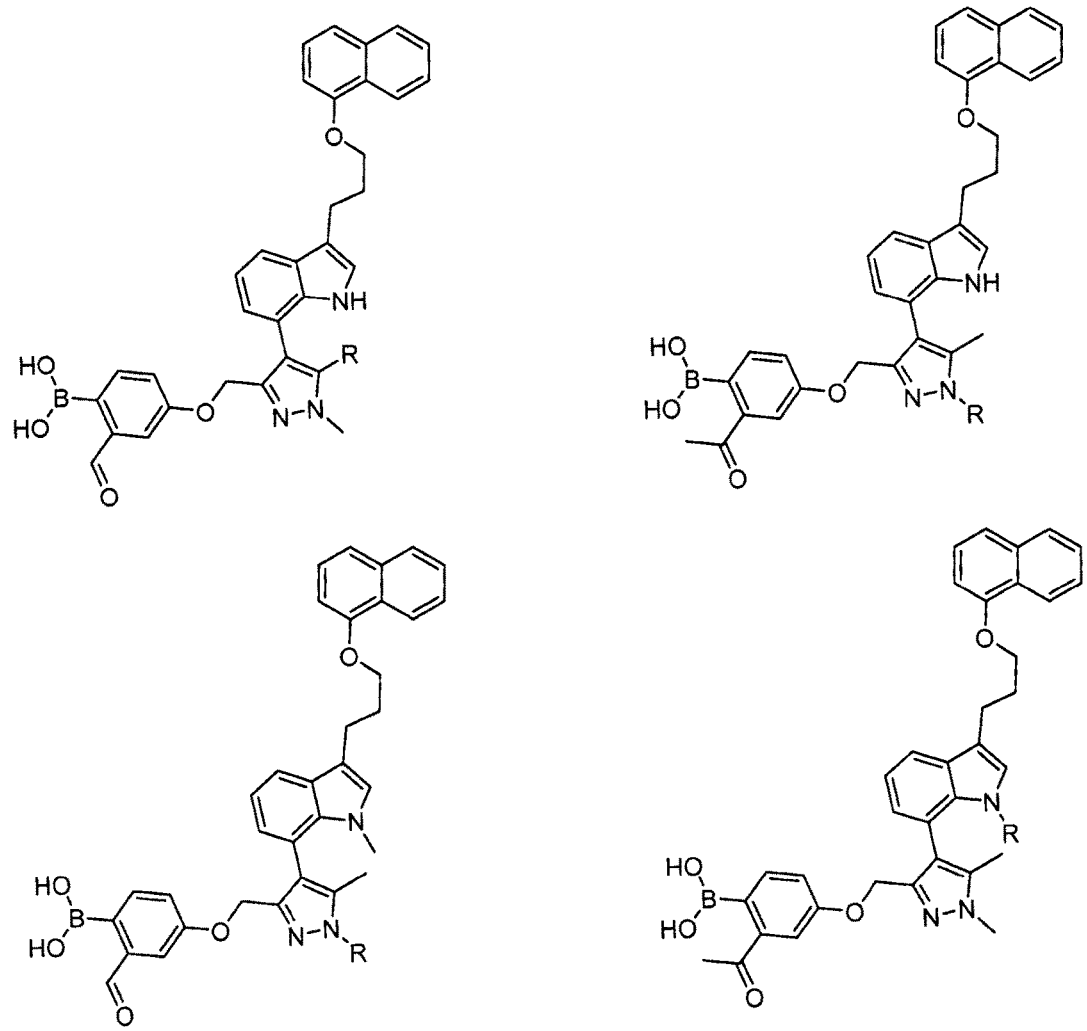
Figure 3T:
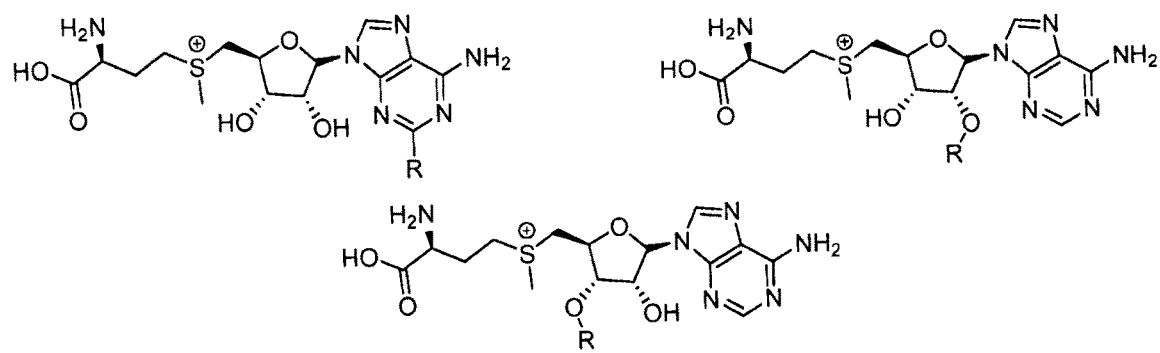
Figure 3U:
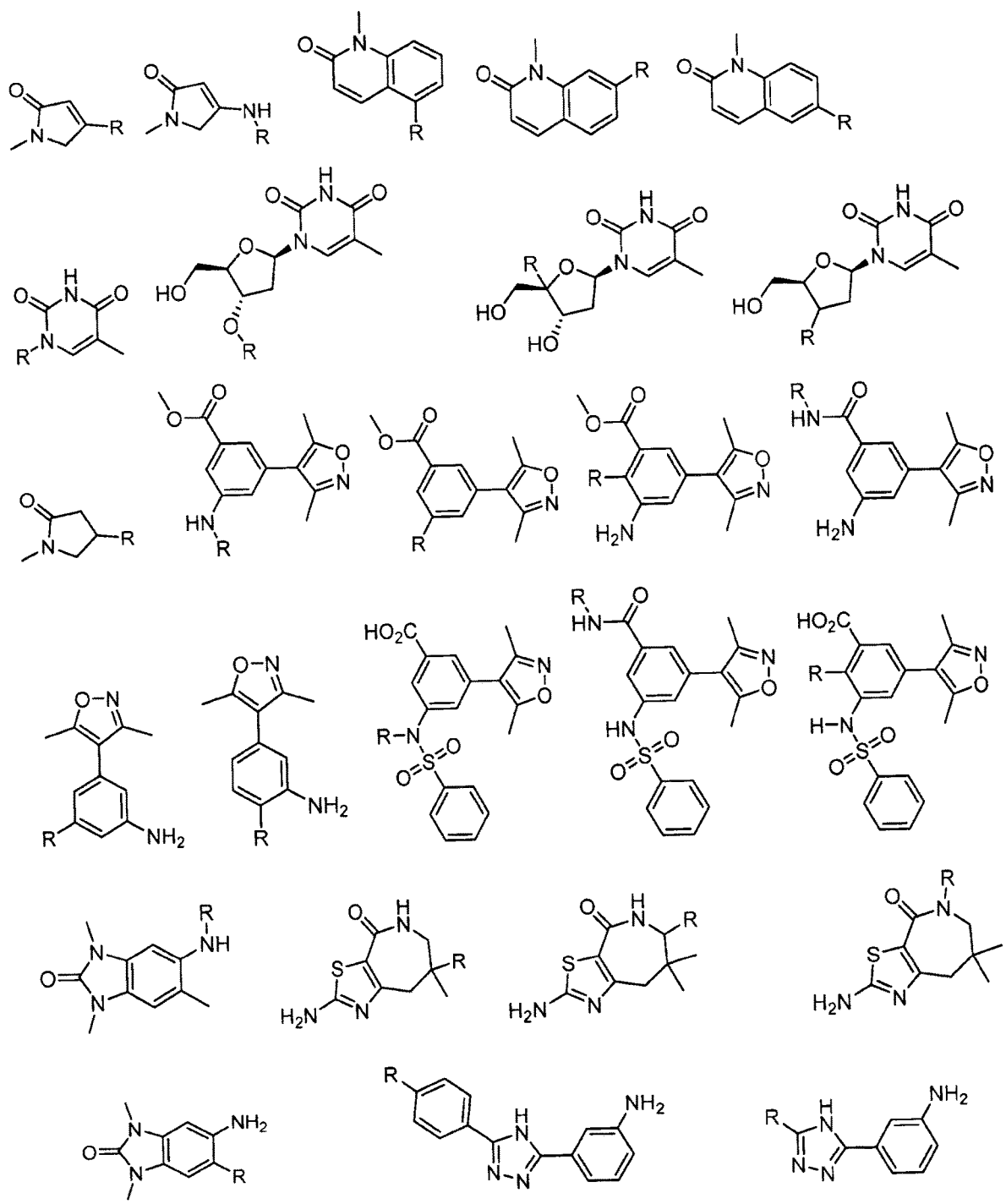
Figure 3V:
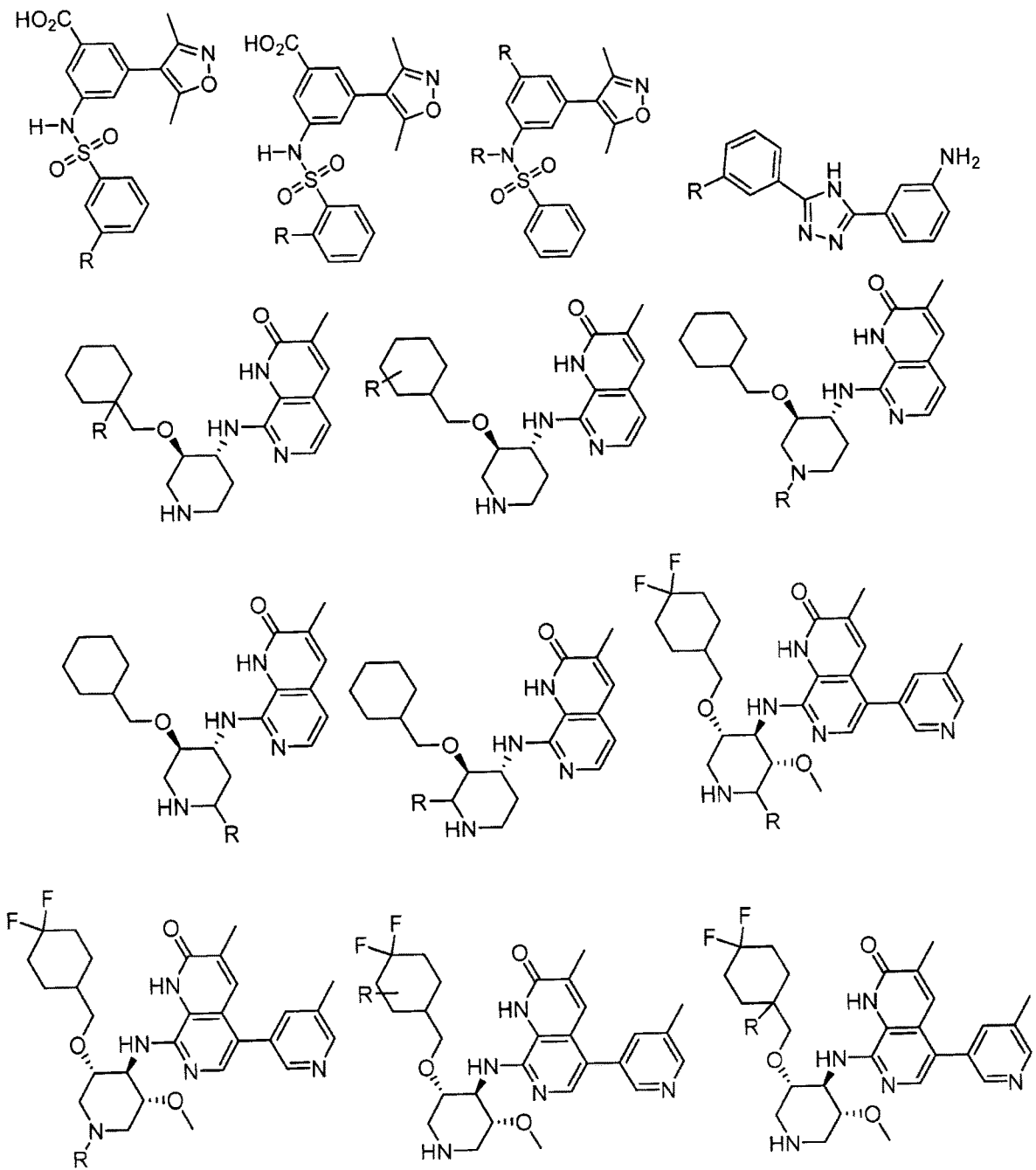
Figure 3W:
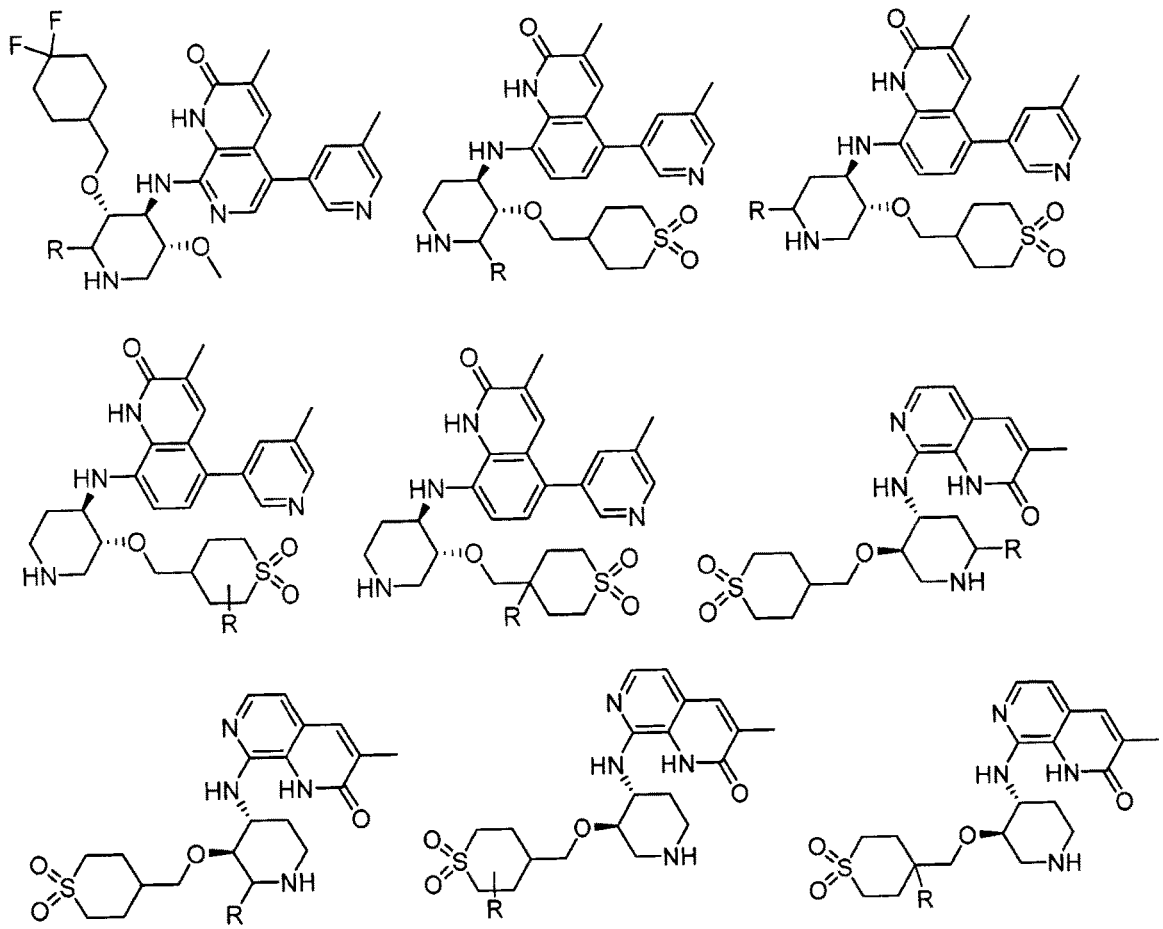
Figure 3X:
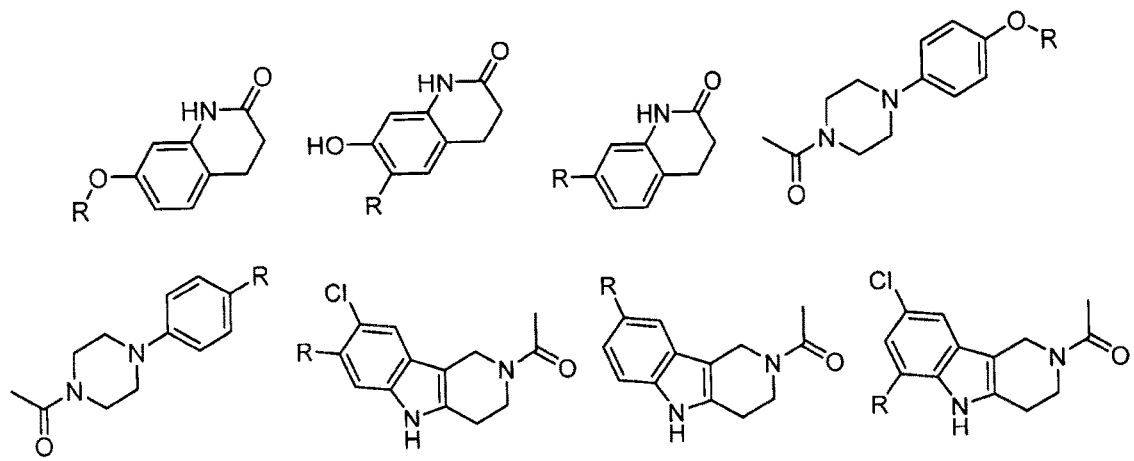
Figure 3Y:
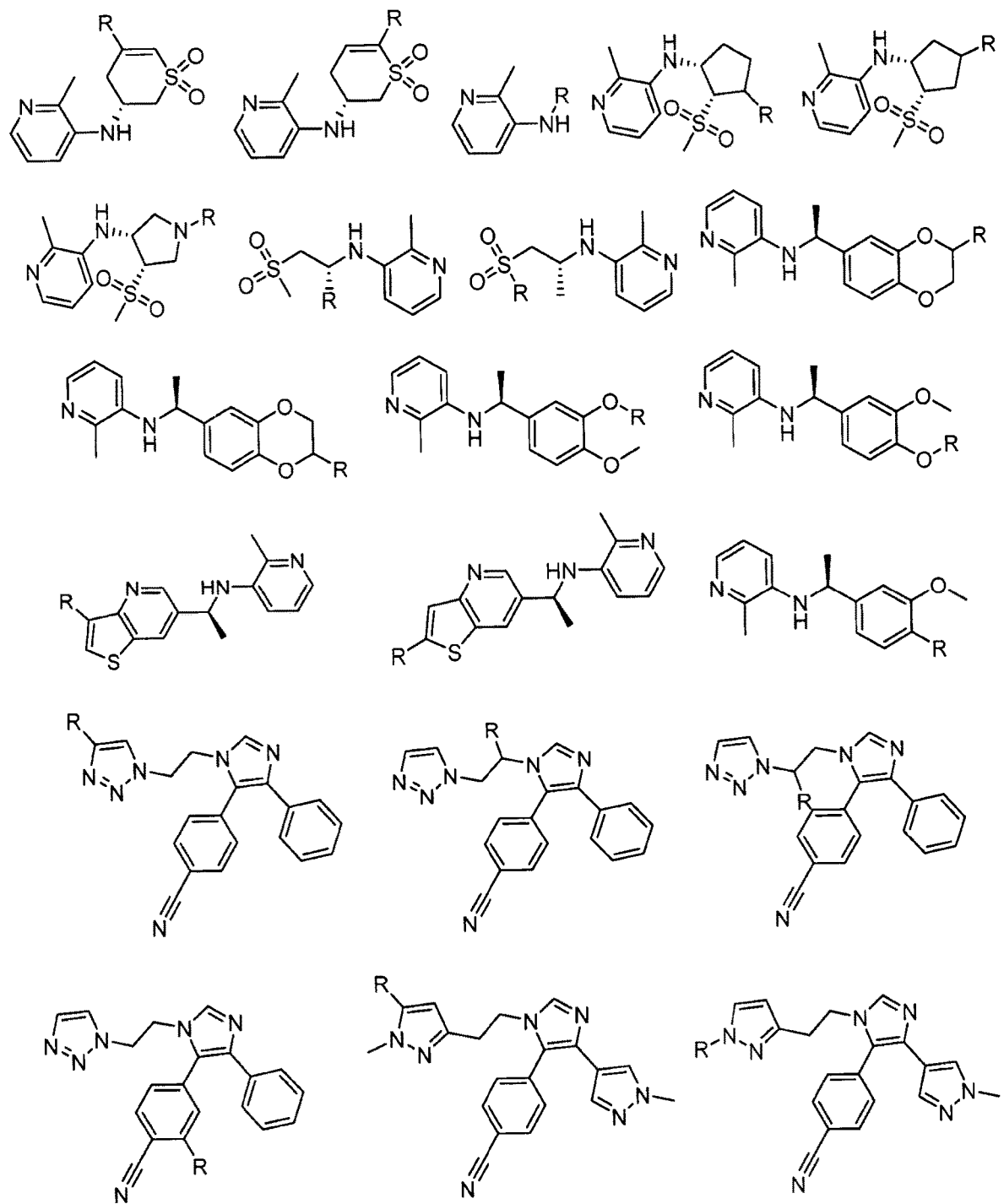
Figure 3Z:
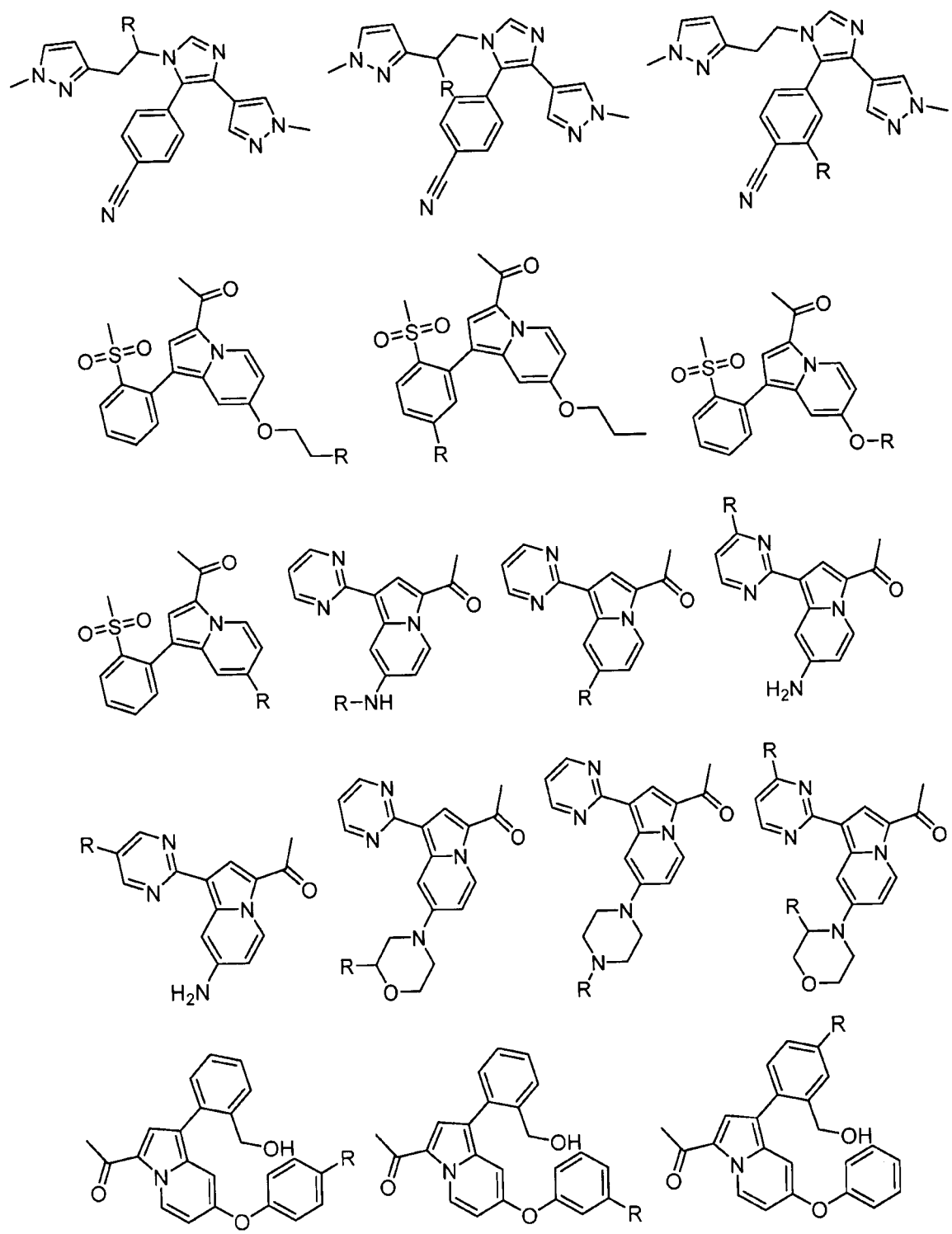

FIG. 3H-3I present examples of KSR1 Targeting Ligands wherein R is the point at which the Linker is attached.

FIG. 3J-3L present examples of CNNTB1 Targeting Ligands wherein R is the point at which the Linker is attached.

FIG. 3M presents examples of BCL6 Targeting Ligands wherein R is the point at which the Linker is attached.

FIG. 3N-3O present examples of PAK1 Targeting Ligands wherein R is the point at which the Linker is attached.

FIG. 3P-3R present examples of PAK4 Targeting Ligands wherein R is the point at which the Linker is attached.

FIG. 3S-3T present examples of TNIK Targeting Ligands wherein R is the point at which the Linker is attached.

FIG. 3U presents examples of MEN1 Targeting Ligands wherein R is the point at which the Linker is attached.

FIG. 3V-3W present examples of ERK1 Targeting Ligands wherein R is the point at which the Linker is attached.

FIG. 3X presents examples of IDO1 Targeting Ligands wherein R is the point at which the Linker is attached.

FIG. 3Y presents examples of CBP Targeting Ligands wherein R is the point at which the Linker is attached.

FIG. 3Z-3SS present examples of MCL1 Targeting Ligands wherein R is the point at which the Linker is attached. For additional examples and related ligands, see, Tanaka Y. et al "Discovery of potent Mcl-1/Bcl-xL dual inhibitors by using a hybridization strategy based on structural analysis of target proteins." *J. Med. Chem.* 56: 9635-9645 (2013); Friberg A. et al. "Discovery of potent myeloid cell leukemia 1 (Mcl-1) inhibitors using fragment-based methods and structure-based design." *J. Med. Chem.* 56: 15-30 (2013); Petros A. M. et al "Fragment-based discovery of potent inhibitors of the anti-apoptotic MCL-1 protein." *Bioorg. Med. Chem. Lett.* 24: 1484-1488 (2014); Burke J. P. et al. "Discovery of tricyclic indoles that potently inhibit mcl-1 using fragment-based methods and structure-based design." *J. Med. Chem.* 58: 3794-3805 (2015); Pelz N. F. et al. "Discovery of 2-Indole-acylsulfonamide Myeloid Cell Leukemia 1 (Mcl-1) Inhibitors Using Fragment-Based Methods." *J. Med. Chem.* 59: 2054-2066 (2016); Clifton M. C. et al. "A Maltose-Binding Protein Fusion Construct Yields a Robust Crystallography Platform for MCL1." *Plos One* 10: e0125010-e0125010 (2015); Kotschy A et al. "The MCL1 inhibitor S63845 is tolerable and effective in diverse cancer models. *Nature* 538:477-482 (2016); EP 2886545 A1 titled "New thienopyrimidine derivatives a process for their preparation and pharmaceutical compositions containing them"; Jeffrey W. Johannes et al. "Structure Based Design of Non-Natural Peptidic Macrocyclic Mcl-1 Inhibitors" *ACS Med. Chem. Lett.* (2017); DOI: 10.1021/acsmedchemlett.6b00464; Bruncko M. et al. "Structure-Guided Design of a Series of MCL-1 Inhibitors with High Affinity and Selectivity." *J. Med. Chem.* 58: 2180-2194 (2015); Taekyu Lee et al. "Discovery and biological characterization of potent myeloid cell leukemia-1 inhibitors." *FEBS Letters* 591: 240-251 (2017); Chen L. et al. "Structure-Based Design of 3-Carboxy-Substituted 1 2 3 4-Tetrahydroquinolines as Inhibitors of Myeloid Cell Leukemia-1 (Mcl-1)." *Org. Biomol. Chem.* 14:5505-5510 (2016); US 2016/0068545 titled "Tetrahydronaphthalene derivatives that inhibit mcl-1 protein"; WO 2016207217 A1 titled "Preparation of new bicyclic derivatives as pro-apoptotic agents"; Gizem Akgay et al. "Inhibition of Mcl-1 through covalent modification of a noncatalytic lysine side chain" Nature Chemical Biology 12: 931-936 (2016).

FIG. 3TT presents examples of ASH1L Targeting Ligands wherein R is the point at which the Linker is attached. See for example, the crystal structure PDB 4YNM ("Human ASH1L SET domain in complex with S-adenosyl methionine (SAM)" Rogawski D. S. et al.)

FIG. 3UU-3WW present examples of ATAD2 Targeting Ligands wherein R is the point at which the Linker is attached. For additional examples and related ligands, see, Chaikuad A. et al. "Structure-based approaches towards identification of fragments for the low-druggability ATAD2 bromodomain" *Med Chem Comm* 5: 1843-1848 (2014); Poncet-Montange G. et al. "Observed bromodomain flexibility reveals histone peptide- and small molecule ligand-compatible forms of ATAD2." *Biochem. J.* 466: 337-346 (2015); Harner M. J. et al. "Fragment-Based Screening of the Bromodomain of ATAD2." *J. Med. Chem.* 57: 9687-9692 (2014); Demont E. H. et al. "Fragment-Based Discovery of Low-Micromolar Atad2 Bromodomain Inhibitors." *J. Med. Chem.* 58: 5649 (2015); and, Bamborough P. et al. "Structure-Based Optimization of Naphthyridones into Potent Atad2 Bromodomain Inhibitors." *J. Med. Chem.* 58: 6151 (2015).

FIG. 3XX-3AAA present examples of BAZ2A and BAZ2B Targeting Ligands wherein R is the point at which the Linker is attached. For additional examples and related ligands, see, the crystal structure PDB 4CUU ("Human Baz2B in Complex with Fragment-6 N09645" Bradley A. et al.); the crystal structure PDB 5CUA ("Second Bromodomain of Bromodomain Adjacent to Zinc Finger Domain Protein 2B (BAZ2B) in complex with 1-Acetyl-4-(4-hydroxyphenyl)piperazine". Bradley A. et al.); Ferguson F. M. et al. "Targeting low-druggability bromodomains: fragment based screening and inhibitor design against the BAZ2B bromodomain." *J. Med. Chem.* 56: 10183-10187 (2013); Marchand J. R. et al. "Derivatives of 3-Amino-2-methylpyridine as BAZ2B Bromodomain Ligands: In Silico Discovery and in Crystallo Validation." *J. Med Chem.* 59: 9919-9927 (2016); Drouin L. et al. "Structure Enabled Design of BAZ2-ICR A Chemical Probe Targeting the Bromodomains of BAZ2A and BAZ2B." *J. Med Chem.* 58: 2553-2559 (2015); Chen P. et al. "Discovery and characterization of GSK2801 a selective chemical probe for the bromodomains BAZ2A and BAZ2B." *J. Med Chem.* 59:1410-1424 (2016).

FIG. 3BBB presents examples of BRD1 Targeting Ligands wherein R is the point at which the Linker is attached. For additional examples and related ligands, see, the crystal structure PDB 5AME ("the Crystal Structure of the Bromodomain of Human Surface Epitope Engineered Brd1A in Complex with 3D Consortium Fragment 4-Acetyl-Piperazin-2-One Pearce", N. M. et al.); the crystal structure PDB 5AMF ("Crystal Structure of the Bromodomain of Human Surface Epitope Engineered Brd1A in Complex with 3D Consortium Fragment Ethyl 4 5 6 7-Tetrahydro-1H-Indazole-5-Carboxylate", Pearce N. M. et al.); the crystal structure PDB 5FG6 ("the Crystal structure of the bromodomain of human BRD1 (BRPF2) in complex with OF-1 chemical probe.", Tallant C. et al.); Filippakopoulos P. et al. "Histone recognition and large-scale structural analysis of the human bromodomain family." *Cell,* 149: 214-231 (2012).

FIG. 3CCC-3EEE present examples of BRD2 Bromodomain 1 Targeting Ligands wherein R is the point at which the Linker is attached. For additional examples and related ligands, see, the crystal structure PDB 2ydw; the crystal structure PDB 2yek; the crystal structure PDB 4a9 h; the crystal structure PDB 4a9f; the crystal structure PDB 4a9i; the crystal structure PDB 4a9m; the crystal structure PDB 4akn; the crystal structure PDB 4alg, and the crystal structure PDB 4uyf.

FIG. 3FFF-3HHH present examples of BRD2 Bromodomain 2 Targeting Ligands wherein R is the point at which the Linker is attached. For additional examples and related ligands, see, the crystal structure PDB 3oni; Filippakopoulos P. et al. "Selective Inhibition of BET Bromodomains." *Nature* 468: 1067-1073 (2010); the crystal structure PDB 4jlp; McLure K. G. et al. "RVX-208: an Inducer of ApoA-I in Humans is a BET Bromodomain Antagonist." *Plos One* 8: e83190-e83190 (2013); Baud M. G. et al. "Chemical biology. A bump-and-hole approach to engineer controlled selectivity of BET bromodomain chemical probes" *Science* 346: 638-641 (2014); Baud M. G. et al. "New Synthetic Routes to Triazolo-benzodiazepine Analogues: Expanding the Scope of the Bump-and-Hole Approach for Selective Bromo and Extra-Terminal (BET) Bromodomain Inhibition" *J. Med Chem.* 59: 1492-1500 (2016); Gosmini R. et al. "The Discovery of I-Bet726 (Gsk1324726A) a Potent Tetrahydroquinoline Apoa1 Up-Regulator and Selective Bet Bromodomain Inhibitor" *J. Med Chem.* 57: 8111 (2014); the crystal structure PDB 5EK9 ("Crystal structure of the second bromodomain of human BRD2 in complex with a hydroquinolinone inhibitor", Tallant C. et al); the crystal structure PDB 5BT5; the crystal structure PDB 5dfd; Baud M. G. et al. "New Synthetic Routes to Triazolo-benzodiazepine Analogues: Expanding the Scope of the Bump-and-Hole Approach for Selective Bromo and Extra-Terminal (BET) Bromodomain Inhibition" *J. Med. Chem.* 59: 1492-1500 (2016).

FIG. 3III-3JJJ present examples of BRD4 Bromodomain 1 Targeting Ligands wherein R is the point at which the Linker is attached. For additional examples and related ligands, see, the crystal structure PDB 5WUU and the crystal structure PDB 5F5Z.

FIG. 3KKK-3LLL present examples of BRD4 Bromodomain 2 Targeting Ligands wherein R is the point at which the Linker is attached. For additional examples and related ligands, see, Chung C. W. et al. "Discovery and Characterization of Small Molecule Inhibitors of the Bet Family Bromodomains" *J. Med Chem.* 54: 3827 (2011) and Ran X. et al. "Structure-Based Design of gamma-Carboline Analogues as Potent and Specific BET Bromodomain Inhibitors" *J. Med Chem.* 58: 4927-4939 (2015).

FIG. 3MMM presents examples of BRDT Targeting Ligands wherein R is the point at which the Linker is attached. For additional examples and related ligands, see, the crystal structure PDB 4flp and the crystal structure PDB 4kcx.

FIG. 3NNN-3QQQ present examples of BRD9 Targeting Ligands wherein R is the point at which the Linker is attached. For additional examples and related ligands, see, the crystal structure PDB 4ngn; the crystal structure PDB 4uit; the crystal structure PDB 4uiu; the crystal structure PDB 4uiv; the crystal structure PDB 4z6h; the crystal structure PDB 4z6i; the crystal structure PDB 5e9v; the crystal structure PDB 5eu1; the crystal structure PDB 5f1h; and, the crystal structure PDB 5fp2.

FIG. 3RRR presents examples of SMARCA4 PB1 and/or SMARCA2 Targeting Ligands wherein R is the point at which the Linker is attached, A is N or CH, and m is 0 1 2 3 4 5 6 7 or 8.

FIG. 3SSS-3XXX present examples of additional Bromodomain Targeting Ligands wherein R is the point at which the Linker is attached. For additional examples and related ligands, see, Hewings et al. "3 5-Dimethylisoxazoles Act as Acetyl-lysine Bromodomain Ligands." *J. Med. Chem.* 54 6761-6770 (2011); Dawson et al. "Inhibition of BET Recruitment to Chromatin as an Effective Treatment for MLL-fusion Leukemia." *Nature,* 478, 529-533 (2011); US 2015/0256700; US 2015/0148342; WO 2015/074064; WO 2015/067770; WO 2015/022332; WO 2015/015318; and, WO 2015/011084.

FIG. 3YYY presents examples of PB1 Targeting Ligands wherein R is the point at which the Linker is attached. For additional examples and related ligands, see, the crystal structure PDB 3mb4; the crystal structure PDB 4q0n; and, the crystal structure PDB 5fh6.

FIG. 3ZZZ presents examples of SMARCA4 Targeting Ligands wherein R is the point at which the Linker is attached. For additional examples and related ligands, see, the crystal structure 3uvd and the crystal structure 5dkd.

FIG. 3AAAA presents examples of SMARCA2 Targeting Ligands wherein R is the point at which the Linker is attached. For additional examples and related ligands, see, the crystal structure 5dkc and the crystal structure 5dkh.

FIG. 3BBBB presents examples of TRIM24 (TIF1a) and/or BRPF1 Targeting Ligands wherein R is the point at which the Linker is attached and m is 0 1 2 3 4 5 6 7 or 8.

FIG. 3CCC presents examples of TRIM24 (TIF1a) Targeting Ligands wherein R is the point at which the Linker is attached. For additional examples and related ligands, see, Palmer W. S. et al. "Structure-Guided Design of IACS-9571: a Selective High-Affinity Dual TRIM24-BRPF1 Bromodomain Inhibitor." *J. Med. Chem.* 59: 1440-1454 (2016).

FIG. 3DDDD-3FFFF present examples of BRPF1 Targeting Ligands wherein R is the point at which the Linker is attached. For additional examples and related ligands, see, the crystal structure PDB 4uye; the crystal structure PDB 5c7n; the crystal structure PDB 5c87; the crystal structure PDB 5c89; the crystal structure PDB 5d7x; the crystal structure PDB 5dya; the crystal structure PDB 5epr; the crystal structure PDB 5eq1; the crystal structure PDB 5etb; the crystal structure PDB 5ev9; the crystal structure PDB 5eva; the crystal structure PDB 5ewv; the crystal structure PDB 5eww; the crystal structure PDB 5ffy; the crystal structure PDB 5fg5; and, the crystal structure PDB 5 g4r.

FIG. 3GGGG presents examples of CECR2 Targeting Ligands wherein R is the point at which the Linker is attached. For additional examples and related ligands, see, Moustakim M. et al. *Med. Chem. Comm.* 7:2246-2264 (2016) and Crawford T. et al. *Journal of Med. Chem.* 59; 5391-5402 (2016).

FIG. 3HHHH-3OOOO present examples of CREBBP Targeting Ligands wherein R is the point at which the Linker is attached, A is N or CH, and m is 0 1 2 3 4 5 6 7 or 8. For additional examples and related ligands, see, the crystal structure PDB 3p1d; the crystal structure PDB 3svh; the crystal structure PDB 4nr4; the crystal structure PDB 4nr5; the crystal structure PDB 4ts8; the crystal structure PDB 4nr6; the crystal structure PDB 4nr7; the crystal structure PDB 4nyw; the crystal structure PDB 4nyx; the crystal structure PDB 4tqn; the crystal structure PDB 5cgp; the crystal structure PDB 5dbm; the crystal structure PDB 5ep7; the crystal structure PDB 5i83; the crystal structure PDB 5i86; the crystal structure PDB 5i89; the crystal structure PDB 5i8 g; the crystal structure PDB 5j0d; the crystal structure PDB 5ktu; the crystal structure PDB 5ktw; the crystal structure PDB 5ktx; the crystal structure PDB 5tb6.

FIG. 3PPPP presents examples of EP300 Targeting Ligands wherein R is the point at which the Linker is attached. For additional examples and related ligands, see, the crystal structure PDB 5BT3.

FIG. 3QQQQ presents examples of PCAF Targeting Ligands wherein R is the point at which the Linker is attached. See for example, M. Ghizzoni et al. *Bioorg. Med. Chem.* 18: 5826-5834 (2010).

FIG. 3RRRR presents examples of PHIP Targeting Ligands wherein R is the point at which the Linker is attached. For additional examples and related ligands, see, *Mol Cancer Ther.* 7(9): 2621-2632 (2008).

FIG. 3SSSS presents examples of TAF1 and TAF1L Targeting Ligands wherein R is the point at which the Linker is attached. For additional examples and related ligands, see, Picaud S. et al. *Sci Adv* 2: e1600760-e1600760 (2016).

FIG. 3TTTT presents examples of Histone Deacetylase 2 (HDAC2) Targeting Ligands wherein R is the point at which the Linker is attached. For additional examples and related ligands, see, Lauffer B. E. *J. Biol. Chem.* 288: 26926-26943 (2013); Wagner F. F. *Bioorg. Med Chem.* 24: 4008-4015 (2016); Bressi J. C. *Bioorg. Med Chem. Lett.* 20: 3142-3145 (2010); and, Lauffer B. E. *J. Biol. Chem.* 288: 26926-26943 (2013).

FIG. 3UUUU-3VVVV present examples of Histone Deacetylase 4 (HDAC4) Targeting Ligands wherein R is the point at which the Linker is attached. For additional examples and related ligands, see, Burli R. W. *J. Med Chem.* 56: 9934 (2013); Luckhurst C. A. *ACS Med Chem. Lett.* 7: 34 (2016); Bottomley M. J. *J. Biol. Chem.* 283: 26694-26704 (2008).

FIG. 3WWWW presents examples of Histone Deaceytlase 6 Targeting Ligands wherein R is the point at which the Linker is attached. For additional examples and related ligands, see, Harding R. J. (to be published); Hai Y. *Nat. Chem. Biol.* 12: 741-747, (2016); and, Miyake Y. *Nat. Chem. Biol.* 12: 748 (2016).

FIG. 3XXXX-3YYYY presents examples of Histone Deacetylase 7 Targeting Ligands wherein R is the point at which the Linker is attached. For additional examples and related ligands, see, Lobera M. *Nat. Chem. Biol.* 9: 319 (2013) and Schuetz A. *J. Biol. Chem.* 283: 11355-11363 (2008).

FIG. 3ZZZZ-3DDDDD present examples of Histone Deacetylase 8 Targeting Ligands wherein R is the point at which the Linker is attached. For additional examples and related ligands, see, Whitehead L. *Biol. Med Chem.* 19: 4626-4634 (2011); Tabackman A. A. *J. Struct. Biol.* 195: 373-378 (2016); Dowling D. P. *Biochemistry* 47, 13554-13563 (2008); Somoza J. R. *Biochemistry* 12, 1325-1334 (2004); Decroos C. *Biochemistry* 54: 2126-2135 (2015); Vannini A. *Proc. Natl Acad Sci.* 101: 15064 (2004); Vannini A. *EMBO Rep.* 8: 879 (2007); the crystal structure PDB 5BWZ; Decroos A. *ACS Chem. Biol.* 9: 2157-2164 (2014); Somoza J. R. *Biochemistry* 12: 1325-1334 (2004); Decroos C. *Biochemistry* 54: 6501-6513 (2015); Decroos A. *ACS Chem. Biol.* 9: 2157-2164 (2014); and, Dowling D. P. *Biochemistry* 47: 13554-13563 (2008).

FIG. 3EEEEE presents examples of Histone Acetyltransferase (KAT2B) Targeting Ligands wherein R is the point at which the Linker is attached. For additional examples and related ligands, see, Chaikuad A. *J. Med. Chem.* 59: 1648-1653 (2016); the crystal structure PDB 1ZS5; and, Zeng L. *J. Am. Chem. Soc.* 127: 2376-2377 (2005).

FIG. 3FFFFF-3GGGGG present examples of Histone Acetyltransferase (KAT2A) Targeting Ligands wherein R is the point at which the Linker is attached. For additional examples and related ligands, see, Ringel A. E. *Acta Crystallogr. D.* Struct. Biol. 72: 841-848 (2016).

FIG. 3HHHHH presents examples of Histone Acetyltransferase Type B Catalytic Unit (HAT1) Targeting Ligands wherein R is the point at which the Linker is attached. For additional examples and related ligands, see, the crystal structure PDB 2POW.

FIG. 3IIIII presents examples of Cyclic AMP-dependent Transcription Factor (ATF2) Targeting Ligands wherein R is the point at which the Linker is attached.

FIG. 3JJJJJ presents examples of Histone Acetyltransferase (KAT5) Targeting Ligands wherein R is the point at which the Linker is attached.

FIG. 3KKKKK-3MMMMM present examples of Lysine-specific histone demethylase 1A (KDM1A) Targeting Ligands wherein R is the point at which the Linker is attached. For additional examples and related ligands, see, Mimasu S. Biochemistry 49: 6494-6503 (2010); Sartori L. *J. Med. Chem.* 60:1673-1693 (2017); and, Vianello P. *J. Med. Chem.* 60: 1693-1715 (2017).

FIG. 3NNNNN presents examples of HDAC6 Zn Finger Domain Targeting Ligands wherein R is the point at which the Linker is attached.

FIG. 3OOOOO-3PPPPP present examples of general Lysine Methyltransferase Targeting Ligands wherein R is the point at which the Linker is attached.

FIG. 3QQQQQ-3TTTTT present examples of DOT1L Targeting Ligands wherein R is the point at which the Linker is attached, A is N or CH, and m is 0 1 2 3 4 5 6 7 or 8. For additional examples and related ligands, see, the crystal structure PDB 5MVS ("Dot1L in complex with adenosine and inhibitor CPD1" Be C. et al.); the crystal structure PDB 5MW4 ("Dot1L in complex inhibitor CPD7" Be C. et al.); the crystal structure PDB 5DRT ("Dot1L in complex inhibitor CPD2" Be C. et al.); Be C. et al. *ACS Med. Lett.* 8: 338-343 (2017); the crystal structure PDB 5JUW "(Dot1L in complex with SS148" Yu W. et al. Structural Genomics Consortium).

FIG. 3UUUUU presents examples of EHMT1 Targeting Ligands wherein R is the point at which the Linker is attached. For additional examples and related ligands, see, the crystal structure PDB 5TUZ ("EHMT1 in complex with inhibitor MS0124", Babault N. et al.).

FIG. 3VVVVV presents examples of EHMT2 Targeting Ligands wherein R is the point at which the Linker is attached. For additional examples and related ligands, see, the crystal structure PDB 5TUY ("EHMT2 in complex with inhibitor MS0124", Babault N. et al.); the PDB crystal structure 5TTF ("EHMT2 in complex with inhibitor MS012", Dong A. et al.); the PDB crystal structure 3RJW (Dong A. et al., Structural Genomics Consortium); the PDB crystal structure 3K5K; Liu F. et al. *J. Med. Chem.* 52: 7950-7953 (2009); and, the PDB crystal structure 4NVQ ("EHMT2 in complex with inhibitor A-366" Sweis R. F. et al.).

FIG. 3WWWWW presents examples of SETD2 Targeting Ligands wherein R is the point at which the Linker is attached. For additional examples and related ligands, see, the PDB crystal structure 5LSY ("SETD2 in complex with cyproheptadine", Tisi D. et al.); Tisi D. et al. *ACS Chem. Biol.* 11: 3093-3105 (2016); the crystal structures PDB 5LSS, 5LSX, 5LSZ, 5LT6, 5LT7, and 5LT8; the PDB crystal structure 4FMU; and, Zheng W. et al. *J. Am. Chem. Soc.* 134: 18004-18014 (2012).

FIG. 3XXXXX-3YYYYY present examples of SETD7 Targeting Ligands wherein R is the point at which the Linker is attached. For additional examples and related ligands, see, the PDB crystal structure 5AYF ("SETD7 in complex with cyproheptadine." Niwa H. et al.); the PDB crystal structure 4JLG ("SETD7 in complex with (R)-PFI-2", Dong A. et al.); the PDB crystal structure 4JDS (Dong A. et. al Structural Genomics Consortium); the PDB crystal structure 4E47 (Walker J. R. et al. Structural Genomics Consortium; the PDB crystal structure 3VUZ ("SETD7 in complex with AAM-1." Niwa H. et al.); the PDB crystal structure 3VVO; and, Niwa H et al. *Acta Crystallogr. Sect. D* 69: 595-602 (2013).

FIG. 3ZZZZZ presents examples of SETD8 Targeting Ligands wherein R is the point at which the Linker is attached. For additional examples and related ligands, see, the PDB crystal structure 5TH7 ("SETD8 in complex with MS453", Yu W. et al.) and the PDB crystal structure 5T5G (Yu W et. al.; to be published).

Figure 4B:
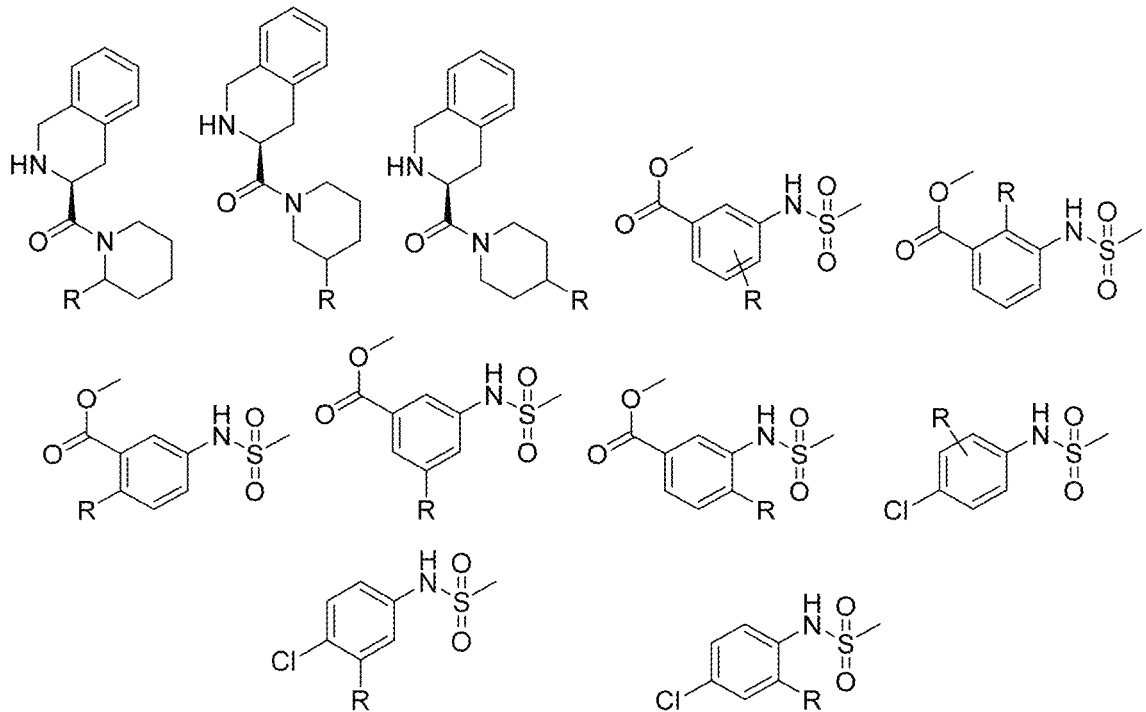
Figure 4C:
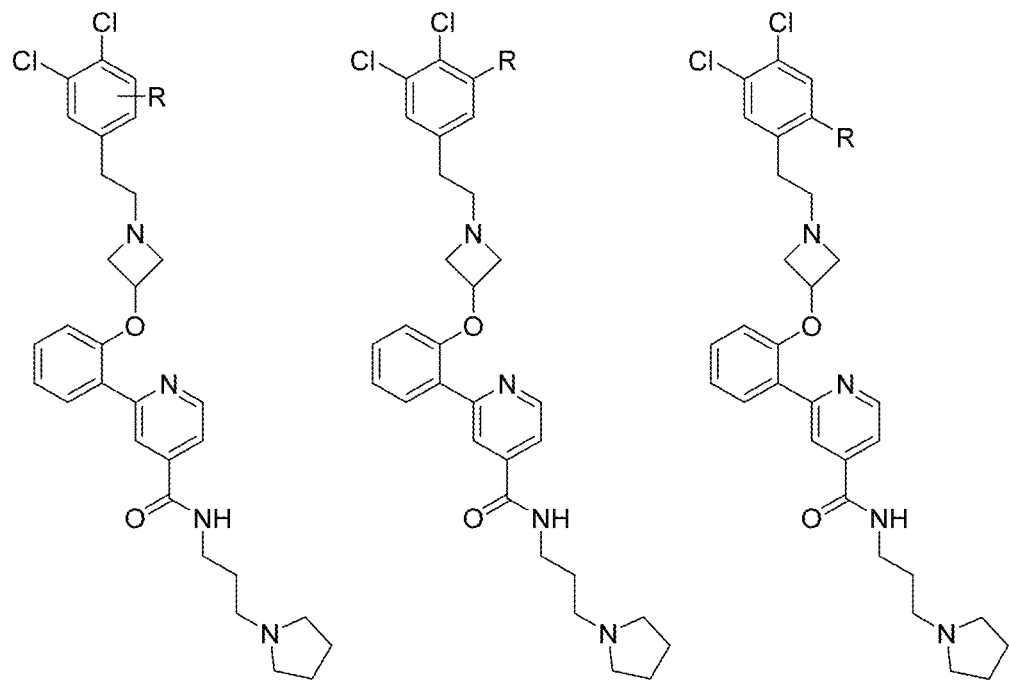
Figure 4D:
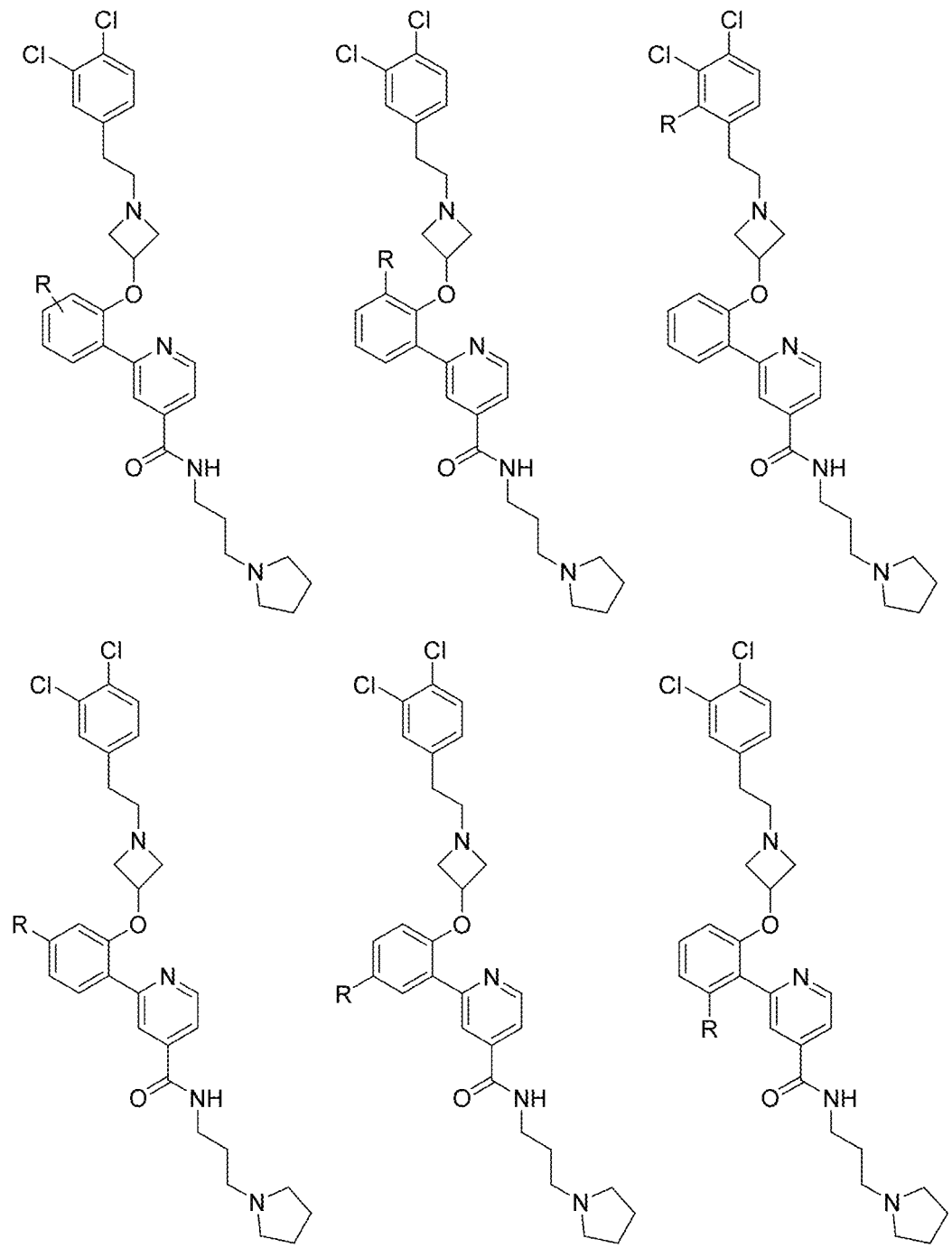
Figure 4E:
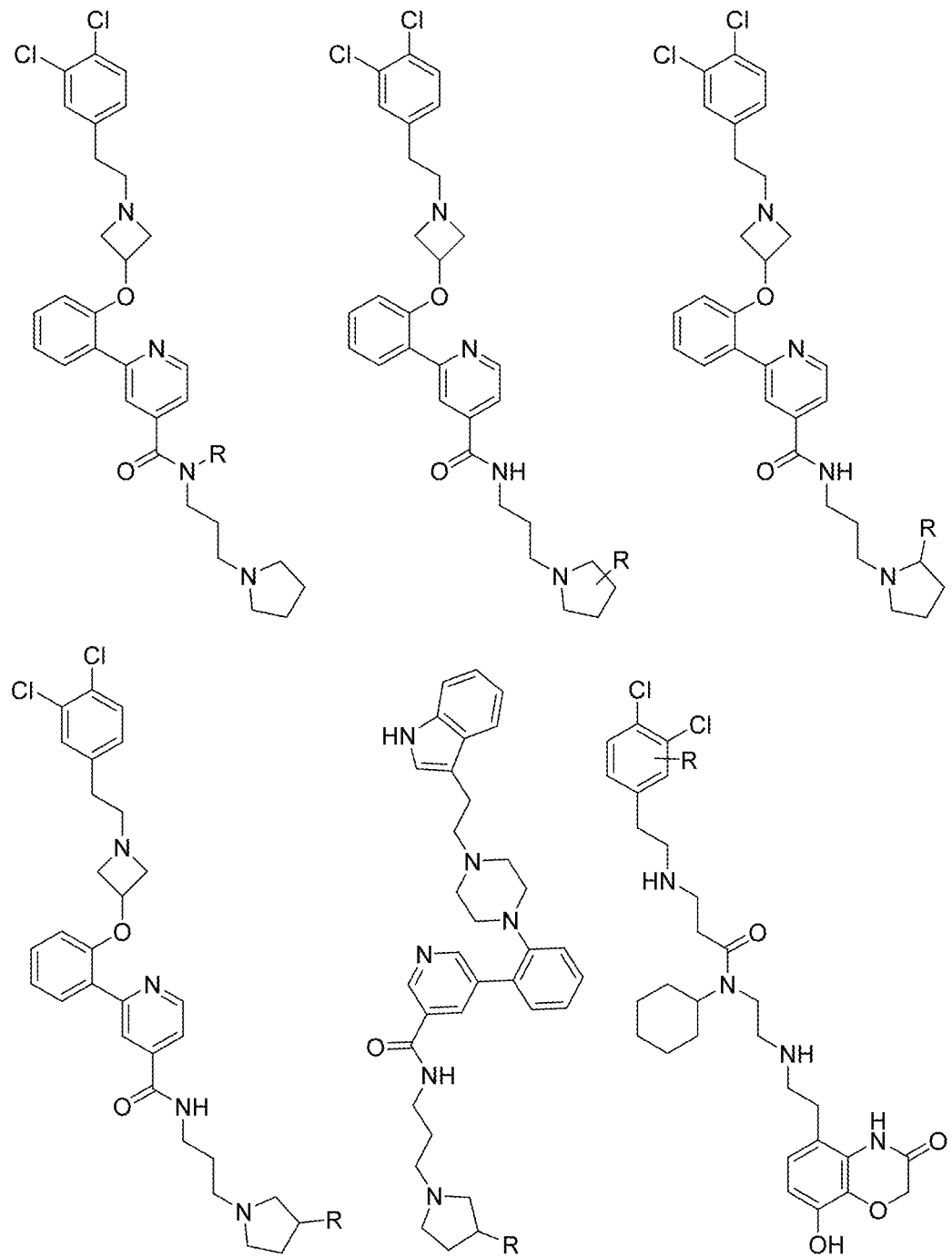
Figure 4F:
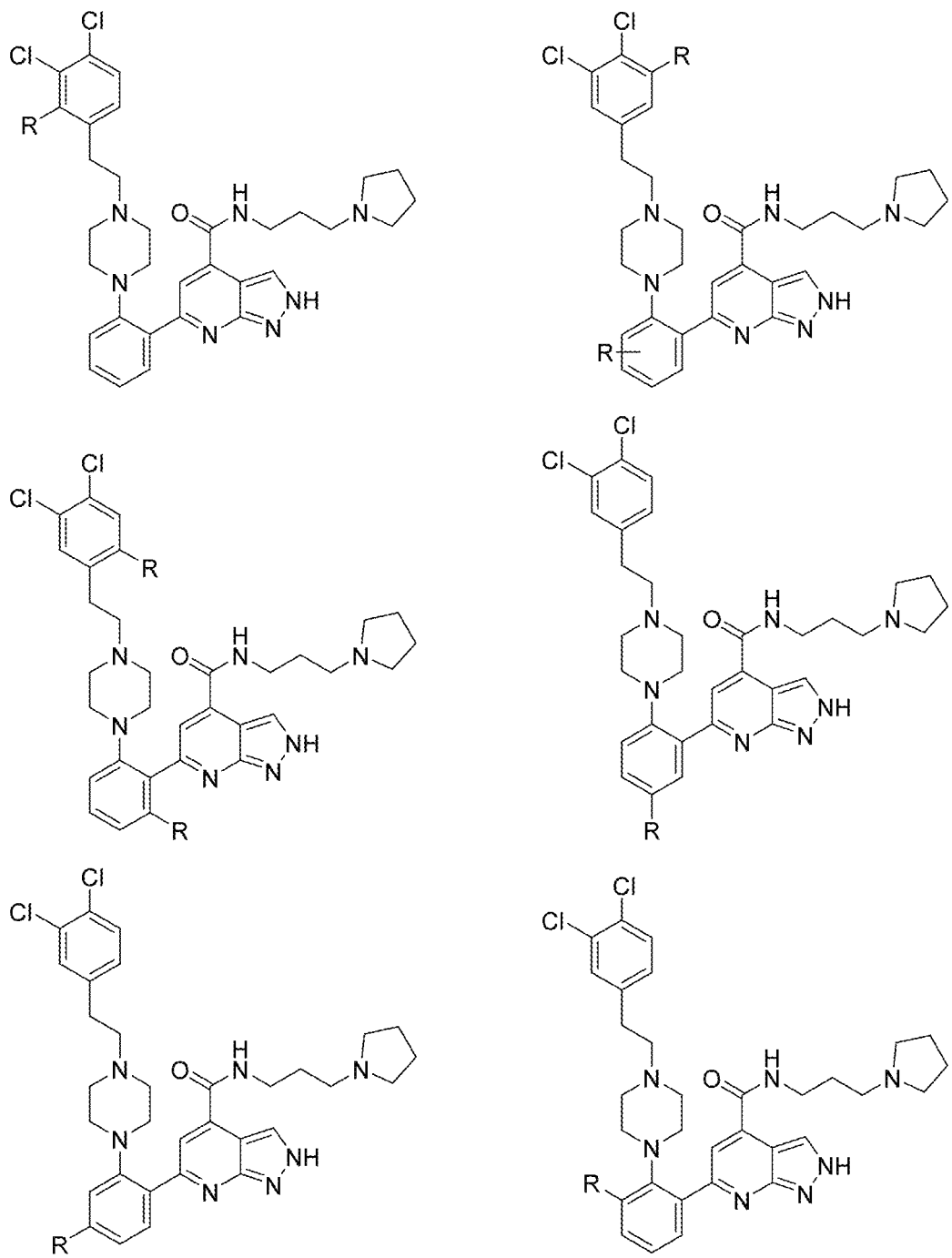
Figure 4G:
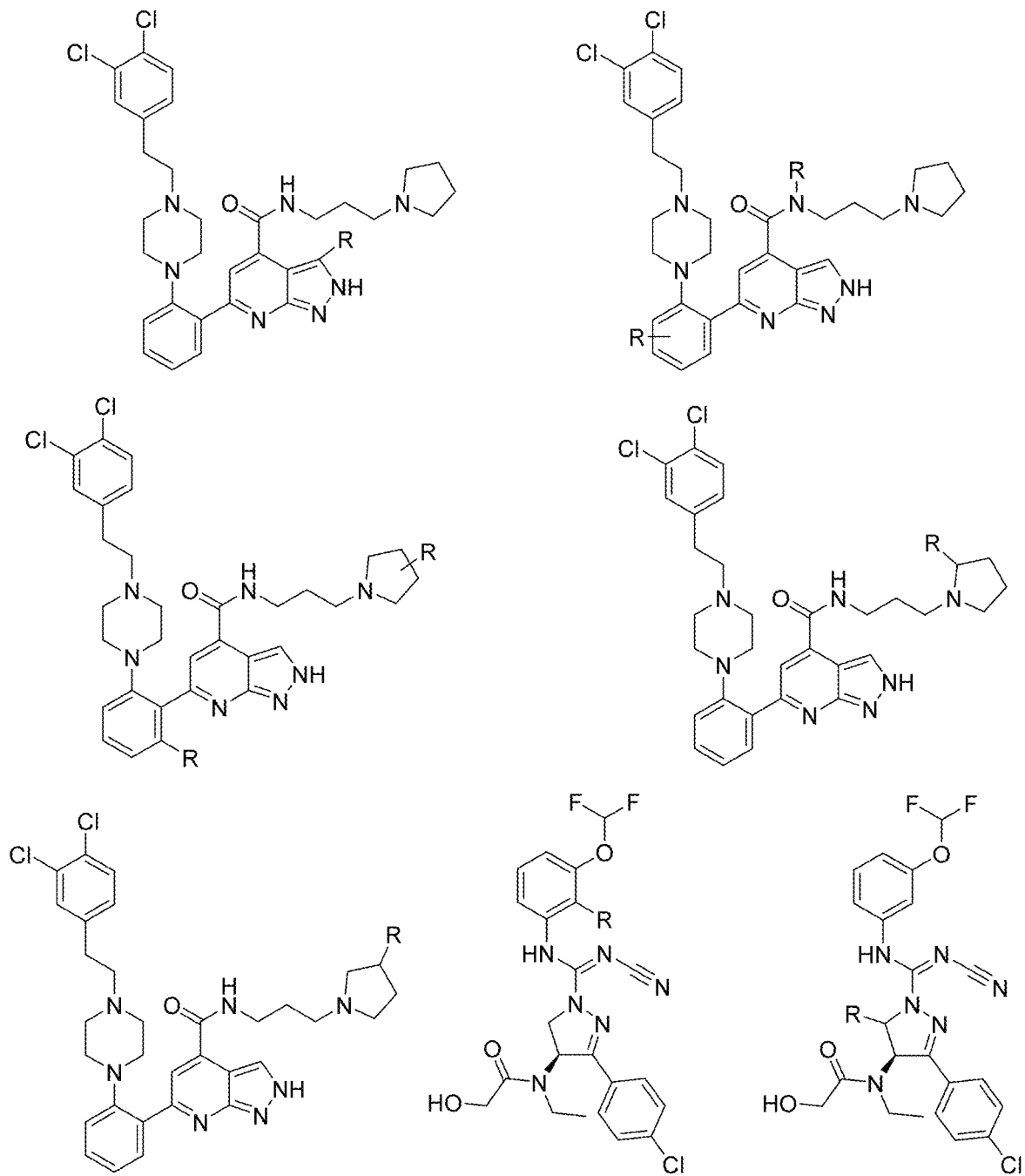
Figure 4H:
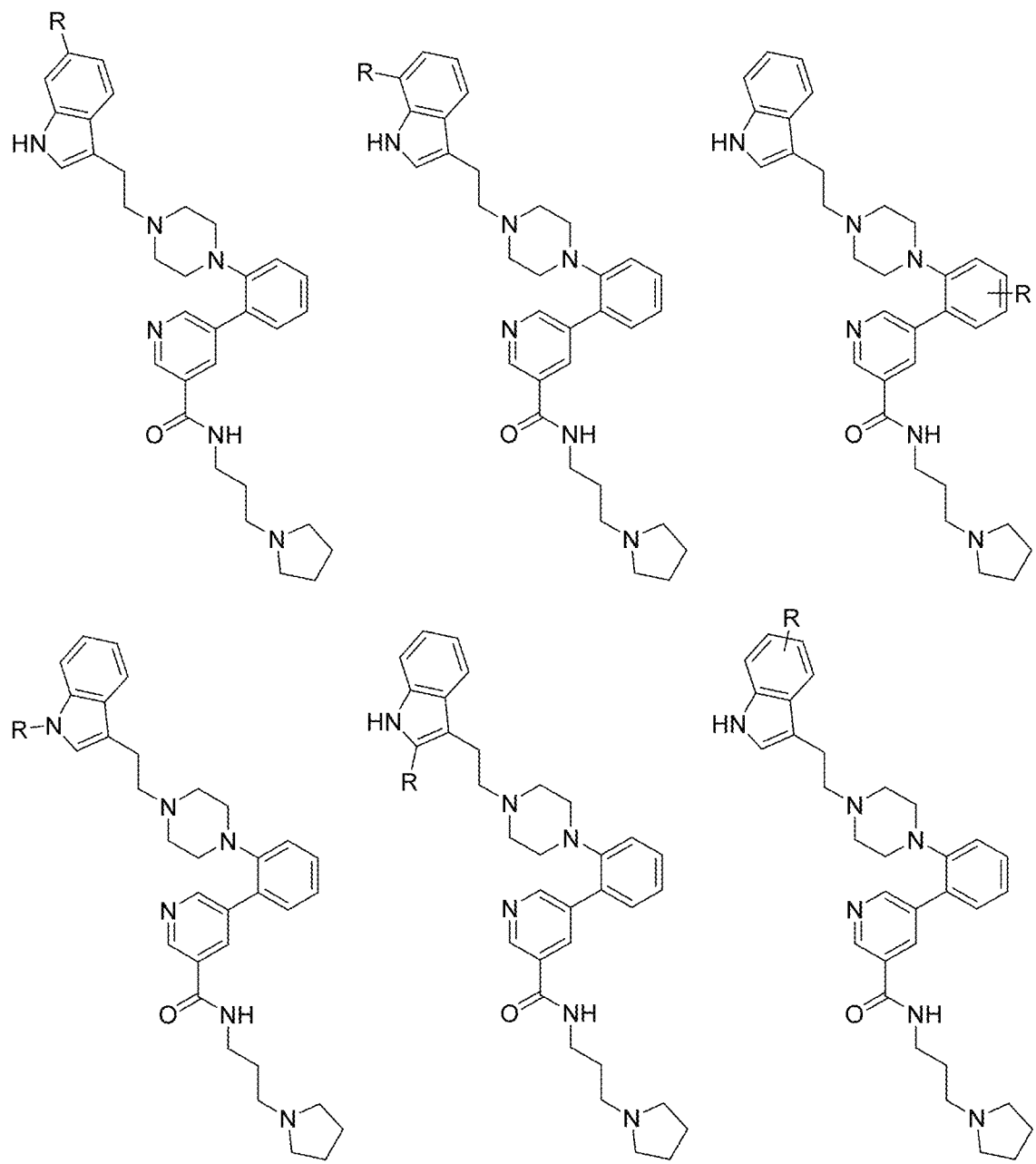
Figure 4I:
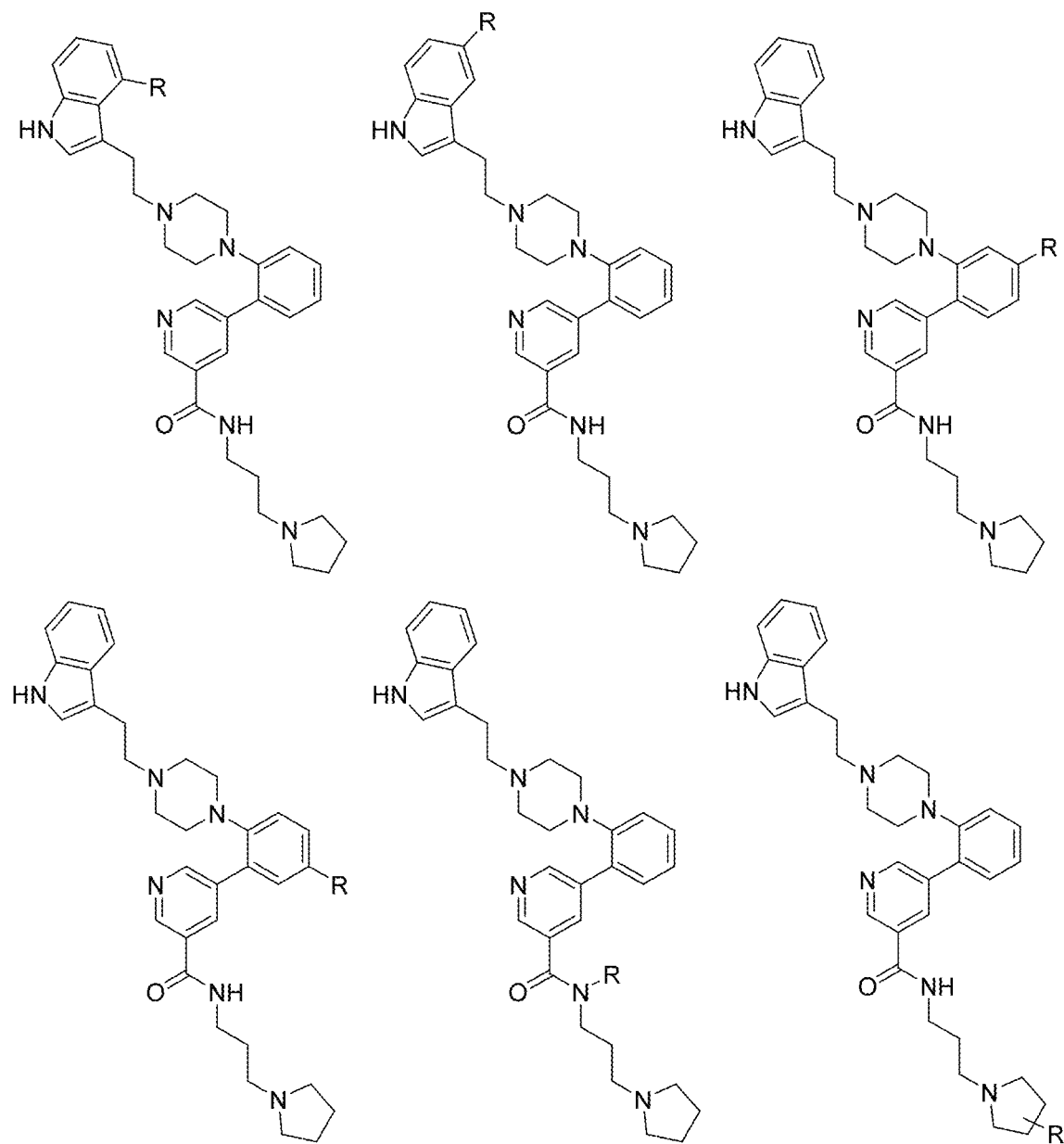
Figure 4J:
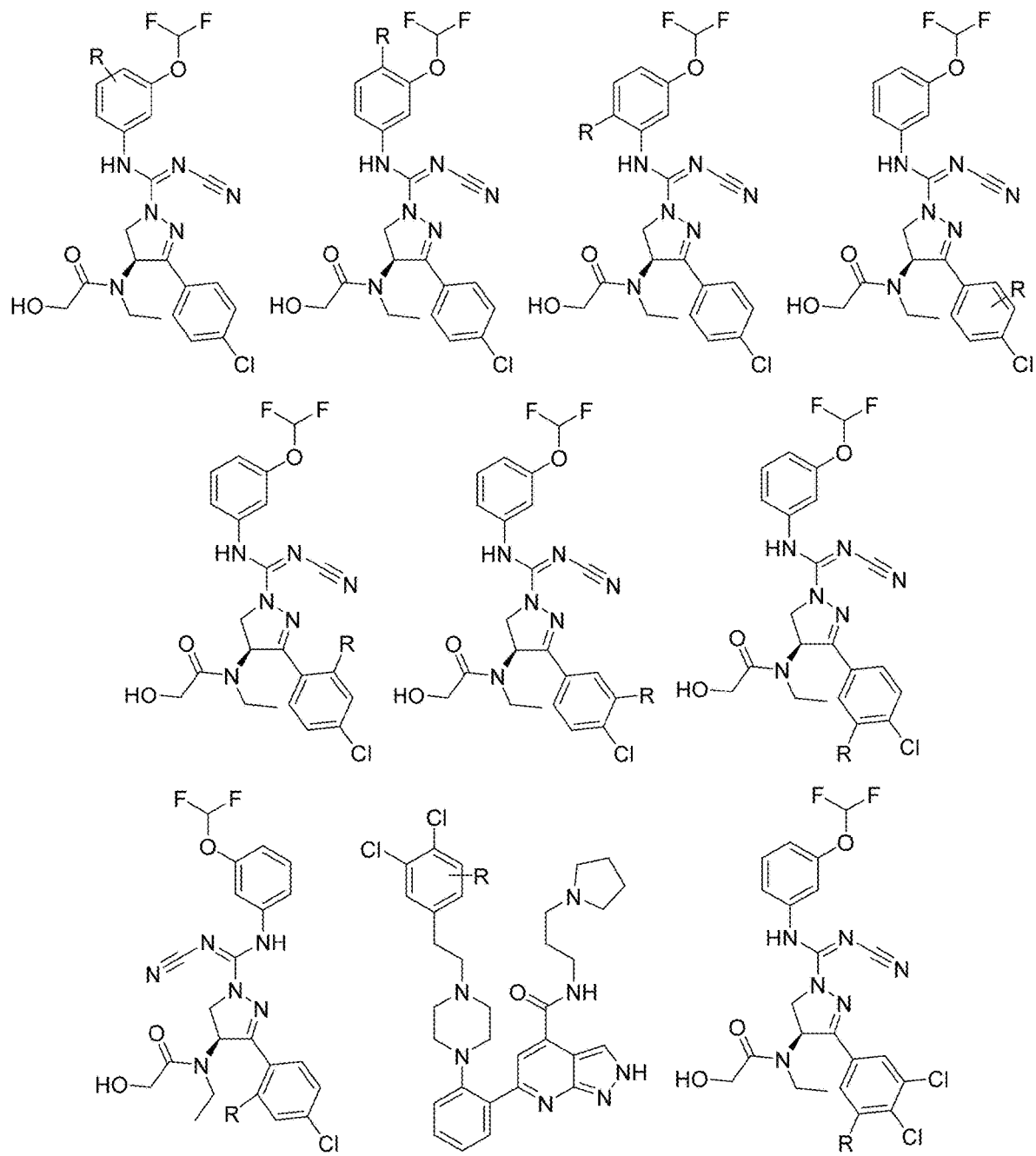
Figure 4K:
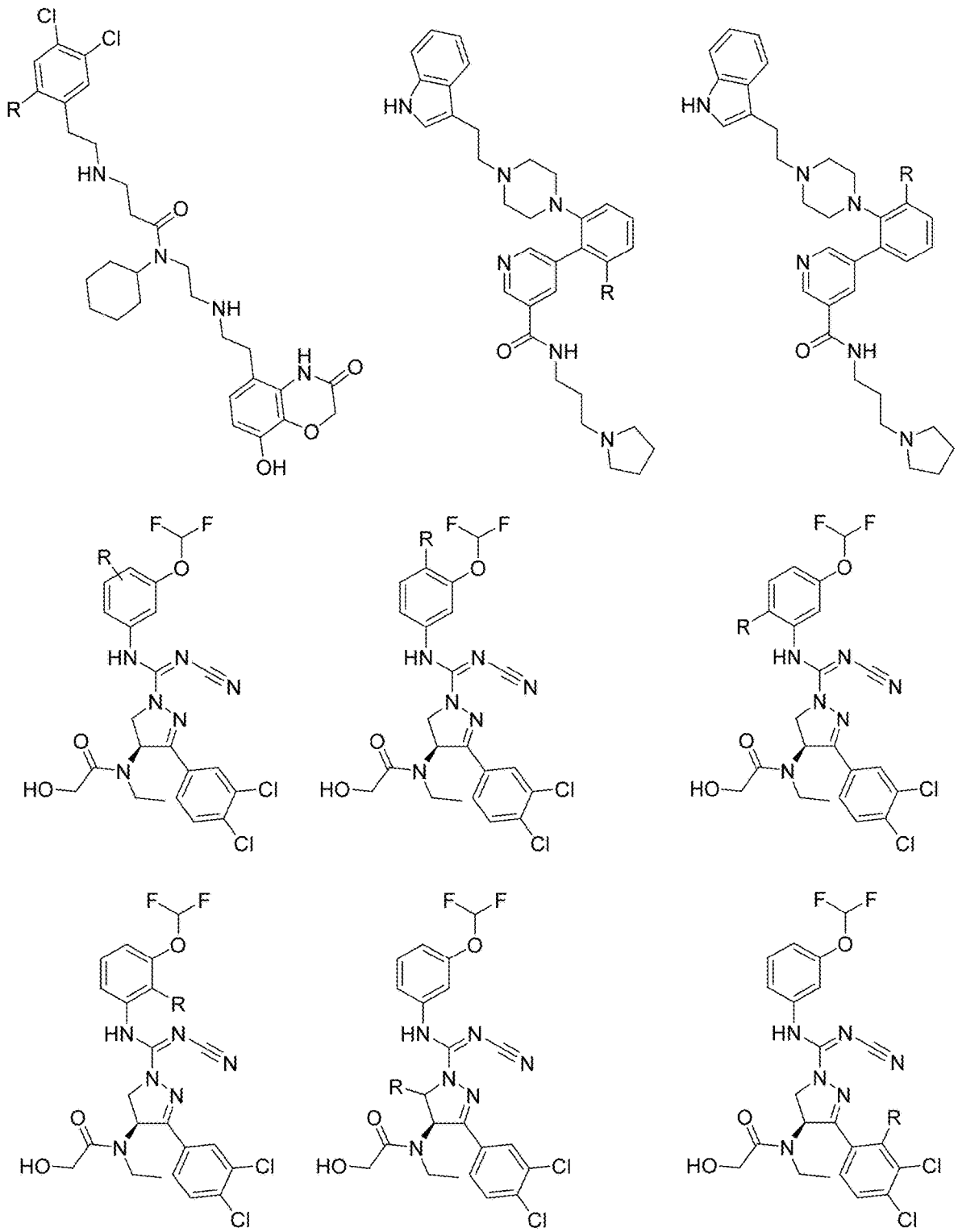
Figure 4L:
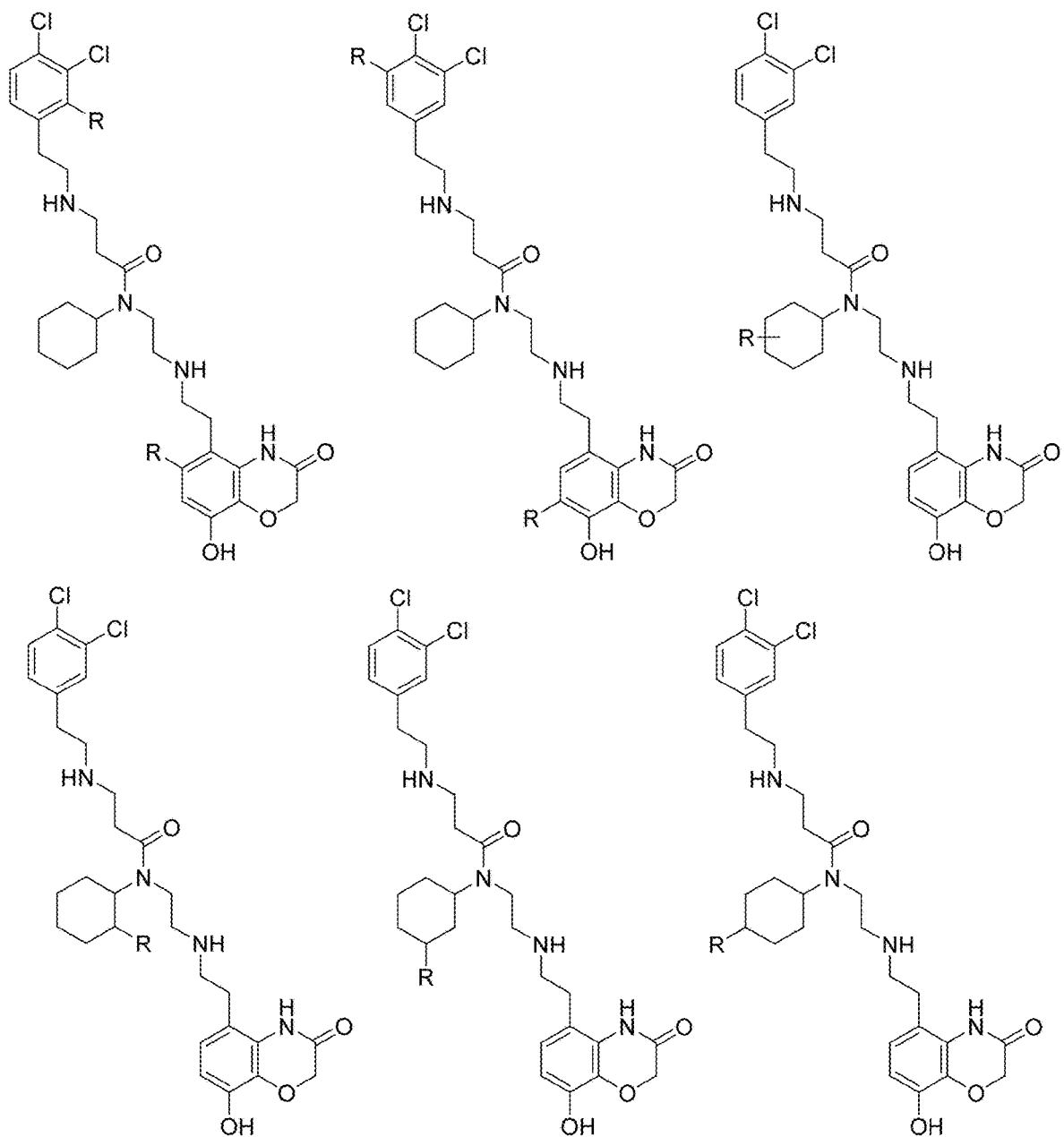
Figure 4M:
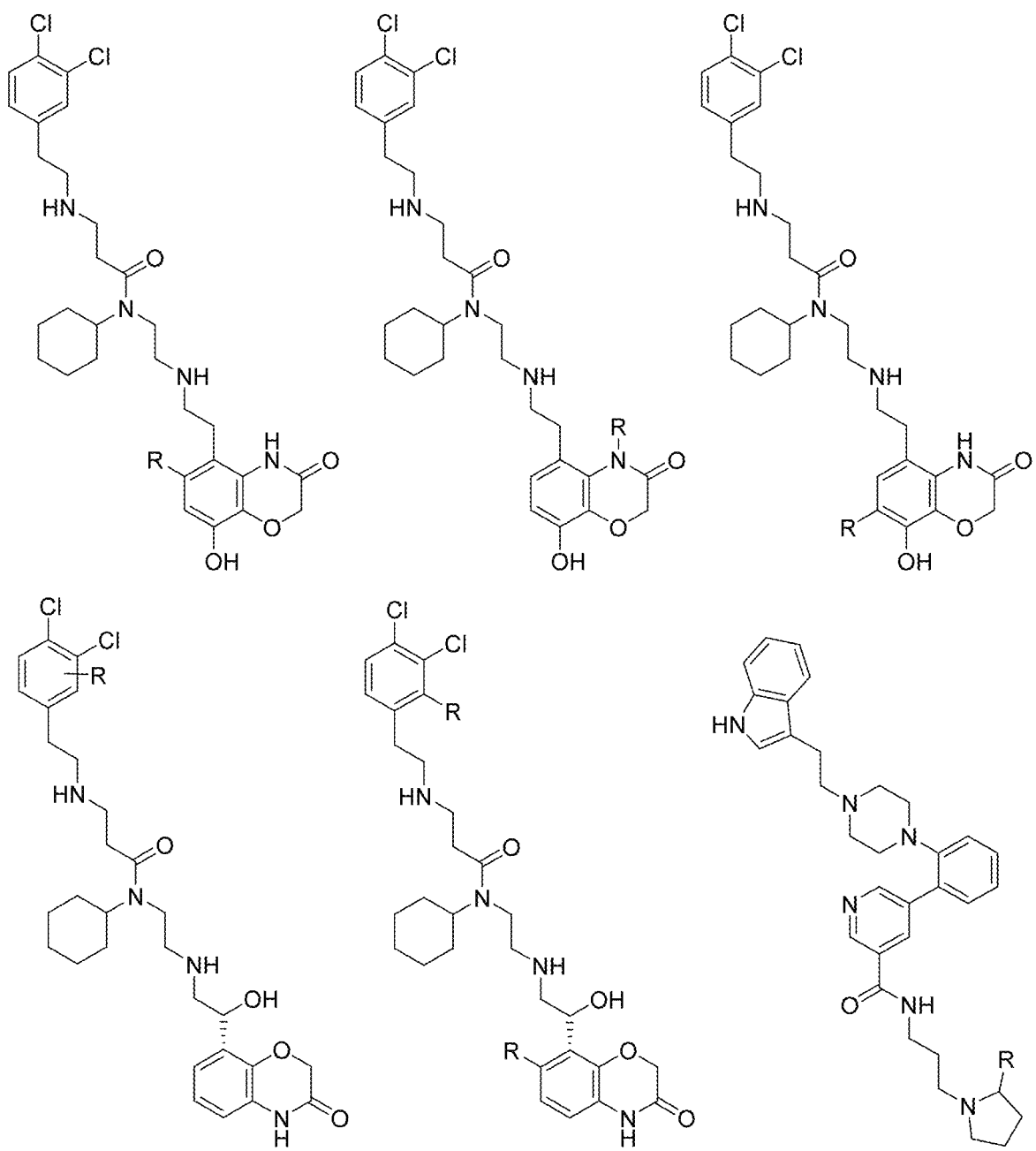
Figure 4N:
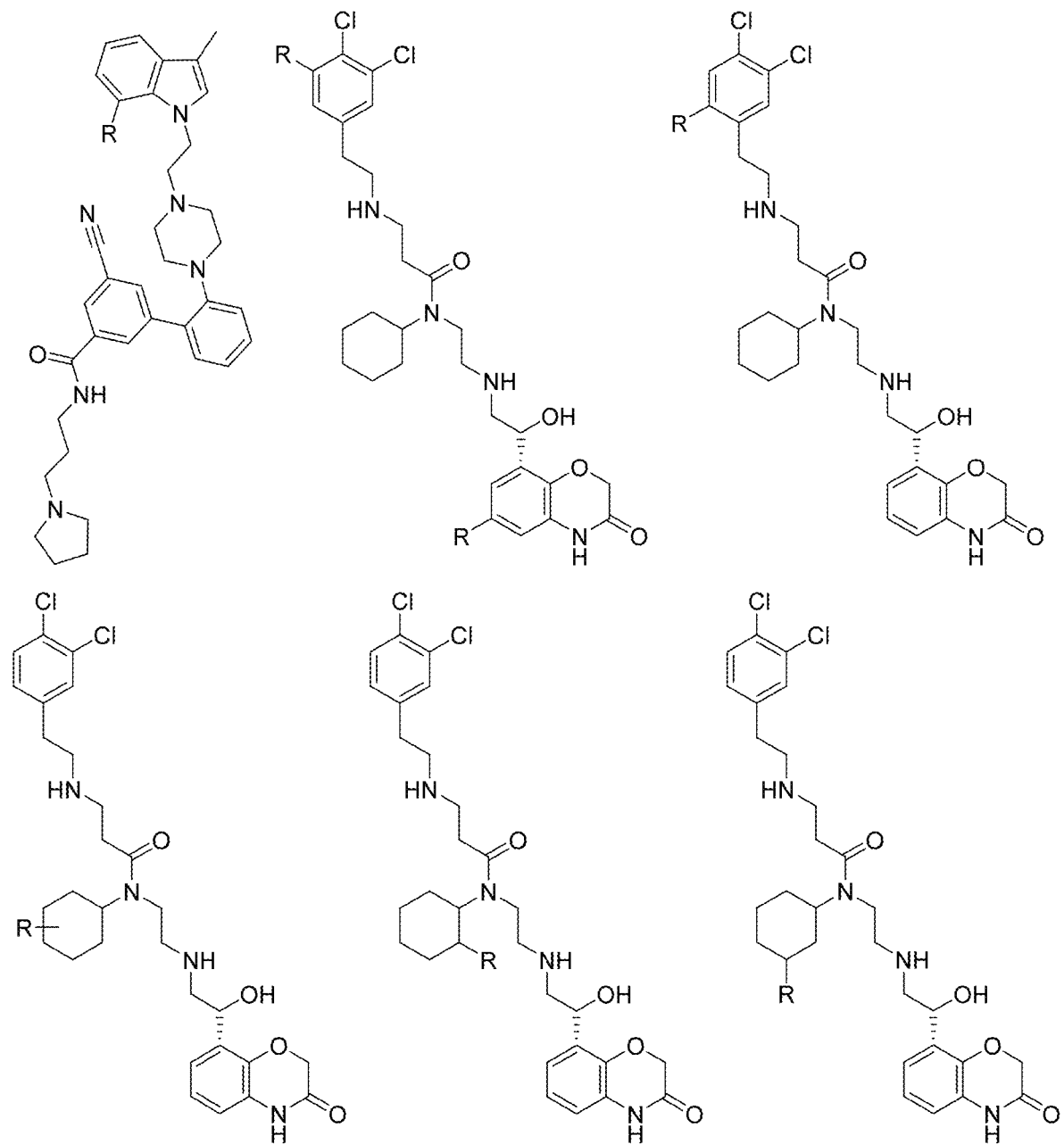
Figure 4O:
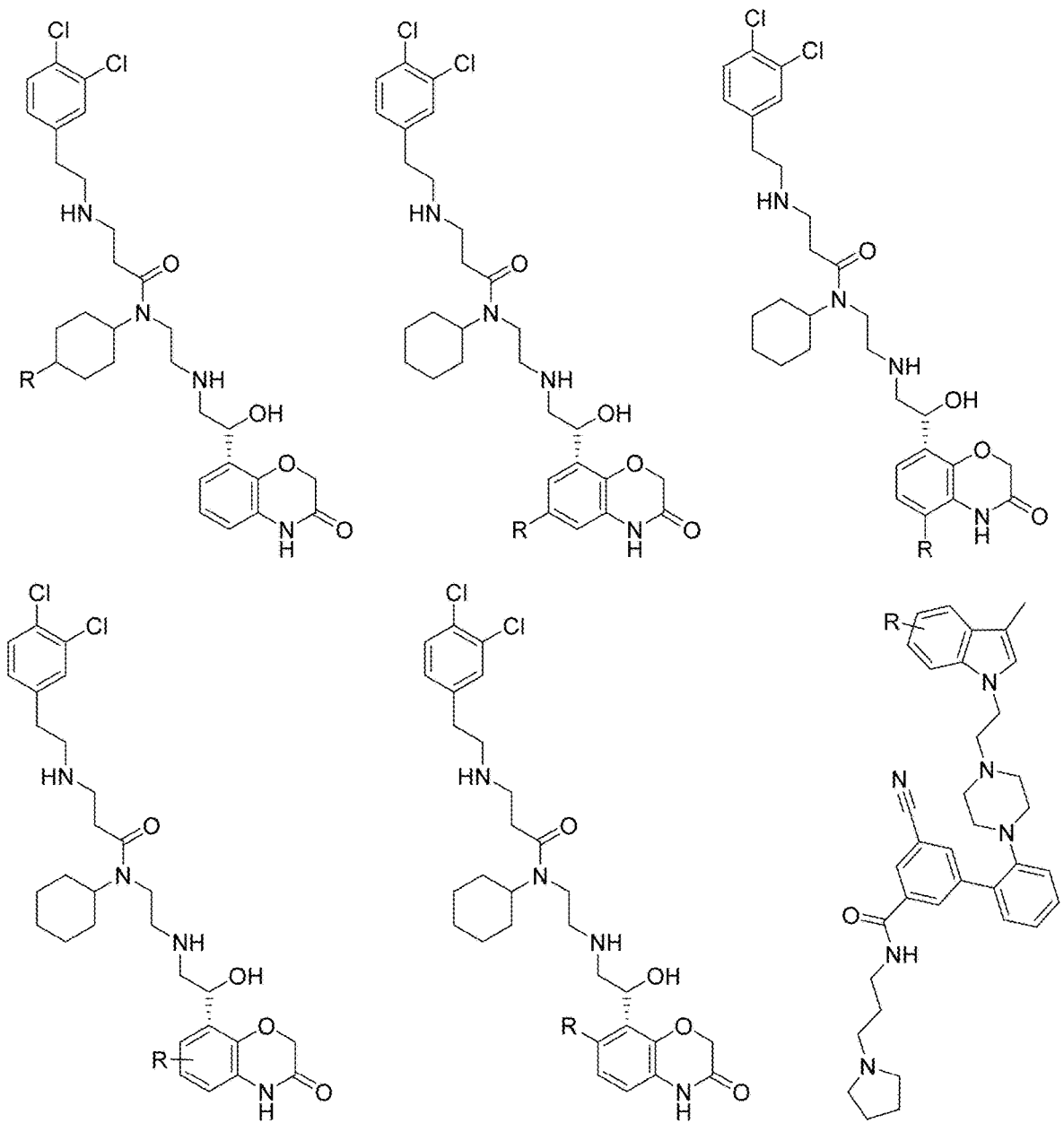
Figure 4P:
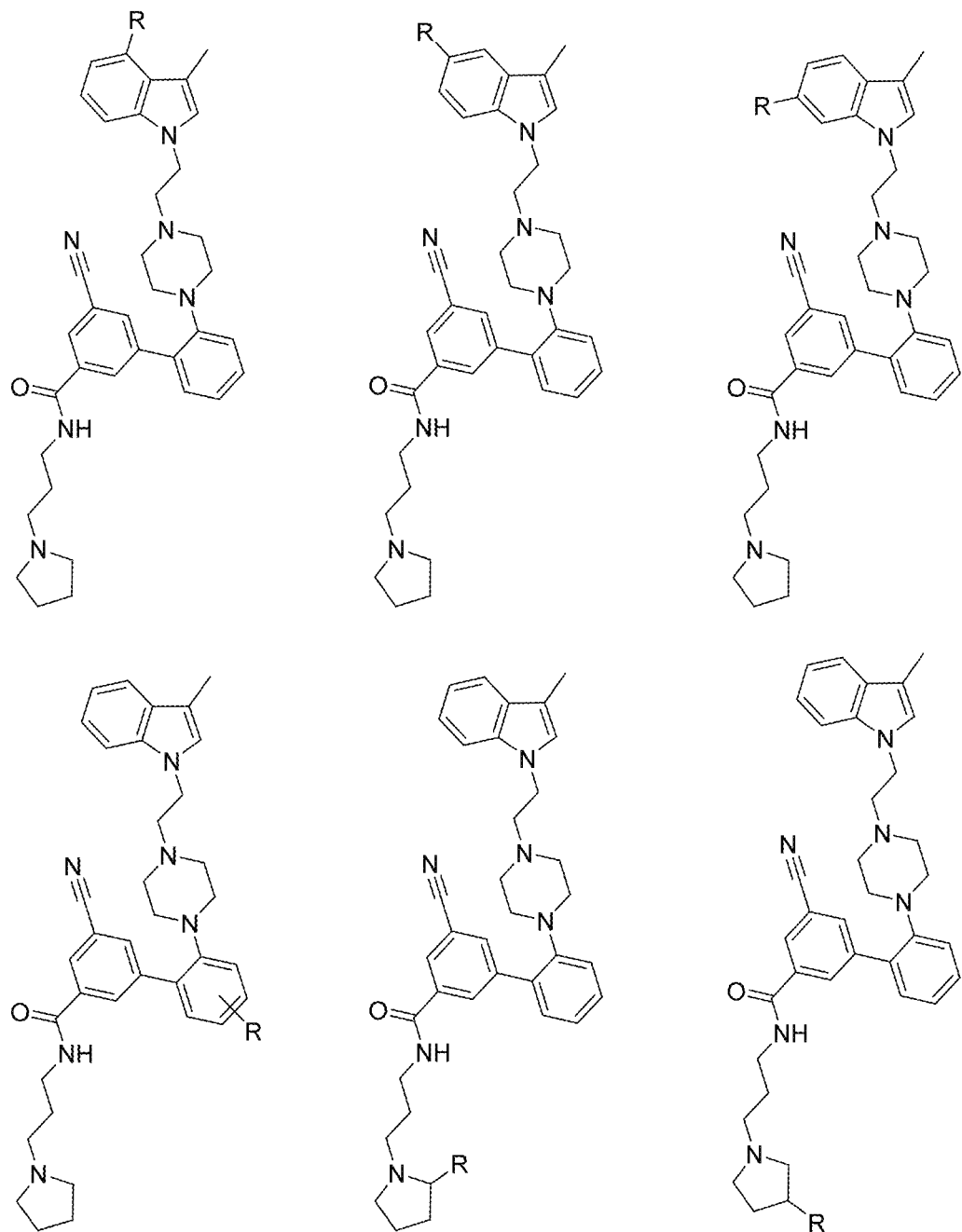
Figure 4Q:
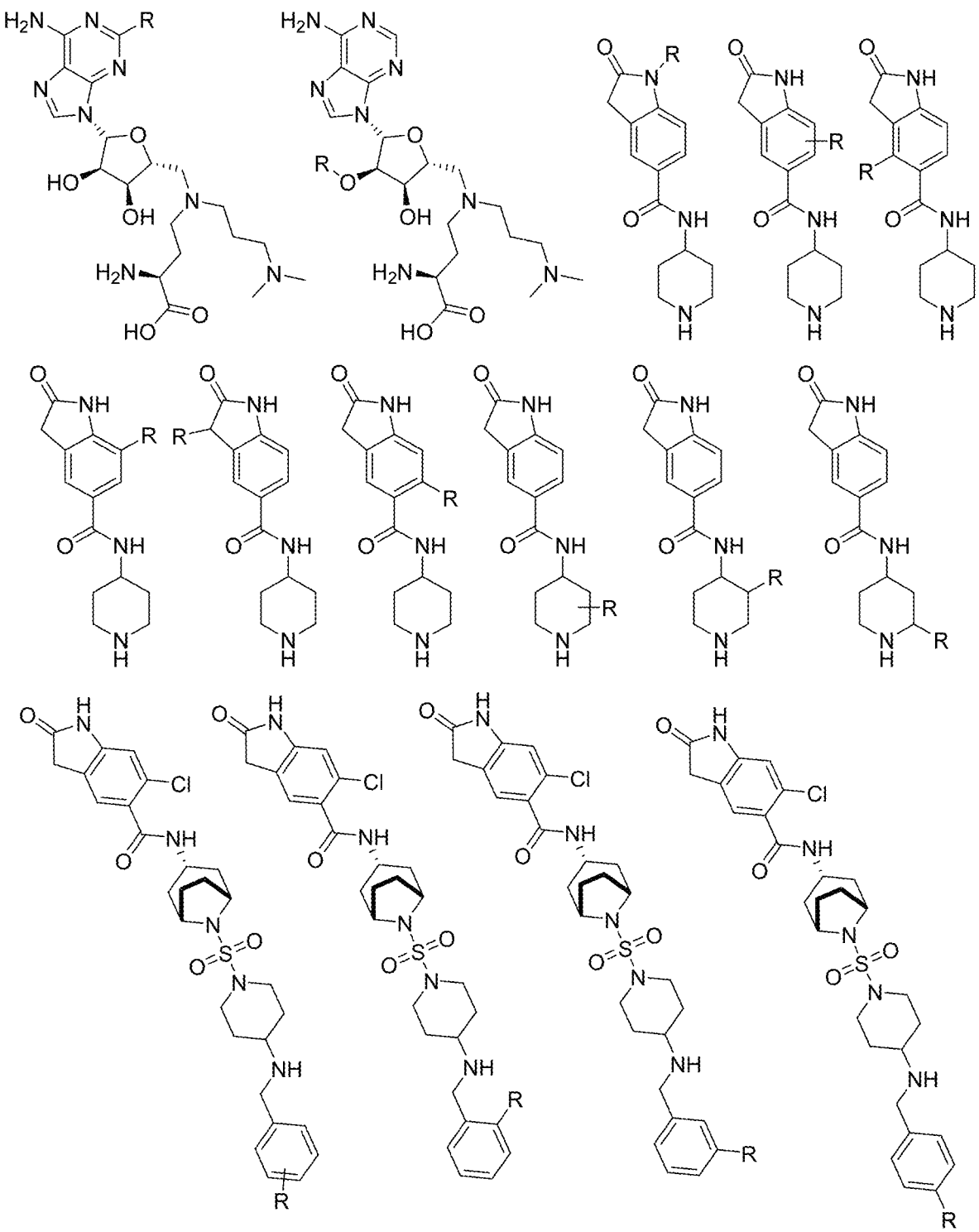
Figure 4R:
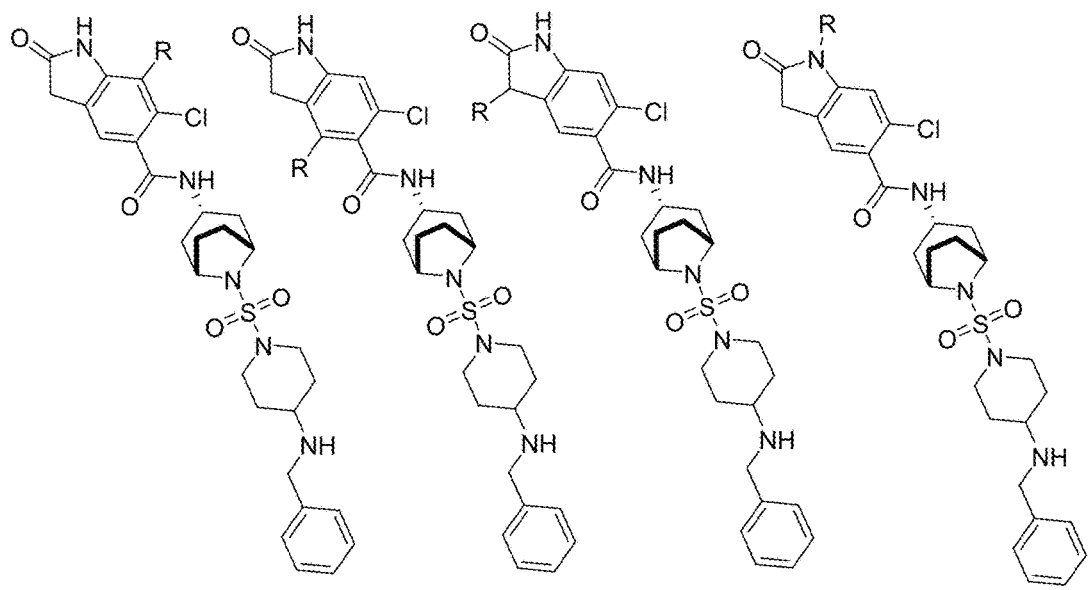
Figure 4S:
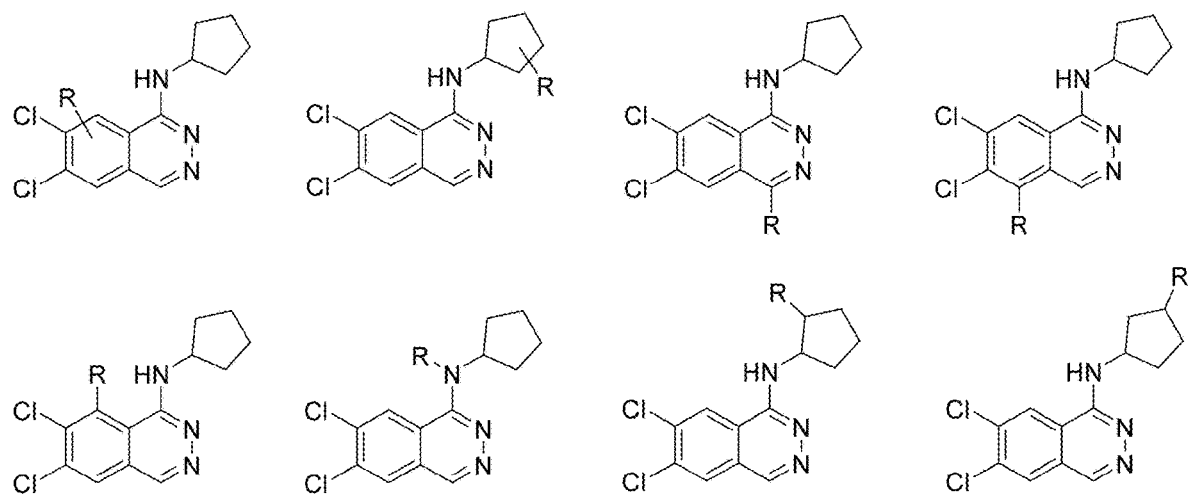
Figure 4T:
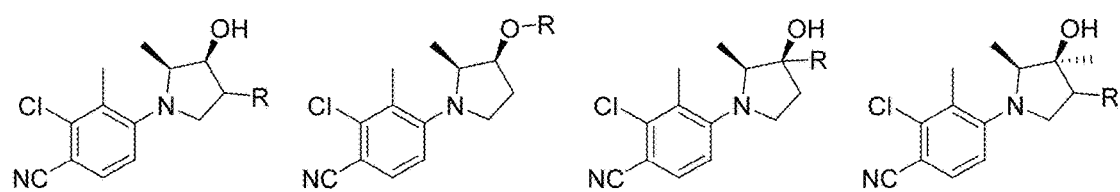
Figure 4U:
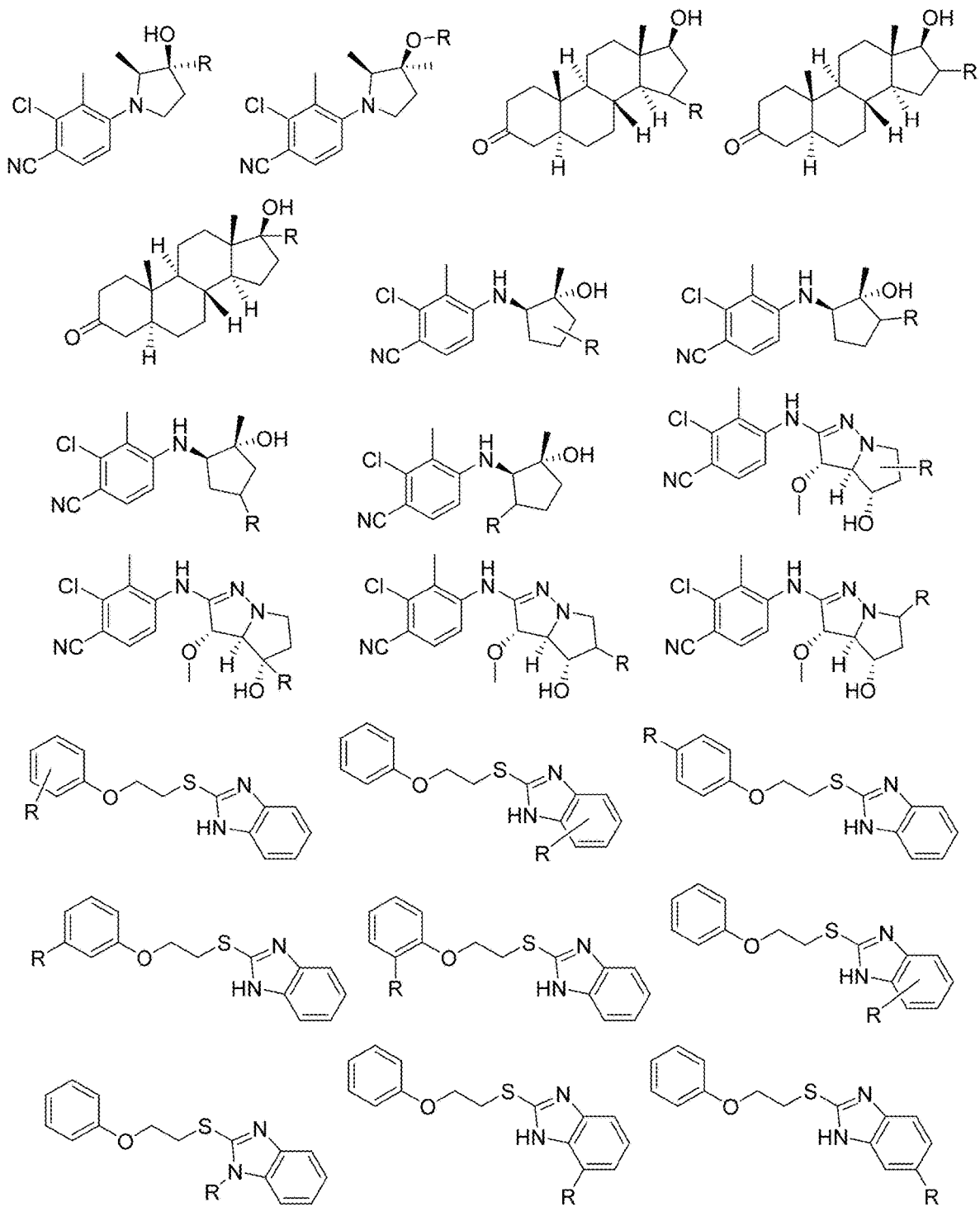
Figure 4V:
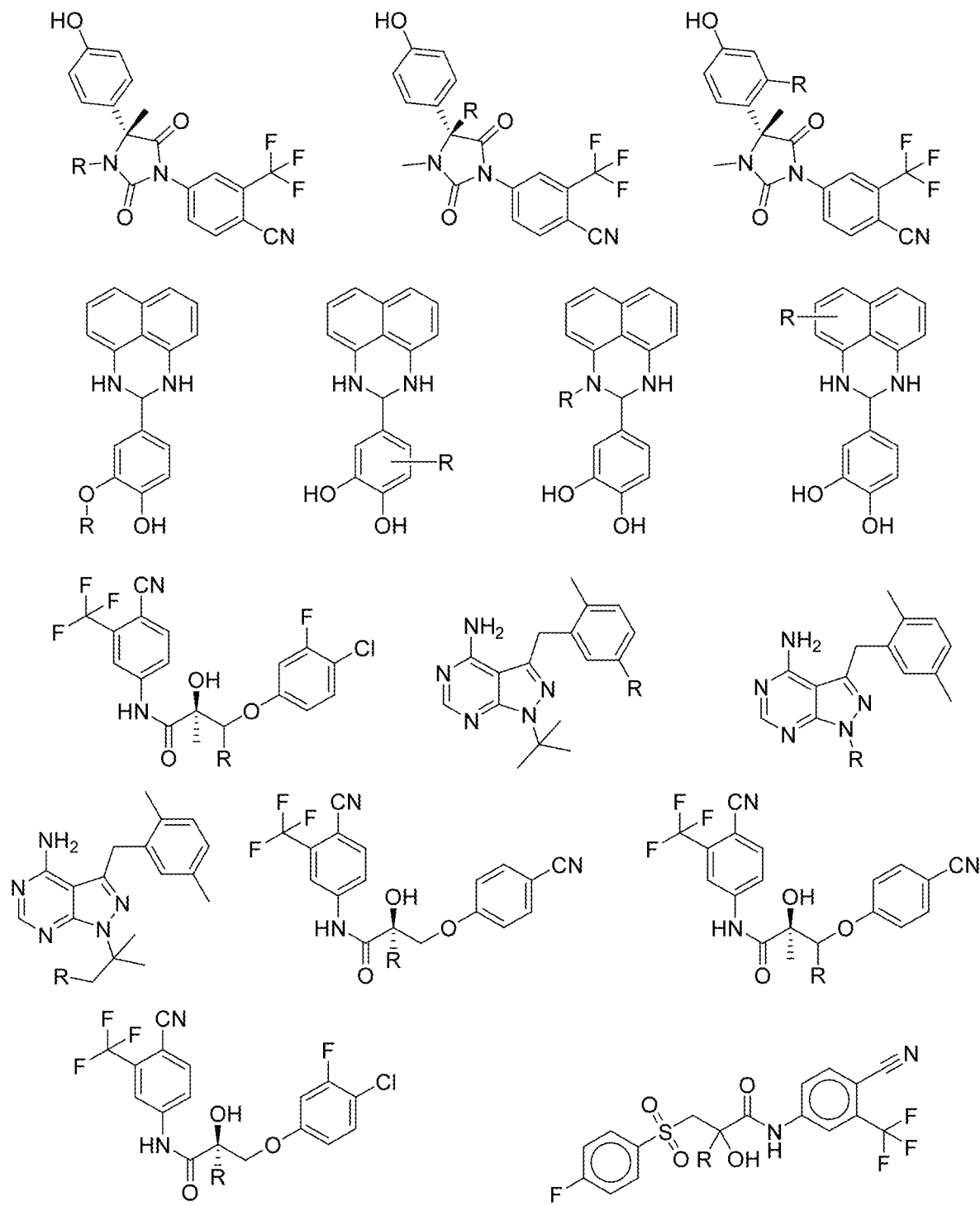
Figure 4W:
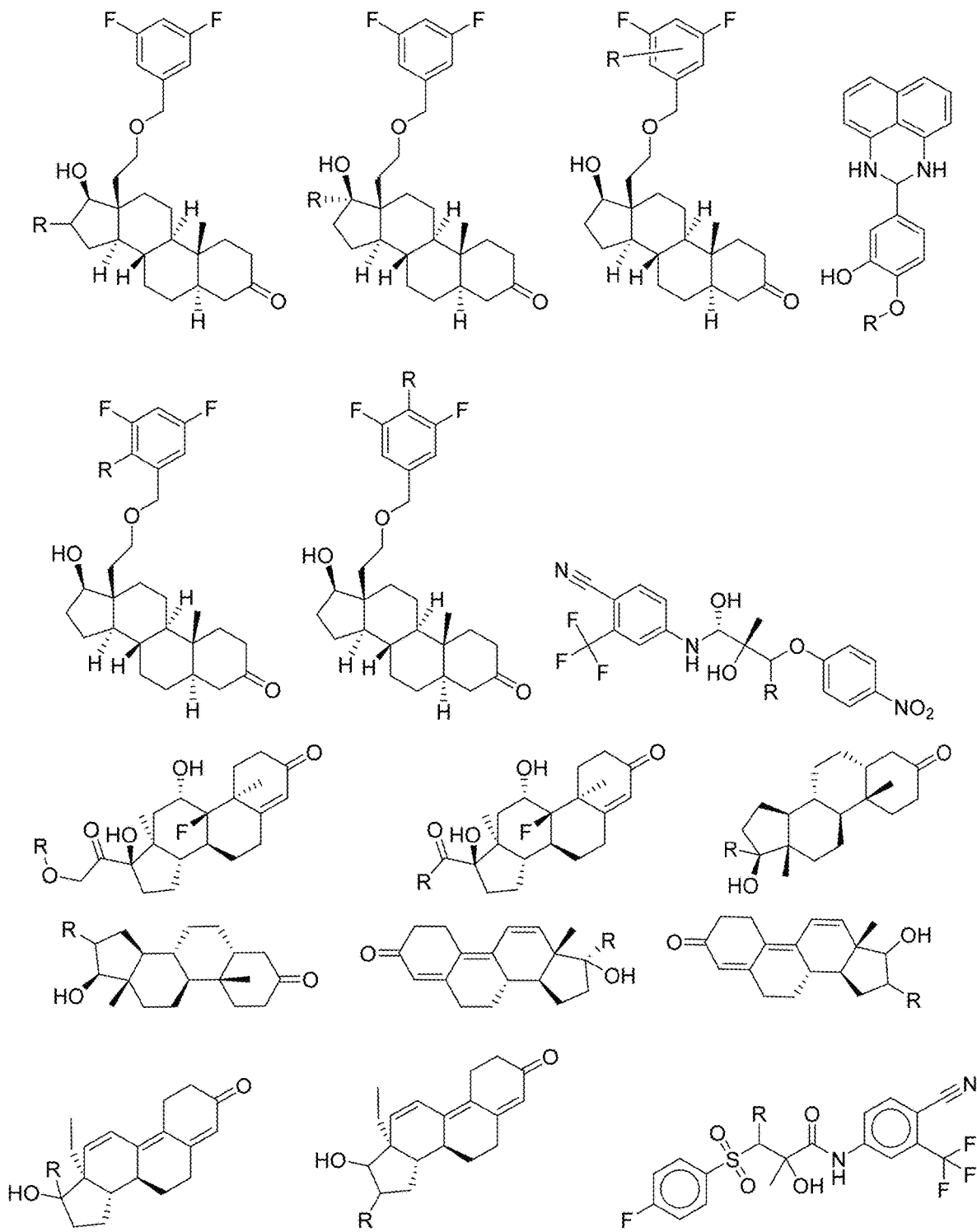
Figure 4X:
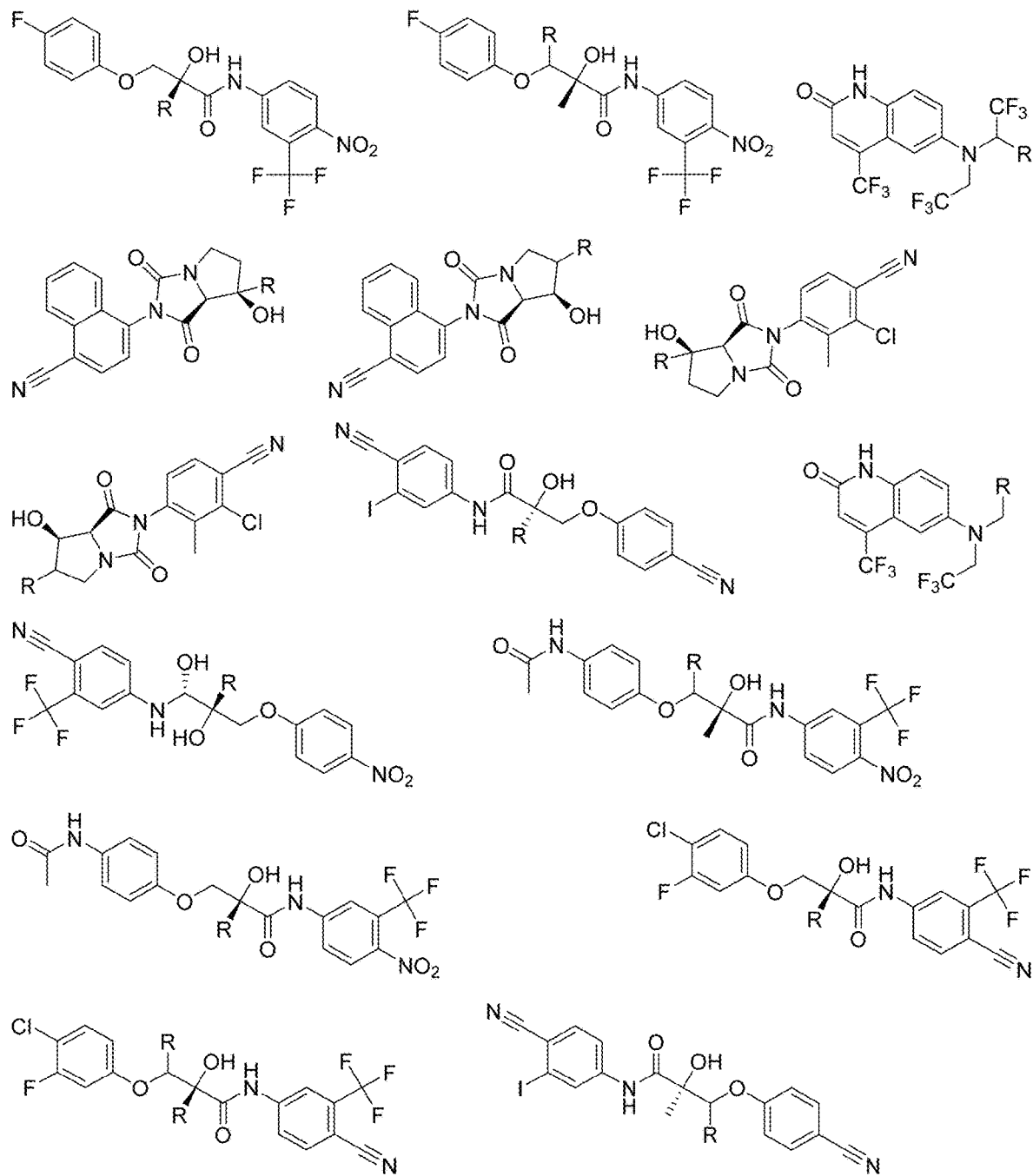
Figure 4Y:
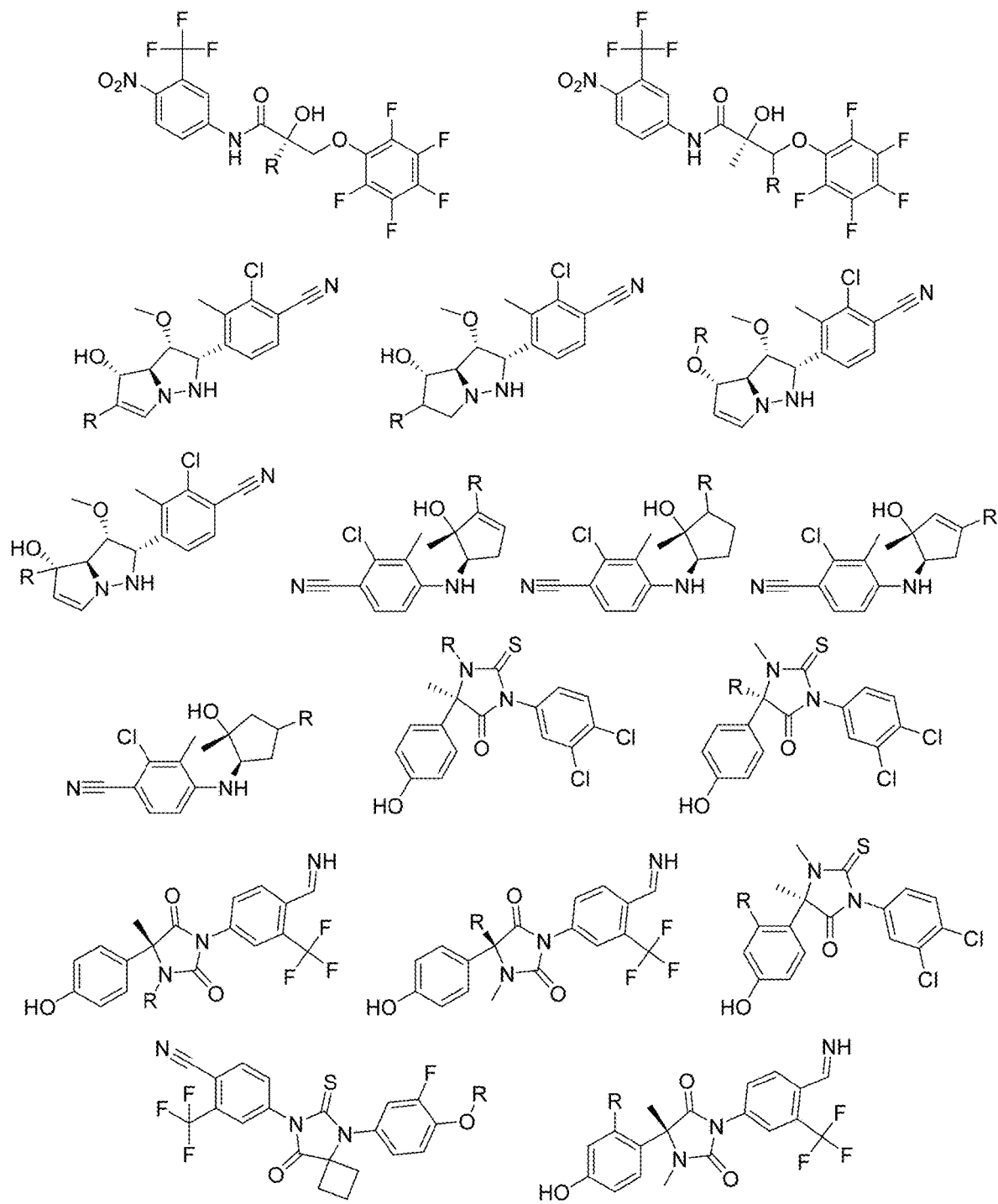
Figure 4Z:
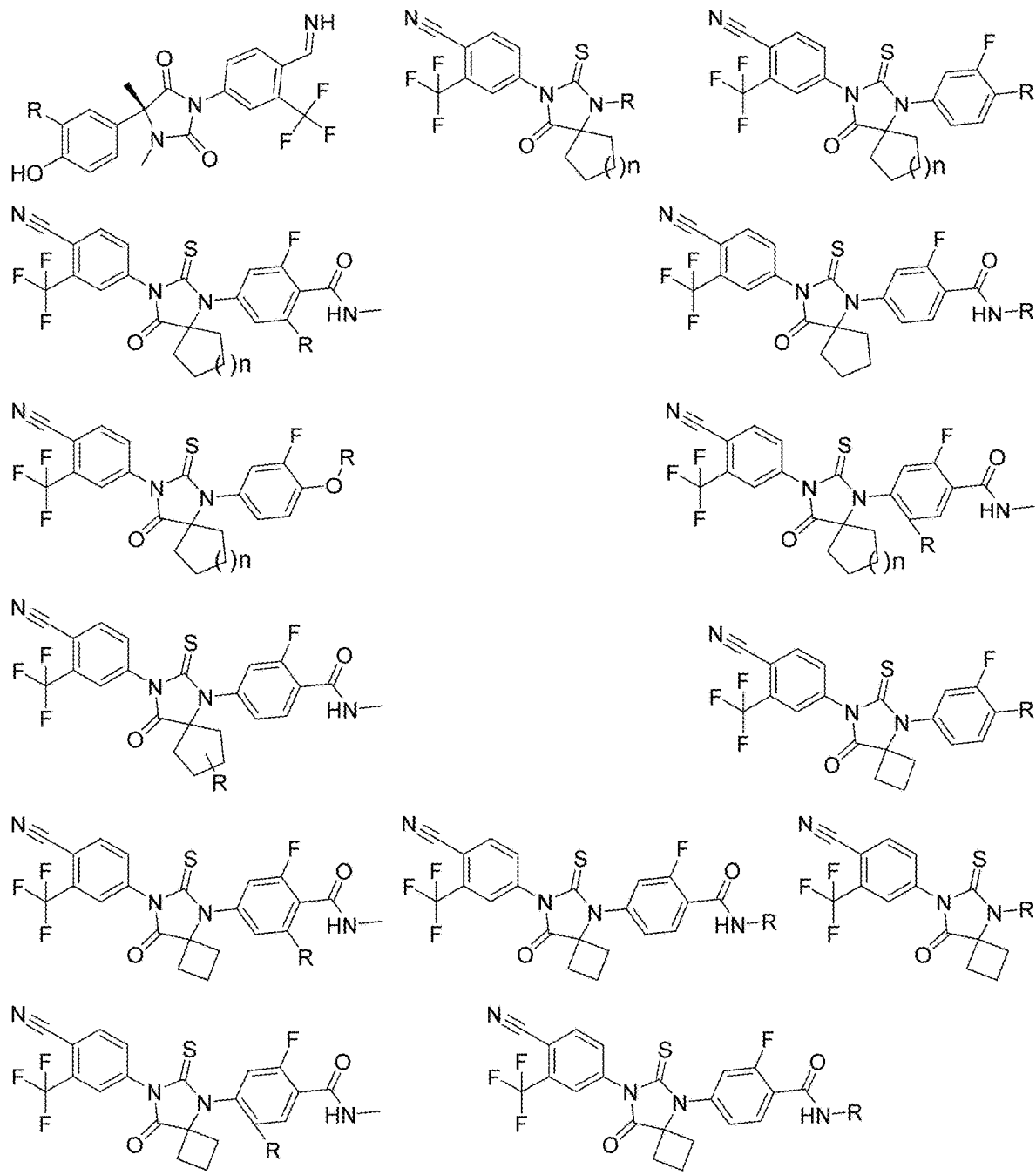
Figure 4A:
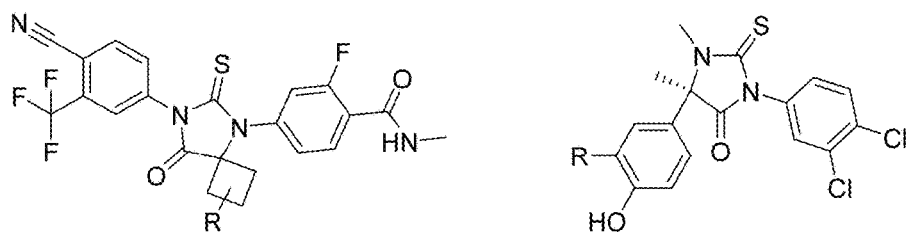
Figure 4B:
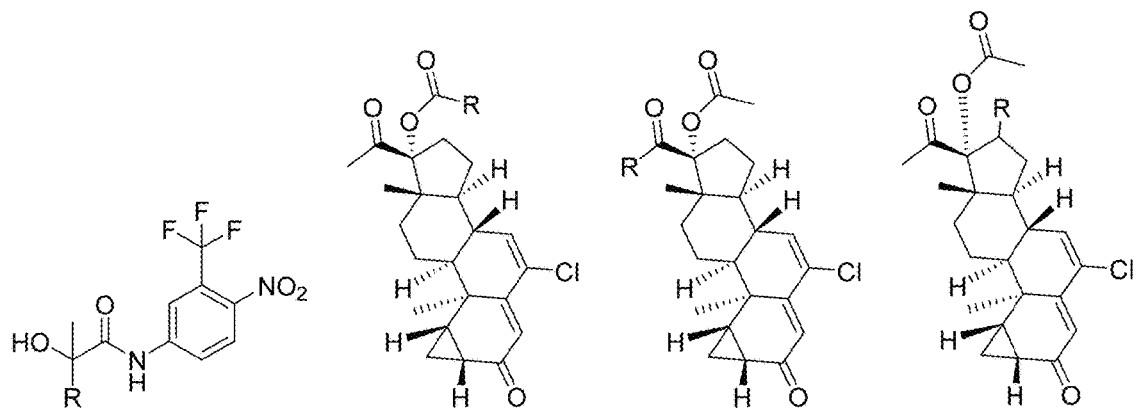
Figure 4C:
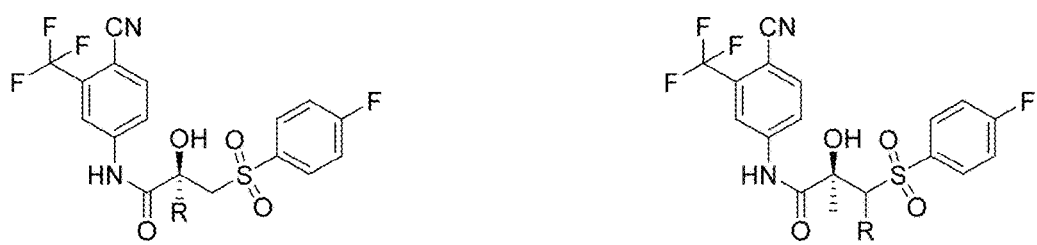
Figure 4D:
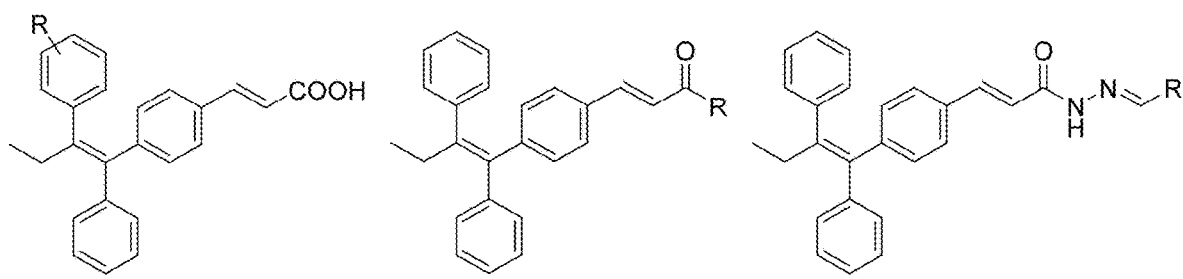
Figure 4E:
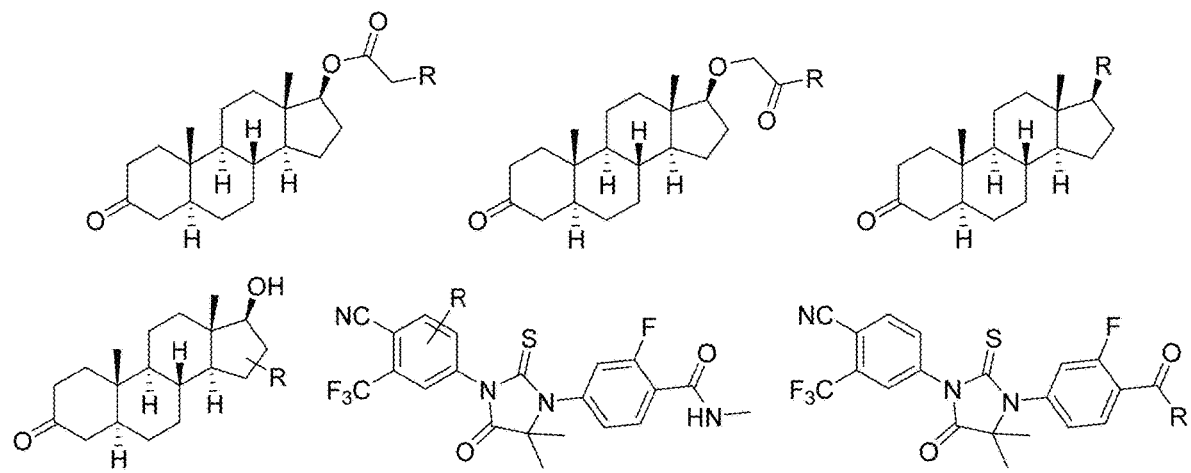

FIG. 4A-4B present examples of SETDB1 Targeting Ligands wherein R is the point at which the Linker is attached. For additional examples and related ligands, see, the PDB crystal structure 5KE2 ("SETDB1 in complex with inhibitor XST06472A", Iqbal A. et al.); the PDB crystal structure 5KE3 ("SETDB1 in complex with fragment MRT0181a", Iqbal A. et al.); the PDB crystal structure 5KH6 ("SETDB1 in complex with fragment methyl 3-(methylsulfonylamino)benzoate", Walker J. R. et al. Structural Genomics Consortium); and, the PDB crystal structure 5KCO ("SETDB1 in complex with [N]-(4-chlorophenyl)methanesulfonamide", Walker J. R. et al.)

FIG. 4C-4P present examples of SMYD2 Targeting Ligands wherein R is the point at which the Linker is attached. For additional examples and related ligands, see, the PDB crystal structure 5KJK ("SMYD2 in complex with inhibitor AZ13450370", Cowen S. D. et al.); the PDB crystal structure 5KJM ("SMYD2 in complex with AZ931", Cowen S. D. et al.); the PDB crystal structure 5KJN ("SMYD2 in complex with AZ506", Cowen S. D. et al.); the PDB crystal structure 5ARF ("SMYD2 in complex with N-[3-(4-chlorophenyl)-1-{N'-cyano-N-[3-(difluoromethoxy)phenyl]carbamimidoyl}-4 5-dihydro-1H-pyrazol-4-YL]-N-ethyl-2-hydroxyacetamide", Eggert E. et al.); the PDB crystal structure 5ARG ("SMYD2 in complex with BAY598", Eggert E. et al.); the PDB crystal structure 4YND ("SMYD2 in complex with A-893", Sweis R. F. et al.); the PDB crystal structure 4WUY ("SMYD2 in complex with LLY-507", Nguyen H. et al.); and, the PDB crystal structure 3S7B ("N-cyclohexyl-N3~-[2-(3 4-dichlorophenyl)ethyl]-N-(2-{[2-(5-hydroxy-3-oxo-3 4-dihydro-2H-1 4-benzoxazin-8-yl)ethyl]amino}ethyl)-beta-alaninamide", Ferguson A. D. et al.).

FIG. 4Q-4R present examples of SMYD3 Targeting Ligands wherein R is the point at which the Linker is attached. For additional examples and related ligands, see, the crystal structure 5H17 ("SMYD3 in complex with 5'-{[(3S)-3-amino-3-carboxypropyl][3-(dimethylamino)propyl]amino}-5'-deoxyadenosine", Van Aller G. S. et al.); the crystal structure 5CCL ("SMYD3 in complex with oxindole compound", Mitchell L. H. et al.); and, the crystal structure 5CCM ("Crystal structure of SMYD3 with SAM and EPZ030456").

FIG. 4S presents examples of SUV4-20H1 Targeting Ligands wherein R is the point at which the Linker is attached. For additional examples and related ligands, see, the PDB crystal structure 5CPR ("SUV4-20H1 in complex with inhibitor A-196", Bromberg K. D. et al.).

FIG. 4T-4AA present examples of Wild Type Androgen Receptor Targeting Ligands wherein R is the point at which the Linker is attached. For additional examples and related ligands, see, the PDB crystal structures 5T8E and 5T8J ("Androgen Receptor in complex with 4-(pyrrolidin-1-yl) benzonitrile derivatives", Asano M. et al.); Asano M. et al. *Bioorg. Med. Chem. Lett.* 27: 1897-1901 (2017); the PDB crystal structure 5JJM ("Androgen Receptor", Nadal M. et al.); the PDB crystal structure 5CJ6 ("Androgen Receptor in complex with 2-Chloro-4-[[(1R 2R)-2-hydroxy-2-methyl-cyclopentyl]amino]-3-methyl-benzonitrile derivatives", Saeed A. et al.); the PDB crystal structure 4QL8 ("Androgen Receptor in complex with 3-alkoxy-pyrrolo[1 2-b]pyrazolines derivatives", Ullrich T. et al.); the PDB crystal structure 4HLW ("Androgen Receptor Binding Function 3 (BF3) Site of the Human Androgen Receptor through Virtual Screening", Munuganti R. S. et al.); the PDB crystal structure 3V49 ("Androgen Receptor lbd with activator peptide and sarm inhibitor 1", Nique F. et al.); Nique F. et al. *J. Med Chem.* 55: 8225-8235 (2012); the PDB crystal structure 2YHD ("Androgen Receptor in complex with AF2 small molecule inhibitor", Axerio-Cilies P. et al.); the PDB crystal structure 3RLJ ("Androgen Receptor ligand binding domain in complex with SARM S-22", Bohl C. E. et al.); Bohl C. E. et al. *J. Med Chem.* 54: 3973-3976 (2011); the PDB crystal structure 3B5R ("Androgen Receptor ligand binding domain in complex with SARM C-31", Bohl C. E. et al.); Bohl C. E. et al. *Bioorg. Med Chem. Lett.* 18: 5567-5570 (2008); the PDB crystal structure 2PIP ("Androgen Receptor ligand binding domain in complex with small molecule", Estebanez-Perpina E. et al.); Estebanez-Perpina. E. *Proc. Natl. Acad Sci.* 104:16074-16079 (2007); the PDB crystal structure 2PNU ("Androgen Receptor ligand binding domain in complex with EM5744", Cantin L. et al.); and, the PDB crystal structure 2HVC ("Androgen Receptor ligand binding domain in complex with LGD2226", Wang F. et al.). For additional related ligands, see, Matias P. M. et al. "Structural Basis for the Glucocorticoid Response in a Mutant Human Androgen Receptor (Ar(Ccr)) Derived from an Androgen-Independent Prostate Cancer." *J. Med Chem.* 45: 1439 (2002); Sack J. S. et al. "Crystallographic structures of the ligand-binding domains of the androgen receptor and its T877A mutant complexed with the natural agonist dihydrotestosterone." *Proc. Natl. Acad Sci.* 98: 4904-4909

(2001); He B. et al. "Structural basis for androgen receptor interdomain and coactivator interactions suggests a transition in nuclear receptor activation function dominance." *Mol. Cell* 16: 425-438 (2004); Pereira de Jesus-Tran K. "Comparison of crystal structures of human androgen receptor ligand-binding domain complexed with various agonists reveals molecular determinants responsible for binding affinity." *Protein Sci.* 15: 987-999 (2006); Bohl C. E. et al. "Structural Basis for Accommodation of Nonsteroidal Ligands in the Androgen Receptor." *Mol Pharmacol.* 63(1): 211-23 (2003); Sun C. et al. "Discovery of potent orally-active and muscle-selective androgen receptor modulators based on an N-aryl-hydroxybicyclohydantoin scaffold." *J. Med Chem.* 49: 7596-7599 (2006); Nirschl A. A. et al. "N-aryl-oxazolidin-2-imine muscle selective androgen receptor modulators enhance potency through pharmacophore reorientation." *J. Med Chem.* 52: 2794-2798 (2009); Bohl C. E. et al. "Effect of B-ring substitution pattern on binding mode of propionamide selective androgen receptor modulators." *Bioorg. Med Chem. Lett.* 18: 5567-5570 (2008); Ullrich T. et al. "3-alkoxy-pyrrolo[1 2-b]pyrazolines as selective androgen receptor modulators with ideal physicochemical properties for transdermal administration." *J. Med Chem.* 57: 7396-7411 (2014); Saeed A. et al. "2-Chloro-4-[[(1R 2R)-2-hydroxy-2-methyl-cyclopentyl] amino]-3-methyl-benzonitrile: A Transdermal Selective Androgen Receptor Modulator (SARM) for Muscle Atrophy." *J. Med Chem.* 59: 750-755 (2016); Nique et al. "Discovery of diarylhydantoins as new selective androgen receptor modulators." *J. Med Chem.* 55: 8225-8235 (2012); and, Michael E. Jung et al. "Structure-Activity Relationship for Thiohydantoin Androgen Receptor Antagonists for Castration-Resistant Prostate Cancer (CRPC)." *J. Med Chem.* 53: 2779-2796 (2010).

FIG. 4BB presents examples of Mutant T877A Androgen Receptor Targeting Ligands wherein R is the point at which the Linker is attached. For additional examples and related ligands, see, the PDB crystal structure 4OGH ('Androgen Receptor T877A-AR-LBD", Hsu C. L. et al.) and the PDB crystal structure 2OZ7 ("Androgen Receptor T877A-AR-LBD", Bohl C. E. et al.).

FIG. 4CC presents examples of Mutant W741L Androgen Receptor Targeting Ligands wherein R is the point at which the Linker is attached. For additional examples and related ligands, see, the PDB crystal structure 4OJB ("Androgen Receptor T877A-AR-LBD", Hsu C. L. et al.).

FIG. 4DD-4EE presents examples of Estrogen and/or Androgen Targeting Ligands wherein R is the point at which the Linker is attached.

Figure 5A:
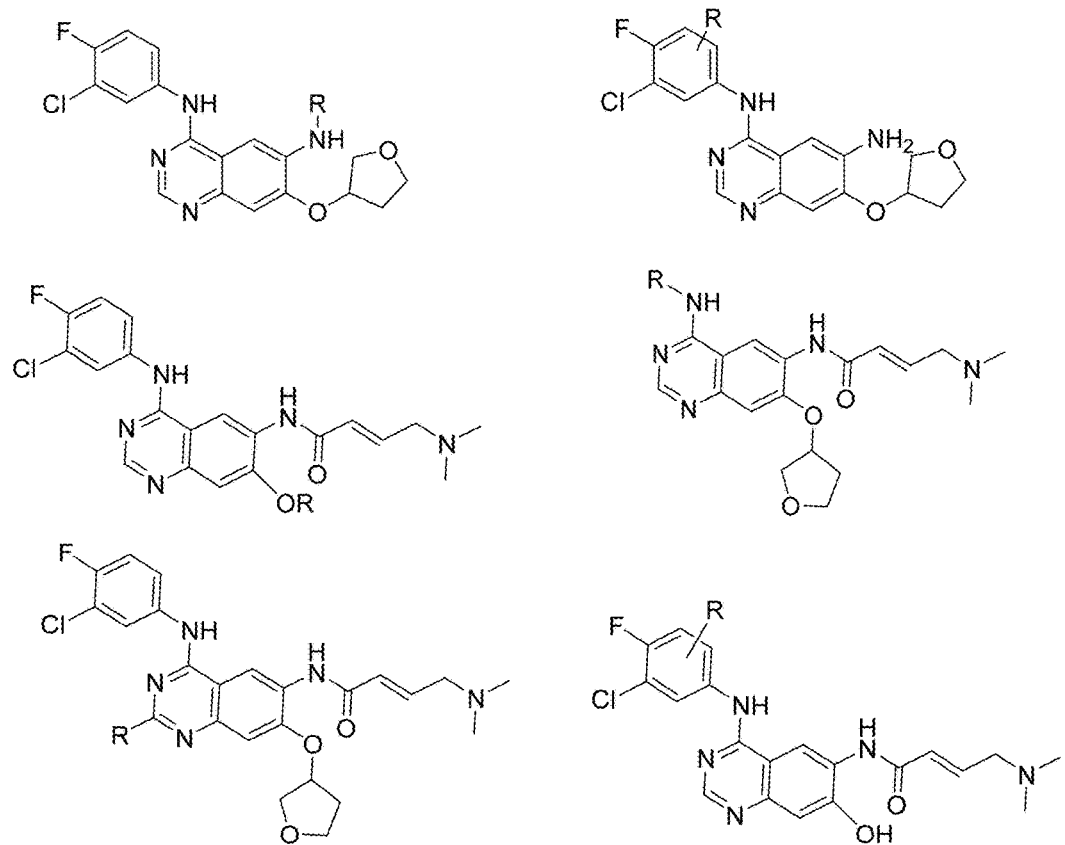

FIG. 5A presents examples of Afatinib, a Targeting Ligands for the EGFR and ErbB2/4 receptors. R is the point at which the Linker is attached.

Figure 5B:
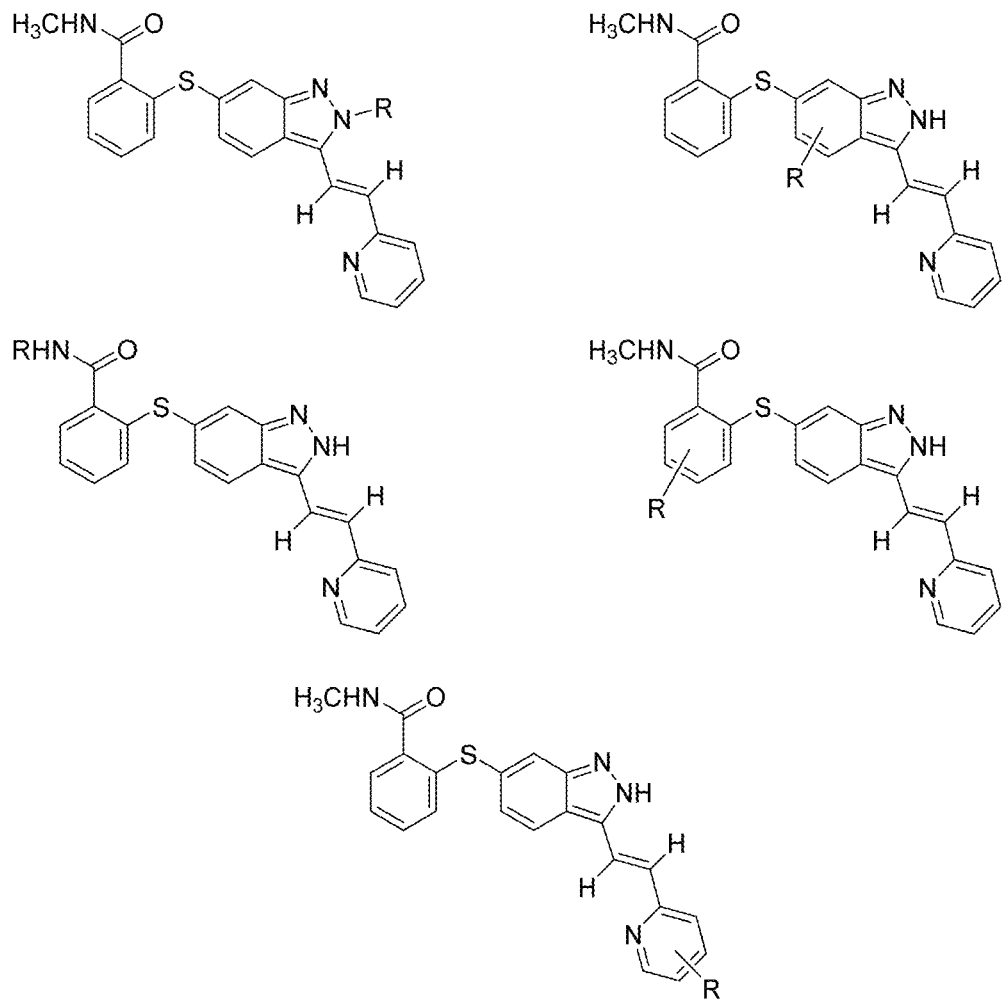

FIG. 5B presents examples of Axitinib, a Targeting Ligands for the VEGFR1/2/3, PDGFRβ, and Kit receptors. R is the point at which the Linker is attached.

Figure 5C:
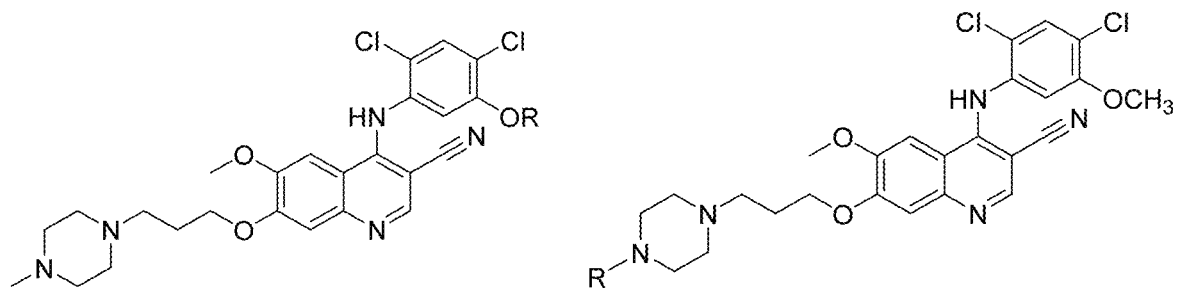
Figure 5D:
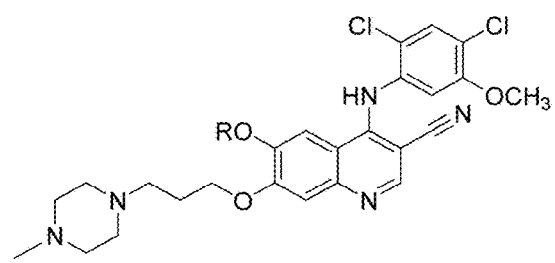

FIG. 5C-5D present examples of Bosutinib, a Targeting Ligands for the BCR-Abl, Src, Lyn and Hck receptors. R is the point at which the Linker is attached.

Figure 5E:
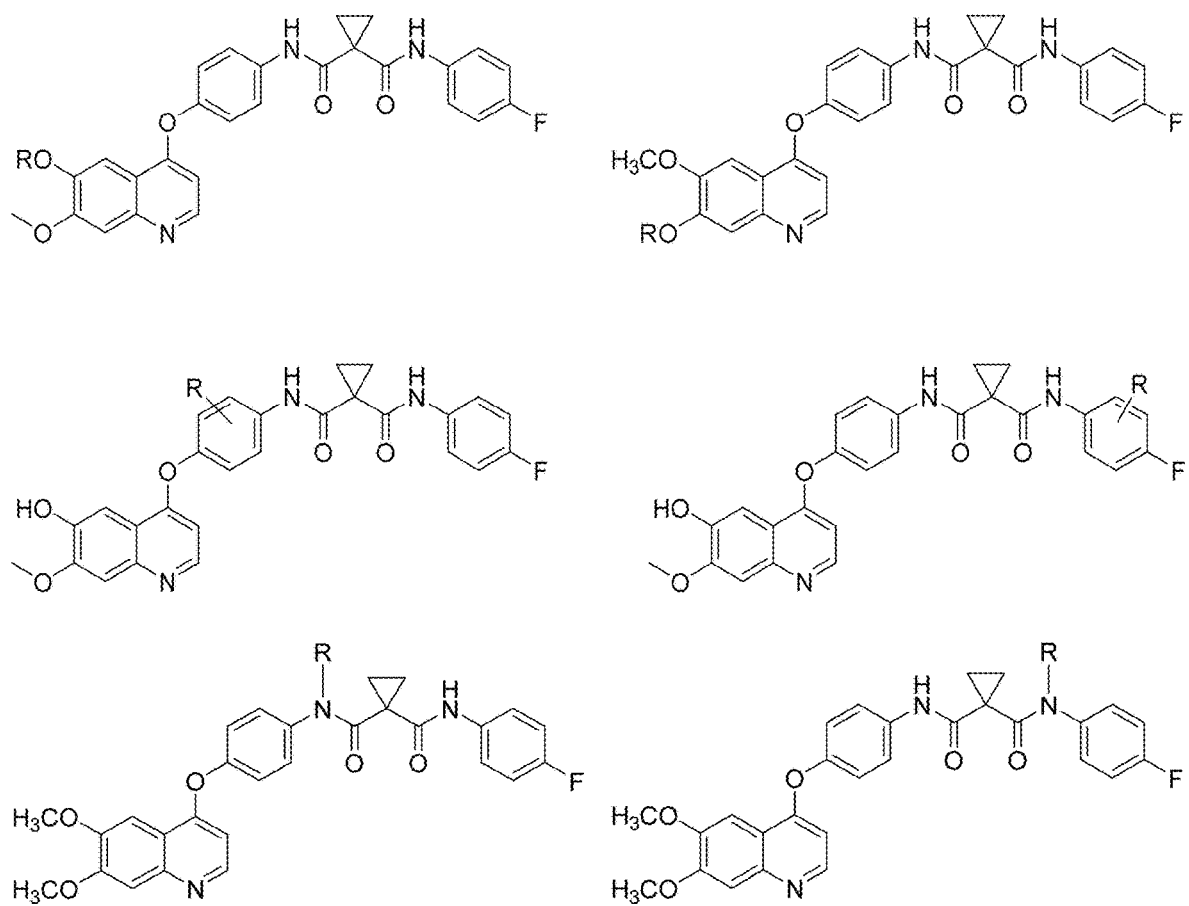

FIG. 5E presents examples of Cabozantinib, a Targeting Ligands for the RET, c-Met, VEGFR1/2/3, Kit, TrkB, Flt3, Axl, and Tie 2 receptors. R is the point at which the Linker is attached.

Figure 5F:
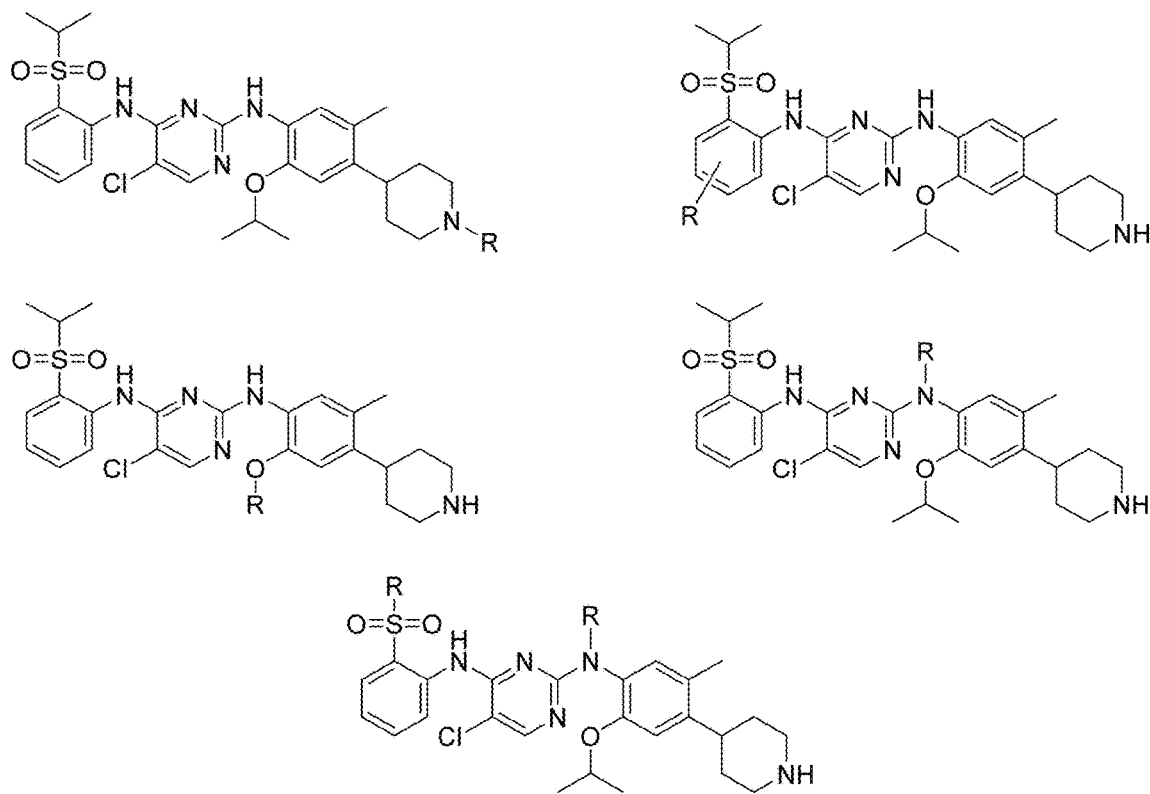

FIG. 5F presents examples of Ceritinib, a Targeting Ligands for the ALK, IGF-1R, InsR, and ROS1 receptors. R is the point at which the Linker is attached.

Figure 5G:
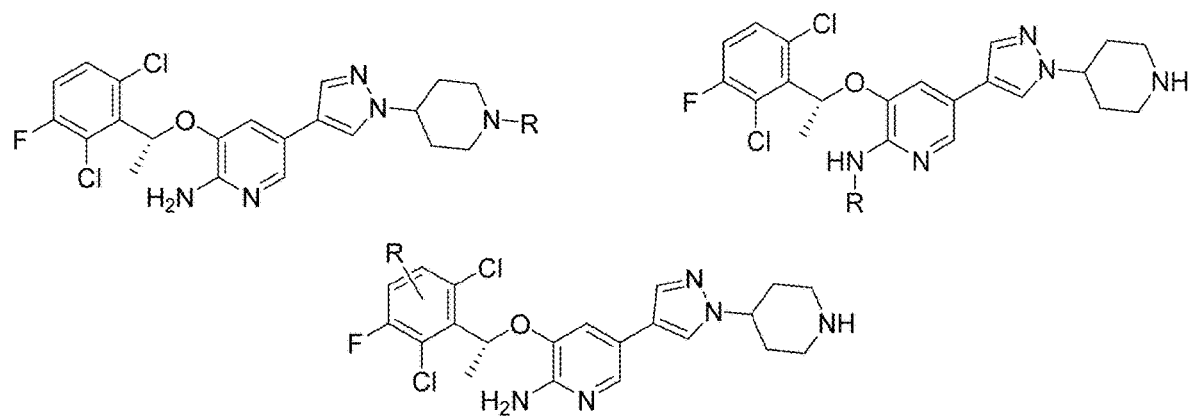

FIG. 5G presents examples of Crizotinib, a Targeting Ligands for the ALK, c-Met, HGFR, ROS1, and MST1R receptors. R is the point at which the Linker is attached.

Figure 5H:
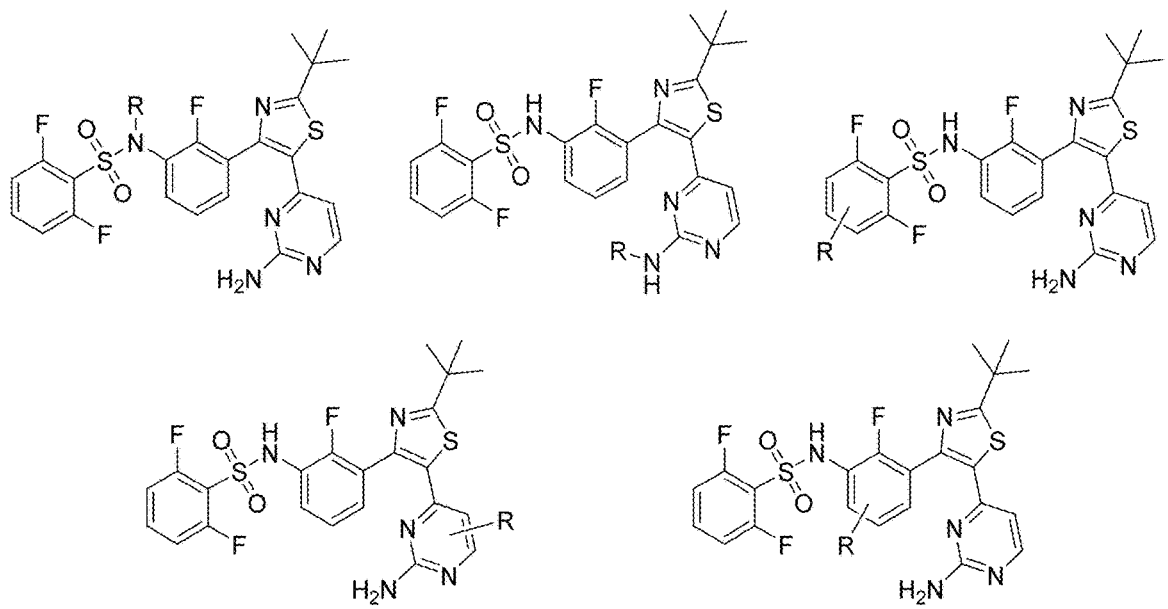

FIG. 5H presents examples of Dabrafenib, a Targeting Ligands for the B-Raf receptor. R is the point at which the Linker is attached.

Figure 5I:
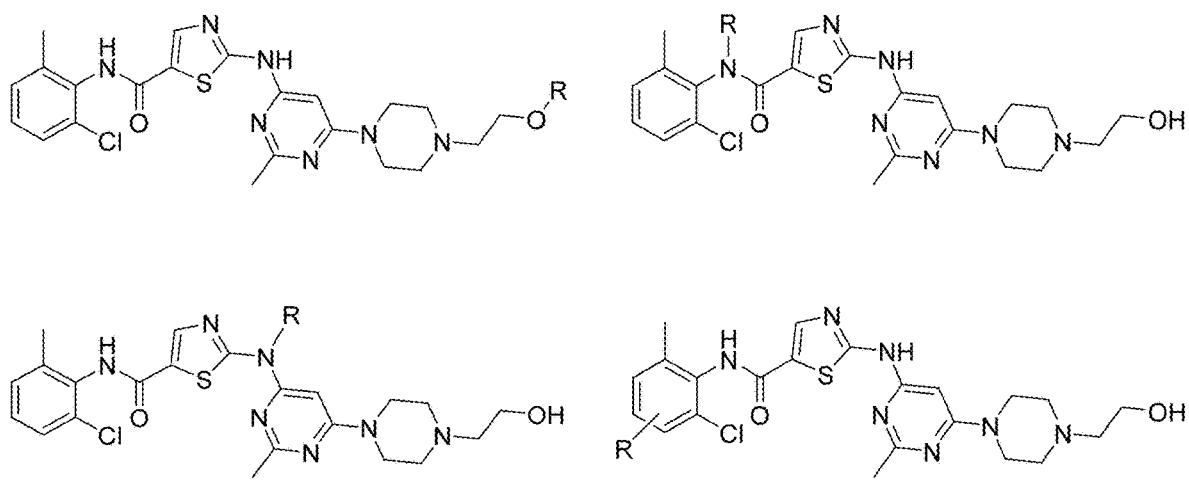

FIG. 5I presents examples of Dasatinib, a Targeting Ligands for the BCR-Abl, Src, Lck, Lyn, Yes, Fyn, Kit, EphA2, and PDGFRβ receptors. R is the point at which Linker is attached.

Figure 5J:
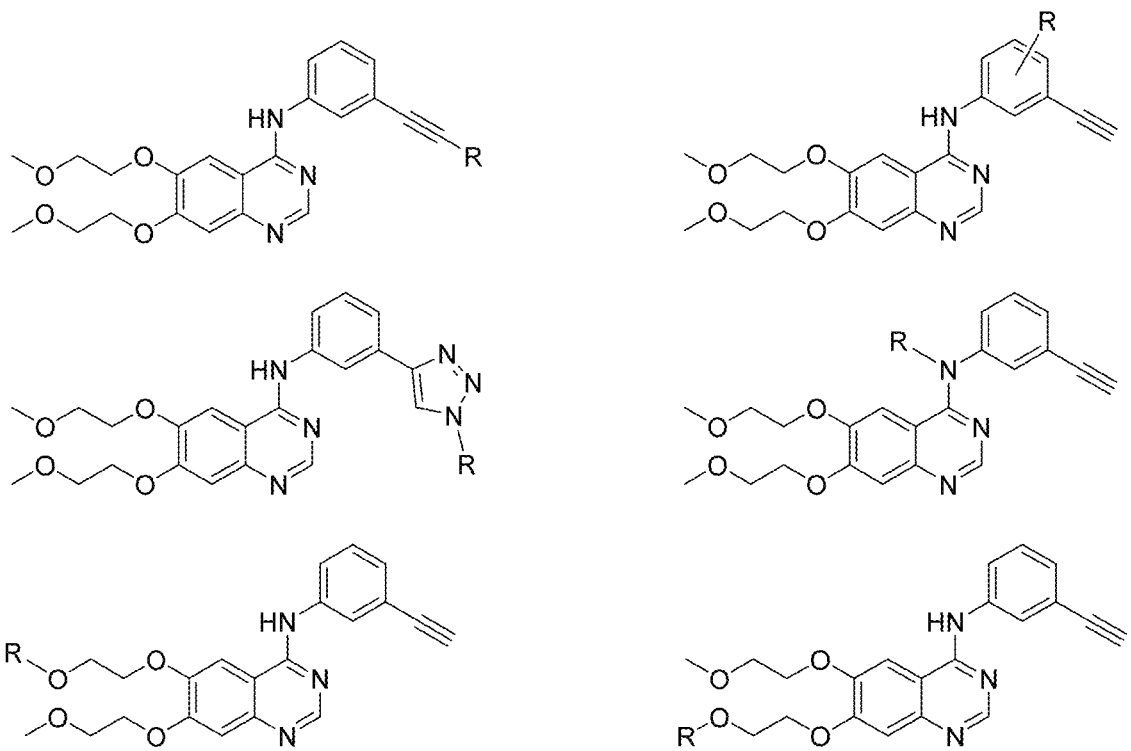

FIG. 5J presents examples of Erlotinib, a Targeting Ligands for the EGFR receptor. R is the point at which the Linker is attached.

Figure 5K:
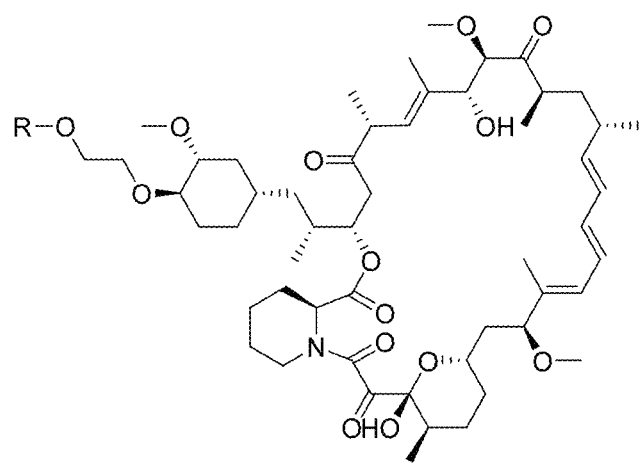
Figure 5O:
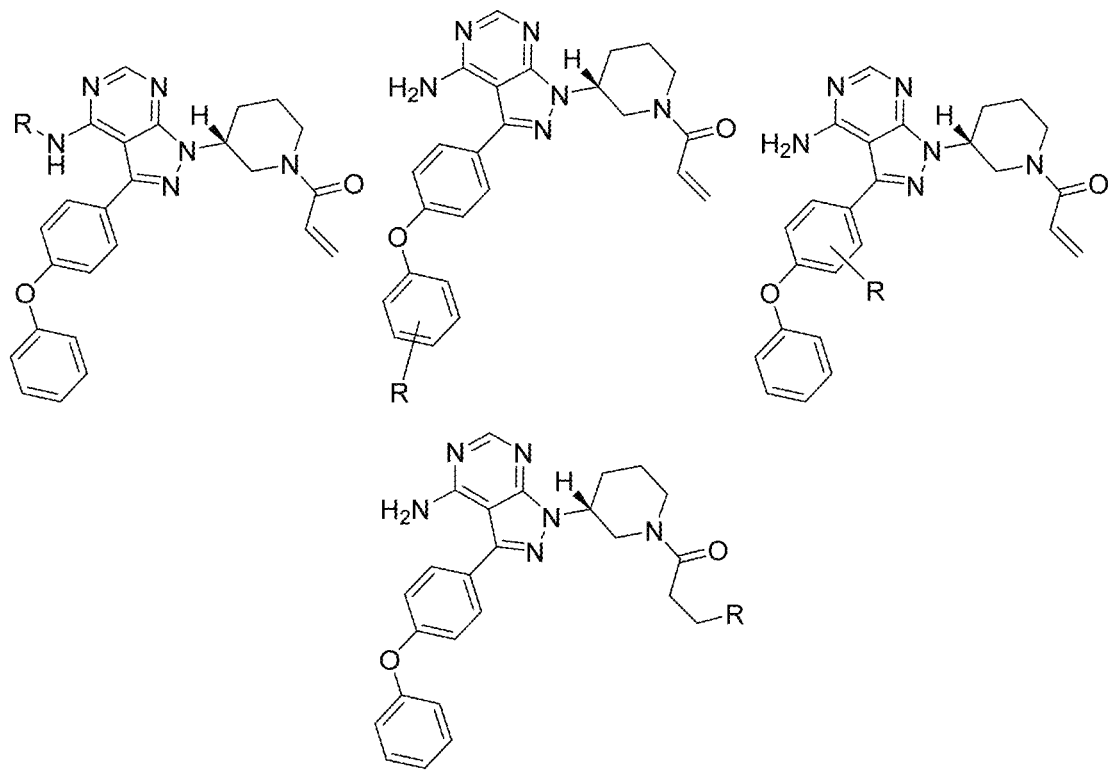
Figure 5P:
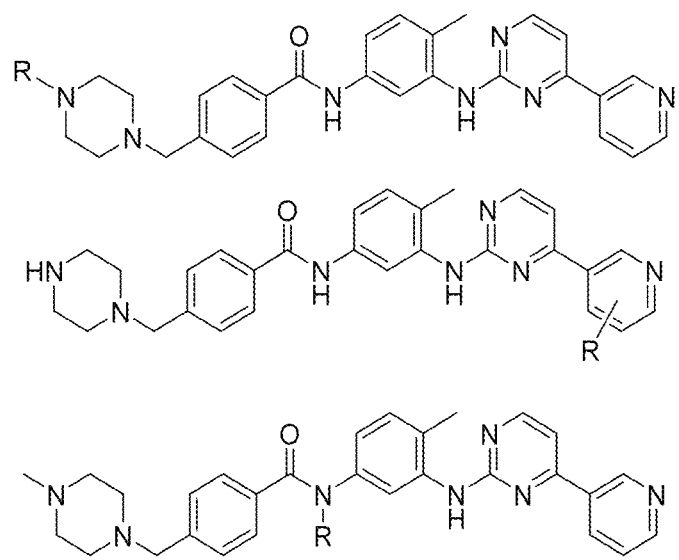
Figure 5Q:
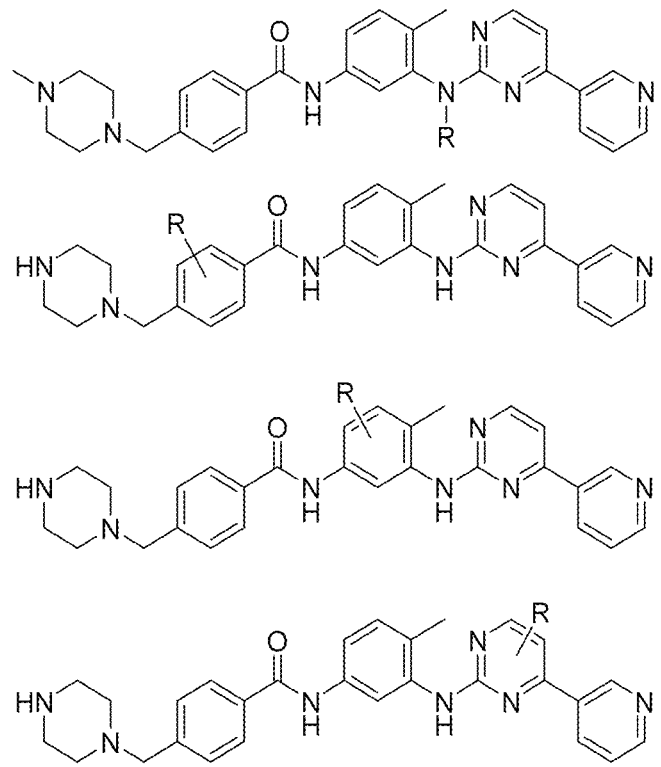
Figure 5R:
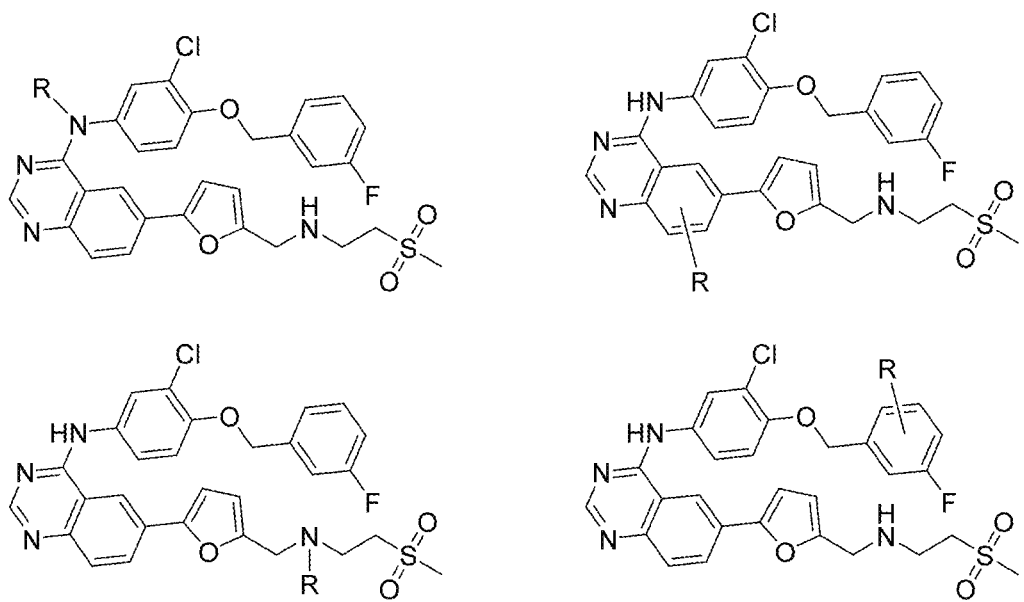
Figure 5S:
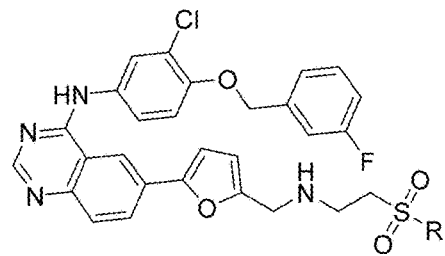
Figure 5T:
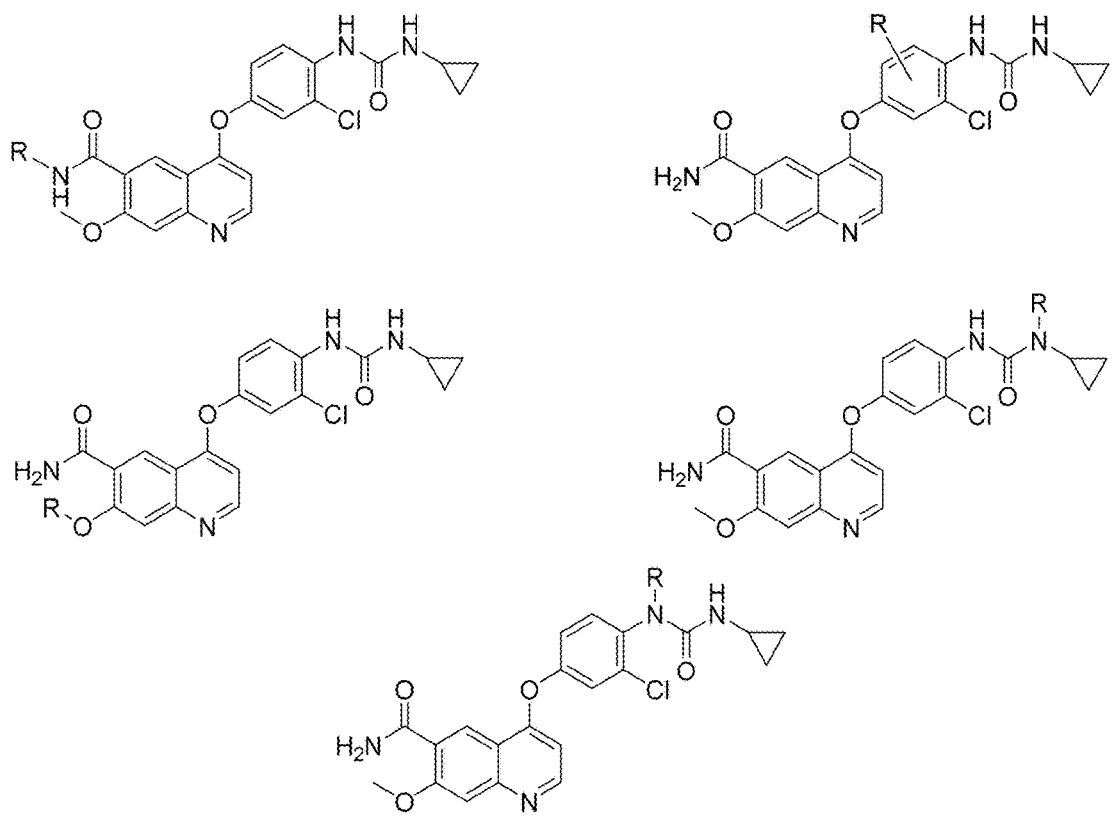
Figure 5U:
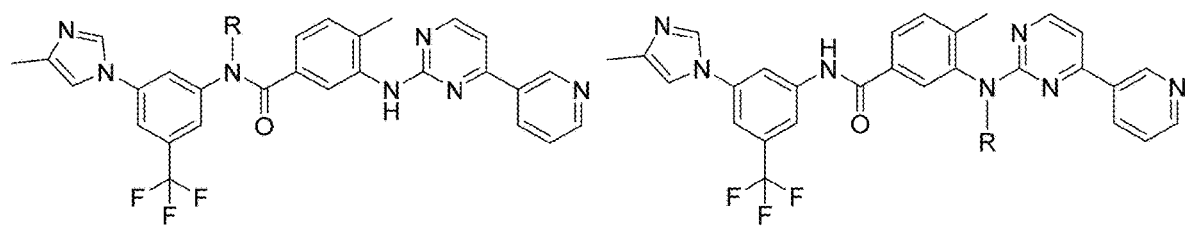
Figure 5V:
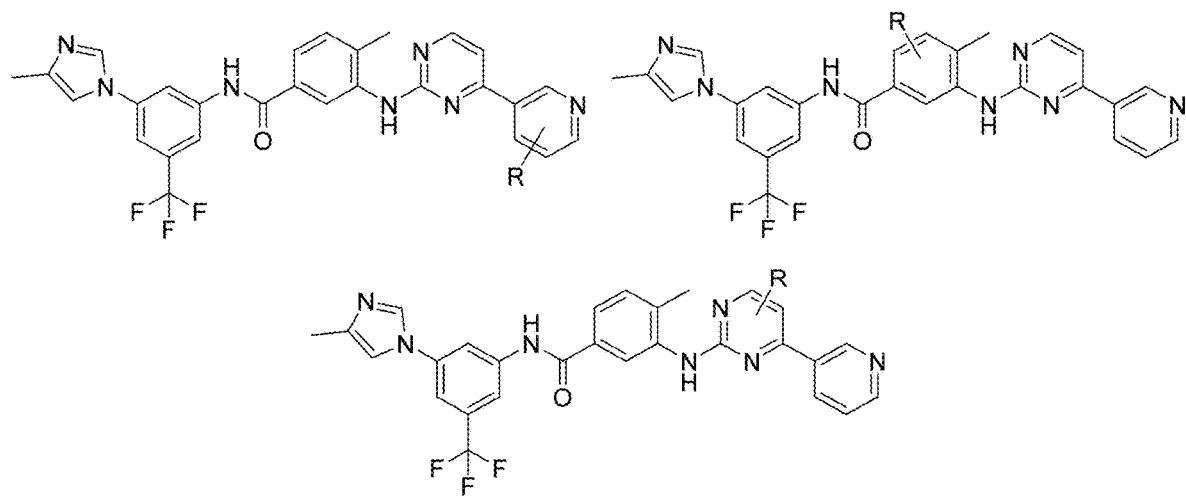
Figure 5W:
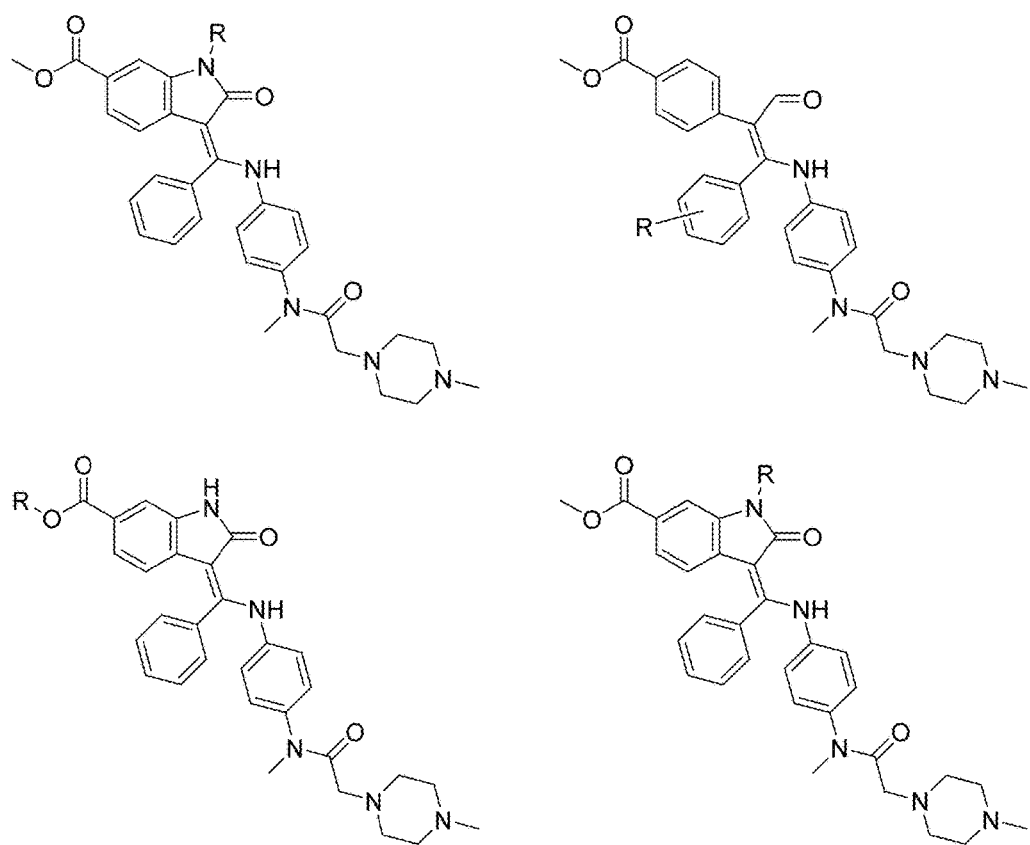
Figure 5X:
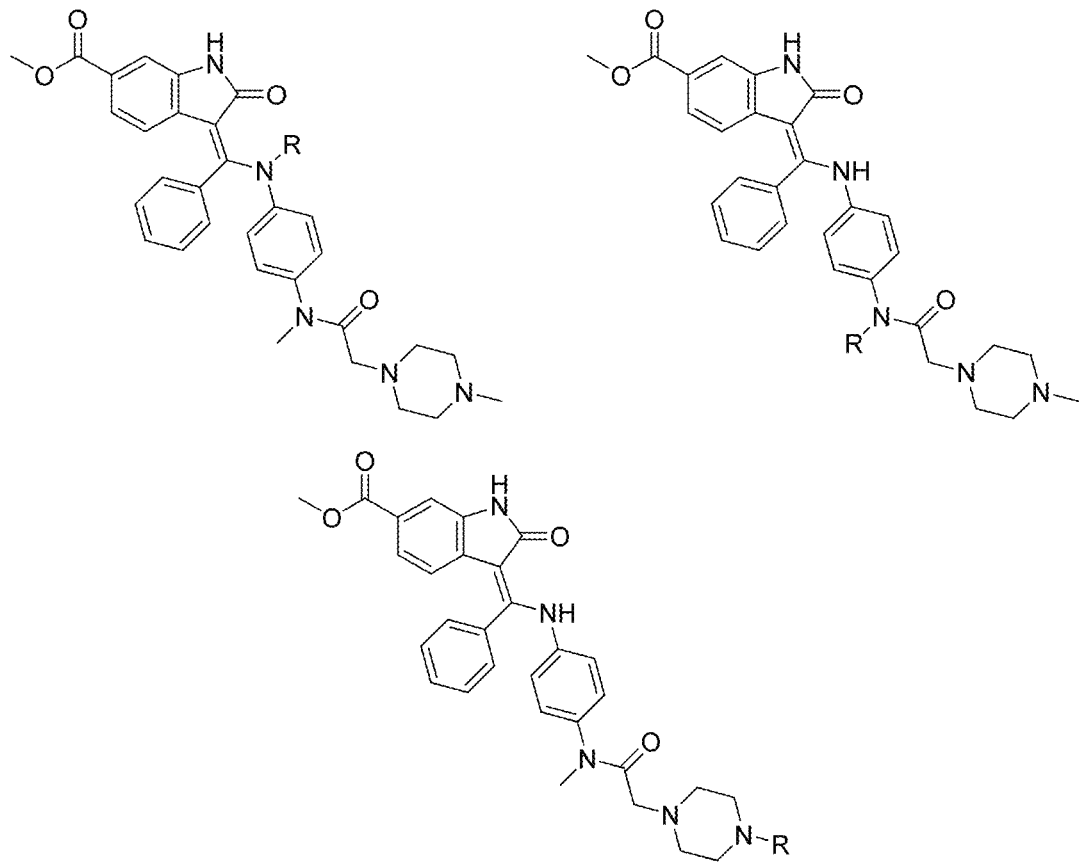
Figure 5Y:
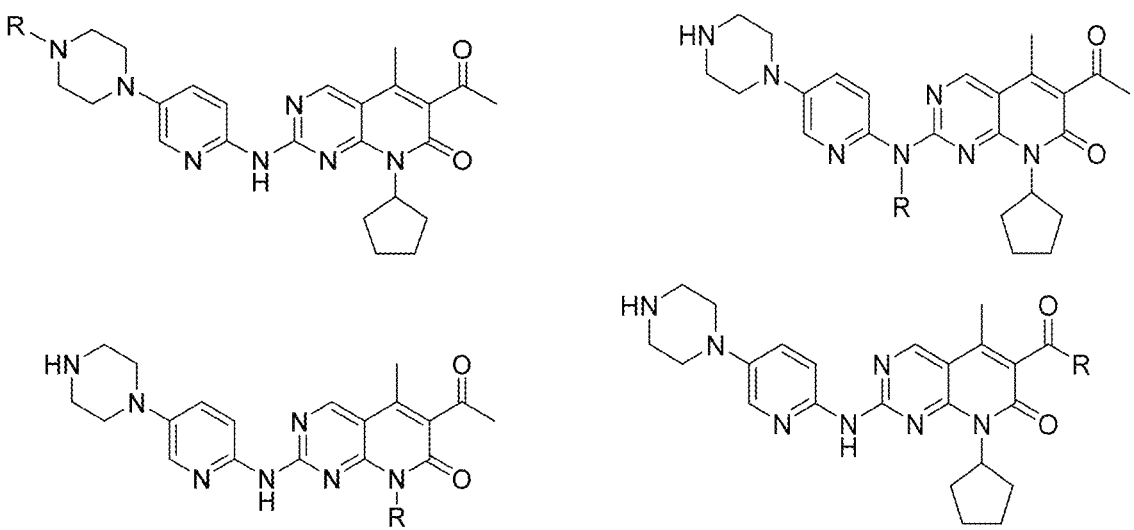
Figure 5Z:
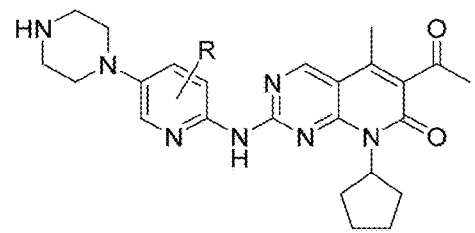
Figure 5A:
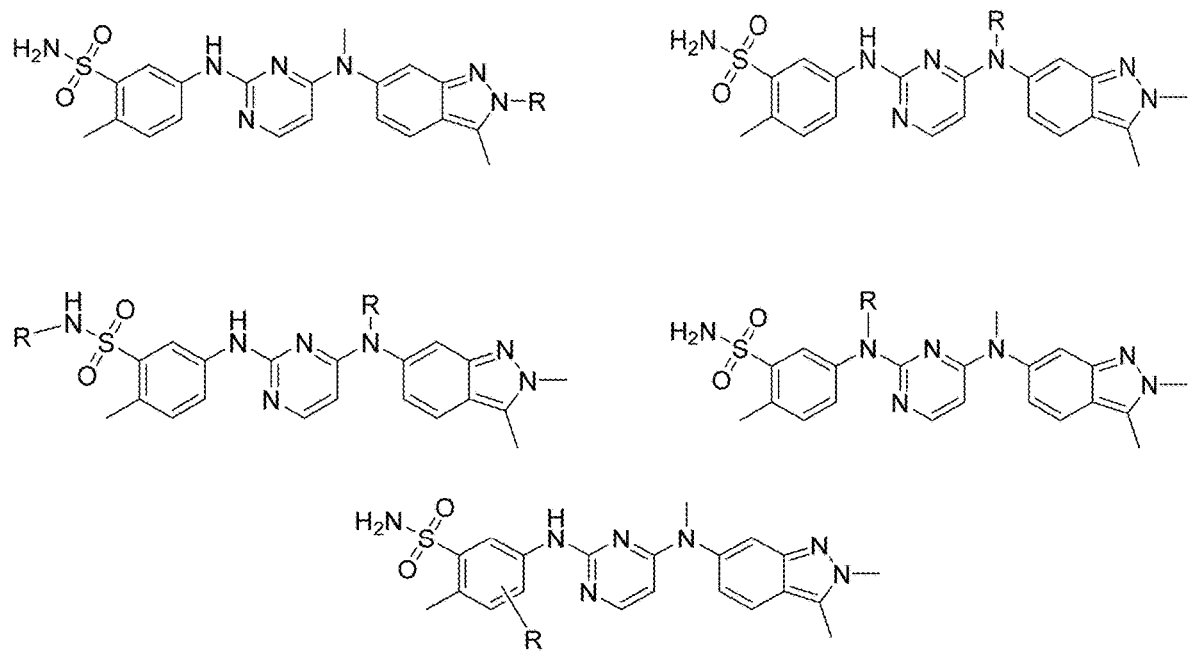
Figure 5B:
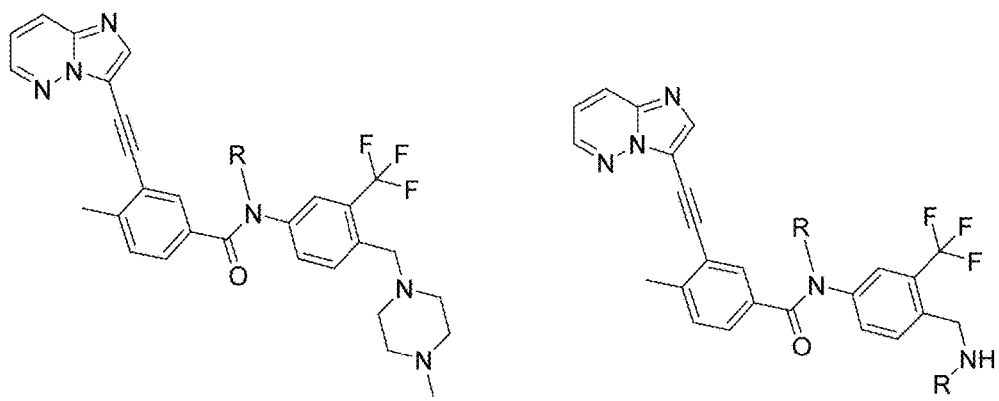
Figure 5C:
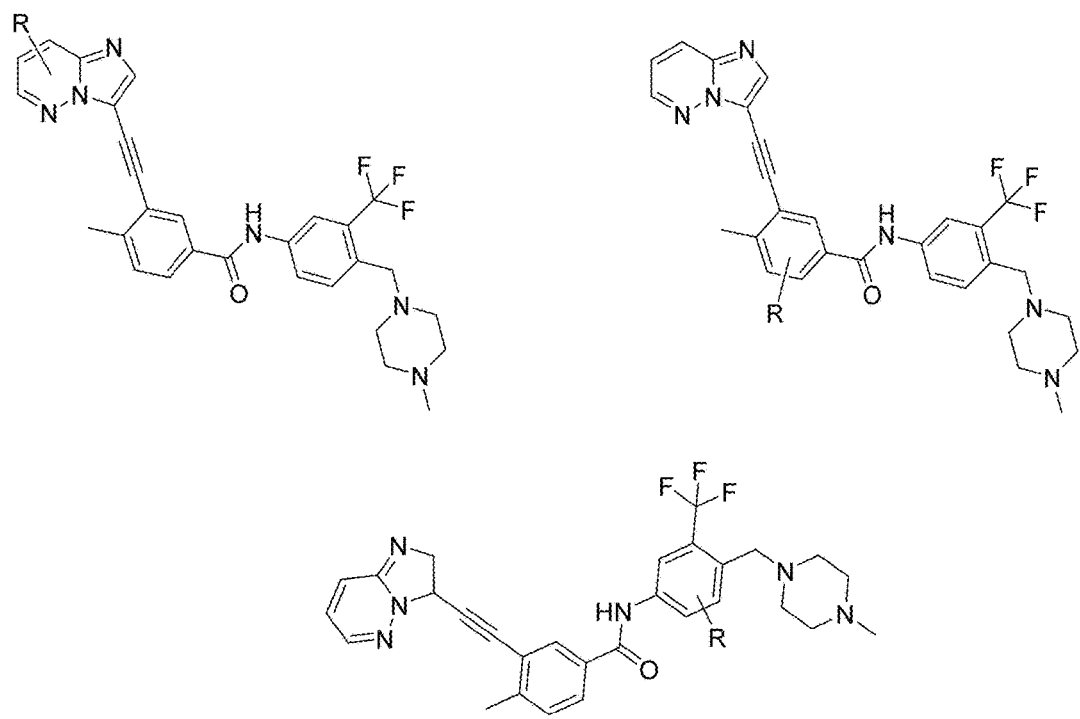
Figure 5D:
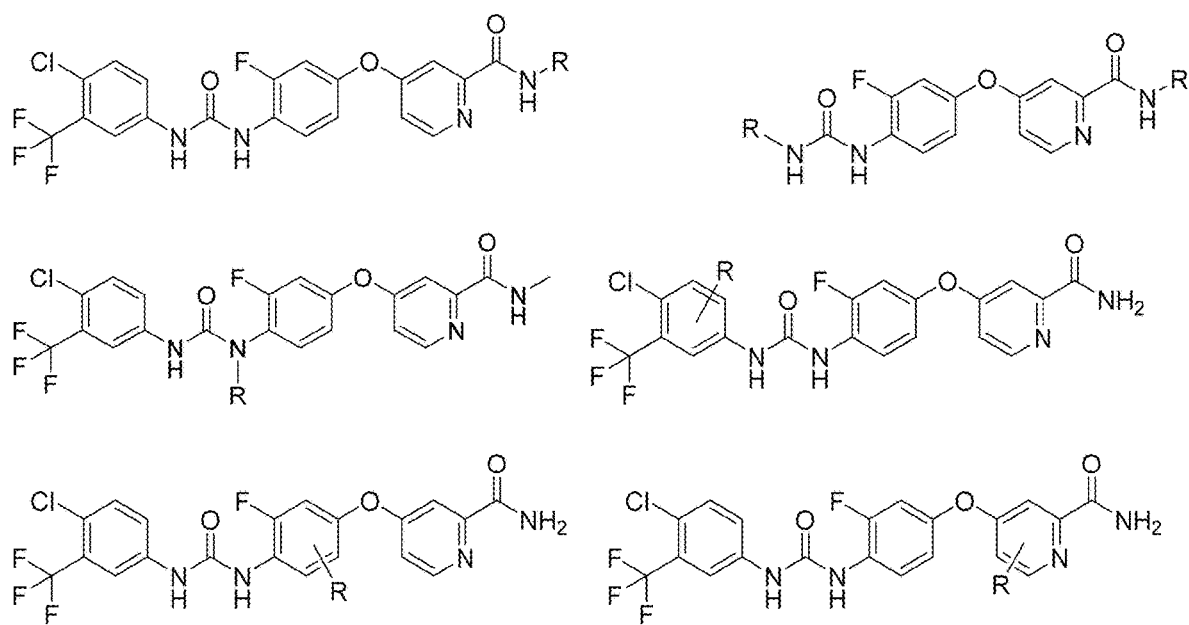
Figure 5E:
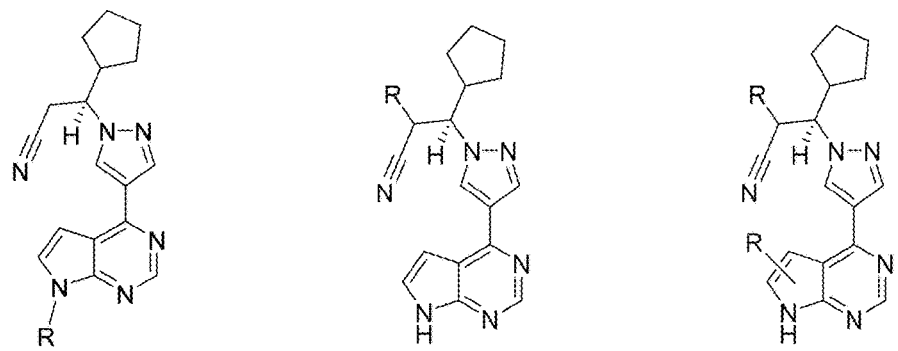
Figure 5F:
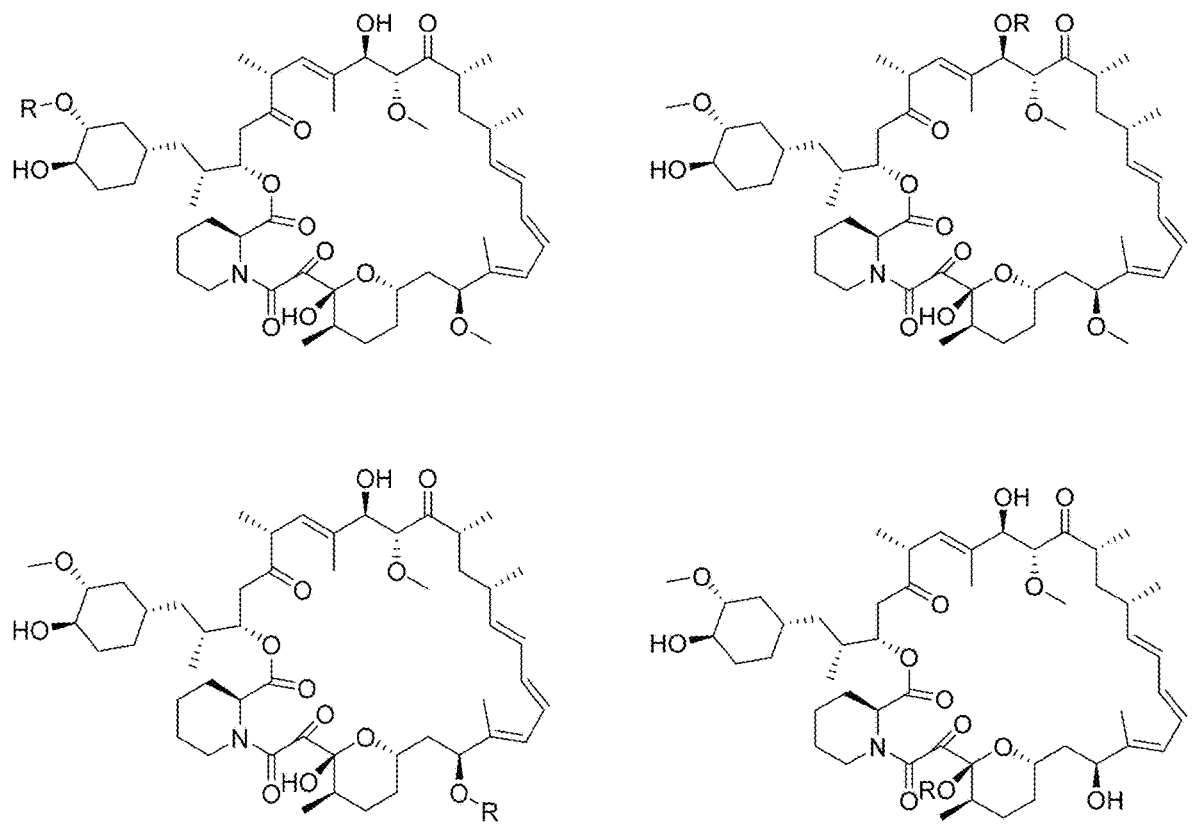
Figure 5G:
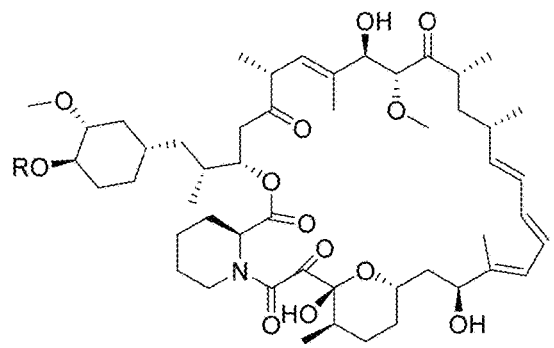
Figure 5H:
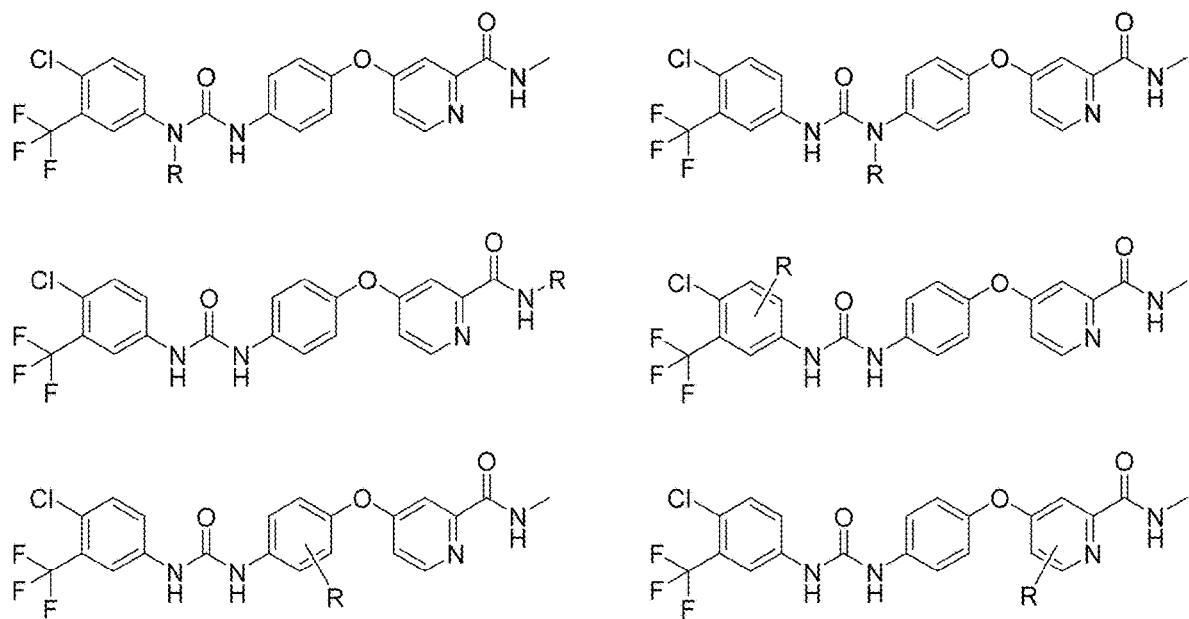
Figure 5I:
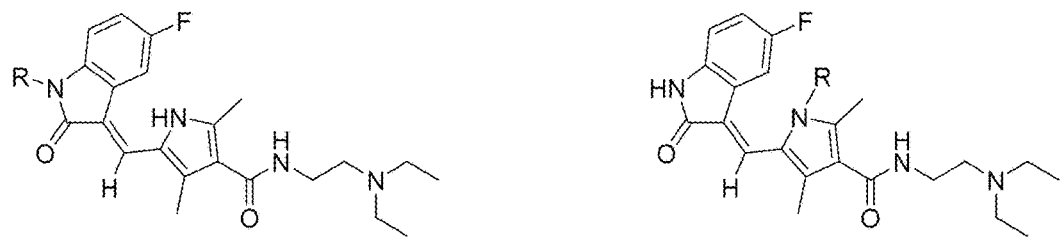
Figure 5L:
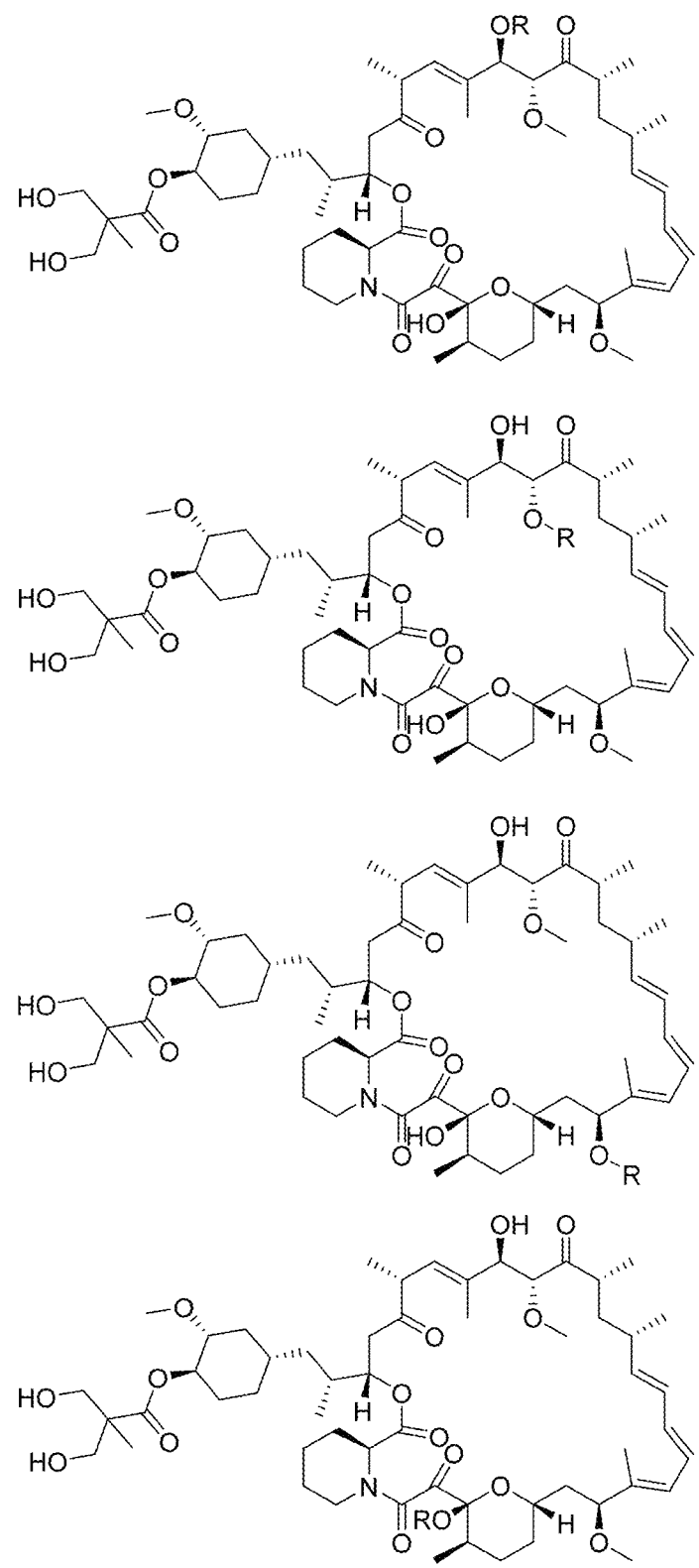
Figure 5M:
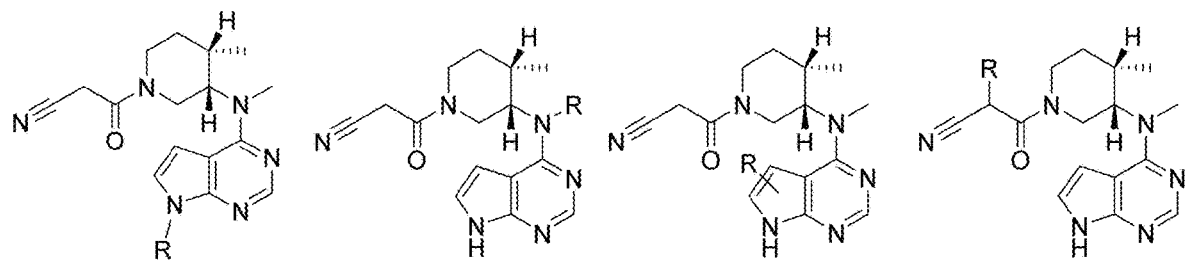

FIG. 5K-5M presents examples of Everolimus, a Targeting Ligands for the HER2 breast cancer receptor, the PNET receptor, the RCC receptors, the RAML receptor, and the SEGA receptor. R is the point at which the Linker is attached.

Figure 5N:
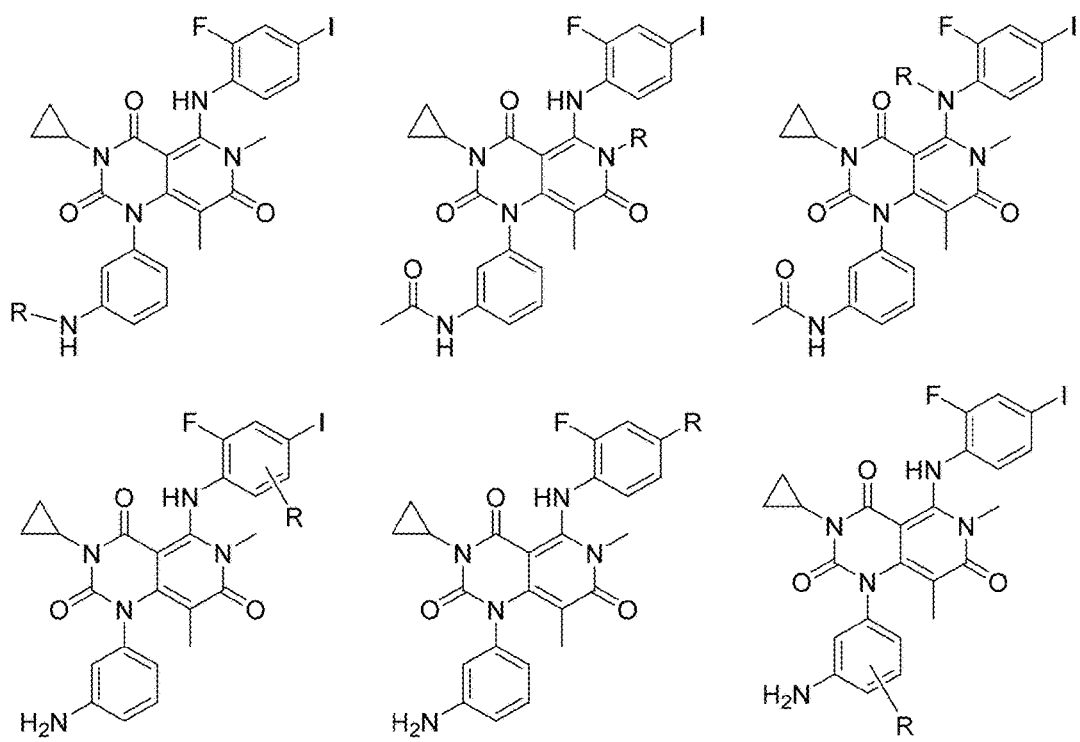
Figure 5O:
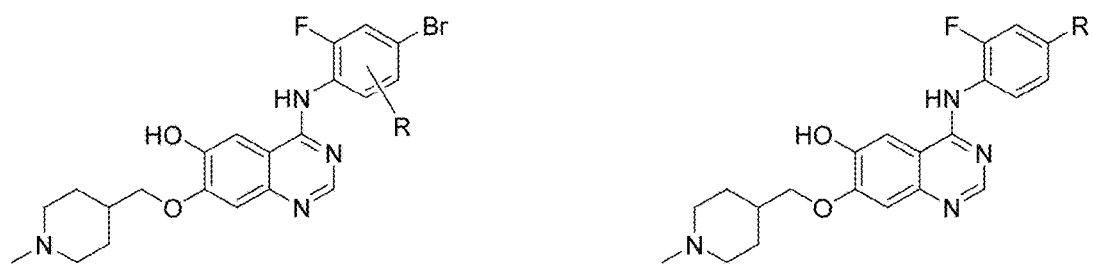
Figure 5P:
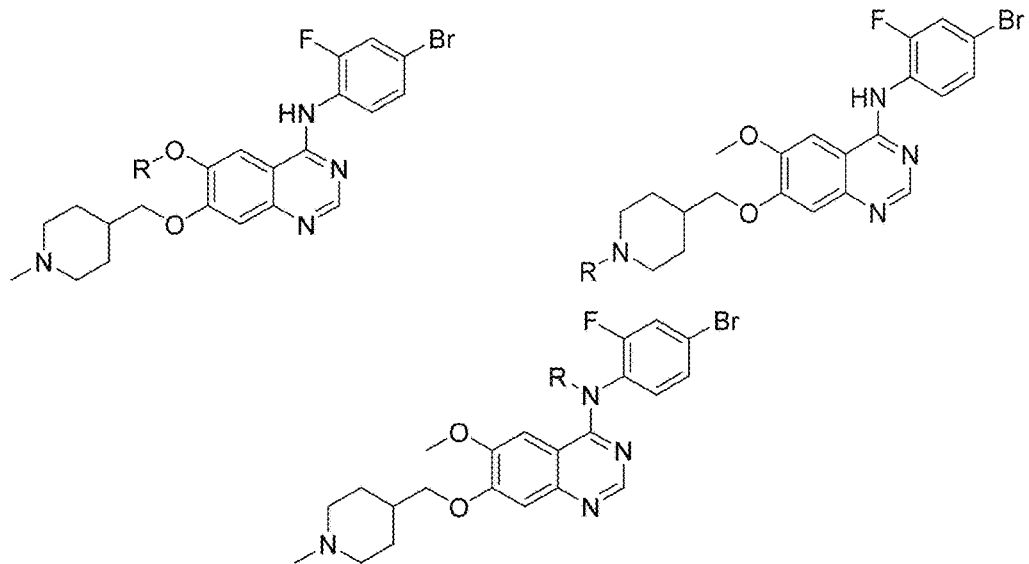
Figure 5Q:
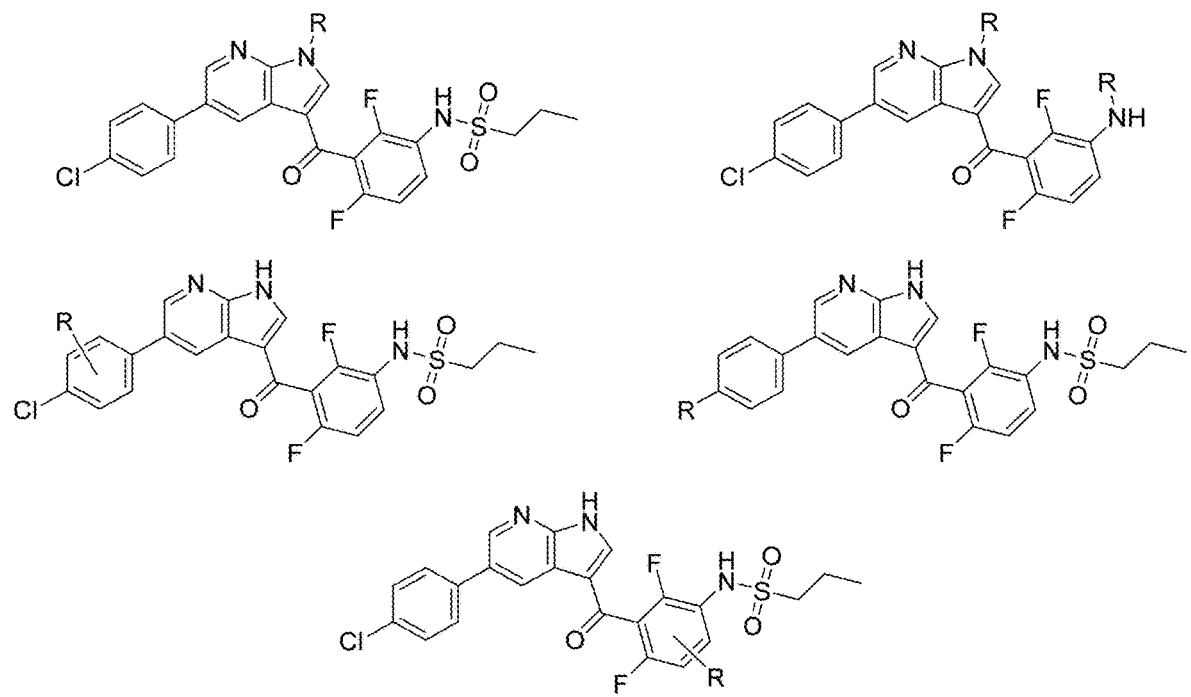
Figure 5R:
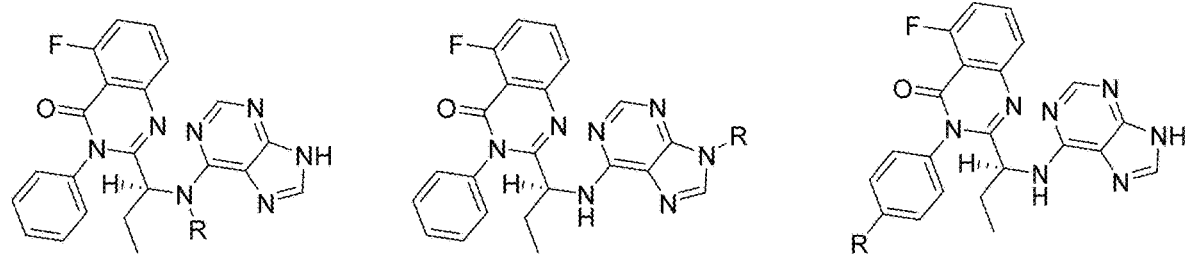
Figure 5S:
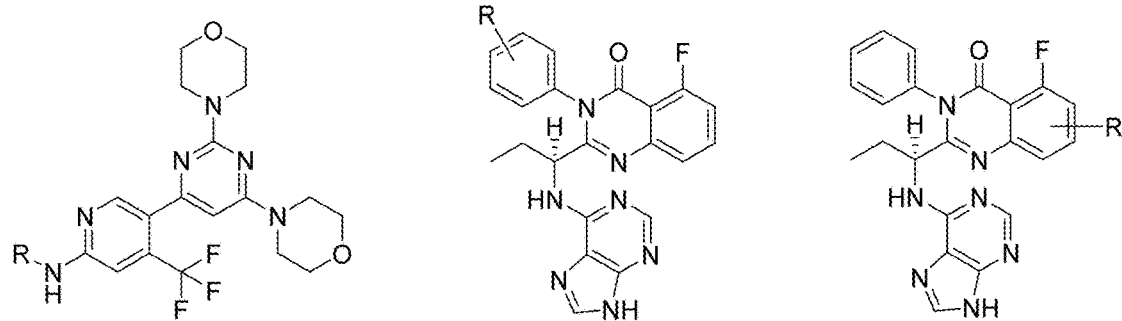
Figure 5T:
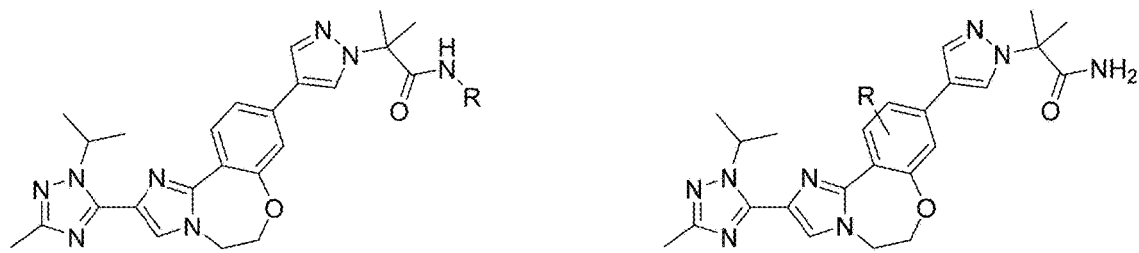
Figure 5U:
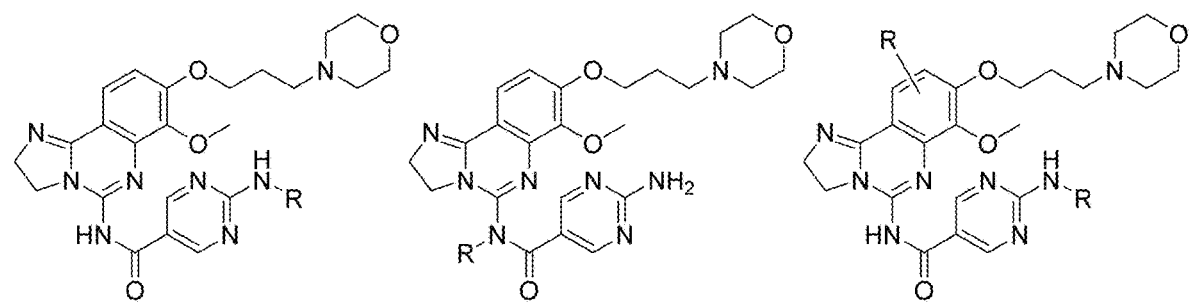
Figure 5V:
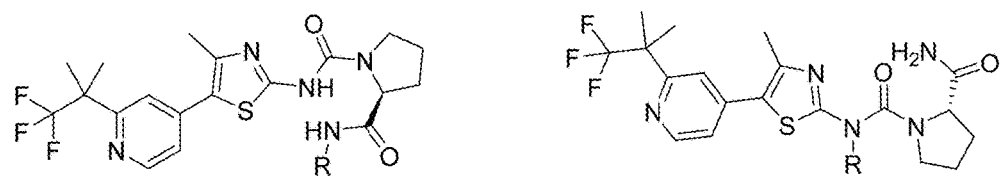
Figure 5W:
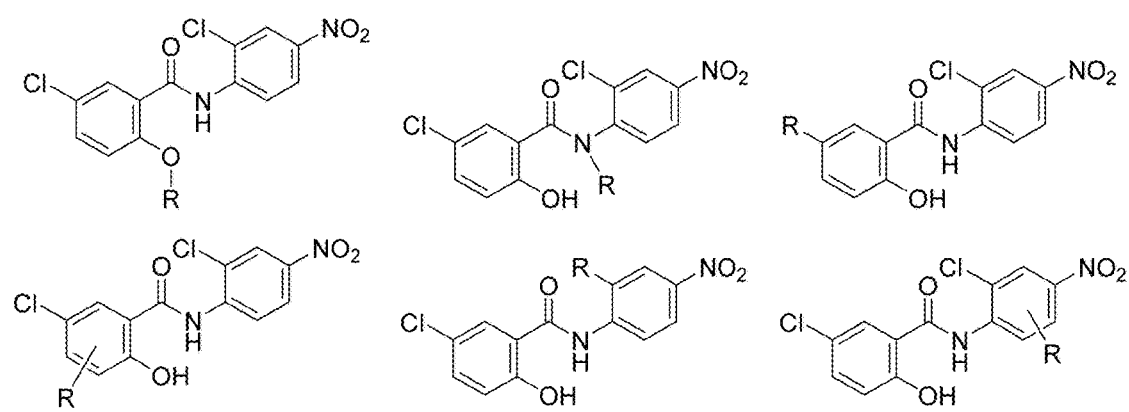

FIG. 5N presents examples of Gefitinib, a Targeting Ligands for the EGFR and PDGFR receptors. R is the point at which the Linker is attached.

FIG. 5O presents examples of Ibrutinib, a Targeting Ligands for the BTK receptor. R is the point at which the Linker is attached.

FIG. 5P-5Q present examples of Imatinib, a Targeting Ligands for the BCR-Abl, Kit, and PDGFR receptors. R is the point at which the Linker is attached.

FIG. 5R-5S present examples of Lapatinib, a Targeting Ligands for the EGFR and ErbB2 receptors. R is the point at which the Linker is attached.

FIG. 5T presents examples of Lenvatinib, a Targeting Ligands for the VEGFR1/2/3, FGFR1/2/3/4, PDGFRα, Kit, and RET receptors. R is the point at which the Linker is attached.

FIG. 5U-5V a present examples of Nilotinib, a Targeting Ligands for the BCR-Abl, PDGRF, and DDR1 receptors. R is the point at which the Linker is attached.

FIG. 5W-5X present examples of Nintedanib, a Targeting Ligands for the FGFR1/2/3, Flt3, Lck, PDGFRα/p, and VEGFR1/2/3 receptors. R is the point at which the Linker is attached.

FIG. 5Y-5Z present examples of Palbociclib, a Targeting Ligands for the CDK4/6 receptor. R is the point at which the Linker is attached.

FIG. 5AA presents examples of Pazopanib, a Targeting Ligands for the VEGFR1/2/3, PDGFRα/β, FGFR1/3, Kit, Lck, Fms, and Itk receptors. R is the point at which the Linker is attached.

FIG. 5BB-5CC present examples of Ponatinib, a Targeting Ligands for the BCR-Abl, T315I VEGFR, PDGFR, FGFR, EphR, Src family kinases, Kit, RET, Tie2, and Flt3 receptors. R is the point at which the Linker is attached.

FIG. 5DD presents examples of Regorafenib, a Targeting Ligands for the VEGFR1/2/3, BCR-Abl, B-Raf, B-Raf (V600E), Kit, PDGFRα/β, RET, FGFR1/2, Tie2, and Eph2A. R is the point at which the Linker is attached.

FIG. 5EE presents examples of Ruxolitinib, a Targeting Ligands for the JAK1/2 receptors. R is the point at which the Linker is attached.

FIG. 5FF-5GG present examples of Sirolimus, a Targeting Ligands for the FKBP12/mTOR receptors. R is the point at which the Linker is attached.

FIG. 5HH presents examples of Sorafenib, a Targeting Ligands for the B-Raf, CDK8, Kit, Flt3, RET, VEGFR1/2/3, and PDGFR receptors. R is the point at which the Linker is attached.

FIG. 5II-5JJ present examples of Sunitinib, a Targeting Ligands for PDGFRα/β, VEGFR1/2/3, Kit, Flt3, CSF-1R, RET. R is the point at which the Linker is attached.

FIG. 5KK-5LL present examples of Temsirolimus, a Targeting Ligands FKBP12/mTOR. R is the point at which the Linker is attached.

FIG. 5MM presents examples of Tofacitinib, a Targeting Ligands for JAK3 receptors. R is the point at which the Linker is attached.

FIG. 5NN presents examples of Trametinib, a Targeting Ligands for the MEK1/2 receptors. R is the point at which the Linker is attached.

FIG. 5OO-5PP presents examples of Vandetanib, a Targeting Ligands for the EGFR, VEGFR, RET, Tie2, Brk, and EphR. R is the point at which the Linker is attached.

FIG. 5QQ presents examples of Vemurafenib, a Targeting Ligands for the A/B/C-Raf, KSR1, and B-Raf (V600E) receptors. R is the point at which the Linker is attached.

FIG. 5RR presents examples of Idelasib, a Targeting Ligands for the PI3Ka receptor. R is the point at which the Linker is attached.

FIG. 5SS presents examples of Buparlisib, a Targeting Ligands for the PI3Ka receptor. R is the point at which the Linker is attached.

FIG. 5TT presents examples of Taselisib, a Targeting Ligands for the PI3Ka receptor. R is the point at which the Linker is attached.

FIG. 5UU presents examples of Copanlisib, a Targeting Ligands for the PI3Ka. R is the point at which the Linker is attached.

FIG. 5VV presents examples of Alpelisib, a Targeting Ligands for the PI3Ka. R is the point at which the Linker is attached.

FIG. 5WW presents examples of Niclosamide, a Targeting Ligands for the CNNTB1. R is the point at which the Linker is attached.

Figure 6A:
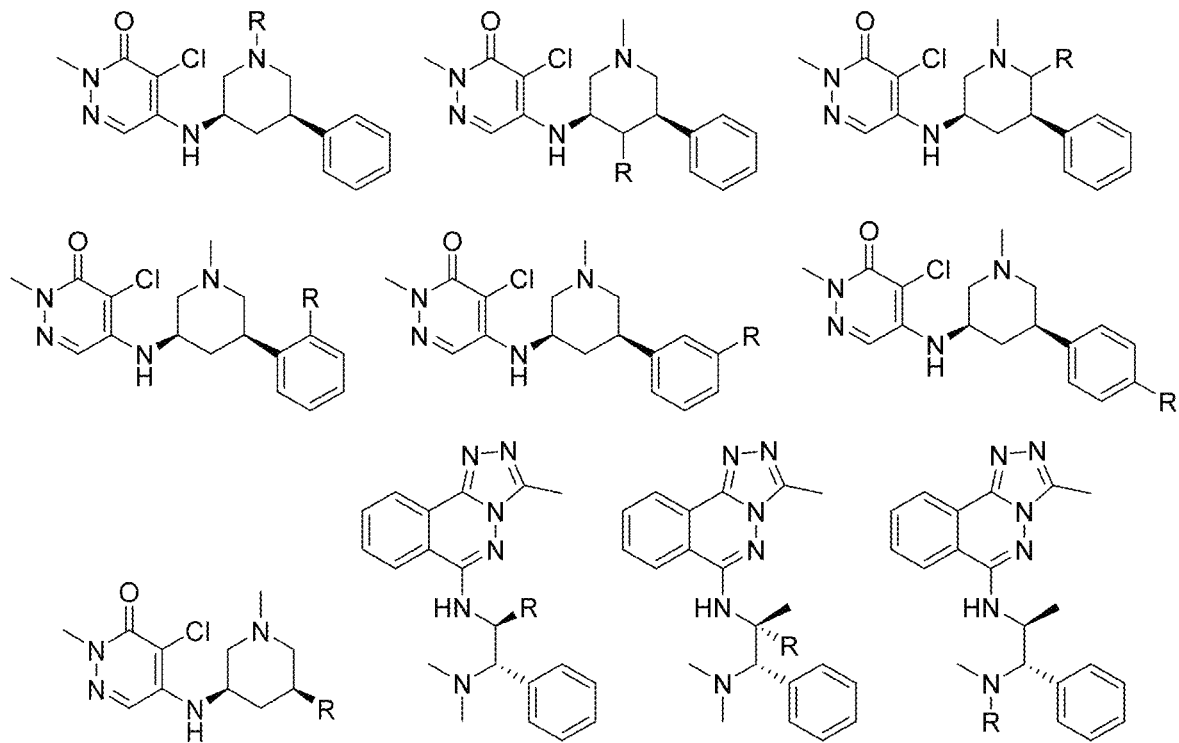
Figure 6B:
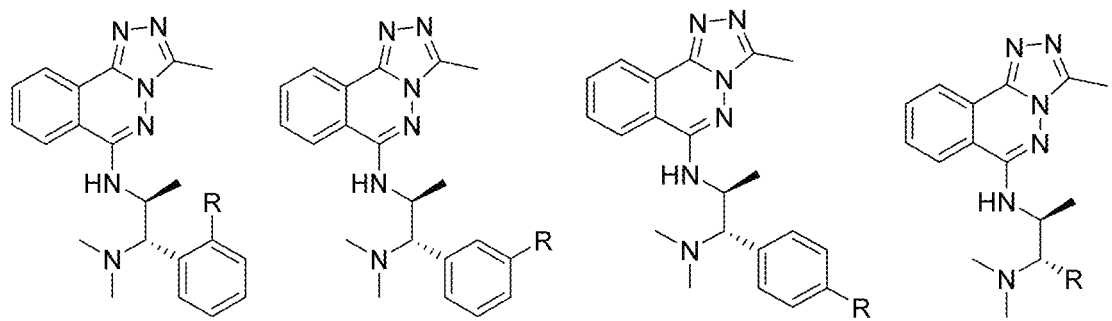

FIG. 6A-6B present examples of the BRD4 Bromodomains of PCAF and GCN5 receptors 1 Targeting Ligands wherein R is the point at which the Linker is attached. For additional examples and related ligands, see, the PDB crystal structure 5tpx ("Discovery of a PCAF Bromodomain Chemical Probe"); Moustakim, M., et al. *Angew. Chem. Int. Ed. Engl.* 56: 827 (2017); the PDB crystal structure 5mlj ("Discovery of a Potent, Cell Penetrant, and Selective p300/CBP-Associated Factor (PCAF)/General Control Nonderepressible 5 (GCN5) Bromodomain Chemical Probe"); and, Humphreys, P. G. et al. *J. Med. Chem.* 60: 695 (2017).

Figure 6C:
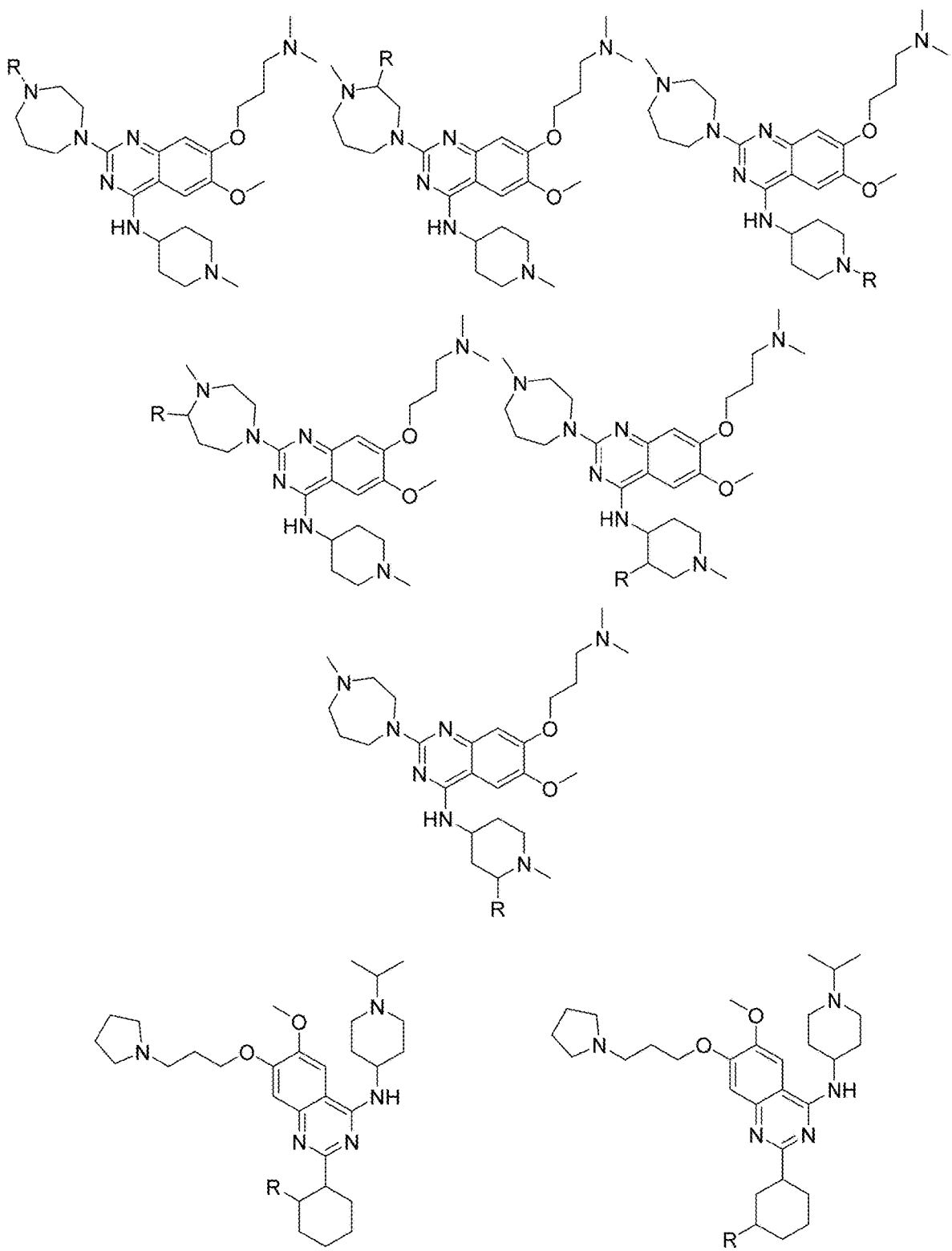
Figure 6D:
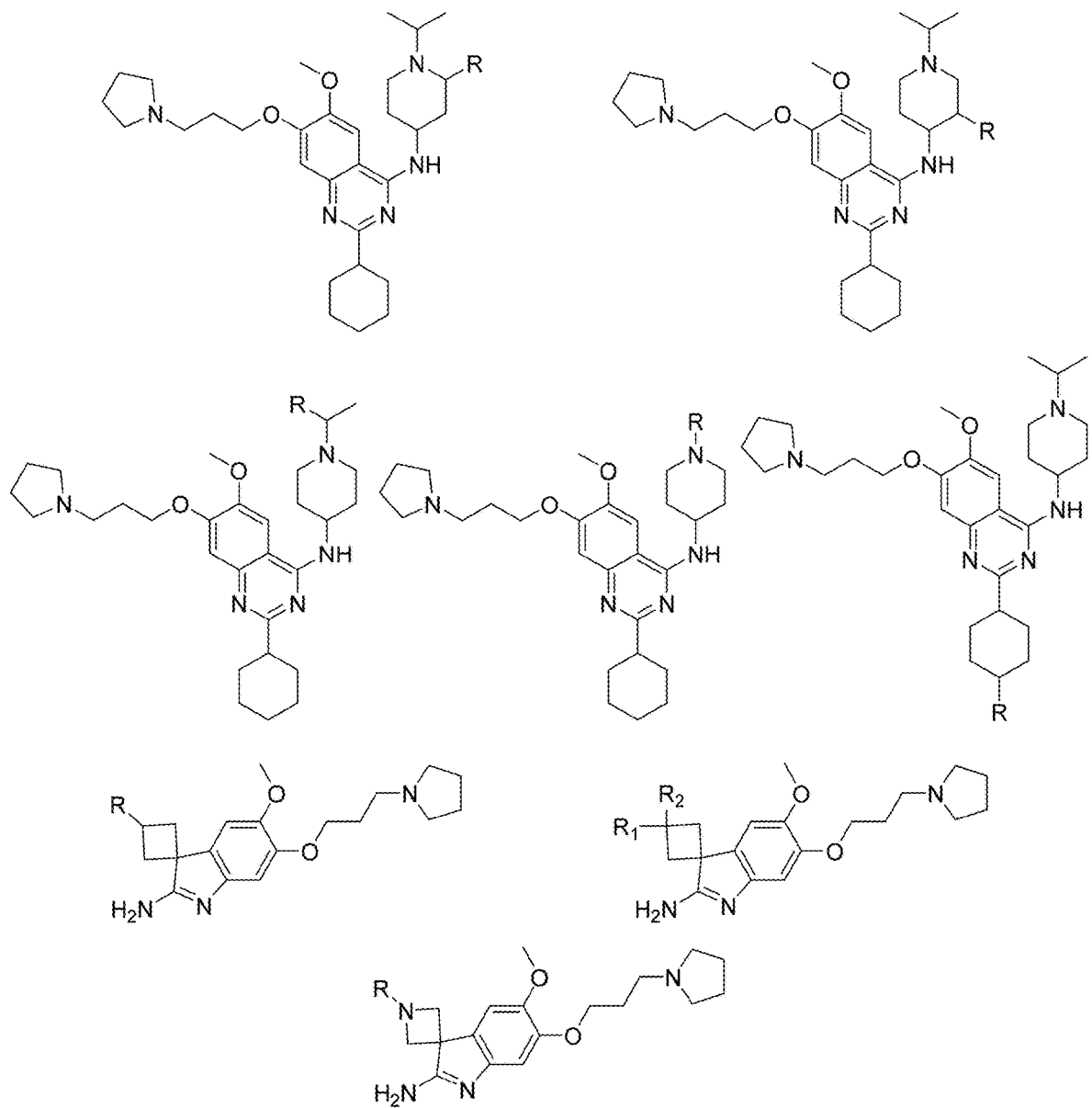

FIG. 6C-6D present examples of G9a (EHMT2) Targeting Ligands wherein R is the point at which the Linker is attached. For additional examples and related ligands, see, the PDB crystal structure 3k5k; ("Discovery of a 2,4-diamino-7-aminoalkoxyquinazoline as a potent and selective inhibitor of histone lysine methyltransferase G9a"); Liu, F. et al. *J. Med. Chem.* 52: 7950 (2009); the PDB crystal structure 3rjw ("A chemical probe selectively inhibits G9a and GLP methyltransferase activity in cells"); Vedadi, M. et al. *Nat. Chem. Biol.* 7: 566 (2011); the PDB crystal structure 4nvq ("Discovery and development of potent and selective inhibitors of histone methyltransferase g9a"); and, Sweis, R. F. et al. *ACS Med Chem Lett* 5: 205 (2014).

Figure 6E:
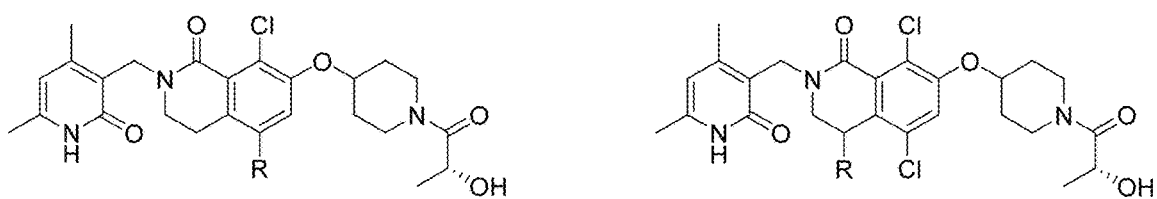
Figure 6F:
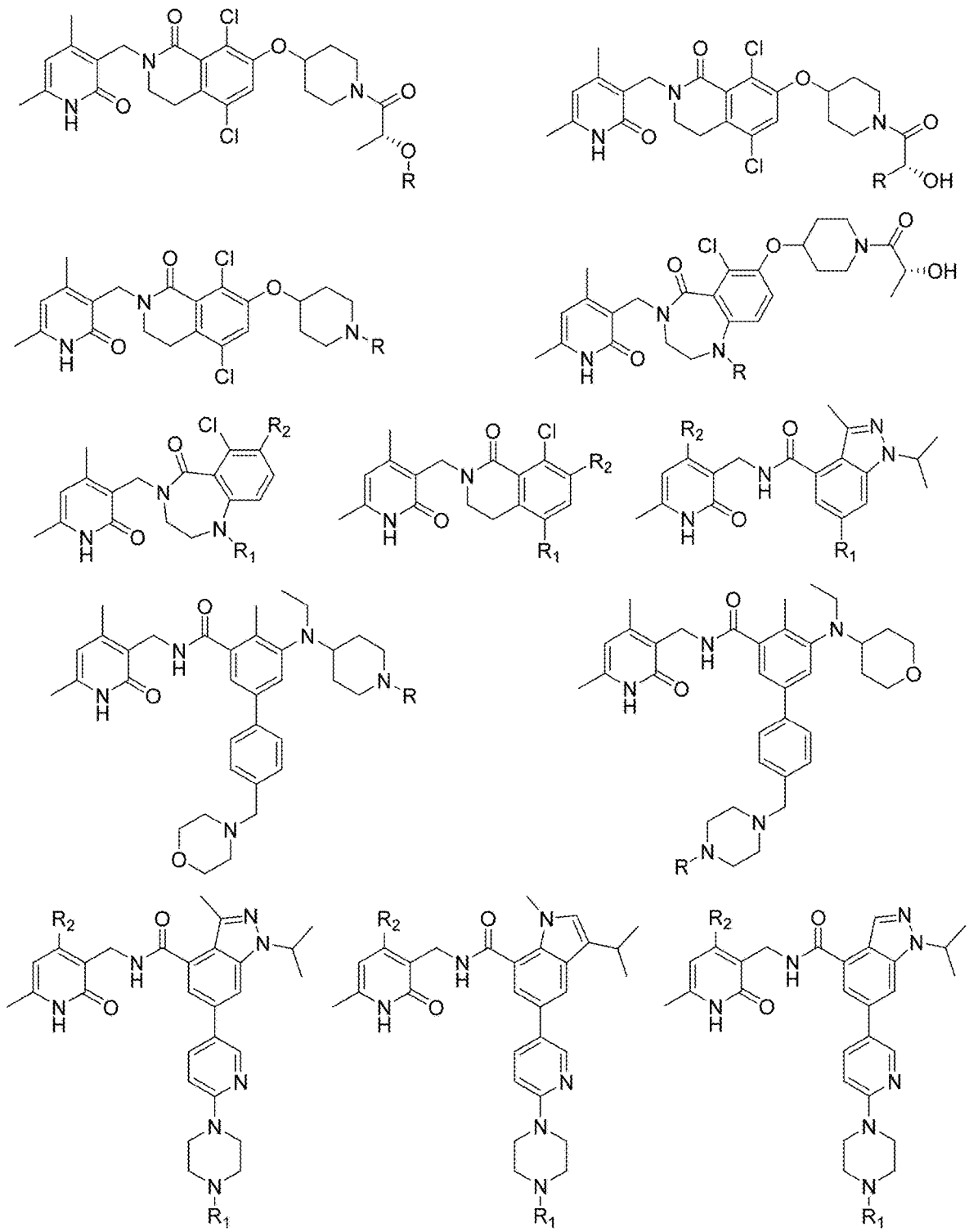
Figure 6G:
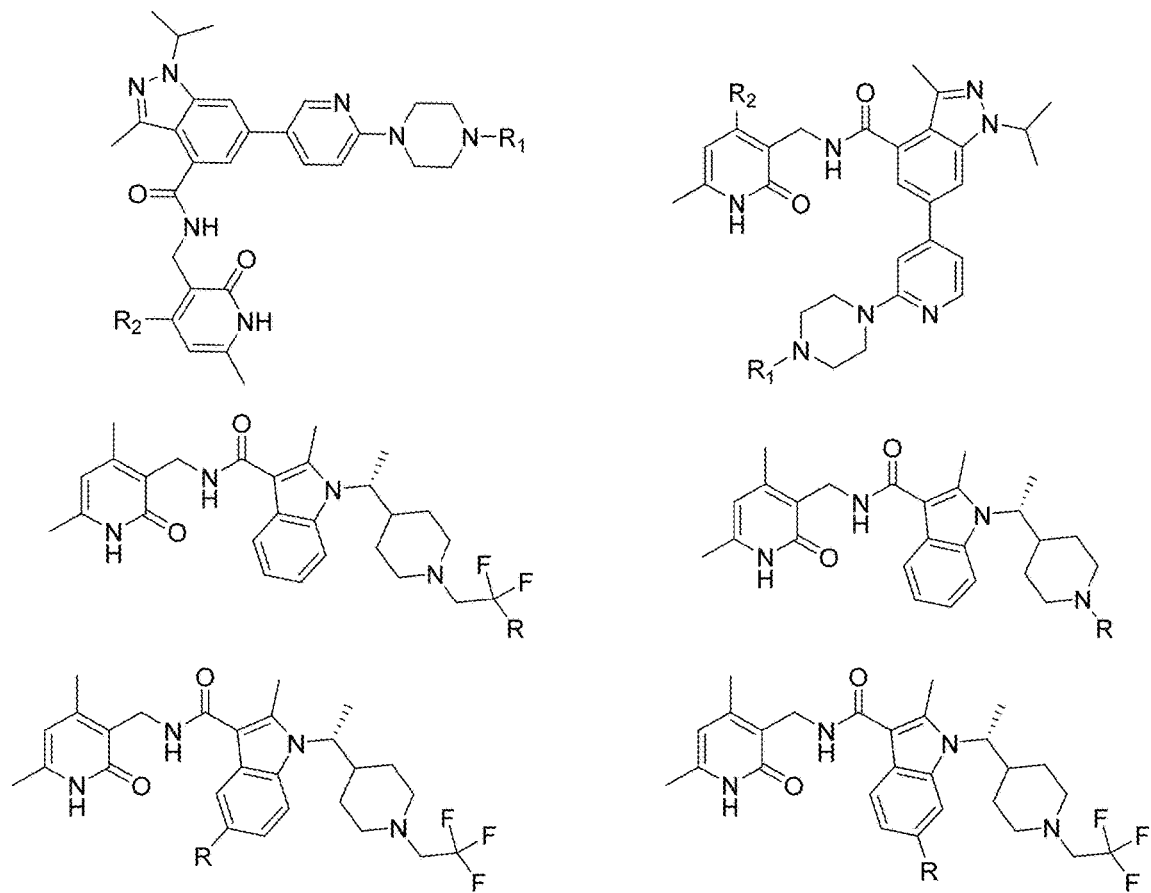

FIG. 6E-6G present examples of EZH2 Targeting Ligands wherein R is the point at which the Linker is attached. For additional examples and related ligands, see, the PDB crystal structure 5ij8 ("Polycomb repressive complex 2 structure with inhibitor reveals a mechanism of activation and drug resistance"); Brooun, A. et al. *Nat Commun* 7: 11384 (2016); the PDB crystal structure 5ls6 ("Identification of (R)—N-((4-Methoxy-6-methyl-2-oxo-1,2-dihydropyridin-3-yl)methyl)-2-methyl-1-(1-(1-(2,2,2-trifluoroethyl)piperidin-4-yl)ethyl)-1H-indole-3-carboxamide (CPI-1205), a Potent and Selective Inhibitor of Histone Methyltransferase EZH2, Suitable for Phase I Clinical Trials for B-Cell Lymphomas"); Vaswani, R. G. et al. *J. Med. Chem.* 59: 9928 (2016); and, the PDB crystal structures 5ij8 and 51s6.

Figure 6H:
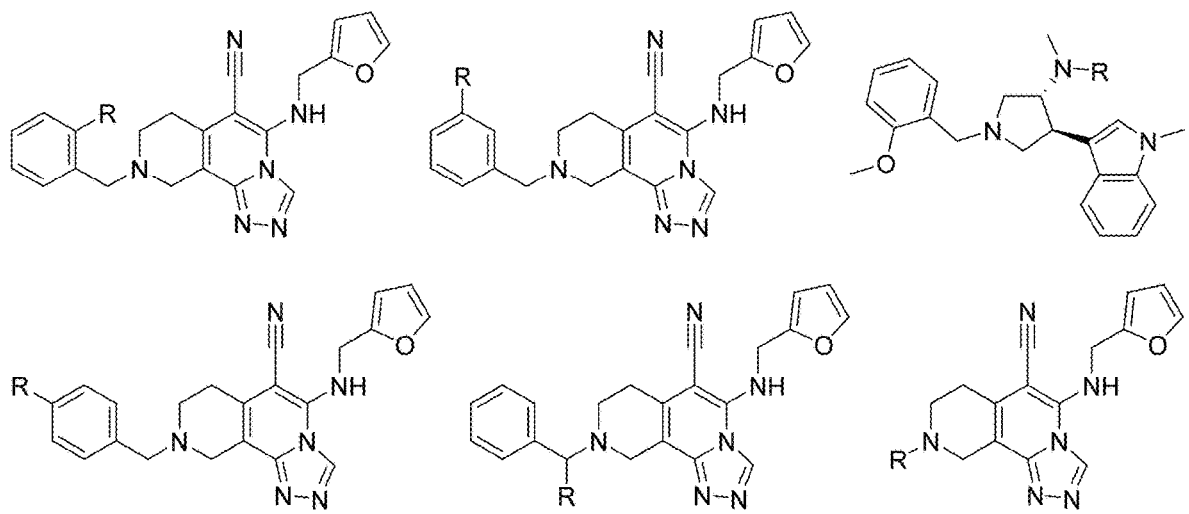
Figure 6I:
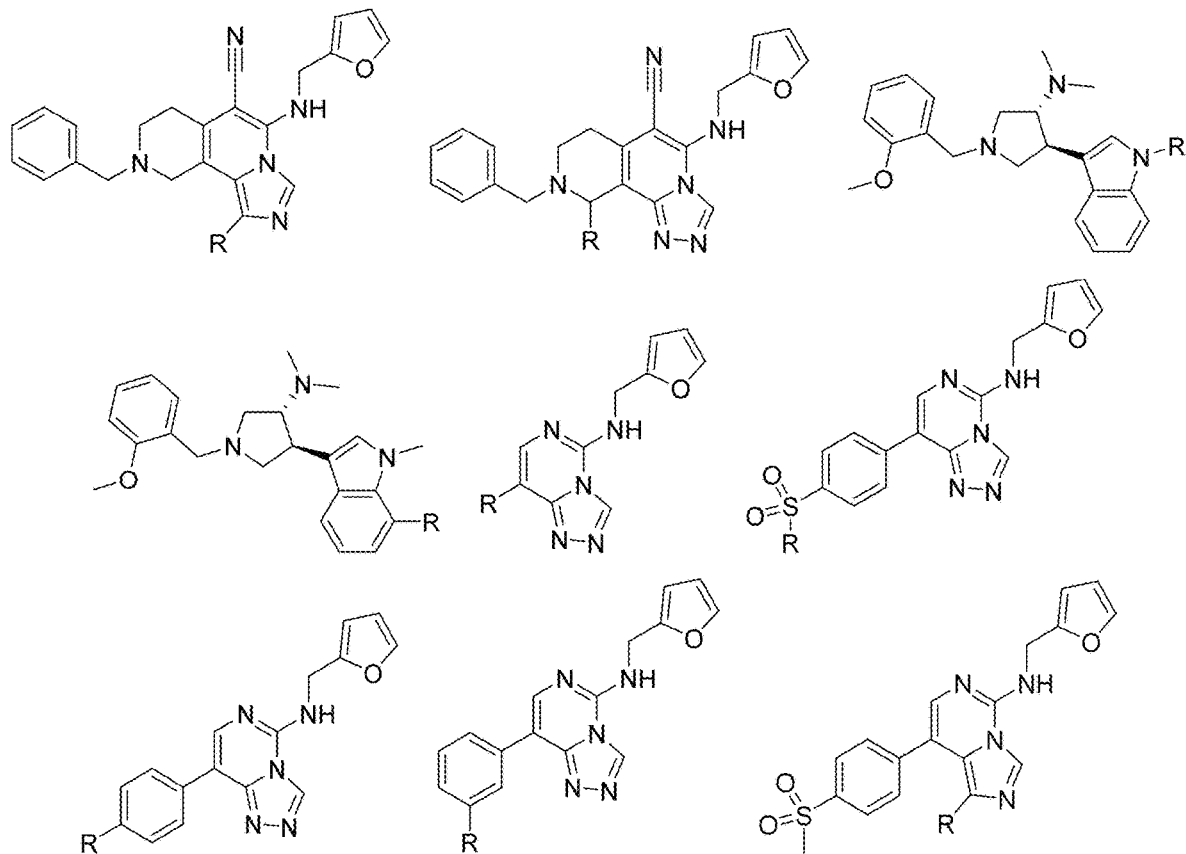

FIG. 6Hz-6I present examples of EED Targeting Ligands wherein R is the point at which the Linker is attached. For additional examples and related ligands, see, the PDB crystal structures 5 h15 and 5 h19 ("Discovery and Molecular Basis of a Diverse Set of Polycomb Repressive Complex 2 Inhibitors Recognition by EED"); Li, L. et al. *PLoS ONE* 12: e0169855 (2017); and, the PDB crystal structure 5 h19.

Figure 6J:
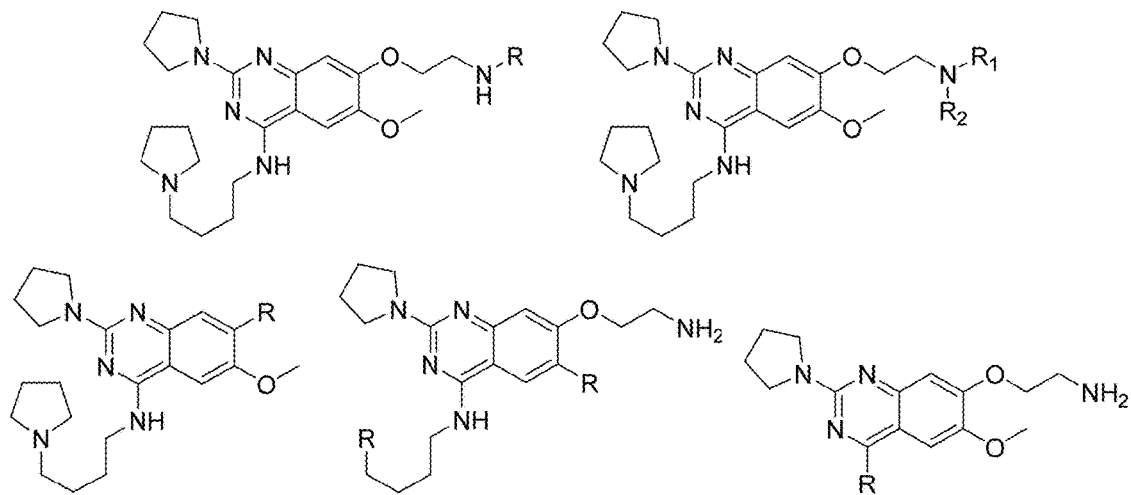

FIG. 6J presents examples of KMT5A (SETD8) Targeting Ligands wherein R is the point at which the Linker is attached. See for example, the PDB crystal structure 5t5 g.

Figure 6K:
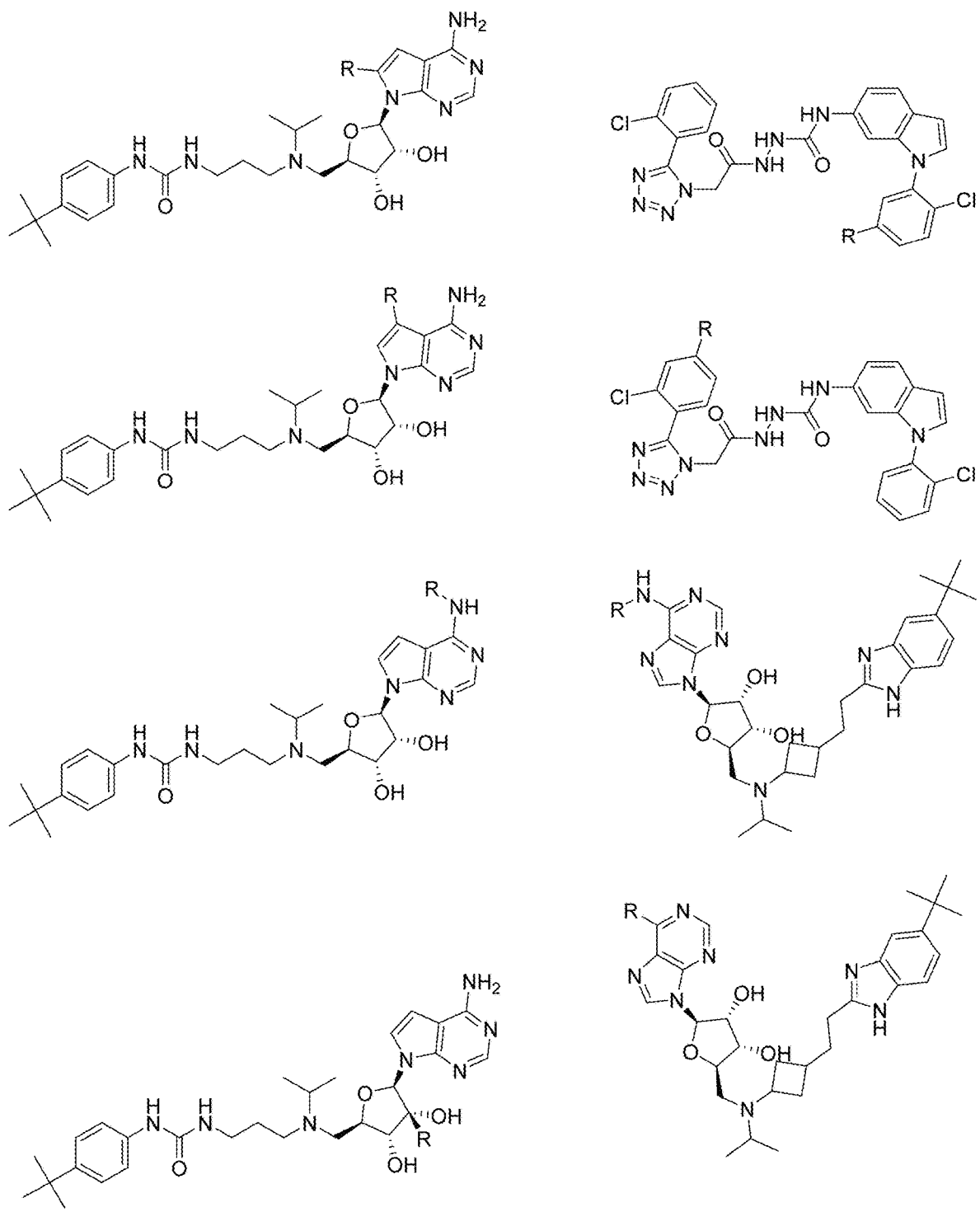
Figure 6L:
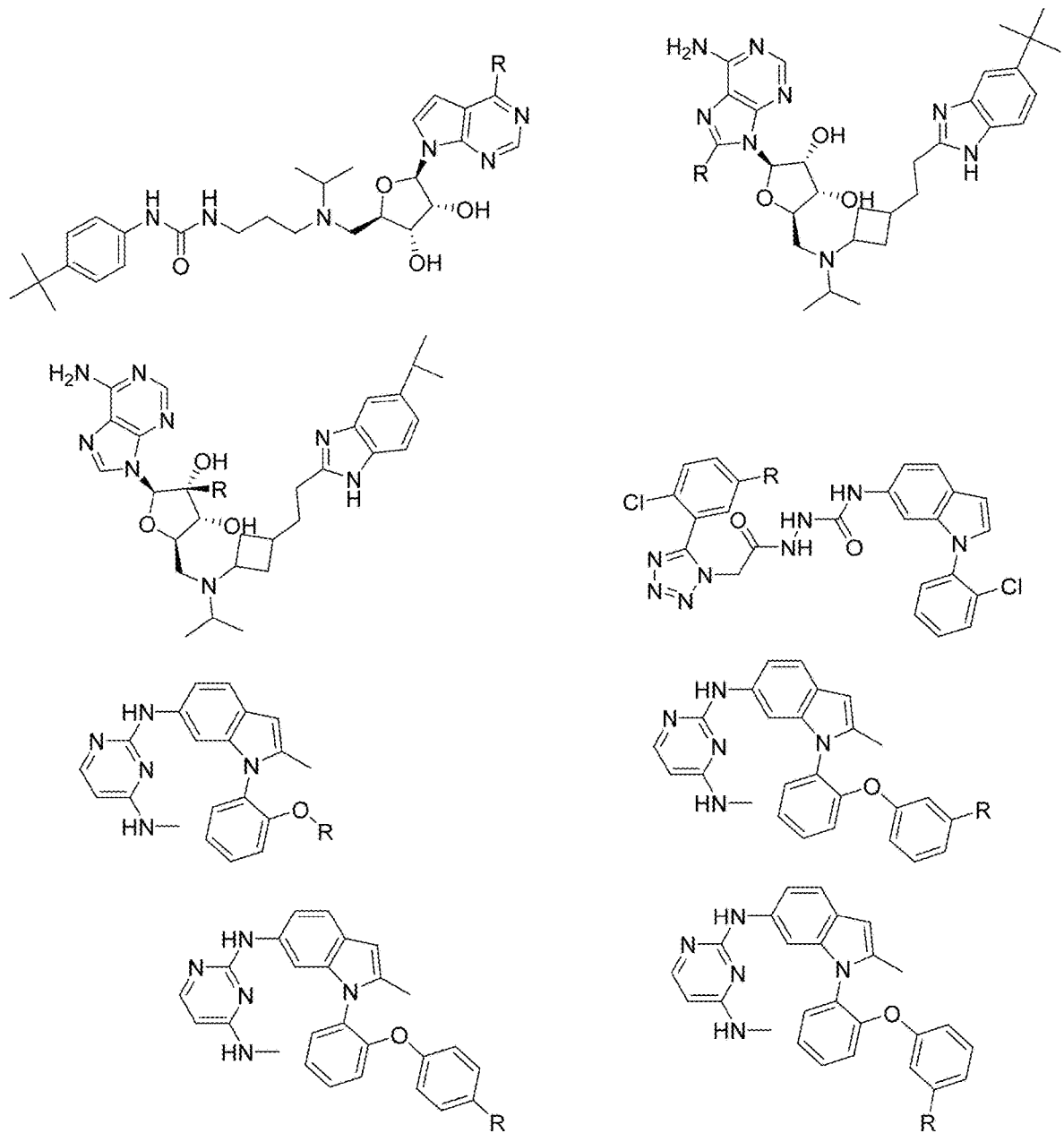

FIG. 6K-6L present examples of DOT1L Targeting Ligands wherein R is the point at which the Linker is attached. For additional examples and related ligands, see, the PDB crystal structure 4eki ("Conformational adaptation drives potent, selective and durable inhibition of the human protein methyltransferase DOT1L"); Basavapathruni, A. et al. *Chem. Biol. Drug Des.* 80: 971 (2012); the PDB crystal structure 4hra ("Potent inhibition of DOT1L as treatment of MLL-fusion leukemia"); Daigle, S. R. et al. *Blood* 122: 1017 (2013); the PDB crystal structure 5dry ("Discovery of Novel Dot1L Inhibitors through a Structure-Based Fragmentation Approach") Chen, C. et al. *ACS Med. Chem. Lett.* 7: 735 (2016); the PDB crystal structure 5dt2 ("Discovery of Novel Dot1L Inhibitors through a Structure-Based Fragmentation Approach"); and, Chen, C. et al. *ACS Med. Chem. Lett.* 7: 735 (2016).

Figure 6M:
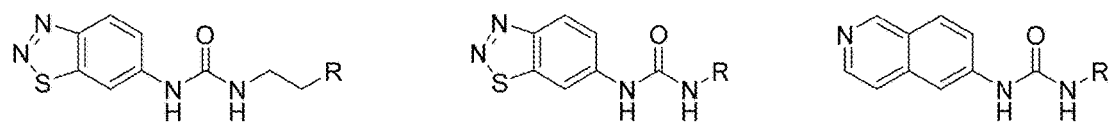

FIG. 6M-6N present examples of PRMT3 Targeting Ligands wherein R is the point at which the Linker is attached. For additional examples and related ligands, see, the PDB crystal structure 3smq ("An allosteric inhibitor of protein arginine methyltransferase 3"); Siarheyeva, A. et al. *Structure* 20: 1425 (2012); PDB crystal structure 4ry ("A Potent, Selective and Cell-Active Allosteric Inhibitor of Protein Arginine Methyltransferase 3 (PRMT3)"); and Kaniskan, H. U. et al. *Angew. Chem. Int. Ed. Engl.* 54: 5166 (2015).

FIG. 6O presents examples of CARM1 (PRMT4) Targeting Ligands wherein R is the point at which the Linker is attached. For additional examples and related ligands, see, the PDB crystal structures 2y1x and 2y1w and related ligands described in "Structural Basis for Carm1 Inhibition by Indole and Pyrazole Inhibitors." Sack, J. S. et al. *Biochem. J.* 436: 331 (2011).

FIG. 6P presents examples of PRMT5 Targeting Ligands wherein R is the point at which the Linker is attached. For additional examples and related ligands, see, the PDB crystal structure 4x61 and related ligands described in "A selective inhibitor of PRMT5 with in vivo and in vitro potency in MCL models". Chan-Penebre, E. *Nat. Chem. Biol.* 11: 432 (2015).

Figure 6Q:
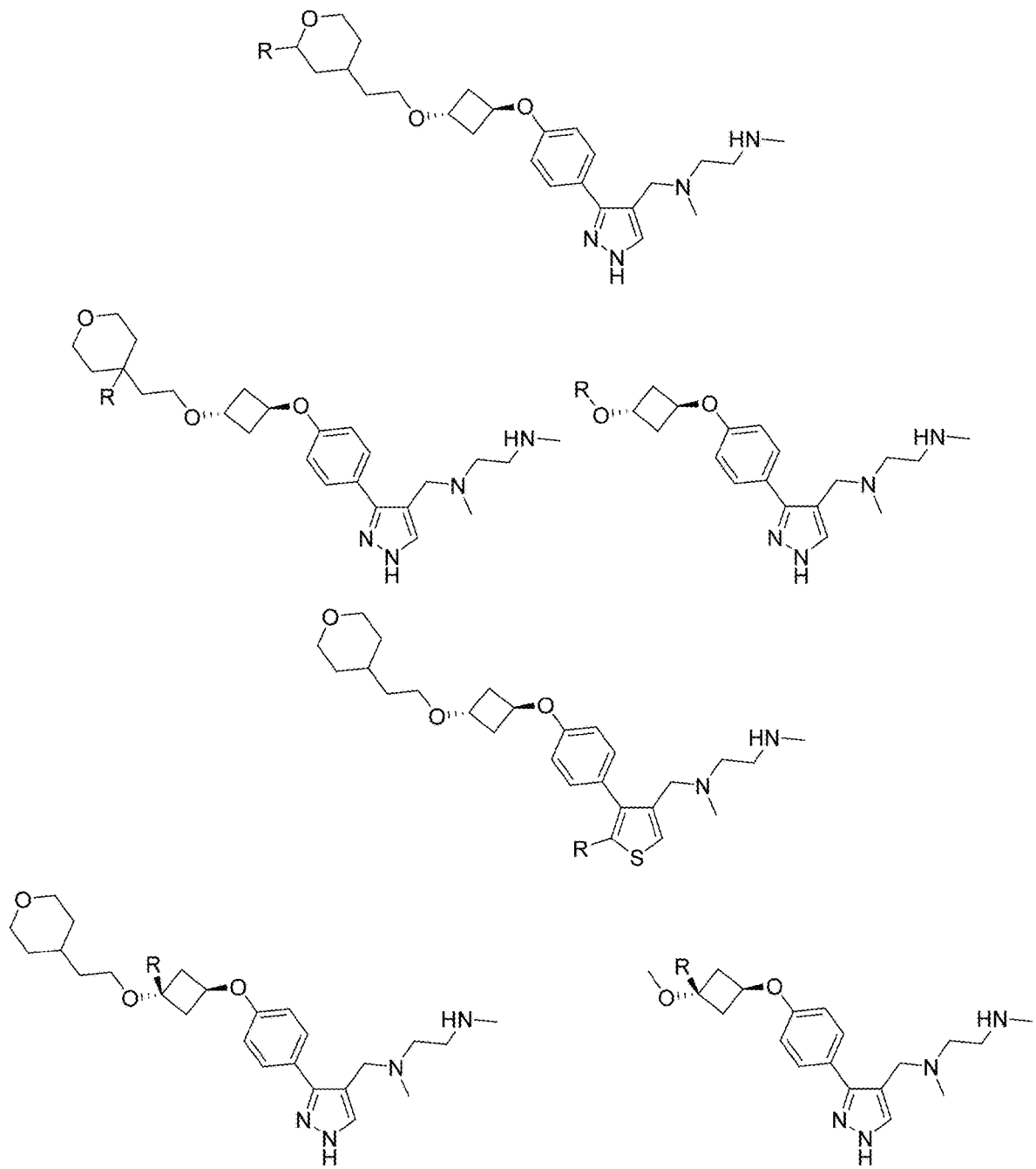

FIG. 6Q presents examples of PRMT6 Targeting Ligands wherein R is the point at which the Linker is attached. For additional examples and related ligands, see, the PDB crystal structure 4y30 and related ligands described in "Aryl Pyrazoles as Potent Inhibitors of Arginine Methyltransferases: Identification of the First PRMT6 Tool Compound". Mitchell, L. H. et al. *ACS Med. Chem. Lett.* 6: 655 (2015).

Figure 6R:
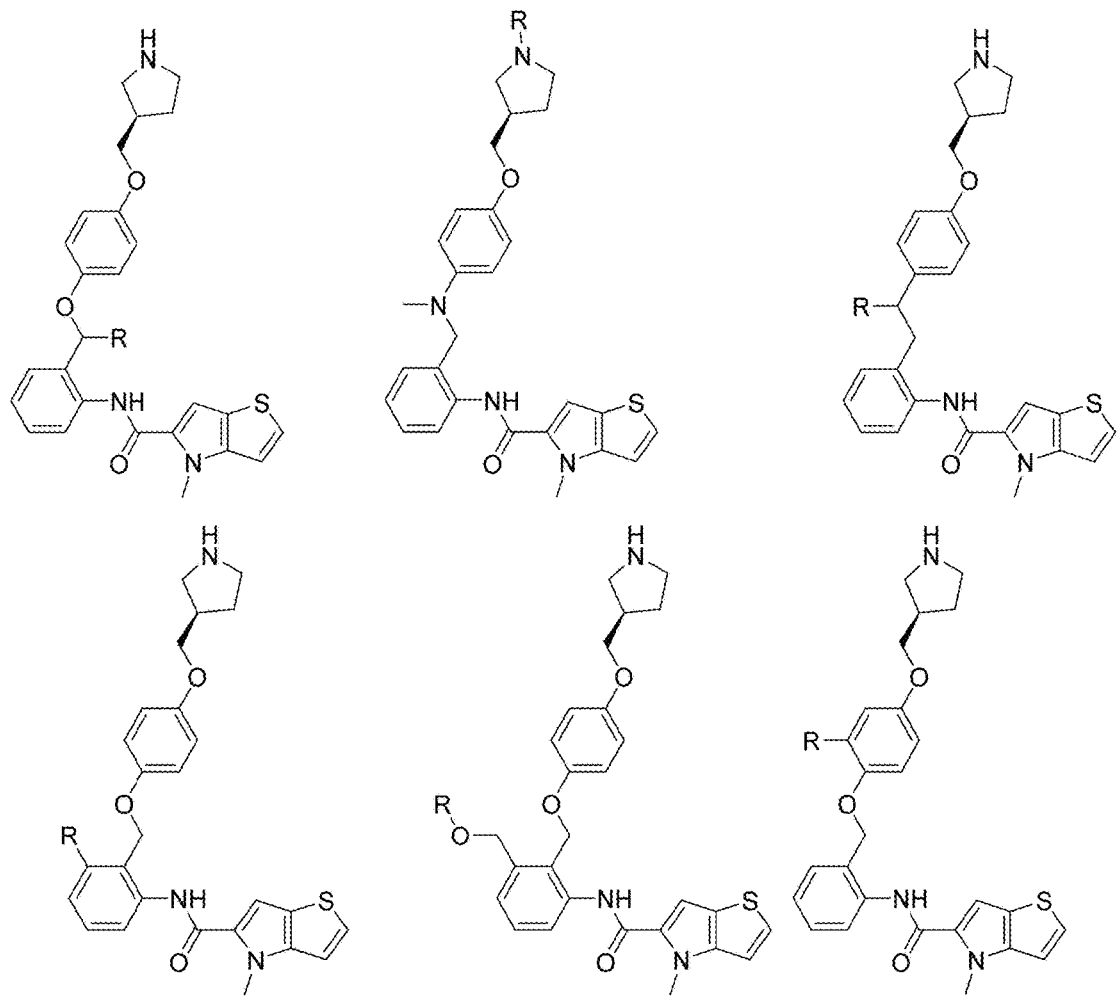

FIG. 6R presents examples of LSD1 (KDM1A) Targeting Ligands wherein R is the point at which the Linker is attached. For additional examples and related ligands, see, the PDB crystal structure 5lgu and related ligands described in "Thieno[3,2-b]pyrrole-5-carboxamides as New Reversible Inhibitors of Histone Lysine Demethylase KDM1A/ LSD1. Part 2: Structure-Based Drug Design and Structure-Activity Relationship". Vianello, P. et al. *J. Med Chem.* 60: 1693 (2017).

Figure 6S:
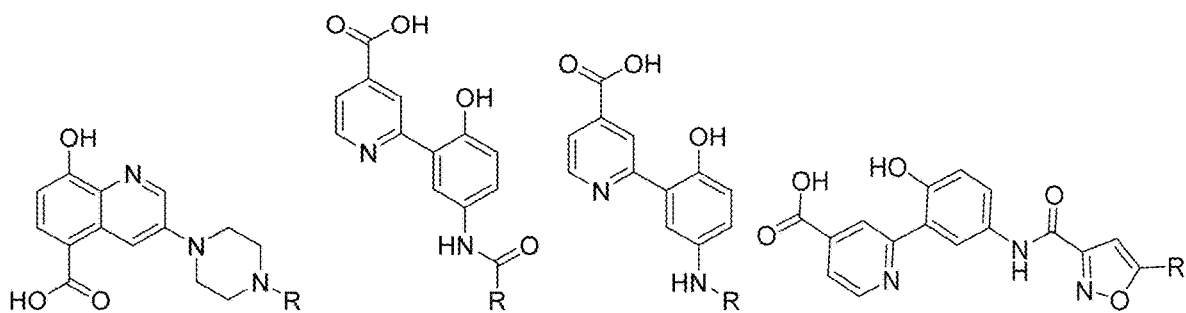
Figure 6T:
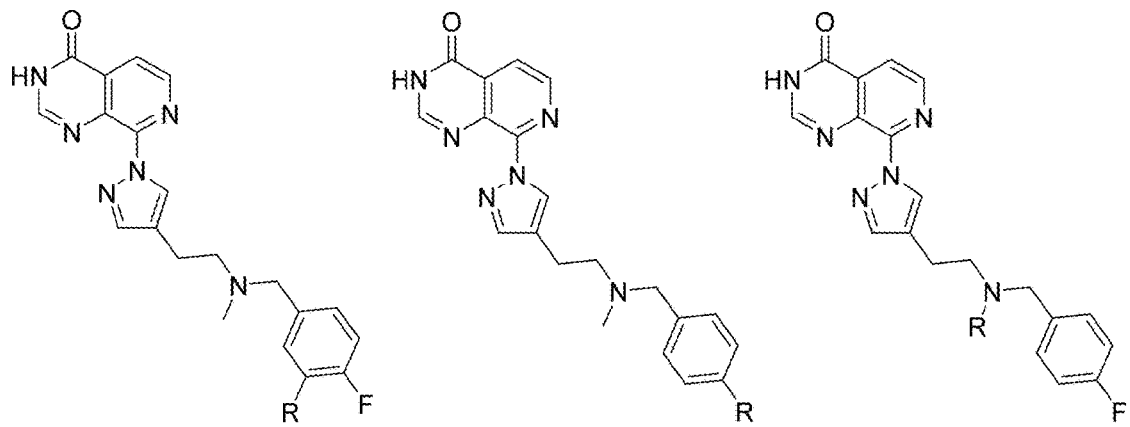

FIG. 6S-6T present examples of KDM4 Targeting Ligands wherein R is the point at which the Linker is attached. For additional examples and related ligands, see, the PDB crystal structure 3rvh; the PDB crystal structure 5a7p and related ligands described in "Docking and Linking of Fragments to Discover Jumonji Histone Demethylase Inhibitors." Korczynska, M., et al. *J. Med Chem.* 59: 1580 (2016); and, the PDB crystal structure 3f3c and related ligands described in "8-Substituted Pyrido[3,4-d]pyrimidin-4(3H)-one Derivatives As Potent, Cell Permeable, KDM4 (JMJD2) and KDM5 (JARID1) Histone Lysine Demethylase Inhibitors." Bavetsias, V. et al. *J. Med Chem.* 59: 1388 (2016).

Figure 6U:
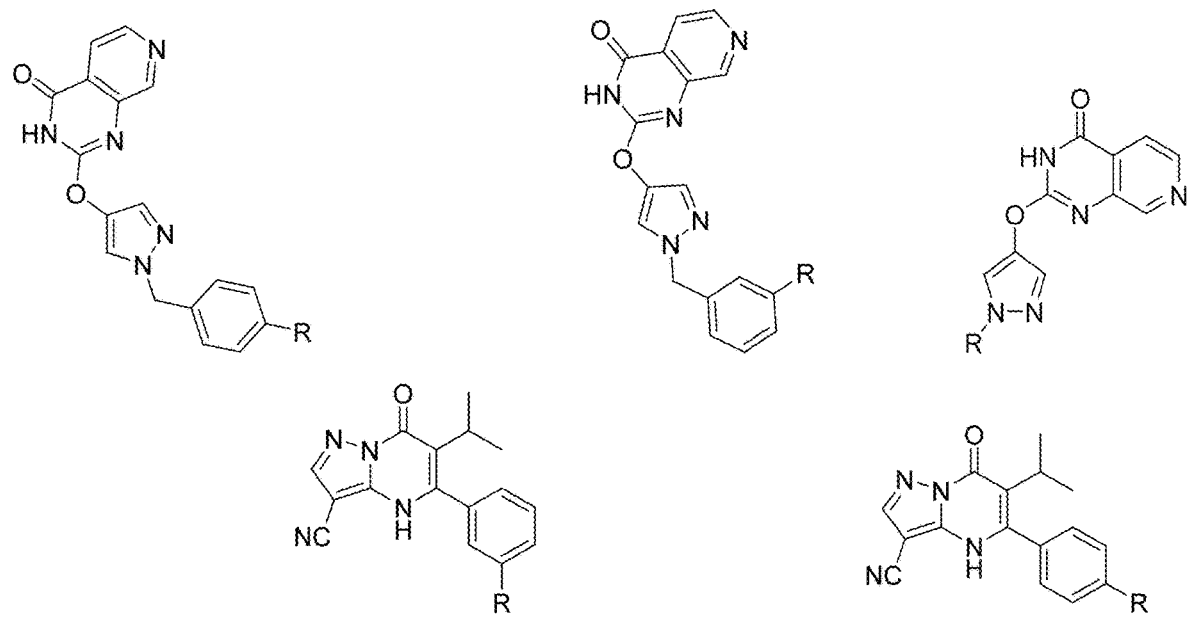

FIG. 6U presents examples of KDM5 Targeting Ligands wherein R is the point at which the Linker is attached. For additional examples and related ligands, see, the PDB crystal structure 3fun and related ligands described in "Structural Analysis of Human Kdm5B Guides Histone Demethylase Inhibitor Development". Johansson, C. et al. *Nat. Chem. Biol.* 12: 539 (2016) and the PDB crystal structure 5ceh and related ligands described in "An inhibitor of KDM5 demethylases reduces survival of drug-tolerant cancer cells". Vinogradova, M. et al. *Nat. Chem. Biol.* 12: 531 (2016).

Figure 6V:
Figure 6W:
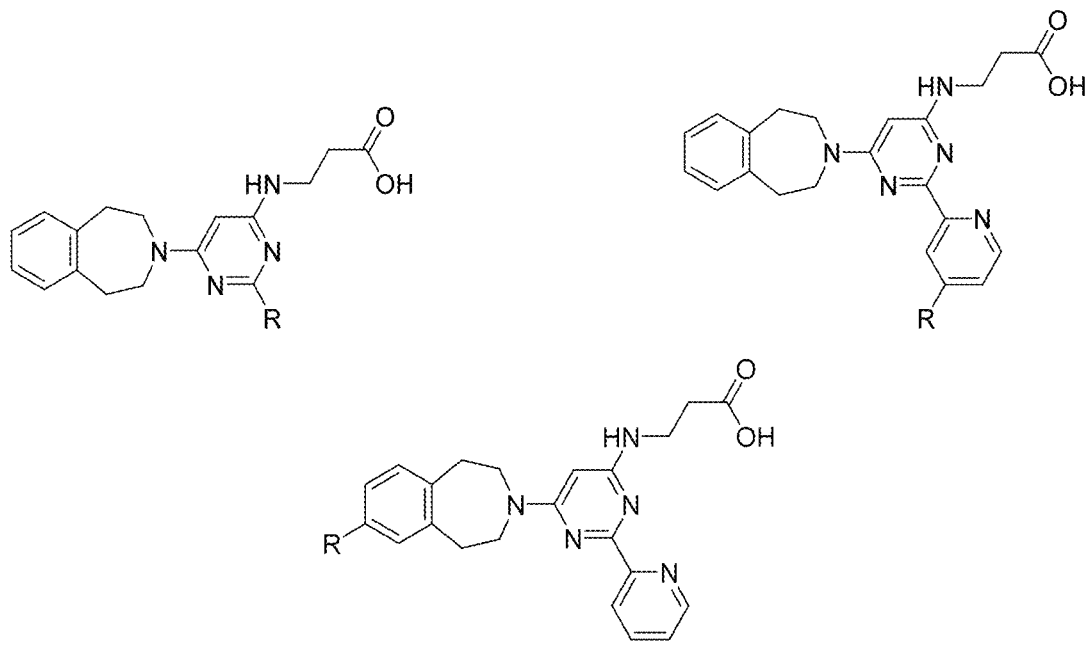

FIG. 6V-6W present examples of KDM6 Targeting Ligands wherein R is the point at which the Linker is attached. For additional examples and related ligands, see, the PDB crystal structure 4ask and related ligands described in "A Selective Jumonji H3K27 Demethylase Inhibitor Modulates the Proinflammatory Macrophage Response". Kruidenier, L. et al. *Nature* 488: 404 (2012).

Figure 6X:
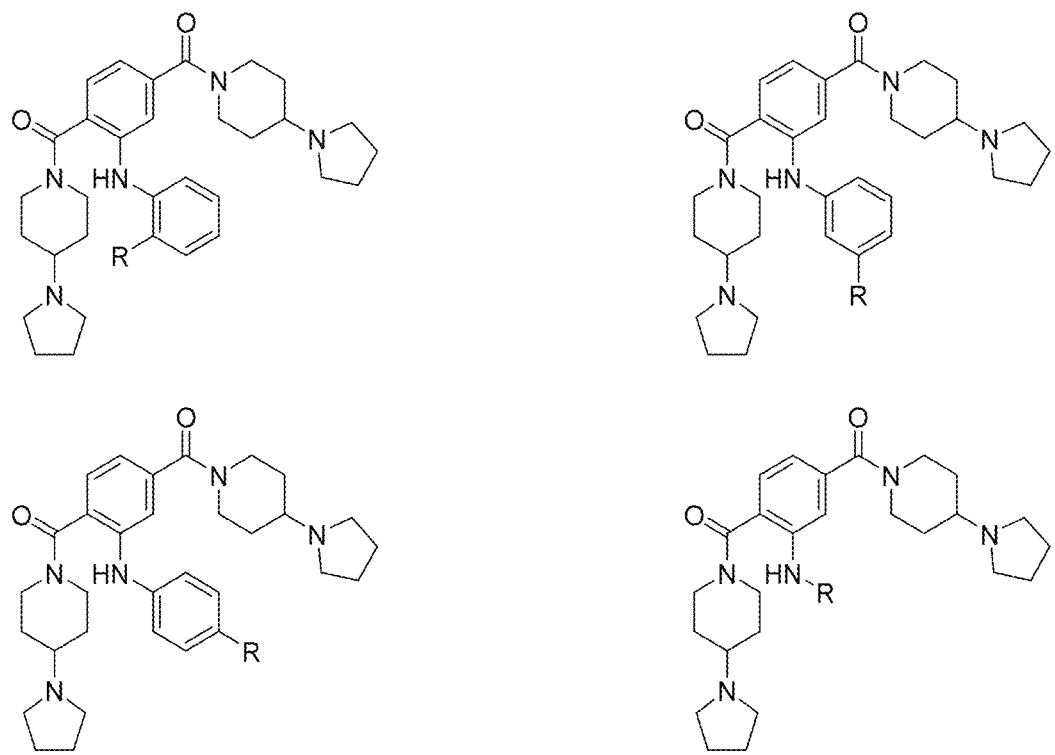

FIG. 6X presents examples of L3MBTL3 targeting ligands wherein R is the point at which the Linker is attached. See for example, the PDB crystal structure 4fl6.

Figure 6Y:
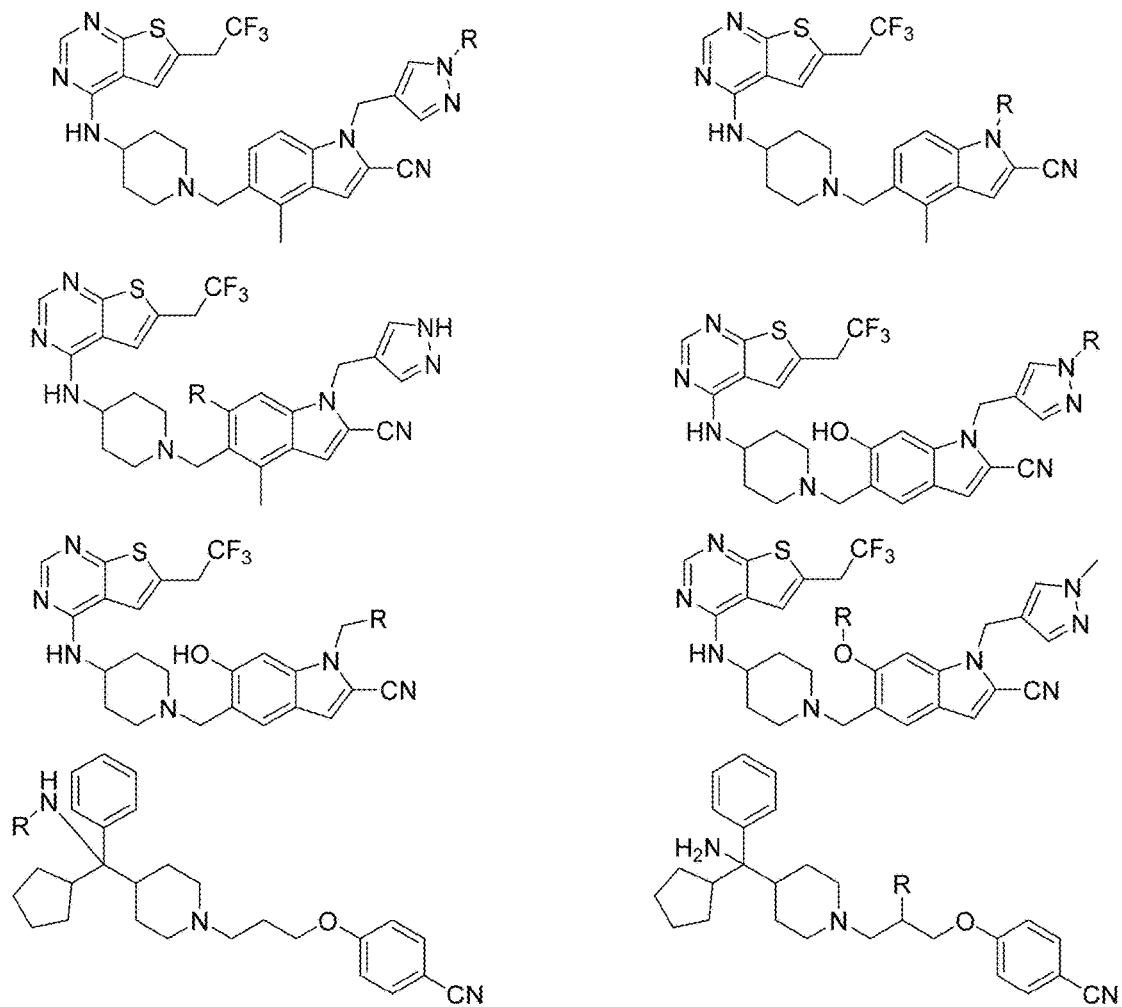

FIG. 6Y presents examples of Menin Targeting Ligands wherein R is the point at which the Linker is attached. For additional examples and related ligands, see the PDB crystal structure 4x5y and related ligands described in "Pharmacologic Inhibition of the Menin-MLL Interaction Blocks Progression of MLL Leukemia In Vivo" Borkin, D. et al. *Cancer Cell* 27: 589 (2015) and the PDB crystal structure 4og8 and related ligands described in "High-Affinity Small-Molecule Inhibitors of the Menin-Mixed Lineage Leukemia (MLL) Interaction Closely Mimic a Natural Protein-Protein Interaction" He, S. et al. *J. Med. Chem.* 57: 1543 (2014).

Figure 6Z:
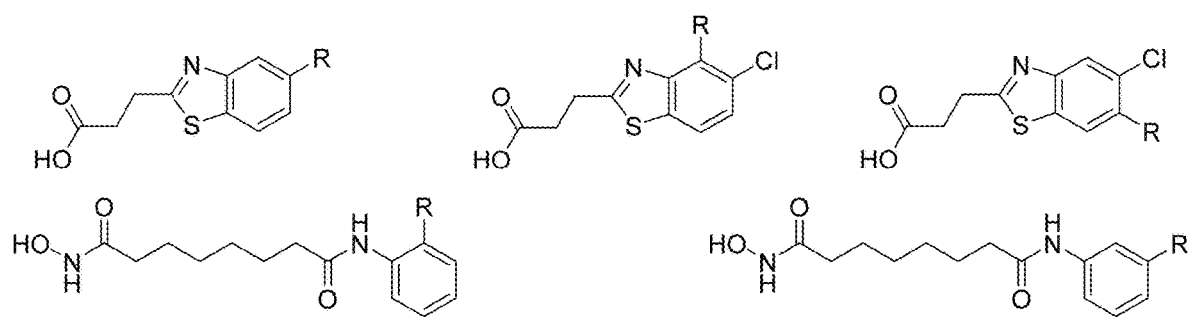
Figure 6A:
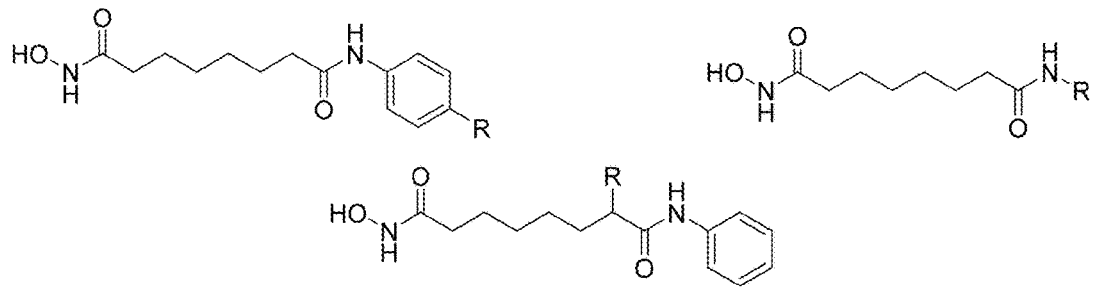
Figure 6B:
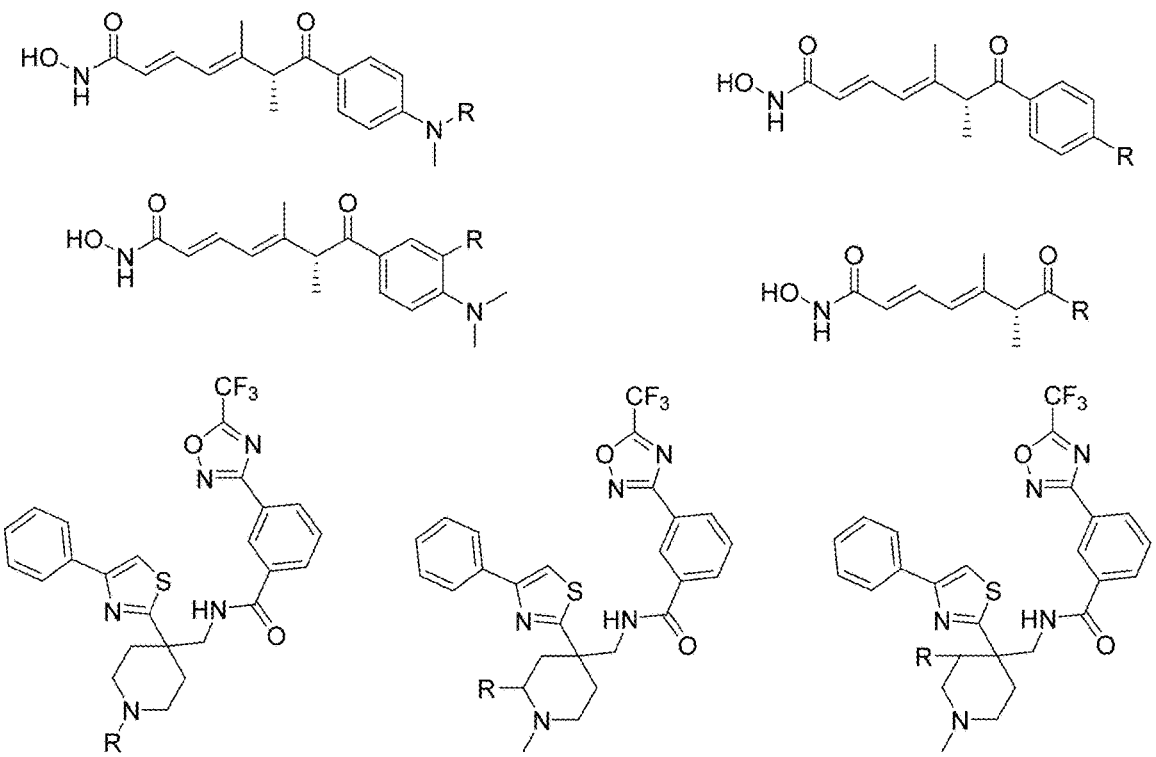

FIG. 6Z-6AA present examples of HDAC6 Targeting Ligands wherein R is the point at which the Linker is attached. See for example, the PDB crystal structures 5kh3 and 5eei.

FIG. 6BB presents examples of HDAC7 Targeting Ligands wherein R is the point at which the Linker is attached. For additional examples and related ligands, see, the PDB crystal structure 3c10 and related ligands described in "Human HDAC7 harbors a class IIa histone deacetylase-specific zinc binding motif and cryptic deacetylase activity." Schuetz, A. et al. *J. Biol. Chem.* 283: 11355 (2008) and the PDB crystal structure PDB 3zns and related ligands described in "Selective Class Iia Histone Deacetylase Inhibition Via a Non-Chelating Zinc Binding Group". Lobera, M. et al. *Nat. Chem. Biol.* 9: 319 (2013).

Figure 7A:
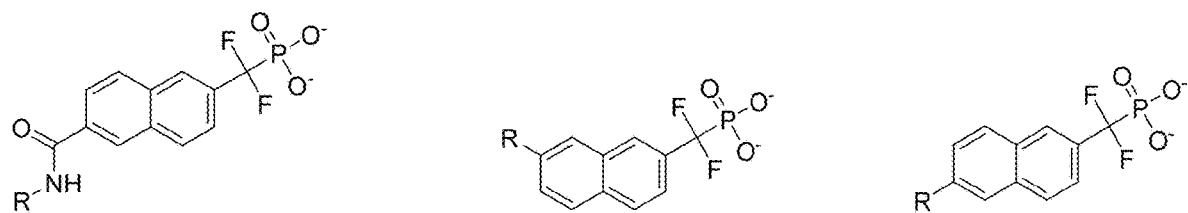
Figure 7B:
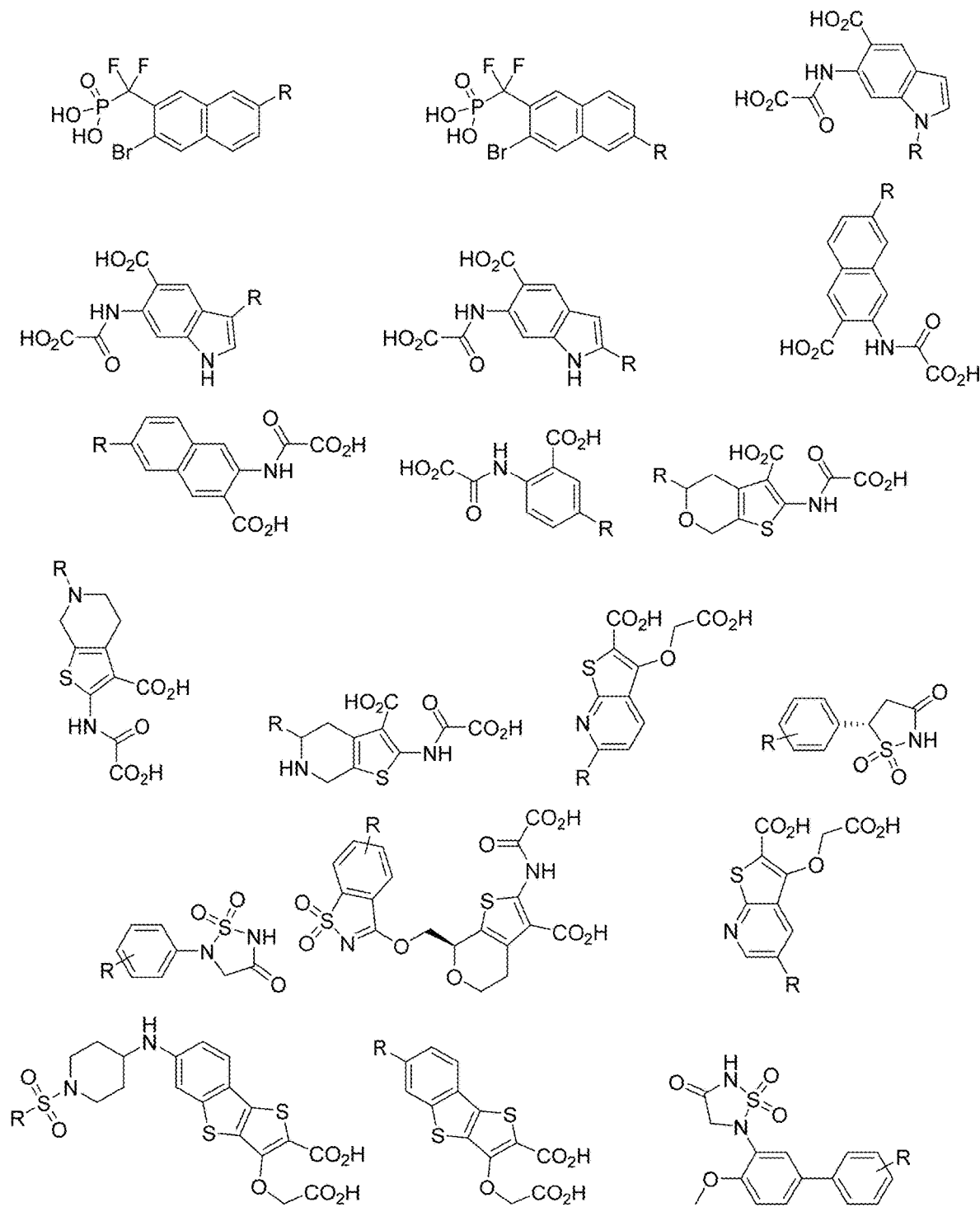
Figure 7C:
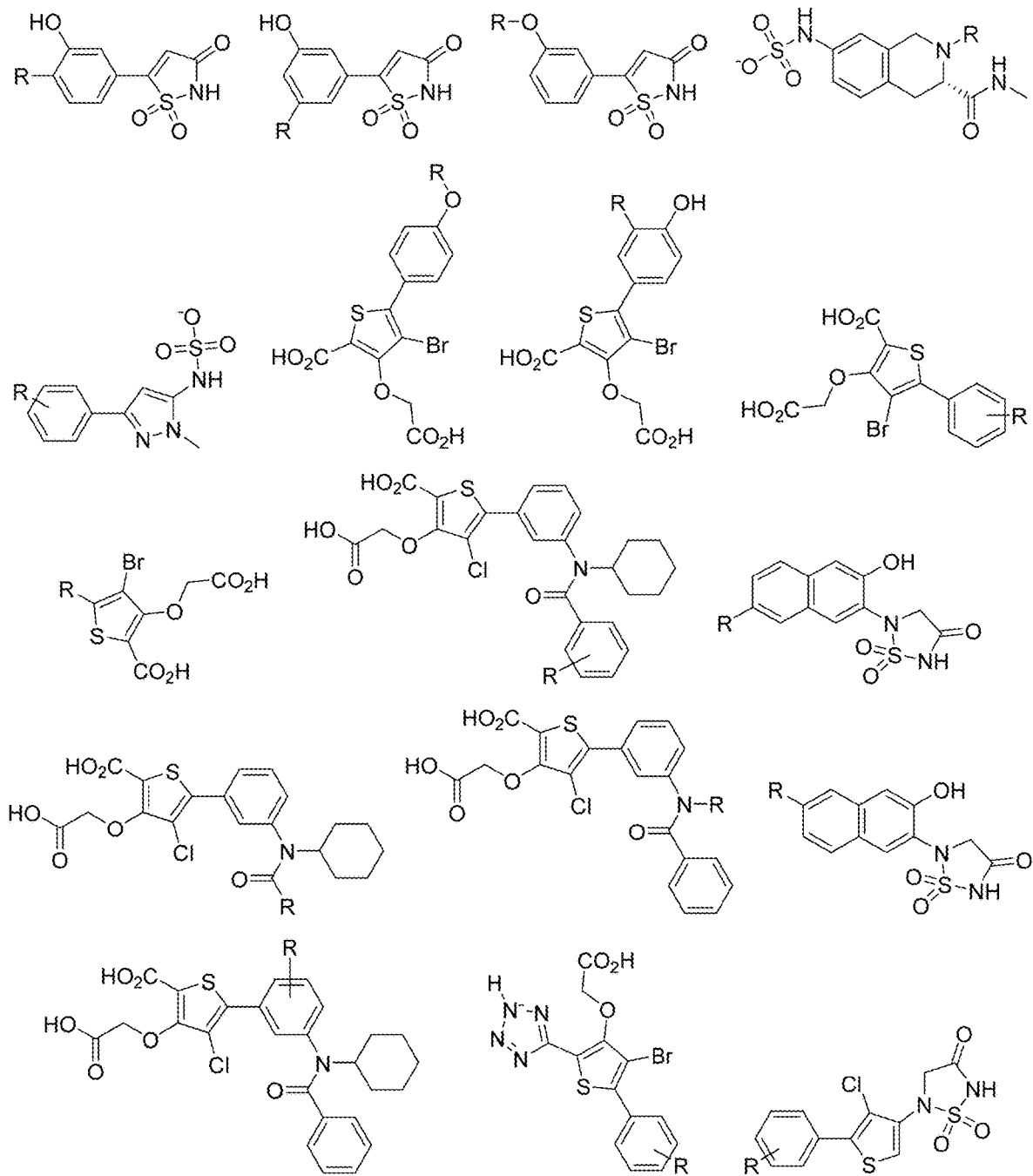

FIG. 7A-7C present examples of Protein Tyrosine Phosphatase, Non-Receptor Type 1, PTP1B Targeting Ligands wherein R is the point at which the Linker is attached. For additional examples and related ligands, see, the PDB crystal structure 1bzj described in "Structural basis for inhibition of the protein tyrosine phosphatase 1B by phosphotyrosine peptide mimetics" Groves, M. R. et al. *Biochemistry* 37: 17773-17783 (1998); the PDB crystal structure 3cwe described in "Discovery of [(3-bromo-7-cyano-2-naphthyl) (difluoro)methyl]phosphonic acid, a potent and orally active small molecule PTP1B inhibitor". Han Y, *Bioorg Med Chem Lett.* 18:3200-5 (2008); the PDB crystal structures 2azr and 2b07 described in "Bicyclic and tricyclic thiophenes as protein tyrosine phosphatase 1B inhibitors." Moretto, A. F. et al. *Bioorg. Med. Chem.* 14: 2162-2177 (2006); the PDB crystal structures PDB 2bgd, 2bge, 2 cm7, 2 cm8, 2cma, 2cmb, 2cmc described in ""Structure-Based Design of Protein Tyrosine Phosphatase-1B Inhibitors". Black, E. et al. *Bioorg. Med. Chem. Lett.* 15: 2503 (2005) and "Structural Basis for Inhibition of Protein-Tyrosine Phosphatase 1B by Isothiazolidinone Heterocyclic Phosphonate Mimetics." Ala, P. J. et al. *J. Biol. Chem.* 281: 32784 (2006); the PDB crystal structures 2f6t and 2f6w described in "1,2,3,4-Tetrahydroisoquinolinyl sulfamic acids as phosphatase PTP1B inhibitors". Klopfenstein, S. R. et al. *Bioorg. Med. Chem. Lett.* 16: 1574-1578 (2006); the PDB crystal structures 2 h4 g, 2 h4k, 2hb1 described in ""Monocyclic thiophenes as protein tyrosine phosphatase 1B inhibitors: Capturing interactions with Asp48." Wan, Z. K. et al. *Bioorg. Med. Chem. Lett.* 16: 4941-4945 (2006); the PDB crystal structures 2zn7 described in "Structure-based optimization of protein tyrosine phosphatase-1 B inhibitors: capturing interactions with arginine 24". Wan, Z. K. et al. *Chem Med Chem.* 3:1525-9 (2008); the PDB crystal structure 2nt7, 2nta described in "Probing acid replacements of thiophene PTP1B inhibitors." Wan, Z. K. et al. *Bioorg. Med. Chem. Lett.* 17: 2913-2920 (2007); and, WO 2008148744 A1 assigned to Novartis AG titled "Thiadiazole derivatives as antidiabetic agents". See also, the PDB crystal structures 1c84, 1c84, 1c85, 1c86, 1c88, 118 g and described in ""2-(oxalylamino)-benzoic acid is a general, competitive inhibitor of protein-tyrosine phosphatases". Andersen, H. S. et al. *J. Biol. Chem.* 275: 7101-7108 (2000); "Structure-based design of a low molecular weight, nonphosphorus, nonpeptide, and highly selective inhibitor of protein-tyrosine phosphatase 1B." Iversen, L. F. et al. *J. Biol. Chem.* 275: 10300-10307 (2000); and, "Steric hindrance as a basis for structure-based design of selective inhibitors of protein-tyrosine phosphatases". Iversen, L. F. et al. *Biochemistry* 40: 14812-14820 (2001).

Figure 7D:
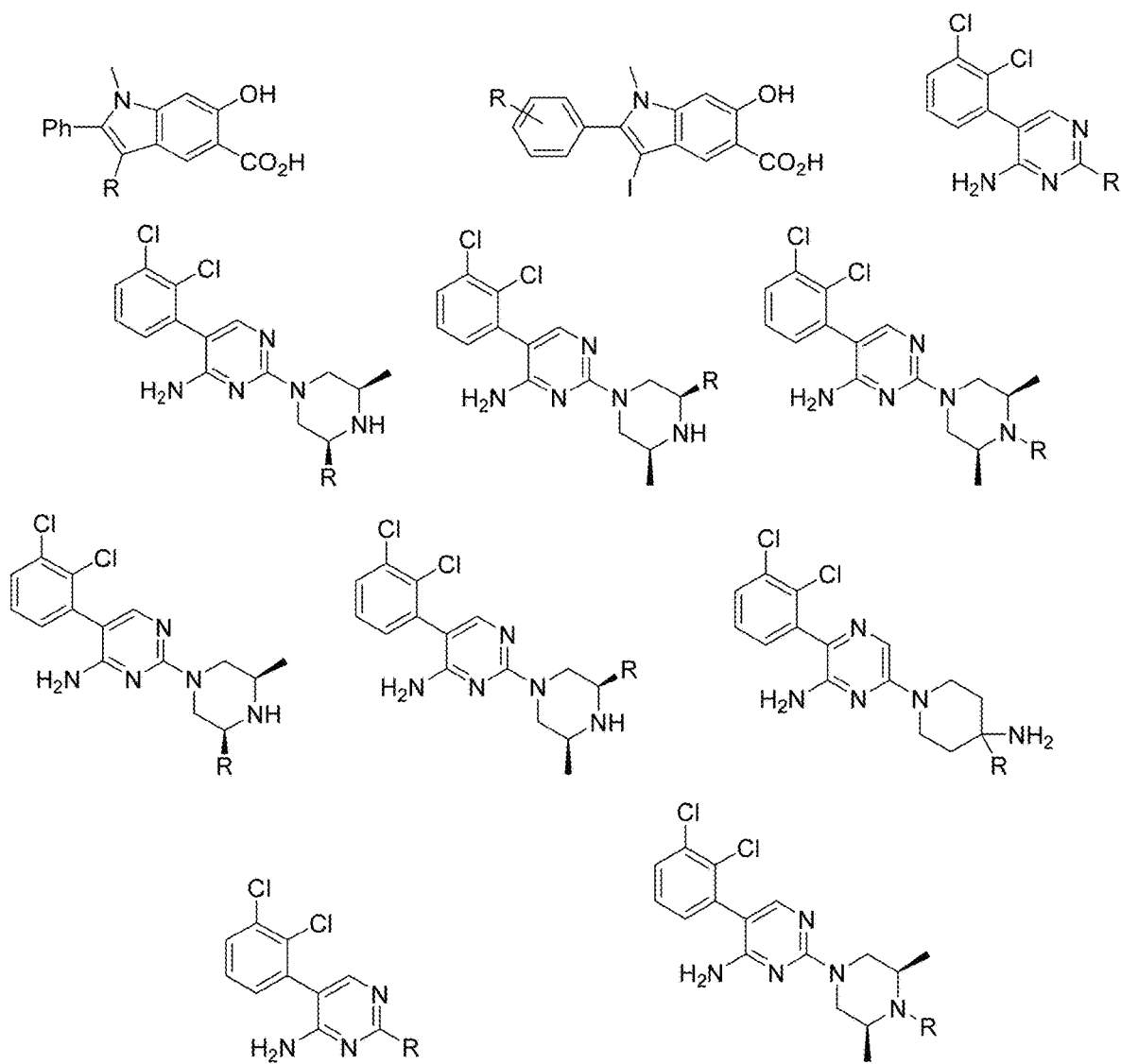

FIG. 7D presents examples of Tyrosine-protein phosphatase non-receptor type 11, SHP2 Targeting Ligands wherein R is the point at which the Linker is attached. For additional examples and related ligands, see, the crystal structures PDB 4pvg and 3O5x and described in "Salicylic acid based small molecule inhibitor for the oncogenic Src homology-2 domain containing protein tyrosine phosphatase-2 (SHP2)." Zhang, X. et al. *J. Med. Chem.* 53: 2482-2493 (2010); and, the crystal structure PDB 5ehr and related ligands described in "Allosteric Inhibition of SHP2: Identification of a Potent, Selective, and Orally Efficacious Phosphatase Inhibitor." Garcia Fortanet, J. et al. *J. Med. Chem.* 59: 7773-7782 (2016). Also, see the crystal structure PDB 5ehr described in "Allosteric Inhibition of SHP2: Identification of a Potent, Selective, and Orally Efficacious Phosphatase Inhibitor." Garcia Fortanet, J. et al. *J. Med. Chem.* 59: 7773-7782 (2016) and "Allosteric inhibition of SHP2 phosphatase inhibits cancers driven by receptor tyrosine kinases." Chen, Y. P. et al. *Nature* 535: 148-152 (2016).

Figure 7E:
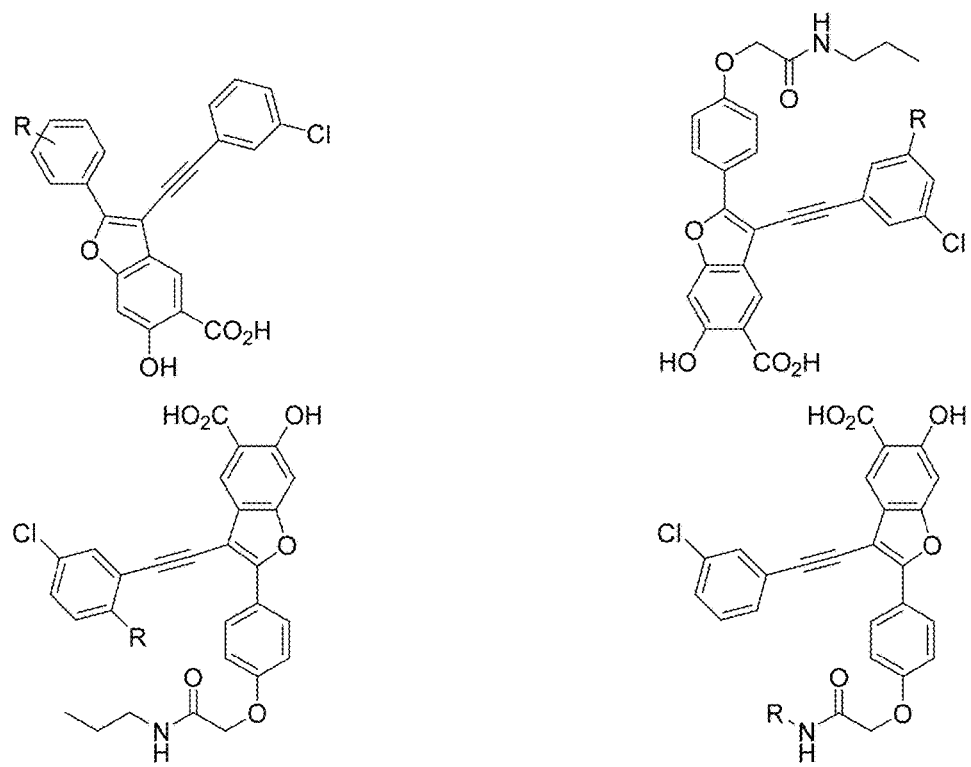

FIG. 7E presents examples of Tyrosine-protein phosphatase non-receptor type 22 Targeting Ligands wherein R is the point at which the Linker is attached. For additional examples and related ligands, see, the crystal structure PDB 4j51 described in "A Potent and Selective Small-Molecule Inhibitor for the Lymphoid-Specific Tyrosine Phosphatase (LYP), a Target Associated with Autoimmune Diseases." He, Y. et al. *J. Med. Chem.* 56: 4990-5008 (2013).

Figure 7F:
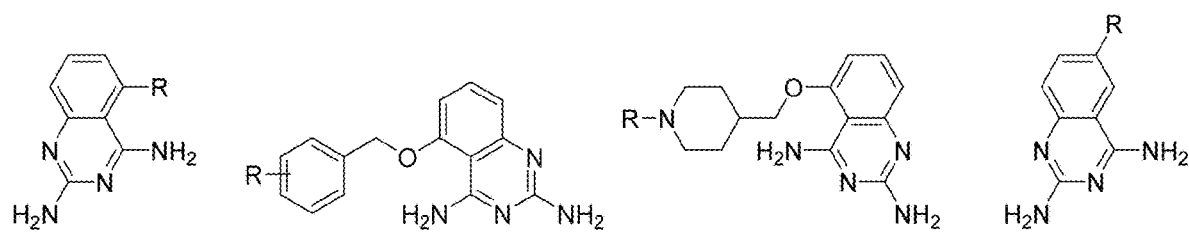

FIG. 7F presents examples of Scavenger mRNA-decapping enzyme DcpS Targeting Ligands wherein R is the point at which the Linker is attached. For additional examples and related ligands, see, the crystal structures PDB 3bl7, 3bl9, 3bla, 4qde, 4qdv, 4qeb and related ligands described in "DcpS as a therapeutic target for spinal muscular atrophy." Singh, J. et al. *ACS Chem. Biol.* 3: 711-722 (2008).

Figure 8A:
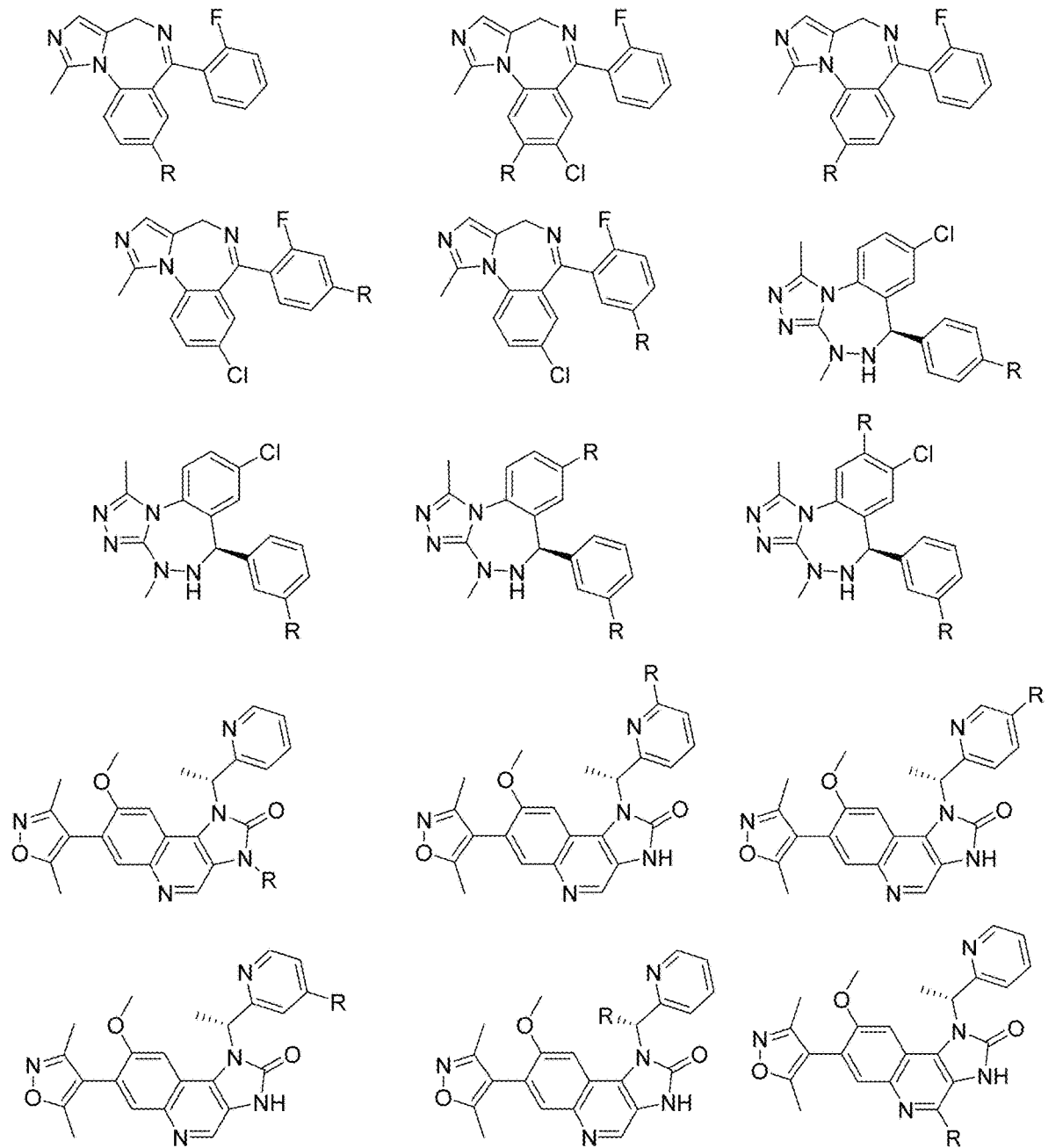
Figure 8B:
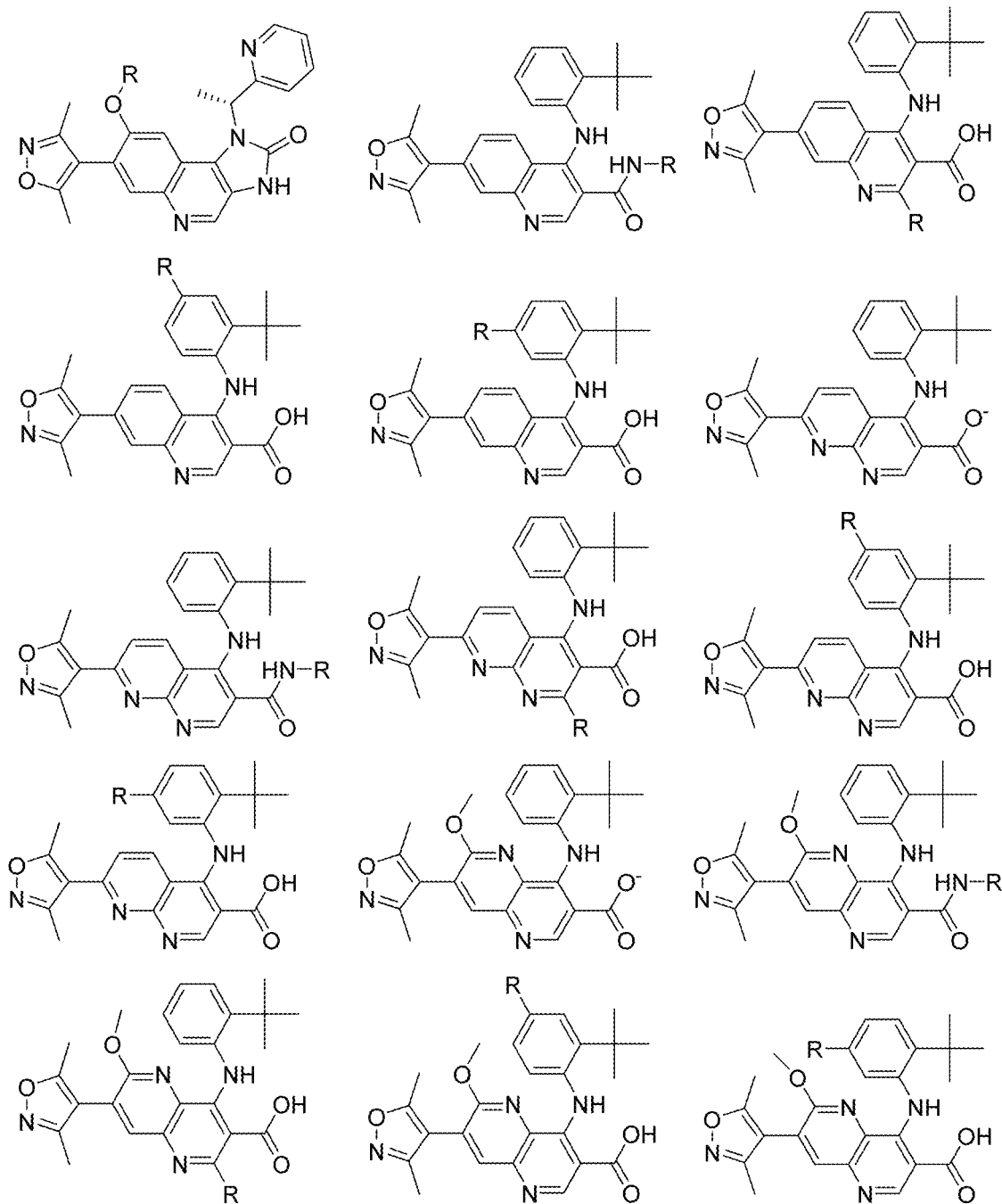
Figure 8C:
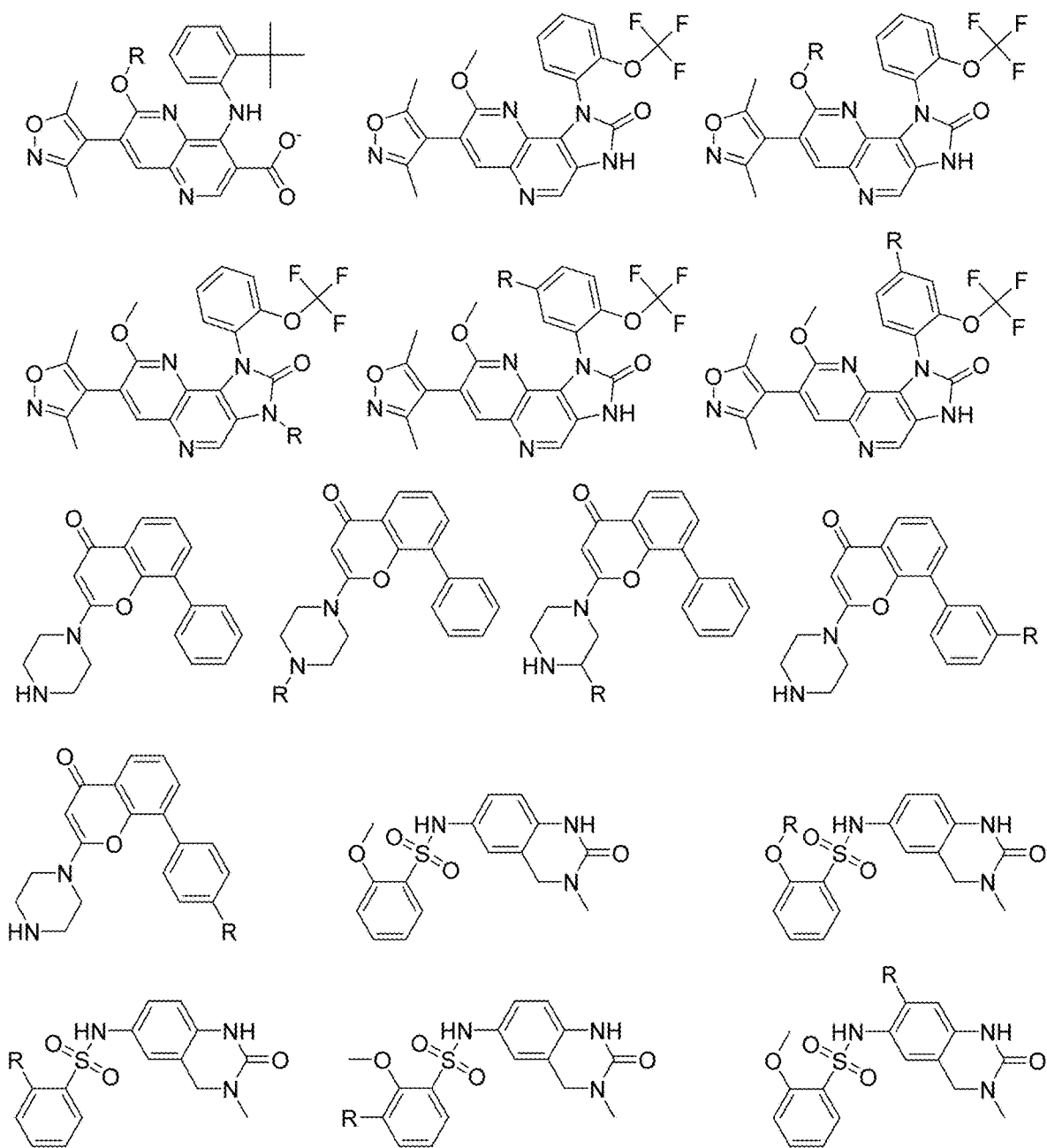
Figure 8D:
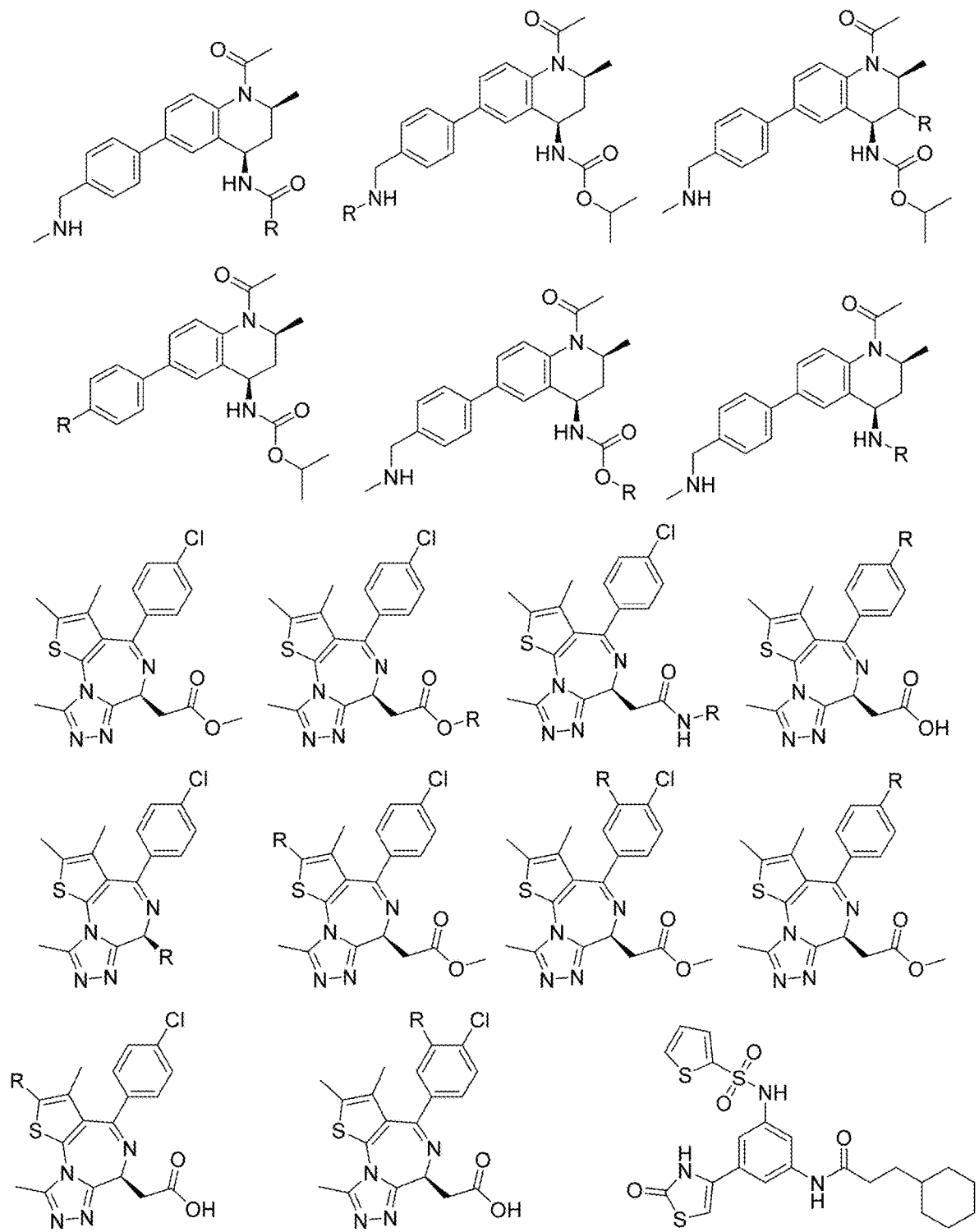
Figure 8E:
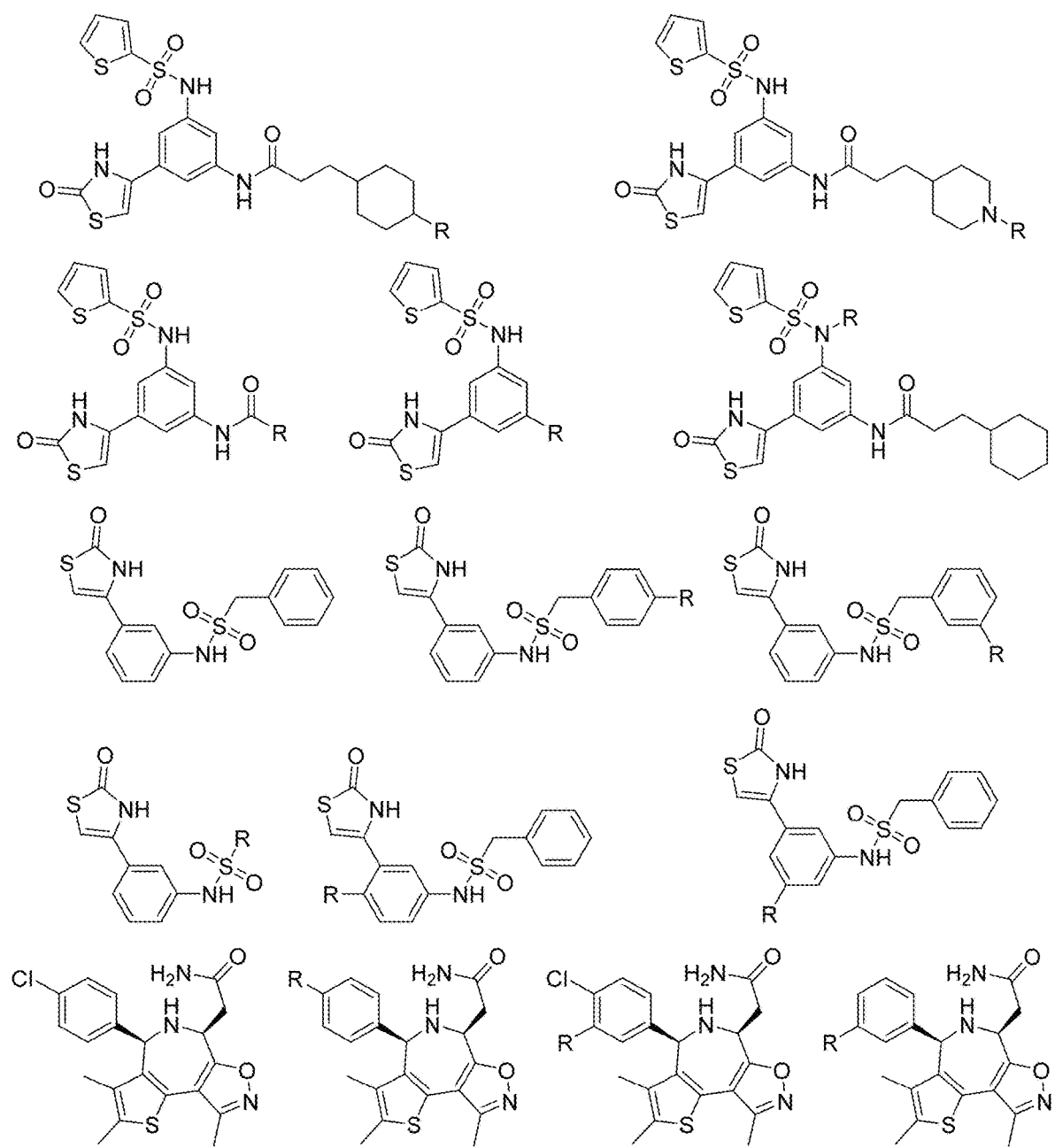
Figure 8F:
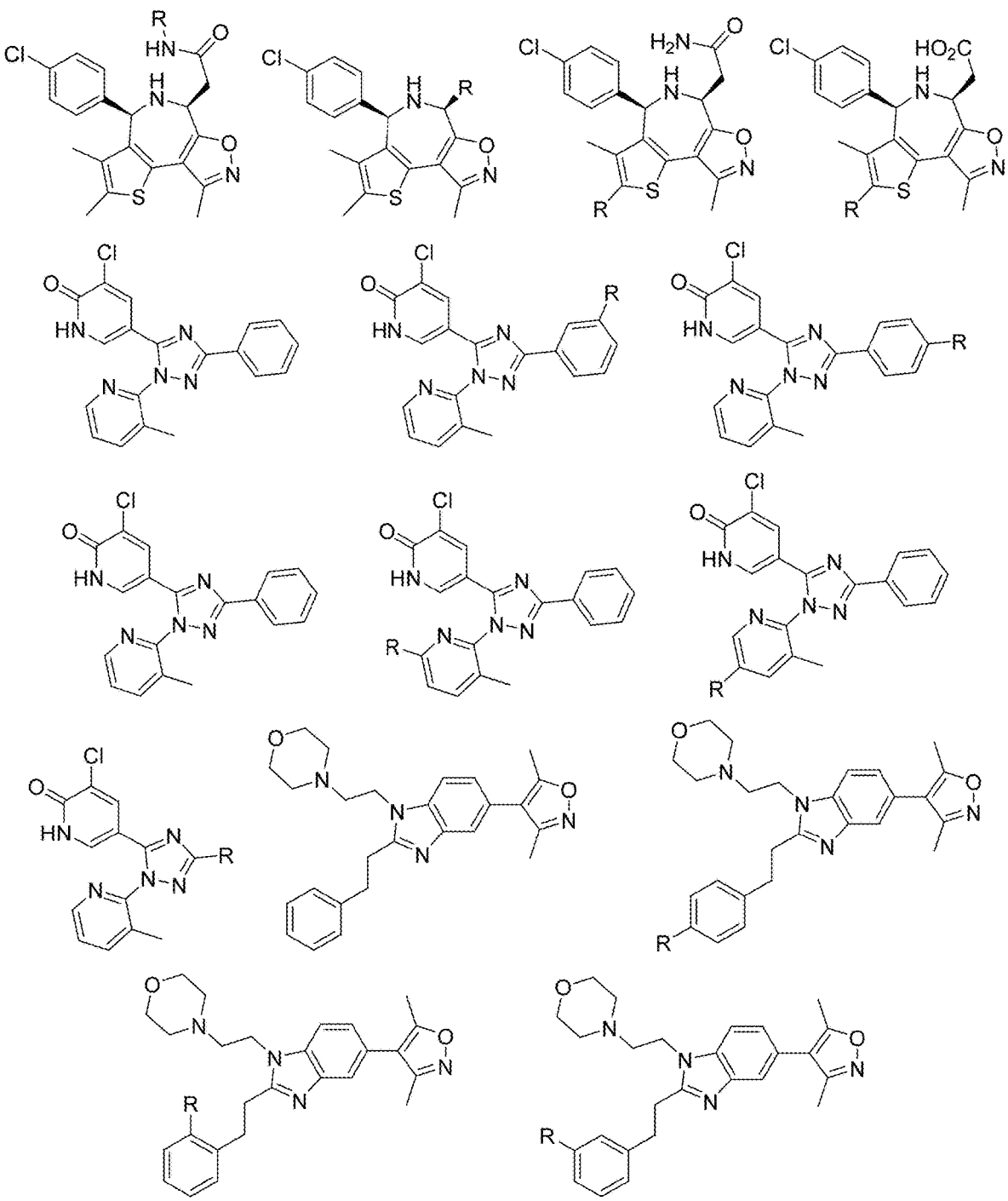
Figure 8G:
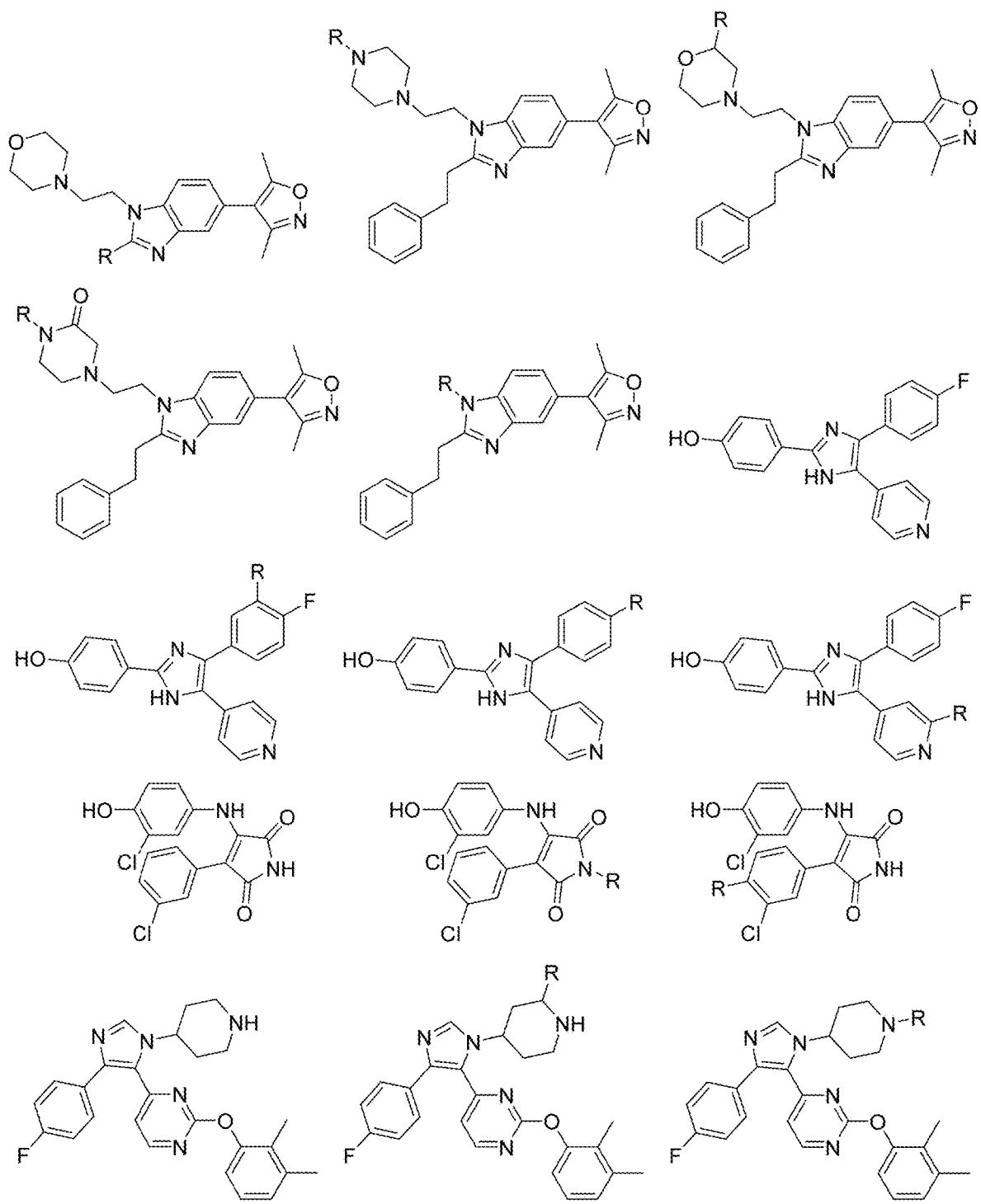
Figure 8H:
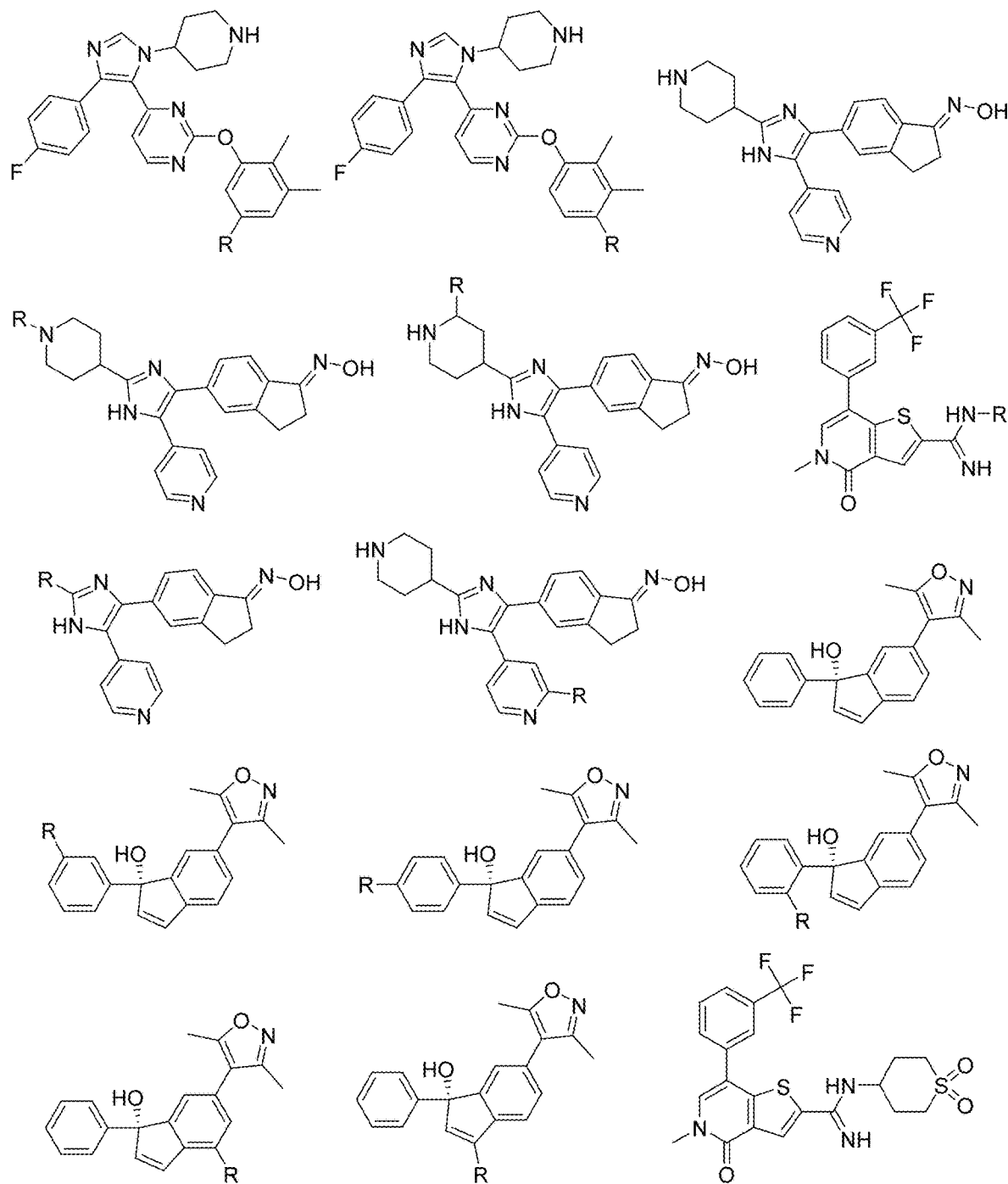
Figure 8I:
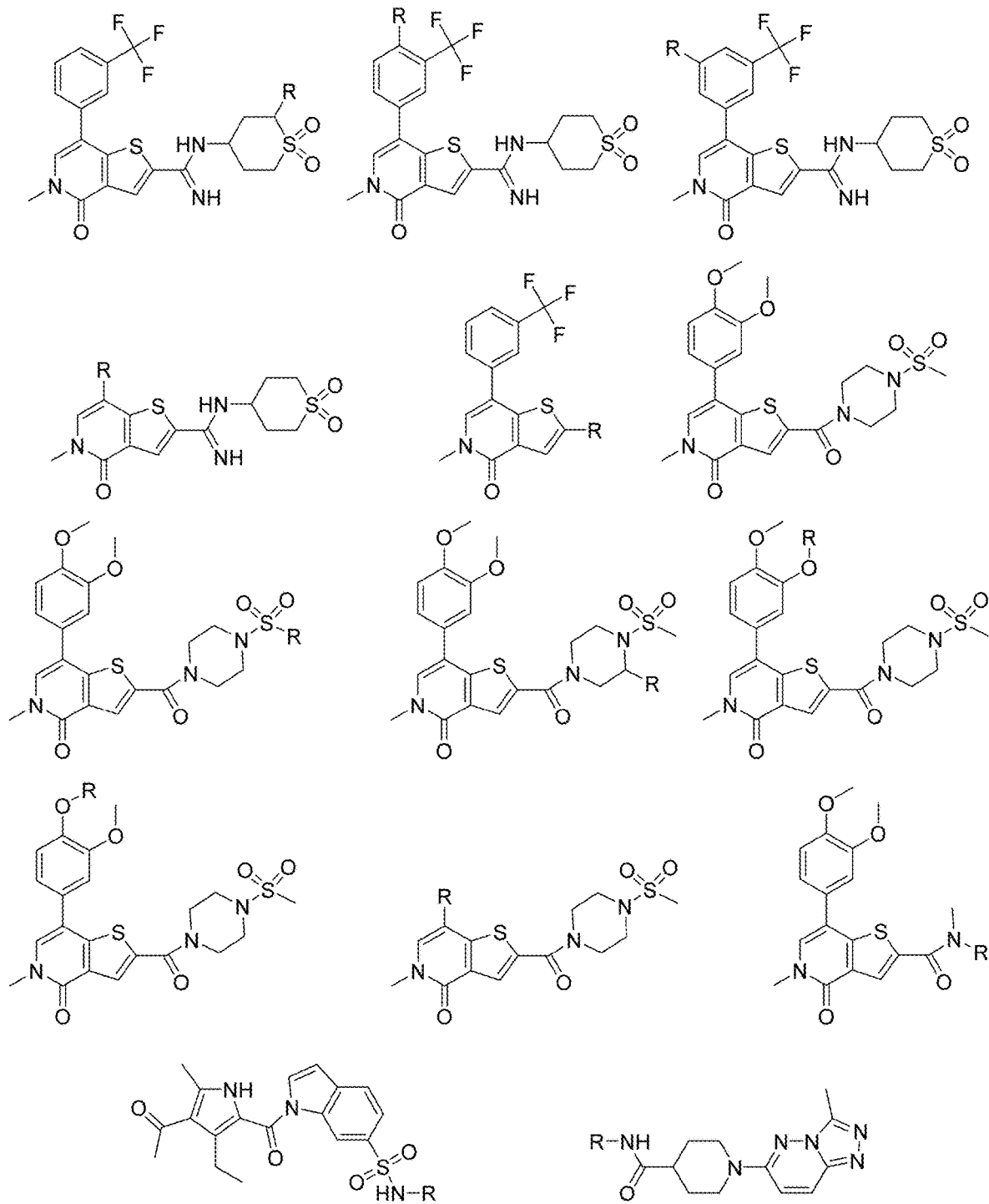
Figure 8J:
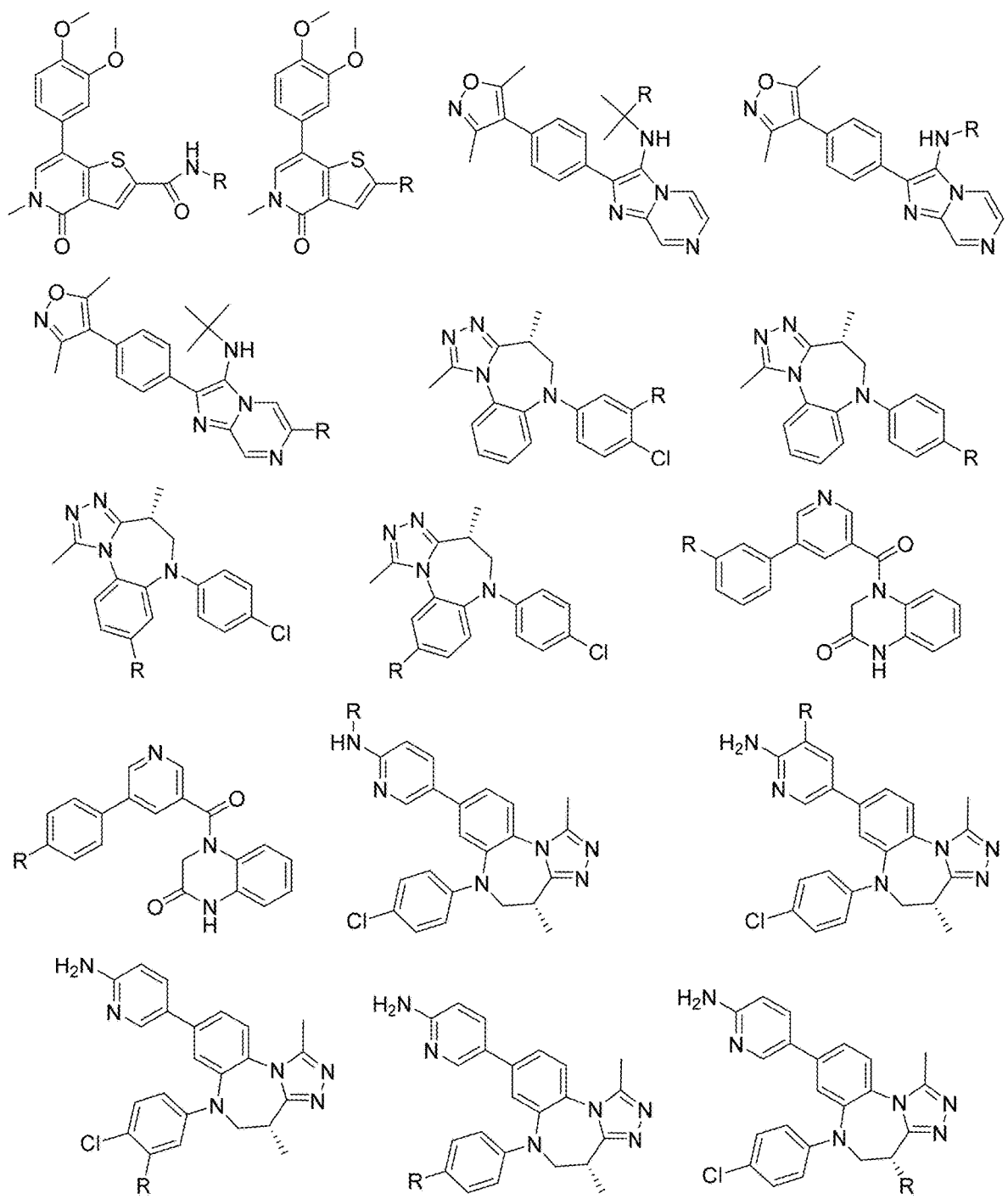
Figure 8K:
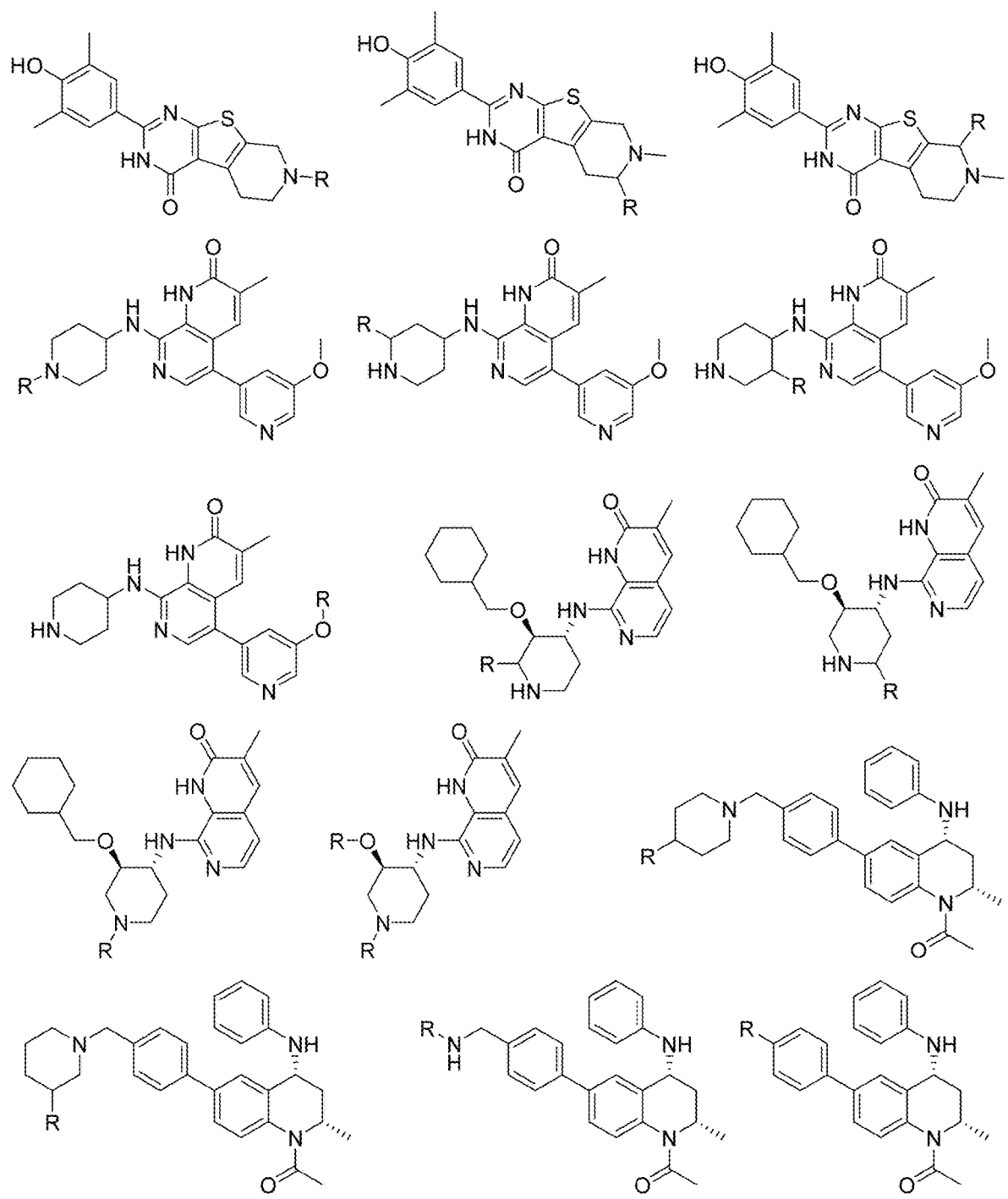
Figure 8L:
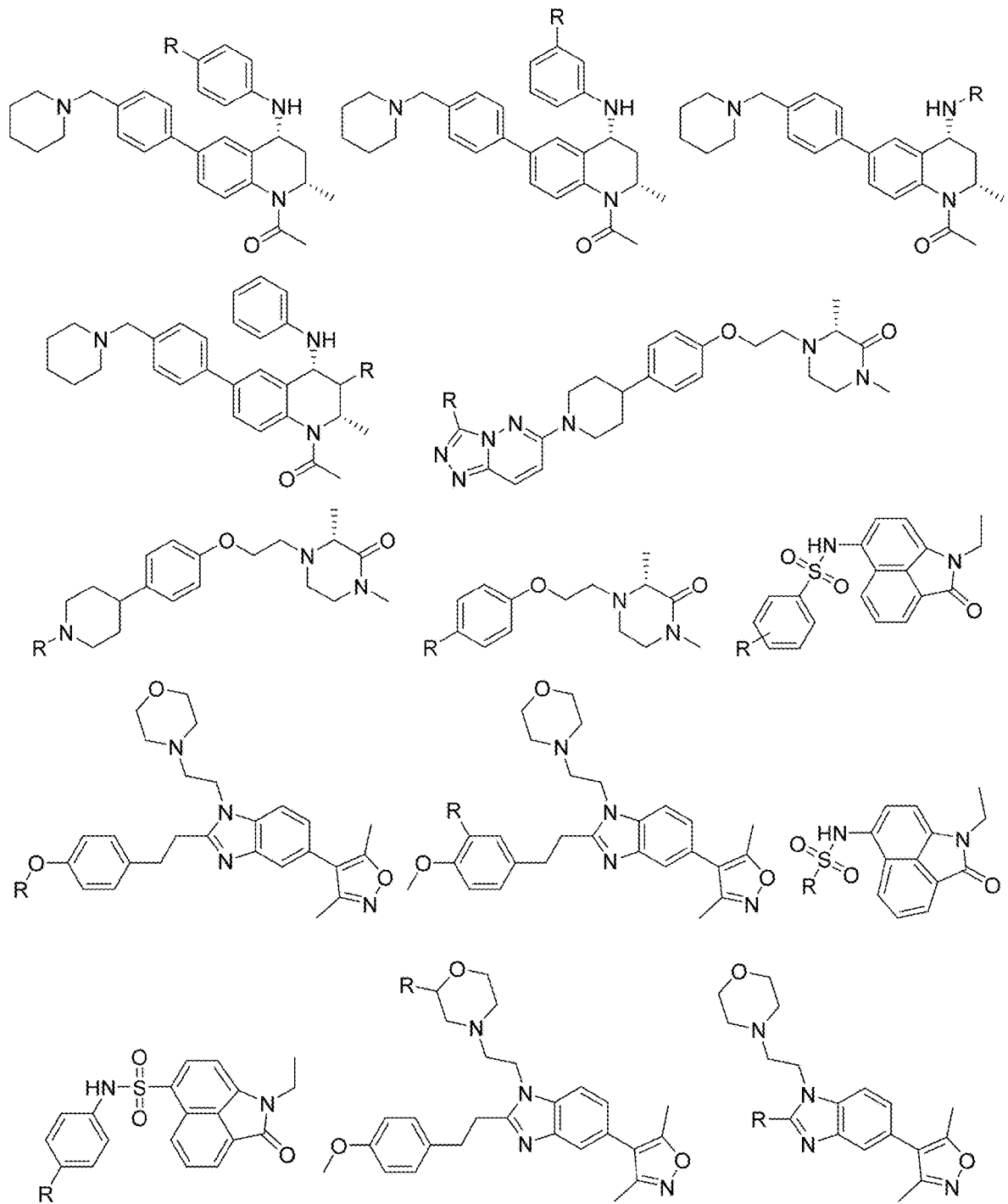
Figure 8M:
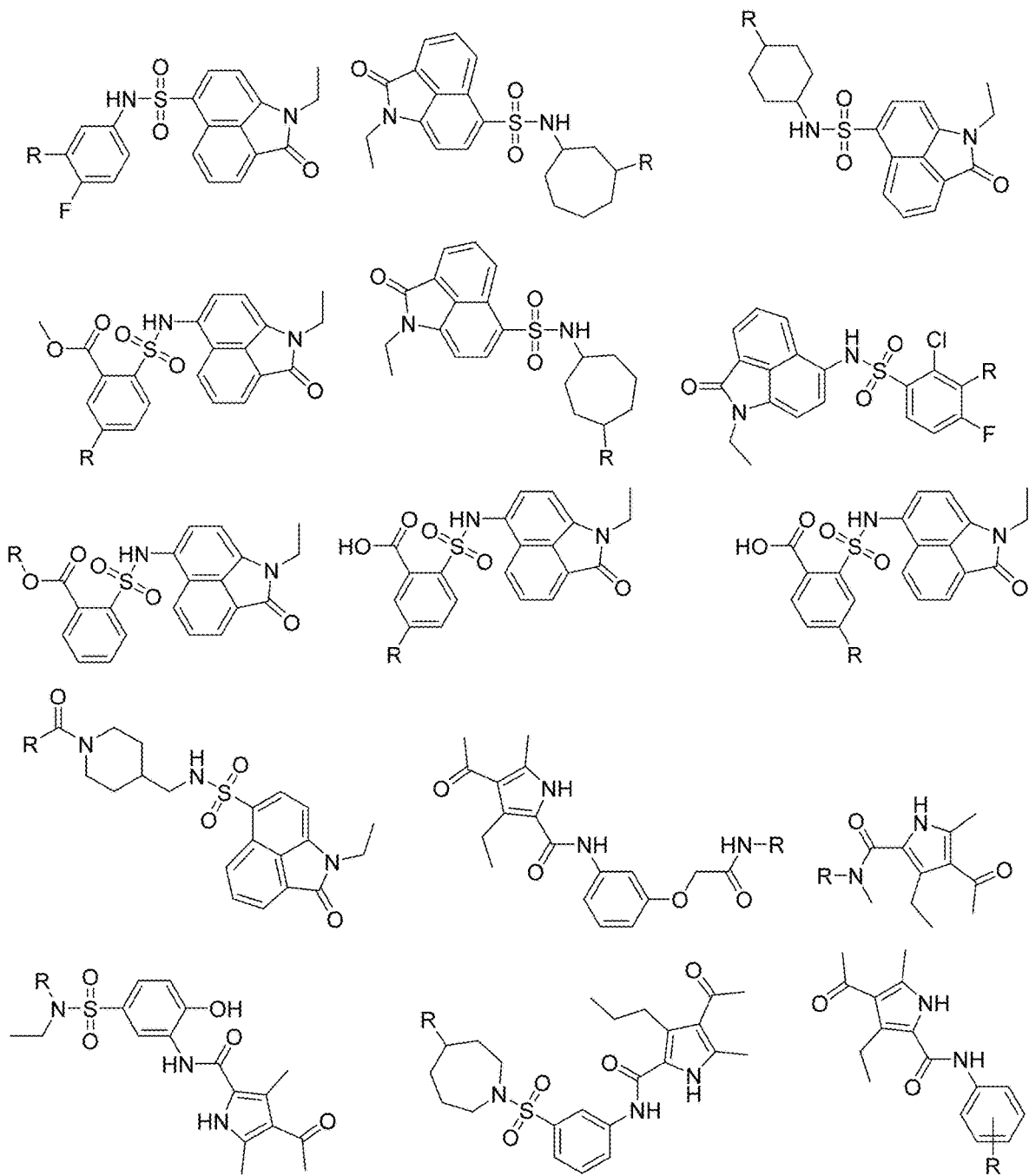
Figure 8N:
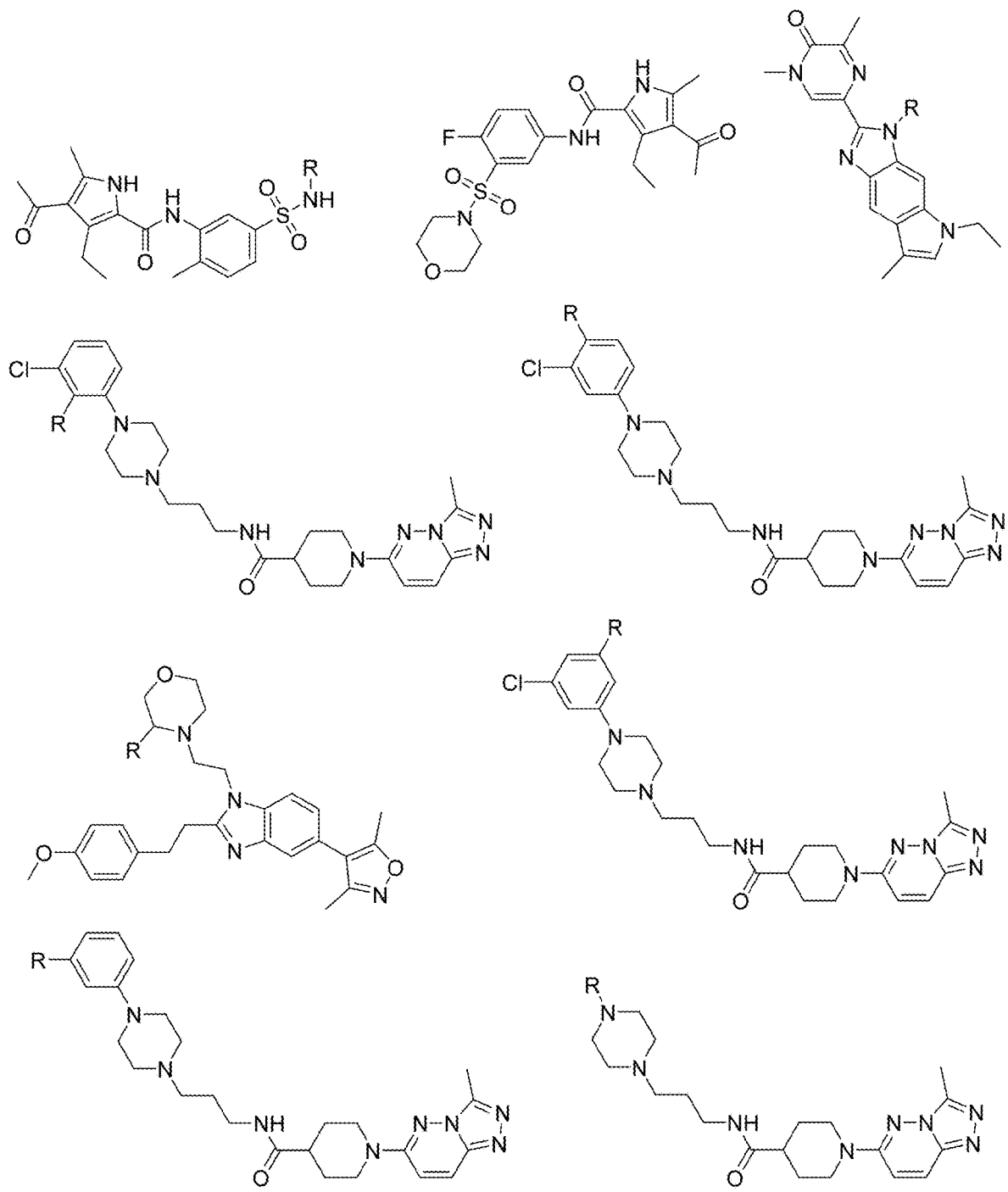
Figure 8O:
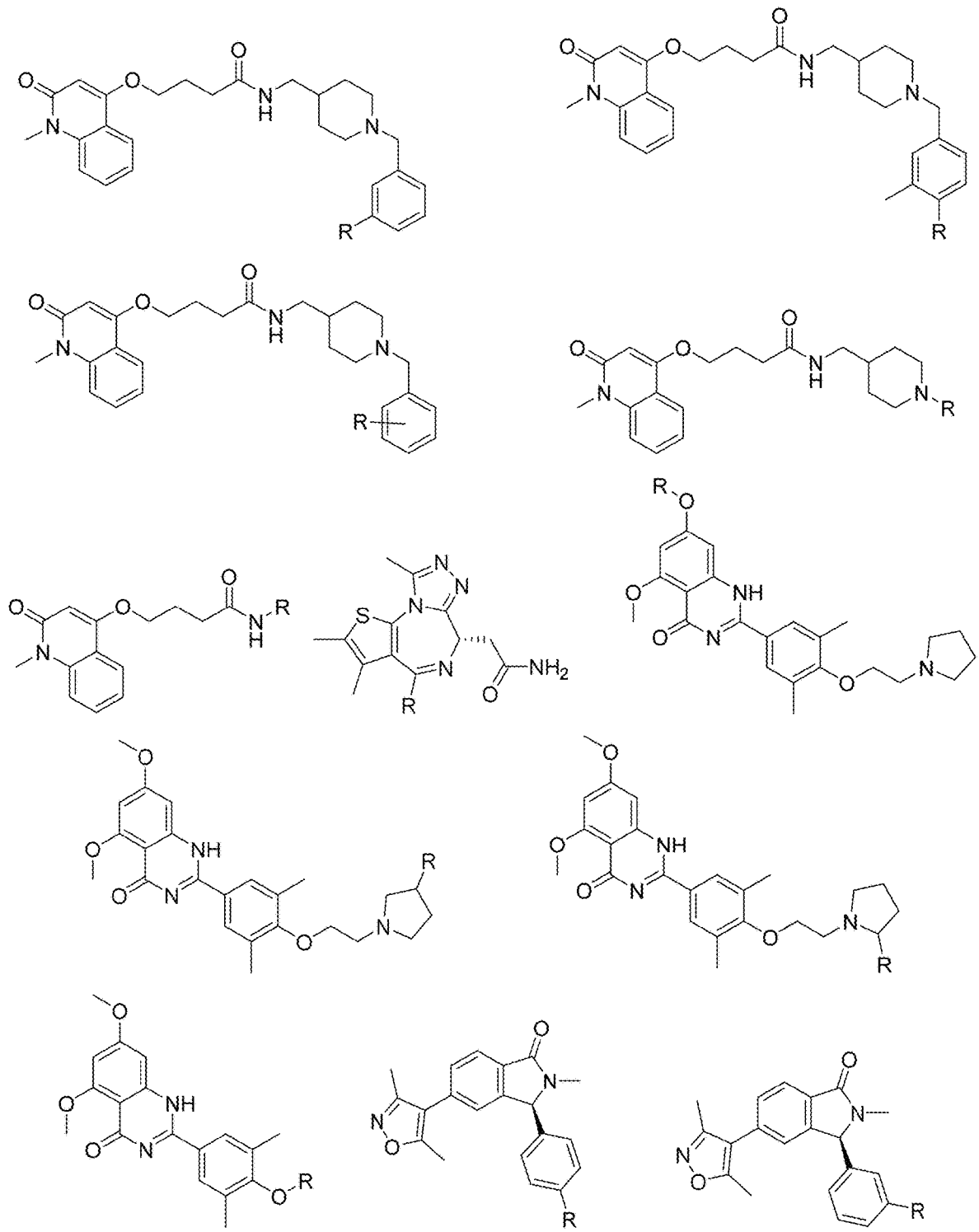
Figure 8P:
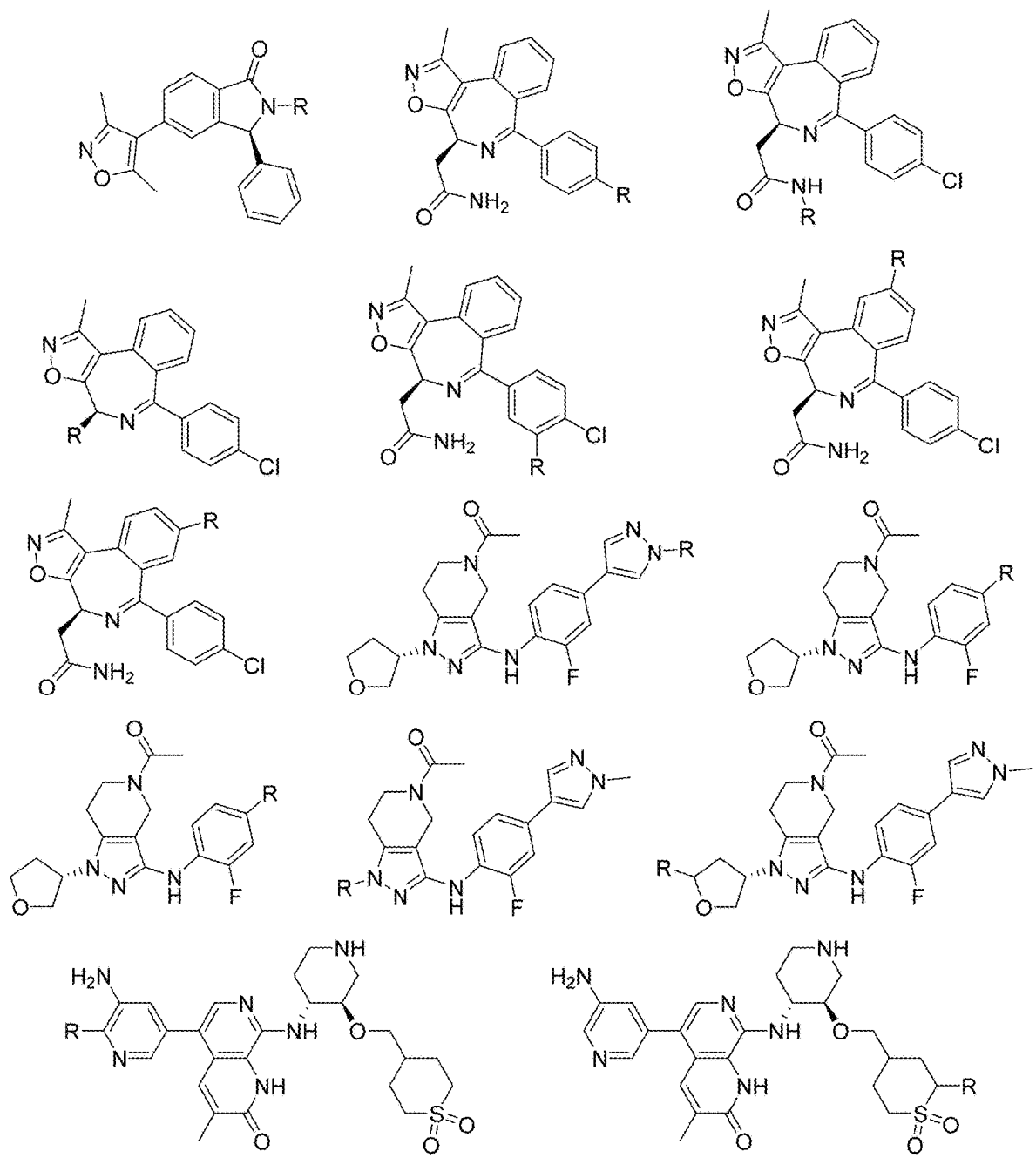
Figure 8Q:
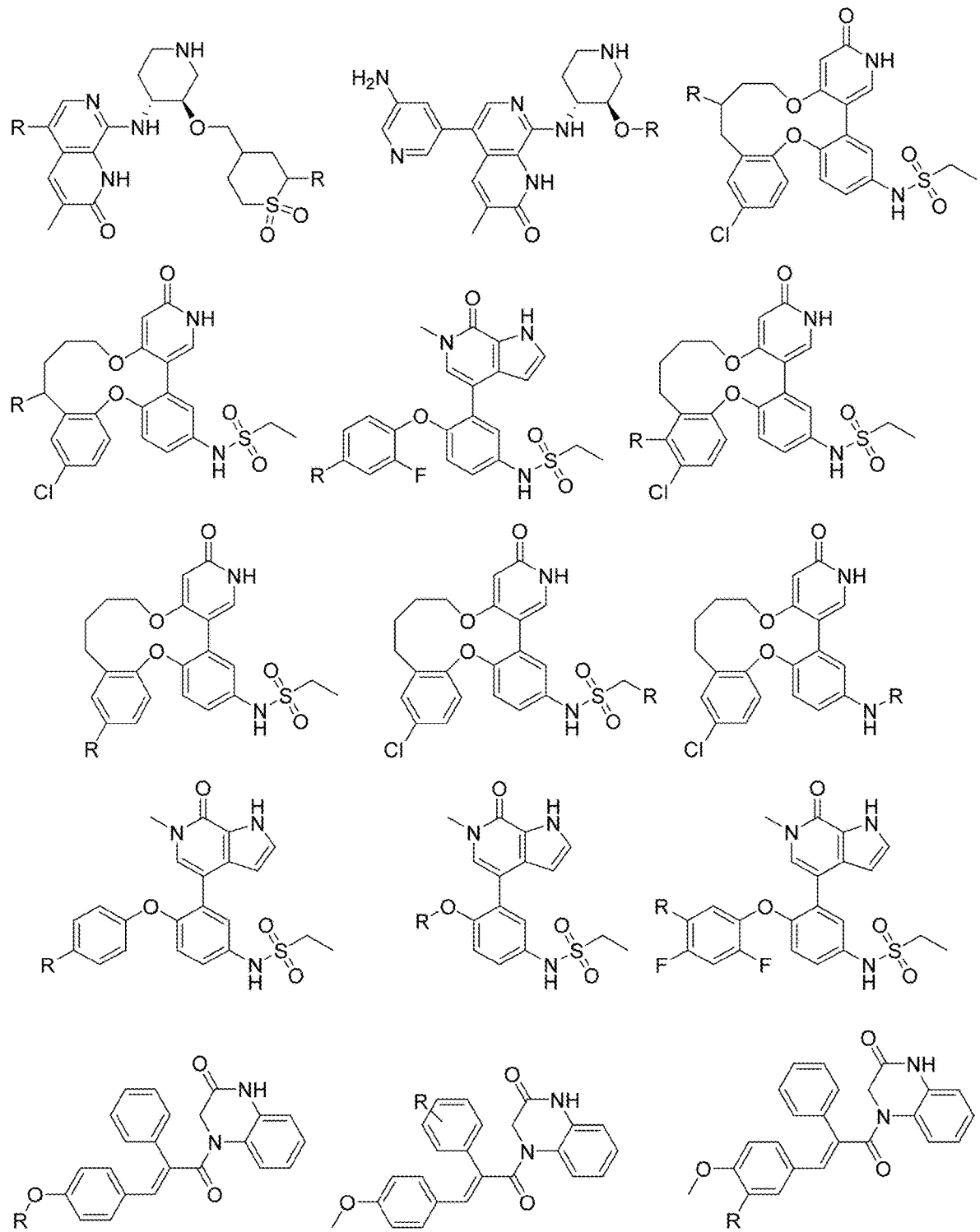
Figure 8R:
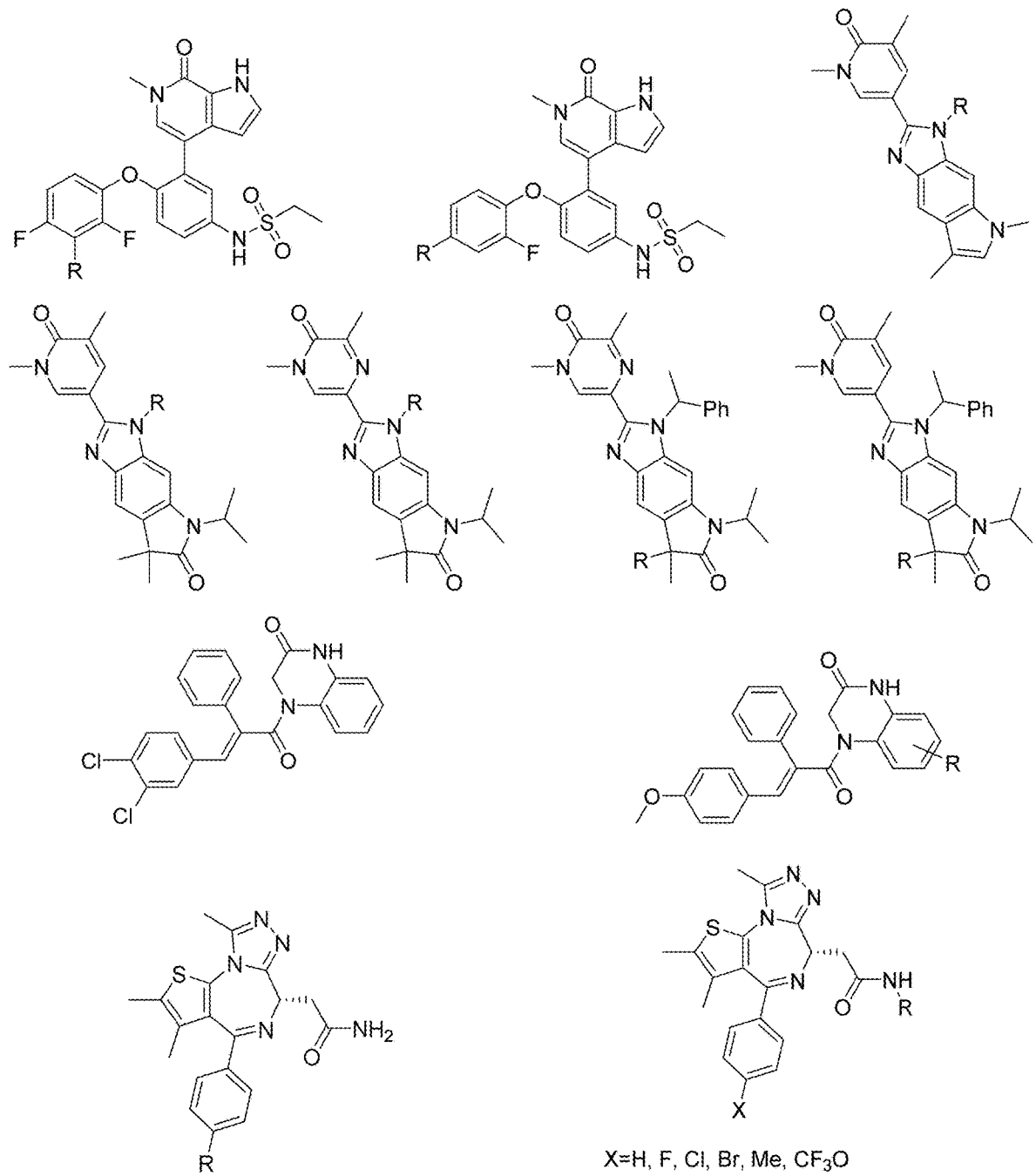
Figure 8U:
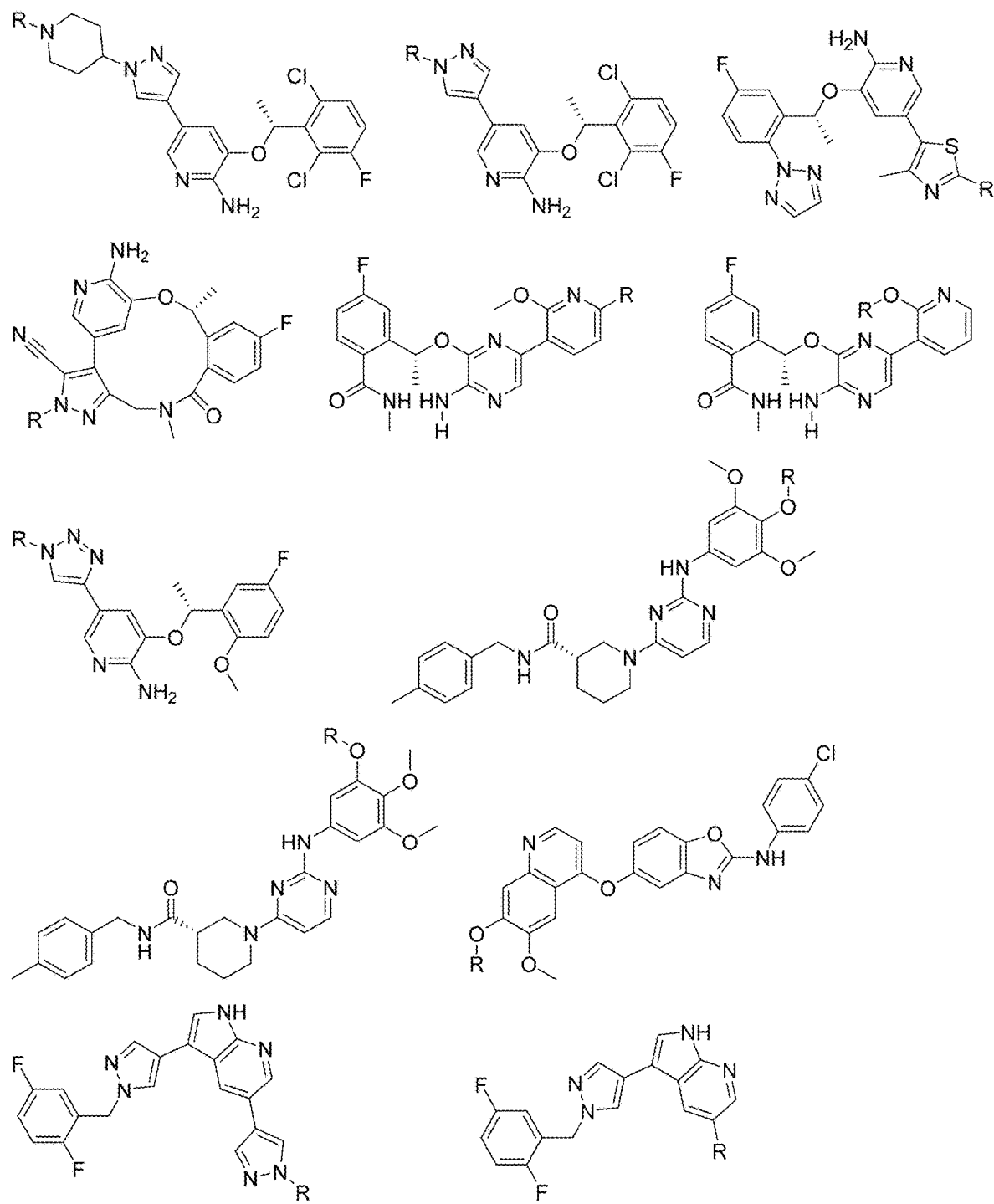
Figure 8V:
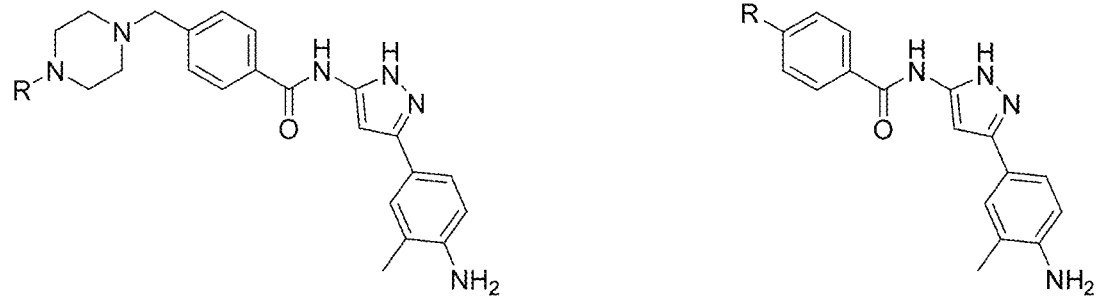
Figure 8W:
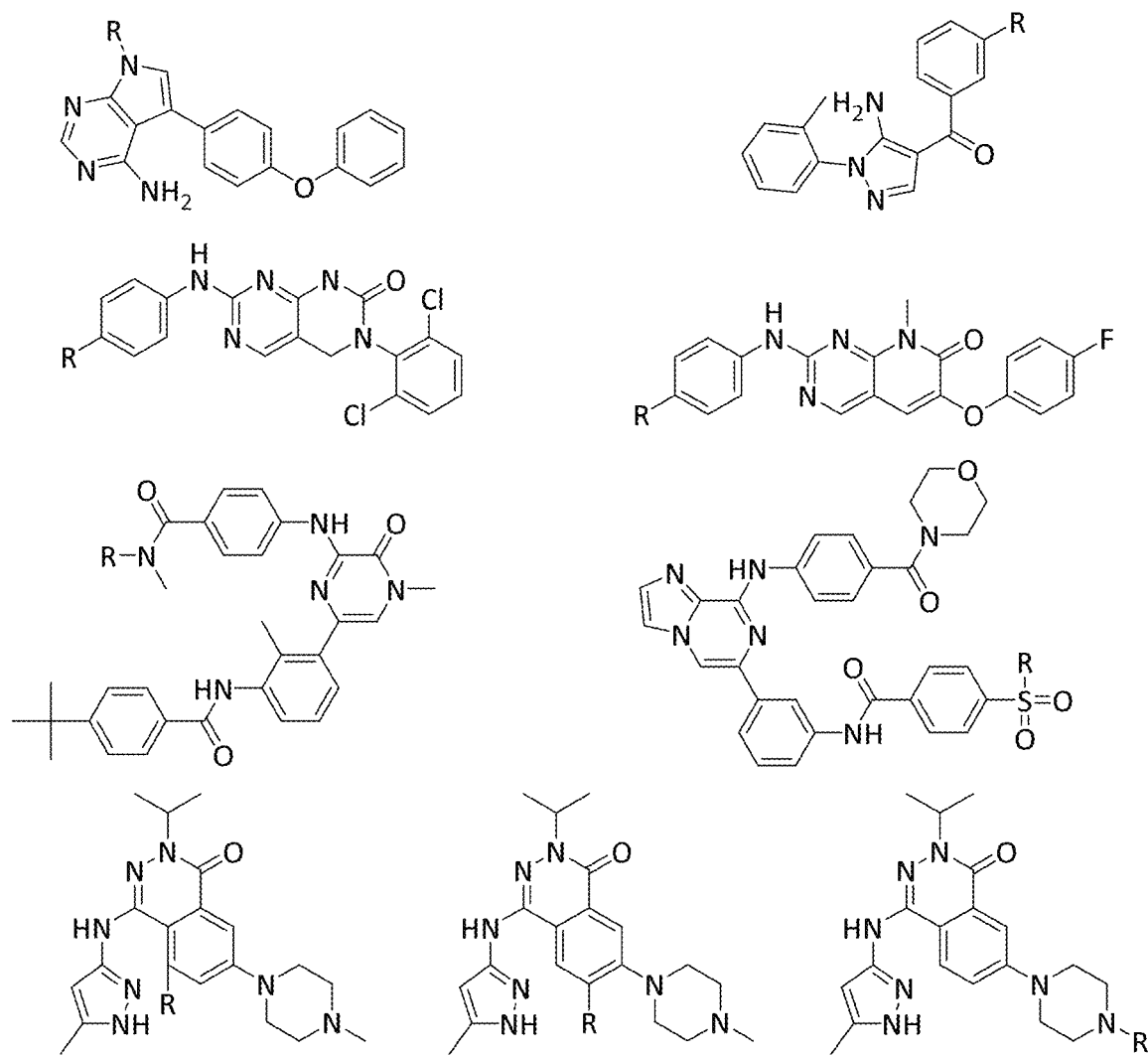
Figure 8X:
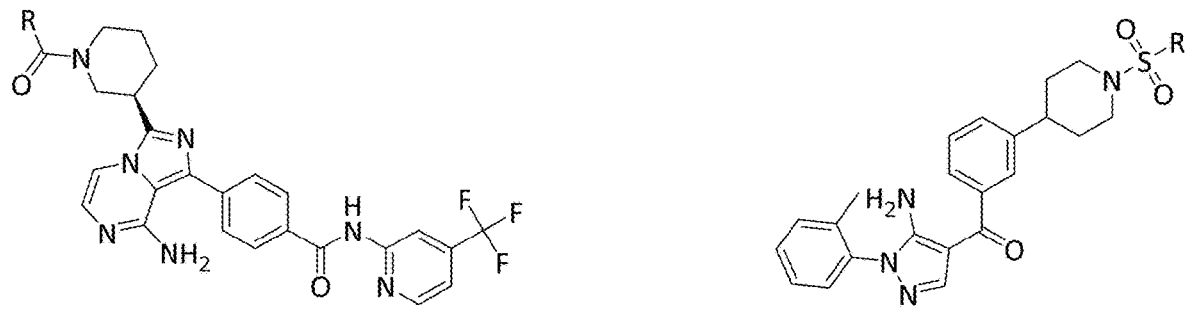
Figure 8Y:
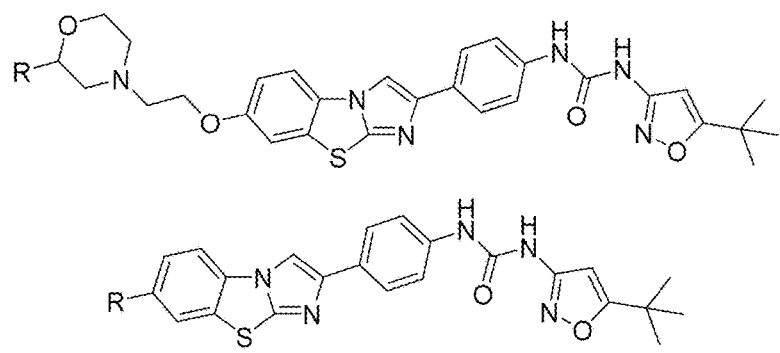
Figure 8Z:
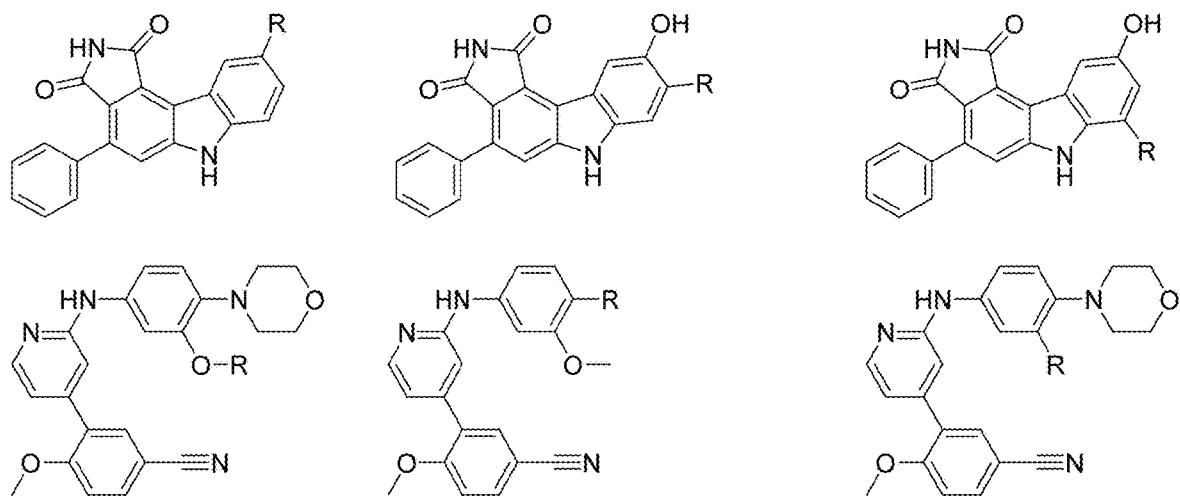
Figure 8A:
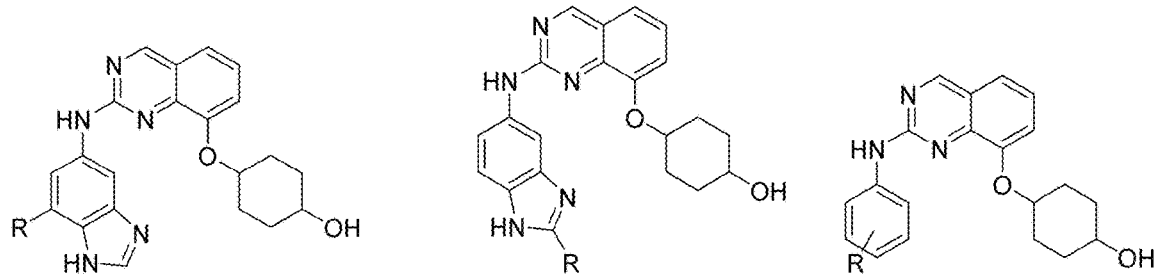
Figure 8B:
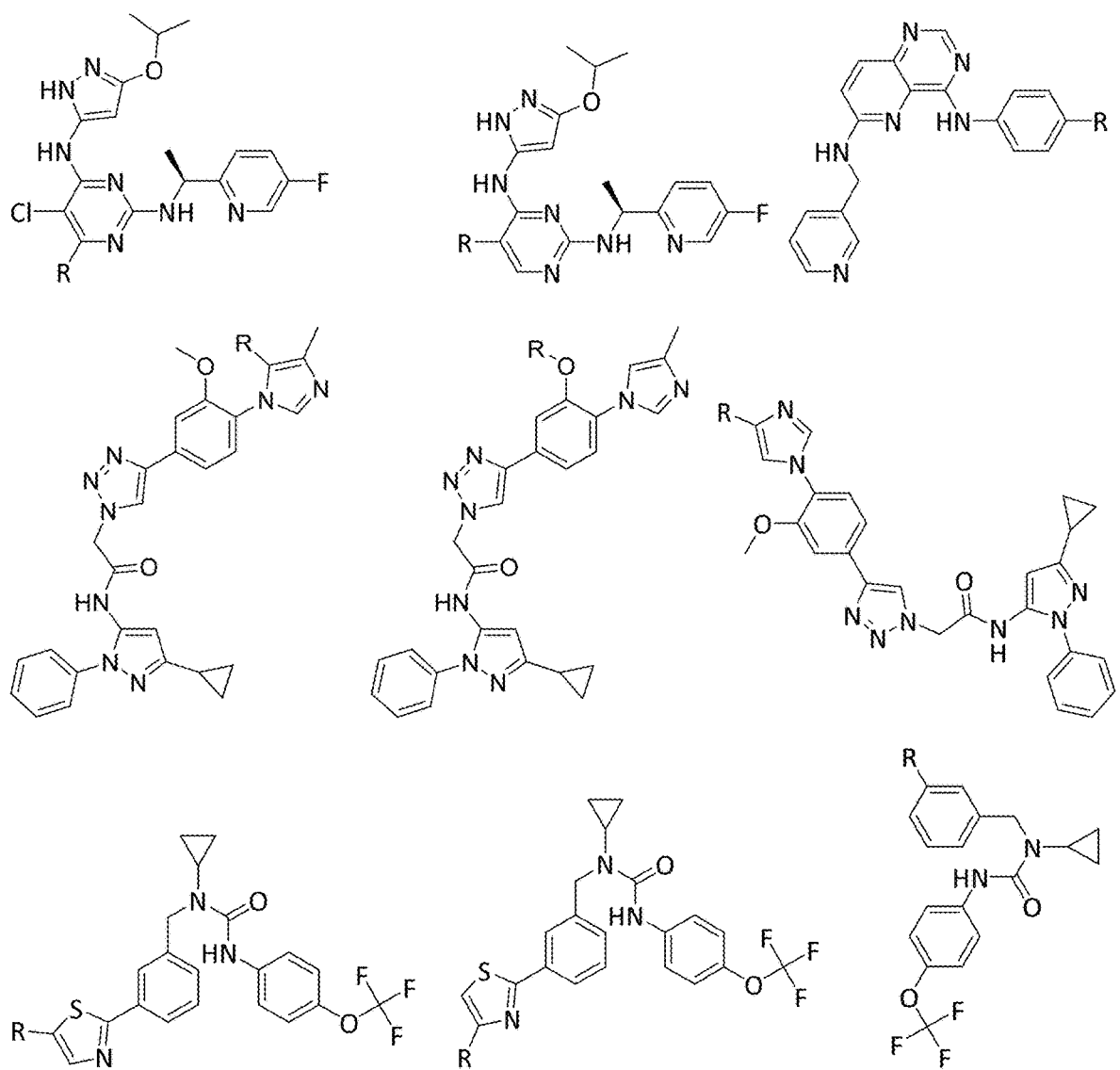
Figure 8C:
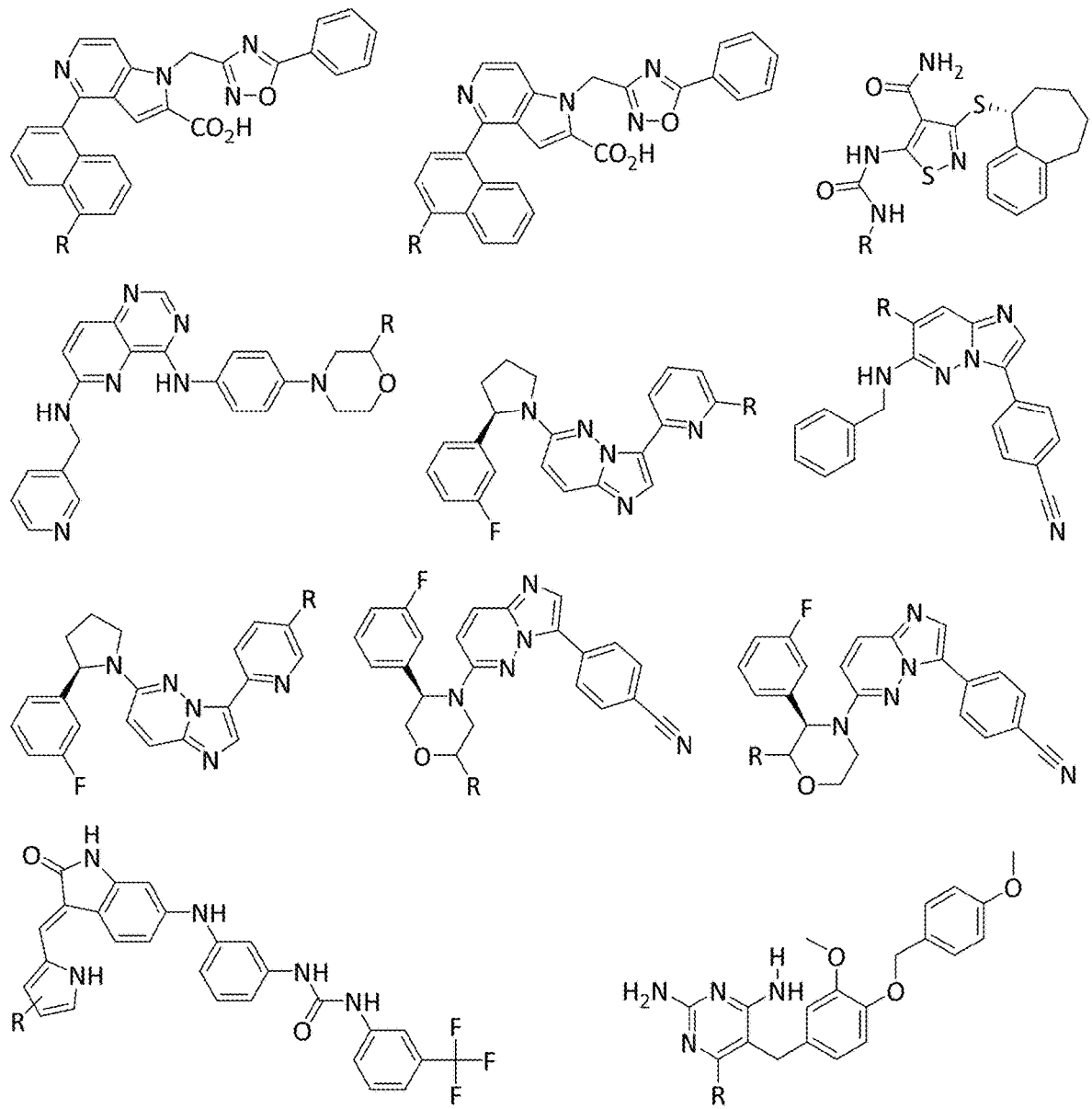
Figure 8D:
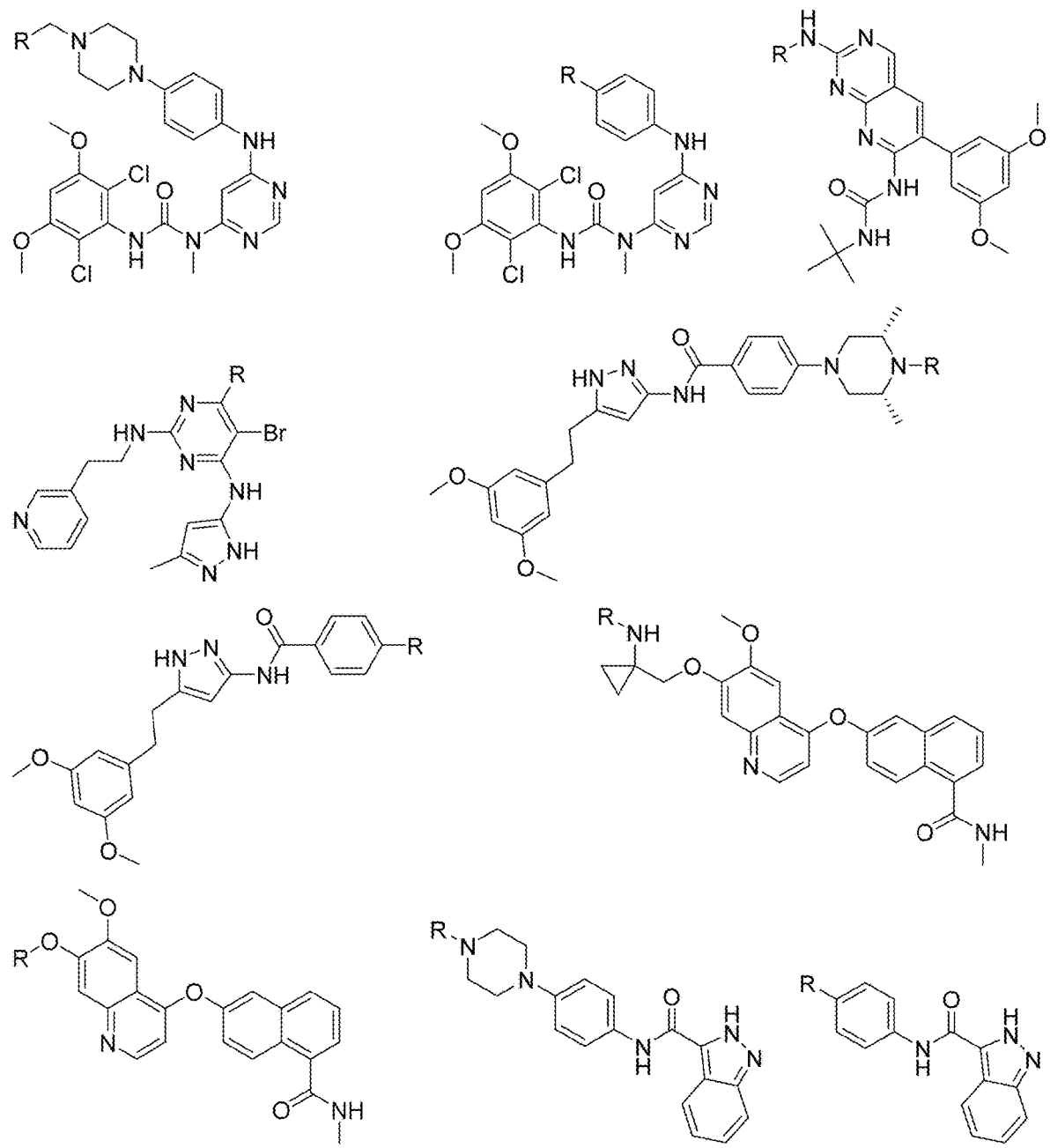
Figure 8E:
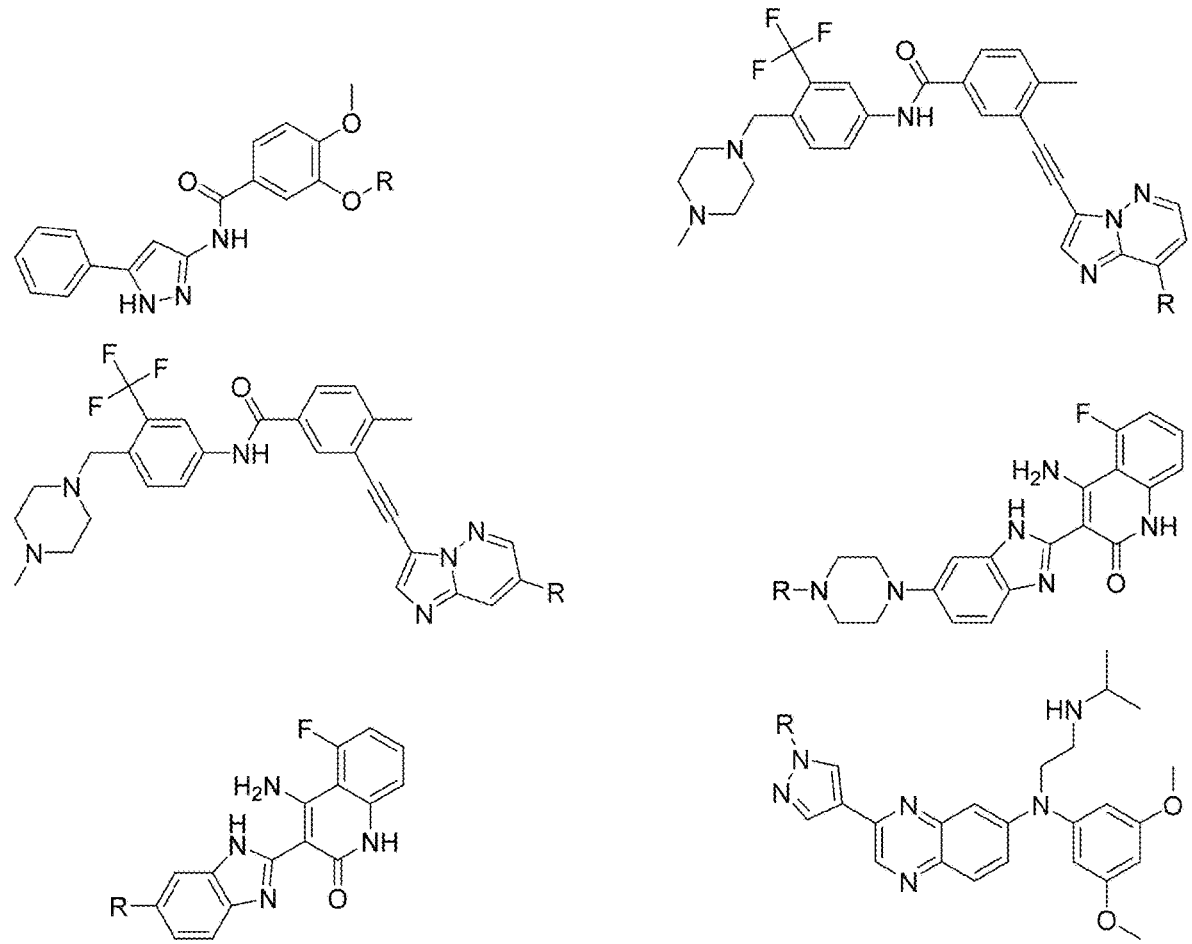
Figure 8F:
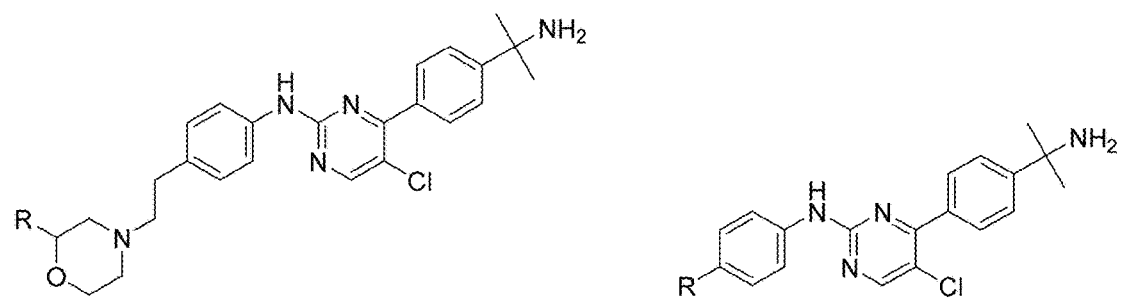
Figure 8G:
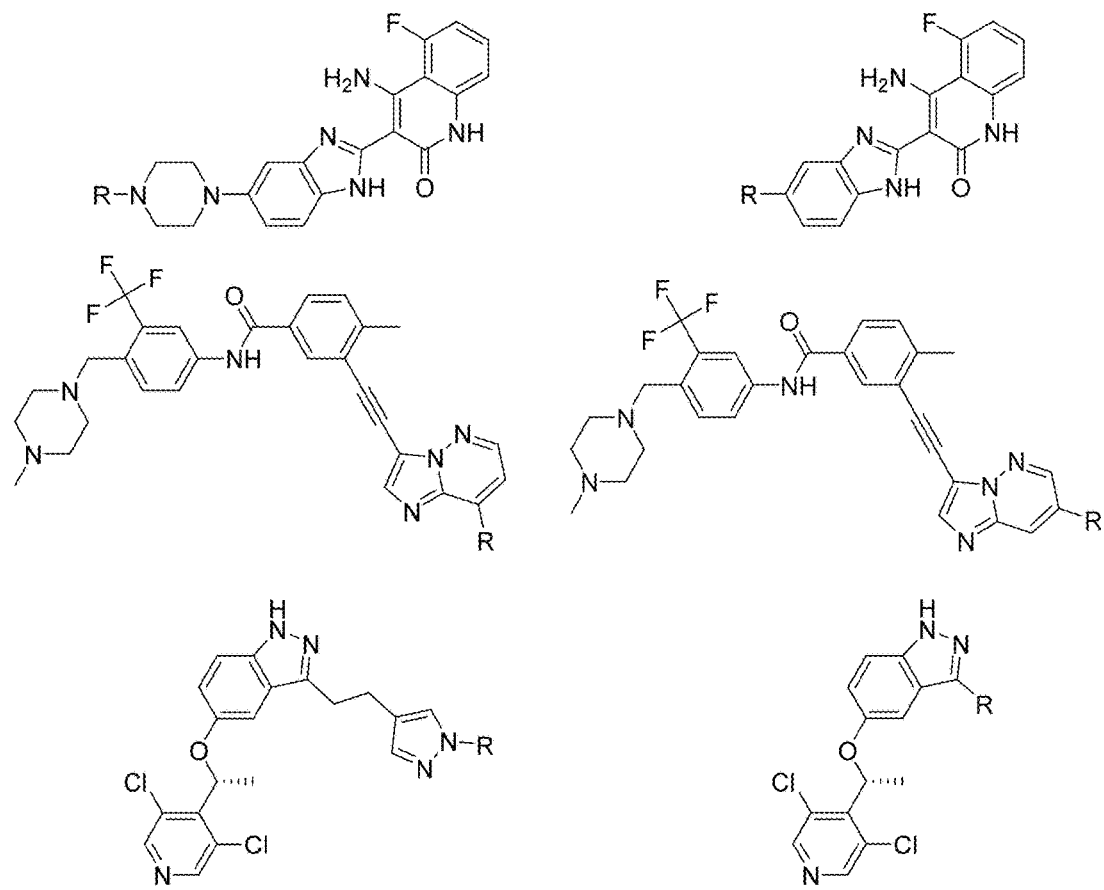
Figure 8H:
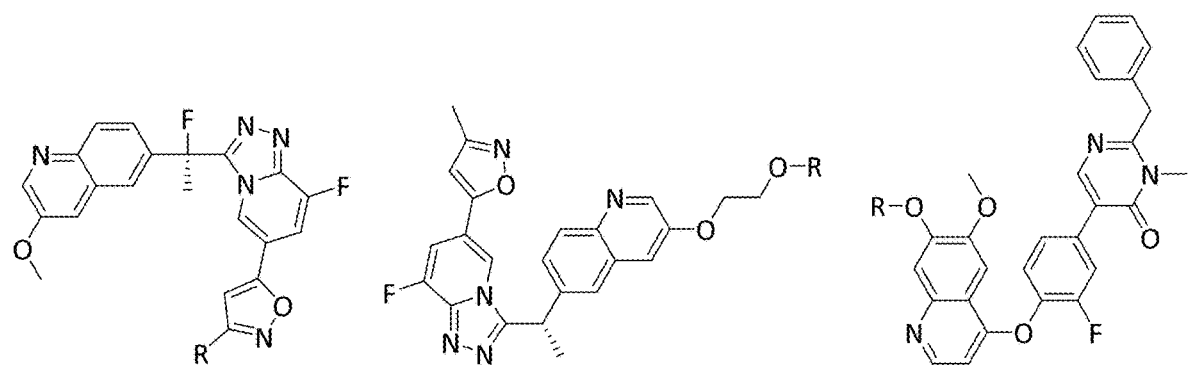
Figure 8I:
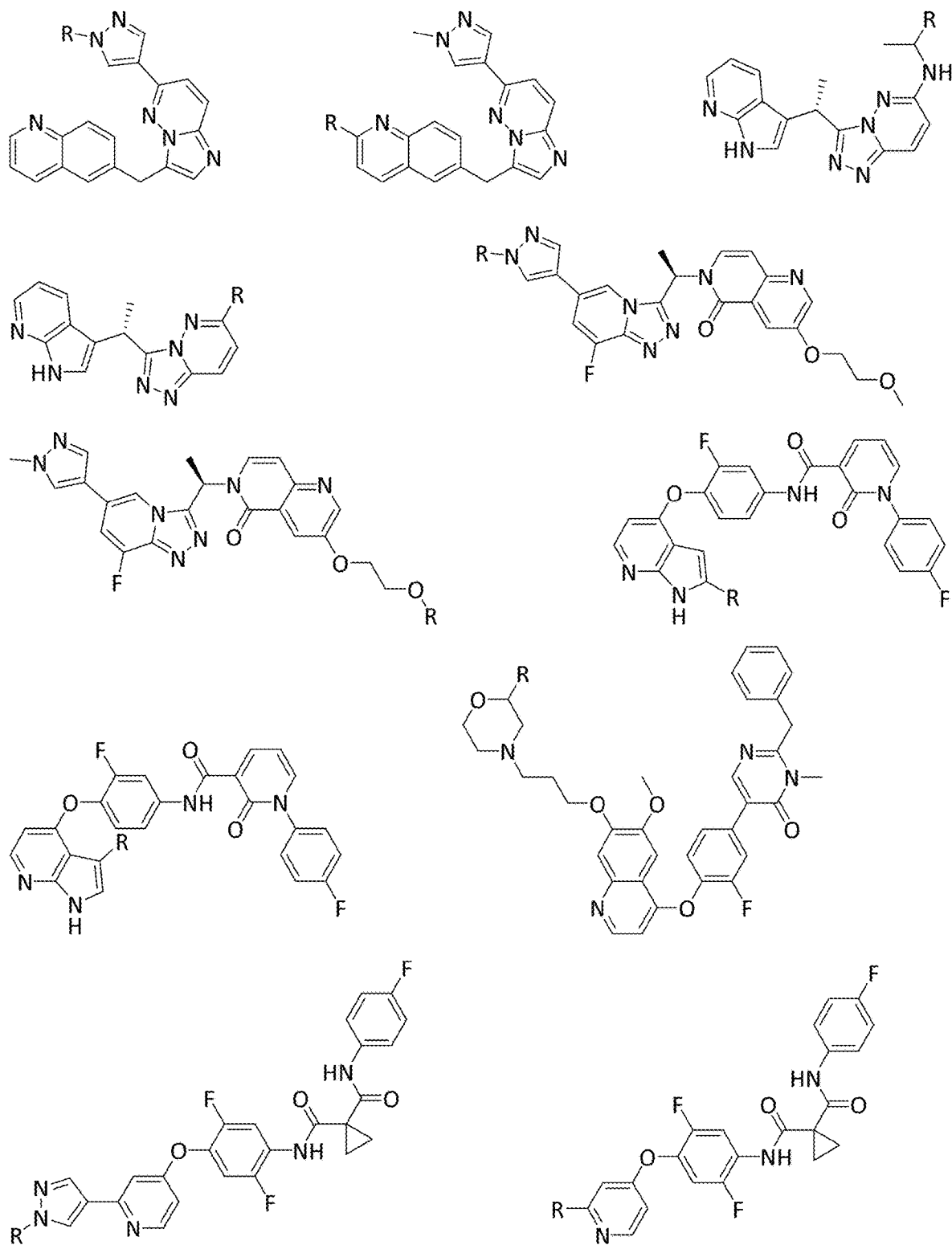
Figure 8J:
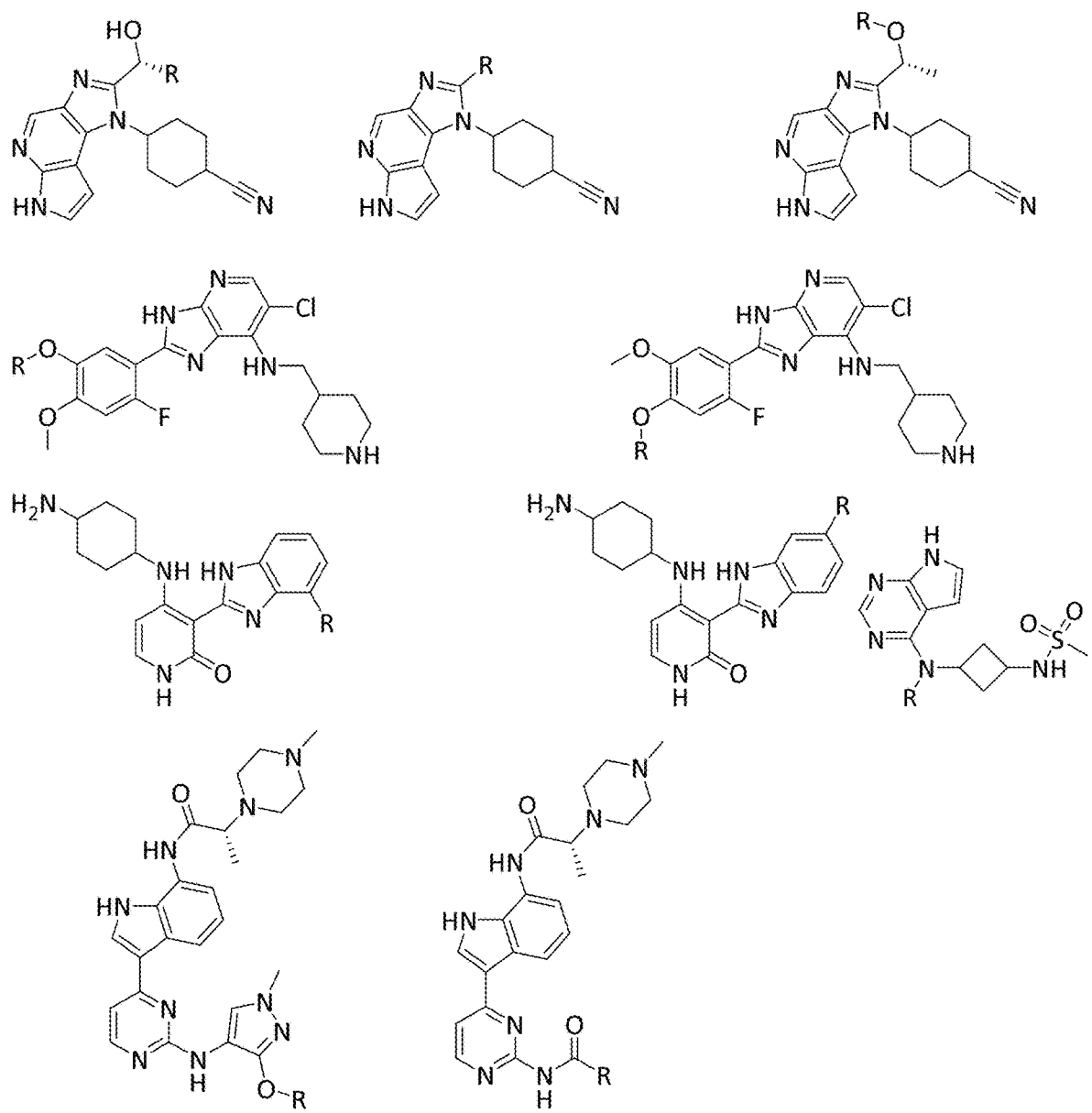
Figure 8K:
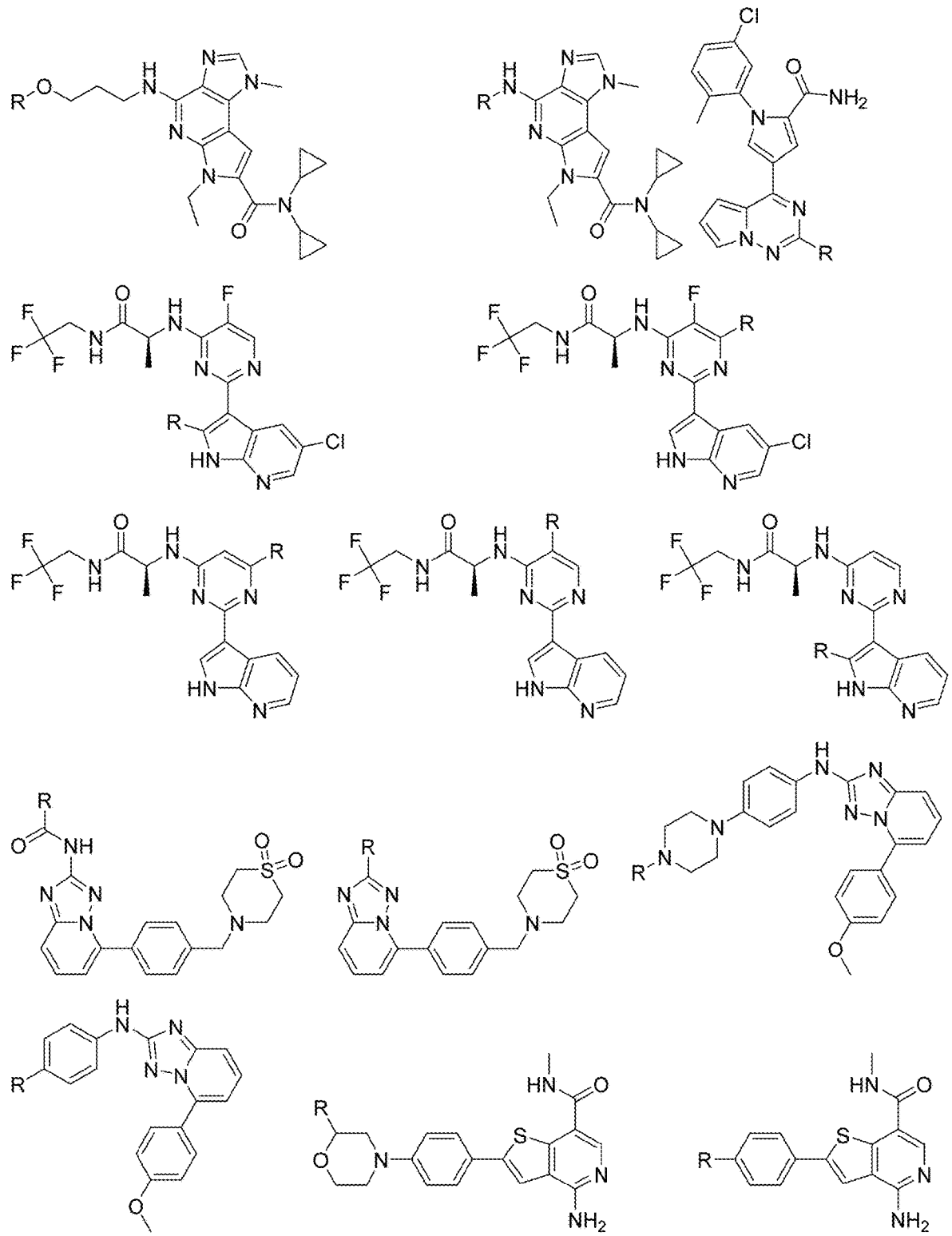
Figure 8L:
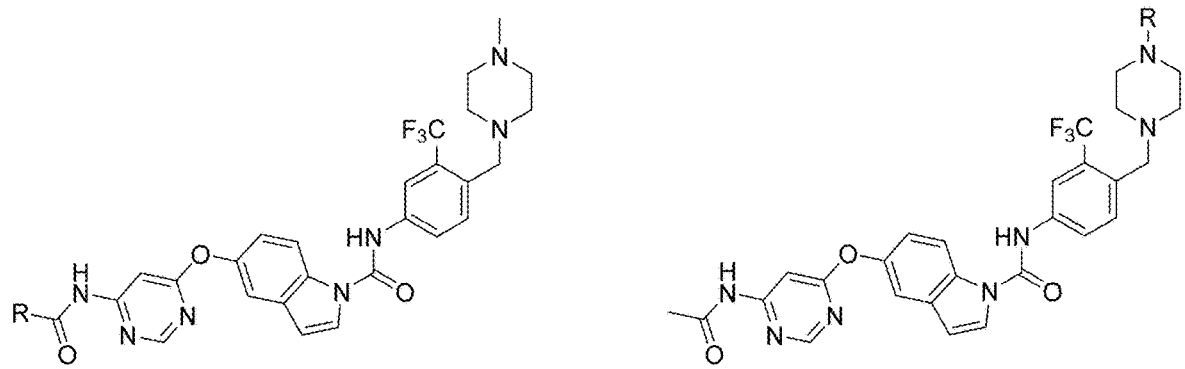
Figure 8M:
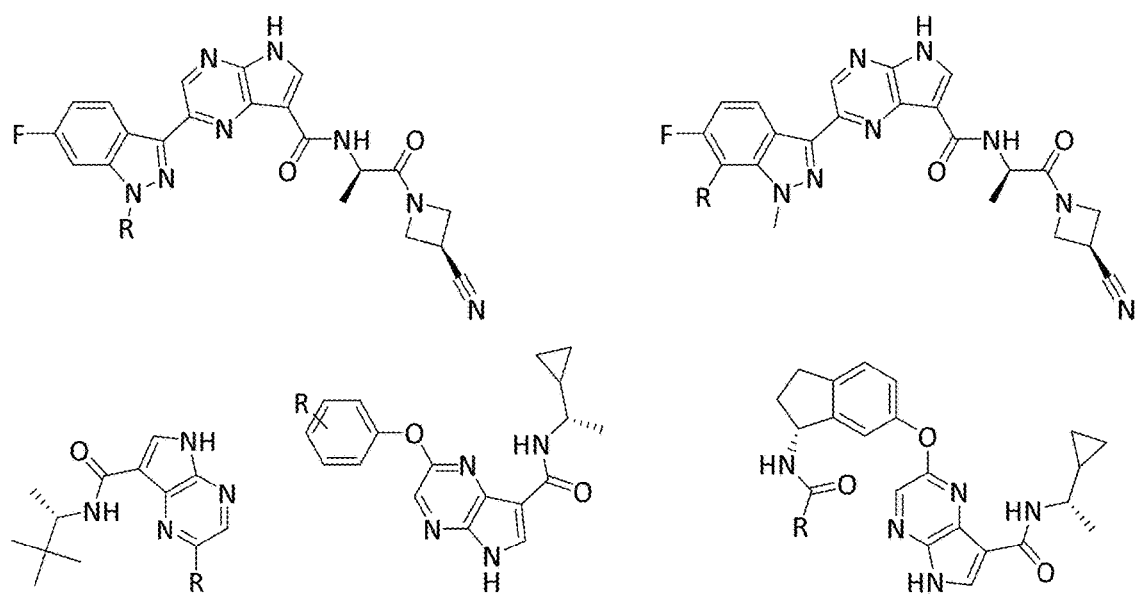
Figure 8N:
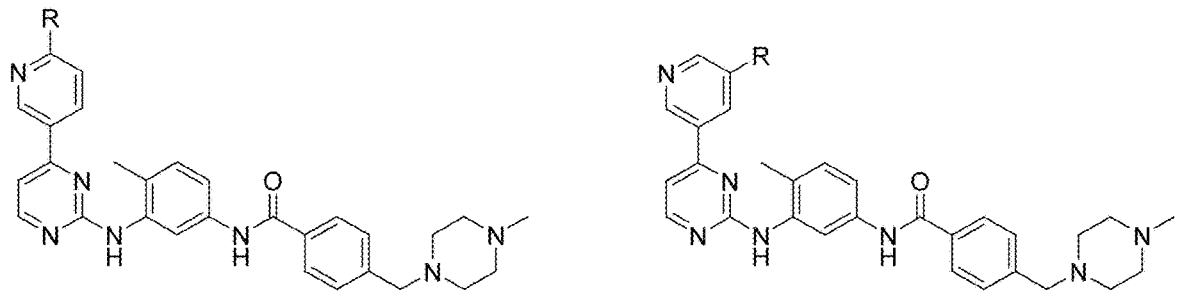
Figure 8O:
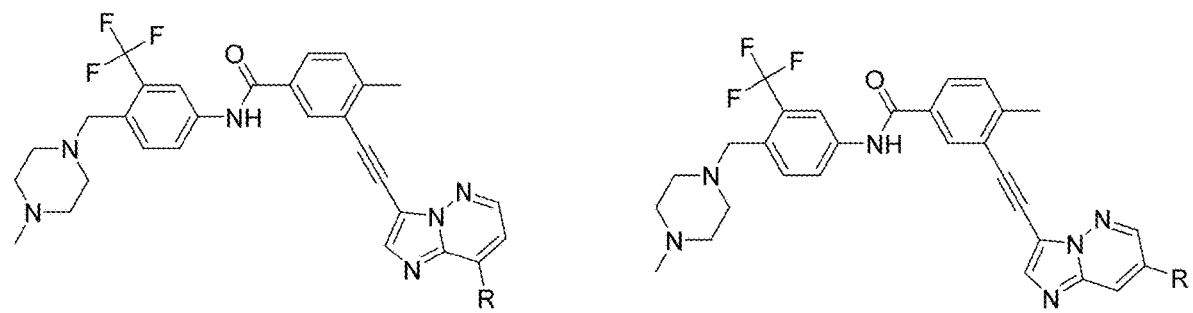
Figure 8P:
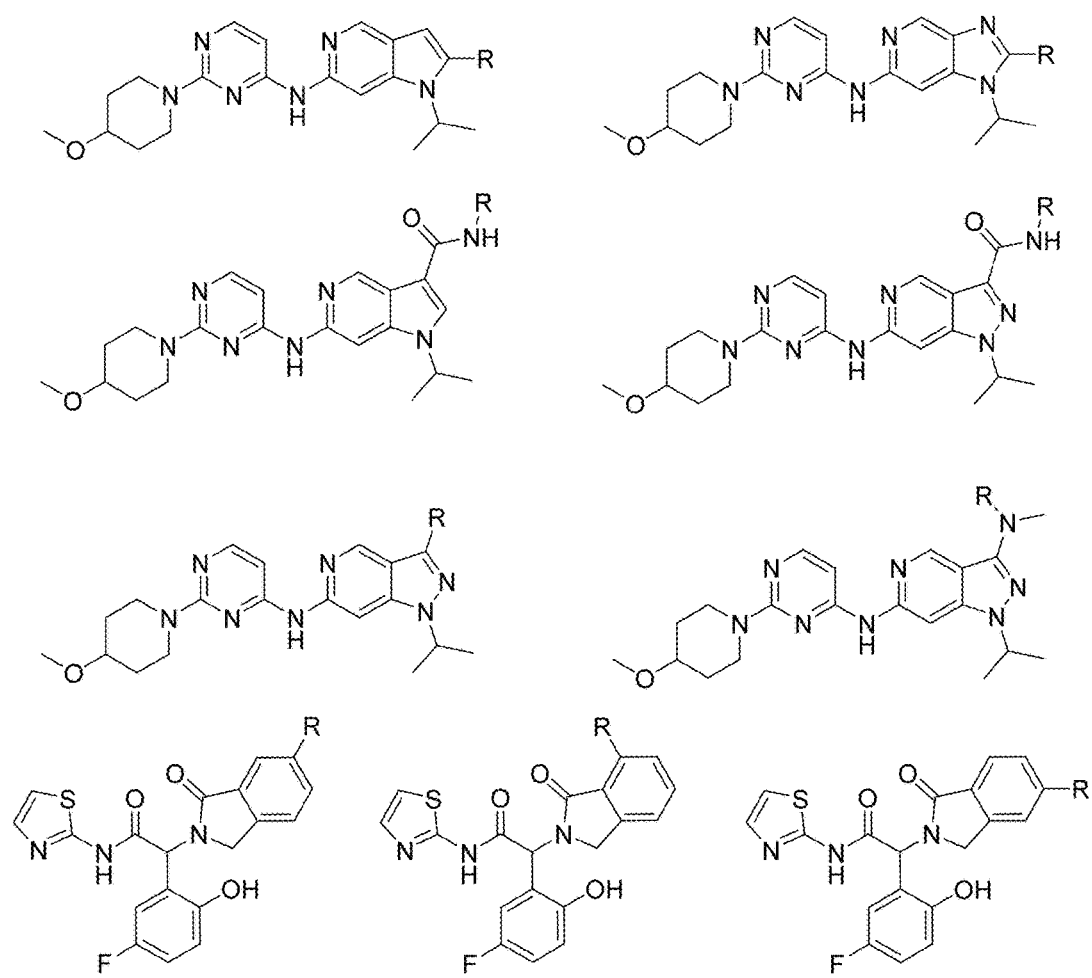
Figure 8Q:
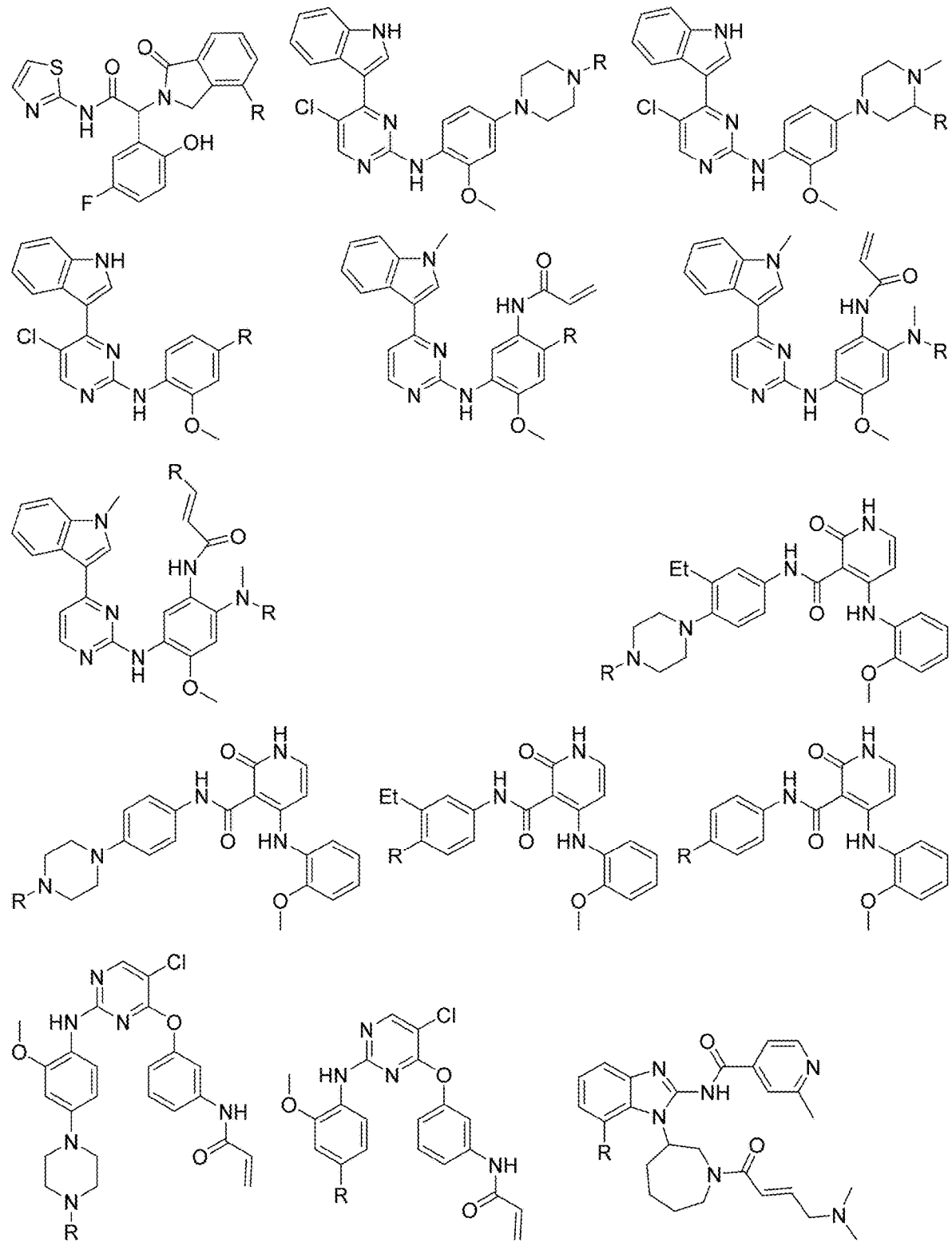
Figure 8R:
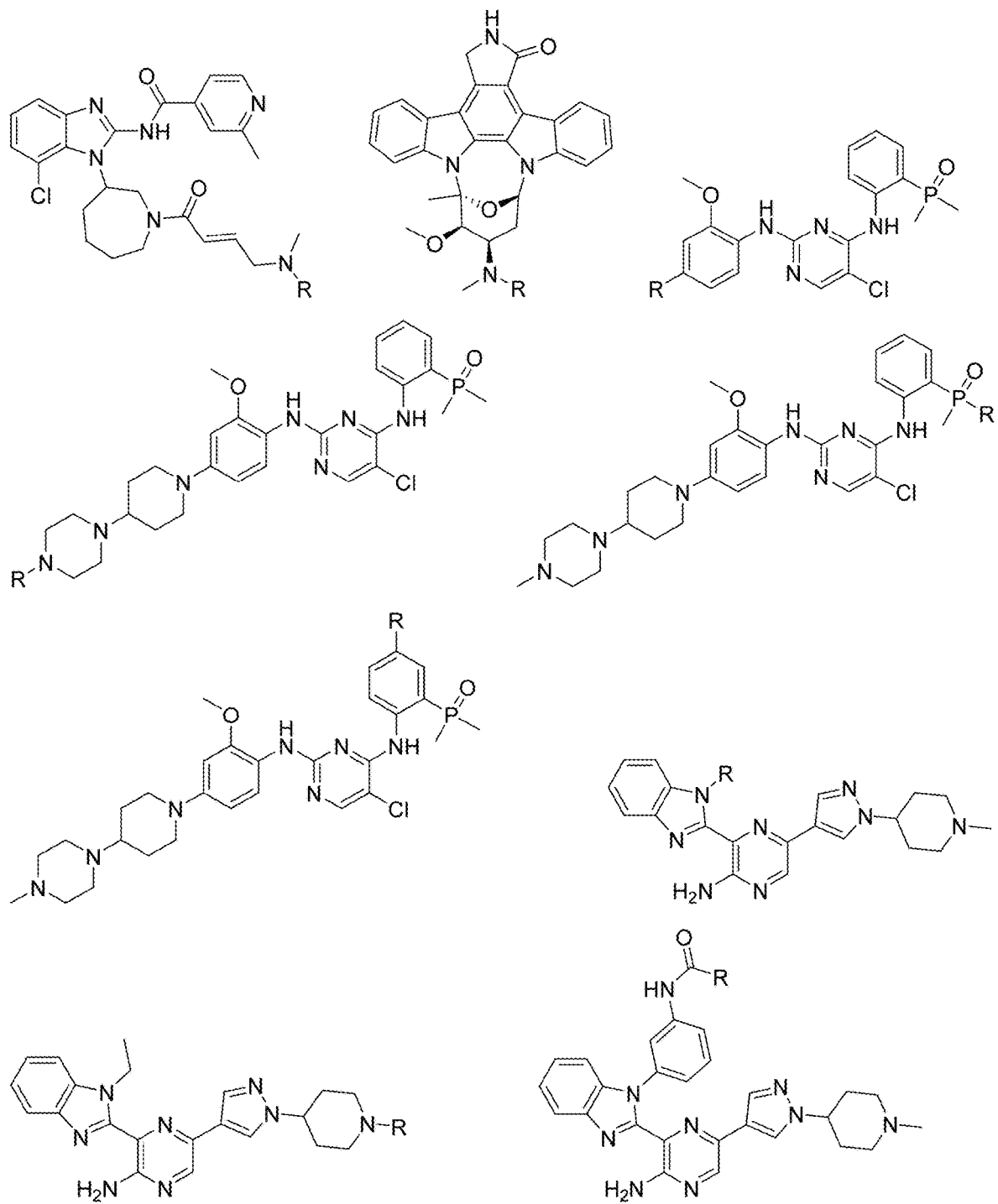
Figure 8S:
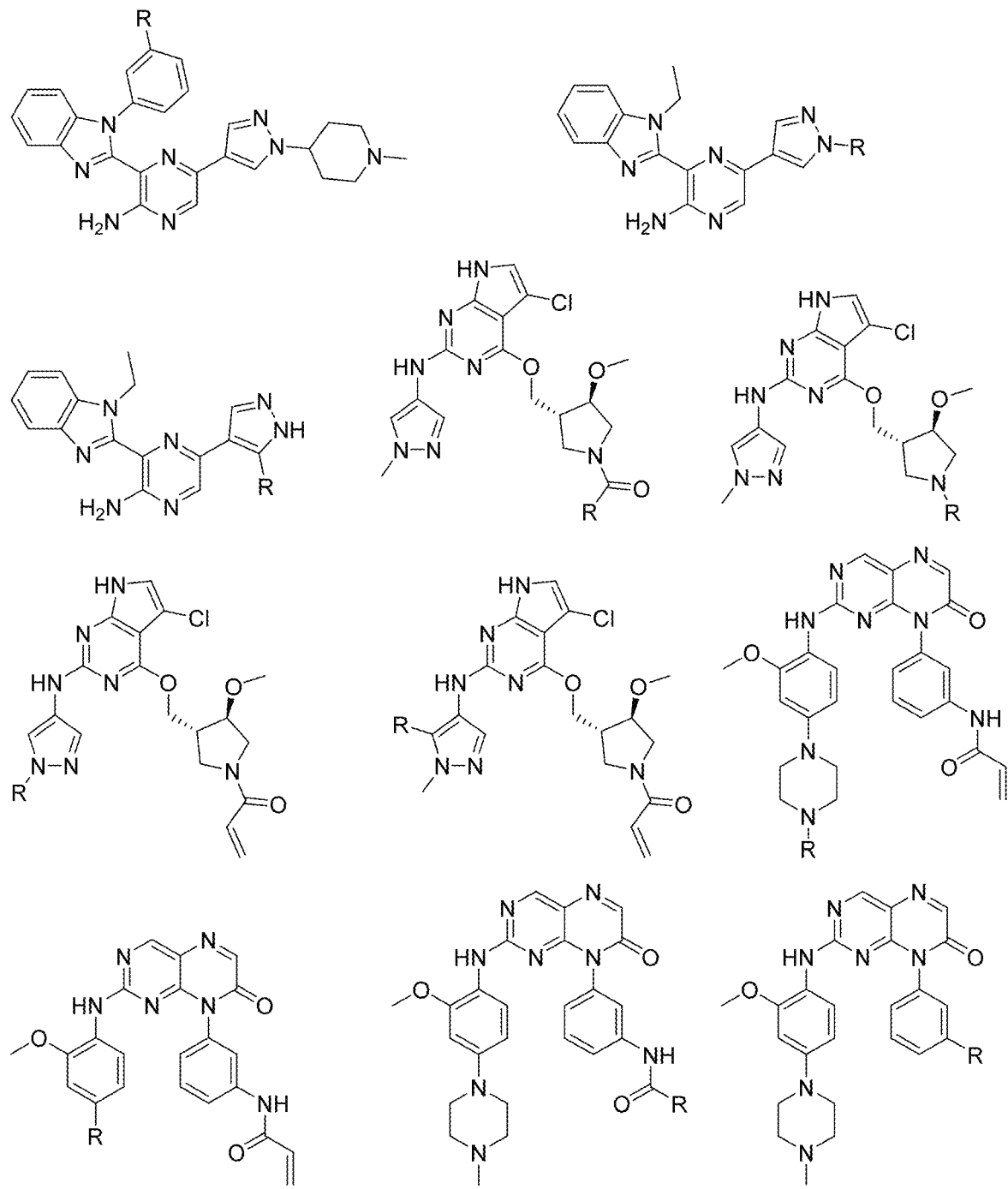

FIG. 8A-8S present examples of BRD4 Bromodomain 1 Targeting Ligands wherein R is the point at which the Linker is attached. For additional examples and related ligands, see, the crystal structures PDB 3u5k and 3u5l and related ligands in Filippakopoulos, P. et al. "Benzodiazepines and benzotriazepines as protein interaction inhibitors targeting bromodomains of the BET family", *Bioorg. Med. Chem.* 20: 1878-1886 (2012); the crystal structure PDB 3u5l; the crystal structure PDB 3zyu and related ligands described in Dawson, M. A. et al. "Inhibition of Bet Recruitment to Chromatin as an Effective Treatment for Mll-Fusion Leukaemia." *Nature* 478: 529 (2011); the crystal structure PDB 4bw1 and related ligands described in Mirguet, O. et al. "Naphthyridines as Novel Bet Family Bromodomain Inhibitors." *Chemmedchem* 9: 589 (2014); the crystal structure PDB 4cfl and related ligands described in Dittmann, A. et al. "The Commonly Used Pi3-Kinase Probe Ly294002 is an Inhibitor of Bet Bromodomains" *ACS Chem. Biol.* 9: 495 (2014); the crystal structure PDB 4e96 and related ligands described in Fish, P. V. et al. "Identification of a chemical probe for bromo and extra C-terminal bromodomain inhibition through optimization of a fragment-derived hit." *J. Med. Chem.* 55: 9831-9837 (2012); the crystal structure PDB 4clb and related ligands described in Atkinson, S. J. et al. "The Structure Based Design of Dual Hdac/Bet Inhibitors as Novel Epigenetic Probes." *Medchemcomm* 5: 342 (2014); the crystal structure PDB 4f3i and related ligands described in Zhang, G. et al. "Down-regulation of NF-{kappa}B Transcriptional Activity in HIV-associated Kidney Disease by BRD4 Inhibition." *J. Biol. Chem.* 287: 28840-28851 (2012); the crystal structure PDB 4hxl and related ligands described in Zhao, L. "Fragment-Based Drug Discovery of 2-Thiazolidinones as Inhibitors of the Histone Reader BRD4 Bromodomain." *J. Med. Chem.* 56: 3833-3851 (2013); the crystal structure PDB 4hxs and related ligands described in Zhao, L. et al. "Fragment-Based Drug Discovery of 2-Thiazolidinones as Inhibitors of the Histone Reader BRD4 Bromodomain." *J. Med. Chem.* 56: 3833-3851 (2013); the crystal structure PDB 4lrg and related ligands described in Gehling, V. S. et al. "Discovery, Design, and Optimization of Isoxazole Azepine BET Inhibitors." *ACS Med Chem Lett* 4: 835-840 (2013); the crystal structure PDB 4mep and related ligands described in Vidler, L. R. "Discovery of Novel Small-Molecule Inhibitors of BRD4 Using Structure-Based Virtual Screening." et al. *J. Med. Chem.* 56: 8073-8088 (2013); the crystal structures PDB 4nr8 and PDB 4c77 and related ligands described in Ember, S. W. et al. "Acetyl-lysine Binding Site of Bromodomain-Containing Protein 4 (BRD4) Interacts with Diverse Kinase Inhibitors." *ACS Chem. Biol.* 9: 1160-1171 (2014); the crystal structure PDB 4o7a and related ligands described in Ember, S. W. et al. "Acetyl-lysine Binding Site of Bromodomain-Containing Protein 4 (BRD4) Interacts with Diverse Kinase Inhibitors." *ACS Chem. Biol.* 9: 1160-1171 (2014); the crystal structure PDB 4o7b and related ligands described in "Acetyl-lysine Binding Site of Bromodomain-Containing Protein 4 (BRD4) Interacts with Diverse Kinase Inhibitors." Ember, S. W. et al. (2014) *ACS Chem. Biol.* 9: 1160-1171; the crystal structure PDB 4o7c and related ligands described in Ember, S. W. et al. "Acetyl-lysine Binding Site of Bromodomain-Containing Protein 4 (BRD4) Interacts with Diverse Kinase Inhibitors". *ACS Chem. Biol.* 9: 1160-1171 (2014); the crystal structure PDB 4gpj; the crystal structure PDB 4uix and related ligands described in Theodoulou, N. H. et al. "The Discovery of I-Brd9, a Selective Cell Active Chemical Probe for Bromodomain Containing Protein 9 Inhibition". *J. Med Chem.* 59: 1425 (2016); the crystal structure PDB 4uiz and related ligands described in Theodoulou, N. H., et al. "The Discovery of I-Brd9, a Selective Cell Active Chemical Probe for Bromodomain Containing Protein 9 Inhibition". *J. Med Chem.* 59: 1425 (2016); the crystal structure PDB 4wiv and related ligands described in McKeown, M. R. et al. "Biased multicomponent reactions to develop novel bromodomain inhibitors." *J. Med Chem.* 57: 9019-9027 (2014); the crystal structure PDB 4x2i and related ligands described in Taylor, A. M. et al. "Discovery of Benzotriazolo[4,3-d][1,4]diazepines as Orally Active Inhibitors of BET Bromodomains." *ACS Med Chem. Lett.* 7: 145-150 (2016); the crystal structure PDB 4yh3; And related ligands described in Duffy, B. C. "Discovery of a new chemical series of BRD4(1) inhibitors using protein-ligand docking and structure-guided design." *Bioorg. Med Chem. Lett.* 25: 2818-2823 (2015); the crystal structure PDB 4yh4 and related ligands described in Duffy, B. C. "Discovery of a new chemical series of BRD4 (1) inhibitors using protein-ligand docking and structure-guided design." *Bioorg. Med Chem. Lett.* 25: 2818-2823 (2015); the crystal structure PDB 4z1q and related ligands described in Taylor, A. M. "Discovery of Benzotriazolo[4,3-d][1,4]diazepines as Orally Active Inhibitors of BET Bromodomains." *ACS Med. Chem. Lett.* 7: 145-150 (2016); the crystal structure PDB 4zw1; the crystal structure PDB 5a5s and related ligands described in Demont, E. H. "Fragment-Based Discovery of Low-Micromolar Atad2 Bromodomain Inhibitors. *J. Med Chem.* 58: 5649 (2015); the crystal structure PDB 5a85 and related ligands described in Bamborough, P. "Structure-Based Optimization of Naphthyridones Into Potent Atad2 Bromodomain Inhibitors" *J. Med Chem.* 58: 6151 (2015); the crystal structure PDB 5acy and related ligands described in Sullivan, J. M. "Autism-Like Syndrome is Induced by Pharmacological Suppression of Bet Proteins in Young Mice." *J. Exp. Med* 212: 1771 (2015); the crystal structure PDB 5ad2 and related ligands described in Waring, M. J. et al. "Potent and Selective Bivalent Inhibitors of Bet Bromodomains". *Nat. Chem. Biol.* 12: 1097 (2016); the crystal structure PDB 5cfw and related ligands described in Chekler, E. L. et al. "Transcriptional Profiling of a Selective CREB Binding Protein Bromodomain Inhibitor Highlights Therapeutic Opportunities." *Chem. Biol.* 22: 1588-1596 (2015); the crystal structure PDB 5cqt and related ligands described in Xue, X. et al. "Discovery of Benzo[cd]indol-2(1H)-ones as Potent and Specific BET Bromodomain Inhibitors: Structure-Based Virtual Screening, Optimization, and Biological Evaluation". *J. Med Chem.* 59: 1565-1579 (2016); the crystal structure PDB 5d3r and related ligands described in Hugle, M. et al. "4-Acyl Pyrrole Derivatives Yield Novel Vectors for Designing Inhibitors of the Acetyl-Lysine Recognition Site of BRD4(1)". *J. Med. Chem.* 59: 1518-1530 (2016); the crystal structure PDB 5dlx and related ligands described in Milhas, S. et al. "Protein-Protein Interaction Inhibition (2P21)-Oriented Chemical Library Accelerates Hit Discovery." (2016) *ACS Chem. Biol.* 11: 2140-2148; the crystal structure PDB 5dlz and related ligands described in Milhas, S. et al. "Protein-Protein Interaction Inhibition (2P21)-Oriented Chemical Library Accelerates Hit Discovery." *ACS Chem. Biol.* 11: 2140-2148 (2016); the crystal structure PDB 5dw2 and related ligands described in Kharenko, O. A. et al. "RVX-297—a novel BD2 selective inhibitor of BET bromodomains." *Biochem. Biophys. Res. Commun.* 477: 62-67 (2016); the crystal structure PDB 5dlx; the crystal structure PDB 5his and related ligands described in Albrecht, B. K. et al. "Identification of a Benzoisoxazoloazepine Inhibitor (CPI-0610) of the Bromodomain and Extra-Terminal (BET) Family as a Candidate for Human Clinical Trials." *J. Med Chem.* 59: 1330-1339 (2016); the crystal structure PDB 5ku3 and related ligands described in Crawford, T. D. et al. "Discovery of a Potent and Selective in Vivo Probe (GNE-272) for the Bromodomains of CBP/EP300". *J. Med Chem.* 59: 10549-10563 (2016); the crystal structure PDB 5lj2 and related ligands described in Bamborough, P. et al. "A Chemical Probe for the ATAD2 Bromodomain." *Angew. Chem. Int. Ed Engl.* 55: 11382-11386 (2016); the crystal structure PDB 5dlx and related ligands described in Wang, L. "Fragment-based, structure-enabled discovery of novel pyridones and pyridone macrocycles as potent bromodomain and extra-terminal domain (BET) family bromodomain inhibitors". *J. Med Chem.* 10.1021/acs.jmedchem.7b00017 (2017); WO 2015169962 A1 titled "Benzimidazole derivatives as BRD4 inhibitors and their preparation and use for the treatment of cancer" assigned to Boehringer Ingelheim International GmbH, Germany; and, WO 2011143669 A2 titled "Azolodiazepine derivatives and their preparation, compositions and methods for treating neoplasia, inflammatory disease and other disorders" assigned to Dana-Farber Cancer Institute, Inc, USA.

Figure 8T:
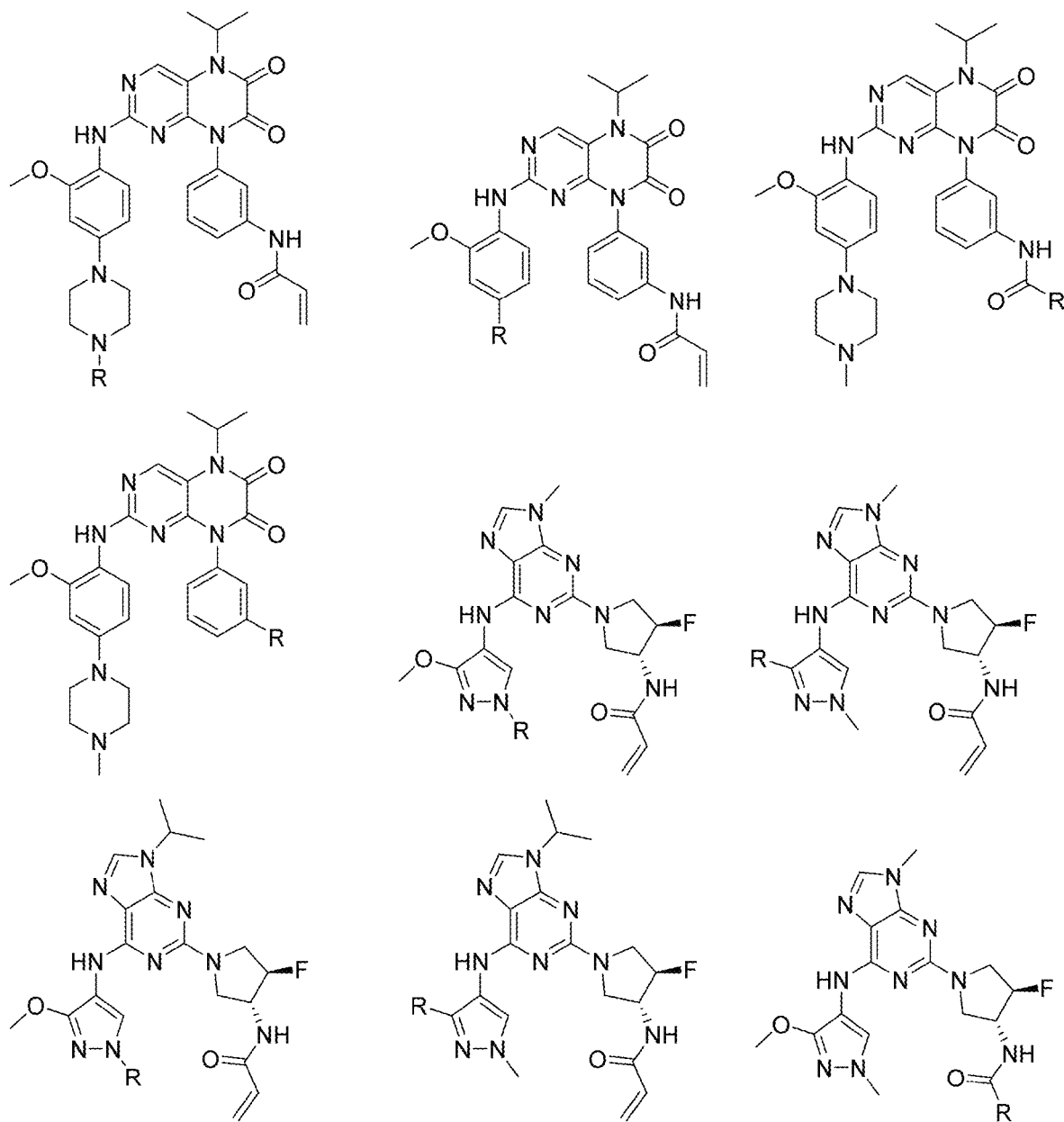
Figure 8U:
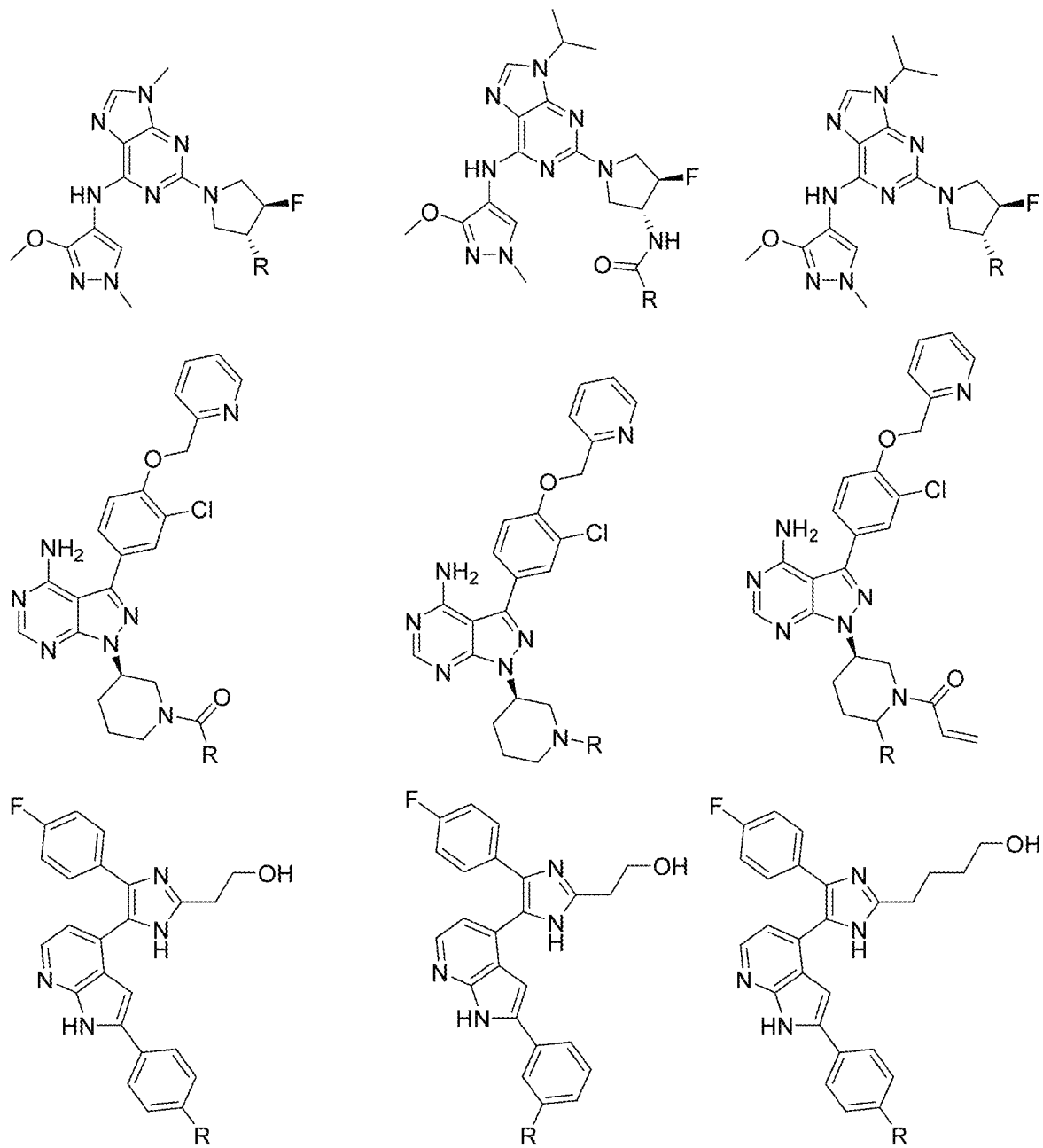
Figure 8V:
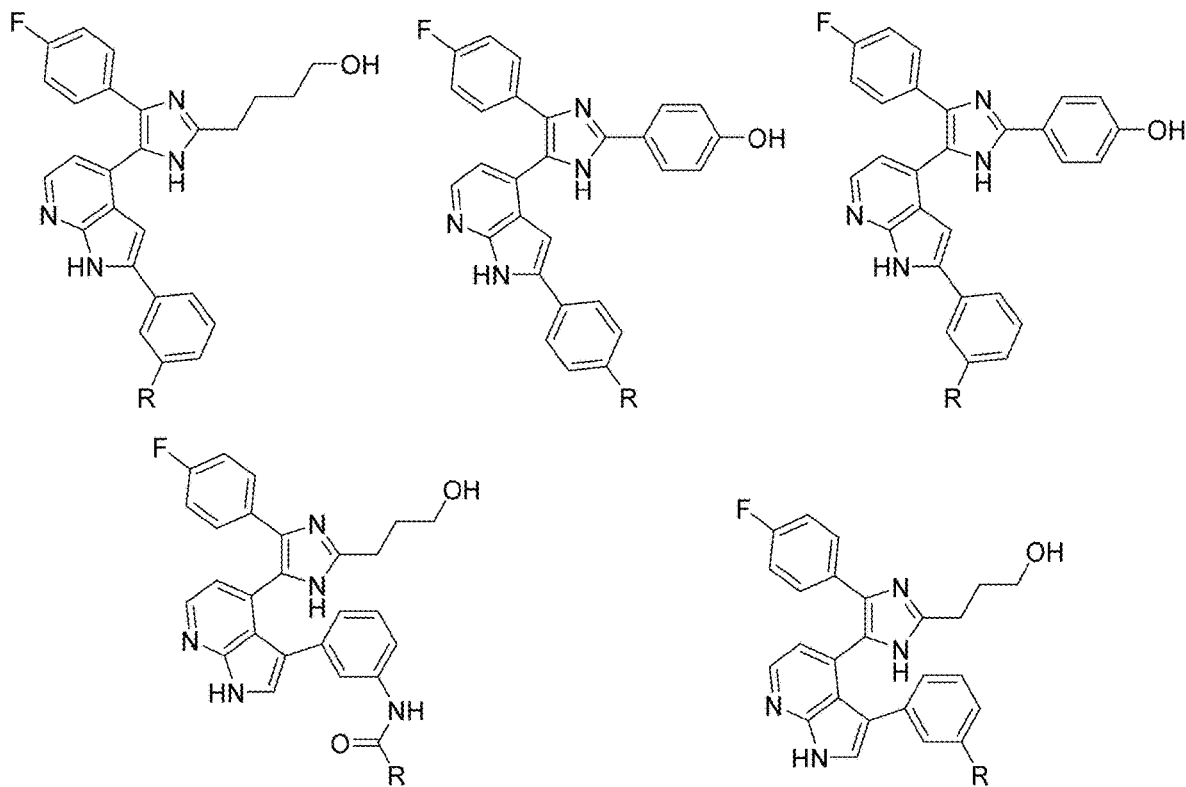
Figure 8W:
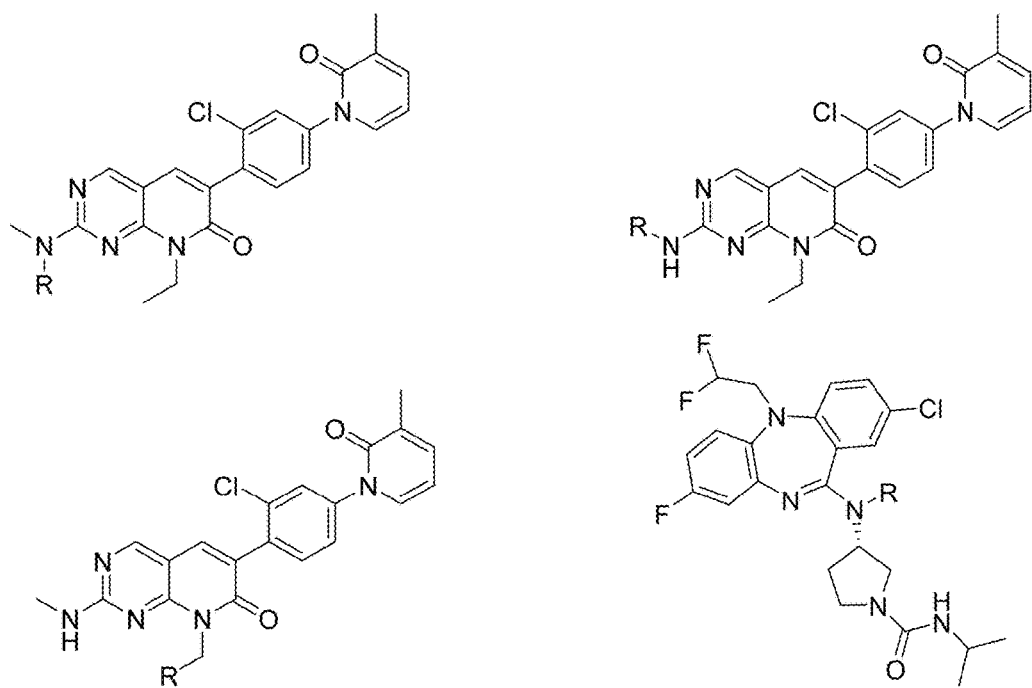
Figure 8X:
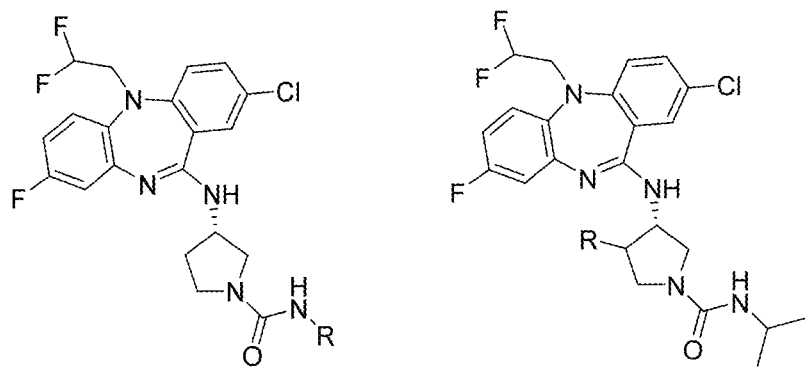
Figure 8Y:
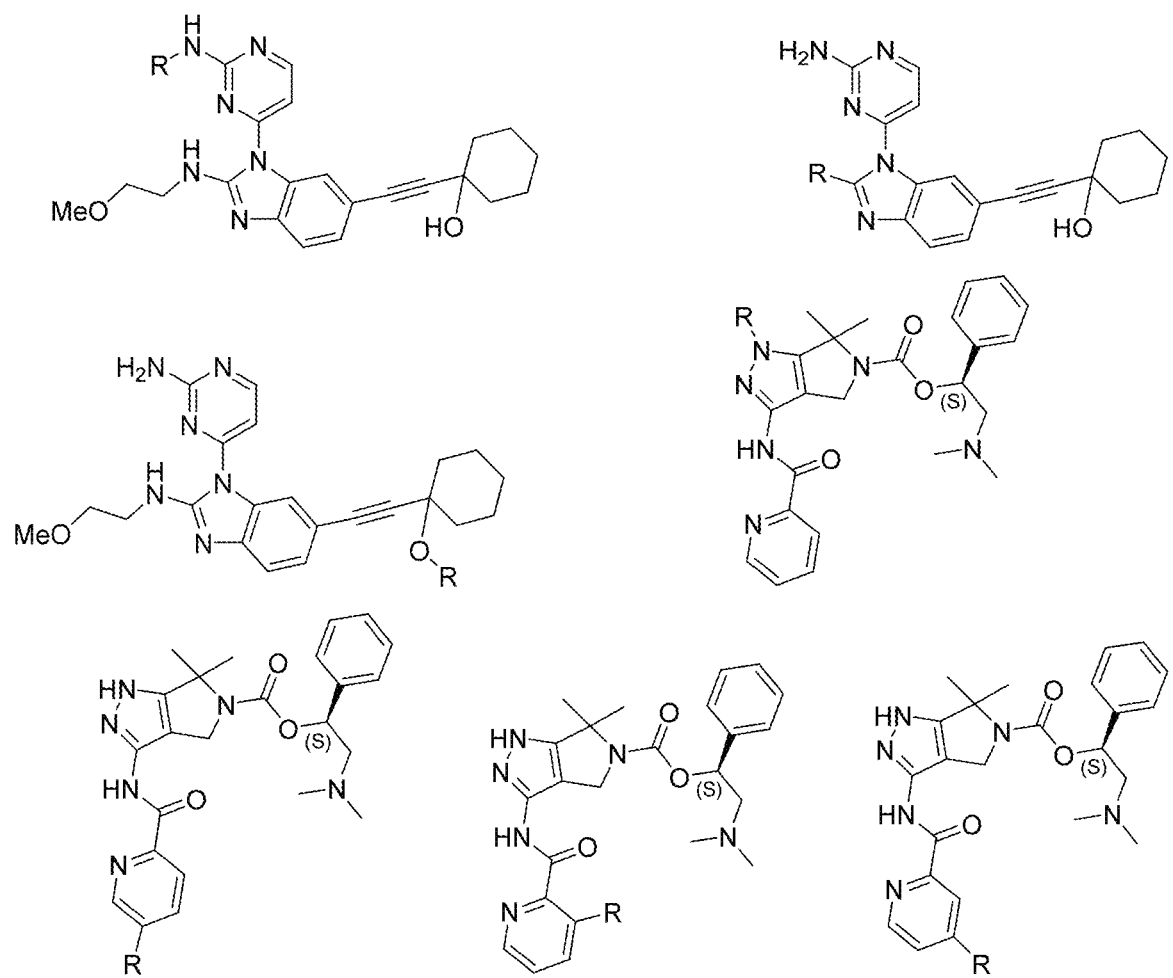
Figure 8Z:
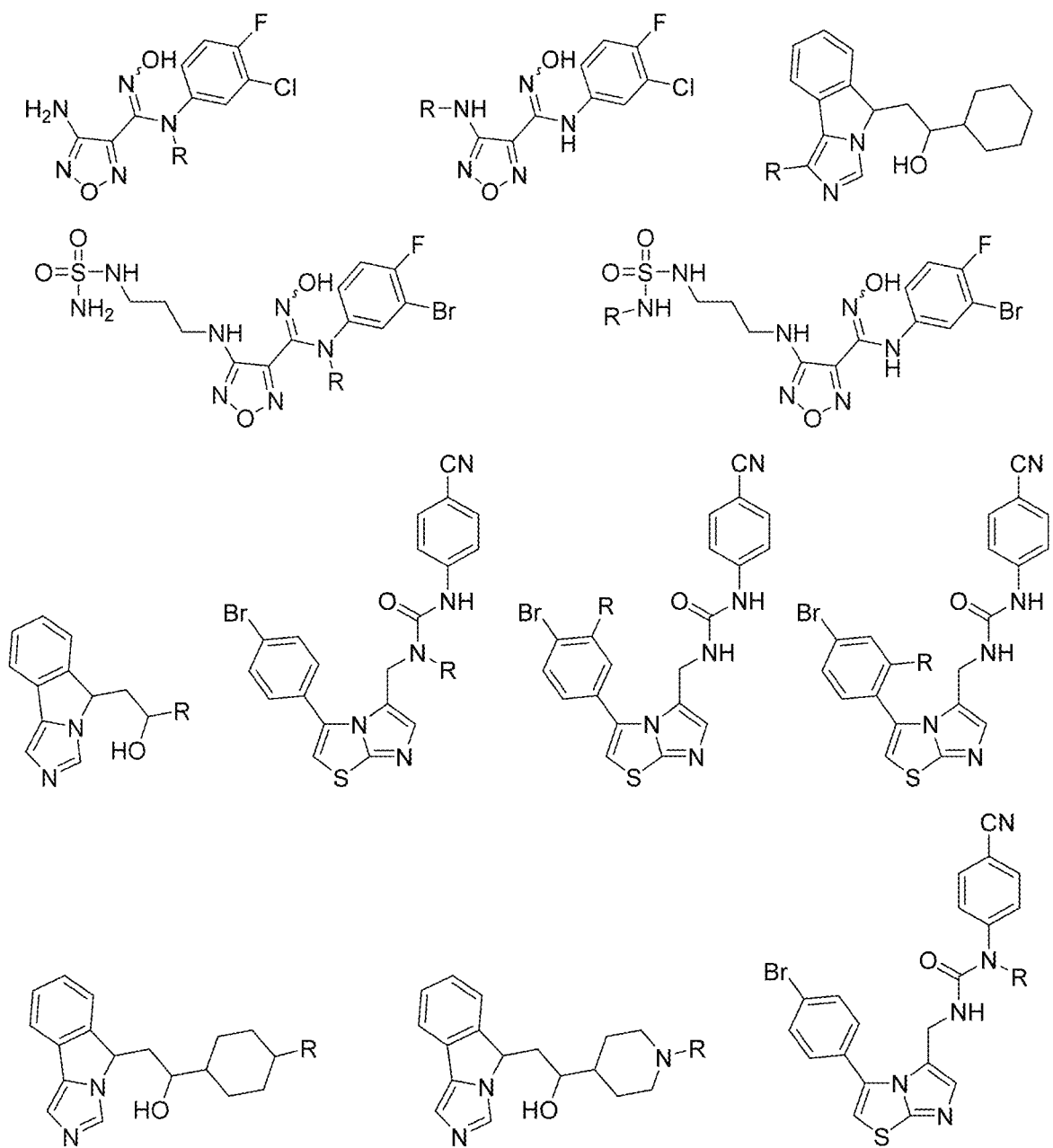

FIG. 8T-8V present examples of ALK Targeting Ligands wherein R is the point at which the Linker is attached. For additional examples and related ligands, see, the crystal structures PDB 2xb7 and 2xba and related ligands described in Bossi, R. T. et al. "Crystal Structures of Anaplastic Lymphoma Kinase in Complex with ATP Competitive Inhibitors" *Biochemistry* 49: 6813-6825 (2010); the crystal structures PDB 2yfx, 4ccb, 4ccu, amd 4cd0 snd related ligands described in Huang, Q. et al. "Design of Potent and Selective Inhibitors to Overcome Clinical Anaplastic Lymphoma Kinase Mutations Resistant to Crizotinib." *J. Med Chem.* 57: 1170 (2014); the crystal structures PDB, 4cli, 4cmo, and 4cnh and related ligands described in Johnson, T. W. et al. "Discovery of (10R)-7-Amino-12-Fluoro-2,10,16-Trimethyl-15-Oxo-10,15,16,17-Tetrahydro-2H-8,4-(Metheno)Pyrazolo[4,3-H][2,5,11]Benzoxadiazacyclotetradecine-3-Carbonitrile (Pf-06463922), a Macrocyclic Inhibitor of Alk/Ros1 with Pre-Clinical Brain Exposure and Broad Spectrum Potency Against Alk-Resistant Mutations." *J. Med Chem.* 57: 4720 (2014); the crystal structure PDB 4fny and related ligands described in Epstein, L. F. et al. "The R1275Q Neuroblastoma Mutant and Certain ATP-competitive Inhibitors Stabilize Alternative Activation Loop Conformations of Anaplastic Lymphoma Kinase." *J. Biol. Chem.* 287: 37447-37457 (2012). the crystal structure PDB 4dce and related ligands described in Bryan, M. C. et al "Rapid development of piperidine carboxamides as potent and selective anaplastic lymphoma kinase inhibitors." *J. Med Chem.* 55: 1698-1705 (2012); the crystal structure PDB 4joa and related ligands described in Gummadi, V. R. et al. "Discovery of 7-azaindole based anaplastic lymphoma kinase (ALK) inhibitors: wild type and mutant (L1196M) active compounds with unique binding mode." (2013) *Bioorg. Med. Chem. Lett.* 23: 4911-4918; and, the crystal structure PDB 5iui and related ligands described in Tu, C. H. et al. "Pyrazolylamine Derivatives Reveal the Conformational Switching between Type I and Type II Binding Modes of Anaplastic Lymphoma Kinase (ALK)." *J. Med. Chem.* 59: 3906-3919 (2016).

FIG. 8W-8X present examples of BTK Targeting Ligands wherein R is the point at which the Linker is attached. For additional examples and related ligands, see, the crystal structure PDB 3gen, 3piz and related ligands described in Marcotte, D. J. et al. "Structures of human Bruton's tyrosine kinase in active and inactive conformations suggest a mechanism of activation for TEC family kinases." *Protein Sci.* 19: 429-439 (2010) and Kuglstatter, A. et al. "Insights into the conformational flexibility of Bruton's tyrosine kinase from multiple ligand complex structures" *Protein Sci.* 20: 428-436" (2011); the crystal structure PDB 3ocs, 4ot6 and related ligands described in Lou, Y. et al. "Structure-Based Drug Design of RN486, a Potent and Selective Bruton's Tyrosine Kinase (BTK) Inhibitor, for the Treatment of Rheumatoid Arthritis" *J. Med. Chem.* 58: 512-516 (2015); the crystal structures PDB 5fbn and 5fbo and related ligands described in Liu, J. et al. "Discovery of 8-Amino-imidazo [1,5-a]pyrazines as Reversible BTK Inhibitors for the Treatment of Rheumatoid Arthritis." *ACS Med. Chem. Lett.* 7: 198-203 (2016); the crystal structure PDB 3pix and related ligands described in Kuglstatter, A. et al. "Insights into the conformational flexibility of Bruton's tyrosine kinase from multiple ligand complex structures." *Protein Sci.* 20: 428-436 (2011); and, the crystal structure PDB 3pij and related ligands described in Bujacz, A. et al. "Crystal structures of the apo form of beta-fructofuranosidase from *Bifidobacterium longum* and its complex with fructose." *Febs J.* 278: 1728-1744 (2011).

FIG. 8Y presents examples of FLT3 Targeting Ligands wherein R is the point at which the Linker is attached. For additional examples and related ligands, see, the crystal structures PDB 4xuf and 4rt7 and related ligands described in Zorn, J. A. et al. "Crystal Structure of the FLT3 Kinase Domain Bound to the Inhibitor Quizartinib (AC220)". *Plos One* 10: e0121177-e0121177 (2015).

FIG. 8Z-8AA present examples of TNIK Targeting Ligands wherein R is the point at which the Linker is attached. For additional examples and related ligands, see, the crystal structure PDB 2x7f; the crystal structures PDB 5ax9 and 5d7a; and, related ligands described in Masuda, M. et al. "TNIK inhibition abrogates colorectal cancer stemness." *Nat Commun* 7: 12586-12586 (2016).

FIG. 8BB-8CC present examples of NTRK1, NTRK2, and NTRK3 Targeting Ligands wherein R is the point at which the Linker is attached. For additional examples and related ligands, see, the crystal structure PDB 4aoj and related ligands described in Wang, T. et al. "Discovery of Disubstituted Imidazo[4,5-B]Pyridines and Purines as Potent Trka Inhibitors." *ACS Med. Chem. Lett.* 3: 705 (2012); the crystal structures PDB 4pmm, 4pmp, 4pms and 4pmt and related ligands described in Stachel, S. J. et al. "Maximizing diversity from a kinase screen: identification of novel and selective pan-Trk inhibitors for chronic pain." *J. Med Chem.* 57: 5800-5816 (2014); the crystal structures PDB 4yps and 4yne snd related ligands described in Choi, H. S. et al. "(R)-2-Phenylpyrrolidine Substituted Imidazopyridazines: A New Class of Potent and Selective Pan-TRK Inhibitors." *ACS Med Chem. Lett.* 6: 562-567 (2015); the crystal structures PDB 4at5 and 4at3 and related ligands described in Bertrand, T. et al. "The Crystal Structures of Trka and Trkb Suggest Key Regions for Achieving Selective Inhibition." *J. Mol. Biol.* 423: 439 (2012); and, the crystal structures PDB 3v5q and 4ymj and related ligands described in Albaugh, P. et al. "Discovery of GNF-5837, a selective TRK Inhibitor with efficacy in rodent cancer tumor models." *ACS Med Chem. Lett.* 3: 140-145 (2012) and Choi, H. S. et al. "(R)-2-Phenylpyrrolidine Substitute Imidazopyridazines: a New Class of Potent and Selective Pan-TRK Inhibitors." *ACS Med Chem Lett* 6: 562-567 (2015).

FIG. 8DD-8EE present examples of FGFR1 Targeting Ligands wherein R is the point at which the Linker is attached. For additional examples and related ligands, see, the crystal structures PDB 3tto and 2fgi and related ligands described in Brison, Y. et al. "Functional and structural characterization of alpha-(1-2) branching sucrase derived from DSR-E glucansucrase." *J. Biol. Chem.* 287: 7915-7924 (2012) and Mohammadi, M. et al. "Crystal structure of an angiogenesis inhibitor bound to the FGF receptor tyrosine kinase domain." *EMBO J.* 17: 5896-5904 (1998); the crystal structure PDB 4fb3; the crystal structure PDB 4rwk and related ligands described in Harrison, C. et al. "Polyomavirus large T antigen binds symmetrical repeats at the viral origin in an asymmetrical manner." *J. Virol.* 87: 13751-13759 (2013); the crystal structure PDB 4rwl and related ligands described in Sohl, C. D. et al. "Illuminating the Molecular Mechanisms of Tyrosine Kinase Inhibitor Resistance for the FGFR1 Gatekeeper Mutation: The Achilles' Heel of Targeted Therapy." *ACS Chem. Biol.* 10: 1319-1329 (2015); the crystal structure PDB 4uwc; the crystal structure PDB 4v01 and related ligands described in Tucker, J. A. et al. "Structural Insights Into Fgfr Kinase Isoform Selectivity: Diverse Binding Modes of Azd4547 and Ponatinib in Complex with Fgfr1 and Fgfr4." *Structure* 22: 1764 (2014); the crystal structure PDB 5a46 and related ligands described in Klein, T. et al. "Structural and Dynamic Insights Into the Energetics of Activation Loop Rearrangement in Fgfr1 Kinase." *Nat. Commun.* 6: 7877 (2015); and, the crystal structure PDB 5ew8 and related ligands described in Patani, H. et al. "Landscape of activating cancer mutations in FGFR kinases and their differential responses to inhibitors in clinical use." *Oncotarget* 7: 24252-24268 (2016).

FIG. 8FF presents examples of FGFR2 Targeting Ligands wherein R is the point at which the Linker is attached. For additional examples and related ligands, see, the crystal structure PDB 2pvf and related ligands described in Chen, H. et al. "A molecular brake in the kinase hinge region regulates the activity of receptor tyrosine kinases." *Mol. Cell* 27: 717-730 (2007).

FIG. 8GG presents examples of FGFR4 Targeting Ligands wherein R is the point at which the Linker is attached. For additional examples and related ligands, see, the crystal structure PDB 4tyi and related ligands described in Lesca, E. et al. "Structural analysis of the human fibroblast growth factor receptor 4 kinase." *J. Mol. Biol.* 426: 3744-3756 (2014).

FIG. 8HH-8II present examples of MET Targeting Ligands wherein R is the point at which the Linker is attached. For additional examples and related ligands, see, the crystal structures PDB 3qti and 3zcl; the crystal structures PDB 4xmo, 4xyf, and 3zc and related ligands described in Peterson, E. A. et al. "Discovery of Potent and Selective 8-Fluorotriazolopyridine c-Met Inhibitors." *J. Med Chem.* 58: 2417-2430 (2015) and Cui, J. J. et al. "Lessons from (S)-6-(1-(6-(1-Methyl-1H-Pyrazol-4-Yl)-[1,2, 4]Triazolo[4,3-B]Pyridazin-3-Yl)Ethyl)Quinoline (Pf-04254644), an Inhibitor of Receptor Tyrosine Kinase C-met with High Protein Kinase Selectivity But Broad Phosphodiesterase Family Inhibition Leading to Myocardial Degeneration in Rats." *J. Med Chem.* 56: 6651 (2013); the crystal structure PDB 5eyd and related ligands described in Boezio, A. A. et al. "Discovery of (R)-6-(1-(8-Fluoro-6-(1-methyl-1H-pyrazol-4-yl)-[1,2,4]triazolo[4,3-a]pyridin-3-yl)ethyl)-3-(2-methoxyethoxy)-1,6-naphthyridin-5(6H)-one (AMG 337), a Potent and Selective Inhibitor of MET with High Unbound Target Coverage and Robust In Vivo Antitumor Activity." *J. Med Chem.* 59: 2328-2342 (2016); the crystal structure PDB 3ce3 and related ligands described in Kim, K. S. et al. "Discovery of pyrrolopyridine-pyridone based inhibitors of Met kinase: synthesis, X-ray crystallographic analysis, and biological activities." *J. Med Chem.* 51: 5330-5341 (2008); the crystal structure PDB 2rfn and related ligands described in Bellon, S. F. et al. "c-Met inhibitors with novel binding mode show activity against several hereditary papillary renal cell carcinoma-related mutations." *J. Biol. Chem.* 283: 2675-2683 (2008); and, the crystal structure PDB 5dg5 and related ligands described in Smith, B. D. et al "Altiratinib Inhibits Tumor Growth, Invasion, Angiogenesis, and Microenvironment-Mediated Drug Resistance via Balanced Inhibition of MET, TIE2, and VEGFR2.". *Mol. Cancer Ther.* 14: 2023-2034 (2015).

FIG. 8JJ presents examples of JAK1 Targeting Ligands wherein R is the point at which the Linker is attached. For additional examples and related ligands, see, the crystal structure PDB 4ivd and related ligands described in Zak, M. et al. "Identification of C-2 Hydroxyethyl Imidazopyrrolopyridines as Potent JAK1 Inhibitors with Favorable Physicochemical Properties and High Selectivity over JAK2." *J. Med Chem.* 56: 4764-4785 (2013); the crystal structure PDB 5e1e and related ligands described in Vasbinder, M. M. et al. "Identification of azabenzimidazoles as potent JAK1 selective inhibitors." *Bioorg. Med Chem. Lett.* 26: 60-67 (2016); the crystal structure PDB 5hx8 and related ligands described in Simov, V., et al. "Structure-based design and development of (benz)imidazole pyridones as JAK1-selective kinase inhibitors." *Bioorg. Med Chem. Lett.* 26: 1803-1808 (2016); the crystal structure PDB 5hx8 and related ligands described in Caspers, N. L. et al. "Development of a high-throughput crystal structure-determination platform for JAK1 using a novel metal-chelator soaking system". *Acta Crystallogr.* Sect. F 72: 840-845 (2016); and, Kettle, J. G. "Discovery of the JAK selective kinase inhibitor AZD4205", AACR National Meeting, April 2017.

FIG. 8KK-8LL present examples of JAK2 Targeting Ligands wherein R is the point at which the Linker is attached. For additional examples and related ligands, see, the crystal structure PDB 3ugc and related ligands described in Andraos, R. et al. "Modulation of activation-loop phosphorylation by JAK inhibitors is binding mode dependent." *Cancer Discov* 2: 512-523 (2012); the crystal structures PDB 5cf4, 5cf5, 5cf6 and 5cf8 and related ligands described in Hart, A. C. et al. "Structure-Based Design of Selective Janus Kinase 2 Imidazo[4,5-d]pyrrolo[2,3-b]pyridine Inhibitors." *ACS Med. Chem. Lett.* 6: 845-849 (2015); the crystal structure PDB 5aep and related ligands described in Brasca, M. G. et al "Novel Pyrrole Carboxamide Inhibitors of Jak2 as Potential Treatment of Myeloproliferative Disorders" *Bioorg. Med Chem.* 23: 2387 (2015); the crystal structures PDB 4ytf, 4yth and 4yti and related ligands described in Farmer, L. J. et al. "Discovery of VX-509 (Decernotinib): A Potent and Selective Janus Kinase 3 Inhibitor for the Treatment of Autoimmune Diseases." *J. Med Chem.* 58: 7195-7216 (2015); the crystal structure PDB 4ytf, 4yth, 4yti and related ligands described in Menet, C. J.

et al. "Triazolopyridines as Selective JAK1 Inhibitors: From Hit Identification to GLPG0634." *J. Med Chem.* 57: 9323-9342 (2014); the crystal structure PDB 4ji9 and related ligands described in Siu, M. et al. "2-Amino-[1,2,4]triazolo [1,5-a]pyridines as JAK2 inhibitors." *Bioorg. Med. Chem. Lett.* 23: 5014-5021 (2013); and, the crystal structures PDB 3io7 and 3iok and related ligands described in Schenkel, L. B. et al. "Discovery of potent and highly selective thienopyridine janus kinase 2 inhibitors." *J. Med. Chem.* 54: 8440-8450 (2011).

FIG. 8MM presents examples of JAK3 Targeting Ligands wherein R is the point at which the Linker is attached. For additional examples and related ligands, see, the crystal structure PDB 3zc6 and related ligands described in Lynch, S. M. et al. "Strategic Use of Conformational Bias and Structure Based Design to Identify Potent Jak3 Inhibitors with Improved Selectivity Against the Jak Family and the Kinome." *Bioorg. Med Chem. Lett.* 23: 2793 (2013); and, the crystal structures PDB 4hvd, 4i6q, and 3zep and related ligands described in Soth, M. et al. "3-Amido Pyrrolopyrazine JAK Kinase Inhibitors: Development of a JAK3 vs JAK1 Selective Inhibitor and Evaluation in Cellular and in Vivo Models." *J. Med. Chem.* 56: 345-356 (2013) and Jaime-Figueroa, S. et al. "Discovery of a series of novel 5H-pyrrolo[2,3-b]pyrazine-2-phenyl ethers, as potent JAK3 kinase inhibitors." *Bioorg. Med Chem. Lett.* 23: 2522-2526 (2013).

FIG. 8NN-8OO present examples of KIT Targeting Ligands wherein R is the point at which the Linker is attached. For additional examples and related ligands, see, the crystal structure PDB 1t46 and related ligands described in Mol, C. D. et al. "Structural basis for the autoinhibition and STI-571 inhibition of c-Kit tyrosine kinase." *J. Biol. Chem.* 279: 31655-31663 (2004); and, the crystal structure PDB 4u0i and related ligands described in Garner, A. P. et al. "Ponatinib Inhibits Polyclonal Drug-Resistant KIT Oncoproteins and Shows Therapeutic Potential in Heavily Pretreated Gastrointestinal Stromal Tumor (GIST) Patients." *Clin. Cancer Res.* 20: 5745-5755 (2014).

FIG. 8PP-8VV present examples of EGFR Targeting Ligands wherein R is the point at which the Linker is attached. For additional examples and related ligands, see, the crystal structures PDB 5hcy, 4rj4, and 5cav; Heald, R., "Noncovalent Mutant Selective Epidermal Growth Factor Receptor Inhibitors: A Lead Optimization Case Study", *J. Med Chem.* 58, 8877-8895 (2015); Hanano, E. J., "Discovery of Selective and Noncovalent Diaminopyrimidine-Based Inhibitors of Epidermal Growth Factor Receptor Containing the T790M Resistance Mutation." *J. Med Chem.*, 57, 10176-10191 (2014); Chan, B. K. et al. "Discovery of a Noncovalent, Mutant-Selective Epidermal Growth Factor Receptor Inhibitor" *J. Med Chem.* 59, 9080 (2016); the crystal structure PDB 5d41 and related ligands described in Jia, Y. et al., "Overcoming EGFR(T790M) and EGFR(C797S) resistance with mutant-selective allosteric inhibitors" *Nature* 534, 129 (2016); Ward, R. A. "Structure- and reactivity-based development of covalent inhibitors of the activating and gatekeeper mutant forms of the epidermal growth factor receptor (EGFR)" *J. Med Chem.* 56, 7025-7048 (2013); the crystal structure PDB 4zau and related ligands described in "Discovery of a Potent and Selective EGFR Inhibitor (AZD9291) of Both Sensitizing and T790M Resistance Mutations That Spares the Wild Type Form of the Receptor" *J. Med. Chem.*, 57 (20), 8249-8267 (2014); the crystal structure PDB 5em7 and related ligands described in Bryan, M. C. et al. "Pyridones as Highly Selective, Noncovalent Inhibitors of T790M Double Mutants of EGFR" *ACS Med Chem. Lett.*, 7 (1), 100-104 (2016); the crystal structure PDB 3IKA and related ligands described in Zhou, W. et al. "Novel mutant-selective EGFR kinase inhibitors against EGFR T790M" *Nature* 462(7276), 1070-1074 (2009); the crystal structure see PDB 5feq and related ligands described in Lelais, G., J. "Discovery of (R,E)-N-(7-Chloro-1-(1-[4-(dimethylamino)but-2-enoyl]azepan-3-yl)-1H-benzo[d]imidazol-2-yl)-2-methylisonicotinamide (EGF816), a Novel, Potent, and WT Sparing Covalent Inhibitor of Oncogenic (L858R, ex19del) and Resistant (T790M) EGFR Mutants for the Treatment of EGFR Mutant Non-Small-Cell Lung Cancers" *Med Chem.*, 59 (14), 6671-6689 (2016); Lee, H.-J. "Noncovalent Wild-type-Sparing Inhibitors of EGFR T790M" *Cancer Discov.* 3(2): 168-181 (2013); the crystal structure PDB 5j7 h and related ligands described in Huang, W-S. et al. "Discovery of Brigatinib (AP26113), a Phosphine Oxide-Containing, Potent, Orally Active Inhibitor of Anaplastic Lymphoma Kinase." *J. Med Chem.* 59: 4948-4964 (2016); the crystal structure PDB 4v0 g and related ligands described in Hennessy, E. J. et al. "Utilization of Structure-Based Design to Identify Novel, Irreversible Inhibitors of EGFR Harboring the T790M Mutation." *ACS. Med Chem. Lett.* 7: 514-519 (2016); the crystal structure PDB 5hg7 and related ligands described in Cheng, H. "Discovery of 1-{(3R,4R)-3-[({5-Chloro-2-[(1-methyl-1H-pyrazol-4-yl)amino]-7H-pyrrolo[2,3-d]pyrimidin-4-yl}oxy) methyl]-4-methoxypyrrolidin-1-yl}prop-2-en-1-one (PF-06459988), a Potent, WT Sparing, Irreversible Inhibitor of T790M-Containing EGFR Mutants." *J. Med Chem.* 59: 2005-2024 (2016); Hao, Y. "Discovery and Structural Optimization of N5-Substituted 6,7-Dioxo-6,7-dihydropteridines as Potent and Selective Epidermal Growth Factor Receptor (EGFR) Inhibitors against L858R/T790M Resistance Mutation." *J. Med Chem.* 59: 7111-7124 (2016); the crystal structure PDB 5ug8, 5ug9, and 5ugc and related ligands described in Planken, S. "Discovery of N-((3R,4R)-4-Fluoro-1-(6-((3-methoxy-1-methyl-1H-pyrazol-4-yl) amino)-9-methyl-9H-purin-2-yl)pyrrolidine-3-yl)acrylamide (PF-06747775) through Structure-Based Drug Design: A High Affinity Irreversible Inhibitor Targeting Oncogenic EGFR Mutants with Selectivity over Wild-Type EGFR." *J. Med Chem.* 60: 3002-3019 (2017); the crystal structure PDB 5gnk and related ligands described in Wang, A. "Discovery of (R)-1-(3-(4-Amino-3-(3-chloro-4-(pyridin-2-ylmethoxy) phenyl)-1H-pyrazolo[3,4-d]pyrimidin-1-yl)piperidin-1-yl) prop-2-en-1-one (CHMFL-EGFR-202) as a Novel Irreversible EGFR Mutant Kinase Inhibitor with a Distinct Binding Mode." *J. Med Chem.* 60: 2944-2962 (2017); and, Juchum, M. "Trisubstituted imidazoles with a rigidized hinge binding motif act as single digit nM inhibitors of clinically relevant EGFR L858R/T790M and L858R/T790M/C797S mutants: An example of target hopping." *J. Med Chem.* DOI: 10.1021/acs.jmedchem.7b00178 (2017).

FIG. 8WW-8XX present examples of PAK1 Targeting Ligands wherein R is the point at which the Linker is attached. For additional examples and related ligands, see, Rudolph, J. et al. "Chemically Diverse Group I p21-Activated Kinase(PAK) Inhibitors Impart Acute Cardiovascular Toxicity with a Narrow Therapeutic Window." *J. Med Chem.* 59, 5520-5541 (2016) and Karpov A S, et al. *ACS Med Chem Lett.* 22; 6(7):776-81 (2015).

FIG. 8YY presents examples of PAK4 Targeting Ligands wherein R is the point at which the Linker is attached. For additional examples and related ligands, see, Staben S T, et al. *J Med Chem.* 13; 57(3):1033-45 (2014) and Guo, C. et al. "Discovery of pyrroloaminopyrazoles as novel PAK inhibitors" *J. Med Chem.* 55, 4728-4739 (2012).

FIG. 8ZZ-8AAA present examples of IDO Targeting Ligands wherein R is the point at which the Linker is attached. For additional examples and related ligands, see, Yue, E. W.; et al. "Discovery of potent competitive inhibitors of indoleamine 2,3-dioxygenase with in vivo pharmacodynamic activity and efficacy in a mouse melanoma model." *J. Med Chem.* 52, 7364-7367 (2009); Tojo, S.; et al. "Crystal structures and structure, and activity relationships of imidazothiazole derivatives as IDO1 inhibitors." *ACS Med Chem. Lett.* 5, 1119-1123 (2014); Mautino, M. R. et al. "NLG919, a novel indoleamine-2,3-dioxygenase (IDO)-pathway inhibitor drug candidate for cancer therapy" Abstract 491, AACR 104th Annual Meeting 2013; Apr. 6-10, 2013; Washington, DC; and, WO2012142237 titled "Fused imidazole derivatives useful as IDO inhibitors".

FIG. 8BBB-8EEE present examples of ERK1 and ERK2 Targeting Ligands wherein R is the point at which the Linker is attached. For additional examples and related ligands, see, the crystal structures PDB 5K4I and 5K4J and related ligands described in Blake, J. F. et al. "Discovery of (S)-1-(1-(4-Chloro-3-fluorophenyl)-2-hydroxyethyl)-4-(2-((1-methyl-1H-pyrazol-5-yl)amino)pyrimidin-4-yl)pyridin-2 (1H)-one (GDC-0994), an Extracellular Signal-Regulated Kinase 1/2 (ERK1/2) Inhibitor in Early Clinical Development" *J. Med Chem.* 59: 5650-5660 (2016); the crystal structure PDB 5BVF and related ligands described in Bagdanoff, J. T. et al. "Tetrahydropyrrolo-diazepenones as inhibitors of ERK2 kinase" *Bioorg. Med Chem. Lett.* 25, 3788-3792 (2015); the crystal structure PDB 4QYY and related ligands described in Deng, Y. et al. "Discovery of Novel, Dual Mechanism ERK Inhibitors by Affinity Selection Screening of an Inactive Kinase" *J. Med Chem.* 57: 8817-8826 (2014); the crystal structures PDB 5HD4 and 5HD7 and the related ligands described in Jha, S. et al. "Dissecting Therapeutic Resistance to ERK Inhibition" *Mol. Cancer Ther.* 15: 548-559 (2016); the crystal structure PDB 4XJ0 and related ligands described in Ren, L. et al. "Discovery of highly potent, selective, and efficacious small molecule inhibitors of ERK1/2." *J. Med Chem.* 58: 1976-1991 (2015); the crystal structures PDB 4ZZM, 4ZZN, 4ZZO and related ligands described in Ward, R. A. et al. "Structure-Guided Design of Highly Selective and Potent Covalent Inhibitors of Erk1/2." *J. Med Chem.* 58: 4790 (2015); Burrows, F. et al. "KO-947, a potent ERK inhibitor with robust preclinical single agent activity in MAPK pathway dysregulated tumors" Poster #5168, AACR National Meeting 2017; Bhagwat, S. V. et al. "Discovery of LY3214996, a selective and novel ERK1/2 inhibitor with potent antitumor activities in cancer models with MAPK pathway alterations." AACR National Meeting 2017; the crystal structures PDB 3FHR and 3FXH and related ligands described in Cheng, R. et al. "High-resolution crystal structure of human Mapkap kinase 3 in complex with a high affinity ligand" *Protein Sci.* 19: 168-173 (2010); the crystal structures PDB 5NGU, 5NHF, 5NHH, 5NHJ, 5NHL, 5NHO, 5NHP, and 5NHV and related ligands described in Ward, R. A. et al. "Structure-Guided Discovery of Potent and Selective Inhibitors of ERK1/2 from a Modestly Active and Promiscuous Chemical Start Point." *J. Med Chem.* 60, 3438-3450 (2017); and, the crystal structures PDB 3 SHE and 3R1N and related ligands described in Oubrie, A. et al. "Novel ATP competitive MK2 inhibitors with potent biochemical and cell-based activity throughout the series." *Bioorg. Med Chem. Lett.* 22: 613-618 (2012).

FIG. 8FFF-8III present examples of ABL1 Targeting Ligands wherein R is the point at which the Linker is attached. For additional examples and related ligands, see, the crystal structure PDB 1fpu and 2e2b and related ligands described in Schindler, T., et al. "Structural mechanism for STI-571 inhibition of abelson tyrosine kinase", *Science* 289: 1938-1942 (2000); and Horio, T. et al. "Structural factors contributing to the Abl/Lyn dual inhibitory activity of 3-substituted benzamide derivatives", *Bioorg. Med. Chem. Lett.* 17: 2712-2717 (2007); the crystal structures PDB 2hzn and 2hiw and related ligands described in Cowan-Jacob, S. W. et al. "Structural biology contributions to the discovery of drugs to treat chronic myelogenous leukaemia", *Acta Crystallog. Sect. D* 63: 80-93 (2007) and Okram, B. et al. "A general strategy for creating", *Chem. Biol.* 13: 779-786 (2006); the crystal structure PDB 3cs9 and related ligands described in Weisberg, E. et al. "Characterization of AMN107, a selective inhibitor of native and mutant Bcr-Abl", *Cancer Cell* 7: 129-14 (2005); the crystal structure PDB 3ik3 and related ligands described in O'Hare, T. et al. "AP24534, a pan-BCR-ABL inhibitor for chronic myeloid leukemia, potently inhibits the T315I mutant and overcomes mutation-based resistance", *Cancer Cell* 16: 401-412 (2009); the crystal structure PDB 3mss and related ligands described in Jahnke, W. et al. "Binding or bending: distinction of allosteric Abl kinase agonists from antagonists by an NMR-based conformational assay", *J. Am. Chem. Soc.* 132: 7043-7048 (2010); the crystal structure PDB 3oy3 and related ligands described in Zhou, T. et al. "Structural Mechanism of the Pan-BCR-ABL Inhibitor Ponatinib (AP24534): Lessons for Overcoming Kinase Inhibitor Resistance", *Chem. Biol. Drug Des.* 77: 1-11 (2011); the crystal structures PDB 3qri and 3qrk and related ligands described in Chan, W. W. et al. "Conformational Control Inhibition of the BCR-ABL1 Tyrosine Kinase, Including the Gatekeeper T315I Mutant, by the Switch-Control Inhibitor DCC-2036", *Cancer Cell* 19: 556-568 (2011); the crystal structure PDB 5hu9 and 2f4j and related ligands described in Liu, F. et al. "Discovery and characterization of a novel potent type II native and mutant BCR-ABL inhibitor (CHMFL-074) for Chronic Myeloid Leukemia (CML)", *Oncotarget* 7: 45562-45574 (2016) and Young, M. A. et al. "Structure of the kinase domain of an imatinib-resistant Abl mutant in complex with the Aurora kinase inhibitor VX-680", *Cancer Res.* 66: 1007-1014 (2006); the crystal structure PDB 2gqg and 2qoh and related ligands described in Tokarski, J. S. et al. "The Structure of Dasatinib (BMS-354825) Bound to Activated ABL Kinase Domain Elucidates Its Inhibitory Activity against Imatinib-Resistant ABL Mutants", *Cancer Res.* 66: 5790-5797 (2006); and Zhou, T. et al. "Crystal Structure of the T315I Mutant of Abl Kinase", *Chem. Biol. Drug Des.* 70: 171-181 (2007); the crystal structure PDB 2gqg and 2qoh and related ligands described in Tokarski, J. S. et al. "The Structure of Dasatinib (BMS-354825) Bound to Activated ABL Kinase Domain Elucidates Its Inhibitory Activity against Imatinib-Resistant ABL Mutants", *Cancer Res.* 66: 5790-5797 (2006) and Zhou, T. et al. "Crystal Structure of the T315I Mutant of Abl Kinase", *Chem. Biol. Drug Des.* 70: 171-181 (2007); the crystal structure PDB 2gqg and 2qoh and related ligands described in Tokarski, J. S. et al. "The Structure of Dasatinib (BMS-354825) Bound to Activated ABL Kinase Domain Elucidates Its Inhibitory Activity against Imatinib-Resistant ABL Mutants", *Cancer Res.* 66: 5790-5797 (2006) and Zhou, T. et al. "Crystal Structure of the T315I Mutant of Abl Kinase", *Chem. Biol. Drug Des.* 70: 171-181(2007); the crystal structures PDB 3dk3 and 3dk8 and related ligands described in Berkholz, D. S. et al. "Catalytic cycle of human glutathione reductase near 1 A resolution" *J. Mol. Biol.* 382: 371-384 (2008); the crystal structure PDB 3ue4 and related ligands described in Levinson, N. M. et al. "Structural and spectroscopic analysis of the kinase inhibitor bosutinib and an isomer of bosutinib binding to the abl tyrosine kinase domain", *Plos One* 7: e29828-e29828 (2012); the crystal structure PDB 4cy8 and related ligands described in Jensen, C. N. et al. "Structures of the Apo and Fad-Bound Forms of 2-Hydroxybiphenyl 3-Monooxygenase (Hbpa) Locate Activity Hotspots Identified by Using Directed Evolution", *Chembiochem* 16: 968 (2015); the crystal structure PDB 2hz0 and related ligands described in Cowan-Jacob, S. W. et al. "Structural biology contributions to the discovery of drugs to treat chronic myelogenous leukaemia", *Acta Crystallogr D Biol Crystallogr.* 63(Pt 1):80-93 (2007); the crystal structure PDB 3pyy and related ligands described in Yang, J. et al. "Discovery and Characterization of a Cell-Permeable, Small-Molecule c-Abl Kinase Activator that Binds to the Myristoyl Binding Site", *Chem. Biol.* 18: 177-186 (2011); and, the crystal structure PDB 5k5v and related ligands described in Kim, M. K., et al. "Structural basis for dual specificity of yeast N-terminal amidase in the N-end rule pathway", *Proc. Natl. Acad. Sci. U.S.A.* 113: 12438-12443 (2016).

FIG. 8JJJ presents examples of ABL2 Targeting Ligands wherein R is the point at which the Linker is attached. For additional examples and related ligands, see, the crystal structure PDB 2xyn and related ligands described in Salah, E. et al. "Crystal Structures of Abl-Related Gene (Abl2) in Complex with Imatinib, Tozasertib (Vx-680), and a Type I Inhibitor of the Triazole Carbothioamide Class", *J Med. Chem.* 54: 2359 (2011); the crystal structure PDB 4xli and related ligands described in Ha, B. H. et al. "Structure of the ABL2/ARG kinase in complex with dasatinib" *Acta Crystallogr. Sect. F* 71: 443-448 (2015); and the crystal structure PDB 3gvu and related ligands described in Salah, E. et al. "The crystal structure of human ABL2 in complex with Gleevec", to be published.

FIG. 8KKK-8MMM present examples of AKT 1 Targeting Ligands wherein R is the point at which the Linker is attached. For additional examples and related ligands, see, Lippa, B. et al. "Synthesis and structure based optimization of novel Akt inhibitors *Bioorg. Med Chem. Lett.* 18: 3359-3363 (2008); Freeman-Cook, K. D. et al. "Design of selective, ATP-competitive inhibitors of Akt", *J. Med Chem.* 53: 4615-4622 (2010); Blake, J. F. et al "Discovery of pyrrolopyrimidine inhibitors of Akt", *Bioorg. Med Chem. Lett.* 20: 5607-5612 (2010); Kallan, N. C. et al. "Discovery and SAR of spirochromane Akt inhibitors", *Bioorg. Med Chem. Lett.* 21: 2410-2414 (2011); Lin, K "An ATP-Site On-Off Switch That Restricts Phosphatase Accessibility of Akt", *Sci. Signal.* 5: ra37-ra37 (2012); Addie, M. et al. "Discovery of 4-Amino-N-[(1S)-1-(4-chlorophenyl)-3-hydroxypropyl]-1-(7H-pyrrolo[2,3-d]pyrimidin-4-yl)piperidine-4-carboxamide (AZD5363), an Orally Bioavailable, Potent Inhibitor of Akt Kinases", *J. Med Chem.* 56: 2059-2073 (2013); Wu, W. I., et al. "Crystal structure of human AKT1 with an allosteric inhibitor reveals a new mode of kinase inhibition. *Plos One* 5: 12913-12913 (2010); Ashwell, M. A. et al. "Discovery and optimization of a series of 3-(3-phenyl-3H-imidazo[4,5-b]pyridin-2-yl)pyridin-2-amines: orally bioavailable, selective, and potent ATP-independent Akt inhibitors", *J. Med Chem.* 55: 5291-5310 (2012); and, Lapierre, J. M. et al. "Discovery of 3-(3-(4-(1-Aminocyclobutyl)phenyl)-5-phenyl-3H-imidazo[4,5-b]pyridin-2-yl)pyridin-2-amine (ARQ 092): An Orally Bioavailable, Selective, and Potent Allosteric AKT Inhibitor", *J. Med Chem.* 59: 6455-6469 (2016).

FIG. 8NNN-8OOO present examples of AKT2 Targeting Ligands wherein R is the point at which the Linker is attached. For additional examples and related ligands, see, the crystal structured PDB 2jdo and 2jdr and related ligands described in Davies, T. G. et al. "A Structural Comparison of Inhibitor Binding to Pkb, Pka and Pka-Pkb Chimera", *J Mol. Biol.* 367: 882 (2007); the crystal structure PDB 2uw9 and related ligands described in Saxty, G. et al "Identification of Inhibitors of Protein Kinase B Using Fragment-Based Lead Discovery", *J. Med Chem.* 50: 2293-2296 (2007); the crystal structure PDB 2x39 and 2xh5 and related ligands described in Mchardy, T. et al. "Discovery of 4-Amino-1-(7H-Pyrrolo[2,3-D]Pyrimidin-4-Yl)Piperidine-4-Carboxamides as Selective, Orally Active Inhibitors of Protein Kinase B (Akt)", *J. Med Chem.* 53: 2239d (2010); the crystal structure PDB 3d03 and related ligands described in Hadler, K. S. et al. "Substrate-promoted formation of a catalytically competent binuclear center and regulation of reactivity in a glycerophosphodiesterase from *Enterobacter aerogenes*', *J. Am. Chem. Soc.* 130: 14129-14138 (2008); and, the crystal structures PDB 3e87, 3e8d and 3e88 and related ligands described in Rouse, M. B. et al. "Aminofurazans as potent inhibitors of AKT kinase" *Bioorg. Med. Chem. Lett.* 19: 1508-1511 (2009).

FIG. 8PPP presents examples of BMX Targeting Ligands wherein R is the point at which the Linker is attached. For additional examples and related ligands, see, the crystal structures PDB 3sxr and 3sxr and related ligands described in Muckelbauer, J. et al. "X-ray crystal structure of bone marrow kinase in the x chromosome: a Tec family kinase", *Chem. Biol. Drug Des.* 78: 739-748 (2011).

FIG. 8QQQ-8SSS present examples of CSF1R Targeting Ligands wherein R is the point at which the Linker is attached. For additional examples and related ligands, see, the crystal structures PDB 2i0v and 2ilm and related ligands described in Schubert, C. et al. "Crystal structure of the tyrosine kinase domain of colony-stimulating factor-1 receptor (cFMS) in complex with two inhibitors", *J. Biol. Chem.* 282: 4094-4101 (2007); the crystal structure PDB 3bea and related ligands described in Huang, H. et al. "Design and synthesis of a pyrido[2,3-d]pyrimidin-5-one class of anti-inflammatory FMS inhibitors", *Bioorg. Med. Chem. Lett.* 18: 2355-2361 (2008); the crystal structure PDB 3dpk and related ligands described in M. T., McKay, D. B. Overgaard, "Structure of the Elastase of *Pseudomonas aeruginosa* Complexed with Phosphoramidon", to be published; the crystal structures PDB 3krj and 3krl and related ligands described in Illig, C. R. et al. "Optimization of a Potent Class of Arylamide Colony-Stimulating Factor-1 Receptor Inhibitors Leading to Anti-inflammatory Clinical Candidate 4-Cyano-N-[2-(1-cyclohexen-1-yl)-4-[1-[(dimethylamino)acetyl]-4-piperidinyl]phenyl]-1H-imidazole-2-carboxamide (JNJ-28312141", *J. Med. Chem.* 54: 7860-7883 (2011); the crystal structure PDB 4r7 h and related ligands described in Tap, W. D. et al. "Structure-Guided Blockade of CSF1R Kinase in Tenosynovial Giant-Cell Tumor, *N Engl J Med* 373: 428-437 (2015); the crystal structure PDB 3lcd and 3lcoa and related ligands described in Meyers, M. J. et al. "Structure-based drug design enables conversion of a DFG-in binding CSF-1R kinase inhibitor to a DFG-out binding mod", *Bioorg. Med. Chem. Lett.* 20: 1543-1547 (2010); the crystal structure PDB 4hw7 and related ligands described in Zhang, C. et al. "Design and pharmacology of a highly specific dual FMS and KIT kinase inhibitor", *Proc. Natl. Acad. Sci. USA* 110: 5689-5694 (2013); and, the crystal structure PDB 4r7i and related ligands described in Tap, W. D. et al. "Structure-Guided Blockade of CSF1R Kinase in Tenosynovial Giant-Cell Tumor", *N Engl J Med* 373: 428-437 (2015).

FIG. 8TTT presents examples of CSK Targeting Ligands wherein R is the point at which the Linker is attached. For additional examples and related ligands, see, Levinson, N. M. et al. "Structural basis for the recognition of c-Src by its inactivator Csk", *Cell* 134: 124-134 (2008).

FIG. 8UUU-8YYY present examples of DDR1 Targeting Ligands wherein R is the point at which the Linker is attached. For additional examples and related ligands, see, the crystal structures PDB 3zos and 4bkj and related ligands described in Canning, P. et al. "Structural Mechanisms Determining Inhibition of the Collagen Receptor Ddr1 by Selective and Multi-Targeted Type II Kinase Inhibitors", *J. Mol. Biol.* 426: 2457 (2014); the crystal structure PDB 4ckr and related ligands described in Kim, H. et al. "Discovery of a Potent and Selective Ddr1 Receptor Tyrosine Kinase Inhibitor", *ACS Chem. Biol.* 8: 2145 (2013); the crystal structure PDB 5bvk, 5bvn and 5bvw and related ligands described in Murray, C. W et al. "Fragment-Based Discovery of Potent and Selective DDR1/2 Inhibitors", *ACS Med. Chem. Lett.* 6: 798-803 (2015); the crystal structure PDB 5fdp and related ligands described in Wang, Z. et al. "Structure-Based Design of Tetrahydroisoquinoline-7-carboxamides as Selective Discoidin Domain Receptor 1 (DDR1) Inhibitors", *J. Med. Chem.* 59: 5911-5916 (2016); and, the crystal structure PDB 5fdx and related ligands described in Bartual, S. G. et al. "Structure of DDR1 receptor tyrosine kinase in complex with D2164 inhibitor at 2.65 Angstroms resolution", to be published.

FIG. 8ZZZ-8CCCC present examples of EPHA2 Targeting Ligands wherein R is the point at which the Linker is attached. For additional examples and related ligands, see, the crystal structures PDB 5i9x, 5i9y, 5ia0 and 5ia1 and related ligands described in Heinzlmeir, S. et al. "Chemical Proteomics and Structural Biology Define EPHA2 Inhibition by Clinical Kinase Drug", *ACS Chem. Biol.* 11: 3400-3411 (2016); the crystal structure PDB 5i9z and related ligands described in Heinzlmeir, S. et al. "Crystal Structure of Ephrin A2 (EphA2) Receptor Protein Kinase with danusertib (PHA739358)", *ACS Chem Biol* 11 3400-3411 (2016); and, the crystal structures PDB 5ia2, 5ia3, 5ia4, and 5ia5 and related ligands described in Heinzlmeir, S. et al. "Chemical Proteomics and Structural Biology Define EPHA2 Inhibition by Clinical Kinase Drug", *ACS Chem. Biol.* 11: 3400-3411 (2016).

FIG. 8DDDD-8FFFF present examples of EPHA3 Targeting Ligands wherein R is the point at which the Linker is attached. For additional examples and related ligands, see, the crystal structure PDB 4 g2f and related ligands described in Zhao, H. et al. "Discovery of a novel chemotype of tyrosine kinase inhibitors by fragment-based docking and molecular dynamics", *ACS Med Chem. Lett.* 3: 834-838 (2012); the crystal structure PDB 4gk2 and 4gk3 and related ligands described in Lafleur, K. et al. "Optimization of Inhibitors of the Tyrosine Kinase EphB4. 2. Cellular Potency Improvement and Binding Mode Validation by X-ray Crystallography", *J. Med Chem.* 56: 84-96 (2013); the crystal structure PDB 4gk3 and related ligands described in Lafleur, K. et al. "Optimization of Inhibitors of the Tyrosine Kinase EphB4. 2. Cellular Potency Improvement and Binding Mode Validation by X-ray Crystallography", *J. Med Chem.* 56: 84-96 (2013); the crystal structure PDB 4p4c and 4p5q and related ligands described in Unzue, A. et al. "Pyrrolo[3,2-b]quinoxaline Derivatives as Types II 1/2 and II Eph Tyrosine Kinase Inhibitors: Structure-Based Design, Synthesis, and in Vivo Validation", *J. Med Chem.* 57: 6834-6844 (2014); the crystal structure PDB 4p5z and related ligands described in Unzue, A. et al. "Pyrrolo[3,2-b]quinoxaline Derivatives as Types I1/2 and II Eph Tyrosine Kinase Inhibitors: Structure-Based Design, Synthesis, and in Vivo Validation", *J. Med Chem.* 57: 6834-6844 (2014); the crystal structure PDB 4twn and related ligands described in Dong, J. et al. "Structural Analysis of the Binding of Type I, I1/2, and II Inhibitors to Eph Tyrosine Kinases", *ACS Med Chem. Lett.* 6: 79-83 (2015); the crystal structure PDB 3dzq and related ligands described in Walker, J. R. "Kinase Domain of Human Ephrin Type-A Receptor 3 (Epha3) in Complex with ALW-II-38-3", to be published.

FIG. 8GGGG presents examples of EPHA4 Targeting Ligands wherein R is the point at which the Linker is attached. For additional examples and related ligands, see, the crystal structure PDB 2y60 and related ligands described in Clifton, I. J. et al. "The Crystal Structure of Isopenicillin N Synthase with Delta((L)-Alpha-Aminoadipoyl)-(L)-Cysteinyl-(D)-Methionine Reveals Thioether Coordination to Iron", *Arch. Biochem. Biophys.* 516: 103 (2011) and the crystal structure PDB 2xyu and related ligands described in Van Linden, O. P et al. "Fragment Based Lead Discovery of Small Molecule Inhibitors for the Epha4 Receptor Tyrosine Kinase", *Eur. J. Med Chem.* 47: 493 (2012).

FIG. 8HHHH presents examples of EPHA7 Targeting Ligands wherein R is the point at which the Linker is attached. For additional examples and related ligands, see, the crystal structure PDB 3dko and related ligands described in Walker, J. R. et al. "Kinase domain of human ephrin type-a receptor 7 (epha7) in complex with ALW-II-49-7", to be published.

FIG. 8IIII-8LLLL presents examples of EPHB4 Targeting Ligands wherein R is the point at which the Linker is attached. For additional examples and related ligands, see, the crystal structure PDB 2vx1 and related ligands described in Bardelle, C. et al. "Inhibitors of the Tyrosine Kinase Ephb4. Part 2: Structure-Based Discovery and Optimisation of 3,5-Bis Substituted Anilinopyrimidines", *Bioorg. Med Chem. Lett.* 18: 5717(2008); the crystal structure PDB 2x9f and related ligands described in Bardelle, C. et al. "Inhibitors of the Tyrosine Kinase Ephb4. Part 3: Identification of Non-Benzodioxole-Based Kinase Inhibitors", *Bioorg. Med Chem. Lett.* 20: 6242-6245 (2010); the crystal structure PDB 2xvd and related ligands described in Barlaam, B. et al. "Inhibitors of the Tyrosine Kinase Ephb4. Part 4: Discovery and Optimization of a Benzylic Alcohol Series", *Bioorg. Med Chem. Lett.* 21: 2207 (2011); the crystal structure PDB 3zew and related ligands described in Overman, R. C. et al. "Completing the Structural Family Portrait of the Human Ephb Tyrosine Kinase Domains", *Protein Sci.* 23: 627 (2014); the crystal structure PDB 4aw5 and related ligands described in Kim, M. H. et al. "The Design, Synthesis, and Biological Evaluation of Potent Receptor Tyrosine Kinase Inhibitors", *Bioorg. Med Chem. Lett.* 22: 4979 (2012); the crystal structure PDB 4bb4 and related ligands described in Vasbinder, M. M. et al. "Discovery and Optimization of a Novel Series of Potent Mutant B-Raf V600E Selective Kinase Inhibitors" *J. Med Chem.* 56: 1996.", (2013); the crystal structures PDB 2vwu, 2vwv and 2vww and related ligands described in Bardelle, C. et al "Inhibitors of the Tyrosine Kinase Ephb4. Part 1: Structure-Based Design and Optimization of a Series of 2,4-Bis-Anilinopyrimidines", *Bioorg. Med Chem. Lett.* 18: 2776-2780 (2008); the crystal structures PDB 2vwx, 2vwy, and 2vwz and related ligands described in Bardelle, C. et al. "Inhibitors of the Tyrosine Kinase Ephb4. Part 2: Structure-Based Discovery and Optimisation of 3,5-Bis Substituted Anilinopyrimidines", *Bioorg. Med Chem. Lett.* 18: 5717 (2008); and, the crystal structure PDB 2vxo and related ligands described in Welin, M. et al. "Substrate Specificity and Oligomerization of Human Gmp Synthetas", *J. Mol. Biol.* 425: 4323 (2013).

FIG. 8MMMM presents examples of ERBB2 Targeting Ligands wherein R is the point at which the Linker is attached. For additional examples and related ligands, see, the crystal structure and related ligands described in Aertgeerts, K. et al "Structural Analysis of the Mechanism of Inhibition and Allosteric Activation of the Kinase Domain of HER2 Protein", *J. Biol. Chem.* 286: 18756-18765 (2011) and the crystal structure and related ligands described in Ishikawa, T. et al. "Design and Synthesis of Novel Human Epidermal Growth Factor Receptor 2 (HER2)/Epidermal Growth Factor Receptor (EGFR) Dual Inhibitors Bearing a Pyrrolo[3,2-d]pyrimidine Scaffold" *J. Med. Chem.* 54: 8030-8050 (2011).

FIG. 8NNNN presents examples of ERBB3 Targeting Ligands wherein R is the point at which the Linker is attached. For additional examples and related ligands, see, Littlefield, P. et al. "An ATP-Competitive Inhibitor Modulates the Allosteric Function of the HER3 Pseudokinase", *Chem. Biol.* 21: 453-458 (2014).

FIG. 8OOOO presents examples ERBB4 Targeting Ligands wherein R is the point at which the Linker is attached. For additional examples and related ligands, see, Qiu, C. et al. "Mechanism of Activation and Inhibition of the HER4/ErbB4 Kinase", Structure 16: 460-467 (2008) and Wood, E. R. et al. "6-Ethynylthieno[3,2-d]- and 6-ethynylthieno[2,3-d]pyrimidin-4-anilines as tunable covalent modifiers of ErbB kinases", *Proc. Natl. Acad. Sci. Usa* 105: 2773-2778 (2008).

FIG. 8PPPP-8QQQQ present examples of FES Targeting Ligands wherein R is the point at which the Linker is attached. For additional examples and related ligands, see, Filippakopoulos, P. et al "Structural Coupling of SH2-Kinase Domains Links Fes and Abl Substrate Recognition and Kinase Activation." Cell 134: 793-803 (2008) and Hellwig, S. et al. "Small-Molecule Inhibitors of the c-Fes Protein-Tyrosine Kinase", *Chem. Biol.* 19: 529-540 (2012).

FIG. 8RRRR presents examples of FYN Targeting Ligands wherein R is the point at which the Linker is attached. For additional examples and related ligands, see, Kinoshita, T. et. al. "Structure of human Fyn kinase domain complexed with staurosporine", *Biochem. Biophys. Res. Commun.* 346: 840-844 (2006).

FIG. 8SSSS-8VVVV present examples of GSG2 (Haspin) Targeting Ligands wherein R is the point at which the Linker is attached. For additional examples and related ligands, see, the crystal structures PDB 3e7v, PDB 3f2n, 3fmd and related ligands described in Filippakopoulos, P. et al. "Crystal Structure of Human Haspin with a pyrazolo-pyrimidine ligand", to be published; the crystal structure PDB 3iq7 and related ligands described in Eswaran, J. et al. "Structure and functional characterization of the atypical human kinase haspin", *Proc. Natl. Acad. Sci. USA* 106: 20198-20203 (2009); and, the crystal structure PDB 4qtc and related ligands described in Chaikuad, A. et al. "A unique inhibitor binding site in ERK1/2 is associated with slow binding kinetics", *Nat. Chem. Biol.* 10: 853-860 (2014).

FIG. 8WWWW-8AAAAA present examples of HCK Targeting Ligands wherein R is the point at which the Linker is attached. For additional examples and related ligands, see, the crystal structure PDB 1qcf and related ligands described in Schindler, T. et al. "Crystal structure of Hck in complex with a Src family-selective tyrosine kinase inhibitor", *Mol. Cell* 3: 639-648 (1999); the crystal structure PDB 2c0i and 2c0t and related ligands described in Burchat, A. et al. "Discovery of A-770041, a Src-Family Selective Orally Active Lck Inhibitor that Prevents Organ Allograft Rejection", *Bioorg. Med Chem. Lett.* 16: 118 (2006); the crystal structure PDB 2hk5 and related ligands described in Sabat, M. et al. "The development of 2-benzimidazole substituted pyrimidine based inhibitors of lymphocyte specific kinase (Lck)", *Bioorg. Med Chem. Lett.* 16: 5973-5977 (2006); the crystal structures PDB 3vry, 3vs3, 3vs6, and 3vs7 and related ligands described in Saito, Y. et al. "A Pyrrolo-Pyrimidine Derivative Targets Human Primary AML Stem Cells in Vivo", *Sci Transl Med* 5: 181ra52-181ra52 (2013); and, the crystal structure PDB 4lud and related ligands described in Parker, L. J. et al "Kinase crystal identification and ATP-competitive inhibitor screening using the fluorescent ligand SKF86002", *Acta Crystallogr., Sect. D* 70: 392-404 (2014).

FIG. 8BBBBB-8FFFFF present examples of IGF1R Targeting Ligands wherein R is the point at which the Linker is attached. For additional examples and related ligands, see, the crystal structure PDB 2oj9 and related ligands described in Velaparthi, U. et al. "Discovery and initial SAR of 3-(1H-benzo[d]imidazol-2-yl)pyridin-2(1H)-ones as inhibitors of insulin-like growth factor 1-receptor (IGF-1R)", *Bioorg. Med Chem. Lett.* 17: 2317-2321 (2007); the crystal structure PDB 3i81 and related ligands described in Wittman, M. D. et al. "Discovery of a 2,4-disubstituted pyrrolo [1,2-f][1,2,4]triazine inhibitor (BMS-754807) of insulin-like growth factor receptor (IGF-1R) kinase in clinical development.", *J. Med Chem.* 52: 7360-7363 (2009); the crystal structure PDB 3nw5 and related ligands described in Sampognaro, A. J. et al. "Proline isosteres in a series of 2,4-disubstituted pyrrolo[1,2-f][1,2,4]triazine inhibitors of IGF-1R kinase and IR kinase", *Bioorg. Med Chem. Lett.* 20: 5027-5030 (2010); the crystal structure PDB 3qqu and related ligands described in Buchanan, J. L. et al. "Discovery of 2,4-bis-arylamino-1,3-pyrimidines as insulin-like growth factor-1 receptor (IGF-1R) inhibitors", *Bioorg. Med Chem. Lett.* 21: 2394-2399 (2011); the crystal structure PDB 4d2r and related ligands described in Kettle, J. G. et al. "Discovery and Optimization of a Novel Series of Dyrk1B Kinase Inhibitors to Explore a Mek Resistance Hypothesis". *J. Med Chem.* 58: 2834 (2015); the crystal structure PDB 3fxq and related ligands described in Monferrer, D. et al. "Structural studies on the full-length LysR-type regulator TsaR from Comamonas testosteroni T-2 reveal a novel open conformation of the tetrameric LTTR fold", *Mol. Microbiol.* 75: 1199-1214 (2010); the crystal structure PDB 5fxs and related ligands described in Degorce, S. et al. "Discovery of Azd9362, a Potent Selective Orally Bioavailable and Efficacious Novel Inhibitor of Igf-R1", to be published; the crystal structure PDB 2zm3 and related ligands described in Mayer, S. C. et al. "Lead identification to generate isoquinolinedione inhibitors of insulin-like growth factor receptor (IGF-1R) for potential use in cancer treatment", *Bioorg. Med Chem. Lett.* 18: 3641-3645 (2008); the crystal structure PDB 3f5p and related ligands described in "Lead identification to generate 3-cyanoquinoline inhibitors of insulin-like growth factor receptor (IGF-1R) for potential use in cancer treatment" *Bioorg. Med Chem. Lett.* 19: 62-66 (2009); the crystal structure PDB 3lvp and related ligands described in Nemecek, C. et al. "Design of Potent IGF1-R Inhibitors Related to Bis-azaindoles" *Chem. Biol. Drug Des.* 76: 100-106 (2010); the crystal structure PDB 3o23 and related ligands described in Lesuisse, D. et al. "Discovery of the first non-ATP competitive IGF-1R kinase inhibitors: Advantages in comparison with competitive inhibitors", *Bioorg. Med Chem. Lett.* 21: 2224-2228 (2011); the crystal structure PDB 3d94 and related ligands described in Wu, J. et al. "Small-molecule inhibition and activation-loop trans-phosphorylation of the IGF1 receptor", *Embo J.* 27: 1985-1994 (2008); and, the crystal structure PDB 5hzn and related ligands described in Stauffer, F. et al. "Identification of a 5-[3-phenyl-(2-cyclic-ether)-methylether]-4-aminopyrrolo[2,3-d]pyrimidine series of IGF-1R inhibitors", *Bioorg. Med Chem. Lett.* 26: 2065-2067 (2016).

FIG. 8GGGGG-8JJJJJ present examples of INSR Targeting Ligands wherein R is the point at which the Linker is attached. For additional examples and related ligands, see, the crystal structure PDB 2z8c and related ligands described in Katayama, N. et al. "Identification of a key element for hydrogen-bonding patterns between protein kinases and their inhibitors", *Proteins* 73: 795-801 (2008); the crystal structure PDB 3ekk and related ligands described in Chamberlain, S. D. et al. "Discovery of 4,6-bis-anilino-1H-pyrrolo[2,3-d]pyrimidines: Potent inhibitors of the IGF-1R receptor tyrosine kinase", (2009) *Bioorg. Med Chem. Lett.* 19: 469-473; the crystal structure PDB 3ekn and related ligands described in Chamberlain, S. D. et al. "Optimization of 4,6-bis-anilino-1H-pyrrolo[2,3-d]pyrimidine IGF-1R tyrosine kinase inhibitors towards JNK selectivity", *Bioorg. Med Chem. Lett.* 19: 360-364 (2009); the crystal structure PDB 5e1s and related ligands described in Sanderson, M. P. et al. "BI 885578, a Novel IGF1R/INSR Tyrosine Kinase Inhibitor with Pharmacokinetic Properties That Dissociate Antitumor Efficacy and Perturbation of Glucose Homeostasis" *Mol. Cancer Ther.* 14: 2762-2772", (2015); the crystal structure PDB 3eta and related ligands described in Patnaik, S. et al. "Discovery of 3,5-disubstituted-1H-pyrrolo[2,3-b]pyridines as potent inhibitors of the insulin-like growth factor-1 receptor (IGF-1R) tyrosine kinase", *Bioorg. Med Chem. Lett.* 19: 3136-3140 (2009); the crystal structure PDB 5hhw and related ligands described in Stauffer, F. et al. "Identification of a 5-[3-phenyl-(2-cyclic-ether)-methylether]-4-aminopyrrolo[2,3-d]pyrimidine series of IGF-1R inhibitors", *Bioorg. Med Chem. Lett.* 26: 2065-2067 (2016); and, the crystal structure PDB 4ibm and related ligands described in Anastassiadis, T. et al. "A highly selective dual insulin receptor (IR)/insulin-like growth factor 1 receptor (IGF-1R) inhibitor derived from an extracellular signal-regulated kinase (ERK) inhibitor", *J. Biol. Chem.* 288: 28068-28077 (2013).

FIG. 8KKKKK-8PPPPP present examples of HBV Targeting Ligands wherein R is the point at which the Linker is attached, Y is methyl or isopropyl, and X is N or C. For additional examples and related ligands, see, Weber, O.; et al. "Inhibition of human hepatitis B virus (HBV) by a novel non-nucleosidic compound in a transgenic mouse model." *Antiviral Res.* 54, 69-78 (2002); Deres, K.; et al. "Inhibition of hepatitis B virus replication by drug-induced depletion of nucleocapsids." *Science,* 299, 893-896 (2003); Stray, S. J.; Zlotnick, A. "BAY 41-4109 has multiple effects on Hepatitis B virus capsid assembly." *J. Mol. Recognit.* 19, 542-548 (2006); Stray, S. J.; et al. "heteroaryldihydropyrimidine activates and can misdirect hepatitis B virus capsid assembly." *Proc. Natl. Acad Sci. U.S.A.,* 102, 8138-8143 (2005); Guan, H.; et al. "The novel compound Z060228 inhibits assembly of the HBV capsid." *Life Sci.* 133, 1-7 (2015); Wang, X. Y.; et al. "In vitro inhibition of HBV replication by a novel compound, GLS4, and its efficacy against adefovir-dipivoxil-resistant HBV mutations." *Antiviral Ther.* 17, 793-803 (2012); Klumpp, K.; et al. "High-resolution crystal structure of a hepatitis B virus replication inhibitor bound to the viral core protein." 112, 15196-15201 (2015); Qiu, Z.; et al. "Design and synthesis of orally bioavailable 4-methyl heteroaryldihydropyrimidine based hepatitis B virus (HBV) capsid inhibitors." *J. Med. Chem.* 59, 7651-7666 (2016); Zhu, X.; et al. "2,4-Diaryl-4,6,7,8-tetrahydroquinazolin-5 (1H)-one derivatives as anti-HBV agents targeting at capsid assembly." *Bioorg. Med Chem. Lett.* 20, 299-301 (2010); Campagna, M. R.; et al. "Sulfamoylbenzamide derivatives inhibit the assembly of hepatitis B virus nucleocapsids." *J. Virol.* 87, 6931-6942 (2013); Campagna, M. R.; et al. "Sulfamoylbenzamide derivatives inhibit the assembly of hepatitis B virus nucleocapsids." *J. Virol.* 87, 6931-6942 (2013); WO 2013096744 A1 titled "Hepatitis B antivial agents"; WO 2015138895 titled "Hepatitis B core protein allosteric modulators"; Wang, Y. J.; et al. "A novel pyridazinone derivative inhibits hepatitis B virus replication by inducing genome-free capsid formation." *Antimicrob. Agents Chemother.* 59, 7061-7072 (2015); WO 2014033167 titled "Fused bicyclic sulfamoyl derivatives for the treatment of hepatitis"; U.S. 20150132258 titled "Azepane derivatives and methods of treating hepatitis B infections"; and, WO 2015057945 "Hepatitis B viral assembly effector".

Figure 9:
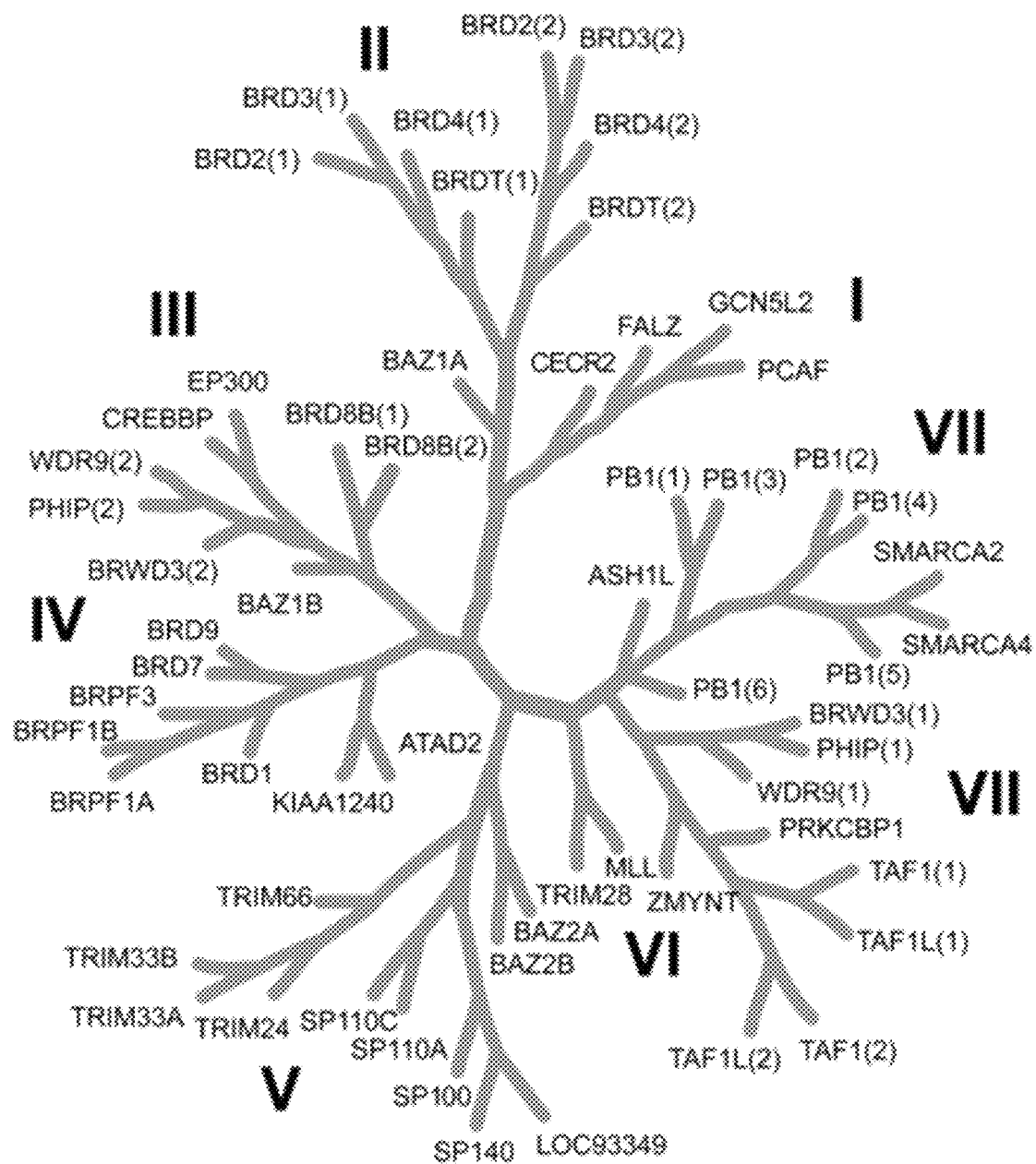

FIG. 9 is a dendrogram of the human bromodomain family of proteins organized into eight sub families, which are involved in epigenetic signaling and chromatin biology. Any of the proteins of the bromodomain family in FIG. 9 can be selected as a Target Protein according to the present invention.

DETAILED DESCRIPTION

I. Definitions

Compounds are described using standard nomenclature. Unless defined otherwise, all technical and scientific terms used herein have the same meaning as is commonly understood by one of skill in the art to which this invention belongs.

The compounds in any of the Formulas described herein may be in the form of a racemate, enantiomer, mixture of enantiomers, diastereomer, mixture of diastereomers, tautomer, N-oxide, isomer; such as rotamer, as if each is specifically described unless specifically excluded by context.

The terms "a" and "an" do not denote a limitation of quantity, but rather denote the presence of at least one of the referenced item. The term "or" means "and/or". Recitation of ranges of values are merely intended to serve as a shorthand method of referring individually to each separate value falling within the range, unless otherwise indicated herein, and each separate value is incorporated into the specification as if it were individually recited herein. The endpoints of all ranges are included within the range and independently combinable. All methods described herein can be performed in a suitable order unless otherwise indicated herein or otherwise clearly contradicted by context. The use of examples, or exemplary language (e.g., "such as"), is intended merely to better illustrate the invention and does not pose a limitation on the scope of the invention unless otherwise claimed.

The present invention includes compounds of Formula I, Formula II, Formula III, and Formula IV with at least one desired isotopic substitution of an atom, at an amount above the natural abundance of the isotope, i.e., enriched. Isotopes are atoms having the same atomic number but different mass numbers, i.e., the same number of protons but a different number of neutrons. Examples of isotopes that can be incorporated into compounds of the invention include isotopes of hydrogen, carbon, nitrogen, oxygen, phosphorous, fluorine, chlorine and iodine such as $^2H$, $^3H$, $^{11}C$, $^{13}C$, $^{14}C$, $^{15}$N, $^{18}$F $^{31}$P, $^{32}$P $^{35}$S, $^{36}$Cl, and $^{125}$I respectively. In one non-limiting embodiment, isotopically labelled compounds can be used in metabolic studies (with, for example $^{14}$C), reaction kinetic studies (with, for example $^{2}$H or $^{3}$H), detection or imaging techniques, such as positron emission tomography (PET) or single-photon emission computed tomography (SPECT) including drug or substrate tissue distribution assays, or in radioactive treatment of patients. In particular, an $^{18}$F labeled compound may be particularly desirable for PET or SPECT studies. Isotopically labeled compounds of this invention and prodrugs thereof can generally be prepared by carrying out the procedures disclosed in the schemes or in the examples and preparations described below by substituting a readily available isotopically labeled reagent for a non-isotopically labeled reagent.

Isotopic substitutions, for example deuterium substitutions, can be partial or complete. Partial deuterium substitution means that at least one hydrogen is substituted with deuterium. In certain embodiments, the isotope is 90, 95 or 99% or more enriched in an isotope at any location of interest. In one non-limiting embodiment, deuterium is 90, 95 or 99% enriched at a desired location.

In one non-limiting embodiment, the substitution of a hydrogen atom for a deuterium atom can be provided in any compound of Formula I-V. In one non-limiting embodiment, the substitution of a hydrogen atom for a deuterium atom occurs within one or more groups selected from any of R's or variables described herein, Linker, and Targeting Ligand. For example, when any of the groups are, or contain for example through substitution, methyl, ethyl, or methoxy, the alkyl residue may be deuterated (in non-limiting embodiments, $CDH_2$, $CD_2H$, $CD_3$, $CH_2CD_3$, $CD_2CD_3$, $CHDCH_2D$, $CH_2CD_3$, $CHDCHD_2$, $OCDH_2$, $OCD_2H$, or $OCD_3$ etc.). In certain other embodiments, when two substituents are combined to form a cycle the unsubstituted carbons may be deuterated.

The compound of the present invention may form a solvate with a solvent (including water). Therefore, in one non-limiting embodiment, the invention includes a solvated form of the compound. The term "solvate" refers to a molecular complex of a compound of the present invention (including a salt thereof) with one or more solvent molecules. Non-limiting examples of solvents are water, ethanol, isopropanol, dimethyl sulfoxide, acetone and other common organic solvents. The term "hydrate" refers to a molecular complex comprising a compound of the invention and water. Pharmaceutically acceptable solvates in accordance with the invention include those wherein the solvent may be isotopically substituted, e.g. $D_2O$, $d_6$-acetone, $d_6$-DMSO. A solvate can be in a liquid or solid form.

A dash ("-") that is not between two letters or symbols is used to indicate a point of attachment for a substituent. For example, —(C═O)NH$_2$ is attached through carbon of the carbonyl (C═O) group.

"Alkyl" is a branched or straight chain saturated aliphatic hydrocarbon group. In one non-limiting embodiment, the alkyl group contains from 1 to about 12 carbon atoms, more generally from 1 to about 6 carbon atoms or from 1 to about 4 carbon atoms. In one non-limiting embodiment, the alkyl contains from 1 to about 8 carbon atoms. In certain embodiments, the alkyl is $C_1$-$C_2$, $C_1$-$C_3$, $C_1$-$C_4$, $C_1$—C, or $C_1$-$C_6$. The specified ranges as used herein indicate an alkyl group having each member of the range described as an independent species. For example, the term $C_1$-$C_6$ alkyl as used herein indicates a straight or branched alkyl group having from 1, 2, 3, 4, 5, or 6 carbon atoms and is intended to mean that each of these is described as an independent species and therefore each subset is considered separately disclosed. For example, the term $C_1$-$C_4$ alkyl as used herein indicates a straight or branched alkyl group having from 1, 2, 3, or 4 carbon atoms and is intended to mean that each of these is described as an independent species. Examples of alkyl include, but are not limited to, methyl, ethyl, n-propyl, isopropyl, n-butyl, isobutyl, sec-butyl, t-butyl, n-pentyl, isopentyl, tert-pentyl, neopentyl, n-hexyl, 2-methylpentane, 3-methylpentane, 2,2-dimethylbutane, and 2,3-dimethylbutane. In an alternative embodiment, the alkyl group is optionally substituted. The term "alkyl" also encompasses cycloalkyl or carbocyclic groups. For example, when a term is used that includes "alk" then "cycloalkyl" or "carbocyclic" can be considered part of the definition, unless unambiguously excluded by the context. For example and without limitation, the terms alkyl, alkoxy, haloalkyl, etc. can all be considered to include the cyclic forms of alkyl, unless unambiguously excluded by context.

"Alkenyl" is a linear or branched aliphatic hydrocarbon groups having one or more carbon-carbon double bonds that may occur at a stable point along the chain. The specified ranges as used herein indicate an alkenyl group having each member of the range described as an independent species, as described above for the alkyl moiety. Examples of alkenyl radicals include, but are not limited to ethenyl, propenyl, allyl, propenyl, butenyl and 4-methylbutenyl. The term "alkenyl" also embodies "cis" and "trans" alkenyl geometry, or alternatively, "E" and "Z" alkenyl geometry. In an alternative embodiment, the alkenyl group is optionally substituted. The term "Alkenyl" also encompasses cycloalkyl or carbocyclic groups possessing at least one point of unsaturation.

"Alkynyl" is a branched or straight chain aliphatic hydrocarbon group having one or more carbon-carbon triple bonds that may occur at any stable point along the chain. The specified ranges as used herein indicate an alkynyl group having each member of the range described as an independent species, as described above for the alkyl moiety. Examples of alkynyl include, but are not limited to, ethynyl, propynyl, 1-butynyl, 2-butynyl, 3-butynyl, 1-pentynyl, 2-pentynyl, 3-pentynyl, 4-pentynyl, 1-hexynyl, 2-hexynyl, 3-hexynyl, 4-hexynyl and 5-hexynyl. In an alternative embodiment, the alkynyl group is optionally substituted. The term "Alkynyl" also encompasses cycloalkyl or carbocyclic groups possessing at least one triple bond.

"Alkylene" is a bivalent saturated hydrocarbon. Alkylenes, for example, can be a 1, 2, 3, 4, 5, 6, 7 to 8 carbon moiety, 1 to 6 carbon moiety, or an indicated number of carbon atoms, for example $C_1$-$C_2$alkylene, $C_1$-$C_3$alkylene, $C_1$-$C_4$alkylene, $C_1$-$C_5$alkylene, or $C_1$-$C_6$alkylene.

"Alkenylene" is a bivalent hydrocarbon having at least one carbon-carbon double bond. Alkenylenes, for example, can be a 2 to 8 carbon moiety, 2 to 6 carbon moiety, or an indicated number of carbon atoms, for example $C_2$-$C_4$alkenylene.

"Alkynylene" is a bivalent hydrocarbon having at least one carbon-carbon triple bond. Alkynylenes, for example, can be a 2 to 8 carbon moiety, 2 to 6 carbon moiety, or an indicated number of carbon atoms, for example $C_2$-$C_4$alkynylene.

"Halo" and "Halogen" refers to fluorine, chlorine, bromine or iodine.

"Haloalkyl" is a branched or straight-chain alkyl groups substituted with 1 or more halo atoms described above, up to the maximum allowable number of halogen atoms. Examples of haloalkyl groups include, but are not limited to, fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl and dichloropropyl. "Perhaloalkyl" means an alkyl group having all hydrogen atoms replaced with halogen atoms. Examples include but are not limited to, trifluoromethyl and pentafluoroethyl.

"Chain" indicates a linear chain to which al other chains, long or short or both, may be regarded as being pendant. Where two or more chains could equally be considered to be the main chain, "chain" refers to the one which leads to the simplest representation of the molecule.

"Haloalkoxy" indicates a haloalkyl group as defined herein attached through an oxygen bridge (oxygen of an alcohol radical).

"Heterocycloalkyl" is an alkyl group as defined herein substituted with a heterocyclo group as defined herein.

"Arylalkyl" is an alkyl group as defined herein substituted with an aryl group as defined herein.

"Heteroarylalkyl" is an alkyl group as defined herein substituted with a heteroaryl group as defined herein.

As used herein, "aryl" refers to a radical of a monocyclic or polycyclic (e.g., bicyclic or tricyclic) 4n+2 aromatic ring system (e.g., having 6, 10, or 14 7 electrons shared in a cyclic array) having 6-14 ring carbon atoms and zero heteroatoms provided in the aromatic ring system ("$C_{6-14}$ aryl"). In some embodiments, an aryl group has 6 ring carbon atoms ("$C_6$ aryl"; e.g., phenyl). In some embodiments, an aryl group has 10 ring carbon atoms ("$C_{10}$ aryl"; e.g., naphthyl such as 1-naphthyl and 2-naphthyl). In some embodiments, an aryl group has 14 ring carbon atoms ("C14 aryl"; e.g., anthracyl). "Aryl" also includes ring systems wherein the aryl ring, as defined above, is fused with one or more carbocyclyl or heterocyclyl groups wherein the radical or point of attachment is on the aryl ring, and in such instances, the number of carbon atoms continue to designate the number of carbon atoms in the aryl ring system. The one or more fused carbocyclyl or heterocyclyl groups can be 4 to 7 or 5 to 7-membered saturated or partially unsaturated carbocyclyl or heterocyclyl groups that optionally contain 1, 2, or 3 heteroatoms independently selected from nitrogen, oxygen, phosphorus, sulfur, silicon and boron, to form, for example, a 3,4-methylenedioxyphenyl group. In one non-limiting embodiment, aryl groups are pendant. An example of a pendant ring is a phenyl group substituted with a phenyl group. In an alternative embodiment, the aryl group is optionally substituted as described above. In certain embodiments, the aryl group is an unsubstituted $C_{6-14}$ aryl. In certain embodiments, the aryl group is a substituted $C_{6-14}$ aryl. An aryl group may be optionally substituted with one or more functional groups that include but are not limited to, halo, hydroxy, nitro, amino, cyano, haloalkyl, aryl, heteroaryl, and heterocyclo.

The term "heterocyclyl" (or "heterocyclo") includes saturated, and partially saturated heteroatom-containing ring radicals, where the heteroatoms may be selected from nitrogen, sulfur and oxygen. Heterocyclic rings comprise monocyclic 3-8 membered rings, as well as 5-16 membered bicyclic ring systems (which can include bridged fused and spiro-fused bicyclic ring systems). It does not include rings containing —O—O—, —O—S— or —S—S— portions. Said "heterocyclyl" group may be optionally substituted, for example, with 1, 2, 3, 4 or more substituents that include but are not limited to, hydroxyl, Boc, halo, haloalkyl, cyano, alkyl, aralkyl, oxo, alkoxy, and amino.

Examples of saturated heterocyclo groups include saturated 3- to 6-membered heteromonocyclic groups containing 1 to 4 nitrogen atoms [e.g. pyrrolidinyl, imidazolidinyl, piperidinyl, pyrrolinyl, piperazinyl]; saturated 3 to 6-membered heteromonocyclic group containing 1 to 2 oxygen atoms and 1 to 3 nitrogen atoms [e.g. morpholinyl]; saturated 3 to 6-membered heteromonocyclic group containing 1 to 2 sulfur atoms and 1 to 3 nitrogen atoms [e.g., thiazolidinyl]. Examples of partially saturated heterocyclyl radicals include but are not limited to, dihydrothienyl, dihydropyranyl, dihydrofuryl, and dihydrothiazolyl. Examples of partially saturated and saturated heterocyclo groups include but are not limited to, pyrrolidinyl, imidazolidinyl, piperidinyl, pyrrolinyl, pyrazolidinyl, piperazinyl, morpholinyl, tetrahydropyranyl, thiazolidinyl, dihydrothienyl, 2,3-dihydro-benzo[1,4]dioxanyl, indolinyl, isoindolinyl, dihydrobenzothienyl, dihydrobenzofuryl, isochromanyl, chromanyl, 1,2-dihydroquinolyl, 1,2,3,4-tetrahydroisoquinolyl, 1,2,3,4-tetrahydro-quinolyl, 2,3,4,4a,9,9a-hexahydro-1H-3-aza-fluorenyl, 5,6,7-trihydro-1,2,4-triazolo[3,4-a]isoquinolyl, 3,4-dihydro-2H-benzo[1,4]oxazinyl, benzo[1,4]dioxanyl, 2,3-dihydro-1H-1λ'-benzo[d]isothiazol-6-yl, dihydropyranyl, dihydrofuryl and dihydrothiazolyl.

Heterocyclo groups also include radicals where heterocyclic radicals are fused/condensed with aryl or heteroaryl radicals: such as unsaturated condensed heterocyclic group containing 1 to 5 nitrogen atoms, for example, indoline, isoindoline, unsaturated condensed heterocyclic group containing 1 to 2 oxygen atoms and 1 to 3 nitrogen atoms, unsaturated condensed heterocyclic group containing 1 to 2 sulfur atoms and 1 to 3 nitrogen atoms, and saturated, partially unsaturated and unsaturated condensed heterocyclic group containing 1 to 2 oxygen or sulfur atoms.

The term "heteroaryl" denotes aryl ring systems that contain one or more heteroatoms selected from O, N and S, wherein the ring nitrogen and sulfur atom(s) are optionally oxidized, and nitrogen atom(s) are optionally quarternized. Examples include but are not limited to, unsaturated 5 to 6 membered heteromonocyclyl groups containing 1 to 4 nitrogen atoms, such as pyrrolyl, imidazolyl, pyrazolyl, 2-pyridyl, 3-pyridyl, 4-pyridyl, pyrimidyl, pyrazinyl, pyridazinyl, triazolyl [e.g., 4H-1,2,4-triazolyl, IH-1,2,3-triazolyl, 2H-1,2,3-triazolyl]; unsaturated 5- to 6-membered heteromonocyclic groups containing an oxygen atom, for example, pyranyl, 2-furyl, 3-furyl, etc.; unsaturated 5 to 6-membered heteromonocyclic groups containing a sulfur atom, for example, 2-thienyl, 3-thienyl, etc.; unsaturated 5- to 6-membered heteromonocyclic groups containing 1 to 2 oxygen atoms and 1 to 3 nitrogen atoms, for example, oxazolyl, isoxazolyl, oxadiazolyl [e.g., 1,2,4-oxadiazolyl, 1,3,4-oxadiazolyl, 1,2,5-oxadiazolyl]; unsaturated 5 to 6-membered heteromonocyclic groups containing 1 to 2 sulfur atoms and 1 to 3 nitrogen atoms, for example, thiazolyl, thiadiazolyl [e.g., 1,2,4-thiadiazolyl, 1,3,4-thiadiazolyl, 1,2,5-thiadiazolyl].

The term "optionally substituted" denotes the substitution of a group herein by a moiety including, but not limited to, $C_1$-$C_{10}$ alkyl, $C_2$-$C_{10}$ alkenyl, $C_2$-$C_{10}$ alkynyl, $C_3$-$C_{12}$ cycloalkyl, $C_3$-$C_{12}$ cycloalkenyl, $C_1$-$C_{12}$ heterocycloalkyl, $C_3$-$C_{12}$ heterocycloalkenyl, $C_1$-$C_{10}$ alkoxy, aryl, aryloxy, heteroaryl, heteroaryloxy, amino, $C_1$-$C_{10}$ alkylamino, $C_1$-$C_{10}$ dialkylamino, arylamino, diarylamino, $C_1$-$C_{10}$ alkylsulfonamino, arylsulfonamino, $C_1$-$C_{10}$ alkylimino, arylimino, $C_1$-$C_{10}$ alkylsulfonimino, arylsulfonimino, hydroxyl, halo, thio, $C_1$-$C_{10}$ alkylthio, arylthio, $C_1$-$C_{10}$ alkylsulfonyl, arylsulfonyl, acylamino, aminoacyl, aminothioacyl, amidino, guanidine, ureido, cyano, nitro, azido, acyl, thioacyl, acyloxy, carboxyl, and carboxylic ester.

In one alternative embodiment any suitable group may be present on a "substituted" or "optionally substituted" position if indicated that forms a stable molecule and meets the desired purpose of the invention and includes, but is not limited to, e.g., halogen (which can independently be F, Cl, Br or I); cyano; hydroxyl; nitro; azido; alkanoyl (such as a $C_2$-$C_6$ alkanoyl group); carboxamide; alkyl, cycloalkyl, alkenyl, alkynyl, alkoxy, aryloxy such as phenoxy; thioalkyl including those having one or more thioether linkages; alkylsulfinyl; alkylsulfonyl groups including those having one or more sulfonyl linkages; aminoalkyl groups including groups having more than one N atoms; aryl (e.g., phenyl, biphenyl, naphthyl, or the like, each ring either substituted or unsubstituted); arylalkyl having for example, 1 to 3 separate or fused rings and from 6 to about 14 or 18 ring carbon atoms, with benzyl being an exemplary arylalkyl group; arylalkoxy, for example, having 1 to 3 separate or fused rings with benzyloxy being an exemplary arylalkoxy group; or a saturated or partially unsaturated heterocycle having 1 to 3 separate or fused rings with one or more N, O or S atoms, or a heteroaryl having 1 to 3 separate or fused rings with one or more N, O or S atoms, e.g. coumarinyl, quinolinyl, isoquinolinyl, quinazolinyl, pyridyl, pyrazinyl, pyrimidinyl, furanyl, pyrrolyl, thienyl, thiazolyl, triazinyl, oxazolyl, isoxazolyl, imidazolyl, indolyl, benzofuranyl, benzothiazolyl, tetrahydrofuranyl, tetrahydropyranyl, piperidinyl, morpholinyl, piperazinyl, and pyrrolidinyl. Such groups may be further substituted, e.g. with hydroxy, alkyl, alkoxy, halogen and amino. In certain embodiments "optionally substituted" includes one or more substituents independently selected from halogen, hydroxyl, amino, cyano, —CHO, —COOH, —CONH$_2$, alkyl including C1-$C_6$alkyl, alkenyl including $C_2$-$C_6$alkenyl, alkynyl including $C_2$-$C_6$alkynyl, —$C_1$-$C_6$alkoxy, alkanoyl including $C_2$-$C_6$alkanoyl, $C_1$-$C_6$alkylester, (mono- and di-$C_1$-$C_6$alkylamino)$C_0$-$C_2$alkyl, haloalkyl including $C_1$-$C_6$haloalkyl, hydoxy$C_1$-$C_6$alkyl, ester, carbamate, urea, sulfonamide, —$C_1$-$C_6$alkyl(heterocyclo), $C_1$-$C_6$alkyl(heteroaryl), —$C_1$-$C_6$alkyl($C_3$-$C_7$cycloalkyl), O—$C_1$-$C_6$alkyl ($C_3$-$C_7$cycloalkyl), B(OH)$_2$, phosphate, phosphonate and haloalkoxy including $C_1$-$C_6$haloalkoxy.

"Aliphatic" refers to a saturated or unsaturated, straight, branched, or cyclic hydrocarbon. "Aliphatic" is intended herein to include, but is not limited to, alkyl, alkenyl, alkynyl, cycloalkyl, cycloalkenyl, and cycloalkynyl moieties, and thus incorporates each of these definitions. In one embodiment, "aliphatic" is used to indicate those aliphatic groups having 1-20 carbon atoms. The aliphatic chain can be, for example, mono-unsaturated, di-unsaturated, tri-unsaturated, or polyunsaturated, or alkynyl. Unsaturated aliphatic groups can be in a is or trans configuration. In one embodiment, the aliphatic group contains from 1 to about 12 carbon atoms, more generally from 1 to about 6 carbon atoms or from 1 to about 4 carbon atoms. In one embodiment, the aliphatic group contains from 1 to about 8 carbon atoms. In certain embodiments, the aliphatic group is $C_1$-$C_2$, $C_1$-$C_3$, $C_1$-$C_4$, $C_1$-$C_5$ or $C_1$-$C_6$. The specified ranges as used herein indicate an aliphatic group having each member of the range described as an independent species. For example, the term $C_1$-$C_6$ aliphatic as used herein indicates a straight or branched alkyl, alkenyl, or alkynyl group having from 1, 2, 3, 4, 5, or 6 carbon atoms and is intended to mean that each of these is described as an independent species. For example, the term $C_1$-$C_4$ aliphatic as used herein indicates a straight or branched alkyl, alkenyl, or alkynyl group having from 1, 2, 3, or 4 carbon atoms and is intended to mean that each of these is described as an independent species. In one embodiment, the aliphatic group is substituted with one or more functional groups that results in the formation of a stable moiety.

The term "heteroaliphatic" refers to an aliphatic moiety that contains at least one heteroatom in the chain, for example, an amine, carbonyl, carboxy, oxo, thio, phosphate, phosphonate, nitrogen, phosphorus, silicon, or boron atoms in place of a carbon atom. In one embodiment, the only heteroatom is nitrogen. In one embodiment, the only heteroatom is oxygen. In one embodiment, the only heteroatom is sulfur. "Heteroaliphatic" is intended herein to include, but is not limited to, heteroalkyl, heteroalkenyl, heteroalkynyl, heterocycloalkyl, heterocycloalkenyl, and heterocycloalkynyl moieties. In one embodiment, "heteroaliphatic" is used to indicate a heteroaliphatic group (cyclic, acyclic, substituted, unsubstituted, branched or unbranched) having 1-20 carbon atoms. In one embodiment, the heteroaliphatic group is optionally substituted in a manner that results in the formation of a stable moiety. Nonlimiting examples of heteroaliphatic moieties are polyethylene glycol, polyalkylene glycol, amide, polyamide, polylactide, polyglycolide, thioether, ether, alkyl-heterocycle-alkyl, —O-alkyl-O-alkyl, alkyl-O-haloalkyl, etc.

A "dosage form" means a unit of administration of an active agent. Examples of dosage forms include tablets, capsules, injections, suspensions, liquids, emulsions, implants, particles, spheres, creams, ointments, suppositories, inhalable forms, transdermal forms, buccal, sublingual, topical, gel, mucosal, and the like. A "dosage form" can also include an implant, for example an optical implant.

An "effective amount" as used herein, means an amount which provides a therapeutic or prophylactic benefit.

As used herein "endogenous" refers to any material from or produced inside an organism, cell, tissue or system.

As used herein, the term "exogenous" refers to any material introduced from or produced outside an organism, cell, tissue or system.

By the term "modulating," as used herein, is meant mediating a detectable increase or decrease in the level of a response in a subject compared with the level of a response in the subject in the absence of a treatment or compound, and/or compared with the level of a response in an otherwise identical but untreated subject. The term encompasses perturbing and/or affecting a native signal or response thereby mediating a beneficial therapeutic response in a subject, preferably, a human.

"Parenteral" administration of an immunogenic composition includes, e.g., subcutaneous (s.c.), intravenous (i.v.), intramuscular (i.m.), or intrasternal injection, or infusion techniques.

As used herein, the terms "peptide," "polypeptide," and "protein" are used interchangeably, and refer to a compound comprised of amino acid residues covalently linked by peptide bonds. A protein or peptide must contain at least two amino acids, and no limitation is placed on the maximum number of amino acids that can comprise a protein's or peptide's sequence. Polypeptides include any peptide or protein comprising two or more amino acids joined to each other by peptide bonds. As used herein, the term refers to both short chains, which also commonly are referred to in the art as peptides, oligopeptides and oligomers, for example, and to longer chains, which generally are referred to in the art as proteins, of which there are many types. "Polypeptides" include, for example, biologically active fragments, substantially homologous polypeptides, oligopeptides, homodimers, heterodimers, variants of polypeptides, modified polypeptides, derivatives, analogs, fusion proteins, among others. The polypeptides include natural peptides, recombinant peptides, synthetic peptides, or a combination thereof.

To "treat" a disease as the term is used herein, means to reduce the frequency or severity of at least one sign or symptom of a disease or disorder experienced by a subject.

Ranges: throughout this disclosure, various aspects of the invention can be presented in a range format. It should be understood that the description in range format is merely for convenience and should not be construed as a limitation on the scope of the invention. The description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

As used herein, "pharmaceutical compositions" are compositions comprising at least one active agent, and at least one other substance, such as a carrier. "Pharmaceutical combinations" are combinations of at least two active agents which may be combined in a single dosage form or provided together in separate dosage forms with instructions that the active agents are to be used together to treat any disorder described herein.

As used herein, "pharmaceutically acceptable salt" is a derivative of the disclosed compound in which the parent compound is modified by making inorganic and organic, non-toxic, acid or base addition salts thereof. The salts of the present compounds can be synthesized from a parent compound that contains a basic or acidic moiety by conventional chemical methods. Generally, such salts can be prepared by reacting free acid forms of these compounds with a stoichiometric amount of the appropriate base (such as Na, Ca, Mg, or K hydroxide, carbonate, bicarbonate, or the like), or by reacting free base forms of these compounds with a stoichiometric amount of the appropriate acid. Such reactions are typically carried out in water or in an organic solvent, or in a mixture of the two. Generally, non-aqueous media like ether, ethyl acetate, ethanol, isopropanol, or acetonitrile are typical, where practicable. Salts of the present compounds further include solvates of the compounds and of the compound salts.

Examples of pharmaceutically acceptable salts include, but are not limited to, mineral or organic acid salts of basic residues such as amines; alkali or organic salts of acidic residues such as carboxylic acids; and the like. The pharmaceutically acceptable salts include the conventional non-toxic salts and the quaternary ammonium salts of the parent compound formed, for example, from non-toxic inorganic or organic acids. For example, conventional non-toxic acid salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, mesylic, esylic, besylic, sulfanilic, 2-acetoxybenzoic, fumaric, toluenesulfonic, methanesulfonic, ethane disulfonic, oxalic, isethionic, HOOC—$(CH_2)_n$—COOH where n is 0-4, and the like, or using a different acid that produces the same counterion. Lists of additional suitable salts may be found, e.g., in *Remington's Pharmaceutical Sciences*, 17th ed., Mack Publishing Company, Easton, Pa., p. 1418 (1985).

The term "carrier" applied to pharmaceutical compositions/combinations of the invention refers to a diluent, excipient, or vehicle with which an active compound is provided.

A "pharmaceutically acceptable excipient" means an excipient that is useful in preparing a pharmaceutical composition/combination that is generally safe, non-toxic and neither biologically nor otherwise inappropriate for administration to a host, typically a human. In one embodiment, an excipient is used that is acceptable for veterinary use.

A "patient" or "host" or "subject" is a human or non-human animal in need of treatment or prevention of any of the disorders as specifically described herein, for example that is modulated by a natural (wild-type) or modified (non-wild type) protein that can be degraded according to the present invention, resulting in a therapeutic effect. Typically, the host is a human. A "host" may alternatively refer to for example, a mammal, primate (e.g., human), cow, sheep, goat, horse, dog, cat, rabbit, rat, mice, fish, bird and the like.

A "therapeutically effective amount" of a pharmaceutical composition/combination of this invention means an amount effective, when administered to a host, to provide a therapeutic benefit such as an amelioration of symptoms or reduction or diminution of the disease itself.

Formula I, Formula II, and Formula V

In one aspect of the present invention a compound of Formula I, Formula II, or Formula V is provided:

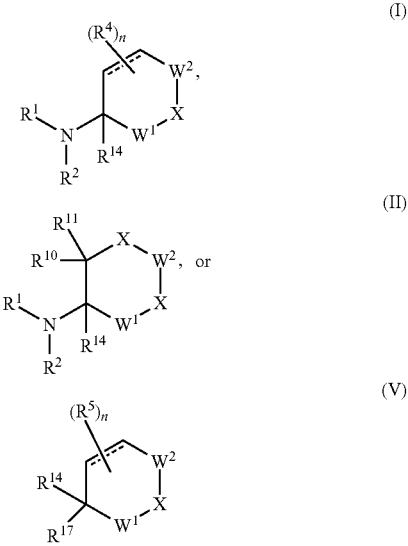

or a pharmaceutically acceptable salt, N-oxide, isotopic derivative, or prodrug thereof, optionally in a pharmaceutically acceptable carrier to form a composition; with variables as defined above.

Linker is a chemical group that attaches the Degron to a Targeting Ligand; and Targeting Ligand is a moiety that binds to a Target Protein, and wherein the Target Protein is a mediator of disease in a host.

Non-limiting examples of compounds of Formula I include:
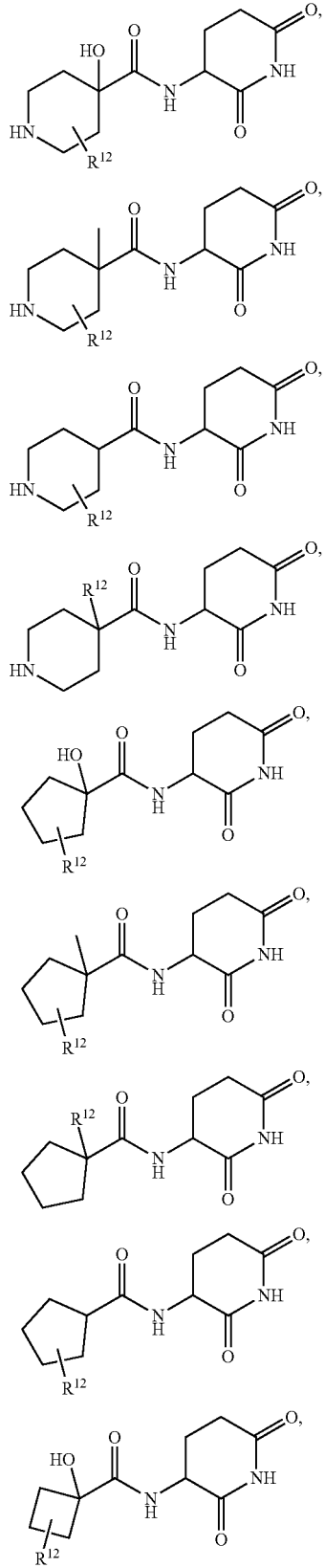
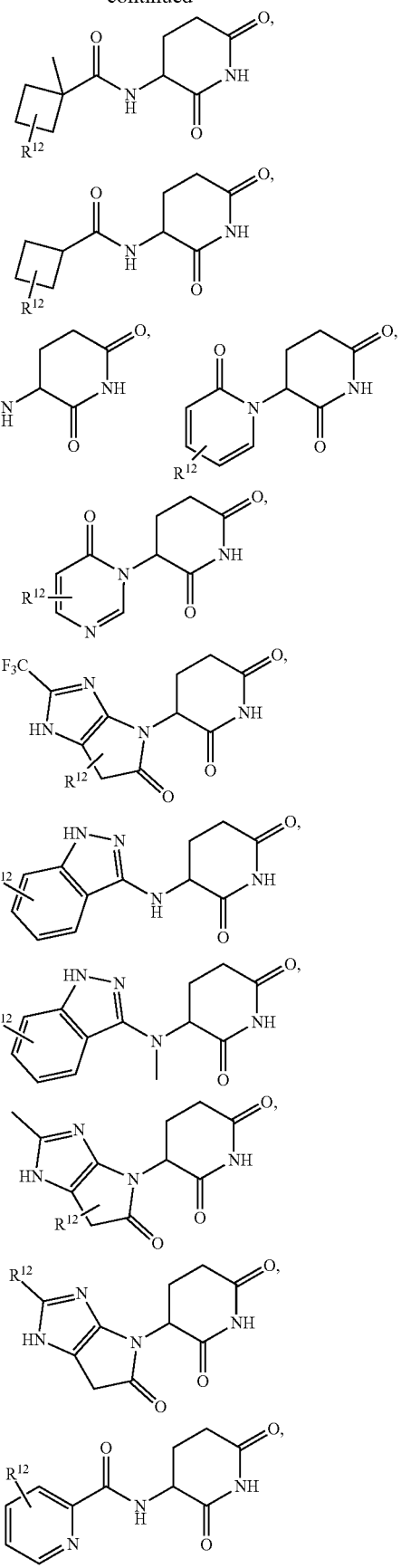

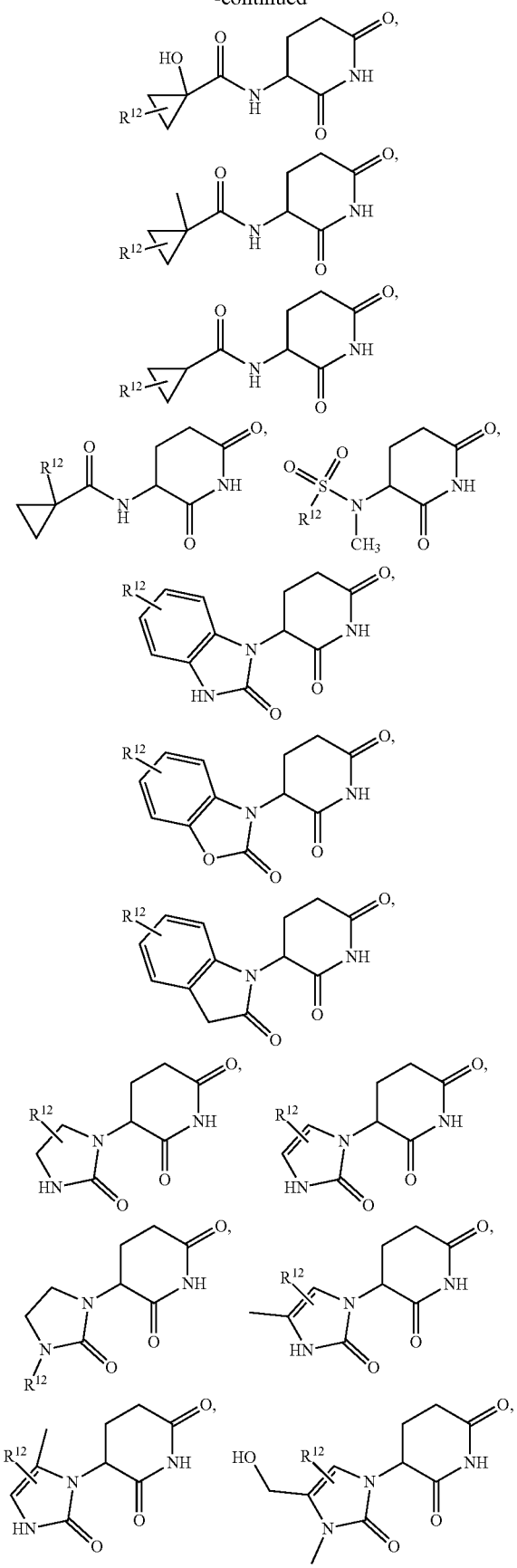
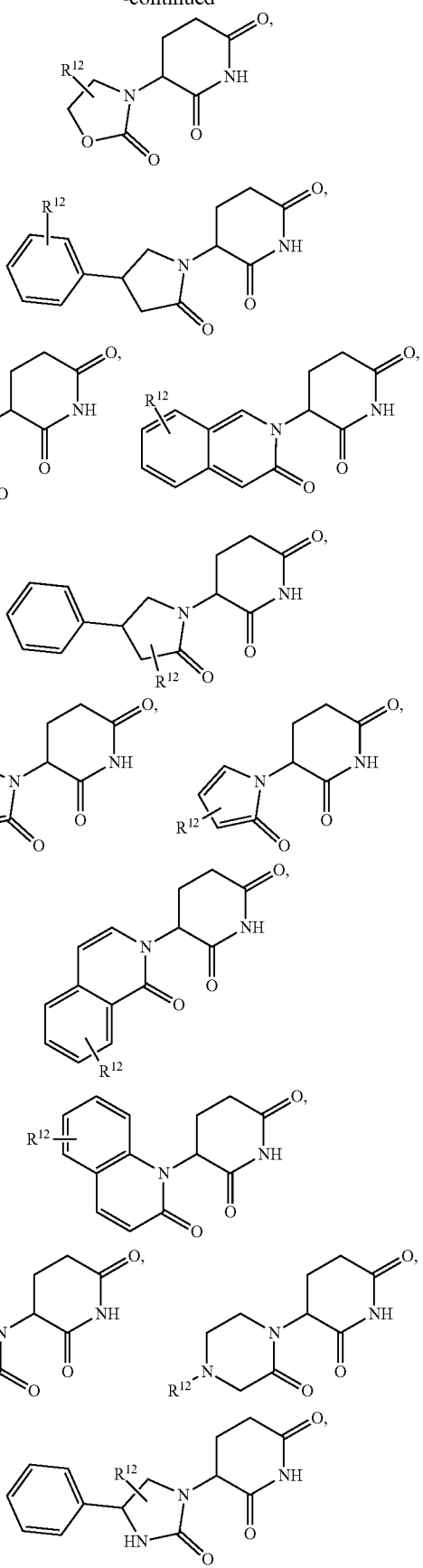

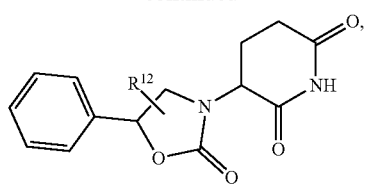
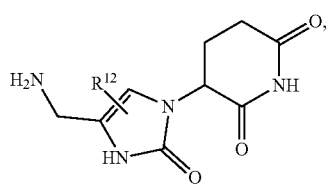
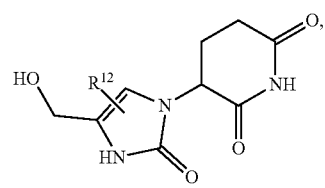
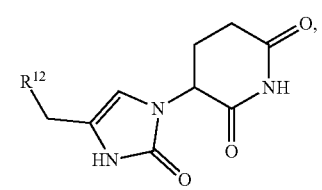
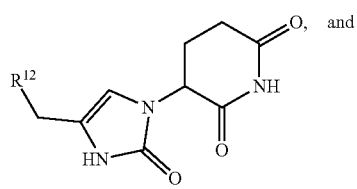
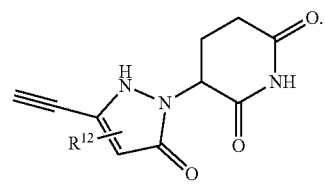
Additional non-limiting examples of compounds of Formula I include:
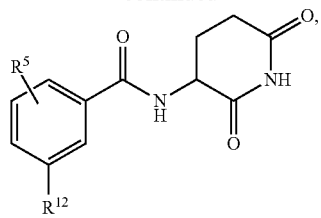
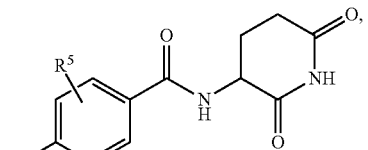
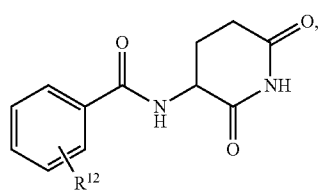
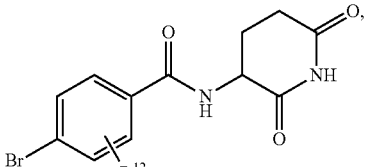
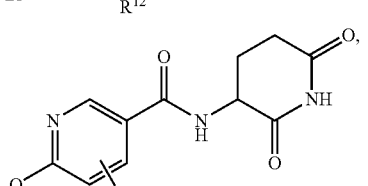
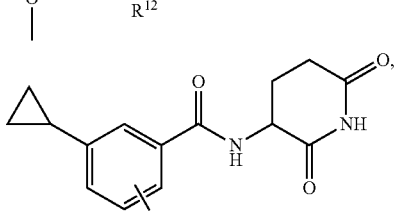
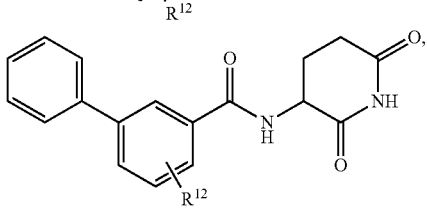
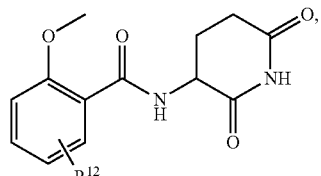
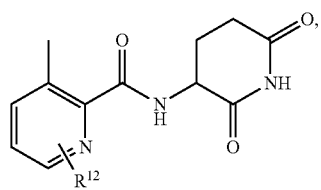

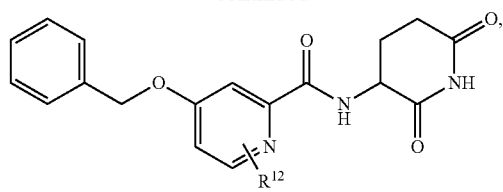
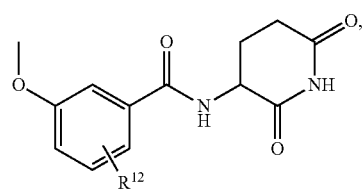
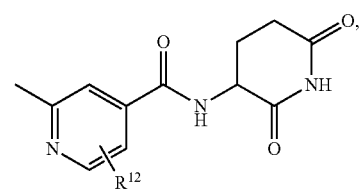
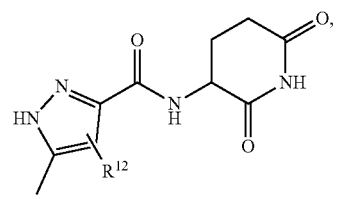
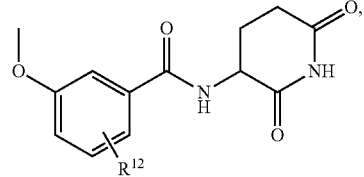
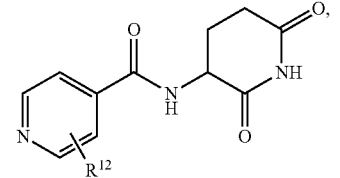
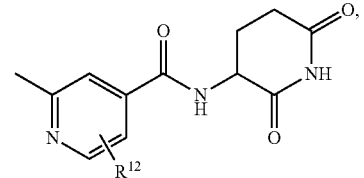
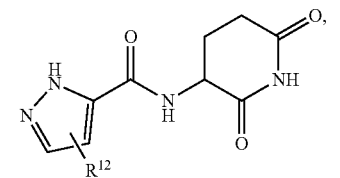
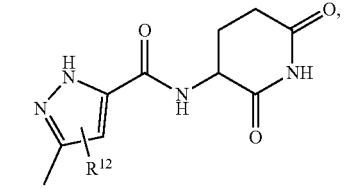
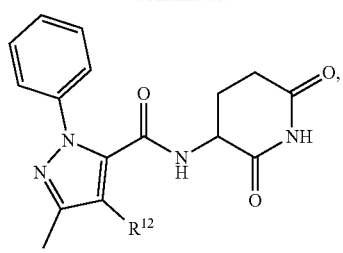
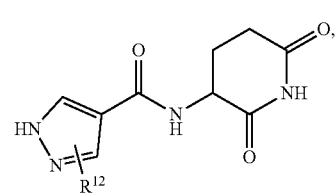
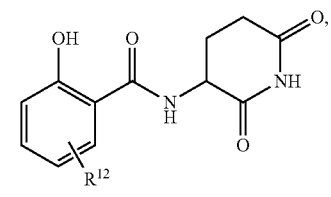
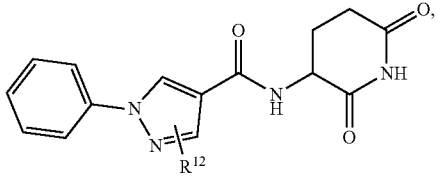
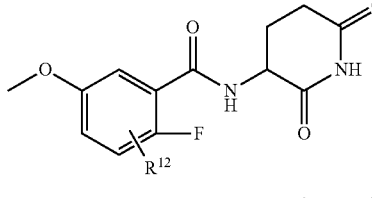
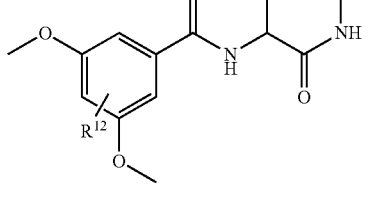
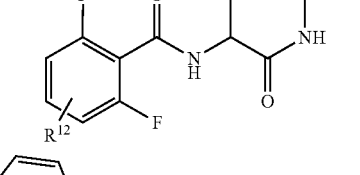
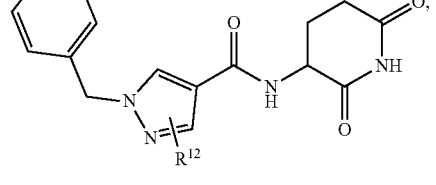

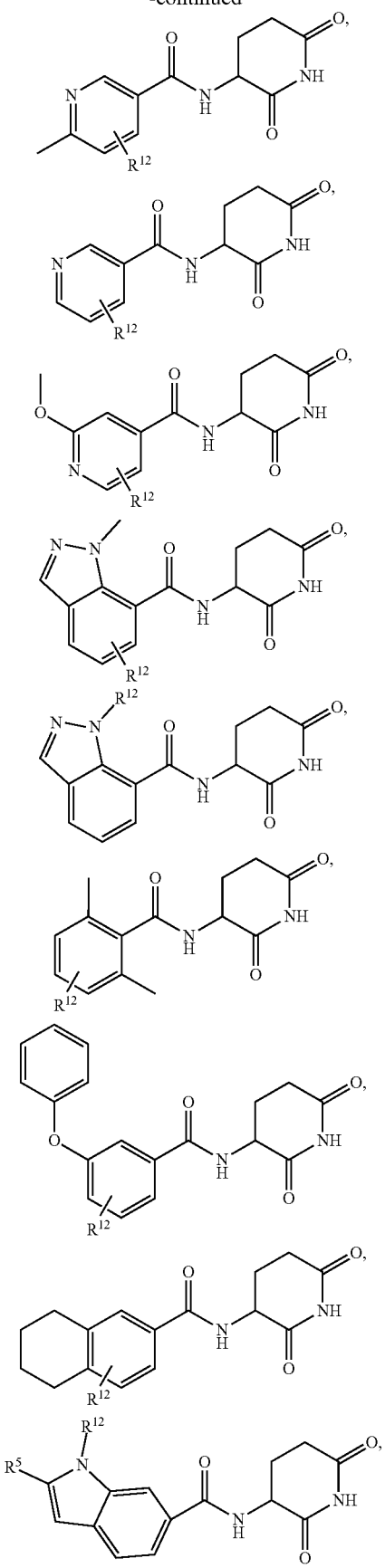
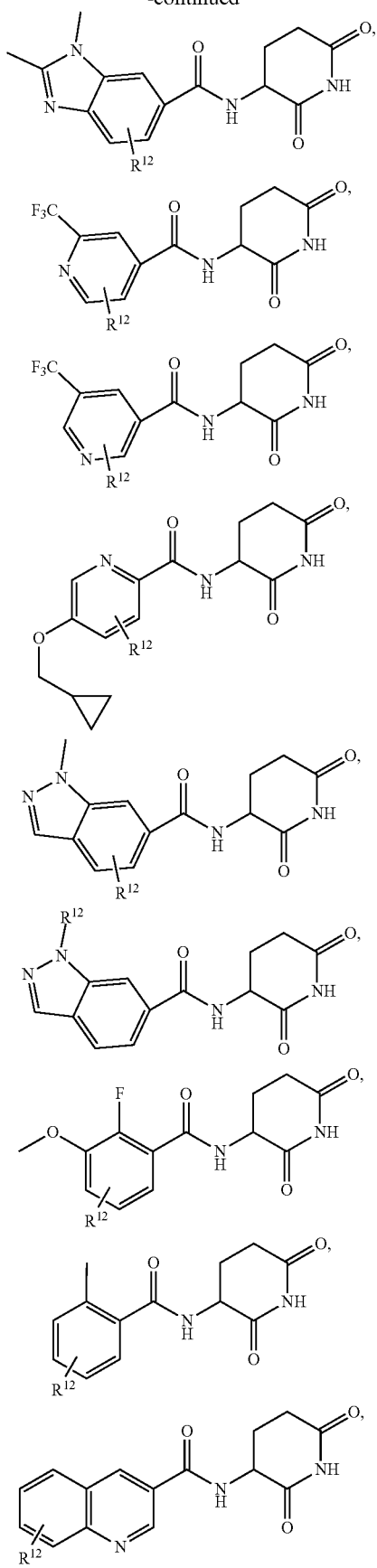

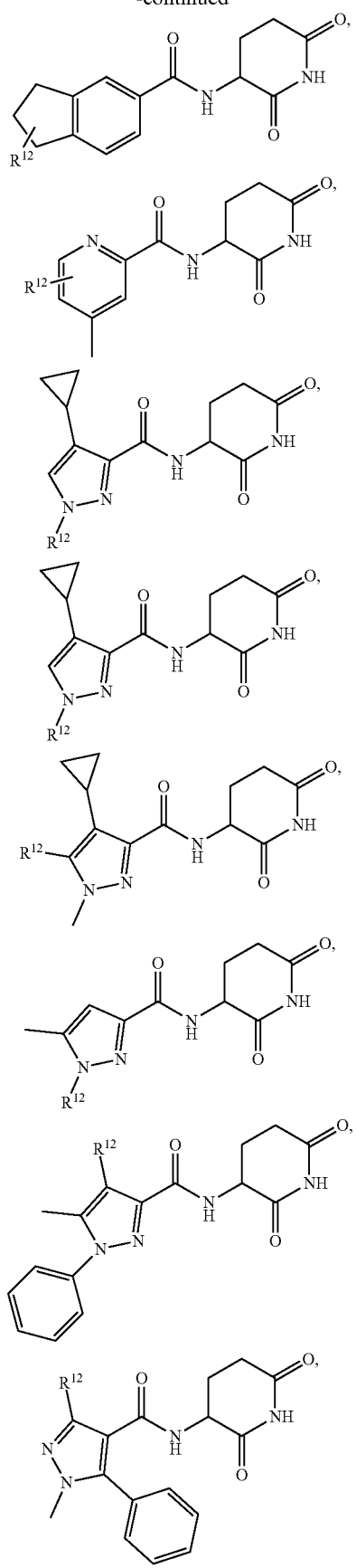
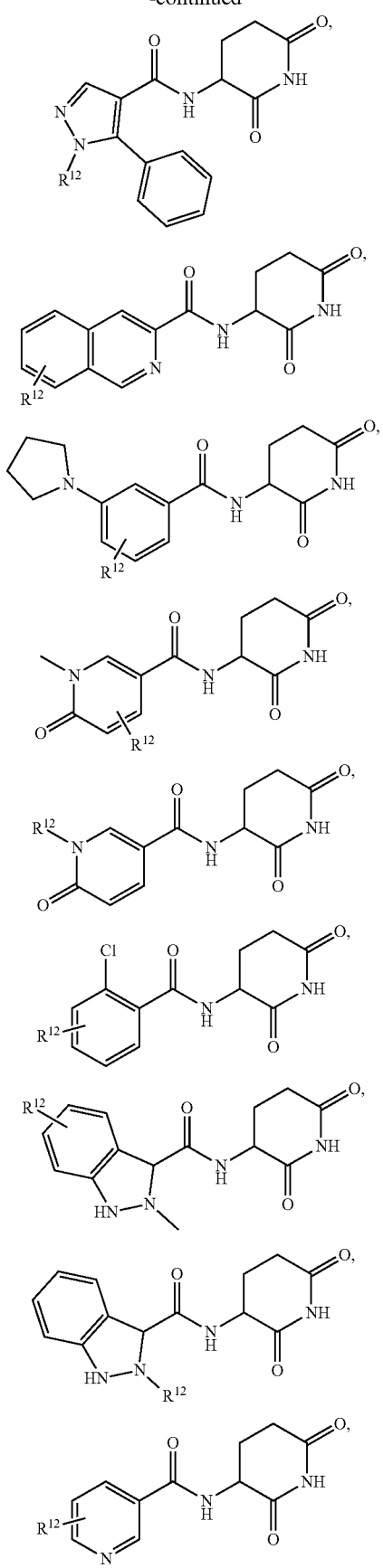

-continued
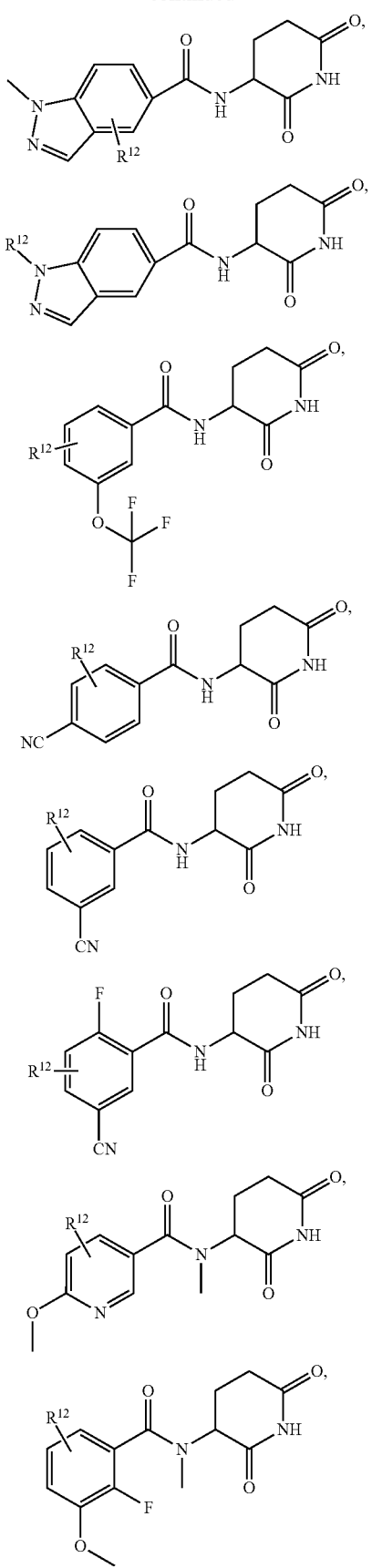
-continued
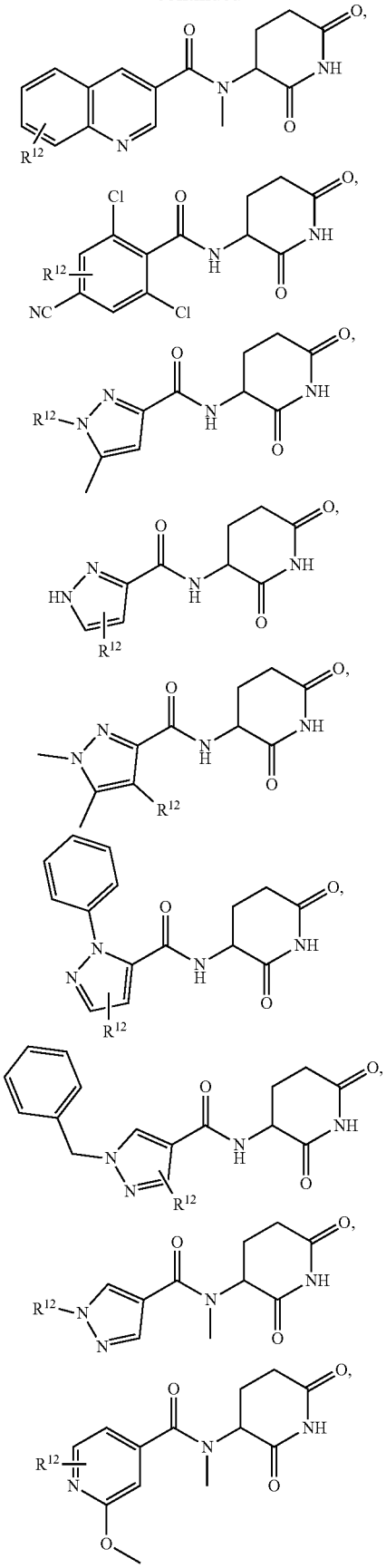

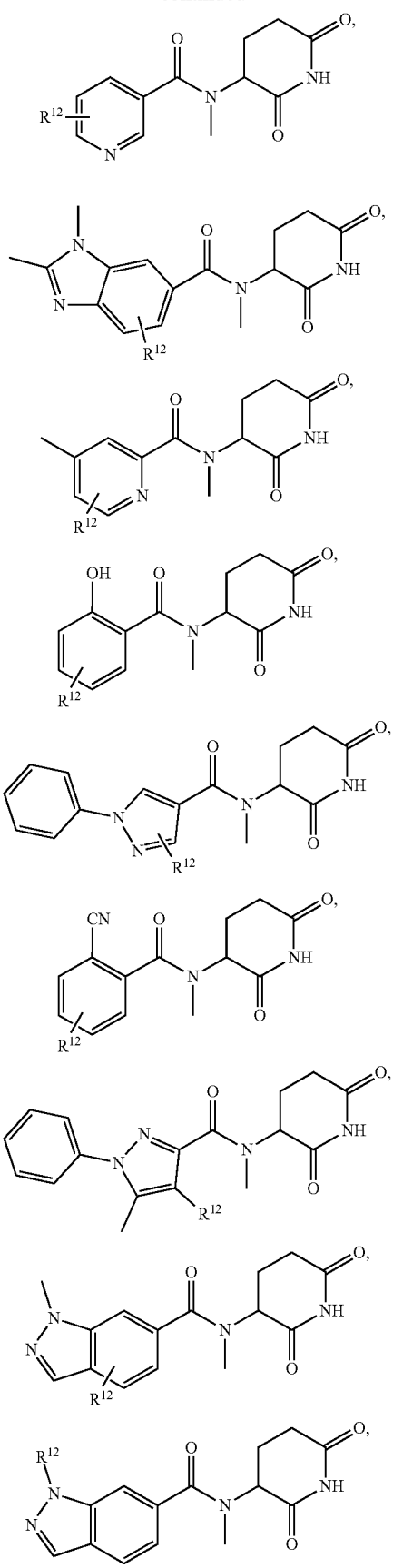
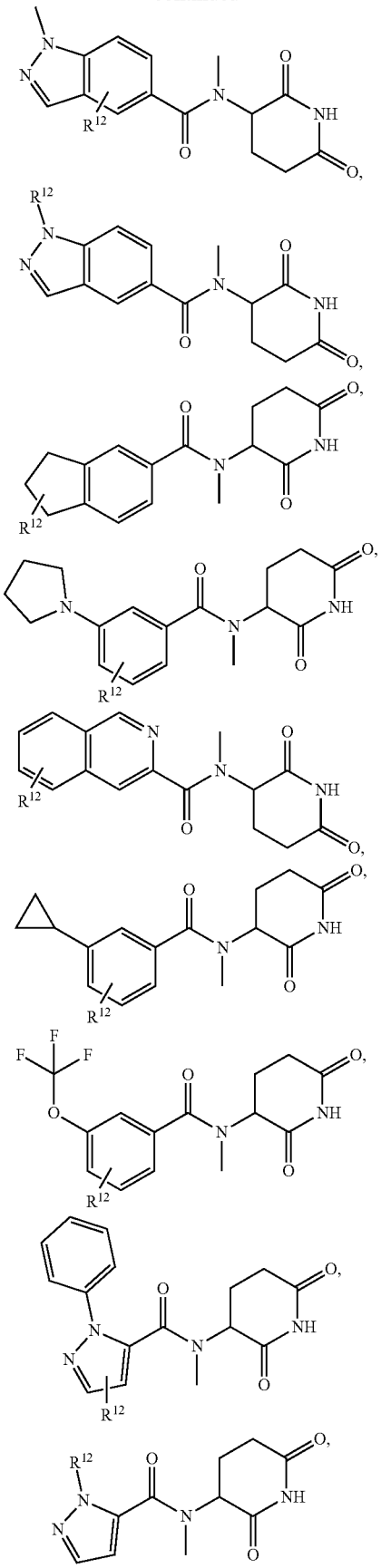

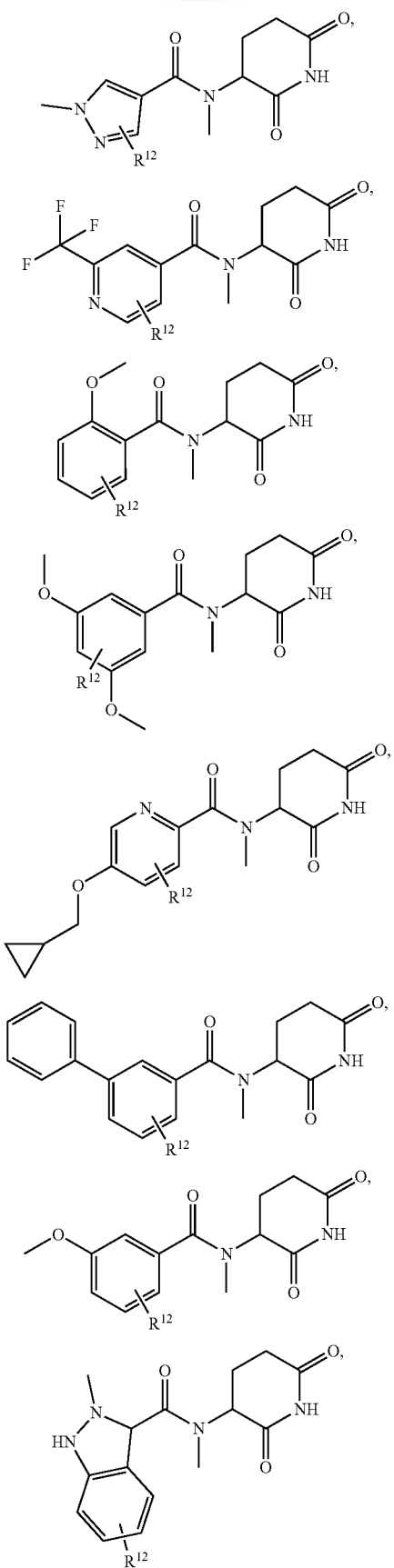
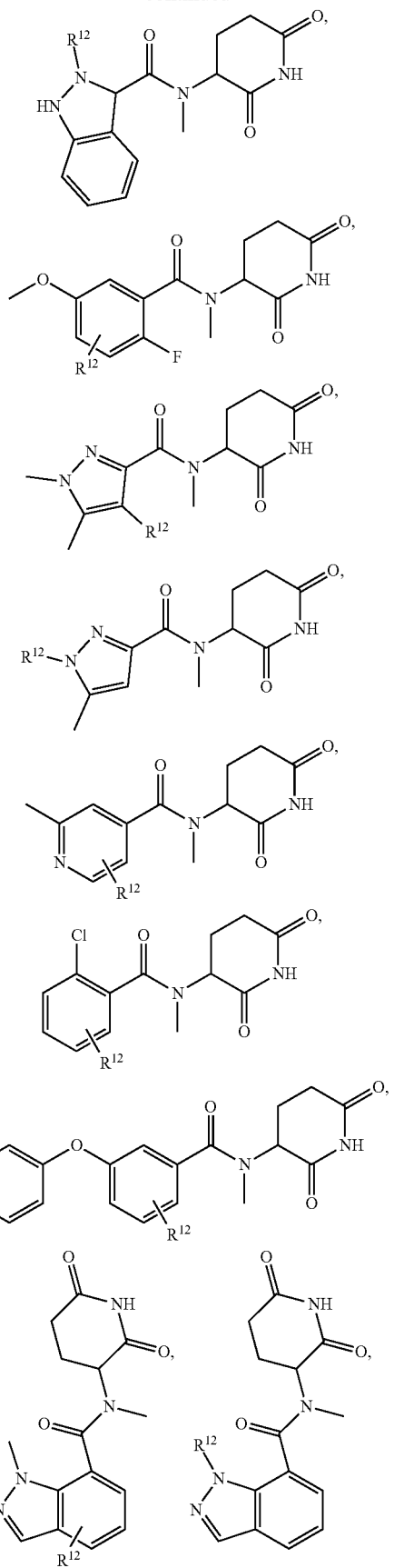

-continued
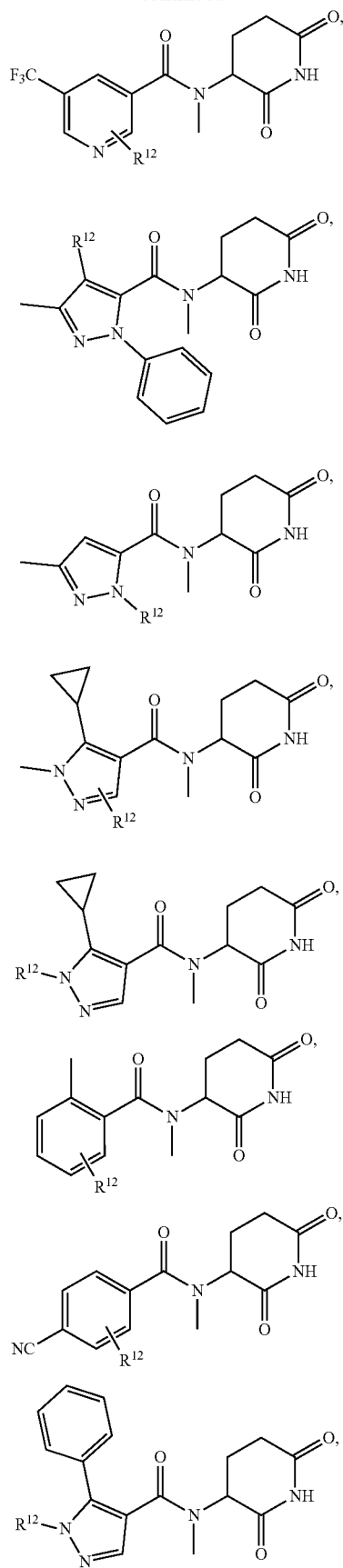
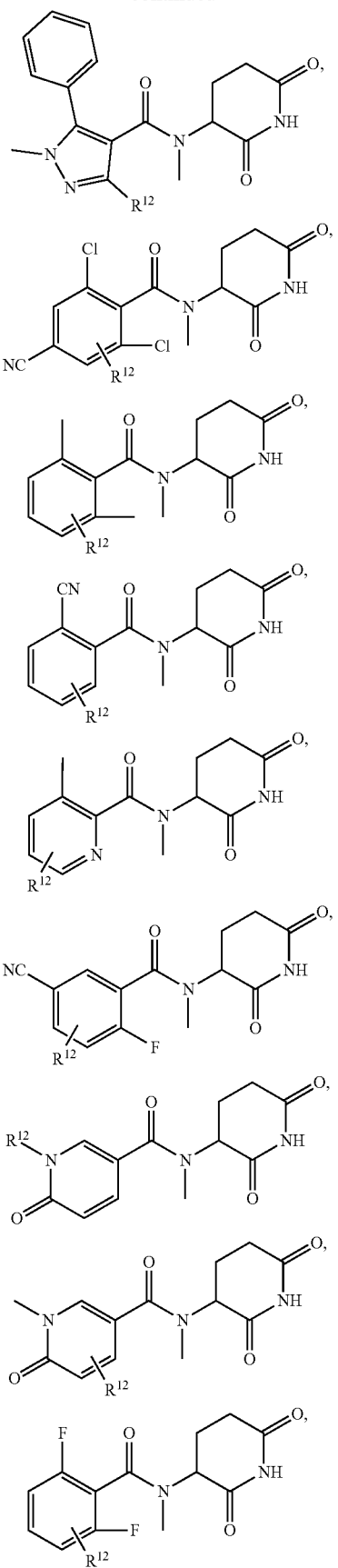

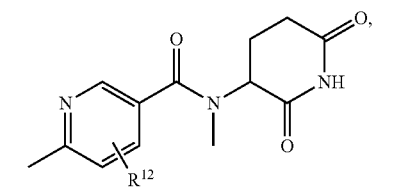
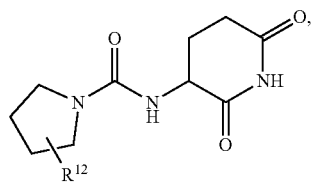
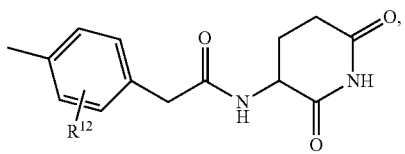
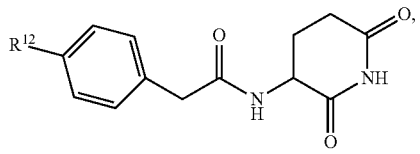
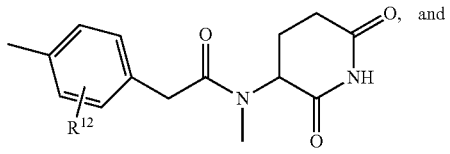
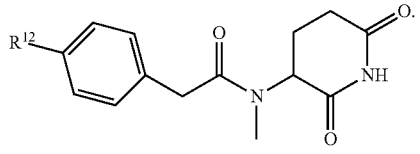
Additional non-limiting examples of compounds of Formula I include:
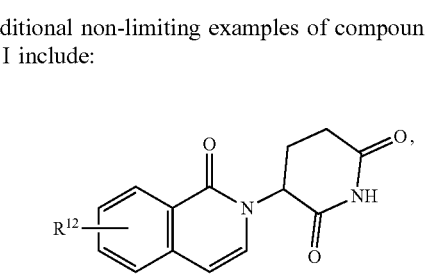
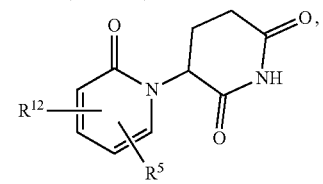
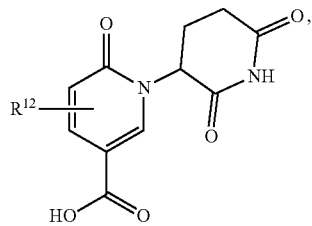
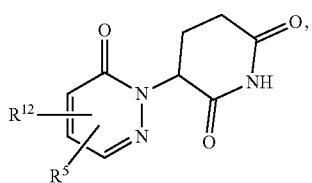
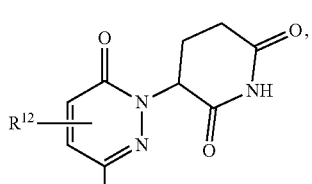
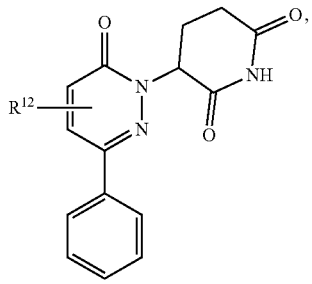
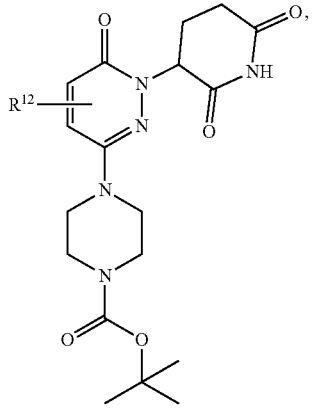
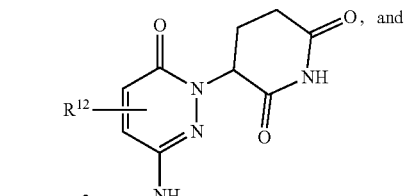
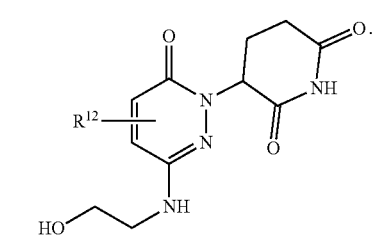

Additional non-limiting examples of compounds of Formula I include:
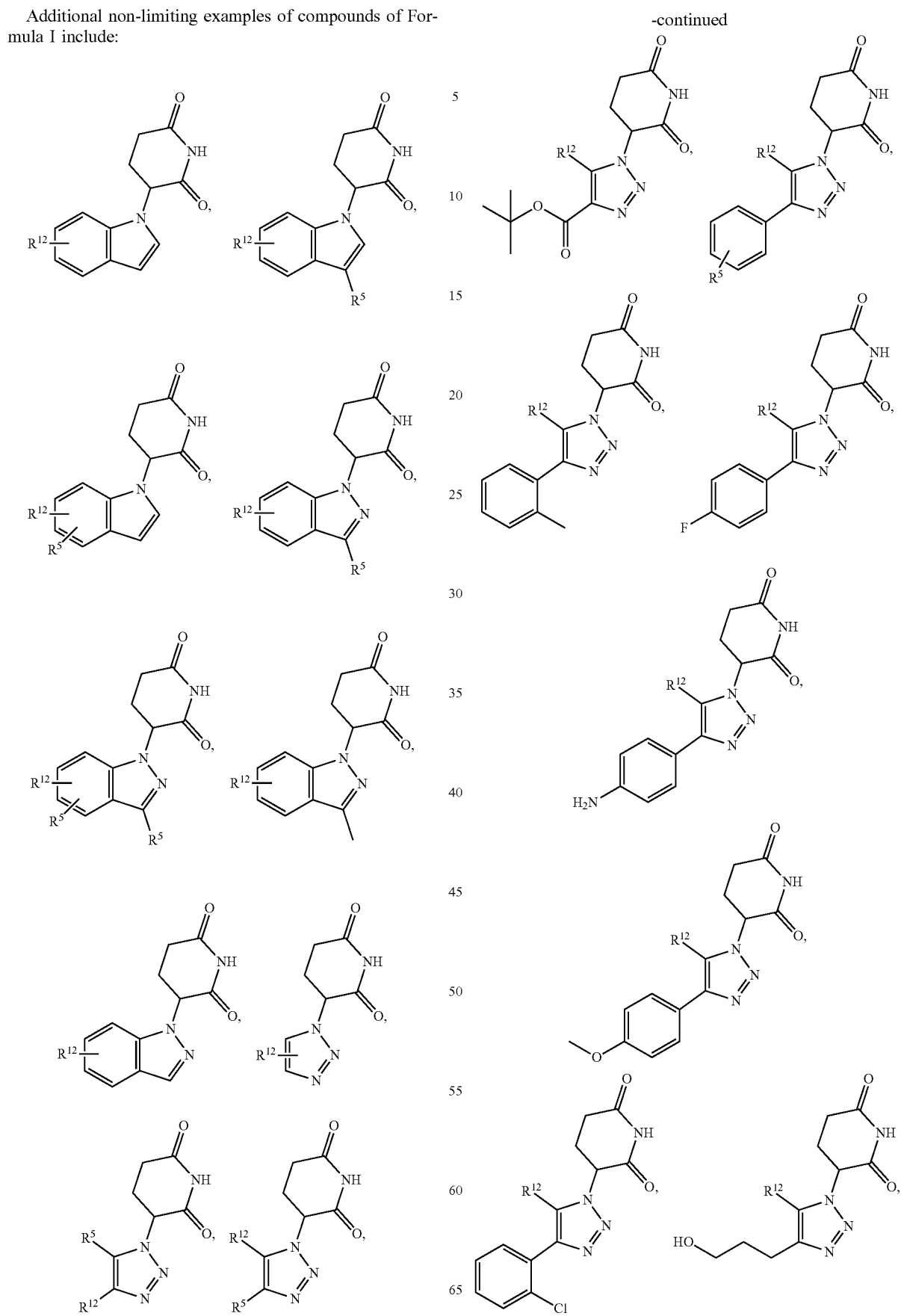

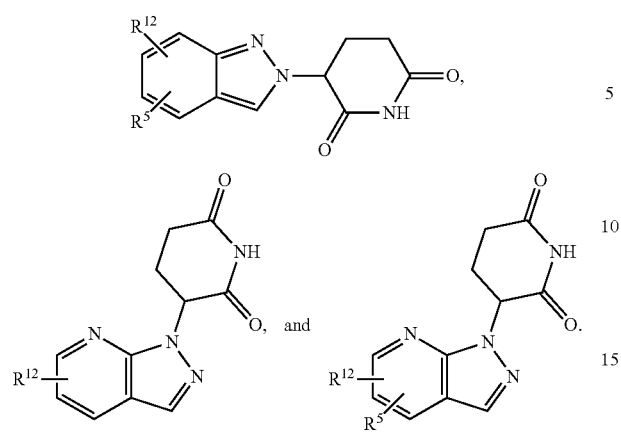
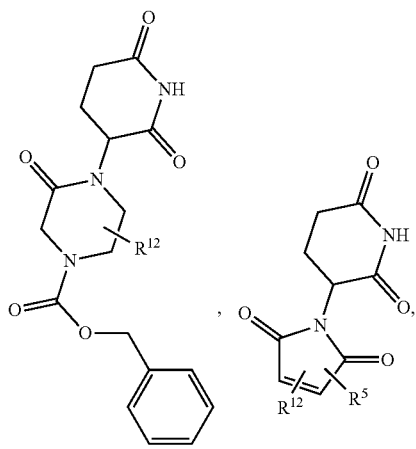
Additional non-limiting examples of compounds of Formula I include:
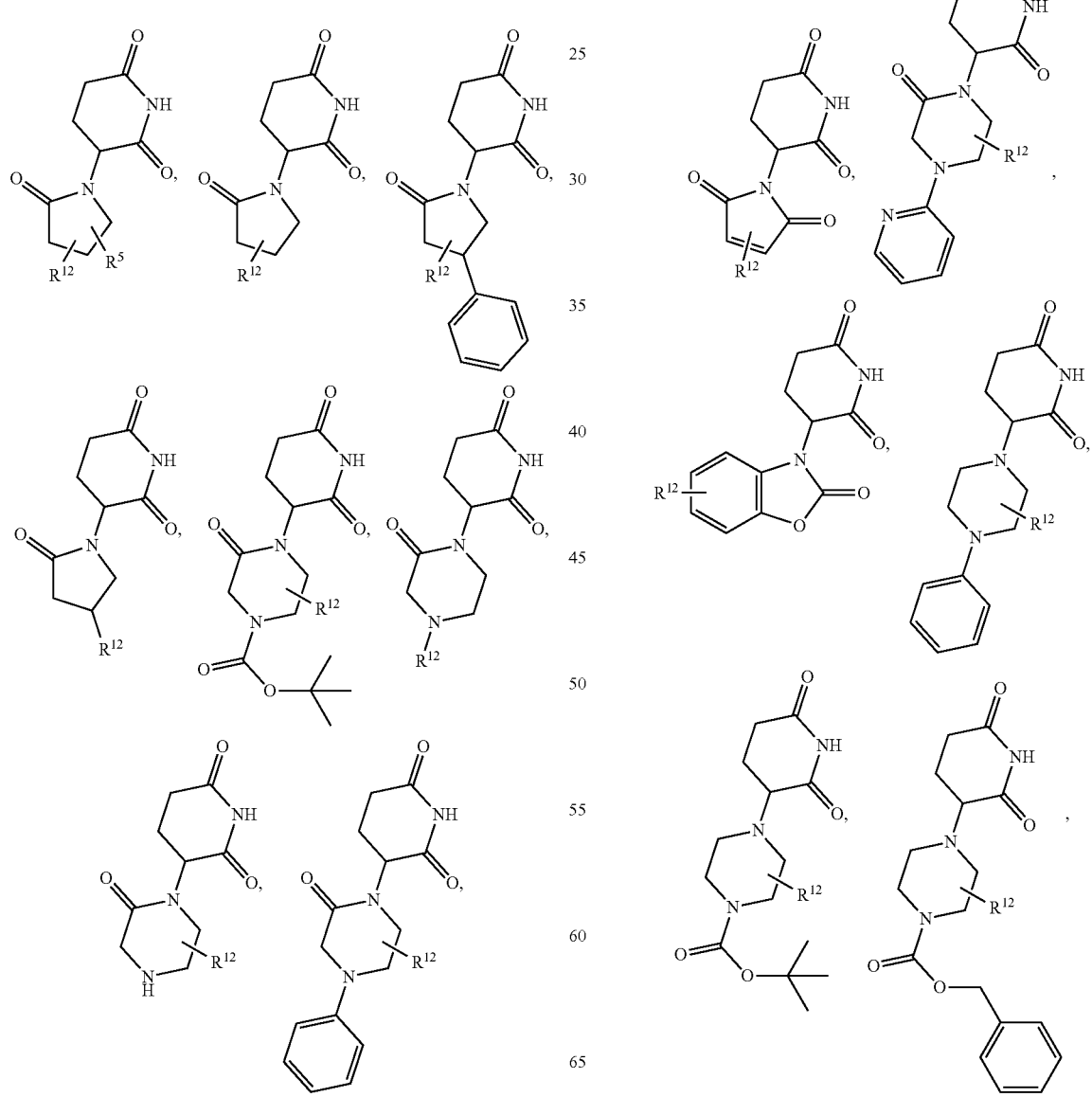

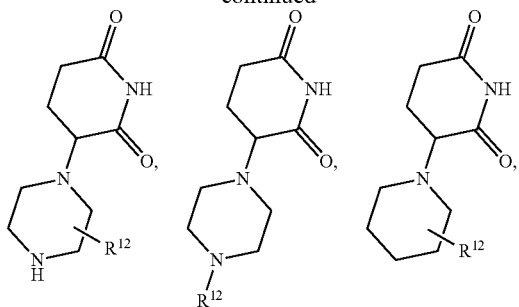
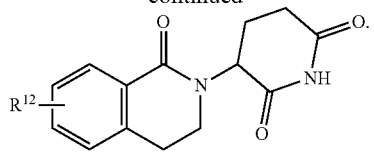
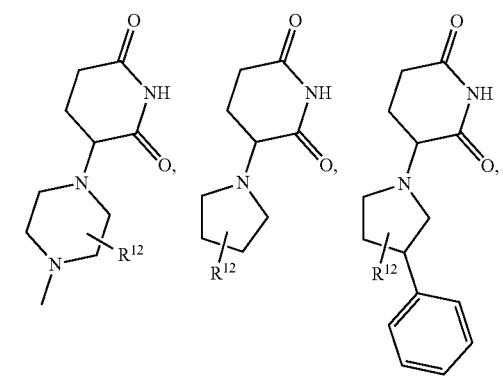
Additional non-limiting examples of compounds of Formula I include:
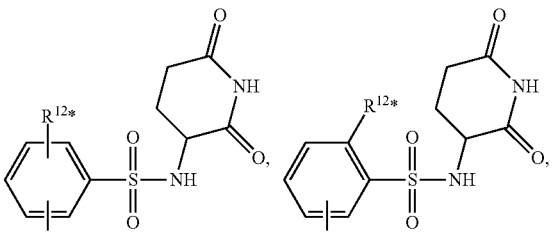
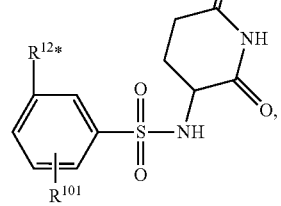
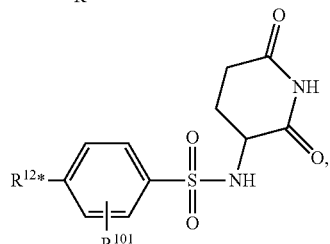
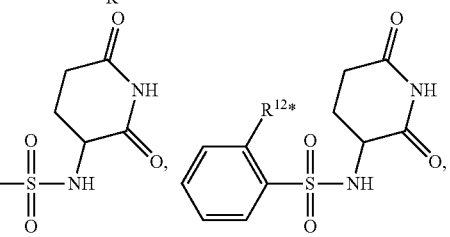
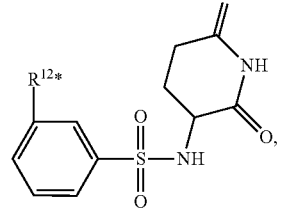
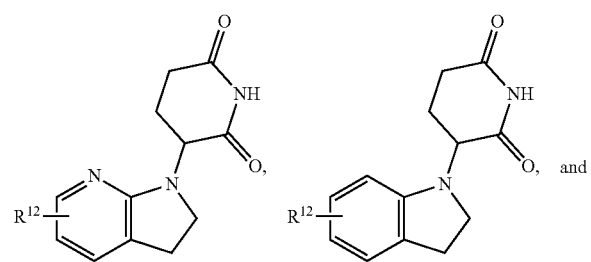

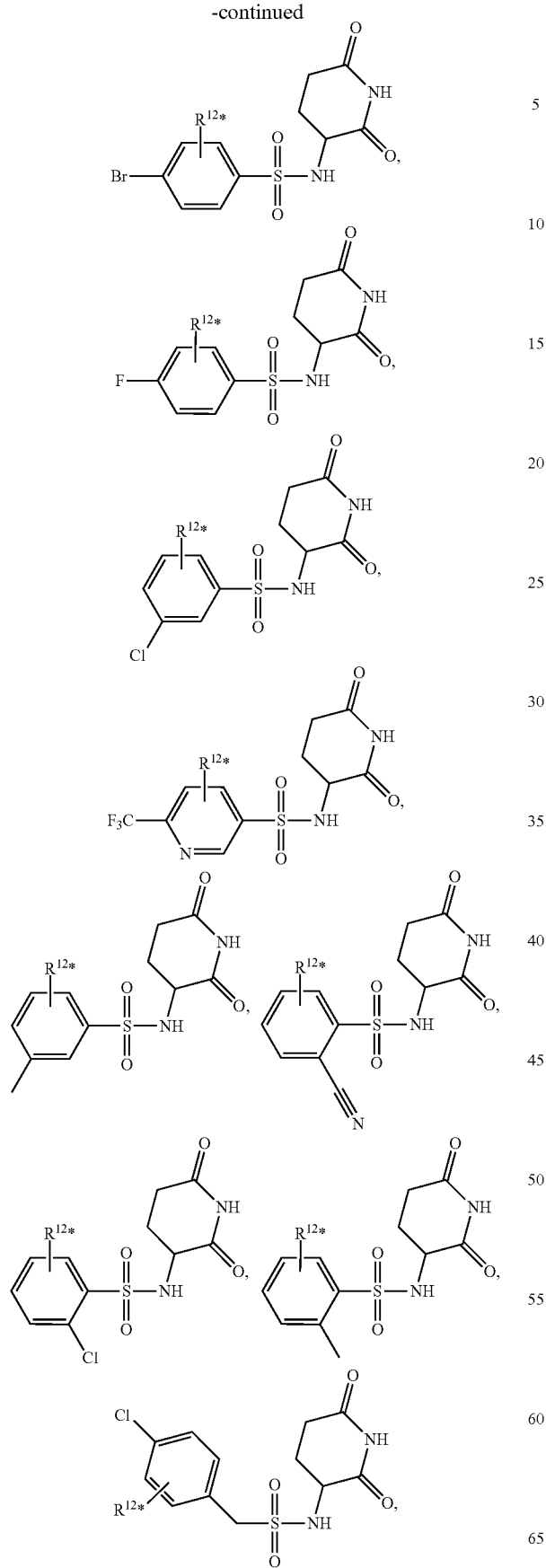
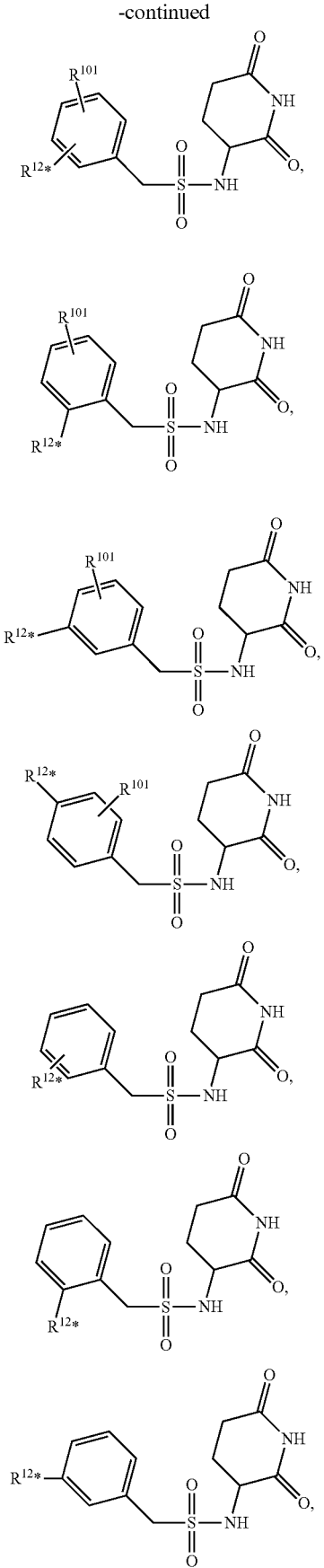

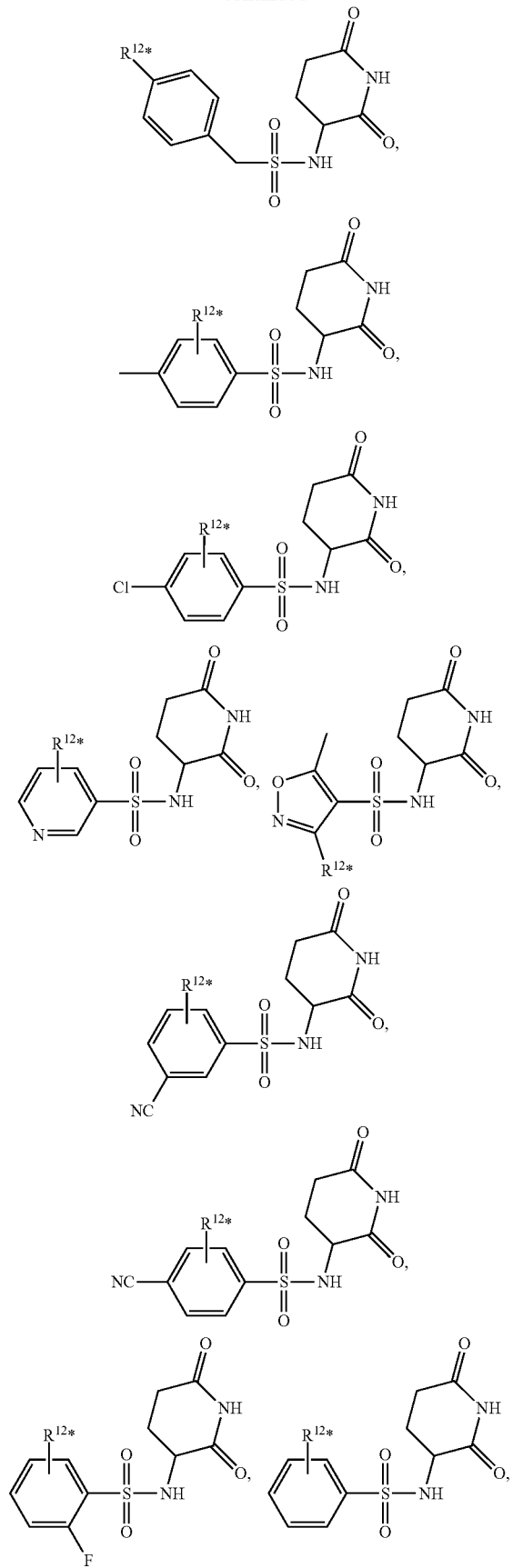
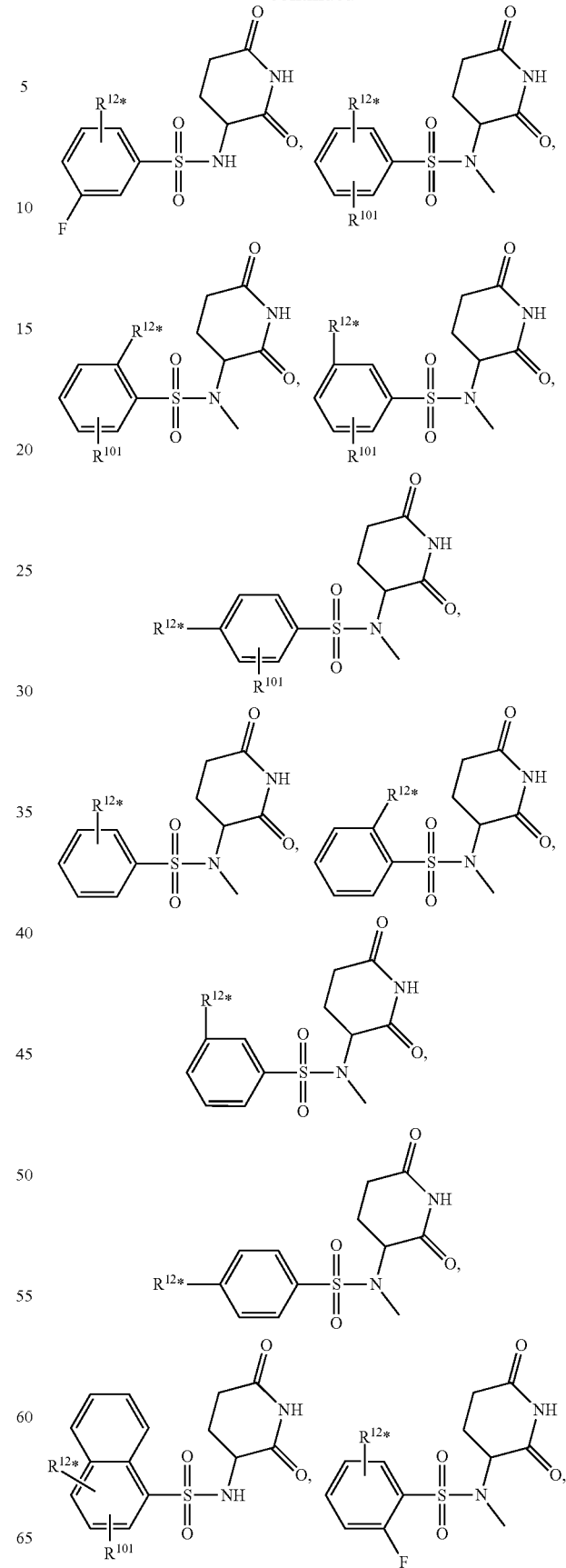

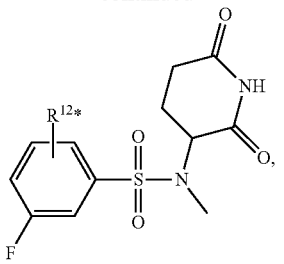
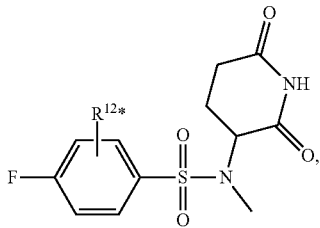
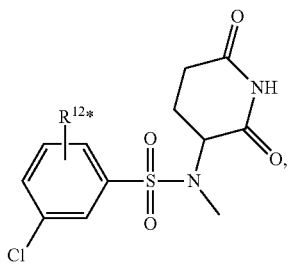
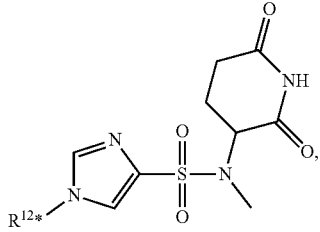
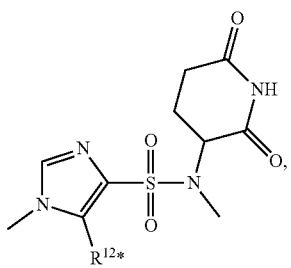
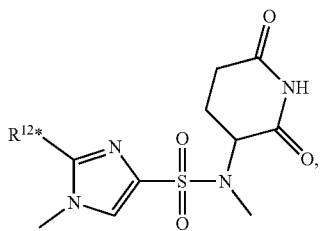
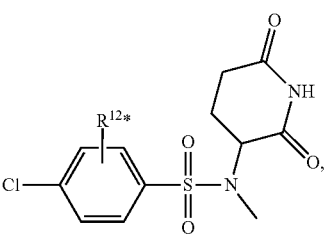
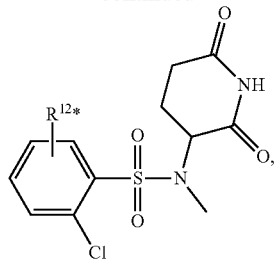
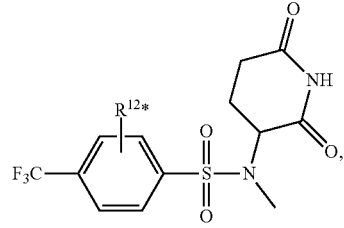
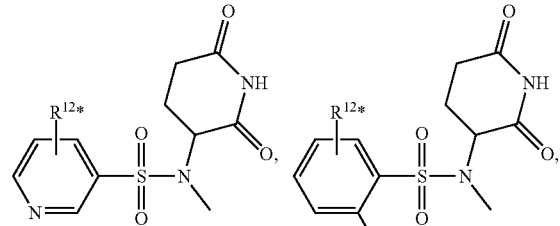
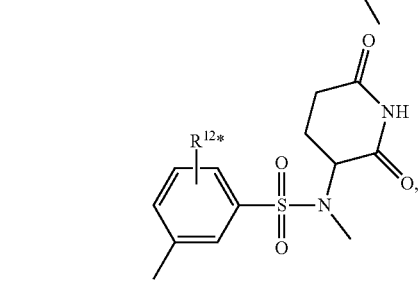
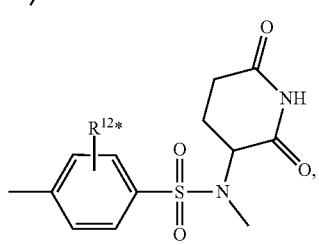
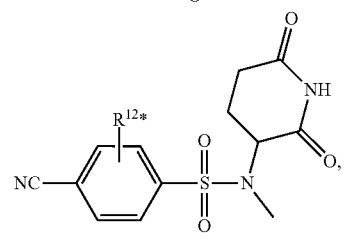
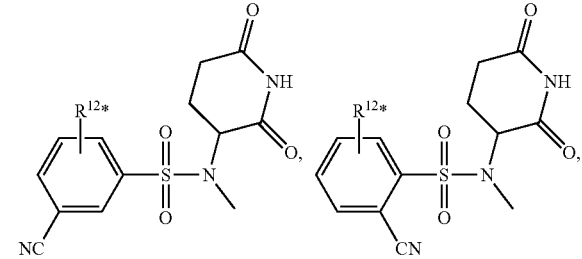

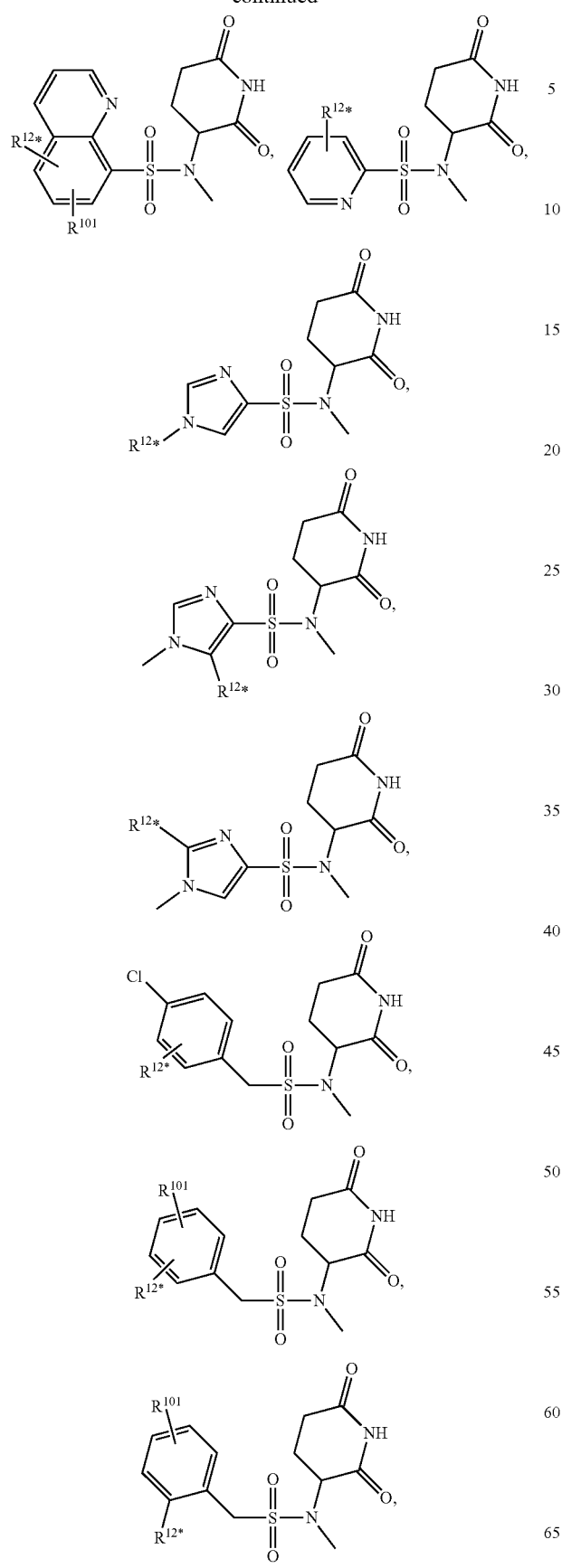
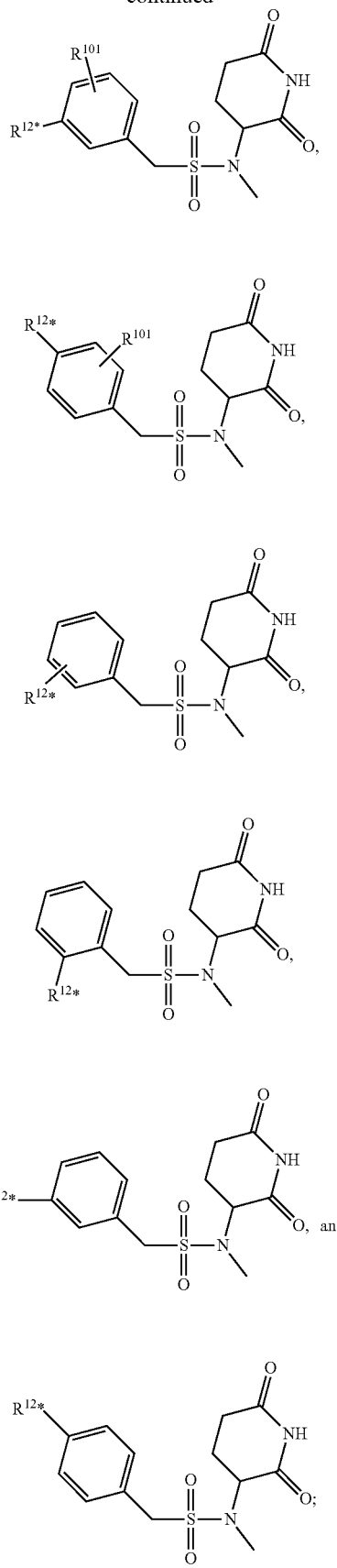

Non-limiting examples of compounds of Formula VII include:
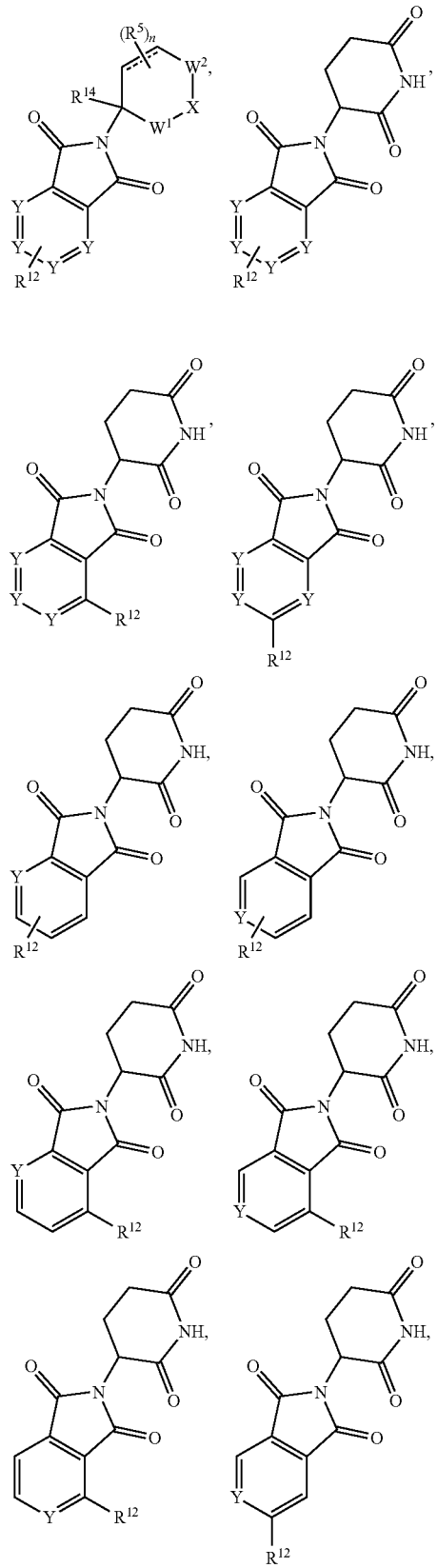
-continued
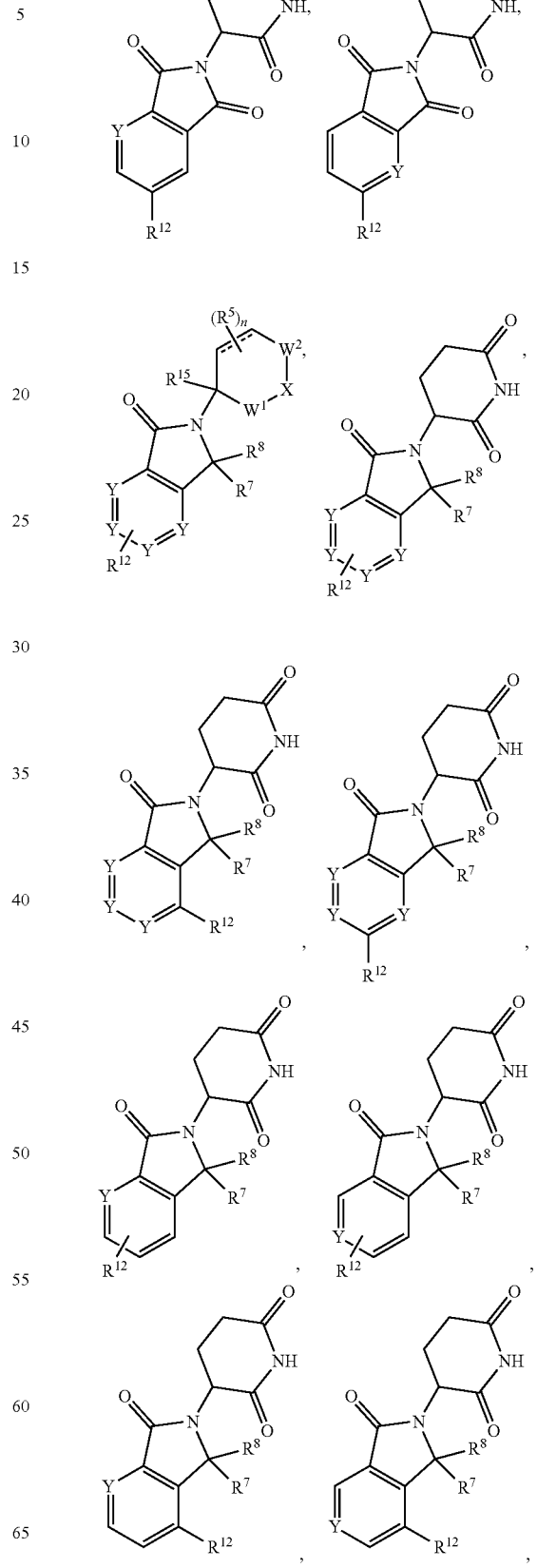

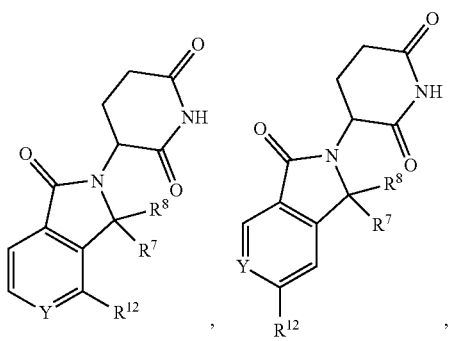
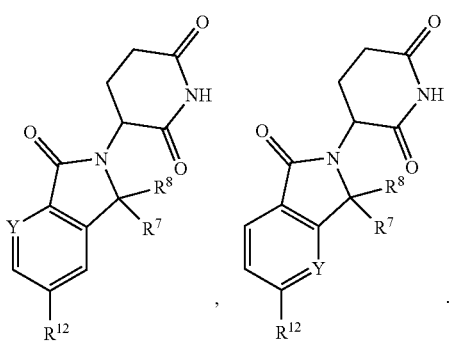
In one embodiment the compound of Formula V is selected from the below:
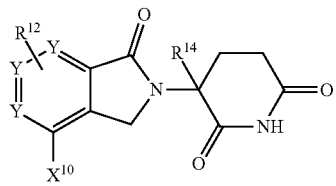
(Va)
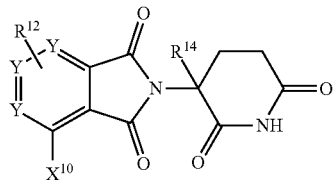
(Vb)
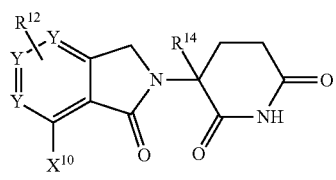
(Vc)
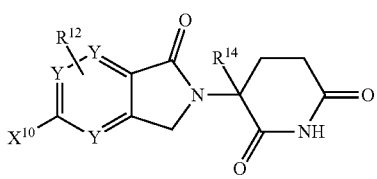
(Vd)
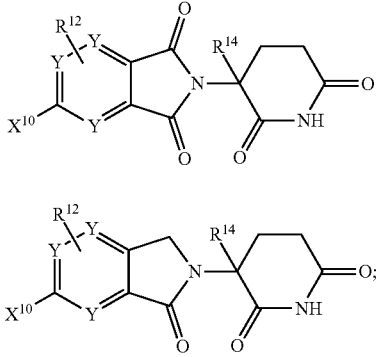
(Ve)
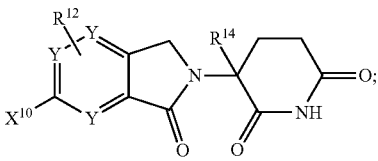
(Vf)
wherein $X^{10}$ is selected from:
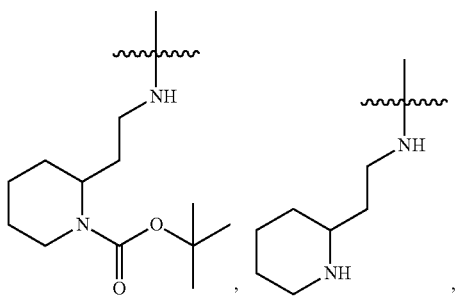
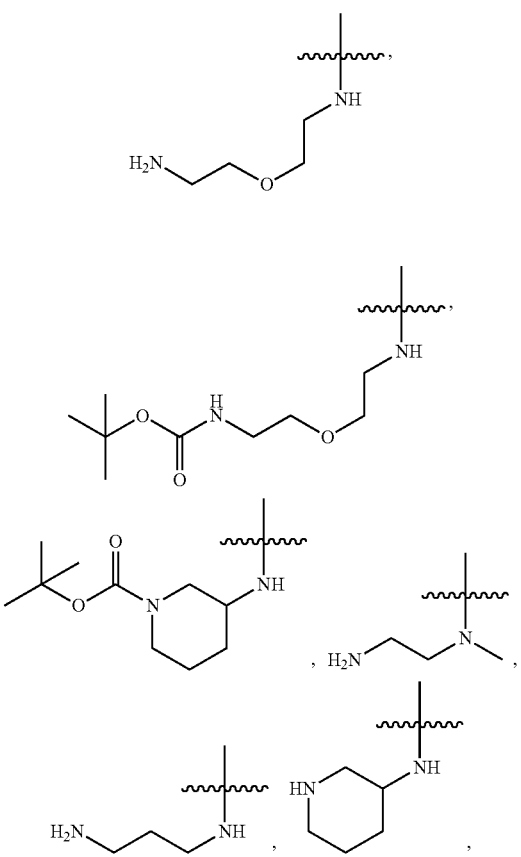

-continued
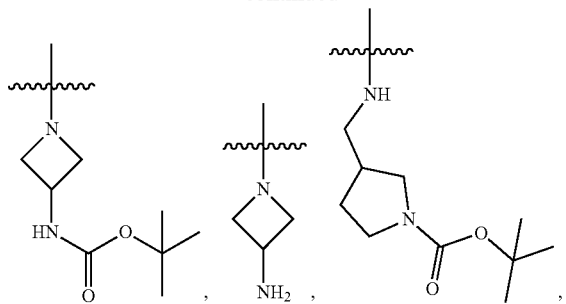
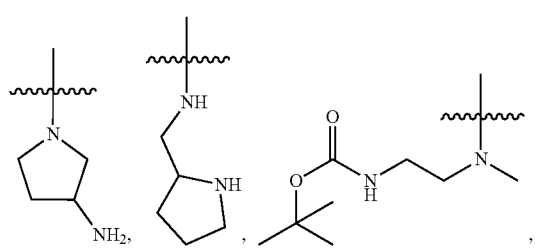
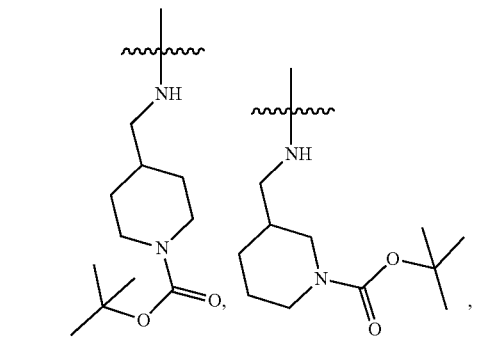
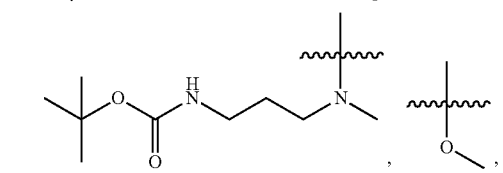
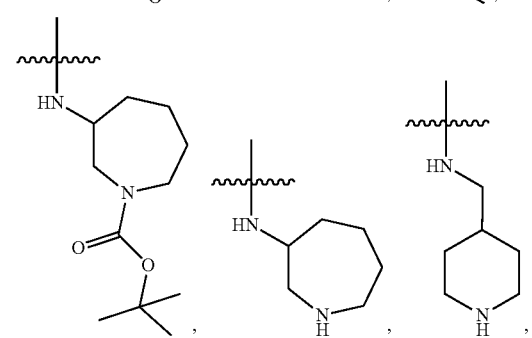
-continued
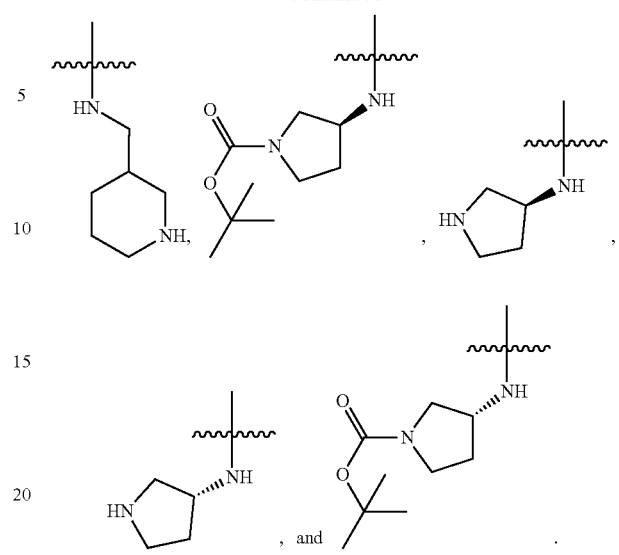
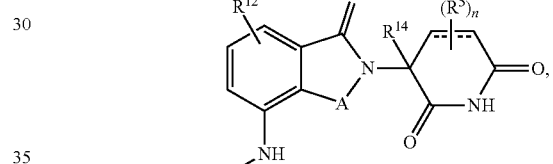
Non limiting examples of compounds of Formula V include:
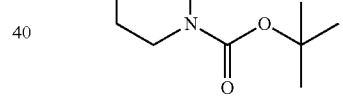
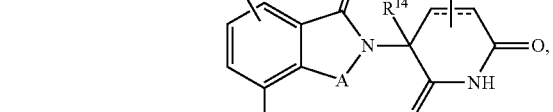
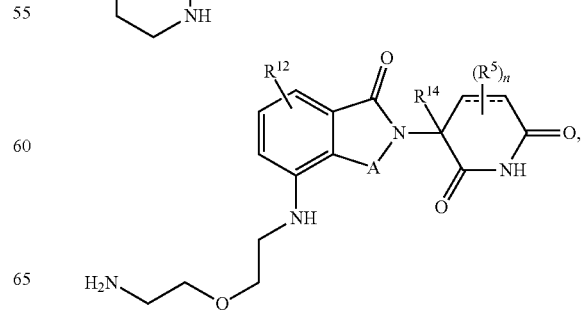

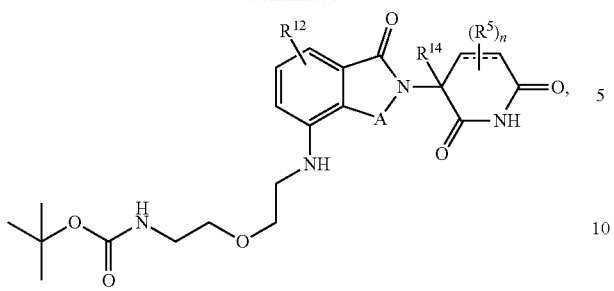
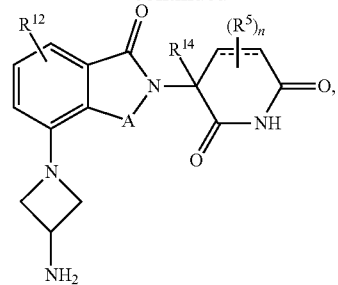
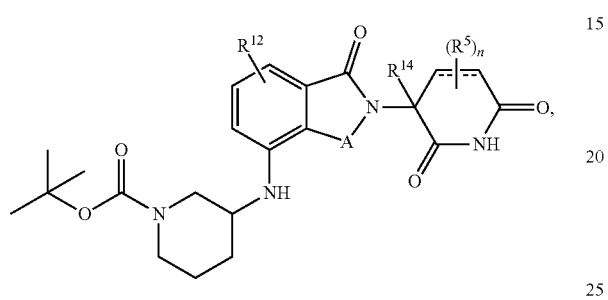
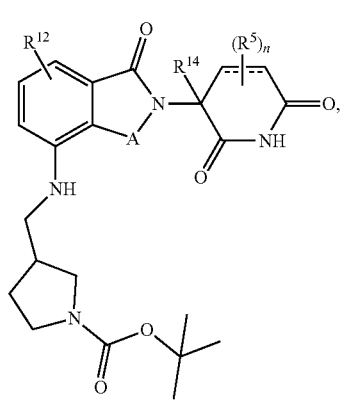
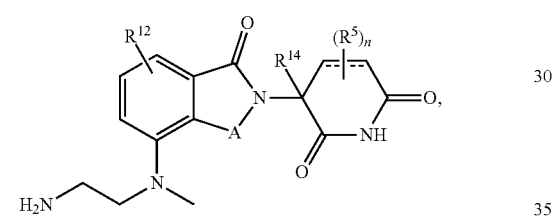
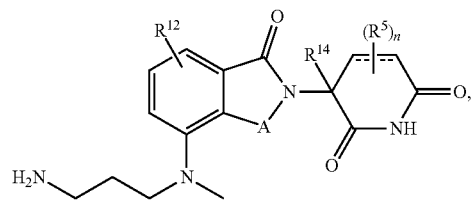
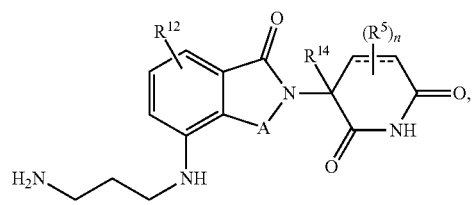
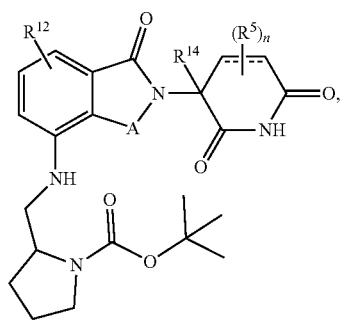
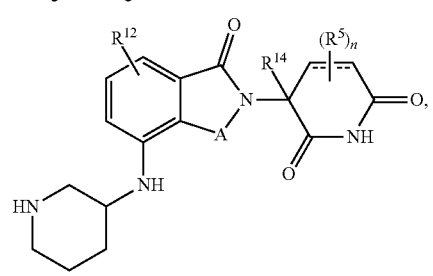
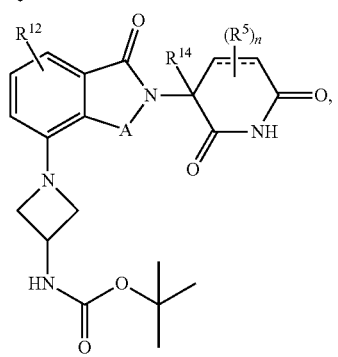
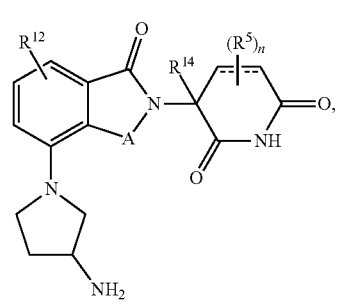

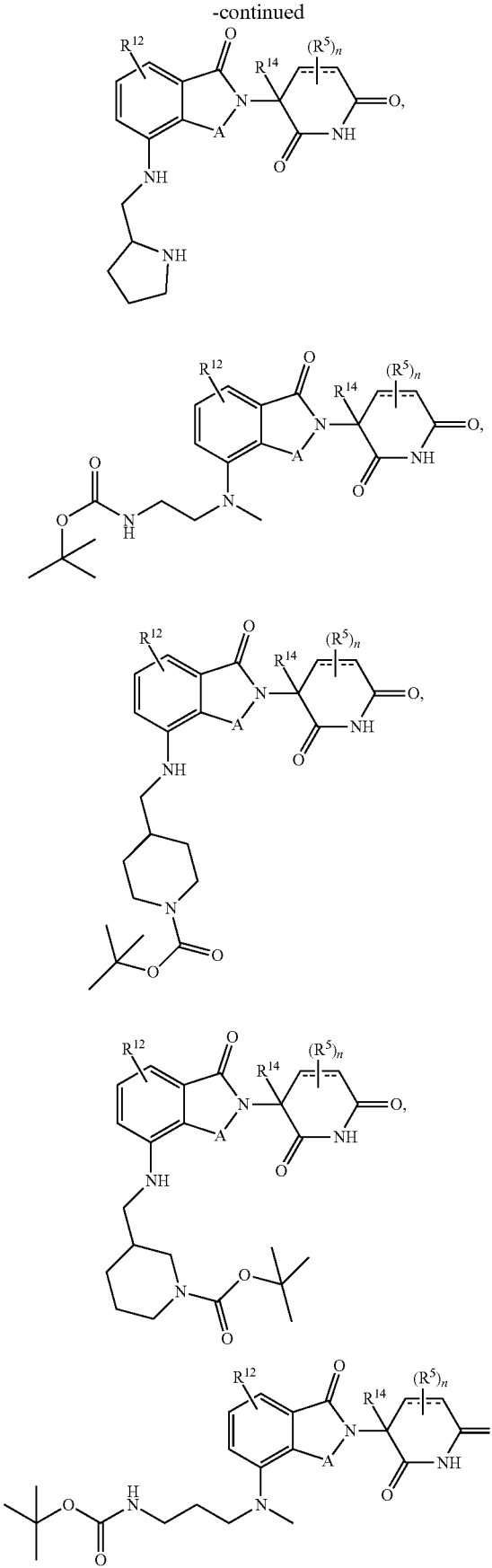
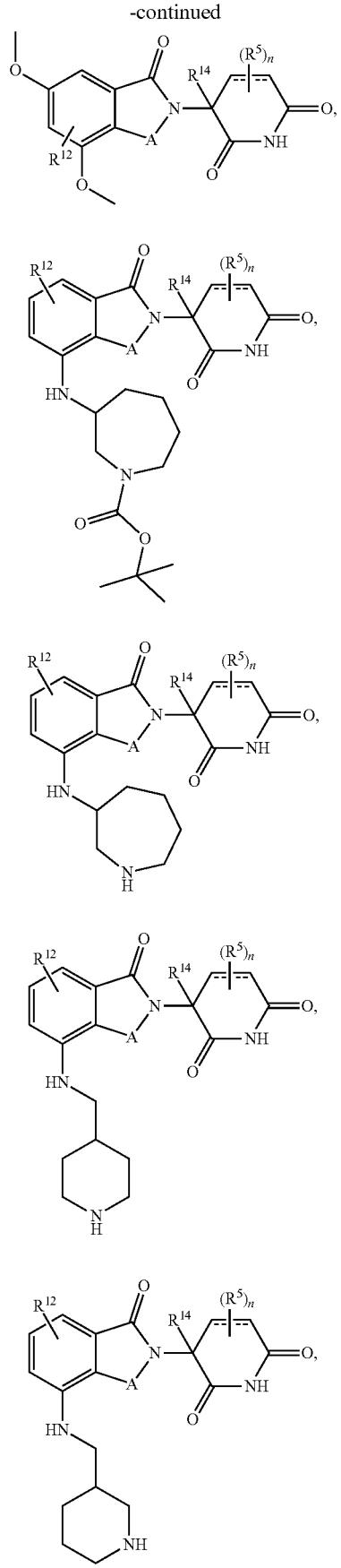

115
-continued
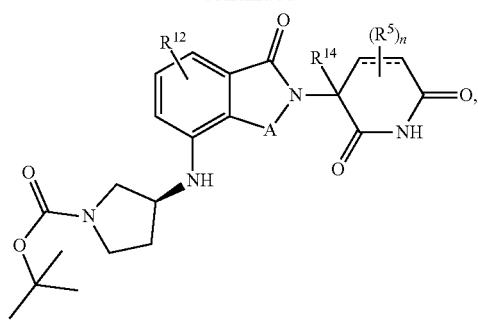
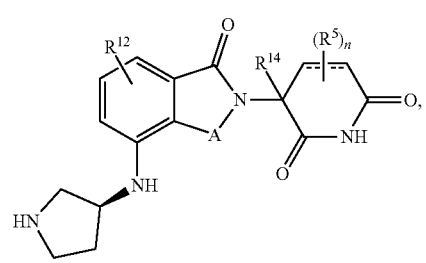
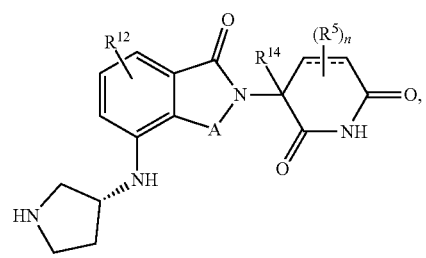
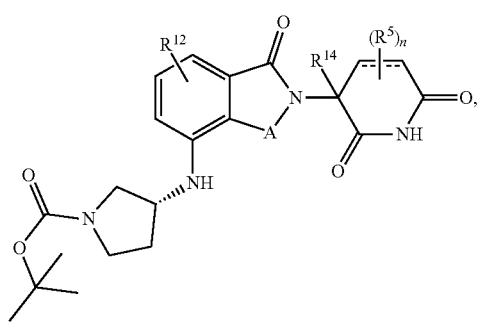
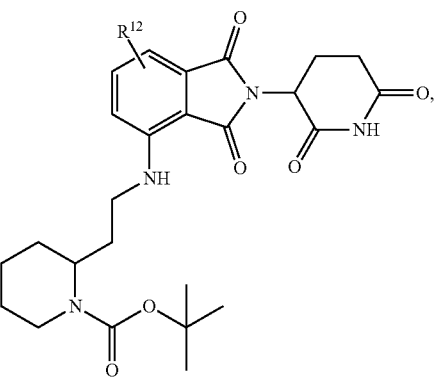
116
-continued
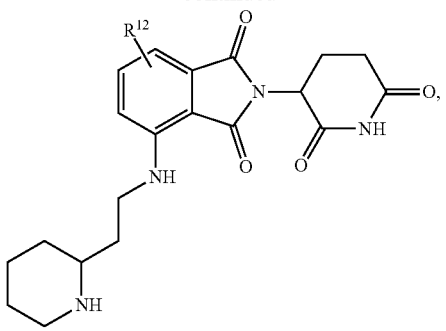
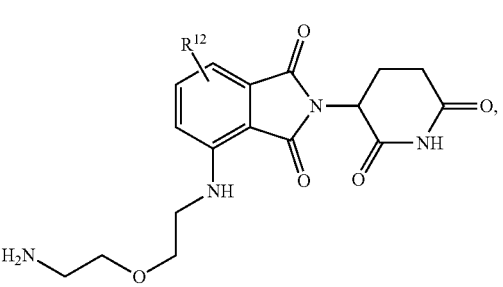
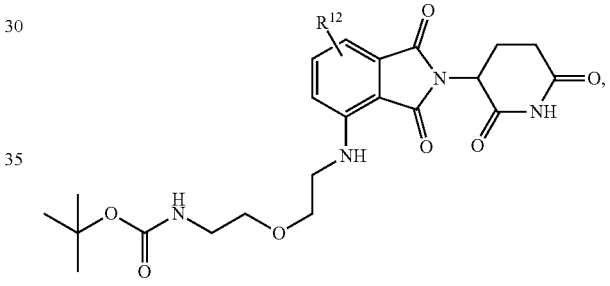
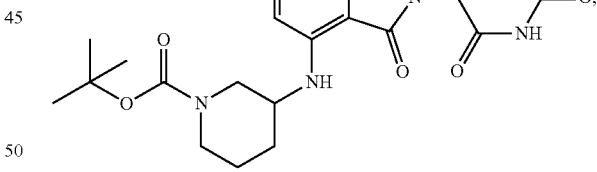
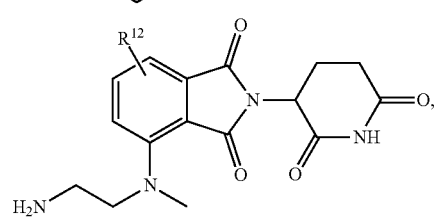
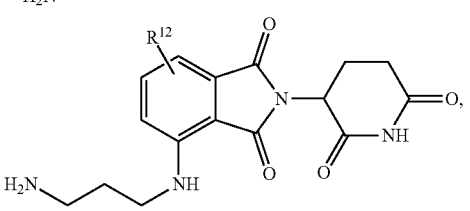

117
-continued
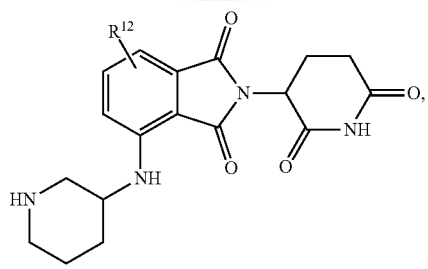
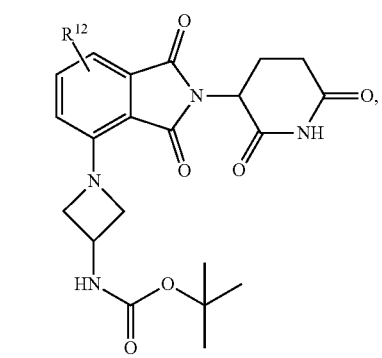
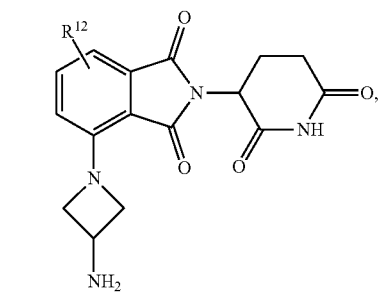
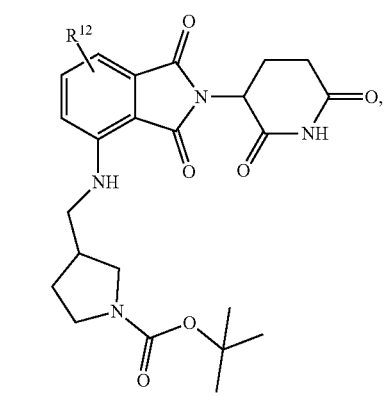
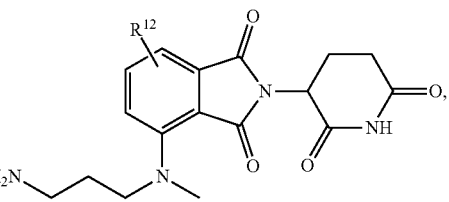
118
-continued
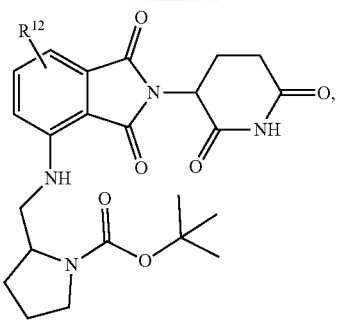
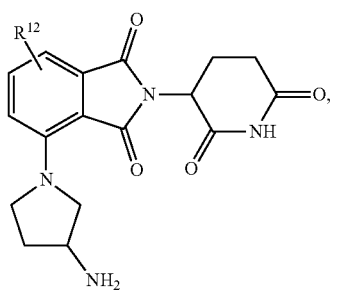
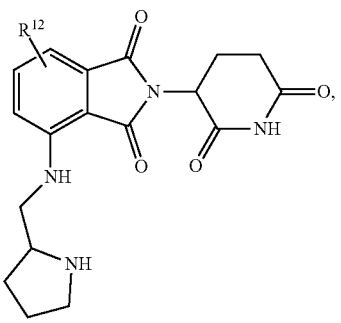
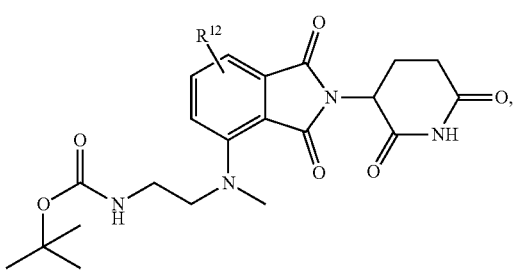
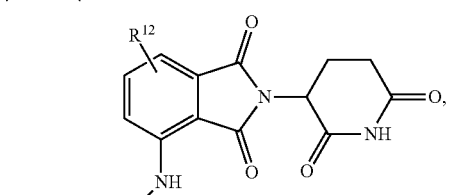
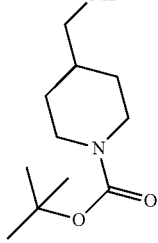

119
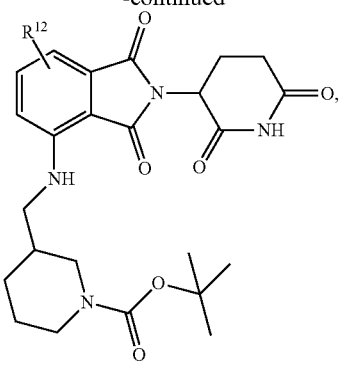
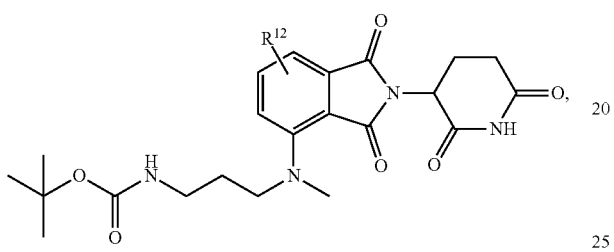
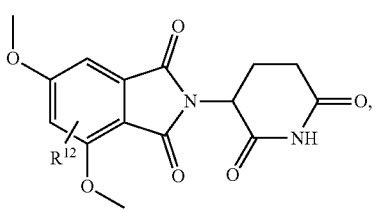
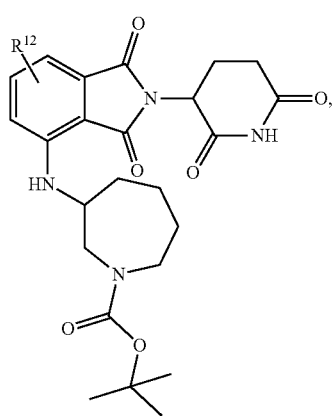
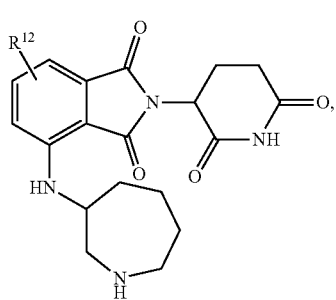
120
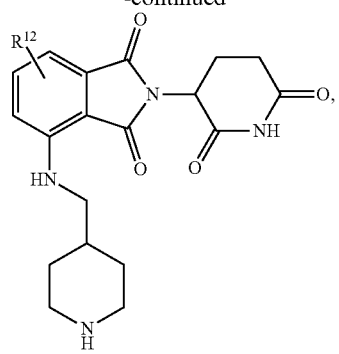
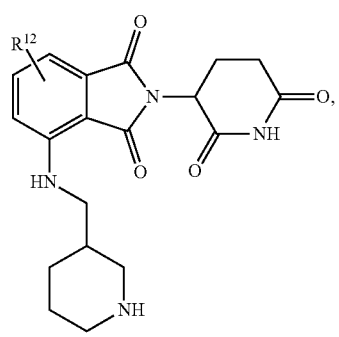
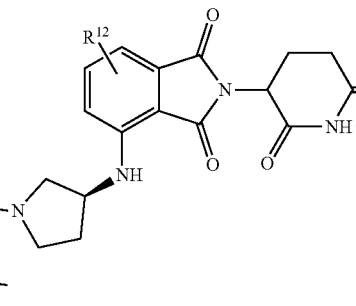
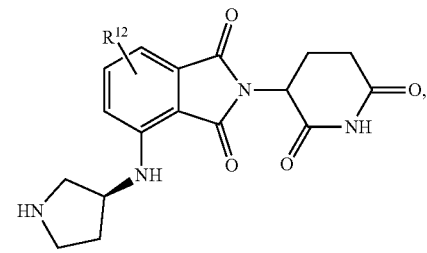
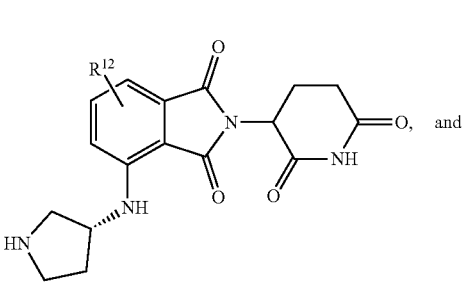, and 121
-continued
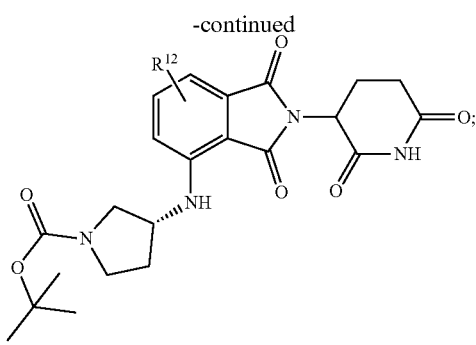
wherein A is CH$_2$ or C(O).
In another embodiment the Degron is selected from:
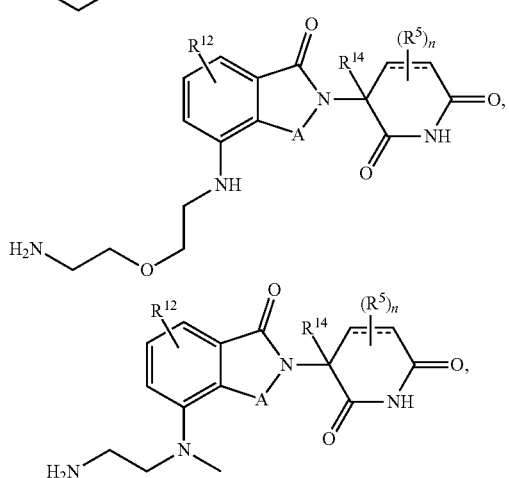
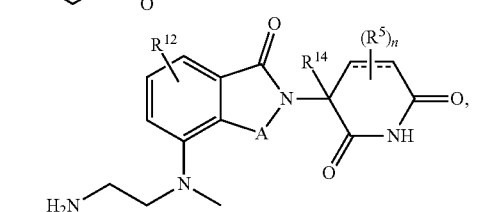
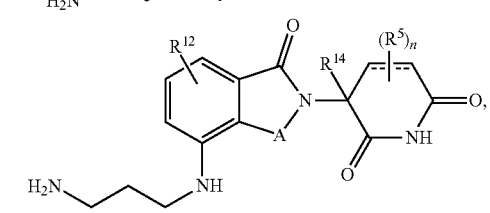
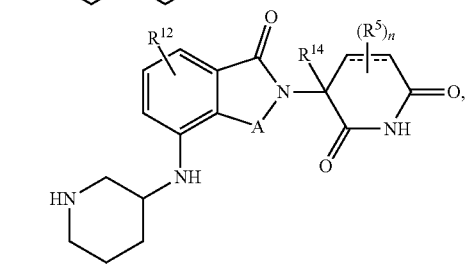

122
-continued
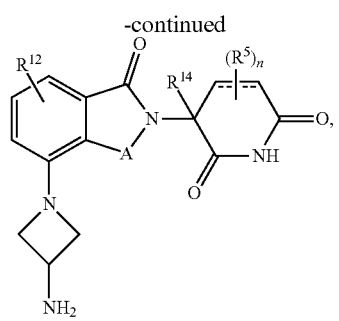
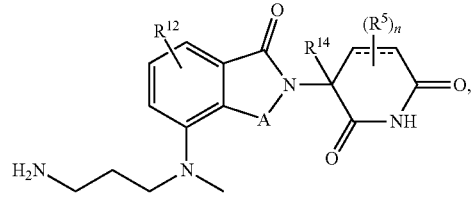
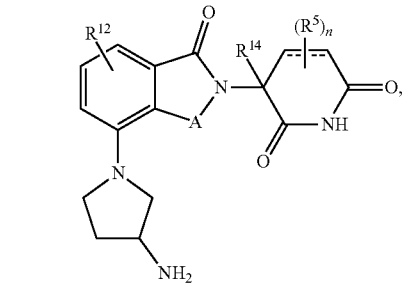
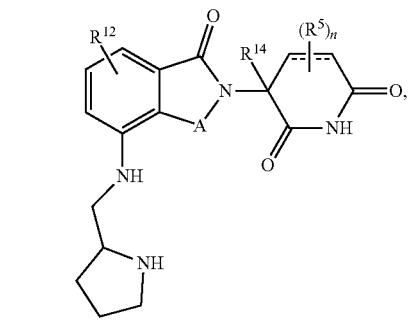
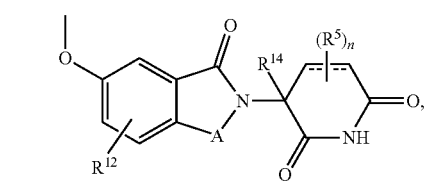
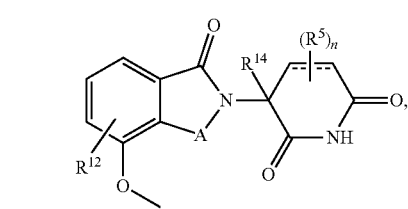


125
-continued
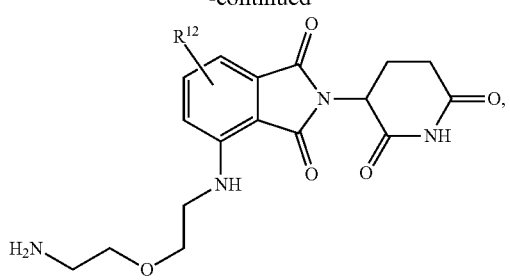
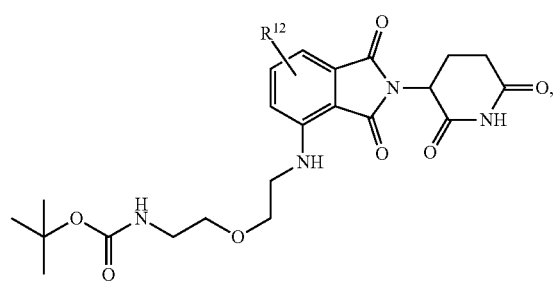
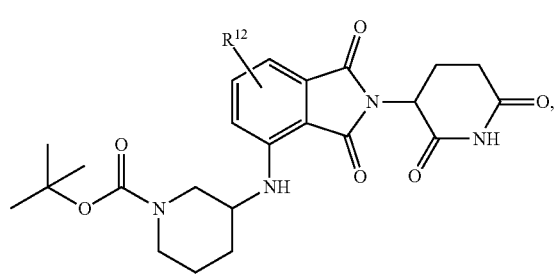
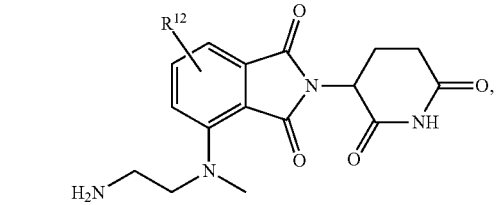
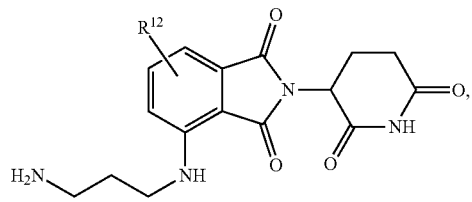
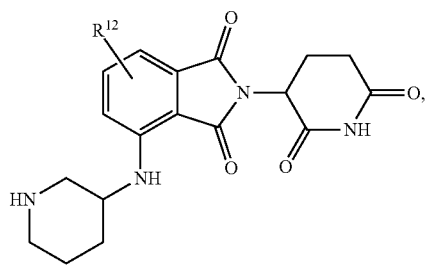
126
-continued
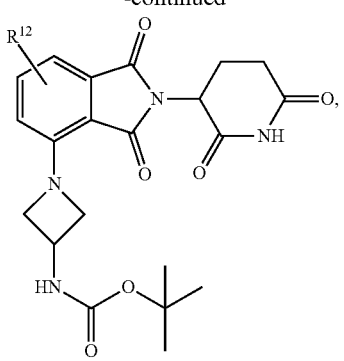
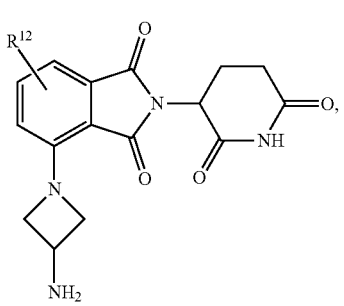
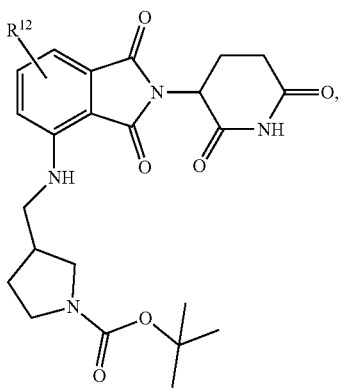
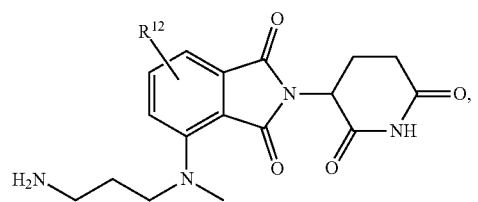
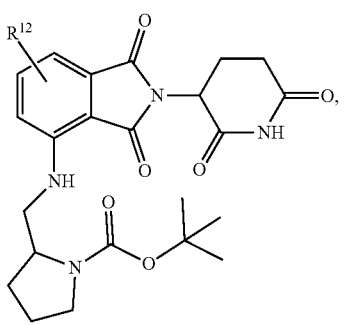

127
-continued
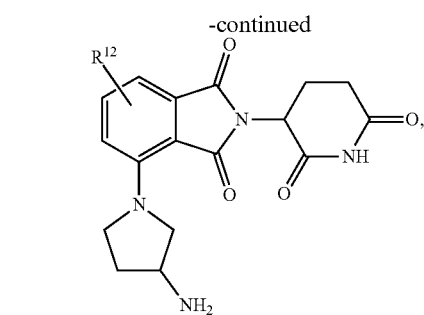
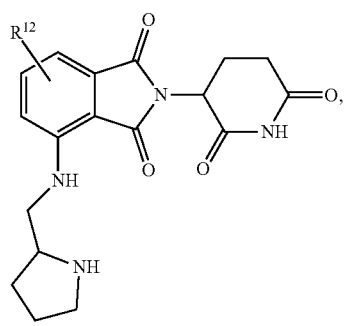
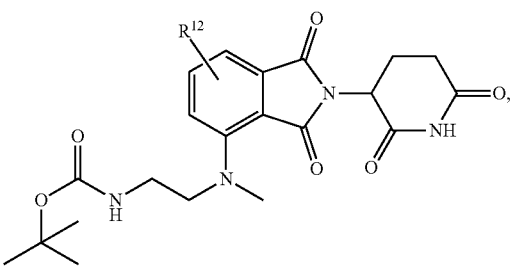
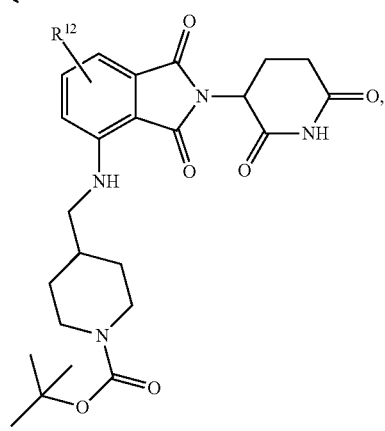
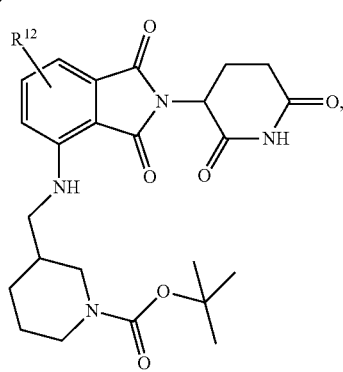
128
-continued
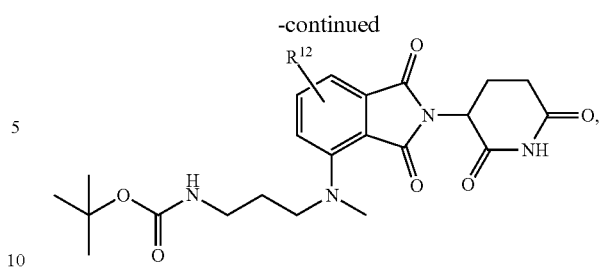
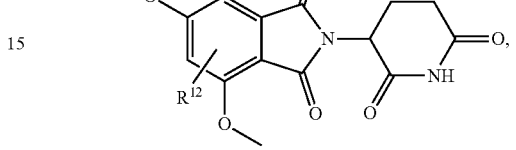
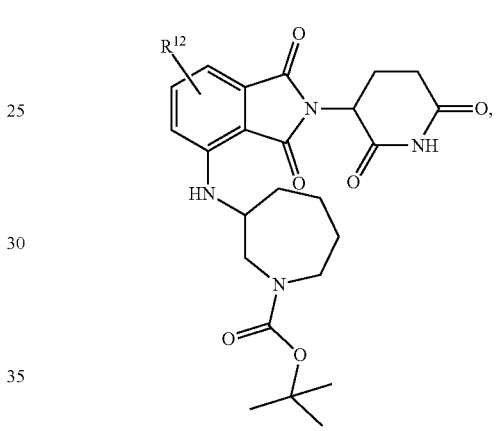
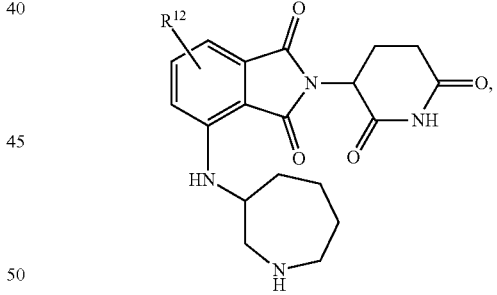
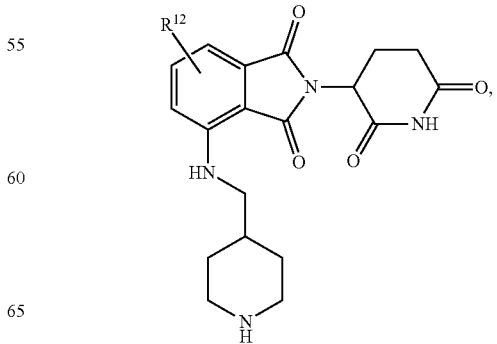

-continued
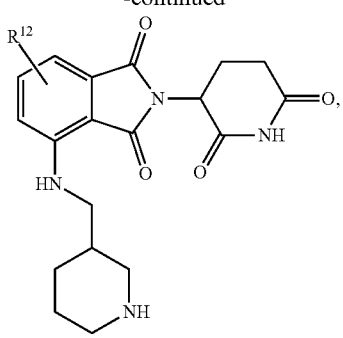
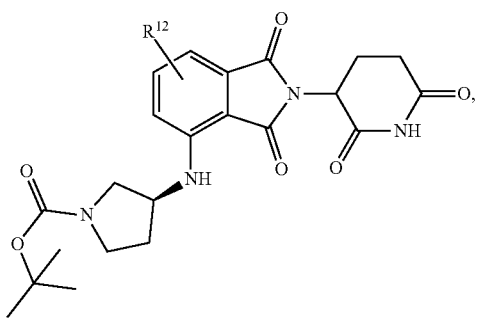
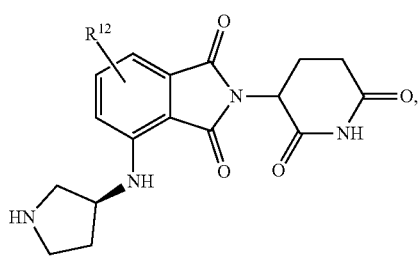
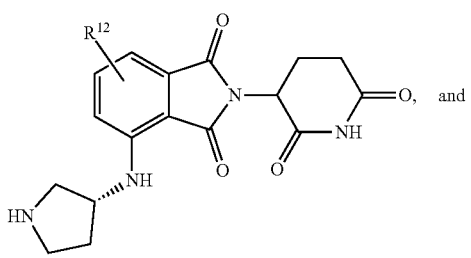
, and
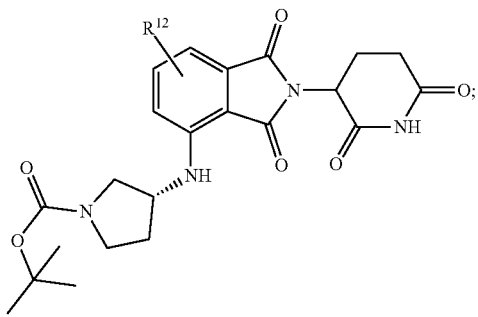
;
wherein A is CH$_2$ or C(O).
Embodiments of NR$^1$R$^2$
Non-limiting examples of R$^1$ include:
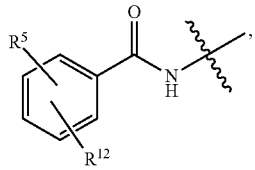
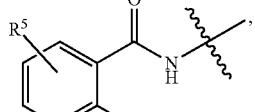
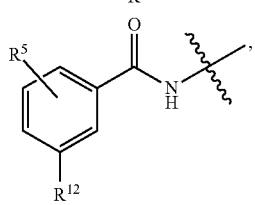
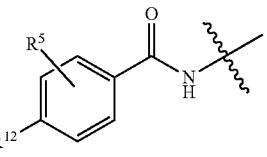
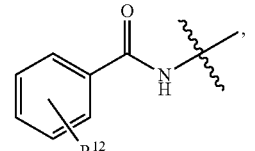
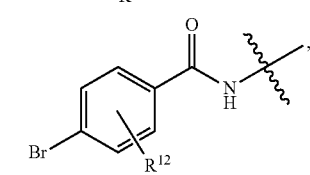
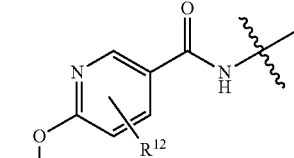
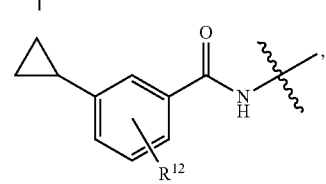
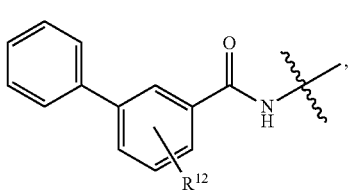

-continued
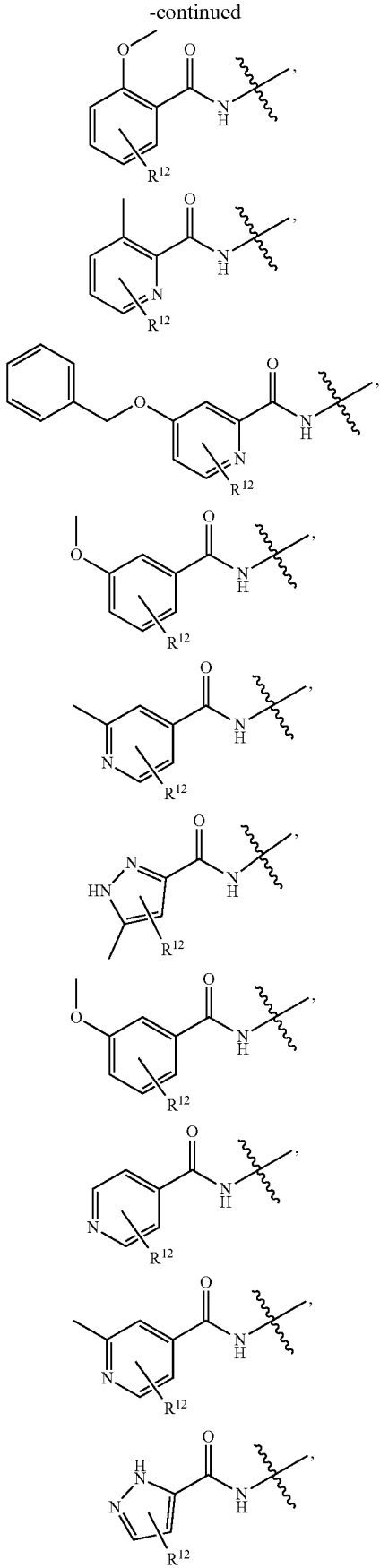
-continued
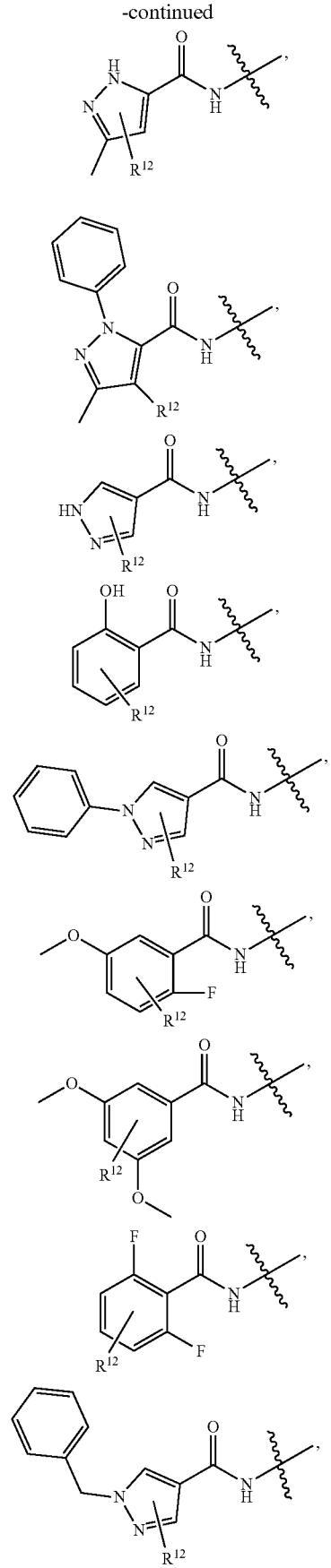

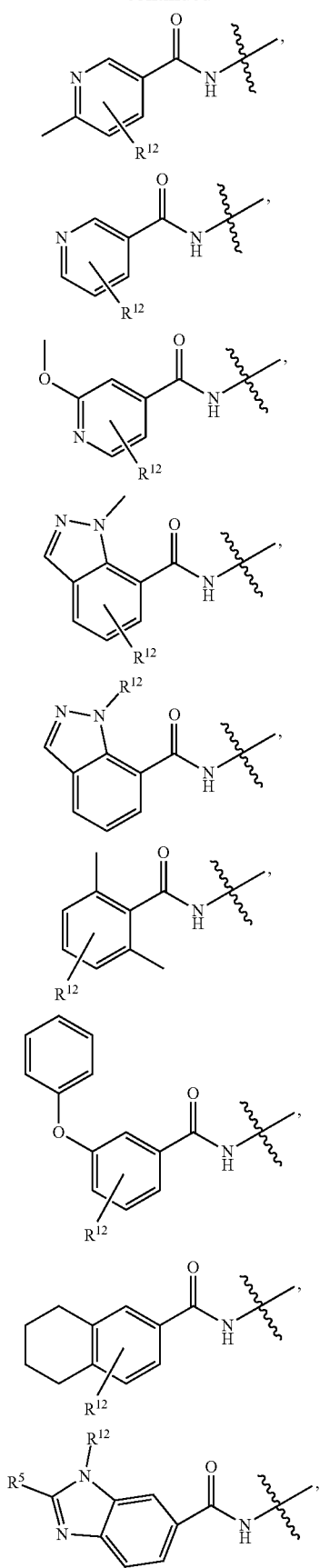
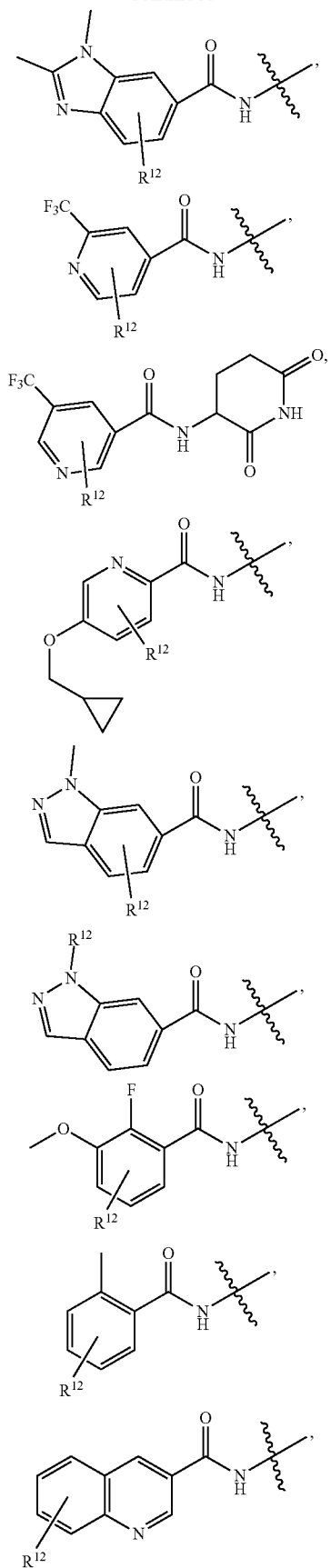

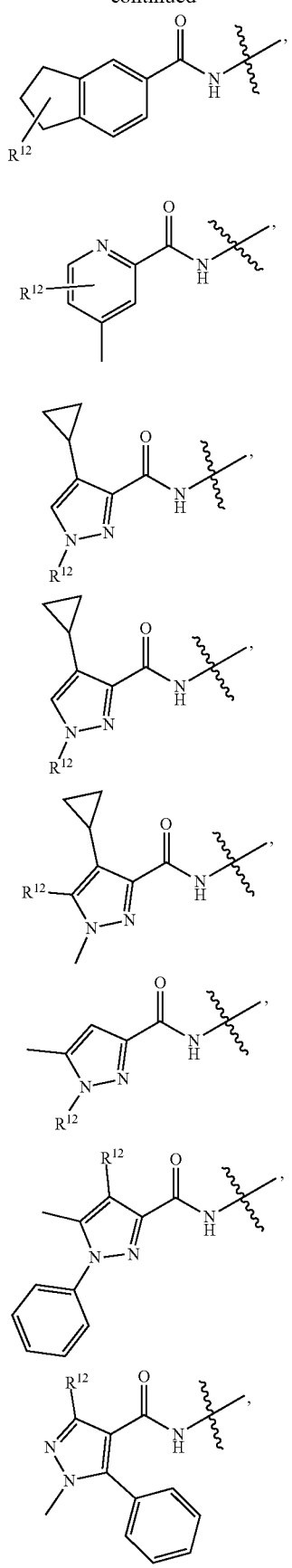
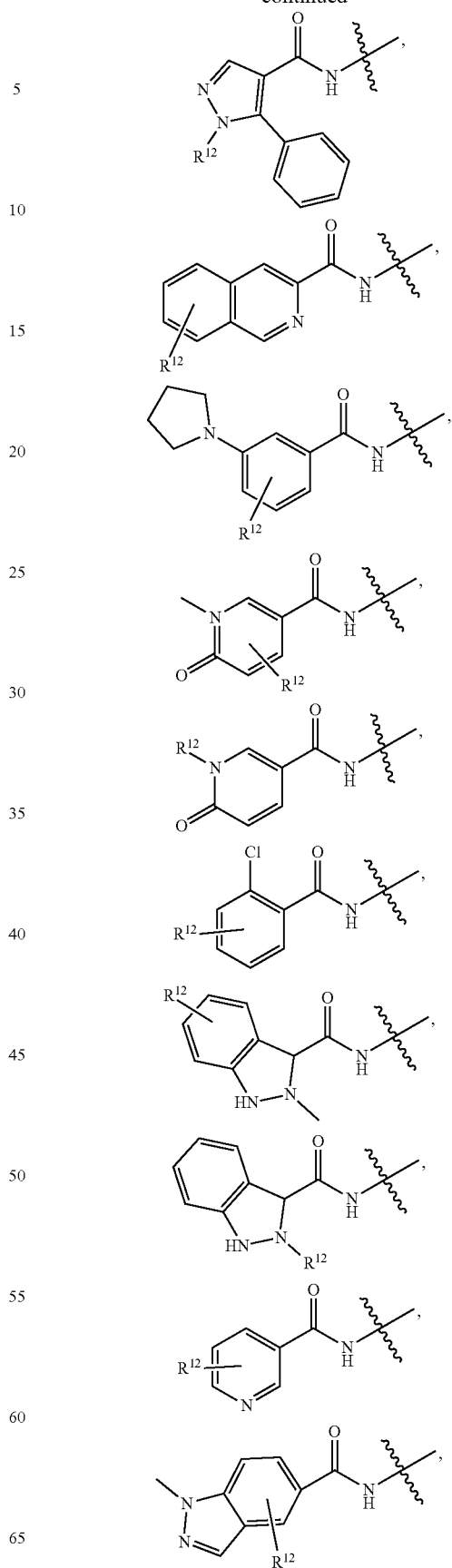

137
-continued
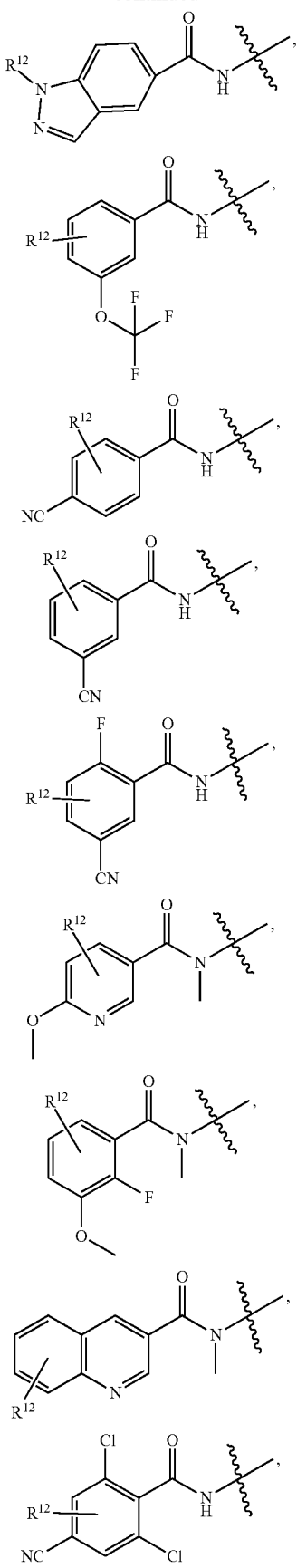
138
-continued
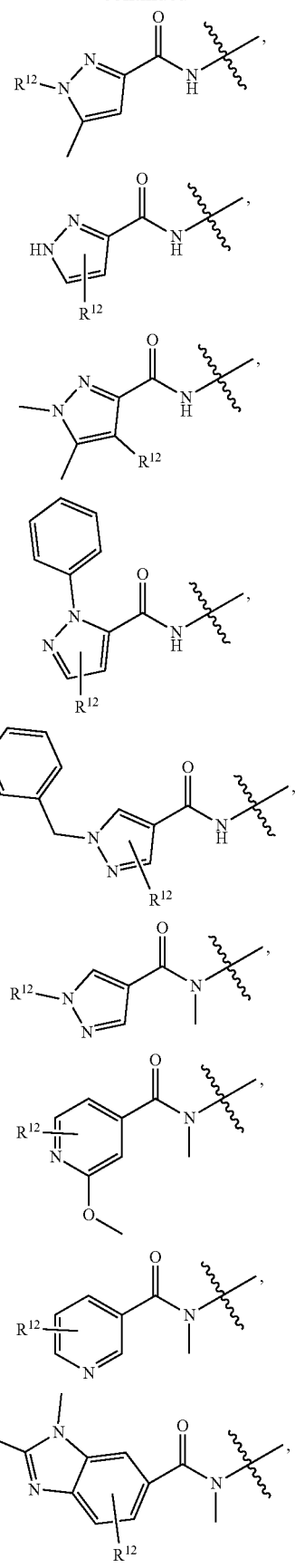

-continued
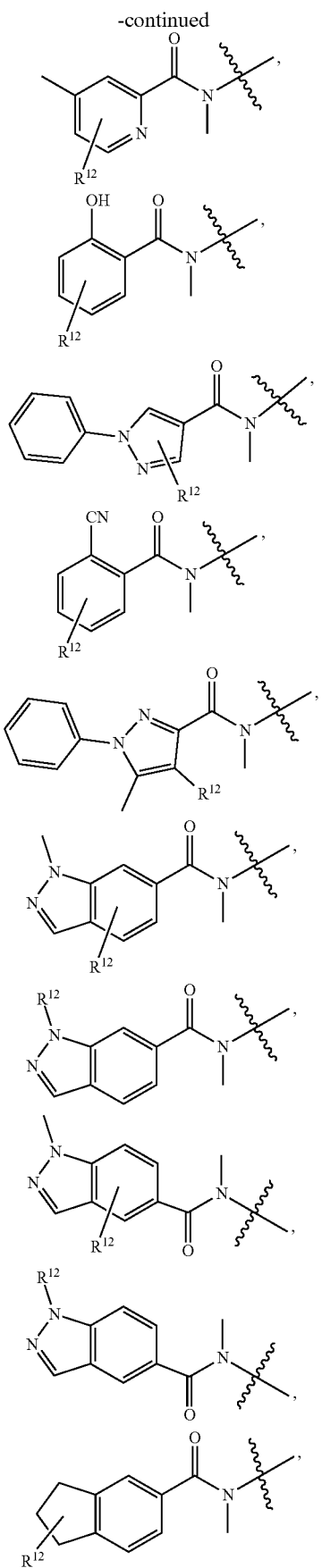
-continued
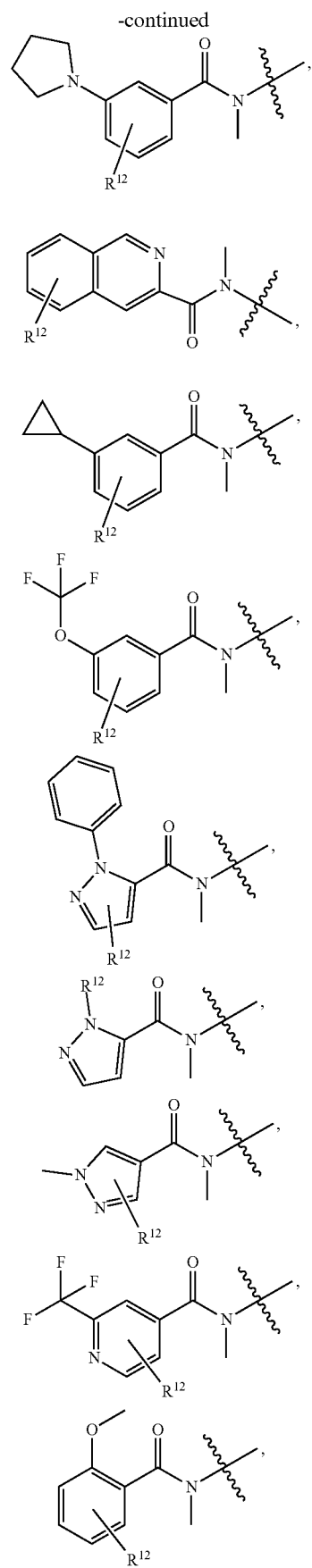

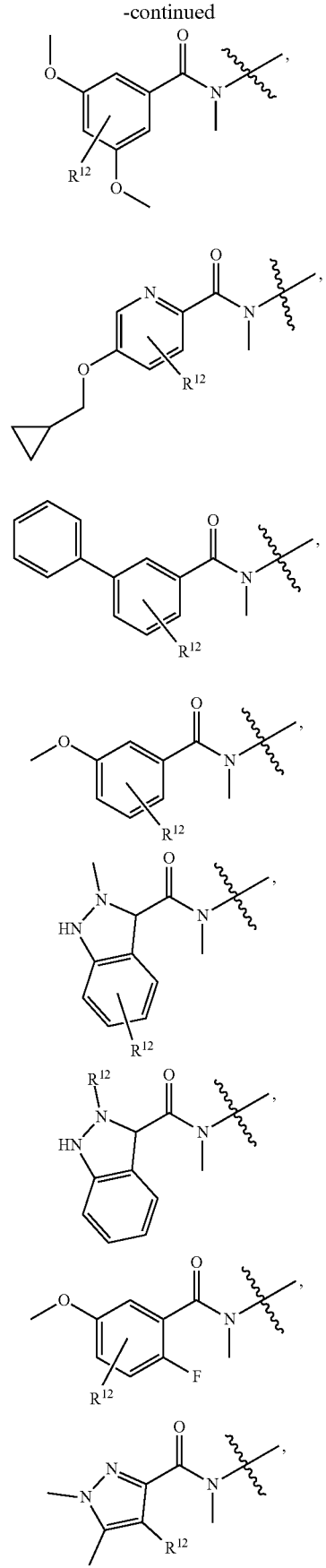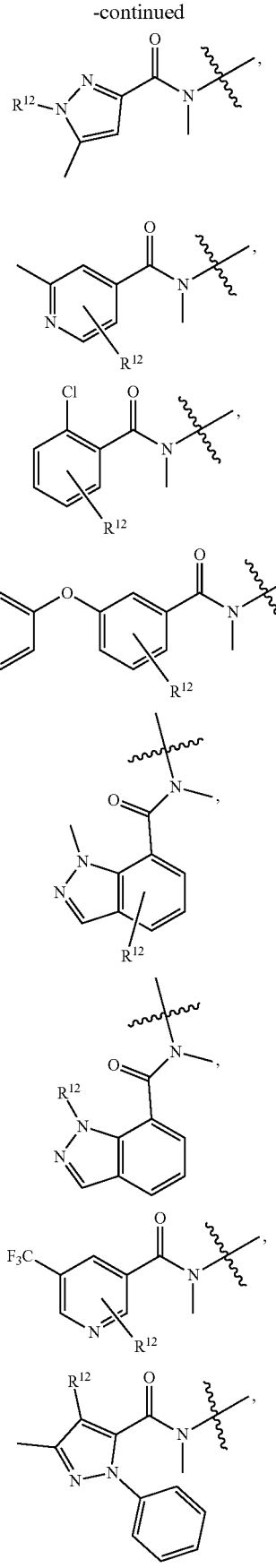

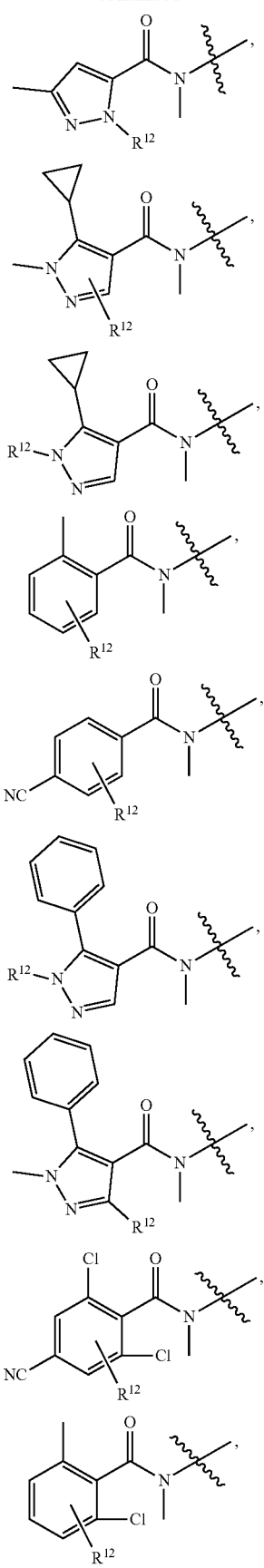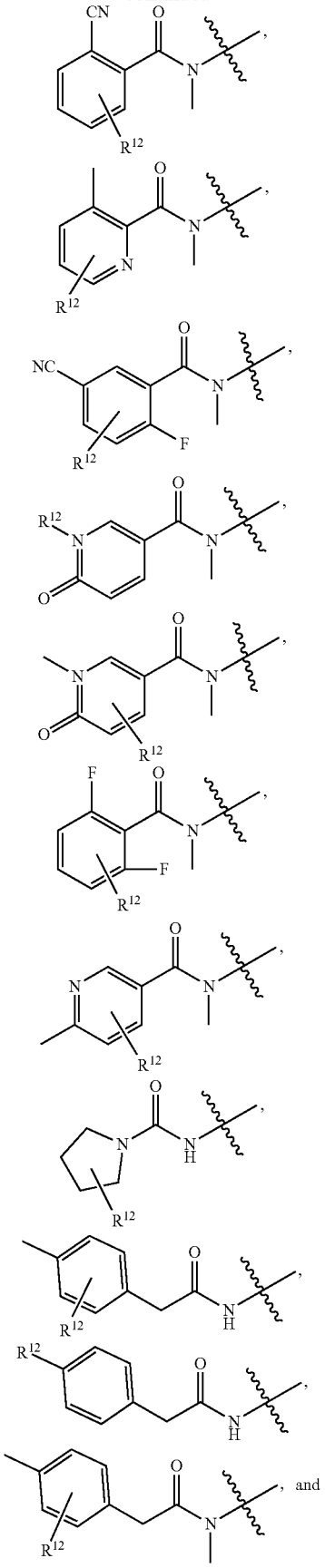

-continued
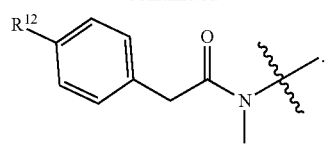
Non-limiting examples of heterocyclo and heteroaryl species formed by combining $R^1$ and $R^2$ include:
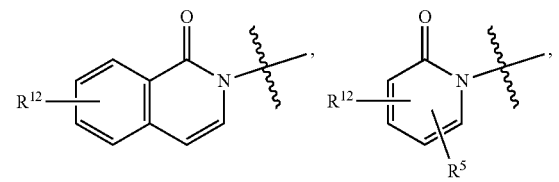
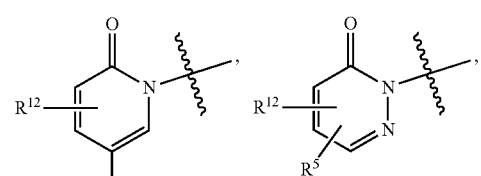
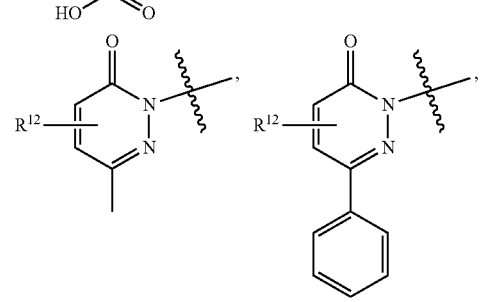
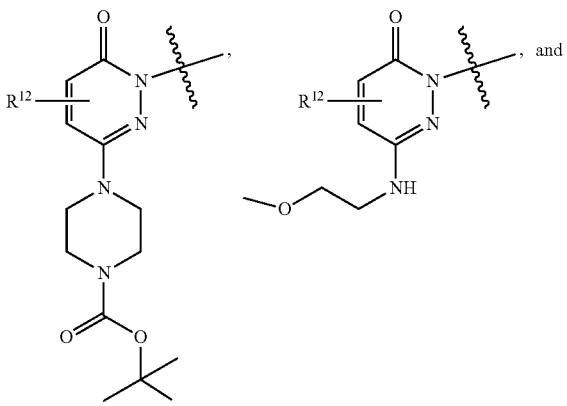
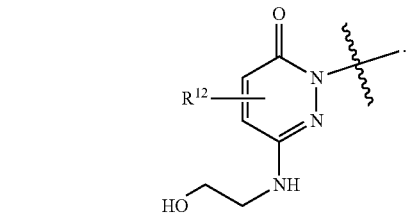
Non-limiting examples of heterocyclo and heteroaryl species formed by combining $R^1$ and $R^2$ include:
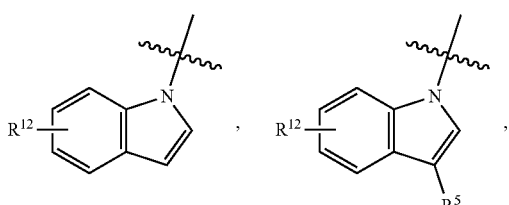
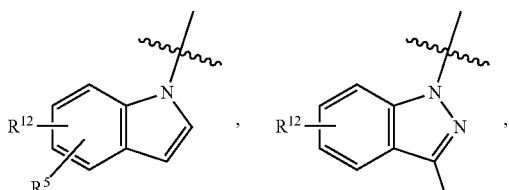
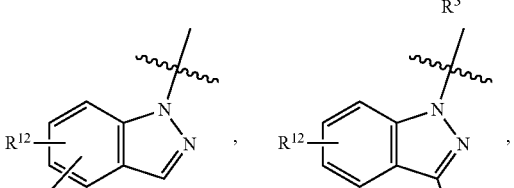
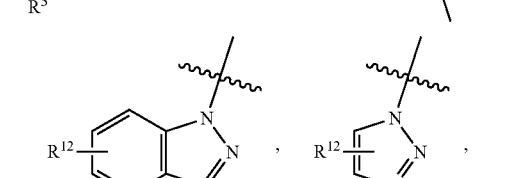
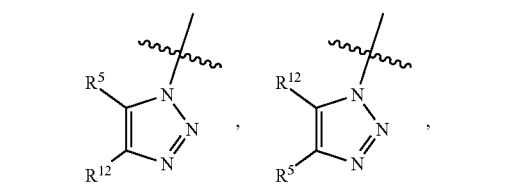
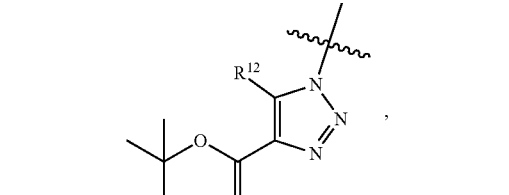
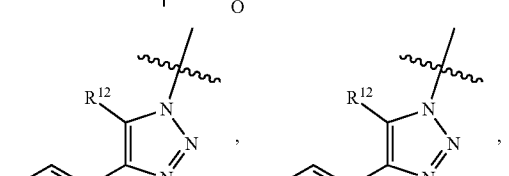
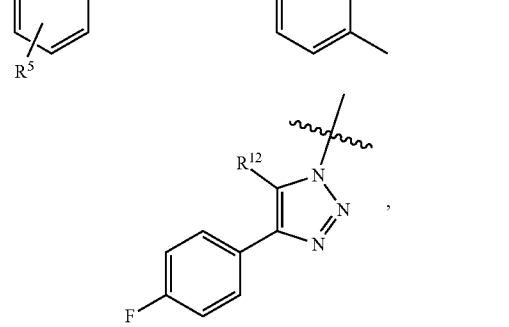

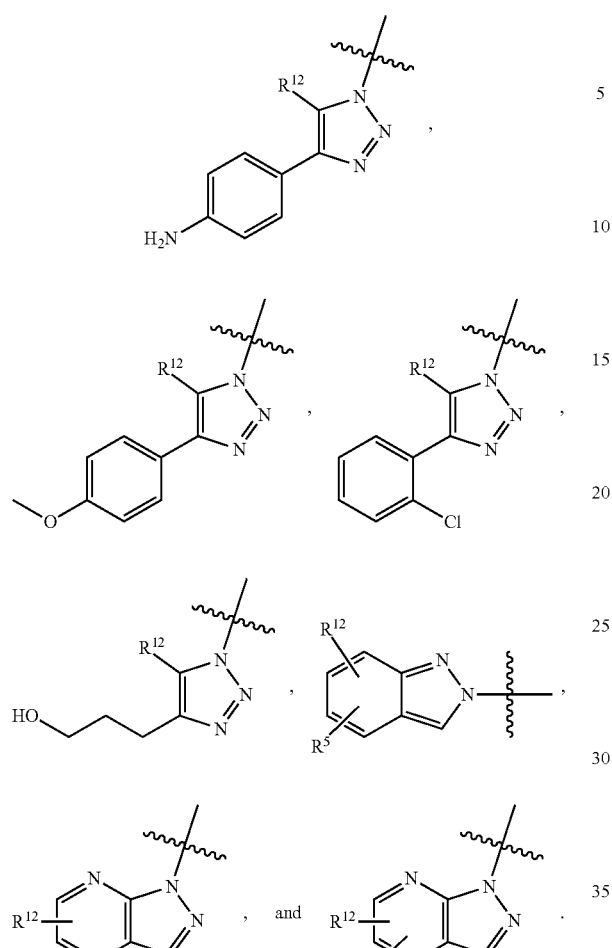
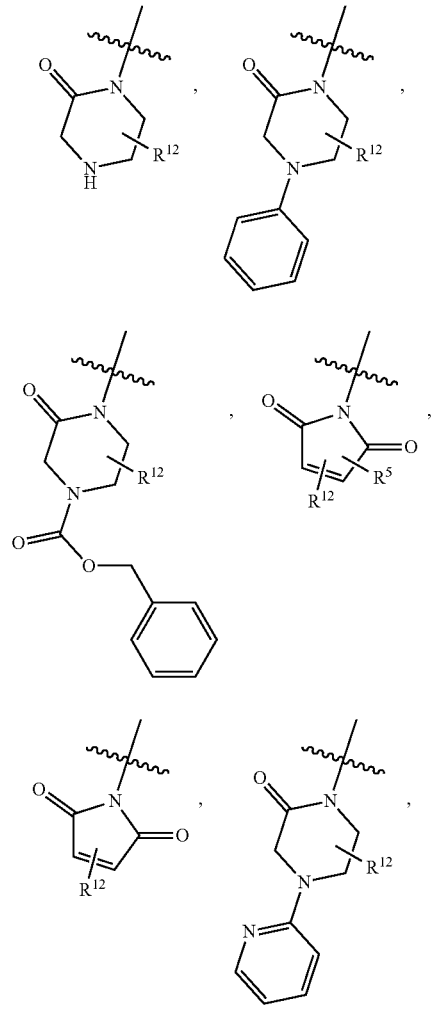
Non-limiting examples of heterocyclo and heteroaryl species formed by combining $R^1$ and $R^2$ include:
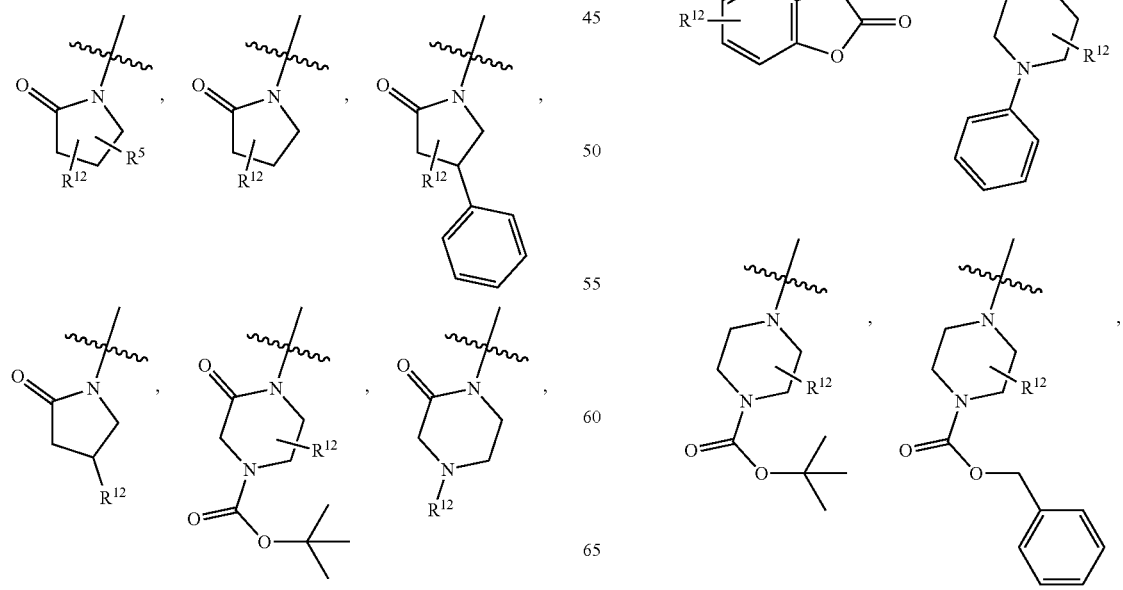

-continued

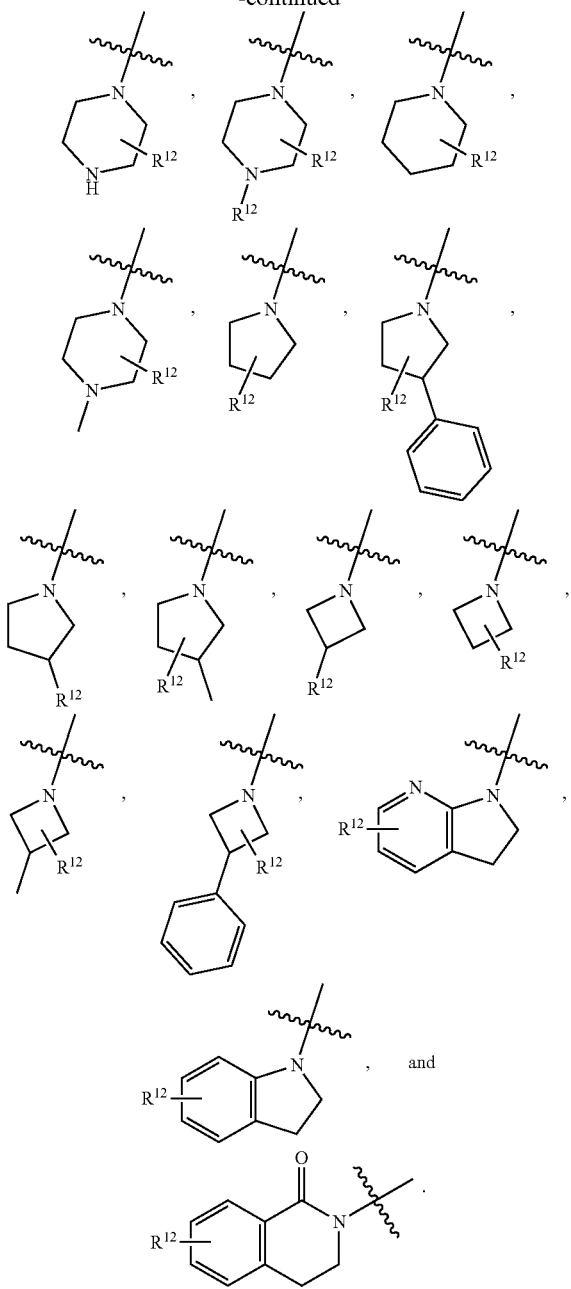

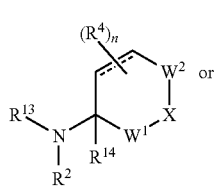

Formula III and Formula IV

In another aspect of the present invention a compound of Formula III or Formula IV is provided:

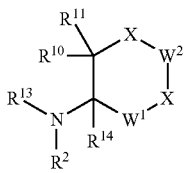
(III)

-continued

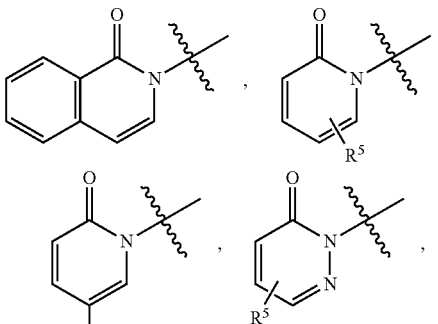
(IV)

or a pharmaceutically acceptable salt, N-oxide, isotopic derivative, or prodrug thereof, optionally in a pharmaceutically acceptable carrier to form a composition as described above.

Non-limiting examples of heterocyclo and heteroaryl species formed by combining $R^{13}$ and $R^2$ include:

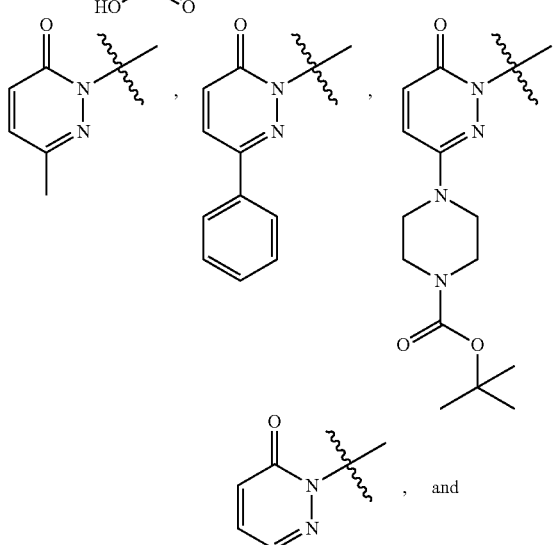

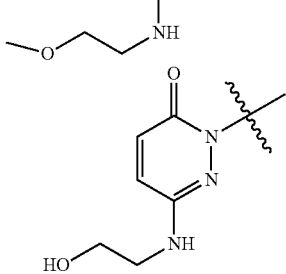

Non-limiting examples of heterocyclo and heteroaryl species formed by combining $R^{13}$ and $R^2$ include:

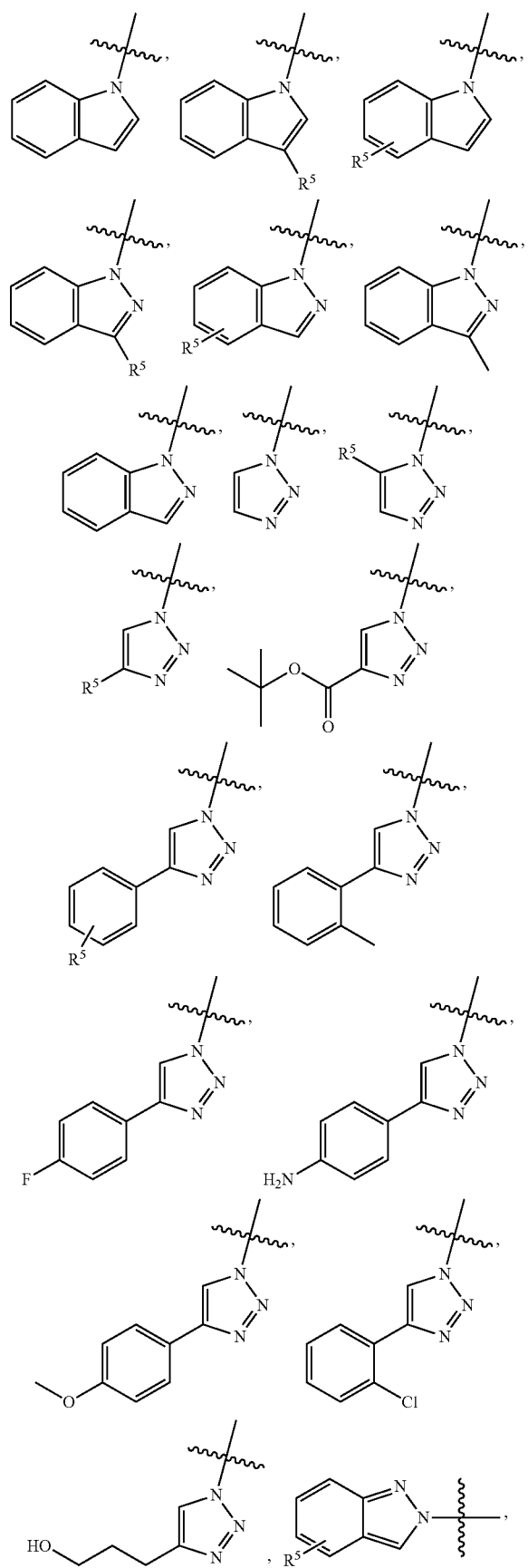
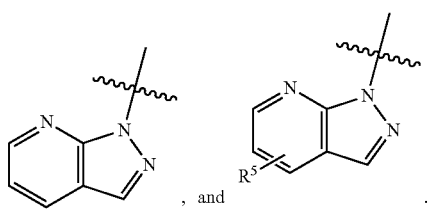
Non-limiting examples of heterocyclo and heteroaryl species formed by combining $R^{13}$ and $R^2$ include:
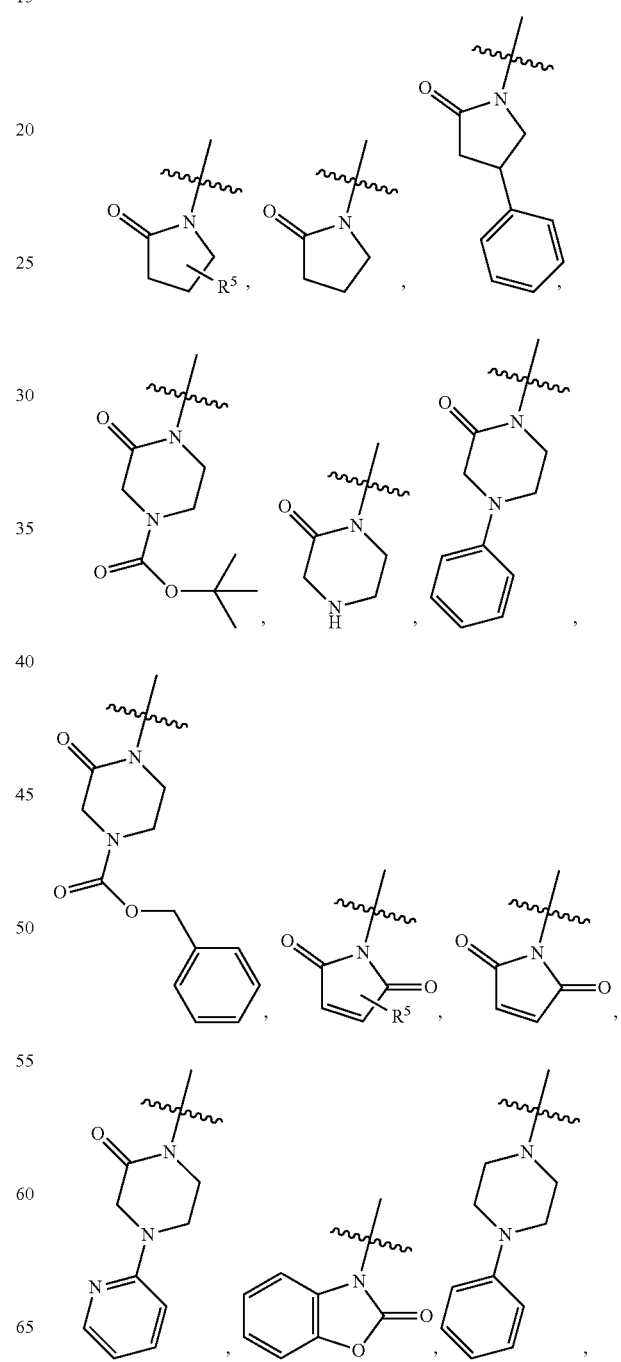

153
-continued
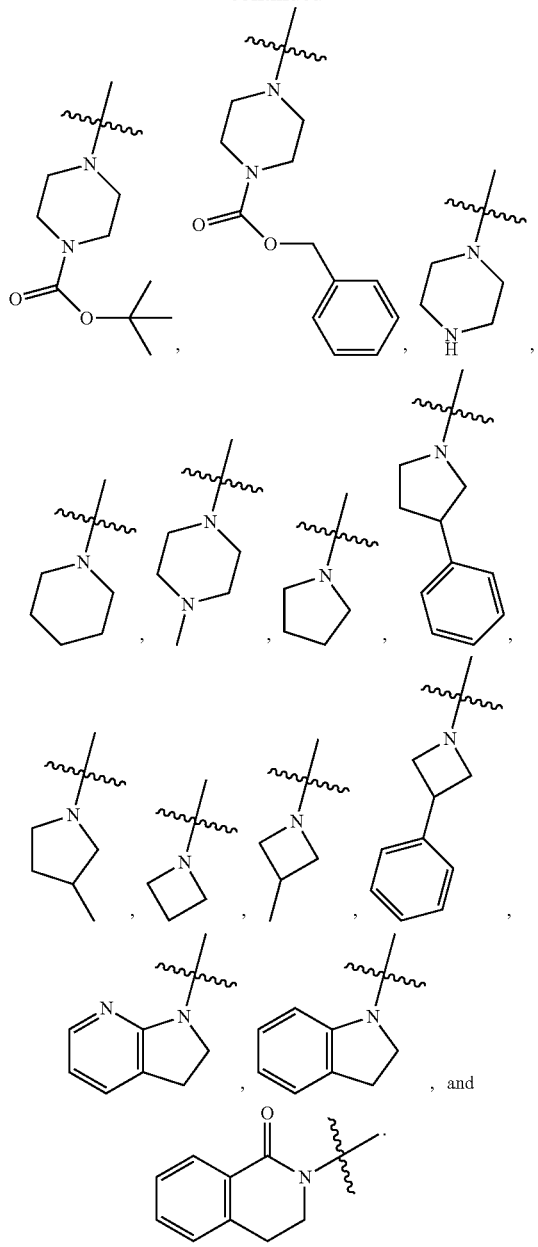
Nonlimiting examples of compounds of Formula III include:
154
-continued
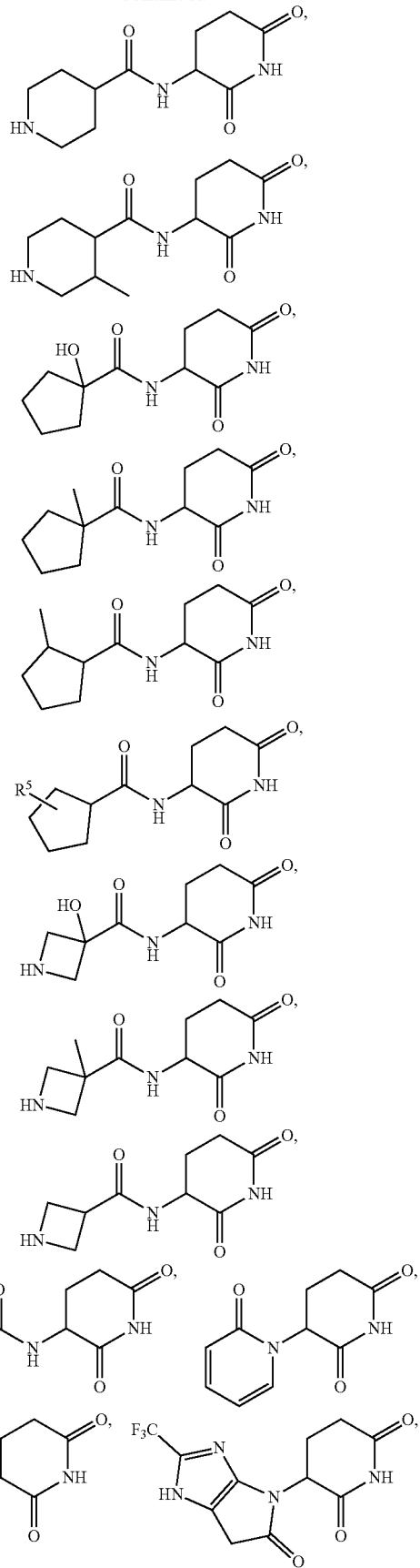

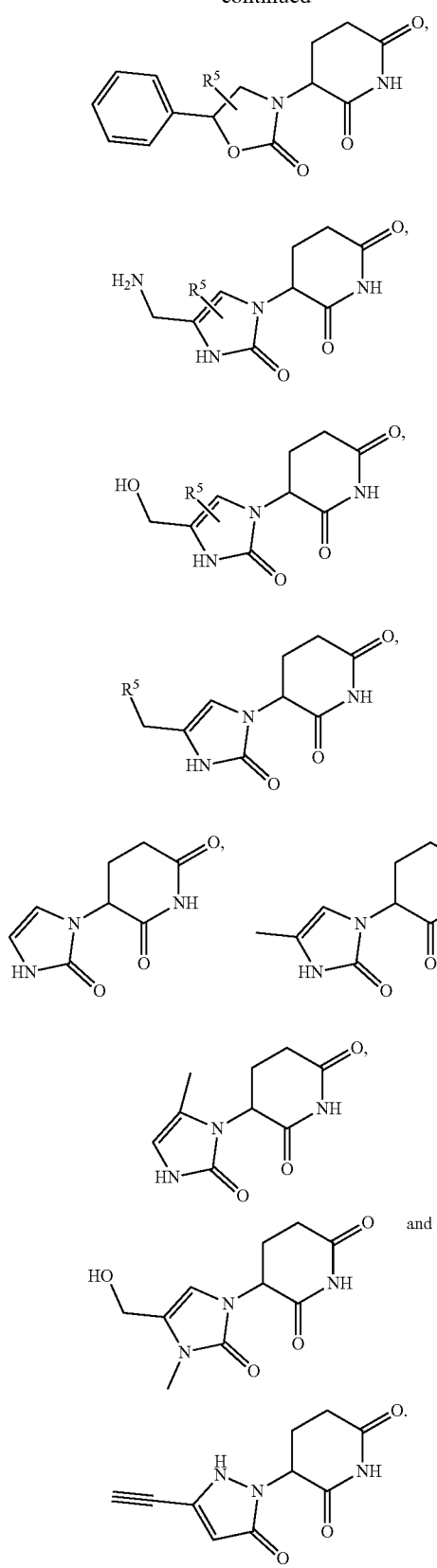
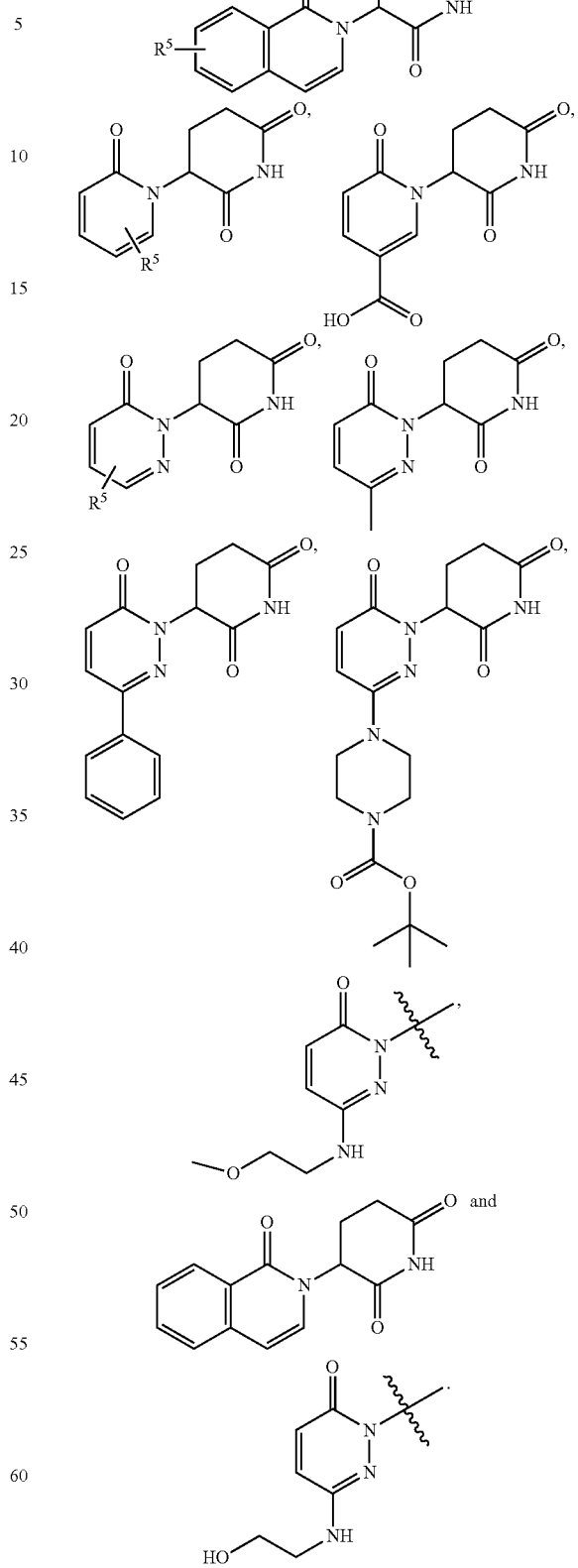
Additional non-limiting examples of compounds of Formula III include:
Additional non-limiting examples of compounds of Formula III include:

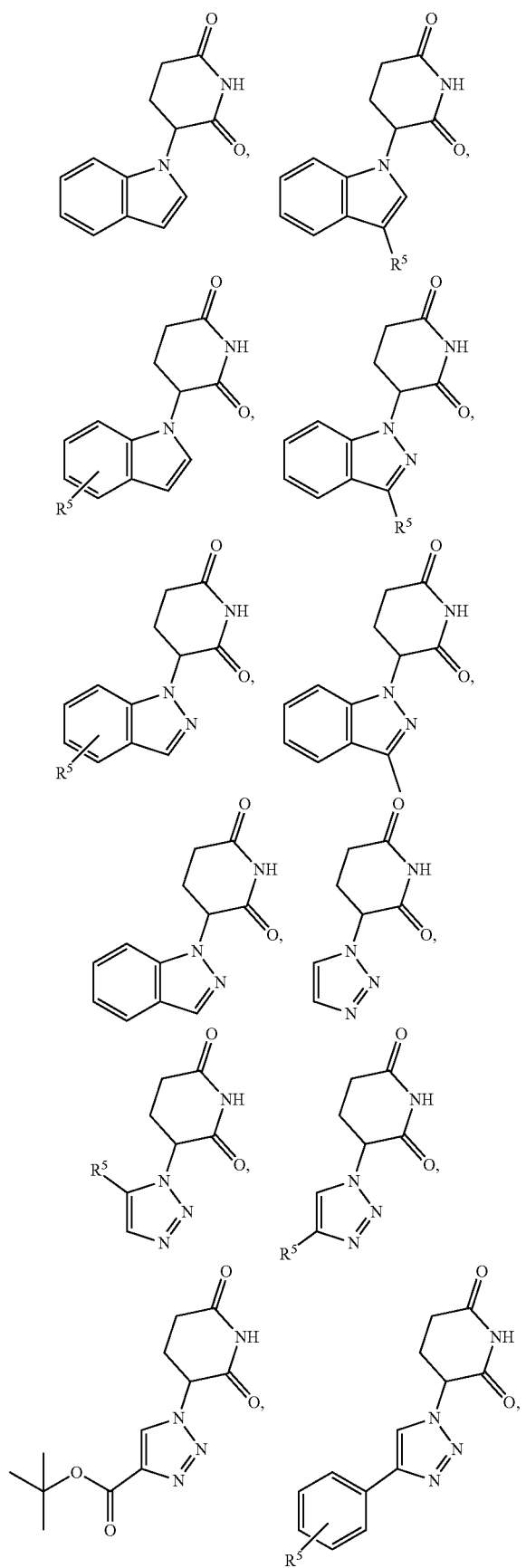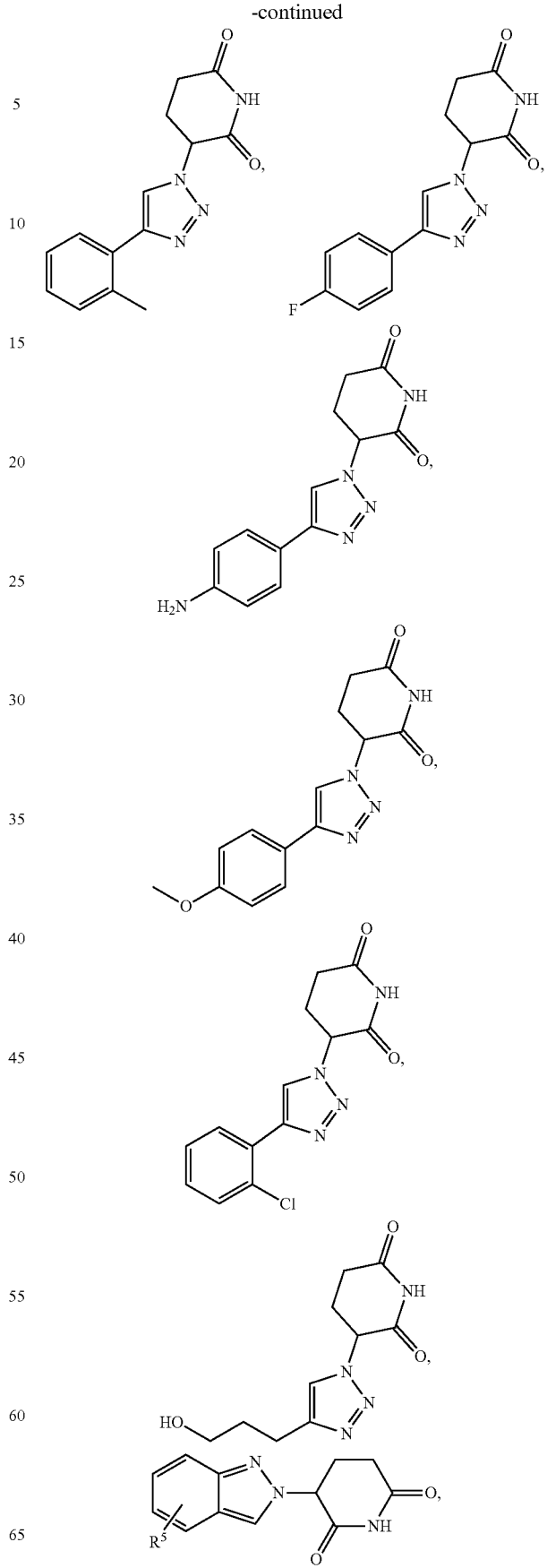

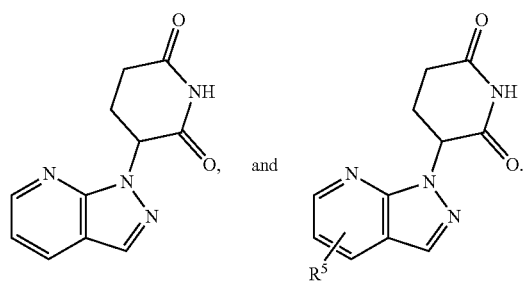
Additional non-limiting examples of compounds of Formula I include:
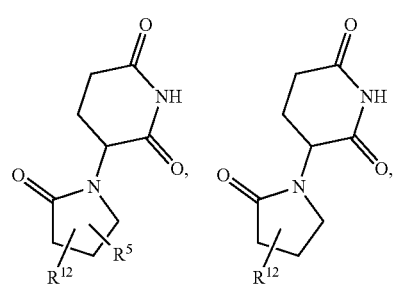
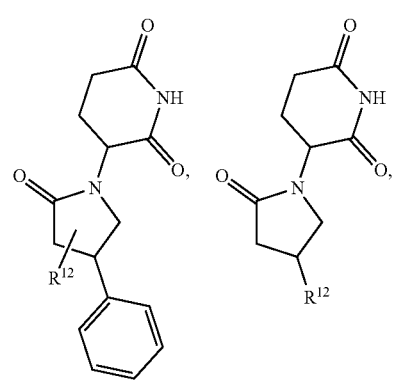
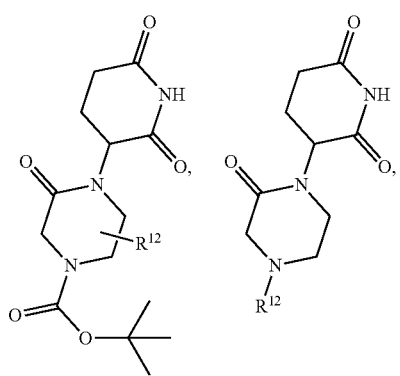
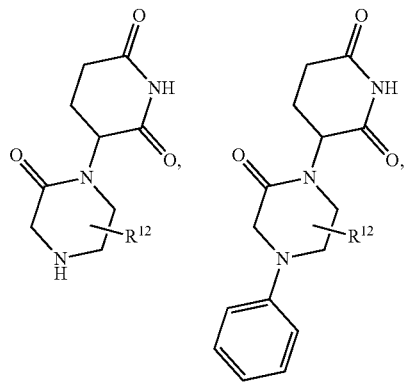
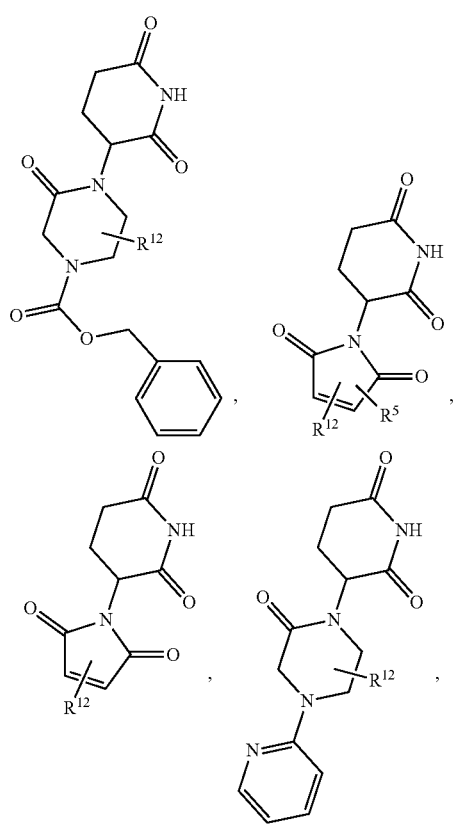
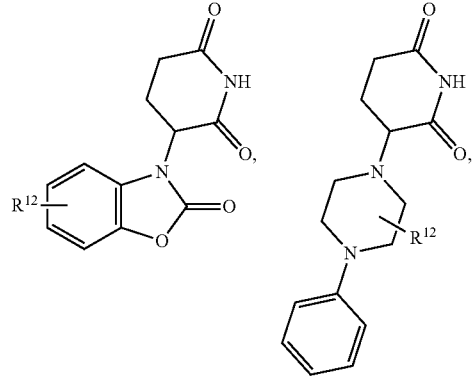

-continued

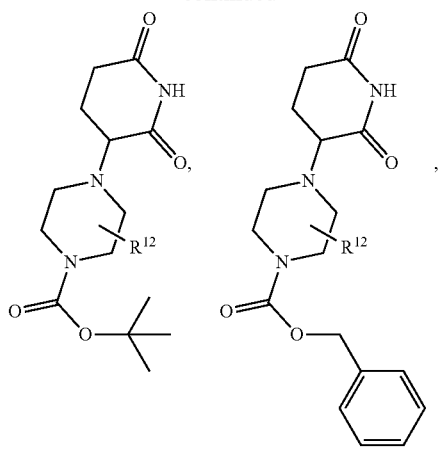

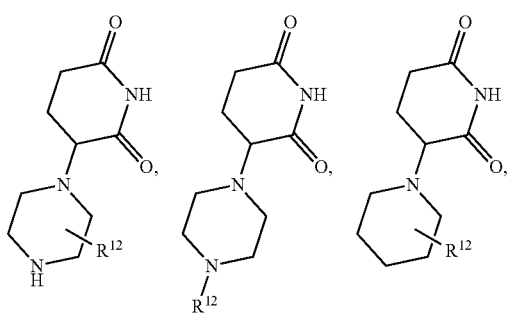

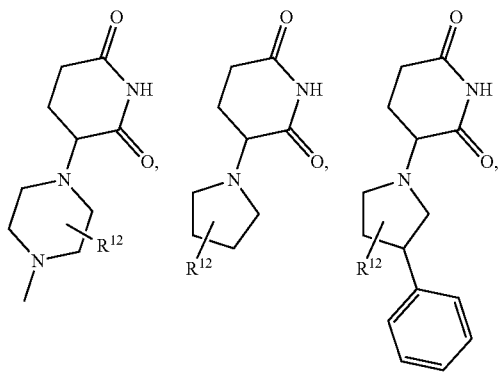

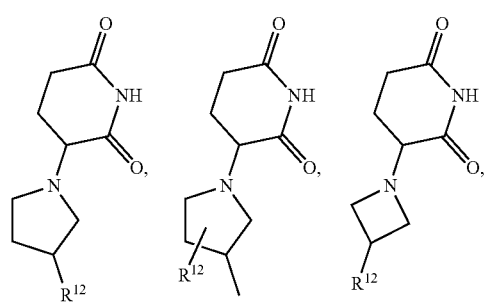

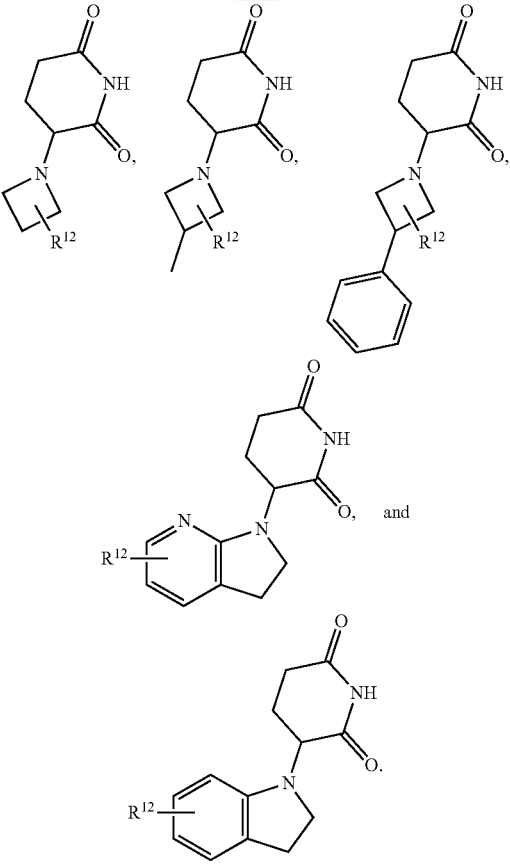

Linker

A Linker is included in the Degronimers of Formula I, II, V and VII. Linker is a bond or a chemically stable group that attaches a Degron to a Targeting Ligand.

Any of the Linkers described herein can be used in either direction, i.e., either the left end is linked to the Degron and the right end to the Target Linker, or the left end is linked to the Target Linker and the right end is linked to the Degron. According to the invention, any desired linker can be used as long as the resulting compound has a stable shelf life for at least 2 months, 3 months, 6 months or 1 year as part of a pharmaceutically acceptable dosage form, and itself is pharmaceutically acceptable.

In a typical embodiment, the Linker has a chain of 2 to 14, 15, 16, 17, 18 or 20 or more carbon atoms of which one or more carbons can be replaced by a heteroatom such as O, N, S, or P. In certain embodiments the chain has 2, 3, 4, 5, 6, 7, 8, 9, 10, 11, 12, 13, 14, 15, 16, 17, 18, 19 or 20 contiguous atoms in the chain. For example, the chain may include 1 or more ethylene glycol units that can be contiguous, partially contiguous or non-contiguous (for example, 2, 3, 4, 5, 6, 7, 8, 9, 10, 11 or 12 ethylene glycol units). In certain embodiments the chain has at least 1, 2, 3, 4, 5, 6, 7, or 8 contiguous chains which can have branches which can be independently alkyl, heteroalkyl, aryl, heteroaryl, alkenyl, or alkynyl, aliphatic, heteroaliphatic, cycloalkyl or heterocyclic substituents.

In other embodiments, the linker can include or be comprised of one or more of ethylene glycol, propylene glycol, lactic acid and/or glycolic acid. In general, propylene glycol adds hydrophobicity, while propylene glycol adds hydrophilicity. Lactic acid segments tend to have a longer half-life than glycolic acid segments. Block and random lactic acid-co-glycolic acid moieties, as well as ethylene glycol and propylene glycol, are known in the art to be pharmaceutically acceptable and can be modified or arranged to obtain the desired half-life and hydrophilicity. In certain aspects, these units can be flanked or interspersed with other moieties, such as aliphatic, including alkyl, heteroaliphatic, aryl, heteroaryl, heterocyclic, cycloalkyl, etc., as desired to achieve the appropriate drug properties.

In one embodiment, the Linker is a moiety selected from Formula LI, Formula LII, Formula LIII, Formula LIV, Formula LV, Formula LVI, and Formula LVII.

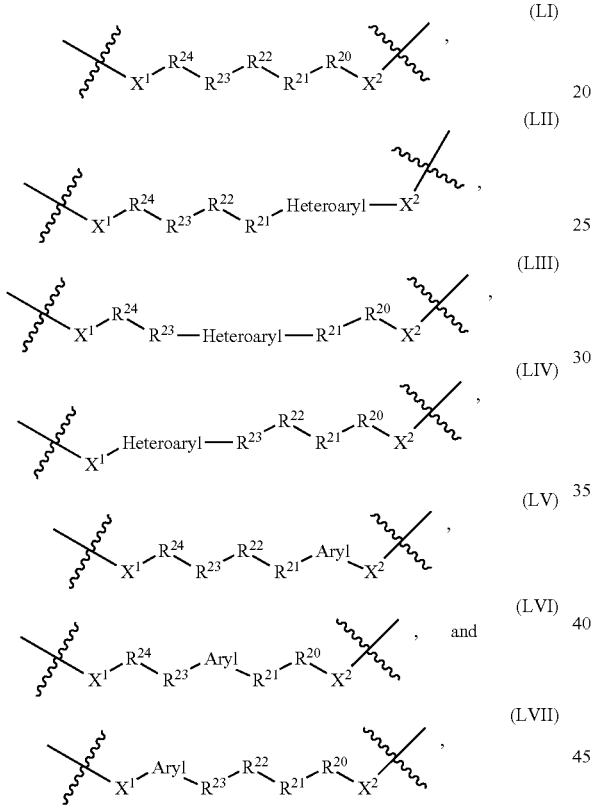

wherein:
$X^1$ and $X^2$ are independently selected from bond, NH, $NR^{25}$, $CH_2$, $CHR^{25}$, $C(R^{25})_2$, O, and S;
$R^{20}$, $R^{21}$, $R^{22}$, $R^{23}$, and $R^{24}$ are independently selected from bond, alkyl, —C(O)— —C(O)O—, —OC(O)—, —C(O)alkyl, —C(O)Oalkyl, —C(S)—, —SO$_2$—, —S(O)—, —C(S)—, —C(O)NH—, —NHC(O)—, —N(alkyl)C(O)—, —C(O)N(alkyl)-, —O—, —S—, —NH—, —N(alkyl)-, —CH(—O—R$^{26}$)—, —CH(—NHR$^{25}$)—, —CH(—NH$_2$)—, —CH(—NR$^{25}$$_2$)—, —C(—O—R$^{26}$)alkyl-, —C(—NHR$^{25}$)alkyl-, —C(—NH$_2$)alkyl-, —C(—NR$^{25}$$_2$)alkyl-, —C(R$^4$R$^4$)—, -alkyl(R$^{27}$)-alkyl(R$^{28}$)—, —C(R$^{27}$R$^{28}$)—, —P(O)(OR$^{26}$)O—, —P(O)(OR$^{26}$)—, —NHC(O)NH—, —N(R$^{25}$)C(O)N(R$^{25}$)—, —N(H)C(O)N(R$^{25}$)—, polyethylene glycol, poly(lactic-co-glycolic acid), alkene, haloalkyl, alkoxy, and alkyne;
or $R^{20}$, $R^{21}$, $R^{22}$, $R^{23}$, and $R^{24}$ can in addition to those above be independently selected from heteroarylalkyl, aryl, arylalkyl, heterocycle, aliphatic, heteroaliphatic, heteroaryl, polypropylene glycol, lactic acid, glycolic acid, carbocycle, or —O—(CH$_2$)$_{1-12}$—O—, —NH—(CH$_2$)$_{1-12}$—NH—, —NH—(CH$_2$)$_{1-12}$—O—, or —O—(CH$_2$)$_{1-12}$—NH—, —S—(CH$_2$)$_{1-12}$—O—, —O—(CH$_2$)$_{1-12}$—S—, —S—(CH$_2$)$_{1-12}$—S—, —S—(CH$_2$)$_{1-12}$—NH—, —NH—(CH$_2$)$_{1-12}$—S—, (and wherein the 1-12 can be independently 1, 2, 3, 4, 5, 6, 7, 8, 9, 10, 11 or 12, and wherein one or more of the CH$_2$ or NH can be modified by substitution of a H for a methyl, ethyl, cyclopropyl, F (if on carbon), etc., as described herein), and optionally, a heteroatom, heteroalkyl, aryl, heteroaryl or cycloaliphatic group is interspersed in the chain). Certain nonlimiting examples include —O—CH(CH$_3$)—CH(CH$_3$)CH—O—, —O—CH$_2$—CH(CH$_3$)CH—O—, —O—CH(CH$_3$)—CH$_2$CH—O—, etc.;

each of which $R^{20}$, $R^{21}$, $R^{22}$, $R^{23}$, and $R^{24}$ is optionally substituted with one or more substituents selected from $R^{1'}$ or alternatively as described in Section 1. Definitions;

$R^{101}$ is independently selected at each occurrence from hydrogen, alkyl, alkene, alkyne, haloalkyl, alkoxy, hydroxyl, aryl, heteroaryl, heterocycle, arylalkyl, heteroarylalkyl, heterocycloalkyl, aryloxy, heteroaryloxy, CN, —COOalkyl, COOH, NO$_2$, F, Cl, Br, I, CF$_3$, NH$_2$, NHalkyl, N(alkyl)$_2$, aliphatic, and heteroaliphatic; and $R^4$ is selected at each instance from: alkyl, alkene, alkyne, halogen, hydroxyl, alkoxy, azide, amino, cyano, —NH(aliphatic, including alkyl), —N(aliphatic, including alkyl)$_2$, —NHSO$_2$(aliphatic, including alkyl), —N(aliphatic, including alkyl)SO$_2$alkyl, —NHSO$_2$(aryl, heteroaryl or heterocyclic), —N(alkyl)SO$_2$(aryl, heteroaryl or heterocyclic) —NHSO$_2$alkenyl, —N(alkyl)SO$_2$alkenyl, —NHSO$_2$alkynyl, —N(alkyl)S$_2$alkynyl, and haloalkyl; and in addition to these can also be selected from aliphatic, heteroaliphatic, aryl, heteroaryl, heteroalkyl and carbocyclic.

In an additional embodiment, the Linker is a moiety selected from Formula LVIII, LIX, and LX:

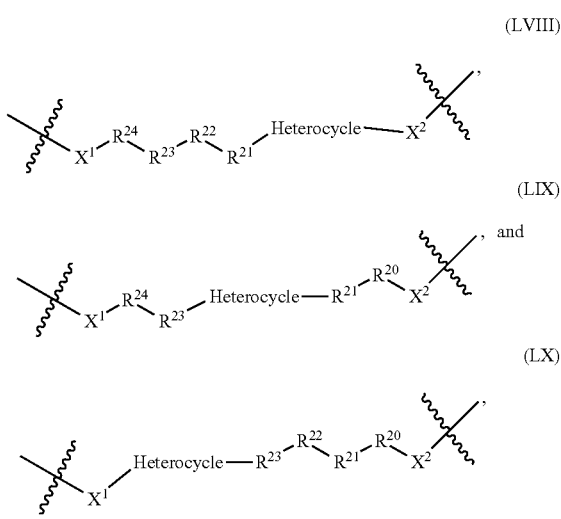

wherein each variable is as it is defined in Formula LI. In alternative embodiments of LVIII, LIX and LX, a carbocyclic ring is used in place of the heterocycle.

The following are non-limiting examples of Linkers that can be used in this invention. Based on this elaboration, those of skill in the art will understand how to use the full breadth of Linkers that will accomplish the goal of the invention.

As certain non-limiting examples, Formula LI, Formula LII, Formula LIII, Formula LIV, Formula LV, Formula LVI, or Formula LVII include:

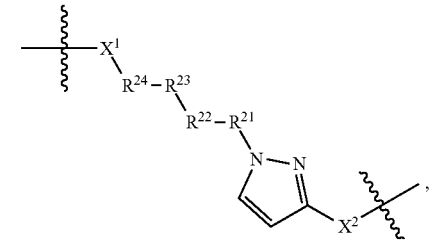

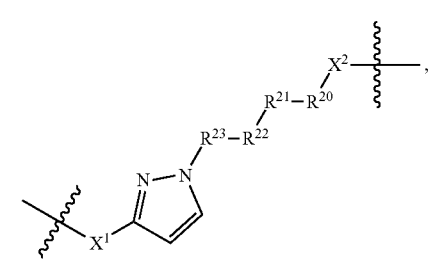

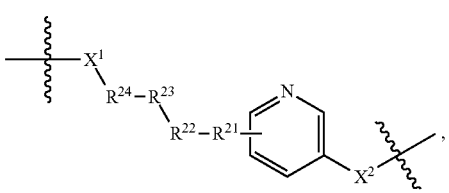

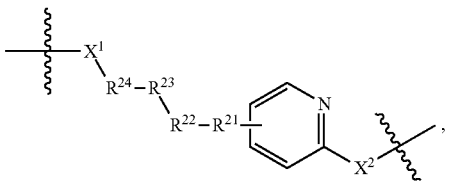

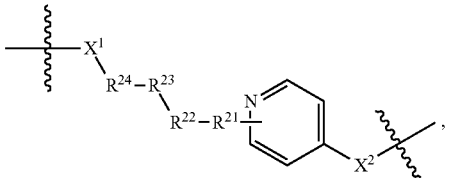

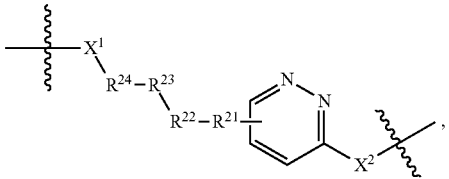

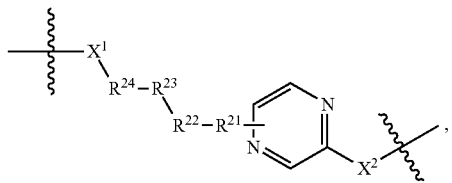

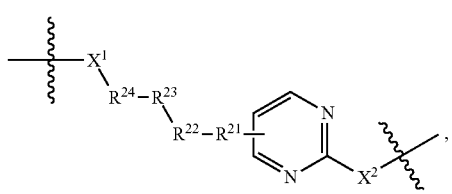

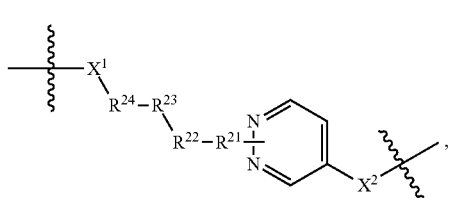

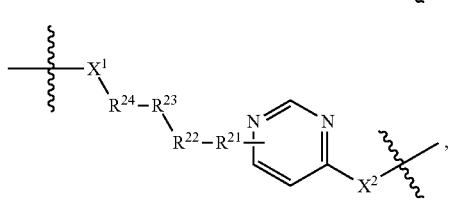

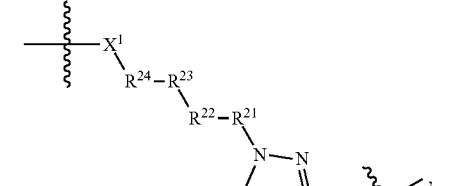

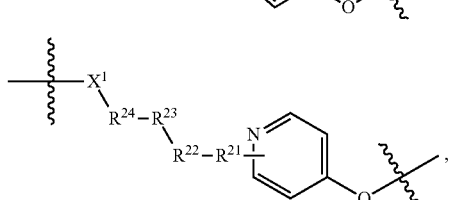

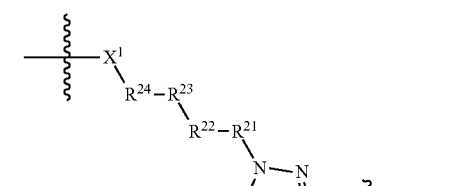

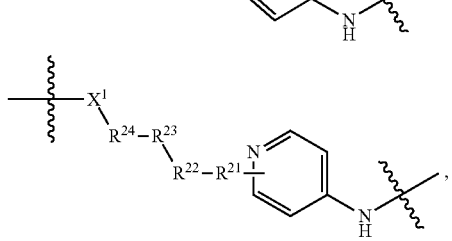

-continued
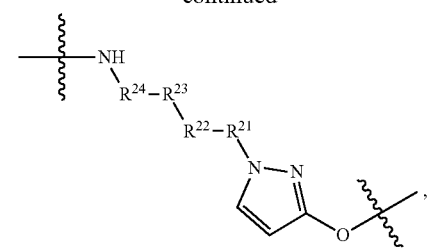
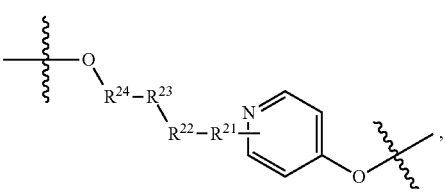
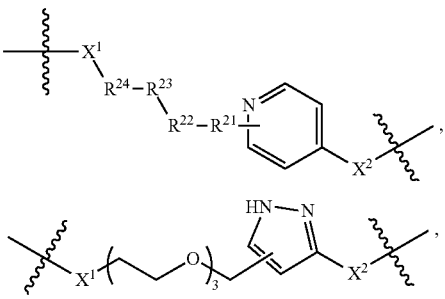
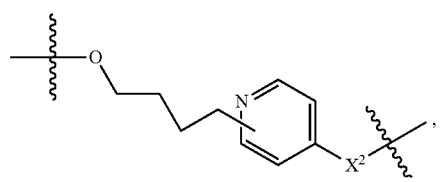
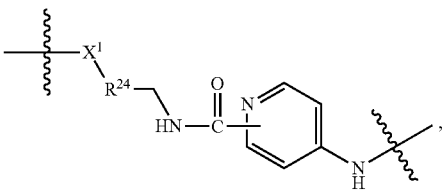
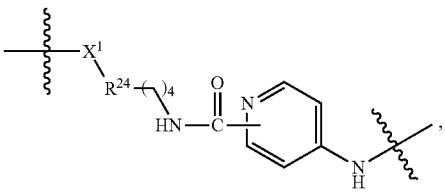
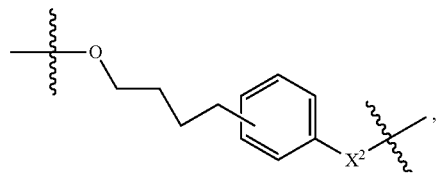
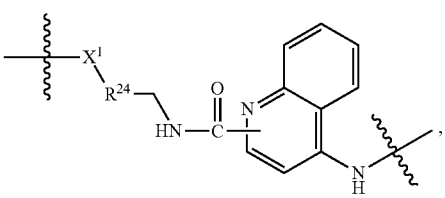
-continued
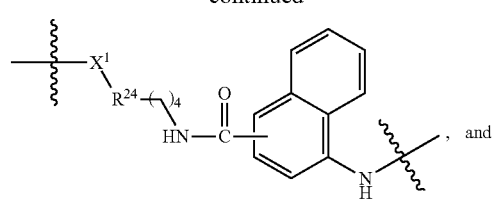
, and
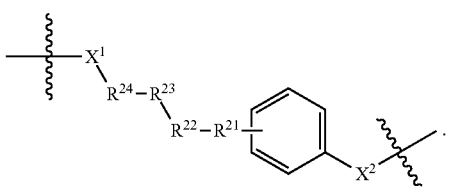
In an additional embodiment Linker is selected from:
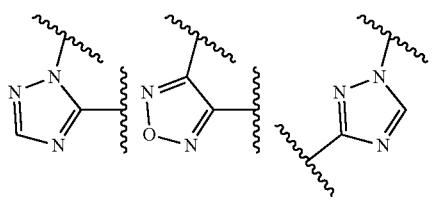
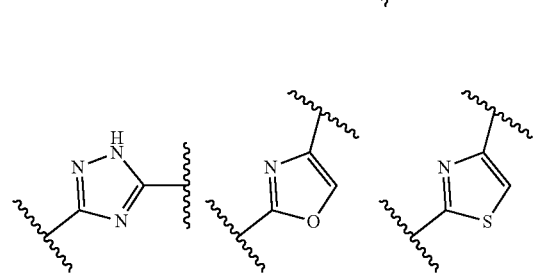
In an additional embodiment Linker is selected from:
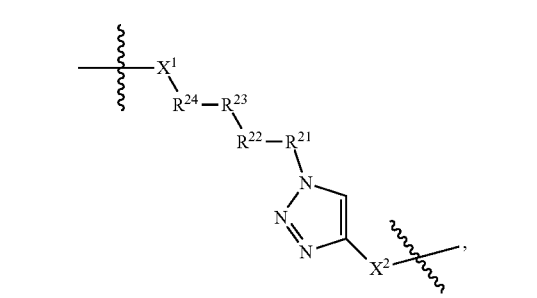

-continued
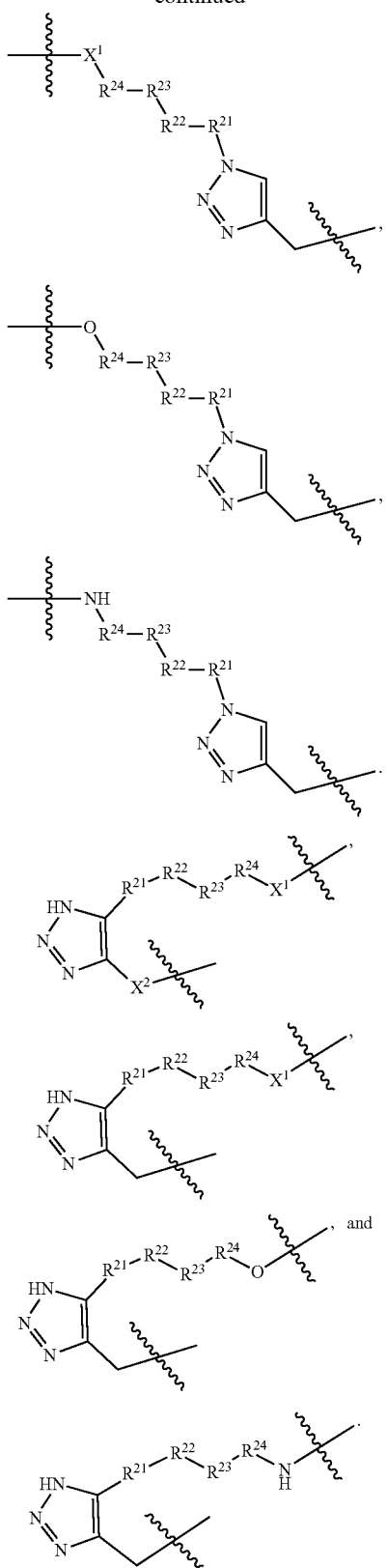
In one embodiment $X^1$ is attached to the Targeting Ligand. In another embodiment $X^2$ is attached to the Targeting Ligand.
Non-limiting examples of moieties of $R^{20}$, $R^{21}$, $R^{22}$, $R^{23}$, and $R^{24}$ include:
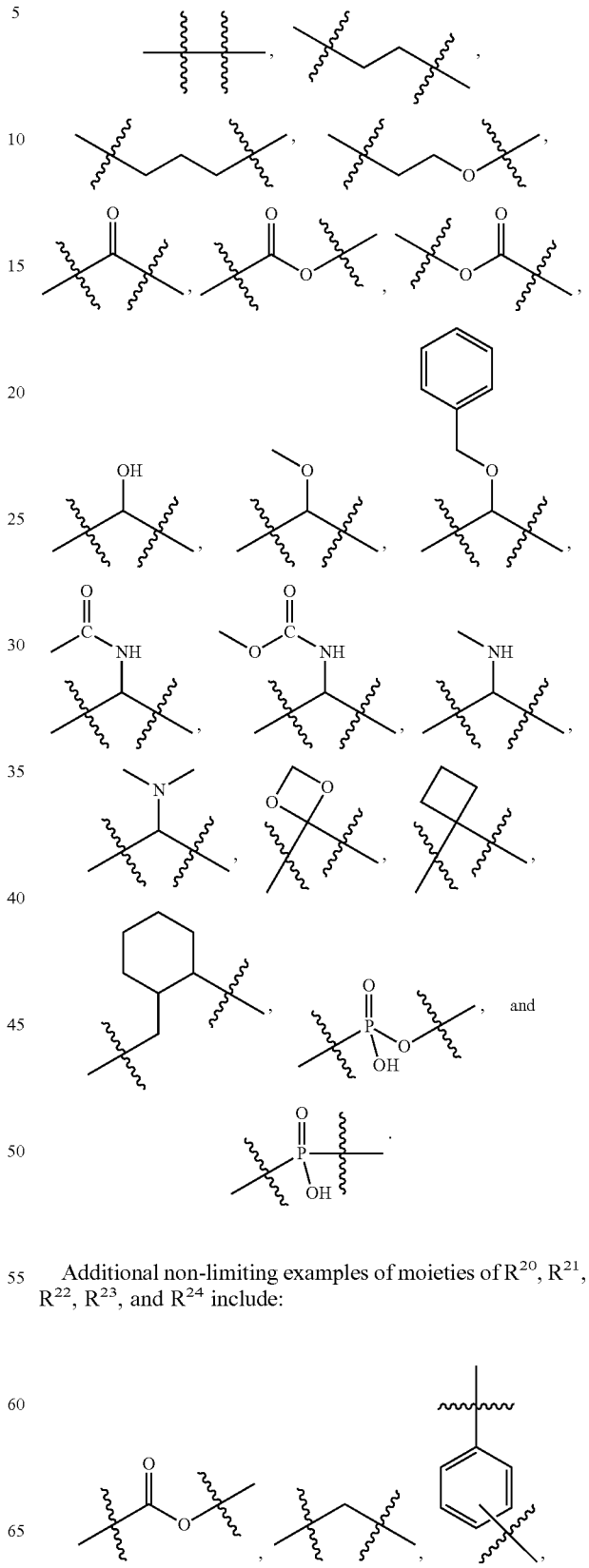
Additional non-limiting examples of moieties of $R^{20}$, $R^{21}$, $R^{22}$, $R^{23}$, and $R^{24}$ include:

-continued
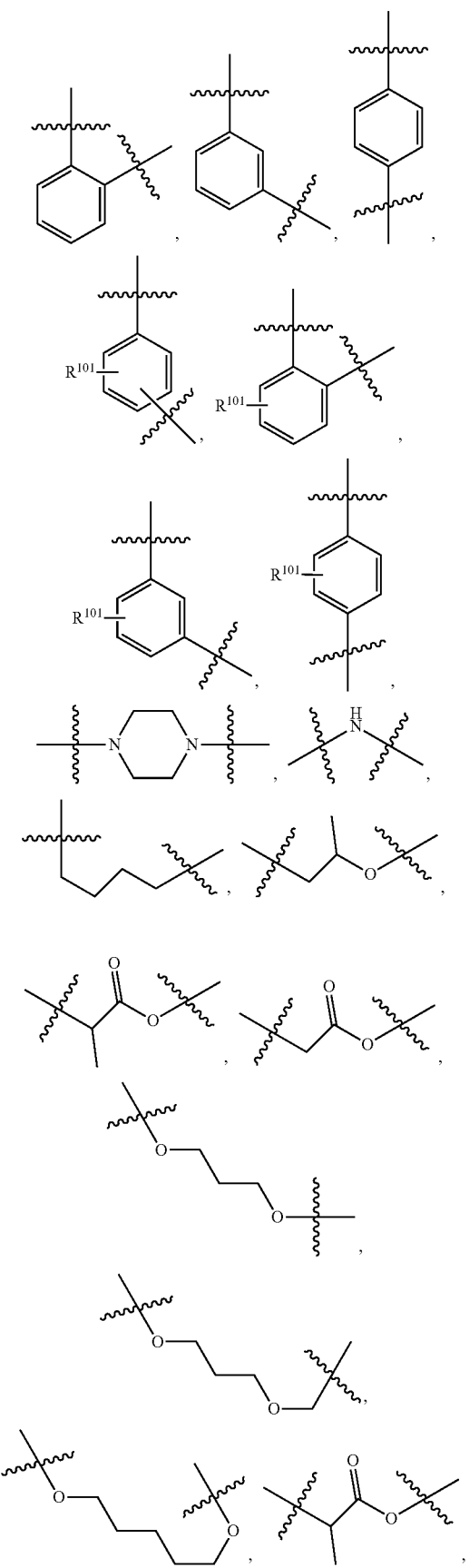
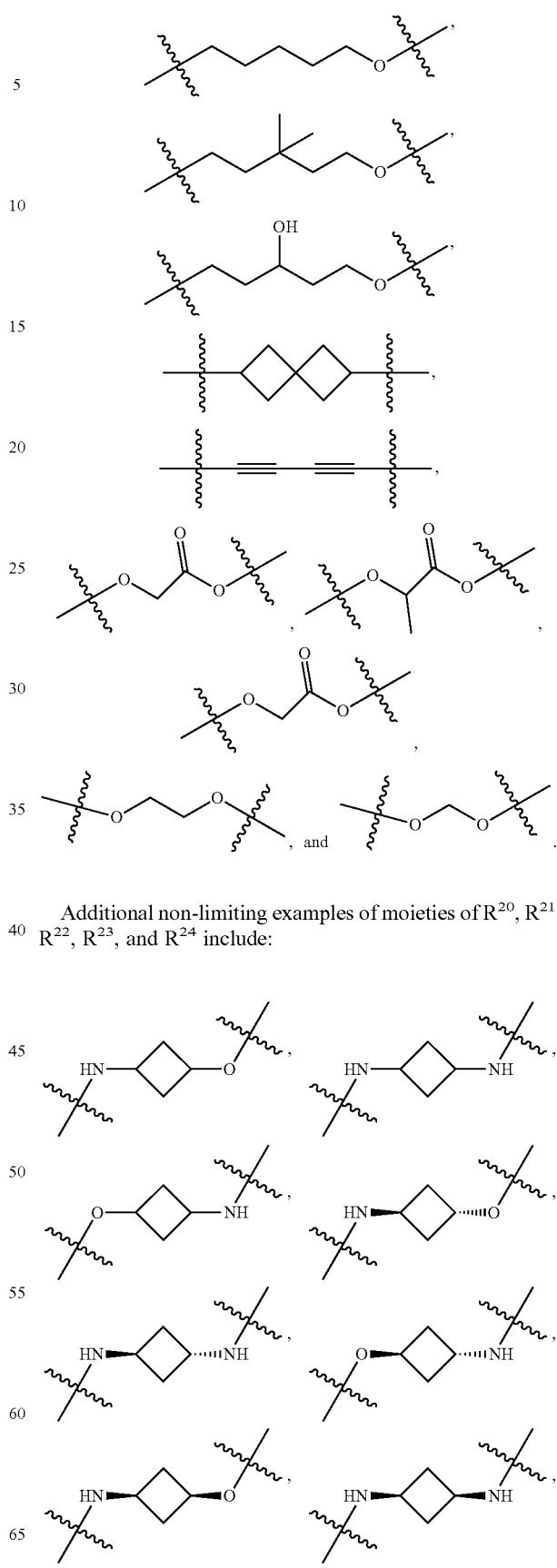
Additional non-limiting examples of moieties of $R^{20}$, $R^{21}$, $R^{22}$, $R^{23}$, and $R^{24}$ include:

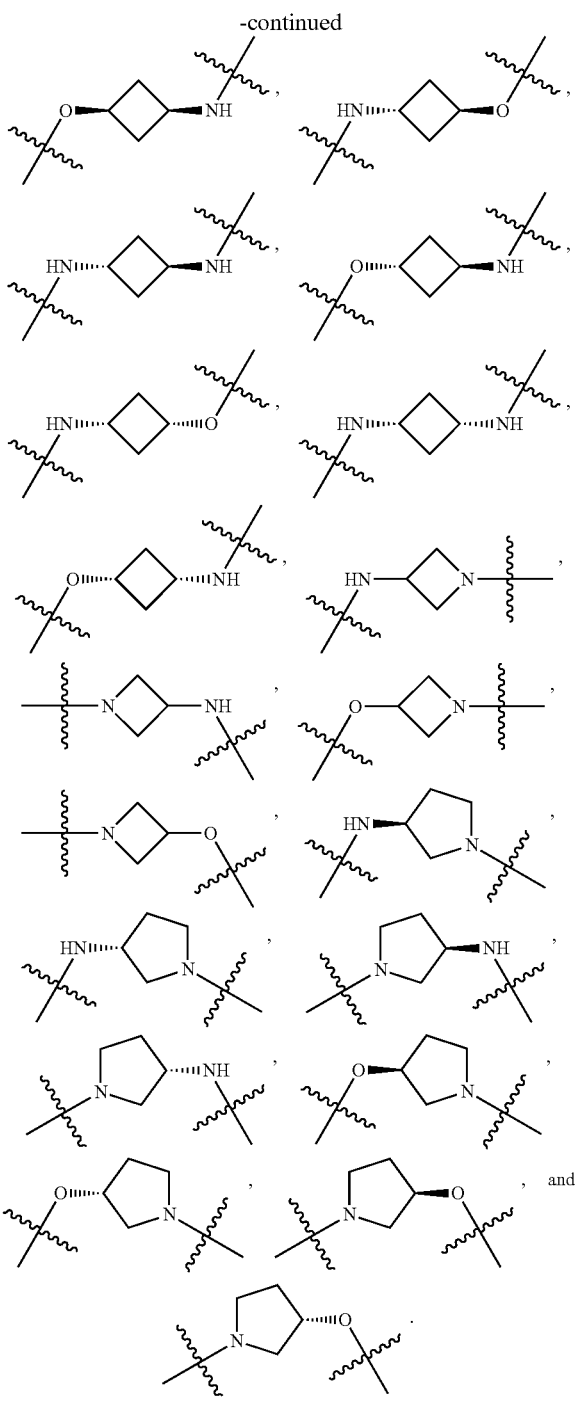

In additional embodiments, the Linker group is an optionally substituted (poly)ethylene glycol having at least 1, at least 2, at least 3, at least 4, at least 5, at least 6, at least 7, at least 8, at least 9, at least 10, ethylene glycol units, or optionally substituted alkyl groups interspersed with optionally substituted, O, N, S, P or Si atoms. In certain embodiments, the Linker is flanked, substituted, or interspersed with an aryl, phenyl, benzyl, alkyl, alkylene, or heterocycle group. In certain embodiments, the Linker may be asymmetric or symmetrical. In some embodiments, the Linker is a substituted or unsubstituted polyethylene glycol group ranging in size from about 1 to about 12 ethylene glycol units, between 1 and about 10 ethylene glycol units, about 2 about 6 ethylene glycol units, between about 2 and 5 ethylene glycol units, between about 2 and 4 ethylene glycol units. In any of the embodiments of the compounds described herein, the Linker group may be any suitable moiety as described herein.

In additional embodiments, the Linker is selected from:
—$NR^{61}(CH_2)_{n1}$-(lower alkyl)-, —$NR^{61}(CH_2)_{n1}$-(lower alkoxyl)-,
—$NR^{61}(CH_2)_{n1}$-(lower alkoxyl)-$OCH_2$—, —$NR^{61}(CH_2)_{n1}$-(lower alkoxyl)-(lower alkyl)-$OCH_2$—,
—$NR^{61}(CH_2)_{n1}$-(cycloalkyl)-(lower alkyl)-$OCH_2$—, —$NR^{61}(CH_2)_{n1}$-(heterocycloalkyl)-,
—$NR^{61}(CH_2CH_2O)_{n1}$-(lower alkyl)-O—$CH_2$—, —$NR^{61}(CH_2CH_2O)_{n1}$-(heterocycloalkyl)-O—$CH_2$—,
—$NR^{61}(CH_2CH_2O)_{n1}$-Aryl-O—$CH_2$—, —$NR^{61}(CH_2CH_2O)_{n1}$-(heteroaryl)-O—$CH_2$—,
—$NR^{61}(CH_2CH_2O)_{n1}$-(cycloalkyl)-O-(heteroaryl)-O—$CH_2$—,
—$NR^{61}(CH_2CH_2O)_{n1}$-(cycloalkyl)-O-Aryl-O—$CH_2$—,
—$NR^{61}(CH_2CH_2O)_{n1}$-(lower alkyl)-NH-Aryl-O—$CH_2$—,
—$NR^6(CH_2CH_2O)_{n1}$-(lower alkyl)-O-Aryl-$CH_2$,
—$NR^{61}(CH_2CH_2O)_{n1}$-cycloalkyl-O-Aryl-, —$NR^6(CH_2CH_2O)_{n1}$-cycloalkyl-heteroaryl-,
—$NR^{61}(CH_2CH_2)_{n1}$-(cycloalkyl)-O-(heterocycle)-$CH_2$,
—$NR^{61}(CH_2CH_2)_{n1}$-(heterocycle)-(heterocycle)-$CH_2$, and —$NR^{61}$-(heterocycle)-$CH_2$;
wherein n1 is 0, 1, 2, 3, 4, 5, 6, 7, 8, 9, or 10; and $R^{61}$ is H, methyl, or ethyl.

In additional embodiments, the Linker is selected from:
—$N(R^{61})$—$(CH_2)_{m1}$—$O(CH_2)_{n2}$—$O(CH_2)_{o1}$—$O(CH_2)_{p1}$—$O(CH_2)_{q1}$—$O(CH_2)_{r1}$—$OCH_2$—;
—O—$(CH_2)_{m1}$—$O(CH_2)_{n2}$—$O(CH_2)_{o1}$—$O(CH_2)_{p1}$—$O(CH_2)_{q1}$—$O(CH_2)_{r1}$—$OCH_2$—;
—O—$(CH_2)_{m1}$—$O(CH_2)_{n2}$—$O(CH_2)_{o1}$—$O(CH_2)_{p1}$—$O(CH_2)_{q1}$—$O(CH_2)_{r1}$—O—;
—$N(R^{61})$—$(CH_2)_{m1}$—$O(CH_2)_{n2}$—$O(CH_2)_{o1}$—$O(CH_2)_{p1}$—$O(CH_2)_{q1}$—$O(CH_2)_{r1}$—O—;
—$(CH_2)_{m1}$—$O(CH_2)_{n2}$—$O(CH_2)_{o1}$—$O(CH_2)_{p1}$—$O(CH_2)_{q1}$—$O(CH_2)_{r1}$—O—;
—$(CH_2)_{m1}$—$O(CH_2)_{n2}$—$O(CH_2)_{o1}$—$O(CH_2)_{p1}$—$O(CH_2)_{q1}$—$O(CH_2)_{r1}$—$OCH_2$—;
—$O(CH_2)_{m1}O(CH_2)_{n2}O(CH_2)_{p1}O(CH_2)_{q1}OCH_2$—;
—$O(CH_2)_{m1}O(CH_2)_{n2}O(CH_2)_{p1}O(CH_2)_{q1}OCH_2$—;
wherein
m1, n2, o1, p1, q1, and r1 are independently 1, 2, 3, 4, or 5; and
$R^{61}$ is H, methyl, or ethyl.
In additional embodiments, the Linker is selected from:

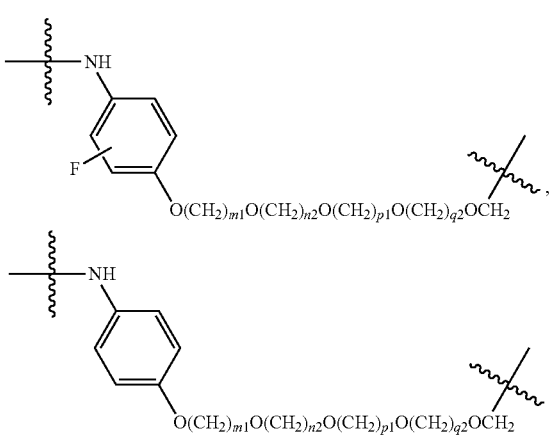

-continued
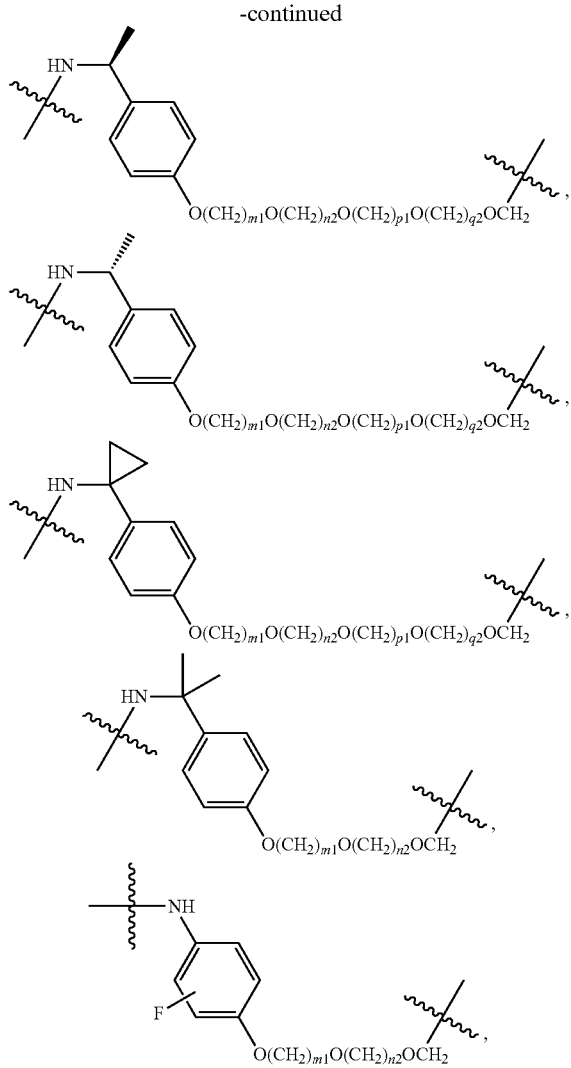
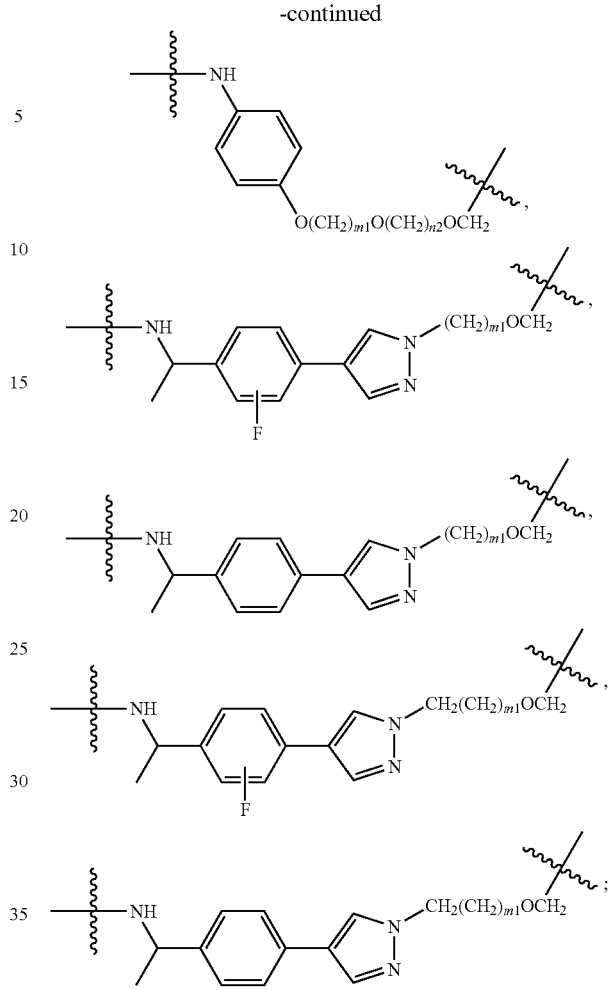
m1, n2, o1, p1, q2, and r1 are independently 1, 2, 3, 4, or 5.
In additional embodiments, the Linker is selected from:
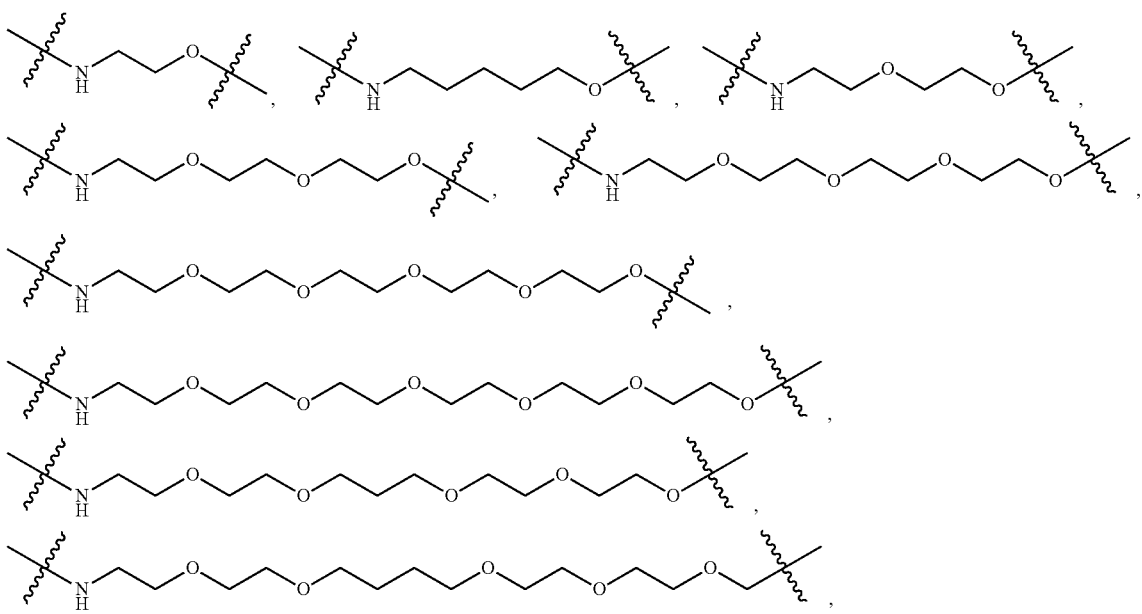

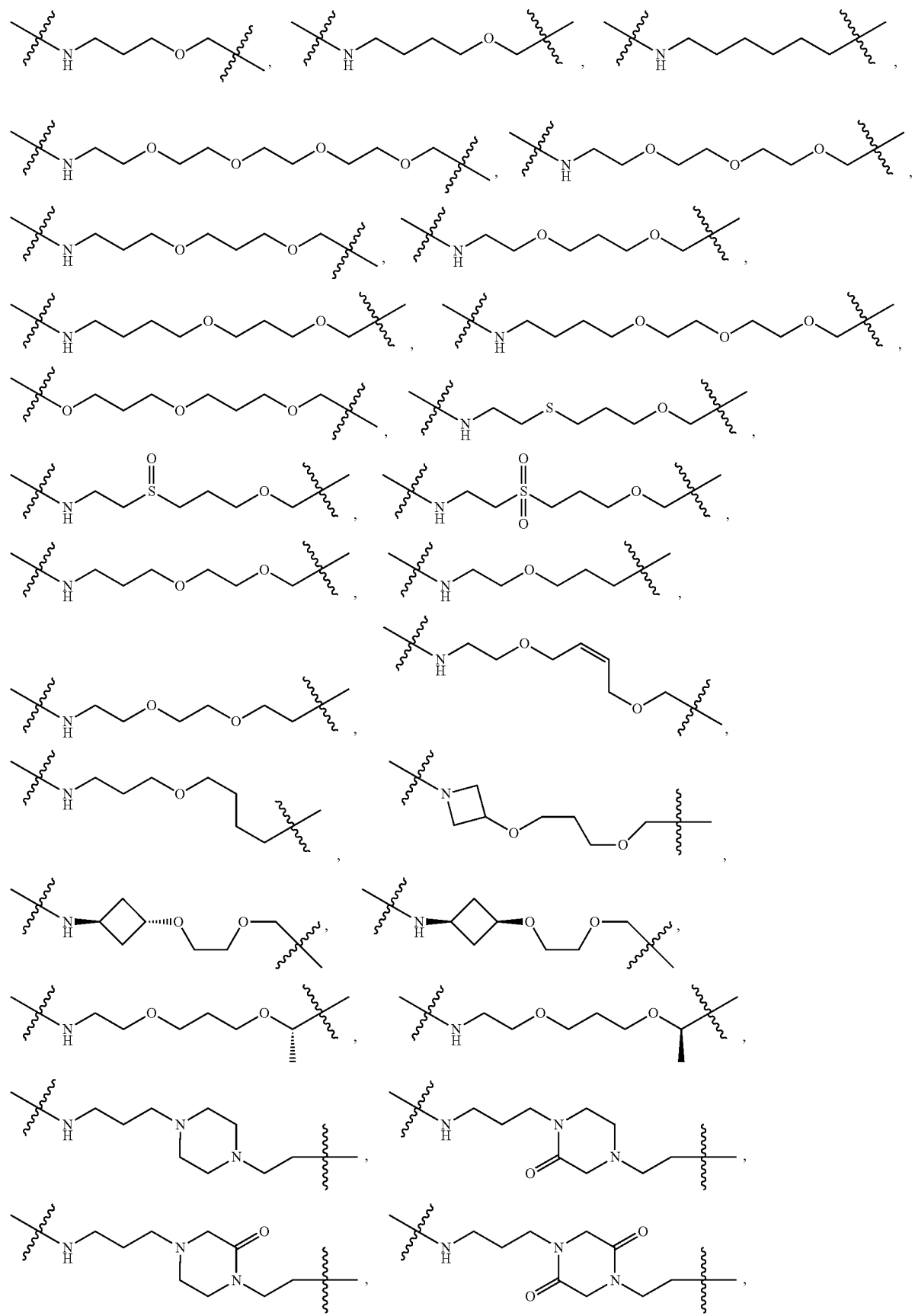

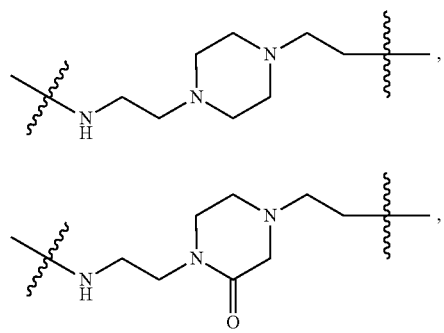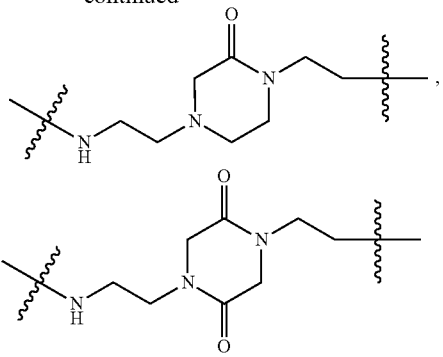
In additional embodiments, the Linker is selected from:
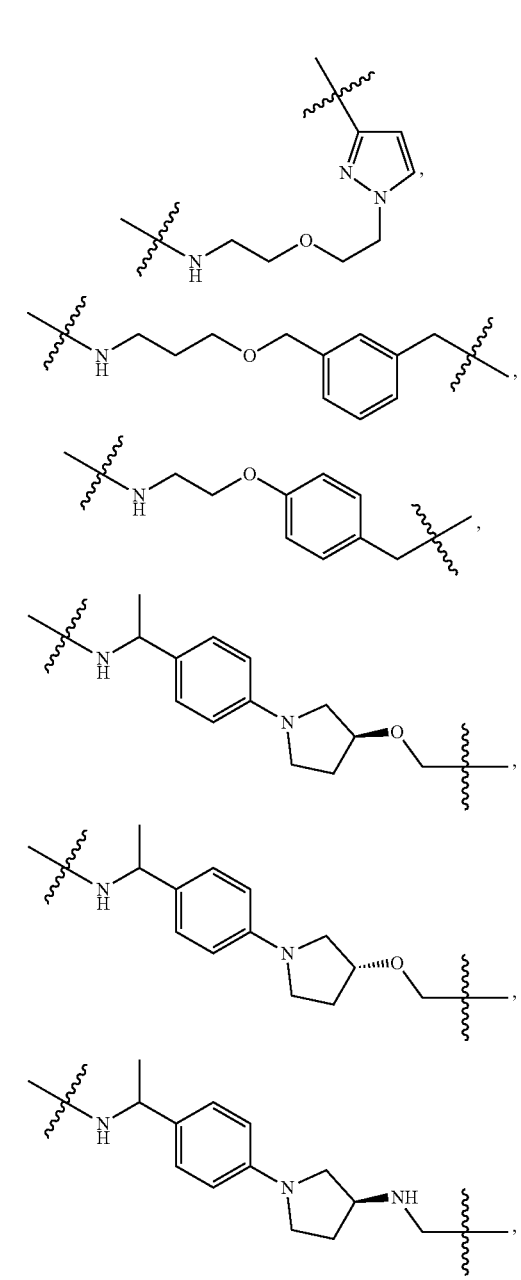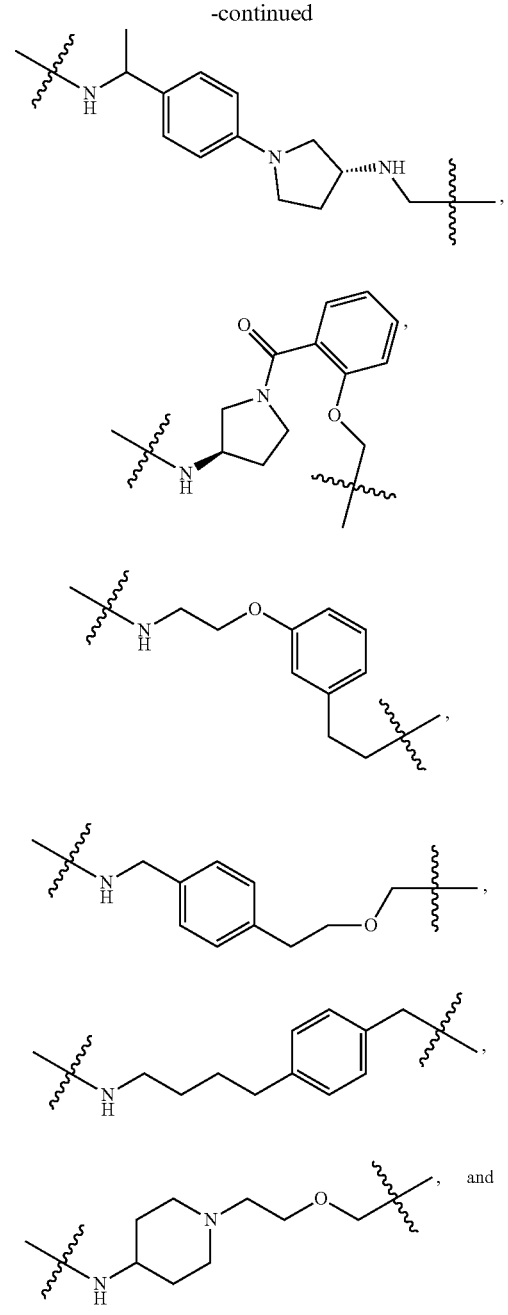

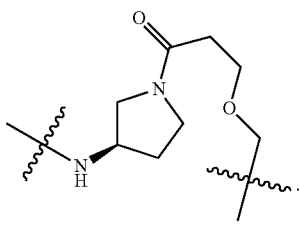
In additional embodiments, the Linker is selected from:
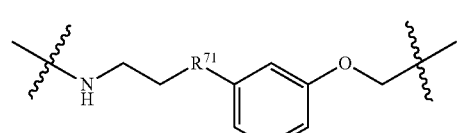
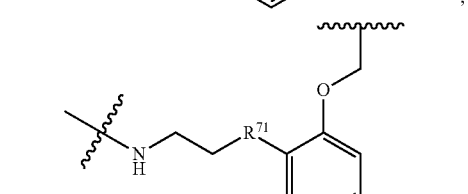

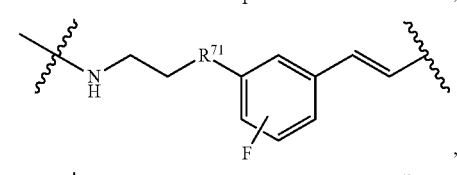
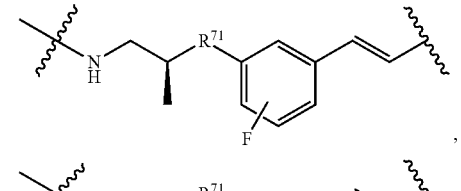
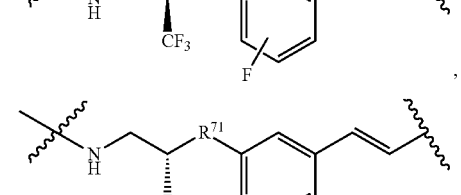
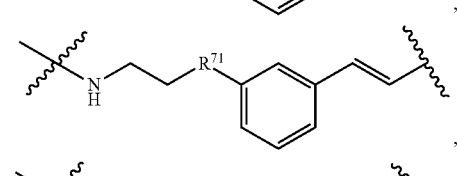
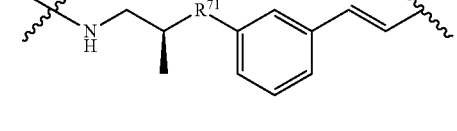
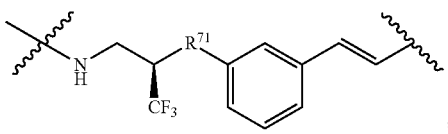
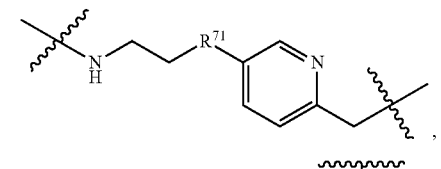
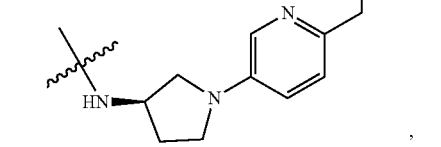
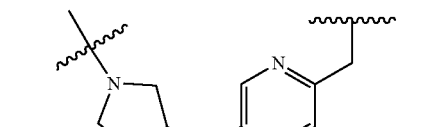
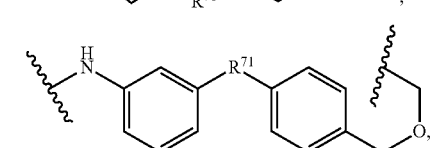
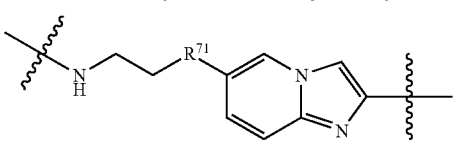
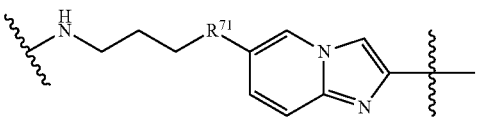
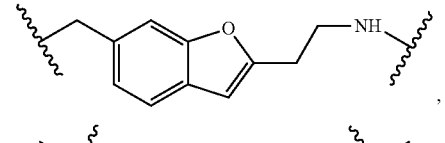
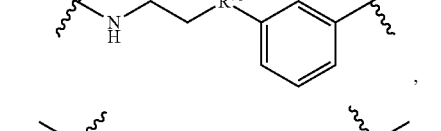
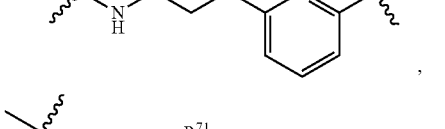
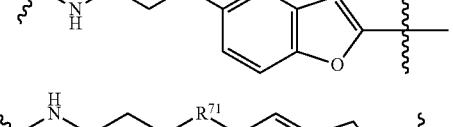
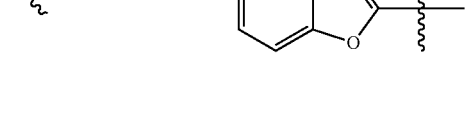

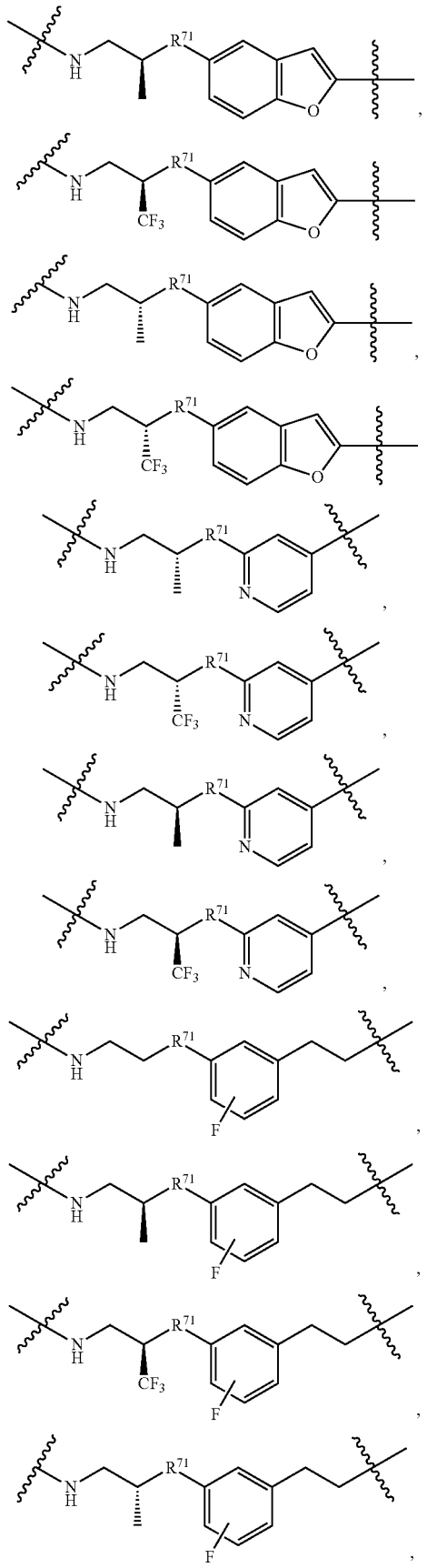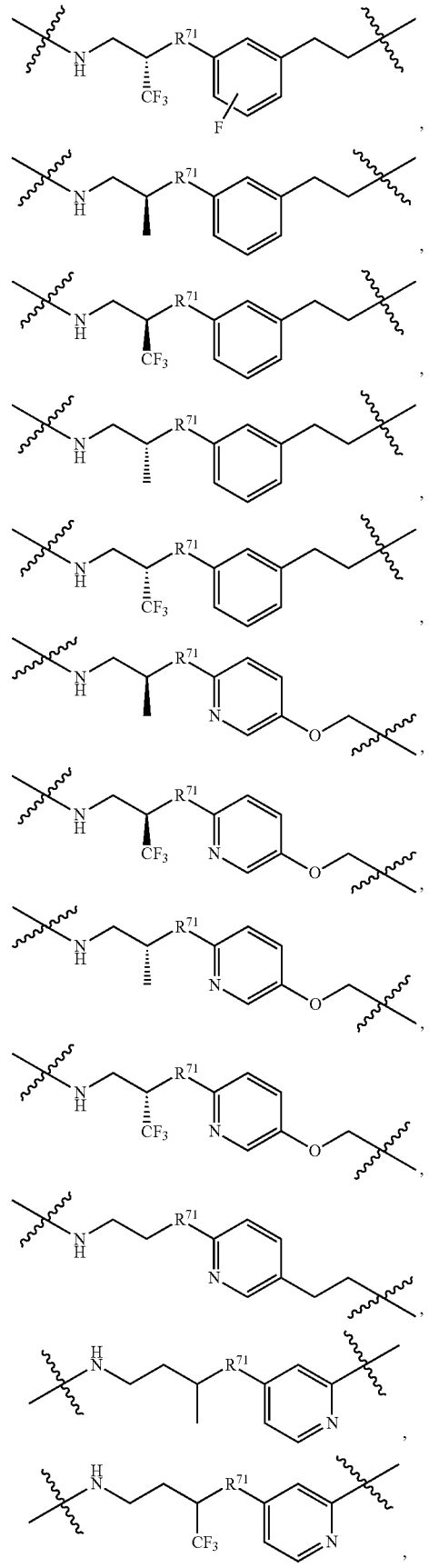

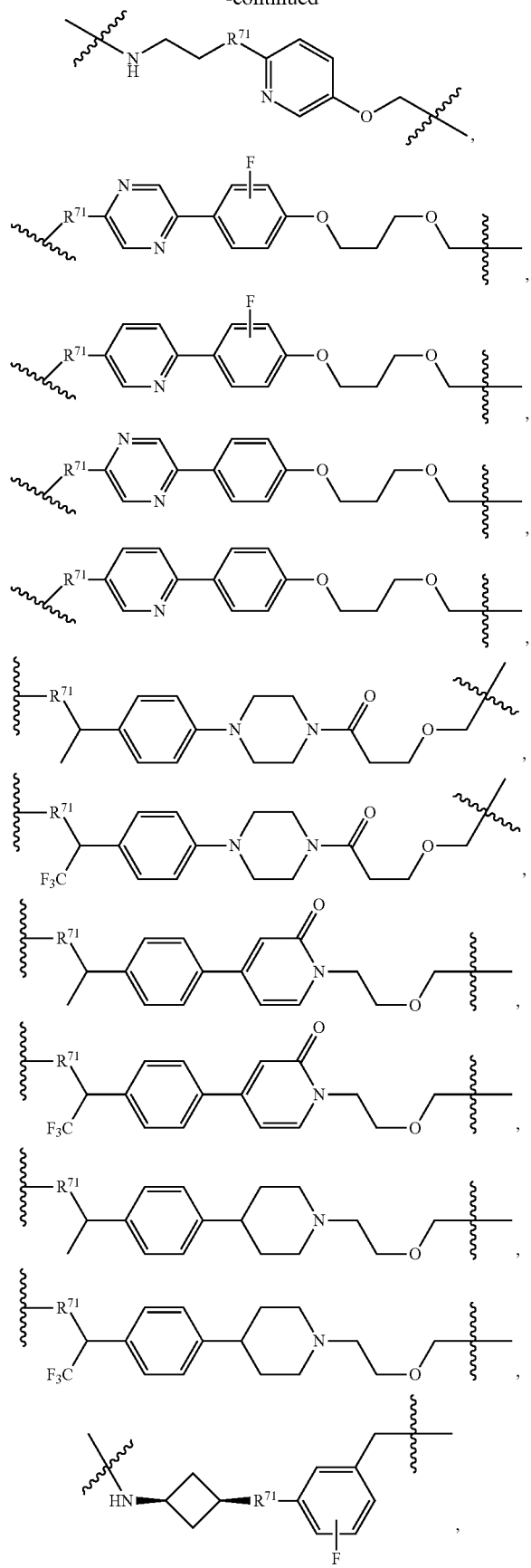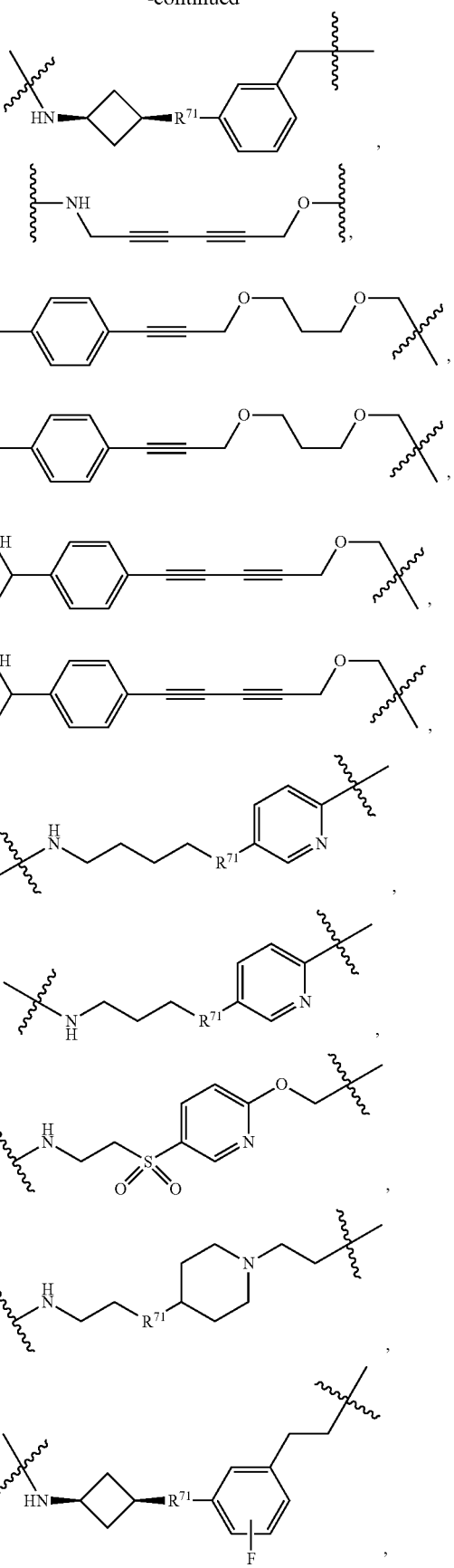

189
-continued
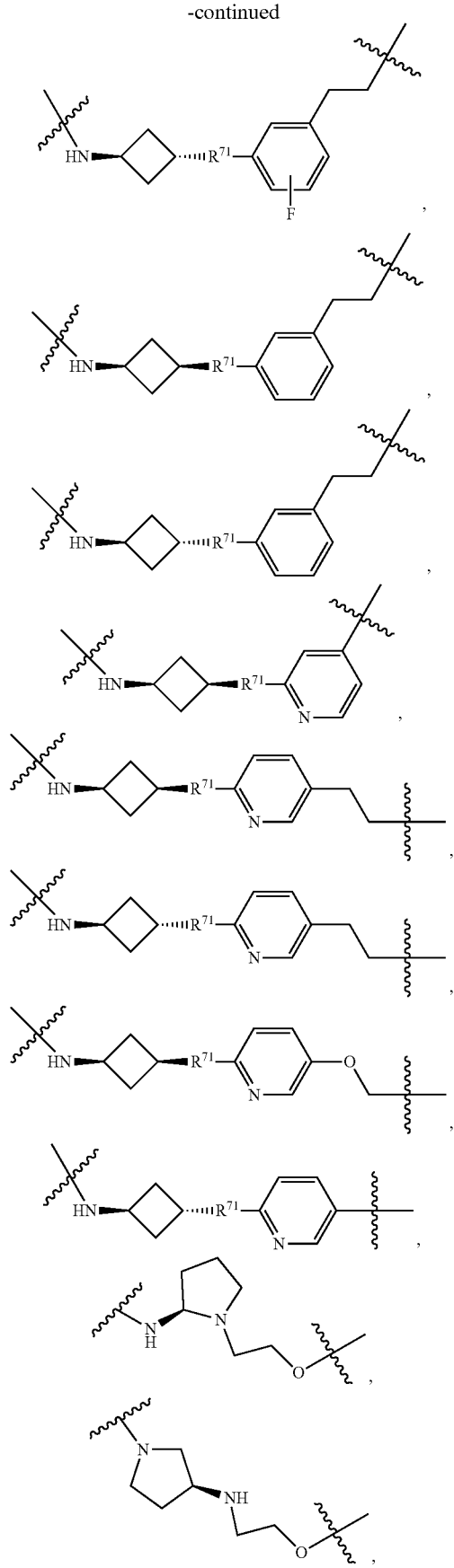
190
-continued
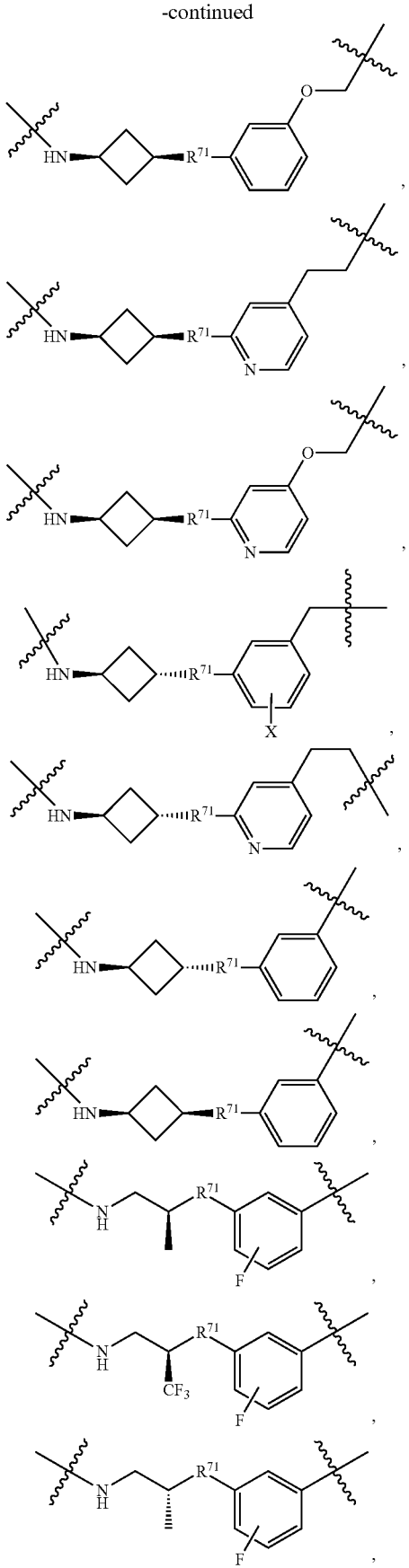

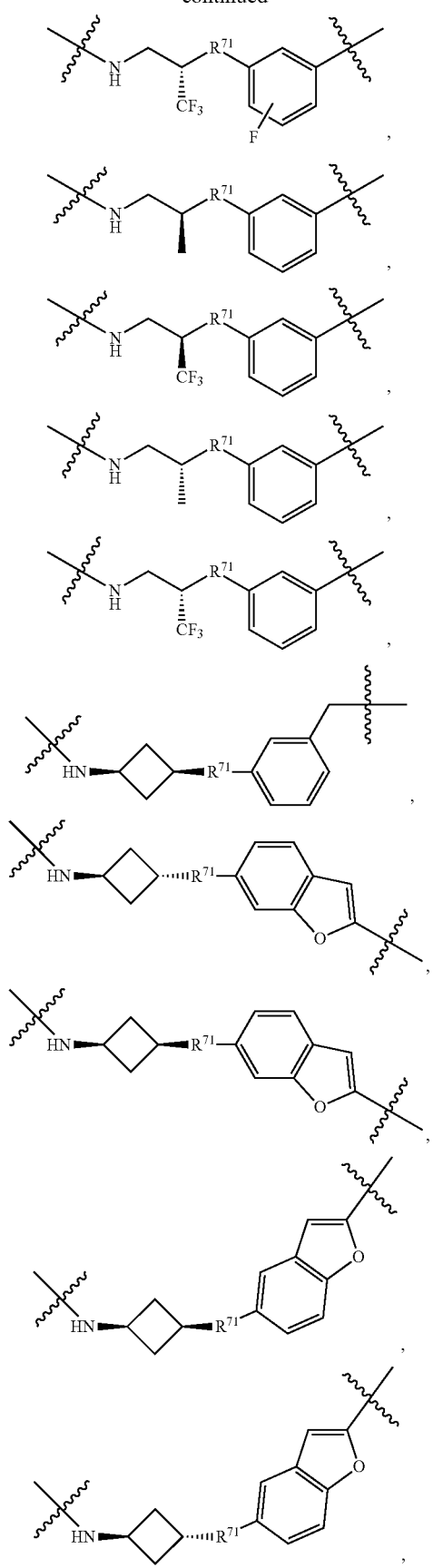
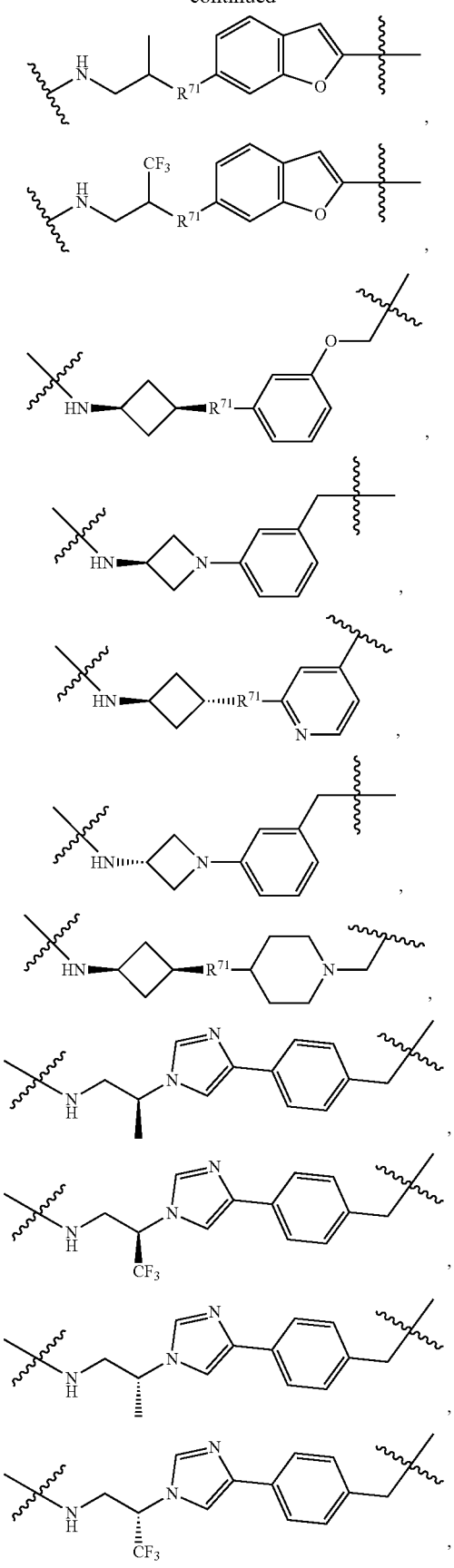

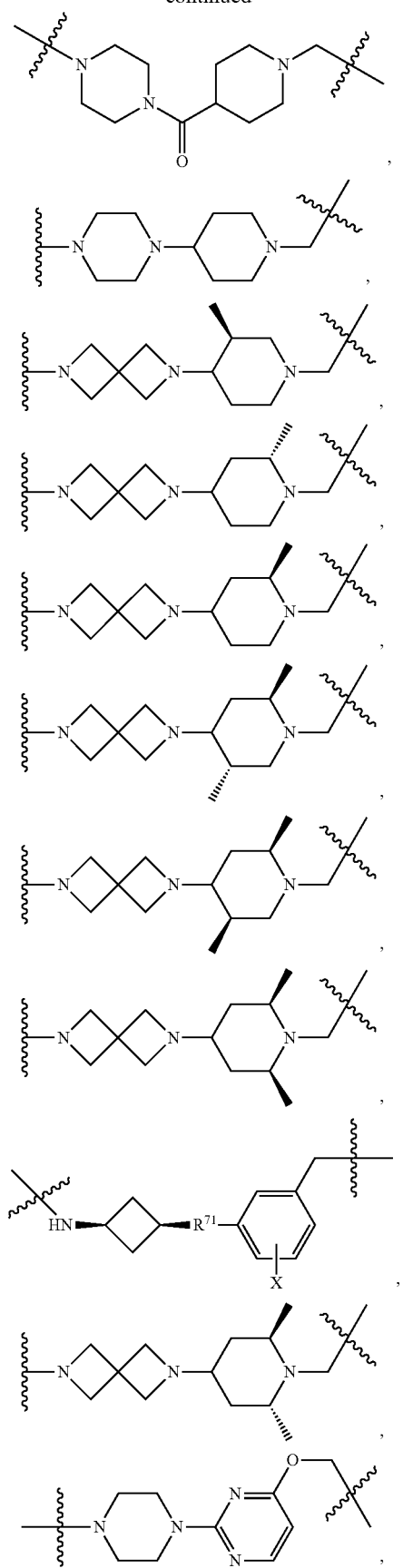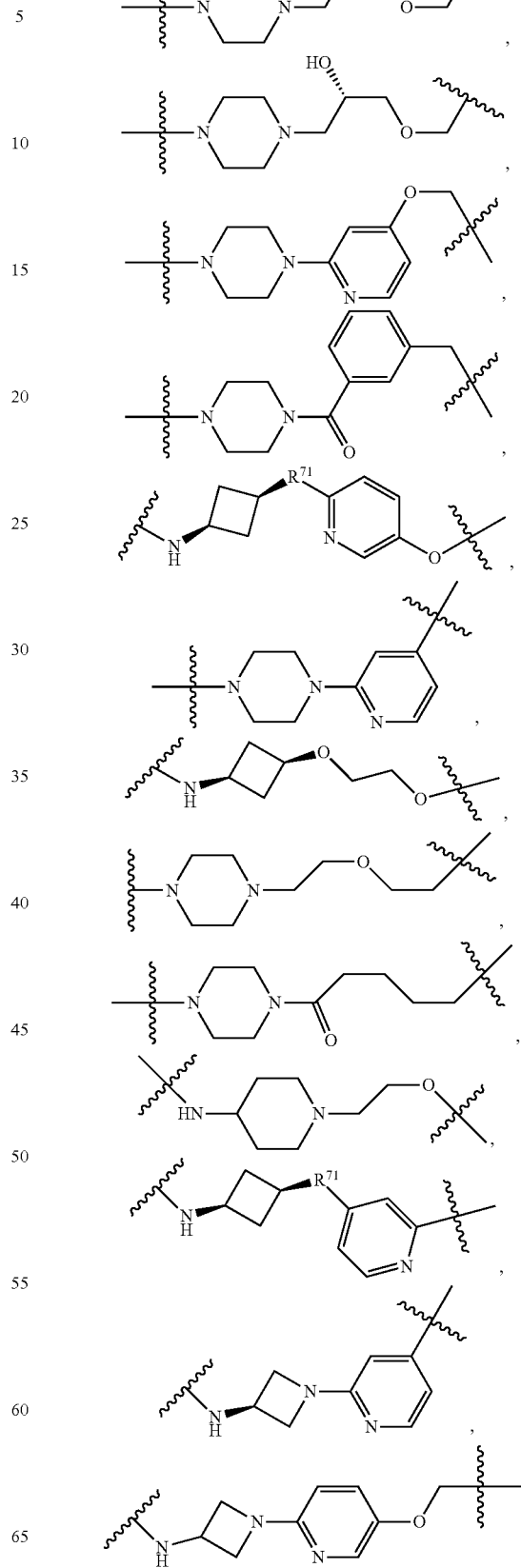

-continued
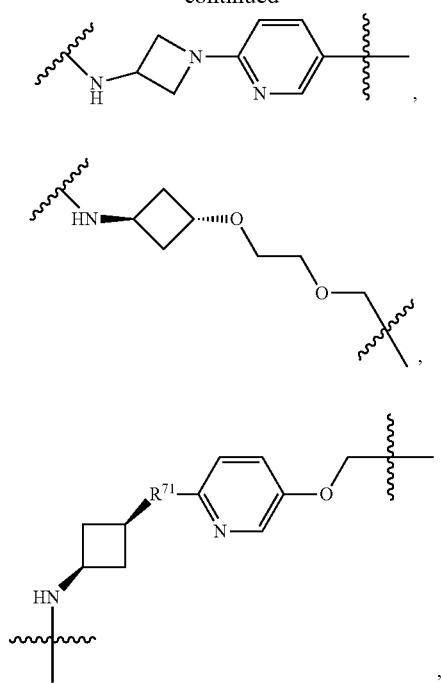
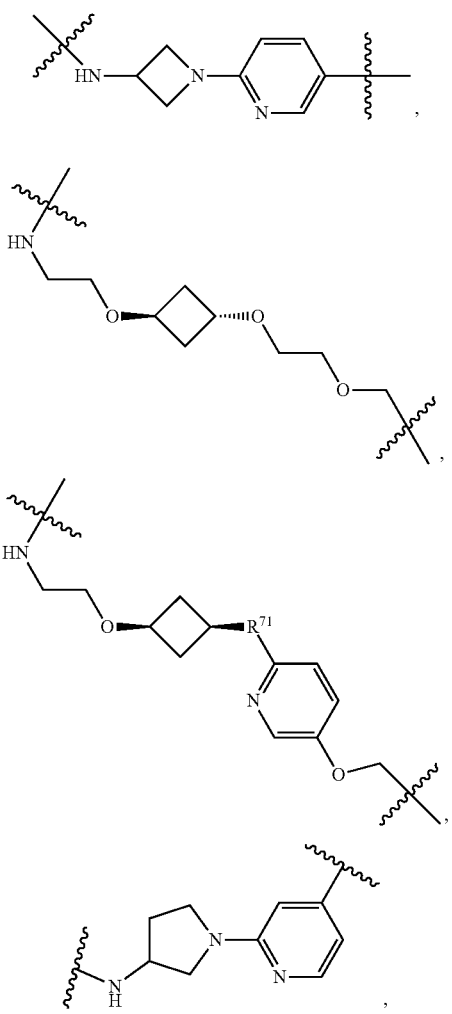
-continued
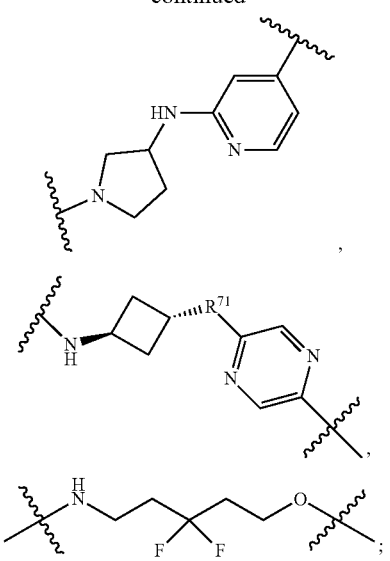
wherein R⁷¹ is —O—, —NH, Nalkyl, heteroaliphatic, aliphatic, or —NMe.
In additional embodiments, the Linker is selected from:
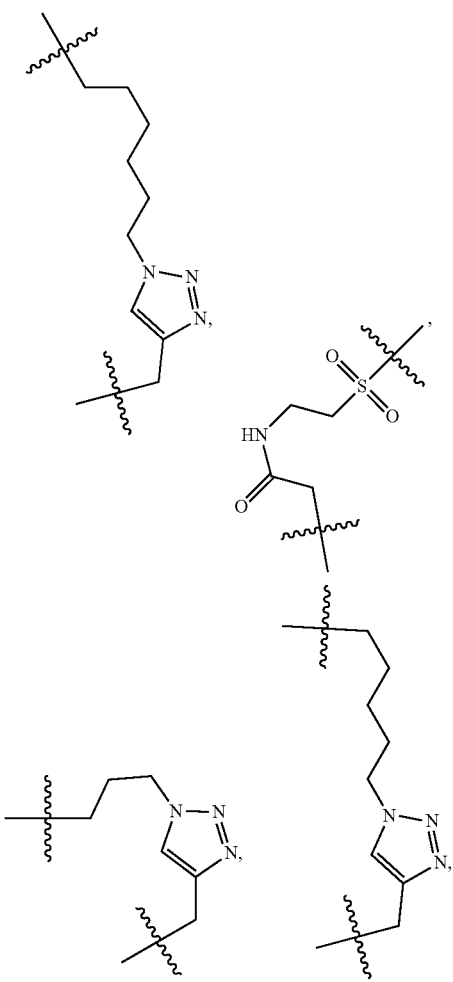

197
-continued
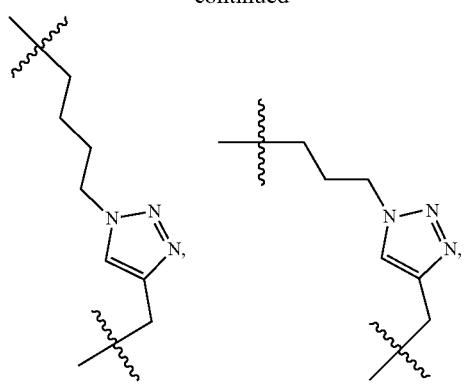
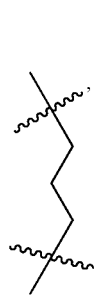
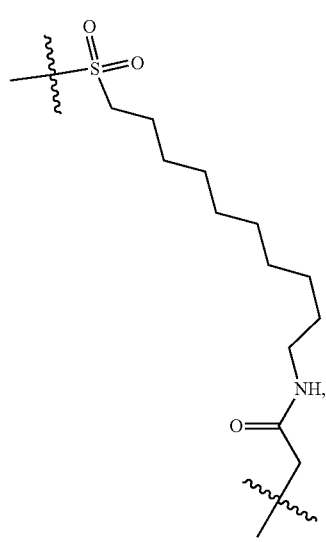
198
-continued
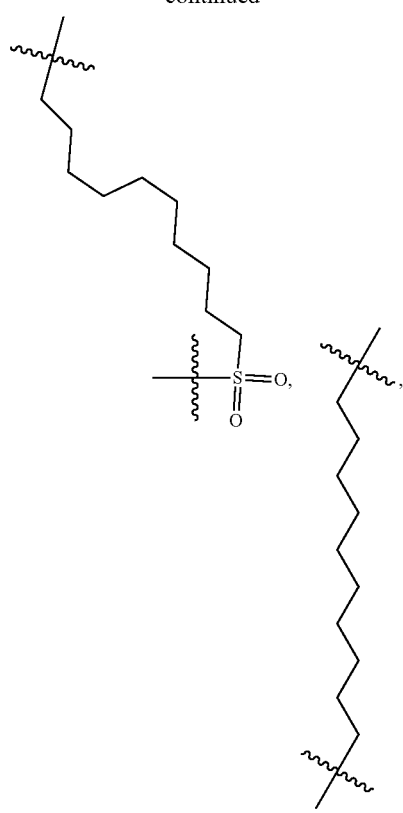
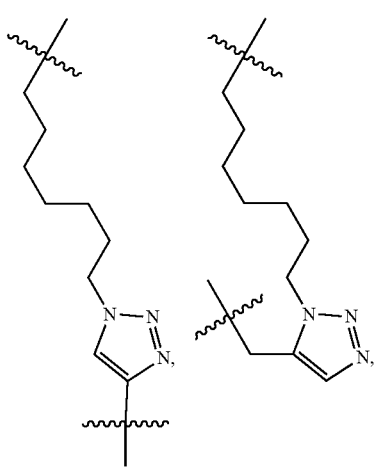

199
-continued
200
-continued
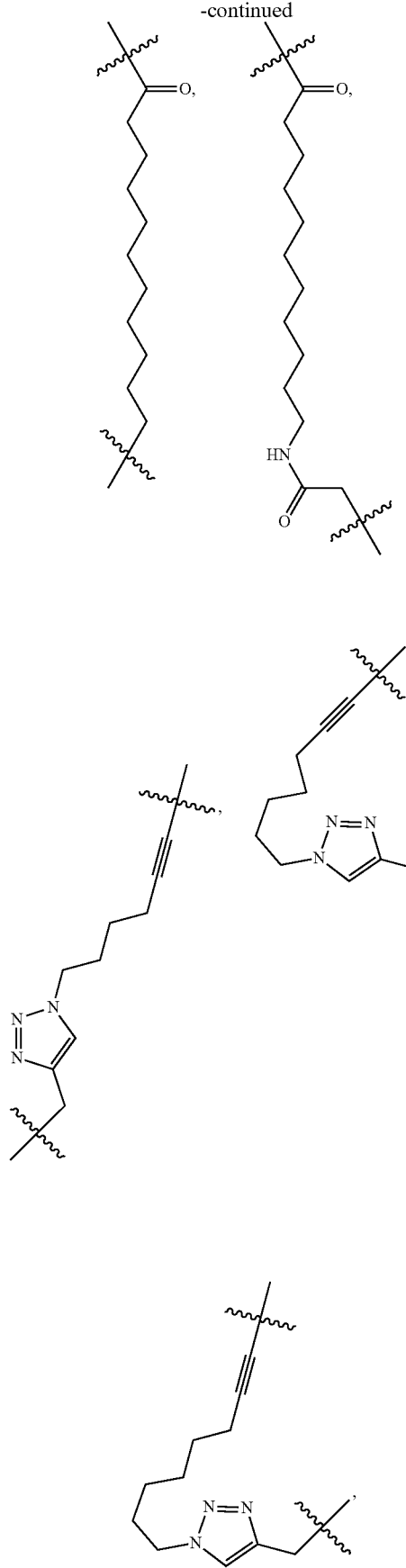
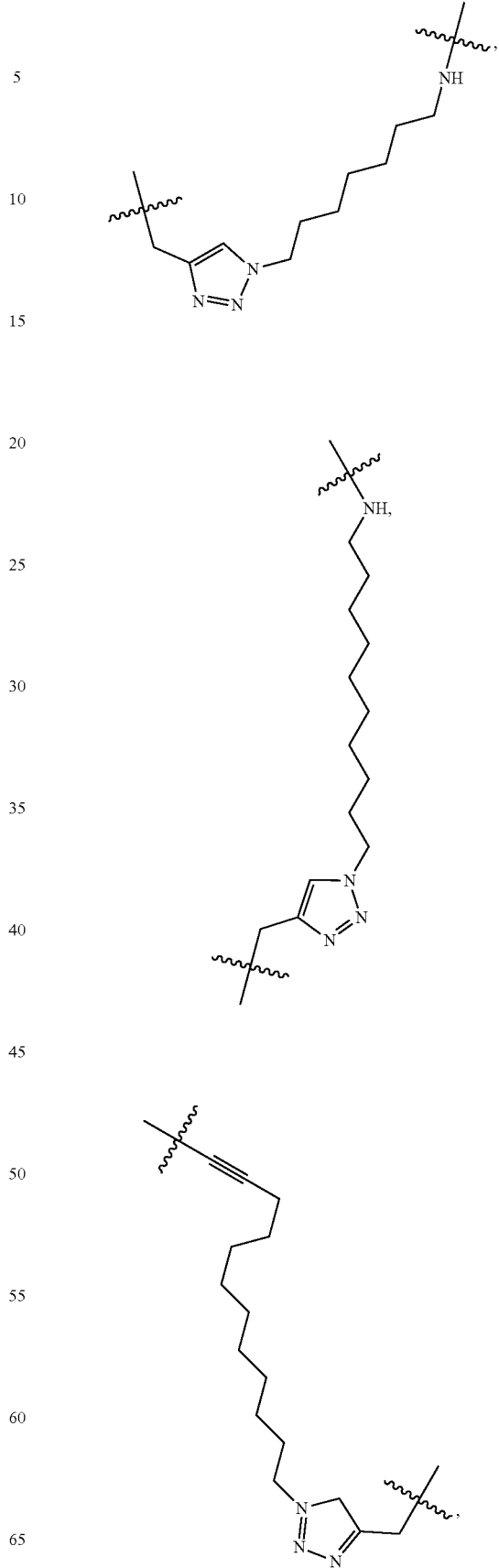

201
-continued
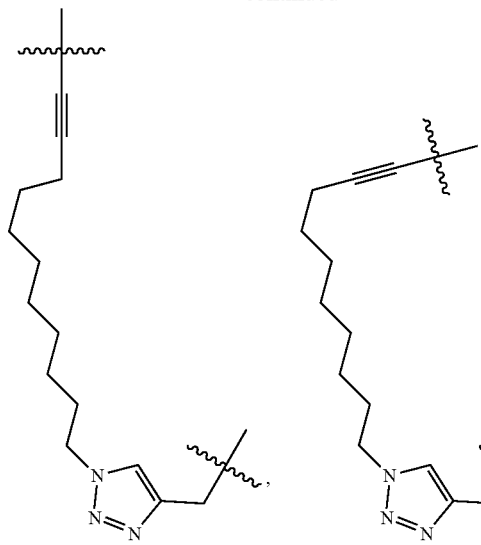
202
-continued
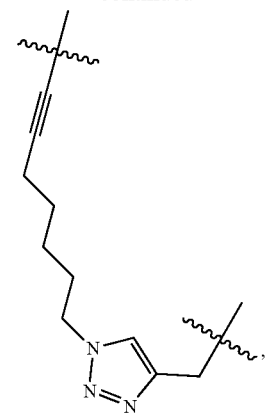
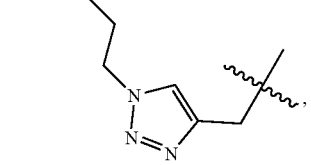
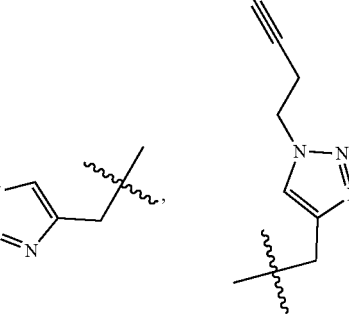
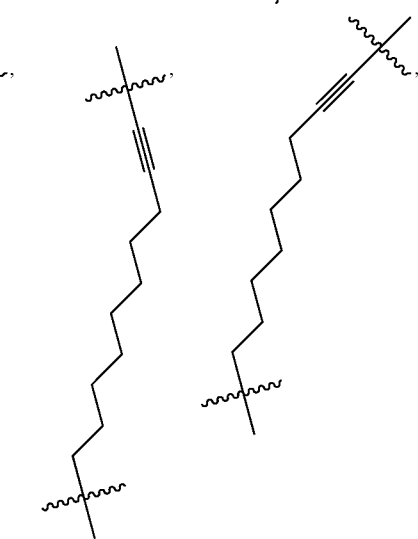

203
-continued
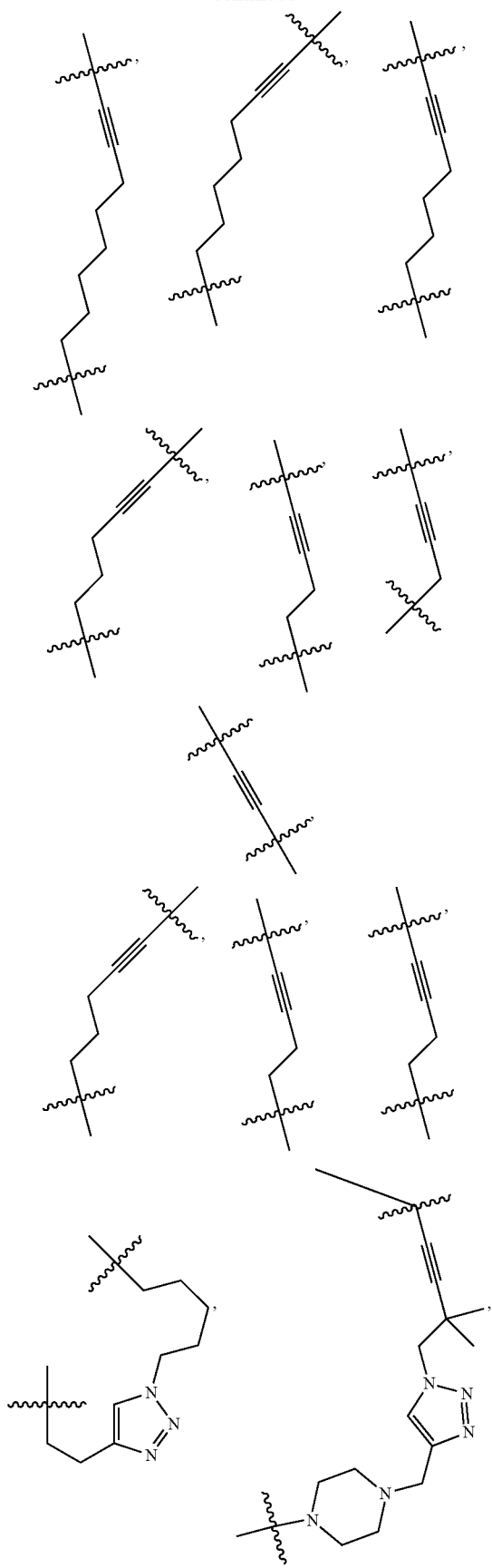
204
-continued
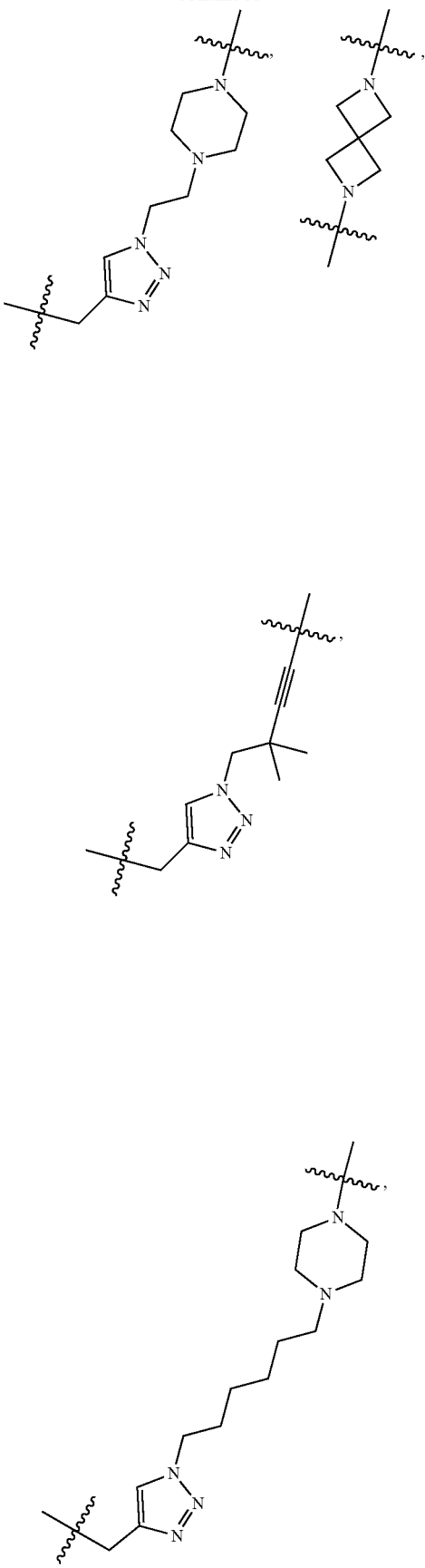

205
-continued
206
-continued
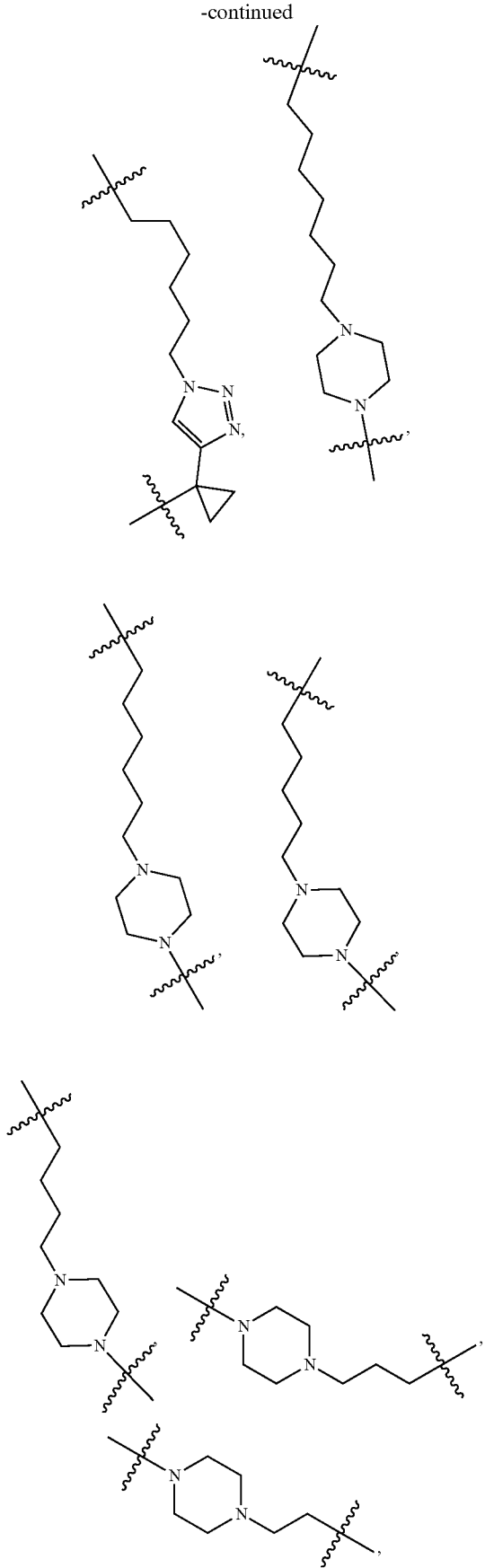
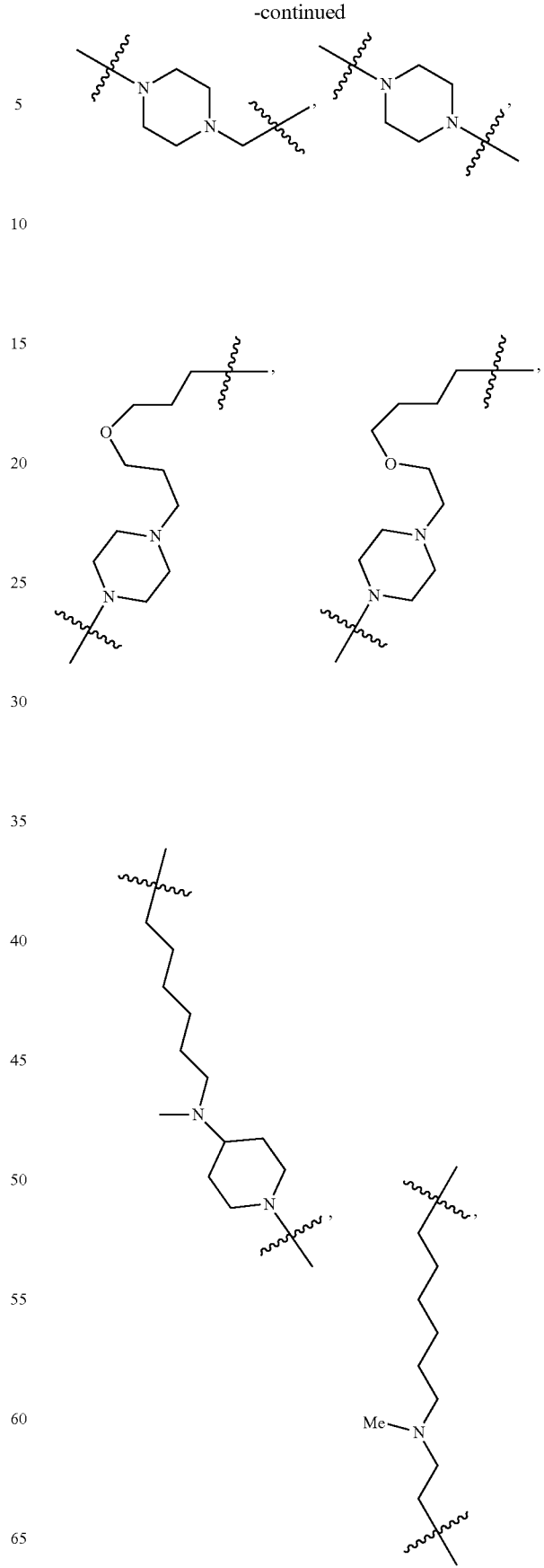

207
-continued
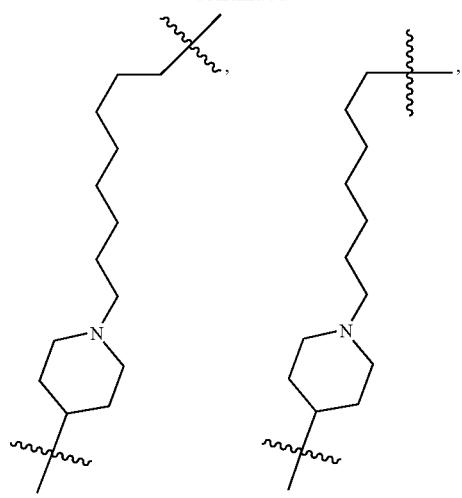
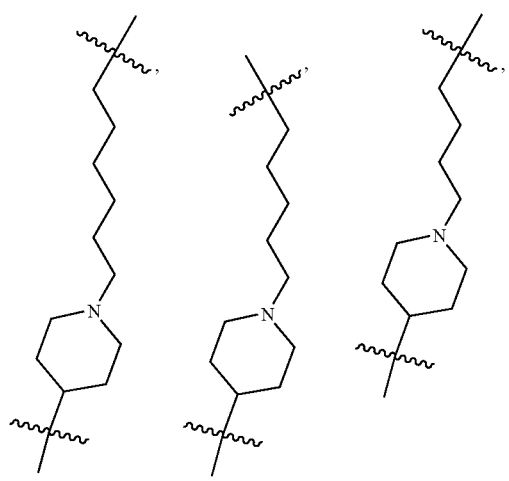
208
-continued
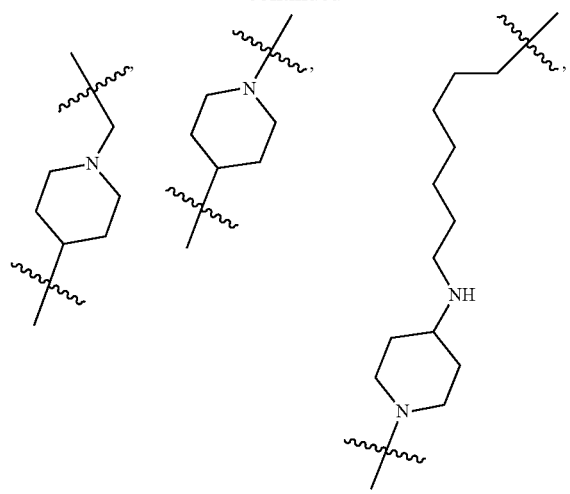
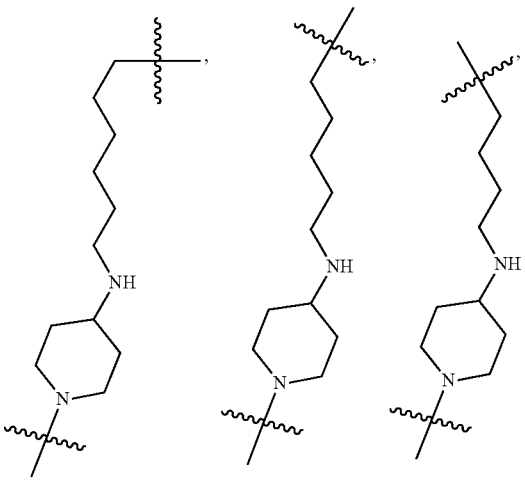
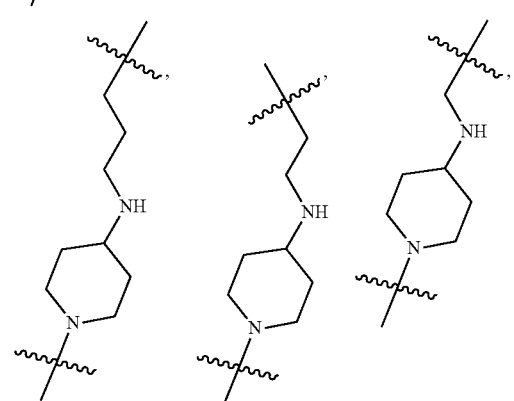
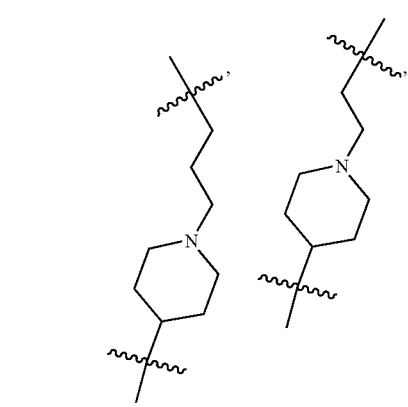
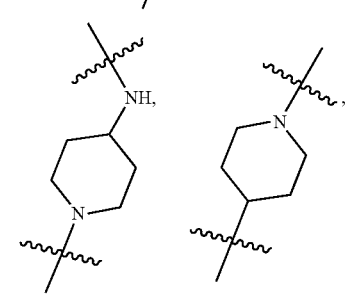

209
-continued
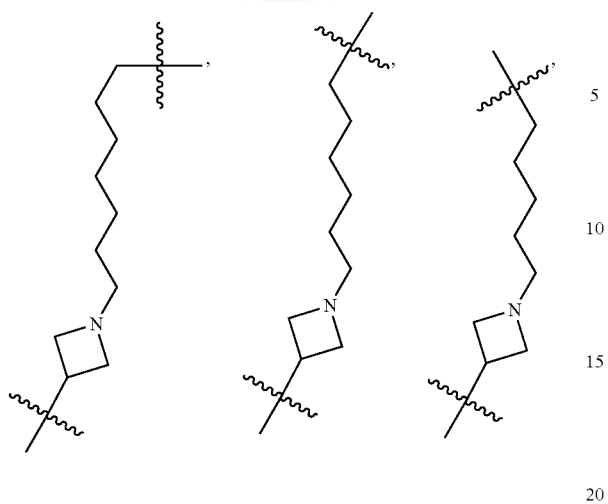
210
-continued
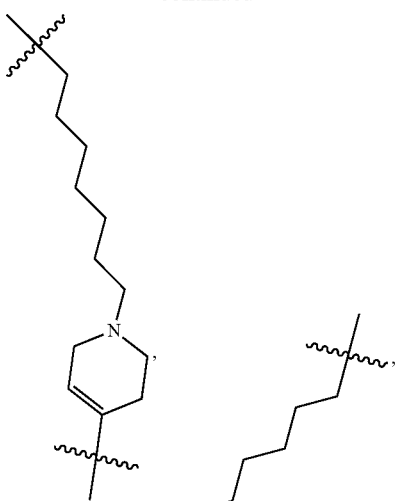
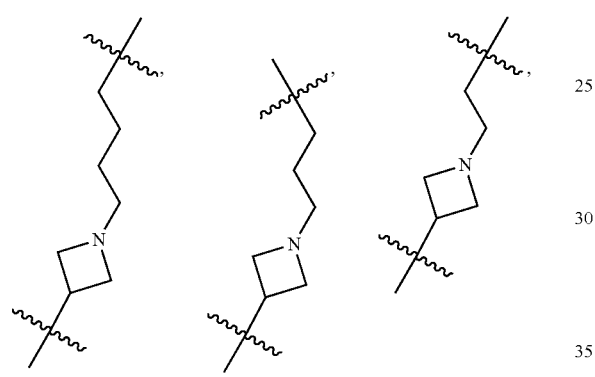
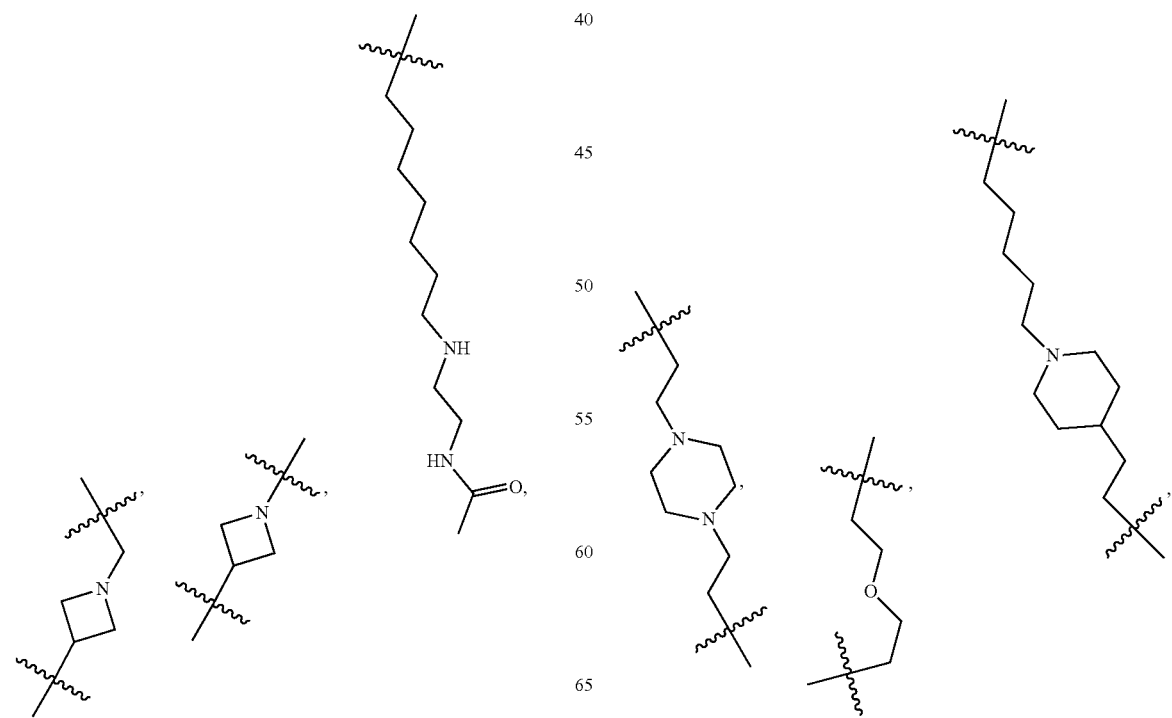

211
-continued
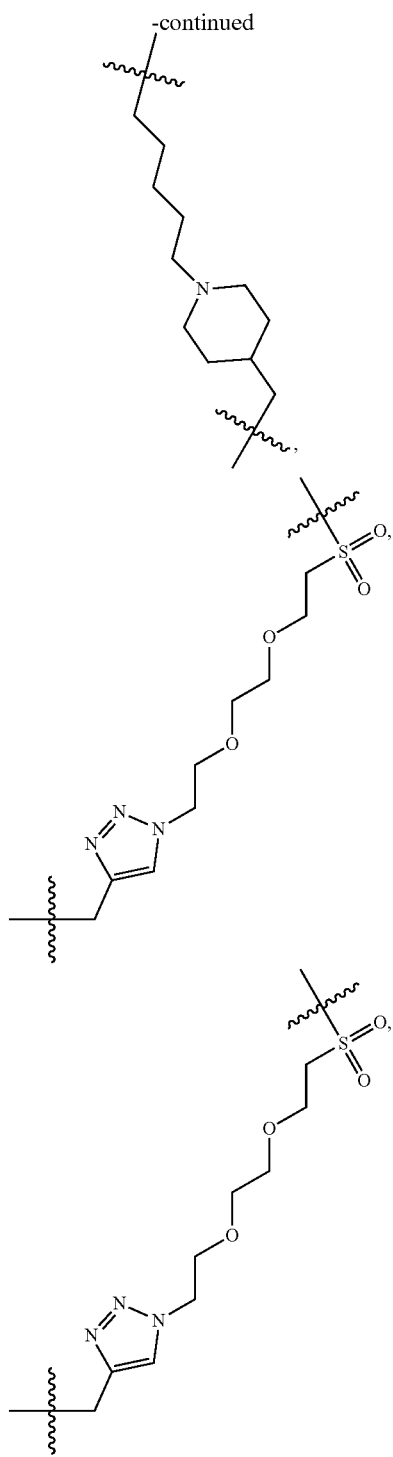
212
-continued
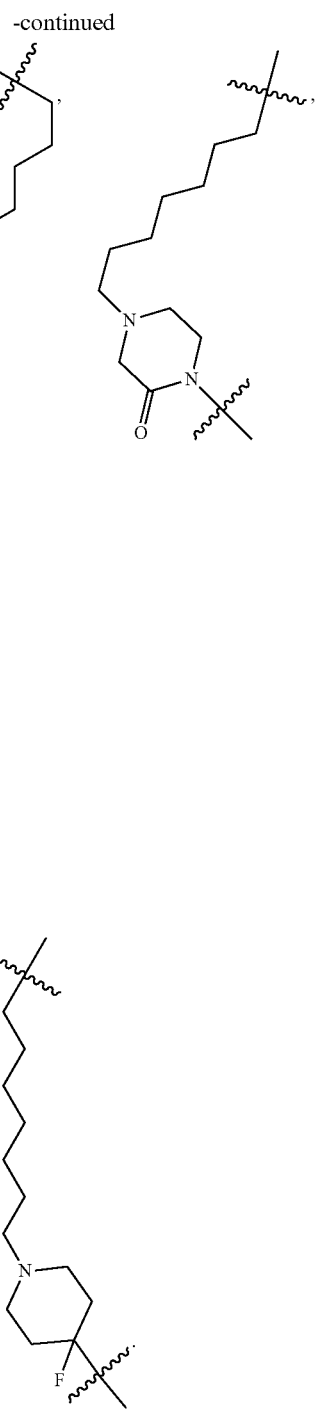
In additional embodiments, the Linker is selected from:
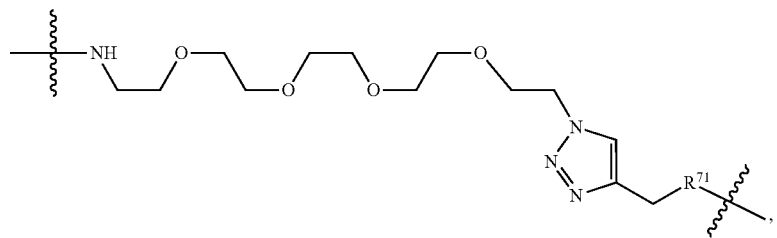

-continued
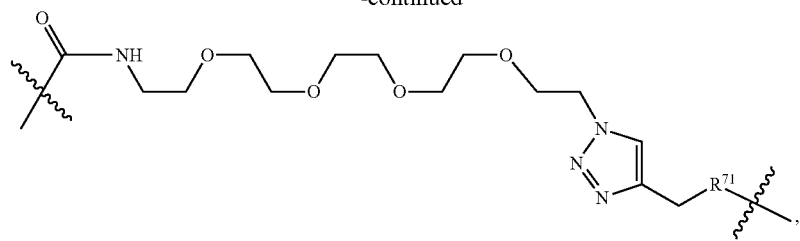
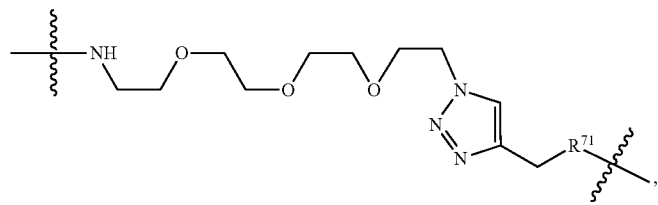
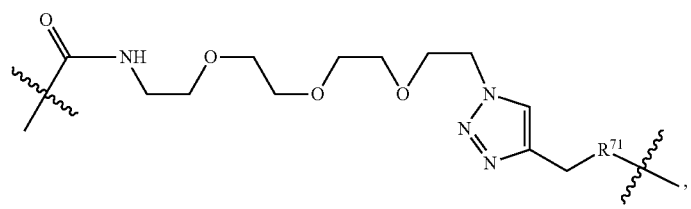
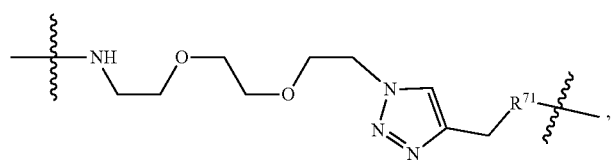
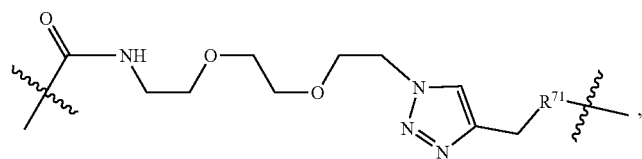
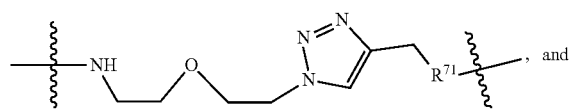, and
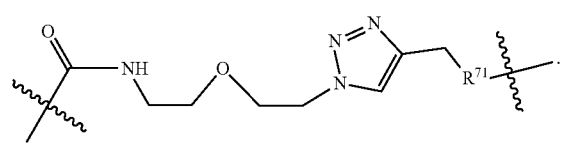.

In additional embodiments, the Linker is selected from:
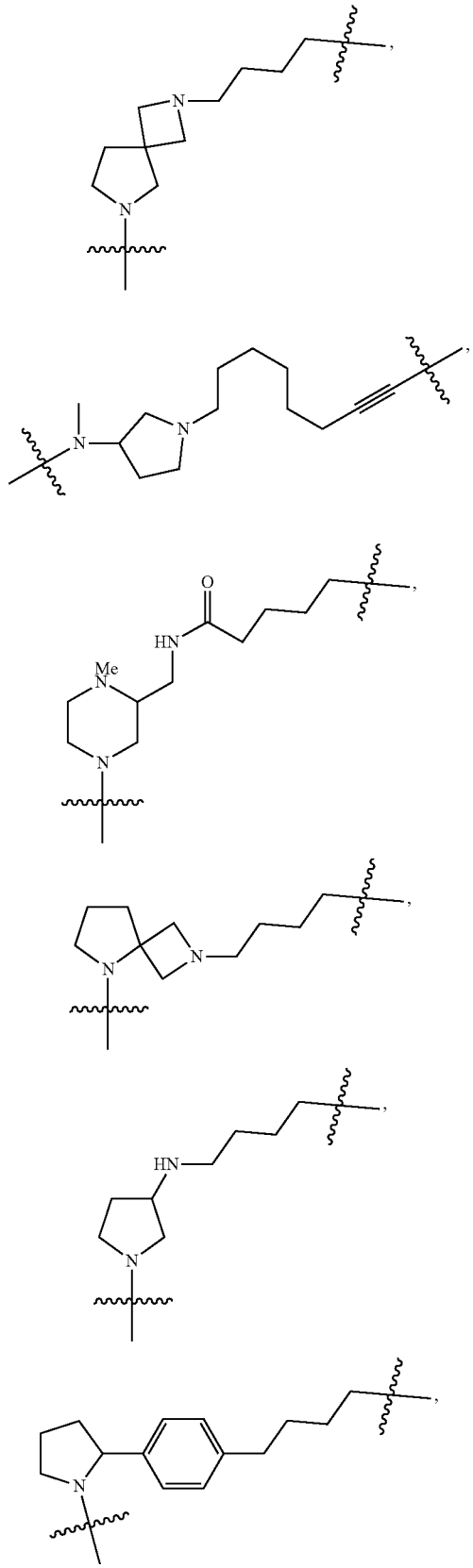
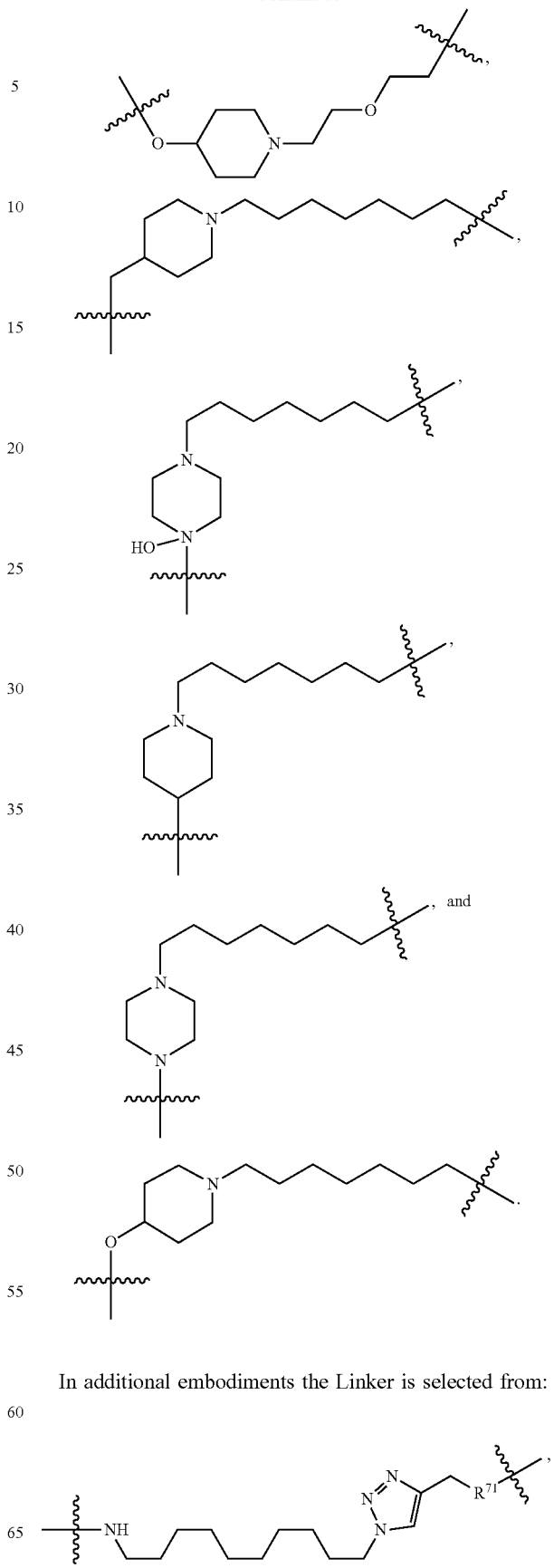
In additional embodiments the Linker is selected from:
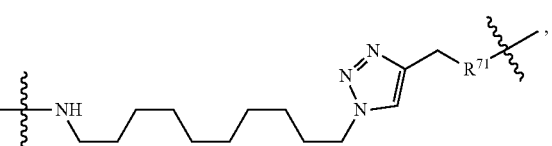

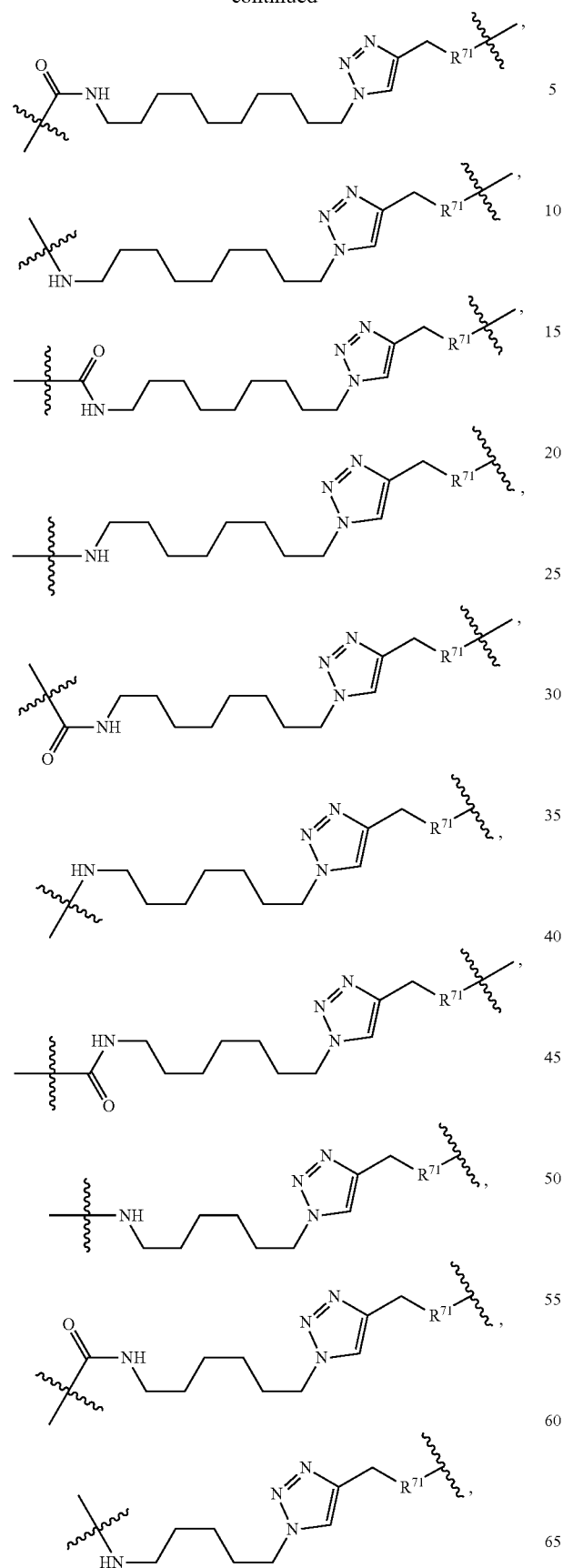
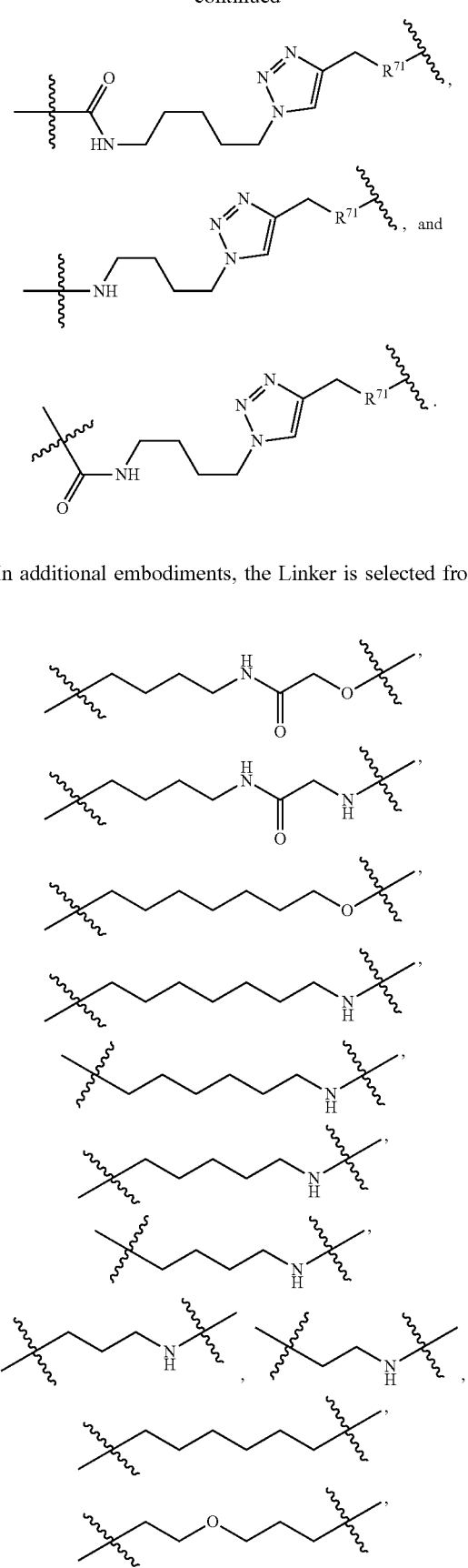
In additional embodiments, the Linker is selected from:

-continued
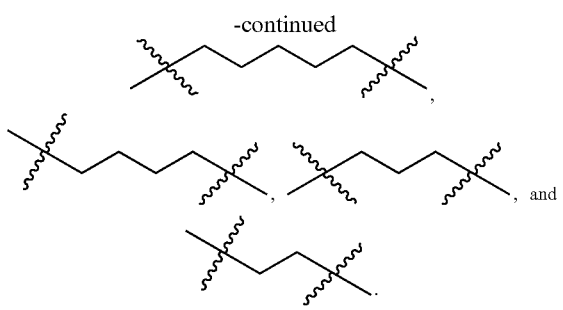
In additional embodiments, the Linker is selected from:
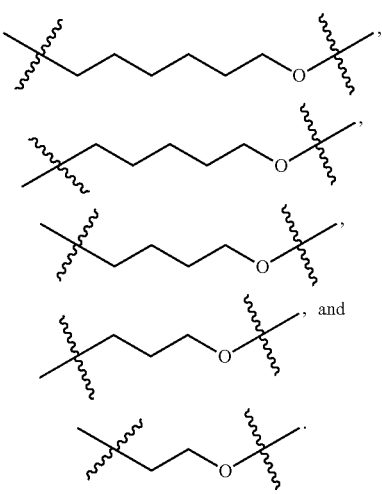
In certain embodiments, the Linker is selected from:
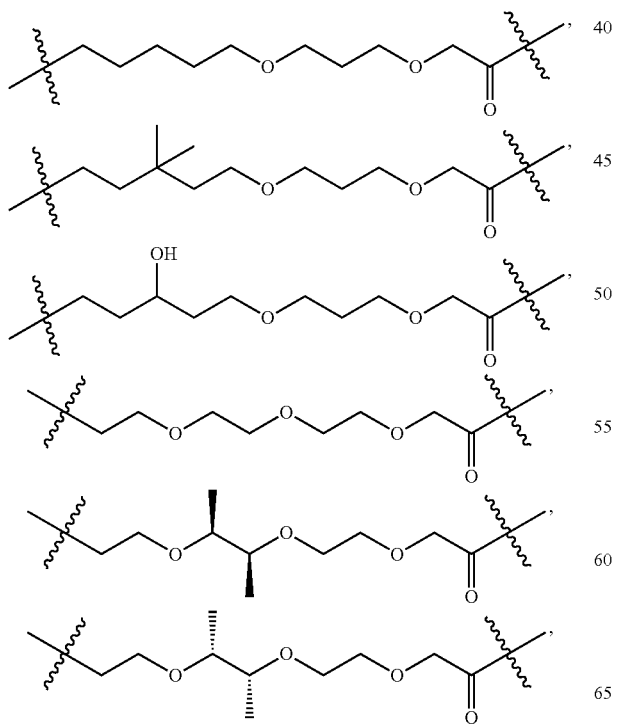
-continued
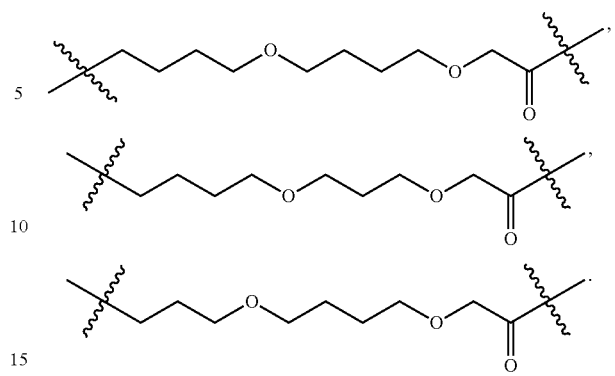
In certain embodiments the Linker is selected from:
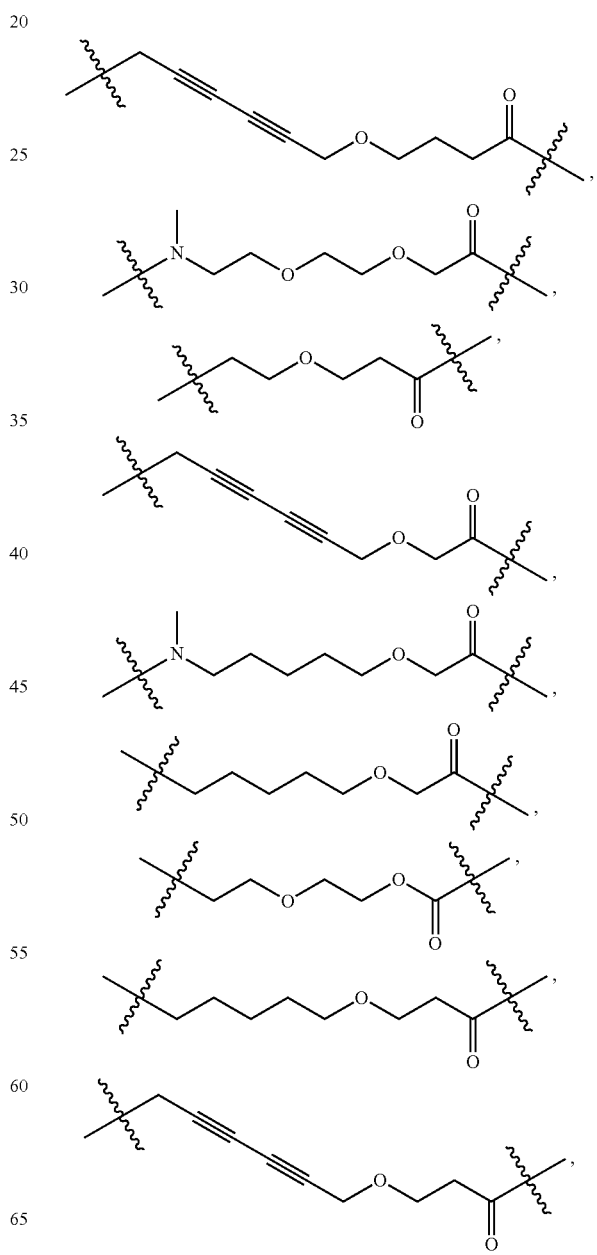

221
-continued
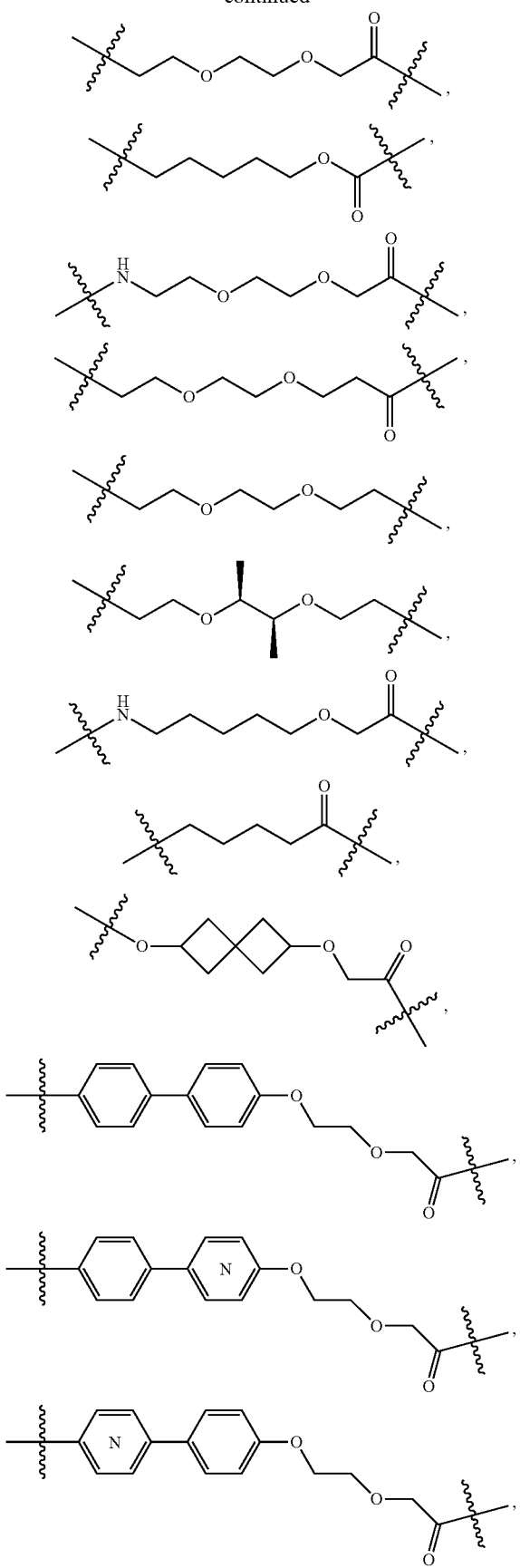
222
-continued
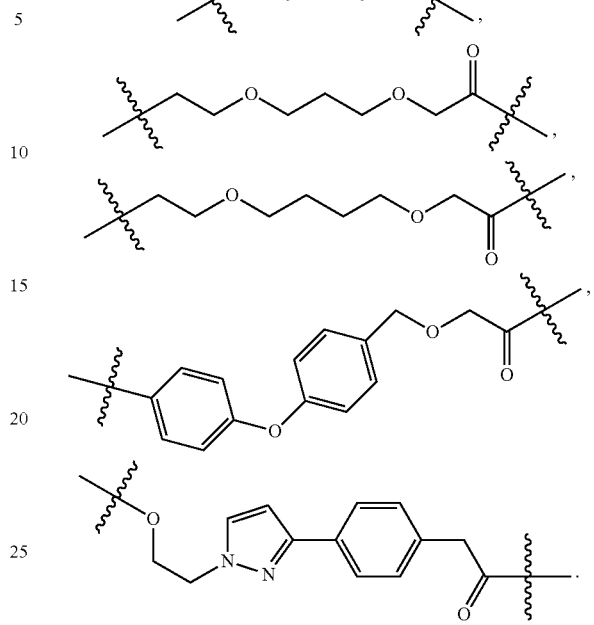
In the above structures
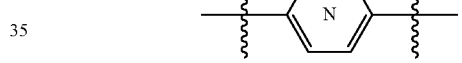
represents
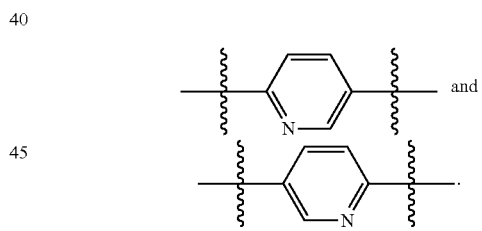
In certain embodiments, Linker can be a 4-24 carbon atom linear chains, wherein one or more the carbon atoms in the linear chain can be replaced or substituted with oxygen, nitrogen, amide, fluorinated carbon, etc., such as the following:
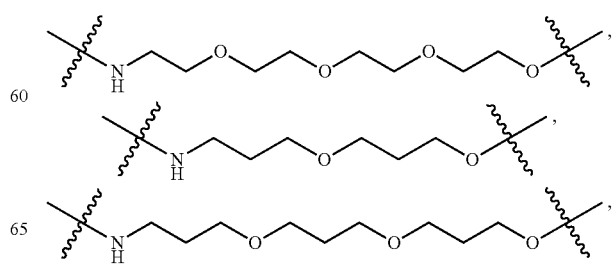

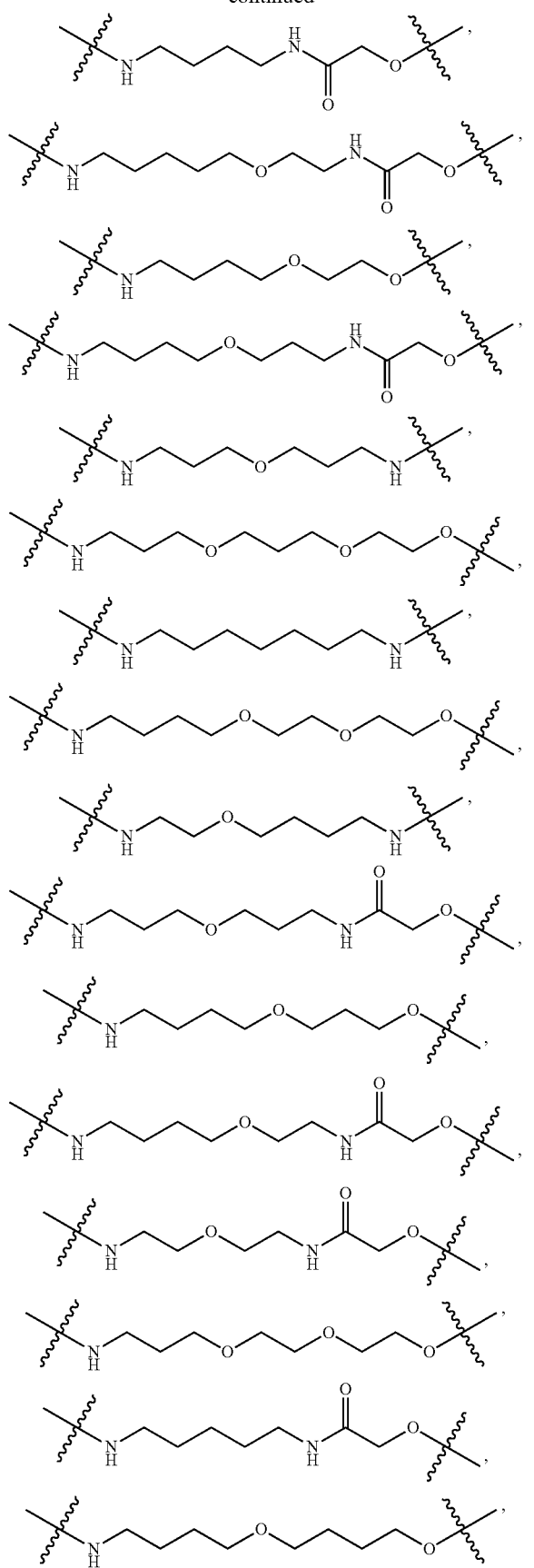
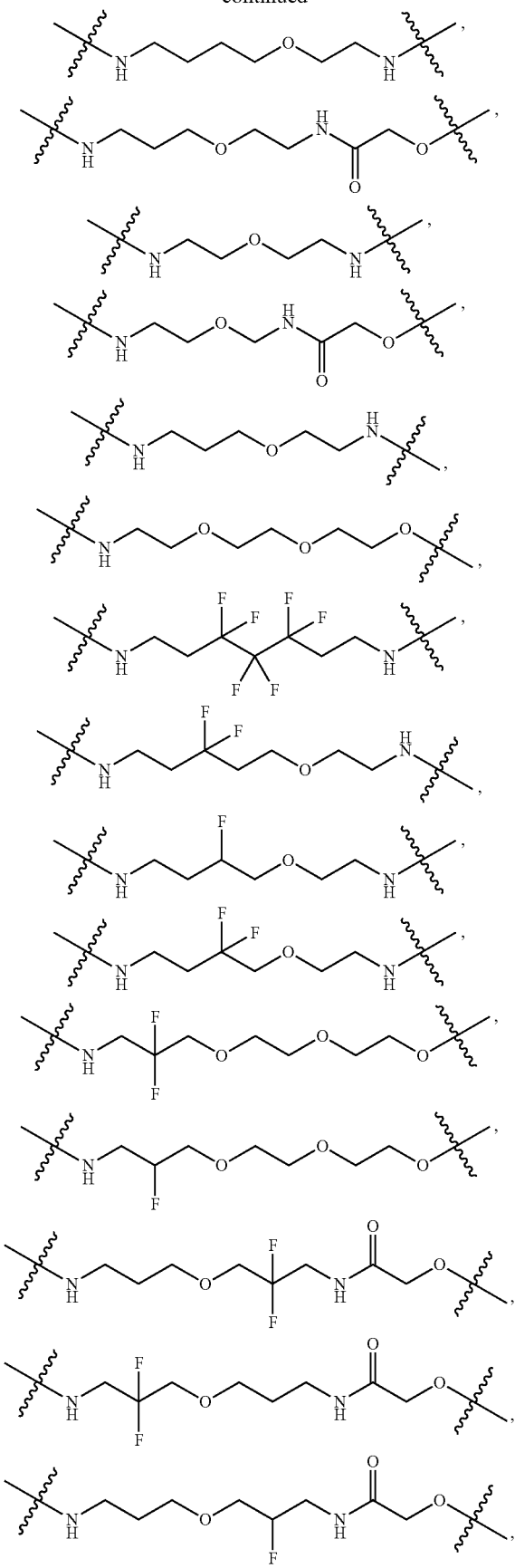

-continued

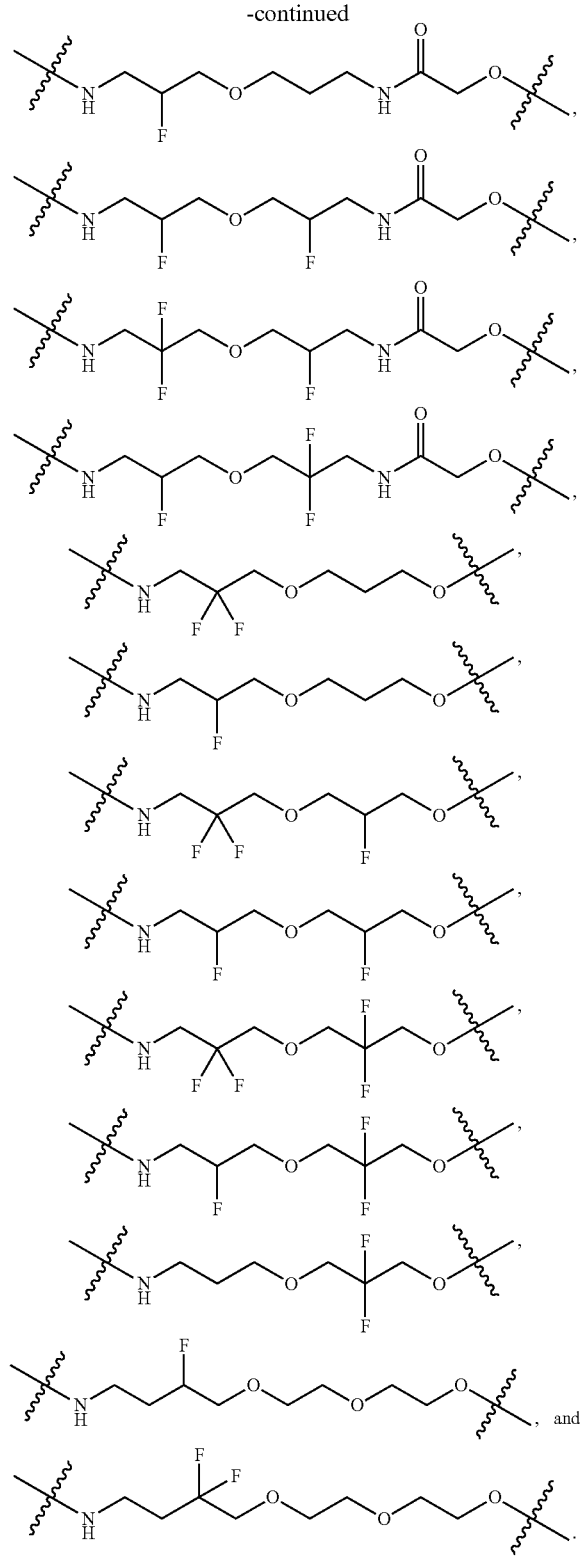

In certain embodiments, Linker can be a nonlinear chain, and can be, or include, aliphatic or aromatic or heteroaromatic cyclic moieties.

In certain embodiments, the Linker may include contiguous, partially contiguous or non-contiguous ethylene glycol unit groups ranging in size from about 1 to about 12 ethylene glycol units, between 1 and about 10 ethylene glycol units, about 2 about 6 ethylene glycol units, between about 2 and 5 ethylene glycol units, between about 2 and 4 ethylene glycol units, for example, 1, 2, 3, 4, 6, 6, 7, 8, 9, 10, 11 or 12 ethylene glycol units.

In certain embodiments, the Linker may have 1, 2, 3, 4, 5, 6, 7, 8, 9, 10, 11, 12, 13, 14, or 15 fluorine substituents. In another embodiment the Linker is perfluorinated. In yet another embodiment the Linker is a partially or fully fluorinated poly ether. Nonlimiting examples of fluorinated Linkers include:

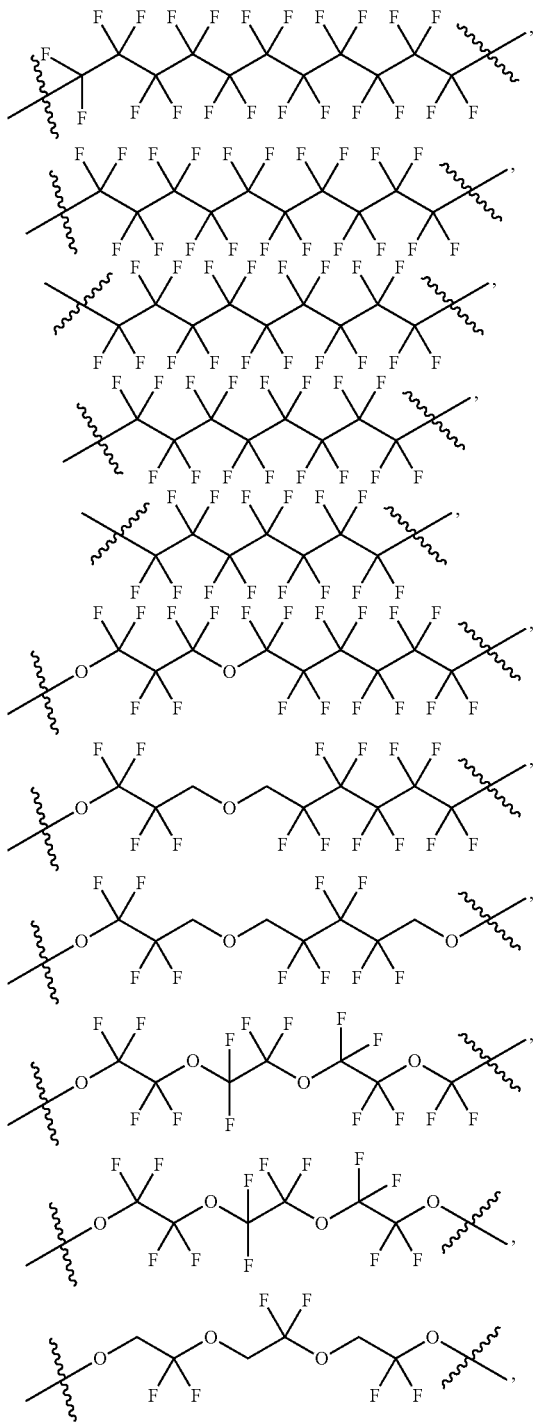

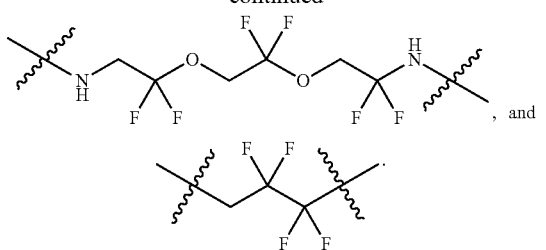

, and

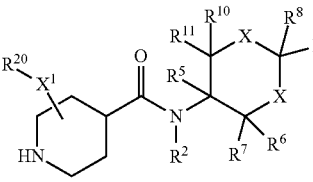

In certain embodiments, where the Target Ligand binds more than one protein (i.e., is not completely selective), selectivity may be enhanced by varying Linker length where the ligand binds some of its targets in different binding pockets, e.g., deeper or shallower binding pockets than others. Therefore, the length can be adjusted as desired.

In certain embodiments, the present invention includes the Degron-Linker (DL) having the following structure:

DLI

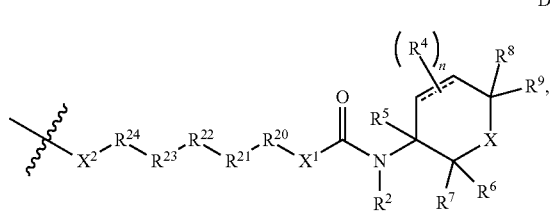

DLII

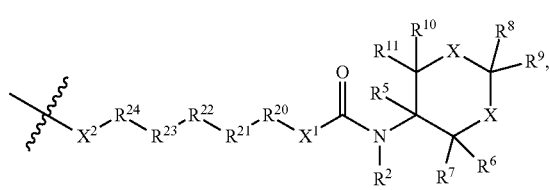

DLIa

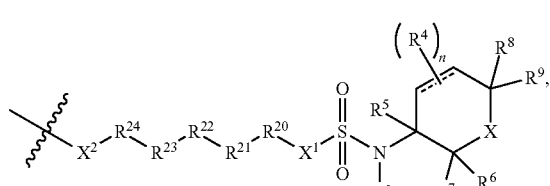

DLIIa

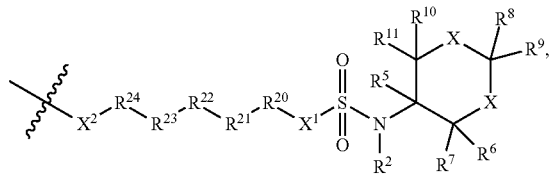

DLIb

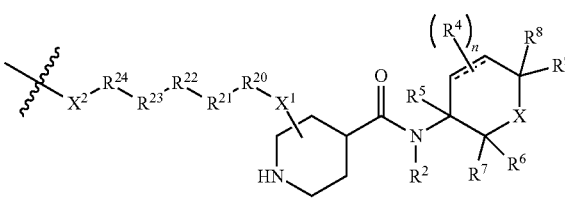

DLIIb

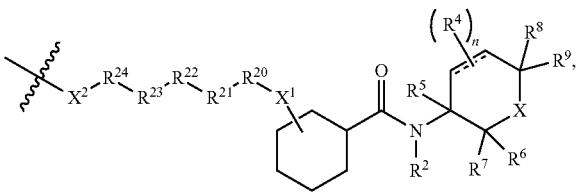

DLIc

DLIIc

DLId

DLIId

DLIe

DLIIe

In another embodiment, the present invention provides the Degron-Linker (DL) having the following structure:

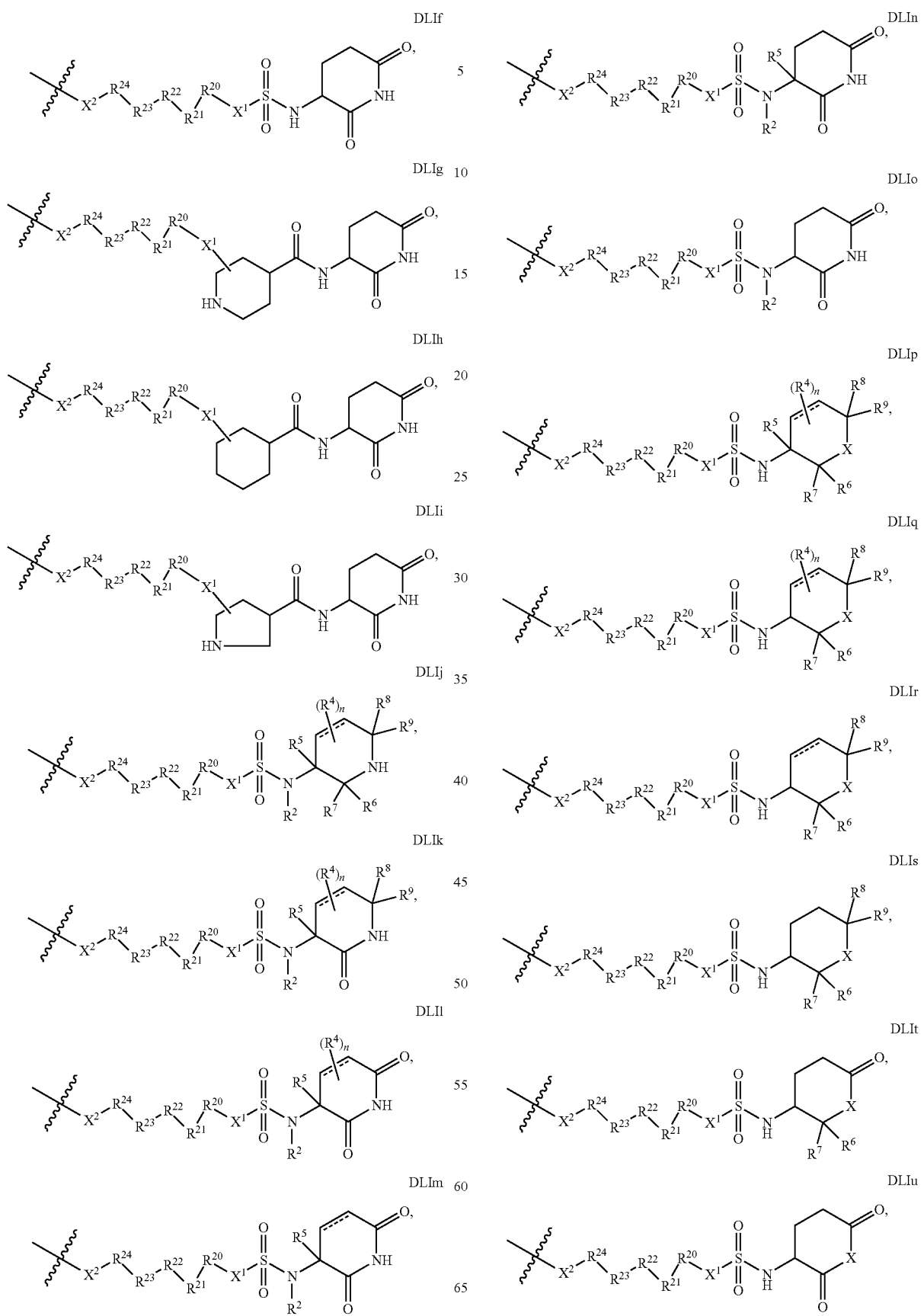

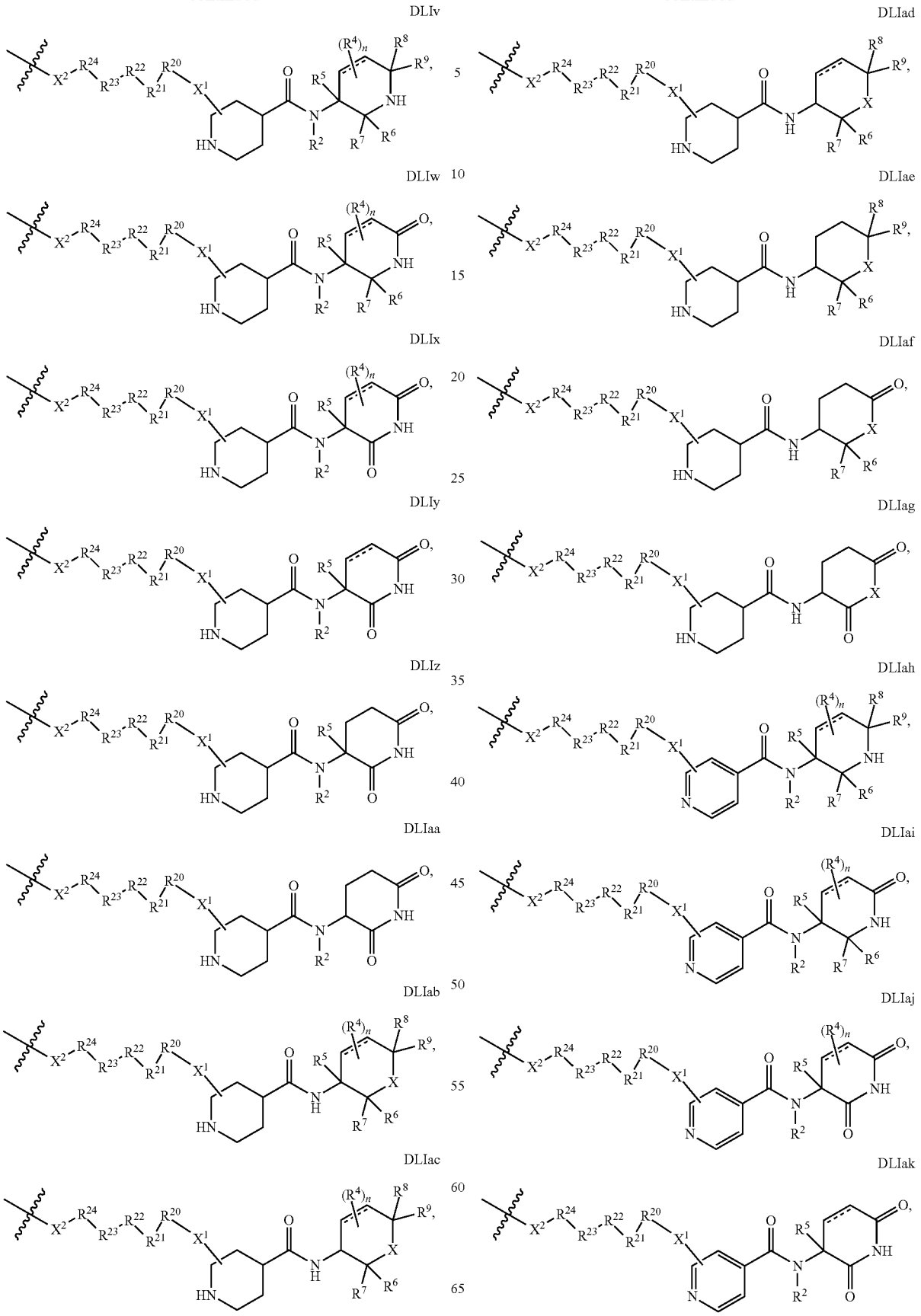

-continued
DLIal
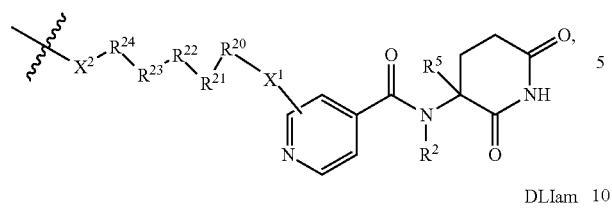
DLIam
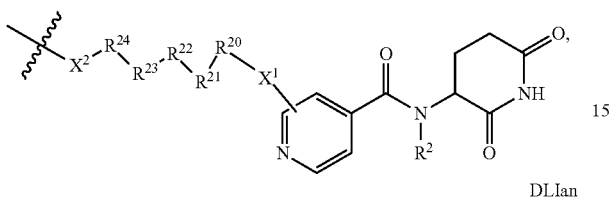
DLIan
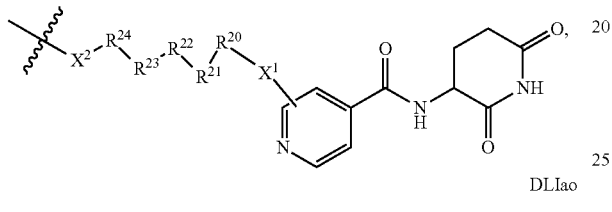
DLIao
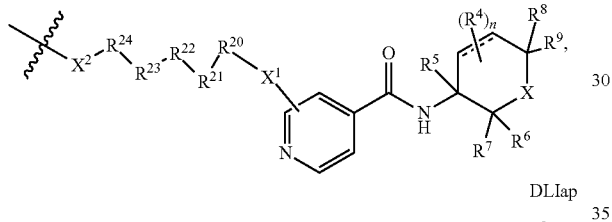
DLIap
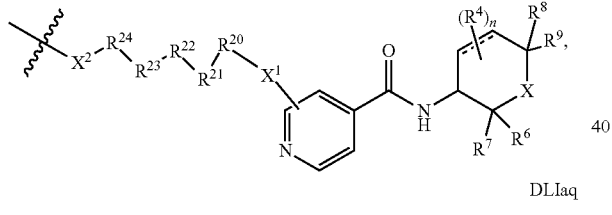
DLIaq
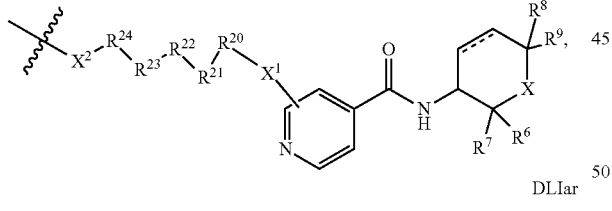
DLIar
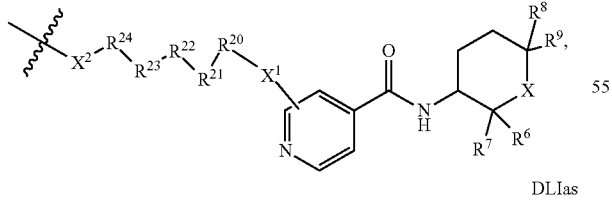
DLIas
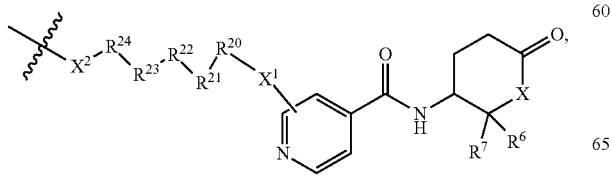
-continued
DLIat
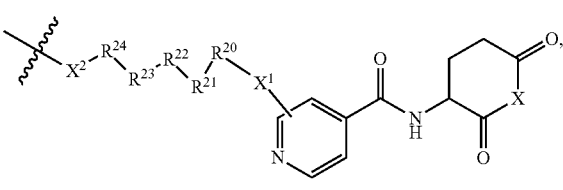
DLIau
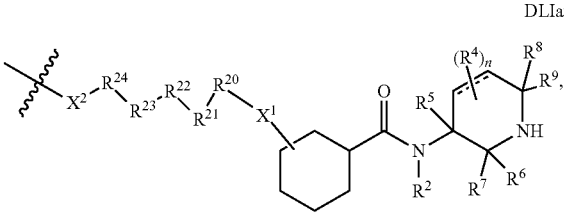
DLIav
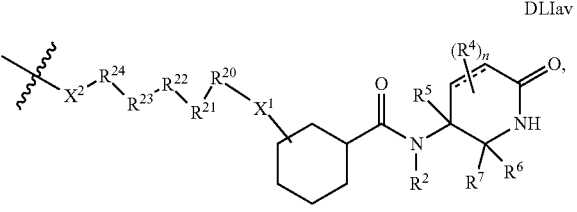
DLIaw
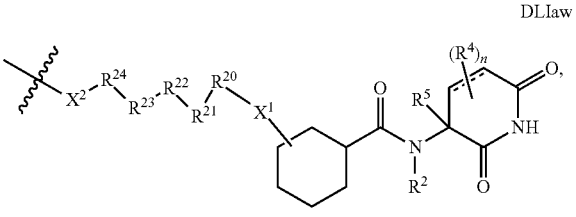
DLIax
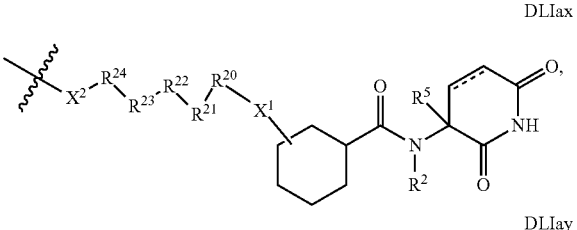
DLIay
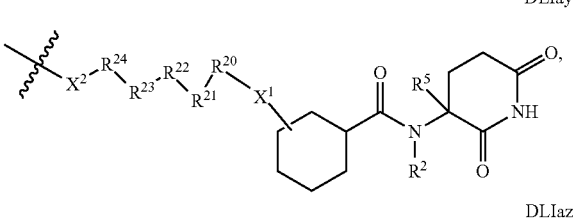
DLIaz
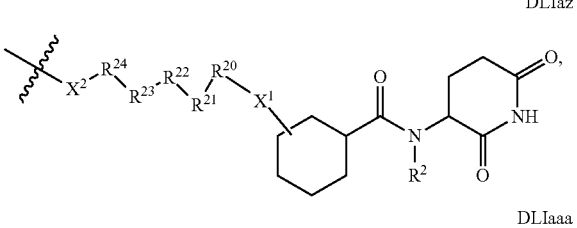
DLIaaa
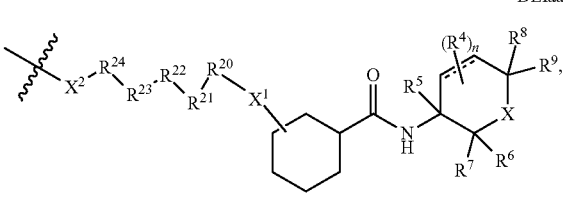

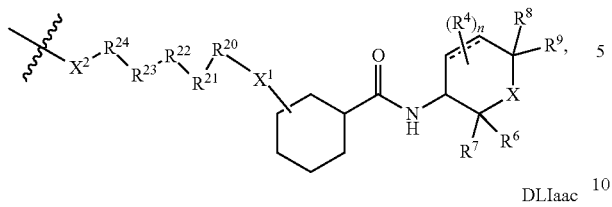
DLIaab

DLIaac
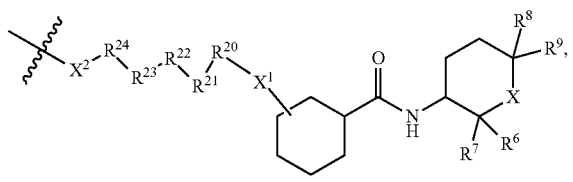
DLIaad
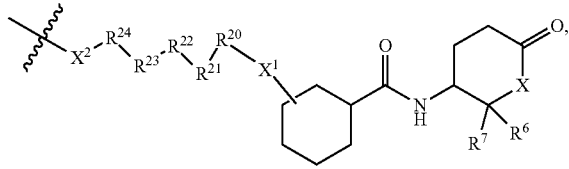
DLIaae
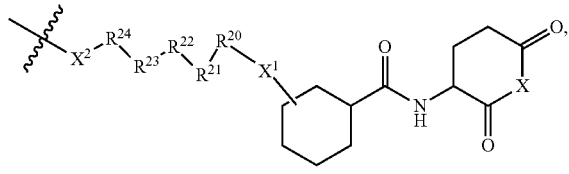
DLIaaf
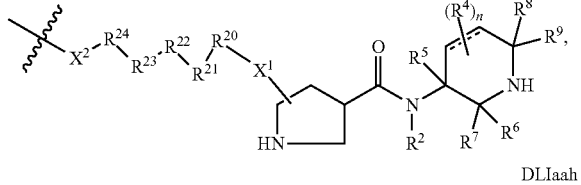
DLIaag
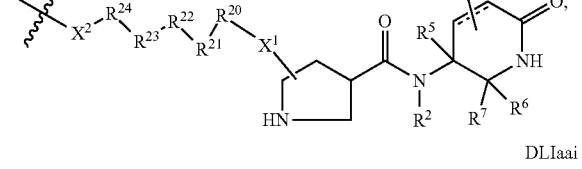
DLIaah
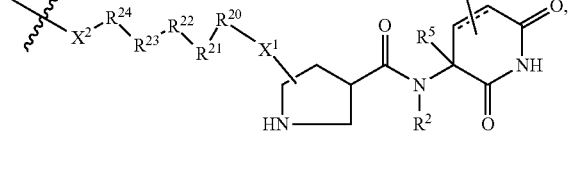
DLIaai
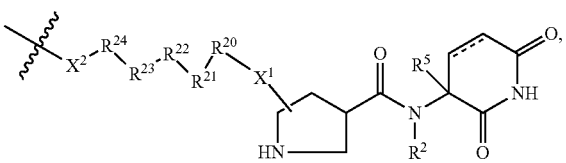
DLIaaj
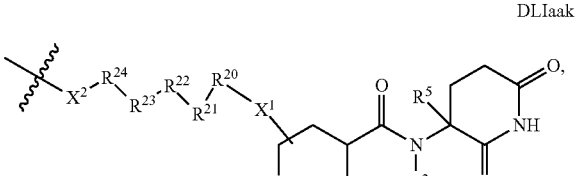
DLIaak
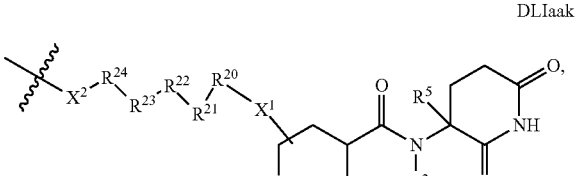
DLIaal
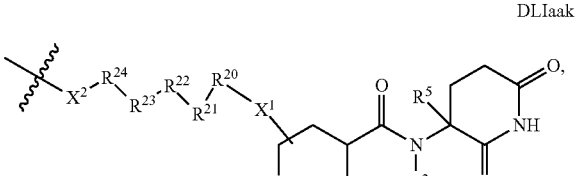
DLIaam
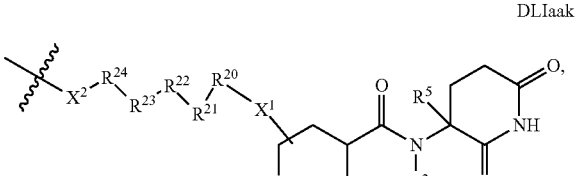
DLIaan
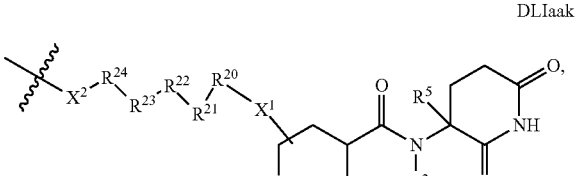
DLIaao
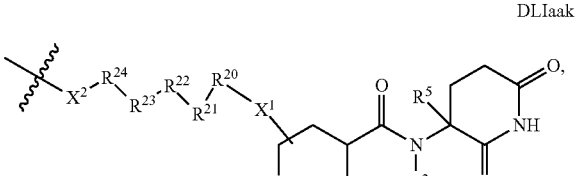
DLIaap
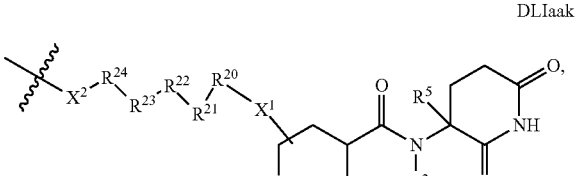
DLIaaq -continued

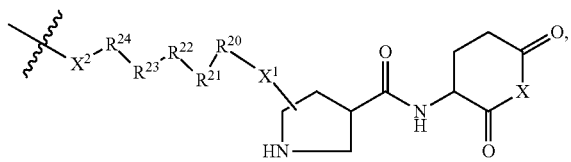
DLIaar wherein each of the variables is as described above in Formula I and Formula LI, and a Targeting Ligand is covalently bonded to the DL with the

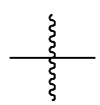

next to $X^2$.

Target Proteins

Degradation of cellular proteins is required for cell homeostasis and normal cell function, such as proliferation, differentiation and cell death. When this system becomes dysfunctional or does not identify and abate abnormal protein behavior in vivo, a disease state can arise in a host, such as a human. A large range of proteins can cause, modulate or amplify diseases in vivo, as well known to those skilled in the art, published in literature and patent filings as well as presented in scientific presentations.

Therefore, in one embodiment, a selected Degronimer compound of the present invention can be administered in vivo in an effective amount to a host in need thereof to degrade a selected protein that mediates a disorder to be treated. The selected protein target may modulate a disorder in a human via a mechanism of action such as modification of a biological pathway, pathogenic signaling or modulation of a signal cascade or cellular entry. In one embodiment, the Target Protein is a protein that is not drugable in the classic sense in that it does not have a binding pocket or an active site that can be inhibited or otherwise bound, and cannot be easily allosterically controlled. In another embodiment, the Target Protein is a protein that is drugable in the classic sense, yet for therapeutic purposes, degradation of the protein is preferred to inhibition.

The Target Protein is recruited with a Targeting Ligand, which is a ligand for the Target Protein. Typically the Targeting Ligand binds the Target Protein in a non-covalent fashion. In an alternative embodiment, the Target Protein is covalently bound to the Degron in a manner that can be irreversible or reversible.

In one embodiment, the selected Target Protein is expressed from a gene that has undergone an amplification, translocation, deletion, or inversion event which causes or is caused by a medical disorder. In certain aspects, the selected Target Protein has been post-translationally modified by one, or a combination, of phosphorylation, acetylation, acylation including propionylation and crotylation, N-linked glycosylation, amidation, hydroxylation, methylation and poly-methylation, O-linked glycosylation, pyrogultamoylation, myristoylation, farnesylation, geranylgeranylation, ubiquitination, sumoylation, or sulfation which causes or is caused by a medical disorder.

As contemplated herein, the present invention includes an Degronimer with a Targeting Ligand that binds to a Target Protein of interest. The Target Protein is any amino acid sequence to which an Degronimer can be bound which by degradation thereof, causes a beneficial therapeutic effect in vivo. In one embodiment, the Target Protein is a non-endogenous peptide such as that from a pathogen or toxin. In another embodiment, the Target Protein can be an endogenous protein that mediates a disorder. The endogenous protein can be either the normal form of the protein or an aberrant form. For example, the Target Protein can be a mutant protein found in cancer cells, or a protein, for example, where a partial, or full, gain-of-function or loss-of-function is encoded by nucleotide polymorphisms. In some embodiments, the Degronimer targets the aberrant form of the protein and not the normal form of the protein. In another embodiment, the Target Protein can mediate an inflammatory disorder or an immune disorder, including an auto-immune disorder. In one embodiment, the Target Protein is a non-endogenous protein from a virus, as non-limiting examples, HIV, HBV, HCV, RSV, HPV, CMV, flavivirus, pestivirus, coronavirus, noroviridae, etc. In one embodiment, the Target Protein is a non-endogenous protein from a bacteria, which may be for example, a gram positive bacteria, gram negative bacteria or other, and can be a drug-resistant form of bacteria. In one embodiment, the Target Protein is a non-endogenous protein from a fungus. In one embodiment, the Target Protein is a non-endogenous protein from a prion. In one embodiment, the Target Protein is a protein derived from a eukaryotic pathogen, for example a protist, helminth, etc.

In one aspect, the Target Protein mediates chromatin structure and function. The Target Protein may mediate an epigenetic action such as DNA methylation or covalent modification of histones. An example is histone deacetylase (HDAC 1, 2, 3, 4, 5, 6, 7, 8, 9, 10 or 11). Alternatively, the Target Protein may be a bromodomain, which are readers of lysine acetylation (for example, BRD1, 2, 3, 4, 5, 6, 7, 8, 9 and T. FIG. 9 illustrates the proteins of the bromodomain family, which, for example, can act as Target Proteins according to the present invention.

Other nonlimiting examples of Target Proteins are a structural protein, receptor, enzyme, cell surface protein, a protein involved in apoptotic signaling, aromatase, helicase, mediator of a metabolic process (anabolism or catabolism), antioxidant, protease, kinase, oxidoreductase, transferase, hydrolase, lyase, isomerase, ligase, enzyme regulator, signal transducer, structural molecule, binding activity (protein, lipid carbohydrate), cell motility protein, membrane fusion protein, cell communication mediator, regulator of biological processes, behavioral protein, cell adhesion protein, protein involved in cell death, protein involved in transport (including protein transporter activity, nuclear transport, ion transporter, channel transporter, carrier activity, permease, secretase or secretion mediator, electron transporter, chaperone regulator, nucleic acid binding, transcription regulator, extracellular organization and biogenesis regulator, and translation regulator).

In one embodiment, the Target Protein is a modulator of a signaling cascade related to a known disease state. In another embodiment, the Target Protein mediates a disorder by a mechanism different from modulating a signaling cascade. Any protein in a eukaryotic system or a microbial system, including a virus, bacteria or fungus, as otherwise described herein, are targets for proteasomal degradation using the present invention. The Target Protein may be a eukaryotic protein, and in some embodiments, a human protein.

In one embodiment, the Target Protein is RXR, DHFR, Hsp90, a kinase, HDM2, MDM2, BET bromodomain-containing protein, HDAC, IDH1, Mcl-1, human lysine methyltransferase, a nuclear hormone receptor, aryl hydrocarbon receptor (AHR), RAS, RAF, FLT, SMARC, KSR, NF2L, CTNB, CBLB, BCL.

In one embodiment, a bromodomain containing protein has histone acetyl transferase activity.

In one embodiment, the bromodomain containing protein is BRD2, BRD3, BRD4, BRDT or ASH1L.

In one embodiment, the bromodomain containing protein is a non-BET protein.

In one embodiment, the non-BET protein is BRD7 or BRD9.

In one embodiment, the FLT is not FLT 3. In one embodiment, the RAS is not RASK. In one embodiment, the RAF is not RAF1. In one embodiment, the SMARC is not SMARC2. In one embodiment, the KSR is not KSR1. In one embodiment, the NF2L is not NF2L2. In one embodiment, the CTNB is not CTNB1. In one embodiment, the BCL is not BCL6.

In one embodiment, the Target Protein is selected from: EGFR, FLT3, RAF1, SMRCA2, KSR1, NF2L2, CTNB1, CBLB, BCL6, and RASK.

In another embodiment, the Target Protein is not selected from: EGFR, FLT3, RAF1, SMRCA2, KSR1, NF2L2, CTNB1, CBLB, BCL6, and RASK.

In one embodiment, the Targeting Ligand is an EGFR ligand, a FLT3 ligand, a RAF1 ligand, a SMRCA2 ligand, a KSR1 ligand, a NF2L2 ligand, a CTNB1 ligand, a CBLB ligand, a BCL6 ligand, or a RASK ligand.

In one embodiment, the Targeting Ligand is not a EGFR ligand, a FLT3 ligand, a RAF1 ligand, a SMRCA2 ligand, a KSR1 ligand, a NF2L2 ligand, a CTNB1 ligand, a CBLB ligand, a BCL6 ligand, or a RASK ligand.

The present invention may be used to treat a wide range of disease states and/or conditions, including any disease state and/or condition in which a protein is dysregulated and where a patient would benefit from the degradation of proteins.

For example, a Target Protein can be selected that is a known target for a human therapeutic, and the therapeutic can be used as the Targeting Ligand when incorporated into the Degronimer according to the present invention. These include proteins which may be used to restore function in a polygenic disease, including for example B7.1 and B7, TINFR1m, TNFR2, NADPH oxidase, Bcl2/Bax and other partners in the apoptosis pathway, C5a receptor, HMG-CoA reductase, PDE V phosphodiesterase type, PDE IV phosphodiesterase type 4, PDE I, PDEII, PDEIII, squalene cyclase inhibitor, CXCR1, CXCR2, nitric oxide (NO) synthase, cyclo-oxygenase 1, cyclo-oxygenase 2, 5HT receptors, dopamine receptors, G Proteins, e.g., Gq, histamine receptors, 5-lipoxygenase, tryptase serine protease, thymidylate synthase, purine nucleoside phosphorylase, GAPDH trypanosomal, glycogen phosphorylase, Carbonic anhydrase, chemokine receptors, JAW STAT, RXR and similar, HIV 1 protease, HIV 1 integrase, influenza, neuraminidase, hepatitis B reverse transcriptase, sodium channel, multi drug resistance (MDR), protein P-glycoprotein (and MRP), tyrosine kinases, CD23, CD124, tyrosine kinase p56 lck, CD4, CD5, IL-2 receptor, IL-1 receptor, TNF-alphaR, ICAM1, Cat+ channels, VCAM, VLA-4 integrin, selectins, CD40/CD40L, neurokinins and receptors, inosine monophosphate dehydrogenase, p38 MAP Kinase, Ras/Raf/MER/ERK pathway, interleukin-1 converting enzyme, caspase, HCV, NS3 protease, HCV NS3 RNA helicase, glycinamide ribonucleotide formyl transferase, rhinovirus 3C protease, herpes simplex virus-1 (HSV-I), protease, cytomegalovirus (CMV) protease, poly (ADP-ribose) polymerase, cyclin dependent kinases, vascular endothelial growth factor, oxytocin receptor, microsomal transfer protein inhibitor, bile acid transport inhibitor, 5 alpha reductase inhibitors, angiotensin 11, glycine receptor, noradrenaline reuptake receptor, endothelin receptors, neuropeptide Y and receptor, estrogen receptors, androgen receptors, adenosine receptors, adenosine kinase and AMP deaminase, purinergic receptors (P2Y1, P2Y2, P2Y4, P2Y6, P2X1-7), farnesyltransferases, geranylgeranyl transferase, TrkA a receptor for NGF, beta-amyloid, tyrosine kinase Flk-IIKDR, vitronectin receptor, integrin receptor, Her-2/neu, telomerase inhibition, cytosolic phospholipaseA2 and EGF receptor tyrosine kinase. Additional protein targets include, for example, ecdysone 20-monooxygenase, ion channel of the GABA gated chloride channel, acetylcholinesterase, voltage-sensitive sodium channel protein, calcium release channel, and chloride channels. Still further Target Proteins include Acetyl-CoA carboxylase, adenylosuccinate synthetase, protoporphyrinogen oxidase, and enolpyruvylshikimate-phosphate synthase.

In certain embodiments, the Target Protein is derived from a kinase to which the Targeting Ligand is capable of binding or binds including, but not limited to, a tyrosine kinase (e.g., AATK, ABL, ABL2, ALK, AXL, BLK, BMX, BTK, CSF1R, CSK, DDR1, DDR2, EGFR, EPHA1, EPHA2, EPHA3, EPHA4, EPHA5, EPHA6, EPHA7, EPHA8, EPHA10, EPHB1, EPHB2, EPHB3, EPHB4, EPHB6, ERBB2, ERBB3, ERBB4, FER, FES, FGFR1, FGFR2, FGFR3, FGFR4, FGR, FLT1, FLT3, FLT4, FRK, FYN, GSG2, HCK, IGF1R, ILK, INSR, INSRR, IRAK4, ITK, JAK1, JAK2, JAK3, KDR, KIT, KSR1, LCK, LMTK2, LMTK3, LTK, LYN, MATK, MERTK, MET, MLTK, MST1R, MUSK, NPR1, NTRK1, NTRK2, NTRK3, PDGFRA, PDGFRB, PLK4, PTK2, PTK2B, PTK6, PTK7, RET, ROR1, ROR2, ROS1, RYK, SGK493, SRC, SRMS, STYK1, SYK, TEC, TEK, TEX14, TIE1, TNK1, TNK2, TNNI3K, TXK, TYK2, TYRO3, YES1, or ZAP70).

In certain embodiments, the Target Protein is derived from a kinase to which the Targeting Ligand is capable of binding or binds including, but not limited to, a serine/threonine kinase (e.g., casein kinase 2, protein kinase A, protein kinase B, protein kinase C, Raf kinases, CaM kinases, AKT1, AKT2, AKT3, ALK1, ALK2, ALK3, ALK4, Aurora A, Aurora B, Aurora C, CHK1, CHK2, CLK1, CLK2, CLK3, DAPK1, DAPK2, DAPK3, DMPK, ERK1, ERK2, ERK5, GCK, GSK3, HIPK, KHS1, LKB1, LOK, MAPKAPK2, MAPKAPK, MNK1, MSSK1, MST1, MST2, MST4, NDR, NEK2, NEK3, NEK6, NEK7, NEK9, NEK11, PAK1, PAK2, PAK3, PAK4, PAK5, PAK6, PIM1, PIM2, PLK1, RIP2, RIP5, RSK1, RSK2, SGK2, SGK3, SIK1, STK33, TAO1, TAO2, TGF-beta, TLK2, TSSK1, TSSK2, ULK1, or ULK2).

In certain embodiments, the Target Protein is derived from a kinase to which the Targeting Ligand is capable of binding or binds including, but not limited to a cyclin dependent kinase for example CDK1, CDK2, CDK3, CDK4, CDK5, CDK6, CDK7, CDK8, CDK9, CDK10, CDK11, CDK12, or CDK13.

In certain embodiments, the Target Protein is derived from a kinase to which the Targeting Ligand is capable of binding or binds including, but not limited to a leucine-rich repeat kinase (e.g., LRRK2).

In certain embodiments, the Target Protein is derived from a kinase to which the Targeting Ligand is capable of binding or binds including, but not limited to a lipid kinase (e.g., PIK3CA, PIK3CB) or a sphingosine kinase (e.g. S1P).

In certain embodiments, the Target Protein is derived from a BET bromodomain-containing protein to which the Targeting Ligand is capable of binding or binds including, but not limited to, ASH1L, ATAD2, BAZ1A, BAZ1B, BAZ2A, BAZ2B, BRD1, BRD2, BRD3, BRD4, BRD5, BRD6, BRD7, BRD8, BRD9, BRD10, BRDT, BRPF1, BRPF3, BRWD3, CECR2, CREBBP, EP300, FALZ, GCN5L2, KIAA1240, LOC93349, MLL, PB1, PCAF, PHIP, PRKCBP1, SMARCA2, SMARCA4, SP100, SP110, SP140, TAF1, TAF1L, TIF1a, TRIM28, TRIM33, TRIM66, WDR9, ZMYND11, and MLL4. In certain embodiments, a BET bromodomain-containing protein is BRD4.

In certain embodiments, the Target Protein is derived from a nuclear protein to which the Targeting Ligand is capable of binding or binds including, but not limited to, BRD2, BRD3, BRD4, Antennapedia Homeodomain Protein, BRCA1, BRCA2, CCAAT-Enhanced-Binding Proteins, histones, Polycomb-group proteins, High Mobility Group Proteins, Telomere Binding Proteins, FANCA, FANCD2, FANCE, FANCF, hepatocyte nuclear factors, Mad2, NF-kappa B, Nuclear Receptor Coactivators, CREB-binding protein, p55, p107, p130, Rb proteins, p53, c-fos, c-jun, c-mdm2, c-myc, and c-rel.

In certain embodiments, the Target Protein is a member of the Retinoid X Receptor (RXR) family and the disorder treated is a neuropsychiatric or neurodegenerative disorder. In certain embodiments, the Target Protein is a member of the Retinoid X Receptor (RXR) family and the disorder treated is schizophrenia.

In certain embodiments, the Target Protein is dihydrofolate reductase (DHFR) and the disorder treated is cancer. In certain embodiments, the Target Protein is dihydrofolate reductase (DHFR) and the disorder treated is microbial.

In certain embodiments, the Target Protein is dihydrofolate reductase from *Bacillus anthracis* (BaDHFR) and the disorder treated is anthrax.

In certain embodiments, the Target Protein is Heat Shock Protein 90 (HSP90) and the disorder treated is cancer.

In certain embodiments, the Target Protein is a kinase or phosphatase and the disorder treated is cancer.

In certain embodiments, the Target Protein is HDM2 and or MDM2 and the disorder treated is cancer.

In certain embodiments, the Target Protein is a BET bromodomain containing protein and the disorder treated is cancer.

In certain embodiments, the Target Protein is a lysine methyltransferase and the disorder treated is cancer.

In certain embodiments, the Target Protein belongs to the RAF family and the disorder treated is cancer.

In certain embodiments, the Target Protein belongs to the FKBP family and the disorder treated is an autoimmune disorder. In certain embodiments, the Target Protein belongs to the FKBP family and the disorder treated is organ rejection. In certain embodiments, the Target Protein belongs to the FKBP family and the compound is given prophylactically to prevent organ failure.

In certain embodiments, the Target Protein is an androgen receptor and the disorder treated is cancer.

In certain embodiments, the Target Protein is an estrogen receptor and the disorder treated is cancer.

In certain embodiments, the Target Protein is a viral protein and the disorder treated is a viral infection. In certain embodiments, the Target Protein is a viral protein and the disorder treated is HIV, HPV, or HCV.

In certain embodiments, the Target Protein is an AP-1 or AP-2 transcription factor and the disorder treated is cancer.

In certain embodiments, the Target Protein is a HIV protease and the disorder treated is a HIV infection. In certain embodiments, the Target Protein is a HIV integrase and the disorder treated is a HIV infection. In certain embodiments, the Target Protein is a HCV protease and the disorder treated is a HCV infection. In certain embodiments, the treatment is prophylactic and the Target Protein is a viral protein.

In certain embodiments, the Target Protein is a member of the histone deacetylase (HDAC) family and the disorder is a neurodegenerative disorder. In certain embodiments, the Target Protein is a member of the histone deacetylase (HDAC) family and the disorder is Huntingon's, Parkinson's, Kennedy disease, amyotropic lateral sclerosis, Rubinstein-Taybi syndrome, or stroke.

In certain embodiments, the Target Protein as referred to herein is named by the gene that expresses it. The person skilled in the art will recognize that when a gene is referred to as a Target Protein, the protein encoded by the gene is the Target Protein. For example, ligands for the protein SMCA2 which is encoded by SMRCA2 are referred to as SMRCA2 Targeting Ligands.

Targeting Ligands

In certain aspects, the Targeting Ligand is a ligand which covalently or non-covalently binds to a Target Protein which has been selected for proteasomal degradation by the selected Degronimer. A Targeting Ligand is a small molecule or moiety (for example a peptide, nucleotide, antibody, antibody fragment, aptamer, biomolecule or other chemical structure) that binds to a Target Protein, and wherein the Target Protein is a mediator of disease in a host as described in detail below. Exemplary Target Ligands are provided in FIGS. 1A-8PPPPP.

In one embodiment, the Targeting Ligand binds to an endogenous protein which has been selected for degradation as a means to achieve a therapeutic effect on the host. Illustrative Targeting Ligands include: RXR ligands, DHFR ligands, Hsp90 inhibitors, kinase inhibitors, HDM2 and MDM2 inhibitors, compounds targeting Human BET bromodomain-containing proteins, HDAC inhibitors, ligands of MerTK, ligands of IDH1, ligands of Mcl-1, ligands of SMRCA2, ligands of EGFR, ligands of RAF, ligands of cRAF, human lysine methyltransferase inhibitors, angiogenesis inhibitors, nuclear hormone receptor compounds, immunosuppressive compounds, and compounds targeting the aryl hydrocarbon receptor (AHR), among numerous others. Targeting Ligands also considered to include their pharmaceutically acceptable salts, prodrugs and isotopic derivatives.

In certain aspects, the Targeting Ligand binds to a dehalogenase enzyme in a patient or subject or in a diagnostic assay and is a haloalkane (preferably a $C_1$-$C_{10}$ alkyl group which is substituted with at least one halo group, preferably a halo group at the distal end of the alkyl group (i.e., away from the Linker). In still other embodiments, the Targeting Ligand is a haloalkyl group, wherein said alkyl group generally ranges in size from about 1 or 2 carbons to about 12 carbons in length, often about 2 to 10 carbons in length, often about 3 carbons to about 8 carbons in length, more often about 4 carbons to about 6 carbons in length. The haloalkyl groups are generally linear alkyl groups (although branched-chain alkyl groups may also be used) and are end-capped with at least one halogen group, preferably a single halogen group, often a single chloride group. Haloalkyl PT, groups for use in the present invention are preferably represented by the chemical structure $(CH_2)_v$—Halo where v is any integer from 2 to about 12, often about 3 to about 8, more often about 4 to about 6. Halo may be any halogen, but is preferably Cl or Br, more often Cl.

In certain embodiments, the Targeting Ligand is a retinoid X receptor (RXR) agonist or antagonist. Non-limiting examples include retinol, retinoic acid, bexarotene, docosahexenoic acid, compounds disclosed in WO 9929324, the publication by Canan Koch et al. (*J. Med. Chem.* 1996, 39, 3229-3234) titled "Identification of the First Retinoid X Receptor Homodimer Antagonist", WO 9712853, EP 0947496A1, WO 2016002968, and analogs thereof.

In certain embodiments, the Targeting Ligand is a DHFR agonist or antagonist. Non-limiting examples include folic acid, methotrexate, 8,10-dideazatetrahydrofolate compounds disclosed by Tian et al. (Chem. Biol. Drug Des. 2016, 87, 444-454) titled "Synthesis, Antifolate and Anticancer Activities of N5-Substituted 8,10-Dideazatetrahydrofolate Analogues", compounds prepared by Kaur et al. (Biorg. Med. Chem. Lett. 2016, 26, 1936-1940) titled "Rational Modification of the Lead Molecule: Enhancement in the Anticancer and Dihydrofolate Reductase Inhibitory Activity", WO 2016022890, compounds disclosed by Zhang et al. (Int. J. Antimicrob. Agents 46, 174-182) titled "New Small-Molecule Inhibitors of Dihydrofolate Reductase Inhibit Streptococcus Mutans", modified trimethoprim analogs developed by Singh et al. (J. Med. Chem. 2012, 55, 6381-6390) titled "Mechanism Inspired Development of Rationally Designed Dihydrofolate Reductase Inhibitors as Anticancer Agents", WO20111153310, and analogs thereof.

In certain embodiments, the Targeting Ligand derived from estrogen, an estrogen analog, SERM (selective estrogen receptor modulator), a SERD (selective estrogen receptor degrader), a complete estrogen receptor degrader, or another form of partial or complete estrogen antagonist or agonist. Examples are the partial anti-estrogens raloxifene and tamoxifen and the complete antiestrogen fulvestrant. Non-limiting examples of anti-estrogen compounds are provided in WO 2014/19176 assigned to Astra Zeneca, WO2013/090921, WO 2014/203129, WO 2014/203132, and US2013/0178445 assigned to Olema Pharmaceuticals, and U.S. Pat. Nos. 9,078,871, 8,853,423, and 8,703,810, as well as US 2015/0005286, WO 2014/205136, and WO 2014/205138. Additional non-limiting examples of anti-estrogen compounds include: SERMS such as anordrin, bazedoxifene, broparestriol, chlorotrianisene, clomiphene citrate, cyclofenil, lasofoxifene, ormeloxifene, raloxifene, tamoxifen, toremifene, and fulvestrant; aromatase inhibitors such as aminoglutethimide, testolactone, anastrozole, exemestane, fadrozole, formestane, and letrozole; and antigonadotropins such as leuprorelin, cetrorelix, allylestrenol, chloromadinone acetate, cyproterone acetate, delmadinone acetate, dydrogesterone, medroxyprogesterone acetate, megestrol acetate, nomegestrol acetate, norethisterone acetate, progesterone, and spironolactone. Other estrogenic ligands that can be used according to the present invention are described in U.S. Pat. Nos. 4,418,068; 5,478,847; 5,393,763; and 5,457,117, WO2011/156518, U.S. Pat. Nos. 8,455,534 and 8,299,112, 9,078,871; 8,853,423; 8,703,810; US 2015/0005286; and WO 2014/205138, US2016/0175289, US2015/0258080, WO 2014/191726, WO 2012/084711; WO 2002/013802; WO 2002/004418; WO 2002/003992; WO 2002/003991; WO 2002/003990; WO 2002/003989; WO 2002/003988; WO 2002/003986; WO 2002/003977; WO 2002/003976; WO 2002/003975; WO 2006/078834; U.S. Pat. No. 6,821,989; US 2002/0128276; U.S. Pat. No. 6,777,424; US 2002/0016340; U.S. Pat. Nos. 6,326,392; 6,756,401; US 2002/0013327; U.S. Pat. Nos. 6,512,002; 6,632,834; US 2001/0056099; U.S. Pat. Nos. 6,583,170; 6,479,535; WO 1999/024027; U.S. Pat. No. 6,005,102; EP 0802184; U.S. Pat. Nos. 5,998,402; 5,780,497, 5,880,137, WO 2012/048058 and WO 2007/087684.

In certain embodiments, the Targeting Ligand is a HSP90 inhibitor identified in Vallee et al. (*J. Med. Chem.* 2011, 54, 7206-7219) titled "Tricyclic Series of Heat Shock Protein 90 (Hsp90) Inhibitors Part I: Discovery of Tricyclic Imidazo [4,5-C]Pyridines as Potent Inhibitors of the Hsp90 Molecular Chaperone", including YKB (N-[4-(3H-imidazo[4,5-C]Pyridin-2-yl)-9H-Fluoren-9-yl]-succinamide), a HSP90 inhibitors (modified) identified in Brough et al. (*J. Med. Chem.* 2008, 51, 196-218) titled "4,5-Diarylisoxazole Hsp90 Chaperone Inhibitors: Potential Therapeutic Agents for the Treatment of Cancer", including compound 2GJ (5-[2,4-dihydroxy-5-(1-methylethyl)phenyl]-n-ethyl-4-[4-(morpholin-4-ylmethyl)phenyl]isoxazole-3-carboxamide), the HSP90 inhibitor geldanamycin ((4E,6Z,8S,9S,10E,12S,13R,14S,16R)-13-hydroxy-8,14,19-trimethoxy-4,10,12,16-tetramethyl-3,20,22-trioxo-2-azabicyclo[16.3.1] (derivatized) or any of its derivatives (e.g. 17-alkylamino-17-desmethoxygeldanamycin ("17-AAG") or 17-(2-dimethylaminoethyl)amino-17-desmethoxygeldanamycin ("17-DMAG")), or a HSP90 inhibitor (modified) identified in Wright et al. (*Chem. Biol.* 2004, 11, 775-785) titled "Structure-Activity Relationships in Purine-Based Inhibitor Binding to Hsp90 Isoforms", including the HSP90 inhibitor PU3. Other non-limiting examples of Hsp90 Targeting Ligands include SNX5422 currently in phase I clinical trials Reddy et al. (*Clin. Lymphoma Myeloma Leuk.* 2013, 13, 385-391) titled "Phase I Trial of the Hsp90 Inhibitor Pf-04929113 (Snx5422) in Adult Patients with Recurrent, Refractory Hematologic Malignancies", or NVP-AUY922 whose anti-cancer activity was assessed by Jensen et al. (*Breast Cancer Research: BCR* 2008, 10, R33-R[33]) titled "Nvp-Auy922: A Small Molecule Hsp90 Inhibitor with Potent Antitumor Activity in Preclinical Breast Cancer Models".

In certain embodiments, the Targeting Ligand is a kinase inhibitor identified in Millan et al. (*J. Med Chem.* 2011, 54, 7797-7814) titled "Design and Synthesis of Inhaled P38 Inhibitors for the Treatment of Chronic Obstructive Pulmonary Disease", including the kinase inhibitors Y1W and Y1X, a kinase inhibitor identified in Schenkel et al. (*J. Med Chem.* 2011, 54, 8440-8450) titled "Discovery of Potent and Highly Selective Thienopyridine Janus Kinase 2 Inhibitors", including the compounds 6TP and 0TP, a kinase inhibitor identified in van Eis et al. (*Biorg. Med Chem. Lett.* 2011, 21, 7367-7372) titled "2,6-Naphthyridines as Potent and Selective Inhibitors of the Novel Protein Kinase C Isozymes", including the kinase inhibitors 07U and YCF identified in Lountos et al. (*J. Struct. Biol.* 2011, 176, 292-301) titled "Structural Characterization of Inhibitor Complexes with Checkpoint Kinase 2 (Chk2), a Drug Target for Cancer Therapy", including the kinase inhibitors XK9 and NXP, afatinib, fostamatinib, gefitinib, lenvatinib, vandetanib, Gleevec, pazopanib, AT-9283, TAE684, nilotanib, NVP-BSK805, crizotinib, JNJ FMS, foretinib, OSI-027, OSI-930, or OSI-906.

In certain embodiments, the Targeting Ligand is a HDM2/MDM2 inhibitor identified in Vassilev et al. (*Science* 2004, 303, 844-848) titled "In Vivo Activation of the P53 Pathway by Small-Molecule Antagonists of Mdm2", and Schneekloth et al. (*Bioorg. Med Chem. Lett.* 2008, 18, 5904-5908) titled "Targeted Intracellular Protein Degradation Induced by a Small Molecule: En Route to Chemical Proteomics", including the compounds nutlin-3, nutlin-2, and nutlin-1.

In certain embodiments, the Targeting Ligand is a Human BET Bromodomain Targeting Ligand identified in Filippakopoulos et al. (*Nature* 2010, 468, 1067-1073) titled "Selective Inhibition of Bet Bromodomains" such as JQ1; a ligand identified in Nicodeme et al. (*Nature* 2010, 468, 1119-1123) titled "Suppression of Inflammation by a Synthetic Histone Mimic"; Chung et al. (*J. Med Chem.* 2011, 54, 3827-3838) titled "Discovery and Characterization of Small Molecule Inhibitors of the Bet Family Bromodomains"; a compound disclosed in Hewings et al. (*J. Med Chem.* 2011, 54, 6761-6770) titled "3,5-Dimethylisoxazoles Act as Acetyl-Lysine-Mimetic Bromodomain Ligands"; a ligand identified in Dawson et al. (*Nature* 2011, 478, 529-533) titled "Inhibition of Bet Recruitment to Chromatin as an Effective Treatment for MLL-Fusion Leukaemia"; or a ligand identified in the following patent applications US 2015/0256700, US 2015/0148342, WO 2015/074064, WO 2015/067770, WO 2015/022332, WO 2015/015318, and WO 2015/011084.

In certain embodiments, the Targeting Ligand is a HDAC Targeting Ligand identified in Finnin et al. (*Nature* 1999, 401, 188-193) titled "Structures of a Histone Deacetylase Homologue Bound to the Tsa and Saha Inhibitors", or a ligand identified as Formula (I) in PCT WO0222577.

In certain embodiments, the Targeting Ligand is a Human Lysine Methyltransferase ligand identified in Chang et al. (*Nat Struct Mol Biol* 2009, 16, 312-317) titled "Structural Basis for G9a-Like Protein Lysine Methyltransferase Inhibition by Bix-01294", a ligand identified in Liu et al. (*J Med Chem* 2009, 52, 7950-7953) titled "Discovery of a 2,4-Diamino-7-Aminoalkoxyquinazoline as a Potent and Selective Inhibitor of Histone Lysine Methyltransferase G9a", azacitidine, decitabine, or an analog thereof.

In certain embodiments, the Targeting Ligand is an angiogenesis inhibitor. Non-limiting examples of angiogenesis inhibitors include: GA-1, estradiol, testosterone, ovalicin, fumagillin, and analogs thereof.

In certain embodiments, the Targeting Ligand is an immunosuppressive compound. Non-limiting examples of immunosuppressive compounds include: AP21998, hydrocortisone, prednisone, prednisolone, methylprednisolone, beclometasone dipropionate, methotrexate, ciclosporin, tacrolimus, actinomycin, and analogues thereof.

In certain embodiments, the Targeting Ligand is an Aryl Hydrocarbon Receptor (AHR) ligand. Non-limiting examples of AHR ligands include: apigenin, SR1, LGC006, and analogues thereof.

In certain embodiments, the Targeting Ligand is a MerTK or Mer Targeting ligand. Non-limiting examples of MerTK Targeting Ligands are included in WO2013/177168 and WO2014/085225, both titled "Pyrimidine Compounds for the Treatment of Cancer" filed by Wang, et al.

In certain embodiments, the Targeting Ligand is an EGFR ligand. In certain embodiments the Targeting Ligand is an EGRF ligand selected from Afatinib, Dacomitinib, Neratinib, Poziotinib, and Canertinib, or derivatives thereof.

In certain embodiments, the Targeting Ligand is a FLT3 Ligand. In certain embodiments, the Targeting Ligand is a FLT3 ligand selected from Tandutinib, Lestaurtinib, Sorafenib, Midostaurin, Quizartinib, and Crenolanib.

In certain embodiments, the Targeting Ligand is a RAF inhibitor. In certain embodiments the Targeting Ligand is a RAF inhibitor selected from Dabrafenib, Regorafenib, and Vemurafenib. In certain embodiments the Targeting Ligand is a cRAF inhibitor.

In some embodiments, the Targeting Ligand is an Ubc9 SUMO E2 ligase 5F6D Targeting Ligand including but not limited to those described in "Insights Into the Allosteric Inhibition of the SUMO E2 Enzyme Ubc9." by Hewitt, W. M., et. al. (2016) Angew. Chem. Int. Ed. Engl. 55: 5703-5707

In another embodiment, the Targeting Ligand is a Tank1 Targeting Ligand including but not limited to those described in "Structure of human tankyrase 1 in complex with small-molecule inhibitors PJ34 and XAV939." Kirby, C. A., Cheung, A., Fazal, A., Shultz, M. D., Stams, T, (2012) Acta Crystallogr., Sect. F 68: 115-118; and "Structure-Efficiency Relationship of [1,2,4]Triazol-3-ylamines as Novel Nicotinamide Isosteres that Inhibit Tankyrases." Shultz, M. D., et al. (2013) J. Med. Chem. 56: 7049-7059.

In another embodiment, the Targeting Ligand is a SH2 domain of pp60 Src Targeting Ligand including but not limited to those described in "Requirements for Specific Binding of Low Affinity Inhibitor Fragments to the SH2 Domain of pp60Src Are Identical to Those for High Affinity Binding of Full Length Inhibitors," Gudrun Lange, et al., *J. Med. Chem.* 2003, 46, 5184-5195.

In another embodiment, the Targeting Ligand is a Sec7 domain Targeting Ligand including but not limited to those described in "The Lysosomal Protein Saposin B Binds Chloroquine," Huta, B. P., et al., (2016) Chemmedchem 11: 277.

In another embodiment, the Targeting Ligand is a Saposin-B Targeting Ligand including but not limited to those described in "The structure of cytomegalovirus immune modulator UL141 highlights structural Ig-fold versatility for receptor binding" I. Nemcovicova and D. M. Zajonc Acta Cryst. (2014). D70, 851-862.

In another embodiment, the Targeting Ligand is a Protein S100-A7 2OWS Targeting Ligand including but not limited to those described in "2WOS STRUCTURE OF HUMAN S100A7 IN COMPLEX WITH 2,6 ANS" DOI: 10.2210/pdb2wos/pdb; and "Identification and Characterization of Binding Sites on S100A7, a Participant in Cancer and Inflammation Pathways." Leon, R., Murray, et al., (2009) Biochemistry 48: 10591-10600.

In another embodiment, the Targeting Ligand is a Phospholipase A2 Targeting Ligand including but not limited to those described in "Structure-based design of the first potent and selective inhibitor of human non-pancreatic secretory phospholipase A2" Schevitz, R. W., et al., Nat. Struct. Biol. 1995, 2, 458-465.

In another embodiment, the Targeting Ligand is a PHIP Targeting Ligand including but not limited to those described in "A Poised Fragment Library Enables Rapid Synthetic Expansion Yielding the First Reported Inhibitors of PHIP(2), an Atypical Bromodomain" Krojer, T.; et al. Chem. Sci. 2016, 7, 2322-2330.

In another embodiment, the Targeting Ligand is a PDZ Targeting Ligand including but not limited to those described in "Discovery of Low-Molecular-Weight Ligands for the AF6 PDZ Domain" Mangesh Joshi, et al. Angew. Chem. Int. Ed. 2006, 45, 3790-3795.

In another embodiment, the Targeting Ligand is a PARP15 Targeting Ligand including but not limited to those described in "Structural Basis for Lack of ADP-ribosyltransferase Activity in Poly(ADP-ribose) Polymerase-13/Zinc Finger Antiviral Protein." Karlberg, T., et al., (2015) J. Biol. Chem. 290: 7336-7344.

In another embodiment, the Targeting Ligand is a PARP14 Targeting Ligand including but not limited to those described in "Discovery of Ligands for ADP-Ribosyltransferases via Docking-Based Virtual Screening." Andersson, C. D., et al., (2012) J. Med. Chem. 55: 7706-7718; "Family-wide chemical profiling and structural analysis of PARP and tankyrase inhibitors." Wahlberg, E., et al. (2012) Nat. Biotechnol. 30: 283-288; "Discovery of Ligands for ADP-Ribosyltransferases via Docking-Based Virtual Screening." Andersson, C. D., et al. (2012) *J. Med. Chem.* 55: 7706-7718.

In another embodiment, the Targeting Ligand is a MTH1 Targeting Ligand including but not limited to those described in "MTH1 inhibition eradicates cancer by preventing sanitation of the dNTP pool" Helge Gad, et. al. Nature, 2014, 508, 215-221.

In another embodiment, the Targeting Ligand is a mPGES-1 Targeting Ligand including but not limited to those described in "Crystal Structures of mPGES-1 Inhibitor Complexes Form a Basis for the Rational Design of Potent Analgesic and Anti-Inflammatory Therapeutics." Luz, J. G., et al., (2015) J. Med. Chem. 58: 4727-4737.

In another embodiment, the Targeting Ligand is a FLAP-5-lipoxygenase-activating protein Targeting Ligand including but not limited to those described in "Crystal structure of inhibitor-bound human 5-lipoxygenase-activating protein," Ferguson, A. D., McKeever, B. M., Xu, S., Wisniewski, D., Miller, D. K., Yamin, T. T., Spencer, R. H., Chu, L., Ujjainwalla, F., Cunningham, B. R., Evans, J. F., Becker, J. W. (2007) Science 317: 510-512.

In another embodiment, the Targeting Ligand is a FA Binding Protein Targeting Ligand including but not limited to those described in "A Real-World Perspective on Molecular Design." Kuhn, B.; et al. J. Med. Chem. 2016, 59, 4087-4102.

In another embodiment, the Targeting Ligand is a BCL2 Targeting Ligand including but not limited to those described in "ABT-199, a potent and selective BCL-2 inhibitor, achieves antitumor activity while sparing platelets." Souers, A. J., et al. (2013) NAT. MED. (N.Y.) 19: 202-208.

In another embodiment, the Targeting Ligand is a NF2L2 Targeting Ligand.

In another embodiment, the Targeting Ligand is a CTNNB1 Targeting Ligand.

In another embodiment, the Targeting Ligand is a CBLB Targeting Ligand.

In another embodiment, the Targeting Ligand is a BCL6 Targeting Ligand.

In another embodiment, the Targeting Ligand is a RASK Targeting Ligand.

In another embodiment, the Targeting Ligand is a TNIK Targeting Ligand.

In another embodiment, the Targeting Ligand is a MEN1 Targeting Ligand.

In another embodiment, the Targeting Ligand is a PI3Ka Targeting Ligand.

In another embodiment, the Targeting Ligand is a IDO1 Targeting Ligand.

In another embodiment, the Targeting Ligand is a MCL1 Targeting Ligand.

In another embodiment, the Targeting Ligand is a PTPN2 Targeting Ligand.

In another embodiment, the Targeting Ligand is a HER2 Targeting Ligand.

In another embodiment, the Targeting Ligand is an EGFR Targeting Ligand. In one embodiment the Targeting Ligand is selected from erlotinib (Tarceva), gefitinib (Iressa), afatinib (Gilotrif), rociletinib (CO-1686), osimertinib (Tagrisso), olmutinib (Olita), naquotinib (ASP8273), nazartinib (EGF816), PF-06747775 (Pfizer), icotinib (BPI-2009), neratinib (HKI-272; PB272); avitinib (AC0010), EAI045, tarloxotinib (TH-4000; PR-610), PF-06459988 (Pfizer), tesevatinib (XL647; EXEL-7647; KD-019), transtinib, WZ-3146, WZ8040, CNX-2006, and dacomitinib (PF-00299804; Pfizer). The linker can be placed on these Targeting Ligands in any location that does not interfere with the Ligands binding to EGFR. Non-limiting examples of Linker binding locations are provided in the below tables. In one embodiment, the EGFR Targeting Ligand binds the L858R mutant of EGFR. In another embodiment, the EGFR Targeting Ligand binds the T790M mutant of EGFR. In another embodiment, the EGFR Targeting Ligand binds the C797G or C797S mutant of EGFR. In one embodiment, the EGFR Targeting Ligand is selected from erlotinib, gefitinib, afatinib, neratinib, and dacomitinib and binds the L858R mutant of EGFR. In another embodiment, the EGFR Targeting Ligand is selected from osimertinib, rociletinib, olmutinib, naquotinib, nazartinib, PF-06747775, Icotinib, Neratinib, Avitinib, Tarloxotinib, PF-0645998, Tesevatinib, Transtinib, WZ-3146, WZ8040, and CNX-2006 and binds the T790M mutant of EGFR. In another embodiment, the EGFR Targeting Ligand is EAI045 and binds the C797G or C797S mutant of EGFR.

In one embodiment, the protein target and Targeting Ligand pair are chosen by screening a library of ligands. Such a screening is exemplified in "Kinase Inhibitor Profiling Reveals Unexpected Opportunities to Inhibit Disease-Associated Mutant Kinases" by Duong-Ly et al.; Cell Reports 14, 772-781 Feb. 2, 2016.

In one embodiment, the protein target and Targeting Ligand pair are discovered by screening promiscuous kinase binding ligands for context-specific degradation. Non-limiting examples of targeting ligands are shown below and are found in *Optimized Chemical Proteomics Assay for Kinase Inhibitor Profiling* Guillaume Médard, Fiona Pachl, Benjamin Ruprecht, Susan Klaeger, Stephanie Heinzlmeir, Dominic Helm, Huichao Qiao, Xin Ku, Mathias Wilhelm, Thomas Kuehne, Zhixiang Wu, Antje Dittmann, Carsten Hopf, Karl Kramer, and Bernhard Kuster J. Proteome Res., 2015, 14(3), pp 1574-1586:

249 250
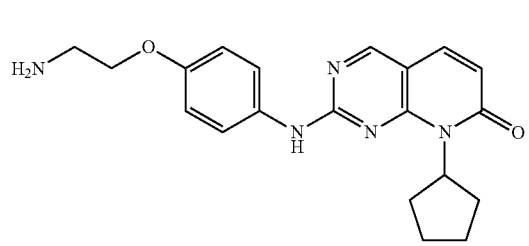
VI16743
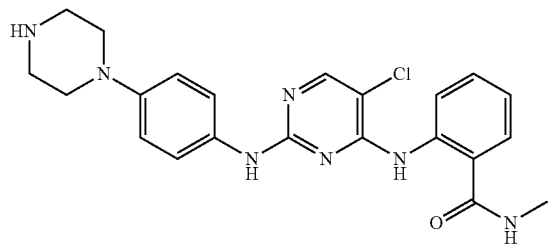
CTx-0294885
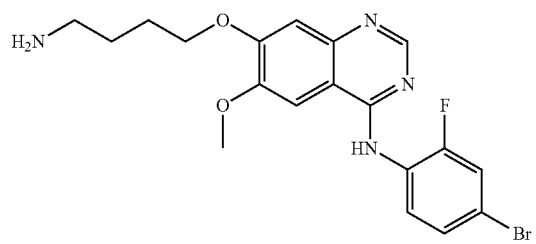
Vandetanib
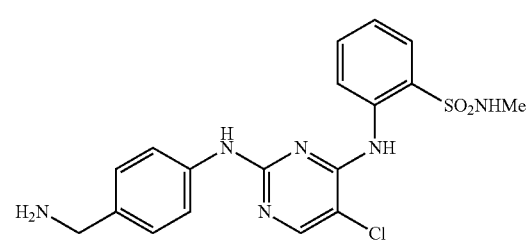
CTx-related
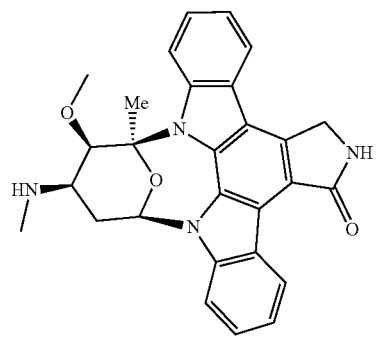
Staurosporine
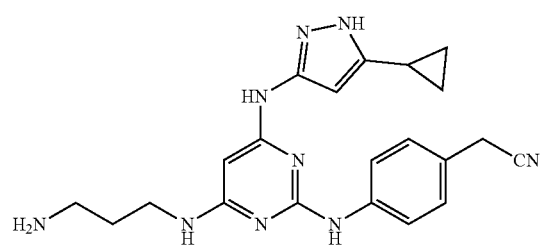
DOI: 10.1021/acschembio.5b00847
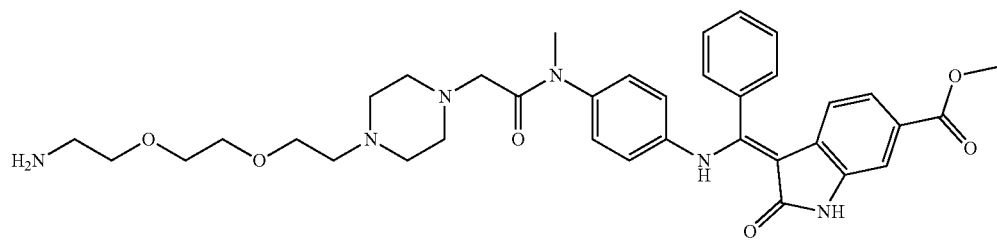
Nintedanib
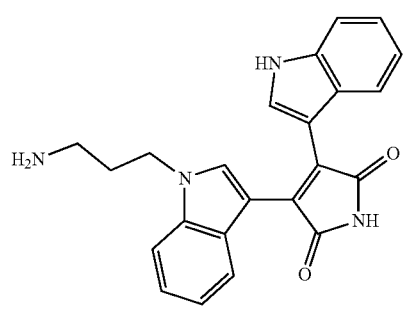
bisindolylmaleimide III
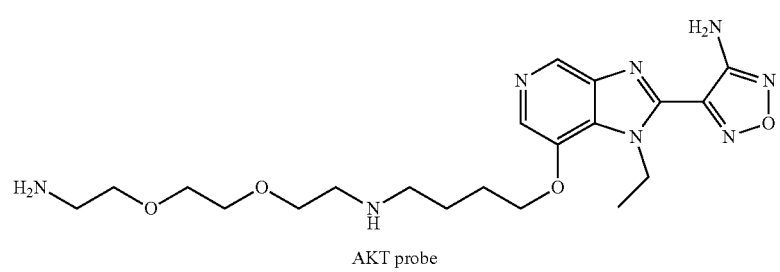
AKT probe -continued
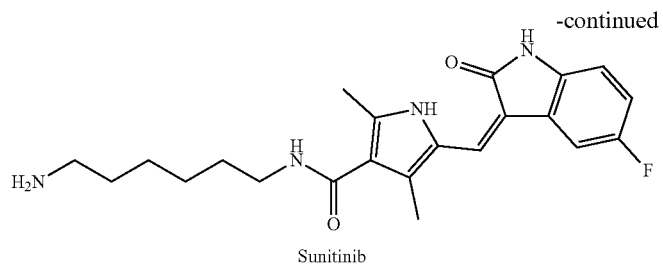
Sunitinib
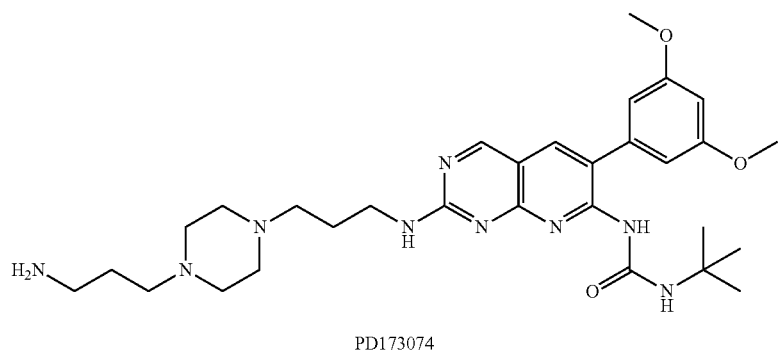
PD173074
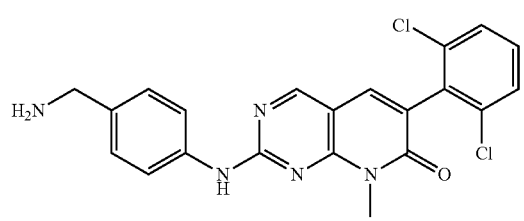
PD173955
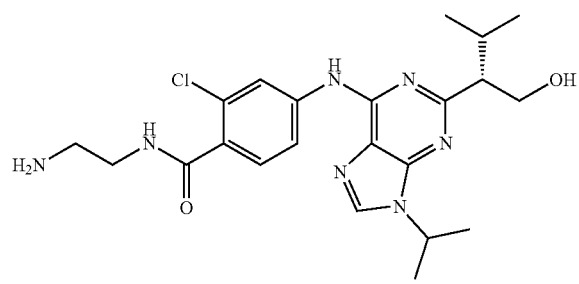
Purvalanol B
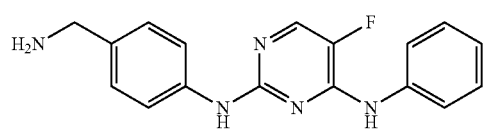
CZC8004
These ligands can be attached to linkers as shown below:
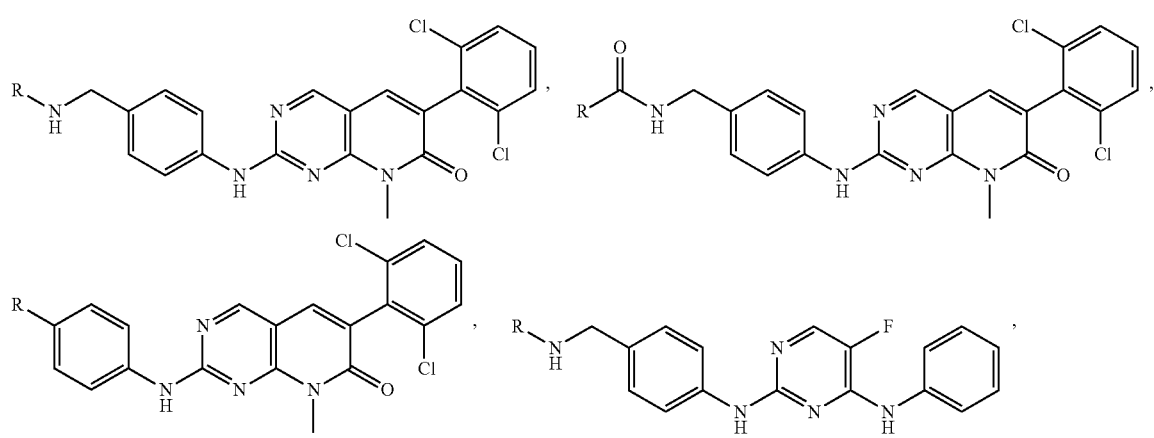

-continued
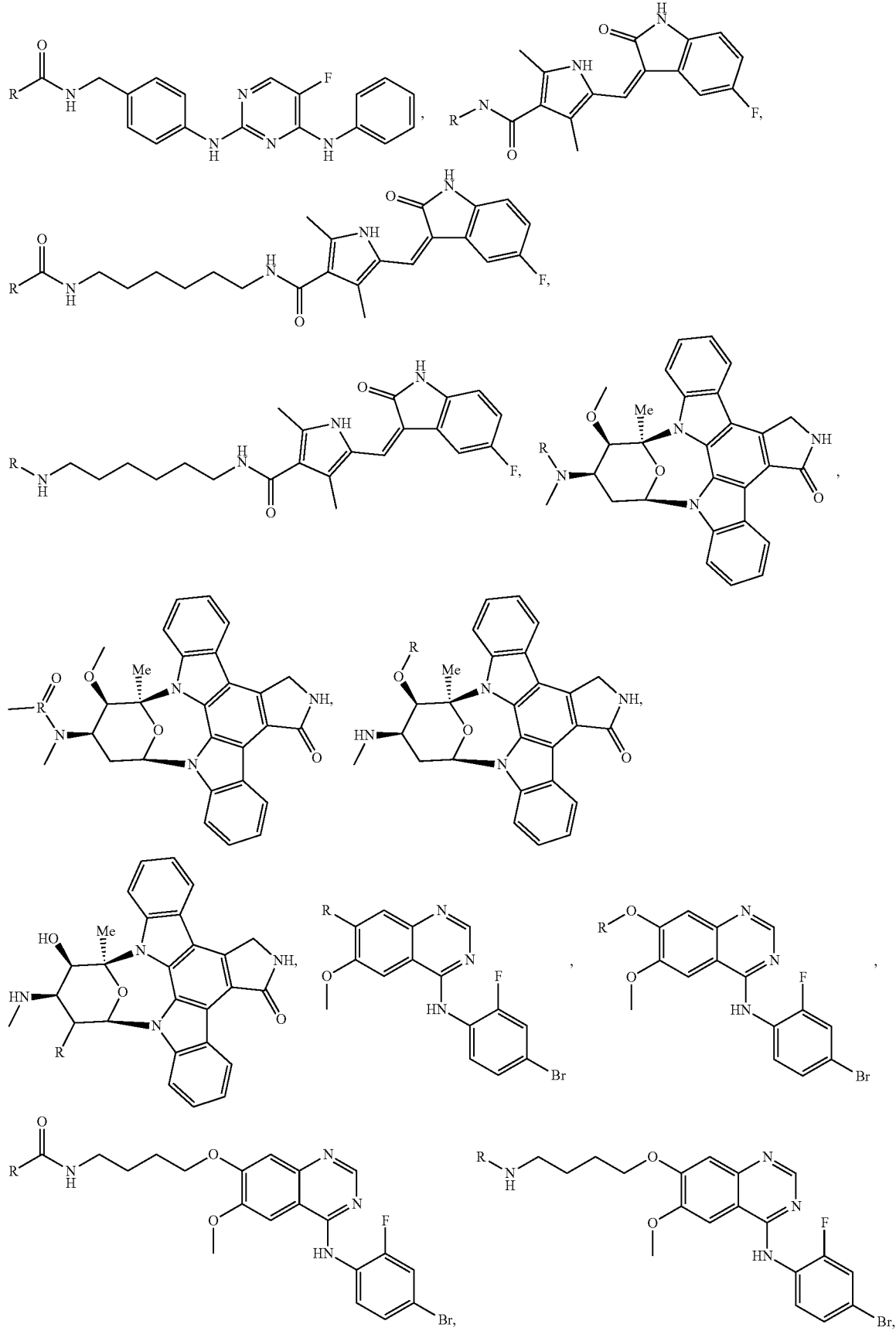

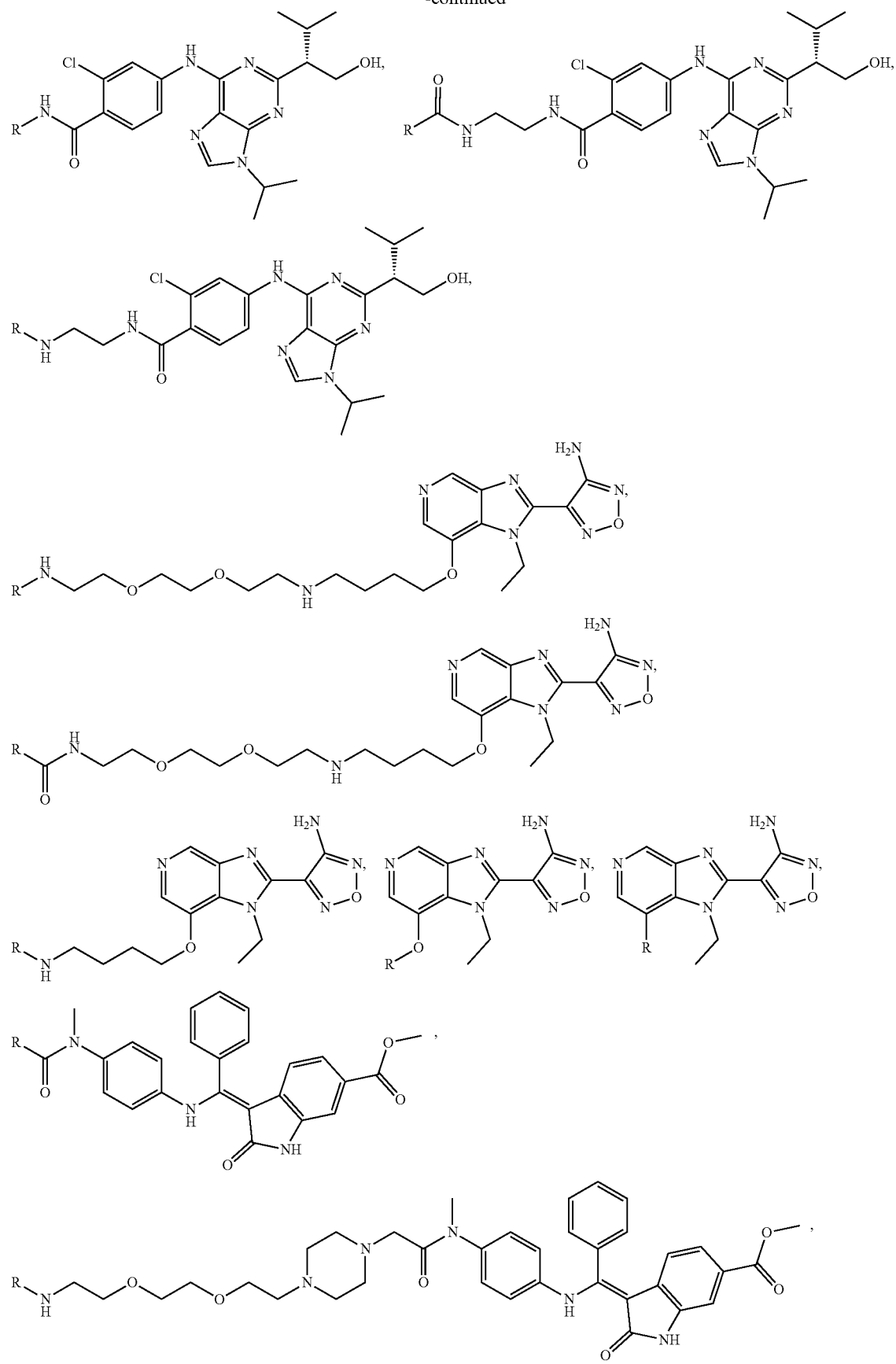

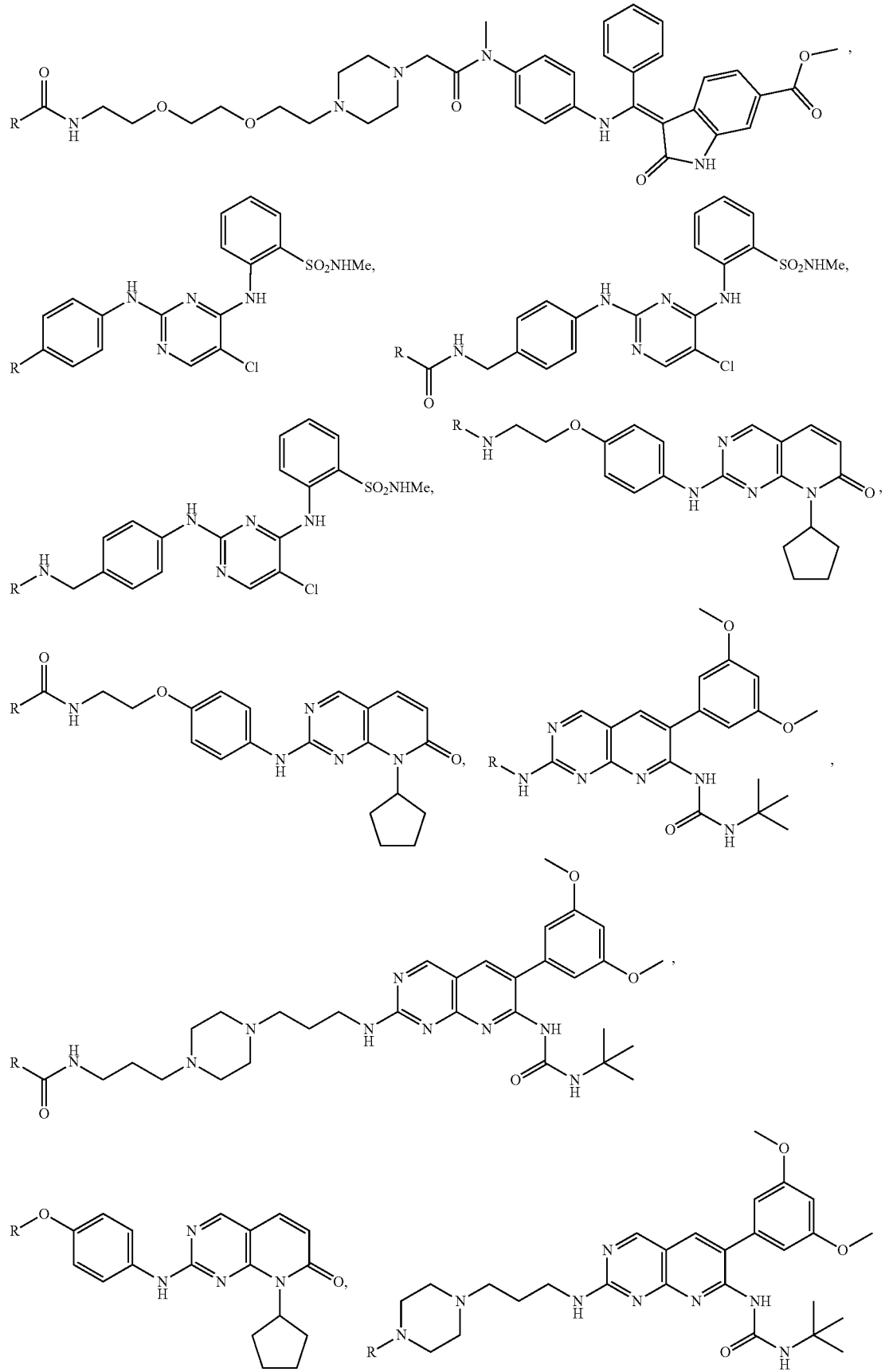

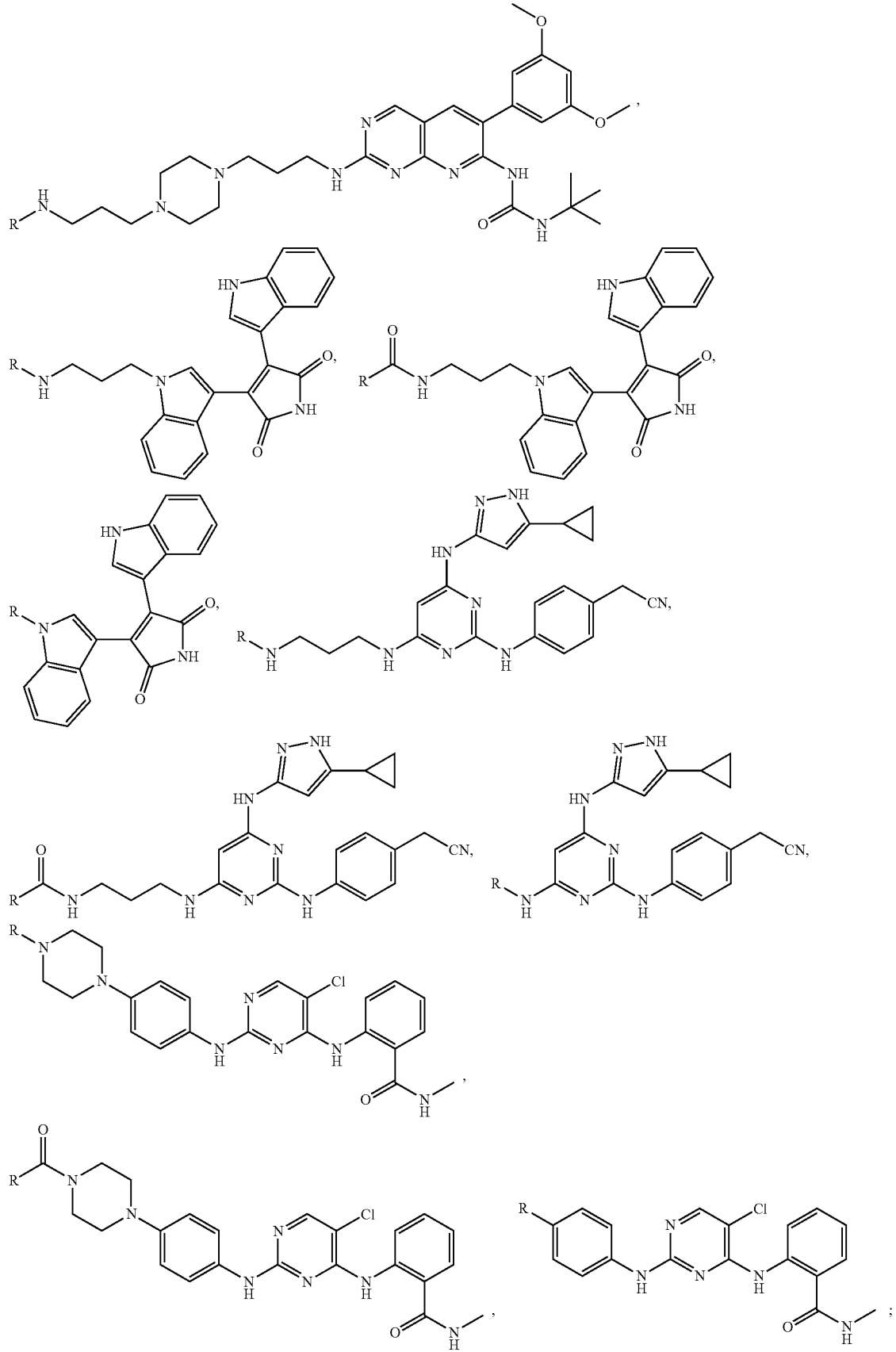

wherein:

R is the point at which the Linker is attached.

According to the present invention, the Targeting Ligand can be covalently bound to the Linker in any manner that achieves the desired results of the Degronimer for therapeutic use. In certain non-limiting embodiments, the Targeting Ligand is bound to the Linker with a functional group that does not adversely affect the binding of the Ligand to the Target Protein. The attachment points below are exemplary in nature and one of ordinary skill in the art would be able to determine different appropriate attachment points.

The non-limiting compounds described below exemplify some of the members of these types of small molecule Targeting Ligands. In the Tables below, R is the point at which the Linker is attached to the Targeting Ligand.

In certain embodiments, the Targeting Ligand is a compound of Formula TL-I:

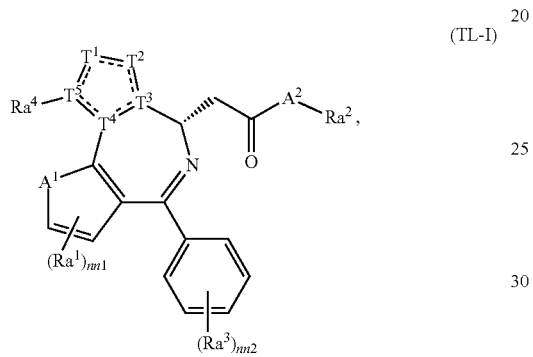

(TL-I)

or a pharmaceutically acceptable salt thereof, wherein:

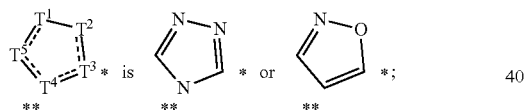

$A^1$ is S or C=C;
$A^2$ is $NR^{a5}$ or O;
nn1 is 0, 1, or 2;
each $Ra^1$ is independently $C_1$-$C_3$ alkyl, $(CH_2)_{0-3}$—CN, $(CH_2)_{0-3}$-halogen, $(CH_2)_{0-3}$—OH, $(CH_2)_{0-3}$—$C_1$-$C_3$ alkoxy, or R;
$Ra^2$ is H, $C_1$-$C_6$ alkyl, $(CH_2)_{0-3}$-heterocyclyl, $(CH_2)_{0-3}$-phenyl, or R, wherein the heterocyclyl comprises one saturated 5- or 6-membered ring and 1-2 heteroatoms selected from N, O, and S and is optionally substituted with $C_1$-$C_3$ alkyl and wherein the phenyl is optionally substituted with $C_1$-$C_3$ alkyl, CN, halogen, OH, $C_1$-$C_3$ alkoxy;
nn2 is 0, 1, 2, or 3;
each $Ra^3$ is independently $C_1$-$C_3$ alkyl, $(CH_2)_{0-3}$—CN, $(CH_2)_{0-3}$-halogen, or R;
$Ra^4$ is $C_1$-$C_3$ alkyl;
$Ra^5$ is H or $C_1$-$C_3$ alkyl; and
R is the point at which the Linker is attached.
wherein the compound of Formula TL-I is substituted with only one R.

In certain embodiments, the Targeting Ligand is a compound of Formula TL-VIII or Formula TL-IX:

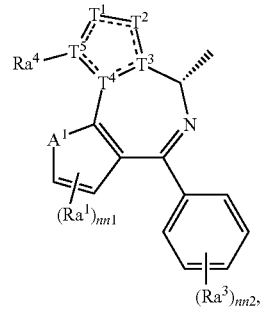

(TL-VIII)

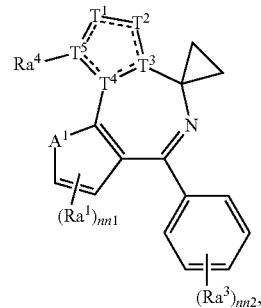

(TL-IX)

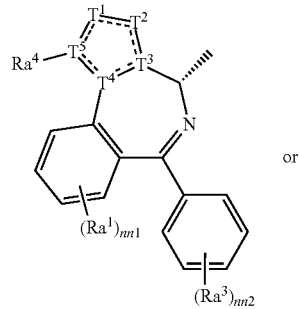

(TL-X)

or

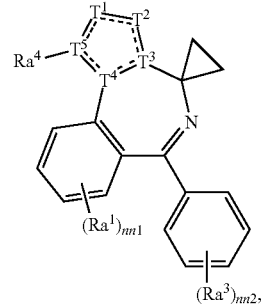

(TL-XI)

wherein the compound of Formula TL-VIII or TL-IX is substituted with only one R.

In certain embodiments, is

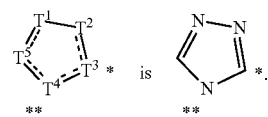

In certain embodiments, is

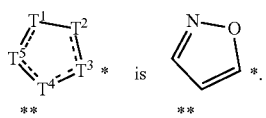

In certain embodiments, $A^1$ is S.
In certain embodiments, $A^1$ is C=C.
In certain embodiments, $A^1$ is $NRa^5$. In further embodiments, $Ra^5$ is H. In other embodiments, $Ra^5$ is $C_1$-$C_3$ alkyl (e.g., methyl, ethyl, propyl, or i-propyl). In further embodiments, $Ra^5$ is methyl.
In certain embodiments, $A^2$ is O.
In certain embodiments, nn1 is 0.
In certain embodiments, nn1 is 1.
In certain embodiments, nn1 is 2.
In certain embodiments, at least one $Ra^1$ is $C_1$-$C_3$ alkyl (e.g., methyl, ethyl, propyl, or i-propyl). In further embodiments, at least one $Ra^1$ is methyl. In further embodiments, two $Ra^1$ are methyl.
In certain embodiments, at least one $Ra^1$ is CN, $(CH_2)$—CN, $(CH_2)_2$—CN, or $(CH_2)_3$—CN. In further embodiments, at least one $Ra^1$ is $(CH_2)$—CN.
In certain embodiments, at least one $Ra^1$ is halogen (e.g., F, Cl, or Br), $(CH_2)$-halogen, $(CH_2)_2$-halogen, or $(CH_2)_3$-halogen. In further embodiments, at least one $Ra^1$ is Cl, $(CH_2)$—Cl, $(CH_2)_2$—Cl, or $(CH_2)_3$—Cl.
In certain embodiments, at least one $Ra^1$ is OH, $(CH_2)$—OH, $(CH_2)_2$—OH, or $(CH_2)_3$—OH.
In certain embodiments, at least one $Ra^1$ is $C_1$-$C_3$ alkoxy (e.g., methoxy, ethoxy, or propoxy), $(CH_2)$—$C_1$-$C_3$ alkoxy, $(CH_2)_2$—$C_1$-$C_3$ alkoxy, or $(CH_2)_3$—$C_1$-$C_3$ alkoxy. In certain embodiments, at least one $Ra^1$ is methoxy.
In further embodiments, $Ra^5$ is H. In other embodiments, $Ra^5$ is $C_1$-$C_3$ alkyl (e.g., methyl, ethyl, propyl, or i-propyl).
In further embodiments, $Ra^5$ is H. In other embodiments, $Ra^5$ is $C_1$-$C_3$ alkyl (e.g., methyl, ethyl, propyl, or i-propyl). In other embodiments, $Ra^5$ is methyl.
In certain embodiments, one $Ra^1$ is R.
In certain embodiments, $Ra^2$ is H.
In certain embodiments, $Ra^2$ is straight-chain $C1$-$C_6$ or branched $C_3$-$C_6$ alkyl (e.g., methyl, ethyl, propyl, i-propyl, butyl, i-butyl, t-butyl, pentyl, or hexyl). In further embodiments, $Ra^2$ is methyl, ethyl, or t-butyl.
In certain embodiments, $Ra^2$ is heterocyclyl, $(CH_2)$-heterocyclyl, $(CH_2)_2$-heterocyclyl, or $(CH_2)_3$-heterocyclyl. In further embodiments, $Ra^2$ is $(CH_2)_3$-heterocyclyl. In further embodiments, the heterocyclyl is selected from pyrrolidinyl, pyrazolidinyl, imidazolidinyl, oxazolidinyl, isoxazolidinyl, thiazolidinyl, isothiazolidinyl, piperidinyl, piperazinyl, hexahydropyrimidinyl, morpholinyl, and thiomorpholinyl. In further embodiments, the heterocyclyl is piperazinyl.
In certain embodiments, the heterocyclyl is substituted with $C_1$-$C_3$ alkyl (e.g., methyl, ethyl, propyl, or i-propyl).
In certain embodiments, $Ra^2$ is phenyl, $(CH_2)$-phenyl, $(CH_2)_2$-phenyl, or $(CH_2)_3$-phenyl. In further embodiments, $Ra^2$ is phenyl.
In certain embodiments, the phenyl is substituted with $C_1$-$C_3$ alkyl (e.g., methyl, ethyl, propyl, or i-propyl). In certain embodiments, the phenyl is substituted with CN. In certain embodiments, the phenyl is substituted with halogen (e.g., F, Cl, or Br). In certain embodiments, the phenyl is substituted with OH. In certain embodiments, the phenyl is substituted with $C_1$-$C_3$ alkoxy (e.g., methoxy, ethoxy, or propoxy).
In certain embodiments, $Ra^2$ is R.
In certain embodiments, nn2 is 0.
In certain embodiments, nn2 is 1.
In certain embodiments, nn2 is 2.
In certain embodiments, nn2 is 3.
In certain embodiments, at least one $Ra^3$ is $C_1$-$C_3$ alkyl (e.g., methyl, ethyl, propyl, or i-propyl). In further embodiments, at least one $Ra^3$ is methyl.
In certain embodiments, at least one $Ra^3$ is CN, $(CH_2)$—CN, $(CH_2)_2$—CN, or $(CH_2)_3$—CN. In further embodiments, at least one $Ra^3$ is CN.
In certain embodiments, at least one $Ra^3$ is halogen (e.g., F, Cl, or Br), $(CH_2)$-halogen, $(CH_2)_2$-halogen, or $(CH_2)_3$-halogen. In further embodiments, at least one $Ra^3$ is Cl, $(CH_2)$—Cl, $(CH_2)_2$—Cl, or $(CH_2)_3$—Cl. In further embodiments, at least one $Ra^3$ is Cl.
In certain embodiments, one $Ra^3$ is R.
In further embodiments, $Ra^5$ is H. In other embodiments, $Ra^5$ is $C_1$-$C_3$ alkyl (e.g., methyl, ethyl, propyl, or i-propyl).
In certain embodiments, $Ra^4$ is $C_1$-$C_3$ alkyl (e.g., methyl, ethyl, propyl, or i-propyl). In further embodiments, $Ra^4$ is methyl.
In certain embodiments, $Ra^5$ is H.
In certain embodiments, $Ra^5$ is $C_1$-$C_3$ alkyl (e.g., methyl, ethyl, propyl, or i-propyl). In further embodiments, $Ra^5$ is methyl.
In certain embodiments,

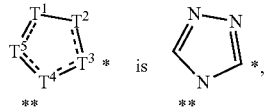

and $A^1$ is S.
In certain embodiments,

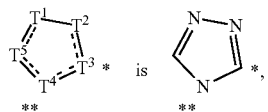

and A is C=C.
In certain embodiments,

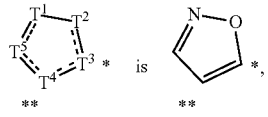

and A is C=C.
In certain embodiments, $A^2$ is NH, and $Ra^2$ is $(CH_2)_{0-3}$-heterocyclyl. In further embodiments, $Ra^2$ is $(CH_2)_3$-heterocyclyl.
In certain embodiments, $A^2$ is NH, and $Ra^2$ is $(CH_2)_{0-3}$-phenyl. In further embodiments, $Ra^2$ is phenyl. In further embodiments, the phenyl is substituted with OH.
In certain embodiments, $A^2$ is NH, and $Ra^2$ is R.
In certain embodiments, $A^2$ is NH, and $Ra^2$ is H or $C_1$-$C_6$ alkyl. In further embodiments, $Ra^2$ is $C_1$-$C_4$ alkyl.
In certain embodiments, $A^2$ is O, and $Ra^2$ is H or $C_1$-$C_6$ alkyl. In further embodiments, $Ra^2$ is $C_1$-$C_4$ alkyl.

II. Methods of Treatment

The N(substituted)$_2$-C$^3$-glutarimide or defined analogue thereof of Formula I, II, III, IV and V can be used in an effective amount to treat a host, including a human, in need thereof, optionally in a pharmaceutically acceptable carrier to treat any of the disorders described herein.

The terms "treat", "treating", and "treatment", etc., as used herein, refer to any action providing a benefit to a patient for which the present compounds may be administered, including the treatment of any disease state or condition which is modulated through the protein to which the present compounds bind. Illustrative non-limiting disease states or conditions, including cancer, which may be treated using compounds according to the present invention are set forth hereinabove.

The N(substituted)$_2$-C$^3$-glutarimide or defined analogue thereof of Formula I and Formula II compositions as described herein can be used to degrade a Target Protein which is a mediator of the disorder affecting the patient, such as a human. The control of protein level afforded by the Formula I, Formula II, or Formula V Degronimers of the present invention provides treatment of a disease state or condition, which is modulated through the Target Protein by lowering the level of that protein in the cell, e.g., cell of a patient. In certain embodiments, the method comprises administering an effective amount of the compound as described herein, optionally including a pharmaceutically acceptable excipient, carrier, adjuvant, i.e., a pharmaceutically acceptable composition, optionally in combination with another bioactive agent or combination of agents.

The term "disease state or condition" when used in connection with a Formula I, Formula II, or Formula V compound is meant to refer to any disease state or condition wherein protein dysregulation (i.e., the amount of protein expressed in a patient is elevated) occurs via a Target Protein and where degradation of such protein in a patient may provide beneficial therapy or relief of symptoms to a patient in need thereof. In certain instances, the disease state or condition may be cured. The compounds of Formula I and Formula II, are for example useful as therapeutic agents when administered in an effective amount to a host, including a human, to treat a myelo- or lymphoproliferative disorder such as B- or T-cell lymphomas, multiple myeloma, Waldenstrom's macroglobulinemia, Wiskott-Aldrich syndrome, or a post-transplant lymphoproliferative disorder; an immune disorder, including autoimmune disorders such as Addison disease, Celiac disease, dermatomyositis, Graves disease, thyroiditis, multiple sclerosis, pernicious anemia, reactive arthritis, lupus, or type I diabetes; a disease of cardiologic malfunction, including hypercholesterolemia; an infectious disease, including viral and/or bacterial infections; an inflammatory condition, including asthma, chronic peptic ulcers, tuberculosis, rheumatoid arthritis, periodontitis, ulcerative colitis, Crohn's disease, or hepatitis.

The term "disease state or condition" when used in connection with a Formula III or Formula IV compound for example, refers to any therapeutic indication which can be treated by decreasing the activity of cereblon or a cereblon-containing E3 Ligase, including but not limited to uses known for the cereblon binders thalidomide, pomalidomide or lenalidomide. Nonlimiting examples of uses for cereblon binders are multiple myeloma, a hematological disorder such as myelodysplastic syndrome, cancer, tumor, abnormal cellular proliferation, HIV/AIDS, HBV, HCV, hepatitis, Crohn's disease, sarcoidosis, graft-versus-host disease, rheumatoid arthritis, Behcet's disease, tuberculosis, and myelofibrosis. Other indications include a myelo- or lymphoproliferative disorder such as B- or T-cell lymphomas, Waldenstrom's macroglobulinemia, Wiskott-Aldrich syndrome, or a post-transplant lymphoproliferative disorder; an immune disorder, including autoimmune disorders such as Addison disease, Celiac disease, dermatomyositis, Graves disease, thyroiditis, multiple sclerosis, pernicious anemia, arthritis, and in particular rheumatoid arthritis, lupus, or type I diabetes; a disease of cardiologic malfunction, including hypercholesterolemia; an infectious disease, including viral and/or bacterial infection, as described generally herein; an inflammatory condition, including asthma, chronic peptic ulcers, tuberculosis, rheumatoid arthritis, periodontitis and ulcerative colitis.

In certain embodiments, the present invention provides for administering a compound of Formulas I, II, III or IV to a method of treating a patient, for example, a human, having an infectious disease, wherein the therapy targets a protein of the infectious agent, optionally in combination with another bioactive agent. The disease state or condition may be a disease caused by a microbial agent or other exogenous agent such as a virus (as non-limiting examples, HIV, HBV, HCV, HSV, HPV, RSV, CMV, Ebola, Flavivirus, Pestivirus, Rotavirus, Influenza, Coronavirus, EBV, viral pneumonia, drug-resistant viruses, Bird flu, RNA virus, DNA virus, adenovirus, poxvirus, Picornavirus, Togavirus, Orthomyxovirus, Retrovirus or Hepadnovirus), bacteria (Gram-negative, Gram-positive, fungus, protozoa, helminth, worms, prion, parasite, or other microbe or may be a disease state, which is caused by overexpression of a protein, which leads to a disease state and/or condition In certain embodiments, the condition treated with a compound of the present invention is a disorder related to abnormal cellular proliferation. Abnormal cellular proliferation, notably hyperproliferation, can occur as a result of a wide variety of factors, including genetic mutation, infection, exposure to toxins, autoimmune disorders, and benign or malignant tumor induction.

There are a number of skin disorders associated with cellular hyperproliferation. Psoriasis, for example, is a benign disease of human skin generally characterized by plaques covered by thickened scales. The disease is caused by increased proliferation of epidermal cells of unknown cause. Chronic eczema is also associated with significant hyperproliferation of the epidermis. Other diseases caused by hyperproliferation of skin cells include atopic dermatitis, lichen planus, warts, pemphigus vulgaris, actinic keratosis, basal cell carcinoma and squamous cell carcinoma.

Other hyperproliferative cell disorders include blood vessel proliferation disorders, fibrotic disorders, autoimmune disorders, graft-versus-host rejection, tumors and cancers.

Blood vessel proliferative disorders include angiogenic and vasculogenic disorders. Proliferation of smooth muscle cells in the course of development of plaques in vascular tissue cause, for example, restenosis, retinopathies and atherosclerosis. Both cell migration and cell proliferation play a role in the formation of atherosclerotic lesions.

Fibrotic disorders are often due to the abnormal formation of an extracellular matrix. Examples of fibrotic disorders include hepatic cirrhosis and mesangial proliferative cell disorders. Hepatic cirrhosis is characterized by the increase in extracellular matrix constituents resulting in the formation of a hepatic scar. Hepatic cirrhosis can cause diseases such as cirrhosis of the liver. An increased extracellular matrix resulting in a hepatic scar can also be caused by viral infection such as hepatitis. Lipocytes appear to play a major role in hepatic cirrhosis.

Mesangial disorders are brought about by abnormal proliferation of mesangial cells. Mesangial hyperproliferative cell disorders include various human renal diseases, such as glomerulonephritis, diabetic nephropathy, malignant nephrosclerosis, thrombotic micro-angiopathy syndromes, transplant rejection, and glomerulopathies.

Another disease with a proliferative component is rheumatoid arthritis. Rheumatoid arthritis is generally considered an autoimmune disease that is thought to be associated with activity of autoreactive T cells, and to be caused by autoantibodies produced against collagen and IgE.

Other disorders that can include an abnormal cellular proliferative component include Bechet's syndrome, acute respiratory distress syndrome (ARDS), ischemic heart disease, post-dialysis syndrome, leukemia, acquired immune deficiency syndrome, vasculitis, lipid histiocytosis, septic shock and inflammation in general.

Cutaneous contact hypersensitivity and asthma are just two examples of immune responses that can be associated with significant morbidity. Others include atopic dermatitis, eczema, Sjogren's Syndrome, including keratoconjunctivitis sicca secondary to Sjogren's Syndrome, alopecia areata, allergic responses due to arthropod bite reactions, Crohn's disease, aphthous ulcer, iritis, conjunctivitis, keratoconjunctivitis, ulcerative colitis, cutaneous lupus erythematosus, scleroderma, vaginitis, proctitis, and drug eruptions. These conditions may result in any one or more of the following symptoms or signs: itching, swelling, redness, blisters, crusting, ulceration, pain, scaling, cracking, hair loss, scarring, or oozing of fluid involving the skin, eye, or mucosal membranes.

In atopic dermatitis, and eczema in general, immunologically mediated leukocyte infiltration (particularly infiltration of mononuclear cells, lymphocytes, neutrophils, and eosinophils) into the skin importantly contributes to the pathogenesis of these diseases. Chronic eczema also is associated with significant hyperproliferation of the epidermis. Immunologically mediated leukocyte infiltration also occurs at sites other than the skin, such as in the airways in asthma and in the tear producing gland of the eye in keratoconjunctivitis sicca.

In one non-limiting embodiment compounds of the present invention are used as topical agents in treating contact dermatitis, atopic dermatitis, eczematous dermatitis, psoriasis, Sjogren's Syndrome, including keratoconjunctivitis sicca secondary to Sjogren's Syndrome, alopecia areata, allergic responses due to arthropod bite reactions, Crohn's disease, aphthous ulcer, iritis, conjunctivitis, keratoconjunctivitis, ulcerative colitis, asthma, allergic asthma, cutaneous lupus erythematosus, scleroderma, vaginitis, proctitis, and drug eruptions. The novel method may also be useful in reducing the infiltration of skin by malignant leukocytes in diseases such as mycosis fungoides. These compounds can also be used to treat an aqueous-deficient dry eye state (such as immune mediated keratoconjunctivitis) in a patient suffering therefrom, by administering the compound topically to the eye.

Disease states of conditions which may be treated using compounds according to the present invention include, for example, asthma, autoimmune diseases such as multiple sclerosis, various cancers, ciliopathies, cleft palate, diabetes, heart disease, hypertension, inflammatory bowel disease, mental retardation, mood disorder, obesity, refractive error, infertility, Angelman syndrome, Canavan disease, Coeliac disease, Charcot-Marie-Tooth disease, Cystic fibrosis, Duchenne muscular dystrophy, Haemochromatosis, Haemophilia, Klinefelter's syndrome, Neurofibromatosis, Phenylketonuria, Polycystic kidney disease 1 (PKD1) or 2 (PKD2) Prader-Willi syndrome, Sickle-cell disease, Tay-Sachs disease, Turner syndrome.

Further disease states or conditions which may be treated by compounds according to the present invention include Alzheimer's disease, Amyotrophic lateral sclerosis (Lou Gehrig's disease), Anorexia nervosa, Anxiety disorder, Atherosclerosis, Attention deficit hyperactivity disorder, Autism, Bipolar disorder, Chronic fatigue syndrome, Chronic obstructive pulmonary disease, Crohn's disease, Coronary heart disease, Dementia, Depression, Diabetes mellitus type 1, Diabetes mellitus type 2, Epilepsy, Guillain-Barre syndrome, Irritable bowel syndrome, Lupus, Metabolic syndrome, Multiple sclerosis, Myocardial infarction, Obesity, Obsessive-compulsive disorder, Panic disorder, Parkinson's disease, Psoriasis, Rheumatoid arthritis, Sarcoidosis, Schizophrenia, Stroke, Thromboangiitis obliterans, Tourette syndrome, Vasculitis.

Still additional disease states or conditions which can be treated by compounds according to the present invention include aceruloplasminemia, Achondrogenesis type II, achondroplasia, Acrocephaly, Gaucher disease type 2, acute intermittent porphyria, Canavan disease, Adenomatous Polyposis *Coli*, ALA dehydratase deficiency, adenylosuccinate lyase deficiency, Adrenogenital syndrome, Adrenoleukodystrophy, ALA-D porphyria, ALA dehydratase deficiency, Alkaptonuria, Alexander disease, Alkaptonuric ochronosis, alpha 1-antitrypsin deficiency, alpha-1 proteinase inhibitor, emphysema, amyotrophic lateral sclerosis Alstrom syndrome, Alexander disease, Amelogenesis imperfecta, ALA dehydratase deficiency, Anderson-Fabry disease, androgen insensitivity syndrome, Anemia Angiokeratoma Corporis Diffusum, Angiomatosis retinae (von Hippel-Lindau disease) Apert syndrome, Arachnodactyly (Marfan syndrome), Stickler syndrome, Arthrochalasis multiplex congenital (Ehlers-Danlos syndrome #arthrochalasia type) ataxia telangiectasia, Rett syndrome, primary pulmonary hypertension, Sandhoff disease, neurofibromatosis type II, Beare-Stevenson cutis gyrata syndrome, Mediterranean fever, familial, Benjamin syndrome, beta-thalassemia, Bilateral Acoustic Neurofibromatosis (neurofibromatosis type II), factor V Leiden thrombophilia, Bloch-Sulzberger syndrome (incontinentia pigmenti), Bloom syndrome, X-linked sideroblastic anemia, Bonnevie-Ullrich syndrome (Turner syndrome), Bourneville disease (tuberous sclerosis), prion disease, Birt-Hogg-Dube syndrome, Brittle bone disease (osteogenesis imperfecta), Broad Thumb-Hallux syndrome (Rubinstein-Taybi syndrome), Bronze Diabetes/Bronzed Cirrhosis (hemochromatosis), Bulbospinal muscular atrophy (Kennedy's disease), Burger-Grutz syndrome (lipoprotein lipase deficiency), CGD Chronic granulomatous disorder, Campomelic dysplasia, biotinidase deficiency, Cardiomyopathy (Noonan syndrome), Cri du chat, CAVD (congenital absence of the vas deferens), Caylor cardiofacial syndrome (CBAVD), CEP (congenital erythropoietic porphyria), cystic fibrosis, congenital hypothyroidism, Chondrodystrophy syndrome (achondroplasia), otospondylomegaepiphyseal dysplasia, Lesch-Nyhan syndrome, galactosemia, Ehlers-Danlos syndrome, Thanatophoric dysplasia, Coffin-Lowry syndrome, Cockayne syndrome, (familial adenomatous polyposis), Congenital erythropoietic porphyria, Congenital heart disease, Methemoglobinemia/ Congenital methaemoglobinaemia, achondroplasia, X-linked sideroblastic anemia, Connective tissue disease, Conotruncal anomaly face syndrome, Cooley's Anemia (beta-thalassemia), Copper storage disease (Wilson's disease), Copper transport disease (Menkes disease), hereditary coproporphyria, Cowden syndrome, Craniofacial dysarthrosis (Crouzon syndrome), Creutzfeldt-Jakob disease (prion disease), Cockayne syndrome, Cowden syndrome, Curschmann-Batten-Steinert syndrome (myotonic dystrophy), Beare-Stevenson cutis gyrata syndrome, primary hyperoxaluria, spondyloepimetaphyseal dysplasia (Strudwick type), muscular dystrophy, Duchenne and Becker types (DBMD), Usher syndrome, Degenerative nerve diseases including de Grouchy syndrome and Dejerine-Sottas syndrome, developmental disabilities, distal spinal muscular atrophy, type V, androgen insensitivity syndrome, Diffuse Globoid Body Sclerosis (Krabbe disease), Di George's syndrome, Dihydrotestosterone receptor deficiency, androgen insensitivity syndrome, Down syndrome, Dwarfism, erythropoietic protoporphyria Erythroid 5-aminolevulinate synthetase deficiency, Erythropoietic porphyria, erythropoietic protoporphyria, erythropoietic uroporphyria, Friedreich's ataxia-familial paroxysmal polyserositis, porphyria cutanea tarda, familial pressure sensitive neuropathy, primary pulmonary hypertension (PPH), Fibrocystic disease of the pancreas, fragile X syndrome, galactosemia, genetic brain disorders, Giant cell hepatitis (Neonatal hemochromatosis), Gronblad-Strandberg syndrome (pseudoxanthoma elasticum), Gunther disease (congenital erythropoietic porphyria), haemochromatosis, Hallgren syndrome, sickle cell anemia, hemophilia, hepatoerythropoietic porphyria (HEP), Hippel-Lindau disease (von Hippel-Lindau disease), Huntington's disease, Hutchinson-Gilford progeria syndrome (progeria), Hyperandrogenism, Hypochondroplasia, Hypochromic anemia, Immune system disorders, including X-linked severe combined immunodeficiency, Insley-Astley syndrome, Jackson-Weiss syndrome, Joubert syndrome, Lesch-Nyhan syndrome, Jackson-Weiss syndrome, Kidney diseases, including hyperoxaluria, Klinefelter's syndrome, Kniest dysplasia, Lacunar dementia, Langer-Saldino achondrogenesis, ataxia telangiectasia, Lynch syndrome, Lysyl-hydroxylase deficiency, Machado-Joseph disease, Metabolic disorders, including Kniest dysplasia, Marfan syndrome, Movement disorders, Mowat-Wilson syndrome, cystic fibrosis, Muenke syndrome, Multiple neurofibromatosis, Nance-Insley syndrome, Nance-Sweeney chondrodysplasia, Niemann-Pick disease, Noack syndrome (Pfeiffer syndrome), Osler-Weber-Rendu disease, Peutz-Jeghers syndrome, Polycystic kidney disease, polyostotic fibrous dysplasia (McCune-Albright syndrome), Peutz-Jeghers syndrome, Prader-Labhart-Willi syndrome, hemochromatosis, primary hyperuricemia syndrome (Lesch-Nyhan syndrome), primary pulmonary hypertension, primary senile degenerative dementia, prion disease, progeria (Hutchinson Gilford Progeria Syndrome), progressive chorea, chronic hereditary (Huntington) (Huntington's disease), progressive muscular atrophy, spinal muscular atrophy, propionic acidemia, protoporphyria, proximal myotonic dystrophy, pulmonary arterial hypertension, PXE (pseudoxanthoma elasticum), Rb (retinoblastoma), Recklinghausen disease (neurofibromatosis type I), Recurrent polyserositis, Retinal disorders, Retinoblastoma, Rett syndrome, RFALS type 3, Ricker syndrome, Riley-Day syndrome, Roussy-Levy syndrome, severe achondroplasia with developmental delay and acanthosis nigricans (SADDAN), Li-Fraumeni syndrome, sarcoma, breast, leukemia, and adrenal gland (SBLA) syndrome, sclerosis tuberose (tuberous sclerosis), SDAT, SED congenital (spondyloepiphyseal dysplasia congenita), SED Strudwick (spondyloepimetaphyseal dysplasia, Strudwick type), SEDc (spondyloepiphyseal dysplasia congenita) SEMD, Strudwick type (spondyloepimetaphyseal dysplasia, Strudwick type), Shprintzen syndrome, Skin pigmentation disorders, Smith-Lemli-Opitz syndrome, South-African genetic porphyria (variegate porphyria), infantile-onset ascending hereditary spastic paralysis, Speech and communication disorders, sphingolipidosis, Tay-Sachs disease, spinocerebellar ataxia, Stickler syndrome, stroke, androgen insensitivity syndrome, tetrahydrobiopterin deficiency, beta-thalassemia, Thyroid disease, Tomaculous neuropathy (hereditary neuropathy with liability to pressure palsies), Treacher Collins syndrome, Triplo X syndrome (triple X syndrome), Trisomy 21 (Down syndrome), Trisomy X, VHL syndrome (von Hippel-Lindau disease), Vision impairment and blindness (Alstrom syndrome), Vrolik disease, Waardenburg syndrome, Warburg Sjo Fledelius Syndrome, Weissenbacher-Zweymuller syndrome, Wolf-Hirschhorn syndrome, Wolff Periodic disease, Weissenbacher-Zweymuller syndrome and Xeroderma pigmentosum, among others.

The term "neoplasia" or "cancer" is used throughout the specification to refer to the pathological process that results in the formation and growth of a cancerous or malignant neoplasm, i.e., abnormal tissue that grows by cellular proliferation, often more rapidly than normal and continues to grow after the stimuli that initiated the new growth cease. Malignant neoplasms show partial or complete lack of structural organization and functional coordination with the normal tissue and most invade surrounding tissues, metastasize to several sites, and are likely to recur after attempted removal and to cause the death of the patient unless adequately treated. As used herein, the term neoplasia is used to describe all cancerous disease states and embraces or encompasses the pathological process associated with malignant hematogenous, ascitic and solid tumors. Exemplary cancers which may be treated by the present compounds either alone or in combination with at least one additional anti-cancer agent include squamous-cell carcinoma, basal cell carcinoma, adenocarcinoma, hepatocellular carcinomas, and renal cell carcinomas, cancer of the bladder, bowel, breast, cervix, colon, esophagus, head, kidney, liver, lung, neck, ovary, pancreas, prostate, and stomach; leukemias; benign and malignant lymphomas, particularly Burkitt's lymphoma and Non-Hodgkin's lymphoma; benign and malignant melanomas; myeloproliferative diseases; sarcomas, including Ewing's sarcoma, hemangiosarcoma, Kaposi's sarcoma, liposarcoma, myosarcomas, peripheral neuroepithelioma, synovial sarcoma, gliomas, astrocytomas, oligodendrogliomas, ependymomas, gliobastomas, neuroblastomas, ganglioneuromas, gangliogliomas, medulloblastomas, pineal cell tumors, meningiomas, meningeal sarcomas, neurofibromas, and Schwannomas; bowel cancer, breast cancer, prostate cancer, cervical cancer, uterine cancer, lung cancer, ovarian cancer, testicular cancer, thyroid cancer, astrocytoma, esophageal cancer, pancreatic cancer, stomach cancer, liver cancer, colon cancer, melanoma; carcinosarcoma, Hodgkin's disease, Wilms' tumor and teratocarcinomas. Additional cancers which may be treated using compounds according to the present invention include, for example, T-lineage Acute lymphoblastic Leukemia (T-ALL), T-lineage lymphoblastic Lymphoma (T-LL), Peripheral T-cell lymphoma, Adult T-cell Leukemia, Pre-B ALL, Pre-B Lymphomas, Large B-cell Lymphoma, Burkitts Lymphoma, B-cell ALL, Philadelphia chromosome positive ALL and Philadelphia chromosome positive CML.

The term "bioactive agent" is used to describe an agent, other than a compound according to the present invention, which is used in combination with the present compounds as an agent with biological activity to assist in effecting an intended therapy, inhibition and/or prevention/prophylaxis for which the present compounds are used. Preferred bioactive agents for use herein include those agents which have pharmacological activity similar to that for which the present compounds are used or administered and include for example, anti-cancer agents, antiviral agents, especially including anti-HIV agents and anti-HCV agents, antimicrobial agents, antifungal agents, etc.

III. Combination Therapy

The amine compounds of Formula I, II, III, IV and V can be used in an effective amount alone or in combination to treat a host such as a human with a disorder as described herein.

The disclosed compounds described herein can be used in an effective amount alone or in combination with another compound of the present invention or another bioactive agent to treat a host such as a human with a disorder as described herein.

The term "bioactive agent" is used to describe an agent, other than the selected compound according to the present invention, which can be used in combination or alternation with a compound of the present invention to achieve a desired result of therapy. In one embodiment, the compound of the present invention and the bioactive agent are administered in a manner that they are active in vivo during overlapping time periods, for example, have time-period overlapping Cmax, Tmax, AUC or other pharmacokinetic parameter. In another embodiment, the compound of the present invention and the bioactive agent are administered to a host in need thereof that do not have overlapping pharmacokinetic parameter, however, one has a therapeutic impact on the therapeutic efficacy of the other.

In one aspect of this embodiment, the bioactive agent is an immune modulator, including but not limited to a checkpoint inhibitor, including as non-limiting examples, a PD-1 inhibitor, PD-L1 inhibitor, PD-L2 inhibitor, CTLA-4 inhibitor, LAG-3 inhibitor, TIM-3 inhibitor, V-domain Ig suppressor of T-cell activation (VISTA) inhibitors, small molecule, peptide, nucleotide, or other inhibitor. In certain aspects, the immune modulator is an antibody, such as a monoclonal antibody.

PD-1 inhibitors that blocks the interaction of PD-1 and PD-L1 by binding to the PD-1 receptor, and in turn inhibit immune suppression include, for example, nivolumab (Opdivo), pembrolizumab (Keytruda), pidilizumab, AMP-224 (AstraZeneca and MedImmune), PF-06801591 (Pfizer), MEDI0680 (AstraZeneca), PDR001 (Novartis), REGN2810 (Regeneron), SHR-12-1 (Jiangsu Hengrui Medicine Company and Incyte Corporation), TSR-042 (Tesaro), and the PD-Li/VISTA inhibitor CA-170 (Curis Inc.). PD-L1 inhibitors that block the interaction of PD-1 and PD-L1 by binding to the PD-L1 receptor, and in turn inhibits immune suppression, include for example, atezolizumab (Tecentriq), durvalumab (AstraZeneca and MedImmune), KN035 (Alphamab), and BMS-936559 (Bristol-Myers Squibb). CTLA-4 checkpoint inhibitors that bind to CTLA-4 and inhibits immune suppression include, but are not limited to, ipilimumab, tremelimumab (AstraZeneca and MedImmune), AGEN1884 and AGEN2041 (Agenus). LAG-3 checkpoint inhibitors, include, but are not limited to, BMS-986016 (Bristol-Myers Squibb), GSK2831781 (GlaxoSmithKline), IMP321 (Prima BioMed), LAG525 (Novartis), and the dual PD-1 and LAG-3 inhibitor MGD013 (MacroGenics). An example of a TIM-3 inhibitor is TSR-022 (Tesaro).

In yet another embodiment, one of the active compounds described herein can be administered in an effective amount for the treatment of abnormal tissue of the female reproductive system such as breast, ovarian, endometrial, or uterine cancer, in combination or alternation with an effective amount of an estrogen inhibitor including but not limited to a SERM (selective estrogen receptor modulator), a SERD (selective estrogen receptor degrader), a complete estrogen receptor degrader, or another form of partial or complete estrogen antagonist or agonist. Partial anti-estrogens like raloxifene and tamoxifen retain some estrogen-like effects, including an estrogen-like stimulation of uterine growth, and also, in some cases, an estrogen-like action during breast cancer progression which actually stimulates tumor growth. In contrast, fulvestrant, a complete anti-estrogen, is free of estrogen-like action on the uterus and is effective in tamoxifen-resistant tumors. Non-limiting examples of anti-estrogen compounds are provided in WO 2014/19176 assigned to Astra Zeneca, WO2013/090921, WO 2014/203129, WO 2014/203132, and US2013/0178445 assigned to Olema Pharmaceuticals, and U.S. Pat. Nos. 9,078,871, 8,853,423, and 8,703, 810, as well as US 2015/0005286, WO 2014/205136, and WO 2014/205138. Additional non-limiting examples of anti-estrogen compounds include: SERMS such as anordrin, bazedoxifene, broparestriol, chlorotrianisene, clomiphene citrate, cyclofenil, lasofoxifene, ormeloxifene, raloxifene, tamoxifen, toremifene, and fulvestratnt; aromatase inhibitors such as aminoglutethimide, testolactone, anastrozole, exemestane, fadrozole, formestane, and letrozole; and antigonadotropins such as leuprorelin, cetrorelix, allylestrenol, chloromadinone acetate, cyproterone acetate, delmadinone acetate, dydrogesterone, medroxyprogesterone acetate, megestrol acetate, nomegestrol acetate, norethisterone acetate, progesterone, and spironolactone. Other estrogenic ligands that can be used according to the present invention are described in U.S. Pat. Nos. 4,418,068; 5,478, 847; 5,393,763; and 5,457,117, WO2011/156518, U.S. Pat. Nos. 8,455,534 and 8,299,112, 9,078,871; 8,853,423; 8,703, 810; US 2015/0005286; and WO 2014/205138, US2016/0175289, US2015/0258080, WO 2014/191726, WO 2012/084711; WO 2002/013802; WO 2002/004418; WO 2002/003992; WO 2002/003991; WO 2002/003990; WO 2002/003989; WO 2002/003988; WO 2002/003986; WO 2002/003977; WO 2002/003976; WO 2002/003975; WO 2006/078834; U.S. Pat. No. 6,821,989; US 2002/0128276; U.S. Pat. No. 6,777,424; US 2002/0016340; U.S. Pat. Nos. 6,326, 392; 6,756,401; US 2002/0013327; U.S. Pat. Nos. 6,512, 002; 6,632,834; US 2001/0056099; U.S. Pat. Nos. 6,583, 170; 6,479,535; WO 1999/024027; U.S. Pat. No. 6,005,102; EP 0802184; U.S. Pat. Nos. 5,998,402; 5,780,497, 5,880, 137, WO 2012/048058 and WO 2007/087684.

In another embodiment, an active compounds described herein can be administered in an effective amount for the treatment of abnormal tissue of the male reproductive system such as prostate or testicular cancer, in combination or alternation with an effective amount of an androgen (such as testosterone) inhibitor including but not limited to a selective androgen receptor modulator, a selective androgen receptor degrader, a complete androgen receptor degrader, or another form of partial or complete androgen antagonist. In one embodiment, the prostate or testicular cancer is androgen-resistant. Non-limiting examples of anti-androgen compounds are provided in WO 2011/156518 and U.S. Pat. Nos. 8,455,534 and 8,299,112. Additional non-limiting examples of anti-androgen compounds include: enzalutamide, apalutamide, cyproterone acetate, chlormadinone acetate, spironolactone, canrenone, drospirenone, ketoconazole, topilutamide, abiraterone acetate, and cimetidine.

In one embodiment, the bioactive agent is an ALK inhibitor. Examples of ALK inhibitors include but are not limited to Crizotinib, Alectinib, ceritinib, TAE684 (NVP-TAE684), GSK1838705A, AZD3463, ASP3026, PF-06463922, entrectinib (RXDX-101), and AP26113.

In one embodiment, the bioactive agent is an EGFR inhibitor. Examples of EGFR inhibitors include erlotinib (Tarceva), gefitinib (Iressa), afatinib (Gilotrif), rociletinib (CO-1686), osimertinib (Tagrisso), olmutinib (Olita), naquotinib (ASP8273), nazartinib (EGF816), PF-06747775 (Pfizer), icotinib (BPI-2009), neratinib (HKI-272; PB272); avitinib (AC0010), EAI045, tarloxotinib (TH-4000; PR-610), PF-06459988 (Pfizer), tesevatinib (XL647; EXEL-7647; KD-019), transtinib, WZ-3146, WZ8040, CNX-2006, and dacomitinib (PF-00299804; Pfizer).

In one embodiment, the bioactive agent is an HER-2 inhibitor. Examples of HER-2 inhibitors include trastuzumab, lapatinib, ado-trastuzumab emtansine, and pertuzumab.

In one embodiment, the bioactive agent is a CD20 inhibitor. Examples of CD20 inhibitors include obinutuzumab, rituximab, fatumumab, ibritumomab, tositumomab, and ocrelizumab.

In one embodiment, the bioactive agent is a JAK3 inhibitor. Examples of JAK3 inhibitors include tasocitinib.

In one embodiment, the bioactive agent is a BCL-2 inhibitor. Examples of BCL-2 inhibitorsincludevenetoclax, ABT-199(4-[4-[[2-(4-Chlorophenyl)-4,4-dimethylcyclohex-1-en-1-yl]methyl]piperazin-1-yl]-N-[[3-nitro-4-[[(tetrahydro-2H-pyran-4-yl)methyl]amino]phenyl]sulfonyl]-2-[(1H-pyrrolo[2,3-b]pyridin-5-yl)oxy]benzamide), ABT-737 (4-[4-[[2-(4-chlorophenyl)phenyl]methyl]piperazin-1-yl]-N-[4-[[(2R)-4-(dimethylamino)-1-phenylsulfanylbutan-2-yl] amino]-3-nitrophenyl]sulfonylbenzamide) (navitoclax), ABT-263 ((R)-4-(4-((4'-chloro-4,4-dimethyl-3,4,5,6-tetrahydro-[1,1'-biphenyl]-2-yl)methyl)piperazin-1-yl)-N-((4-((4-morpholino-1-(phenylthio)butan-2-yl)amino)-3((trifluoromethyl)sulfonyl)phenyl)sulfonyl)benzamide), GX15-070 (obatoclaxmesylate, (2Z)-2-[(5Z)-5-[(3,5-dimethyl-1H-pyrrol-2-yl)methylidene]-4-methoxypyrrol-2-ylidene] indole; methanesulfonic acid))), 2-methoxy-antimycin A3, YC137 (4-(4,9-dioxo-4,9-dihydronaphtho[2,3-d]thiazol-2-ylamino)-phenyl ester), pogosin, ethyl 2-amino-6-bromo-4-(1-cyano-2-ethoxy-2-oxoethyl)-4H-chromene-3-carboxylate, Nilotinib-d3, TW-37 (N-[4-[[2-(1,1-Dimethylethyl) phenyl]sulfonyl]phenyl]-2,3,4-trihydroxy-5-[[2-(1-methylethyl)phenyl]methyl]benzamide), Apogossypolone (ApoG2), HA14-1, AT101, sabutoclax, gambogic acid, or G3139 (Oblimersen).

In one embodiment, the bioactive agent is a kinase inhibitor. In one embodiment, the kinase inhibitor is selected from a phosphoinositide 3-kinase (PI3K) inhibitor, a Bruton's tyrosine kinase (BTK) inhibitor, or a spleen tyrosine kinase (Syk) inhibitor, or a combination thereof.

Examples of PI3 kinase inhibitors include but are not limited to Wortmannin, demethoxyviridin, perifosine, idelalisib, Pictilisib, Palomid 529, ZSTK474, PWT33597, CUDC-907, and AEZS-136, duvelisib, GS-9820, BKM120, GDC-0032 (Taselisib) (2-[4-[2-(2-Isopropyl-5-methyl-1,2,4-triazol-3-yl)-5,6-dihydroimidazo[1,2-d][1,4]benzoxazepin-9-yl]pyrazol-1-yl]-2-methylpropanamide), MLN-1117 ((2R)-1-Phenoxy-2-butanyl hydrogen (S)-methylphosphonate; or Methyl(oxo) {[(2R)-1-phenoxy-2-butanyl] oxy}phosphonium)), BYL-719 ((2S)—N1-[4-Methyl-5-[2-(2,2,2-trifluoro-1,1-dimethylethyl)-4-pyridinyl]-2-thiazolyl]-1,2-pyrrolidinedicarboxamide), GSK2126458 (2,4-Difluoro-N-{2-(methyloxy)-5-[4-(4-pyridazinyl)-6-quinolinyl]-3-pyridinyl}benzenesulfonamide) (omipalisib), TGX-221 (( )-7-Methyl-2-(morpholin-4-yl)-9-(1-phenylaminoethyl)-pyrido[1,2-a]-pyrimidin-4-one), GSK2636771 (2-Methyl-1-(2-methyl-3-(trifluoromethyl) benzyl)-6-morpholino-1H-benzo[d]imidazole-4-carboxylic acid dihydrochloride), KIN-193 ((R)-2-((1-(7-methyl-2-morpholino-4-oxo-4H-pyrido[1,2-a]pyrimidin-9-yl)ethyl) amino)benzoic acid), TGR-1202/RP5264, GS-9820 ((S)-1-(4-((2-(2-aminopyrimidin-5-yl)-7-methyl-4-mohydroxypropan-1-one), GS-1101 (5-fluoro-3-phenyl-2-([S)]-1-[9H-purin-6-ylamino]-propyl)-3H-quinazolin-4-one), AMG-319, GSK-2269557, SAR245409 (N-(4-(N-(3-((3,5-dimethoxyphenyl)amino)quinoxalin-2-yl)sulfamoyl) phenyl)-3-methoxy-4 methylbenzamide), BAY80-6946 (2-amino-N-(7-methoxy-8-(3-morpholinopropoxy)-2,3-dihydroimidazo[1,2-c]quinaz), AS 252424 (5-[1-[5-(4-Fluoro-2-hydroxy-phenyl)-furan-2-yl]-meth-(Z)-ylidene]-thiazolidine-2,4-dione), CZ 24832 (5-(2-amino-8-fluoro-[1,2,4] triazolo[1,5-a]pyridin-6-yl)-N-tert-butylpyridine-3-sulfonamide), Buparlisib (5-[2,6-Di(4-morpholinyl)-4-pyrimidinyl]-4-(trifluoromethyl)-2-pyridinamine), GDC-0941 (2-(1H-Indazol-4-yl)-6-[[4-(methylsulfonyl)-1-piperazinyl]methyl]-4-(4-morpholinyl)thieno[3,2-d] pyrimidine), GDC-0980 ((S)-1-(4-((2-(2-aminopyrimidin-5-yl)-7-methyl-4-morpholinothieno[3,2-d]pyrimidin-6 yl)methyl)piperazin-1-yl)-2-hydroxypropan-1-one (also known as RG7422)), SF1126 ((8S,14S,17S)-14-(carboxymethyl)-8-(3-guanidinopropyl)-17-(hydroxymethyl)-3,6,9,12, 15-pentaoxo-1-(4-(4-oxo-8-phenyl-4H-chromen-2-yl)morpholino-4-ium)-2-oxa-7,10,13,16-tetraazaoctadecan-18-oate), PF-05212384 (N-[4-[[4-(Dimethylamino)-1-piperidinyl]carbonyl]phenyl]-N'-[4-(4,6-di-4-morpholinyl-1,3,5-triazin-2-yl)phenyl]urea) (gedatolisib), LY3023414, BEZ235 (2-Methyl-2-{4-[3-methyl-2-oxo-8-(quinolin-3-yl)-2,3-dihydro-1H-imidazo[4,5-c]quinolin-1-yl] phenyl}propanenitrile) (dactolisib), XL-765 (N-(3-(N-(3-(3, 5-dimethoxyphenylamino)quinoxalin-2-yl)sulfamoyl) phenyl)-3-methoxy-4-methylbenzamide), and GSK1059615 (5-[[4-(4-Pyridinyl)-6-quinolinyl]methylene]-2,4-thiazolidenedione), PX886 ([(3aR,6E,9S,9aR,10R,11aS)-6-[[bis (prop-2-enyl)amino]methylidene]-5-hydroxy-9-(methoxymethyl)-9a,11a-dimethyl-1,4,7-trioxo-2,3,3a,9,10, 11-hexahydroindeno[4,5h]isochromen-10-yl] acetate (also known as sonolisib)), LY294002, AZD8186, PF-4989216, pilaralisib, GNE-317, PI-3065, PI-103, NU7441 (KU-57788), HS 173, VS-5584 (SB2343), CZC24832, TG100-115, A66, YM201636, CAY10505, PIK-75, PIK-93, AS-605240, BGT226 (NVP-BGT226), AZD6482, voxtalisib, alpelisib, IC-87114, TGI100713, CH5132799, PKI-402, copanlisib (BAY 80-6946), XL 147, PIK-90, PIK-293, PIK-294, 3-MA (3-methyladenine), AS-252424, AS-604850, apitolisib (GDC-0980; RG7422), and the structure described in WO2014/071109 having the formula:

Compound 292

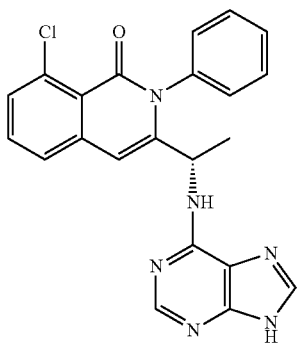

Examples of BTK inhibitors include ibrutinib (also known as PCI-32765)(Imbruvica™)(1-[(3R)-3-[4-amino-3-(4-phenoxy-phenyl)pyrazolo[3,4-d]pyrimidin-1-yl]piperidin-1-yl]prop-2-en-1-one), dianilinopyrimidine-based inhibitors such as AVL-101 and AVL-291/292 (N-(3-((5-fluoro-2-((4-(2-methoxyethoxy)phenyl)amino)pyrimidin-4-yl)amino)phenyl)acrylamide) (Avila Therapeutics) (see US Patent Publication No 2011/0117073, incorporated herein in its entirety), Dasatinib ([N-(2-chloro-6-methylphenyl)-2-(6-(4-(2-hydroxyethyl)piperazin-1-yl)-2-methylpyrimidin-4-ylamino)thiazole-5-carboxamide], LFM-A13 (alpha-cyano-beta-hydroxy-beta-methyl-N-(2,5-ibromophenyl)propenamide), GDC-0834 ([R—N-(3-(6-(4-(1,4-dimethyl-3-oxopiperazin-2-yl)phenylamino)-4-methyl-5-oxo-4,5-dihydropyrazin-2-yl)-2-methylphenyl)-4,5,6,7-tetrahydrobenzo[b]thiophene-2-carboxamide], CGI-560 4-(tert-butyl)-N-(3-(8-(phenylamino)imidazo[1,2-a]pyrazin-6-yl)phenyl)benzamide, CGI-1746 (4-(tert-butyl)-N-(2-methyl-3-(4-methyl-6-((4-(morpholine-4-carbonyl)phenyl)amino)-5-oxo-4,5-dihydropyrazin-2-yl)phenyl)benzamide), CNX-774 (4-(4-((4-((3-acrylamidophenyl)amino)-5-fluoropyrimidin-2-yl)amino)phenoxy)-N-methylpicolinamide), CTA056 (7-benzyl-1-(3-(piperidin-1-yl)propyl)-2-(4-(pyridin-4-yl)phenyl)-1H-imidazo[4,5-g]quinoxalin-6(5H)-one), GDC-0834 ((R)—N-(3-(6-((4-(1,4-dimethyl-3-oxopiperazin-2-yl)phenyl)amino)-4-methyl-5-oxo-4,5-dihydropyrazin-2-yl)-2-methylphenyl)-4,5,6,7-tetrahydrobenzo[b]thiophene-2-carboxamide), GDC-0837 ((R)—N-(3-(6-((4-(1,4-dimethyl-3-oxopiperazin-2-yl)phenyl)amino)-4-methyl-5-oxo-4,5-dihydropyrazin-2-yl)-2-methylphenyl)-4,5,6,7-tetrahydrobenzo[b]thiophene-2-carboxamide), HM-71224, ACP-196, ONO-4059 (Ono Pharmaceuticals), PRT062607 (4-((3-(2H-1,2,3-triazol-2-yl)phenyl)amino)-2-(((1R,2S)-2-aminocyclohexyl)amino)pyrimidine-5-carboxamide hydrochloride), QL-47 (1-(1-acryloylindolin-6-yl)-9-(1-methyl-1H-pyrazol-4-yl)benzo[h][1,6]naphthyridin-2 (1H)-one), and RN486 (6-cyclopropyl-8-fluoro-2-(2-hydroxymethyl-3-{1-methyl-5-[5-(4-methyl-piperazin-1-yl)-pyridin-2-ylamino]-6-oxo-1,6-dihydro-pyridin-3-yl}-phenyl)-2H-isoquinolin-1-one), and other molecules capable of inhibiting BTK activity, for example those BTK inhibitors disclosed in Akinleye et ah, Journal of Hematology & Oncology, 2013, 6:59, the entirety of which is incorporated herein by reference.

Syk inhibitors include, for example, Cerdulatinib (4-(cyclopropylamino)-2-((4-(4-(ethylsulfonyl)piperazin-1-yl)phenyl)amino)pyrimidine-5-carboxamide), entospletinib (6-(1H-indazol-6-yl)-N-(4-morpholinophenyl)imidazo[1,2-a]pyrazin-8-amine), fostamatinib ([6-({5-Fluoro-2-[(3,4,5-trimethoxyphenyl)amino]-4-pyrimidinyl}amino)-2,2-dimethyl-3-oxo-2,3-dihydro-4H-pyrido[3,2-b][1,4]oxazin-4-yl]methyl dihydrogen phosphate), fostamatinib disodium salt (sodium (6-((5-fluoro-2-((3,4,5-trimethoxyphenyl)amino)pyrimidin-4-yl)amino)-2,2-dimethyl-3-oxo-2H-pyrido[3,2-b][1,4]oxazin-4(3H)-yl)methyl phosphate), BAY 61-3606 (2-(7-(3,4-Dimethoxyphenyl)-imidazo[1,2-c]pyrimidin-5-ylamino)-nicotinamide HCl), RO9021 (6-[(1R, 2S)-2-Amino-cyclohexylamino]-4-(5,6-dimethyl-pyridin-2-ylamino)-pyridazine-3-carboxylic acid amide), imatinib (Gleevac; 4-[(4-methylpiperazin-1-yl)methyl]-N-(4-methyl-3-{[4-(pyridin-3-yl)pyrimidin-2-yl]amino}phenyl)benzamide), staurosporine, GSK143 (2-(((3R,4R)-3-aminotetrahydro-2H-pyran-4-yl)amino)-4-(p-tolylamino)pyrimidine-5-carboxamide), PP2 (1-(tert-butyl)-3-(4-chlorophenyl)-1H-pyrazolo[3,4-d]pyrimidin-4-amine), PRT-060318 (2-(((1R, 2S)-2-aminocyclohexyl)amino)-4-(m-tolylamino)pyrimidine-5-carboxamide), PRT-062607 (4-((3-(2H-1,2,3-triazol-2-yl)phenyl)amino)-2-(((1R,2S)-2-aminocyclohexyl)amino)pyrimidine-5-carboxamide hydrochloride), R112 (3,3'-((5-fluoropyrimidine-2,4-diyl)bis(azanediyl))diphenol), R348 (3-Ethyl-4-methylpyridine), $R^{406}$ (6-((5-fluoro-2-((3,4,5-trimethoxyphenyl)amino)pyrimidin-4-yl)amino)-2,2-dimethyl-2H-pyrido[3,2-b][1,4]oxazin-3(4H)-one), piceatannol (3-Hydroxyresveratol), YM193306(see Singh et al. Discovery and Development of Spleen Tyrosine Kinase (SYK) Inhibitors, J. Med. Chem. 2012, 55, 3614-3643), 7-azaindole, piceatannol, ER-27319 (see Singh et al. Discovery and Development of Spleen Tyrosine Kinase (SYK) Inhibitors, J. Med. Chem. 2012, 55, 3614-3643 incorporated in its entirety herein), Compound D (see Singh et al. Discovery and Development of Spleen Tyrosine Kinase (SYK) Inhibitors, J. Med. Chem. 2012, 55, 3614-3643 incorporated in its entirety herein), PRT060318 (see Singh et al. Discovery and Development of Spleen Tyrosine Kinase (SYK) Inhibitors, J. Med. Chem. 2012, 55, 3614-3643 incorporated in its entirety herein), luteolin (see Singh et al. Discovery and Development of Spleen Tyrosine Kinase (SYK) Inhibitors, J. Med. Chem. 2012, 55, 3614-3643 incorporated in its entirety herein), apigenin (see Singh et al. Discovery and Development of Spleen Tyrosine Kinase (SYK) Inhibitors, J. Med. Chem. 2012, 55, 3614-3643 incorporated in its entirety herein), quercetin (see Singh et al. Discovery and Development of Spleen Tyrosine Kinase (SYK) Inhibitors, J. Med. Chem. 2012, 55, 3614-3643 incorporated in its entirety herein), fisetin (see Singh et al. Discovery and Development of Spleen Tyrosine Kinase (SYK) Inhibitors, J. Med. Chem. 2012, 55, 3614-3643 incorporated in its entirety herein), myricetin (see Singh et al. Discovery and Development of Spleen Tyrosine Kinase (SYK) Inhibitors, J. Med. Chem. 2012, 55, 3614-3643 incorporated in its entirety herein), morin (see Singh et al. Discovery and Development of Spleen Tyrosine Kinase (SYK) Inhibitors, J. Med. Chem. 2012, 55, 3614-3643 incorporated in its entirety herein).

In one embodiment, the bioactive agent is a EK inhibitor. MEK inhibitors are well known, and include, for example, trametinib/GSK1120212 (N-(3-{3-Cyclopropyl-5-[(2-fluoro-4-iodophenyl)amino]-6,8-dimethyl-2,4,7-trioxo-3,4, 6,7-tetrahydropyrido[4,3-d]pyrimidin-(2H-yl}phenyl)acetamide), selumetinib (6-(4-bromo-2-chloroanilino)-7-fluoro-N-(2-hydroxyethoxy)-3-methylbenzimidazole-5-carboxamide), pimasertib/AS703026/MSC 1935369 ((S)—N-(2,3-dihydroxypropyl)-3-((2-fluoro-4-iodophenyl)amino) isonicotinamide), XL-518/GDC-0973 (1-({3,4-difluoro-2-[(2-fluoro-4-iodophenyl)amino]phenyl}carbonyl)-3-[(2S)-piperidin-2-yl]azetidin-3-ol), refametinib/BAY869766/RDEAl 19 (N-(3,4-difluoro-2-(2-fluoro-4- iodophenylamino)-6-methoxyphenyl)-1-(2,3-dihydroxypropyl)cyclopropane-1-sulfonamide), PD-0325901 (N-[(2R)-2,3-Dihydroxypropoxy]-3,4-difluoro-2-[(2-fluoro-4-iodophenyl)amino]-benzamide), TAK733 ((R)-3-(2,3-Dihydroxypropyl)-6-fluoro-5-(2-fluoro-4-iodophenylamino)-8-methylpyrido[2,3-d]pyrimidine-4,7(3H,8H)-dione), MEK162/ARRY438162 (5-[(4-Bromo-2-fluorophenyl)amino]-4-fluoro-N-(2-hydroxyethoxy)-1-methyl-1H-benzimidazole-6-carboxamide), RO5126766 (3-[[3-Fluoro-2-(methylsulfamoylamino)-4-pyridyl]methyl]-4-methyl-7-pyrimidin-2-yloxychromen-2-one), WX-554, R04987655/CH4987655 (3,4-difluoro-2-((2-fluoro-4-iodophenyl)amino)-N-(2-hydroxyethoxy)-5-((3-oxo-1,2-oxazinan-2yl)methyl)benzamide), or AZD8330 (2-((2-fluoro-4-iodophenyl)amino)-N-(2 hydroxyethoxy)-1, 5-dimethyl-6-oxo-1,6-dihydropyridine-3-carboxamide), U0126-EtOH, PD184352 (CI-1040), GDC-0623, BI-847325, cobimetinib, PD98059, BIX 02189, BIX 02188, binimetinib, SL-327, TAK-733, PD318088.

In one embodiment, the bioactive agent is a Raf inhibitor. Raf inhibitors are known and include, for example, Vemurafinib (N-[3-[[5-(4-Chlorophenyl)-1H-pyrrolo[2,3-b]pyridin-3-yl]carbonyl]-2,4-difluorophenyl]-1-propanesulfonamide), sorafenib tosylate (4-[4-[[4-chloro-3-(trifluoromethyl)phenyl]carbamoylamino]phenoxy]-N-methylpyridine-2-carboxamide; 4-methylbenzenesulfonate), AZ628 (3-(2-cyanopropan-2-yl)-N-(4-methyl-3-(3-methyl-4-oxo-3,4-dihydroquinazolin-6-ylamino)phenyl) benzamide), NVP-BHG712 (4-methyl-3-(1-methyl-6-(pyridin-3-yl)-1H-pyrazolo[3,4-d]pyrimidin-4-ylamino)-N-(3-(trifluoromethyl)phenyl)benzamide), RAF-265(1-methyl-5-[2-[5-(trifluoromethyl)-1H-imidazol-2-yl]pyridin-4-yl]oxy-N-[4-(trifluoromethyl)phenyl]benzimidazol-2-amine),2-Bromoaldisine (2-Bromo-6,7-dihydro-1H,5H-pyrrolo[2,3-c]azepine-4,8-dione), Raf Kinase Inhibitor IV (2-chloro-5-(2-phenyl-5-(pyridin-4-yl)-1H-imidazol-4-yl)phenol), Sorafenib N-Oxide (4-[4-[[[[4-Chloro-3(trifluoroMethyl) phenyl]aMino]carbonyl]aMino]phenoxy]-N-Methyl-2pyridinecarboxaMide 1-Oxide), PLX-4720, dabrafenib (GSK2118436), GDC-0879, RAF265, AZ 628, SB590885, ZM336372, GW5074, TAK-632, CEP-32496, LY3009120, and GX818 (Encorafenib).

In one embodiment, the bioactive agent is an AKT inhibitor, including but not limited to, MK-2206, GSK690693, Perifosine, (KRX-0401), GDC-0068, Triciribine, AZD5363, Honokiol, PF-04691502, and Miltefosine, a FLT-3 inhibitor, including but not limited to, P406, Dovitinib, Quizartinib (AC220), Amuvatinib (MP-470), Tandutinib (MLN518), ENMD-2076, and KW-2449, or a combination thereof.

In one embodiment, the bioactive agent is an mTOR inhibitor. Examples of mTOR inhibitors include but are not limited to rapamycin and its analogs, everolimus (Afinitor), temsirolimus, ridaforolimus, sirolimus, and deforolimus. Examples of MEK inhibitors include but are not limited to tametinib/GSK1120212 (N-(3-{3-Cyclopropyl-5-[(2-fluoro-4-iodophenyl)amino]-6,8-dimethyl-2,4,7-trioxo-3,4,6,7-tetrahydropyrido[4,3-d]pyrimidin-(2H-yl}phenyl)acetamide), selumetinob(6-(4-bromo-2-chloroanilino)-7-fluoro-N-(2-hydroxyethoxy)-3-methylbenzimidazole-5-carboxamide), pimasertib/AS703026/MSC1935369 ((S)—N-(2,3-dihydroxypropyl)-3-((2-fluoro-4-iodophenyl)amino) isonicotinamide), XL-518/GDC-0973 (1-({3,4-difluoro-2-[(2-fluoro-4-iodophenyl)amino]phenyl}carbonyl)-3-[(2S)-piperidin-2-yl]azetidin-3-ol)(cobimetinib), refametinib/BAY869766/RDEA119(N-(3,4-difluoro-2-(2-fluoro-4-iodophenylamino)-6-methoxyphenyl)-1-(2,3-dihydroxypropyl)cyclopropane-1-sulfonamide), PD-0325901 (N-[(2R)-2,3-Dihydroxypropoxy]-3,4-difluoro-2-[(2-fluoro-4-iodophenyl)amino]-benzamide), TAK733((R)-3-(2,3-Dihydroxypropyl)-6-fluoro-5-(2-fluoro-4-iodophenylamino)-8-methylpyrido[2,3d]pyrimidine-4,7(3H,8H)-dione), MEK162/ARRY438162 (5-[(4-Bromo-2-fluorophenyl)amino]-4-fluoro-N-(2-hydroxyethoxy)-1-methyl-1H-benzimidazole-6 carboxamide), RO5126766 (3-[[3-Fluoro-2-(methylsulfamoylamino)-4-pyridyl]methyl]-4-methyl-7-pyrimidin-2-yloxychromen-2-one), WX-554, R04987655/CH4987655 (3,4-difluoro-2-((2-fluoro-4-iodophenyl)amino)-N-(2-hydroxyethoxy)-5-((3-oxo-1,2-oxazinan-2 yl)methyl)benzamide), or AZD8330 (2-((2-fluoro-4-iodophenyl)amino)-N-(2-hydroxyethoxy)-1,5-dimethyl-6-oxo-1,6-dihydropyridine-3-carboxamide).

In one embodiment, the bioactive agent is a RAS inhibitor. Examples of RAS inhibitors include but are not limited to Reolysin and siG12D LODER.

In one embodiment, the bioactive agent is a HSP inhibitor. HSP inhibitors include but are not limited to Geldanamycin or 17-N-Allylamino-17-demethoxygeldanamycin (17AAG), and Radicicol.

Additional bioactive compounds include, for example, everolimus, trabectedin, abraxane, TLK 286, AV-299, DN-101, pazopanib, GSK690693, RTA 744, ON 0910.Na, AZD 6244 (ARRY-142886), AMN-107, TKI-258, GSK461364, AZD 1152, enzastaurin, vandetanib, ARQ-197, MK-0457, MLN8054, PHA-739358, R-763, AT-9263, a FLT-3 inhibitor, a VEGFR inhibitor, an aurora kinase inhibitor, a PIK-1 modulator, an HDAC inhibitor, a c-MET inhibitor, a PARP inhibitor, a Cdk inhibitor, an IGFR-TK inhibitor, an anti-HGF antibody, a focal adhesion kinase inhibitor, a Map kinase kinase (mek) inhibitor, a VEGF trap antibody, pemetrexed, panitumumab, amrubicin, oregovomab, Lep-etu, nolatrexed, azd2171, batabulin, ofatumumab, zanolimumab, edotecarin, tetrandrine, rubitecan, tesmilifene, oblimersen, ticilimumab, ipilimumab, gossypol, Bio 111, 131-I-TM-601, ALT-110, BIO 140, CC 8490, cilengitide, gimatecan, IL13-PE38QQR, INO 1001, IPdR₁KRX-0402, lucanthone, LY317615, neuradiab, vitespan, Rta 744, Sdx 102, talampanel, atrasentan, Xr 311, romidepsin, ADS-100380, sunitinib, 5-fluorouracil, vorinostat, etoposide, gemcitabine, doxorubicin, liposomal doxorubicin, 5'-deoxy-5-fluorouridine, vincristine, temozolomide, ZK-304709, seliciclib; PD0325901, AZD-6244, capecitabine, L-Glutamic acid, N-[4-[2-(2-amino-4,7-dihydro-4-oxo-1H-pyrrolo[2,3-d]pyrimidin-5-yl)ethyl]benzoyl]—, disodium salt, heptahydrate, camptothecin, PEG-labeled irinotecan, tamoxifen, toremifene citrate, anastrazole, exemestane, letrozole, DES(diethylstilbestrol), estradiol, estrogen, conjugated estrogen, bevacizumab, IMC-1C11, CHIR-258); 3-[5-(methylsulfonylpiperadinemethyl)-indolyl-quinolone, vatalanib, AG-013736, AVE-0005, goserelin acetate, leuprolide acetate, triptorelin pamoate, medroxyprogesterone acetate, hydroxyprogesterone caproate, megestrol acetate, raloxifene, bicalutamide, flutamide, nilutamide, megestrol acetate, CP-724714; TAK-165, HKI-272, erlotinib, lapatanib, canertinib, ABX-EGF antibody, erbitux, EKB-569, PKI-166, GW-572016, Ionafarnib, BMS-214662, tipifarnib; amifostine, NVP-LAQ824, suberoyl analide hydroxamic acid, valproic acid, trichostatin A, FK-228, SU11248, sorafenib, KRN951, aminoglutethimide, arnsacrine, anagrelide, L-asparaginase, *Bacillus* Calmette-Guerin (BCG) vaccine, adriamycin, bleomycin, buserelin, busulfan, carboplatin, carmustine, chlorambucil, cisplatin, cladribine, clodronate, cyproterone, cytarabine, dacarbazine, dactinomycin, daunorubicin, diethylstilbestrol, epirubicin, fludarabine, fludrocortisone, fluoxymesterone, flutamide, gleevec, gemcitabine, hydroxyurea, idarubicin, ifosfamide, imatinib, leuprolide, levamisole, lomustine, mechlorethamine, melphalan, 6-mercaptopurine, mesna, methotrexate, mitomycin, mitotane, mitoxantrone, nilutamide, octreotide, oxaliplatin, pamidronate, pentostatin, plicamycin, porfimer, procarbazine, raltitrexed, rituximab, streptozocin, teniposide, testosterone, thalidomide, thioguanine, thiotepa, tretinoin, vindesine, 13-cis-retinoic acid, phenylalanine mustard, uracil mustard, estramustine, altretamine, floxuridine, 5-deooxyuridine, cytosine arabinoside, 6-mecaptopurine, deoxycoformycin, calcitriol, valrubicin, mithramycin, vinblastine, vinorelbine, topotecan, razoxin, marimastat, COL-3, neovastat, BMS-275291, squalamine, endostatin, SU5416, SU6668, EMD121974, interleukin-12, IM862, angiostatin, vitaxin, droloxifene, idoxyfene, spironolactone, finasteride, cimitidine, trastuzumab, denileukin diftitox, gefitinib, bortezimib, paclitaxel, cremophor-free paclitaxel, docetaxel, epithilone B, BMS-247550, BMS-310705, droloxifene, 4-hydroxytamoxifen, pipendoxifene, ERA-923, arzoxifene, fulvestrant, acolbifene, lasofoxifene, idoxifene, TSE-424, HMR-3339, ZK186619, topotecan, PTK787/ZK 222584, VX-745, PD 184352, rapamycin, 40-O-(2-hydroxyethyl)-rapamycin, temsirolimus, AP-23573, RAD001, ABT-578, BC-210, LY294002, LY292223, LY292696, LY293684, LY293646, wortmannin, ZM336372, L-779,450, PEG-filgrastim, darbepoetin, erythropoietin, granulocyte colony-stimulating factor, zolendronate, prednisone, cetuximab, granulocyte macrophage colony-stimulating factor, histrelin, pegylated interferon alfa-2a, interferon alfa-2a, pegylated interferon alfa-2b, interferon alfa-2b, azacitidine, PEG-L-asparaginase, lenalidomide, gemtuzumab, hydrocortisone, interleukin-11, dexrazoxane, alemtuzumab, all-transretinoic acid, ketoconazole, interleukin-2, megestrol, immune globulin, nitrogen mustard, methylprednisolone, ibritgumomab tiuxetan, androgens, decitabine, hexamethylmelamine, bexarotene, tositumomab, arsenic trioxide, cortisone, editronate, mitotane, cyclosporine, liposomal daunorubicin, Edwina-asparaginase, strontium 89, casopitant, netupitant, an NK-1 receptor antagonist, palonosetron, aprepitant, diphenhydramine, hydroxyzine, metoclopramide, lorazepam, alprazolam, haloperidol, droperidol, dronabinol, dexamethasone, methylprednisolone, prochlorperazine, granisetron, ondansetron, dolasetron, tropisetron, pegfilgrastim, erythropoietin, epoetin alfa, darbepoetin alfa and mixtures thereof.

In one embodiment, the bioactive agent is selected from, but are not limited to, Imatinib mesylate (Gleevac®), Dasatinib (Sprycel®), Nilotinib (Tasigna®), Bosutinib (Bosulif®), Trastuzumab (Herceptin®), trastuzumab-DM1, Pertuzumab (Perjeta™), Lapatinib (Tykerb®), Gefitinib (Iressa®), Erlotinib (Tarceva®), Cetuximab (Erbitux®), Panitumumab (Vectibix®), Vandetanib (Caprelsa®), Vemurafenib (Zelboraf®), Vorinostat (Zolinza®), Romidepsin (Istodax®), Bexarotene (Tagretin®), Alitretinoin (Panretin®), Tretinoin (Vesanoid®), Carfilizomib (Kyprolis™), Pralatrexate (Folotyn®), Bevacizumab (Avastin®), Ziv-aflibercept (Zaltrap®), Sorafenib (Nexavar®), Sunitinib (Sutent®), Pazopanib (Votrient®), Regorafenib (Stivarga®), and Cabozantinib (Cometriq™).

In certain aspects, the bioactive agent is an anti-inflammatory agent, a chemotherapeutic agent, a radiotherapeutic, an additional therapeutic agent, or an immunosuppressive agent.

Suitable chemotherapeutic bioactive agents include, but are not limited to, a radioactive molecule, a toxin, also referred to as cytotoxin or cytotoxic agent, which includes any agent that is detrimental to the viability of cells, and liposomes or other vesicles containing chemotherapeutic compounds. General anticancer pharmaceutical agents include: Vincristine (Oncovin®) or liposomal vincristine (Marqibo®), Daunorubicin (daunomycin or Cerubidine®) or doxorubicin (Adriamycin®), Cytarabine (cytosine arabinoside, ara-C, or Cytosar®), L-asparaginase (Elspar®) or PEG-L-asparaginase (pegaspargase or Oncaspar®), Etoposide (VP-16), Teniposide (Vumon®), 6-mercaptopurine (6-MP or Purinethol®), Methotrexate, Cyclophosphamide (Cytoxan®), Prednisone, Dexamethasone (Decadron), imatinib (Gleevec®), dasatinib (Sprycel®), nilotinib (Tasigna®), bosutinib (Bosulif®), and ponatinib (Iclusig™). Examples of additional suitable chemotherapeutic agents include but are not limited to 1-dehydrotestosterone, 5-fluorouracil decarbazine, 6-mercaptopurine, 6-thioguanine, actinomycin D, adriamycin, aldesleukin, an alkylating agent, allopurinol sodium, altretamine, amifostine, anastrozole, anthramycin (AMC)), an anti-mitotic agent, cis-dichlorodiamine platinum (II) (DDP) cisplatin), diamino dichloro platinum, anthracycline, an antibiotic, an antimetabolite, asparaginase, BCG live (intravesical), betamethasone sodium phosphate and betamethasone acetate, bicalutamide, bleomycin sulfate, busulfan, calcium leucouorin, calicheamicin, capecitabine, carboplatin, lomustine (CCNU), carmustine (BSNU), Chlorambucil, Cisplatin, Cladribine, Colchicin, conjugated estrogens, Cyclophosphamide, Cyclothosphamide, Cytarabine, Cytarabine, cytochalasin B, Cytoxan, Dacarbazine, Dactinomycin, dactinomycin (formerly actinomycin), daunirubicin HCL, daunorucbicin citrate, denileukin diftitox, Dexrazoxane, Dibromomannitol, dihydroxy anthracin dione, Docetaxel, dolasetron mesylate, doxorubicin HCL, dronabinol, E. coli L-asparaginase, emetine, epoetin-α, Erwinia L-asparaginase, esterified estrogens, estradiol, estramustine phosphate sodium, ethidium bromide, ethinyl estradiol, etidronate, etoposide citrororum factor, etoposide phosphate, filgrastim, floxuridine, fluconazole, fludarabine phosphate, fluorouracil, flutamide, folinic acid, gemcitabine HCL, glucocorticoids, goserelin acetate, gramicidin D, granisetron HCL, hydroxyurea, idarubicin HCL, ifosfamide, interferon α-2b, irinotecan HCL, letrozole, leucovorin calcium, leuprolide acetate, levamisole HCL, lidocaine, lomustine, maytansinoid, mechlorethamine HCL, medroxyprogesterone acetate, megestrol acetate, melphalan HCL, mercaptipurine, mesna, methotrexate, methyltestosterone, mithramycin, mitomycin C, mitotane, mitoxantrone, nilutamide, octreotide acetate, ondansetron HCL, paclitaxel, pamidronate disodium, pentostatin, pilocarpine HCL, plimycin, polifeprosan 20 with carmustine implant, porfimer sodium, procaine, procarbazine HCL, propranolol, rituximab, sargramostim, streptozotocin, tamoxifen, taxol, teniposide, tenoposide, testolactone, tetracaine, thioepa chlorambucil, thioguanine, thiotepa, topotecan HCL, toremifene citrate, trastuzumab, tretinoin, valrubicin, vinblastine sulfate, vincristine sulfate, and vinorelbine tartrate.

Additional therapeutic agents that can be administered in combination with a degronimer disclosed herein can include bevacizumab, sutinib, sorafenib, 2-methoxyestradiol or 2ME2, finasunate, vatalanib, vandetanib, aflibercept, volociximab, etaracizumab (MEDI-522), cilengitide, erlotinib, cetuximab, panitumumab, gefitinib, trastuzumab, dovitinib, figitumumab, atacicept, rituximab, alemtuzumab, aldesleukine, atlizumab, tocilizumab, temsirolimus, everolimus, lucatumumab, dacetuzumab, HLL1, huN901-DM1, atiprimod, natalizumab, bortezomib, carfilzomib, marizomib, tanespimycin, saquinavir mesylate, ritonavir, nelfinavir mesylate, indinavir sulfate, belinostat, panobinostat, mapatumumab, lexatumumab, dulanermin, ABT-737, oblimersen, plitidepsin, talmapimod, P276-00, enzastaurin, tipifarnib, perifosine, imatinib, dasatinib, lenalidomide, thalidomide, simvastatin, celecoxib, bazedoxifene, AZD4547, rilotumumab, oxaliplatin (Eloxatin), PD0332991, ribociclib (LEE011), amebaciclib (LY2835219), HDM201, fulvestrant (Faslodex), exemestane (Aromasin), PIM447, ruxolitinib (INC424), BGJ398, necitumumab, pemetrexed (Alimta), and ramucirumab (IMC-1121B).

In one aspect of the invention, the disclosed compound is administered in combination with an anti-infective agent, for example but not limited to an anti-HIV agent, anti-HCV agent, anti-HBV agent, or other anti-viral or anti-bacterial agent. In one embodiment, the anti-HIV agent can be, but is not limited to, for example, a nucleoside reverse transcriptase inhibitor (NRTI), other non-nucloeoside reverse transcriptase inhibitor, protease inhibitor, fusion inhibitor, among others. Nucleoside/Nucleotide Reverse Transcriptase Inhibitors (NRTIs) include, but are not limited to, Abacavir or ABC (Ziagen), Didanosine or ddI (Videx), Emtricitabine or FTC (Emtriva), Lamivudine or 3TC (Epivir), ddC (zalcitabine), Stavudine or d4T (Zerit), Tenofovircor TDF (Viread), D-D4FC (Reverset), and Zidovudine or AZT or ZDV (Retrovir). Non-nucleoside Reverse Transcriptase Inhibitors (NNRTIs) include, but are not limited to, Delavirdine (Rescriptor), Efavirenz (Sustiva), Etravirine (Intelence), Nevirapine (Viramune), and Rilpivirine (Edurant). Anti-HIV Protease Inhibitors (PIs) include, but are not limited to, Atazanavir or ATV (Reyataz), Darunavir or DRV (Prezista), Fosamprenavir or FPV (Lexiva), Indinavir or IDV (Crixivan), Lopinavir+ritonavir, or LPV/r (Kaletra), Nelfinavir or NFV (Viracept), Ritonavir or RTV (Norvir), Saquinavir or SQV (Invirase), Tipranavir, or TPV (Aptivus), Cobicistat (Tybost), Atazanavir+cobicistat, or ATV/COBI (Evotaz), Darunavir+cobicistat, or DRV/COBI (Prezcobix). Anti-HIV Fusion Inhibitors include, but are not limited to, Enfuvirtide or ENF or T-20 (Fuzeon). Anti-HIV also include, but are not limited to, Maraviroc or MVC (Selzentry). Anti-HIV Integrase Inhibitors include, but are not limited to Dolutegravir (Tivicay), Elvitegravir (Vitekta), Raltegravir (Isentress). Anti-HIV combinations agents include Abacavir+Dolutegravir+lamivudine, or ABC/DTG/3TC (Triumeq), Abacavir+lamivudine or ABC/3TC (Epzicom), Abacavir+lamivudine+zidovudine, or ABC/3TC/ZDV (Trizivir), Efavirenz+emtricitabine+tenofovir or EFV/FTC/TDF (Atripla, Tribuss), elvitegravir, cobicistat, emtricitabine, tenofovir alafenamide or EVG/COBI/FTC/TAF or ECF/TAF (Genvoya; (Stribild), emtricitabine+rilpivirine+tenofovir or FTC/RPV/TAF (Odefsey); Emtricitabine+rilpivirine+tenofovir or FTC/RPV/TDF (Complera), Emtricitabine+tenofovir or TAF/FTC (Descovy), emtricitabine and tenofovir disoproxil fumarate (Truvada), and Lamivudine+zidovudine or 3TC/ZDV (Combivir). Other anti-HIV compounds include, but are not limited to Racivir, L-FddC, L-FD4C, SQVM (Saquinavir mesylate), IDV (Indinavir), SQV (Saquinavir), APV (Amprenavir), LPV (Lopinavir), fusion inhibitors such as T20, among others, fuseon and mixtures thereof, including anti-HIV compounds presently in clinical trials or in development.

Other anti-HIV agents which may be used in co-administration with the disclosed compounds according to the present invention. NNRTIs may be selected from the group consisting of nevirapine (BI-R6-587), delavirdine (U-90152S/T), efavirenz (DMP-266), UC-781 (N-[4-chloro-3-(3-methyl-2-butenyloxy)phenyl]-2methyl3-furan-carbothiamide), etravirine (TMC125), Trovirdine (Ly300046.HCl), HI-236, HI-240, HI-280, HI-281, rilpivirine (TMC-278), MSC-127, HBY 097, DMP266, Baicalin (TJN-151) ADAM-II (Methyl 3',3'-dichloro-4',4"-dimethoxy-5',5"-bis(methoxycarbonyl)-6,6-diphenylhexenoate), Methyl 3-Bromo-5-(1-5-bromo-4-methoxy-3-(methoxycarbonyl)phenyl)hept-1-enyl)-2-methoxybenzoate (Alkenyl-diarylmethane analog, Adam analog), (5-chloro-3-(phenylsulfinyl)-2'-indolecarboxamide), AAP-BHAP (U-104489 or PNU-104489), Capravirine (AG-1549, S-1153), atevirdine (U-87201E), aurin tricarboxylic acid (SD-095345), 1-[(6-cyano-2-indolyl)carbonyl]-4-[3-(isopropylamino)-2-pyridinyl]piperazine, 1-[5-[[N-(methyl)methylsulfonylamino]-2-indolylcarbonyl-4-[3-(isopropylamino)-2-pyridinyl]piperazine, 1-[3-(Ethylamino)-2-[pyridinyl]-4-[(5-hydroxy-2-indolyl)carbonyl]piperazine, 1-[(6-Formyl-2-indolyl)carbonyl]-4-[3-(isopropylamino)-2-pyridinyl]piperazine, 1-[[5-(Methylsulfonyloxy)-2-indoyly)carbonyl]-4-[3-(isopropylamino)-2-pyridinyl]piperazine, U88204E, Bis(2-nitrophenyl)sulfone (NSC 633001), Calanolide A (NSC675451), Calanolide B, 6-Benzyl-5-methyl-2-(cyclohexyloxy)pyrimidin-4-one (DABO-546), DPC 961, E-EBU, E-EBU-dm, E-EPSeU, E-EPU, Foscarnet (Foscavir), HEPT (1-[(2-Hydroxyethoxy)methyl]-6-(phenylthio)thymine), HEPT-M (1-[(2-Hydroxyethoxy)methyl]-6-(3-methylphenyl)thio)thymine), HEPT-S(1-[(2-Hydroxyethoxy)methyl]-6-(phenylthio)-2-thiothymine), Inophyllum P, L-737,126, Michellamine A (NSC650898), Michellamine B (NSC649324), Michellamine F, 6-(3,5-Dimethylbenzyl)-1-[(2-hydroxyethoxy)methyl]-5-isopropyluracil, 6-(3,5-Dimethylbenzyl)-1-(ethyoxymethyl)-5-isopropyluracil, NPPS, E-BPTU (NSC 648400), Oltipraz (4-Methyl-5-(pyrazinyl)-3H-1,2-dithiole-3-thione), N-{2-(2-Chloro-6-fluorophenethyl]-N'-(2-thiazolyl)thiourea (PETT Cl, F derivative), N-{2-(2,6-Difluorophenethyl]-N'-[2-(5-bromopyridyl)]thiourea {PETT derivative), N-{2-(2,6-Difluorophenethyl]-N'-[2-(5-methylpyridyl]thiourea {PETT Pyridyl derivative), N-[2-(3-Fluorofuranyl)ethyl]-N'-[2-(5-chloropyridyl)]thiourea, N-[2-(2-Fluoro-6-ethoxyphenethyl)]-N'-[2-(5-bromopyridyl)]thiourea, N-(2-Phenethyl)-N'-(2-thiazolyl)thiourea (LY-73497), L-697,639, L-697,593, L-697,661, 342-(4, 7-Difluorobenzoxazol-2-yl)ethyl}-5-ethyl-6-methyl (pypridin-2(1H)-thione (2-Pyridinone Derivative), 3-[[(2-Methoxy-5,6-dimethyl-3-pyridyl)methyl]amine]-5-ethyl-6-methyl(pypridin-2(1H)-thione, R82150, R82913, R87232, R88703, R89439 (Loviride), R90385, S-2720, Suramin Sodium, TBZ (Thiazolobenzimidazole, NSC 625487), Thiazoloisoindol-5-one, (+)(R)-9b-(3,5-Dimethylphenyl-2,3-dihydrothiazolo[2,3-a]isoindol-5 (9bH)-one, Tivirapine (R86183), UC-38 and UC-84, among others.

In one aspect of the invention, the disclosed compound when used to treat an HCV infection can be administered in combination with another anti-HCV agent. Anti-HCV agents are known in the art. To date, a number of fixed dose drug combinations have been approved for the treatment of HCV. Harvoni® (Gilead Sciences, Inc.) contains the NS5A inhibitor ledipasvir and the NS5B inhibitor sofosbuvir. Technivie™ (AbbVie, Inc.) is a fixed-dose combination containing ombitasvir, an NS5A inhibitor; paritaprevir, an NS3/4A protease inhibitor; and ritonavir, a CYP3A inhibitor. Daklinza™ (daclatasvir, Bristol-Myers Squibb) is a HCV NS5A inhibitor indicated for use with sofosbuvir for the treatment of chronic genotype 3 infection. Zepatier™ (Merck & Co.) has recently been approved for the treatment of chronic HCV genotypes 1 and 4. Zepatier™ is a fixed-dose combination product containing elbasvir, an HCV NS5A inhibitor, and grazoprevir, an HCV NS3/4A protease inhibitor. Zepatier™ is indicated with or without ribavirin. Epclusa®

(Gilead Sciences, Inc.) is a fixed-dose combination tablet containing sofosbuvir and velpatasvir. Additional anti-HCV agents and combinations thereof include those described in U.S. Pat. Nos. 9,382,218; 9,321,753; 9,249,176; 9,233,974; 9,221,833; 9,211,315; 9,194,873; 9,186,369; 9,180,193; 9,156,823; 9,138,442; 9,133,170; 9,108,999; 9,090,559; 9,079,887; 9,073,943; 9,073,942; 9,056,090; 9,051,340; 9,034,863; 9,029,413; 9,011,938; 8,987,302; 8,945,584; 8,940,718; 8,927,484; 8,921,341; 8,884,030; 8,841,278; 8,822,430; 8,772,022; 8,765,722; 8,742,101; 8,741,946; 8,674,085; 8,673,288; 8,669,234; 8,663,648; 8,618,275; 8,580,252; 8,575,195; 8,575,135; 8,575,118; 8,569,302; 8,524,764; 8,513,298; 8,501,714; 8,404,651; 8,273,341; 8,257,699; 8,197,861; 8,158,677; 8,105,586; 8,093,353; 8,088,368; 7,897,565; 7,871,607; 7,846,431; 7,829,081; 7,829,077; 7,824,851; 7,572,621; and 7,326,536; Patents assigned to Alios: U.S. Pat. Nos. 9,365,605; 9,346,848; 9,328,119; 9,278,990; 9,249,174; 9,243,022; 9,073,960; 9,012,427; 8,980,865; 8,895,723; 8,877,731; 8,871,737; 8,846,896 and 8,772,474; Achillion U.S. Pat. Nos. 9,273,082; 9,233,136; 9,227,952; 9,133,115; 9,125,904; 9,115,175; 9,085,607; 9,006,423; 8,946,422; 8,835,456; 8,809,313; 8,785,378; 8,614,180; 8,445,430; 8,435,984; 8,183,263; 8,173,636; 8,163,693; 8,138,346; 8,114,888; 8,106,209; 8,088,806; 8,044,204; 7,985,541; 7,906,619; 7,902,365; 7,767,706; 7,741,334; 7,718,671; 7,659,399; 7,476,686; 7,439,374; 7,365,068; 7,199,128; and 7,094,807; Cocrystal Pharma Inc. 9,181,227; 9,173,893; 9,040,479 and 8,771,665; Gilead Sciences U.S. Pat. Nos. 9,353,423; 9,346,841; 9,321,800; 9,296,782; 9,296,777; 9,284,342; 9,238,039; 9,216,996; 9,206,217; 9,161,934; 9,145,441; 9,139,604; 9,090,653; 9,090,642; 9,085,573; 9,062,092; 9,056,860; 9,045,520; 9,045,462; 9,029,534; 8,980,878; 8,969,588; 8,962,652; 8,957,046; 8,957,045; 8,946,238; 8,933,015; 8,927,741; 8,906,880; 8,889,159; 8,871,785; 8,841,275; 8,815,858; 8,809,330; 8,809,267; 8,809,266; 8,779,141; 8,765,710; 8,759,544; 8,759,510; 8,735,569; 8,735,372; 8,729,089; 8,722,677; 8,716,264; 8,716,263; 8,716,262; 8,697,861; 8,664,386; 8,642,756; 8,637,531; 8,633,309; 8,629,263; 8,618,076; 8,592,397; 8,580,765; 8,569,478; 8,563,530; 8,551,973; 8,536,187; 8,513,186; 8,513,184; 8,492,539; 8,486,938; 8,481,713; 8,476,225; 8,420,597; 8,415,322; 8,338,435; 8,334,270; 8,329,926; 8,329,727; 8,324,179; 8,283,442; 8,263,612; 8,232,278; 8,178,491; 8,173,621; 8,163,718; 8,143,394; patents assigned to Idenix, acquired by Merck, include U.S. Pat. Nos. 9,353,100; 9,309,275; 9,296,778; 9,284,307; 9,249,173; 9,243,025; 9,211,300; 9,187,515; 9,187,496, 9,109,001; 8,993,595; 8,951,985; 8,691,788; 8,680,071; 8,637,475; 8,507,460; 8,377,962; 8,362,068; 8,343,937; 8,299,038; 8,193,372; 8,093,379; 7,951,789; 7,932,240; 7,902,202; 7,662,798; 7,635,689; 7,625,875; 7,608,600; 7,608,597; 7,582,618; 7,547,704; 7,456,155; 7,384,924; 7,365,057; 7,192,936; 7,169,766; 7,163,929; 7,157,441; 7,148,206; 7,138,376; 7,105,493; 6,914,054 and 6,812,219; patents assigned to Merck include U.S. Pat. Nos. 9,364,482; 9,339,541; 9,328,138; 9,265,773; 9,254,292; 9,243,002; 9,242,998; 9,242,988; 9,242,917; 9,238,604; 9,156,872; 9,150,603; 9,139,569; 9,120,818; 9,090,661; 9,073,825; 9,061,041; 8,987,195; 8,980,920; 8,927,569; 8,871,759; 8,828,930; 8,772,505; 8,715,638; 8,697,694; 8,637,449; 8,609,635; 8,557,848; 8,546,420; 8,541,434; 8,481,712; 8,470,834; 8,461,107; 8,404,845; 8,377,874; 8,377,873; 8,354,518; 8,309,540; 8,278,322; 8,216,999; 8,148,349; 8,138,164; 8,080,654; 8,071,568; 7,973,040; 7,935,812; 7,915,400; 7,879,815; 7,879,797; 7,632,821; 7,569,374; 7,534,767; 7,470,664 and 7,329,732; patent application publication US 2013/0029904 to Boehringer Ingelheim GMBH and US 2014/0113958 to Stella Aps.

In one embodiment, the additional therapy is a monoclonal antibody (MAb). Some MAbs stimulate an immune response that destroys cancer cells. Similar to the antibodies produced naturally by B cells, these MAbs may "coat" the cancer cell surface, triggering its destruction by the immune system. For example, bevacizumab targets vascular endothelial growth factor(VEGF), a protein secreted by tumor cells and other cells in the tumor's microenvironment that promotes the development of tumor blood vessels. When bound to bevacizumab, VEGF cannot interact with its cellular receptor, preventing the signaling that leads to the growth of new blood vessels. Similarly, cetuximab and panitumumab target the epidermal growth factor receptor (EGFR), and trastuzumab targets the human epidermal growth factor receptor 2 (HER-2). MAbs that bind to cell surface growth factor receptors prevent the targeted receptors from sending their normal growth-promoting signals. They may also trigger apoptosis and activate the immune system to destroy tumor cells.

In one aspect of the present invention, the bioactive agent is an immunosuppressive agent. The immunosuppressive agent can be a calcineurin inhibitor, e.g. a cyclosporin or an ascomycin, e.g. Cyclosporin A (NEORAL®), FK506 (tacrolimus), pimecrolimus, a mTOR inhibitor, e.g. rapamycin or a derivative thereof, e.g. Sirolimus (RAPAMUNE®), Everolimus (Certican®), temsirolimus, zotarolimus, biolimus-7, biolimus-9, a rapalog, e.g. ridaforolimus, azathioprine, campath 1H, a S1P receptor modulator, e.g. fingolimod or an analogue thereof, an anti IL-8 antibody, mycophenolic acid or a salt thereof, e.g. sodium salt, or a prodrug thereof, e.g. Mycophenolate Mofetil (CELLCEPT®), OKT3 (ORTHOCLONE OKT3@), Prednisone, ATGAM®, THYMOGLOBULIN, Brequinar Sodium, OKT4, T10B9.A-3A, 33B3.1, 15-deoxyspergualin, tresperimus, Leflunomide ARAVA®, CTLAI-Ig, anti-CD25, anti-IL2R, Basiliximab (SVIMULECT®), Daclizumab (ZENAPAX®), mizorbine, methotrexate, dexamethasone, ISAtx-247, SDZ ASM 981 (pimecrolimus, Elidel®), CTLA4lg (Abatacept), belatacept, LFA3lg, etanercept (sold as Enbrel® by Immunex), adalimumab (Humira®), infliximab (Remicade®), an anti-LFA-1 antibody, natalizumab (Antegren®), Enlimomab, gavilimomab, antithymocyte immunoglobulin, siplizumab, Alefacept efalizumab, pentasa, mesalazine, asacol, codeine phosphate, benorylate, fenbufen, naprosyn, diclofenac, etodolac and indomethacin, aspirin and ibuprofen.

IV. Pharmaceutical Compositions

The N(substituted)$_2$-C$^3$-glutarimide compounds of Formula I, II, III, IV and V as disclosed herein can be administered as the neat chemical, but are more typically administered as a pharmaceutical composition, that includes an effective amount for a host, typically a human, in need of such treatment for any of the disorders described herein. Accordingly, the disclosure provides pharmaceutical compositions comprising an effective amount of compound or pharmaceutically acceptable salt together with at least one pharmaceutically acceptable carrier for any of the uses described herein. The pharmaceutical composition may contain a compound or salt as the only active agent, or, in an alternative embodiment, the compound and at least one additional active agent.

In certain embodiments the pharmaceutical composition is in a dosage form that contains from about 0.1 mg to about 2000 mg, from about 10 mg to about 1000 mg, from about 100 mg to about 800 mg, or from about 200 mg to about 600 mg of the active compound and optionally from about 0.1 mg to about 2000 mg, from about 10 mg to about 1000 mg, from about 100 mg to about 800 mg, or from about 200 mg to about 600 mg of an additional active agent in a unit dosage form. Examples are dosage forms with at least 0.1, 1, 5, 10, 25, 50, 100, 200, 250, 300, 400, 500, 600, 700, or 750 mg of active compound, or its salt. The pharmaceutical composition may also include a molar ratio of the active compound and an additional active agent. For example the pharmaceutical composition may contain a molar ratio of about 0.5:1, about 1:1, about 2:1, about 3:1 or from about 1.5:1 to about 4:1 of an anti-inflammatory or immunosuppressing agent. Compounds disclosed herein may be administered orally, topically, parenterally, by inhalation or spray, sublingually, via implant, including ocular implant, transdermally, via buccal administration, rectally, as an ophthalmic solution, injection, including ocular injection, intraveneous, intra-aortal, intracranial, subdermal, intraperitioneal, subcutaneous, transnasal, sublingual, or rectal or by other means, in dosage unit formulations containing conventional pharmaceutically acceptable carriers. For ocular delivery, the compound can be administered, as desired, for example, via intravitreal, intrastromal, intracameral, sub-tenon, subretinal, retrobulbar, peribulbar, suprachorodial, conjunctival, subconjunctival, episcleral, periocular, transscleral, retrobulbar, posterior juxtascleral, circumcorneal, or tear duct injections, or through a mucus, mucin, or a mucosal barrier, in an immediate or controlled release fashion or via an ocular device.

The pharmaceutical composition may be formulated as any pharmaceutically useful form, e.g., as an aerosol, a cream, a gel, a pill, an injection or infusion solution, a capsule, a tablet, a syrup, a transdermal patch, a subcutaneous patch, a dry powder, an inhalation formulation, in a medical device, suppository, buccal, or sublingual formulation, parenteral formulation, or an ophthalmic solution. Some dosage forms, such as tablets and capsules, are subdivided into suitably sized unit doses containing appropriate quantities of the active components, e.g., an effective amount to achieve the desired purpose.

Carriers include excipients and diluents and must be of sufficiently high purity and sufficiently low toxicity to render them suitable for administration to the patient being treated. The carrier can be inert or it can possess pharmaceutical benefits of its own. The amount of carrier employed in conjunction with the compound is sufficient to provide a practical quantity of material for administration per unit dose of the compound.

Classes of carriers include, but are not limited to binders, buffering agents, coloring agents, diluents, disintegrants, emulsifiers, flavorants, glidents, lubricants, preservatives, stabilizers, surfactants, tableting agents, and wetting agents. Some carriers may be listed in more than one class, for example vegetable oil may be used as a lubricant in some formulations and a diluent in others. Exemplary pharmaceutically acceptable carriers include sugars, starches, celluloses, powdered tragacanth, malt, gelatin; talc, and vegetable oils. Optional active agents may be included in a pharmaceutical composition, which do not substantially interfere with the activity of the compound of the present invention.

The pharmaceutical compositions/combinations can be formulated for oral administration. These compositions can contain any amount of active compound that achieves the desired result, for example between 0.1 and 99 weight % (wt. %) of the compound and usually at least about 5 wt. % of the compound. Some embodiments contain from about 25 wt. % to about 50 wt. % or from about 5 wt. % to about 75 wt. % of the compound.

Formulations suitable for rectal administration are typically presented as unit dose suppositories. These may be prepared by admixing the active compound with one or more conventional solid carriers, for example, cocoa butter, and then shaping the resulting mixture.

Formulations suitable for topical application to the skin preferably take the form of an ointment, cream, lotion, paste, gel, spray, aerosol, or oil. Carriers which may be used include petroleum jelly, lanoline, polyethylene glycols, alcohols, transdermal enhancers, and combinations of two or more thereof.

Formulations suitable for transdermal administration may be presented as discrete patches adapted to remain in intimate contact with the epidermis of the recipient for a prolonged period of time. Formulations suitable for transdermal administration may also be delivered by iontophoresis (see, for example, *Pharmaceutical Research* 3 (6):318 (1986)) and typically take the form of an optionally buffered aqueous solution of the active compound. In one embodiment, microneedle patches or devices are provided for delivery of drugs across or into biological tissue, particularly the skin. The microneedle patches or devices permit drug delivery at clinically relevant rates across or into skin or other tissue barriers, with minimal or no damage, pain, or irritation to the tissue.

Formulations suitable for administration to the lungs can be delivered by a wide range of passive breath driven and active power driven single/-multiple dose dry powder inhalers (DPI). The devices most commonly used for respiratory delivery include nebulizers, metered-dose inhalers, and dry powder inhalers. Several types of nebulizers are available, including jet nebulizers, ultrasonic nebulizers, and vibrating mesh nebulizers. Selection of a suitable lung delivery device depends on parameters, such as nature of the drug and its formulation, the site of action, and pathophysiology of the lung.

Many methods and devices for drug delivery are known in the art. Non-limiting examples are described in the following patents and patent applications (fully incorporated herein by reference). Examples are U.S. Pat. No. 8,192,408 titled "Ocular trocar assembly" (Psivida Us, Inc.); U.S. Pat. No. 7,585,517 titled "Transcleral delivery" (Macusight, Inc.); U.S. Pat. Nos. 5,710,182 and 5,795,913 titled "Ophthalmic composition" (Santen OY); U.S. Pat. No. 8,663,639 titled "Formulations for treating ocular diseases and conditions", U.S. Pat. No. 8,486,960 titled "Formulations and methods for vascular permeability-related diseases or conditions", U.S. Pat. Nos. 8,367,097 and 8,927,005 titled "Liquid formulations for treatment of diseases or conditions", U.S. Pat. No. 7,455,855 titled "Delivering substance and drug delivery system using the same" (Santen Pharmaceutical Co., Ltd.); WO/2011/050365 titled "Conformable Therapeutic Shield For Vision and Pain" and WO/2009/145842 titled "Therapeutic Device for Pain Management and Vision" (Forsight Labs, LLC); U.S. Pat. Nos. 9,066,779 and 8,623,395 titled "Implantable therapeutic device", WO/2014/160884 titled "Ophthalmic Implant for Delivering Therapeutic Substances", U.S. Pat. Nos. 8,399,006, 8,277, 830, 8,795,712, 8,808,727, 8,298,578, and WO/2010/088548 titled "Posterior segment drug delivery", WO/2014/152959 and US20140276482 titled "Systems for Sustained Intraocular Delivery of Low Solubility Compounds from a Port Delivery System Implant", U.S. Pat. Nos. 8,905,963 and 9,033,911 titled "Injector apparatus and method for drug delivery", WO/2015/057554 titled "Formulations and Methods for Increasing or Reducing Mucus", U.S. Pat. Nos. 8,715,712 and 8,939,948 titled "Ocular insert apparatus and methods", WO/2013/116061 titled "Insertion and Removal Methods and Apparatus for Therapeutic Devices", WO/2014/066775 titled "Ophthalmic System for Sustained Release of Drug to the Eye", WO/2015/085234 and WO/2012/019176 titled "Implantable Therapeutic Device", WO/2012/065006 titled "Methods and Apparatus to determine Porous Structures for Drug Delivery", WO/2010/141729 titled "Anterior Segment Drug Delivery", WO/2011/050327 titled "Corneal Denervation for Treatment of Ocular Pain", WO/2013/022801 titled "Small Molecule Delivery with Implantable Therapeutic Device", WO/2012/019047 titled "Subconjunctival Implant for Posterior Segment Drug Delivery", WO/2012/068549 titled "Therapeutic Agent Formulations for Implanted Devices", WO/2012/019139 titled "Combined Delivery Methods and Apparatus", WO/2013/040426 titled "Ocular Insert Apparatus and Methods", WO/2012/019136 titled "Injector Apparatus and Method for Drug Delivery", WO/2013/040247 titled "Fluid Exchange Apparatus and Methods" (ForSight Vision4, Inc.); US/2014/0352690 titled "Inhalation Device with Feedback System", U.S. Pat. No. 8,910,625 and US/2015/0165137 titled "Inhalation Device for Use in Aerosol Therapy" (Vectura GmbH); U.S. Pat. No. 6,948,496 titled "Inhalers", US/2005/0152849 titled "Powders comprising anti-adherent materials for use in dry powder inhalers", U.S. Pat. Nos. 6,582,678, 8,137,657, US/2003/0202944, and US/2010/0330188 titled "Carrier particles for use in dry powder inhalers", U.S. Pat. No. 6,221,338 titled "Method of producing particles for use in dry powder inhalers", U.S. Pat. No. 6,989,155 titled "Powders", US/2007/0043030 titled "Pharmaceutical compositions for treating premature ejaculation by pulmonary inhalation", U.S. Pat. No. 7,845,349 titled "Inhaler", US/2012/0114709 and U.S. Pat. No. 8,101,160 titled "Formulations for Use in Inhaler Devices", US/2013/0287854 titled "Compositions and Uses", US/2014/0037737 and U.S. Pat. No. 8,580,306 titled "Particles for Use in a Pharmaceutical Composition", US/2015/0174343 titled "Mixing Channel for an Inhalation Device", U.S. Pat. No. 7,744,855 and US/2010/0285142 titled "Method of making particles for use in a pharmaceutical composition", U.S. Pat. No. 7,541,022, US/2009/0269412, and US/2015/0050350 titled "Pharmaceutical formulations for dry powder inhalers" (Vectura Limited).

Additional non-limiting examples of how to deliver the active compounds are provided in WO/2015/085251 titled "Intracameral Implant for Treatment of an Ocular Condition" (Envisia Therapeutics, Inc.); WO/2011/008737 titled "Engineered Aerosol Particles, and Associated Methods", WO/2013/082111 titled "Geometrically Engineered Particles and Methods for Modulating Macrophage or Immune Responses", WO/2009/132265 titled "Degradable compounds and methods of use thereof, particularly with particle replication in non-wetting templates", WO/2010/099321 titled "Interventional drug delivery system and associated methods", WO/2008/100304 titled "Polymer particle composite having high fidelity order, size, and shape particles", WO/2007/024323 titled "Nanoparticle fabrication methods, systems, and materials" (Liquidia Technologies, Inc. and the University of North Carolina at Chapel Hill); WO/2010/009087 titled "Iontophoretic Delivery of a Controlled-Release Formulation in the Eye", (Liquidia Technologies, Inc. and Eyegate Pharmaceuticals, Inc.) and WO/2009/132206 titled "Compositions and Methods for Intracellular Delivery and Release of Cargo", WO/2007/133808 titled "Nanoparticles for cosmetic applications", WO/2007/056561 titled "Medical device, materials, and methods", WO/2010/065748 titled "Method for producing patterned materials", WO/2007/081876 titled "Nanostructured surfaces for biomedical/biomaterial applications and processes thereof" (Liquidia Technologies, Inc.).

Additional non-limiting examples of drug delivery devices and methods include, for example, US20090203709 titled "Pharmaceutical Dosage Form For Oral Administration Of Tyrosine Kinase Inhibitor" (Abbott Laboratories); US20050009910 titled "Delivery of an active drug to the posterior part of the eye via subconjunctival or periocular delivery of a prodrug", US 20130071349 titled "Biodegradable polymers for lowering intraocular pressure", U.S. Pat. No. 8,481,069 titled "Tyrosine kinase microspheres", U.S. Pat. No. 8,465,778 titled "Method of making tyrosine kinase microspheres", U.S. Pat. No. 8,409,607 titled "Sustained release intraocular implants containing tyrosine kinase inhibitors and related methods", U.S. Pat. No. 8,512,738 and US 2014/0031408 titled "Biodegradable intravitreal tyrosine kinase implants", US 2014/0294986 titled "Microsphere Drug Delivery System for Sustained Intraocular Release", U.S. Pat. No. 8,911,768 titled "Methods For Treating Retinopathy With Extended Therapeutic Effect" (Allergan, Inc.); U.S. Pat. No. 6,495,164 titled "Preparation of injectable suspensions having improved injectability" (Alkermes Controlled Therapeutics, Inc.); WO 2014/047439 titled "Biodegradable Microcapsules Containing Filling Material" (Akina, Inc.); WO 2010/132664 titled "Compositions And Methods For Drug Delivery" (Baxter International Inc. Baxter Healthcare SA); US20120052041 titled "Polymeric nanoparticles with enhanced drugloading and methods of use thereof" (The Brigham and Women's Hospital, Inc.); US20140178475, US20140248358, and US20140249158 titled "Therapeutic Nanoparticles Comprising a Therapeutic Agent and Methods of Making and Using Same" (BIND Therapeutics, Inc.); U.S. Pat. No. 5,869,103 titled "Polymer microparticles for drug delivery" (Danbiosyst UK Ltd.); U.S. Pat. No. 8,628,801 titled "Pegylated Nanoparticles" (Universidad de Navarra); US2014/0107025 titled "Ocular drug delivery system" (Jade Therapeutics, LLC); U.S. Pat. No. 6,287,588 titled "Agent delivering system comprised of microparticle and biodegradable gel with an improved releasing profile and methods of use thereof", U.S. Pat. No. 6,589,549 titled "Bioactive agent delivering system comprised of microparticles within a biodegradable to improve release profiles" (Macromed, Inc.); U.S. Pat. Nos. 6,007,845 and 5,578,325 titled "Nanoparticles and microparticles of non-linear hydrophilichydrophobic multiblock copolymers" (Massachusetts Institute of Technology); US20040234611, US20080305172, US20120269894, and US20130122064 titled "Ophthalmic depot formulations for periocular or subconjunctival administration (Novartis Ag); U.S. Pat. No. 6,413,539 titled "Block polymer" (Poly-Med, Inc.); US 20070071756 titled "Delivery of an agent to ameliorate inflammation" (Peyman); US 20080166411 titled "Injectable Depot Formulations And Methods For Providing Sustained Release Of Poorly Soluble Drugs Comprising Nanoparticles" (Pfizer, Inc.); U.S. Pat. No. 6,706,289 titled "Methods and compositions for enhanced delivery of bioactive molecules" (PR Pharmaceuticals, Inc.); and U.S. Pat. No. 8,663,674 titled "Microparticle containing matrices for drug delivery" (Surmodics).

V. General Synthesis

The compounds described herein can be prepared by methods known by those skilled in the art. In one non-limiting example the disclosed compounds can be made using the schemes below.

Compounds of the present invention with stereocenters may be drawn without stereochemistry for convenience. One skilled in the art will recognize that pure enantiomers and diastereomers can be prepared by methods known in the art. Examples of methods to obtain optically active materials include at least the following.

i) physical separation of crystals—a technique whereby macroscopic crystals of the individual enantiomers are manually separated. This technique can be used if crystals of the separate enantiomers exist, i.e., the material is a conglomerate, and the crystals are visually distinct;
  ii) simultaneous crystallization—a technique whereby the individual enantiomers are separately crystallized from a solution of the racemate, possible only if the latter is a conglomerate in the solid state;
  iii) enzymatic resolutions—a technique whereby partial or complete separation of a racemate by virtue of differing rates of reaction for the enantiomers with an enzyme;
  iv) enzymatic asymmetric synthesis—a synthetic technique whereby at least one step of the synthesis uses an enzymatic reaction to obtain an enantiomerically pure or enriched synthetic precursor of the desired enantiomer;
  v) chemical asymmetric synthesis—a synthetic technique whereby the desired enantiomer is synthesized from an achiral precursor under conditions that produce asymmetry (i.e., chirality) in the product, which may be achieved using chiral catalysts or chiral auxiliaries;
  vi) diastereomer separations—a technique whereby a racemic compound is reacted with an enantiomerically pure reagent (the chiral auxiliary) that converts the individual enantiomers to diastereomers. The resulting diastereomers are then separated by chromatography or crystallization by virtue of their now more distinct structural differences and the chiral auxiliary later removed to obtain the desired enantiomer;
  vii) first- and second-order asymmetric transformations—a technique whereby diastereomers from the racemate equilibrate to yield a preponderance in solution of the diastereomer from the desired enantiomer or where preferential crystallization of the diastereomer from the desired enantiomer perturbs the equilibrium such that eventually in principle all the material is converted to the crystalline diastereomer from the desired enantiomer. The desired enantiomer is then released from the diastereomer;
  viii) kinetic resolutions—this technique refers to the achievement of partial or complete resolution of a racemate (or of a further resolution of a partially resolved compound) by virtue of unequal reaction rates of the enantiomers with a chiral, non-racemic reagent or catalyst under kinetic conditions;
  ix) enantiospecific synthesis from non-racemic precursors—a synthetic technique whereby the desired enantiomer is obtained from non-chiral starting materials and where the stereochemical integrity is not or is only minimally compromised over the course of the synthesis;
  x) chiral liquid chromatography—a technique whereby the enantiomers of a racemate are separated in a liquid mobile phase by virtue of their differing interactions with a stationary phase (including via chiral HPLC). The stationary phase can be made of chiral material or the mobile phase can contain an additional chiral material to provoke the differing interactions;
  xi) chiral gas chromatography—a technique whereby the racemate is volatilized and enantiomers are separated by virtue of their differing interactions in the gaseous mobile phase with a column containing a fixed non-racemic chiral adsorbent phase;
  xii) extraction with chiral solvents—a technique whereby the enantiomers are separated by virtue of preferential dissolution of one enantiomer into a particular chiral solvent;
  xiii) transport across chiral membranes—a technique whereby a racemate is placed in contact with a thin membrane barrier. The barrier typically separates two miscible fluids, one containing the racemate, and a driving force such as concentration or pressure differential causes preferential transport across the membrane barrier. Separation occurs as a result of the non-racemic chiral nature of the membrane that allows only one enantiomer of the racemate to pass through.
  xiv) simulated moving bed chromatography, is used in one embodiment. A wide variety of chiral stationary phases are commercially available.

General Scheme 1

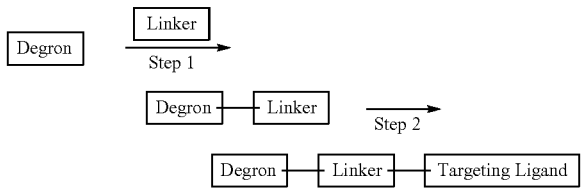

General Scheme 2

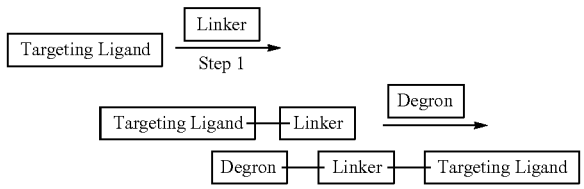

As shown in General Scheme 1 compounds for use in the present invention can be prepared by chemically combining a Degron and a Linker followed by subsequent addition of a Targeting Ligand. Similarly, in General Scheme 2 compounds for use in the present invention are prepared by chemically combing a Targeting Ligand and Linker first, followed by subsequent addition of a Degron. As illustrated in the above and following schemes, compounds for use in the present invention can readily be synthesized by one skilled in the art in a variety of methods and chemical reactions.

General Scheme 3

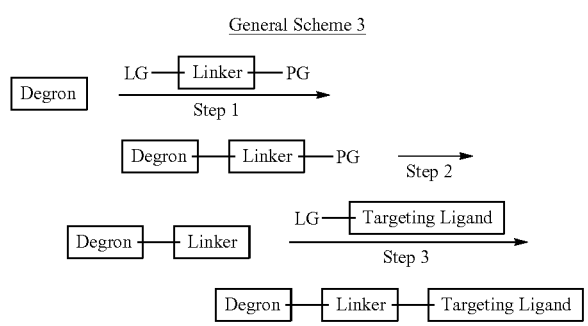

General Scheme 3: In Step 1, a nucleophilic Degron displaces a leaving group on the Linker to make a Degron Linker fragment. In Step 2, the protecting group is removed by methods known in the art to free a nucleophilic site on the Linker. In Step 3, the nucleophilic Degron Linker fragment displaces a leaving group on the Targeting Ligand to form a compound for use in the present invention. In an alternative embodiment Step 1 and/or Step 2 is accomplished by a coupling reaction instead of a nucleophilic attack.

General Scheme 4

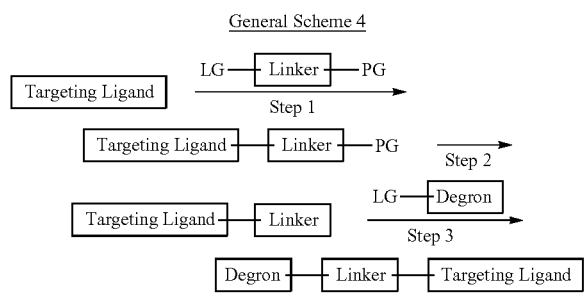

General Scheme 4: In Step 1, a nucleophilic Targeting Ligand displaces a leaving group on the Linker to make a Targeting Ligand Linker fragment. In Step 2, the protecting group is removed by methods known in the art to free a nucleophilic site on the Linker. In Step 3, the nucleophilic Targeting Ligand Linker fragment displaces a leaving group on the Degron to form a compound for use in the present invention. In an alternative embodiment Step 1 and/or Step 2 is accomplished by a coupling reaction instead of a nucleophilic attack.

General Scheme 5

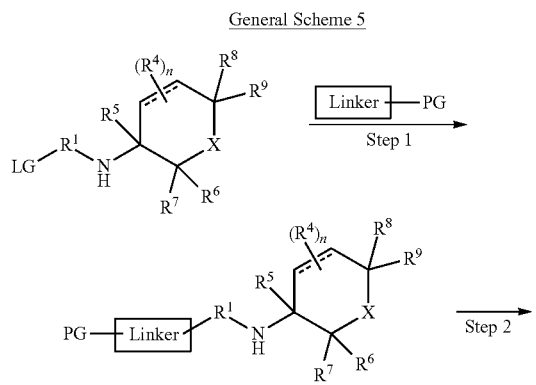

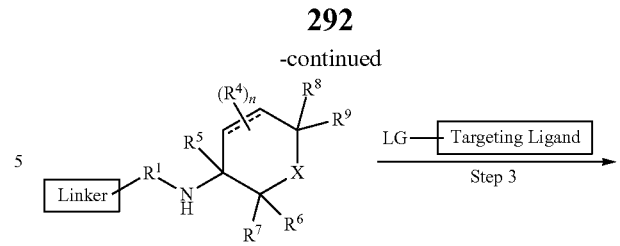

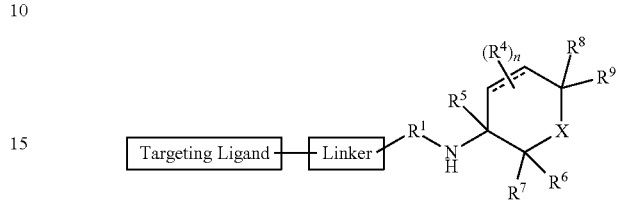

General Scheme 6

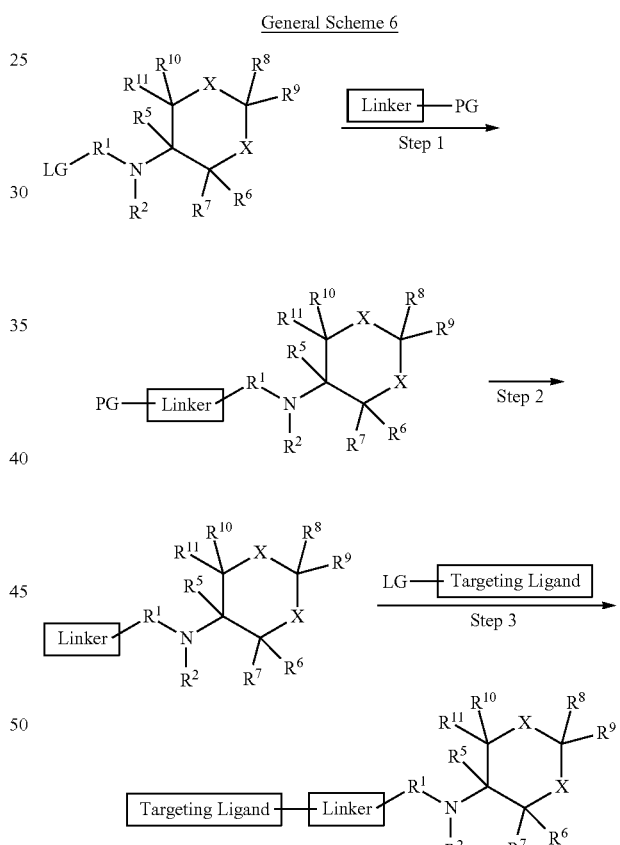

General Scheme 5 and General Scheme 6: In Step 1, a nucleophilic Linker displaces a leaving group on the Degron to make a Degron Linker fragment. In Step 2, the protecting group is removed by methods known in the art to free a nucleophilic site on the Linker. In Step 3, the nucleophilic Degron Linker fragment displaces a leaving group on the Targeting Ligand to form a compound of Formula I, Formula II, or Formula V. In an alternative embodiment Step 1 and/or Step 2 is accomplished by a coupling reaction instead of a nucleophilic attack.

VI. Exemplary Methods for Linking Targeting Ligand and Degron Through a Linker
Linking Scheme 1
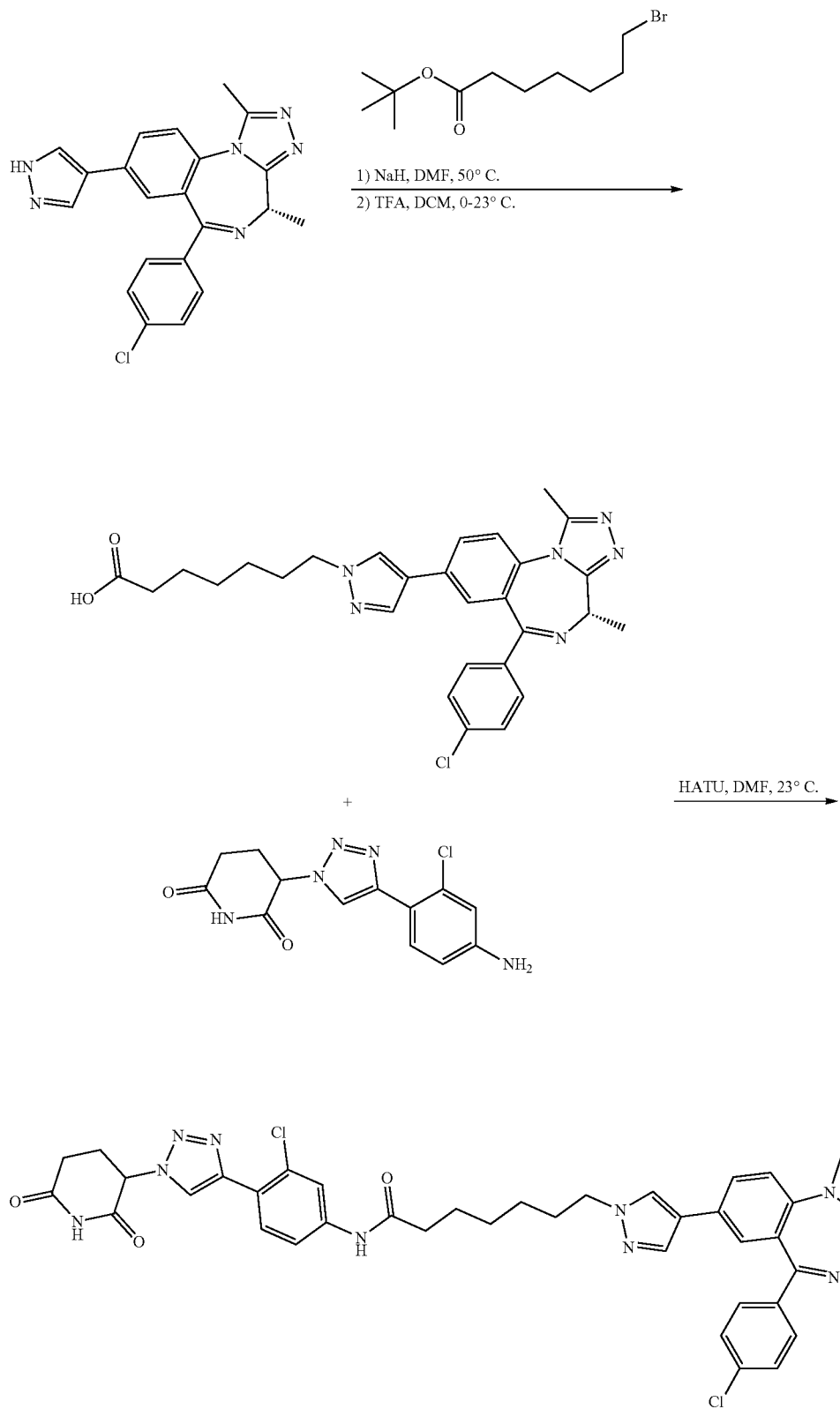

Linking Scheme 2
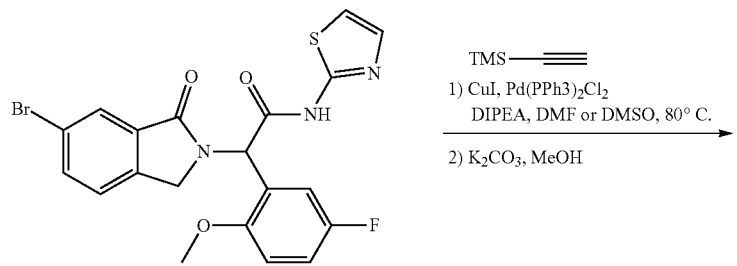
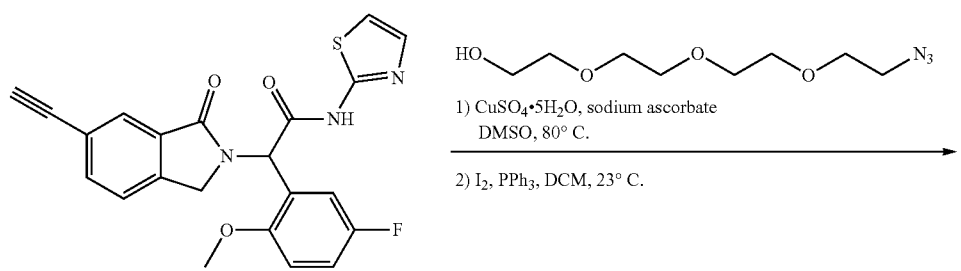
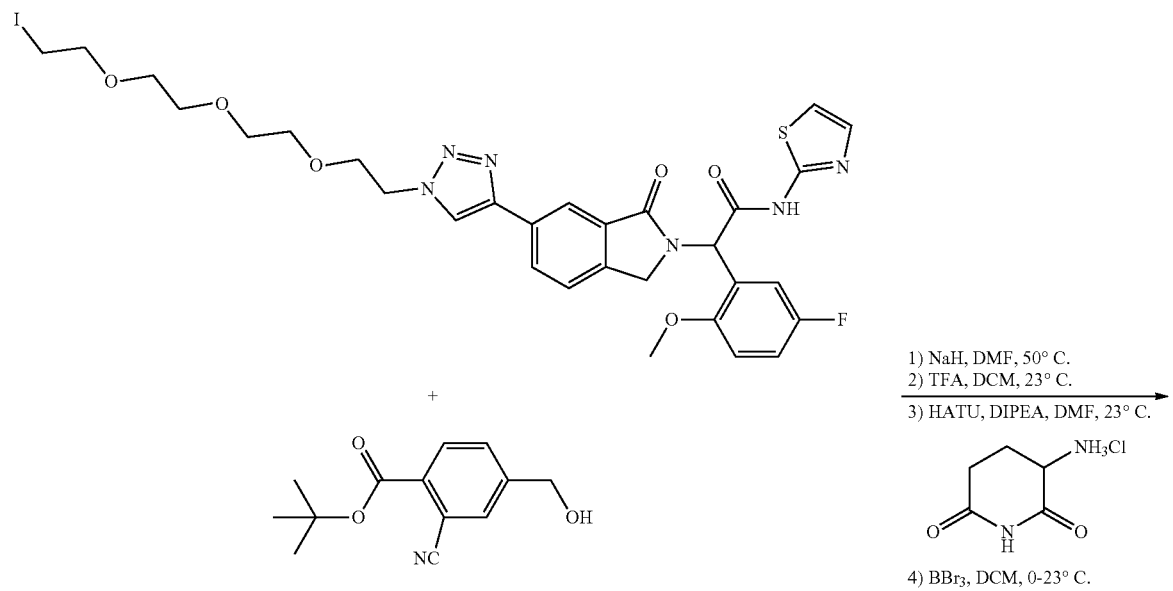
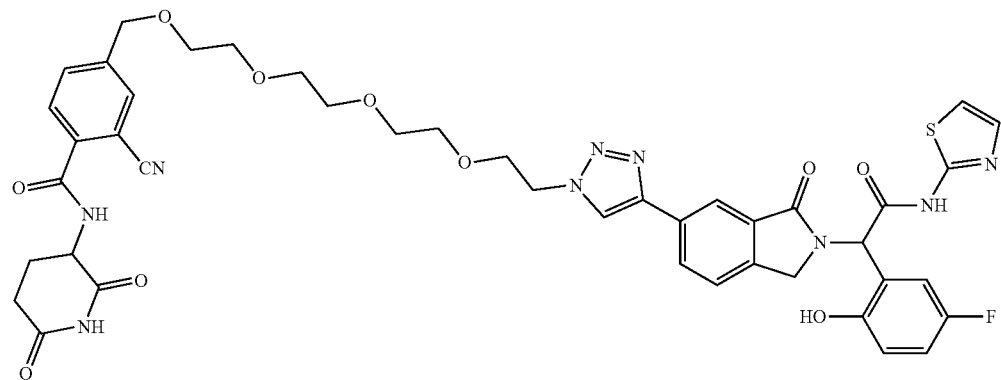

297 298
Linking Scheme 3
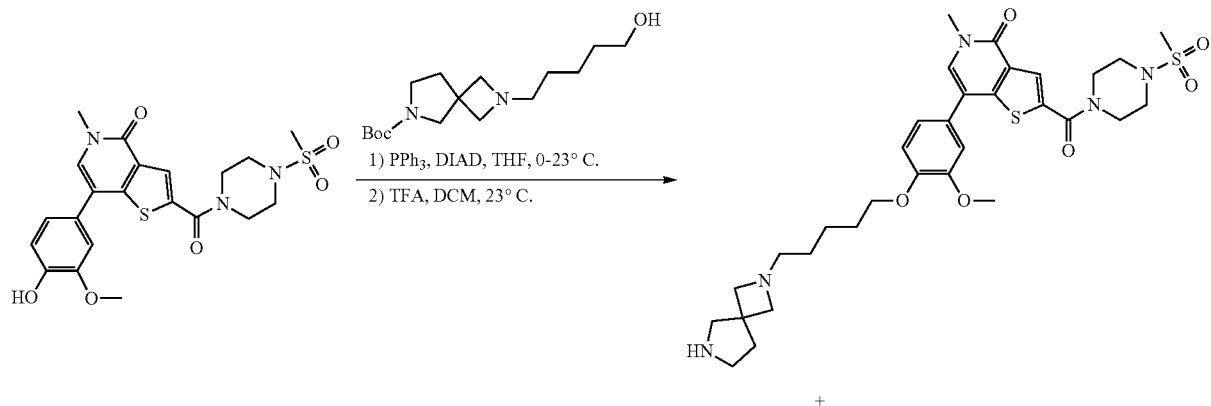
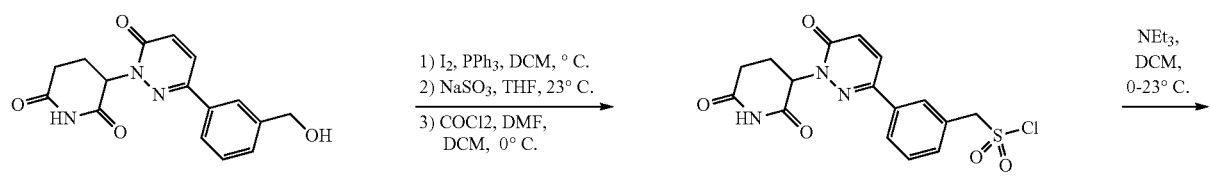
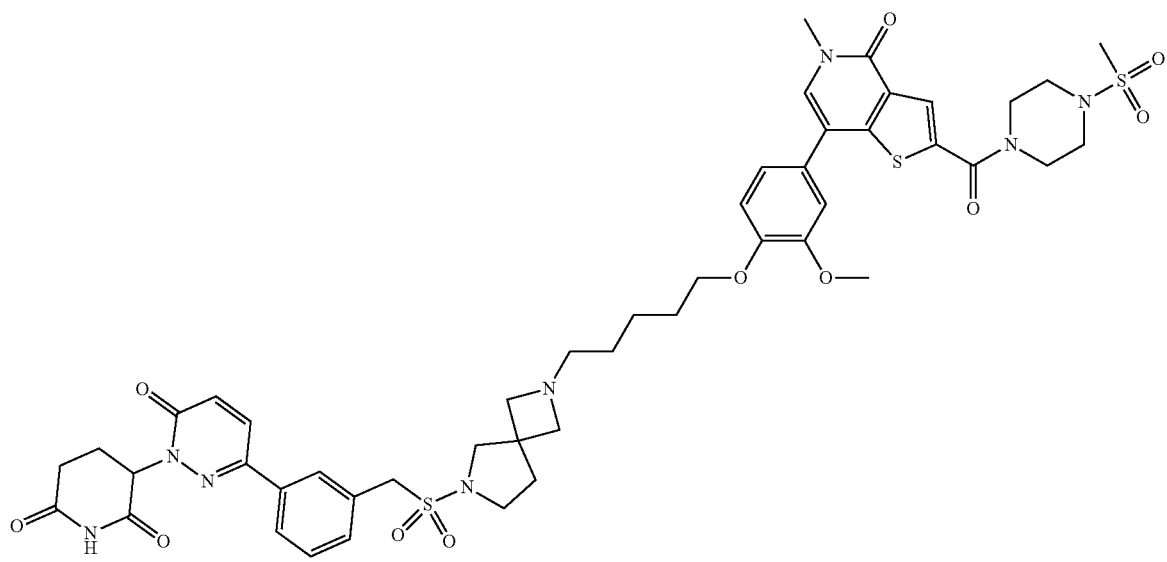

Linking Scheme 4
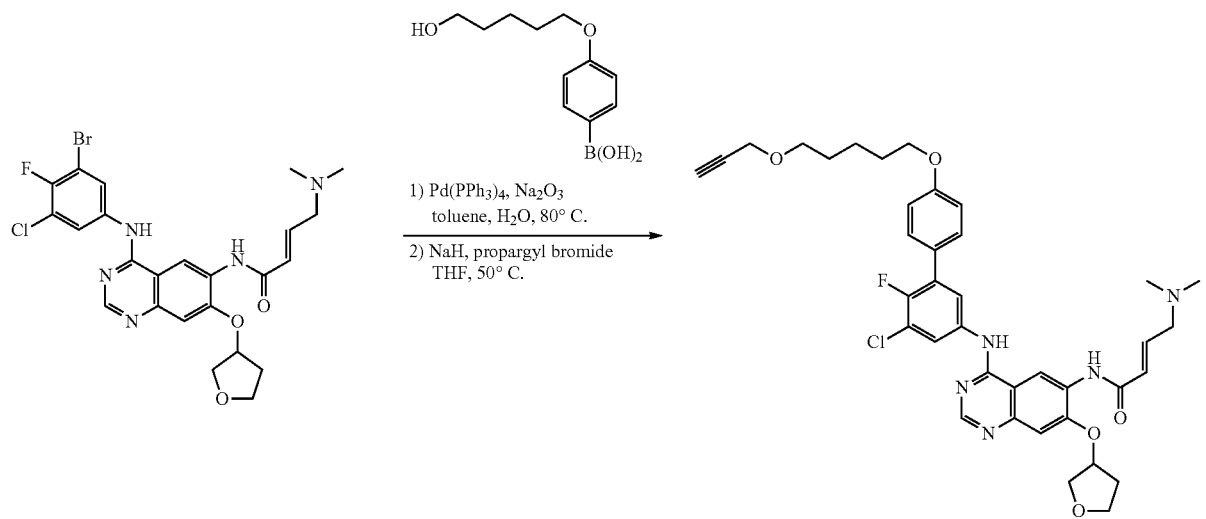
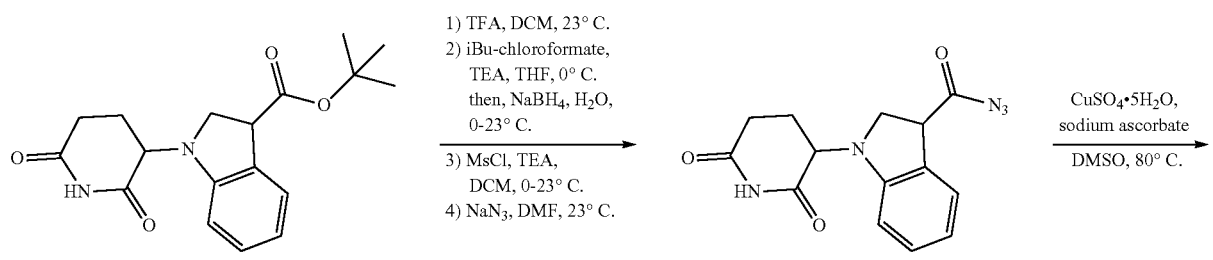
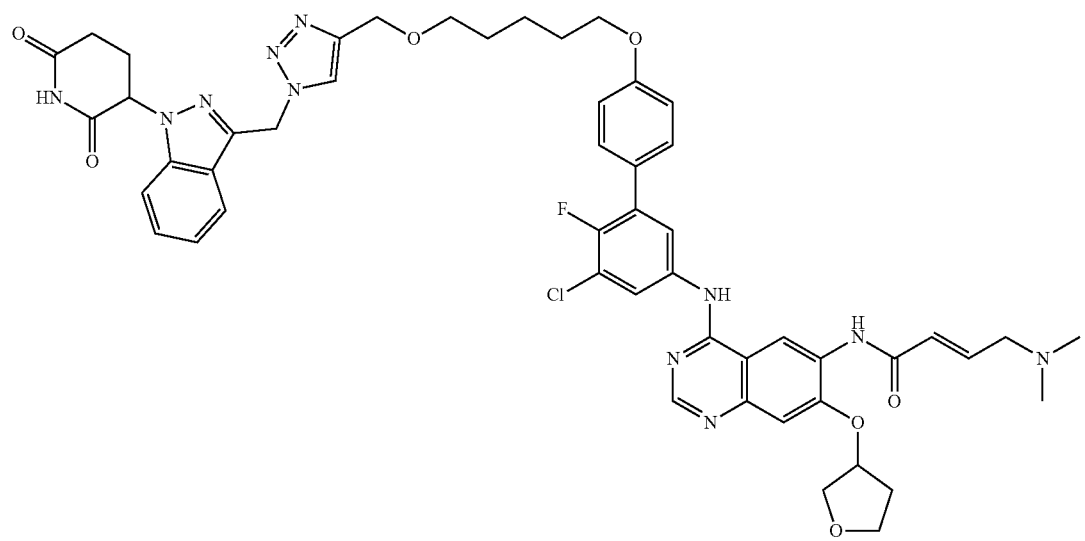

Linking Scheme 5
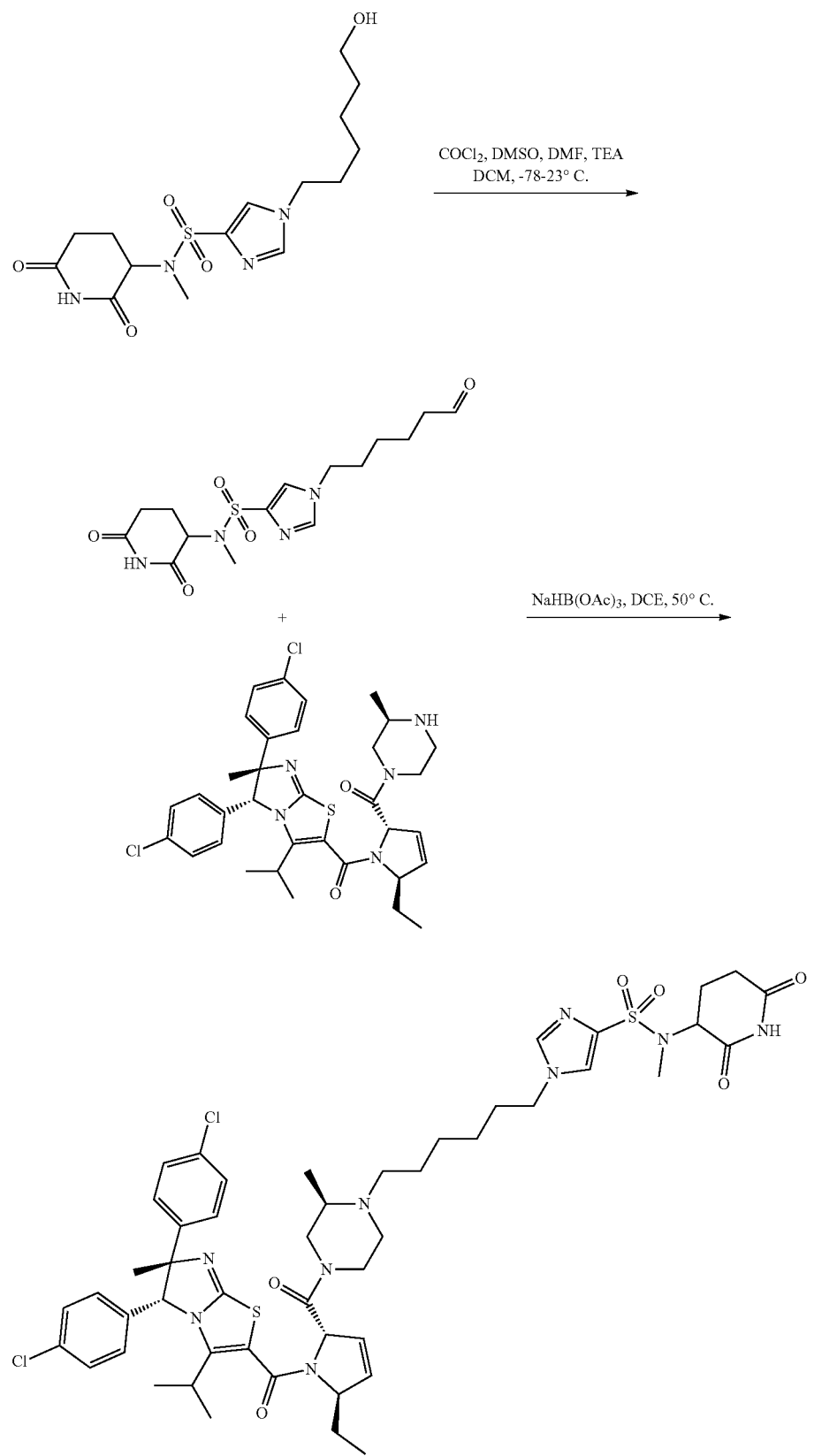

Linking Scheme 6
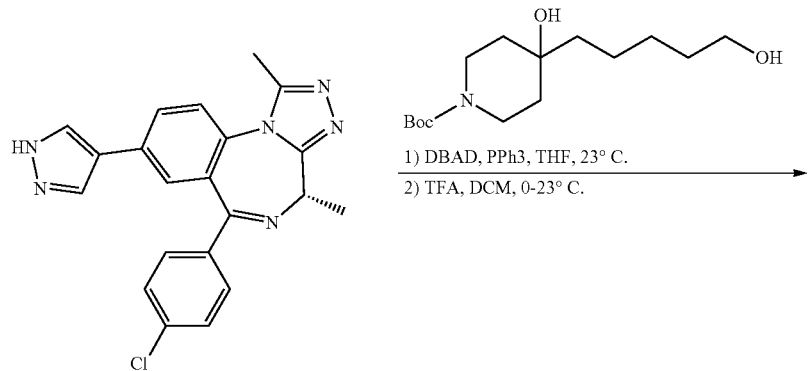
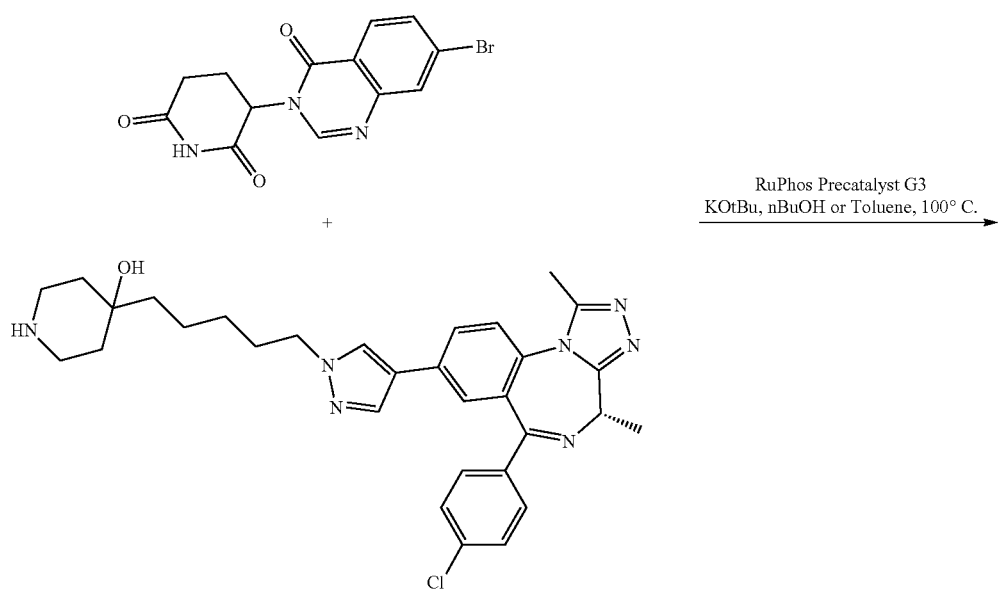
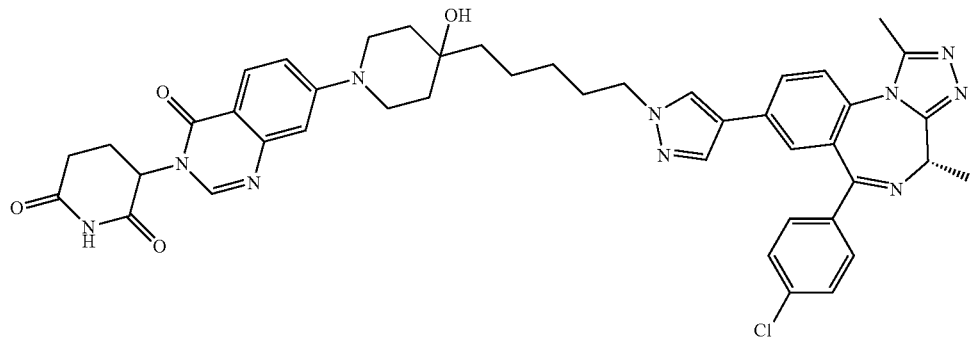

Linking Scheme 7
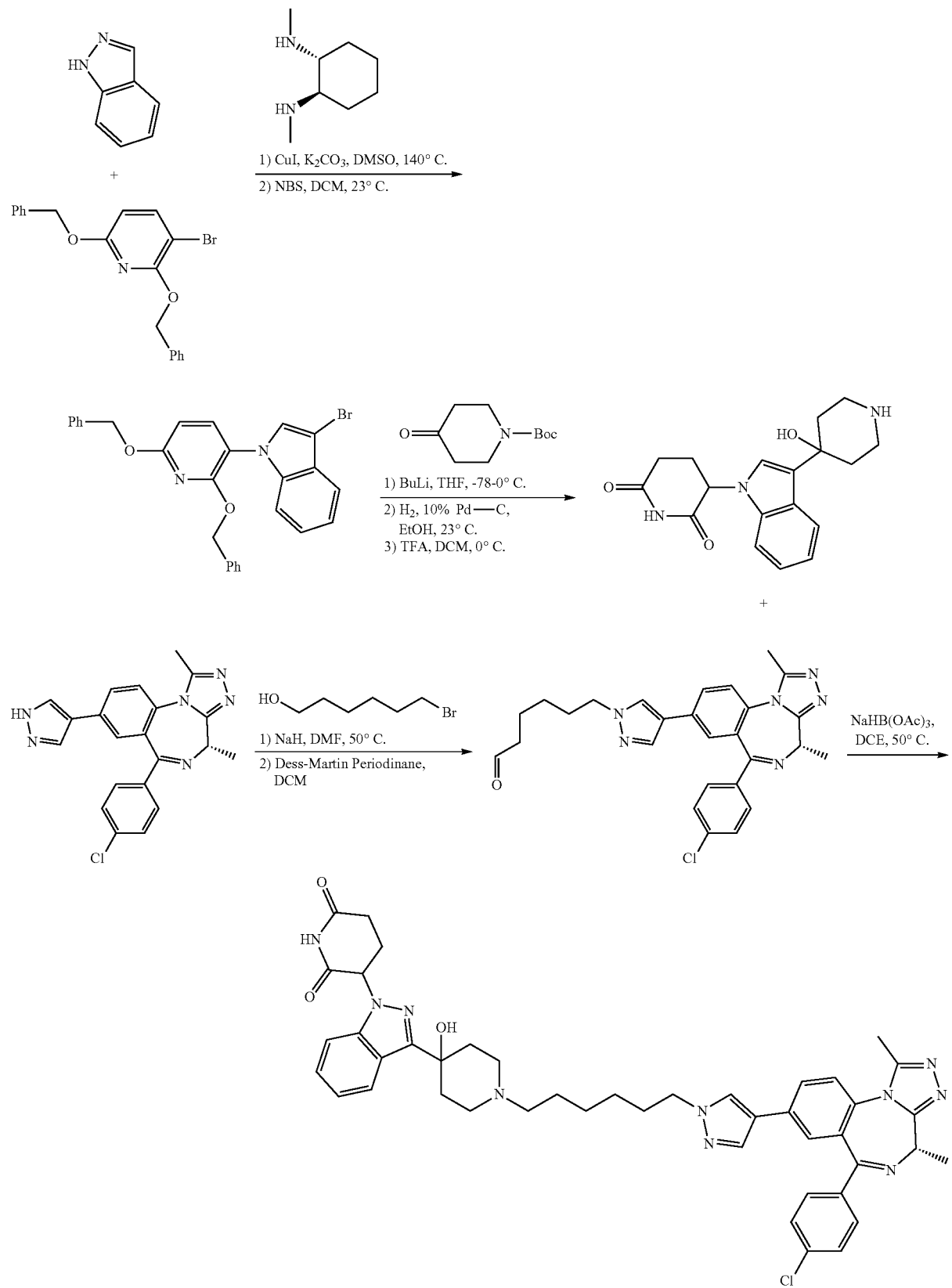

Linking Scheme 8

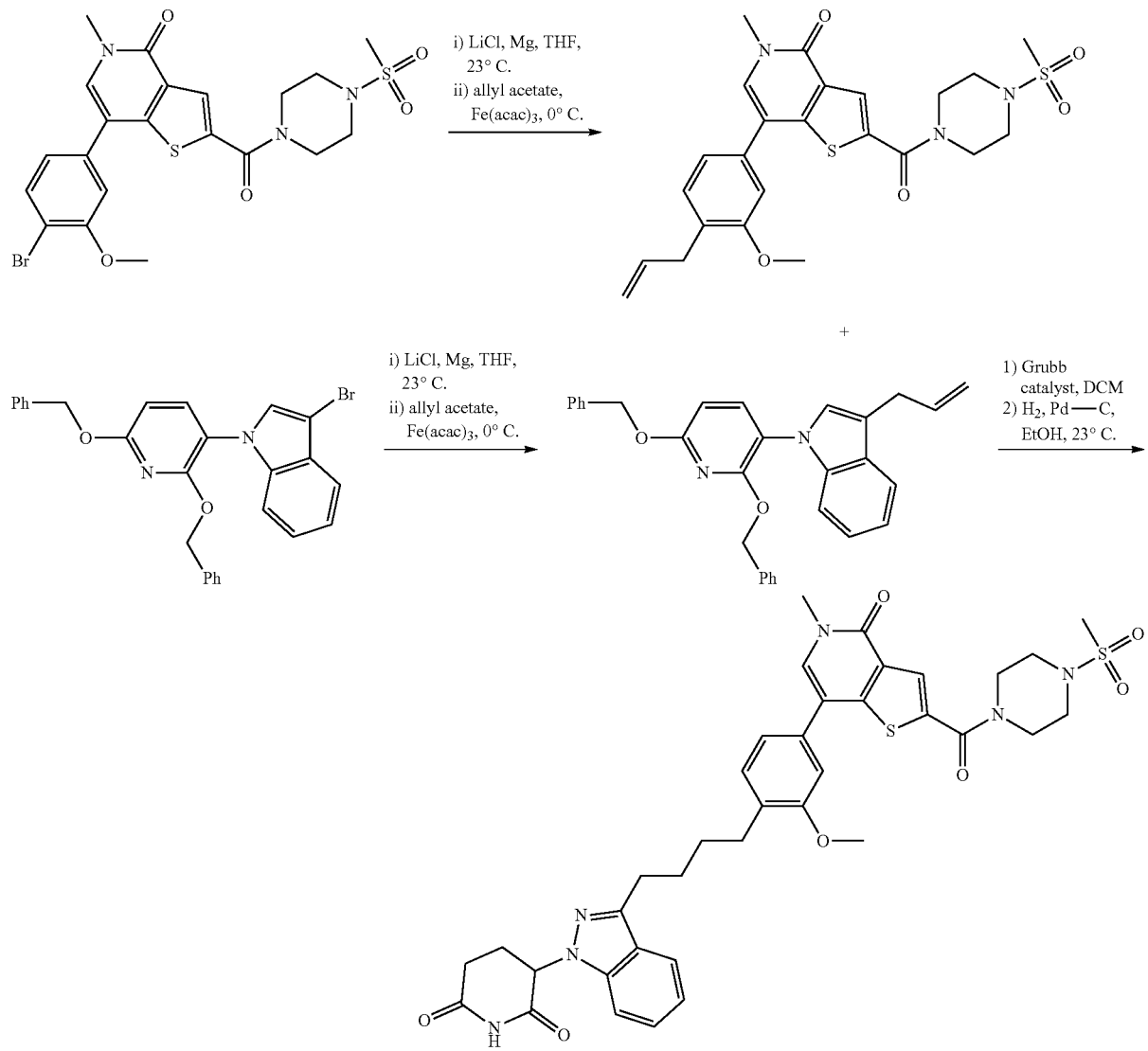

VII. Synthesis of Representative Compounds

The compounds of the present invention can be prepared, for example, using methods provided below or routine modifications of these methods.

Scheme 1

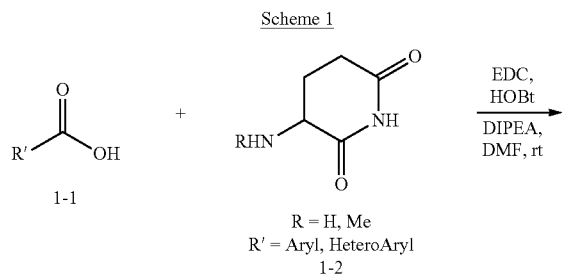

-continued

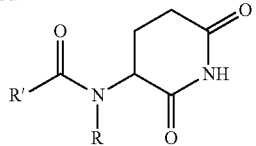

General Procedure:
To the mixture of 1-1 (100 mg) and 1-2 (1.1 eq.) in DMF (2 ml) were added EDC·HCl (2.5 eq), HOBT (1.5 eq), and this was followed by the addition of DIPEA (3 eq). The reaction mixture was stirred at room temperature for 16 hours to produce 1-3. After completion, crude 1-3 was purified by preparative HPLC to afford 1-3.

General Methods for Prep HPLC Purification:
Method-1
Preparative HPLC was conducted on Waters auto purification instrument equipped with a—YMC-Actus Triart C18

(100×30 mm, 5μ) column operating at ambient temperature and a flow rate of 30.0 ml/min. Mobile phase: A=20 mM NH₄HCO₃ in water, B=Acetonitrile; Gradient Profile: Mobile phase initial composition of 80% A and 20% B, then to 65% A and 35% B in 2 minutes, then to 25% A and 75% B in 12 minutes, then to 5% A and 95% B in 13 minutes. This was maintained up to 15 minutes for column washing and the solvent mixture was returned to the initial composition for 16 minutes and maintained until 18 minutes.

Method-2

Preparative HPLC was conducted on Waters auto purification instrument equipped with a —YMC-Actus Triart C18 (250×20 mm, 5μ) column operating at ambient temperature and flow rate of 20.0 ml/min. Mobile phase: A=10 mM NH₄OAc in water, B=Acetonitrile; Gradient Profile: Mobile phase initial composition of 70% A and 30% B, then to 45% A and 55% B in 3 minutes, then to 25% A and 75% B in 18 minutes, then to 5% A and 95% B in 19 minutes. This was maintained for up to 21 minutes for column washing and the solvent mixture was returned to the initial composition for 22 minutes and maintained until 25 minutes.

Method-3

Preparative HPLC was conducted on Waters auto purification instrument equipped with a—YMC-Actus Triart C18 (250×20 mm, 5μ) column operating at ambient temperature and flow rate of 20.0 ml/min. Mobile phase: A=0.1% Formic acid in water, B=Acetonitrile; Gradient Profile: Mobile phase initial composition of 80% A and 20% B, then to 70% A and 30% B in 3 minutes, then to 25% A and 75% B in 18 minutes, then to 5% A and 95% B in 19 minutes. This was maintained for up to 21 minutes for column washing and the solvent mixture was returned to the initial composition for 22 minutes and maintained until 25 minutes.

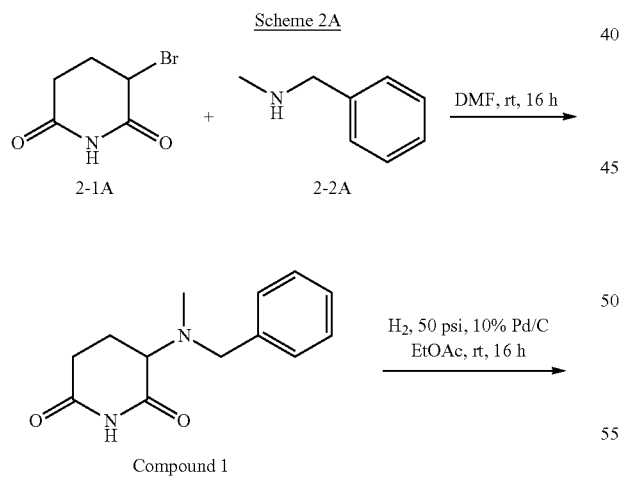

Scheme 2A

Preparation of 3-(Benzyl-methyl-amino)-piperidine-2,6-dione (Compound 1)

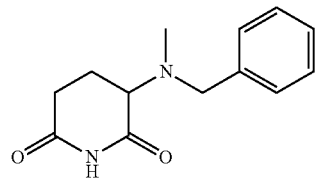 [SMILES: CN(Cc1ccccc1)C1CCC(=O)NC1=O]

A solution of 3-bromo-piperidine-2,6-dione (2-1) (6 g, 31.25 mmol) and benzyl-methylamine (2-2) (10 g, 78.125 mmol) in DMF (30 mL) was stirred at ambient temperature 16 hours. The reaction mixture was then concentrated under reduced pressure and the crude mixture was purified by column chromatography (silica, gradient: 0-25% EtOAc in hexane) to afford 3-(benzyl-methyl-amino)-piperidine-2,6-dione (Compound 1) (6 g, 83%) as a grey solid. ¹H NMR (400 MHz, DMSO-d6) δ 10.63 (s, 1H), 7.32 (s, 4H), 7.23 (brs, 1H), 3.76 (s, 2H), 3.60 (dd, J=11.74, 4.34 Hz, 1H), 2.63-2.51 (m, 1H), 2.46-2.41 (m, 1H), 2.13-2.03 (m, 1H), 1.95-1.91 (m, 1H); LC MS: ES+ 233.2.

Preparation of 3-Methylamino-piperidine-2,6-dione (2-3)

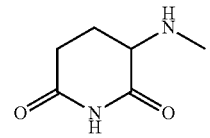

An ethyl acetate solution (100 mL) of 3-(benzyl-methyl-amino)-piperidine-2,6-dione (Compound 1) (2.5 g, 10.763 mmol) in a Parr shaker vessel was degassed with argon for about 15 minutes and this was followed by the addition of 10% Pd/C (700 mg). The reaction vessel was backfilled with hydrogen and reaction mixture was subjected to hydrogenolysis on a Parr hydrogenator for 16 hours at 50 psi hydrogen pressure at ambient temperature. The reaction mixture was filtered through a bed of celite and washed with ethyl acetate. The combined filtrates were concentrated under reduced pressure to afford 3-methylamino-piperidine-2,6-dione (2-3) (1.5 g, 98%) as a grey solid.

The following compounds were made according the general procedure of Scheme 1:

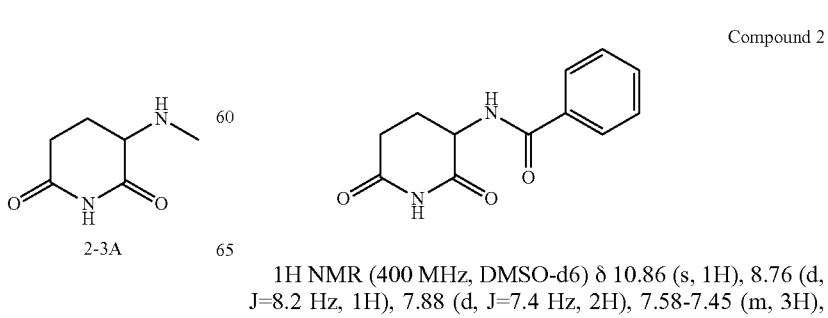

1H NMR (400 MHz, DMSO-d6) δ 10.86 (s, 1H), 8.76 (d, J=8.2 Hz, 1H), 7.88 (d, J=7.4 Hz, 2H), 7.58-7.45 (m, 3H), 4.85-4.65 (m, 1H), 2.83-2.76 (m, 1H), 2.57-2.50 (m, 1H), 2.18-2.12 (m, 1H), 2.01-1.90 (s, 1H); LC MS: ES+ 233.2.

Compound 3

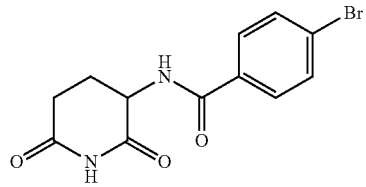

1H NMR (400 MHz, DMSO-d6) δ 10.88 (s, 1H), 8.87 (d, J=8.2 Hz, 1H), 7.82 (d, J=8.2 Hz, 2H), 7.72 (d, J=8.2 Hz, 2H), 4.78 (ddd, J=13.1, 8.2, 5.3 Hz, 1H), 2.80 (ddd, J=18.2, 13.4, 5.5 Hz, 1H), 2.57-2.50 (m, 1H), 2.11 (td, J=13.3, 8.8 Hz, 1H), 1.97 (d, J=12.6 Hz, 1H); LC MS: ES− 308.8 (Br pattern observed).

Compound 4

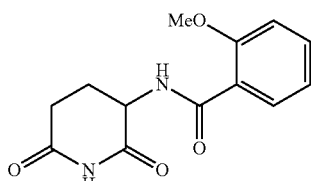

1H NMR (400 MHz, DMSO-d6) δ 10.88 (s, 1H), 8.79 (d, J=8.3 Hz, 1H), 8.69 (d, J=2.6 Hz, 1H), 8.14 (dd, J=8.9, 2.8 Hz, 1H), 6.92 (d, J=8.7 Hz, 1H), 4.78 (dq, J=13.1, 6.1, 5.5 Hz, 1H), 3.92 (s, 3H), 2.80 (td, J=15.2, 13.3, 5.2 Hz, 1H), 2.57-2.50 (m, 1H), 2.16-2.05 (m, 1H), 2.03-1.94 (m, 1H); LC MS: 264.1.

Compound 5

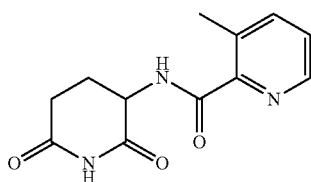

1H NMR (400 MHz, DMSO-d6) δ 10.86 (s, 1H), 8.71 (d, J=8.4 Hz, 1H), 7.63 (d, J=7.7 Hz, 1H), 7.55 (d, J=1.8 Hz, 1H), 7.35 (t, J=7.7 Hz, 1H), 7.28 (d, J=7.7 Hz, 1H), 4.77 (ddd, J=13.1, 8.3, 5.4 Hz, 1H), 2.80 (ddd, J=18.2, 13.3, 5.5 Hz, 1H), 2.56 (t, J=3.7 Hz, 1H), 2.20-2.05 (m, 1H), 1.99 (tt, J=8.3, 5.2 Hz, 2H), 1.04-0.94 (m, 2H), 0.77-0.68 (m, 2H); LC MS: ES−271.2.

Compound 6

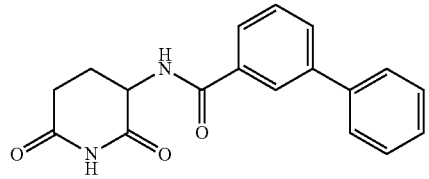

1H NMR (400 MHz, DMSO-d6) δ 10.89 (s, 1H), 8.90 (d, J=8.4 Hz, 1H), 8.16 (s, 1H), 7.87 (t, J=6.8 Hz, 2H), 7.78-7.71 (m, 2H), 7.59 (t, J=7.7 Hz, 1H), 7.51 (dd, J=8.4, 6.8 Hz, 2H), 7.41 (t, J=7.3 Hz, 1H), 4.89-4.77 (m, 1H), 2.82 (ddd, J=18.2, 13.3, 5.5 Hz, 1H), 2.58-2.50 (m, 1H), 2.13 (td, J=12.9, 4.3 Hz, 1H), 2.05-1.99 (m, 1H); LC MS: ES− 307.2.

Compound 7

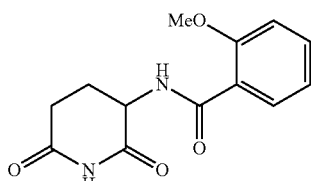

1H NMR (400 MHz, DMSO-d6) δ 10.89 (s, 1H), 8.62 (d, J=7.3 Hz, 1H), 7.85 (dd, J=7.7, 1.9 Hz, 1H), 7.51 (ddd, J=8.8, 7.4, 1.9 Hz, 1H), 7.17 (d, J=8.3 Hz, 1H), 7.06 (t, J=7.4 Hz, 1H), 4.81-4.69 (m, 1H), 3.92 (s, 3H), 2.85-2.71 (m, 1H), 2.55 (t, J=3.5 Hz, 1H), 2.10 (ddd, J=12.4, 8.9, 4.2 Hz, 2H); LC MS: ES− 261.1.

Compound 8

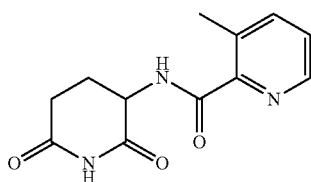

1H NMR (400 MHz, DMSO-d6) δ 10.86 (s, 1H), 8.96 (d, J=8.2 Hz, 1H), 8.48 (d, J=4.7 Hz, 1H), 7.77 (d, J=7.7 Hz, 1H), 7.49 (dd, J=7.8, 4.5 Hz, 1H), 4.74 (ddd, J=12.8, 8.2, 5.1 Hz, 1H), 2.79 (ddd, J=18.9, 13.7, 5.6 Hz, 1H), 2.57-2.55 (m, 4H), 2.24-2.10 (m, 1H), 2.02 (t, J=7.1 Hz, 1H); LC MS: ES+ 248.1.

Compound 9

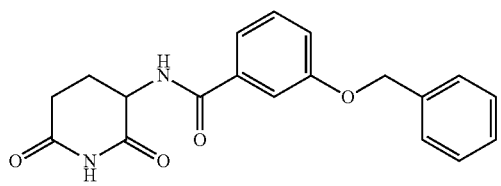

1H NMR (400 MHz, DMSO-d6) δ 10.87 (s, 1H), 8.76 (d, J=8.4 Hz, 1H), 7.55-7.44 (m, 4H), 7.45-7.36 (m, 3H), 7.34 (dd, J=8.7, 5.5 Hz, 1H), 7.20 (dd, J=7.9, 2.7 Hz, 1H), 5.16 (s, 2H), 4.83-4.73 (m, 1H), 2.83-2.75 (m, 1H), 2.56-2.50 (m, 1H), 2.11 (dt, J=13.1, 6.6 Hz, 1H), 2.01-1.95 (m, 1H); LC MS: ES− 337.2.

Compound 10

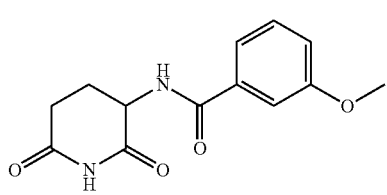

1H NMR (400 MHz, DMSO-d6) δ 10.87 (s, 1H), 8.76 (d, J=8.3 Hz, 1H), 7.49-7.36 (m, 3H), 7.16-7.08 (m, 1H), 4.78 (q, J=11.4, 8.8 Hz, 1H), 3.32 (s, 3H), 2.80 (td, J=13.1, 6.6 Hz, 1H), 2.56-2.50 (m, 1H), 2.17-2.05 (m, 1H), 1.98 (s, 1H); LC MS: ES– 261.1.

Compound 11

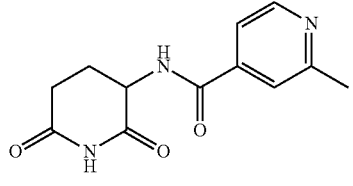

1H NMR (400 MHz, DMSO-d6) δ 10.90 (s, 1H), 9.00 (d, J=8.2 Hz, 1H), 8.60 (d, J=5.1 Hz, 1H), 7.64 (s, 1H), 7.56 (d, J=5.0 Hz, 1H), 4.81 (d, J=8.7 Hz, 1H), 2.81 (t, J=13.5 Hz, 1H), 2.55-2.50 (m, 4H), 2.10 (t, J=13.5 Hz, 1H), 1.99 (s, 1H); LC MS: ES– 246.1.

Compound 12

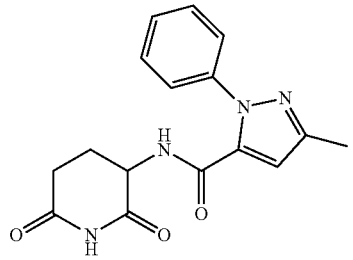

1H NMR (400 MHz, DMSO-d6) δ 10.87 (s, 1H), 8.91 (d, J=8.3 Hz, 1H), 7.42 (d, J=8.6 Hz, 3H), 7.42-7.32 (m, 2H), 6.68 (s, 1H), 4.67-4.64 (m, 1H), 2.76-2.74 (m, 1H), 2.56-2.50 (m, 1H), 2.27 (s, 3H), 2.07-2.04 (m, 1H), 1.97-1.96 (m, 1H); LC MS: ES+ 313.1.

Compound 13

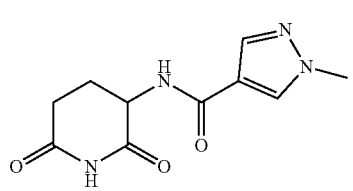

1H NMR (400 MHz, DMSO-d6) δ 10.84 (s, 1H), 8.35 (d, J=8.3 Hz, 1H), 8.14 (s, 1H), 7.84 (s, 1H), 4.71 (ddd, J=13.2, 8.6, 5.3 Hz, 1H), 3.86 (s, 3H), 2.78 (ddd, J=17.7, 13.2, 5.4 Hz, 1H), 2.50-2.49 (m, 1H), 2.09-1.93 (m, 2H); LC MS: ES– 235.1.

Compound 14

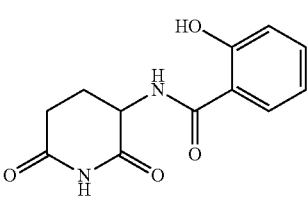

1H NMR (400 MHz, DMSO-d6) δ 12.19 (s, 1H), 10.94 (s, 1H), 9.11 (d, J=7.6 Hz, 1H), 7.87 (d, J=7.8 Hz, 1H), 7.42 (t, J=7.5 Hz, 1H), 6.92 (t, J=7.9 Hz, 2H), 4.82 (dt, J=12.8, 6.4 Hz, 1H), 2.81 (ddd, J=18.1, 12.9, 5.9 Hz, 1H), 2.57 (d, J=4.5 Hz, 1H), 2.12 (ddd, J=27.7, 14.2, 9.2 Hz, 2H); LC MS: ES– 247.1.

Compound 15

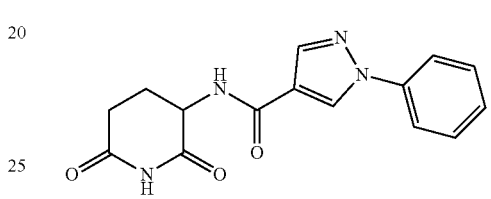

1H NMR (400 MHz, DMSO-d6) δ 10.89 (s, 1H), 8.96 (d, J=4.0 Hz, 1H), 8.54 (d, J=8.2 Hz, 1H), 8.17 (d, J=4.1 Hz, 1H), 7.87 (d, J=8.0 Hz, 2H), 7.53 (t, J=7.8 Hz, 2H), 7.37 (t, J=7.4 Hz, 1H), 4.80-4.75 (m, 1H), 2.84-2.74 (m, 1H), 2.57-2.49 (m, 1H), 2.13-2.04 (m, 2H); LC MS: ES-297.1.

Compound 16

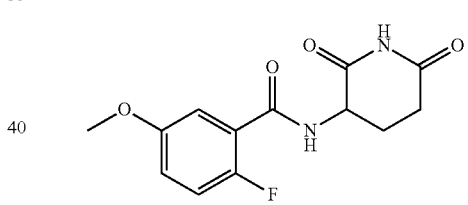

1H NMR (400 MHz, DMSO-d6) δ 10.87 (s, 1H), 8.55 (dd, J=8.2, 3.6 Hz, 1H), 7.25 (t, J=9.6 Hz, 1H), 7.13 (ddd, J=21.9, 7.4, 4.2 Hz, 2H), 4.76 (p, J=5.9 Hz, 1H), 3.32 (d, J=3.6 Hz, 3H), 2.78 (td, J=12.5, 6.3 Hz, 1H), 2.56-2.50 (m, 1H), 2.10 (dd, J=12.8, 4.2 Hz, 1H), 2.05-1.99 (m, 1H); LC MS: ES– 279.1.

Compound 17

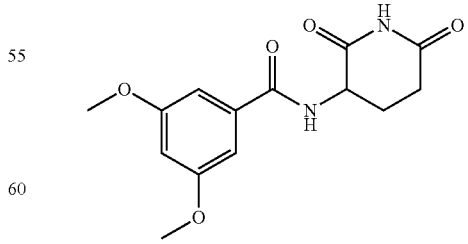

1H NMR (400 MHz, DMSO-d6) δ 10.87 (s, 1H), 8.73 (d, J=8.2 Hz, 1H), 7.03 (s, 2H), 6.67 (s, 1H), 4.75 (m, 1H), 3.79 (s, 6H), 2.83-2.76 (m, 1H), 2.55 (m, 1H), 2.13-1.97 (m, 2H); LC MS: ES-291.1.

Compound 18

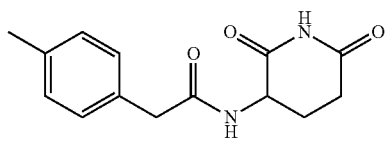

1H NMR (400 MHz, DMSO-d6) δ 10.81 (s, 1H), 8.38 (d, J=8.0 Hz, 1H), 7.16 (d, J=7.7 Hz, 2H), 7.10 (d, J=7.5 Hz, 2H), 4.54 (q, J=8.5 Hz, 1H), 3.43 (s, 2H), 2.72 (dd, J=17.6, 9.2 Hz, 1H), 2.49-2.46 (m, 1H), 2.26 (s, 3H), 1.90 (s, 2H); LC MS: ES− 259.1.

Compound 19

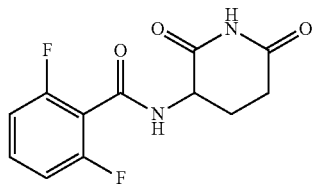

1H NMR (400 MHz, DMSO-d6) δ 10.88 (s, 1H), 9.07 (d, J=8.3 Hz, 1H), 7.54-7.51 (m, 1H), 7.18 (t, J=8.3 Hz, 2H), 4.81-4.72 (m, 1H), 2.78 (m, 1H), 2.53-2.49 (m, 1H), 2.10-2.00 (m, 1H); LC MS: ES+ 269.0.

Compound 20

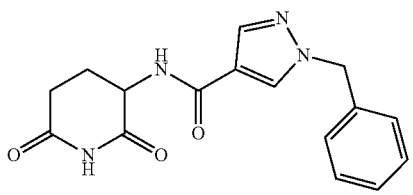

1H NMR (400 MHz, DMSO-d6) δ 10.84 (s, 1H), 8.39 (d, J=8.4 Hz, 1H), 8.27 (s, 1H), 7.89 (s, 1H), 7.41-7.23 (m, 5H), 5.36 (s, 2H), 4.77-4.68 (m, 1H), 2.80-2.72 (m, 1H), 2.49-2.46 (m, 1H), 2.02-1.94 (m, 2H); LC MS: ES− 311.1.

Compound 21

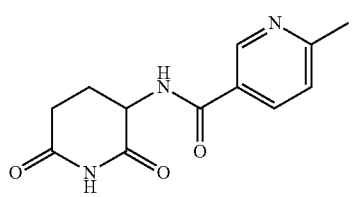

1H NMR (400 MHz, DMSO-d6) δ 10.88 (s, 1H), 8.94-8.85 (m, 2H), 8.11 (dd, J=8.1, 2.4 Hz, 1H), 7.38 (d, J=8.1 Hz, 1H), 4.80 (ddd, J=12.8, 8.2, 5.4 Hz, 1H), 2.81 (ddd, J=18.2, 13.1, 5.5 Hz, 1H), 2.57 (m, 1H), 2.53 (s, 3H), 2.20-1.95 (m, 2H); LC MS: ES− 246.1.

Compound 22

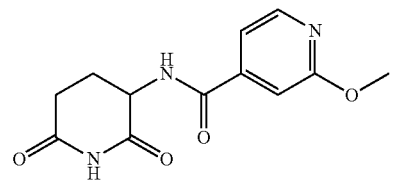

1H NMR (400 MHz, DMSO-d6) δ 10.90 (s, 1H), 9.00 (d, J=8.0 Hz, 1H), 8.32 (d, J=5.2 Hz, 1H), 7.37 (d, J=5.2 Hz, 1H), 7.20 (s, 1H), 4.78 (p, J=6.0 Hz, 1H), 3.90 (s, 3H), 2.80 (td, J=13.3, 7.0 Hz, 1H), 2.57 (m, 1H), 2.11-1.99 (m, 2H); LC MS: ES+ 364.03.

Compound 23

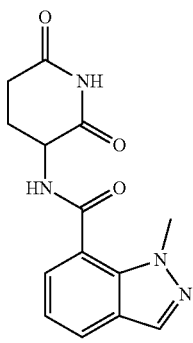

1H NMR (400 MHz, DMSO-d6) δ 10.90 (s, 1H), 9.02 (d, J=8.4 Hz, 1H), 8.15 (s, 1H), 7.89 (d, J=8.0 Hz, 1H), 7.49 (d, J=7.0 Hz, 1H), 7.19 (t, J=7.6 Hz, 1H), 4.88-4.76 (m, 1H), 4.07 (s, 3H), 2.84 (ddd, J=18.2, 13.0, 5.9 Hz, 1H), 2.57-2.49 (m, 1H), 2.23-2.03 (m, 2H); LC MS: ES+ 287.1.

Compound 24

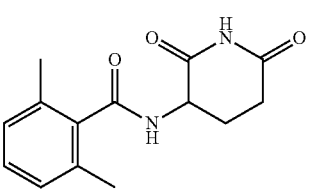

1H NMR (400 MHz, DMSO-d6) δ 10.82 (s, 1H), 8.64 (d, J=8.4 Hz, 1H), 7.21-7.12 (m, 1H), 7.04 (d, J=7.6 Hz, 2H), 4.73 (ddd, J=12.1, 8.3, 5.5 Hz, 1H), 2.79 (ddd, J=17.2, 12.9, 5.7 Hz, 1H), 2.55 (d, J=3.8 Hz, 1H), 2.28 (s, 6H), 2.15-1.93 (m, 2H); LC MS: ES− 259.1.

Compound 25

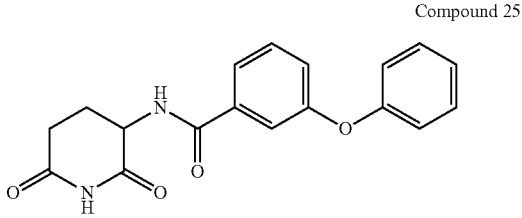 [SMILES: O=C1CCC(NC(=O)c2cccc(Oc3ccccc3)c2)C(=O)N1]

1H NMR (400 MHz, DMSO-d6) δ 10.86 (s, 1H), 8.81 (d, J=8.3 Hz, 1H), 7.66 (d, J=7.7 Hz, 1H), 7.56-7.46 (m, 2H), 7.42 (t, J=7.9 Hz, 2H), 7.25-7.13 (m, 2H), 7.05 (d, J=8.0 Hz, 2H), 4.76 (ddd, J=12.9, 8.2, 5.3 Hz, 1H), 2.79 (ddd, J=18.0, 13.2, 5.5 Hz, 1H), 2.55 (d, J=3.8 Hz, 1H), 2.11 (qd, J=13.0, 4.5 Hz, 1H), 2.00-1.91 (m, 1H); LC MS: ES− 323.1.

(ddd, J=17.9, 13.4, 5.5 Hz, 1H), 2.62-2.52 (m, 1H), 2.11-1.99 (m, 2H); LC MS: ES− 300.1.

Compound 26

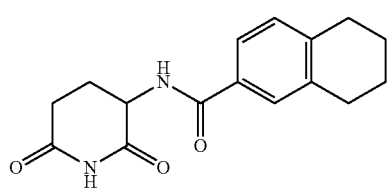

1H NMR (400 MHz, DMSO-d6) δ 10.85 (s, 1H), 8.63 (d, J=8.4 Hz, 1H), 7.58-7.56 (m, 2H), 7.15 (d, J=7.8 Hz, 1H), 4.77 (ddd, J=13.1, 8.2, 5.1 Hz, 1H), 2.82-2.76 (m, 5H), 2.55-2.50 (m, 1H), 2.18-2.05 (m, 1H), 1.99-1.91 (m, 1H), 1.75-1.73 (m, 4H); LC MS: ES− 285.1.

Compound 30

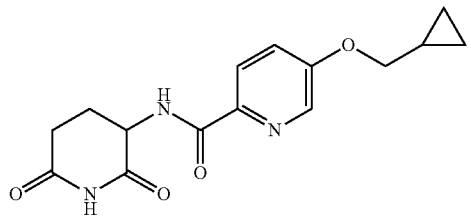

1H NMR (400 MHz, DMSO-d6) δ 10.86 (s, 1H), 8.88 (d, J=8.3 Hz, 1H), 8.33 (d, J=2.8 Hz, 1H), 8.00 (d, J=8.6 Hz, 1H), 7.53 (dd, J=8.7, 3.0 Hz, 1H), 4.76 (dt, J=13.3, 5.8 Hz, 1H), 3.99 (d, J=7.0 Hz, 2H), 2.79 (td, J=14.3, 13.4, 8.0 Hz, 1H), 2.51-2.49 (m, 1H), 2.20-2.18 (m, 1H), 2.02-1.99 (m, 1H), 1.29-1.20 (m, 1H), 0.60 (q, J=4.1 Hz, 2H), 0.37 (q, J=4.8 Hz, 2H); LC MS: ES+ 304.1.

Compound 27

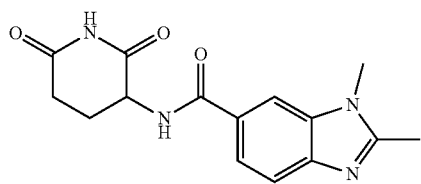

1H NMR (400 MHz, DMSO-d6) δ 10.88 (s, 1H), 8.72 (d, J=8.1 Hz, 1H), 8.04 (s, 1H), 7.72 (d, J=8.4 Hz, 1H), 7.57 (d, J=8.5 Hz, 1H), 4.83-4.80 (m, 1H), 3.78 (s, 3H), 3.00-2.82 (m, 1H), 2.56 (s, 3H), 2.56-2.50 (m, 1H), 2.14 (dt, J=13.4, 6.7 Hz, 1H), 2.00 (d, J=11.8 Hz, 1H); LC MS: ES+301.1.

Compound 31

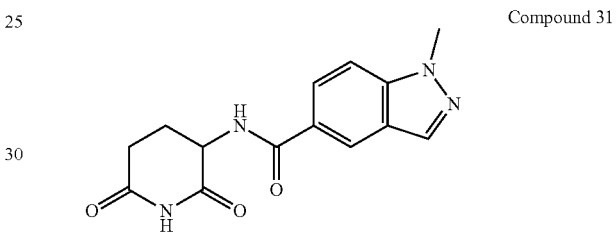

1H NMR (400 MHz, DMSO-d6) δ 10.87 (s, 1H), 8.79 (d, J=8.2 Hz, 1H), 8.36 (s, 1H), 8.22 (s, 1H), 7.92 (d, J=8.7 Hz, 1H), 7.72 (d, J=8.7 Hz, 1H), 4.86-4.80 (m, 1H), 4.08 (s, 3H), 2.91-2.70 (m, 1H), 2.57-2.49 (m, 1H), 2.14-1.98 (m, 2H); LC MS: ES− 285.1; LC MS: ES− 279.1.

Compound 28

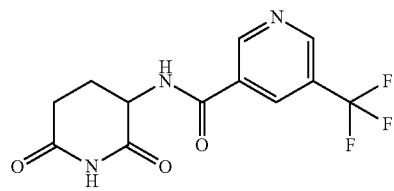

1H NMR (400 MHz, DMSO-d6) δ 10.95 (s, 1H), 9.28 (dd, J=24.7, 5.2 Hz, 2H), 9.18 (s, 1H), 8.60 (s, 1H), 4.86 (ddd, J=13.2, 8.3, 5.4 Hz, 1H), 2.83 (ddd, J=18.3, 12.7, 5.3 Hz, 1H), 2.62-2.52 (m, 1H), 2.09 (ddd, J=30.0, 11.4, 5.6 Hz, 2H); LC MS: ES− 300.1.

Compound 32

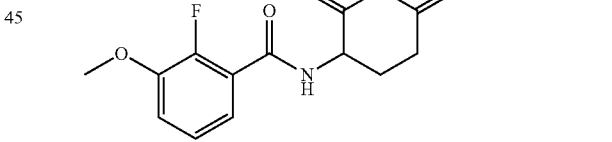

1H NMR (400 MHz, DMSO-d6) δ 10.87 (s, 1H), 8.61 (d, J=8.2 Hz, 1H), 7.31 (s, 1H), 7.22 (t, J=8.0 Hz, 1H), 7.15 (t, J=6.5 Hz, 1H), 4.81-4.69 (m, 1H), 3.87 (s, 3H), 2.78 (ddd, J=18.2, 12.8, 5.5 Hz, 1H), 2.56-2.52 (m, 1H), 2.12-2.01 (m, 2H).

Compound 29

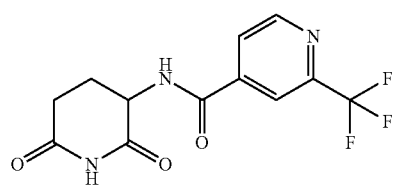

1H NMR (400 MHz, DMSO-d6) δ 10.95 (s, 1H), 9.34 (d, J=8.2 Hz, 1H), 8.98 (d, J=5.0 Hz, 1H), 8.27 (s, 1H), 8.12 (d, J=5.0 Hz, 1H), 4.85 (ddd, J=13.1, 8.4, 5.4 Hz, 1H), 2.82

Compound 33

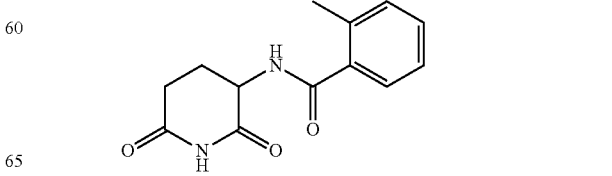

1H NMR (400 MHz, DMSO-d6) δ 10.85 (s, 1H), 8.54 (d, J=8.4 Hz, 1H), 7.40-7.30 (m, 2H), 7.26 (d, J=7.4 Hz, 2H), 4.76-4.70 (m, 1H), 2.80 (ddd, J=18.4, 13.1, 5.8 Hz, 1H), 2.55 (m, 1H), 2.37 (s, 3H), 2.11-1.90 (m, 2H); LC MS: ES− 245.1.

1H NMR (400 MHz, DMSO-d6) δ 10.82 (s, 1H), 8.02 (d, J=8.3 Hz, 1H), 7.66 (s, 1H), 4.75-4.65 (m, 1H), 3.83 (s, 3H), 2.77 (td, J=15.1, 13.1, 5.5 Hz, 1H), 2.55-2.49 (m, 1H), 2.15-1.85 (m, 3H), 1.05-0.95 (m, 2H), 0.80 (d, J=3.04 Hz, 2H); LC MS: ES− 275.1.

Compound 34

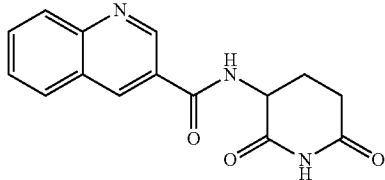

1H NMR (400 MHz, DMSO-d6) δ 10.94 (s, 1H), 9.30 (s, 1H), 9.16 (d, J=8.3 Hz, 1H), 8.87 (s, 1H), 8.12 (t, J=9.4 Hz, 2H), 7.89 (t, J=7.6 Hz, 1H), 7.72 (t, J=7.5 Hz, 1H), 4.94-4.84 (m, 1H), 2.87-2.80 (m, 1H), 2.60-2.49 (m, 1H), 2.18-1.97 (m, 2H); LC MS: ES− 282.2.

Compound 38

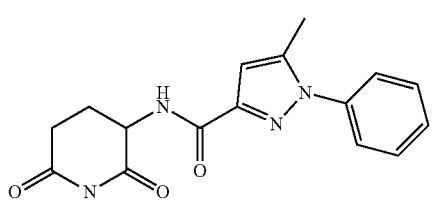

1H NMR (400 MHz, DMSO-d6) δ 10.81 (s, 1H), 8.44 (d, J=8.4 Hz, 1H), 7.58-7.50 (m, 5H), 6.68 (s, 1H), 4.75-4.72 (m, 1H), 2.82-2.72 (m, 1H), 2.33 (s, 3H), 2.20-2.11 (m, 1H), 1.99-1.95 (m, 1H); 1H NMR (400 MHz, MeOD) δ 7.53-7.48 (m, 5H), 6.71 (s, 1H), 4.82-4.77 (m, 1H), 2.82-2.75 9M, 1H), 2.72-2.65 (m, 1H), 2.35 (s, 3H), 2.24-2.13 (m, 2H); LC MS: ES+ 313.1.

Compound 35

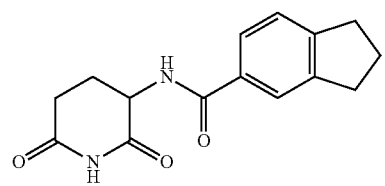

1H NMR (400 MHz, DMSO-d6) δ 10.85 (s, 1H), 8.65 (d, J=8.4 Hz, 1H), 7.73 (s, 1H), 7.65 (d, J=7.8 Hz, 1H), 7.32 (d, J=7.7 Hz, 1H), 4.79-4.75 (m, 1H), 2.90 (t, J=7.4 Hz, 4H), 2.85-2.72 (m, 1H), 2.55-2.49 (m, 1H), 2.16-2.04 (m, 1H), 2.16-1.97 (m, 4H); LC MS: ES− 271.1.

Compound 39

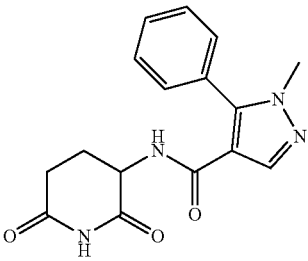

1H NMR (400 MHz, DMSO-d6) δ 10.79 (s, 1H), 8.13 (d, J=8.1 Hz, 1H), 7.97 (s, 1H), 7.60-7.35 (m, 5H), 4.61-4.55 (m, 1H), 3.66 (s, 3H), 2.71-2.69 (m, 1H), 2.51-2.49 (m, 1H), 1.99-1.92 (m, 2H); LC MS: ES+ 313.1.

Compound 36

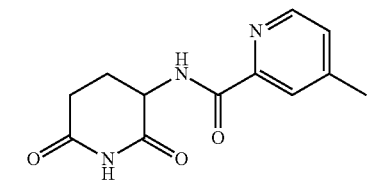

1H NMR (400 MHz, DMSO-d6) δ 10.87 (s, 1H), 9.04 (d, J=8.4 Hz, 1H), 8.52 (d, J=5.0 Hz, 1H), 7.91 (s, 1H), 7.46 (d, J=4.9 Hz, 1H), 4.88-4.72 (m, 1H), 2.88-2.73 (m, 1H), 2.50-2.46 (m, 1H), 2.42 (s, 3H), 2.25-2.15 (m, 1H), 2.08-1.91 (m, 1H); LC MS: ES+ 248.0.

Compound 40

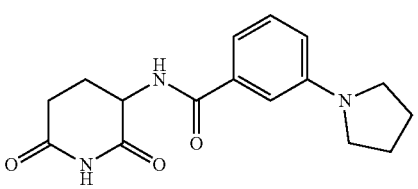

1H NMR (400 MHz, DMSO-d6) δ 10.85 (s, 1H), 8.61 (d, J=8.5 Hz, 1H), 7.24 (t, J=7.9 Hz, 1H), 7.08 (d, J=7.6 Hz, 1H), 7.00 (s, 1H), 6.69 (dd, J=8.2, 2.5 Hz, 1H), 4.81-4.71 (m, 1H), 3.26 (s, 3H), 3.26 (d, J=12.6 Hz, 1H), 2.86-2.73 (m, 1H), 2.56-2.50 (m, 1H), 2.14-2.11 (m, 1H), 2.01-1.93 (m, 5H), LC MS: ES− 300.1.

Compound 37

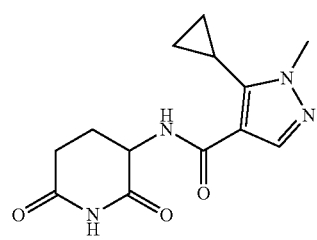

Compound 41

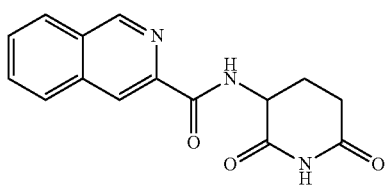

1H NMR (400 MHz, DMSO-d6) δ 10.90 (s, 1H), 9.42 (s, 1H), 9.23 (d, J=8.3 Hz, 1H), 8.61 (s, 1H), 8.25 (dd, J=19.2, 8.1 Hz, 2H), 7.90 (t, J=7.4 Hz, 1H), 7.83 (t, J=7.5 Hz, 1H), 4.88 (ddd, J=13.3, 8.1, 5.2 Hz, 1H), 2.91-2.77 (m, 1H), 2.57-2.55 (m, 1H), 2.34-2.19 (m, 1H), 2.07-2.04 (m, 1H); LC MS: ES+ 284.0.

Compound 42

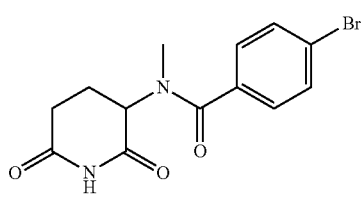

1H NMR (400 MHz, DMSO-d6, 100° C.) δ 10.49 (s, 1H), 7.63 (d, J=8.28 Hz, 2H), 7.35 (d, J=8.12 Hz, 2H), 4.81 (brs, 1H), 2.84 (s, 3H), 2.77-2.69 (m, 1H), 2.57-2.51 (m, 1H), 2.43-2.32 (m, 1H), 2.04-2.00 (m, 1H); LC MS:ES+ 325.0 (Br pattern observed).

Compound 43

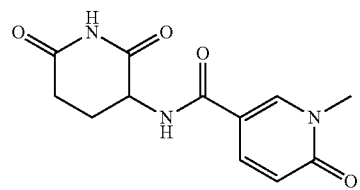

1H NMR (400 MHz, DMSO-d6) δ 10.86 (s, 1H), 8.53 (d, J=8.2 Hz, 1H), 8.38 (d, J=2.8 Hz, 1H), 7.86 (dd, J=9.6, 2.7 Hz, 1H), 6.43 (d, J=9.5 Hz, 1H), 4.79-4.69 (m, 1H), 3.49 (s, 3H), 2.79 (ddd, J=18.2, 13.2, 5.5 Hz, 1H), 2.53-2.47 (m, 1H), 2.05-1.92 (m, 2H); LC MS: ES− 262.1; LC MS: ES− 265.0.

Compound 44

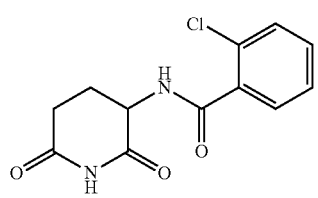

1H NMR (400 MHz, DMSO-d6) δ 10.86 (s, 1H), 8.76 (d, J=8.4 Hz, 1H), 7.55-7.38 (m, 4H), 4.75 (q, J=8.6 Hz, 1H), 2.78 (ddt, J=18.3, 13.4, 6.9 Hz, 1H), 2.56 (d, J=3.7 Hz, 1H), 2.0-1.90 (m, 2H).

Compound 45

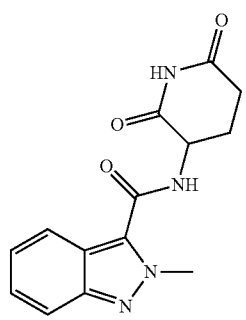

1H NMR (400 MHz, DMSO-d6) δ 10.94 (s, 1H), 8.78 (d, J=8.4 Hz, 1H), 7.93 (d, J=8.4 Hz, 1H), 7.70 (d, J=8.6 Hz, 1H), 7.33 (t, J=6.9 Hz, 1H), 7.24 (t, J=7.5 Hz, 1H), 4.93-4.90 (m, 1H), 4.32 (s, 3H), 2.89-2.80 (m, 1H), 2.59-2.50 (m, 1H), 2.23-2.14 (m, 2H); LC MS: ES− 285.1.

Compound 46

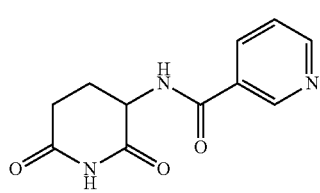

1H NMR (400 MHz, DMSO-d6) δ 10.91 (s, 1H), 9.01 (dd, J=15.3, 5.3 Hz, 2H), 8.74 (dd, J=4.9, 1.8 Hz, 1H), 8.21 (dt, J=7.8, 2.1 Hz, 1H), 7.54 (dd, J=7.9, 4.8 Hz, 1H), 4.82 (dd, J=12.2, 5.8 Hz, 1H), 2.87-2.75 (m, 1H), 2.58-2.50 (m, 1H), 2.15-1.99 (m, 2H); LC MS: ES+ 234.0.

Compound 47

1H NMR (400 MHz, DMSO-d6) δ 10.90 (s, 1H), 8.87 (d, J=8.2 Hz, 1H), 8.19 (s, 1H), 8.13 (s, 1H), 7.85 (d, J=8.4 Hz, 1H), 7.64 (d, J=8.4 Hz, 1H), 4.85 (q, J=9.2, 8.3 Hz, 1H), 4.11 (s, 3H), 2.82 (d, J=12.9 Hz, 1H), 2.57 (d, J=16.2 Hz, 1H), 2.21-2.11 (m, 1H), 2.10-2.03 (m, 1H); LC MS: ES− 285.1.

Compound 48

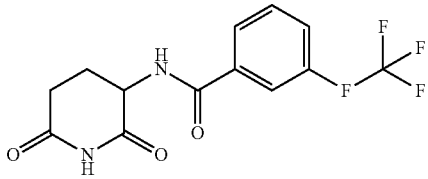

1H NMR (400 MHz, DMSO-d6) δ 10.90 (s, 1H), 8.97 (d, J=8.3 Hz, 1H), 7.93 (d, J=7.7 Hz, 1H), 7.83 (s, 1H), 7.66 (t, J=8.2 Hz, 1H), 7.60-7.56 (m, 1H), 4.83-4.76 (m, 1H), 2.84-2.76 (m, 1H), 2.57-2.50 (m, 1H), 2.19-2.10 (m, 1H), 2.09-2.00 (m, 1H); LC MS: ES− 315.1.

Compound 49

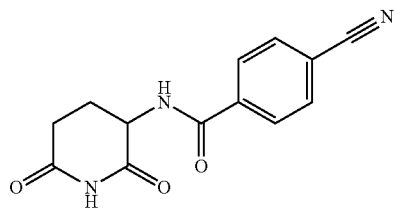

1H NMR (400 MHz, DMSO-d6) δ 10.91 (s, 1H), 9.05 (d, J=8.2 Hz, 1H), 8.06-7.95 (m, 4H), 4.81 (ddd, J=13.0, 8.5, 5.3 Hz, 1H), 2.88-2.67 (m, 1H), 2.57-2.54 (m, 1H), 2.13-2.08 (m, 1H), 2.00-1.99 (m 1H); LC MS: ES− 256.1.

Compound 50

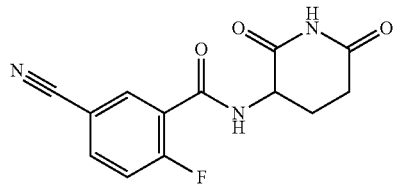

1H NMR (400 MHz, DMSO-d6) δ 10.91 (s, 1H), 8.87 (d, J=8.2 Hz, 1H), 8.15-8.05 (m, 2H), 7.59 (t, J=9.24 Hz, 1H), 4.82-4.74 (m, 1H), 2.84-2.75 (m, 1H), 2.56-2.50 (m, 1H), 2.08-2.03 (m, 2H); LC MS: ES− 274.1.

Compound 51

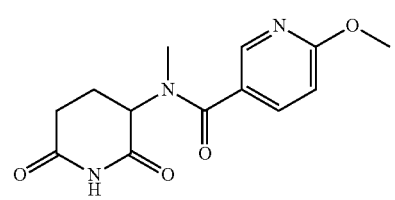

1H NMR (400 MHz, DMSO-d6) δ 10.90 (s, 1H), 8.31-8.18 (m, 1H), 7.82-7.66 (m, 1H), 6.90-6.85 (m, 1H), 5.00-4.64 (m, 1H), 3.89 (s, 3H), 2.89-2.80 (m, 4H), 2.79-2.50 (m, 1H), 2.49-2.44 (m, 1H), 2.01-1.98 (m, 1H); LC MS: ES=278.1.

Compound 52

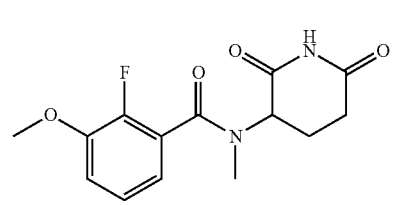

1H NMR (400 MHz, DMSO-d6) δ 10.92 (s, 1H), 7.29-7.12 (m, 2H), 6.93-6.84 (m, 1H), 5.15-4.44 (m, 1H), 3.86 (s, 3H), 2.86-2.74 (m, 4H), 2.57-2.45 (m, 1H), 2.40-2.37 (m, 1H), 1.98-1.91 (m, 1H); LC MS: ES+ 295.1.

Compound 53

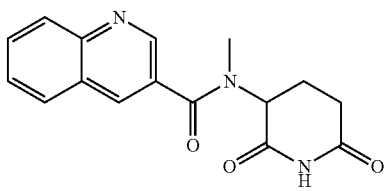

1H NMR (400 MHz, DMSO-d6) δ 10.94 (s, 1H), 8.94-8.83 (m, 1H), 8.55-8.35 (m, 1H), 8.13-8.08 (m, 2H), 7.85-7.81 (m, 1H), 7.71-7.65 (m, 1H), 5.20-4.73 (m, 1H), 2.94-2.85 (m, 4H), 2.58-2.49 (m, 1H), 2.49-2.44 (m, 1H), 2.08-2.00 (m, 1H); LC MS: ES+ 298.1.

Compound 54

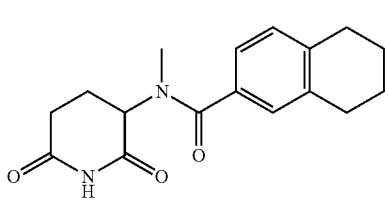

1H NMR (400 MHz, DMSO-d6) δ 10.46 (brs, 1H), 7.10-7.09 (m, 3H), 4.84 (brs, 1H), 2.84 (s, 3H), 2.79-2.61 (m, 5H), 2.59-2.52 (m, 1H), 2.42-2.31 (m, 1H), 2.03-1.98 (m, 1H), 1.77-1.71 (m, 4H); LC MS: ES+ 301.1.

Compound 55

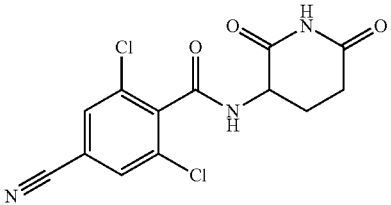

1H NMR (400 MHz, DMSO-d6) δ 10.90 (s, 1H), 9.26 (d, J=8.0 Hz, 1H), 8.18 (d, J=2.9 Hz, 2H), 4.79 (dt, J=12.6, 6.2 Hz, 1H), 2.80-2.71 (m, 1H), 2.56-2.50 (m, 1H), 2.08-2.00 (m, 1H), 2.00-1.96 (m, 1H); LC MS: ES+ 324.0 (Cl pattern observed).

Compound 56

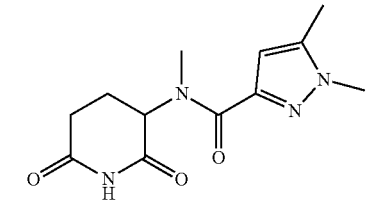

1H NMR (400 MHz, DMSO-d6) δ 10.80 (s, 1H), 8.20 (d, J=8.2 Hz, 1H), 6.43 (s, 1H), 4.75-4.70 (m, 1H), 3.78 (s, 3H), 2.83-2.69 (m, 1H), 2.28 (s, 3H), 2.56-2.50 (m, 1H), 2.18-2.07 (m, 1H), 2.00-1.92 (m, 1H); LC MS: ES+ 251.1.

Compound 57

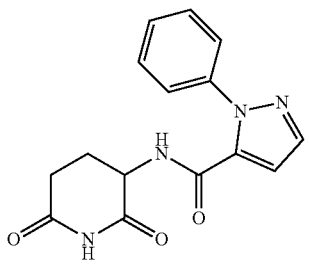

1H NMR (400 MHz, DMSO-d6) δ 10.88 (s, 1H), 8.97 (d, J=8.4 Hz, 1H), 7.76 (d, J=1.9 Hz, 1H), 7.52-7.34 (m, 4H), 6.90 (d, J=1.9 Hz, 1H), 4.69-4.63 (m, 1H), 2.80-2.71 (m, 1H), 2.51-2.49 (m, 1H), 2.08-1.95 (m, 2H); LC MS: ES− 297.1.

Compound 58

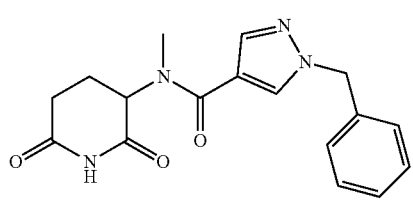

1H NMR (400 MHz, DMSO-d6 at 100° C.) δ 10.44 (s, 1H), 8.15 (s, 1H), 7.73 (s, 1H), 7.37-7.27 (m, 5H), 5.36 (s, 2H), 5.2-4.98 (m, 1H), 3.03 (s, 3H), 2.81-2.72 (m, 1H), 2.67-2.55 (m, 1H), 2.41-2.30 (m, 1H), 2.03-1.94 (m, 1H); LC MS: ES− 325.2.

Compound 59

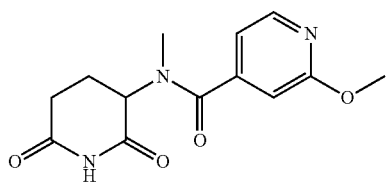

1H NMR (400 MHz, DMSO-d6, 100° C.) δ 10.53 (s, 1H), 8.25 (d, J=5.0 Hz, 1H), 6.93 (d, J=4.6 Hz, 1H), 6.73 (s, 1H), 4.98 (brs, 1H), 3.92 (s, 3H), 2.83 (s, 3H), 2.66-2.58 (m, 1H), 2.56-2.50 (m, 1H), 2.43-2.33 (m, 1H), 2.04-2.01 (m, 1H); LC MS: ES− 276.1.

Compound 60

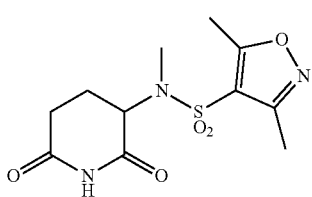

1H NMR (400 MHz, MeOD) δ 4.93-4.89 (m, 1H), 2.88-2.80 (m, 1H), 2.78 (s, 3H), 2.71-2.63 (m, 1H), 2.61 (s, 3H), 2.39-2.31 (m, 4H); LC MS: ES− 300.1.

Compound 61

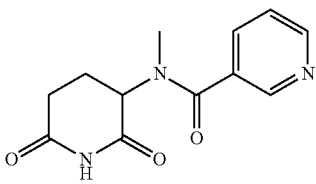

1H NMR (400 MHz, DMSO-d6) δ 10.92 (s, 1H), 8.67-8.54 (m, 1H), 7.89-7.74 (m, 1H), 7.52-7.44 (m, 1H), 5.13-4.53 (m, 1H), 2.89-2.83 (m, 4H), 2.67-2.55 (m, 1H), 2.50-2.34 (m, 2H), 2.07-2.02 (m, 1H); LC MS: ES+ 248.1.

Compound 62

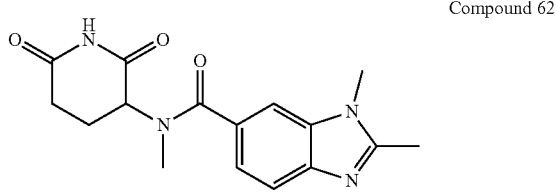 [SMILES: Cc1nc2ccc(C(=O)N(C)C3CCC(=O)NC3=O)cc2n1C]

1H NMR (400 MHz, DMSO-d6 100° C.) δ 10.47 (s, 1H), 7.54 (d, J=8.2 Hz, 1H), 7.50 (s, 1H), 7.21 (d, J=8.2 Hz, 1H), 4.90-4.87 (m, 1H), 3.75 (s, 3H), 2.89 (s, 3H), 2.75-2.69 (m, 1H), 2.60-2.54 (m, 1H), 2.55 (s, 3H), 2.43-2.32 (m, 1H), 2.07-2.05 (m, 1H); LC MS: ES+ 315.2.

Compound 63

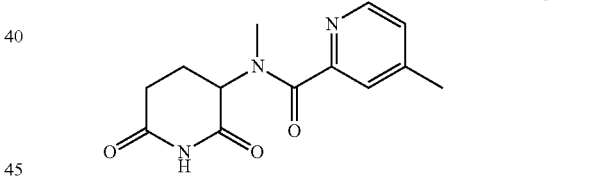

1H NMR (400 MHz, DMSO-d6, 100 C) δ 10.46 (s, 1H), 8.43 (s, 1H), 7.40 (s, 1H), 7.29 (d, J=4.7 Hz, 1H), 5.04-5.02 (m, 1H), 2.91 (s, 3H), 2.84-2.73 (m, 1H), 2.64-2.60 (m, 1H), 2.51-2.38 (m, 4H), 2.11-1.99 (m, 1H); LC MS: ES+ 262.1.

Compound 64

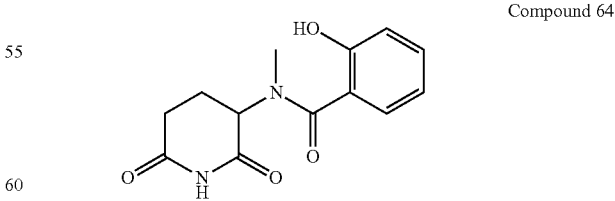

1H NMR (400 MHz, DMSO-d6, 100° C.) 10.41 (s, 1H), 9.36 (s, 1H), 7.23 (t, J=8.1 Hz, 1H), 7.13 (d, J=7.6 Hz, 1H), 6.91-6.83 (m, 2H), 4.90-4.82 (m, 1H), 2.81 (s, 3H), 2.76-2.67 (m, 1H), 2.60-2.56 (m, 1H), 2.41-2.32 (m, 1H), 2.03-2.00 (m, 1H); LC MS: ES− 261.1.

Compound 65

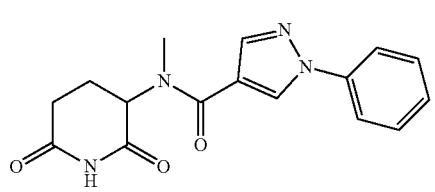

1H NMR (400 MHz, DMSO-d6 100° C.) δ 10.82 (s, 1H), 8.68 (s, 1H), 7.97 (s, 1H), 7.87 (d, J=8.0 Hz, 2H), 7.52 (t, J=7.6 Hz, 2H), 7.36 (t, J=7.2 Hz, 1H), 5.06 (dd, J=5.4, 12.5 Hz, 1H), 3.08 (brs, 3H), 2.85-2.76 (m, 1H), 2.67-2.57 (m, 1H), 2.45-2.32 (m, 1H), 2.05-2.02 (m, 1H); LC MS: ES+ 313.1.

Compound 66

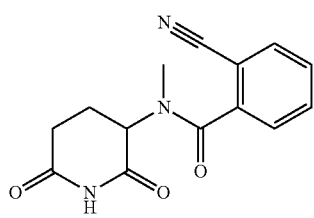

1H NMR (400 MHz, DMSO-d6, 100° C.) δ 10.54 (s, 1H), 7.91 (d, J=16.1, 7.8 Hz, 1H), 7.80-7.76 (m, 1H), 7.63 (t, J=7.9 Hz, 1H), 7.58-7.50 (m, 1H), 5.10-4.91 (m, 1H), 2.85-2.70 (m, 4H), 2.62-2.50 (m, 1H), 2.49-2.37 (m, 1H), 2.07-2.03 (m, 1H); LC MS: ES− 270.1.

Compound 67

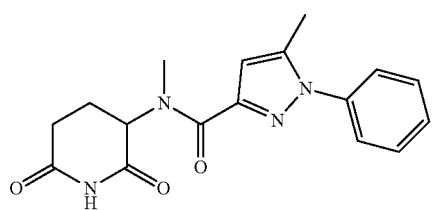

1H NMR (400 MHz, DMSO-d6, 100° C.) δ 10.84 (s, 1H), 7.56-7.54 (m, 4H), 7.49-7.45 (m, 1H), 6.66 (s, 1H), 5.08 (brs, 1H), 3.40-3.00 (m, 3H), 2.80-2.57 (m, 2H), 2.44-2.34 (m, 1H), 2.34 (s, 3H), 2.10-1.99 (m, 1H); LC MS: ES+ 327.1.

Compound 68

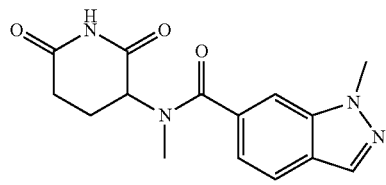

1H NMR (400 MHz, DMSO-d6, 100° C.) δ 10.49 (s, 1H), 8.06 (s, 1H), 7.81 (d, J=8.2 Hz, 1H), 7.64 (m, 1H), 7.14 (d, J=8.1 Hz, 1H), 4.88 (brs, 1H), 4.07 (s, 3H), 2.89 (s, 3H), 2.78-2.50 (m, 2H), 2.44-2.32 (m, 1H), 2.09-1.98 (m, 1H); LC MS: ES+ 301.1.

Compound 69

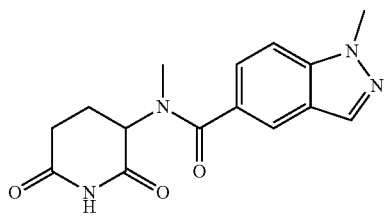

1H NMR (400 MHz, DMSO-d6) δ 10.89 (s, 1H), 8.18-8.11 (m, 1H), 7.89-7.77 (m, 1H), 7.69-7.61 (m, 1H), 7.47-7.38 (m, 1H), 5.10-5.03 (m, 1H), 4.07 (s, 3H), 2.88-2.86 (m, 4H), 2.62-2.49 (m, 1H), 2.48-2.33 (m, 1H), 2.00-1.99 (m, 1H); LC MS: ES+ 301.1.

Compound 70

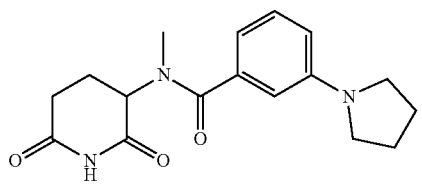

1H NMR (400 MHz, DMSO-d6, 100° C.) δ 10.47 (s, 1H), 7.21 (t, J=7.7 Hz, 1H), 6.60 (t, J=8.9 Hz, 1H), 6.52 (s, 1H), 4.91-4.80 (m, 1H), 3.25-3.23 (m, 4H), 2.84 (s, 3H), 2.71-2.59 (m, 1H), 2.54-2.50 (m, 2H), 2.42-2.33 (m, 1H), 2.00-1.95 (m, 5H); LC MS: ES+ 316.1.

Compound 71

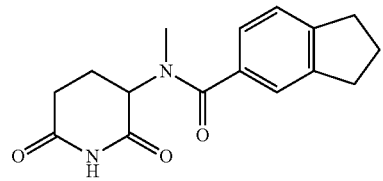

1H NMR (400 MHz, DMSO-d6, 100° C.) δ 10.46 (s, 1H), 7.27 (t, J=7.6 Hz, 1H), 7.15 (d, J=7.6 Hz, 1H), 4.91-4.85 (m, 1H), 2.95-2.89 (m, 4H), 2.84 (s, 3H), 2.76-2.67 (m, 1H), 2.65-2.50 (m, 1H), 2.49-2.32 (m, 2H), 2.10-2.00 (m, 3H); LC MS: ES+ 287.1.

Compound 72

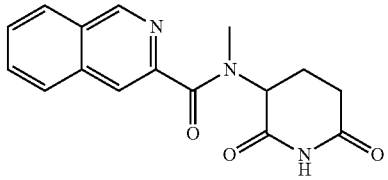

1H NMR (400 MHz, DMSO-d6) δ 10.92 (s, 0.5H), 10.80 (s, 0.5H), 9.36 (s, 0.5H), 9.30 (s, 0.5H), 8.20 (t, J=8.0 Hz, 2H), 8.11-8.09 (m, 2H), 7.88-7.76 (m, 2H), 5.21-5.11 (m, 0.5H), 4.98-4.93 (m, 0.5H), 2.92 (s, 1.5H), 2.88 (s, 1.5H), 2.66-2.37 (m, 3H), 2.21-2.15 (m, 0.5H), 2.01-1.99 (m, 0.5H); LC MS: ES+ 298.1.

Compound 73

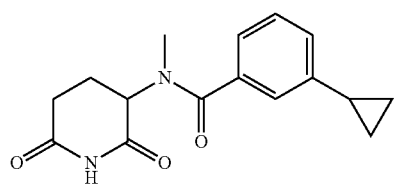

1H NMR (400 MHz, DMSO-d6, 100° C.) δ 10.47 (s, 1H), 7.31 (t, J=7.6 Hz, 1H), 7.18-7.15 (m, 2H), 7.11 (s, 1H), 4.90-4.70 (m, 1H), 2.83 (s, 3H), 2.72-2.49 (m, 2H), 2.40-2.32 (m, 1H), 2.04-1.97 (m, 2H), 0.99-0.95 (m, 2H), 0.69-0.67 (m, 2H); LC MS: ES+ 287.1.

Compound 74

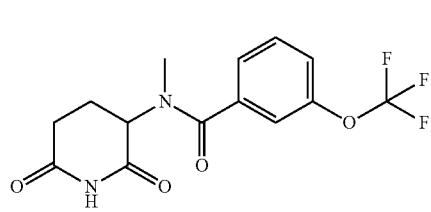

1H NMR (400 MHz, DMSO-d6, 100° C.) δ 10.52 (s, 1H), 7.60 (t, J=8.1 Hz, 1H), 7.43 (d, J=7.4 Hz, 2H), 7.33 (s, 1H), 4.91-4.82 (m, 1H), 2.85 (s, 3H), 2.74-2.69 (m, 1H), 2.60-2.50 (m, 1H), 2.44-2.34 (m, 1H), 2.00-2.03 (m, 1H); LC MS: ES− 329.1.

Compound 75

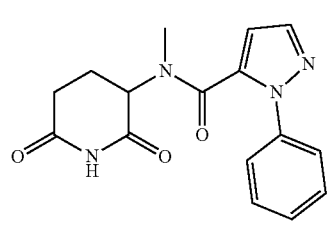

1H NMR (400 MHz, DMSO-d6) δ 10.96-1.93 (m, 1H), 7.80-7.76 (m, 1H), 7.56-7.54 (m, 2H), 7.49-7.46 (m, 2H), 7.40-7.36 (m, 1H), 6.75-6.65 (m, 1H), 5.10-4.86 (m, 1H), 2.79 (s, 3H), 2.72-2.63 (m, 1H), 2.56-2.50 (m, 1H), 2.36-2.26 (m, 1H), 1.86-1.71 (m, 1H); LC MS: ES+ 313.1.

Compound 76

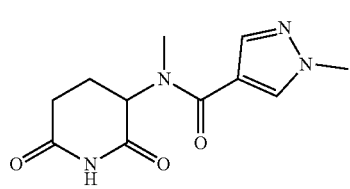

1H NMR (400 MHz, DMSO-d6) δ 10.84 (s, 1H), 8.18 (s, 1H), 7.77 (s, 1H), 5.12-5.13 (m, 1H), 3.86 (s, 3H), 3.07 (s, 3H), 2.83-2.71 (m, 2H), 2.41-2.32 (m, 1H), 2.01-1.87 (m, 1H); LC MS: ES−249.1.

Compound 77

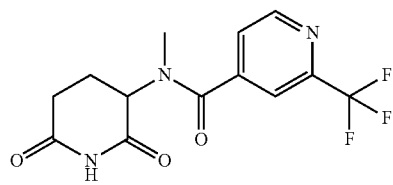

1H NMR (400 MHz, DMSO-d6) δ 10.97 (s, 1H), 8.87 (dd, J=23.6, 4.9 Hz, 1H), 7.78 (s, 1H), 5.17-4.49 (m, 1H), 2.88-2.79 (m, 4H), 2.66-2.56 (m, 1H), 2.49-2.35 (m, 2H), 2.10-1.98 (m, 1H); LC MS: ES− 314.1.

Compound 78

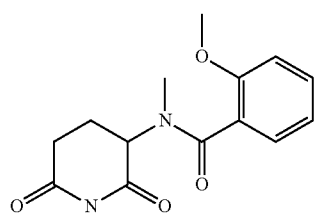

1H NMR (400 MHz, DMSO-d6, 100° C.) δ 10.86 (s, 1H), 7.39 (t, J=7.1 Hz, 1H), 7.16 (d, J=6.28 Hz, 1H), 7.10-6.98 (m, 2H), 5.08-4.28 (m, 1H), 3.82 (s, 3H), 2.83-2.62 (m, 4H), 2.57-2.49 (m, 1H), 2.37-2.04 (m, 1H), 2.02-1.91 (m, 1H); LC MS: ES+ 277.1.

Compound 79

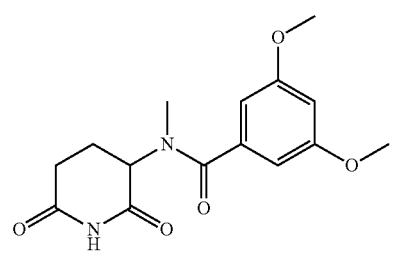

1H NMR (400 MHz, DMSO-d6) δ 10.90 (s, 1H), 6.57 (d, J=12.1 Hz, 1H), 6.54-6.44 (m, 2H), 5.10-4.54 (m, 1H), 3.77-3.75 (m, 6H), 2.86-2.78 (m, 4H), 2.66-2.57 (m, 1H), 2.49-2.32 (m, 1H), 2.00-1.96 (m, 1H); LC MS: ES+ 307.1.

Compound 80

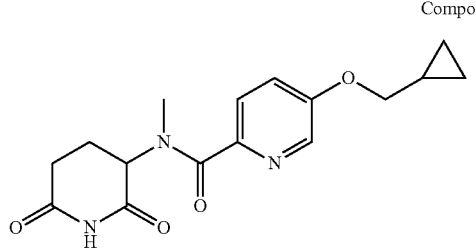

1H NMR (400 MHz, DMSO-d6) δ 10.88 (s, 1H), 8.28-8.22 (m, 1H), 7.5-7.57 (m, 1H), 7.48-7.46 (m, 1H), 5.13-5.09 (m, 1H), 3.96-3.92 (m, 2H), 2.95-2.81 (m, 4H), 2.65-

2.61 (m, 1H), 2.49-2.33 (m, 1H), 2.11-1.94 (m, 1H), 1.29-1.22 (m, 1H), 0.64-0.55 (m, 2H), 0.35-0.33 (m, 2H); LC MS: ES+ 318.2.

Compound 81

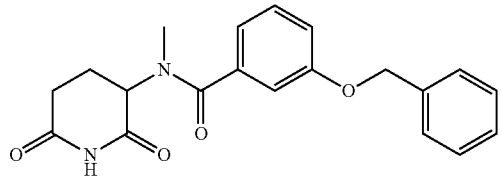

1H NMR (400 MHz, DMSO-d6) δ 10.90 (s, 1H), 7.40 (ddd, J=33.4, 17.4, 7.5 Hz, 6H), 7.11 (d, J=9.1 Hz, 1H), 7.04-6.88 (m, 2H), 5.15-4.48 (m, 3H), 2.83-2.76 (m, 4H), 2.57-2.49 (m, 1H), 2.39-2.32 (m, 1H), 2.00-1.93 (m, 1H); LC MS: ES− 351.2.

Compound 82

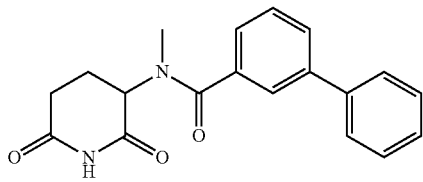

1H NMR (400 MHz, DMSO-d6) δ 10.92 (s, 1H), 7.78 (t, J=7.9 Hz, 1H), 7.74-7.62 (m, 3H), 7.64-7.45 (m, 3H), 7.43-7.34 (m, 2H), 5.13-4.60 (m, 1H), 2.87-2.85 (m, 4H), 2.66-2.55 (m, 1H), 2.49-2.39 (m, 1H), 2.02-1.96 (m, 1H); LC MS: ES+ 323.1.

Compound 83

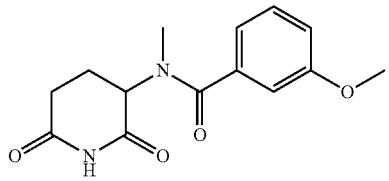

1H NMR (400 MHz, DMSO-d6) δ 10.87 (s, 1H), 7.34 (dt, J=16.5, 7.9 Hz, 1H), 6.95 (dt, J=34.5, 12.8 Hz, 3H), 5.10-4.51 (m, 1H), 3.76-3.72 (m, 3H), 2.84-2.75 (m, 4H), 2.66-2.56 (m, 1H), 2.49-2.31 (m, 1H), 2.00-1.94 (m, 1H); LC MS: ES+ 277.1.

Compound 84

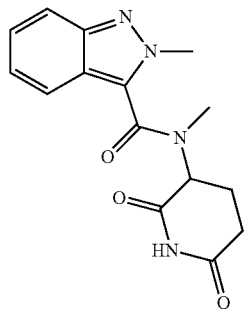

1H NMR (400 MHz, DMSO-d6, 100° C.) δ 10.55 (s, 1H), 7.66-7.61 (m, 2H), 7.30-7.28 (m, 1H), 7.18-7.16 (m, 1), 5.02-4.98 (m, 1H), 4.17 (s, 3H), 2.94 (s, 3H), 2.76-2.62 (m, 1H), 2.60-2.49 (m, 2H), 2.00-2.12 (m, 1H); LC MS: ES+ 301.1.

Compound 85

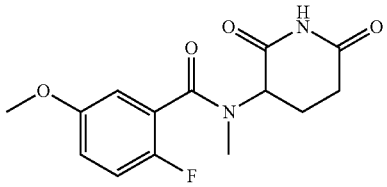

1H NMR (400 MHz, DMSO-d6, 100° C.) δ 10.51 (s, 1H), 7.20-7.15 (m, 1H), 7.10-7.02 (m, 1H), 7.00-6.85 (m, 1H), 5.15-4.43 (m, 1H), 3.77 (s, 3H), 2.83-2.81 (m, 4H), 2.70-2.50 (m, 1H), 2.40-2.37 (m, 1H), 2.09-1.91 (m, 1H); LC MS: ES+ 295.1.

Compound 86

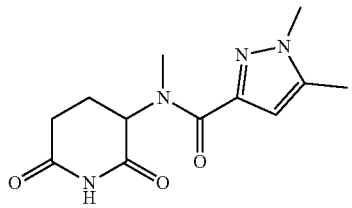

1H NMR (400 MHz, DMSO-d6) δ 10.8-10.83 (m, 1H), 6.37-6.35 (m, 1H), 5.90-5.03 (m, 1H), 3.77-3.74 (m, 3H), 3.19 (s, 2H), 2.83-2.66 (m, 3H), 2.60-2.50 (m, 1H), 2.40-2.33 (m, 1H), 2.26-2.25 (m, 4H), 2.03-1.89 (m, 1H); LC MS: ES+ 265.1.

Compound 87

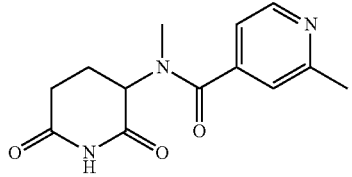

1H NMR (400 MHz, DMSO-d6, 100° C.) δ 10.00 (brs, 1H), 8.52 (d, J=4.8 Hz, 1H), 7.20 (s, 1H), 7.12 (s, 1H), 4.97 (brs, 1H), 2.83 (s, 3H), 2.79-2.71 (m, 1H), 2.61-2.50 (m, 1H), 2.52 (s, 3H), 2.43-2.32 (m, 1H), 2.04-2.01 (m, 1H); LC MS: ES+ 262.1.

Compound 88

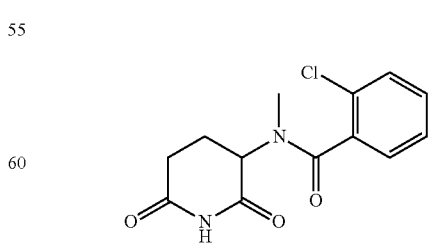

1H NMR (400 MHz, DMSO-d6, 100° C.) δ 10.48 (brs, 1H), 7.50-7.35 (m, 4H), 5.09 (brs, 0.6H), 4.26 (brs, 0.4H), 2.95-2.01 (m, 8H); LC MS: ES+ 281.1.

Compound 89

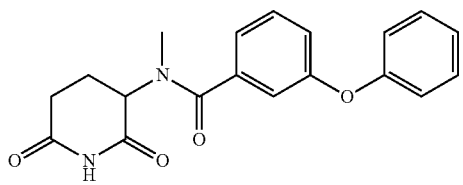

1H NMR (400 MHz, DMSO-d6, 100° C.) δ 10.48 (brs, 1H), 7.47-7.39 (m, 3H), 7.18-7.05 (m, 5H), 6.97 (s, 1H), 4.93-4.79 (m, 1H), 2.95 (s, 3H), 2.73-2.69 (m, 1H), 2.58-2.49 (m, 1H), 2.40-2.34 (m, 1H), 2.02-1.98 (m, 1H); LC MS: ES– 337.2.

Compound 90

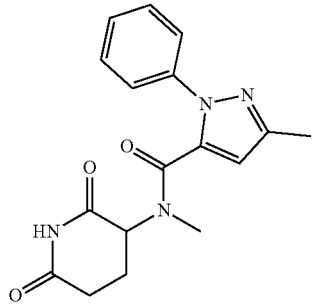

1H NMR (400 MHz, DMSO-d6) δ 10.96-10.84 (m, 1H), 8.14-8.10 (m, 1H), 7.87-7.83 (m, 1H), 7.34-7.31 (m, 1H), 7.23-7.13 (m, 1H), 5.35-5.25 (m, 0.5H), 4.67-4.59 (m, 0.5H), 4.04-4.01 (m, 3H), 2.94-2.79 (m, 4H), 2.62-2.58 (m, 1H), 2.45-2.37 (m, 1H), 2.13-2.05 (m, 1H); LC MS: ES+301.1.

Compound 91

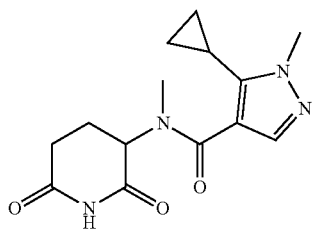

1H NMR (400 MHz, DMSO-d6, 100° C.) δ 10.34 (brs, 1H), 7.15-7.09 (m, 4H), 4.94-4.90 (m, 1H), 3.69 (s, 2H), 2.95 (s, 3H), 2.74-2.67 (m, 1H), 2.56-2.49 (m, 1H), 2.28 (s, 3H), 2.25-2.21 (m, 1H), 1.88-1.79 (m, 1H); LC MS: ES+ 275.2.

Compound 92

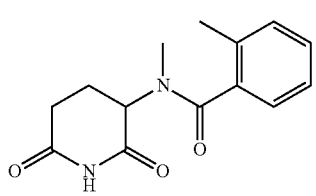

1H NMR (400 MHz, DMSO-d6) δ 10.96 (s, 0.5H), 10.94 (s, 0.5H), 5.19-5.11 (m, 0.5H), 4.60-4.56 (m, 0.5H), 2.88-2.82 (m, 4H), 2.66-2.56 (m, 1H), 2.43-2.32 (m, 2H), 2.05-2.02 (m, 1H); LC MS: ES– 314.1.

Compound 93

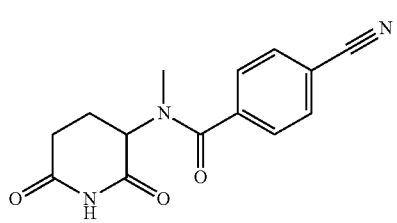

1H NMR (400 MHz, DMSO-d6, 100° C.) δ 10.51 (brs, 1H), 7.53 (d, J=7.88 Hz, 2H), 7.44 (t, J=7.78, 2H), 7.34 (t, J=7.24, 1H), 6.43 (s, 1H), 4.95 (brs, 1H), 2.81 (s, 3H), 2.73-2.63 (m, 1H), 2.53-2.49 (m, 1H), 2.32-2.24 (m, 4H), 1.91-1.85 (m, 1H); LC MS: ES+ 327.2.

Compound 94

1H NMR (400 MHz, DMSO-d6) δ 10.83 (s, 1H), 7.40-7.28 (m, 1H), 5.02-4.65 (m, 1H), 3.83-3.81 (m, 3H), 2.87-2.65 (m, 4H), 2.57-2.50 (m, 1H), 2.43-2.31 (m, 1H), 1.95-1.79 (m, 2H), 0.97-0.84 (m, 2H), 0.79-0.52 (m, 2H); LC MS: ES+ 291.2.

Compound 95

1H NMR (400 MHz, DMSO-d6) δ 10.88 (brs, 1H), 7.31-7.08 (m, 4H), 5.14 (brs, 0.6H), 4.25 (brs, 0.4H), 2.83-1.95 (m, 11H); LC MS: ES– 259.1.

Compound 96

1H NMR (400 MHz, DMSO-d6) δ 10.92 (s, 1H), 7.96-7.90 (m, 2H), 7.61 (d, J=7.36 Hz, 1H), 7.51 (d, J=7.60 Hz, 1H), 5.13 (m, 0.5H), 4.44-4.42 (m, 0.5H), 2.82 (s, 1.5H), 2.78 (s, 1.5H), 2.66-2.33 (m, 3H), 1.98 (brs, 1H); LC MS: ES− 270.1.

Compound 97

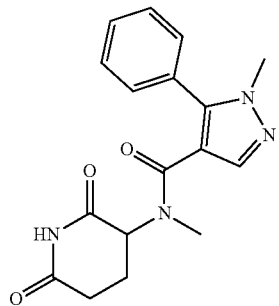

1H NMR (400 MHz, DMSO-d6) δ 10.80 (brs, 1H), 7.68 (s, 0.5H), 7.55 (s, 0.5H), 7.48 (s, 5H), 4.95 (brs, 0.5H), 4.63-461 (m, 0.5H), 3.80 (s, 1.5H), 3.75 (s, 1.5H), 2.75-2.60 (m, 4H), 2.32-2.05 (m, 2H), 1.73-1.70 (m, 0.5H), 0.79-0.75 (m, 0.5H); LC MS: ES− 325.2; LC MS: ES− 338.1.

Compound 98

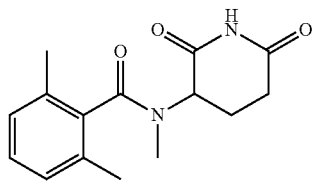

1H NMR (400 MHz, DMSO-d6) δ 10.8 (brs, 1H), 8.24 (d, J=2.4 Hz, 1H), 5.25 (d, J=11.6 Hz, 1H), 2.84-2.79 (m, 1H), 2.73 (s, 2H), 2.61-2.51 (m, 1H), 2.42-2.38 (m, 1H), 1.96-1.88 (m, 1H).

Compound 99

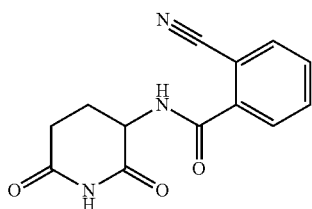

1H NMR (400 MHz, DMSO-d6) δ 10.89 (s, 1H), 7.19 (t, J=7.6 Hz, 1H), 7.08 (d, J=7.6 Hz, 2H), 5.14 (brs, 1H), 2.91-2.77 (m, 1H), 2.64 (s, 3H), 2.61-2.52 (m, 1H), 2.42 (m, 1H), 2.24 (s, 3H), 2.18 (s, 3H), 1.95 (s, 1H); LC MS: ES+ 275.2.

Compound 100

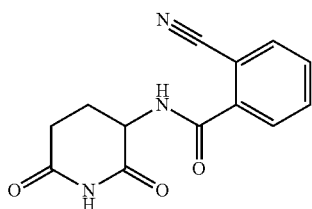

1H NMR (400 MHz, DMSO-d6) δ 1.75 (brs, 1H), 7.94-7.90 (m, 4H), 5.16 (dd, J=12.8, 5.08 Hz, 1M), 2.94-2.85 (m, 1H), 2.62-2.51 (m, 2H), 2.08-2.05 (m, 1H); LC MS: ES− 257.1.

Compound 101

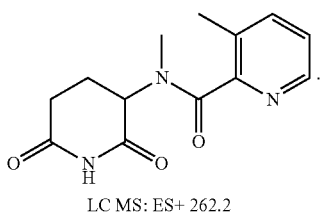

LC MS: ES+ 262.2

Compound 102

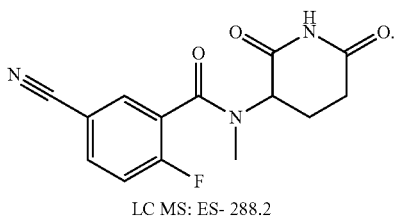

LC MS: ES− 288.2

Compound 103

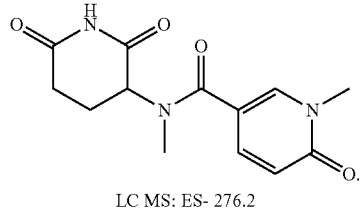

LC MS: ES− 276.2

Compound 104

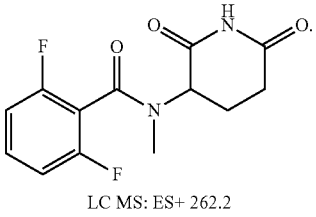

LC MS: ES+ 262.2

Compound 105

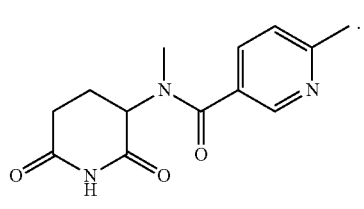

LC MS: ES+ 283.0

Scheme 2B

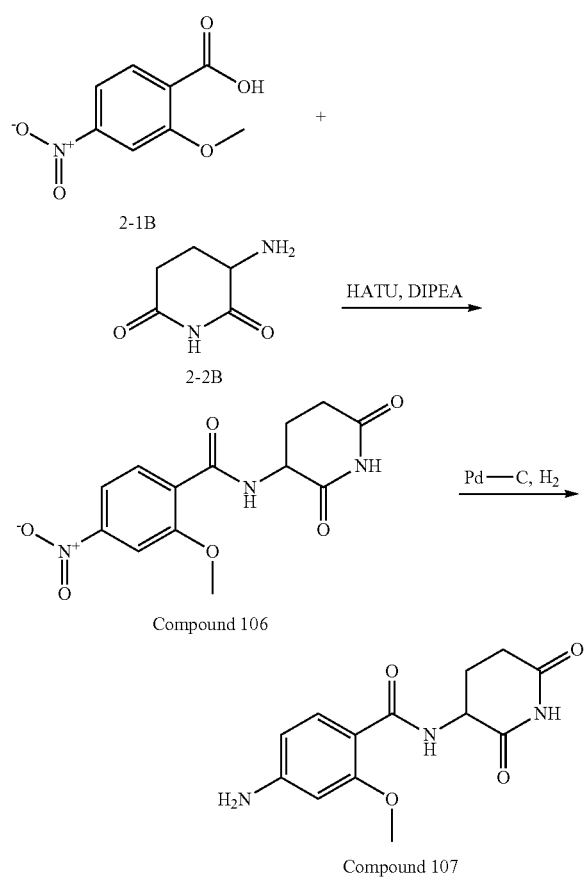

4-amino-N-(2,6-dioxo-3-piperidyl)-2-methoxy-benzamide (compound 107) $^1$H NMR (400 MHz, DMSO-$d_6$) δ 10.81 (s, 1H), 8.31 (d, J=6.9 Hz, 1H), 7.63 (dd, J=8.5, 1.0 Hz, 1H), 6.23 (d, J=1.9 Hz, 1H), 4.66 (ddd, J=12.2, 6.6, 5.3 Hz, 1H), 3.82 (s, 3H), 2.71 (m, 2H), 2.17-1.94 (m, 2H). LC MS: ES+ 278.1.

Scheme 3

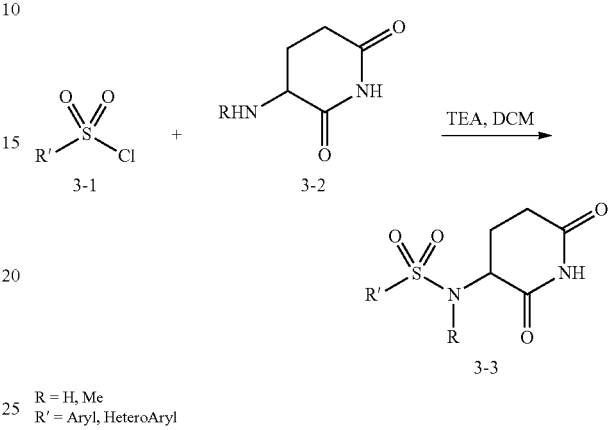

R = H, Me
R' = Aryl, HeteroAryl

General Procedure:

To the mixture of compound amine (100 mg) in DCM (3 ml) were added TEA (3 eq) and sulfonyl chloride (1.1 eq) under ice cold condition. The reaction mixture was stirred at RT for 16 h. At completion, reaction mixture was evaporated and dissolved in DMF. Crude material was submitted for prep-HPLC purification.

General Methods for Prep HPLC Purification:

Method-1

Preparative HPLC was done on Waters auto purification instrument. Column name:—YMC-Actus Triart C18 (100× 30 mm, 5μ) operating at ambient temperature and flow rate of 30.0 ml/min. Mobile phase: A=20 mM $NH_4HCO_3$ in water, B=Acetonitrile; Gradient Profile: Mobile phase initial composition of 80% A and 20% B, then to 65% A and 35% B in 2 min., then to 25% A and 75% B in 12 min., then to 5% A and 95% B in 13 min., held this composition up to 15 min. for column washing, then returned to initial composition in 16 min. and held till 18 min.

Method-2

Preparative HPLC was done on Waters auto purification instrument. Column name: —YMC-Actus Triart C18 (250× 20 mm, 5μ) operating at ambient temperature and flow rate of 20.0 ml/min. Mobile phase: A=10 mM $NH_4OAc$ in water, B=Acetonitrile; Gradient Profile: Mobile phase initial composition of 70% A and 30% B, then to 45% A and 55% B in 3 min., then to 25% A and 75% B in 18 min., then to 5% A and 95% B in 19 min., held this composition up to 21 min. for column washing, then returned to initial composition in 22 min. and held till 25 min.

Method-3

Preparative HPLC was done on Waters auto purification instrument. Column name: —YMC-Actus Triart C18 (250× 20 mm, 5μ) operating at ambient temperature and flow rate of 20.0 ml/min. Mobile phase: A=0.1% Formic acid in water, B=Acetonitrile; Gradient Profile: Mobile phase initial composition of 80% A and 20% B, then to 70% A and 30% B in 3 min., then to 25% A and 75% B in 18 min., then to 5% A and 95% B in 19 min., held this composition up to 21

Step 1: Preparation of Compound 106

2-Methoxy-4-nitro-benzoic acid (474.33 mg, 2.41 mmol) and 3-aminopiperidine-2,6-dione (330 mg, 2.00 mmol, HCl) mixed in DMF (5 mL) at 0° C., followed by HATU (991.06 mg, 2.61 mmol) and diisopropylethylamine (777.37 mg, 6.01 mmol, 1.05 mL). The reaction mixture was stirred at room temp for 2 hrs, from [15:34]. HPLC and MS indicate all starting materials were consumed and product present as the main peak. Dilute with 15 mL EtOAc, isolate via filtration. cake was washed by water 3 times (10 mL each). Obtain compound 106 as white solid N-(2,6-dioxo-3-piperidyl)-2-methoxy-4-nitro-benzamide (495 mg, 1.61 mmol, 80.35% yield) $^1$H NMR (400 MHz, DMSO-$d_6$) δ 10.88 (s, 1H), 8.73 (d, J=7.8 Hz, 1H), 8.02-7.80 (m, 2H), 4.76 (dt, J=11.5, 6.9 Hz, 1H), 4.00 (s, 3H), 2.77 (ddd, J=24.3, 12.4, 6.5 Hz, 1H), 2.54 (d, J=3.8 Hz, 1H), 2.23-2.00 (m, 2H). LC MS: ES+ 308.2.

Step 2: Preparation of Compound 107

Add N-(2,6-dioxo-3-piperidyl)-2-methoxy-4-nitro-benzamide (300 mg, 976.38 umol) and Palladium, 5% on activated carbon paste, 5R437 (2.08 mg, 19.53 umol) to 20 mL vial, followed by DMF (4 mL), then purge with nitrogen at room temp for 15 mins. Hydrogen/vacuum purge 3 times, then let reaction mixture stirred at room temp under hydrogen atmosphere. The final product was isolated after celite pad filtration and concentration to afford white foam

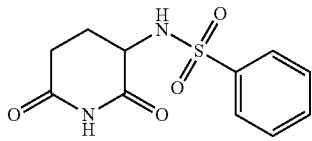

Compound 108

1H NMR (400 MHz, DMSO-d6) δ 10.77 (s, 1H), 8.15 (d, J=8.4 Hz, 1H), 7.88-7.81 (m, 2H), 7.66-7.58 (m, 1H), 7.57 (dd, J=8.2, 6.4 Hz, 2H), 4.24 (q, J=8.5 Hz, 1H), 2.65 (dt, J=17.8, 9.3 Hz, 1H), 2.49-2.38 (m, 1H), 1.80 (dt, J=10.5, 5.2 Hz, 2H); LC MS: ES+ 269.0.

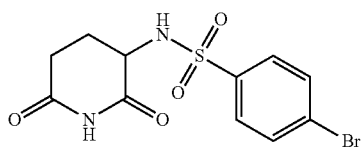

Compound 109

1H NMR (400 MHz, DMSO-d6) δ 10.77 (s, 1H), 8.29 (d, J=8.5 Hz, 1H), 7.82-7.72 (m, 4H), 4.26 (ddd, J=11.0, 8.4, 6.1 Hz, 1H), 2.67 (ddd, J=17.9, 11.7, 6.3 Hz, 1H), 2.49-2.39 (m, 1H), 1.90-1.74 (m, 2H); LC MS: ES− 345.0.

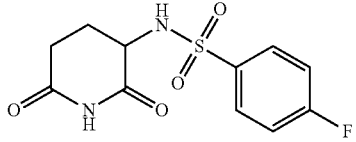

Compound 110

1H NMR (400 MHz, DMSO-d6) δ 10.78 (s, 1H), 8.12 (s, 1H), 7.89 (dt, J=8.7, 4.4 Hz, 2H), 7.41 (dd, J=10.1, 7.2 Hz, 2H), 4.25 (dd, J=10.7, 6.4 Hz, 1H), 2.73-2.59 (m, 1H), 2.44 (dd, J=17.5, 4.0 Hz, 1H), 1.88-1.76 (m, 2H); LC MS: ES− 285.1.

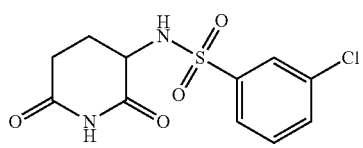

Compound 111

1H NMR (400 MHz, DMSO-d6) δ 10.79 (s, 1H), 8.38 (d, J=7.8 Hz, 1H), 7.87 (t, J=2.1 Hz, 1H), 7.79 (d, J=7.8 Hz, 1H), 7.70 (dd, J=7.9, 2.3 Hz, 1H), 7.60 (t, J=8.0 Hz, 1H), 4.32 (d, J=15.2 Hz, 1H), 2.68 (ddd, J=17.8, 11.6, 6.5 Hz, 1H), 2.46 (d, J=21.4 Hz, 1H), 1.85 (dq, J=13.0, 8.5, 6.1 Hz, 2H); LC MS: ES− 301.0 (Cl pattern observed).

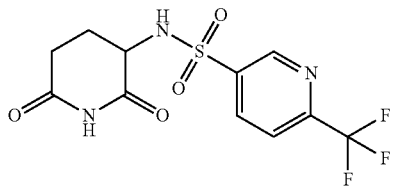

Compound 112

1H NMR (400 MHz, DMSO-d6) δ 10.79 (s, 1H), 9.14 (d, J=2.1 Hz, 1H), 8.76 (d, J=8.8 Hz, 1H), 8.47 (dd, J=8.3, 2.1 Hz, 1H), 8.15 (d, J=8.3 Hz, 1H), 4.43 (ddd, J=12.0, 8.7, 5.5 Hz, 1H), 2.51-2.48 (m, 1H), 2.70 (ddd, J=18.1, 12.8, 5.8 Hz, 1H), 2.04-1.82 (m, 2H); LC MS: ES− 336.1.

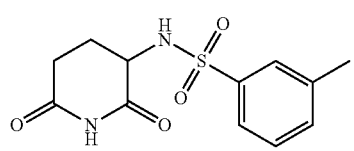

Compound 113

1H NMR (400 MHz, DMSO-d6) δ 10.78 (s, 1H), 8.12-8.06 (m, 1H), 7.69-7.61 (m, 2H), 7.47-4.43 (m, 2H), 4.29-4.20 (m, 1H), 2.65 (dt, J=18.0, 9.4 Hz, 1H), 2.48-2.38 (m, 1H), 2.38 (s, 3H), 1.80 (dt, J=11.1, 5.4 Hz, 2H); LC MS: ES− 281.1.

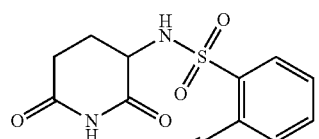

Compound 114

1H NMR (400 MHz, DMSO-d6) δ 10.79 (s, 1H), 8.56 (s, 1H), 8.08 (dd, J=7.8, 4.0 Hz, 2H), 7.88 (t, J=7.8 Hz, 1H), 7.80 (t, J=7.6 Hz, 1H), 4.31 (t, J=8.7 Hz, 1H), 2.49-2.46 (m, 1H), 2.76-2.62 (m, 1H), 1.96 (dt, J=13.6, 6.6 Hz, 2H); LC MS: ES− 301.0.

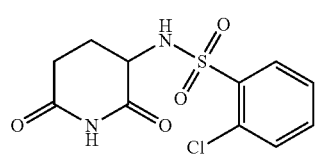

Compound 115

1H NMR (400 MHz, DMSO-d6) δ 10.78 (s, 1H), 8.29-8.25 (m, 1H), 8.03 (d, J=7.8 Hz, 1H), 7.69-7.57 (m, 2H), 7.51 (t, J=7.5 Hz, 1H), 4.26 (d, J=10.0 Hz, 1H), 2.70-2.62 (m, 1H), 2.49-2.43 (m, 1H), 1.96-1.88 (m, 2H); LC MS: ES− 301.1 (Cl pattern observed).

Compound 116

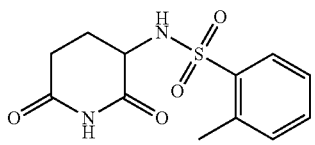

1H NMR (400 MHz, DMSO-d6) δ 10.77 (s, 1H), 8.20-8.13 (m, 1H), 7.90 (d, J=7.8 Hz, 1H), 7.50 (t, J=7.5 Hz, 1H), 7.42-7.30 (m, 2H), 4.19-4.14 (m, 1H), 2.64-2.56 (m, 4H), 2.48-2.38 (m, 1H), 1.84 (tt, J=7.6, 4.1 Hz, 2H); LC MS: ES− 281.1.

Compound 117

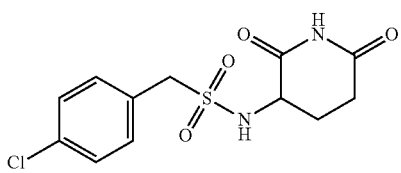

1H NMR (400 MHz, DMSO-d6) δ 10.92 (s, 1H), 7.71-7.69 (m, 1H), 7.48-7.40 (m, 4H), 4.47 (s, 2H), 4.30 (d, J=11.4 Hz, 1H), 2.71-2.66 (m, 1H), 2.52-2.49 (m, 1H), 2.00-1.99 (m, 1H), 1.99-1.90 (m, 1H); LC MS: ES− 315.1 (Cl pattern observed).

Compound 118

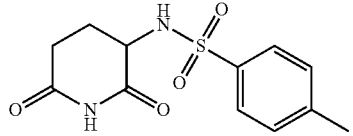

1H NMR (400 MHz, DMSO-d6) δ 10.76 (s, 1H), 8.04 (s, 1H), 7.72 (d, J=8.1 Hz, 2H), 7.37 (d, J=8.0 Hz, 2H), 4.20-4.17 (m, 1H), 2.71-2.57 (m, 1H), 2.43 (dt, J=17.2, 3.9 Hz, 1H), 2.38 (s, 3H), 1.78 (td, J=11.5, 10.1, 4.5 Hz, 2H); LC MS: ES− 281.1.

Compound 119

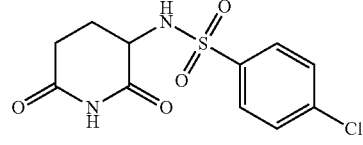

1H NMR (400 MHz, DMSO-d6) δ 10.77 (s, 1H), 8.29 (s, 1H), 7.88-7.80 (m, 2H), 7.68-7.61 (m, 2H), 4.26 (dd, J=11.1, 6.2 Hz, 1H), 2.67 (ddd, J=18.0, 11.7, 6.4 Hz, 1H), 2.44 (dd, J=17.4, 4.0 Hz, 1H), 1.89-1.74 (m, 2H); LC MS: ES− 301.0.

Compound 120

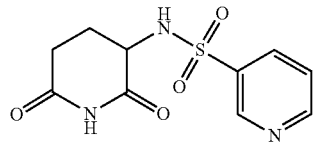

1H NMR (400 MHz, DMSO-d6) δ 10.77 (s, 1H), 8.98 (d, J=2.4 Hz, 1H), 8.78 (d, J=4.8 Hz, 1H), 8.47 (s, 1H), 8.20 (d, J=8.0 Hz, 1H), 7.61 (dd, J=8.2, 4.8 Hz, 1H), 4.36-4.33 (m, 1H), 2.73-2.62 (m, 1H), 2.50-2.44 (m, 1H), 1.89-1.87 (m, 2H); LC MS: ES+ 270.1.

Compound 121

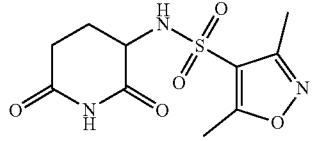

1H NMR (400 MHz, DMSO-d6) δ 10.81 (s, 1H), 8.46 (s, 1H), 4.16 (dd, J=12.0, 5.5 Hz, 1H), 2.71 (ddd, J=17.6, 12.3, 5.6 Hz, 1H), 2.57 (s, 3H), 2.49-2.46 (m, 1H), 2.36 (s, 3H), 1.91 (ddd, J=24.7, 10.2, 4.4 Hz, 2H); LC MS: ES− 286.0.

Compound 122

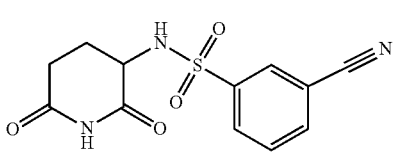

1H NMR (400 MHz, DMSO-d6) 10.79 (s, 1H), 8.47 (s, 1H), 8.25 (s, 1H), 8.12 (t, J=9.3 Hz, 2H), 7.79 (t, J=7.8 Hz, 1H), 4.35 (dd, J=11.8, 5.8 Hz, 1H), 2.70-2.67 (m, 1H), 2.64 (d, J=5.9 Hz, 1H), 1.93-1.80 (m, 2H); LC MS: ES− 292.1.

Compound 123

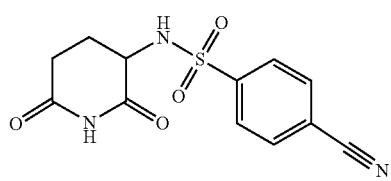

1H NMR (400 MHz, DMSO-d6) δ 10.79 (s, 1H), 8.53 (d, J=8.0 Hz, 1H), 8.07 (d, J=8.2 Hz, 2H), 7.99 (d, J=8.0 Hz, 2H), 4.31 (t, J=5.8 Hz, 1H), 2.72-2.63 (m, 1H), 2.49-2.45 (m, 1H), 1.91-1.86 (m, 2H); LC MS: ES− 292.1.

Compound 124

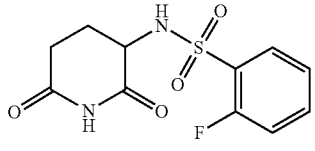

1H NMR (400 MHz, DMSO-d6) δ 10.76 (s, 1H), 8.41-8.36 (m, 1H), 7.82 (t, J=7.5 Hz, 1H), 7.67 (d, J=7.8 Hz, 1H), 7.41 (t, J=9.4 Hz, 1H), 7.34 (t, J=7.7 Hz, 1H), 4.26 (t, J=8.7 Hz, 1H), 2.71 (dd, J=17.8, 9.3 Hz, 1H), 2.46-2.43 (m, 1H), 1.90 (t, J=5.8 Hz, 2H); LC MS: ES− 285.0.

Compound 125

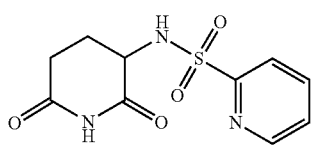

1H NMR (400 MHz, DMSO-d6) δ 10.75 (s, 1H), 8.70 (d, J=4.6 Hz, 1H), 8.29 (s, 1H), 8.06 (td, J=7.8, 1.7 Hz, 1H), 7.94 (d, J=7.9 Hz, 1H), 7.64 (dd, J=7.5, 4.5 Hz, 1H), 4.33 (dd, J=11.7, 5.4 Hz, 1H), 2.68 (ddd, J=17.7, 12.4, 5.6 Hz, 1H), 2.50-2.40 (m, 1H), 1.98-1.76 (m, 2H); LC MS: ES+ 270.0.

Compound 126

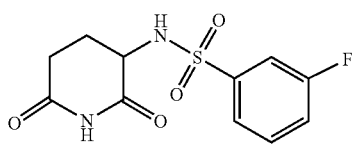

1H NMR (400 MHz, DMSO-d6) δ 10.80 (s, 1H), 8.35 (d, J=8.3 Hz, 1H), 7.72-7.58 (m, 3H), 7.54-7.44 (m, 1H), 4.31 (q, J=8.3 Hz, 1H), 2.65 (s, 1H), 2.50-2.40 (m, 1H), 1.89-1.78 (m, 2H); LC MS: ES− 285.1.

Compound 127

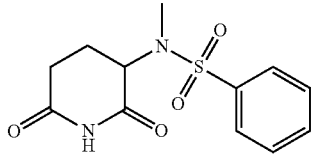

1H NMR (400 MHz, DMSO-d6) δ 10.82 (s, 1H), 7.87-7.80 (m, 2H), 7.67 (t, J=7.3 Hz, 1H), 7.59 (t, J=7.6 Hz, 2H), 4.94 (dd, J=13.1, 5.1 Hz, 1H), 2.84-2.76 (m, 1H), 2.66 (s, 3H), 2.47-2.46 (m, 1H), 2.22 (dd, J=13.6, 9.2 Hz, 1H), 1.63-1.60 (m, 1H); LC MS: ES− 281.1.

Compound 128

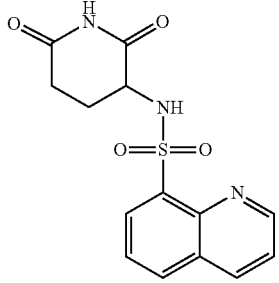

1H NMR (400 MHz, DMSO-d6) δ 10.73 (s, 1H), 9.09 (dd, J=4.4, 1.9 Hz, 1H), 8.55 (dd, J=8.4, 1.9 Hz, 1H), 8.31 (dd, J=13.3, 7.7 Hz, 2H), 7.79-7.67 (m, 3H), 4.38 (dt, J=12.2, 6.2 Hz, 1H), 2.69-2.61 (m, 1H), 2.42 (d, J=17.7 Hz, 1H), 1.95-1.83 (m, 2H); LC MS: ES+ 320.0.

Compound 129

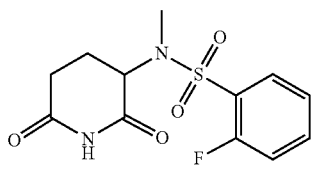

1H NMR (400 MHz, DMSO-d6) δ 10.84 (s, 1H), 7.84 (t, J=7.1 Hz, 1H), 7.71 (dt, J=12.5, 6.6 Hz, 1H), 7.48-7.33 (m, 2H), 4.87 (dd, J=13.1, 5.2 Hz, 1H), 2.85 (ddd, J=18.4, 13.8, 5.2 Hz, 1H), 2.76 (s, 3H), 2.56-2.50 (m, 1H), 2.30 (dd, J=13.0, 4.4 Hz, 1H), 1.80-1.72 (m, 1H); LC MS: ES− 299.0.

Compound 130

1H NMR (400 MHz, DMSO-d6) δ 10.82 (s, 1H), 7.90 (ddd, J=8.1, 5.2, 2.5 Hz, 2H), 7.48-7.38 (m, 2H), 4.94 (dd, J=13.1, 5.1 Hz, 1H), 2.81 (ddd, J=17.9, 13.7, 5.2 Hz, 1H), 2.67 (s, 3H), 2.48-2.45 (m, 1H), 2.23 (qd, J=13.0, 4.4 Hz, 1H), 1.73-1.64 (m, 1H); LC MS: ES− 299.0.

Compound 131

1H NMR (400 MHz, DMSO-d6) δ 10.83 (s, 1H), 7.72-7.61 (m, 3H), 7.54 (s, 1H), 4.97 (dd, J=13.0, 5.1 Hz, 1H), 2.80 (td, J=13.5, 7.0 Hz, 1H), 2.69 (d, J=4.0 Hz, 3H), 2.55-2.50 (m, 1H), 2.25 (dd, J=13.1, 4.5 Hz, 1H), 1.74-1.65 (m, 1H); LC MS: ES− 299.1.

Compound 132

1H NMR (400 MHz, DMSO-d6) δ 10.83 (s, 1H), 7.87 (d, J=2.4 Hz, 1H), 7.77 (dd, J=21.4, 7.9 Hz, 2H), 7.62 (dd, J=9.8, 6.0 Hz, 1H), 4.99 (dd, J=13.0, 5.2 Hz, 1H), 2.85-2.76 (m, 1H), 2.70 (s, 3H), 2.55-2.50 (m, 1H), 2.25 (dt, J=14.4, 7.1 Hz, 1H), 1.72 (dd, J=10.1, 5.2 Hz, 1H); LC MS: ES− 315.0.

Compound 133

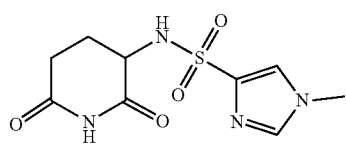

1H NMR (400 MHz, DMSO-d6) δ 10.78 (s, 1H), 7.76-7.71 (m, 2H), 7.10-7.70 (m, 1H), 4.19-4.12 (m, 1H), 3.69 (s, 3H), 2.68-2.58 (m, 1H), 2.49-2.43 (m, 1H), 1.93-1.95 (m, 1H), 1.83-1.80 (m, 1H); LC MS: ES− 271.0.

Compound 134

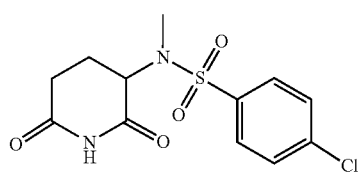

1H NMR (400 MHz, DMSO-d6) δ 10.82 (s, 1H), 7.87-7.80 (m, 2H), 7.70-7.62 (m, 2H), 4.94 (dd, J=13.0, 5.1 Hz, 1H), 2.81 (ddd, J=17.6, 13.7, 5.0 Hz, 1H), 2.68 (s, 3H), 2.49-2.45 (m, 1H), 2.31-2.17 (m, 1H), 1.69-1.67 (m, 1H); LC MS: ES+ 315.0 (Cl pattern observed).

Compound 135

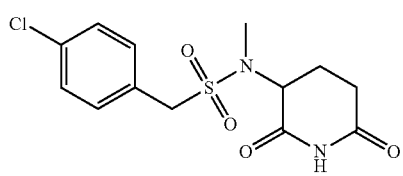

1H NMR (400 MHz, DMSO-d6) δ 10.96 (s, 1H), 7.46 (s, 4H), 4.73 (dd, J=13.0, 5.1 Hz, 1H), 4.57 (d, J=13.8 Hz, 1H), 4.46 (d, J=13.7 Hz, 1H), 2.80-2.72 (m, 1H), 2.67 (s, 3H), 2.56-2.50 (m, 1H), 2.35-2.20 (m, 1H), 1.81-1.75 (m, 1H); LC MS: ES− 329.0 (Cl pattern observed).

Compound 136

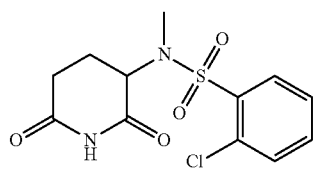

1H NMR (400 MHz, DMSO-d6) δ 10.88 (s, 1H), 8.08 (d, J=7.6 Hz, 1H), 7.71-7.62 (m, 2H), 7.59-7.49 (m, 1H), 4.90 (dd, J=13.2, 5.0 Hz, 1H), 2.85 (ddd, J=17.8, 13.5, 5.2 Hz, 1H), 2.74 (s, 3H), 2.59-2.48 (m, 1H), 2.38-2.23 (m, 1H), 1.84-1.76 (m, 1H); LC MS: ES− 315.0 (Cl pattern observed).

Compound 137

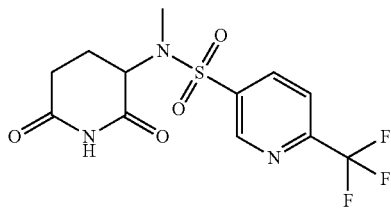

1H NMR (400 MHz, DMSO-d6) δ 10.84 (s, 1H), 9.16 (s, 1H), 8.50 (dd, J=8.4, 2.2 Hz, 1H), 8.16 (d, J=8.3 Hz, 1H), 5.05 (dd, J=13.0, 5.2 Hz, 1H), 2.83-2.79 (m, 1H), 2.76 (s, 3H), 2.59-2.56 (m, 1H), 2.36-2.30 (m, 1H), 1.86-1.84 (m, 1H); LC MS: ES− 350.0.

Compound 138

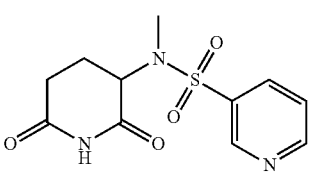

1H NMR (400 MHz, DMSO-d6) δ 10.82 (s, 1H), 8.98 (s, 1H), 8.82 (s, 1H), 8.21 (d, J=8.0 Hz, 1H), 7.67-7.60 (m, 1H), 5.00-4.98 (m, 1H), 3.31-3.00 (m, 1H), 2.98 (s, 3H), 2.50-2.49 (m, 1H), 2.29-2.07 (m, 1H), 1.80-1.71 (m, 1H); LC MS: ES− 282.1.

Compound 139

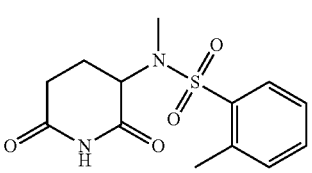

1H NMR (400 MHz, DMSO-d6) δ 10.87 (s, 1H), 7.95 (d, J=7.8 Hz, 1H), 7.55 (t, J=7.4 Hz, 1H), 7.46-7.35 (m, 2H), 4.83 (dd, J=12.8, 5.1 Hz, 1H), 2.86-2.81 (m, 1H), 2.68 (s, 3H), 2.57 (s, 3H), 2.50-2.49 (m, 1H), 2.33-2.28 (m, 1H), 1.81-1.80 (m, 1H); LC MS: ES− 295.1.

Compound 140

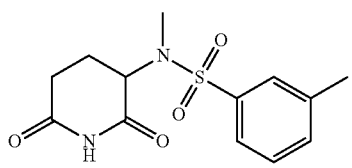

1H NMR (400 MHz, DMSO-d6) δ 10.81 (s, 1H), 7.65 (d, J=12.8 Hz, 2H), 7.47 (d, J=4.6 Hz, 2H), 4.92 (dd, J=13.2, 5.0 Hz, 1H), 2.84-2.80 (m, 1H), 2.66 (s, 3H), 2.49-2.46 (m, 1H), 2.39 (s, 3H), 2.23-2.15 (m, 1H), 1.62-1.59 (m, 1H); LC MS: ES− 295.1.

Compound 141

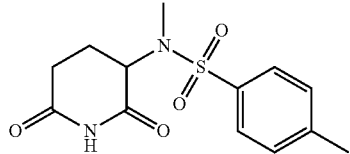

1H NMR (400 MHz, DMSO-d6) δ 10.80 (s, 1H), 7.72 (d, J=7.8 Hz, 2H), 7.39 (d, J=7.9 Hz, 2H), 4.91 (dd, J=13.1, 5.0 Hz, 1H), 2.83-2.80 (m, 1H), 2.64 (s, 3H), 2.49-2.43 (m, 1H), 2.39 (s, 3H), 2.22-2.14 (m, 1H), 1.62-1.60 (m, 1H); LC MS: ES− 295.1.

Compound 142

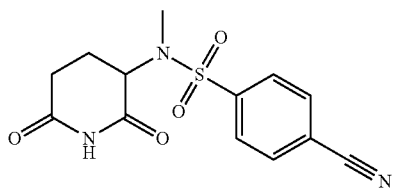

1H NMR (400 MHz, DMSO-d6) δ 10.83 (s, 1H), 8.08 (d, J=7.9 Hz, 2H), 8.00 (d, J=8.1 Hz, 2H), 4.97 (dd, J=13.0, 5.1 Hz, 1H), 2.84-2.77 (m, 1H), 2.71 (s, 3H), 2.49-2.46 (m, 1H), 2.35-2.22 (m, 1H), 1.78-1.69 (m, 1H); LC MS: ES− 306.1.

Compound 143

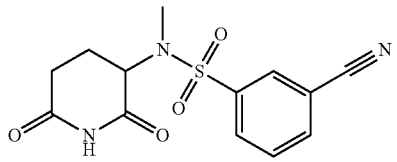

1H NMR (400 MHz, DMSO-d6) δ 10.83 (s, 1H), 8.30 (s, 1H), 8.14 (d, J=7.8 Hz, 2H), 7.80 (t, J=7.9 Hz, 1H), 5.00 (dd, J=13.0, 5.0 Hz, 1H), 2.88-2.74 (m, 1H), 2.71 (s, 3H), 2.49-2.46 (m, 1H), 2.32-2.08 (m, 1H), 1.77-1.75 (m, 1H); LC MS: ES− 306.1.

Compound 144

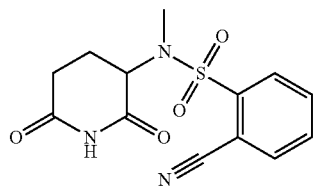

1H NMR (400 MHz, DMSO-d6) δ 10.87 (s, 1H), 8.11 (dd, J=7.7, 3.4 Hz, 2H), 7.88 (dt, J=24.5, 7.6 Hz, 2H), 4.92 (dd, J=12.9, 5.1 Hz, 1H), 2.84-2.78 (m, 4H), 2.58-2.52 (m, 1H), 2.41-2.26 (m, 1H), 1.90-1.81 (m, 1H); LC MS: ES− 306.1.

Compound 145

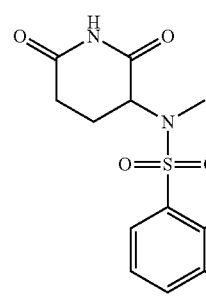

1H NMR (400 MHz, DMSO-d6) δ 10.77 (s, 1H), 9.08 (d, J=4.2 Hz, 1H), 8.53 (d, J=8.3 Hz, 1H), 8.39 (d, J=7.2 Hz, 1H), 8.29 (d, J=8.1 Hz, 1H), 7.79-7.65 (m, 2H), 5.36 (dd, J=13.4, 4.8 Hz, 1H), 2.96-2.83 (m, 1H), 2.76 (s, 3H), 2.49-2.46 (m, 1H), 2.20-2.05 (m, 1H), 1.63 (s, 1H); LC MS: ES+ 334.1.

Compound 146

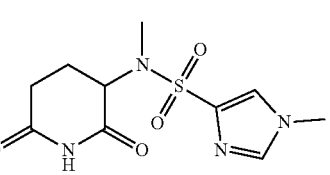

1H NMR (400 MHz, DMSO-d6) δ 10.82 (s, 1H), 7.78 (d, J=5.1 Hz, 2H), 4.80 (dd, J=13.7, 4.8 Hz, 1H), 3.70 (s, 3H), 2.79-2.66 (m, 1H), 2.62 (s, 3H), 2.49-2.46 (m, 1H), 2.13-2.05 (m, 1H), 1.89-1.86 (m, 1H); LC MS: ES+ 287.1.

Compound 147

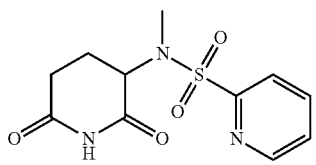

1H NMR (400 MHz, DMSO-d6) δ 10.82 (s, 1H), 8.73 (d, J=4.5 Hz, 1H), 8.12-8.04 (m, 1H), 7.93 (d, J=7.8 Hz, 1H), 7.67 (dd, J=7.6, 4.6 Hz, 1H), 4.89 (dd, J=13.2, 5.0 Hz, 1H), 3.09-2.80 (m, 1H), 2.77 (s, 3H), 2.47-2.43 (m, 1H), 2.31-2.16 (m, 1H), 1.81-1.75 (m, 1H); LC MS: ES+ 284.1.

Example 3: Illustrative Preparation of 3-Substituted-2,6-Dioxopiperdine Intermediates Via LHMDS Mediated SN2 on 3-Br-Glutarimide Scheme 4

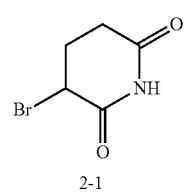

2-1

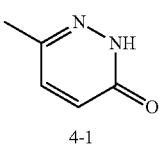

4-1

1. LiHMDS
   THF, -30° C., 1 h
2. 70° C., ON
→

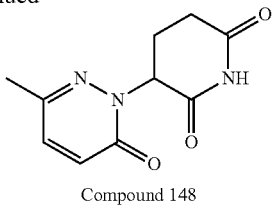

Compound 148

Preparation of 3-(3-Methyl-6-oxopyridazin-1(6H)-yl)piperidine-2,6-dione (Compound 148)

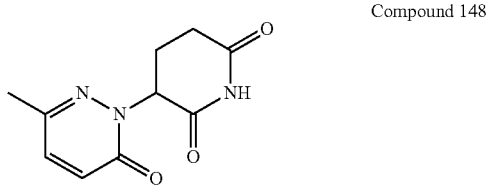 [SMILES: Cc1ccc(=O)n(C2CCC(=O)NC2=O)n1]

Compound 148

To a stirred solution of 6-methylpyridazin-3(2H)-one 4-1 (300 mg, 2.72 mmol)) in THF (10 ml) at −30° C. was added LiHMDS (4.08 ml, 4.08 mmol), reaction mixture stirred for 1 h followed by addition of 3-bromopiperidine-2,6-dione 2-1 (522 mg, 2.72 mmol), gradually warming up to room temperature and finally heating under reflux overnight. After complete consumption of 4-1 as evident from TLC, the reaction mass was quenched with ice water, volatiles stripped off, residue partitioned between ethyl acetate and water, combined organic extracts dried over sodium sulphate, concentrated, the residual crude purified by column chromatography (elution with 2% MeOH/DCM) to afford 3-(3-methyl-6-oxopyridazin-1(6H)-yl)piperidine-2,6-dione Compound 148 (80.0 mg, 361 μmol, 13.3%) as an off white solid. $^1$H NMR (400 MHz, DMSO-$d_6$) δ 10.99 (brs, 1H), 7.36 (d, J=9.44 Hz, 1H), 6.93 (d, J=9.44 Hz, 1H), 5.60-5.62 (m, 1H), 2.82-2.89 (m, 1H), 2.44-2.66 (m, 2H), 2.25 (s, 3H), 2.05 (m, 1H). LC MS: ES+ 222.3.

Scheme 5

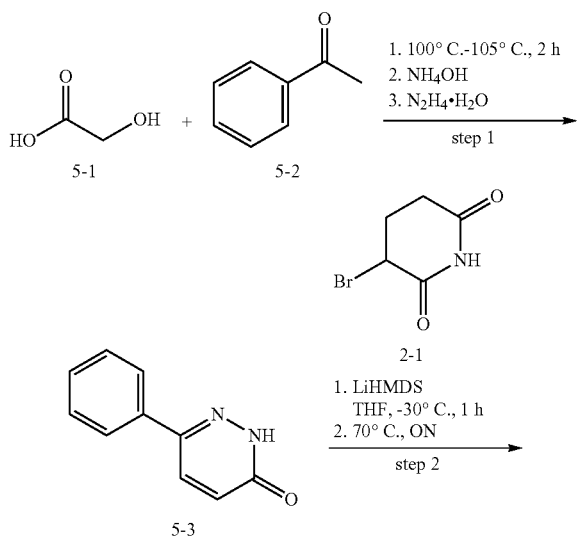

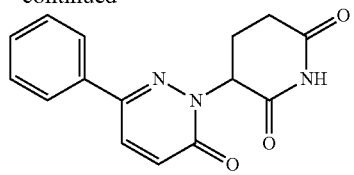

Compound 149

Preparation of 6-Phenylpyridazin-3(2H)-one 5-3

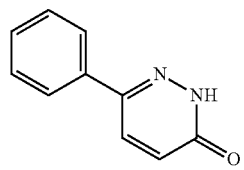 [SMILES: O=c1ccc(-c2ccccc2)n[nH]1]

A mixture of Cpd-5-1(1 g, 13.5 mmol) and 5-2 (4.88 g, 40.5 mmol) was heated at 110° C. for 2 h, cooled down to 40° C. followed by addition of water (4.5 ml) and concentrated aqueous ammonia (1 ml). The reaction mixture was thereafter extracted with DCM, organic part was separated and the ammoniacal aqueous layer was treated with hydrazine hydrate (676 mg, 13.5 mmol) followed by heating at 100° C. for 2 h, reaction mass cooled down to room temperature, precipitate formed was collected by filtration, residue dried under vacuum to afford 6-phenylpyridazin-3(2H)-one 5-3 (417 mg, 2.42 mmol, 17.9%) as an off-white solid. LC MS: ES+ 173.3.

Preparation of 3-(6-Oxo-3-phenylpyridazin-1(6H)-yl)piperidine-2,6-dione (Compound 149)

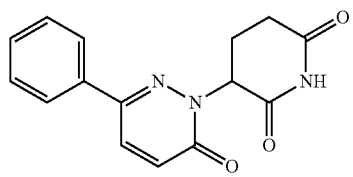 [SMILES: O=C1CCC(n2nc(-c3ccccc3)ccc2=O)C(=O)N1]

To a stirred solution of 6-phenylpyridazin-3(2H)-one 3 (200 mg, 1.16 mmol) in THF(5 mL) at −30° C. was added LiHMDS (1.74 mL, 1.74 mmol), stirred for 1 h followed by addition of 3-bromopiperidine-2,6-dione 4 (266 mg, 1.39 mmol). The reaction mixture was thereafter gradually warmed up to room temperature followed by heating under reflux overnight. After complete consumption of Cpd-3 as evident from TLC, the reaction mixture was quenched with ice water, volatiles stripped off, residue partitioned between ethyl acetate and water, combined organic extracts dried over sodium sulphate, concentrated, the residual crude purified by preparative TLC to afford 3-(6-oxo-3-phenylpyridazin-1(6H)-yl)piperidine-2,6-dione (Compound 149) (69.4 mg, 245 μmol, 21.1%) as an off-white solid. $^1$H NMR (400 MHz, DMSO-$d_6$) δ 11.08 (s, 1H), 8.10 (d, J=9.72 Hz, 1H), 7.87-7.88 (m, 2H), 7.48-7.50 (m, 3H), 7.13 (d, J=9.96 Hz), 5.80-5.83 (m, 1H), 2.89-2.92 (m, 1H), 2.61-2.64 (m, 2H), 2.17 (m, 1H). LC MS: ES+ 284.3.

Scheme 6

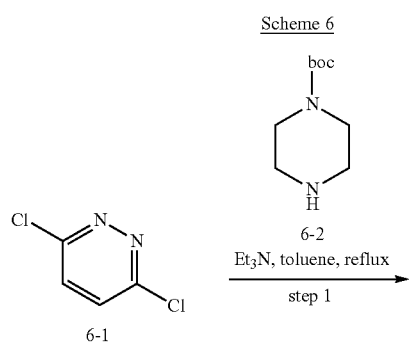

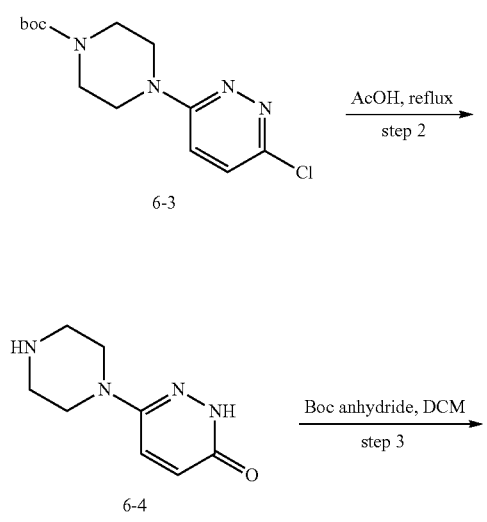

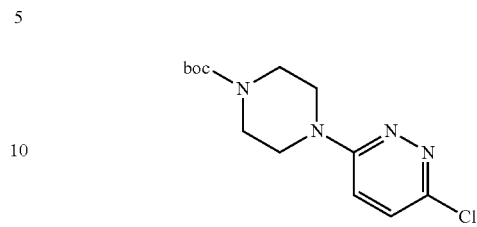

Preparation of tert-Butyl 4-(6-chloropyridazin-3-yl)piperazine-1-carboxylate 6-3

A stirred mixture of 3,6-dichloropyridazine 6-1 (2.0 g, 13.4 mmol), tert-butyl piperazine-1-carboxylate 6-2 (3.72 g, 20.0 mmol) and triethylamine (2.78 mL, 20.0 mmol) in toluene (20 mL) was heated at 110° C. for 16 h. After complete consumption of 6-1 as evident from TLC, the volatiles were stripped off, residue partitioned between ethyl acetate and water, combined organic extracts evaporated to afford a crude residue which was purified column chromatography (elution with 30% ethyl acetate/Hexane) to afford tert-butyl 4-(6-chloropyridazin-3-yl)piperazine-1-carboxylate 6-3 (2.52 g, 8.46 mmol, 63.0%) as an off-white solid. LC MS: ES+299.2.

Preparation of 6-(Piperazin-1-yl)pyridazin-3(2H)-one 6-4

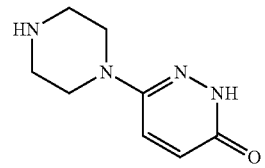 [SMILES: O=c1ccc(N2CCNCC2)n[nH]1]

A solution of tert-butyl 4-(6-chloropyridazin-3-yl)piperazine-1-carboxylate 6-3 (2.2 g, 7.36 mmol) in acetic acid (20 mL) was heated at 120° C. for 16 h. After complete consumption of Cpd-3 as evident from TLC, the volatiles were stripped off, residue partitioned between ethyl acetate and water, combined organic extracts evaporated to afford a crude residue which was purified over neutral alumina (elution with 30% methanol/DCM) to afford 6-(piperazin-1-yl)pyridazin-3(2H)-one 6-4 (871 mg, 4.83 mmol, 65.9%) as a brown solid. LC MS: ES+ 181.1.

Preparation of 6-(Piperazin-1-yl)pyridazin-3(2H)-one 6-5

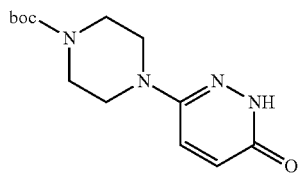

A solution of 6-(piperazin-1-yl)pyridazin-3(2H)-one 6-4 (1 g, 5.54 mmol) in DCM (10 mL) was treated with Boc anhydride (1.32 g, 6.09 mmol) and the mixture stirred for 2 h at rt in presence of Et₃N (848 μL, 6.09 mmol). After complete consumption of 6-4 as evident from TLC, the volatiles were stripped off, residue partitioned between methylene chloride and water, combined organic extracts evaporated to afford a crude residue which was purified over silica (elution with 3% MeOH:DCM) to afford tert-butyl-4-(6-oxo-1,6-dihydropyridazin-3-yl)piperazine-1-carboxylate 6-5 (896 mg, 3.19 mmol, 57.8%) as a white solid. LC MS: ES+ 281.0.

Preparation of Tert-Butyl 4-(1-(2,6-dioxopiperidin-3-yl)-6-oxo-1,6-dihydropyridazin-3-yl)piperazine-1-carboxylate (Compound 150)

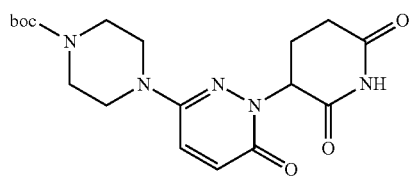

To a stirred solution of tert-butyl 4-(6-oxo-1,6-dihydropyridazin-3-yl)piperazine-1-carboxylate 6-5 (150 mg, 535 µmol) in THF (5 mL) at −30° C. was added LiHMDS (802 µL, 802 µmol), stirred for 1 h followed by addition of 3-bromopiperidine-2,6-dione 2-1 (123 mg, 642 µmol). The reaction mixture was thereafter gradually warmed up to room temperature followed by heating under reflux overnight. After complete consumption of 6-5 as evident from TLC, the reaction mixture was quenched with ice water, volatiles stripped off, residue partitioned between ethyl acetate and water, combined organic extracts dried over sodium sulphate, concentrated, the residual crude purified by preparative HPLC to afford tert-butyl 4-(1-(2,6-dioxopiperidin-3-yl)-6-oxo-1,6-dihydropyridazin-3-yl)piperazine-1-carboxylate (Compound 150) (89.3 mg, 228 µmol, 42.7%) as an off-white solid. $^1$H NMR (400 MHz, DMSO-$d_6$) δ 10.95 (brs, 1H), 7.55 (d, J=9.92 Hz, 1H), 6.91 (d, J=9.92 Hz, 1H), 5.56-5.57 (m, 1H), 3.38 (s, 4H), 3.19 (s, 4H), 2.82-2.88 (m, 1H), 2.59-2.50 (m, 2H), 2.02 (m, 1H), 1.40 (s, 9H). LC MS: ES+ 390.5; LCMS: calculated for [M−H]$^+$ 390.19; found 390.5.

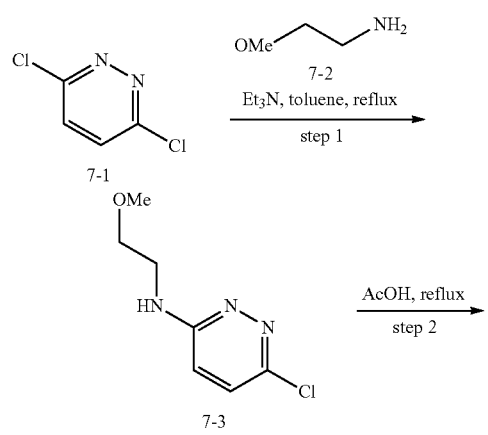

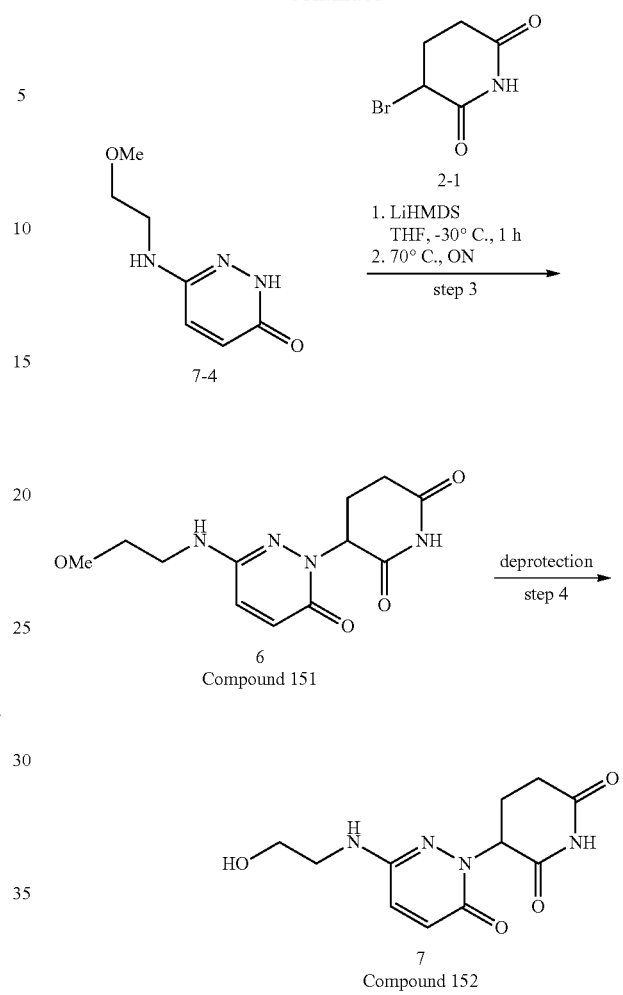

Preparation of 6-Chloro-N-(2-methoxyethyl)pyridazin-3-amine 7-3

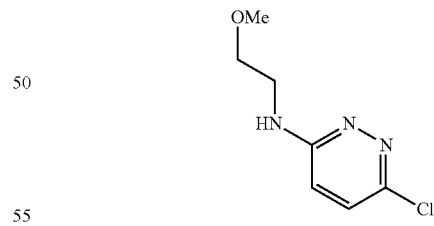

A stirred solution of 7-1 (2 g, 13.4 mmol) and 7-2 (1.20 g, 16.0mmol) in toluene (10 ml) was heated at 120° C. overnight in presence of triethylamine (1.35 g, 13.4 mmol). After complete consumption of 7-1 as evident from TLC, the volatiles were stripped off, residue partitioned between ethyl acetate and water, combined organic extracts evaporated to afford a crude residue which was purified over silica (elution with 2% MeOH/DCM) to afford 6-chloro-N-(2-methoxyethyl)pyridazin-3-amine 7-3 (1.50 g, 7.99 mmol, 59.7%) as an off white solid. LC MS: ES+ 188.1.

Preparation of 6-((2-Methoxyethyl)amino)pyridazin-3(2H)-one 7-4

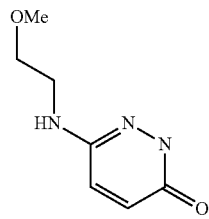 [SMILES: COCCNc1ccc(=O)[nH]n1]

A solution of 6-chloro-N-(2-methoxyethyl)pyridin-2-amine 7-3 (1.5 g, 8.03 mmol) in acetic acid (30 ml) was heated at 120° C. for 2 days. After complete consumption of 7-3 as evident from TLC & LCMS, the reaction mass was concentrated, residue partitioned between ethyl acetate and sodium bicarbonate, combined organic extracts evaporated to afford a crude residue which was purified over silica (elution with 5% MeOH/DCM to afford 6-((2-methoxyethyl)amino)pyridazin-3(2H)-one 7-4 (71.0 mg, 419 µmol, 52.5%) as a light yellow solid. LC MS: ES+ 170.1.

Preparation of 3-(3-((2-Methoxyethyl)amino)-6-oxopyridazin-1(6H)-yl)piperidine-2,6-dione (Compound 151)

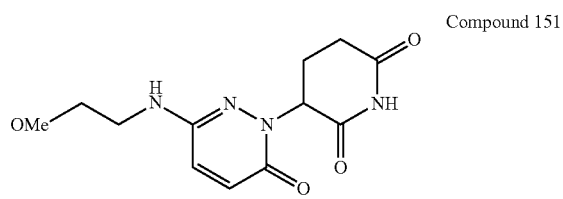 [SMILES: COCCNc1ccc(=O)n(C2CCC(=O)NC2=O)n1]

To a stirred solution of compound 6-((2-methoxyethyl)amino)pyridazin-3(2H)-one 7-4 (400 mg, 2.36 mmol) in THF (3 ml) at −30° C. was added LiHMDS (578 mg, 3.54 mmol) stirred for 1 h followed by addition of 3-bromopiperidine-2,6-dione 2-1 (497 mg, 2.59 mmol. The reaction mixture was thereafter gradually warmed up to room temperature followed by refluxing overnight. After complete consumption of 7-4 as evident from TLC, the reaction mass was quenched with ice water, volatiles stripped off, residue partitioned between ethyl acetate and water, combined organic extracts dried over sodium sulphate, concentrated, the residual crude purified over silica (elution with 2% MeOH/DCM) to afford 3-(3-((2-methoxyethyl)amino)-6-oxopyridazin-1(6H)-yl)piperidine-2,6-dione Compound 151 (300 mg, 1.07 mmol, 45.3%) as an off white solid. $^1$H NMR (400 MHz, DMSO-$d_6$) δ 10.92 (brs, 1H), 7.03 (d, J=9.76 Hz, 1H), 6.77 (d, J=9.64 Hz, 1H), 6.55 (m, 1H), 5.49-5.50 (m, 1H), 3.41-3.42 (m, 2H), 3.25 (s, 3H), 3.17-3.18 (m, 2H), 2.79-2.86 (m, 1H), 2.43-2.59 (m, 2H), 1.98 (m, 1H). LC MS: ES+ 281.3.

Preparation of 3-(3-((2-Hydroxyethyl)amino)-6-oxopyridazin-1(6H)-yl)piperidine-2,6-dione (Compound 152)

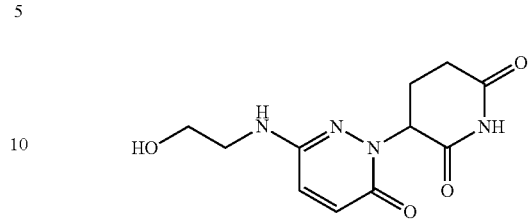

A solution of compound 3-(3-((2-methoxyethyl)amino)-6-oxopyridazin-1(6H)-yl)piperidine-2,6-dione Compound 151 (100 mg, 356 µmol) in DCM (10 ml) at 0° C. was treated with boron tribromide (178 mg, 712 µmol). After complete consumption of Compound 151 as evident from TLC, the reaction mass was concentrated, residue partitioned between ethyl acetate and sodium bicarbonate, combined organic extracts dried over sodium sulphate, concentrated, the residual crude purified over silica (elution with 7% MeOH/DCM to afford 3-(3-((2-hydroxyethyl)amino)-6-oxopyridazin-1(6H)-yl)piperidine-2,6-dione Compound 152 (70.0 mg, 262 µmol, 73.9%) as an off white solid. $^1$H NMR (400 MHz, DMSO-$d_6$) δ 10.91 (brs, 1H), 7.03 (d, J=9.80 Hz, 1H), 6.76 (d, J=9.72 Hz, 1H), 6.50 (m, 1H), 5.48-5.50 (m, 1H), 4.65 (t, J=5.16 Hz, 1H, —OH), 3.48 (q, J=5.44 Hz, 2H), 3.07 (q, J=5.24 Hz, 2H), 2.79-2.86 (m, 1H), 2.44-2.59 (m, 2H), 1.99 (m, 1H). LC MS: ES+ 267.1.

Scheme 8

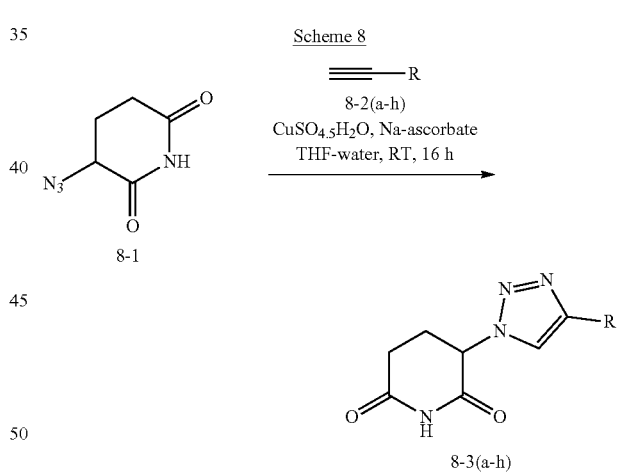

General Procedure (Click Reaction)

A mixture of 8-1 (1 mmol), 8-2 (a-h) (1.1 mmol), CuSO4.5H2O (0.1 mmol) and Na-ascorbate (0.4 mmol) in THF-water (3:1, 3 mL) was stirred at room temperature for 16 hours to produce 8-3 (a-h). Reaction mixture was filtered through a short plug of celite. The filtrate was partitioned between Ethyl acetate and water. The organic layer was separated, dried over anhydrous Na2SO4 and concentrated under reduced pressure. Crude mass was purified doing column chromatography (silica, gradient: 0-2% MeOH in DCM) to afford 8-3(a-h) as pure solids.

The following compounds (8a-h) were prepared according to the general procedure shown in Scheme 8

(Compound 153)

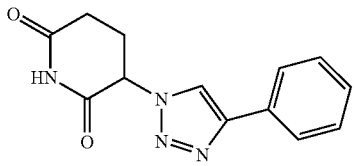

Yield: 60%

¹H NMR (400 MHz, DMSO-d₆) δ 11-26 (s, 1H), 8.68 (s, 1H), 7.85 (d, J=7.72 Hz, 2H), 7.46 (t, J=7.54 Hz, 2H), 7.35 (t, J=7.26 Hz, 1H), 5.86 (dd, J=12.96, 5.16 Hz, 1H0, 2.95-2.86 (m, 1H), 2.73-2.49 (m, 2H), 2.38-2.36 (m, 1H); LC MS: ES+ 257.1.

(Compound 154)

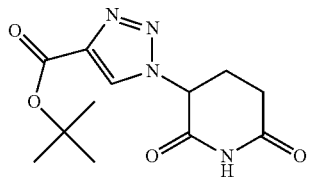

Yield: 19%

¹H NMR (400 MHz, DMSO-d₆) δ 11.27 (s, 1H), 8.80 (s, 1H), 5.89 (dd, J=12.52, 4.92 Hz, 1H), 2.89-2.83 (m, 1H), 2.72-2.66 (m, 2H), 2.33-2.28 (m, 1H0, 1.54 (s, 9H); LC MS: ES+ 281.0.

(Compound 155)

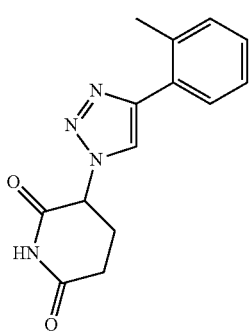

Yield: 73%

¹H NMR (400 MHz, DMSO-d6) δ 11.26 (s, 1H), 8.51 (s, 1H), 7.76 (d, J=5.6 Hz, 1H), 7.31-0.722 (m, 2H), 5.89-5.86 (m, 1H), 2.93-2.85 (m, 1H), 2.79-2.67 (m, 2H), 2.43 (s, 3H), 3.39-2.34 (m, 1H); LC MS: ES+ 271.

(Compound 156)

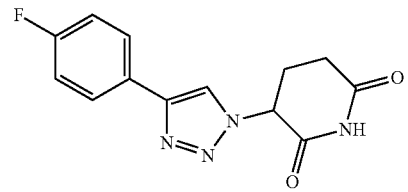

Yield: 67%

¹H NMR (400 MHz, DMSO-d6) δ 11.27 (s, 1H), 8.68 (s, 1H), 7.89 (t, J=6.62 Hz, 2H), 7.31 (t, J=8.66 Hz, 2H), 5.86 (dd, 12.12, 4.32 Hz, 1H), 2.93-2.85 (m, 1H), 2.72-2.63 (m, 2H), 2.38-2.35 (m, 1H); LC MS: ES+ 275.1.

(Compound 157)

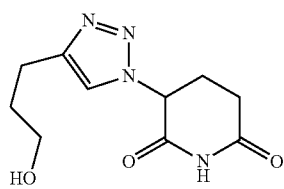

Yield: 19%

¹H NMR (400 MHz, DMSO-d6) δ 11.18 (s, 1H), 7.93 (s, 1H), 5.73 (dd, J=12.36, 4.72 Hz, 1H), 4.49-4.46 (m, 1H), 3.46-3.41 (m, 2H), 2.88-2.80 (m, 1H), 2.69-2.55 (m, 4H), 2.27-2.23 (m, 1H), 1.78-1.71 (m, 2H); LC MS: ES+ 239.1.

(Compound 158)

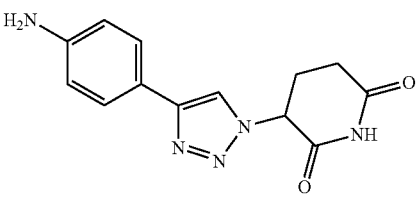

Yield: 36%

¹H NMR (400 MHz, DMSO-d6) δ 11.23 (s, 1H), 8.35 (s, 1H), 7.48 (d, J=8.4 Hz, 2H), 6.61 (d, J=8.44 Hz, 2H), 5.78 (dd, J=12.44, 5.04 Hz, 1H0, 5.24 (brs, 2H), 2.89-2.83 (m, 1H), 2.72-2.61 (m, 2H), 2.35-2.30 (m, 1H); LC MS: ES+ 272.2.

(Compound 159)

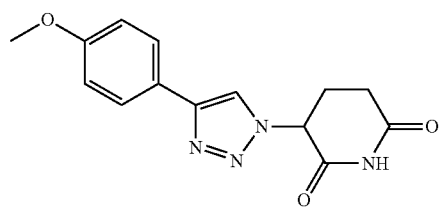

Yield: 68%

¹H NMR (400 MHz, DMSO-d6) δ 11.25 (s, 1H0, 8.56 (s, 1H), 7.77 (d, J=8.68 Hz, 2H), 7.02 (d, J=8.72 Hz, 2H), 5.83

(dd, J=12.56, 5.16 Hz, 1H), 0.79 (s, 3H), 2.91-2.85 (m, 1H), 2.73-2.63 (m, 2H), 2.36-2.32 (m, 1H); LC MS: ES+ 287.2.

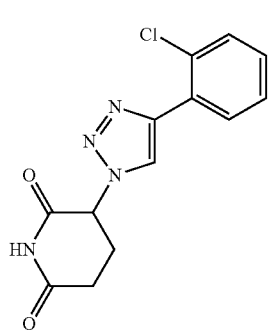
(Compound 160)

Yield: 67%
$^1$H NMR (400 MHz, DMSO-d6) δ 11.26 (s, 1H), 8.80 (s, 1H), 8.11 (dd, J=7.76, 1.4 Hz, 1H), 7.58 (d, J=7.84 Hz, 1H), 7.48 (t, J=7.14 Hz, 1H), 7.42-7.38 (m, 1H), 5.91 (dd, J=12.28, 5.08 Hz, 1H), 2.90-2.67 (m, 3H), 2.37-2.33 (m, 1H); LC MS: ES+ 291.1.

Scheme 9

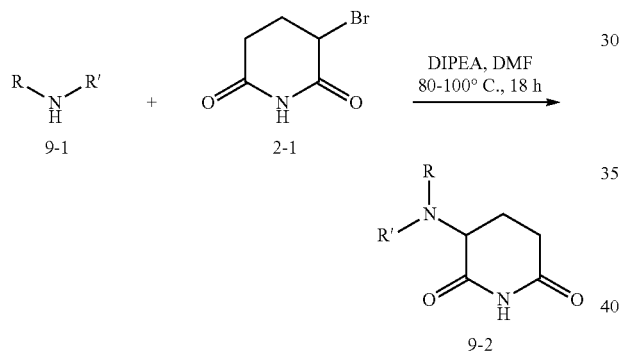

General Procedure—A

To a stirred solution of 2-1 (1.0 mmol) in DMF (3 mL) was added Anilines 9-1 (2.5 mmol). The resulting solution was heated at 80° C.-100° C. for 5-24 hours to produce 9-2. Reaction mixture was then cooled to room temperature and evaporated under reduced pressure. Crude reaction mass was purified by reverse phase preparative HPLC, following the methods as are given below, to afford pure 9-3.

General Procedure—B

To a stirred solution of 2-1 (1.0 mmol) in Dioxane (3 mL) was added Anilines 9-1 (2.5 mmol). The resulting solution was heated at 70° C.-100° C. for 5-24 hours to produce 9-2. Reaction mixture was then cooled to room temperature and evaporated under reduced pressure. Crude reaction mass was purified by reverse phase preparative HPLC, following the methods as are given below, to afford pure 9-3.

General Methods for Prep HPLC Purification:

Method 1

Preparative HPLC was done on Waters auto purification instrument. Column name: —YMC-Actus Triart C18 (250× 20 mm, 5μ) operating at ambient temperature and flow rate of 20.0 ml/min. Mobile phase: A=10 mM NH$_4$OAc in water, B=Acetonitrile; Gradient Profile: Mobile phase initial composition of 70% A and 30% B, then to 45% A and 55% B in 3 min., then to 25% A and 75% B in 18 min., then to 5% A and 95% B in 19 min., held this composition up to 21 min. for column washing, then returned to initial composition in 22 min. and held till 25 min.

Method 2

Preparative HPLC was done on Waters auto purification instrument. Column name: —YMC-Actus Triart C18 (250× 20 mm, 5μ) operating at ambient temperature and flow rate of 20.0 ml/min. Mobile phase: A=0.1% Formic acid in water, B=Acetonitrile; Gradient Profile: Mobile phase initial composition of 80% A and 20% B, then to 70% A and 30% B in 3 min., then to 25% A and 75% B in 18 min., then to 5% A and 95% B in 19 min., held this composition up to 21 min. for column washing, then returned to initial composition in 22 min. and held till 25 min. Use of basic buffer (NH$_4$HCO$_3$) causes hydrolysis of the Glutarimide ring either during prep HPLC run or during post purification evaporation.

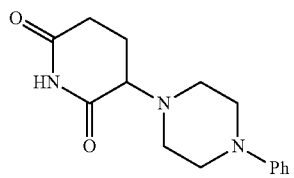
Compound 161

Compound 161 was synthesized following General approach (DMF/heating). Yield: 28%; $^1$H NMR (400 MHz, DMSO-d6) δ 10.65 (s, 1H), 7.19 (t, J=7.76 Hz, 2H), 6.92 (d, J=8.04 Hz, 2H), 6.76 (t, J=7.10 Hz, 1H), 3.44 (dd, J=10.42, 3.86 Hz, 1H), 3.10 (brs, 4H), 2.84-2.77 (m, 2H), 2.77-2.72 (m, 2H), 2.54-2.49 (m, 2H), 2.08-2.01 (m, 1H), 1.90-1.85 (m, 1H); LC MS: ES+ 274.0.

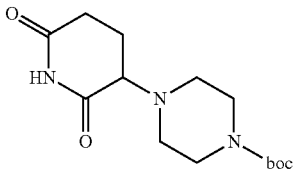
Compound 162

Compound 162 was synthesized following General approach (DMF/heating). Yield: 36%; $^1$H NMR (400 MHz, DMSO-d6) δ 10.63 (s, 1H), 3.46 (dd, J=10.96, 3.92 Hz, 1H), 2.69-2.63 (m, 2H), 2.56-2.49 (m, 4H), 2.04-1.98 (m, 1H), 1.87-1.81 (m, 1H), 1.39 (s, 9H); LC MS: ES+ 298.1.

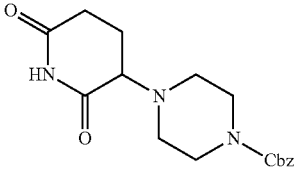
Compound 163

Compound 163 was synthesized following General approach (DMF/heating). Yield: 52%; 1H NMR (400 MHz, DMSO-d6) δ 10.63 (s, 1H), 7.35 (brs 5H), 3.47 (dd, J=11.04, 3.88 Hz, 1), 3.37 (brs, 4H), 2.73-2.68 (m, 2H), 2.59-2.51 (m, 2H), 2.50-2.46 (m, 2H), 2.04-2.00 (m, 1H), 1.88-1.82 (m, 1H); LC MS: ES+ 332.2.

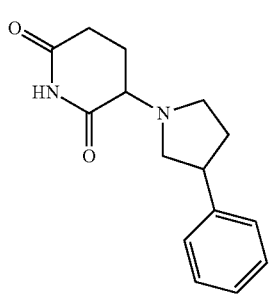

Compound 164

Compound 164 was synthesized following General approach (DIPEA/Dioxane). Yield: 30%; ¹H NMR (400 MHz, DMSO-d6) δ 10.66 (d, J=9.84 Hz, 1H), 7.27 (s, 4H), 7.18 (s, 1H), 3.32-3.25 (m, 2H), 3.12-3.02 (m, 1H), 2.89-2.85 (m, 2H), 2.70-2.65 (m, 1H), 2.56-2.48 (m, 2H), 2.23-2.19 (m, 1H), 2.01-1.97 (m, 2H), 1.81-1.77 (m, 1H); LC MS: ES+ 259.3.

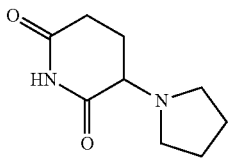

Compound 165

Compound 165 was synthesized following General approach (DIPEA/Dioxane). Yield: 21%; ¹H NMR (400 MHz, DMSO-d6) δ 10.61 (s, 1H), 3.13-3.08 (m, 1H), 2.63-2.58 (m, 4H), 2.50-2.42 (m, 2H), 1.98-1.93 (m, 2H), 1.69 (brs, 4H); LC MS: ES+ 183.3.

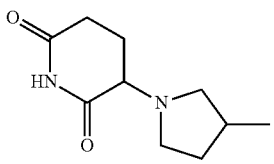

Compound 166

Compound 166 was synthesized following General approach (DIPEA/Dioxane). Yield: 12%; ¹H NMR (400 MHz, DMSO-d6) δ 10.61 (s, 1H), 3.11 (brs, 1H), 2.88-2.2.77 (m, 1H), 2.73-2.65 (m, 2H), 2.50-2.44 (m, 2H), 2.18-2.13 (m, 2H), 1.98-1.92 (m, 3H), 1.32-1.27 (m, 1H), 0.97 (d, J=6.2 Hz, 3H); LC MS: ES+ 197.3.

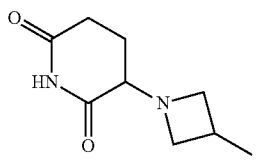

Compound 167

Compound 167 was synthesized following General approach (DIPEA/Dioxane). Yield: 16%; ¹H NMR (400 MHz, DMSO-d6) δ 10.60 (s, 1H), 3.44-3.40 (m, 2H), 2.93-2.82 (m, 3H), 2.53-2.33 (m, 3H), 1.89-1.85 (m, 1H), 1.66-1.61 (m, 1H), 1.09 (d, J=6.64 Hz, 3H); LC MS: ES+ 183.3.

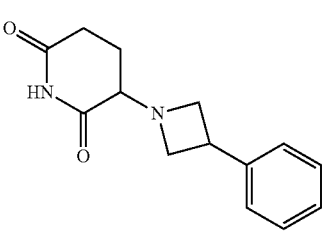

Compound 168

Compound 168 was synthesized following General approach (DMF/Heating). Yield: 16%; ¹H NMR (400 MHz, DMSO-d6) δ 10.65 (s, 1H), 7.33 (brs, 4H), 7.21 (brs, 1H), 3.77-3.61 (m, 3H), 3.28-3.22 (m, 2H), 3.07 (brs, 1H), 2.55-2.50 (m, 1H), 2.48-2.3.9 (m, 1H), 1.96-1.90 (m, 1H), 1.73-1.68 (m, 1H); LC MS: ES+ 245.2.

Compound 169

Compound 169 was synthesized following General approach (DIPEA/Dioxane). Yield: 11%; ¹H NMR (400 MHz, DMSO-d6) δ 10.59 (s, 1H), 3.25-3.19 (m, 4H), 2.91 (brs, 1H), 2.47-2.31 (m, 2H), 1.98-1.94 (m, 2H), 1.89-1.83 (m, 1H), 1.68-1.59 (m, 1H); LC MS: ES+ 169.0.

Compound 170

Compound 170 was synthesized following General approach (DMF/heating). Yield: 20%; LC MS: ¹H NMR (400 MHz, MeOD 6 3.47-3.41 (m, 1H), 2.69-2.54 (m, 6H), 2.09-2.02 (m, 2H), 1.60 (brs, 4H), 1.49-1.44 (m, 2H); LC MS: ES+ 197.0.

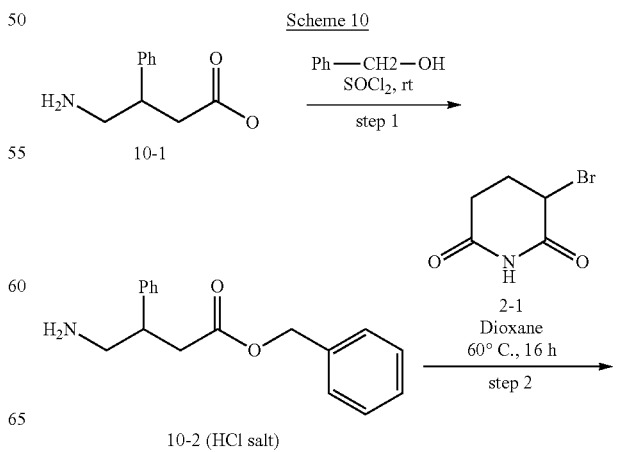

Scheme 10

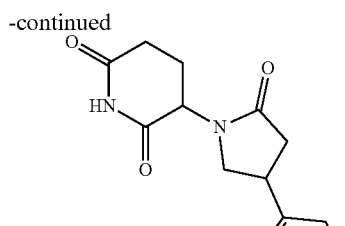

Compound 171

Step-1

To a stirred solution of 10-1 (1 g, 5.587 mmol) in BnOH (10 mL) was added SOCl$_2$ (0.69 mL, 8.38 mmol) at 0° C. Then the reaction mixture was stirred at room temperature for 16 hours. Reaction mixture was evaporated in reduced pressure to get 10-2 as off white solid. Yield: 66%; LC MS: ES+ 269.8.

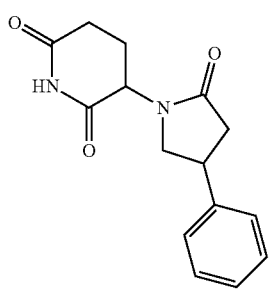

Compound 171

Step-2

Compound 171 was synthesized by general procedure (DIPEA/Dioxane). Yield: 8%; $^1$H NMR (400 MHz, DMSO-d6) δ 10.90 (s, 1H), 7.37-7.31 (m, 4H, 7.24 (brs, 1H), 4.92-4.86 (m, 1H), 3.75-0.71 (m, 1H), 3.62-3.58 (m, 2H), 3.22-3.18 (m, 1H), 2.86-2.73 (m, 2H), 2.48-2.38 (m, 2H), 2.28-2.21 (m, 1H), 1.89-1.85 (m, 1H); LC MS: ES− 271.3.

Scheme 11

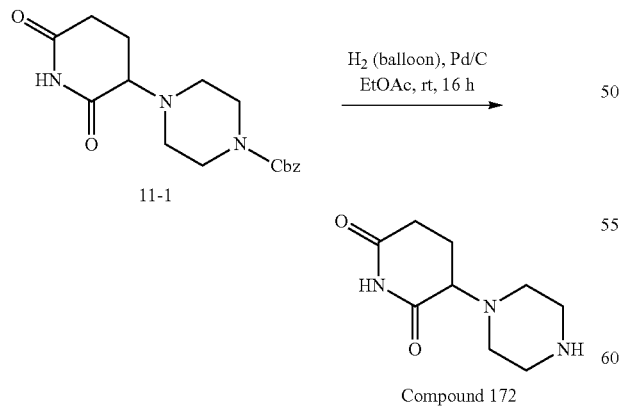

A stirred solution of 11-1 (70 mg, 0.211 mmol) in Ethyl acetate was degassed with argon for 10 minutes. 10% Pd/C (30 Wt %) was added to the reaction mixture and it was subjected to hydrogenation under hydrogen balloon for 16 hours. It was filtered through celite and concentrated under reduced pressure to obtain compound 172 as off white solid. Yield: 72%; $^1$H NMR (400 MHz, MeOD) δ 3.43 (dd, J=10.36, 4.8 Hz, 1H), 2.88-2.81 (m, 4H), 2.74-2.68 (m, 4H), 2.67-2.55 (m, 2H), 2.11-2.05 (m, 2H); GC MS: m/z 197.

Scheme 12

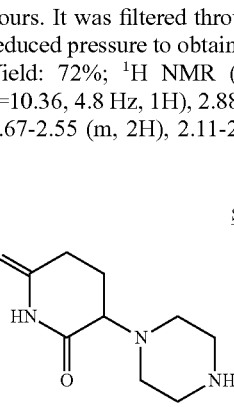

Compound 172

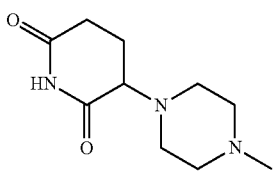

Compound 173

Step-1

To a stirred solution of Compound 172 (60 mg, 0.304 mmol) in acetonitrile (5 mL) were added acetic acid (0.243 mL, 4.259 mmol) and 37% Formaldehyde (91.249 mg, 3.042 mmol). It was stirred at room temperature for 30 minutes. Then to it was added NaCNBH$_4$ and stirred at room temperature for 16 hours. It was diluted with Ethyl acetate, washed with saturated NaHCO$_3$, water and brine. It was dried over Na2SO4 and concentrated under reduced pressure. It was purified by column chromatography (silica, gradient 0%-1.5% Methanol in DCM) to afford Compound 173 as yellow sticky gum. Yield: 47%; $^1$H NMR (400 MHz, DMSO-d6) δ 10.59 (s, 1H), 3.32-3.28 (m, 1H), 2.67-2.58 (m, 4H), 2.51-2.48 (m, 2H), 2.32 (brs, 4H), 2.15 (s, 3H), 2.06-2.01 (m, 1H), 1.86-1.81 (m, 1H); LC MS: ES+ 212.0.

Scheme 13

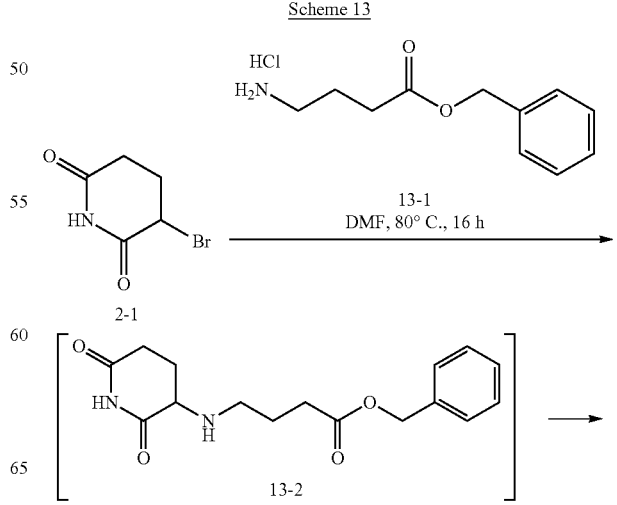

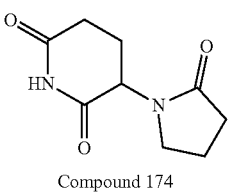

Compound 174

To a stirred solution of 2-1 (400 mg, 2.083 mmol) in dioxane (2 mL) was added DIPEA (1.088 mL, 6.25 mmol) at 0° C. in a sealed tube. 13-1 (525 mg, 2.292 mmol) was added to the reaction mixture. It was heated at 70° C. for 16 hours. It was concentrated under reduced pressure and purified by column chromatography using (silica, gradient 0%-2% Methanol in DCM) to obtain Compound 174 as a white solid. Yield: 2%; $^1$H NMR (400 MHz, DMSO-d6) δ 10.88 (s, 1H), 4.78 (dd, J=13.04, 4.80 Hz, 1H), 3.31-3.24 (m, 1H), 3.22-3.16 (m, 1H), 2.85-2.76 (m, 1H), 2.55-2.49 (m, 1H), 2.29-2.15 (m, 3H), 1.999-1.91 (m, 2H), 1.82-1.76 (m, 1H); LC MS: ES+197.26.

followed by 14-4 (81 mg, 0.721 mmol). It was stirred at room temperature for 16 hours. It was concentrated under reduced pressure, diluted with Ethyl acetate, washed with saturated aqueous NaHCO$_3$ solution and concentrated under reduced pressure. It was purified by column chromatography (silica, gradient 0%-1% Methanol in DCM) to afford 14-5 as bluish gum. Yield: 62%; LC MS: ES+ 382.0.

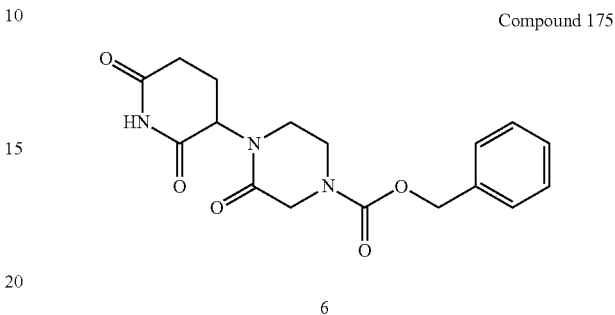

Compound 175

Step-3

To stirred solution of 14-5 (75 mg, 0.196 mmol) in THF (5 mL) was added NaH (60% in oil) (16 mg, 0.393 mmol) at 0° C. It was stirred at room temperature for 16 hours. It was diluted with Ethyl acetate, washed with water, dried over Na$_2$SO$_4$ and concentrated under reduced pressure. It was purified by column chromatography (silica, gradient 0%-2% Methanol in DCM) and then Preparative TLC Plate (eluting with 3% Methanol in DCM) to afford Compound 175 as off white solid. Yield: 14%; $^1$H NMR (400 MHz, DMSO-d6) δ 10.89 (s, 1H), 7.38-7.32 (m, 5H), 5.11 (s, 2H), 5.07-4.99 (m, 1H), 4.09-4.05 (m, 2H), 3.72-3.67 (m, 1H), 3.57-3.51 (m, 1H), 3.36-3.27 (m, 2H), 2.81-2.73 (m, 1H), 2.55-2.49 (m, 1H), 2.32-2.26 (m, 1H), 1.88-1.82 (m, 1H); LC MS: ES– 344.2.

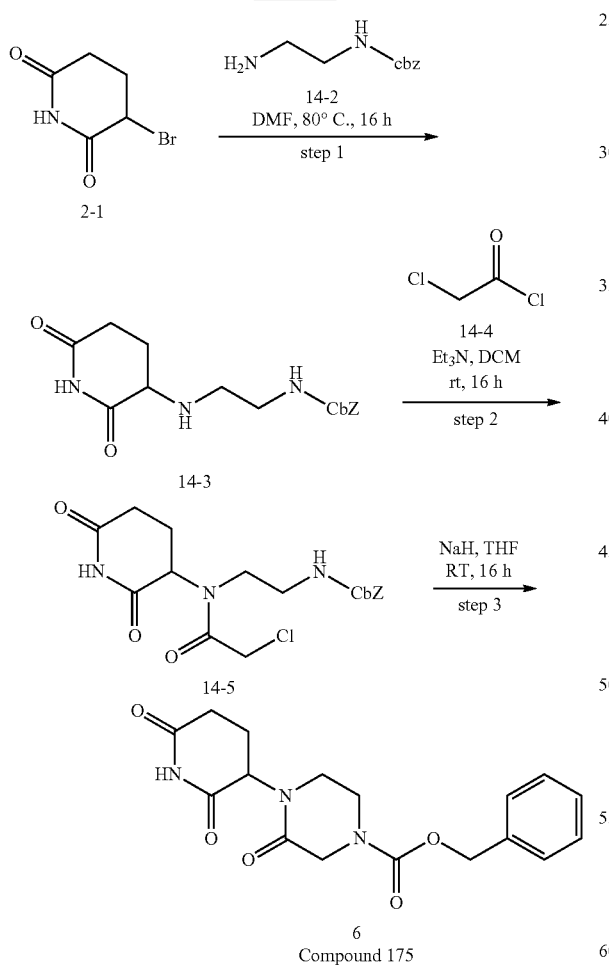

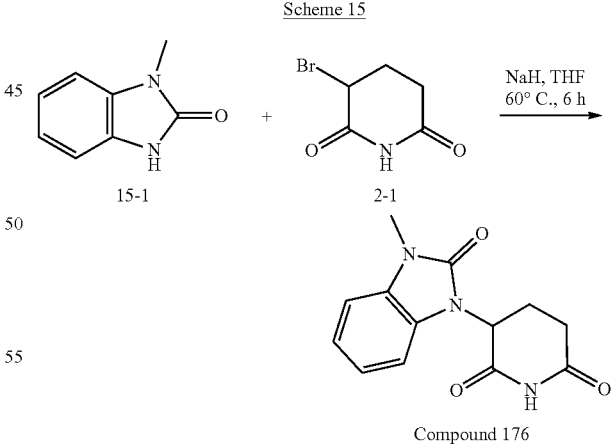

Compound 176

Step-1

Compound 14-3 was synthesized by general procedure (DMF/heating). Yield: 69%; LC MS: ES+ 306.2.

Step-2

To a stirred solution of 14-3 (200 mg, 0.655 mmol) in DCM (5 mL) was added Et$_3$N (0.099 mL, 0.983 mmol) and To a THF solution (2 mL) of 15-1 (100 mg, 674 μmol) was added NaH (13.4 mg, 337 μmol) under Nitrogen atmosphere. The resultant solution was heated at 60° C. for 30 minutes. To the hot reaction mixture was added a THF solution (2 mL) of 2-1 (64.7 mg, 337 μmol) drop wise and the heating was continued for another 5 hours to produce Compound 176. It was then cooled to room temperature, diluted with 20% IPA-DCM solution, washed with water and brine. The organic layer was dried over anhydrous Na₂SO₄ and concentrated under reduced pressure. Crude mass was purified by column chromatography (silica, gradient: 0-3% MeOH in DCM) to afford Compound 176 (3.5 mg, 13 μmol, 5%). ¹H NMR (400 MHz, DMSO-d₆) δ 11.10 (s, 1H), 7.19 (d, J=7.6 Hz, 1H), 7.15-7.01 (m, 3H), 5.38 (s, 1H), 3.25 (s, 3H), 2.90-2.87 (m, 1H), 2.72-2.50 (m, 2H), 2.07-2.05 (m, 1H). LC MS: ES+ 260.3.

Compound 177

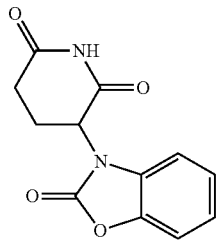

Compound 177 was synthesized following General approach (NaH, reverse addition protocol). Yield: 7%; ¹H NMR (400 MHz, DMSO-d6) δ 11.21 (s, 1H), 7.39 (d, J=7.76 Hz, 1H), 7.14-7.28 (m, 3H), 5.35-5.40 (m, 1H), 2.85-2.93 (m, 1H), 2.63-2.74 (m, 2H), 2.13-2.19 (m, 1H). LC MS: ES– 245.4.

Compound 178

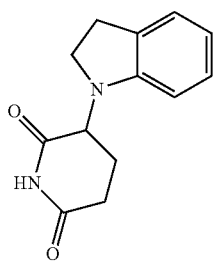

Yield: 8%; ¹H NMR (400 MHz, DMSO-d6) δ 10.79 (s, 1H), 7.00 (d, J=6.72 Hz, 1H), 6.93 (t, J=7.68 Hz, 1H), 6.53 (t, J=7.32 Hz, 1H), 6.47 (d, J=7.60 Hz, 1H), 4.60-4.64 (m, 1H), 3.25-3.42 (m, 2H), 2.91-2.95 (m, 2H), 2.81-2.84 (m, 1H), 2.54-2.59 (m, 1H), 2.15-2.25 (m, 1H), 1.89-1.96 (m, 1H); LC MS: ES+ 231.3.

Compound 179

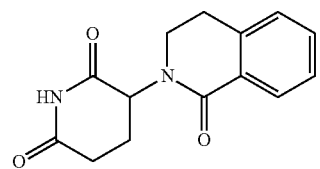

Yield: 7%; 1H NMR (400 MHz, DMSO-d6) δ 10.89 (s, 1H), 7.87 (d, J=7.6 Hz, 1H), 7.50 (t, J=7.22 Hz, 1H), 7.38-7.30 (m, 2H), 5.21 (brs, 1H), 3.52-3.44 (m, 2H), 3.03-2.95 (m, 2H), 2.85-2.95 (m, 1H), 2.55-2.39 (m, 2H), 1.95-1.91 (m, 1H); LC MS: ES+ 259.2.

Compound 180

Yield: 18%; ¹H NMR (400 MHz, DMSO-d6) δ 11.04 (s, 1H), 7.49 (d, J=7.88 Hz, 1H), 7.38 (d, J=8.2 Hz, 1H), 7.13-7.09 (m, 2H), 7.02 (t, J=7.28 Hz, 1H), 5.55 (dd, J=12.4, J₂=4.6 Hz, 1H), 2.90-2.86 (m, 1H), 2.67-2.64 (m, 1H), 2.24 (s, 3H), 2.11-2.08 (m, 1H); LC MS: ES+ 243.4.

Compound 181

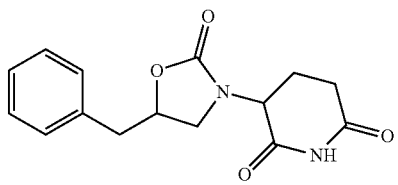

Yield: 2.15%; ¹H NMR (400 MHz, DMSO-d6) δ 10.95-10.92 (d, J=12.6 Hz, 1H), 7.30-7.25 (m, 5H), 4.87-4.82 (m, 2H), 4.61-4.52 (m, 2H), 3.56-3.52 (m, 1H), 3.48-3.44 (m, 1H), 3.31-3.21 (m, 1H), 3.13-3.11 (m, 1H), 3.05-2.95 (m, 3H), 2.84-2.75 (m, 1H), 2.18-2.14 (m, 1H), 1.88 (br m, 1H), 1.72 (br m, 1H); LC MS: ES+ 289.3.

Compound 182

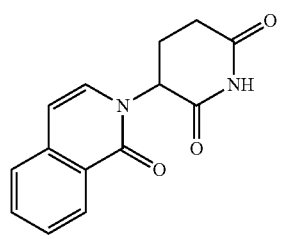

Yield: 52% ¹H NMR (400 MHz, DMSO-d₆) δ 11.04 (s, 1H), 8.20 (d, J=8.2 Hz, 1H), 7.76-7.72 (m, 1H), 7.68-7.66 (m, 1H), 7.52 (t, J=7.48 Hz, 1H), 7.41 (d, J=7.4 Hz, 1H), 6.67 (d, J=7.2 Hz, 1H), 5.51-5.47 (br, 1H), 2.91-2.83 (m, 1H), 2.63-2.59 (m, 2H), 2.05 (m, 1H); LC MS: ES+ 257.1.

Compound 183

Yield: 3%; ¹H NMR (400 MHz, DMSO-d₆) δ 11.19 (s, 1H), 8.27 (s, 1H), 7.67 (d, J=6.88 Hz, 1H), 7.54 (d, J=7.92 Hz, 1H), 7.25-7.21 (m, 2H), 5.71-5.68 (m, 1H), 2.90-2.78 (m, 3H), 2.25-2.15 (m, 1H); LC MS: ES+ 230.0.

Compound 184

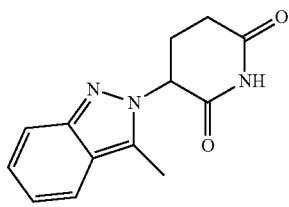

Yield: 57%; ¹H NMR (400 MHz, DMSO-d₆) δ 7.70 (d, J=8.04 Hz, 1H), 7.50 (d, J=8.56 Hz, 1H), 7.41 (t, J=7.36 Hz, 1H), 7.16 (t, J=7.52 Hz, 1H), 5.63 (dd, J=11.92, 5.28 Hz, 1H), 2.93-2.76 (m, 3H), 2.53 (s, 3H), 2.36-2.32 (m, 1H); LC MS: ES+ 244.1.

Compound 185

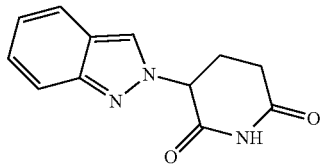

Yield: 7%; ¹H NMR (400 MHz, DMSO-d₆) δ 11.17 (s, 1H), 8.45 (s, 1H), 7.73 (d, J=8.96 Hz, 1H), 7.59 (d, J=8.28 Hz), 7.25 (t, J=7.32 Hz, 1H), 7.07-7.03 (m, 1H), 5.73 (m, 1H), 2.85-2.67 (m, 3H), 2.33 (m, 1H); LC MS: ES+ 230.1.

Compound 186

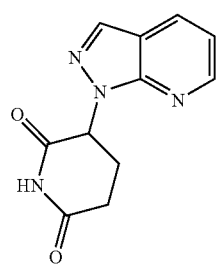

Yield: 35%; ¹H NMR (400 MHz, DMSO-d₆) δ 11.07 (s, 1H), 8.53-8.52 (m, 1H), 8.27 (d, J=8.08 Hz, 1H), 8.21 (s, 1H), 7.26-7.23 (m, 1H), 5.96-5.93 (m, 1H), 2.96-2.92 (m, 1H), 2.79-2.76 (m, 1H), 2.68-2.64 (m, 1H), 2.23 (m, 1H); LC MS: ES+ 231.3.

Compound 187

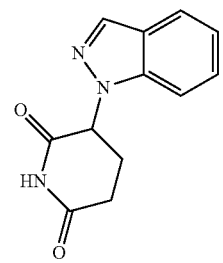

Yield: 51%; ¹H NMR (400 MHz, DMSO-d₆) δ 11.07 (s, 1H), 8.10 (s, 1H), 7.76 (d, J=7.76 Hz, 1H), 7.60 (d, J=8.16 Hz, 1H), 7.38 (t, J=6.72 Hz, 1H), 7.14 (d, J=7.0 Hz, 1H), 5.83-5.82 (m, 1H), 2.85-2.67 (m, 3H), 2.25-2.24 (m, 1H); LC MS: ES+ 230.3.

Compound 188

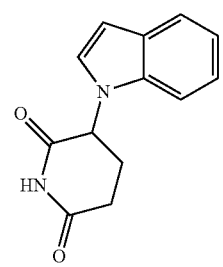

Yield: 4%; ¹H NMR (400 MHz, DMSO-d₆) δ 11.07 (s, 1H), 7.55 (d, J=7.48 Hz, 1H), 7.44 (d, J=7.36 Hz, 1H), 7.37 (br s, 1H), 7.12-7.10 (m, 1H), 7.05-7.03 (m, 1H), 6.48 (br s, 1H), 5.64-5.62 (m, 1H), 2.91-2.87 (m, 1H), 2.81-2.66 (m, 2H), 2.13-2.07 (m, 1H); LC MS: ES+ 229.3.

(Compound 189)

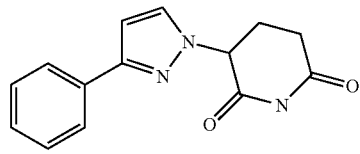

Yield: 20%

¹H NMR (400 MHz, DMSO-d₆) δ 11.08 (s, 1H), 7.85 (d, J=2.5 Hz, 1H), 7.79 (d, J=7.6 Hz, 2H), 7.40 (t, J=7.5 Hz, 2H), 7.30 (t, J=7.3 Hz, 1H), 6.77 (d, J=2.4 Hz, 1H), 5.43 (dd, J=12.1, 5.2 Hz, 1H), 2.82 (dq, J=12.9, 6.7, 5.5 Hz, 1H), 2.74-2.57 (m, 2H), 2.32-2.23 (m, 1H); LC MS: ES+ 256.

Scheme 16

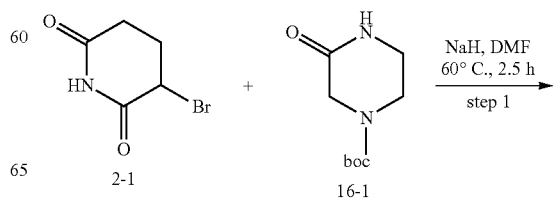

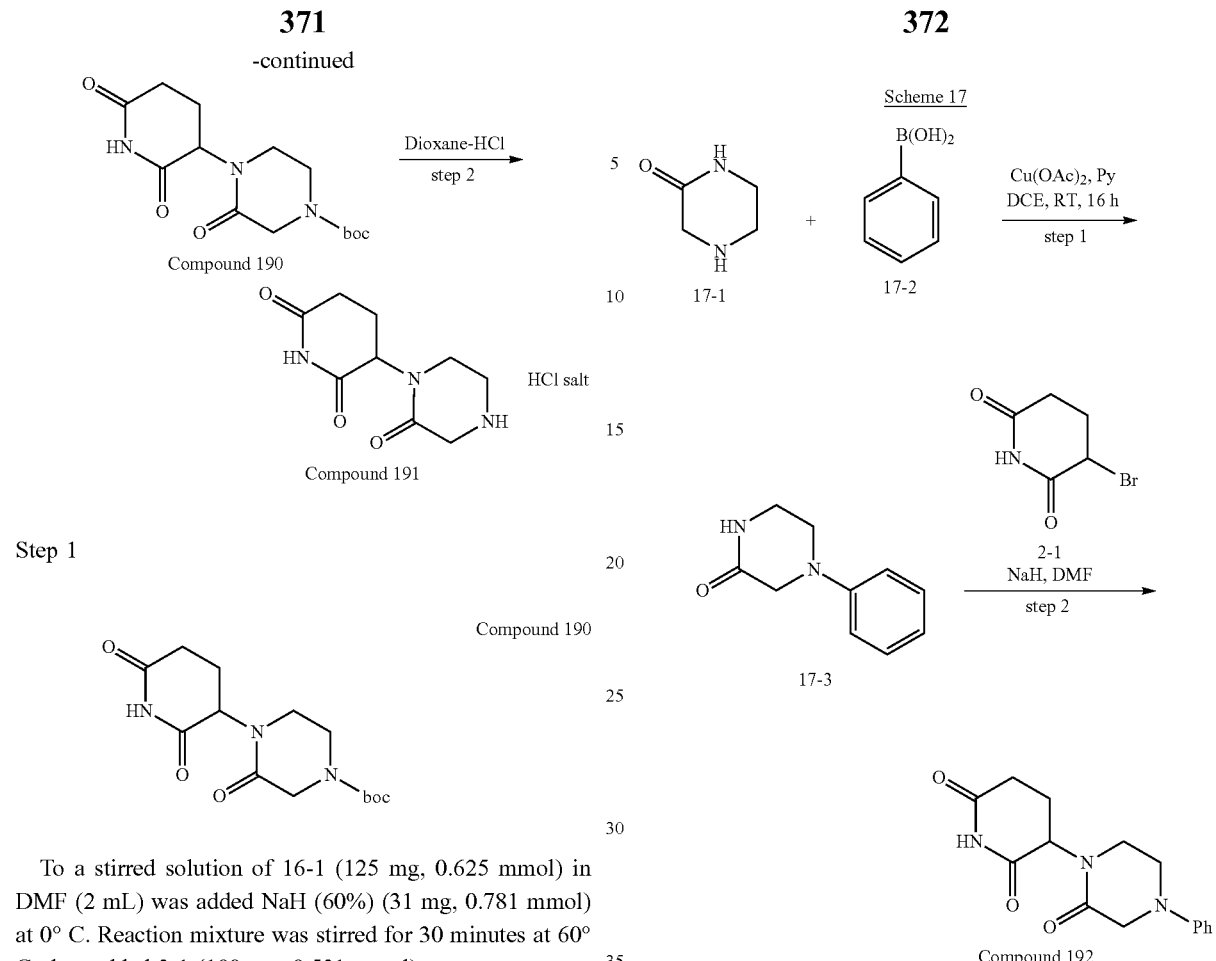

Step 1

Compound 190

To a stirred solution of 16-1 (125 mg, 0.625 mmol) in DMF (2 mL) was added NaH (60%) (31 mg, 0.781 mmol) at 0° C. Reaction mixture was stirred for 30 minutes at 60° C. then added 2-1 (100 mg, 0.521 mmol) at same temperature. It was then heated at 60° C. for 4 hours. Reaction mixture was diluted with water and extracted with 20% IPA/DCM. Organic part was washed with brine, followed by dried over anhydrous sodium sulfate and concentrated, crude was isolated via column chromatography by using (silica, gradient 0%-1% Methanol in Ethyl acetate to afford Compound 190 as off white solid. Yield: 15%.

Step-2

Compound 191

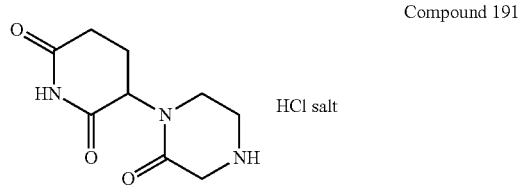 [SMILES: O=C1CCC(N2CCNCC2=O)C(=O)N1]

To a stirred solution of Compound 190 (60 mg, 0.193 mmol) in 1,4-Dioxane (1 mL) was added 1,4-Dioxane in HCl (0.5 mL) at 0° C. It was stirred at room temperature for 16 hours. The reaction mixture was concentrated under reduced pressure, washed with n-pentane and dried under reduced pressure to afford Compound 191 as off white solid. Yield: 99%; $^1$H NMR (400 MHz, DMSO-d6) δ 10.94 (s, 1H), 9.52 (brs, 2H), 5.09-5.03 (m, 1H), 3.86-3.75 (m, 2H), 3.53-3.34 (m, 4H), 2.83-2.73 (m, 1H), 2.5-2.50 (m, 1H), 2.36-2.28 (m, 1H), 1.86-1.81 (m, 1H); LC MS: ES+212.25.

Step-1

To a stirred solution of 17-1 (200 mg, 2.0 mmol) and 17-2 (366 mg, 3.0 mmol) in DCE (10 mL) was added pyridine (0.805 mL, 10.0 mmol). Cu(OAc)$_2$·H$_2$O (40 mg, 0.2 mmol) was added to the reaction mixture. Reaction mixture was stirred at room temperature for 72 hours. It was diluted with DCM, washed with water, dried over Na$_2$SO$_4$ and concentrated under reduced pressure. Crude was purified by column chromatography (silica, gradient 0%-2% Methanol in DCM) to provide 17-3 as off white solid. Yield: 21%; LC MS: ES+ 177.0.

Step-2

To a stirred solution of 17-3 (70 mg, 397 μmol) in DMF (5 mL) was added sodium hydride (31.6 mg, 794 μmol). The reaction was heated to 60° C. under nitrogen for 30 minutes. 2-1 (76.2 mg, 397 μmol) was added to the reaction mixture and the heating was continued for 3 hours. It was cooled to room temperature and quenched with ice water (10 mL). It was extracted with ethyl acetate. Organic part was dried over sodium sulfate, reduced in vacuo. The crude residue was purified by column chromatography (silica, gradient 0%-2% Methanol in DCM) to provide (Compound 192) as a white solid. Yield: 12%; $^1$H NMR (400 MHz, DMSO-d6) δ 10.90 (s, 1H), 7.24 (t, J=7.2 Hz, 2H), 6.94 (d, J=7.25 Hz, 2H), 6.80 (d, J=7.0 Hz, 1H), 5.05 (brs, 1H), 3.89-0.79 (m, 2H), 3.55-3.51 (m, 1H), 3.43-3.32 (m, 3H), 2.84-2.76 (m, 1H), 2.56-2.49 (m, 1H), 2.42-2.33 (m, 1H), 1.90-1.85 (m, 1H); LC MS: ES+ 288.26.

Scheme 18

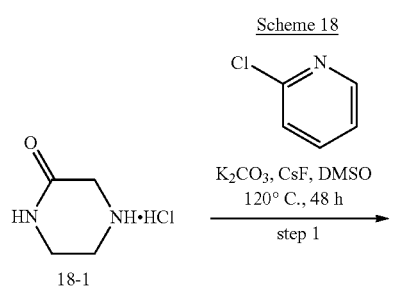

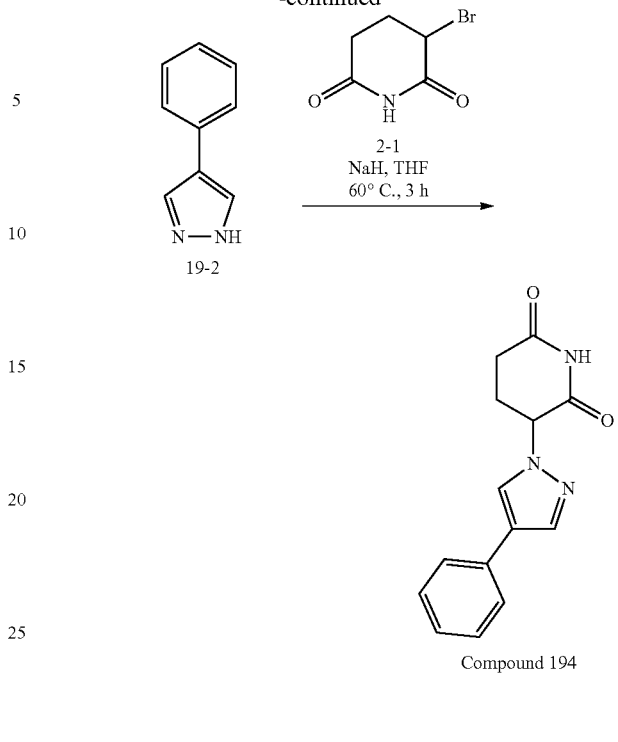

Step-1

To a stirred solution of 18-1 (881 mg, 8.80 mmol) in Dimethyl Sulfoxide (5 mL) was added 2-chloropyridine (1 g, 8.80 mmol) and potassium carbonate (3.64 g, 26.4 mmol). The reaction mixture was heated to 120° C. under nitrogen atmosphere for 16 hours. Reaction mixture was diluted with water and extracted with 20% IPA/DCM, dried over $Na_2SO_4$ and concentrated. The crude was purified by column chromatography (silica, gradient 0%-1% Methanol in DCM) to provide 18-2 as a liquid. Yield: 7%; LC MS: ES+ 178.0.

Step-2

Compound 193 was synthesized following General approach (NaH, reverse addition protocol). Yield: 14%; 1H NMR (400 MHz, DMSO-d6) δ 10.90 (s, 1H), 8.13 (brs, 1H), 7.57 (brs, 1H), 6.82 (d, J=7.32 Hz, 1H), 6.68 (brs, 1H), 5.07 (brs, 1H), 4.20-4.06 (m, 2H), 3.86 (brs, 1H), 3.69 (brs, 1H), 3.42) brs, 2H), 2.81-2.74 (m, 1H), 2.52-2.49 (m, 1H), 2.37-2.31 (m, 1H), 1.87 (m, 1H); LC MS: ES+ 289.20.

Scheme 19

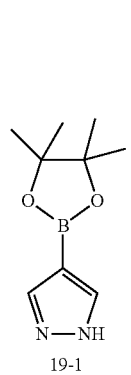

Step 1: Preparation of 4-Phenyl-4H-pyrazole

Compound 19-2 was synthesized according to Scheme 19. Yield: 10%; LC MS: ES+145.4.

Step-2

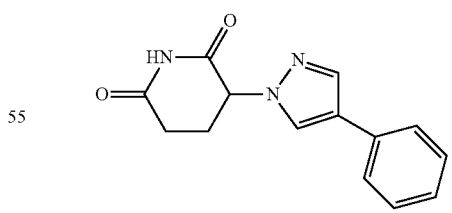

Compound 194

Compound 194 was synthesized following general procedure (NaH/THF, reverse addition protocol). Yield: 86%; $^1$H NMR (400 MHz, DMSO-d6) δ 11.09 (s, 1H), 8.25 (s, 1H), 7.94 (s, 1H), 7.59-7.58 (m, 2H), 7.36 (t, J=7.44 Hz, 2H), 7.20 (t, J=7.36 Hz, 1H), 5.41-5.37 (m, 1H), 2.86-2.78 (m, 1H), 2.69-2.57 (m, 1H), 2.32-2.25 (m, 1H); LC MS: ES+ 256.3.

Synthesis of Compound 195

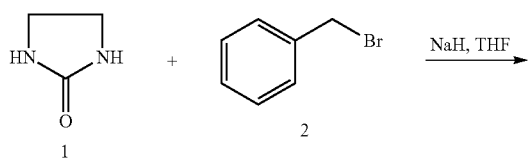

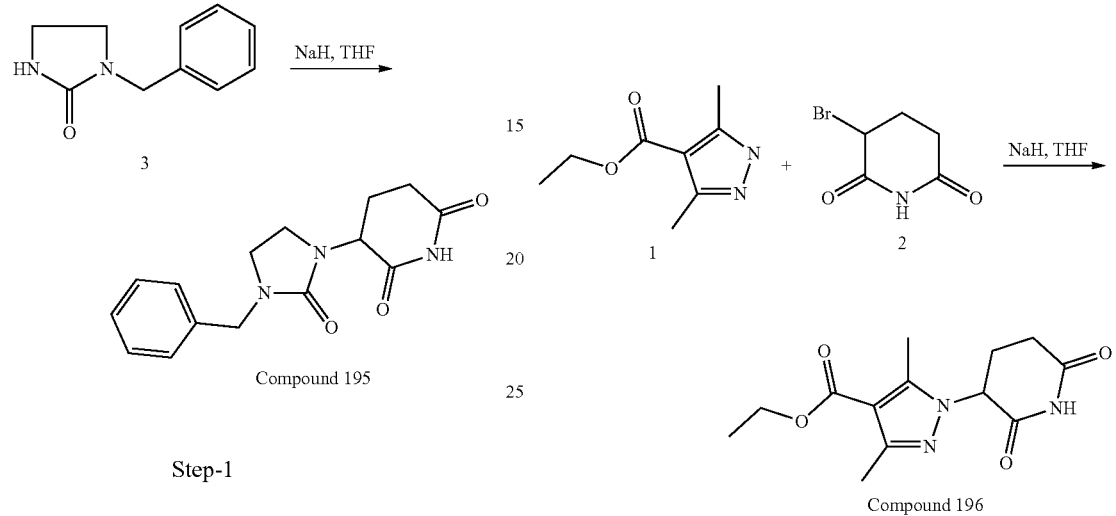

Compound 195

Step-1
Preparation of 1-Benzyl-imidazolidin-2-one (3)

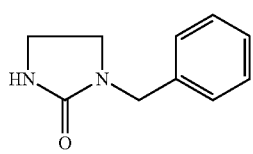 [SMILES: O=C1NCCN1Cc1ccccc1]

A stirred solution of (1) (2 g, 23.23 mmol) was added to a stirred solution of NaH (613 mg, 25.55 mmol) in THF (20 mL) under argon. The reaction mixture was stirred for one hour at room temperature and a solution of 2 (3.03 mL, 25.55 mmol) in THF (10 mL) was added drop wise. The reaction mixture was refluxed for overnight. After cooling, water was added and it was extracted with diethyl ether (3*20 ml). Combined organic layers were dried with Na2SO4, concentrated under reduced pressure. Crude mass was purified by column chromatography (0%-100% ethyl acetate in hexane) to afford 400 mg compound 3 as off white solid. Yield: 10%; $^1$H NMR (400 MHz, DMSO-d6) δ 7.37-7.32 (m, 2H), 7.29-7.20 (m, 3H), 6.40 (br s, 1H), 4.22 (s, 2H), 3.24-3.16 (m, 4H).

Step-2: Preparation of Compound 195

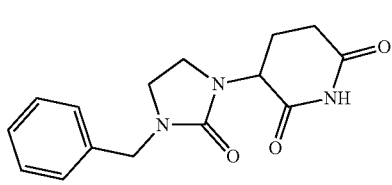 [SMILES: O=C1CCC(N2CCN(Cc3ccccc3)C2=O)C(=O)N1]

Compound 195 was synthesized following general protocol (NaH, reverse addition). Yield: 2%; $^1$H NMR (400 MHz, DMSO-d6) δ 10.85 (s, 1H), 7.36-7.32 (m, 2H), 7.30-7.25 (m, 3H), 4.62-4.58 (m, 1H), 4.30 (s, 2H), 3.32-3.24 (m, 2H), 3.21-3.15 (m, 2H), 2.84-2.80 (m, 1H), 2.52-2.50 (m, 1H), 2.22-2.16 (m, 1H), 1.88-1.86 (m, 1H); LC MS: ES+ 288.2.

Synthesis of Compound 196

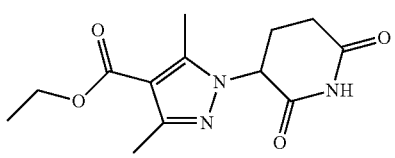

Compound 196

Preparation of Compound 196

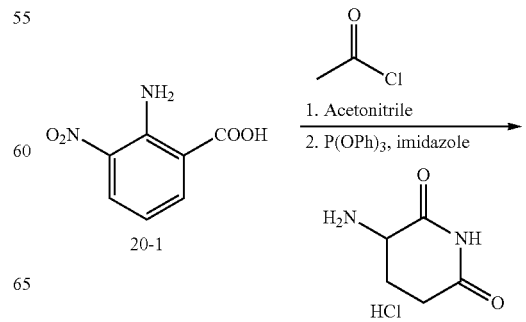

Compound 196

Compound 196 was synthesized according to the scheme above. Yield: 20%; $^1$H NMR (400 MHz, DMSO-$d_6$) δ 11.07 (s, 1H), 5.41-5.37 (m, 1H), 4.21 (q, J=7 Hz, 2H), 2.78 (m, 1H), 2.66-2.61 (m, 2H), 2.45 (s, 3H), 2.27 (s, 3H), 2.25 (m, 1H), 1.27 (t, J=7.04 Hz, 3H). LC MS: ES+ 280.1.

Scheme 20

-continued

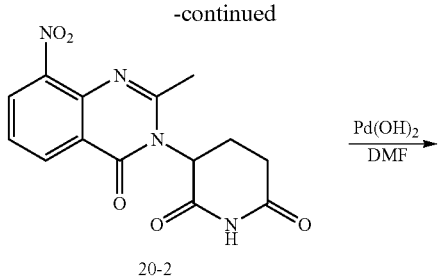
20-2

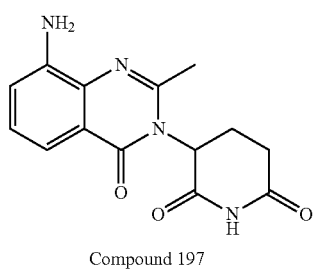
Compound 197

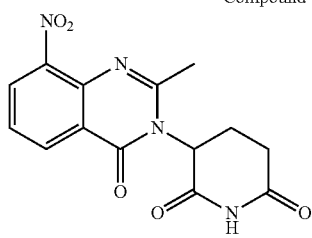

Preparation of 20-2

To a stirred mixture of 2-amino-3-nitrobenzoic acid (2 g, 10.9 mmol) and imidazole (1.2 eq.) in Acetonitrile (20 mL) was added acetyl chloride (927 μL, 13.0 mmol); the solid suspension slowly dissolved; stirred at rt overnight; add 3-aminopiperidine-2,6-dione hydrochloride (1.79 g, 10.9 mmol); followed by rest of 2.4 eq, make it total 1H-Imidazole (2.66 g, 39.2 mmol); add Phosphorous acid, triphenyl ester (3.40 mL, 13.0 mmol) heat to reflux; pdt peak as the major peak based on UV, but major impurity 259 (M+1, ES+); add 60 mL water, light yellow solid precipitated, wash with water and EtOAc; solid still has the 259 peak, but all other impurities gone; crude 3-(2-methyl-8-nitro-4-oxoquinazolin-3(4H)-yl)piperidine-2,6-dione (2.07 g, 6.54 mmol, 60.1%).

Compound 197

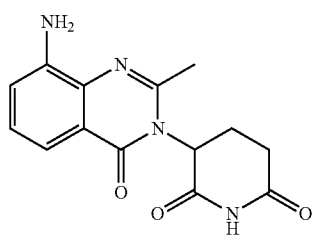

Charge crude 3-(2-methyl-8-nitro-4-oxoquinazolin-3(4H)-yl)piperidine-2,6-dione (2 g, 6.32 mmol) to 100 mL RBF; charge N,N-dimethylformamide (35 mL, 6.32 mmol) under nitrogen flow, purge; stir form light yellow solution; add dihydroxypalladium (879 mg, 1.26 mmol) on carbon; purge with nitrogen; purge with hydrogen; rxn complete overnight; filter off solid, concentrate and subject to FCC, MeOH/DCM 2-30%; isolate as off-white solid 3-(8-amino-2-methyl-4-oxoquinazolin-3(4H)-yl)piperidine-2,6-dione (Compound 197) (796 mg, 2.78 mmol, 44.2%). 1H NMR (500 MHz, DMSO-d6): δ 10.96 (s, 1H), 7.7.18-7.09 (m, 2H), 6.94 (dd, J=2.0 Hz, 7.0 Hz, 1H), 5.64 (s, 1H), 5.20 (dd, J=10.0, 4.0 Hz, 1H), 2.87-2.75 (m, 2H), 2.63-2.50 (m, 5H), 2.16-2.10 (m, 1H). LC/MS (ES+): m/z 287.1 [M+H]⁺.

Scheme 21: Preparation of Compound 198

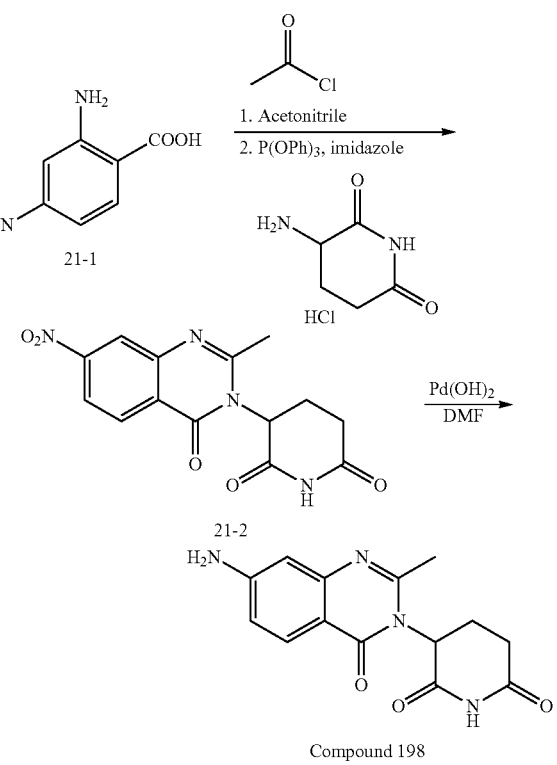
Compound 198

Step 1: Preparation of 21-2

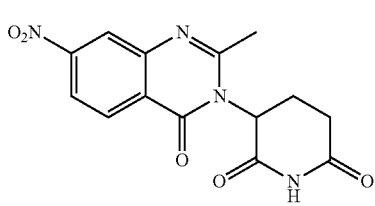
21-2

To a stirred mixture of 2-amino-4-nitrobenzoic acid (2.0 g, 10.9 mmol) and imidazole (0.88 g, 12.84 mmol) in acetonitrile (40 mL), was added Acetyl chloride (1.02 g, 13.0 mmol) at room temperature. The mixture was stirred at room temperature overnight. To the mixture, was added 3-amino-piperidine-2,6-dione hydrogen chloride (1.78 g, 10.9 mmol), imidazole (1.60 g, 23.24 mmol) and Phosphorous acid, triphenyl ester (4.03 g, 13.0 mmol), and heated to reflux overnight. Water (200 mL) was added to the mixture. The suspension was filtered and the solid was stirred for 20 min in CH3CN(25 mL). The mixture was filtrated to give 3-(2-methyl-7-nitro-4-oxoquinazolin-3(4H)-yl)piperidine-2,6-dione 21-2 (1.70 g, 5.37 mmol, 49.4%) as an off-white solid. LC/MS (ES+): m/z 317.2 [M+H]$^+$.

Step 2: Preparation of Compound 198

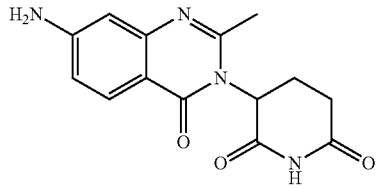

Compound 198

To a solution of 3-(2-methyl-7-nitro-4-oxoquinazolin-3(4H)-yl)piperidine-2,6-dione (1.4 g, 4.42 mmol) in DMF(17 mL) was added Palladium hydroxide (310 mg, 2.21 mmol) and Cyclohexene (4.4 mL, 44.0 mmol). The mixture was stirred at 125° C. overnight. The mixture was poured into water and stirred for 15 min. The mixture was filtrated and the solid was collected to give 3-(7-amino-2-methyl-4-oxoquinazolin-3(4H)-yl)piperidine-2,6-dione (Compound 198) (946 mg, 3.30 mmol, 75.0%) as white solid. 1H NMR (500 MHz, DMSO-d6): δ 10.93 (s, 1H), 7.65 (d, 9.0 Hz, 1H), 6.67 (dd, J=2.0 Hz, 7.0 Hz, 1H), 6.53 (d, J=2.0 Hz, 1H), 6.12 (s, 2H), 5.12-5.08 (m, 1H), 2.81-2.77 (m, 1H), 2.63-2.50 (m, 5H), 2.11-2.09 (m, 1H). LC/MS (ES+): m/z 287.1 [M+H]$^+$.

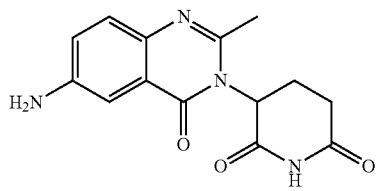

Compound 199

Compound 199 was prepared according to the procedure in Scheme 21. Yield 72.1%. 1H NMR (500 MHz, DMSO-d6): δ 10.97 (s, 1H), 7.33-7.31 (m, 1H), 7.06-7.04 (m, 2H), 5.60 (s, 2H), 5.18-5.14 (m, 1H), 2.83-2.79 (m, 1H), 2.65-2.53 (m, 5H), 2.12-2.10 (m, 1H). LC/MS (ES+): m/z 287.2 [M+H]$^+$.

Scheme 22

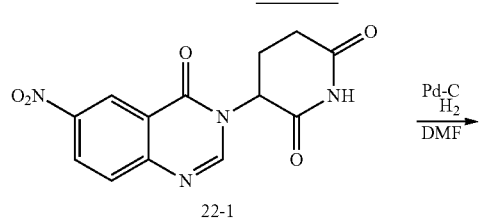

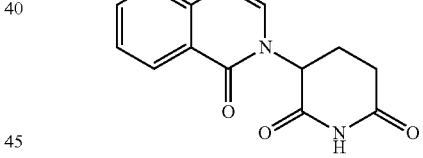

Compound 200

In a 50 mL RB flask was added 3-(6-nitro-4-oxoquinazolin-3(4H)-yl)piperidine-2,6-dione (200 mg, 661 μmol) in DMF (10 mL). 10% Pd/C (100 mg) was added. The mixture was stirred at r.t. under a hydrogen atmosphere for 6 hours. Reaction mixture was filtered through celite and wash with ethyl acetate (10 mL), The filtrate was concentrated under a vacuum, Then added ether and drop wise methanol. Solid was formed, filtered and washed with pentane to give 3-(6-amino-4-oxoquinazolin-3(4H)-yl)piperidine-2,6-dione (Compound 200) (27.4 mg, 100 μmol, 15.3%) as a green solid. $^1$H NMR (400 MHz, DMSO-d6) δ 2.07-2.11 (m, 1H), 2.59-2.66 (m, 2H), 2.79-2.88 (m, 1H), 5.40 (bs, 1H), 5.72 (s, 2H), 7.09 (dd, J=6.0 Hz & 2.4 Hz, 1H), 7.18 (d, J=2.4 Hz, 1H), 7.40 (d, 8.8 Hz, 1H), 7.99 (s, 1H), 11.10 (s, 1H). ES-MS (m/z): 273.24 (M+H$^+$).

Preparation of 3-(8-Amino-4-oxoquinazolin-3(4H)-yl)piperidine-2,6-dione (Compound 201)

Compound 201

[Compound 201 structure]

Compound 201 was prepared as an off white solid according to procedure in Scheme 22. Yield 79.0%. $^1$H NMR (400 MHz, DMSO-d6) δ 2.11-2.15 (m, 1H), 2.65-2.68 (m, 2H), 2.69-2.73 (m, 1H), 2.81-2.86 (m, 1H), 5.76 (s, 2H), 7.00 (t, J=8.0 Hz, 1H), 7.23 (d, J=8.0 Hz, 2H), 8.22 (s, 1H), 11.14 (s, 1H). ES-MS (m/z): 273.21 (M+H$^+$).

Scheme 23: Preparation of 3-(7-Nitro-4-oxoquinazolin-3(4H)-yl)piperidine-2,6-dione (Compound 202)

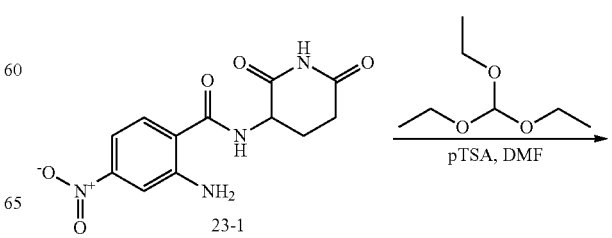

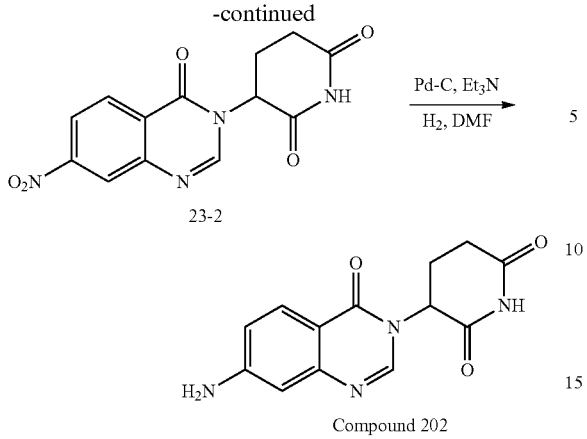

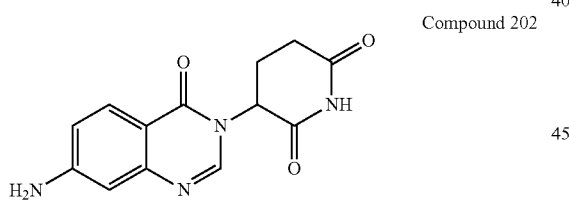

Compound 202

Step 1

To a solution of 2-amino-N-(2,6-dioxopiperidin-3-yl)-4-nitrobenzamide 23-1 (4 g, 13.6 mmol)) in DMF (40 mL) in a vial, triethylorthoformate (40 ml, 270 µmol) and PTSA (2.34 g, 13.6 mmol) were added under nitrogen condition and sealed the vial. Then the reaction was heated at 150° C. for 4 hr. The reaction was monitored by TLC. After consumption of SM, the reaction mixture was poured in ice cold water (100 mL), the resulting solid was filtered, washed with ACN, and dried under high vacuum to obtain 3-(7-nitro-4-oxoquinazolin-3(4H)-yl)piperidine-2,6-dione 23-2 (2.57 g, 8.51 mmol, 62.5%) as grey colored solid. LC/MS (ES+): m/z 303.07 [M+H]$^+$.

Step 2: Preparation of Compound 202

To a solution of 2-amino-N-(2,6-dioxopiperidin-3-yl)-4-nitrobenzamide 23-2 (0.5 g, 1.71 mmol) in DMF (8 mL) in RB flask, TEA (0.02 ml) was added under nitrogen at RT. After adding 10% Pd on carbon (0.25 g, 2.34 mmol) the reaction was hydrogenated for 18 hr at RT using balloon pressure. The reaction was monitored by TLC. After complete consumption of SM, the reaction was filtered through celite bed and washed with Ethylacetate (10 mL). The filtrate was concentrated under high vacuum at 55° C. and resulting residue was washed with methanol (10 mL) and diethyl ether (10 mL) and dried under high vacuum to obtain 3-(7-amino-4-oxoquinazolin-3(4H)-yl)piperidine-2,6-dione (Compound 202) (300 mg, 1.10 mmol, 64.5%) as brown colored solid. $^1$H NMR (400 MHz, DMSO-d6) δ 2.06-2.10 (m, 1H), 2.58-2.63 (m, 2H), 2.79-2.88 (m, 1H), 5.33-5.35 (m, 1H), 6.19 (s, 2H), 6.62 (s, 1H), 6.74 (d, J=6.8 Hz, 1H), 7.76 (d, J=8.0 Hz, 1H), 8.10 (s, 1H), 11.08 (s, 1H). ES-MS (m/z): 273.23 (M+H$^+$).

Scheme 24

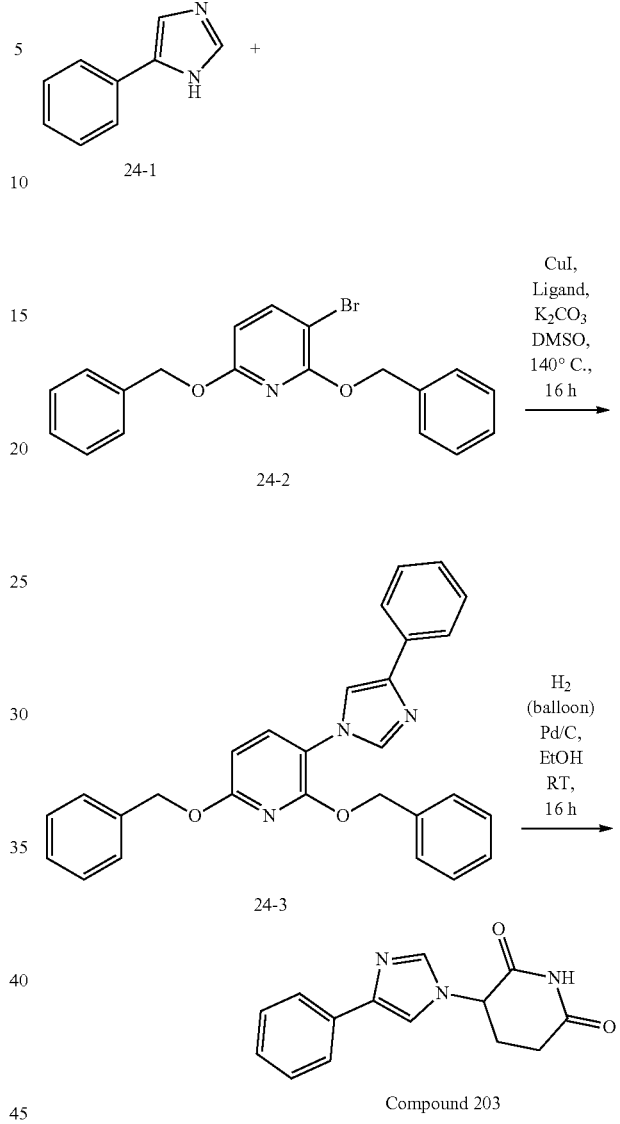

Step 1: Preparation of 2,6-Bis-benzyloxy-3-(5-phenyl-imidazol-1-yl)-pyridine (24-3)

A stirred solution of 24-1 (100 mg, 693 µmol), 24-2 (256 mg, 693 µmol) and K$_2$CO$_3$ (285 mg, 2.07 mmol) in DMSO (15 mL) was with Argon for about 10 minutes followed by the addition of CuI (26.2 mg, 138 µmol) and 2-Acetylcyclohexanone (48.5 mg, 346 µmol). The resulting mixture was heated at 140° C. in a sealed tube for 20 hours. It was then cooled to room temperature, diluted with water and extracted with Ethyl acetate. The combined Ethyl acetate extract was washed with water, brine, dried over anhydrous Na$_2$SO$_4$ and concentrated under reduced pressure. Crude mass was purified by column chromatography (silica, gradient: 0-20% Ethyl acetate in Hexane) to afford 24-3 (60 mg, 138 µmol, 20%) as off white solid. LC MS: ES+ 434.2.

Step 2: Preparation of 3-(4-Phenyl-imidazol-1-yl)-piperidine-2,6-dione (Compound 203)

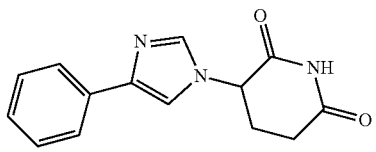 [SMILES: O=C1CCC(n2cnc(-c3ccccc3)c2)C(=O)N1]

A solution of 24-3 (55 mg, 126 µmol) in Ethanol (5 mL) was degassed with Argon for about 10 minutes followed by the addition of 10% Pd/C (27 mg). The resulting mixture was purged with hydrogen (balloon) and stirred under Hydrogen atmosphere at ambient temperature for 16 hours to produce Compound 203. Reaction mixture was filtered through a short bed of celite and the filtrate was concentrated under reduced pressure. Crude mass was purified by column chromatography (silica, gradient: 0-3% MeOH in DCM) to afford Compound 203 (10.0 mg, 39.1 µmol, 31%) as light brown solid. $^1$H NMR (400 MHz, DMSO-$d_6$) δ 11.14 (s, 1H), 7.78-7.68 (m, 4H), 7.35 (t, J=7.6 Hz, 2H), 7.19 (t, J=7.3 Hz, 1H), 5.32 (dd, J=13.3, 5.0 Hz, 1H), 2.90-2.76 (m, 1H), 2.64 (dd, J=25.2, 15.0 Hz, 2H), 2.32-2.24 (m, 1H). LC MS: ES+ 256.21.

Scheme 25: Preparation of Compound 204

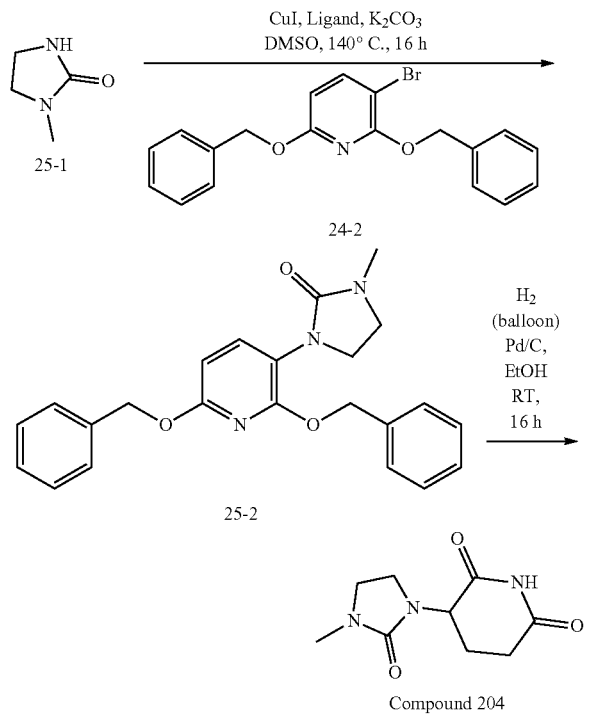

Preparation of 25-2

To a stirred solution of 24-2 (455 mg, 1.22 mmol) in toluene was added 25-1 (100 mg, 860.86 µmol) and K$_3$PO$_4$.H$_2$O (494 mg, 215 µmol) and the resulting mixture was degassed with Argon for 10 minutes. To this were added CuI (0.05 mg, 0.26 µmol) and trans-N,N'-dimethylcyclo-hexane-1,2-diamine (17 mg, 120 µmol) and heated to 100° C. for 16 hours to produce 25-2. Reaction mixture was cooled to room temperature and filtered through a short bed of celite. The filtrate was diluted with Ethyl acetate, washed with water and brine, dried over anhydrous Na$_2$SO$_4$ and concentrated under reduced pressure. Crude mass was purified doing column chromatography (silica, gradient: 0-20% Ethyl acetate in Hexane) to afford 25-2 (200 mg, 514 µmol, 60%) as sticky off-white solid. LC MS: ES+ 390.2.

Preparation of Compound 204

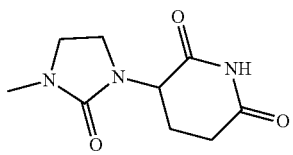

Compound 204 was synthesized following the usual hydrogenation protocol (Yield: 59%) as off white solid. $^1$H NMR (400 MHz, DMSO-d6) δ 10.82 (s, 1H), 4.53 (dd, J=13.4, 5.1 Hz, 1H), 3.37-3.18 (m, 1H), 3.25-3.20 (m, 2H), 3.13 (dd, J=11.3, 4.2 Hz, 1H), 2.81 (ddd, J=18.5, 14.0, 5.4 Hz, 1H), 2.67 (s, 3H), 2.55-2.50 (m, 1H), 2.17 (qd, J=13.2, 4.4 Hz, 1H), 1.81 (dd, J=9.9, 4.5 Hz, 1H); LC MS: ES+ 212.3.

Scheme 26: Synthesis of Compound 205

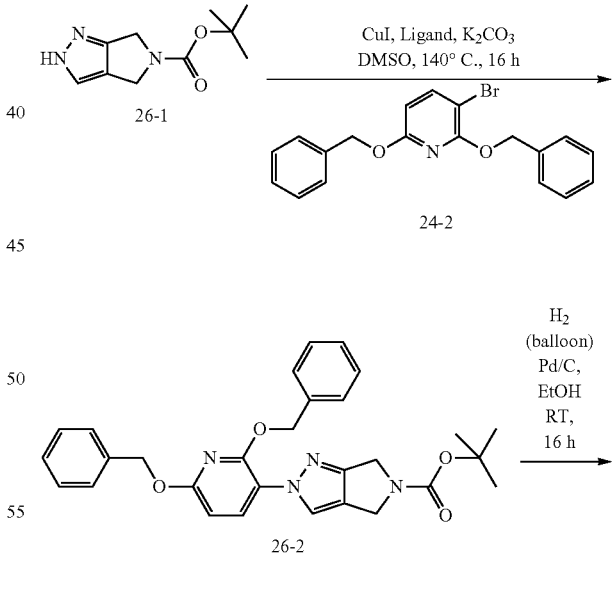

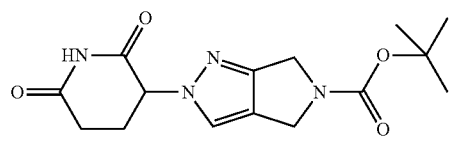

Step-1: Preparation of 2-(2,6-Bis-benzyloxy-pyridin-3-yl)-2,6-dihydro-4H-pyrrolo[3,4-c]pyrazole-5-carboxylic Acid Tert-Butyl Ester (26-2)

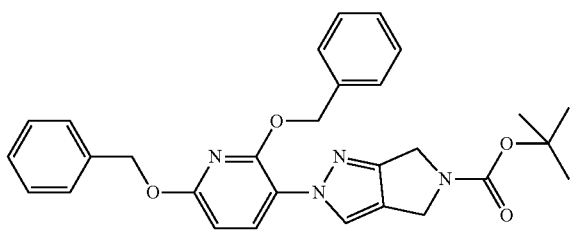 [SMILES: CC(C)(C)OC(=O)N1Cc2cn(-c3ccc(OCc4ccccc4)nc3OCc3ccccc3)nc2C1]

Compound 26-2 was synthesized according to Scheme 26. Yield: 12%; LC MS: ES+ 499.3.

Step-2: Preparation of 2-(2,6-Dioxo-piperidin-3-yl)-2,6-dihydro-4H-pyrrolo[3,4-c]pyrazole-5-carboxylic Acid Tert-Butyl Ester (Compound 205)

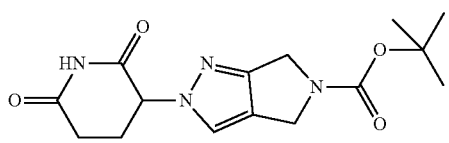 [SMILES: CC(C)(C)OC(=O)N1Cc2cn(C3CCC(=O)NC3=O)nc2C1]

Compound 205 was synthesized following general procedure (hydrogenation) shown in Scheme 26. Yield: 20%; $^1$H NMR (400 MHz, DMSO-d6) δ 11.04 (s, 1H), 7.60 (d, J=8.88 Hz, 1H), 5.33 (m, 1H), 4.33-4.31 (m, 4H), 2.80 (m, 1H), 2.60 (m, 1H), 2.23 (m, 1H), 1.44 (s, 9H); LC MS: ES+ 321.2.

Scheme 27: Synthesis of Compound 206

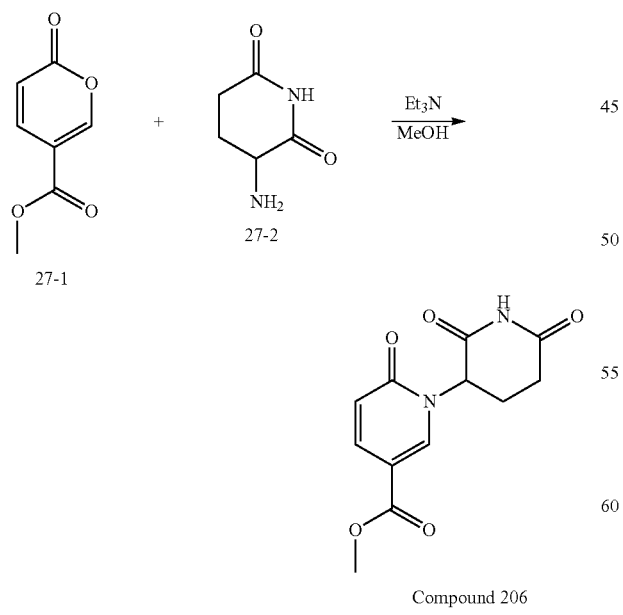

A solution of methyl coumalate 27-1 (200 mg, 1 equiv.) in MeOH (12 ml) was treated with 3-aminopiperidine-2,6-dione 27-2 (216 mg, 1.2 equiv.) and TEA (196 uL, 1.5 equiv.). The reaction was stirred at 23° C. under nitrogen. After 16 h, the reaction was concentrated and triturated with MTBE:Ethylacetate mixture, The solid was suspended in acetonitrile:water, frozen and lyophilized, affording methyl 1-(2,6-dioxopiperidin-3-yl)-6-oxo-1,6-dihydropyridine-3-carboxylate (Compound 206) (86 mg, 23.1%). (M+H). $^1$H NMR (400 MHz, DMSO-d$_6$) δ 11.04 (s, 1H), 8.46 (d, J=2.5 Hz, 1H), 7.79 (dd, J=9.6, 2.5 Hz, 1H), 6.44 (d, J=9.6 Hz, 1H), 5.45 (s, 1H), 3.75 (s, 3H), 2.73 (s, 1H), 2.66-2.45 (m, 2H), 2.11-1.87 (m, 1H). LCMS: MS (ESI+): 265.2.

Scheme 28: Synthesis of Compound 207

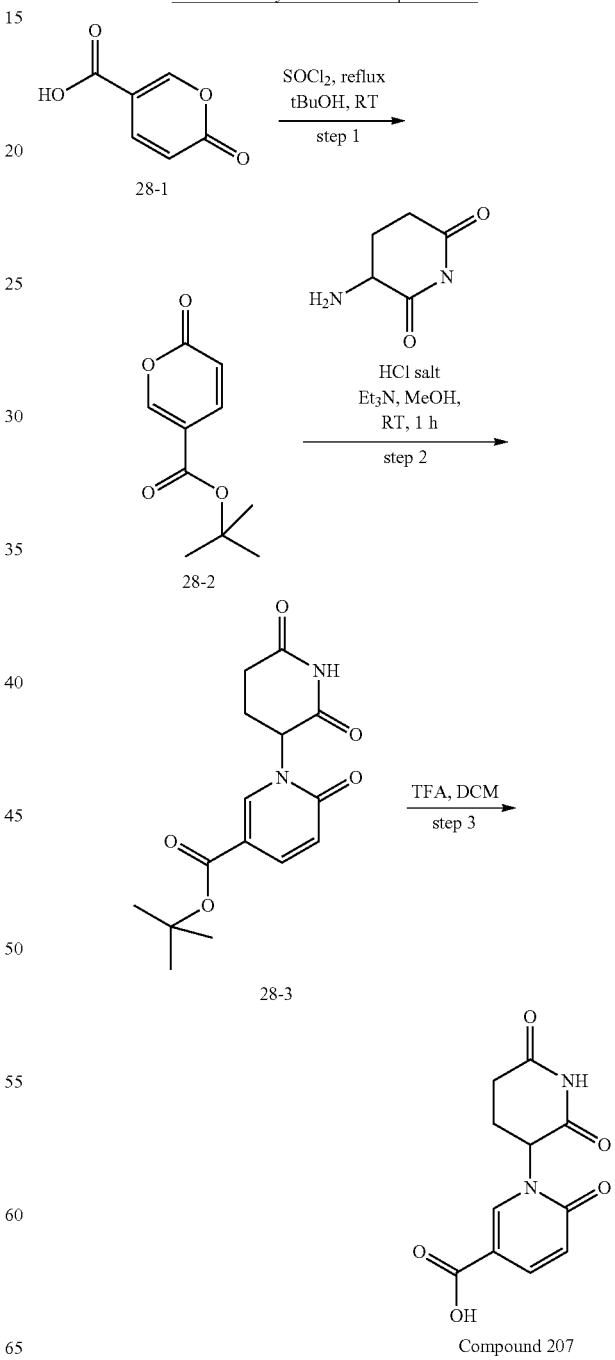

Step-1: 28-2

A stirred solution of 28-1 (5.0 g, 35.6 mmol) in SOCl2 (30.0 mL) was refluxed for 2 hours. Then reaction mass was concentrated in vacuo under inert atmosphere. To this crude acid chloride in THE (30.0 mL) were added Pyridine (11.4 mL, 142 mmol) and Tertiary butanol (33.9 mL, 356 mmol) and the reaction mixture was heated at same temperature for 16 hours. It was concentrated, diluted with saturated aqueous NaHCO$_3$ solution, ethyl acetate. Organic layer was separated and washed with 2N aqueous HCl solution, water, brine, dried over sodium sulfate. It was concentrated to afford 28-2 (3 g) as reddish brown semisolid. Yield: 43%; LC MS: ES+ 197.2.

Step-2: 28-3

To a stirred solution of 28-2 (3.0 g, 15.2 mmol) in Methanol (20.0 mL) were added triethyl amine (3.28 mL, 22.8 mmol) and 3-aminopiperidine-2,6-dione (2.50 g, 15.2 mmol). The reaction mixture was stirred at room temperature for 1 hour. It was concentrated under reduced pressure and diluted with ethyl acetate, water. Layers were separated and organic layer was washed with brine solution. It was dried over sodium sulfate and concentrated. Crude material was purified by column chromatography using (silica, gradient 0%-1% MeOH/DCM) to afford 1.03 g of 28-3 (1 g) as off white solid. Yield: 22%; LC MS: ES+ 307.3.

Step-3: Compound 207

To a stirred solution of 28-3 (1.0 g, 3.26 mmol) in DCM (30.0 mL) was added TFA (10.0 mL) at 0° C. and the reaction mixture was stirred at room temperature for 3 hours. It was concentrated under reduced pressure and triturated with ether to afford Compound 207 (650 mg) as brown solid. Yield: 80%, $^1$H NMR (400 MHz, DMSO-d$_6$) δ 12.92 (br, 1H), 11.05 (s, 1H), 8.42 (m, 1H), 7.83-7.80 (m, 1H), 6.46 (d, J=9.48 Hz, 1H), 5.45 (br, 1H), 2.80-2.74 (m, 1H), 2.67-2.57 (m, 2H), 2.06-2.03 (m, 1H); LC MS: ES+ 251.1.

Scheme 29

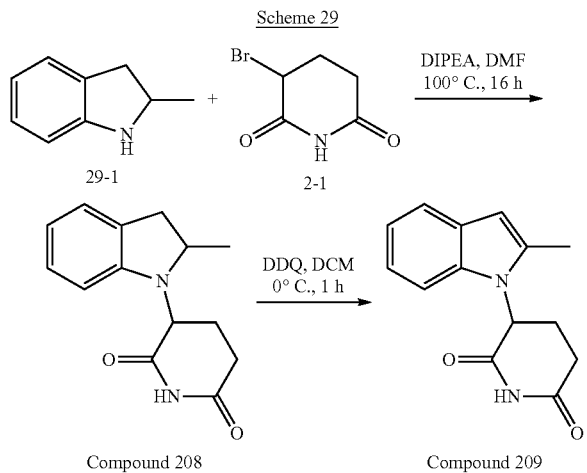

Compound 208     Compound 209

Preparation of 3-(2-Methyl-2,3-dihydro-indol-1-yl)-piperidine-2,6-dione (Compound 208)

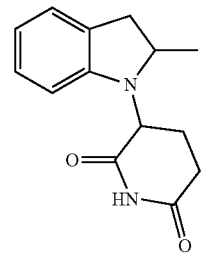 [SMILES: CC1Cc2ccccc2N1C1CCC(=O)NC1=O]

To a mixture of 29-1 (300 mg, 2.25 mmol) and 2-1 (432 mg, 2.25 mmol) in DMF (2 mL) was added N,N-Diisopropylethylamine (0.77 µL, 4.50 mmol). The resulting solution was heated in a sealed tube at 80° C. for 16 hours to produce Compound 208. Reaction mixture was then cooled to room temperature, diluted with water and extracted with Ethyl acetate. The combined Ethyl acetate extract was washed with brine, dried over anhydrous Na$_2$SO$_4$ and concentrated under reduced pressure. Crude mass was purified by column chromatography (silica, gradient: 0-20% Ethyl acetate in Hexane) to afford Compound 208 (65.0 mg, 266 µmol, 12%) as brown solid. $^1$H NMR (400 MHz, DMSO-d$_6$) δ 10.80 (d, J=9.7 Hz, 1H), 6.98-6.97 (m, 1H), 6.88 (d, J=9.2 Hz, 1H), 6.57-6.47 (m, 1H), 6.30-6.19 (m, 1H), 4.39 (t, J=14.1 Hz, 1H), 3.93-3.80 (m, 1H), 3.25-3.09 (m, 2H), 2.79-2.74 (m, 2H), 2.24-2.20 (m, 1H), 1.89-1.81 (m, 1H), 1.22 (d, J=6.3 Hz, 3H). LC MS: ES+ 245.32.

Preparation of 3-(2-Methyl-indol-1-yl)-piperidine-2,6-dione (Compound 209)

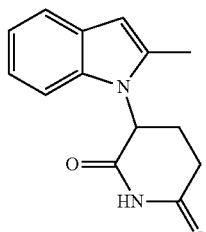

A DCM solution (5 mL) of Compound 208 (45 mg, 184 µmol) was cooled to 0° C. and to it was added DDQ (41.7 mg, 184 µmol) and the resulting mixture was stirred at the same temperature for 1 hour to produce Compound 209. Reaction mass was diluted with DCM, washed with aqueous saturated NaHCO$_3$ solution, water and brine. The organic layer was dried over anhydrous Na$_2$SO$_4$, concentrated under reduced pressure and the resultant solid was triturated with Diethyl ether and Pentane to afford Compound 209 (28.0 mg, 115 µmol, 63%) as brown solid. $^1$H NMR (400 MHz, DMSO-d$_6$) δ 11.14 (s, 1H), 7.43 (d, J=7.8 Hz, 1H), 7.10-6.96 (m, 3H), 6.24 (s, 1H), 5.44 (brs, 1H), 2.98-2.91 (m, 1H), 2.65-2.60 (m, 2H), 2.39-2.31 (m, 3H), 2.06-2.03 (m, 1H); LC MS: ES+ 243.4.

Scheme 30: Preparation of Compound 210

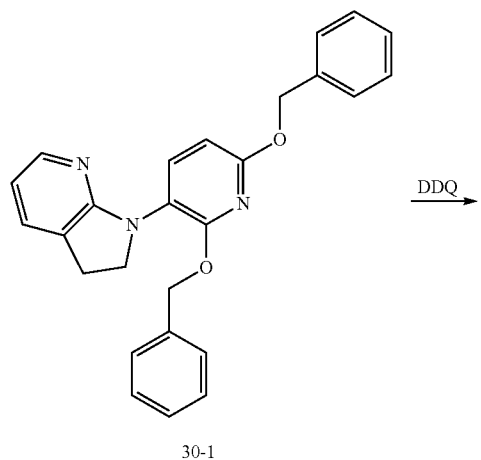

30-1

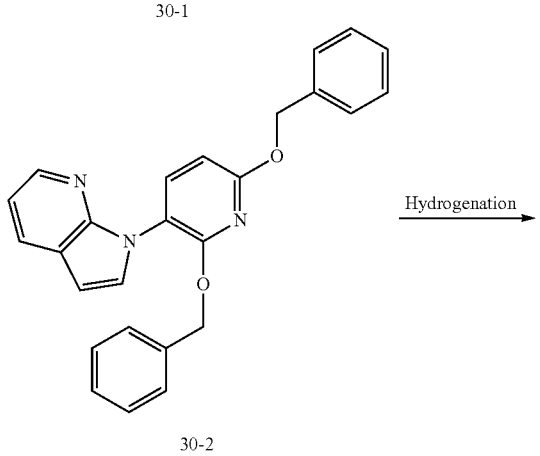

30-2

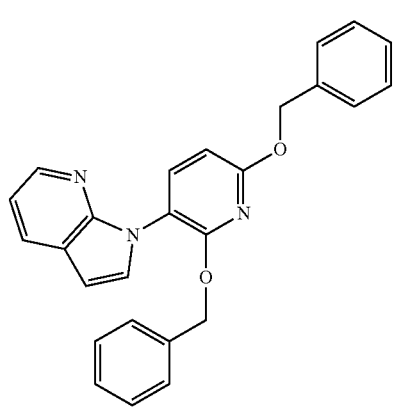 [SMILES: c1ccc(COc2ccc(-n3ccc4cccnc43)c(OCc3ccccc3)n2)cc1]

Compound 210

Preparation of 1-(2,6-Bis-benzyloxy-pyridin-3-yl)-2,3-dihydro-1H-pyrrolo[2,3-b]pyridine (30-2)

30-2 was synthesized according to the procedure followed in Scheme 30 using DDQ (Yield: 71%) as yellowish solid. LC MS: ES+ 408.1.

Preparation of 3-(3H-Pyrrolo[2,3-b]pyridin-1-yl)-piperidine-2,6-dione (Compound 210)

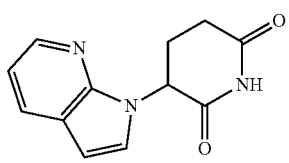

Compound 210

Compound 210 was synthesized according to the usual hydrogenation protocol (Yield: 44%) as an off white solid. $^1$H NMR (400 MHz, DMSO-$d_6$) δ 11.06 (s, 1H), 8.22 (d, J=4.6 Hz, 1H), 7.99 (d, J=7.8 Hz, 1H), 7.58 (d, J=3.6 Hz, 1H), 7.12 (dd, J=8.0, 4.6 Hz, 1H), 6.53 (d, J=3.6 Hz, 1H), 5.78 (dd, J=12.9, 5.1 Hz, 1H), 3.04-2.91 (m, 1H), 2.87-2.80 (m, 1H), 2.67-2.63 (m, 1H), 2.16-2.10 (m, 1H); LCMS: ES+ 230.2.

Scheme 31: Synthesis of Compound 211

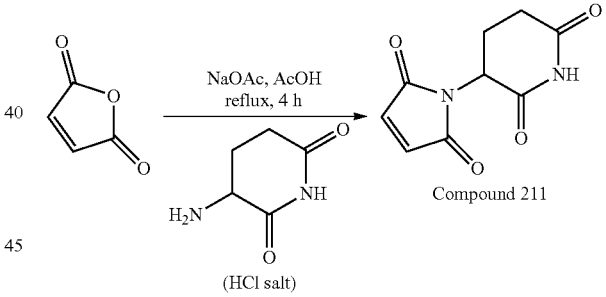

To a stirred solution of 3-aminopiperidine-2,6-dione (168 mg, 1.02 mmol) in acetic acid were added Sodium acetate (250 mg, 3.06 mmol) and furan-2,5-dione (100 mg, 1.02 mmol) and the reaction mixture was heated at 120° C. for 4 hours. It was cooled to room temperature and was concentrated under reduced pressure. It was purified by column chromatography (silica, gradient 0%-40% Ethyl acetate in Hexane) to provide Compound 211 as a white solid. Yield: 29%; $^1$H NMR (400 MHz, DMSO-d6) δ 11.07 (s, 1H), 7.12 (s, 2H), 4.93-4.98 (m, 1H), 2.79-2.88 (m, 1H), 2.53-2.58 (m, 1H), 2.36-2.46 (m, 1H), 1.94-1.99 (m, 1H). GC MS: m/z 208.

Scheme 32

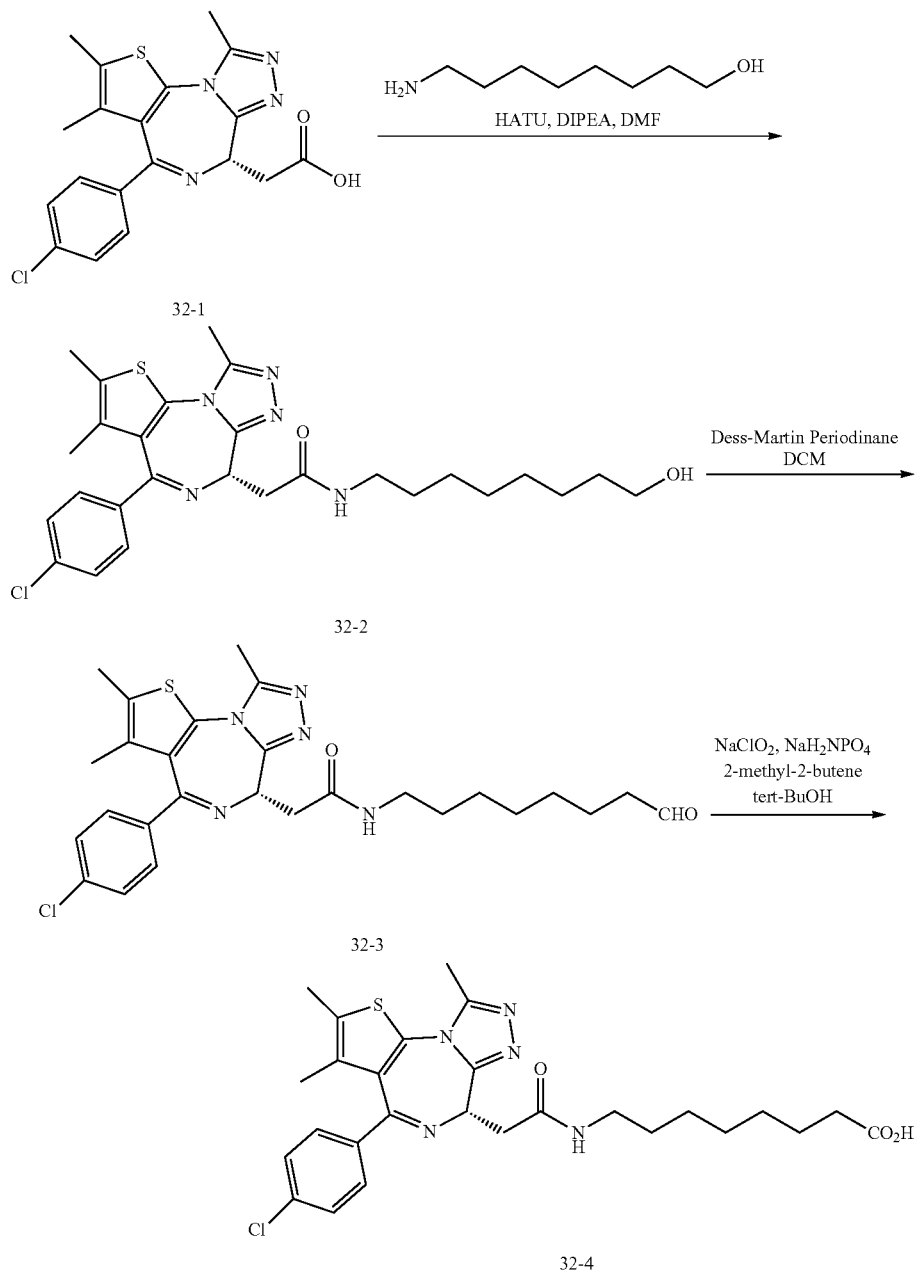

Preparation of (S)-2-(4-(4-Chlorophenyl)-2,3,9-trimethyl-6H-thieno[3,2-f][1,2,4]triazolo[4,3-a][1,4]diazepin-6-yl)-N-(8-hydroxyoctyl)acetamide(32-2)

To a solution of (S)-2-(4-(4-chlorophenyl)-2,3,9-trimethyl-6H-thieno[3,2-f][1,2,4]triazolo[4,3-a][1,4]diazepin-6-yl)acetic acid 32-1 (450 mg, 1.12 mmol) in DMF (2.80 mL) was added 8-aminooctan-1-ol (244 mg, 1.68 mmol), Diisopropylethylamine (389 µL, 2.24 mmol) and HATU (509 mg, 1.34 mmol), The reaction was stirred for 24 h, at which time the reaction was concentrated and purified by isco (24 g column 0-10% MeOH/DCM) to provide (S)-2-(4-(4-chlorophenyl)-2,3,9-trimethyl-6H-thieno[3,2-f][1,2,4]triazolo[4,3-a][1,4]diazepin-6-yl)-N-(3-hydroxypropyl)acetamide (400 mg, 67.6%). LCMS ES+=529.1.

Preparation of (S)-2-(4-(4-Chlorophenyl)-2,3,9-trimethyl-6H-thieno[3,2-f][1,2,4]triazolo[4,3-a][1,4]diazepin-6-yl)-N-(8-oxooctyl)acetamide (32-3)

A 25 mL round bottom flask was charged with (S)-2-(4-(4-chlorophenyl)-2,3,9-trimethyl-6H-thieno[3,2-f][1,2,4]triazolo[4,3-a][1,4]diazepin-6-yl)-N-(8-hydroxyoctyl)acetamide 32-2 (400 mg, 757 µmol) and dichloromethane (4 mL). Dess-Martin Periodinane (0.3 M in DCM, 3.02 mL, 908 µmol) was added and the reaction was stirred at rt for 1 h, then quenched with 0.5 mL isopropanol, sat'd sodium thiosulfate, and sat'd sodium bicarbonate. The reaction was extracted 3×DCM, organics were dried over Na$_2$SO$_4$, filtered and concentrated to provide (S)-2-(4-(4-chlorophenyl)-2,3,9-trimethyl-6H-thieno[3,2-f][1,2,4]triazolo[4,3-a][1,4]diazepin-6-yl)-N-(8-oxooctyl)acetamide (390 mg, 741 mmol, 98% yield) (32-3), which was used in subsequent reactions without further purification. LCMS ES+ 527.3.

Preparation of (S)-8-(2-(4-(4-Chlorophenyl)-2,3,9-trimethyl-6H-thieno[3,2-f][1,2,4]triazolo[4,3-a][1,4]diazepin-6-yl)acetamido)octanoic acid (32-4)

A 25 mL round bottom flask was charged with (S)-2-(4-(4-chlorophenyl)-2,3,9-trimethyl-6H-thieno[3,2-f][1,2,4]triazolo[4,3-a][1,4]diazepin-6-yl)-N-(8-oxooctyl)acetamide 32-3 (250 mg, 475 μmol), NaClO$_2$ (128 mg, 1.425 mmol), NaH$_2$PO$_4$ (202 mg, 1.425 mmol), 2-methyl-2-butene (71 μL, 1.425 mmol) and tert-butanol (5 mL). The reaction was stirred at rt for 18 h, acidified with 1N HCl and extracted with ethyl acetate. The combined organics were dried over Na$_2$SO$_4$, filtered and concentrated. The crude residue was purified by reverse-phase isco (5-100% MeCN/H$_2$O containing 0.01% TFA) to provide (S)-8-(2-(4-(4-chlorophenyl)-2,3,9-trimethyl-6H-thieno[3,2-f][1,2,4]triazolo[4,3-a][1,4]diazepin-6yl)acetamido)octanoic acid (32-4) (200 mg, 368 mmol, 77% yield) as a white solid. LCMS ES+=543.3.

Preparation of Tert-Butyl (S)-(8-(2-(4-(4-Chlorophenyl)-2,3,9-trimethyl-6H-thieno[3,2-f][1,2,4]triazolo[4,3-a][1,4]diazepin-6-yl)acetamido)octyl)carbamate(33-2)

To a solution of (S)-2-(4-(4-chlorophenyl)-2,3,9-trimethyl-6H-thieno[3,2-f][1,2,4]triazolo[4,3-a][1,4]diazepin-6-yl)acetic acid 33-1 (150 mg, 374 μmol) in DMF (935 L) was added tert-butyl (8-aminooctyl)carbamate (118 mg, 486 μmol), Diisopropylethylamine (130 μL, 748 μmol) and HATU (170 mg, 448 μmol). The reaction was stirred for 24 h, at which time the reaction was concentrated and purified by isco (24 g column 0-10% MeOH/DCM) to provide (S)-2-(4-(4-chlorophenyl)-2,3,9-trimethyl-6H-thieno[3,2-f][1,2,4]triazolo[4,3-a][1,4]diazepin-6-yl)-N-(3-hydroxypropyl)acetamide 33-2 (200 mg, 85.4%).

Preparation of (S)—N-(8-Aminooctyl)-2-(4-(4-chlorophenyl)-2,3,9-trimethyl-6H-thieno[3,2-f][1,2,4]triazolo[4,3-a][1,4]diazepin-6-yl)acetamide(33-3)

To a solution of (S)-2-(4-(4-chlorophenyl)-2,3,9-trimethyl-6H-thieno[3,2-f][1,2,4]triazolo[4,3-a][1,4]diazepin-6-yl)-N-(3-hydroxypropyl)acetamide 33-2 (200 mg, 85%) in 5 mL DCM was added TFA (3 mL). The reaction was stirred at rt for 1 h and then concentrated to provide a TFA salt of (S)—N-(8-aminooctyl)-2-(4-(4-chlorophenyl)-2,3,9-trimethyl-6H-thieno[3,2-f][1,2,4]triazolo[4,3-a][1,4]diazepin-6-yl)acetamide (33-3) (180 mg) which was used in subsequent reactions without further purification.

Scheme 33

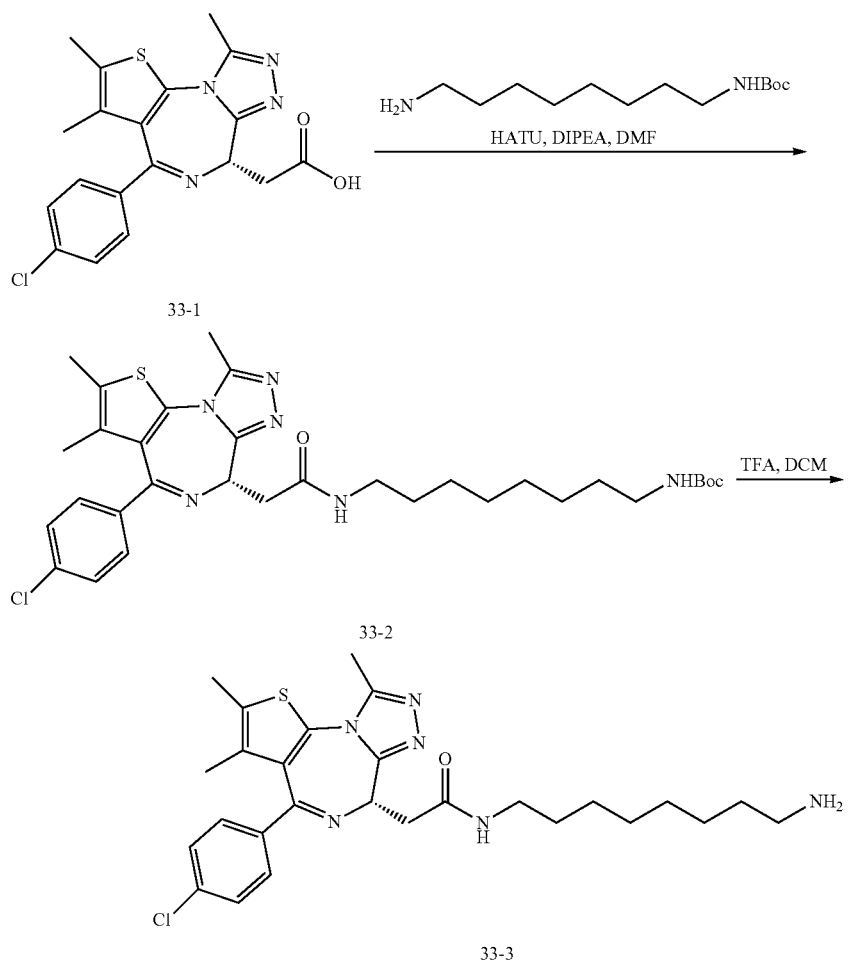

Scheme 34: Preparation of N-(8-(2-((S)-4-(4-Chlorophenyl)-2,3,9-trimethyl-6H-thieno[3,2-f][1,2,4]triazolo[4,3-a][1,4]diazepin-6-yl)acetamido)octyl)-1-(2,6-dioxopiperidin-3-yl)-6-oxo-1,6-dihydropyridine-3-carboxamide (Degronimer 1)

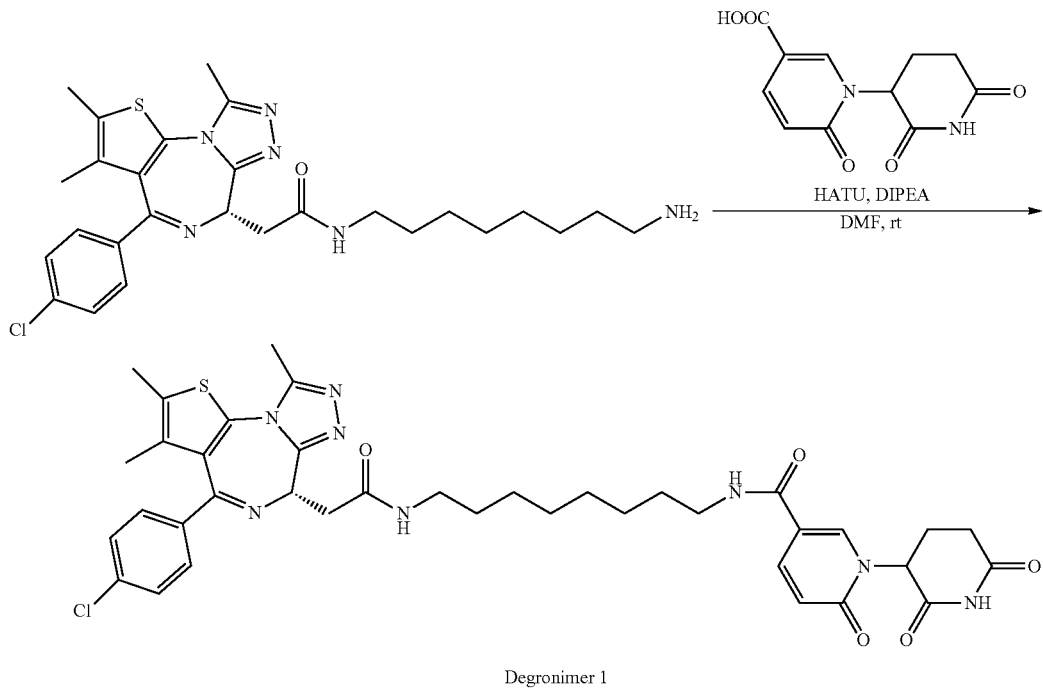

Degronimer 1

(S)—N-(8-aminooctyl)-2-(4-(4-chlorophenyl)-2,3,9-trimethyl-6H-thieno[3,2-f][1,2,4]triazolo[4,3-a][1,4]diazepin-6-yl)acetamide (50 mg, 94.85 umol) and 1-(2,6-dioxo-3-piperidyl)-6-oxo-pyridine-3-carboxylic acid (26.11 mg, 104.34 umol) in DMF (500 uL) were treated with HATU (68.53 mg, 180.22 umol) followed by N,N-Diisopropylethylamine (56.39 mg, 436.33 umol, 76.00 uL). The solution was stirred at rt. Upon completion of the reaction as determined by LCMS, the reaction was purified directly on a reverse-phase C18 column, eluting with 10-100% MeCN in $H_2O$. The product combining fractions were combined, solvent removed and product extracted 3×$CH_2Cl_2$. The organic layers were dried over $Na_2SO_4$, filtered and solvent removed to give N-(8-(2-((S)-4-(4-chlorophenyl)-2,3,9-trimethyl-6H-thieno[3,2-f][1,2,4]triazolo[4,3-a][1,4]diazepin-6-yl)acetamido)octyl)-1-(2,6-dioxopiperidin-3-yl)-6-oxo-1,6-dihydropyridine-3-carboxamide (Degronimer 1) (14.2 mg, 18.70 umol, 19.7% yield) as a light brown solid. 1H NMR (400 MHz, DMSO-d6) δ 11.05 (s, 1H), 8.22 (d, J=2.5 Hz, 1H), 8.18 (t, J=5.5 Hz, 1H), 8.12 (t, J=5.6 Hz, 1H), 7.87 (dd, J=9.6, 2.5 Hz, 1H), 7.50-7.38 (m, 5H), 6.43 (d, J=9.5 Hz, 1H), 5.35 (bs, 1H), 4.52-4.42 (m, 1H), 3.28-3.01 (m, 6H), 2.62-2.54 (m, 4H), 2.39 (s, 2H), 2.22-2.12 (m, 1H), 2.10-1.99 (m, 1H), 1.61 (s, 2H), 1.50-1.38 (m, 4H), 1.26 (s, 6H), 1.22 (s, 6H), 0.92 (t, J=7.5 Hz, 1H), 0.86-0.80 (m, 1H). LC/MS (ES+): m/z 759.2 (M+H)+.

Scheme 35

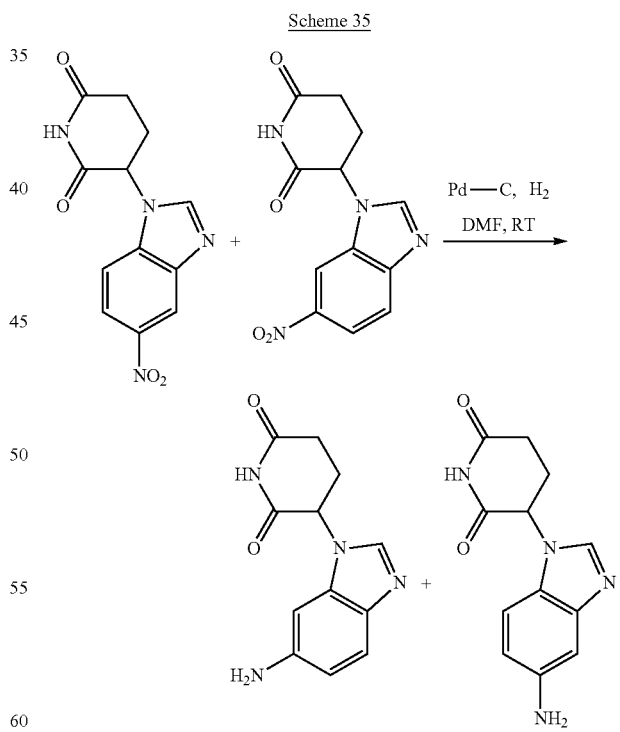

Dissolve 3-(6-nitrobenzimidazol-1-yl)piperidine-2,6-dione and regio isomer (220 mg, 802.24 umol) in DMF (3 mL) with Palladium, 5% on activated carbon paste (16.04 umol), purge with nitrogen three times. Then purge with hydrogen three times, stir at hydrogen atmosphere. Reaction was complete according to LCMS after 4 hrs, filter off pd on carbon via ½ inch celite pad. concentrate down to afford dark green foam crude and directly used for next steps. 3-(6-aminobenzimidazol-1-yl)piperidine-2,6-dione and regio isomer (220 mg, 900.72 umol, 112.28% yield). $^1$H NMR (400 MHz, DMSO-$d_6$) δ 11.33 (d, J=14.9 Hz, 1H), 9.04 (d, J=14.8 Hz, 1H), 7.60 (dd, J=9.0, 3.1 Hz, 1H), 7.15 (s, 1H), 7.08-6.91 (m, 2H), 5.80 (td, J=12.1, 5.0 Hz, 1H), 2.97-2.81 (m, 1H), 2.74 (q, J=14.8, 12.4 Hz, 2H), 2.34 (d, J=7.6 Hz, 1H).

octanoic acid (30 mg, 55.14 umol) and 3-(6-aminobenzimidazol-1-yl)piperidine-2,6-dione (14.81 mg, 60.65 umol) in DMF (300 uL) were treated with HATU (39.83 mg, 104.76 umol) followed by N,N-Diisopropylethylamine (32.78 mg, 253.63 umol, 44.18 uL). The solution was stirred at rt. Upon completion of the reaction by LCMS, the reaction was purified directly on a reverse-phase C18 column, eluting with 10-100% MeCN in H2O. The product combining fractions were combined, solvent removed and product Scheme 36

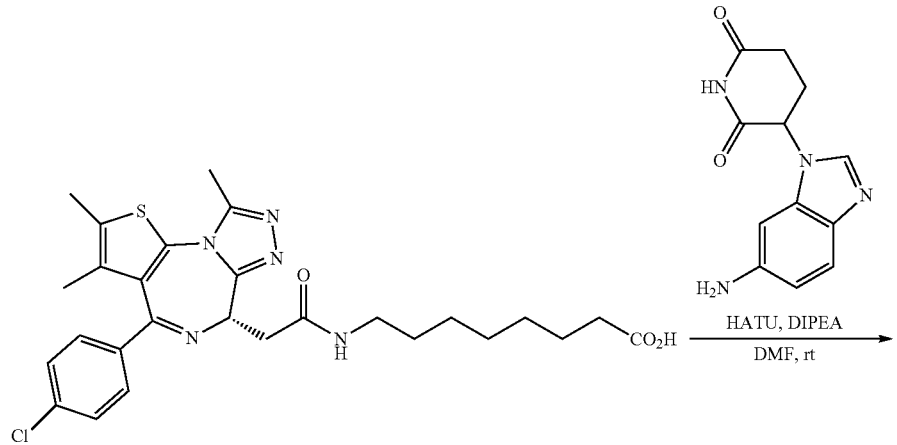

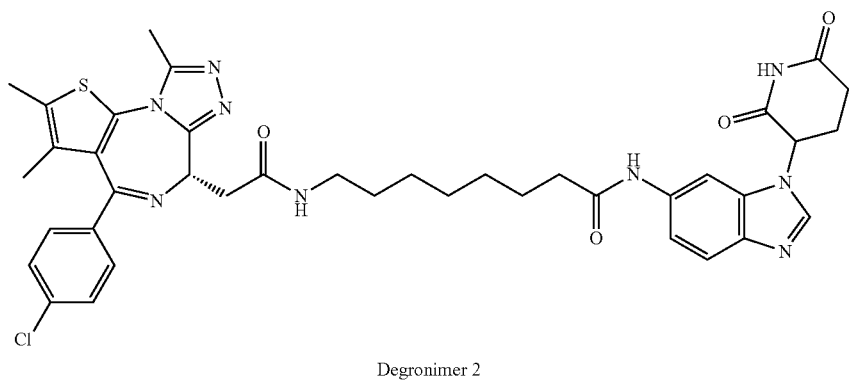

Degronimer 2

8-(2-((S)-4-(4-Chlorophenyl)-2,3,9-trimethyl-6H-thieno[3,2-f][1,2,4]triazolo[4,3-a][1,4]diazepin-6-yl)acetamido)-N-(1-(2,6-dioxopiperidin-3-yl)-1H-benzo[d]imidazol-6-yl)octanamide (Degronimer 2)

(S)-8-(2-(4-(4-chlorophenyl)-2,3,9-trimethyl-6H-thieno[3,2-f][1,2,4]triazolo[4,3-a][1,4]diazepin-6-yl)acetamido)

extracted 3×CH$_2$Cl$_2$. The organic layers were dried over Na$_2$SO$_4$, filtered and solvent removed 8-(2-((S)-4-(4-chlorophenyl)-2,3,9-trimethyl-6H-thieno[3,2-f][1,2,4]triazolo[4,3-a][1,4]diazepin-6-yl)acetamido)-N-(1-(2,6-dioxopiperidin-3-yl)-1H-benzo[d]imidazol-6-yl)octanamide (Degronimer 2) (5.8 mg, 7.53 umol, 13.7% yield) brown solid. LC/MS (ES+): m/z 768.6 (M+H)$^+$.

Scheme 37: 2-((S)-4-(4-Chlorophenyl)-2,3,9-trimethyl-6H-thieno[3,2-f][1,2,4]triazolo[4,3-a][1,4]diazepin-6-yl)-N-(8-(4-(2,6-dioxopiperidin-3-yl)-3-oxopiperazin-1-yl)octyl)acetamide (Degronimer 3)

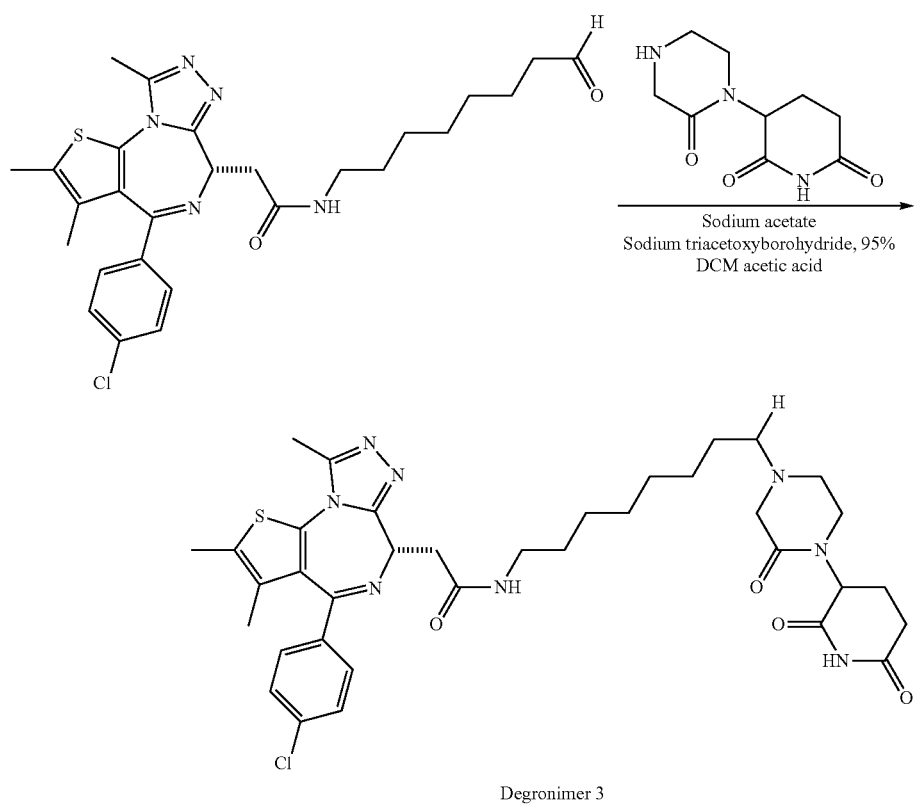

Degronimer 3

2-[4-(4-chlorophenyl)-2,3,9-trimethyl-6H-[1,2,4]triazolothieno[1,4]diazepin-6-yl]-N-(8-oxooctyl)acetamide (15.0 mg, 28.51 umol), 3-(2-oxopiperazin-1-yl)piperidine-2,6-dione (6.02 mg, 28.51 umol), Sodium acetate, anhydrous (11.69 mg, 142.56 umol, 7.64 uL) were added to a vial followed by DCM (95.04 uL) and the reaction stirred for 30 min. Acetic acid (5.14 mg, 85.54 umol, 4.89 uL) was added to the solution and the reaction stirred for an additional 30 min and cooled to 0° C. prior to the addition of Sodium triacetoxyborohydride, 95% (6.65 mg, 31.36 umol) was added and the reaction was gradually warmed to RT and stirred for 12 hours. 1 ml of DMSO was added to the vial and DCM was evaporated under vacuum. Upon completion of the reaction as determined by LCMS, the reaction was purified directly on a reverse-phase C18 column, eluting with 10-100% MeCN in $H_2O$.

The product containing fractions were combined, solvent removed and product extracted 3×$CH_2Cl_2$. The organic layers were dried over $Na_2SO_4$, filtered and solvent removed to give 2-((S)-4-(4-chlorophenyl)-2,3,9-trimethyl-6H-thieno[3,2-f][1,2,4]triazolo[4,3-a][1,4]diazepin-6-yl)-N-(8-(4-(2,6-dioxopiperidin-3-yl)-3-oxopiperazin-1-yl)octyl)acetamide (Degronimer 3) (6 mg, 7.49 umol, 26.26% yield) as a red oil. 1H NMR (400 MHz, DMSO-d6) δ 10.84 (s, 1H), 10.02 (s, 1H), 8.13 (t, J=5.6 Hz, 1H), 8.06 (s, 1H), 7.58 (d, J=8.7 Hz, 1H), 7.46 (d, J=8.5 Hz, 2H), 7.43-7.37 (m, 2H), 4.51-4.44 (m, 1H), 4.29 (dd, J=9.5, 5.1 Hz, 1H), 3.88 (s, 3H), 3.27-3.02 (m, 4H), 2.68-2.60 (m, 2H), 2.57 (s, 2H), 2.37 (s, 2H), 2.35-2.29 (m, 2H), 2.20-2.09 (m, 2H), 1.60 (s, 3H), 1.48-1.40 (m, 2H), 1.30 (s, 4H), 1.22 (s, 5H), 0.91 (t, J=7.4 Hz, 1H), 0.87-0.80 (m, 1H). LC/MS (ES+): m/z 743.5 (M+H+Na)+.

VIII. Additional Synthesis of Representative Compounds

The compounds of the present invention can be prepared, for example, using methods provided below or routine modifications of these methods.

Scheme 38

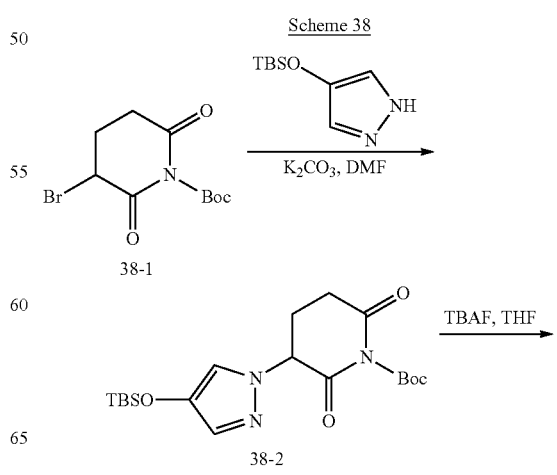

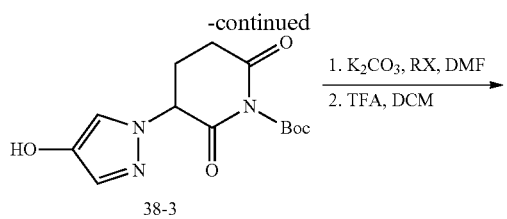

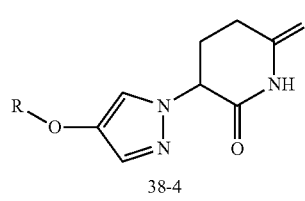

wherein:
R is the point at which the Linker is attached.

Step 1 tert-Butyl 3-(4-((tert-butyldimethylsilyl)oxy)-1H-pyrazol-1-yl)-2,6-dioxopiperidine-1-carboxylate Dry $K_2CO_3$ (1.0 eq.) and tert-butyl 3-bromo-2,6-dioxopiperidine-1-carboxylate (1.0 eq.) (Faming Zhuanli Shenqing, 103554082, 5 Feb. 2014) are added to a stirred solution of 4-((tert-butyldimethylsilyl)oxy)-1H-pyrazole (1.0 eq.) (in DMF (0.2M) at rt. After 2.5 h water is added and the suspension is extracted with AcOEt. The organic phase is dried ($Na_2SO_4$) and evaporated. The residue is chromatographed on silica gel (AcOEt/n-heptane 1/1) to provide tert-butyl 3-(4-((tert-butyldimethylsilyl)oxy)-1H-pyrazol-1-yl)-2,6-dioxopiperidine-1-carboxylate.

Step 2 tert-Butyl 3-(4-hydroxy-1H-pyrazol-1-yl)-2,6-dioxopiperidine-1-carboxylate

Tetra-n-butylammonium fluoride (1.1 M in THF; 1.1 eq.) is added to a solution of tert-butyl 3-(4-((tert-butyldimethylsilyl)oxy)-1H-pyrazol-1-yl)-2,6-dioxopiperidine-1-carboxylate (1.0 eq.) in THF (2.0 M) that has been cooled to 5° C. The resultant mixture is stirred at ambient temperature for 1 hour. The reaction mixture is diluted with a saturated aqueous sodium bicarbonate solution and extracted with ethyl acetate. The organic phase is recovered, washed with water, dried over magnesium sulphate and evaporated to provide tert-butyl 3-(4-hydroxy-1H-pyrazol-1-yl)-2,6-dioxopiperidine-1-carboxylate.

Scheme 38

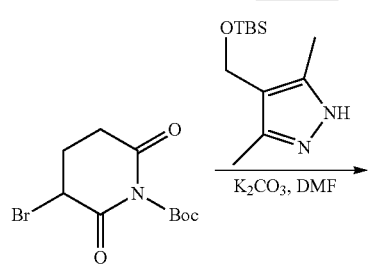

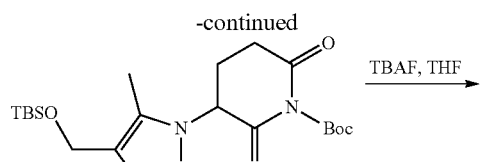

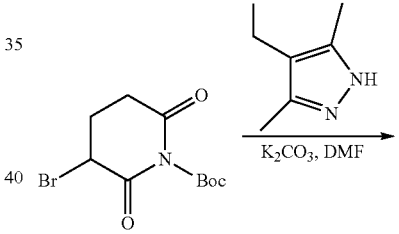

wherein:
R is the point at which the Linker is attached.

Step 1

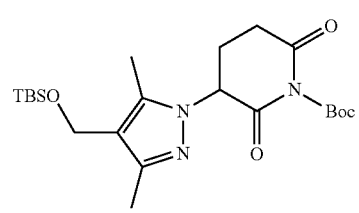

Tert-Butyl 3-(4-(((tert-butyldimethylsilyl)oxy)methyl)-3,5-dimethyl-1H-pyrazol-1-yl)-2,6-dioxopiperidine-1-carboxylate Dry $K_2CO_3$ (1.0 eq.) and tert-butyl 3-bromo-2,6-dioxopiperidine-1-carboxylate (1.0 eq.) are added to a stirred solution of 4-(((tert-butyldimethylsilyl)oxy)methyl)-3,5-dimethyl-1H-pyrazole (1.0 eq.) (Journal of Organometallic Chemistry, 694(2), 199-206; 2009) in DMF (0.2M) at rt. After 2.5 h water is added and the suspension is extracted with AcOEt. The organic phase is dried ($Na_2SO_4$) and evaporated. The residue is chromatographed on silica gel (AcOEt/n-heptane 1/1) to provide tert-butyl 3-(4-(((tert-butyldimethylsilyl)oxy)methyl)-3,5-dimethyl-1H-pyrazol-1-yl)-2,6-dioxopiperidine-1-carboxylate.

Step 2

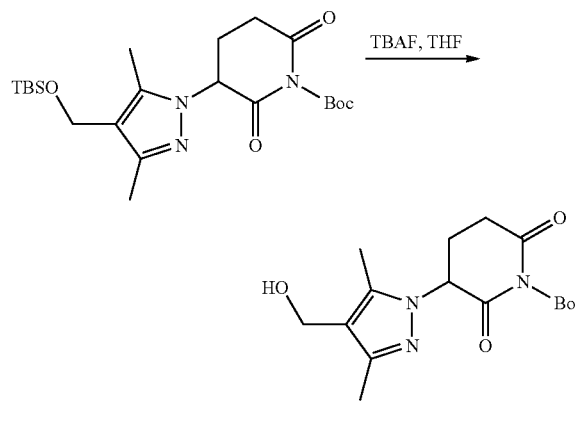

Tert-Butyl 3-(4-(hydroxymethyl)-3,5-dimethyl-1H-pyrazol-1-yl)-2,6-dioxopiperidine-1-carboxylate Tetra-n-butylammonium fluoride (1.1 M in THF; 1.1 eq.) is added to a solution of tert-butyl 3-(4-(((tert-butyldimethylsilyl)oxy)methyl)-3,5-dimethyl-1H-pyrazol-1-yl)-2,6-dioxopiperidine-1-carboxylate (1.0 eq.) in THF (2.0 M) that has been cooled to 5° C. The resultant mixture is stirred at ambient temperature for 1 hour. The reaction mixture is diluted with a saturated aqueous sodium bicarbonate solution and extracted with ethyl acetate. The organic phase is recovered, washed with water, dried over magnesium sulphate and evaporated to provide tert-butyl 3-(4-(hydroxymethyl)-3,5-dimethyl-1H-pyrazol-1-yl)-2,6-dioxopiperidine-1-carboxylate.

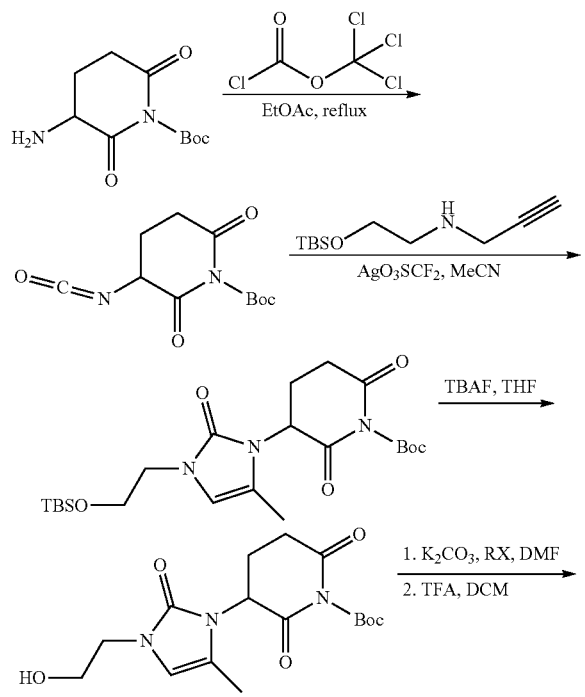

-continued

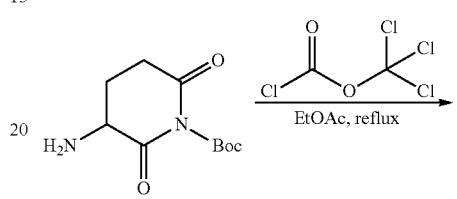

wherein:
R is the point at which the Linker is attached.

Step 1

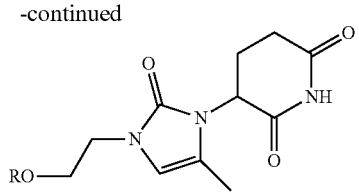

Tert-Butyl 3-isocyanato-2,6-dioxopiperidine-1-carboxylate

Following the example procedure of J. Med. Chem. 1999, 42, 593-600: To a solution of trichloromethyl chloroformate (1.3 eq.) and a catalytic amount of activated charcoal in 20 mL of dry ethyl acetate is added rapidly tert-butyl 3-amino-2,6-dioxopiperidine-1-carboxylate (1.0 eq.) as a solid or a solution of the corresponding amine (2.5 mmol) in 10 mL of dry ethyl acetate. The reaction mixture is heated to reflux for 4-5 h, cooled, filtered, and the solvent is evaporated carefully under reduced pressure to provide tert-butyl 3-isocyanato-2,6-dioxopiperidine-1-carboxylate.

Step 2

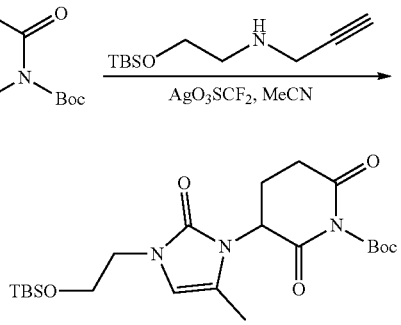

Tert-Butyl 3-(3-(2-((tert-butyldimethylsilyl)oxy)ethyl)-5-methyl-2-oxo-2,3-dihydro-1H-imidazol-1-yl)-2,6-dioxopiperidine-1-carboxylate Following the general procedure: Journal of Organic Chemistry, 76(14), 5867-5872; 2011 To a solution of N-(2-

((tert-butyldimethylsilyl)oxy)ethyl)prop-2-yn-1-amine (ref: Tetrahedron Letters, 52(46), 6185-6189; 2011) (1 eq.) in dry MeCN (2.0 M) is added tert-butyl 3-isocyanato-2,6-dioxopiperidine-1-carboxylate (1.1 eq.) at 0-5° C. The glass tube containing the reaction mixture is degassed and flushed with argon. After 5 min of stirring, silver triflate (26 mg, 0.1 mmol) is added, and the reaction mixture is sealed and stirred for 2 h at 80° C. Upon completion of the reaction, MeCN is removed under reduced pressure. The crude product is loaded onto a silica gel column for chromatography to provide tert-butyl 3-(3-(2-((tert-butyldimethylsilyl)oxy)ethyl)-5-methyl-2-oxo-2,3-dihydro-1H-imidazol-1-yl)-2,6-dioxopiperidine-1-carboxylate.

Step 3

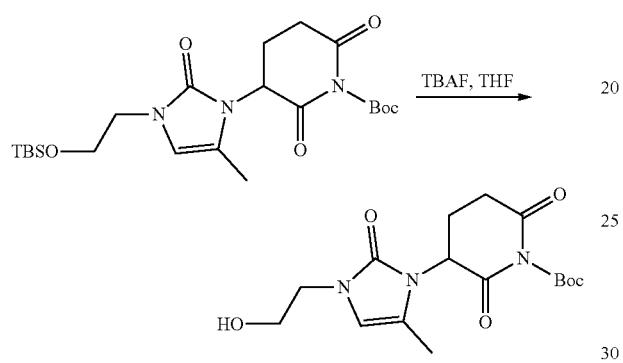

Tert-Butyl 3-(3-(2-hydroxyethyl)-5-methyl-2-oxo-2,3-dihydro-1H-imidazol-1-yl)-2,6-dioxopiperidine-1-carboxylate Tetra-n-butylammonium fluoride (1.1 M in THF; 1.1 eq.) is added to a solution of tert-butyl 3-(3-(2-((tert-butyldimethylsilyl)oxy)ethyl)-5-methyl-2-oxo-2,3-dihydro-1H-imidazol-1-yl)-2,6-dioxopiperidine-1-carboxylate (1.0 eq.) in TH (2.0 M) that has been cooled to 5° C. The resultant mixture is stirred at ambient temperature for 1 hour. The reaction mixture is diluted with a saturated aqueous sodium bicarbonate solution and extracted with ethyl acetate. The organic phase is recovered, washed with water, dried over magnesium sulphate and evaporated to provide

Tert-Butyl 3-(3-(2-hydroxyethyl)-5-methyl-2-oxo-2,3-dihydro-1H-imidazol-1-yl)-2,6-dioxopiperidine-1-carboxylate -continued

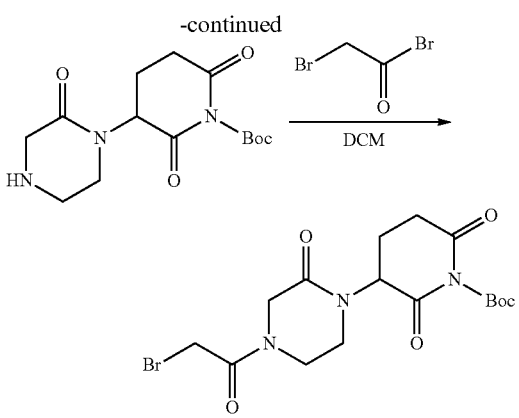

Step 1

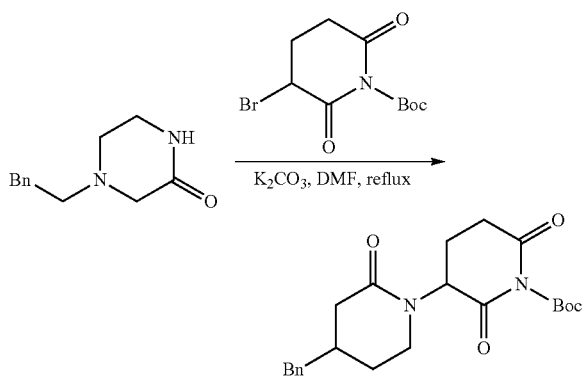

Tert-Butyl 3-(4-benzyl-2-oxopiperazin-1-yl)-2,6-dioxopiperidine-1-carboxylate Dry $K_2CO_3$ (1.0 eq.) and 4-phenethylpiperazin-2-one (1.0 eq.) are added to a stirred solution of (1.0 eq.) tert-butyl 3-bromo-2,6-dioxopiperidine-1-carboxylate in DMF (0.2M) at rt. After 2.5 h, water is added and the suspension is extracted with AcOEt. The organic phase is dried ($Na_2SO_4$) and evaporated. The residue is chromatographed on silica gel (AcOEt/n-heptane 1/1) to provide tert-butyl 3-(4-benzyl-2-oxopiperazin-1-yl)-2,6-dioxopiperidine-1-carboxylate.

Step 2

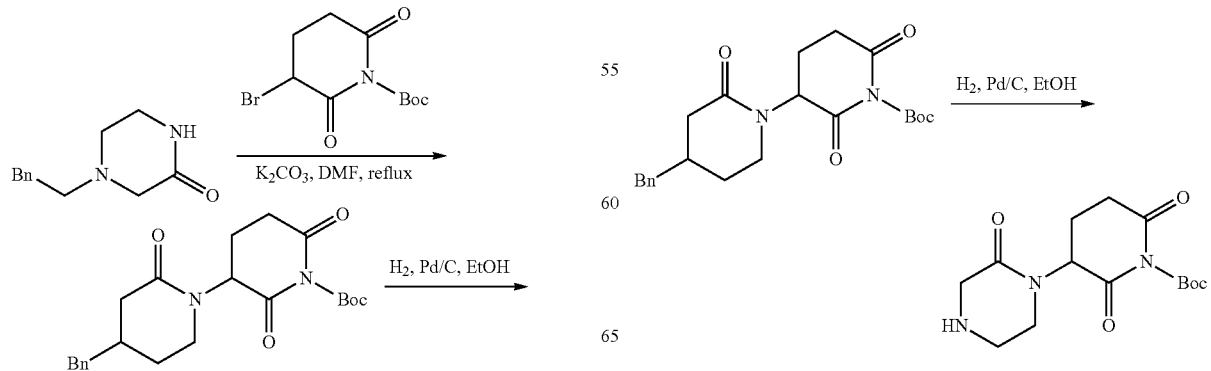

Tert-Butyl 2,6-dioxo-3-(2-oxopiperazin-1-yl)piperidine-1-carboxylate (Example procedure: Journal of Organic Chemistry, 70(5), 1897-1900; 2005) A mixture of tert-butyl 3-(4-benzyl-2-oxopiperazin-1-yl)-2,6-dioxopiperidine-1-carboxylate (1.0 eq.), 10% Pd—C catalyst (0.1 eq Pd) in EtOH (0.2 M) under $H_2$ is stirred at room temperature and atmospheric pressure until the absorption of hydrogen ceased. After the catalyst is filtered out through Celite®, the filtrate is evaporated to provide tert-butyl 2,6-dioxo-3-(2-oxopiperazin-1-yl)piperidine-1-carboxylate.

Step 3

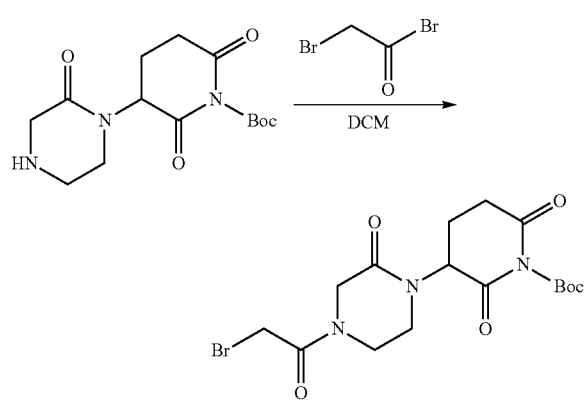

Tert-Butyl 3-(4-(2-bromoacetyl)-2-oxopiperazin-1-yl)-2,6-dioxopiperidine-1-carboxylate (Example procedure: Tetrahedron, 63(2), 337-346; 2007) To a stirred solution of bromoacetyl bromide (1.0 eq.) in DCM (0.2M) at −10° C. is added tert-butyl 2,6-dioxo-3-(2-oxopiperazin-1-yl)piperidine-1-carboxylate (1 eq.). The reaction is stirred overnight and quenched with water. The aqueous layer is extracted with DCM and the organics are dried (MgSO4) and concentrated in vacuo to afford tert-butyl 3-(4-(2-bromoacetyl)-2-oxopiperazin-1-yl)-2,6-dioxopiperidine-1-carboxylate.

Step 1

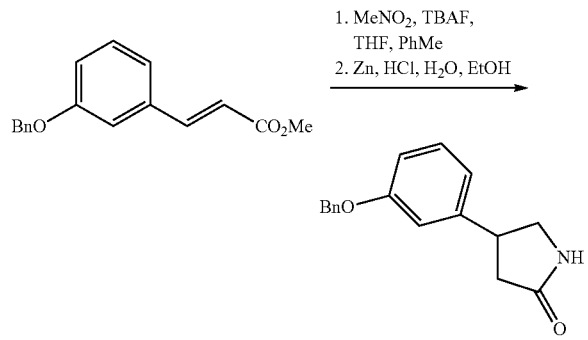

4-(3-(Benzyloxy)phenyl)pyrrolidin-2-one (Angewandte Chemie, International Edition, 54(2), 678-682; 2015): A solution of methyl (E)-3-(3-(benzyloxy)phenyl)acrylate (1 eq.), nitromethane (10 eq.) and tetrabutylammonium (1.2 eq.) (1 M in THF) in toluene (12.3 mL) is stirred at 50° C. for 8 h. This mixture is poured into a 1 M solution of HCl (20 mL) and the phases are separated. The aqueous layer is extracted with toluene (2×15 mL). The combined organic layers are dried over $Na_2SO_4$. The organic layers are concentrated and the product is purified by flash chromatography (hexane/EtOAc 8:2) to provide methyl 3-(3-(benzyloxy)phenyl)-4-nitrobutanoate.

(Organic Letters, 14(20), 5180-5183; 2012): (1 eq.) methyl 3-(3-(benzyloxy)phenyl)-4-nitrobutanoate is dissolved in EtOH (0.1 M) and diluted with HCl (10%/wt) via syringe at 25° C. Zn dust (10 eq.) is added in small portions and the reaction mixture is stirred at 25° C. overnight. When the reaction is complete, $Na_2CO_3$(aq) is added to the mixture until the pH=9. The reaction mixture is extracted with ethyl acetate (3×50 mL), dried with $MgSO_4$, concentrated, and purified by silica gel column chromatography (hexane/EA/$NEt_3$=5/1/1) to provide 4-(3-(benzyloxy)phenyl)pyrrolidin-2-one.

Step 2

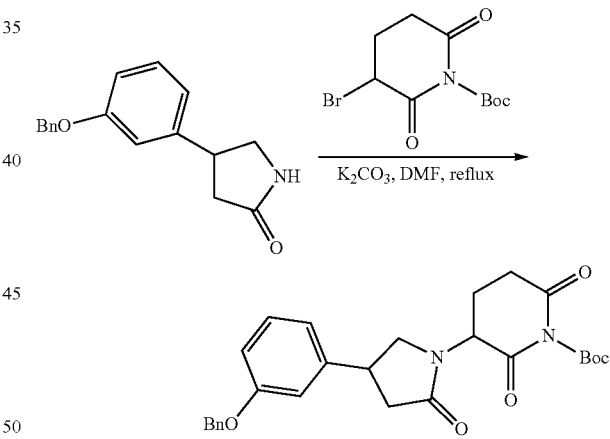

Tert-Butyl 3-(4-(3-(benzyloxy)phenyl)-2-oxopyrrolidin-1-yl)-2,6-dioxopiperidine-1-carboxylate (Following the procedure from Faming Zhuanli Shenqing, 103601717, 26 Feb. 2014). Dry $K_2CO_3$ (1.0 eq.) and 4-(3-(benzyloxy)phenyl)pyrrolidin-2-one (1.0 eq.) are added to a stirred solution of (1.0 eq.) tert-butyl 3-bromo-2,6-dioxopiperidine-1-carboxylate in DMF (0.2M) at rt. After 2.5 h, water is added and the suspension is extracted with AcOEt. The organic phase is dried ($Na_2SO_4$) and evaporated. The residue is chromatographed on silica gel (AcOEt/n-heptane 1/1) to provide tert-butyl 3-(4-(3-(benzyloxy)phenyl)-2-oxopyrrolidin-1-yl)-2,6-dioxopiperidine-1-carboxylate.

Step 3

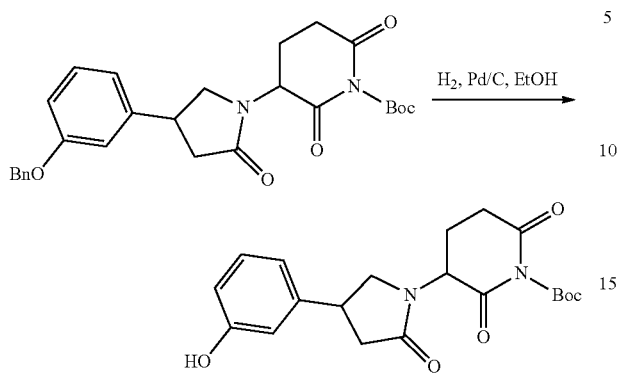

Tert-Butyl 3-(4-(3-hydroxyphenyl)-2-oxopyrrolidin-1-yl)-2,6-dioxopiperidine-1-carboxylate (Example procedure: Journal of Organic Chemistry, 70(5), 1897-1900; 2005) A mixture of tert-butyl 3-(4-(3-(benzyloxy)phenyl)-2-oxopyrrolidin-1-yl)-2,6-dioxopiperidine-1-carboxylate (1.0 eq.), 10% Pd—C catalyst (0.1 eq Pd) in EtOH (0.2 M) under H₂ is stirred at room temperature and atmospheric pressure until the absorption of hydrogen ceased. After the catalyst is filtered out through Celite®, the filtrate is evaporated to provide tert-butyl 3-(4-(3-hydroxyphenyl)-2-oxopyrrolidin-1-yl)-2,6-dioxopiperidine-1-carboxylate.

Step 1

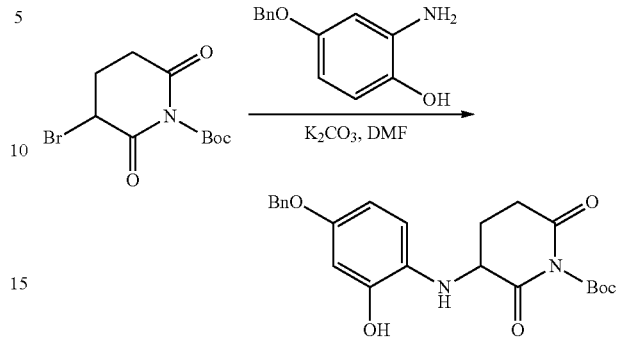

Tert-Butyl 3-((4-(benzyloxy)-2-hydroxyphenyl)amino)-2,6-dioxopiperidine-1-carboxylate Dry $K_2CO_3$ (1.0 eq.) and 2-amino-4-(benzyloxy)phenol (1.0 eq.) are added to a stirred solution of (1.0 eq.) tert-butyl 3-bromo-2,6-dioxopiperidine-1-carboxylate in DMF (0.2M) at rt. After 2.5 h, water is added and the suspension is extracted with AcOEt. The organic phase is dried ($Na_2SO_4$) and evaporated. The residue is chromatographed on silica gel (AcOEt/n-heptane 1/1) to provide tert-butyl 3-((4-(benzyloxy)-2-hydroxyphenyl)amino)-2,6-dioxopiperidine-1-carboxylate.

Step 2

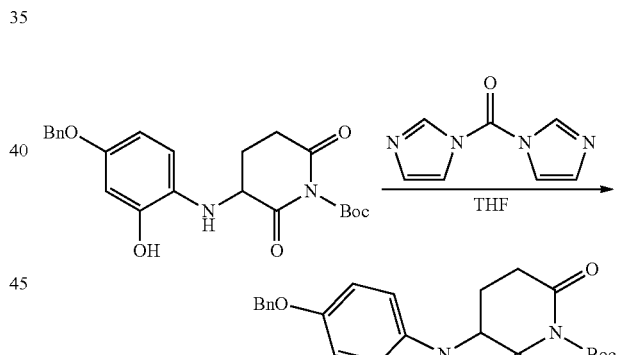

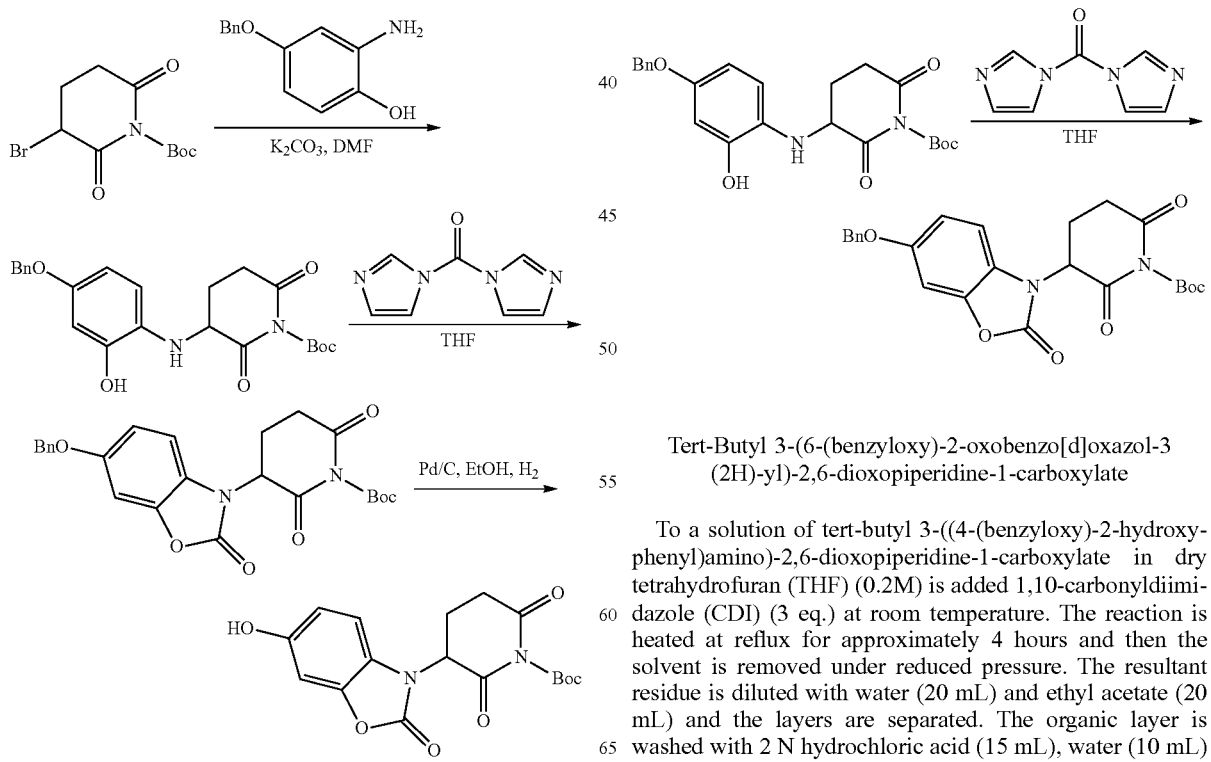

Tert-Butyl 3-(6-(benzyloxy)-2-oxobenzo[d]oxazol-3(2H)-yl)-2,6-dioxopiperidine-1-carboxylate To a solution of tert-butyl 3-((4-(benzyloxy)-2-hydroxyphenyl)amino)-2,6-dioxopiperidine-1-carboxylate in dry tetrahydrofuran (THF) (0.2M) is added 1,10-carbonyldiimidazole (CDI) (3 eq.) at room temperature. The reaction is heated at reflux for approximately 4 hours and then the solvent is removed under reduced pressure. The resultant residue is diluted with water (20 mL) and ethyl acetate (20 mL) and the layers are separated. The organic layer is washed with 2 N hydrochloric acid (15 mL), water (10 mL) and dried over anhydrous sodium sulfate. The mixture is reduced and purified by silica gel column chromatography using hexane: ethyl acetate as eluent to tert-butyl 3-(6-(benzyloxy)-2-oxobenzo[d]oxazol-3(2H)-yl)-2,6-dioxopiperidine-1-carboxylate.

Step 3

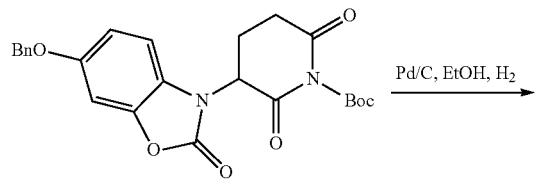

Tert-Butyl 3-(6-hydroxy-2-oxobenzo[d]oxazol-3 (2H)-yl)-2,6-dioxopiperidine-1-carboxylate A mixture of tert-butyl 3-(6-(benzyloxy)-2-oxobenzo[d] oxazol-3(2H)-yl)-2,6-dioxopiperidine-1-carboxylate (1.0 eq.), 10% Pd—C catalyst (0.1 eq Pd) in EtOH (0.2 M) under H$_2$ is stirred at room temperature and atmospheric pressure until the absorption of hydrogen ceased. After the catalyst is filtered out through Celite®, the filtrate is evaporated to provide tert-butyl 3-(6-hydroxy-2-oxobenzo[d]oxazol-3 (2H)-yl)-2,6-dioxopiperidine-1-carboxylate.

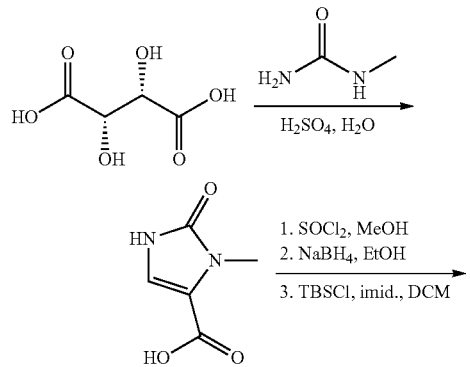

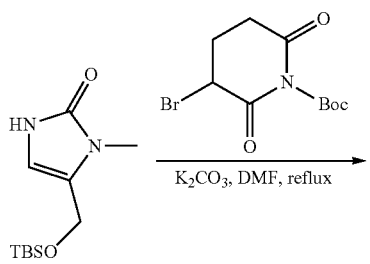

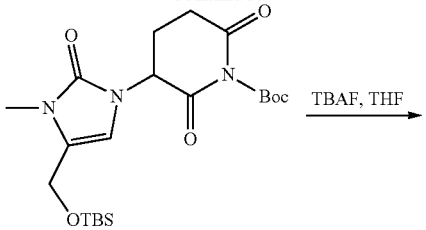

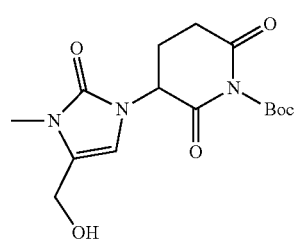

Step 1

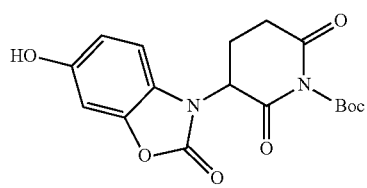

Methyl 3-methyl-2-oxo-2,3-dihydro-1H-imidazole-4-carboxylate (Angewandte Chemie, International Edition, 51(28), 6870-6873, S6870/1-56870/29; 2012) A solid mixture of (±)-tartaric acid 16 (100 g, 0.66 mol, 1.0 equiv) and N-methyl urea 17 (55.69 g, 0.73 mol, 1.1 equiv) is added in 6 portions via scoopula (waiting 10-15 min before addition of another portion) to a stirred solution of concentrated sulfuric acid (0.2M) maintaining the temperature below 45° C. without external cooling. The mixture is then heated to 80° C. and stirred for 3 h at this temperature. The dark brown homogeneous reaction mixture is allowed to cool to 23° C., poured onto ice, and the resulting solids are filtered to provide methyl 3-methyl-2-oxo-2,3-dihydro-1H-imidazole-4-carboxylate.

Step 2

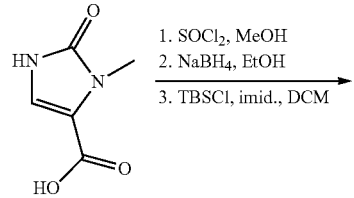

Methyl 3-methyl-2-oxo-2,3-dihydro-1H-imidazole-4-carboxylate

Add dropwise SOCl$_2$ (1 eq.) to a cooled solution of L-pyroglutamic acid (1 eq.) in dry MeOH (80 mL) with magnetic stirring at room temperature for 2 hours. Concentrate the mixture under vacuum to obtain methyl 3-methyl-2-oxo-2,3-dihydro-1H-imidazole-4-carboxylate as a clear oil.

Step 3

5-(Hydroxymethyl)-1-methyl-1,3-dihydro-2H-imidazol-2-one

Methyl 3-methyl-2-oxo-2,3-dihydro-1H-imidazole-4-carboxylate is dissolved in dry EtOH (0.2 M) and NaBH$_4$ (3.0 eq.) is added portionwise. The reaction mixture is stirred at room temperature for 2 hours. The mixture is acidified with concentrated HCl to pH 1 and concentrated under vacuum. The product is purified by flash chromatography (15% MeOH, CH$_2$Cl$_2$) to obtain 5-(hydroxymethyl)-1-methyl-1,3-dihydro-2H-imidazol-2-one.

Step 4

5-(((tert-Butyldimethylsilyl)oxy)methyl)-1-methyl-1,3-dihydro-2H-imidazol-2-one Tert-butyldimethylsilyl chloride (1.1 eq.) is added to a solution of 5-(hydroxymethyl)-1-methyl-1,3-dihydro-2H-imidazol-2-one (1.0 eq.) and imidazole (1.5 eq.) in CH$_2$Cl2 (0.2 M). The reaction mixture is stirred at room temperature for 3 h, then 2 g of silica gel is added and the volatiles are removed in vacuo. The residue is purified by silica chromatography (0-50% EtOAc:Hex) to afford 5-(((tert-butyldimethylsilyl)oxy)methyl)-1-methyl-1,3-dihydro-2H-imidazol-2-one.

Step 5

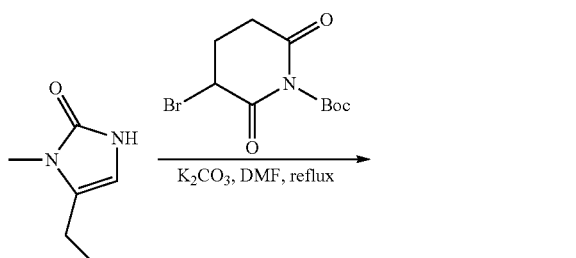

Tert-Butyl 3-(4-(((tert-butyldimethylsilyl)oxy)methyl)-3-methyl-2-oxo-2,3-dihydro-1H-imidazol-1-yl)-2,6-dioxopiperidine-1-carboxylate Dry K$_2$CO$_3$ (1.0 eq.) and 5-(((tert-butyldimethylsilyl)oxy)methyl)-1-methyl-1,3-dihydro-2H-imidazol-2-one (1.0 eq.) are added to a stirred solution of (1.0 eq.) tert-butyl 3-bromo-2,6-dioxopiperidine-1-carboxylate in DMF (0.2M) at rt. After 2.5 h, water is added and the suspension is extracted with AcOEt. The organic phase is dried (Na$_2$SO$_4$) and evaporated. The residue is chromatographed on silica gel (AcOEt/n-heptane 1/1) to provide tert-butyl 3-(4-(((tert-butyldimethylsilyl)oxy)methyl)-3-methyl-2-oxo-2,3-dihydro-1H-imidazol-1-yl)-2,6-dioxopiperidine-1-carboxylate.

Step 6

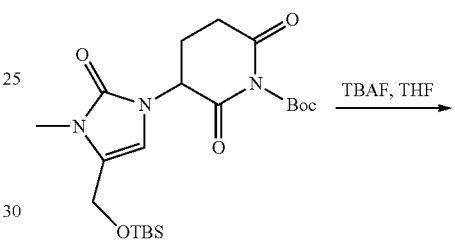

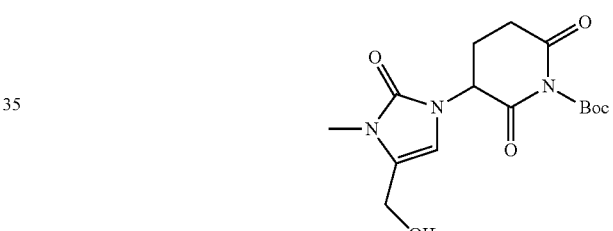

Tert-Butyl 3-(4-(hydroxymethyl)-3-methyl-2-oxo-2,3-dihydro-1H-imidazol-1-yl)-2,6-dioxopiperidine-1-carboxylate Tetra-n-butylammonium fluoride (1.1 M in THF; 1.1 eq.) is added to a solution of tert-butyl 3-(4-(((tert-butyldimethylsilyl)oxy)methyl)-3-methyl-2-oxo-2,3-dihydro-1H-imidazol-1-yl)-2,6-dioxopiperidine-1-carboxylate (1.0 eq.) in TH (2.0 M) that has been cooled to 5° C. The resultant mixture is stirred at ambient temperature for 1 hour. The reaction mixture is diluted with a saturated aqueous sodium bicarbonate solution and extracted with ethyl acetate. The organic phase is recovered, washed with water, dried over magnesium sulphate and evaporated to provide tert-butyl 3-(4-(hydroxymethyl)-3-methyl-2-oxo-2,3-dihydro-1H-imidazol-1-yl)-2,6-dioxopiperidine-1-carboxylate.

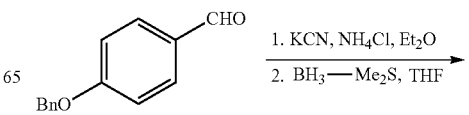

415

-continued

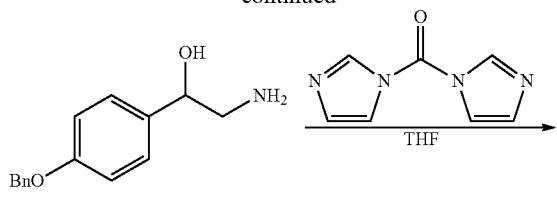

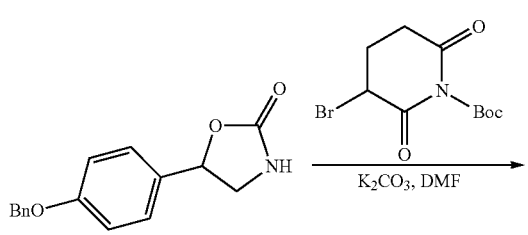

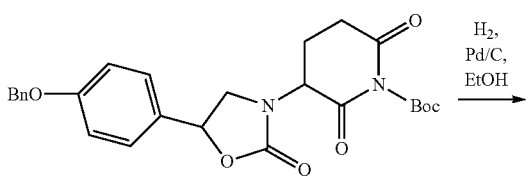

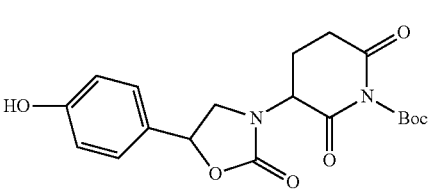

Step 1

2-Amino-1-(4-(benzyloxy)phenyl)ethan-1-ol (Procedure from PCT Int. Appl., 2008087512, 24 Jul. 2008) 2-Amino-1-(4-benzyloxyphenyl)ethanol, potassium cyanide (1 eq.) and ammonium chloride (1 eq.) are dissolved in water (0.1M) to which is added 4-benzyloxybenzaldehyde (1.0 eq.) followed by diethyl ether (100 ml). The reaction mixture is stirred vigorously for 48 hours at room temperature before extracting with ethyl acetate (2×200 ml). The combined organic layers are dried over anhydrous magnesium sulphate, filtered and concentrated in vacuo to afford the cyanohydrin intermediate.

The cyanohydrin is dissolved in dry THE (0.1M) and borane-methyl sulphide complex (2.0 eq.) added. The reaction mixture is heated at reflux for 2 hours before being quenched with methanol (10 eq.). Water (100 eq.) was added followed by conc. HCl (40 ml) and the reaction mixture is stirred for 2 hours until the exotherm subsides. The reaction mixture is concentrated in vacuo and the residue diluted with water. The aqueous solution is then basified by addition of NH₄OH, and extracted with ethyl acetate (3×150 ml). The organic extracts are dried over anhydrous magnesium sulphate, filtered and concentrated in vacuo to afford 2-amino-1-(4-(benzyloxy)phenyl)ethan-1-ol.

416

Step 2

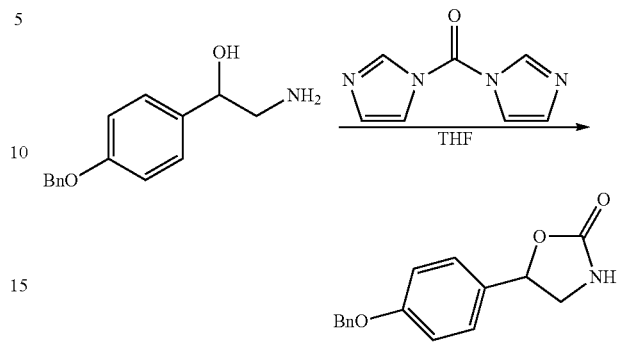

5-(4-(Benzyloxy)phenyl)oxazolidin-2-one

To a solution of 2-amino-1-(4-(benzyloxy)phenyl)ethan-1-ol in dry tetrahydrofuran (THF) (0.2M) is added 1,10-carbonyldiimidazole (CDI) (3 eq.) at room temperature. The reaction is refluxed for approximately 4 hours and then the solvent is removed under reduced pressure. The resultant residue is diluted with water (20 mL) and ethyl acetate (20 mL) and the layers are separated. The organic layer is washed with 2 N hydrochloric acid (15 mL), water (10 mL) and dried over anhydrous sodium sulfate. The mixture is reduced and purified by silica gel column chromatography using hexane: ethyl acetate as eluent to afford 5-(4-(benzyloxy)phenyl)oxazolidin-2-one.

Step 3

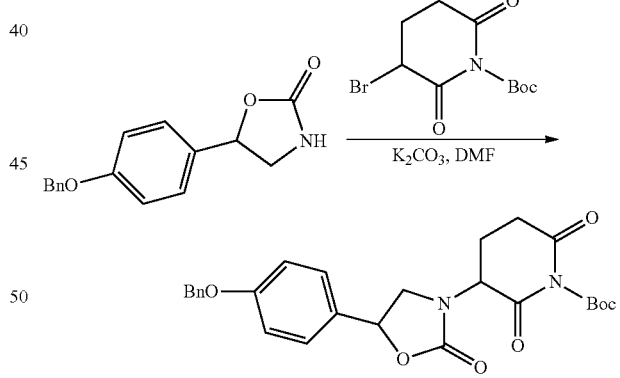

tert-Butyl 3-(5-(4-(benzyloxy)phenyl)-2-oxooxazolidin-3-yl)-2,6-dioxopiperidine-1-carboxylate Dry K₂CO₃ (1.0 eq.) and 5-(4-(benzyloxy)phenyl)oxazolidin-2-one (1.0 eq.) are added to a stirred solution of (1.0 eq.) tert-butyl 3-bromo-2,6-dioxopiperidine-1-carboxylate in DMF (0.2M) at rt. After 2.5 h, water is added and the suspension is extracted with AcOEt. The organic phase is dried (Na₂SO₄) and evaporated. The residue is chromatographed on silica gel (AcOEt/n-heptane 1/1) to provide tert-butyl 3-(5-(4-(benzyloxy)phenyl)-2-oxooxazolidin-3-yl)-2,6-dioxopiperidine-1-carboxylate.

Step 4

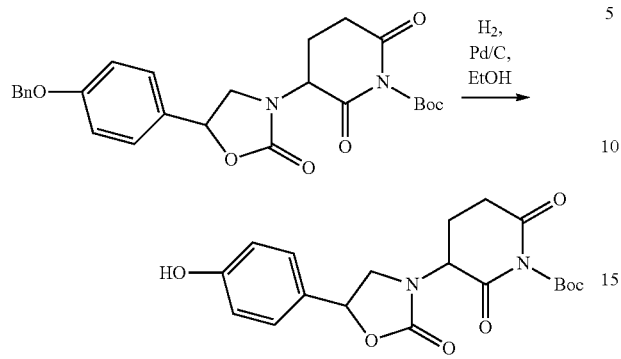

Tert-Butyl 3-(5-(4-hydroxyphenyl)-2-oxooxazolidin-3-yl)-2,6-dioxopiperidine-1-carboxylate A mixture of 5-(4-(benzyloxy)phenyl)oxazolidin-2-one (1.0 eq.), 10% Pd—C catalyst (0.1 eq Pd) in EtOH (0.2 M) under $H_2$ is stirred at room temperature and atmospheric pressure until the absorption of hydrogen ceased. After the catalyst is filtered out through Celite®, the filtrate is evaporated to provide tert-butyl 3-(5-(4-hydroxyphenyl)-2-oxooxazolidin-3-yl)-2,6-dioxopiperidine-1-carboxylate.

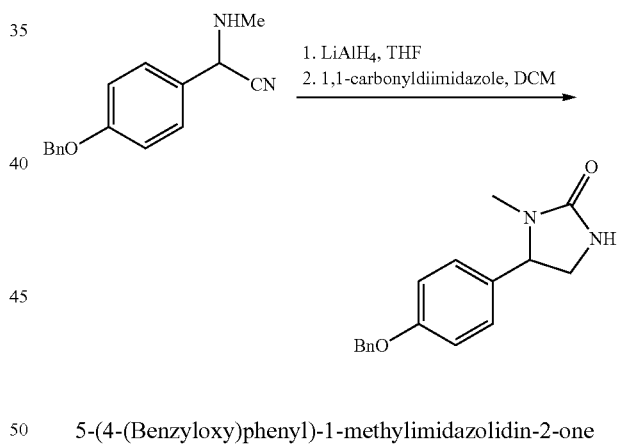

-continued

STEP 1

2-(4-(Benzyloxy)phenyl)-2-(methylamino)acetonitrile (Example procedure: PCT Int. Appl., 2008046758, 24 Apr. 2008) To a solution of 4-(benzyloxy)benzaldehyde (1 eq.) in 50 mL methanol is slowly added at room temperature a solution of potassium cyanide (2 eq.) and methylamine·HCl (1.5 eq.) in water (50 mL). The reaction mixture is heated at 40° C. for 2 h and then at room temperature for 18 h and monitored by TLC. After completion, the reaction mixture is extracted with 3×100 mL dichloromethane. The organic layer is dried over $Na_2SO_4$ and concentrated to afford the desired 2-(4-(benzyloxy)phenyl)-2-(methylamino)acetonitrile which is used in the next step without further purification.

Step 2

5-(4-(Benzyloxy)phenyl)-1-methylimidazolidin-2-one

A solution of 2-(4-(benzyloxy)phenyl)-2-(methylamino)acetonitrile (1.0 equiv.) in THF (0.4 M) is added to a suspension of $LiAlH_4$ (6.0 equiv.) in THF (0.4 M) at 0° C. The reaction is heated at reflux overnight. The reaction is quenched with $Na_2SO_4 \cdot 10H_2O$ and passed through a pad of Celite® which is further eluted with ether. The filtrated is concentrated to provide 1-(4-(benzyloxy)phenyl)-$N^1$-methylethane-1,2-diamine.

Step 3

To a solution of 1-(4-(benzyloxy)phenyl)-$N^1$-methylethane-1,2-diamine in dry tetrahydrofuran (THF) (0.2M) is added 1,10-carbonyldiimidazole (CDI) (3 eq.) at room temperature. The reaction is refluxed for approximately 4 hours and then the solvent is removed under reduced pressure. The resultant residue is diluted with water (20 mL) and ethyl acetate (20 mL) and the layers are separated. The organic layer is washed with 2 N hydrochloric acid (15 mL), water (10 mL) and dried over anhydrous sodium sulfate. The mixture is reduced and purified by silica gel column chromatography using hexane: ethyl acetate as eluent to provide 5-(4-(benzyloxy)phenyl)-1-methylimidazolidin-2-one.

Step 4

Tert-Butyl 3-(4-(4-(benzyloxy)phenyl)-3-methyl-2-oxoimidazolidin-1-yl)-2,6-dioxopiperidine-1-carboxylate Dry K$_2$CO$_3$ (1.0 eq.) and 5-(4-(benzyloxy)phenyl)-1-methylimidazolidin-2-one (1.0 eq.) are added to a stirred solution of (1.0 eq.) tert-butyl 3-bromo-2,6-dioxopiperidine-1-carboxylate in DMF (0.2M) at rt. After 2.5 h, water is added and the suspension is extracted with AcOEt. The organic phase is dried (Na$_2$SO$_4$) and evaporated. The residue is chromatographed on silica gel (AcOEt/n-heptane 1/1) to provide tert-butyl 3-(4-(4-(benzyloxy)phenyl)-3-methyl-2-oxoimidazolidin-1-yl)-2,6-dioxopiperidine-1-carboxylate.

Step 5

Tert-Butyl 3-(4-(4-hydroxyphenyl)-3-methyl-2-oxoimidazolidin-1-yl)-2,6-dioxopiperidine-1-carboxylate A mixture of tert-butyl 3-(4-(4-(benzyloxy)phenyl)-3-methyl-2-oxoimidazolidin-1-yl)-2,6-dioxopiperidine-1-carboxylate (1.0 eq.) and 10% Pd—C catalyst (0.1 eq Pd) in EtOH (0.2 M) under H$_2$ is stirred at room temperature and atmospheric pressure until the absorption of hydrogen ceases. After the catalyst is filtered out through Celite®, the filtrate is evaporated to provide tert-butyl 3-(4-(4-hydroxyphenyl)-3-methyl-2-oxoimidazolidin-1-yl)-2,6-dioxopiperidine-1-carboxylate.

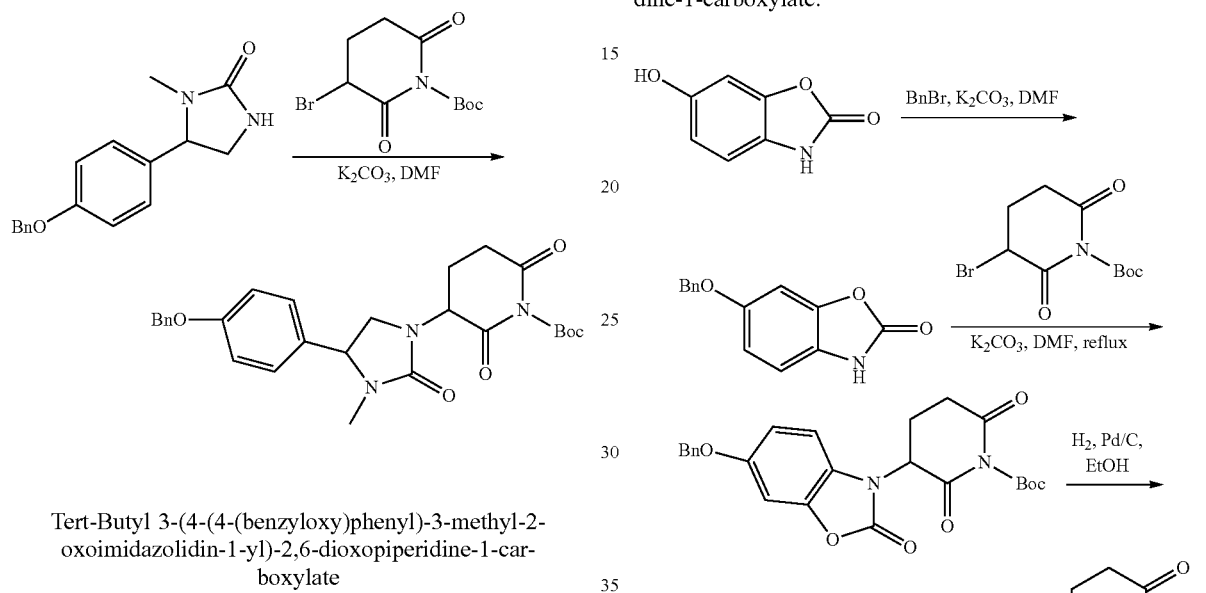

Step 1

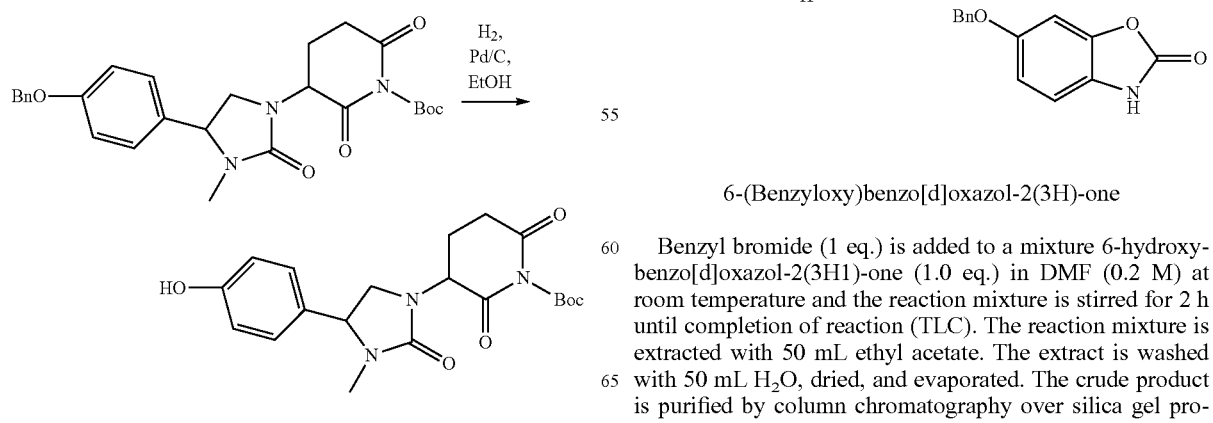

6-(Benzyloxy)benzo[d]oxazol-2(3H)-one

Benzyl bromide (1 eq.) is added to a mixture 6-hydroxybenzo[d]oxazol-2(3H1)-one (1.0 eq.) in DMF (0.2 M) at room temperature and the reaction mixture is stirred for 2 h until completion of reaction (TLC). The reaction mixture is extracted with 50 mL ethyl acetate. The extract is washed with 50 mL H$_2$O, dried, and evaporated. The crude product is purified by column chromatography over silica gel providing 6-benzyloxy)benzo[d]oxazol-2(3H1)-one.

421

Step 2

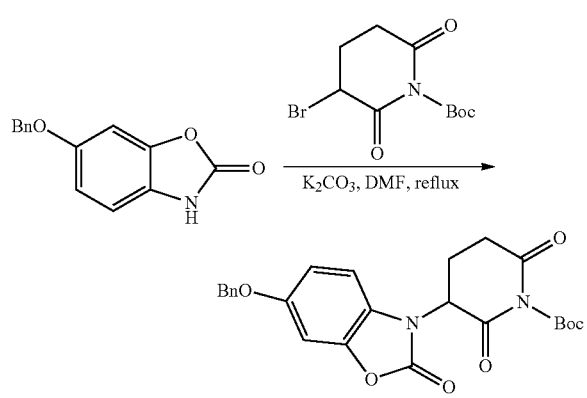

Tert-Butyl 3-(6-(benzyloxy)-2-oxobenzo[d]oxazol-3 (2H)-yl)-2,6-dioxopiperidine-1-carboxylate Dry K₂CO₃ (1.0 eq.) and 6-(benzyloxy)benzo[d]oxazol-2(3H)-one (1.0 eq.) are added to a stirred solution of (1.0 eq.) tert-butyl 3-bromo-2,6-dioxopiperidine-1-carboxylate in DMF (0.2M) at rt. After 2.5 h, water is added and the suspension is extracted with AcOEt. The organic phase is dried (Na₂SO₄) and evaporated. The residue is chromatographed on silica gel (AcOEt/n-heptane 1/1) to provide tert-butyl 3-(6-(benzyloxy)-2-oxobenzo[d]oxazol-3(2H)-yl)-2,6-dioxopiperidine-1-carboxylate.

Step 3

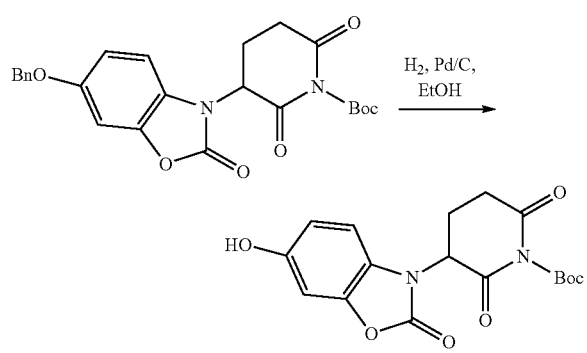

Tert-Butyl 3-(6-hydroxy-2-oxobenzo[d]oxazol-3 (2H)-yl)-2,6-dioxopiperidine-1-carboxylate A mixture of tert-butyl 3-(6-(benzyloxy)-2-oxobenzo[d]oxazol-3(2H)-yl)-2,6-dioxopiperidine-1-carboxylate (1.0 eq.) and 10% Pd—C catalyst (0.1 eq Pd) in EtOH (0.2 M) under H₂ is stirred at room temperature and atmospheric pressure until the absorption of hydrogen ceases. After the catalyst is filtered out through Celite®, the filtrate is evaporated to provide tert-butyl 3-(6-hydroxy-2-oxobenzo[d]oxazol-3(2H)-yl)-2,6-dioxopiperidine-1-carboxylate.

422

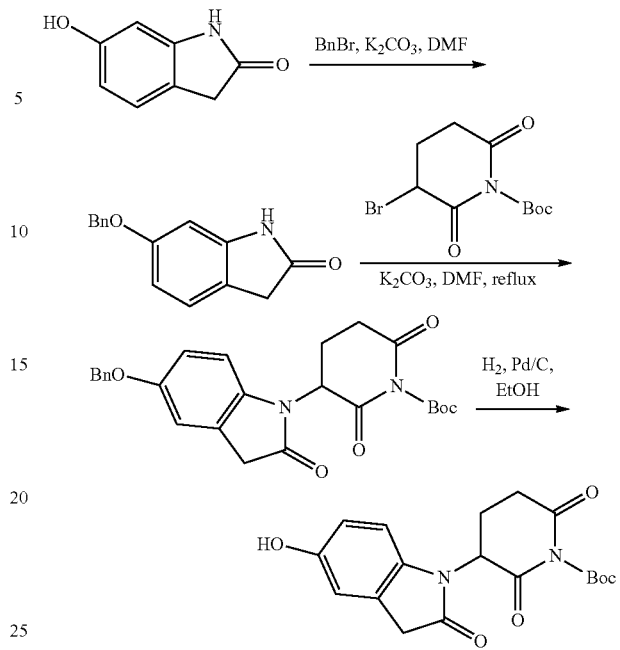

Step 1

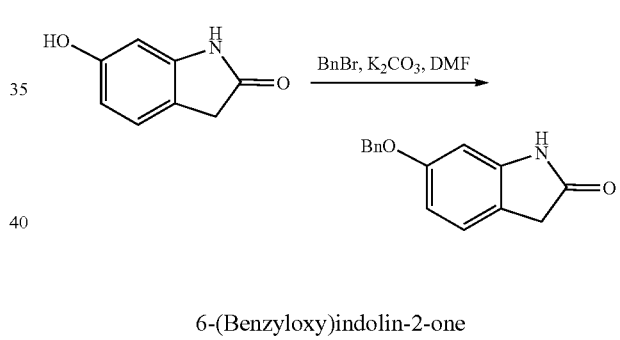

6-(Benzyloxy)indolin-2-one (Tetrahedron, 65(25), 4894-4903; 2009): Benzyl bromide (1 eq.) is added to a mixture 6-hydroxyindolin-2-one (1.0 eq.) in DMF (0.2 M) at room temperature and the reaction mixture is stirred for 2 h until completion of reaction (TLC). The reaction mixture is extracted with 50 mL ethyl acetate. The extract is washed with 50 mL H₂O, dried, and evaporated. The crude product is purified by column chromatography over silica gel providing 6-(benzyloxy)indolin-2-one.

Step 2

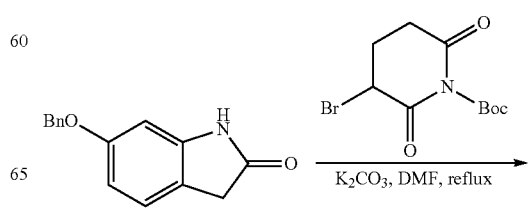

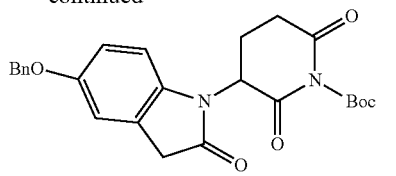

Tert-Butyl 3-(5-(benzyloxy)-2-oxoindolin-1-yl)-2,6-dioxopiperidine-1-carboxylate Dry $K_2CO_3$ (1.0 eq.) and 6-(benzyloxy)indolin-2-one (1.0 eq.) are added to a stirred solution of (1.0 eq.) tert-butyl 3-bromo-2,6-dioxopiperidine-1-carboxylate in DMF (0.2M) at rt. After 2.5 h, water is added and the suspension is extracted with AcOEt. The organic phase is dried ($Na_2SO_4$) and evaporated. The residue is chromatographed on silica gel (AcOEt/n-heptane 1/1) to provide tert-butyl 3-(5-(benzyloxy)-2-oxoindolin-1-yl)-2,6-dioxopiperidine-1-carboxylate.

Step 3

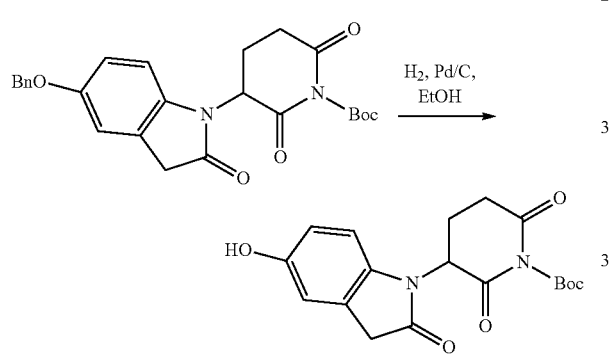

Tert-Butyl 3-(5-hydroxy-2-oxoindolin-1-yl)-2,6-dioxopiperidine-1-carboxylate A mixture of tert-butyl 3-(5-(benzyloxy)-2-oxoindolin-1-yl)-2,6-dioxopiperidine-1-carboxylate (1.0 eq.) and 10% Pd—C catalyst (0.1 eq Pd) in EtOH (0.2 M) under $H_2$ is stirred at room temperature and atmospheric pressure until the absorption of hydrogen ceases. After the catalyst is filtered out through Celite®, the filtrate is evaporated to provide tert-butyl 3-(5-hydroxy-2-oxoindolin-1-yl)-2,6-dioxopiperidine-1-carboxylate.

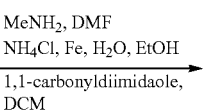

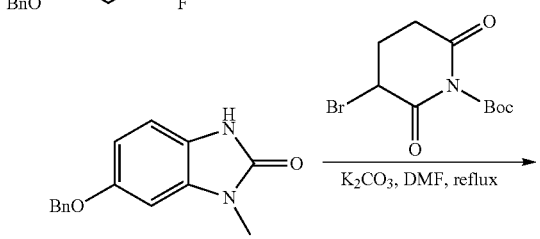

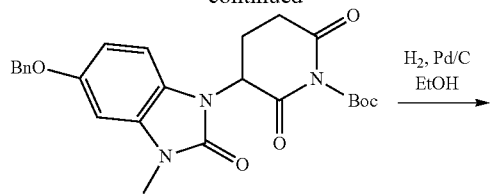

Step 1

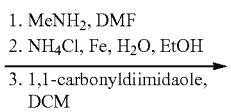

6-(Benzyloxy)-1-methyl-1,3-dihydro-2H-benzo[d]imidazol-2-one

Following the example procedure: Journal of Medicinal Chemistry, 52(18), 5703-5711, 2009. To a solution containing 4-(benzyloxy)-2-fluoro-1-nitrobenzene (1 eq.) in DMF (0.2M) is added methylamine (5 eq.) at room temperature, and the reaction mixture is stirred at room temperature under nitrogen. After 18 h, the reaction mixture is poured into a saturated aqueous solution of sodium chloride and extracted with ethyl acetate. The organic layer is dried over anhydrous sodium sulfate, concentrated in vacuo, and the residue is purified via flash column chromatography (silica, 1% ethyl acetate in hexane) to provide 5-(benzyloxy)-N-methyl-2-nitroaniline.

Step 2

A stirred mixture of 5-(benzyloxy)-N-methyl-2-nitroaniline (1 eq.) and iron powder (5 eq.) in 50% ethanol:water (0.1 M), is heated to 100° C. and concentrated hydrochloric acid (10 eq.) is added. After stirring at 100° C. for 1 hour, the mixture is filtered. The filtrate is concentrated under reduced pressure to provide crude 5-(benzyloxy)-$N^1$-methylbenzene-1,2-diamine.

Step 3

A mixture of 5-(benzyloxy)-$N^1$-methylbenzene-1,2-diamine (1.0 eq.) and N,N'-carbonyldiimidazole (1.5 eq.) in tetrahydrofuran (0.2 M) is stirred at 65° C. for 1 hr. The mixture is diluted with water, and extracted with ethyl acetate. The extract is washed with water, and dried over anhydrous sodium sulfate. The solvent is evaporated under reduced pressure and the obtained residue is purified by flash chromatography (EtOAc/hexanes) to provide 6-(benzyloxy)-1-methyl-1,3-dihydro-2H-benzo[d]imidazol-2-one.

Step 4

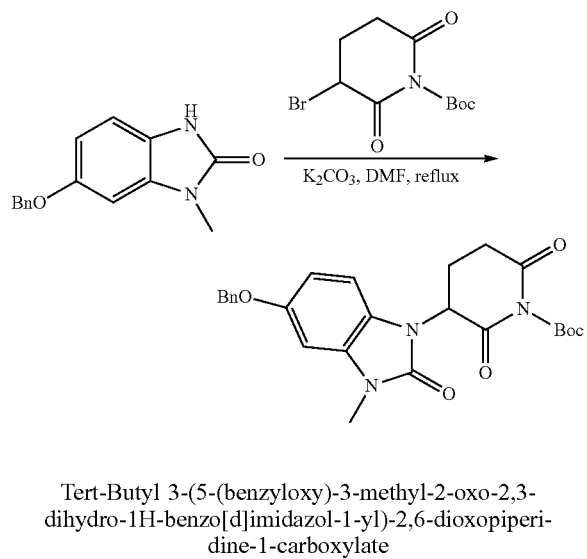

Tert-Butyl 3-(5-(benzyloxy)-3-methyl-2-oxo-2,3-dihydro-1H-benzo[d]imidazol-1-yl)-2,6-dioxopiperidine-1-carboxylate Dry K₂CO₃ (1.0 eq.) and 6-(benzyloxy)-1-methyl-1,3-dihydro-2H-benzo[d]imidazol-2-one (1.0 eq.) are added to a stirred solution of (1.0 eq.) tert-butyl 3-bromo-2,6-dioxopiperidine-1-carboxylate in DMF (0.2M) at rt. After 2.5 h, water is added and the suspension is extracted with AcOEt. The organic phase is dried (Na₂SO₄) and evaporated. The residue is chromatographed on silica gel (AcOEt/n-heptane 1/1) to provide tert-butyl 3-(5-(benzyloxy)-3-methyl-2-oxo-2,3-dihydro-1H-benzo[d]imidazol-1-yl)-2,6-dioxopiperidine-1-carboxylate.

Step 5

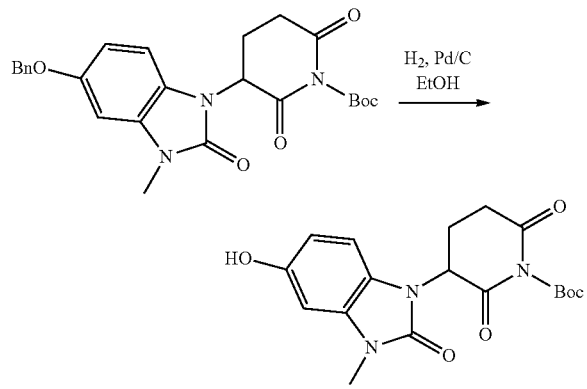

Tert-Butyl 3-(5-hydroxy-3-methyl-2-oxo-2,3-dihydro-1H-benzo[d]imidazol-1-yl)-2,6-dioxopiperidine-1-carboxylate A mixture of tert-butyl 3-(5-(benzyloxy)-3-methyl-2-oxo-2,3-dihydro-1H-benzo[d]imidazol-1-yl)-2,6-dioxopiperidine-1-carboxylate (1.0 eq.) and 10% Pd—C catalyst (0.1 eq Pd) in EtOH (0.2 M) under H₂ is stirred at room temperature and atmospheric pressure until the absorption of hydrogen ceases. After the catalyst is filtered out through Celite®, the filtrate is evaporated to provide tert-butyl 3-(5-hydroxy-3-methyl-2-oxo-2,3-dihydro-H-benzo[d]imidazol-1-yl)-2,6-dioxopiperidine-1-carboxylate.

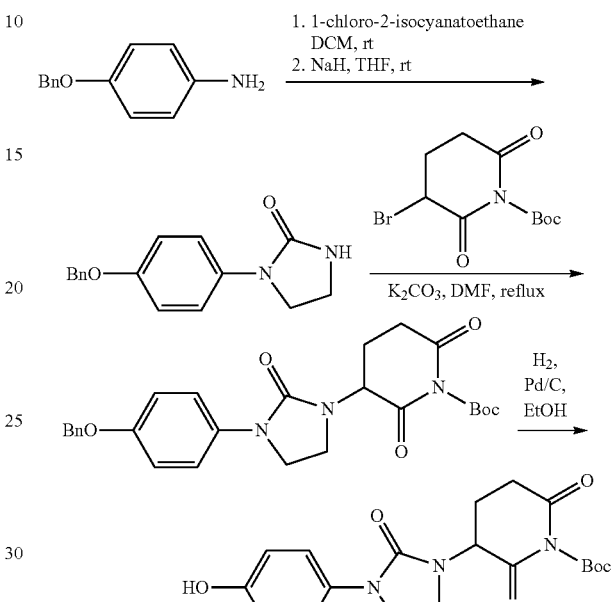

Step 1

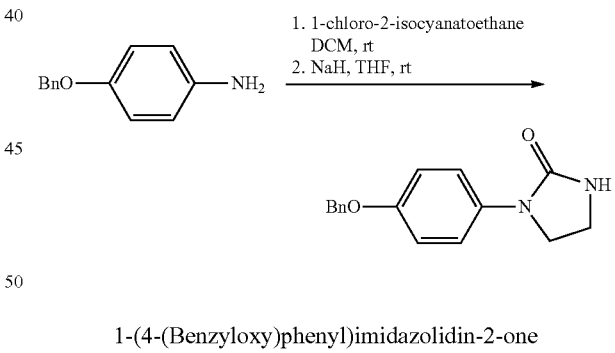

1-(4-(Benzyloxy)phenyl)imidazolidin-2-one 3-chloroethylisocyanate (1.2 eq.) is added dropwise to a cold solution (ice bath) of the 4-(benzyloxy)aniline (1.0 eq) in dry methylene chloride (15 mL per g of aniline). The ice bath is then removed and the reaction mixture is stirred at room temperature for 24 h. After completion of the reaction, the solvent is evaporated under reduced pressure to afford 1-(4-(benzyloxy)phenyl)-3-(2-chloroethyl)urea.

Step 2

To a solution of 1-(4-(benzyloxy)phenyl)-3-(2-chloroethyl)urea in THF (0.05M) at 0° C. is added NaH (1.2 eq, 60 wt % in mineral oil). The reaction is allowed to warm to room temperature, concentrated, and purified by flash chromatography to provide 1-(4-(benzyloxy)phenyl)imidazolidin-2-one.

Step 3

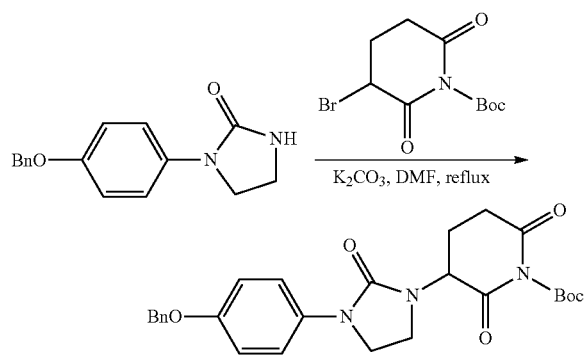

Tert-Butyl 3-(3-(4-(benzyloxy)phenyl)-2-oxoimidazolidin-1-yl)-2-oxopiperidine-1-carboxylate Dry $K_2CO_3$ (1.0 eq.) and 1-(4-(benzyloxy)phenyl)imidazolidin-2-one (1.0 eq.) are added to a stirred solution of (1.0 eq.) tert-butyl 3-bromo-2,6-dioxopiperidine-1-carboxylate in DMF (0.2M) at rt. After 2.5 h, water is added and the suspension is extracted with AcOEt. The organic phase is dried ($Na_2SO_4$) and evaporated. The residue is chromatographed on silica gel (AcOEt/n-heptane 1/1) to provide tert-butyl 3-(3-(4-(benzyloxy)phenyl)-2-oxoimidazolidin-1-yl)-2-oxopiperidine-1-carboxylate.

Step 4

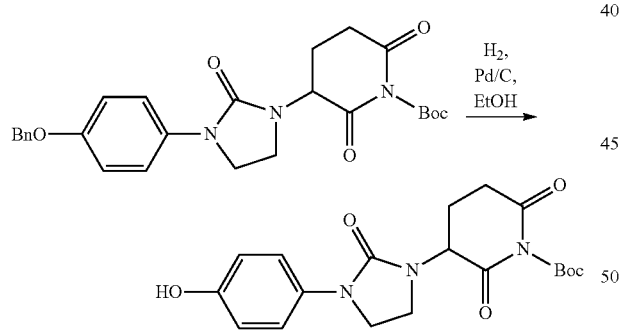

Tert-Butyl 3-(3-(4-hydroxyphenyl)-2-oxoimidazolidin-1-yl)-2,6-dioxopiperidine-1-carboxylate A mixture of tert-butyl 3-(3-(4-(benzyloxy)phenyl)-2-oxoimidazolidin-1-yl)-2-oxopiperidine-1-carboxylate (1.0 eq.) and 10% Pd—C catalyst (0.1 eq Pd) in EtOH (0.2 M) under $H_2$ is stirred at room temperature and atmospheric pressure until the absorption of hydrogen ceases. After the catalyst is filtered out through Celite®, the filtrate is evaporated to provide tert-butyl 3-(3-(4-hydroxyphenyl)-2-oxoimidazolidin-1-yl)-2,6-dioxopiperidine-1-carboxylate. tert-Butyl 3-(3-(4-bromophenyl)-2-oxoimidazolidin-1-yl)-2,6-dioxopiperidine-1-carboxylate

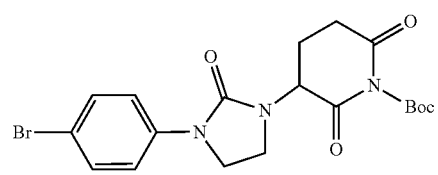 [SMILES: CC(C)(C)OC(=O)N1C(=O)CCC(N2CCN(c3ccc(Br)cc3)C2=O)C1=O]

Step 1

1-(4-Bromophenyl)imidazolidin-2-one

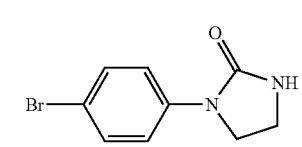

Chloro-2-isocyanatoethane (1.2 eq.) is added dropwise to a cold solution (ice bath) of 4-(bromo)aniline (1.0 eq) in dry methylene chloride (15 mL per g of aniline). The ice bath is then removed and the reaction mixture is stirred at room temperature for 24 h. After completion of the reaction, the solvent is evaporated under reduced pressure to afford 1-(4-bromophenyl)-3-(2-chloroethyl)urea.

Step 2

To a solution of 1-(4-bromophenyl)-3-(2-chloroethyl) in THF (0.05M) at 0° C. is added NaH (1.2 eq, 60 wt % in mineral oil). The reaction is allowed to warm to room temperature, concentrated, and purified by flash chromatography to provide 1-(4-(bromophenyl)imidazolidin-2-one.

Step 3

Tert-Butyl 3-(3-(4-bromophenyl)-2-oxoimidazolidin-1-yl)-2,6-dioxopiperidine-1-carboxylate

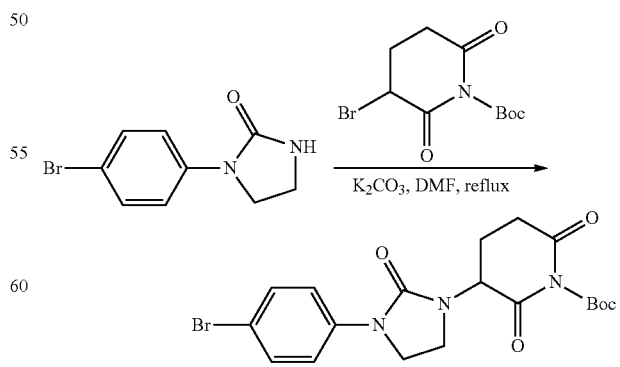

Dry $K_2CO_3$ (1.0 eq.) and 1-(4-(bromo)phenyl)imidazolidin-2-one (1.0 eq.) are added to a stirred solution of (1.0 eq.) tert-butyl 3-bromo-2,6-dioxopiperidine-1-carboxylate in DMF (0.2M) at rt. After 2.5 h, water is added and the suspension is extracted with AcOEt. The organic phase is dried (Na₂SO₄) and evaporated. The residue is chromatographed on silica gel (AcOEt/n-heptane 1/1) to provide tert-butyl 3-(3-(4-bromophenyl)-2-oxoimidazolidin-1-yl)-2,6-dioxopiperidine-1-carboxylate.

Tert-Butyl 3-((2,6-dioxopiperidin-3-yl)amino)-6-nitro-1H-indazole-1-carboxylate

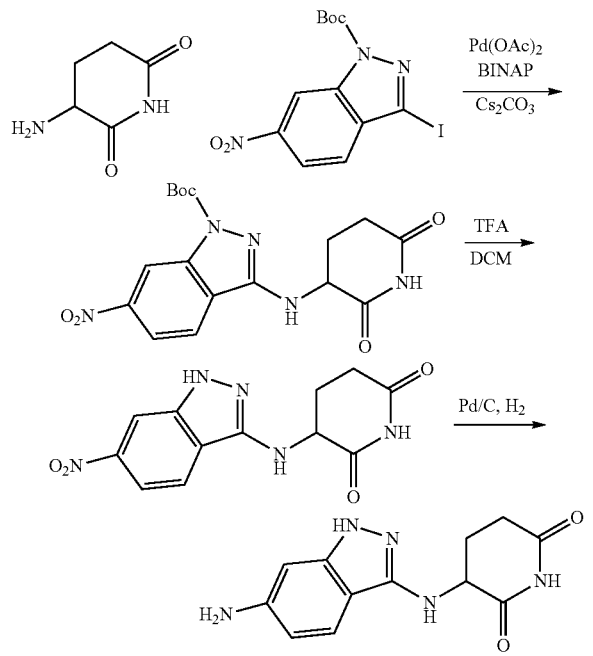

Step 1

Following a general procedure from patent application WO2010007944: 3-aminopiperidine-2,6-dione (1 equiv.), tert-butyl 3-iodo-6-nitro-1H-indazole-1-carboxylate (1 equiv.) and cesium carbonate (2 equiv.) are mixed with dioxane (0.2M). The mixture is purged with N₂ for 10 min. Palladium acetate (0.1 equiv.) and XANTPHOS (0.1 equiv.) are added to the mixture and the mixture is heated at 90° C. for 18 hours. The reaction mixture is cooled to ambient temperature and concentrated under vacuum. The residue is diluted with water and extracted with ethyl acetate (thrice). The organic layers are combined, dried over sodium sulfate and concentrated under vacuum. The residue is purified by flash chromatography on a silica gel column to provide tert-butyl 3-((2,6-dioxopiperidin-3-yl)amino)-6-nitro-1H-indazole-1-carboxylate.

Step 2: 3-((6-Nitro-1H-indazol-3-yl)amino)piperidine-2,6-dione tert-Butyl 3-((2,6-dioxopiperidin-3-yl)amino)-6-nitro-1H-indazole-1-carboxylate (1 equiv.) is dissolved in dichloromethane (0.2 M). Trifluoroacetic acid (50 equiv.) is added to this solution and the reaction is stirred at RT for 2 h. After the completion of the reaction, the volatiles are removed by rotary evaporation to provide 3-((6-nitro-1H-indazol-3-yl)amino)piperidine-2,6-dione.

Step 3: 3-((6-Amino-1H-indazol-3-yl)amino)piperidine-2,6-dione 3-((6-nNtro-1H-indazol-3-yl)amino)piperidine-2,6-dione is dissolved in methanol (0.2 M) and palladium on charcoal (10%) is added. The reaction vessel is placed under a hydrogen atmosphere and stirred for 16 hours. The reaction mixture is filtered through Celite® and evaporated to afford 3-((6-amino-H-indazol-3-yl)amino)piperidine-2,6-dione.

3-((6-Amino-1H-indazol-3-yl)(methyl)amino)piperidine-2,6-dione

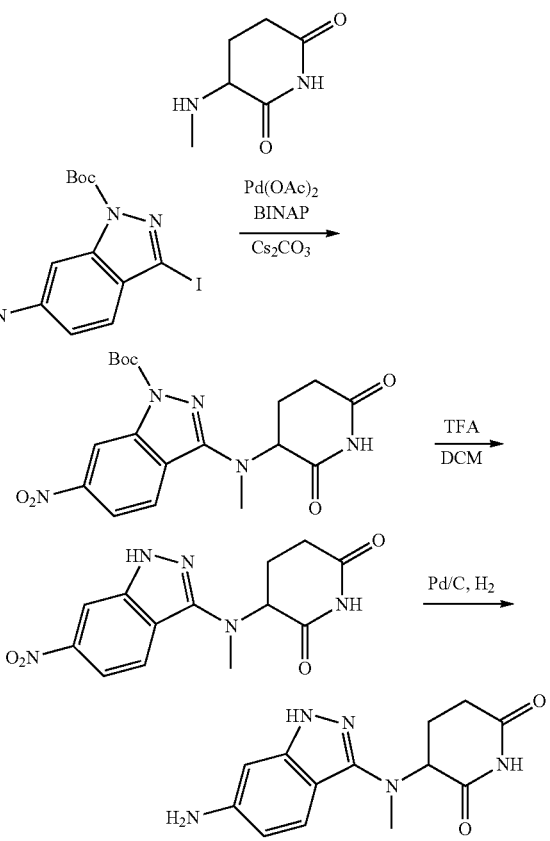

3-((6-amino-1H-indazol-3-yl)(methyl)amino)piperidine-2,6-dione is obtained in a fashion similar as 3-((6-amino-1H-indazol-3-yl)amino)piperidine-2,6-dione, using 3-(methylamino)piperidine-2,6-dione as a starting material instead of 3-aminopiperidine-2,6-dione.

3-((5-amino-1H-indazol-3-yl)amino)piperidine-2,6-dione is obtained in a fashion similar as 3-((6-amino-1H-indazol-3-yl)amino)piperidine-2,6-dione

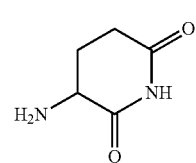

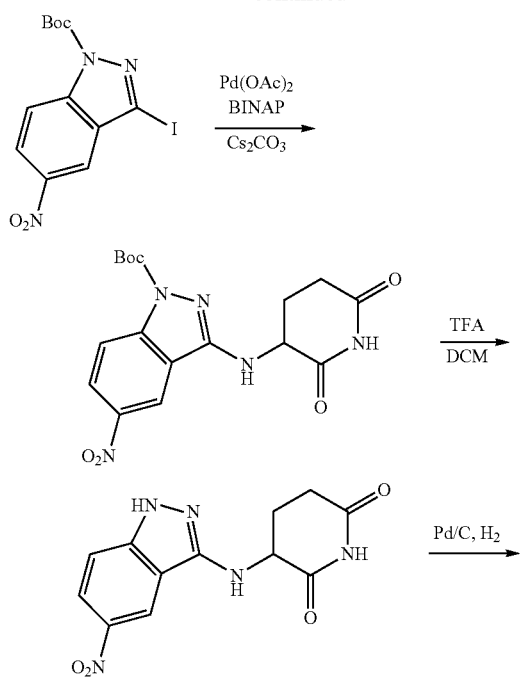

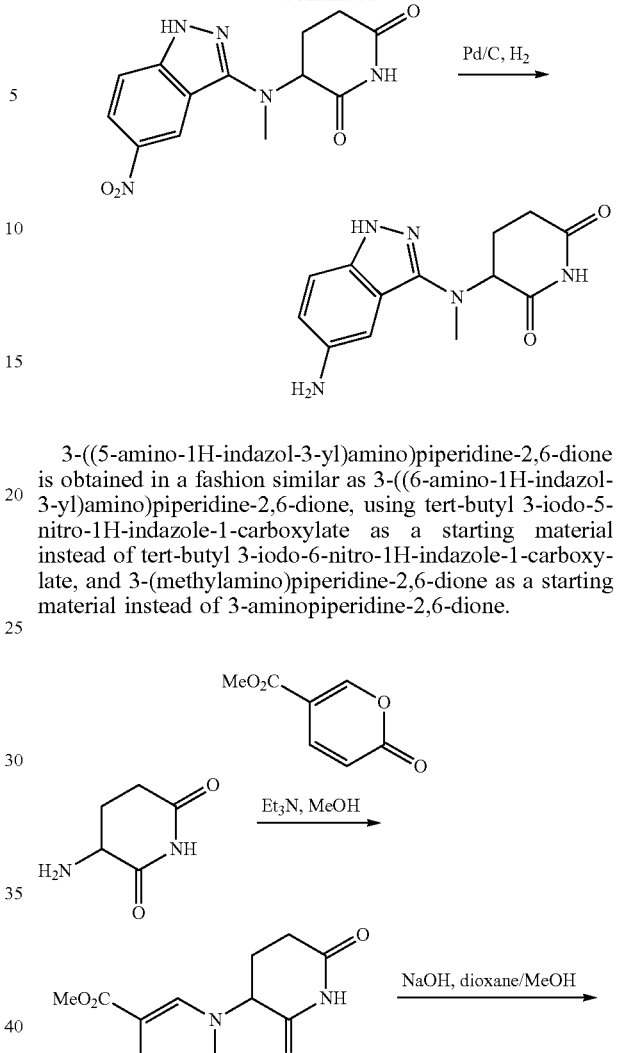

3-((5-amino-1H-indazol-3-yl)amino)piperidine-2,6-dione is obtained in a fashion similar as 3-((6-amino-1H-indazol-3-yl)amino)piperidine-2,6-dione, using tert-butyl 3-iodo-5-nitro-1H-indazole-1-carboxylate as a starting material instead of tert-butyl 3-iodo-6-nitro-1H-indazole-1-carboxylate, and 3-(methylamino)piperidine-2,6-dione as a starting material instead of 3-aminopiperidine-2,6-dione.

3-((5-amino-1H-indazol-3-yl)amino)piperidine-2,6-dione is obtained in a fashion similar as 3-((6-amino-1H-indazol-3-yl)amino)piperidine-2,6-dione, using tert-butyl 3-iodo-5-nitro-H-indazole-1-carboxylate as a starting material instead of tert-butyl 3-iodo-6-nitro-H-indazole-1-carboxylate.

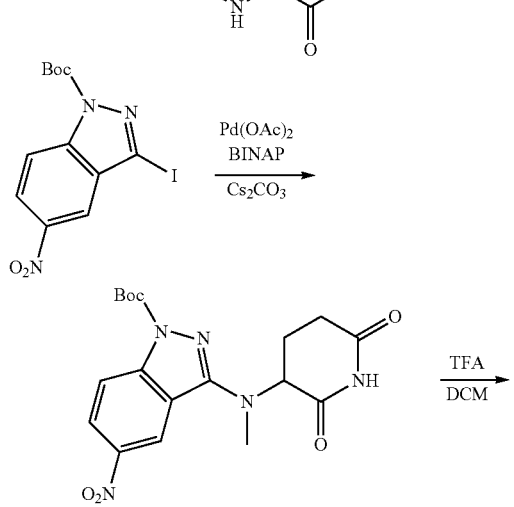

Step 1: Methyl 1-(2,6-dioxopiperidin-3-yl)-6-oxo-1,6-dihydropyridine-3-carboxylate (Following a general procedure from patent application WO2012177893): A solution of methyl coumalate (1 equiv.) in MeOH (0.2 M) is treated with 3-aminopiperidine-2,6-dione (1.25 equiv.) and TEA (1.5 equiv.). The reaction is stirred at 23° C. under nitrogen. After 1 h, the reaction is concentrated and purified by silica gel chromatography to afford methyl 1-(2,6-dioxopiperidin-3-yl)-6-oxo-1,6-dihydropyridine-3-carboxylate.

Step 2: 1-(2,6-Dioxopiperidin-3-yl)-6-oxo-1,6-dihydropyridine-3-carboxylic acid

A solution of methyl 1-(2,6-dioxopiperidin-3-yl)-6-oxo-1,6-dihydropyridine-3-carboxylate (1 equiv.) in 1,4-dioxane and MeOH (3:1 ratio, respectively) is treated with aqueous sodium hydroxide, 5.0 M (1.5 equiv.). The reaction is stirred at 23° C. After 20 h, the reaction is neutralized to pH=6.0 with 2 N HCl, and concentrated in vacuo. The residue is azeotroped with toluene (3×10 mL), suspended in a 1:1 MeOH:DCM solution, and the white NaCl residue is removed by filtration. The filtrate is concentrated affording 1-(2,6-dioxopiperidin-3-yl)-6-oxo-1,6-dihydropyridine-3-carboxylic acid.

3-(8-Amino-1-oxoisoquinolin-2(1H)-yl)piperidine-2,6-dione

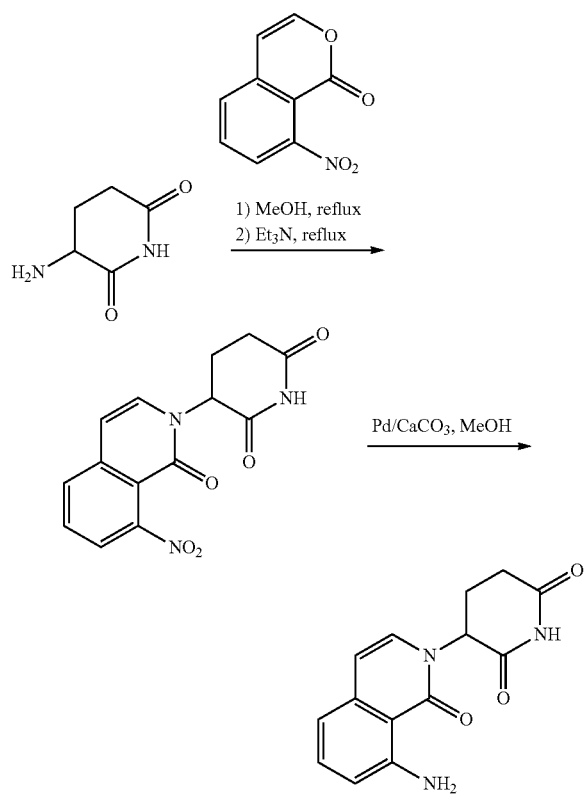

Step 1: 3-(8-Nitro-1-oxoisoquinolin-2(1H)-yl)piperidine-2,6-dione (Following a general procedure from patent WO2012177893): 5-Nitro-isochromen-1-one (1 equiv.) and 3-aminopiperidine-2,6-dione (1 equiv.) are heated at reflux in methanol (0.2 M) for 1 hour. Triethylamine (2 equiv.) is added to the mixture and the reaction mixture is heated at reflux overnight. The volatiles are removed in vacuo and the residue is purified by flash column chromatography (40 g of silica gel, 0-50% EtOAc/Hexane) to afford 2-(1,3-dihydroxypropan-2-yl)-5-nitroisoquinolin-1 (2H)-one.

Step 2: 3-(8-Amino-1-oxoisoquinolin-2(1H)-yl)piperidine-2,6-dione 2-(1,3-dihydroxypropan-2-yl)-5-nitroisoquinolin-1 (2H)-one (1.0 equiv.) is stirred with palladium 10% wt. on calcium carbonate (0.1 equiv.) in methanol (0.2 M) under hydrogen (balloon) over 1 hour at ambient temperature. The catalyst is filtered and the filtrate is concentrated to dryness to afford 3-(8-amino-1-oxoisoquinolin-2(1H)-yl)piperidine-2,6-dione.

3-(5-Amino-1-oxoisoquinolin-2(1H)-yl)piperidine-2,6-dione

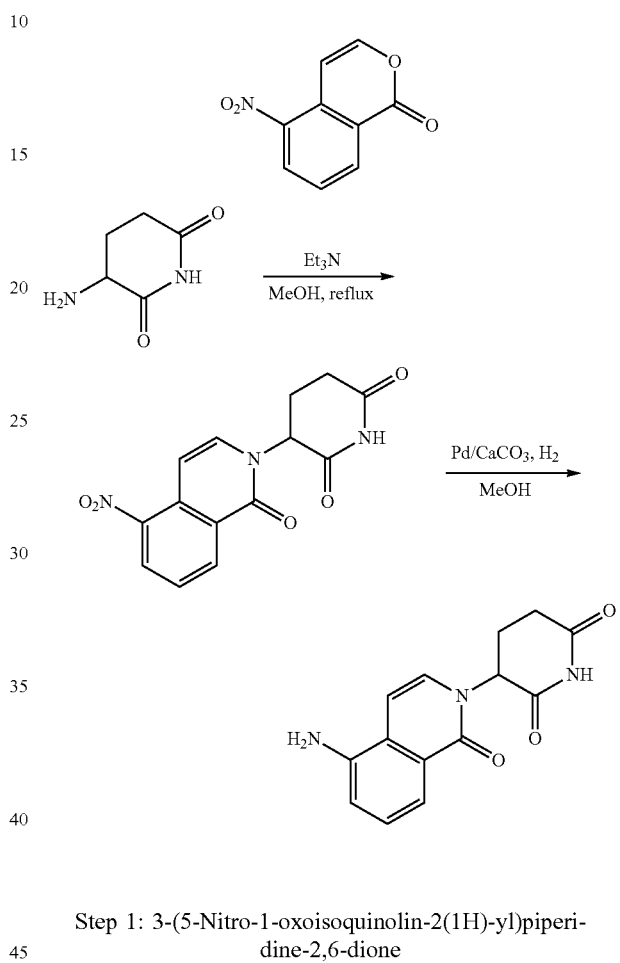

Step 1: 3-(5-Nitro-1-oxoisoquinolin-2(1H)-yl)piperidine-2,6-dione (Following a general procedure from patent WO2008112205): 5-Nitro-1H-isochromen-1-one (1.0 equiv.), 3-aminopiperidine-2,6-dione (1.0 equiv.) and 3-aminopiperidine-2,6-dione (1.2 equiv.) are stirred with trimethylamine (3.5 equiv.) in MeOH (0.2 M) at reflux for 2 hours. After cooling, the precipitated product is filtered and collected to afford 3-(5-nitro-1-oxoisoquinolin-2(1H)-yl)piperidine-2,6-dione.

Step 2: 3-(5-Amino-1-oxoisoquinolin-2(1H)-yl)piperidine-2,6-dione 3-(5-nitro-1-oxoisoquinolin-2(1H)-yl)piperidine-2,6-dione(1.0 equiv.) is stirred with palladium 10% wt. on calcium carbonate (0.1 equiv.) in methanol (0.2 M) under hydrogen (balloon) over 1 hour at ambient temperature. The catalyst is filtered and the filtrate is concentrated to dryness to afford 3-(5-amino-1-oxoisoquinolin-2(1H)-yl)piperidine-2,6-dione.

435

3-(4-Hydroxy-6-methyl-2-oxopyridin-1(2H)-yl)piperidine-2,6-dione

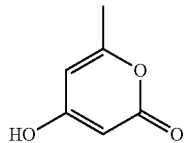

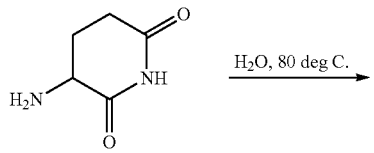

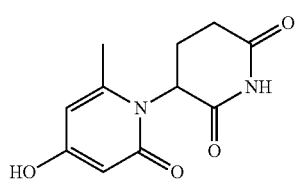

(Following a general procedure from patent application WO2009074812): A mixture of 6-methyl-4-hydroxy pyranone (1 0 eq) and primary amine (1.20 eq) in water (5 times dilution by weight) is heated at 80'C for 16 h. The precipitated solid is filtered, washed with ether and dried under vacuum to obtain the desired 3-(4-hydroxy-6-methyl-2-oxopyridin-1(2H)-yl)piperidine-2,6-dione.

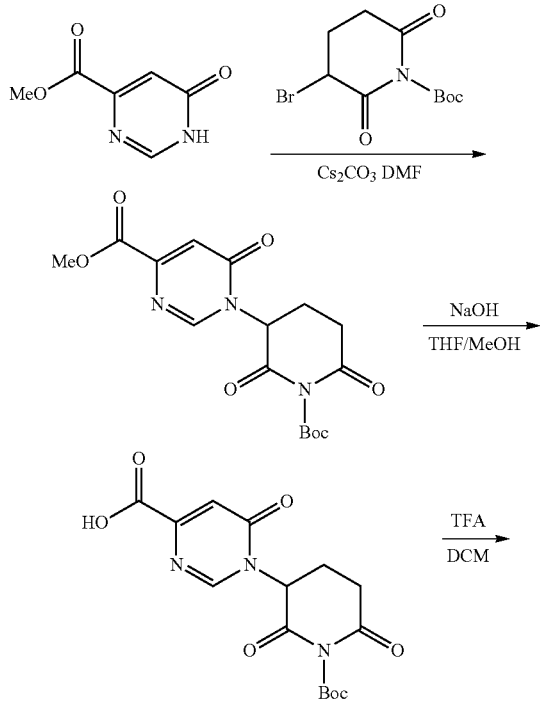

436

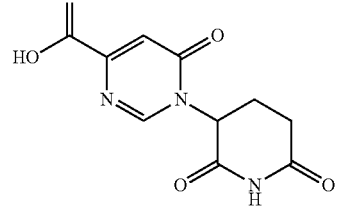

Step 1: Methyl 1-(1-(tert-butoxycarbonyl)-2,6-dioxopiperidin-3-yl)-6-oxo-1,6-dihydropyrimidine-4-carboxylate tert-Butyl 3-bromo-2,6-dioxopiperidine-1-carboxylate (1.0 equiv.) and methyl 6-oxo-1,6-dihydropyrimidine-4-carboxylate (1.0 equiv.) are mixed in DMF (0.2M) and cesium carbonate is added (2.0 equiv.). The reaction mixture is stirred at 60° C. for 16 hours. The reaction mixture is partitioned between brine and ethyl acetate. The organic layer is dried with sodium sulfate, filtered and evaporated under reduced pressure. The crude residue is purified by silica gel column chromatography to afford methyl 1-(1-(tert-butoxycarbonyl)-2,6-dioxopiperidin-3-yl)-6-oxo-1,6-dihydropyrimidine-4-carboxylate.

Step 2: 1-(1-(tert-Butoxycarbonyl)-2,6-dioxopiperidin-3-yl)-6-oxo-1,6-dihydropyrimidine-4-carboxylic Acid Methyl 1-(1-(tert-butoxycarbonyl)-2,6-dioxopiperidin-3-yl)-6-oxo-1,6-dihydropyrimidine-4-carboxylate is dissolved in THF/MeOH (1/1, 0.2M) and sodium hydroxide is added to the reaction mixture and stirred. After 20 h, the reaction is neutralized to pH=6.0 with 2 N HCl, and concentrated in vacuo. The residue is azeotroped with toluene (3×10 mL), suspended in a 1:1 MeOH:DCM solution and the white sodium chloride residue is removed by filtration. The filtrate is concentrated, affording 1-(1-(tert-butoxycarbonyl)-2,6-dioxopiperidin-3-yl)-6-oxo-1,6-dihydropyrimidine-4-carboxylic acid.

Step 3: 1-(2,6-Dioxopiperidin-3-yl)-6-oxo-1,6-dihydropyrimidine-4-carboxylic Acid 1-(1-(tert-butoxycarbonyl)-2,6-dioxopiperidin-3-yl)-6-oxo-1,6-dihydropyrimidine-4-carboxylic acid is dissolved in dichloromethane (0.2M) and TFA (50 equiv.) is added. The reaction mixture is stirred for 2 hours and then evaporated in vacuo to afford 1-(2,6-dioxopiperidin-3-yl)-6-oxo-1,6-dihydropyrimidine-4-carboxylic acid.

Tert-Butyl 3-(7-bromo-3-oxoisoquinolin-2(3H)-yl)-2,6-dioxopiperidine-1-carboxylate

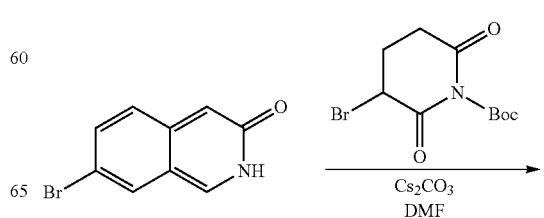

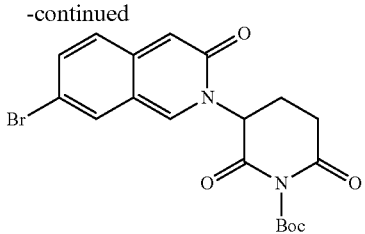

Step 1

(Following procedure from patent application WO2004014378): tert-Butyl 3-bromo-2,6-dioxopiperidine-1-carboxylate (1.0 equiv.) and 7-bromoisoquinolin-3(2H)-one (1.0 equiv.) are mixed in DMF (0.2M), and cesium carbonate is added (2.0 equiv.). The reaction mixture is stirred at 60° C. for 16 hours. The reaction mixture is partitioned between brine and ethyl acetate. The organic layer is dried with sodium sulfate, filtered and evaporated under reduced pressure to afford tert-butyl 3-(7-bromo-3-oxoisoquinolin-2(3H)-yl)-2,6-dioxopiperidine-1-carboxylate.

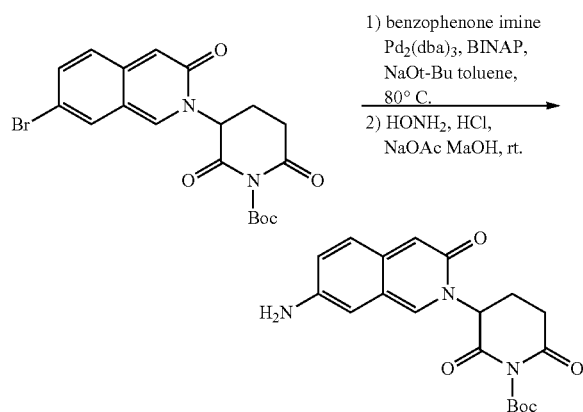

Step 1

A reaction vessel is charged with tert-butyl 3-(7-bromo-3-oxoisoquinolin-2(3H)-yl)-2,6-dioxopiperidine-1-carboxylate (1 equiv.), benzophenone imine (1.2 equiv.), tris(dibenzylideneacetone)dipalladium(0) (1 mol %), BINAP (3 mol %) and sodium tert-butoxide (2 equiv.) and purged by cycling between nitrogen and vacuum 3 times. Toluene is added and the reaction is heated at 80° C. for 18 hours. Ethyl acetate is added and the solids separated by filtration through a plug of Celite®. The filtrate is concentrated and the residue is purified by chromatography to provide tert-butyl 3-(7-((diphenylmethylene)amino)-3-oxoisoquinolin-2(3H)-yl)-2,6-dioxopiperidine-1-carboxylate.

Step 2

A reaction vessel is charged with tert-butyl 3-(7-((diphenylmethylene)amino)-3-oxoisoquinolin-2(3H)-yl)-2,6-dioxopiperidine-1-carboxylate (1 equiv.) and dissolved in MeOH. Hydroxylamine hydrochloride (1.8 equiv.) and sodium acetate (2.4 equiv.) are added and the reaction mixed at ambient temperature for 1 hour. The reaction is quenched by addition of 0.1M aq. NaOH solution and the resultant mixture extracted with ethyl acetate. The combined organic layer is washed with brine, dried over sodium sulfate, filtered, and concentrated. The crude residue is purified by silica gel chromatography to provide tert-butyl 3-(7-amino-3-oxoisoquinolin-2(3H)-yl)-2,6-dioxopiperidine-1-carboxylate. (*PCT Int. Appl.*, 2015002230, 8 Jan. 2015).

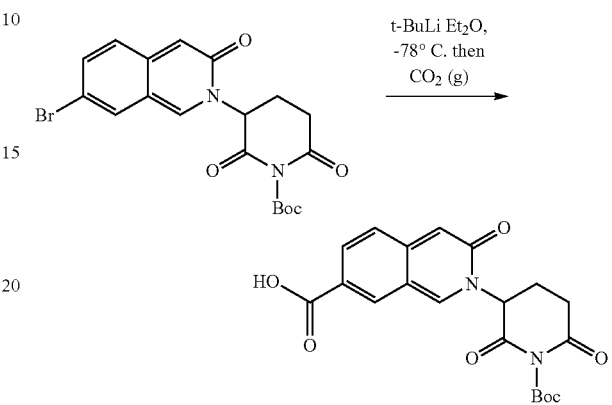

A flame-dried reaction vessel is charged with tert-butyl 3-(7-bromo-3-oxoisoquinolin-2(3H)-yl)-2,6-dioxopiperidine-1-carboxylate (1 equiv.) and the atmosphere is cycled between nitrogen and vacuum three times. Ether is added and the solution is cooled to −78° C. tert-Butyllithium (2 equiv.) is added dropwise and the reaction is mixed for 15 min then carbon dioxide gas is bubbled through the solution for 15 min. The reaction is warmed to ambient temperature allowing excess carbon dioxide gas to slowly evolve from solution. The reaction is quenched with 1 M aq. NaOH solution and washed with ether (2×). The pH of the aqueous layer is adjusted to 3 with hydrochloric acid (1M aq.) and extracted with ethyl acetate (3×). The combined organic layer is dried over sodium sulfate and concentrated to dryness with toluene (3×) to provide 4-(1-(tert-butoxycarbonyl)-2,6-dioxopiperidin-3-yl)benzoic acid.

N-(2,6-Dioxo-piperidin-3-yl)-benzene Sulfonamide

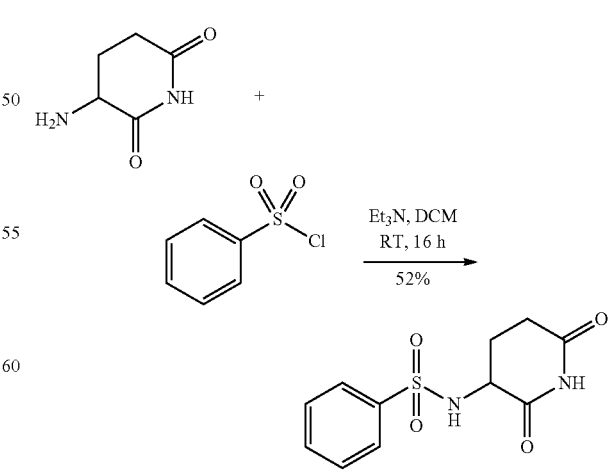

To a stirred solution of 3-amino-piperidine-2,6-dione hydrochloride (100 mg, 0.608 mmol, 1 equiv.) in DCM (5 mL) are added triethylamine (0.25 mL, 1.823 mmol, 3 equiv.) and Benzenesulfonyl chloride (118.03 mg, 0.668 mmol, 1.1 equiv.) sequentially at 0° C. The resulting mixture is stirred at the same temperature for 4 hours. The reaction mixture is then quenched with ice-water and extracted with EtOAc. The combined organics are washed with an aqueous saturated NaHCO$_3$ solution, water, brine, dried over anhydrous Na$_2$SO$_4$ and concentrated under reduced pressure. The crude mass is purified by column chromatography (silica, gradient: 0-1% MeOH-DCM) to afford N-(2,6-Dioxo-piperidin-3-yl)-benzene sulfonamide (55 mg, 34%) as a white solid. $^1$H NMR (400 MHz, DMSO-d$_6$) δ 10.76 (s, 1H), 8.15-8.13 (d, J=8.44 Hz, 1H), 7.85-7.83 (d, J=7.12 Hz, 2H), 7.63-7.54 (m, 3H), 4.26-4.20 (m, 1H), 2.69-2.60 (m, 1H), 2.46-2.40 (m, 1H), 1.82-1.76 (m, 2H); LCMS (M+H): 269.

4-Bromo-N-(2,6-dioxo-piperidin-3-yl)-benzene-sulfonamide

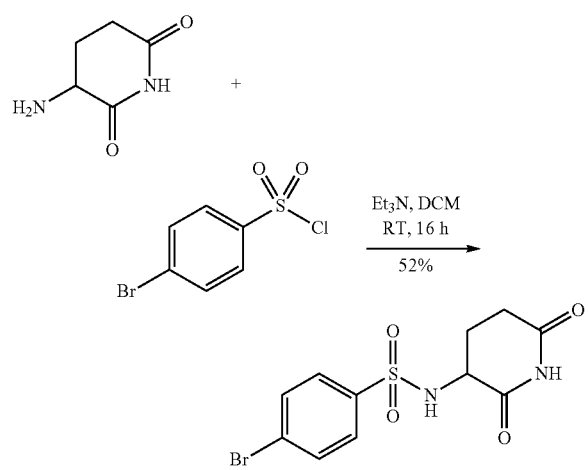

To a stirred solution of 3-amino-piperidine-2,6-dione hydrochloride (100 mg, 0.608 mmol, 1 equiv.) in DCM (5 mL) are sequentially added at 0° C. triethylamine (0.25 mL, 1.823 mmol, 3 equiv.) and 4-bromobenzenesulfonyl chloride (170.76 mg, 0.668 mmol, 1.1 equiv.). The resulting mixture is stirred at the same temperature for 4 hours. The reaction mixture is then quenched with ice-water and extracted with EtOAc. The combined organics are washed with aqueous saturated NaHCO$_3$ solution, water, brine, dried over anhydrous Na$_2$SO$_4$ and concentrated under reduced pressure. The crude mass is purified by column chromatography (silica, gradient: 0-1% MeOH-DCM) to afford 4-bromo-N-(2,6-dioxo-piperidin-3-yl)-benzene sulfonamide (110 mg, 52%) as a white solid. $^1$H NMR (400 MHz, DMSO-d$_6$) δ 10.76 (s, 1H), 8.29-8.27 (d, J=8.52 Hz, 1H), 7.79-7.74 (m, 4H), 4.28-4.22 (m, 1H), 2.70-2.62 (m, 1H), 2.42 (b, 1H), 1.86-1.79 (m, 2H); LCMS (M−H): 345 (Br isotope pattern).

N-(2,6-Dioxo-piperidin-3-yl)-benzamide

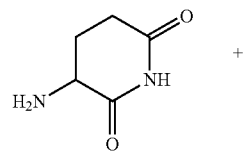

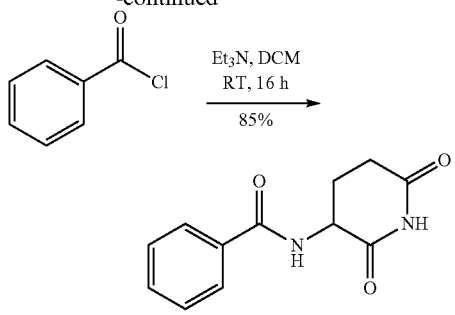

To a stirred solution of 3-amino-piperidine-2,6-dione hydrochloride (100 mg, 0.608 mmol, 1 equiv.) in DCM (5 mL) are added triethylamine (0.25 mL, 1.823 mmol, 3 equiv.) and benzoyl chloride (78 μL, 0.668 mmol, 1.1 equiv.) sequentially at 0° C. The resulting mixture is stirred at ambient temperature for 18 hours. The reaction mixture is then quenched with ice-water and extracted with EtOAc. The combined organics are washed with an aqueous saturated NaHCO$_3$ solution, water, brine, dried over anhydrous Na$_2$SO$_4$ and concentrated under reduced pressure. The residue is triturated with diethyl ether and pentane to afford N-(2,6-dioxo-piperidin-3-yl)-benzamide (105 mg, 74%) as a white solid. $^1$H NMR (400 MHz, DMSO-d$_6$) δ 10.86 (s, 1H), 8.77-8.75 (d, J=8.12 Hz, 1H), 7.88-7.86 (d, J=7.08 Hz, 2H), 7.56-7.54 (d, J=7.28 Hz, 2H), 7.51-7.47 (m, 3H), 4.78 (b, 1H), 2.83-2.76 (bm, 1H), 2.56 (b, 1H), 2.14 (m, 1H), 1.99 (m, 1H); LCMS (M+H): 233.

4-Bromo-N-(2,6-dioxo-piperidin-3-yl)-benzamide

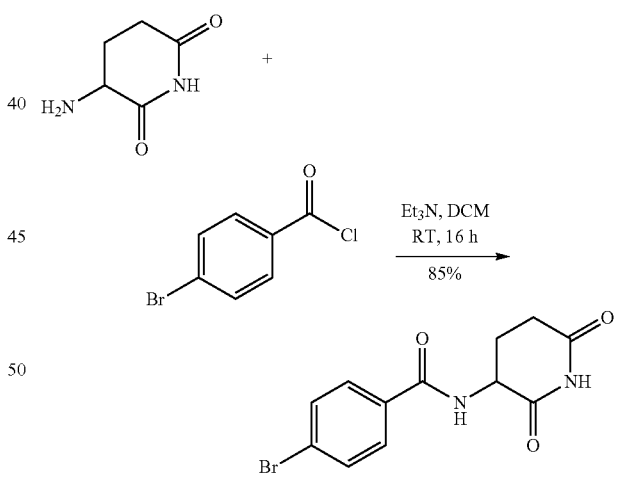

To a stirred solution of 3-amino-piperidine-2,6-dione hydrochloride (100 mg, 0.608 mmol, 1 equiv.) in DCM (5 mL) are added triethylamine (0.25 mL, 1.823 mmol, 3 equiv.) and 4-bromobenzoyl chloride (146.662 mg, 0.668 mmol, 1.1 equiv.) sequentially at 0° C. The resulting mixture is stirred at ambient temperature for 18 hours. The reaction mixture is then quenched with ice-water and extracted with EtOAc. The combined organics are washed with aqueous saturated NaHCO$_3$ solution, water, brine, dried over anhydrous Na$_2$SO$_4$ and concentrated under reduced pressure. The residue is triturated with diethyl ether and pentane to afford 4-bromo-N-(2,6-dioxo-piperidin-3-yl)-benzamide (160 mg, 85%) as a white solid. $^1$H NMR (400 MHz, DMSO-$d_6$) δ 10.88 (s, 1H), 8.87-8.85 (d, J=8.12 Hz, 1H), 7.83-7.80 (d, J=9.12 Hz 2H), 7.72-7.70 (d, J=8.32 Hz, 2H), 4.81-4.75 (m, 1H), 2.83-2.75 (m, 1H), 2.56 (b, 1H), 2.13-2.07 (m, 1H), 2.98 (m, 1H); LCMS (M−H): 309 (Br isotope pattern).

N-(2,6-Dioxopiperidin-3-yl)-N-methylpiperidine-4-carboxamide

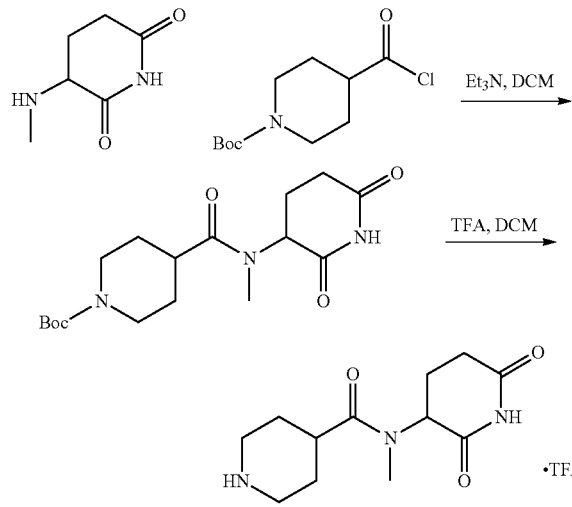

To a stirred solution of 3-(methylamino)piperidine-2,6-dione (1 equiv.) in DCM (0.1M) are added triethylamine (3 equiv.) and tert-butyl 4-(chlorocarbonyl)piperidine-1-carboxylate (1.1 equiv.) sequentially at 0° C. The resulting mixture is stirred at ambient temperature for 18 hours. The reaction mixture is then quenched with ice-water and extracted with EtOAc. The combined organics are washed with aqueous saturated NaHCO$_3$ solution, water, brine, dried over anhydrous Na$_2$SO$_4$ and concentrated under reduced pressure to afford tert-butyl 4-((2,6-dioxopiperidin-3-yl)(methyl)carbamoyl)piperidine-1-carboxylate.

tert-Butyl 4-((2,6-dioxopiperidin-3-yl)(methyl)carbamoyl)piperidine-1-carboxylate is dissolved in DCM/TFA (1/1, 0.2M) and stirred at ambient temperature for 2 hours. The volatiles are evaporated under reduced pressure to afford N-(2,6-dioxopiperidin-3-yl)-N-methylpiperidine-4-carboxamide as trifluoroacetic acid salt.

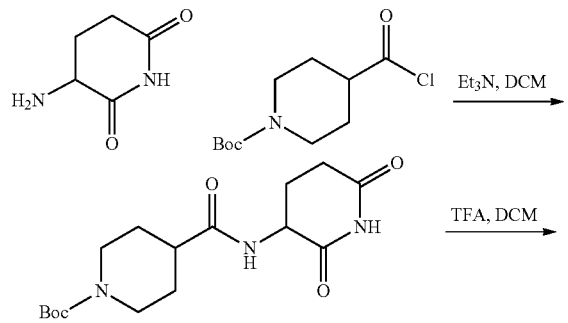

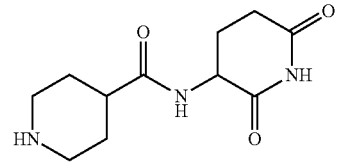

To a stirred solution of 3-amino-piperidine-2,6-dione (1 equiv.) in DCM (0.1 M) are added triethylamine (3 equiv.) and tert-butyl 4-(chlorocarbonyl)piperidine-1-carboxylate (1.1 equiv.) sequentially at 0° C. The resulting mixture is stirred at ambient temperature for 18 hours. The reaction mixture is then quenched with ice-water and extracted with EtOAc. The combined organics are washed with aqueous saturated NaHCO$_3$ solution, water, brine, dried over anhydrous Na$_2$SO$_4$ and concentrated under reduced pressure to afford tert-butyl 4-((2,6-dioxopiperidin-3-yl)carbamoyl)piperidine-1-carboxylate.

tert-Butyl 4-((2,6-dioxopiperidin-3-yl)carbamoyl)piperidine-1-carboxylate is dissolved in DCM/TFA (1/1, 0.2M) and stirred at ambient temperature for 2 hours. The volatiles are evaporated under reduced pressure to afford N-(2,6-dioxopiperidin-3-yl)piperidine-4-carboxamide as a trifluoroacetic acid salt.

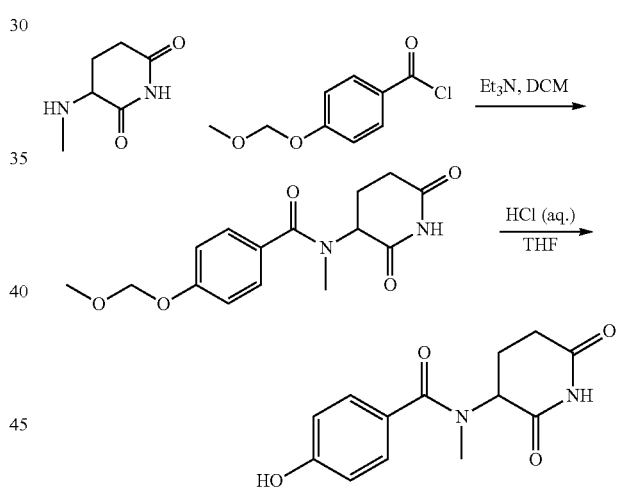

To a stirred solution of 3-(methylamino)piperidine-2,6-dione (1 equiv.) in DCM (0.1M) are added triethylamine (3 equiv.) and tert-butyl 4-(methoxymethoxy)benzoyl chloride (1.1 equiv.) sequentially at 0° C. The resulting mixture is stirred at ambient temperature for 18 hours. The reaction mixture is then quenched with ice-water and extracted with EtOAc. The combined organics are washed with aqueous saturated NaHCO$_3$ solution, water, brine, dried over anhydrous Na$_2$SO$_4$ and concentrated under reduced pressure to afford N-(2,6-dioxopiperidin-3-yl)-4-(methoxymethoxy)-N-methylbenzamide.

N-(2,6-Dioxopiperidin-3-yl)-4-(methoxymethoxy)-N-methylbenzamide is dissolved in methanol (0.2M), hydrochloric acid (1M aq., 10 equiv.) is added and stirred at ambient temperature for 3 hours. The volatiles are evaporated in vacuo to afford N-(2,6-dioxopiperidin-3-yl)-4-hydroxy-N-methylbenzamide.

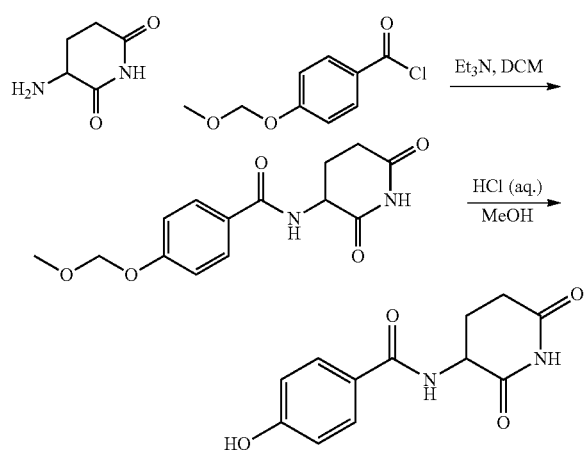

To a stirred solution of 3-amino-piperidine-2,6-dione 1 equiv.) in DCM (0.1M) are added triethylamine (3 equiv.) and tert-butyl 4-(methoxymethoxy)benzoyl chloride (1.1 equiv.) sequentially at 0° C. The resulting mixture is stirred at ambient temperature for 18 hours. The reaction mixture is then quenched with ice-water and extracted with EtOAc. The combined organics are washed with aqueous saturated $NaHCO_3$ solution, water, brine, dried over anhydrous $Na_2SO_4$ and concentrated under reduced pressure to afford N-(2,6-dioxopiperidin-3-yl)-4-(methoxymethoxy)benzamide.

N-(2,6-Dioxopiperidin-3-yl)-4-(methoxymethoxy)benzamide is dissolved in methanol (0.2M), hydrochloric acid (1M aq., 10 equiv.) is added and stirred at ambient temperature for 3 hours. The volatiles are evaporated in vacuo to afford N-(2,6-dioxopiperidin-3-yl)-4-hydroxybenzamide.

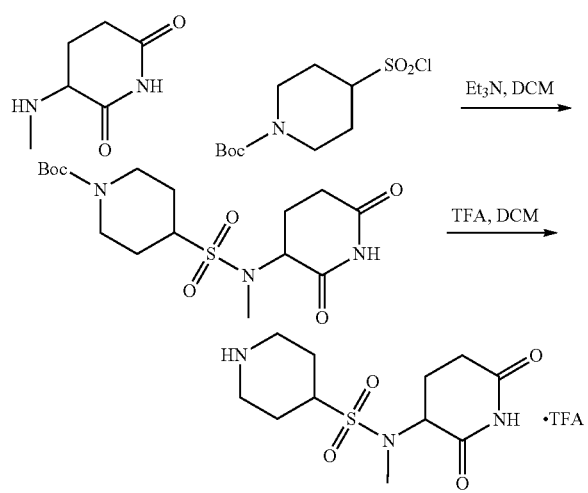

To a stirred solution of 3-(methylamino)piperidine-2,6-dione (1 equiv.) in DCM (0.2 M) are added triethylamine (3 equiv.) and tert-butyl 4-(chlorosulfonyl)piperidine-1-carboxylate (1.1 equiv.) sequentially at 0° C. The resulting mixture is stirred at the same temperature for 4 hours. The reaction mixture is then quenched with ice-water and extracted with EtOAc. The combined organics are washed with aqueous saturated $NaHCO_3$ solution, water, brine, dried over anhydrous $Na_2SO_4$ and concentrated under reduced pressure. The crude residue is purified by column chromatography to afford tert-butyl 4-(N-(2,6-dioxopiperidin-3-yl)-N-methylsulfamoyl)piperidine-1-carboxylate.

tert-Butyl 4-(N-(2,6-dioxopiperidin-3-yl)-N-methylsulfamoyl)piperidine-1-carboxylate is dissolved in DCM/TFA (1/1, 0.2M) and stirred at ambient temperature for 2 hours. The volatiles are evaporated under reduced pressure to afford N-(2,6-dioxopiperidin-3-yl)-N-methylpiperidine-4-sulfonamide.

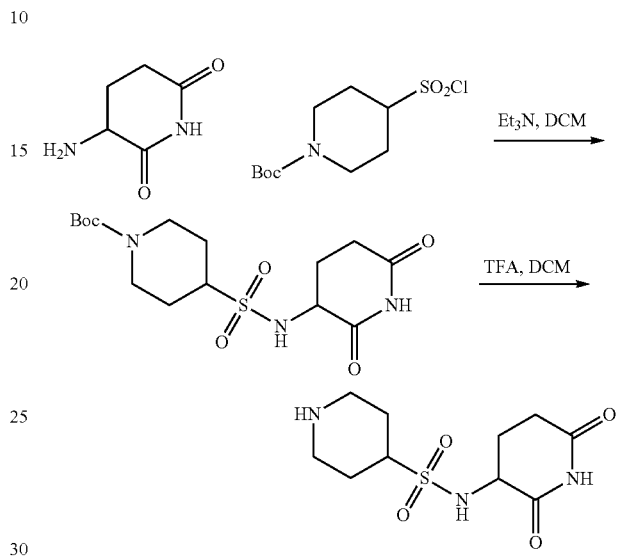

To a stirred solution of 3-aminopiperidine-2,6-dione (1 equiv.) in DCM (0.2 M) are added triethylamine (3 equiv.) and tert-butyl 4-(chlorosulfonyl)piperidine-1-carboxylate (1.1 equiv.) sequentially at 0° C. The resulting mixture is stirred at the same temperature for 4 hours. The reaction mixture is then quenched with ice-water and extracted with EtOAc. The combined organics is washed with aqueous saturated $NaHCO_3$ solution, water, brine, dried over anhydrous $Na_2SO_4$ and concentrated under reduced pressure. The crude residue is purified by column chromatography to afford tert-butyl 4-(N-(2,6-dioxopiperidin-3-yl)sulfamoyl)piperidine-1-carboxylate.

tert-Butyl 4-(N-(2,6-Dioxopiperidin-3-yl)sulfamoyl)piperidine-1-carboxylate is dissolved in DCM/TFA (1/1, 0.2M) and stirred at ambient temperature for 2 hours. The volatiles are evaporated under reduced pressure to afford N-(2,6-dioxopiperidin-3-yl)piperidine-4-sulfonamide.

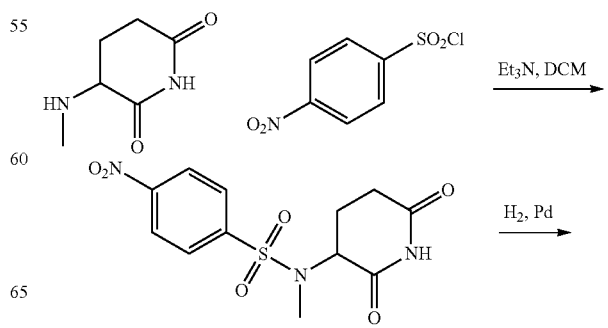

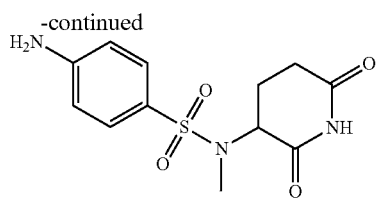

To a stirred solution of 3-(methylamino)piperidine-2,6-dione (1 equiv.) in DCM (0.2 M) are added triethylamine (3 equiv.) and 4-nitrobenzenesulfonyl chloride (1.1 equiv.) sequentially at 0° C. The resulting mixture is stirred at the same temperature for 4 hours. The reaction mixture is then quenched with ice-water and extracted with EtOAc. The combined organics are washed with aqueous saturated NaHCO₃ solution, water, brine, dried over anhydrous Na₂SO₄ and concentrated under reduced pressure. The crude residue is purified by column chromatography to afford N-(2,6-dioxopiperidin-3-yl)-N-methyl-4-nitrobenzenesulfonamide.

N-(2,6-Dioxopiperidin-3-yl)-N-methyl-4-nitrobenzenesulfonamide is dissolved in methanol (0.2 M) and palladium on charcoal (10%) is added. The reaction vessel is placed under a hydrogen atmosphere and stirred for 16 hours. The reaction mixture is filtered through Celite® and evaporated to afford 4-amino-N-(2,6-dioxopiperidin-3-yl)-N-methylbenzenesulfonamide.

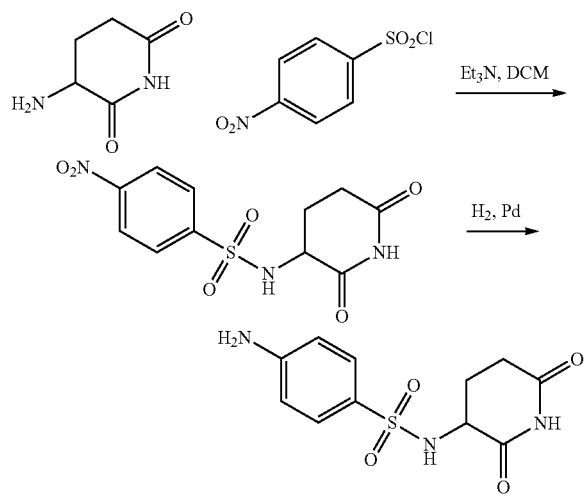

To a stirred solution of 3-aminopiperidine-2,6-dione 1 equiv. in DCM (0.2 M) are added triethylamine (3 equiv.) and 4-nitrobenzenesulfonyl chloride (1.1 equiv.) sequentially at 0° C. The resulting mixture is stirred at the same temperature for 4 hours. The reaction mixture is then quenched with ice-water and extracted with EtOAc. The combined organics are washed with aqueous saturated NaHCO₃ solution, water, brine, dried over anhydrous Na₂SO₄ and concentrated under reduced pressure. The crude residue is purified by column chromatography to afford N-(2,6-dioxopiperidin-3-yl)-4-nitrobenzenesulfonamide.

N-(2,6-Dioxopiperidin-3-yl)-4-nitrobenzenesulfonamide is dissolved in methanol (0.2 M) and palladium on charcoal (10%) is added. The reaction vessel is placed under a hydrogen atmosphere and stirred for 16 hours. The reaction mixture is filtered on Celite® and evaporated to afford 4-amino-N-(2,6-dioxopiperidin-3-yl)benzenesulfonamide.

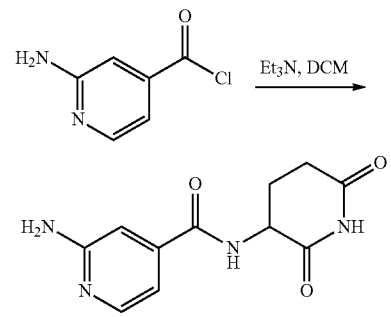

To a stirred solution of 3-amino-piperidine-2,6-dione (1 equiv.) in DCM (0.1M) are added triethylamine (3 equiv.) and 2-aminoisonicotinoyl chloride (1.1 equiv.) sequentially at 0° C. The resulting mixture is stirred at ambient temperature for 18 hours. The reaction mixture is then quenched with ice-water and extracted with EtOAc. The combined organics are washed with aqueous saturated NaHCO₃ solution, water, brine, dried over anhydrous Na₂SO₄ and concentrated under reduced pressure to afford 2-amino-N-(2,6-dioxopiperidin-3-yl)isonicotinamide.

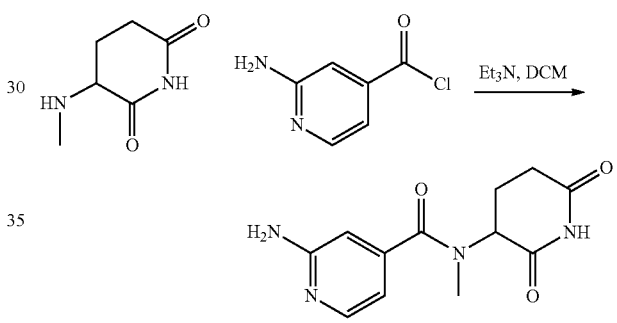

To a stirred solution of 3-(methylamino)piperidine-2,6-dione (1 equiv.) in DCM (0.1M) are added triethylamine (3 equiv.) and 2-aminoisonicotinoyl chloride (1.1 equiv.) sequentially at 0° C. The resulting mixture is stirred at ambient temperature for 18 hours. The reaction mixture is then quenched with ice-water and extracted with EtOAc. The combined organics are washed with aqueous saturated NaHCO₃ solution, water, brine, dried over anhydrous Na₂SO₄ and concentrated under reduced pressure to afford 2-amino-N-(2,6-dioxopiperidin-3-yl)-N-methylisonicotinamide.

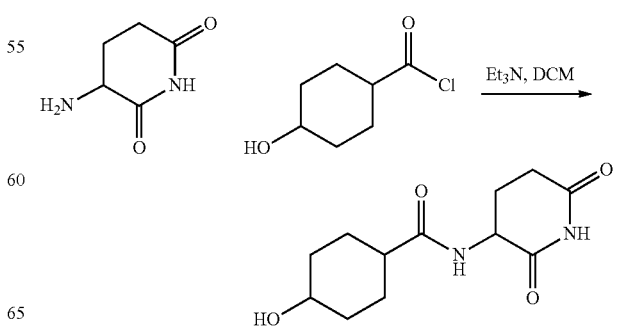

To a stirred solution of 3-amino-piperidine-2,6-dione 1 equiv.) in DCM (0.1M) are added triethylamine (3 equiv.) and 4-hydroxycyclohexane-1-carbonyl chloride (1.1 equiv.) sequentially at 0° C. The resulting mixture is stirred at ambient temperature for 18 hours. The reaction mixture is then quenched with ice-water and extracted with EtOAc. The combined organics are washed with aqueous saturated NaHCO$_3$ solution, water, brine, dried over anhydrous Na$_2$SO$_4$ and concentrated under reduced pressure to afford N-(2,6-dioxopiperidin-3-yl)-4-hydroxycyclohexane-1-carboxamide.

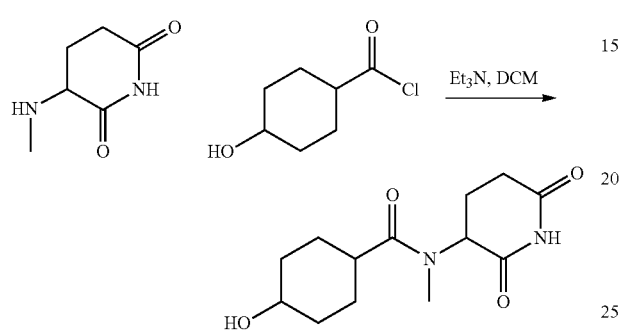

To a stirred solution of 3-(methylamino)piperidine-2,6-dione (1 equiv.) in DCM (0.1M) are added triethylamine (3 equiv.) and 4-hydroxycyclohexane-1-carbonyl chloride (1.1 equiv.) sequentially at 0° C. The resulting mixture is stirred at ambient temperature for 18 hours. The reaction mixture is then quenched with ice-water and extracted with EtOAc. The combined organics are washed with aqueous saturated NaHCO$_3$ solution, water, brine, dried over anhydrous Na$_2$SO$_4$ and concentrated under reduced pressure to afford N-(2,6-dioxopiperidin-3-yl)-4-hydroxy-N-methylcyclohexane-1-carboxamide.

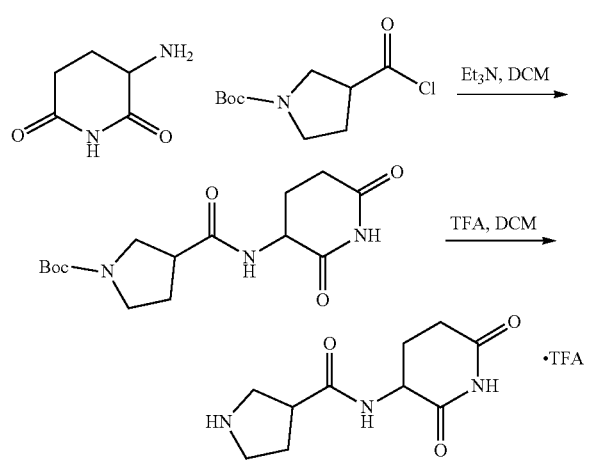

To a stirred solution of 3-amino-piperidine-2,6-dione (1 equiv.) in DCM (0.1 M) are added triethylamine (3 equiv.) and tert-butyl 3-(chlorocarbonyl)pyrrolidine-1-carboxylate (1.1 equiv.) sequentially at 0° C. The resulting mixture is stirred at ambient temperature for 18 hours. The reaction mixture is then quenched with ice-water and extracted with EtOAc. The combined organics are washed with aqueous saturated NaHCO$_3$ solution, water, brine, dried over anhydrous Na$_2$SO$_4$ and concentrated under reduced pressure to afford tert-butyl 3-((2,6-dioxopiperidin-3-yl)carbamoyl)pyrrolidine-1-carboxylate.

3-((2,6-Dioxopiperidin-3-yl)carbamoyl)pyrrolidine-1-carboxylate is dissolved in DCM/TFA (1/1, 0.2M) and stirred at ambient temperature for 2 hours. The volatiles are evaporated under reduced pressure to afford N-(2,6-dioxopiperidin-3-yl)pyrrolidine-3-carboxamide as a trifluoroacetic acid salt.

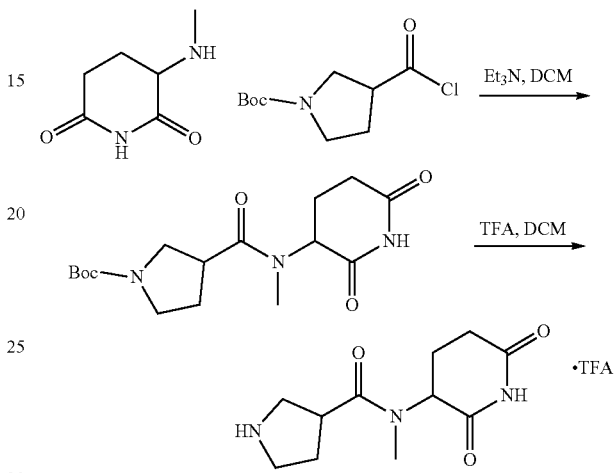

To a stirred solution of 3-(methylamino)piperidine-2,6-dione (1 equiv.) in DCM (0.1 M) are added triethylamine (3 equiv.) and tert-butyl 3-(chlorocarbonyl)pyrrolidine-1-carboxylate (1.1 equiv.) sequentially at 0° C. The resulting mixture is stirred at ambient temperature for 18 hours. The reaction mixture is then quenched with ice-water and extracted with EtOAc. The combined organics are washed with aqueous saturated NaHCO$_3$ solution, water, brine, dried over anhydrous Na$_2$SO$_4$ and concentrated under reduced pressure to afford tert-butyl 3-((2,6-dioxopiperidin-3-yl)(methyl)carbamoyl)pyrrolidine-1-carboxylate.

3-((2,6-Dioxopiperidin-3-yl)carbamoyl)pyrrolidine-1-carboxylate is dissolved in DCM/TFA (1/1, 0.2M) and stirred at ambient temperature for 2 hours. The volatiles are evaporated under reduced pressure to afford N-(2,6-dioxopiperidin-3-yl)-N-methylpyrrolidine-3-carboxamide as a trifluoroacetic acid salt.

Intermediate Functionalization in Preparation for Linker Installation Tert-Butyl 3-(3-(4-aminophenyl)-2-oxoimidazolidin-1-yl)-2,6-dioxopiperidine-1-carboxylate

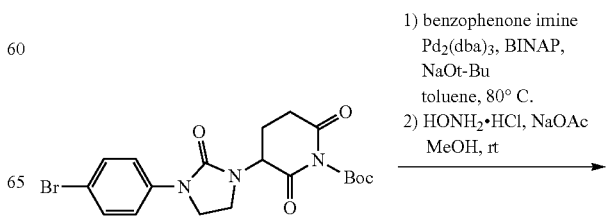

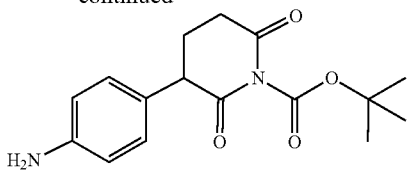

A reaction vessel is charged with tert-butyl 3-(3-(4-bromophenyl)-2-oxoimidazolidin-1-yl)-2,6-dioxopiperidine-1-carboxylate (1 equiv.), benzophenone imine (1.2 equiv.), tris(dibenzylideneacetone)dipalladium(0) (1 mol %), BINAP (3 mol %) and sodium tert-butoxide and purged by cycling between nitrogen and vacuum 3 times. Toluene is added and the reaction is heated at 80° C. for 18 hours. Ethyl acetate is added and the solids separated by filtration through a plug of Celite®. The filtrate is concentrated and the residue is purified by chromatography to provide tert-butyl 3-(3-(4-((diphenylmethylene)amino)phenyl)-2-oxoimidazolidin-1-yl)-2,6-dioxopiperidine-1-carboxylate.

A reaction vessel is charged with tert-butyl 3-(3-(4-((diphenylmethylene)amino)phenyl)-2-oxoimidazolidin-1-yl)-2,6-dioxopiperidine-1-carboxylate·carboxylate (1 equiv.) and dissolved in MeOH. Hydroxylamine hydrochloride (1.8 equiv.) and sodium acetate (2.4 equiv.) are added and the reaction mixed at ambient temperature for 1 hour. The reaction is quenched by addition of 0.1M aq. NaOH solution and the resultant mixture extracted with ethyl acetate. The combined organic layer is washed with brine, dried over sodium sulfate, filtered, and concentrated. The crude residue is purified by silica gel chromatography to provide tert-butyl 3-(3-(4-aminophenyl)-2-oxoimidazolidin-1-yl)-2,6-dioxopiperidine-1-carboxylate. (PCT Int. Appl., 2015002230, 8 Jan. 2015).

Tert-Butyl 3-(3-(4-ethynylphenyl)-2-oxoimidazolidin-1-yl)-2,6-dioxopiperidine-1-carboxylate

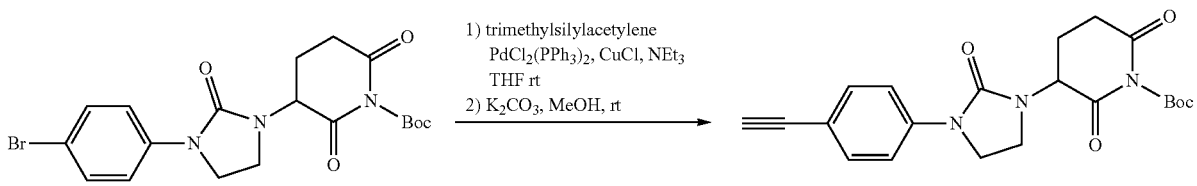 [SMILES: CC(C)(C)OC(=O)N1C(=O)CCC(N2CCN(c3ccc(Br)cc3)C2=O)C1=O ; C#Cc1ccc(N2CCN(C3CCC(=O)N(C(=O)OC(C)(C)C)C3=O)C2=O)cc1]

A reaction vessel is charged with bis(triphenylphosphine)palladium(II) chloride (2 mol %), copper(I) iodide (4 mol %) and tert-butyl 3-(3-(4-bromophenyl)-2-oxoimidazolidin-1-yl)-2,6-dioxopiperidine-1-carboxylate (1 equiv.). The reaction atmosphere is cycled between nitrogen and vacuum 3 times then triethylamine (1.55 equiv.) and trimethylsilylacetylene (1.25 equiv.) are added and the reaction is mixed for 24 hours. When the starting materials are consumed, the reaction is diluted with ethyl acetate and filtered through a plug of Celite®. The filtrate is concentrated and the residue is purified by silica gel chromatography to provide tert-butyl 2,6-dioxo-3-(2-oxo-3-(4-((trimethylsilyl)ethynyl)phenyl)imidazolidin-1-yl)piperidine-1-carboxylate. (Org. Lett. 2014, 16(24), 6302)

A reaction vessel is charged with tert-butyl 2,6-dioxo-3-(2-oxo-3-(4-((trimethylsilyl)ethynyl)phenyl)imidazolidin-1-yl)piperidine-1-carboxylate(1 equiv.), potassium carbonate (4 equiv.) and MeOH. The reaction is mixed at ambient temperature for 8 hours then concentrated. The residue is diluted with water and ethyl acetate. The aqueous layer is extracted with ethyl acetate and the combined organic layer is dried over sodium sulfate, filtered and concentrated. The crude residue is purified by silica gel chromatography to provide tert-butyl 3-(3-(4-ethynylphenyl)-2-oxoimidazolidin-1-yl)-2,6-dioxopiperidine-1-carboxylate.

Tert-Butyl 2,6-dioxo-3-(2-oxo-3-(4-(prop-2-yn-1-yloxy)phenyl)imidazolidin-1-yl)piperidine-1-carboxylate

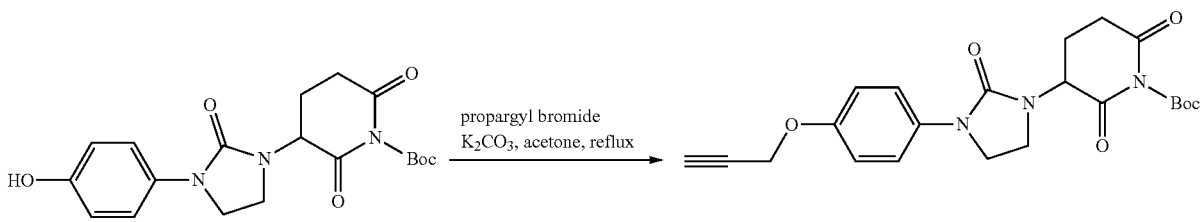 [SMILES: CC(C)(C)OC(=O)N1C(=O)CCC(N2CCN(c3ccc(O)cc3)C2=O)C1=O ; C#CCOc1ccc(N2CCN(C3CCC(=O)N(C(=O)OC(C)(C)C)C3=O)C2=O)cc1]

A reaction vessel is charged with tert-butyl 3-(3-(4-hydroxyphenyl)-2-oxoimidazolidin-1-yl)-2,6-dioxopiperidine-1-carboxylate (1 equiv.) and acetone (0.25 M). To this solution is added sequentially potassium carbonate (4 equiv.) and propargyl bromide (1.2 equiv.). The reaction is refluxed overnight, cooled to ambient temperature, filtered through a medium frit, and concentrated. The crude residue is purified by silica gel chromatography to provide tert-butyl 2,6-dioxo-3-(2-oxo-3-(4-(prop-2-yn-1-yloxy)phenyl)imidazolidin-1-yl)piperidine-1-carboxylate. (J. Med. Chem. 2013, 56(7), 2828).

4-(3-(1-(tert-Butoxycarbonyl)-2,6-dioxopiperidin-3-yl)-2-oxoimidazolidin-1-yl)benzoic Acid

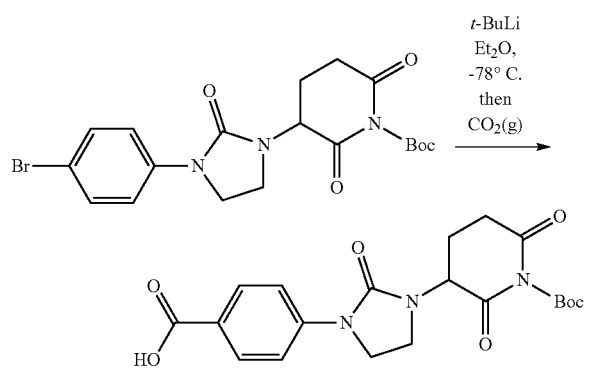

A flame-dried reaction vessel is charged with tert-butyl 3-(3-(4-bromophenyl)-2-oxoimidazolidin-1-yl)-2,6-dioxopiperidine-1-carboxylate (1 equiv.) and the atmosphere is cycled between nitrogen and vacuum three times. Ether is added and the solution is cooled to −78° C. tert-Butyllithium (2 equiv.) is added dropwise and the reaction is mixed for 15 min then carbon dioxide gas is bubbled through the solution for 15 min. The reaction is warmed to ambient temperature allowing excess carbon dioxide gas to slowly evolve from solution. The reaction is quenched with 1 M aq. NaOH solution and washed with ether (2×). The pH of the aqueous layer is adjusted to 3 and extracted with ethyl acetate (3×). The combined organic layer is dried over sodium sulfate and concentrated to dryness with toluene (3×) to provide 4-(3-(1-(tert-butoxycarbonyl)-2,6-dioxopiperidin-3-yl)-2-oxoimidazolidin-1-yl)benzoic acid.

Tert-Butyl 3-(3-(4-(hydroxymethyl)phenyl)-2-oxoimidazolidin-1-yl)-2,6-dioxopiperidine-1-carboxylate

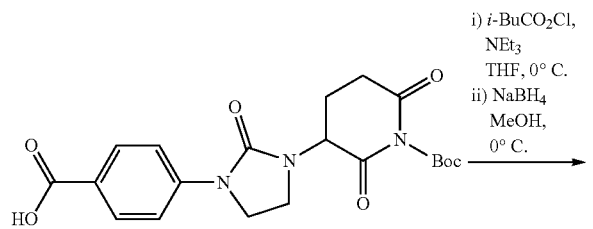

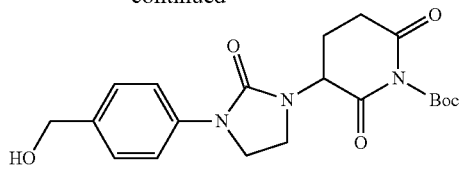

A reaction vessel is charged with 4-(3-(1-(tert-butoxycarbonyl)-2,6-dioxopiperidin-3-yl)-2-oxoimidazolidin-1-yl)benzoic acid (1 equiv.), THF and cool to 0° C. Triethylamine (1.1 equiv.) and isobutylchloroformate (1.1 equiv.) are added and the reaction mixed at ambient temperature for 1 hour. The reaction is filtered through a medium frit and cooled to 0° C. To the solution of mixed anhydride is added a solution of sodium borohydride (2 equiv.) in MeOH. Upon complete reduction to the corresponding benzylic alcohol, the reaction is concentrated then treated with ethyl acetate and 10% aq. HCl. The phases are separated and aqueous solution is extracted with ethyl acetate (3×). The combined organic layer is washed with 5% sodium bicarbonate solution, dried over sodium sulfate, and concentrated. The residue is purified by silica gel chromatography to provide tert-butyl 3-(3-(4-(hydroxymethyl)phenyl)-2-oxoimidazolidin-1-yl)-2,6-dioxopiperidine-1-carboxylate.

Tert-Butyl 3-(3-(4-formylphenyl)-2-oxoimidazolidin-1-yl)-2,6-dioxopiperidine-1-carboxylate

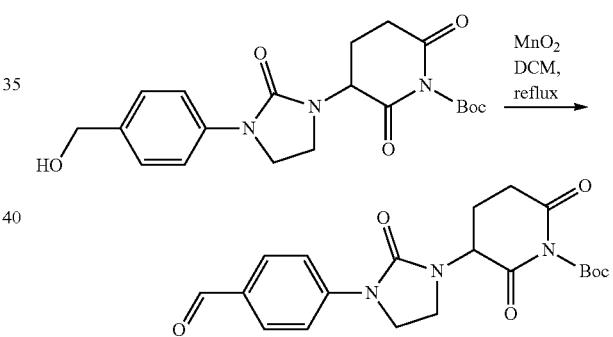

A reaction vessel is charged with tert-butyl 3-(3-(4-(hydroxymethyl)phenyl)-2-oxoimidazolidin-1-yl)-2,6-dioxopiperidine-1-carboxylate (1 equiv.), manganese dioxide (10 equiv.) and DCM. The reaction is heated at reflux overnight then cooled to ambient temperature and filtered. The filtrate is concentrated and purified by silica gel chromatography to provide tert-butyl 3-(3-(4-formylphenyl)-2-oxoimidazolidin-1-yl)-2,6-dioxopiperidine-1-carboxylate.

Tert-Butyl 3-(3-(4-(bromomethyl)phenyl)-2-oxoimidazolidin-1-yl)-2,6-dioxopiperidine-1-carboxylate

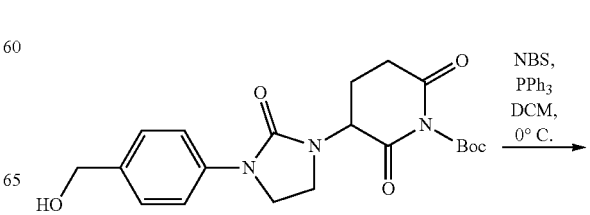

453
-continued

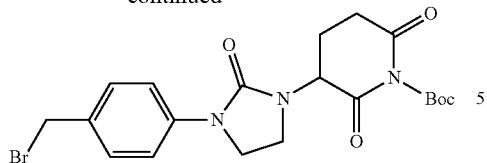

454
-continued

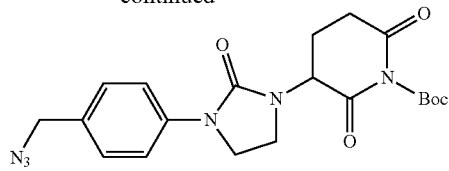

A reaction vessel is charged with tert-butyl 3-(3-(4-(hydroxymethyl)phenyl)-2-oxoimidazolidin-1-yl)-2,6-dioxopiperidine-1-carboxylate (1 equiv.) and DCM. The solution is cooled to 0° C. and N-bromosuccinimide (1.25 equiv.) and triphenylphosphine (1.25 equiv.) are then added. The reaction is mixed for 3 hours then concentrated. The crude residue is purified by silica gel chromatography to provide tert-butyl 3-(3-(4-(bromomethyl)phenyl)-2-oxoimidazolidin-1-yl)-2,6-dioxopiperidine-1-carboxylate. (J. Med. Chem. 2015, 58(3), 1215).

Tert-Butyl 3-(3-(4-(azidomethyl)phenyl)-2-oxoimidazolidin-1-yl)-2,6-dioxopiperidine-1-carboxylate Sodium azide (3 equiv.) is added to a solution of tert-butyl 3-(3-(4-(bromomethyl)phenyl)-2-oxoimidazolidin-1-yl)-2,6-dioxopiperidine-1-carboxylate (1 equiv.) in water and acetone (1:3, 0.25 M). The reaction is heated at 60° C. for 6 hours. The reaction is cooled to ambient temperature and the solvent removed by rotary evaporation. The aqueous layer is extracted with DCM (3×) and the combined organic layer is dried over sodium sulfate and filtered. The filtrate is concentrated and the crude residue is purified by silica gel chromatography to provide tert-butyl 3-(3-(4-(azidomethyl)phenyl)-2-oxoimidazolidin-1-yl)-2,6-dioxopiperidine-1-carboxylate. (Angew. Chem. Int. Ed. 2014, 53(38), 10155).

Linker Installation

Tert-Butyl 3-(3-(4-((8-hydroxyoctyl)oxy)phenyl)-2-oxoimidazolidin-1-yl)-2,6-dioxopiperidine-1-carboxylate

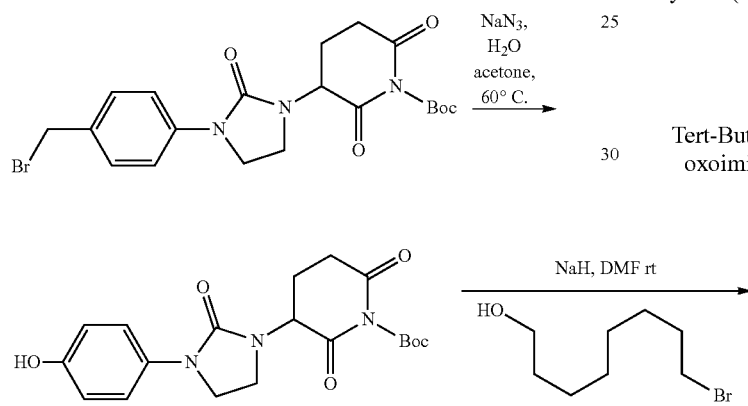

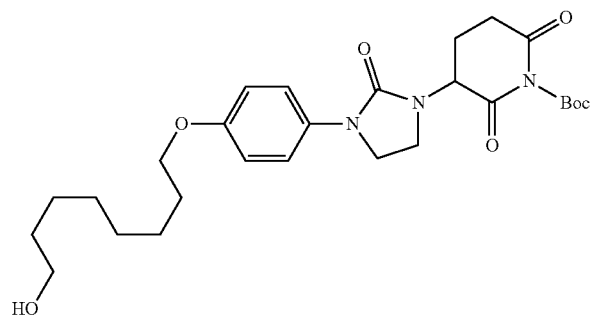

A reaction vessel is charged with tert-butyl 3-(3-(4-hydroxyphenyl)-2-oxoimidazolidin-1-yl)-2,6-dioxopiperidine-1-carboxylate (1 equiv.) and DMF (0.3 M) then cooled to 0° C. Sodium hydride (60% dispersion in mineral oil, 1.1 equiv.) is added and the reaction is warmed to ambient temperature and mixed for 1 hour. The reaction is cooled to 0° C. then 8-bromooctan-1-ol (1.1 equiv.) is added and the reaction is mixed at ambient temperature overnight. DMF is removed by rotary evaporation and the residue is deposited onto silica gel and purified by silica gel chromatography to provide tert-butyl 3-(3-(4-((8-hydroxyoctyl)oxy)phenyl)-2-oxoimidazolidin-1-yl)-2,6-dioxopiperidine-1-carboxylate.

Tert-Butyl 3-(3-(4-(2-(2-(2-hydroxyethoxy)ethoxy)ethoxy)phenyl)-2-oxoimidazolidin-1-yl)-2,6-dioxopiperidine-1-carboxylate

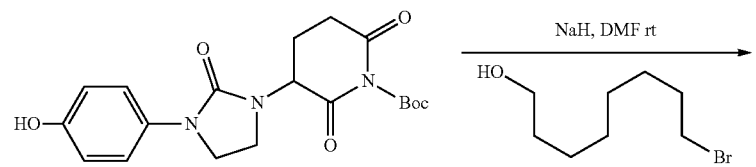

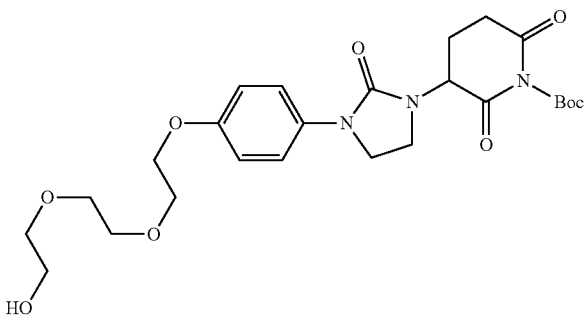

A reaction vessel is charged with tert-butyl 3-(3-(4-hydroxyphenyl)-2-oxoimidazolidin-1-yl)-2,6-dioxopiperidine-1-carboxylate (1 equiv.) and DMF (0.3 M) then cooled to 0° C. Sodium hydride (60% dispersion in mineral oil, 1.1 equiv.) is added and the reaction is warmed to ambient temperature and mixed for 1 hour. The reaction is cooled to 0° C. then 2-(2-(2-bromoethoxy)ethoxy)ethan-1-ol (1.1 equiv.) is added and the reaction is mixed at ambient temperature overnight. DMF is removed by rotary evaporation and the residue is deposited onto silica gel and purified by silica gel chromatography to provide tert-butyl 3-(3-(4-(2-(2-(2-hydroxyethoxy)ethoxy)ethoxy)phenyl)-2-oxoimidazolidin-1-yl)-2,6-dioxopiperidine-1-carboxylate.

Tert-Butyl 3-(3-(4-((1-(3-hydroxypropyl)-1H-1,2,3-triazol-4-yl)methoxy)phenyl)-2-oxoimidazolidin-1-yl)-2,6-dioxopiperidine-1-carboxylate

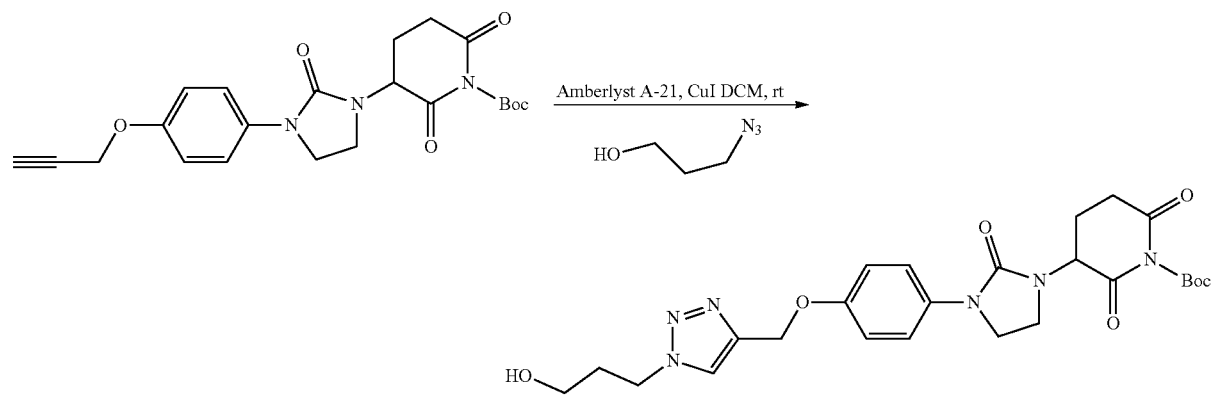

A reaction vessel is charged with the polymer supported catalyst (Amberlyst A-21, 1.23 mmol/g; CuI, 13% mol). The azide (0.5 M in DCM) is added dropwise followed by a solution of the tert-butyl 2,6-dioxo-3-(2-oxo-3-(4-(prop-2-yn-1-yloxy)phenyl)imidazolidin-1-yl)piperidine-1-carboxylate (0.5 M in DCM). The suspension is mixed for 12 hours at ambient temperature. The reaction solution is filtered through a frit and the polymer cake is washed with DCM (2×). The combined filtrate is concentrated and the residue purified by silica gel chromatography to provide tert-butyl 3-(3-(4-((1-(3-hydroxypropyl)-1H-1,2,3-triazol-4-yl)methoxy)phenyl)-2-oxoimidazolidin-1-yl)-2,6-dioxopiperidine-1-carboxylate. (Org. Lett. 2006, 8(8), 1689).

Tert-Butyl 3-(3-(4-(2-(2,4-dihydroxy-2-methylbutoxy)ethoxy)phenyl)-2-oxoimidazolidin-1-yl)-2,6-dioxopiperidine-1-carboxylate

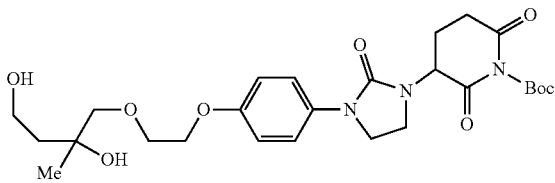 [SMILES: CC(O)(CCO)COCCOc1ccc(N2CCN(C3CCC(=O)N(C(=O)OC(C)(C)C)C3=O)C2=O)cc1]

Tert-Butyl 3-(3-(4-(2-hydroxyethoxy)phenyl)-2-oxoimidazolidin-1-yl)-2,6-dioxopiperidine-1-carboxylate

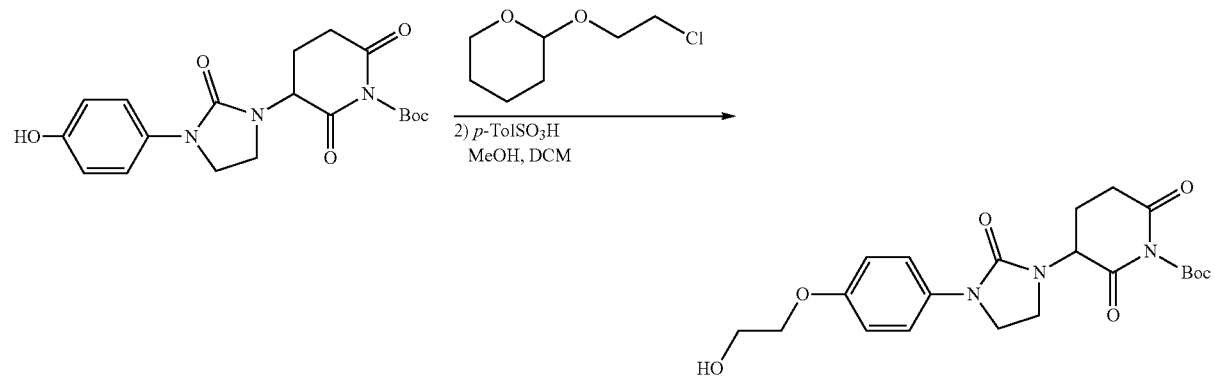

A reaction vessel is charged with tert-butyl 3-(3-(4-hydroxyphenyl)-2-oxoimidazolidin-1-yl)-2,6-dioxopiperidine-1-carboxylate (1 equiv.), potassium carbonate (2 equiv.) and DMF (0.5 M). 2-(2-Chloroethoxy)tetrahydro-2H-pyran (1.1 equiv.) is added and the reaction is heated at 110° C. for 12 hours. The reaction is then cooled to ambient temperature and concentrated. The residue is taken up in water and ethyl acetate and the layers separated. The aqueous layer is extracted with ethyl acetate (2×). The combined organic layer is washed with brine, dried over sodium sulfate, filtered and concentrated. The crude residue is used directly in the following reaction.

A reaction vessel is charged with crude tert-butyl 2,6-dioxo-3-(2-oxo-3-(4-(2-((tetrahydro-2H-pyran-2-yl)oxy)ethoxy)phenyl)imidazolidin-1-yl)piperidine-1-carboxylate (1 equiv.), MeOH and DCM (1:1, 0.2 M). p-Toluenesulfonic acid (0.1 equiv.) is added and the reaction mixed at ambient temperature. Upon completion of the hydrolysis reaction, the volatiles are removed by rotary evaporation and the residue purified by silica gel chromatography to provide tert-butyl 3-(3-(4-(2-hydroxyethoxy)phenyl)-2-oxoimidazolidin-1-yl)-2,6-dioxopiperidine-1-carboxylate.

Tert-Butyl 2,6-dioxo-3-(2-oxo-3-(4-(2-(2-oxopropoxy)ethoxy)phenyl)imidazolidin-1-yl)piperidine-1-carboxylate

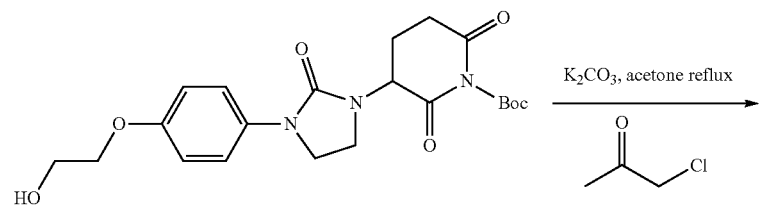

-continued

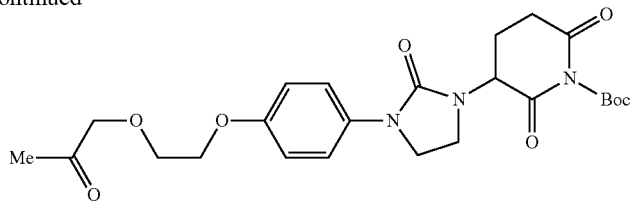

A reaction vessel is charged with tert-butyl 3-(3-(4-(2-hydroxyethoxy)phenyl)-2-oxoimidazolidin-1-yl)-2,6-dioxopiperidine-1-carboxylate (1 equiv.), potassium carbonate (1.2 equiv.) and acetone (0.1 M). Chloroacetone (1.2 equiv.) is then added and the reaction heated at reflux overnight. The reaction is cooled then concentrated and the crude residue partitioned between water and ethyl acetate. The layers were separated and the aqueous layer was extracted with ethyl acetate (2×). The combined organic layers are dried over sodium sulfate, filtered and concentrated. The crude residue is purified by column chromatography to provide tert-butyl 2,6-dioxo-3-(2-oxo-3-(4-(2-(2-oxopropoxy)ethoxy)phenyl) imidazolidin-1-yl)piperidine-1-carboxylate. (J. Med. Chem. 2007, 50(18), 4304).

Tert-Butyl 3-(3-(4-(2-(2,4-dihydroxy-2-methylbutoxy)ethoxy)phenyl)-2-oxoimidazolidin-1-yl)-2,6-dioxopiperidine-1-carboxylate (3×). The combined organic layer is washed with brine, dried over sodium sulfate, filtered and concentrated. The crude residue is purified by silica gel chromatography to provide tert-butyl 3-(3-(4-(2-((2-hydroxy-2-methylbut-3-en-1-yl)oxy)ethoxy)phenyl)-2-oxoimidazolidin-1-yl)-2,6-dioxopiperidine-1-carboxylate.

Cyclohexene (4.2 equiv.) was added to a solution of $BH_3 \cdot THF$ (1 M in THF, 2 equiv.) at 0° C. under argon. After stirring for 1 hour at 0° C., a solution of tert-butyl 3-(3-(4-(2-((2-hydroxy-2-methylbut-3-en-1-yl)oxy)ethoxy)phenyl)-2-oxoimidazolidin-1-yl)-2,6-dioxopiperidine-1-carboxylate. (1 equiv.) in THF (0.15 M) was added to the mixture at 0° C. After stirring for 2 hours at 0° C., 3N NaOH (6 equiv.) and 30% $H_2O_2$ (33% volume of aq. NaOH solution addition) was added to the mixture. This solution is allowed to mix at ambient temperature for 30 min. The reaction is quenched with saturated aqueous $NH_4Cl$ (8 volumes) at 0° C., and the

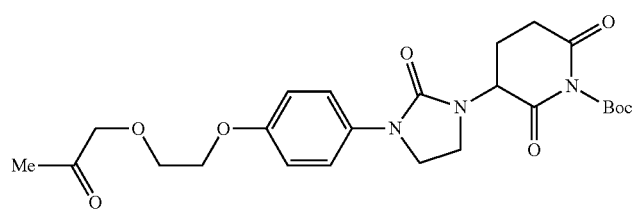

1) vinyl-Mg-Br THF, -78° C.
2) $BH_3$-THF cyclohexane THF, 0° C.
3) NaOH, $H_2O_2$ $H_2O$, 0° C.

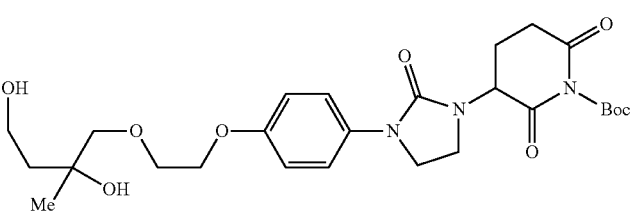

A reaction vessel is charged with tert-butyl 2,6-dioxo-3-(2-oxo-3-(4-(2-(2-oxopropoxy)ethoxy)phenyl)imidazolidin-1-yl)piperidine-1-carboxylate. (1 equiv.), and THF (0.2 M), purged with nitrogen and cooled to −78° C. Vinylmagnesium bromide (4 equiv.) is added dropwise and the reaction is warmed to 0° C. over 1 hour. The reaction is quenched with aq. 1% HCl solution and extracted with ethyl acetate resulting mixture is extracted with ethyl acetate (3×). The combined extracts are washed with brine, dried over sodium sulfate, filtered, and concentrated under reduced pressure. The crude residue is purified by silica gel chromatography to provide tert-butyl 3-(3-(4-(2-(2,4-dihydroxy-2-methylbutoxy)ethoxy)phenyl)-2-oxoimidazolidin-1-yl)-2,6-dioxopiperidine-1-carboxylate. (Org. Lett. 2012, 14(24), 6374).

Tert-Butyl 3-(3-(4-((7-chloro-4-hydroxy-4-methyl-hept-2-yn-1-yl)oxy)phenyl)-2-oxoimidazolidin-1-yl)-2,6-dioxopiperidine-1-carboxylate Ref: Gupta, V. D.; Singh, Joginder; Kinger, Mayank; Arora, Avnish Kumar; Jaswal, Vivek Sheel Asian Journal of Chemistry Volume 27 Issue 12 Pages 4379-4382.

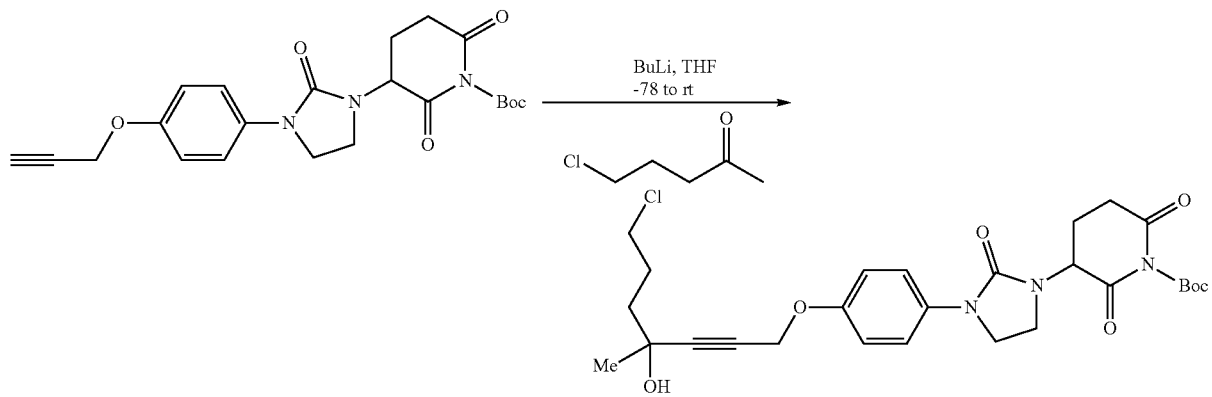

A reaction vessel is charged with tert-butyl 2,6-dioxo-3-(2-oxo-3-(4-(prop-2-yn-1-yloxy)phenyl)imidazolidin-1-yl)piperidine-1-carboxylate (1 equiv.) and the atmosphere cycled between nitrogen and vacuum three times. Anhydrous THF (0.1 M) is added and the reaction cooled to −78° C. Butyllithium (1.05 equiv.) is added and the reaction is mixed for 15 min. 5-Chloro-2-pentanone (1.1 equiv.) in THF (5 volumes) is then added and the reaction is warmed to ambient temperature and quenched with sat. aq. ammonium chloride solution. Ethyl acetate is added and the phases are separated. The aqueous layer is extracted with ethyl acetate (2×). The combined organic layers are washed with brine, dried over sodium sulfate, filtered and concentrated. The crude residue is purified by silica gel chromatography.

(3-(4-((7-Chloro-4-hydroxy-4-methylhept-2-yn-1-yl)oxy)phenyl)-2-oxoimidazolidin-1-yl)-2,6-dioxopiperidine-1-carboxylate

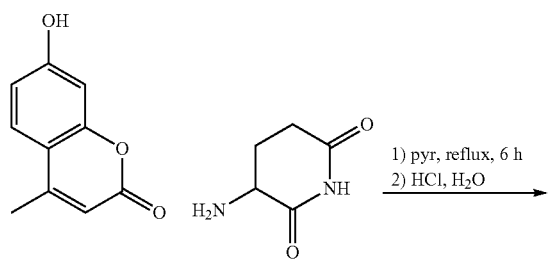

7-Hydroxy-4-methy-2H-chromen-2-one (1.0 equiv.) and 3-aminopiperidine-2,6-dione (1.5 equiv.) are dissolved in pyridine (0.2 M) and heated to reflux for 6 hours. After cooling, hydrochloric acid (1M aq.) is added to the reaction mixture. The solid is filtered under to obtain 3-(7-hydroxy-4-methyl-2-oxoquinolin-1(2H)-yl)piperidine-2,6-dione.

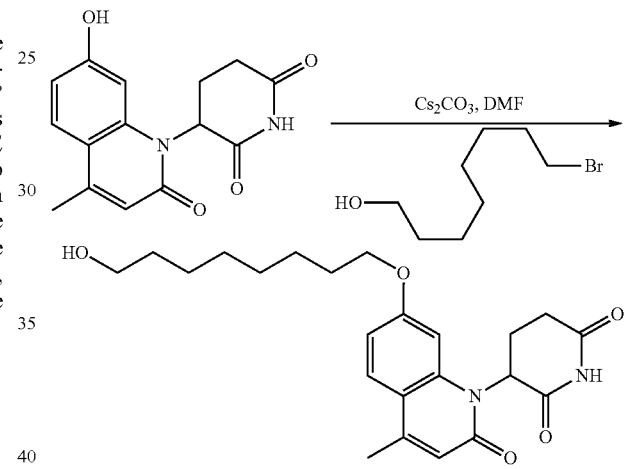

A reaction vessel is charged with 3-(7-hydroxy-4-methyl-2-oxoquinolin-1(2H)-yl)piperidine-2,6-dione (1 equiv.) and DMF (0.3 M). Cesium carbonate (1.2 equiv.) and mixed for 1 hour. 8-bromooctan-1-ol (1.2 equiv.) is added and the reaction is mixed at ambient temperature overnight. DMF is removed by rotary evaporation and the residue is deposited onto silica gel and purified by silica gel chromatography to provide 3-(7-((8-hydroxyoctyl)oxy)-4-methyl-2-oxoquinolin-1(2H)-yl)piperidine-2,6-dione.

3-(7-((8-Iodooctyl)oxy)-4-methyl-2-oxoquinolin-1(2H)-yl)piperidine-2,6-dione

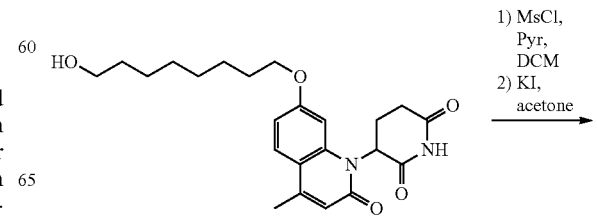

463

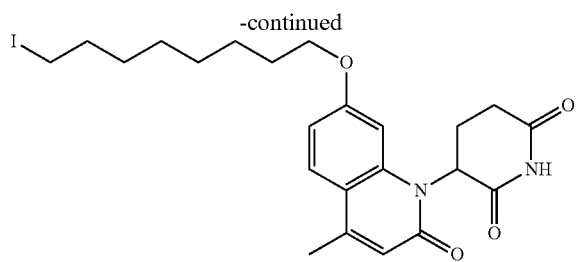

3-(7-((8-hydroxyoctyl)oxy)-4-methyl-2-oxoquinolin-1 (2H)-yl)piperidine-2,6-dione (1.0 equiv.) is dissolved in DCM, pyridine is added (1.1 equiv.), and cooled to 0deg C. Methanesulfnoyl chloride is added, and the reaction mixture is stirred for 2 hours. The volatiles are evaporated and the crude residue is taken up in acetone (0.1M). Potassium iodide (5 equiv.) is added and the reaction mixture is stirred in the dark at ambient temperature for 2 hours. The reaction mixture is impregnated on silica and purified by silica gel column chromatography to afford 3-(7-((8-iodooctyl)oxy)-4-methyl-2-oxoquinolin-1(2H)-yl)piperidine-2,6-dione.

3-(7-((8-Aminooctyl)oxy)-4-methyl-2-oxoquinolin-1 (2H)-yl)piperidine-2,6-dione

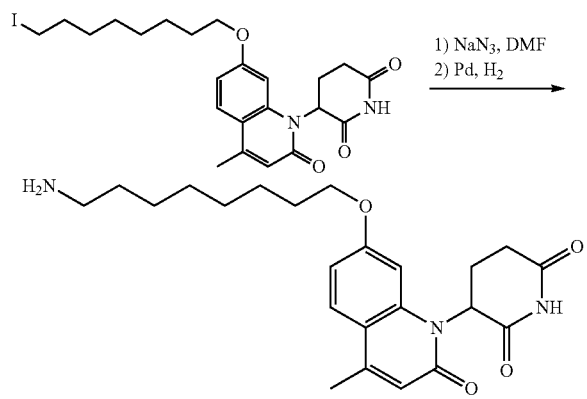

3-(7-((8-Iodooctyl)oxy)-4-methyl-2-oxoquinolin-1(2H)-yl)piperidine-2,6-dione is dissolved DMF (0.2 M), and sodium azide (3 equiv.) is added. The reaction mixture is heated to 60deg C. for 6 hours. The reaction mixture is partitioned between EtOAc and sodium bicarbonate, and the organic phase is washed with brine, dried with sodium sulfate and filtered. The reaction mixture is concentrated under reduced pressure. The residue is redissolved in MeOH and palladium on charcoal (5%) is added. The reaction mixture is placed under an atmosphere of hydrogen. The reaction mixture is filtered on Celite® and the filtrate is evaporated under reduced pressure to afford 3-(7-((8-aminooctyl)oxy)-4-methyl-2-oxoquinolin-1(2H)-yl)piperidine-2,6-dione.

464

3-(7-(2-(2-(2-(2-Hydroxyethoxy)ethoxy)ethoxy) ethoxy)-4-methyl-2-oxoquinolin-1(2H)-yl)piperidine-2,6-dione

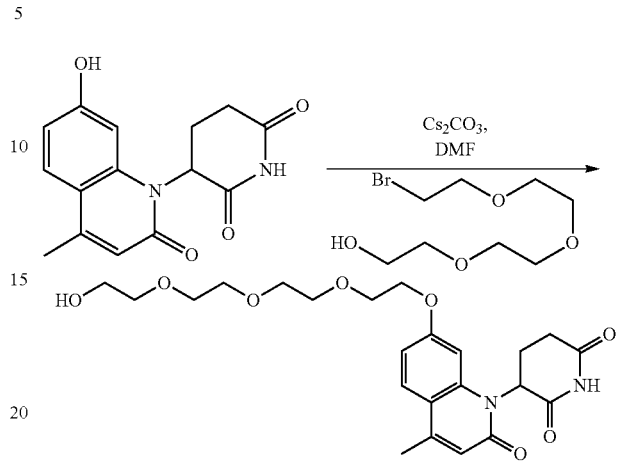

A reaction vessel is charged with 3-(7-hydroxy-4-methyl-2-oxoquinolin-1(2H)-yl)piperidine-2,6-dione (1 equiv.) and DMF (0.3 M). Cesium carbonate (1.2 equiv.) and mixed for 1 hour. 2-(2-(2-(2-bromoethoxy)ethoxy)ethoxy)ethan-1-ol (1.2 equiv.) is added and the reaction is mixed at ambient temperature overnight. DMF is removed by rotary evaporation and the residue is deposited onto silica gel and purified by silica gel chromatography to provide 3-(7-(2-(2-(2-(2-hydroxyethoxy)ethoxy)ethoxy)ethoxy)-4-methyl-2-oxoquinolin-1(2H)-yl)piperidine-2,6-dione.

3-(7-((1-(6-Hydroxyhexyl)-1H-1,2,3-triazol-4-yl) methoxy)-4-methyl-2-oxoquinolin-1(2H)-yl)piperidine-2,6-dione

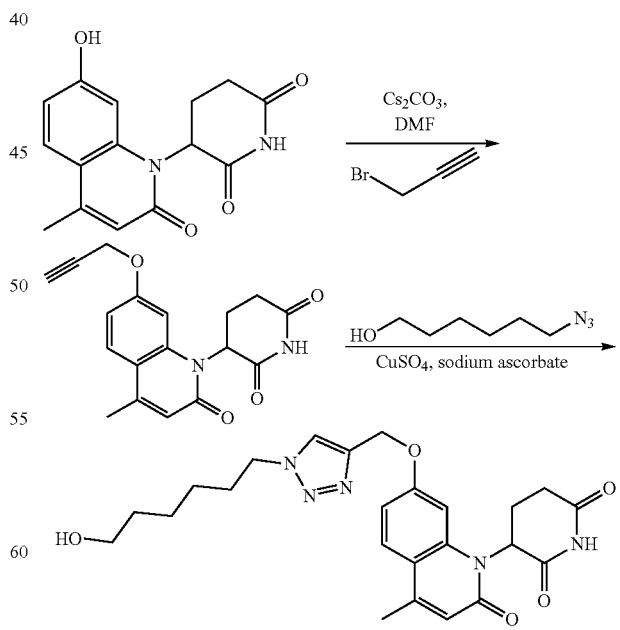

Step 1: A reaction vessel is charged with 3-(7-hydroxy-4-methyl-2-oxoquinolin-1(2H)-yl)piperidine-2,6-dione (1 equiv.) and DMF (0.3 M). Cesium carbonate (1.2 equiv.) and mixed for 1 hour. Propargyl bromide (1.3 equiv.) is added and the reaction is mixed at ambient temperature overnight. DMF is removed by rotary evaporation and the residue is deposited onto silica gel and purified by silica gel chromatography to provide 3-(4-methyl-2-oxo-7-(prop-2-yn-1-yloxy)quinolin-1(2H)-yl)piperidine-2,6-dione.

Step 2: 3-(4-Methyl-2-oxo-7-(prop-2-yn-1-yloxy)quinolin-1(2H)-yl)piperidine-2,6-dione is dissolved with 6-azidohexan-1-ol in a tert-butanol/water mixture. Copper sulfate (0.01 equiv.) and sodium ascorbate (0.1 equiv.) are added and the reaction mixture is stirred at 25° C. for 24 hours. The reaction moisture is diluted with water and extracted with ethyl acetate. The organic layer is washed with brine, dried with sodium sulfate, filtered and evaporated under reduced pressure to afford 3-(7-((1-(6-hydroxyhexyl)-1H-1,2,3-triazol-4-yl)methoxy)-4-methyl-2-oxoquinolin-1(2H)-yl)piperidine-2,6-dione.

Step 2: tert-Butyl 2-((1-(2,6-dioxopiperidin-3-yl)-4-methyl-2-oxo-1,2-dihydroquinolin-7-yl)oxy)acetate (1 equiv.) is dissolved in dioxane:water mixture (10:1, 0.2M) and hydrogen chloride (4M in dioxane, 4 equiv.) is added. The reaction mixture is stirred at 40° C. for 16 hours. The volatiles are evaporated under reduced pressure to afford 2-((1-(2,6-dioxopiperidin-3-yl)-4-methyl-2-oxo-1,2-dihydroquinolin-7-yl)oxy)acetic acid.

Step 3: 2-((1-(2,6-Dioxopiperidin-3-yl)-4-methyl-2-oxo-1,2-dihydroquinolin-7-yl)oxy)acetic acid (1 equiv.) is dissolved in DMF, diisopropylethylamine (2.1 equiv.) is added followed by tert-butyl (3-(2-(2-(3-aminopropoxy)ethoxy)ethoxy)propyl)carbamate (1.3 equiv.). the reaction mixture is cooled to 0° C. and HATU (1-[Bis(dimethylamino)methylene]-1H-1,2,3-triazolo[4,5-b]pyridinium 3-oxid hexafluorophosphate) (1.1 equiv.) is added. The reaction mixture is stirred for 4 hours, while increasing the temperature to 25°

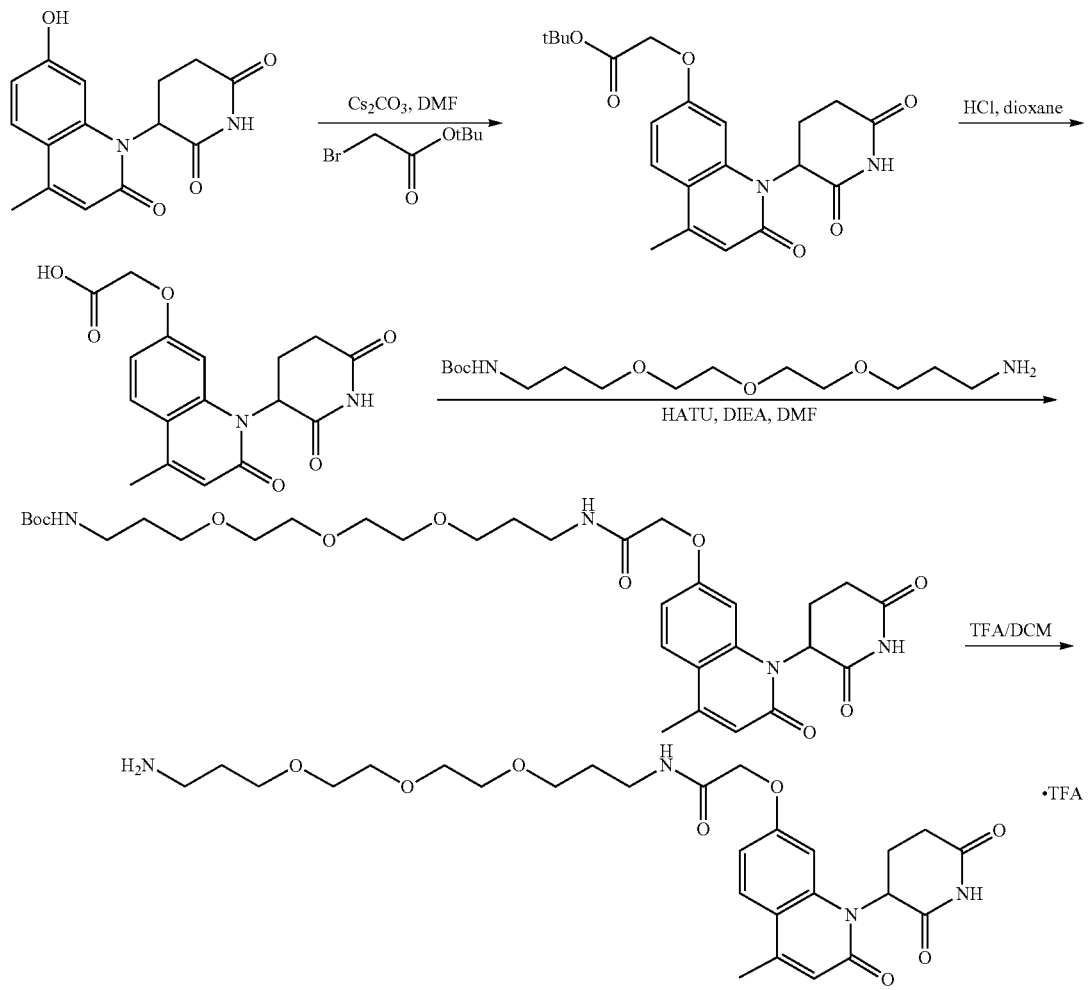

Step 1: A reaction vessel is charged with 3-(7-hydroxy-4-methyl-2-oxoquinolin-1(2H)-yl)piperidine-2,6-dione (1 equiv.) and DMF (0.3 M). Cesium carbonate (1.2 equiv.) and mixed for 1 hour. Methyl bromoacetate (1.3 equiv.) is added and the reaction is mixed at ambient temperature overnight. DMF is removed by rotary evaporation and the residue is deposited onto silica gel and purified by silica gel chromatography to provide tert-butyl 2-((1-(2,6-dioxopiperidin-3-yl)-4-methyl-2-oxo-1,2-dihydroquinolin-7-yl)oxy)acetate.

C. DMF is removed by rotary evaporation and the residue is deposited onto silica gel and purified by silica gel chromatography to provide tert-butyl (1-((1-(2,6-dioxopiperidin-3-yl)-4-methyl-2-oxo-1,2-dihydroquinolin-7-yl)oxy)-2-oxo-7,10,13-trioxa-3-azahexadecan-16-yl)carbamate.

Step 4: tert-butyl (1-((1-(2,6-dioxopiperidin-3-yl)-4-methyl-2-oxo-1,2-dihydroquinolin-7-yl)oxy)-2-oxo-7,10,13-trioxa-3-azahexadecan-16-yl)carbamate is dissolved in a TFA:DCM mixture (1:1, 0.2M), and stirred for 2 hours at ambient temperature. The volatiles are evaporated under reduced pressure to afford N-(3-(2-(2-(3-aminopropoxy)ethoxy)ethoxy)propyl)-2-((1-(2,6-dioxopiperidin-3-yl)-4-methyl-2-oxo-1,2-dihydroquinolin-7-yl)oxy)acetamide as a trifluoroacetic acid salt.

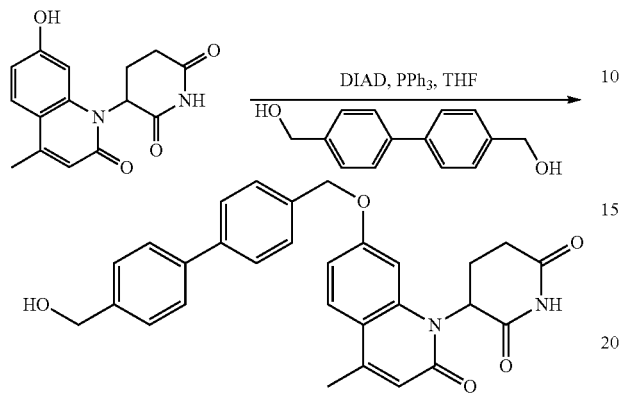

Step 1: 3-(7-hydroxy-4-methyl-2-oxoquinolin-1(2H)-yl)piperidine-2,6-dione (1 equiv.) is dissolved in THF (0.2M) and triphenylphosphine (2.0 equiv.) and [1,1'-biphenyl]-4,4'-diyldimethanol (2.0 equiv.) are added. The reaction mixture is cooled to 0° C. and DIAD (1.2 equiv.) is added dropwise under stirring over 5 minutes. The reaction mixture is stirred while warming to room temperature for 2 hours. The volatiles are evaporated under reduced pressure, the crude material is impregnated on silica and purified using silica gel chromatography to afford 3-(7-((4'-(hydroxymethyl)-[1,1'-biphenyl]-4-yl)methoxy)-4-methyl-2-oxoquinolin-1(2H)-yl)piperidine-2,6-dione.

N-(2-(2 6-Dioxopiperidin-3-yl)-1-oxo-1,2-dihydroisoquinolin-5-yl)-7-hydroxyheptanamide

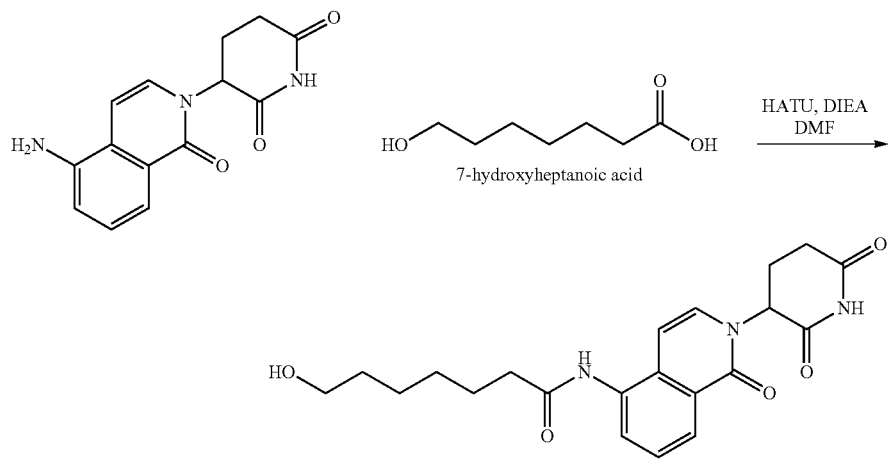

3-(5-amino-1-oxoisoquinolin-2(1H)-yl)piperidine-2,6-dione is dissolved in DMF (0.2 M) and 7-hydroxyheptanoic acid is added. The reaction mixture is cooled to 0deg C., and HATU (1.1 equiv.) is added. After stirred for 15 hours, the reaction mixture is partitioned between EtOAc and sodium bicarbonate (sat. aqueous). The organic phase is washed with brine, dried with sodium sulfate, filtered and evaporated under reduced pressure. The crude material is purified by column chromatography to afford N-(2-(2,6-dioxopiperidin-3-yl)-1-oxo-1,2-dihydroisoquinolin-5-yl)-7-hydroxyheptanamide.

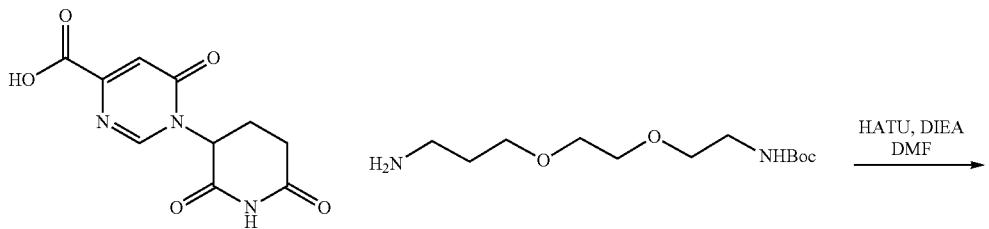

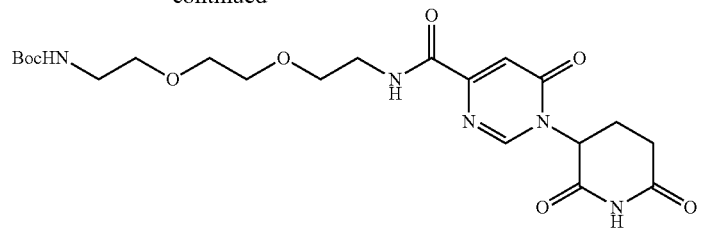

1-(2,6-dioxopiperidin-3-yl)-6-oxo-1,6-dihydropyrimidine-4-carboxylic acid is dissolved in DMF (0.2 M) and tert-butyl (2-(2-(3-aminopropoxy)ethoxy)ethyl)carbamate is added. The reaction mixture is cooled to 0deg C., and HATU (1.1 equiv.) is added. After stirred for 15 hours, the reaction mixture is partitioned between EtOAc and sodium bicarbonate (sat. aqueous). The organic phase is washed with brine, dried with sodium sulfate, filtered and evaporated under reduced pressure. The crude material is purified by column chromatography to afford tert-butyl (2-(2-(2-(1-(2,6-dioxopiperidin-3-yl)-6-oxo-1,6-dihydropyrimidine-4-carboxamido)ethoxy)ethoxy)ethyl)carbamate.

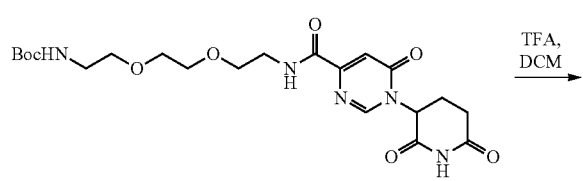

tert-Butyl (2-(2-(2-(1-(2,6-dioxopiperidin-3-yl)-6-oxo-1,6-dihydropyrimidine-4-carboxamido)ethoxy)ethoxy)ethyl) carbamate is dissolved in a TFA:DCM mixture (1:1, 0.2M), and stirred for 2 hours at ambient temperature. The volatiles are evaporated under reduced pressure to afford N-(2-(2-(2-aminoethoxy)ethoxy)ethyl)-1-(2,6-dioxopiperidin-3-yl)-6-oxo-1,6-dihydropyrimidine-4-carboxamide as a trifluoroacetic acid salt.

Final Compound Examples

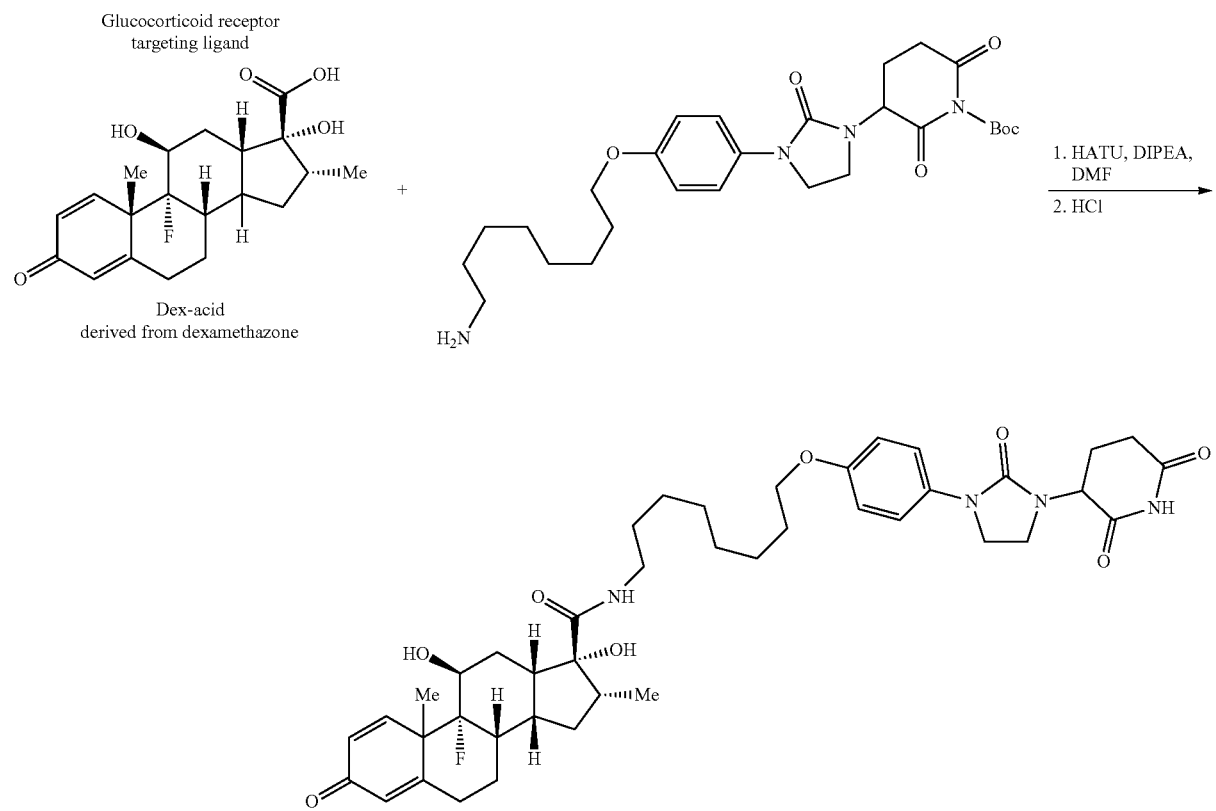

tert-Butyl 3-(3-(4-((8-aminooctyl)oxy)phenyl)-2-oxoimidazolidin-1-yl)-2,6-dioxopiperidine-1-carboxylate (1 equiv.) is dissolved in DMF and added to a solution of Dex-acid (1 equiv.), DIPEA (3 equiv.). HATU (1 equiv.) is then added and the mixture is stirred for 24 hours. The mixture is then diluted with ethyl acetate and washed with saturated sodium bicarbonate solution, water, and then brine. The organic layer is dried over sodium sulfate and concentrated. The crude material is then dissolved in dioxane. HCl (4N in dioxane) is added and the solution stirred at room temperature for 12 hours. The solvent is then evaporated under reduced pressure and the crude product is purified on silica.

saturated sodium bicarbonate solution, water, and then brine. The organic layer is dried over sodium sulfate and concentrated. The crude material is then dissolved in dioxane. HCl (4N in dioxane) is added and the solution stirred at room temperature for 12 hours. The solvent is then evaporated under reduced pressure and the crude product is purified on silica.

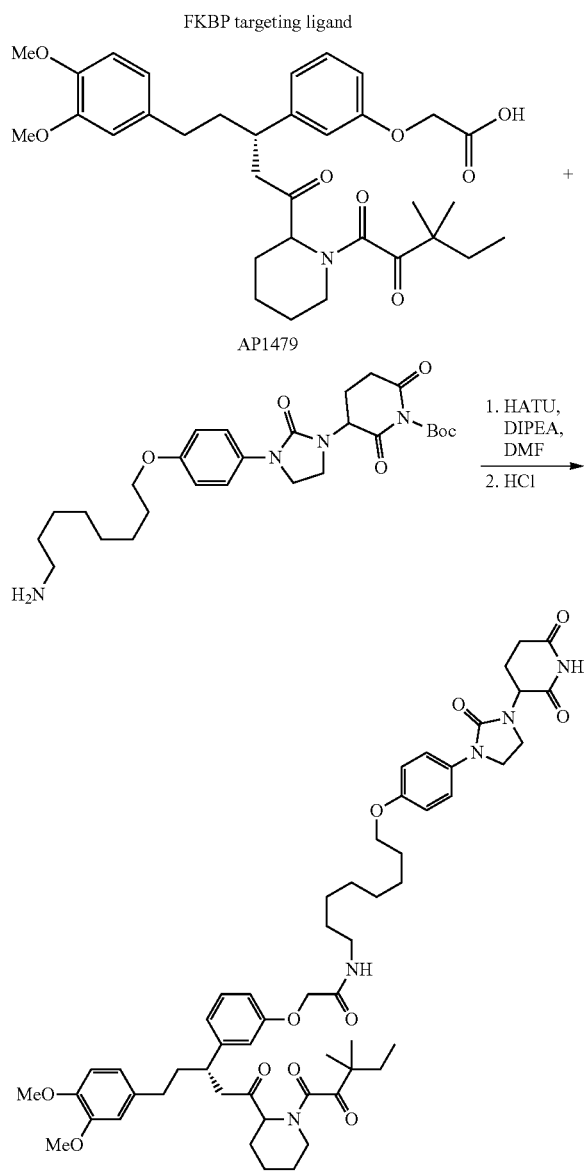

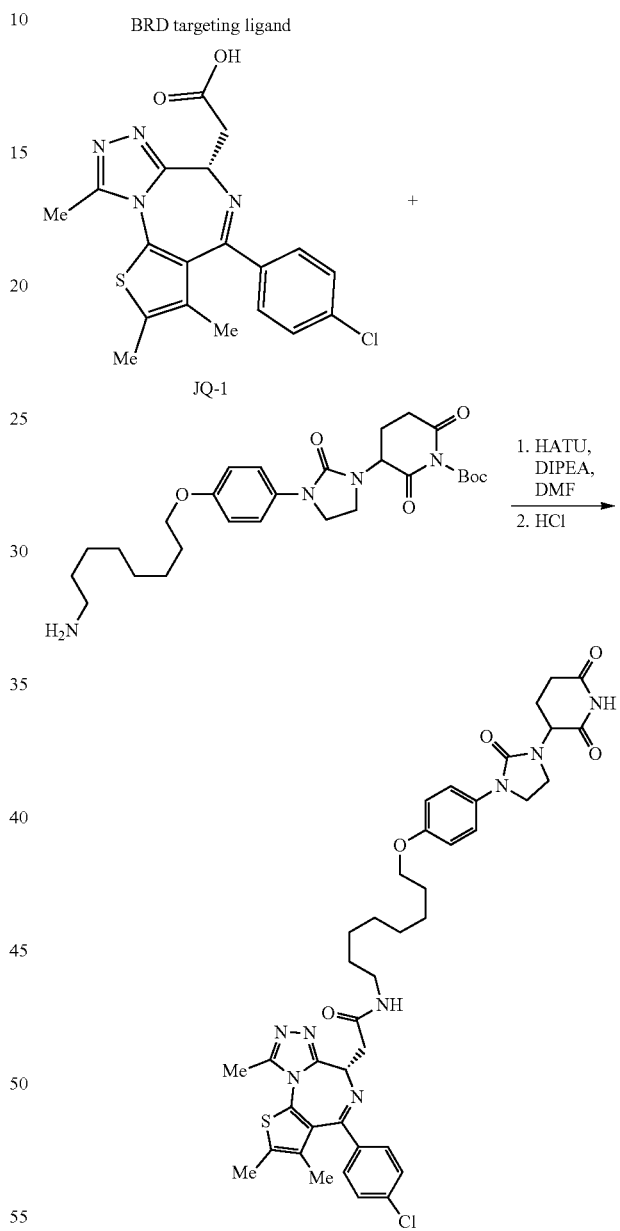

tert-Butyl 3-(3-(4-((8-aminooctyl)oxy)phenyl)-2-oxoimidazolidin-1-yl)-2,6-dioxopiperidine-1-carboxylate (1 equiv.) is dissolved in DMF and added to a solution of AP1479 (1 equiv.), DIPEA (3 equiv.). HATU (1 equiv.) is then added and the mixture is stirred for 24 hours. The mixture is then diluted with ethyl acetate and washed with tert-Butyl 3-(3-(4-((8-aminooctyl)oxy)phenyl)-2-oxoimidazolidin-1-yl)-2,6-dioxopiperidine-1-carboxylate (1 equiv.) is dissolved in DMF and added to a solution of JQ-1 (1 equiv.), DIPEA (3 equiv.). HATU (1 equiv.) is then added and the mixture is stirred for 24 hours. The mixture is then diluted with ethyl acetate and washed with saturated sodium bicarbonate solution, water, and then brine. The organic layer is dried over sodium sulfate and concentrated. The crude material is then dissolved in dioxane. HCl (4N in dioxane) is added and the solution stirred at room temperature for 12 hours. The solvent is then evaporated under reduced pressure and the crude product is purified on silica.

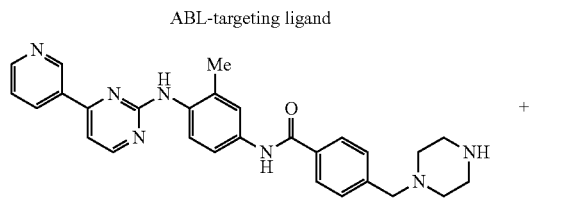

ABL-targeting ligand

+

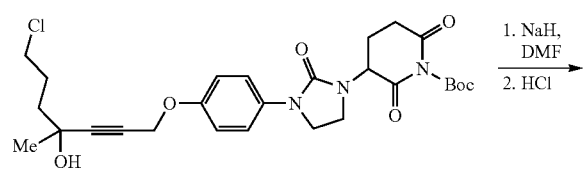

1. NaH, DMF
2. HCl

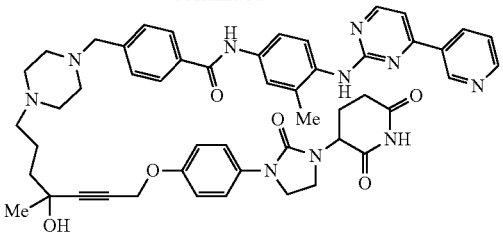

-continued

A reaction vessel is charged with N-(3-methyl-4-((4-(pyridin-3-yl)pyrimidin-2-yl)amino)phenyl)-4-(piperazin-1-ylmethyl)benzamide (1 equiv.) and DMF (0.3 M) then cooled to 0° C. Sodium hydride (60% dispersion in mineral oil, 1.1 equiv.) is added and the reaction is warmed to ambient temperature and mixed for 1 hour. The reaction is cooled to 0° C. then tert-butyl 3-(3-(4-((7-chloro-4-hydroxy-4-methylhept-2-yn-1-yl)oxy)phenyl)-2-oxoimidazolidin-1-yl)-2,6-dioxopiperidine-1-carboxylate (1.1 equiv.) is added and the reaction is mixed at ambient temperature overnight. DMF is removed by rotary evaporation. The crude material is then dissolved in dioxane. HCl (4N in dioxane) is added and the solution stirred at room temperature for 12 hours. The solvent is then evaporated under reduced pressure and the crude product is purified on silica.

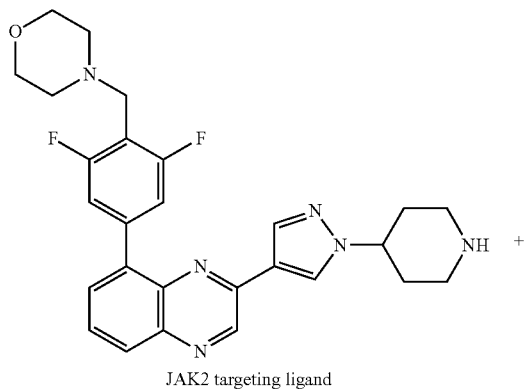

JAK2 targeting ligand

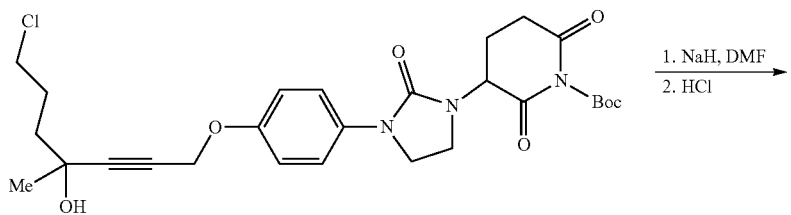

1. NaH, DMF
2. HCl

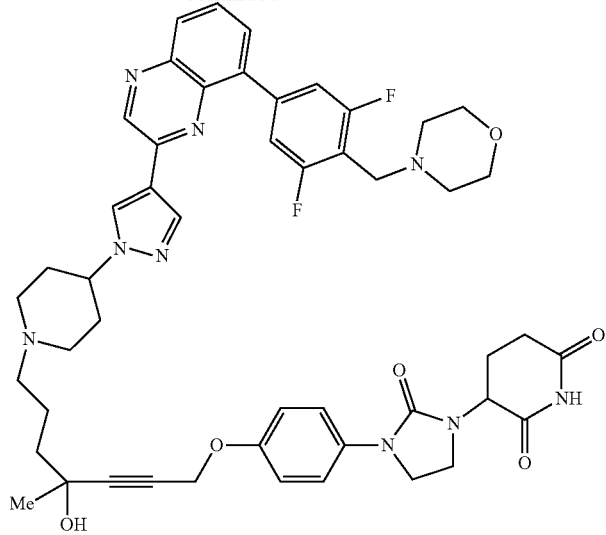

A reaction vessel is charged with 4-(2,6-difluoro-4-(3-(1-(piperidin-4-yl)-1H-pyrazol-4-yl)quinoxalin-5-yl)benzyl)morpholine (1 equiv.) and DMF (0.3 M) then cooled to 0° C. Sodium hydride (60% dispersion in mineral oil, 1.1 equiv.) is added and the reaction is warmed to ambient temperature and mixed for 1 hour. The reaction is cooled to 0° C. then tert-butyl 3-(3-(4-((7-chloro-4-hydroxy-4-methylhept-2-yn-1-yl)oxy)phenyl)-2-oxoimidazolidin-1-yl)-2,6-dioxopiperidine-1-carboxylate (1.1 equiv.) is added and the reaction is mixed at ambient temperature overnight. DMF is removed by rotary evaporation. The crude material is then dissolved in dioxane. HCl (4N in dioxane) is added and the solution stirred at room temperature for 12 hours. The solvent is then evaporated under reduced pressure and the crude product is purified on silica.

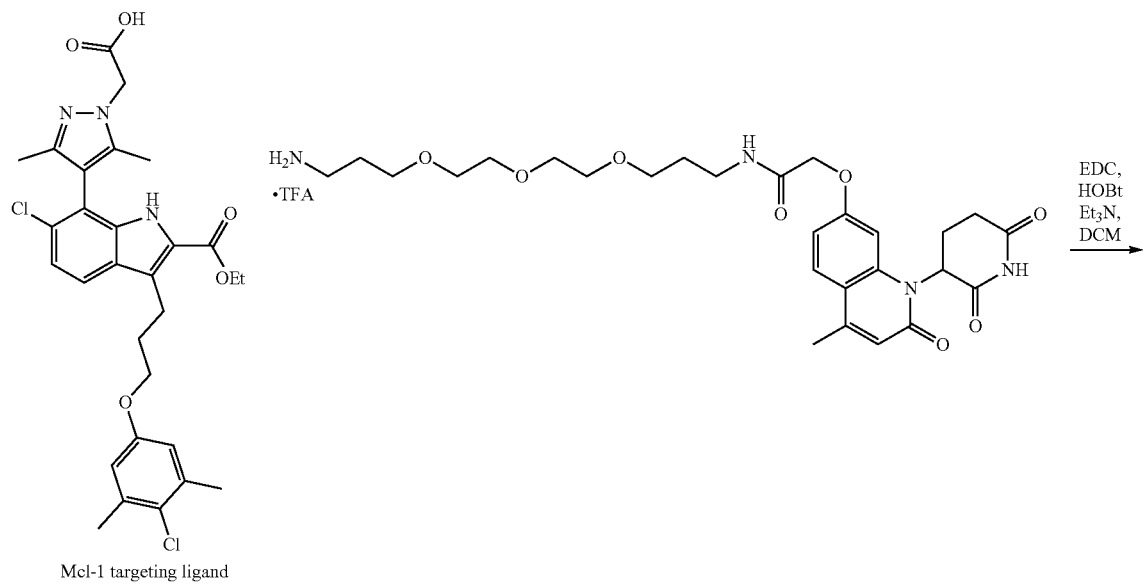

Mcl-1 targeting ligand

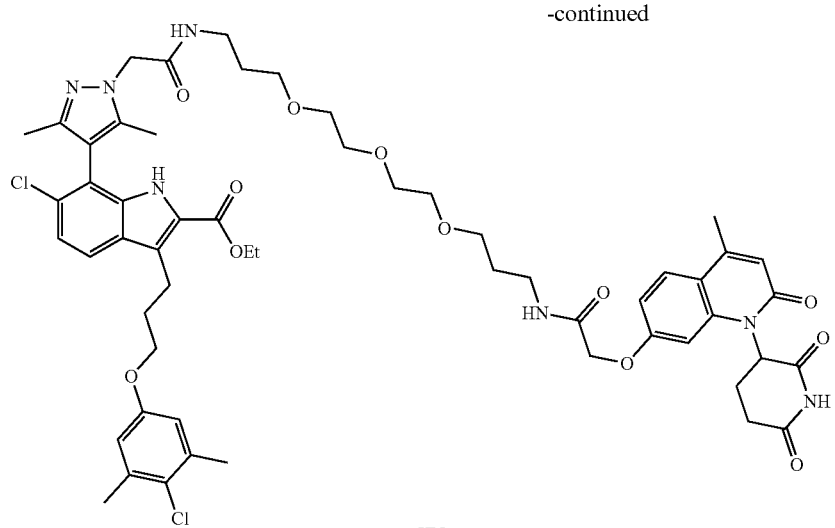

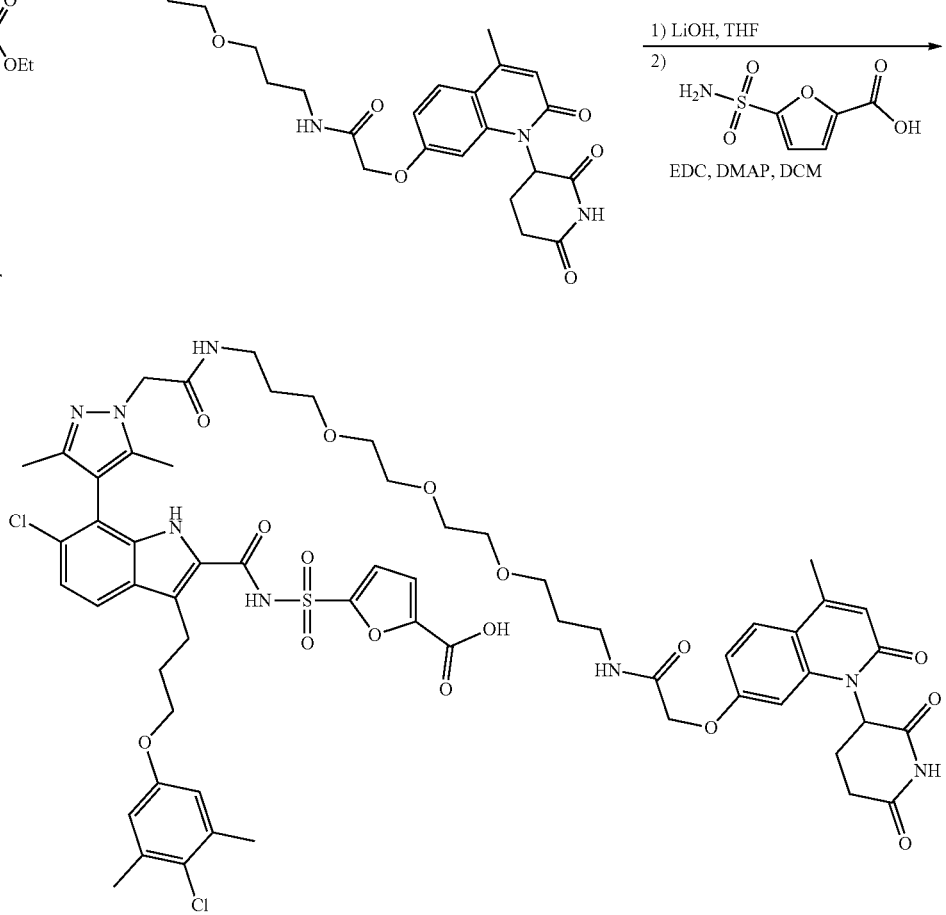

2-(4-(6-chloro-3-(3-(4-chloro-3,5-dimethylphenoxy)propyl)-2-(ethoxycarbonyl)-1H-indol-7-yl)-3,5-dimethyl-1H-pyrazol-1-yl)acetic acid is synthesized according to the procedure reported by N. F. Pelz et al. in *J. Med. Chem.*, 2016, 59, 2054-2066.

Step 1: 2-(4-(6-chloro-3-(3-(4-chloro-3,5-dimethylphenoxy)propyl)-2-(ethoxycarbonyl)-1H-indol-7-yl)-3,5-dimethyl-1H-pyrazol-1-yl)acetic acid (1 equiv.) and trimethylamine are mixed in DCM (0.2M). The reaction mixture is cooled to 0 deg C. and HOBt (1.05 equiv.) and EDC (1.1 equiv.) are added in succession and stirred for 5 minutes. N-(3-(2-(2-(3-aminopropoxy)ethoxy)ethoxy)propyl)-2-((1-(2,6-dioxopiperidin-3-yl)-4-methyl-2-oxo-1,2-dihydroquinolin-7-yl)oxy)acetamide, trifluoroacetic acid salt is added to the reaction mixture, and stirred for 2 hours while warming to room temperature. The volatiles are evaporated under reduced pressure and the compound is purified by preparative HPLC to afford ethyl 6-chloro-3-(3-(4-chloro-3,5-dimethylphenoxy)propyl)-7-(1-(19-((1-(2,6-dioxopiperidin-3-yl)-4-methyl-2-oxo-1,2-dihydroquinolin-7-yl)oxy)-2,18-dioxo-7,10,13-trioxa-3,17-diazanonadecyl)-3,5-dimethyl-1H-pyrazol-4-yl)-1H-indole-2-carboxylate.

Step 2: Ethyl 6-chloro-3-(3-(4-chloro-3,5-dimethylphenoxy)propyl)-7-(1-(19-((1-(2,6-dioxopiperidin-3-yl)-4-methyl-2-oxo-1,2-dihydroquinolin-7-yl)oxy)-2,18-dioxo-7,10,13-trioxa-3,17-diazanonadecyl)-3,5-dimethyl-1H-pyrazol-4-yl)-1H-indole-2-carboxylate is dissolved in THF/MeOH mixture (3/1) and cooled to 0 deg C. An aqueous lithium hydroxide solution (1M, 1.1 equiv.) is added to the reaction mixture. The reaction mixture is stirred for 4 hours while warming to ambient temperature. The mixture is acidified with acetic acid and purified by preparative HPLC to afford 6-chloro-3-(3-(4-chloro-3,5-dimethylphenoxy)propyl)-7-(1-(19-((1-(2,6-dioxopiperidin-3-yl)-4-methyl-2-oxo-1,2-dihydroquinolin-7-yl)oxy)-2,18-dioxo-7,10,13-trioxa-3,17-diazanonadecyl)-3,5-dimethyl-1H-pyrazol-4-yl)-1H-indole-2-carboxylic acid.

Step 3: 6-Chloro-3-(3-(4-chloro-3,5-dimethylphenoxy)propyl)-7-(1-(19-((1-(2,6-dioxopiperidin-3-yl)-4-methyl-2-oxo-1,2-dihydroquinolin-7-yl)oxy)-2,18-dioxo-7,10,13-trioxa-3,17-diazanonadecyl)-3,5-dimethyl-1H-pyrazol-4-yl)-1H-indole-2-carboxylic acid is dissolved in DCM (0.2 M), and DMAP (3.1 equiv.) and EDC (1.05 equiv.) are added and the reaction mixture is stirred for 5 minutes. 5-sulfamoyl-furan-2-carboxylic acid (1.1 equiv.) is added and stirred for 16 hours. The volatiles are evaporated under reduced pressure and the crude mixture is purified by preparative HPLC to afford 5-(N-(6-chloro-3-(3-(4-chloro-3,5-dimethylphenoxy)propyl)-7-(1-(19-((1-(2,6-dioxopiperidin-3-yl)-4-methyl-2-oxo-1,2-dihydroquinolin-7-yl)oxy)-2,18-dioxo-7,10,13-trioxa-3,17-diazanonadecyl)-3,5-dimethyl-1H-pyrazol-4-yl)-1H-indole-2-carbonyl)sulfamoyl)furan-2-carboxylic acid.

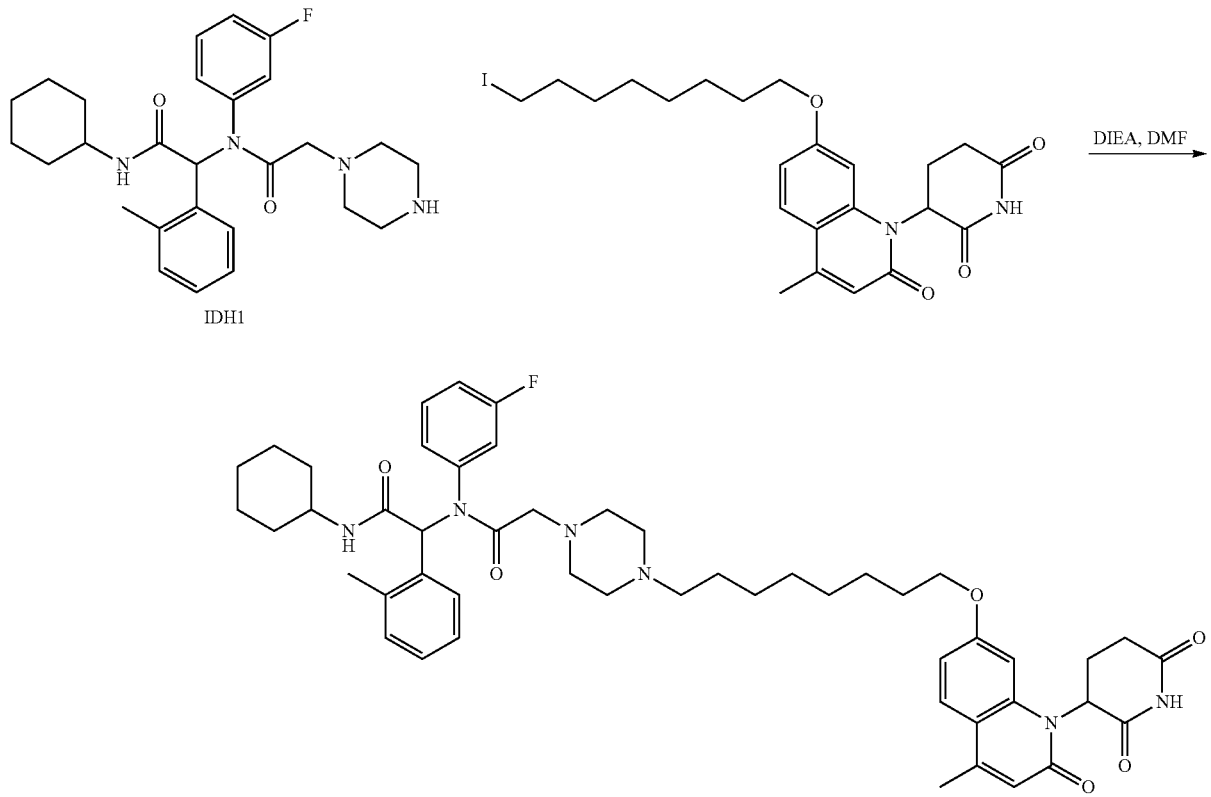

1-(2-((2-(Cyclohexylamino)-2-oxo-1-(o-tolyl)ethyl)(3-fluorophenyl)amino)-2-oxoethyl)-2-methyl-1H-imidazole-4-carboxylic acid is synthesized using the procedures outlined by J. Popovici-Muller, et al. in *ACS Med. Chem. Lett.* 2012, 3, 850.

Step 1: 1-(2-((2-(Cyclohexylamino)-2-oxo-1-(o-tolyl)ethyl)(3-fluorophenyl)amino)-2-oxoethyl)-2-methyl-1H-imidazole-4-carboxylic acid (1 equiv.) and trimethylamine are mixed in DCM (0.2M). The reaction mixture is cooled to 0 deg C. and HOBt (1.05 equiv.) and EDC (1.1 equiv.) are added in succession and stirred for 5 minutes. N-(3-(2-(2-(3-aminopropoxy)ethoxy)ethoxy)propyl)-2-((1-(2,6-dioxopiperidin-3-yl)-4-methyl-2-oxo-1,2-dihydroquinolin-7-yl)oxy)acetamide, trifluoroacetic acid salt, is added to the reaction mixture, and stirred for 2 hours while warming to room temperature. The volatiles are evaporated under reduced pressure and the compound is purified by preparative HPLC to afford 1-(2-((2-(cyclohexylamino)-2-oxo-1-(o-tolyl)ethyl)(3-fluorophenyl)amino)-2-oxoethyl)-N-(1-((1-(2,6-dioxopiperidin-3-yl)-4-methyl-2-oxo-1,2-dihydroquinolin-7-yl)oxy)-2-oxo-7,10,13-trioxa-3-azahexadecan-16-yl)-2-methyl-1H-imidazole-4-carboxamide.

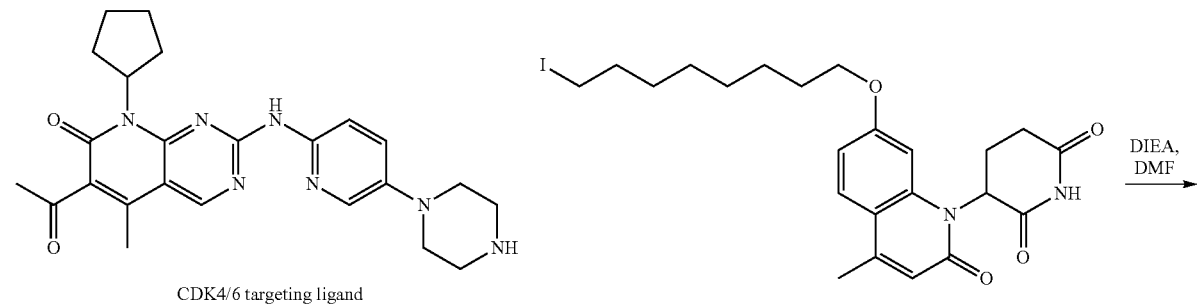

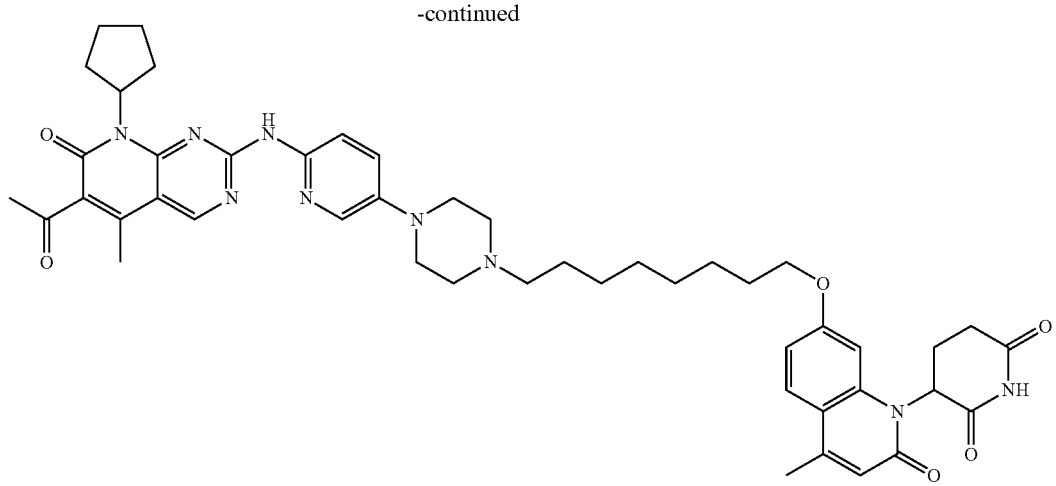

Step 2: 6-Acetyl-8-cyclopentyl-5-methyl-2-((5-(piperazin-1-yl)pyridin-2-yl)amino)pyrido[2,3-d]pyrimidin-7(8H)-one (1.0 equiv.) and 3-(7-((8-iodooctyl)oxy)-4-methyl-2-oxoquinolin-1(2H)-yl)piperidine-2,6-dione (1.0 equiv.) are mixed in DMF and diisopropylethylamine (2.0 equiv.) is added. The reaction mixture is stirred at ambient temperature for 16 hours, and the reaction mixture is purified by preparative HPLC to afford 3-(7-((8-(4-(6-(((6-acetyl-8-cyclopentyl-5-methyl-7-oxo-7,8-dihydropyrido[2,3-d]pyrimidin-2-yl)amino)pyridin-3-yl)piperazin-1-yl)octyl)oxy)-4-methyl-2-oxoquinolin-1(2H)-yl)piperidine-2,6-dione.

(R)-3-(1-(2,6-Dichloro-3-fluorophenyl)ethoxy)-5-(1-(piperidin-4-yl)-1H-pyrazol-4-yl)pyridin-2-amine (1.0 equiv.) and 3-(7-((8-iodooctyl)oxy)-4-methyl-2-oxoquinolin-1(2H)-yl)piperidine-2,6-dione (1.0 equiv.) are mixed in DMF and diisopropylethylamine (2.0 equiv.) is added. The reaction mixture is stirred at ambient temperature for 16 hours, and the reaction mixture is purified by preparative HPLC to afford 3-(7-((8-(4-(4-(6-amino-5-((R)-1-(2,6-dichloro-3-fluorophenyl)ethoxy)pyridin-3-yl)-1H-pyrazol-1-yl)piperidin-1-yl)octyl)oxy)-4-methyl-2-oxoquinolin-1(2H)-yl)piperidine-2,6-dione.

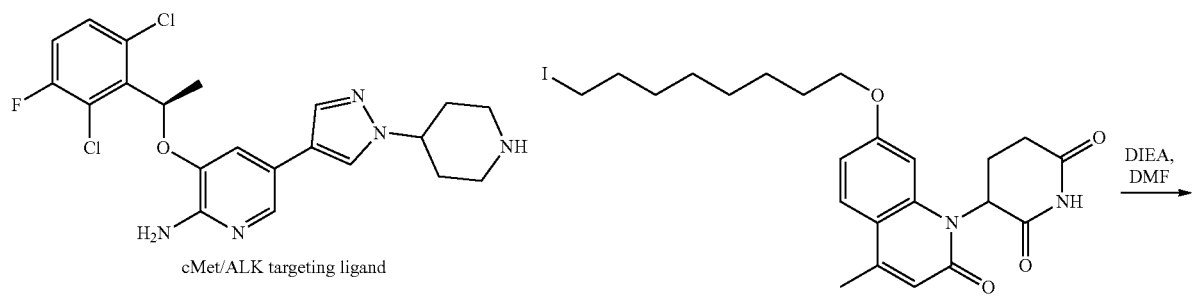

cMet/ALK targeting ligand

DIEA, DMF

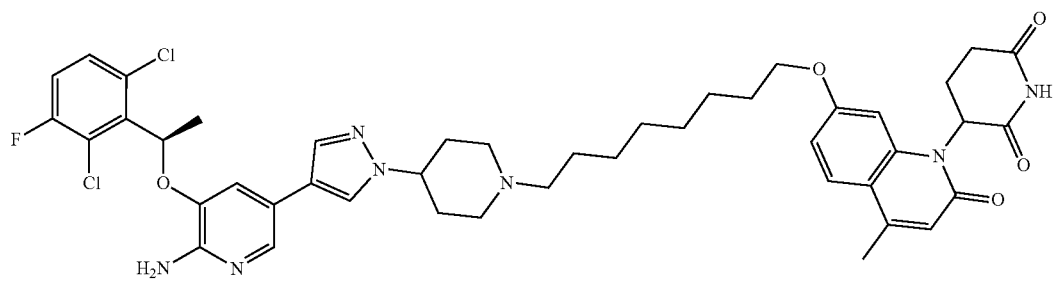

Additional Examples
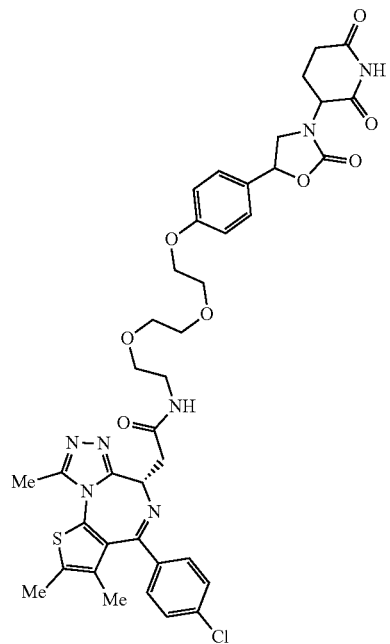
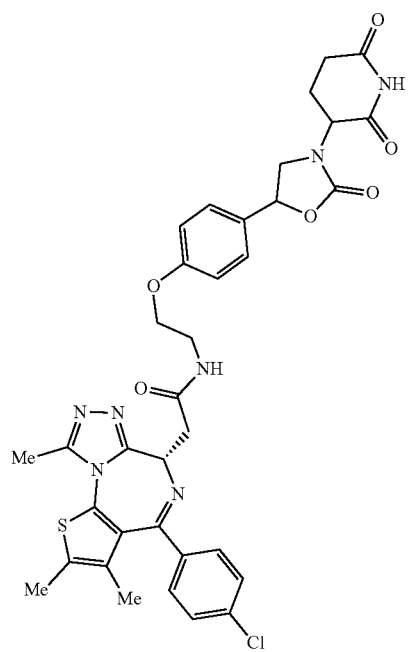

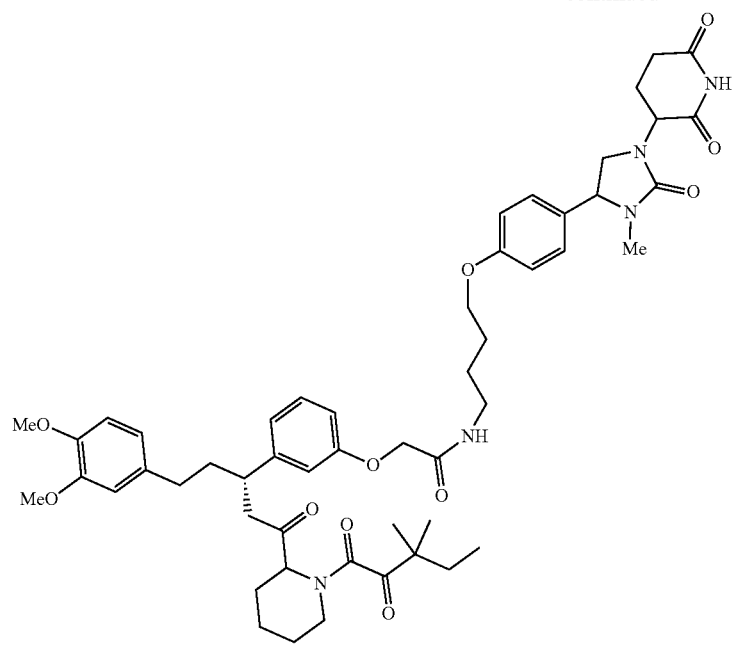
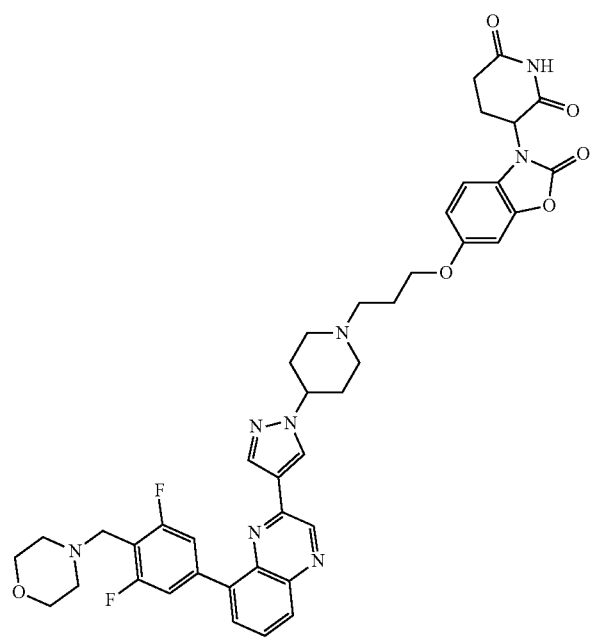

487
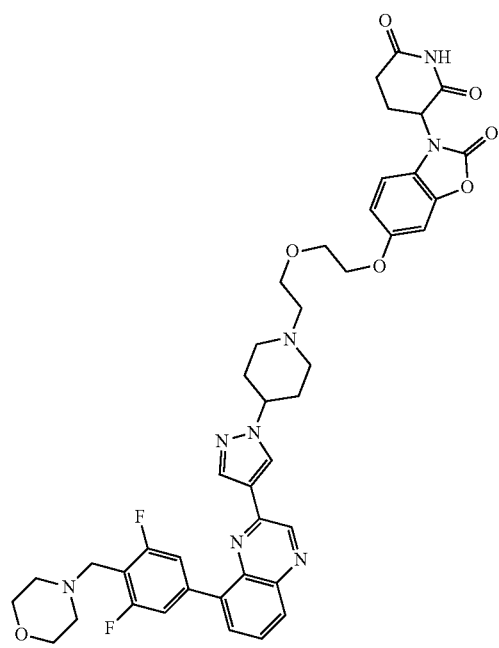
488
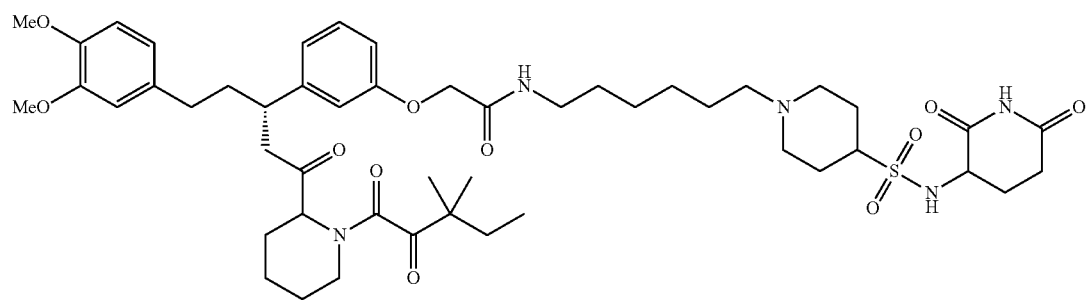
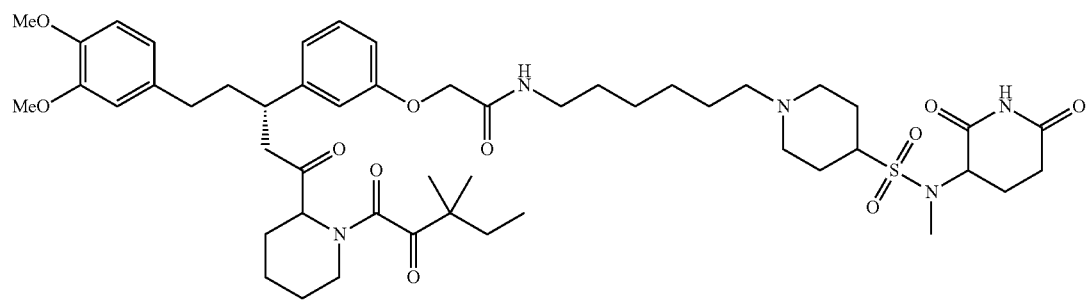
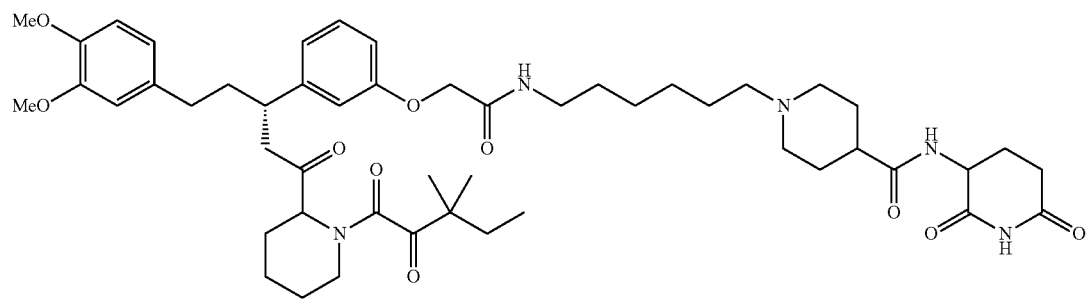

-continued
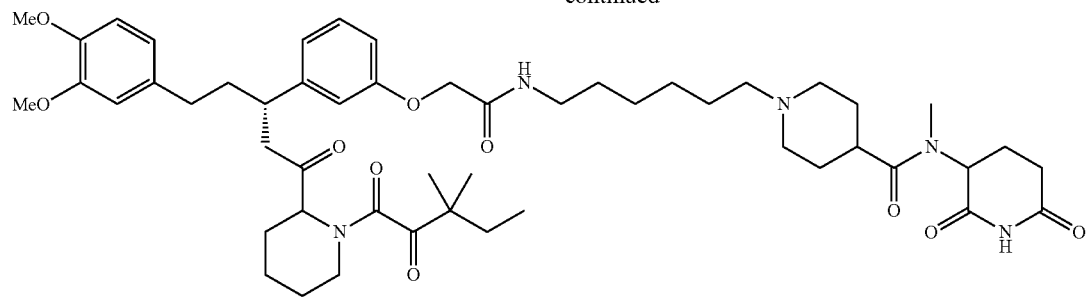
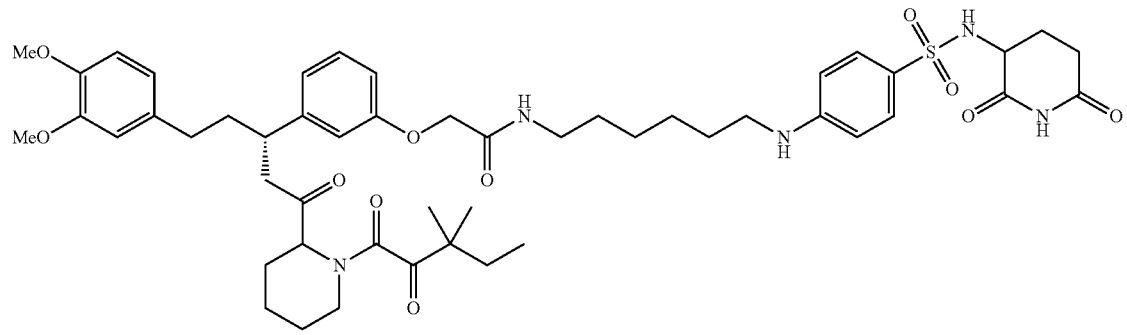
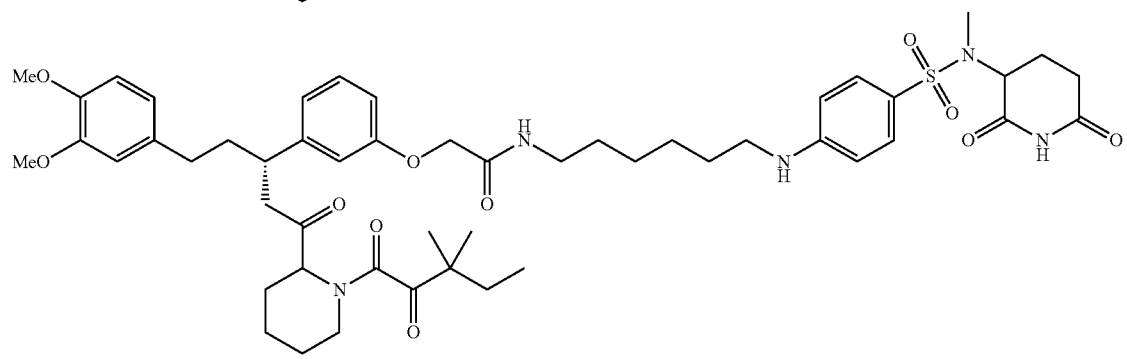
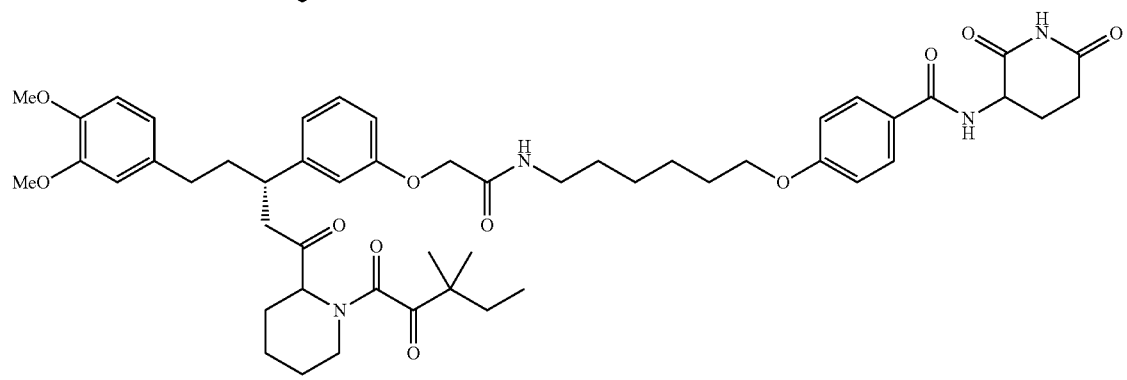
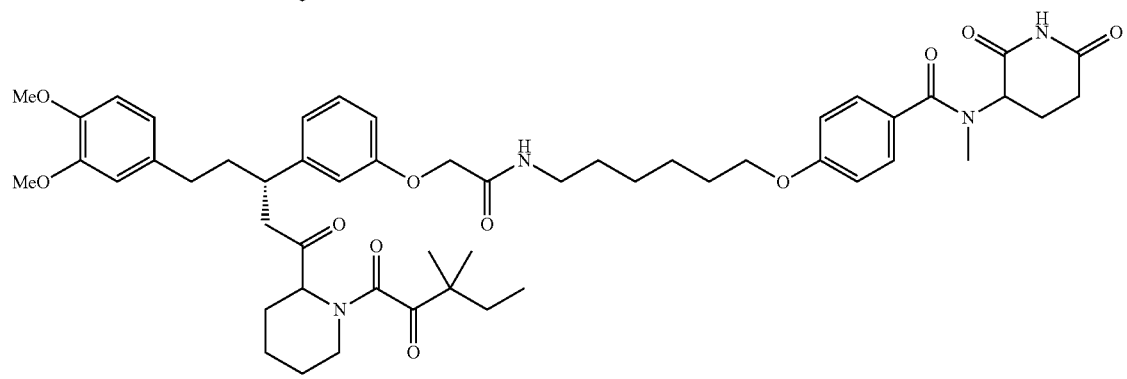

491
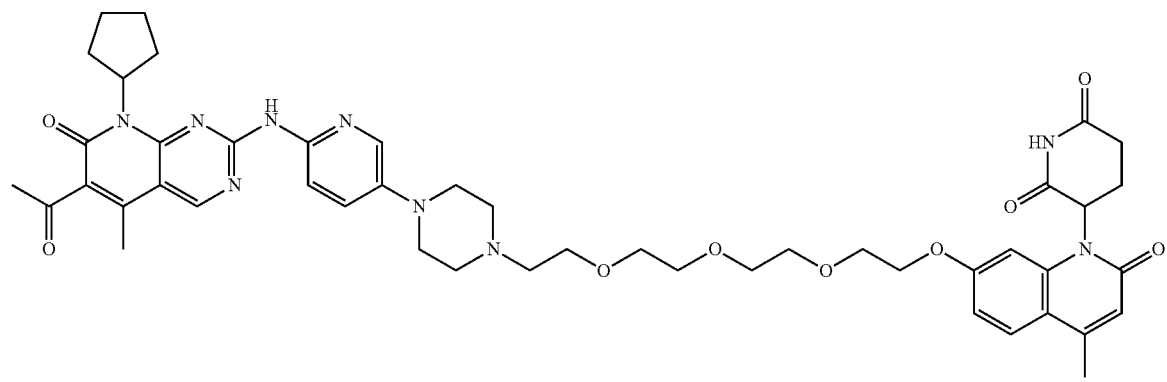
492
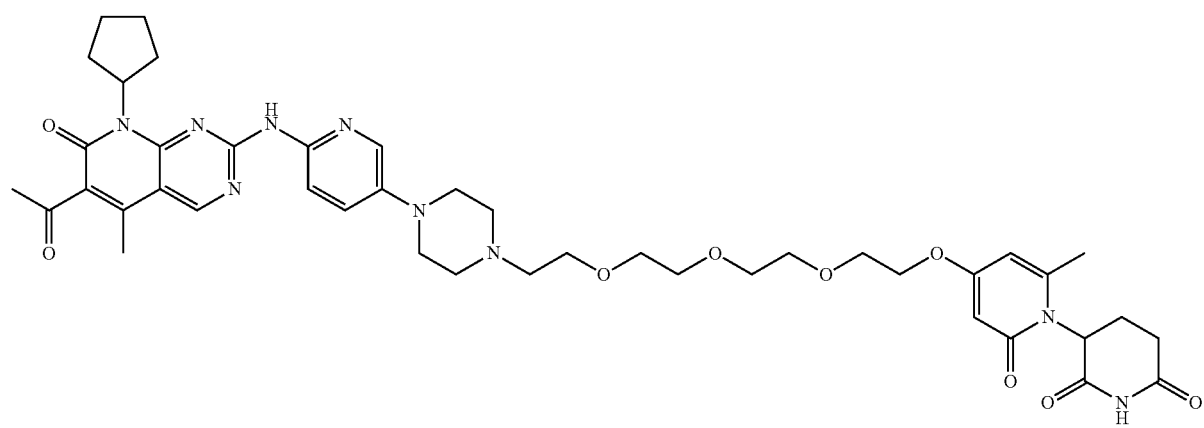
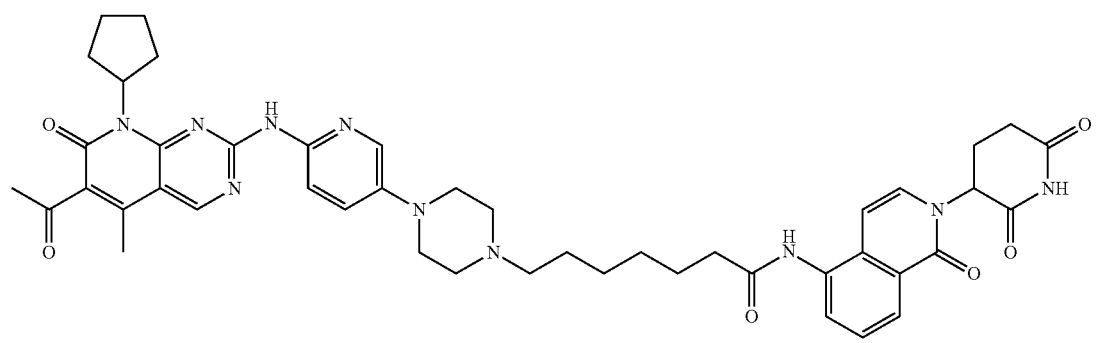

-continued
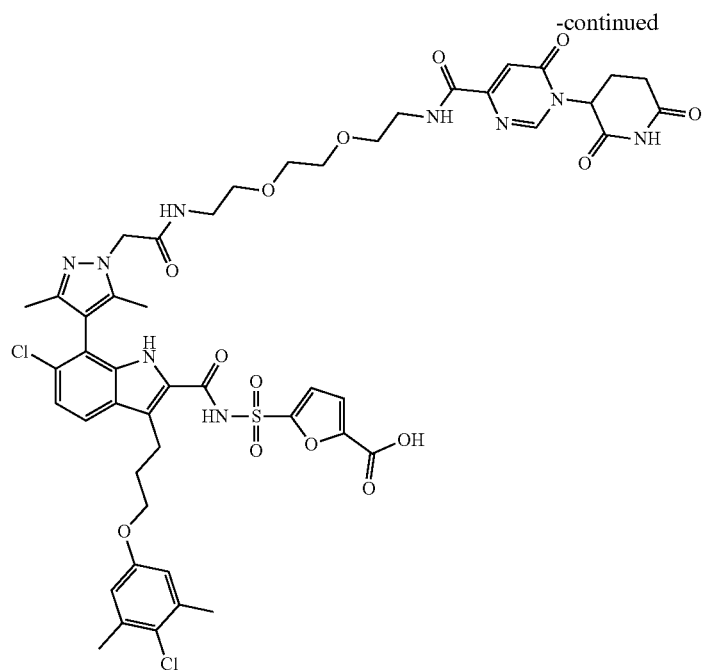
Preparation of Representative Targeting Ligands
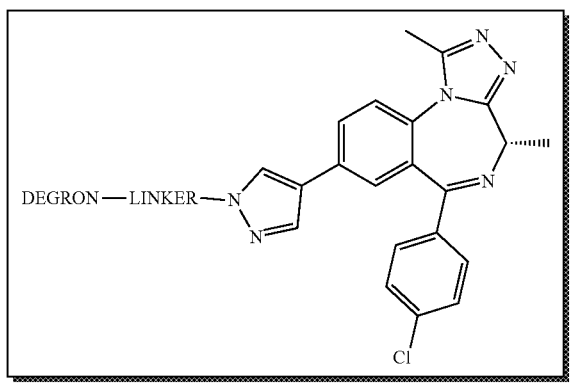
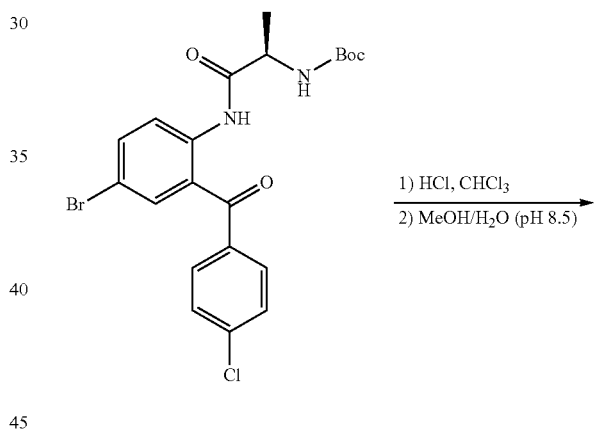
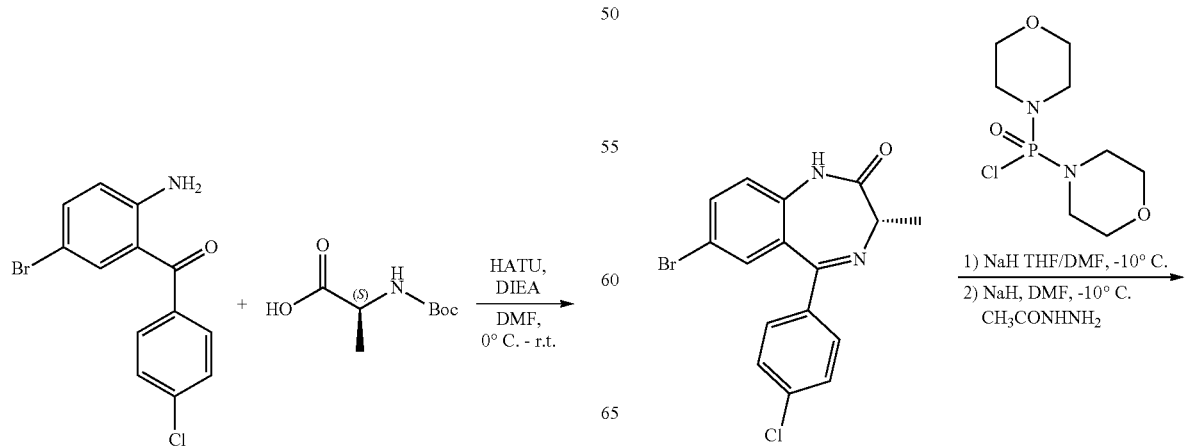

495
-continued

496

Tert-Butyl (R)-(1-((4-bromo-2-(4-chlorobenzoyl)phenyl)amino)-1-oxopropan-2-yl)carbamate

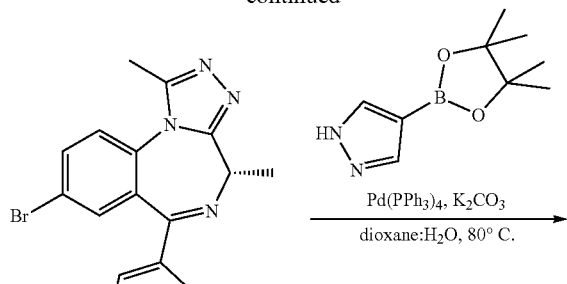

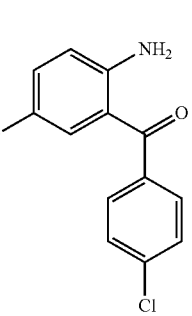

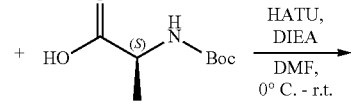

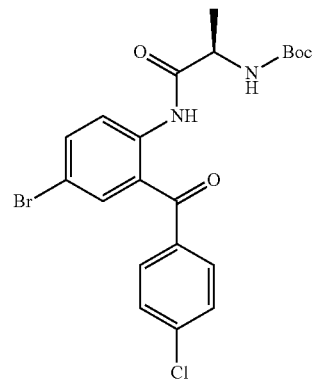

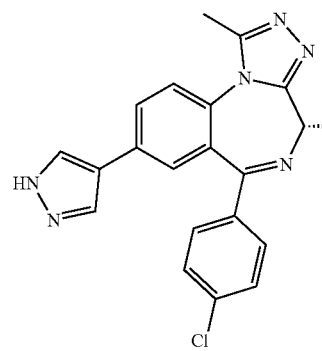

(S)-6-(4-Chlorophenyl)-1,4-dimethyl-8-(1H-pyrazol-4-yl)-4H-benzo[f][1,2,4]triazolo[4,3-a][1,4]diazepine (2-Amino-5-bromophenyl)(4-chlorophenyl)methanone (1.0 equiv.) and Boc-(L)-Ala (1.0 equiv.) is suspended in DMF and cooled to 0° C. DIEA (2.0 equiv.) is added followed by HATU (1.1 equiv.) and the reaction is stirred at reduced temperature for 30 minutes and then warmed to room temperature. When the reaction is judged to be complete it is quenched with aq. ammonium chloride and extracted with ethyl acetate. The combined organic layers are dried over sodium sulfate, concentrated and purified by silica gel chromatography to provide tert-butyl (R)-(1-((4-bromo-2-(4-chlorobenzoyl)phenyl)amino)-1-oxopropan-2-yl)carbamate.

(S)-7-Bromo-5-(4-chlorophenyl)-3-methyl-1,3-dihydro-2H-benzo[e][1,4]diazepin-2-one

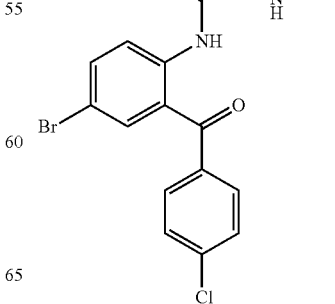

1) HCl, CHCl₃
2) MeOH/H₂O (pH 8.5)

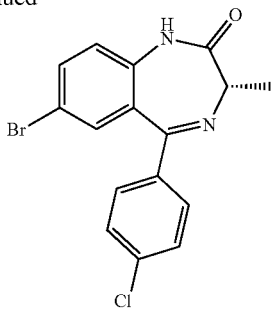

To a stirred solution of boc protected amine in CHCl₃ at r.t., is added hydrogen chloride gas slowly. After 20 minutes the addition is stopped and the reaction is stirred at r.t. until deprotection is complete. The reaction mixture is then washed with saturated bicarbonate solution (2×) and water (2×). The organic layer is concentrated under reduced pressure. The residue is dissolved in 2:1 methanol:water and the pH is adjusted to 8.5 by the addition of 1N aqueous NaOH. The reaction is then stirred at r.t. until the cyclization is complete. MeOH is then removed under reduced pressure and the solution is extracted with DCM (3×). The combined organic layer is dried over sodium sulfate, concentrated and purified by silica gel chromatography to provide (S)-7-bromo-5-(4-chlorophenyl)-3-methyl-1,3-dihydro-2H-benzo[e][1,4]diazepin-2-one (US 2010 0261711).

(S)-8-Bromo-6-(4-chlorophenyl)-1,4-dimethyl-4H-benzo[f][1,2,4]triazolo[4,3-a][1,4]diazepine

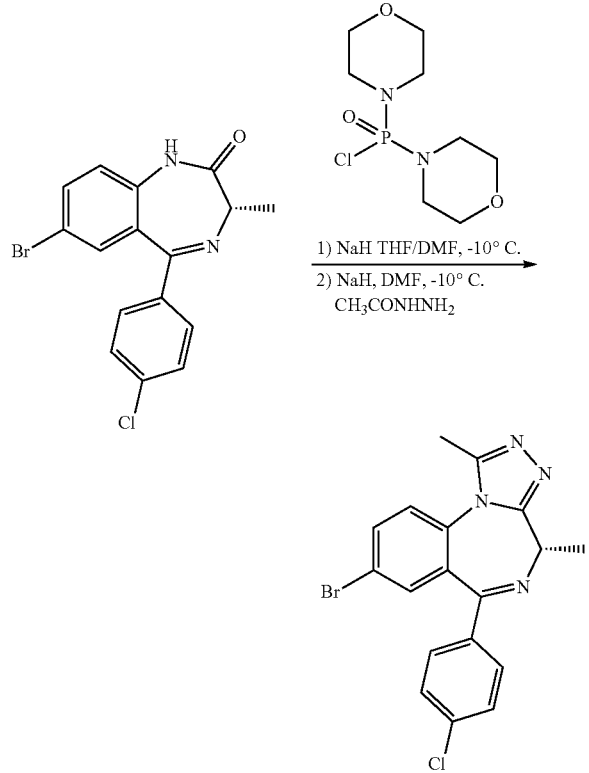

A solution of diazapine (1.0 equiv.) in THF is cooled to −10° C. and NaH (0.85 equiv.) is added in one portion. After an hour at reduced temperature di-4-morphilinylphosphinic chloride (1.07 equiv.) is added at −10° C. and the reaction is allowed to warm to r.t. and stir for 2 hours. To this mixture is added a solution of acetic hydrazide (1.4 equiv.) in n-butanol and stirring is continued for 30 minutes. The solvent is then removed under reduced pressure and the residue dissolved in fresh dry n-butanol before refluxing for the desired time frame. Upon the completion of the reaction the volatiles are removed by rotary evaporation and the residue is partitioned between DCM and brine. The organic layer is dried, concentrated and purified by silica gel chromatography to provide (S)-8-bromo-6-(4-chlorophenyl)-1,4-dimethyl-4H-benzo[f][1,2,4]triazolo[4,3-a][1,4]diazepine (US20100261711).

(S)-6-(4-Chlorophenyl)-1,4-dimethyl-8-(1H-pyrazol-4-yl)-4H-benzo[f][1,2,4]triazolo[4,3-a][1,4]diazepine

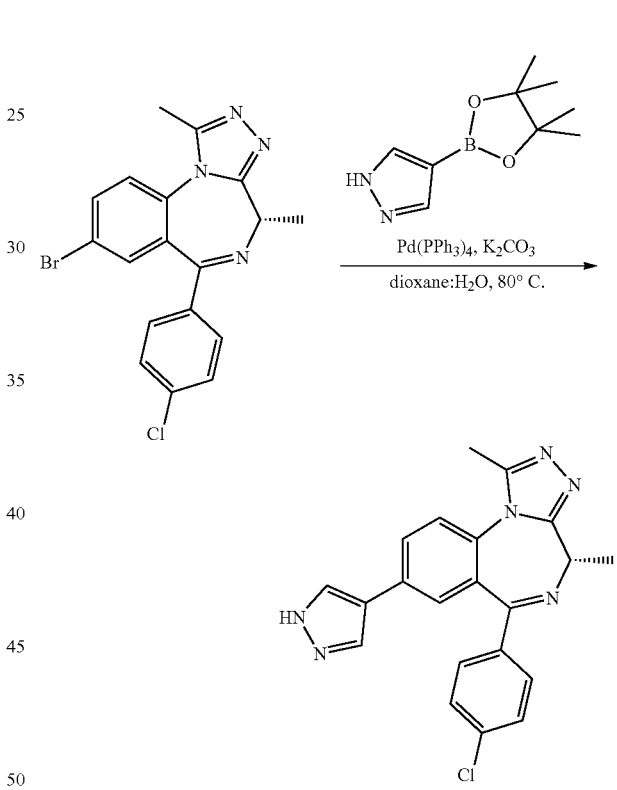

To a vial containing (S)-8-bromo-6-(4-chlorophenyl)-1,4-dimethyl-4H-benzo[f][1,2,4]triazolo[4,3-a][1,4]diazepine (1 equiv.) is added Pd(PPh3)₄ (20 mol %), 4-(4,4,5,5-tetramethyl-1,3,2-dioxaborolan-2-yl)-1H-pyrazole (1.5 equiv.), and potassium carbonate (2.5 equiv.). The vial is then evacuated and purged under N2. To the vial is added dioxane:water (2:1). The contents were once again evacuated and purged under N2 and the reaction mixture was heated to 80° C. until the SM is converted. The mixture is then cooled to room temperature and filtered over a pad of Celite®. The filter pad is rinsed with EtOAc (3×) and the filtrate is concentrate. The crude material is purified by flash chromatography (WO 2015156601).

499
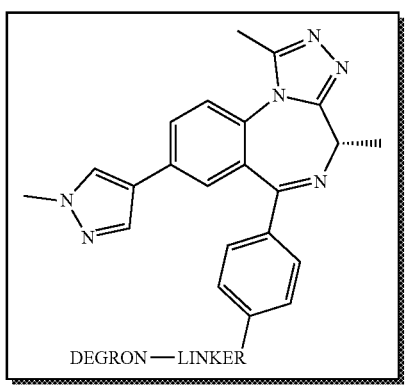
DEGRON—LINKER
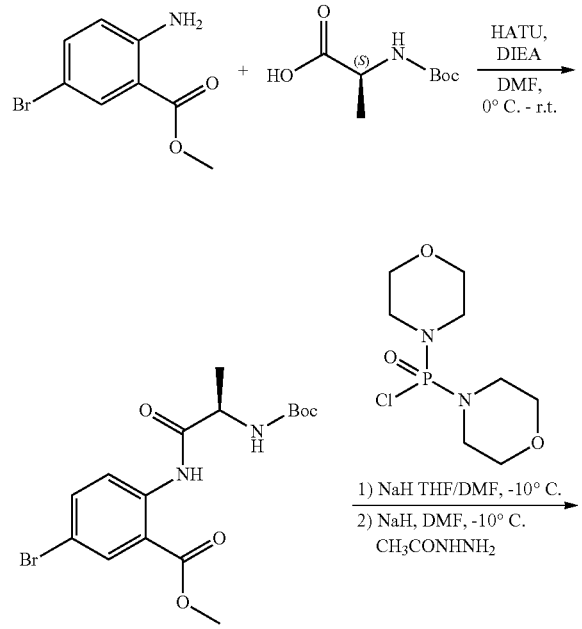
500
-continued
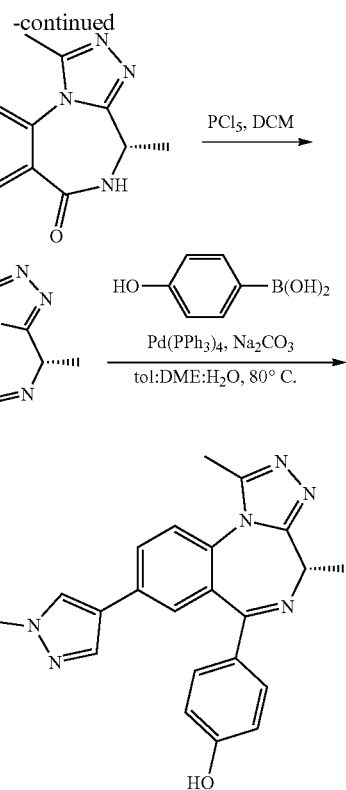
(S)-4-(1,4-dimethyl-8-(1-methyl-1H-pyrazol-4-yl)-4H-benzo[f][1,2,4]triazolo[4,3-a][1,4]diazepin-6-yl)phenol
Methyl (R)-5-bromo-2-(2-((tert-butoxycarbonyl)amino)propanamido)benzoate
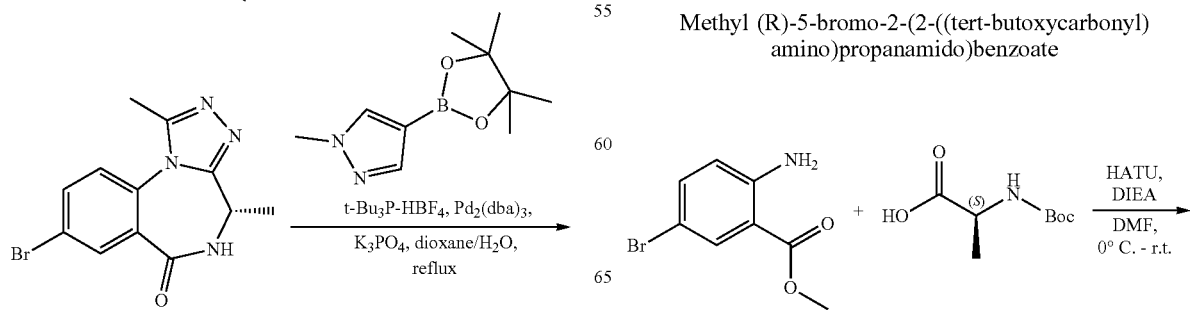

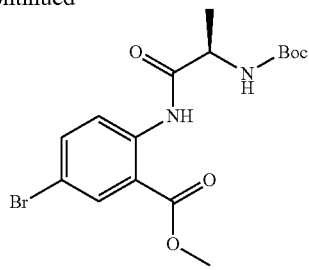

Methyl 2-amino-5-bromobenzoate (1.0 equiv.) and Boc-(L)-Ala (1.0 equiv.) is suspended in DMF and cooled to 0° C. DIEA (2.0 equiv.) is added followed by HATU (1.1 equiv.) and the reaction is stirred at reduced temperature for 30 minutes and then warmed to room temperature. When the reaction is judged to be complete it is quenched with aq. ammonium chloride and extracted with ethyl acetate. The combined organic layers are dried over sodium sulfate, concentrated and purified by silica gel chromatography to provide methyl (R)-5-bromo-2-(2-((tert-butoxycarbonyl)amino)propanamido)benzoate.

Methyl 5-bromo-2-(3-((R)-1-((tert-butoxycarbonyl)amino)ethyl)-5-methyl-4H-1,2,4-triazol-4-yl)benzoate

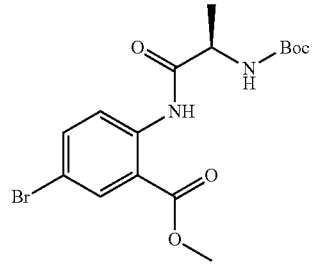

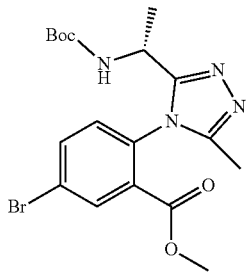

Methyl (R)-5-bromo-2-(2-((tert-butoxycarbonyl)amino)propanamido)benzoate A solution of methyl (R)-5-bromo-2-(2-((tert-butoxycarbonyl)amino)propanamido)benzoate (1.0 equiv.) in THF is cooled to −10° C. and NaH (0.85 equiv.) is added in one portion. After an hour at reduced temperature di-4-morphilinylphosphinic chloride (1.07 equiv.) is added at −10° C. and the reaction is allowed to warm to r.t. and stir for 2 hours. To this mixture is added a solution of acetic hydrazide (1.4 equiv.) in n-butanol and stirring is continued for 30 minutes. The solvent is then removed under reduced pressure and the residue dissolved in fresh dry n-butanol before refluxing for the desired time frame. Upon the completion of the reaction the volatiles are removed by rotary evaporation and the residue is partitioned between DCM and brine. The organic layer is dried, concentrated and purified by silica gel chromatography to provide methyl (R)-5-bromo-2-(2-((tert-butoxycarbonyl)amino)propanamido)benzoate (BMCL 2015, 25, 1842-48).

(S)-8-Bromo-1,4-dimethyl-4,5-dihydro-6H-benzo[f][1,2,4]triazolo[4,3-a][1,4]diazepin-6-one

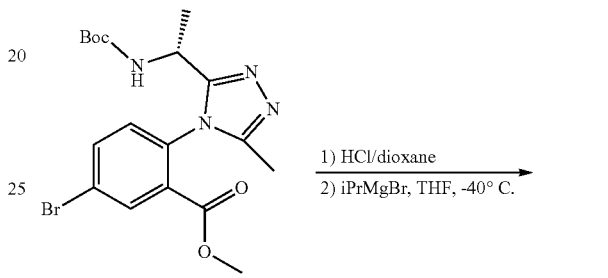

Methyl (R)-5-bromo-2-(2-((tert-butoxycarbonyl)amino)propanamido)benzoate is brought up in DCM and cooled to 0° C. 4M HCl in dioxane is added and the reaction is warmed to r.t. When deprotection is complete the reaction is concentrated and then azeotroped from toluene (2×). The crude amine salt is then dissolved in THF and cooled to −40° C. at which time iPrMgBr solution is added dropwise (2.0 equiv.) and the reaction is stirred at reduced temp until complete conversion (BMCL 2015, 25, 1842-48).

(S)-1,4-Dimethyl-8-(1-methyl-1H-pyrazol-4-yl)-4,5-dihydro-6H-benzo[f][1,2,4]triazolo[4,3-a][1,4]diazepin-6-one

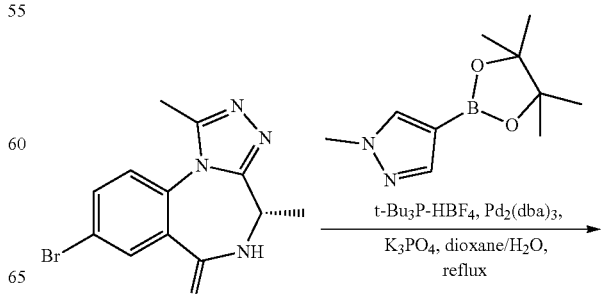

503

-continued

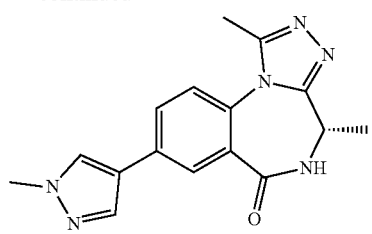

To a vial containing (S)-8-bromo-1,4-dimethyl-4,5-dihydro-6H-benzo[f][1,2,4]triazolo[4,3-a][1,4]diazepin-6-one (1 equiv.) is added Pd2 (dba) 3 (10 mol %), tri-tert-butylphosphonium tetrafluoroborate (20 mol %), 1-methyl-4-(4,4,5,5-tetramethyl-1,3,2-dioxaborolan-2-yl)-1H-pyrazole (1.5 equiv.), and potassium phosphate tribasic, monohydrate (2.5 equiv.). The vial is then evacuated and purged under N2. To the vial is added 20:1 ratio by volume of dioxane:water. The contents were once again evacuated and purged under N2 (g) and the reaction mixture was heated to 100° C. until the SM is converted. The mixture is then cooled to room temperature and filtered over a pad of Celite®. The filter pad is rinsed with EtOAc (3×) and the filtrate is concentrate. The crude material is purified by flash chromatography.

(S)-6-Chloro-1,4-dimethyl-8-(1-methyl-1H-pyrazol-4-yl)-4H-benzo[f][1,2,4]triazolo[4,3-a][1,4]diazepine

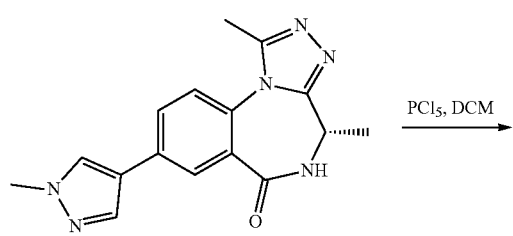

(S)-1,4-dimethyl-8-(1-methyl-1H-pyrazol-4-yl)-4,5-dihydro-6H-benzo[f][1,2,4]triazolo[4,3-a][1,4]diazepin-6-one (1.0 equiv.) is dissolved in DCM and PCl5 (1.7 equiv.) is added in one-portion. After conversion of SM 2M sodium carbonate is added. The biphasic mixture is subsequently extracted with EtOAc (4×). The combined organic layers were dried over sodium sulfate and concentrated to dryness. The resultant residue is purified by flash chromatography.

504

(S)-4-(1,4-Dimethyl-8-(1-methyl-1H-pyrazol-4-yl)-4H-benzo[f][1,2,4]triazolo[4,3-a][1,4]diazepin-6-yl)phenol

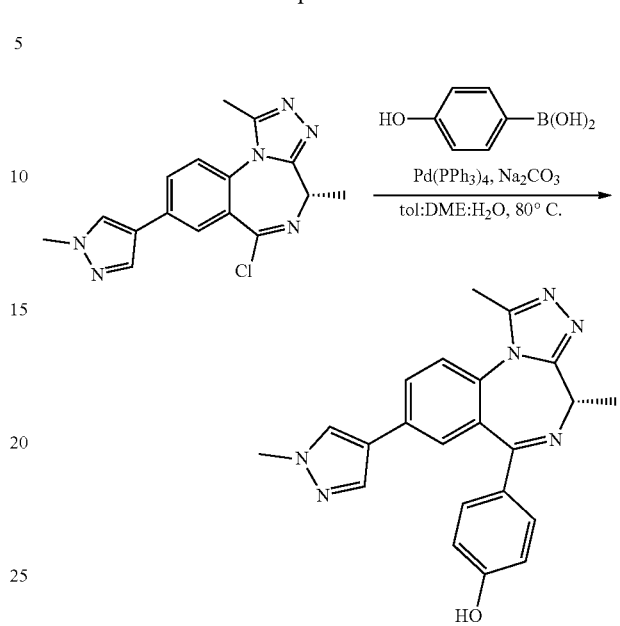

To a vial containing ((S)-6-chloro-1,4-dimethyl-8-(1-methyl-1H-pyrazol-4-yl)-4H-benzo[f][1,2,4]triazolo[4,3-a][1,4]diazepine (1 equiv.) is added Pd(PPh3)4 (20 mol %), 4-hydroxy-Phenyl boronic acid (1.5 equiv.), and sodium carbonate (2.5 equiv.). The vial is then evacuated and purged under N2. To the vial is added tol:DME:water (1:1:5). The contents were once again evacuated and purged under N2 and the reaction mixture was heated to 80° C. until the SM is converted. The mixture is then cooled to room temperature and filtered over a pad of Celite®. The filter pad is rinsed with EtOAc (3×) and the filtrate is concentrate. The crude material is purified by flash chromatography.

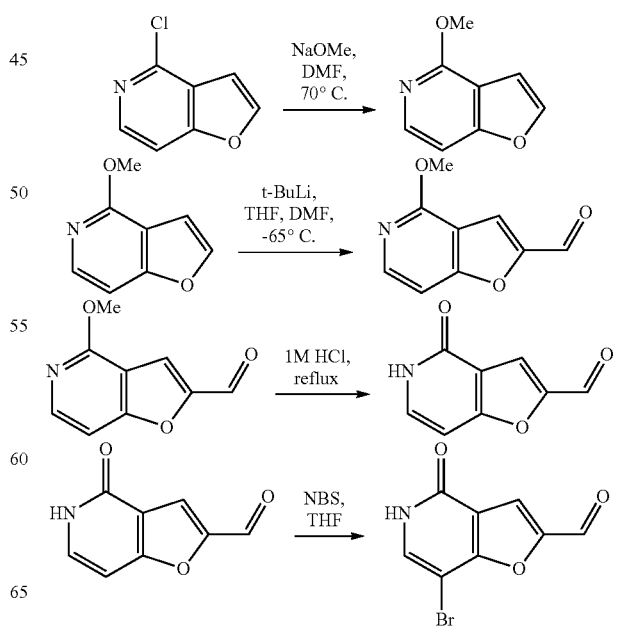

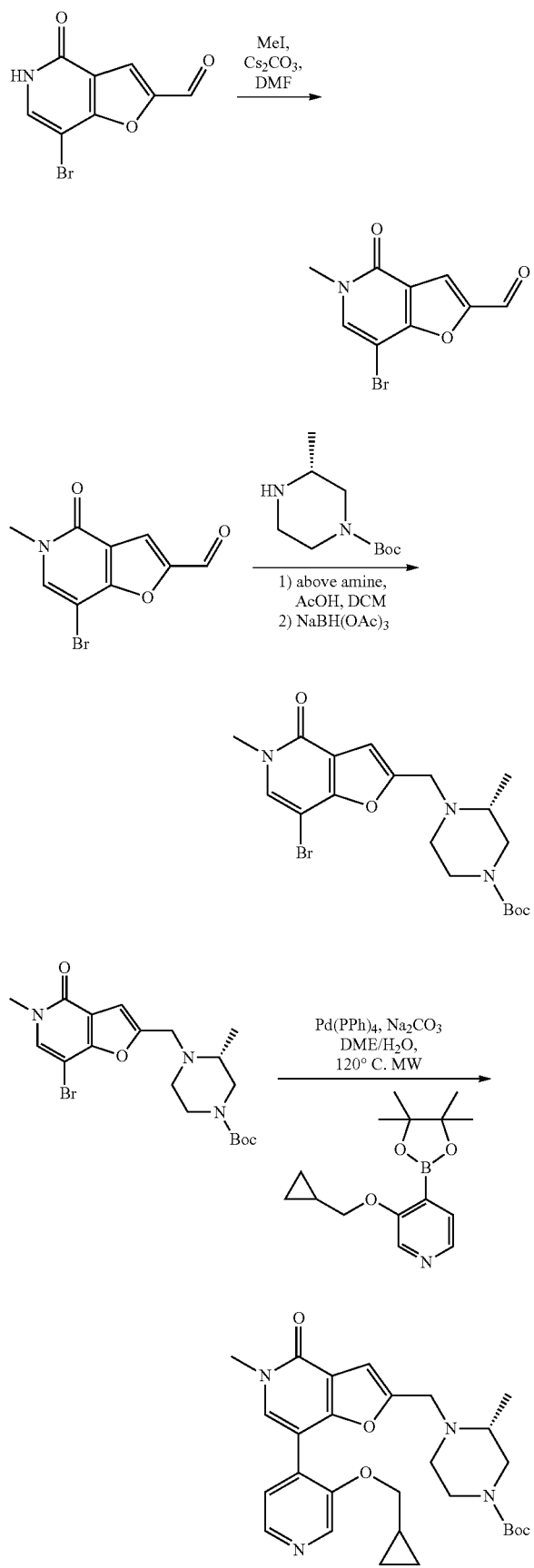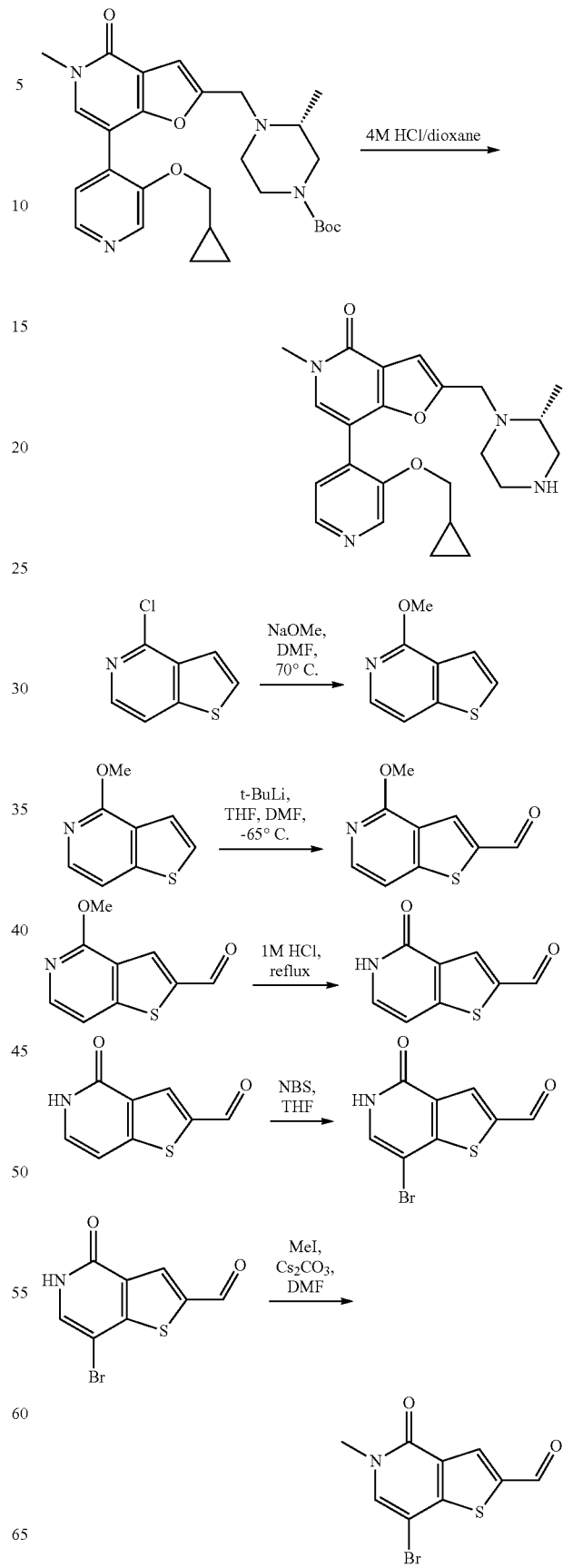

507
-continued
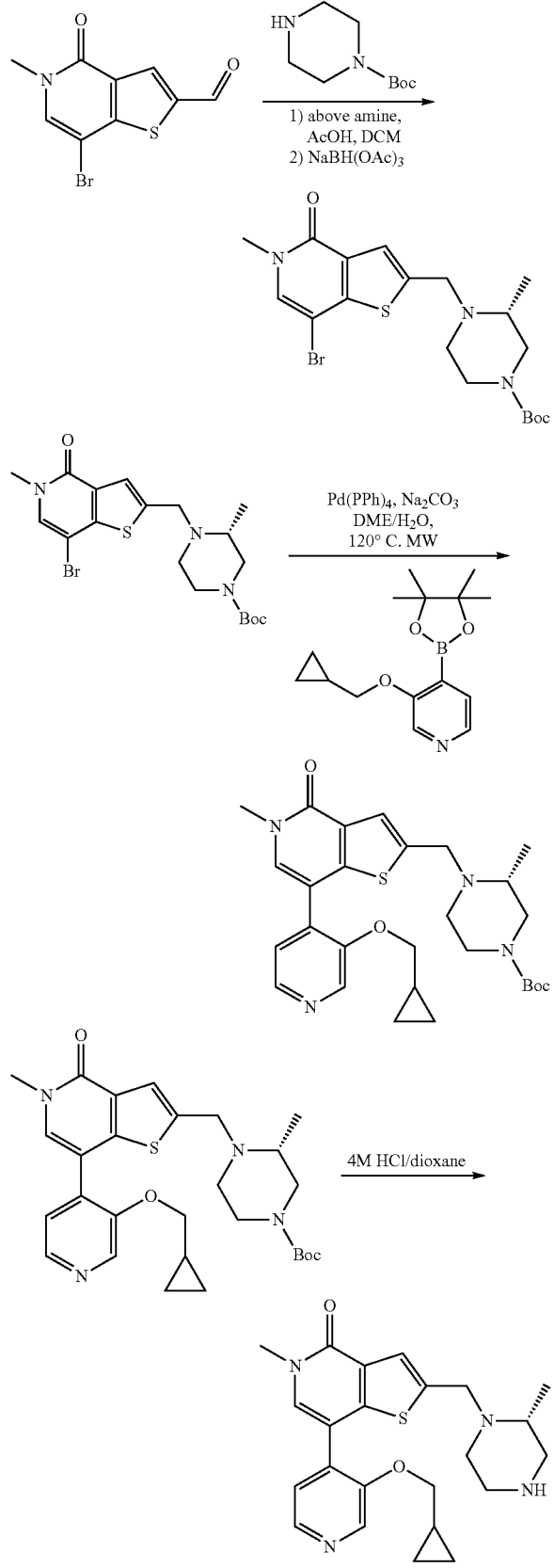
508
Synthesis of Selected Glutarimides
Difluoro
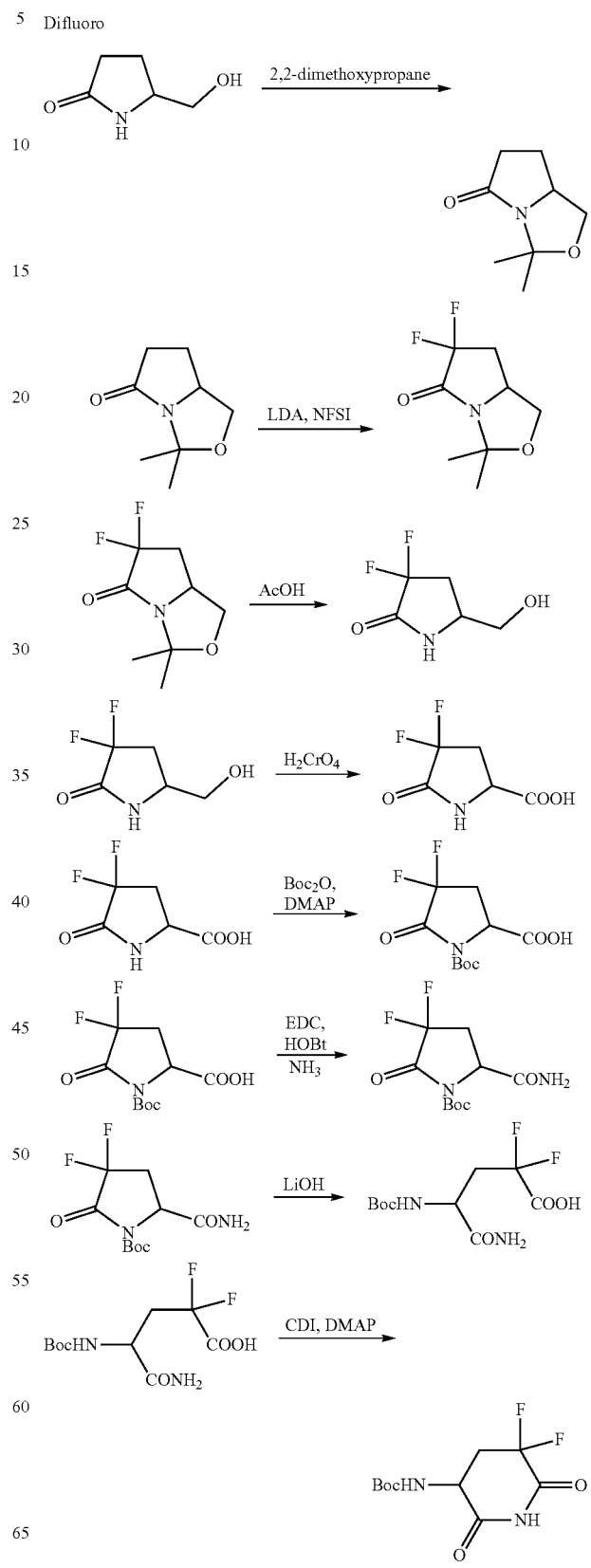

509
-continued
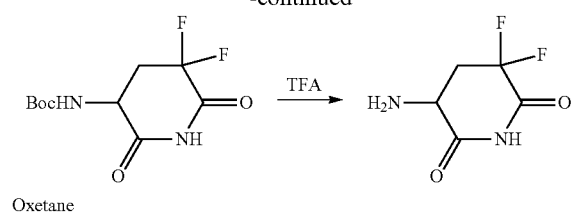
Oxetane
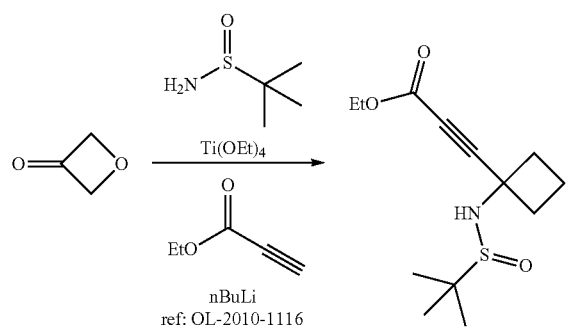
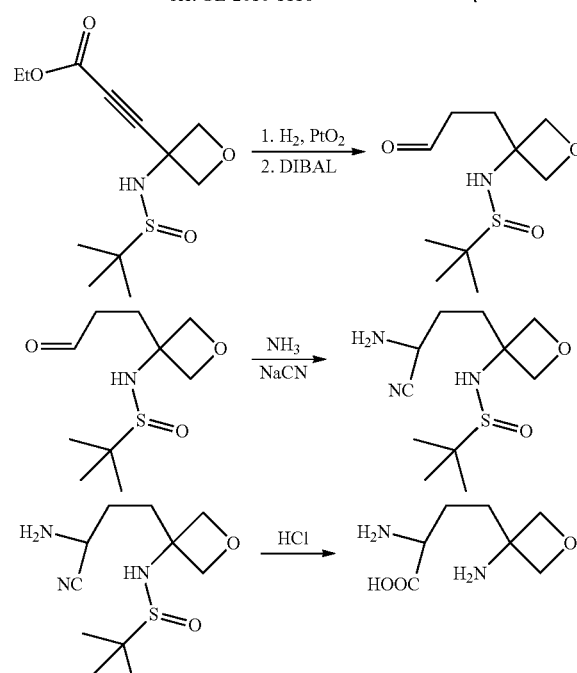
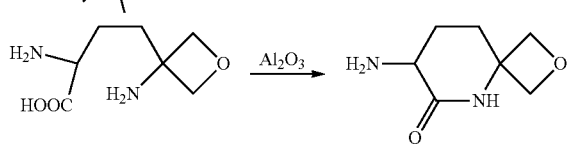
Sulfone
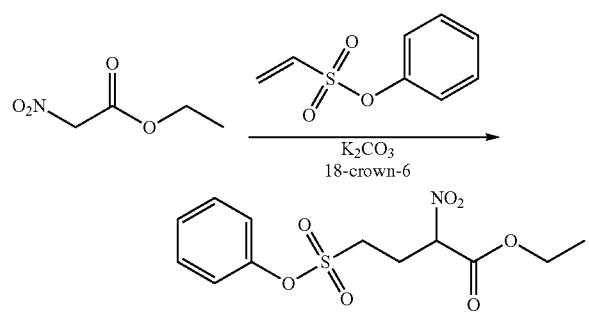
510
-continued
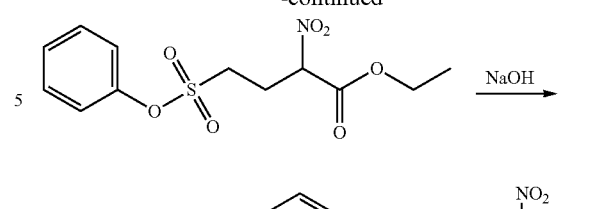
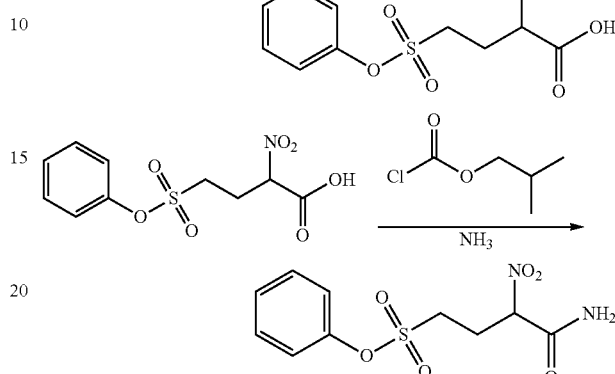
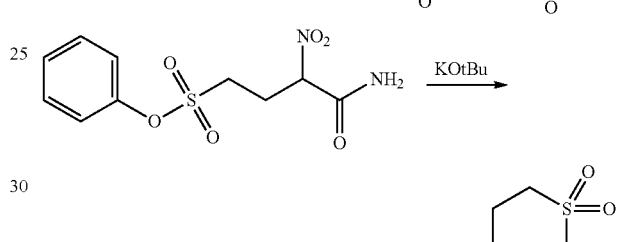
Sulfone 2
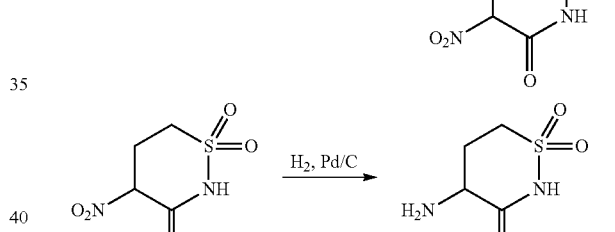
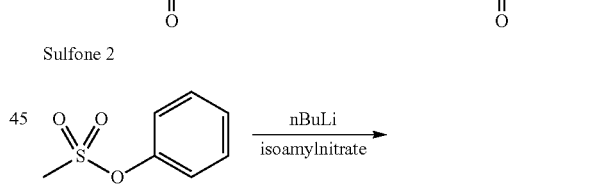
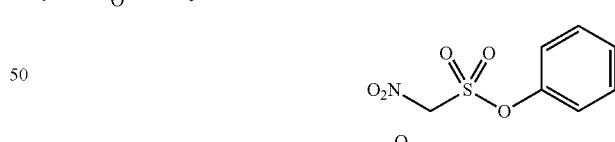
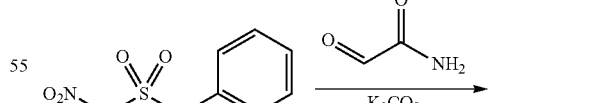
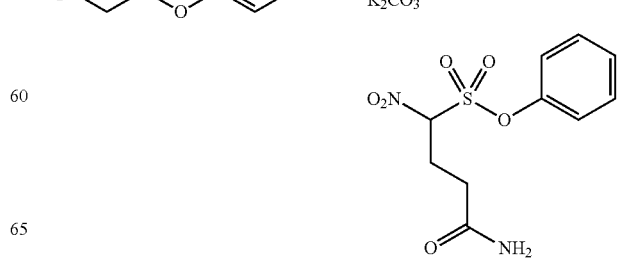

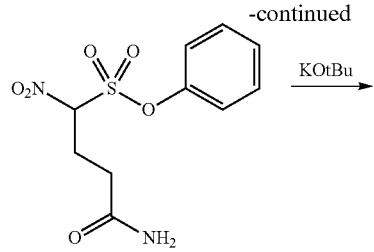
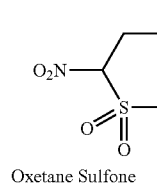
Oxetane Sulfone
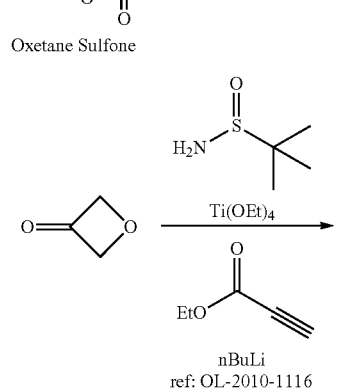
Cyclopropyl
Cyclopropyl 2

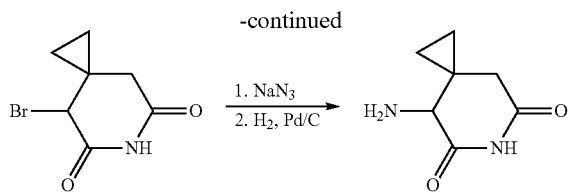

IX. Synthesis of Representative Degrons of Formula V

Illustrative Preparation of 4-Amino-Substituted 2-(2,6-dioxo-piperidin-3-yl)-isoindole-1,3-diones Via SNAr

Example 1

Scheme 1

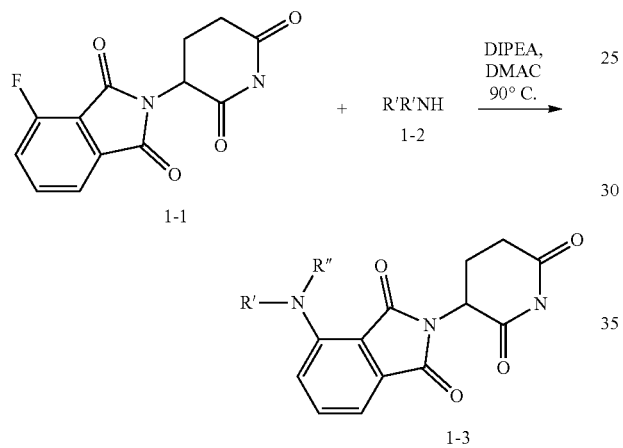

General Procedure:

A mixture of 1-1 (1 mmol) and 1-2 (1 mmol) in Dimethylacetamide was heated at 90° C. in a sealed tube in presence of DIPEA (3 mmol). After complete consumption of 1-1 as evident from TLC, the reaction mixture was cooled, partitioned between ethyl acetate and water, combined organic extracts washed with brine, dried over sodium sulfate and concentrated under reduced pressure. Crude mass was purified by reverse phase preparative HPLC to afford the desired product 1-3 as a solid.

General Methods for Prep HPLC Purification:

Method-1

Preparative HPLC was conducted on Waters auto purification instrument equipped with a —YMC-Actus Triart C18 (100×30 mm, 5μ) column operating at ambient temperature and a flow rate of 30.0 ml/min. Mobile phase: A=20 mM NH$_4$HCO$_3$ in water, B=Acetonitrile; Gradient Profile: Mobile phase initial composition of 80% A and 20% B, then to 65% A and 35% B in 2 minutes, then to 25% A and 75% B in 12 minutes, then to 5% A and 95% B in 13 minutes. This was maintained up to 15 minutes for column washing and the solvent mixture was returned to the initial composition for 16 minutes and maintained until 18 minutes.

Method-2

Preparative HPLC was conducted on Waters auto purification instrument equipped with a —YMC-Actus Triart C18 (250×20 mm, 5μ) column operating at ambient temperature and flow rate of 20.0 ml/min. Mobile phase: A=10 mM NH$_4$OAc in water, B=Acetonitrile; Gradient Profile: Mobile phase initial composition of 70% A and 30% B, then to 45% A and 55% B in 3 minutes, then to 25% A and 75% B in 18 minutes, then to 5% A and 95% B in 19 minutes. This was maintained for up to 21 minutes for column washing and the solvent mixture was returned to the initial composition for 22 minutes and maintained until 25 minutes.

Method-3

Preparative HPLC was conducted on Waters auto purification instrument equipped with a —YMC-Actus Triart C18 (250×20 mm, 5μ) column operating at ambient temperature and flow rate of 20.0 ml/min. Mobile phase: A=0.1% Formic acid in water, B=Acetonitrile; Gradient Profile: Mobile phase initial composition of 80% A and 20% B, then to 70% A and 30% B in 3 minutes, then to 25% A and 75% B in 18 minutes, then to 5% A and 95% B in 19 minutes. This was maintained for up to 21 minutes for column washing and the solvent mixture was returned to the initial composition for 22 minutes and maintained until 25 minutes.

The Following Compounds were Made According the Procedure of Scheme 1 in Example 1:

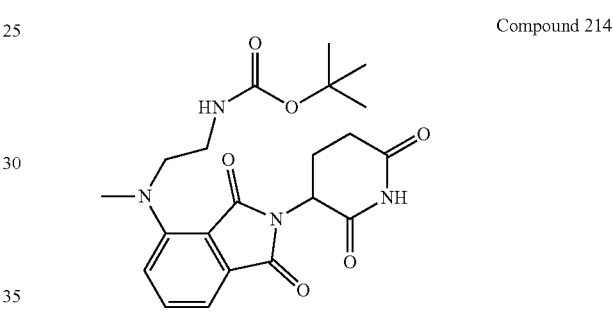

Compound 214

Yield: 20.36%

$^1$H NMR (400 MHz, DMSO-d$_6$) δ 11.06 (s, 1H), 7.60 (t, J=7.9 Hz, 1H), 7.23 (dd, J=14.5, 7.8 Hz, 2H), 6.72 (s, 1H), 5.08 (d, J=8.7 Hz, 1H), 3.58 (brs, 2H), 3.14 (d, J=7.1 Hz, 2H), 3.02 (s, 3H), 2.88-2.85 (m, 1H), 2.60-2.55 (m, 2H), 2.02-1.96 (m, 1H), 1.28 (s, 9H); LCMS: ES+ 431.32.

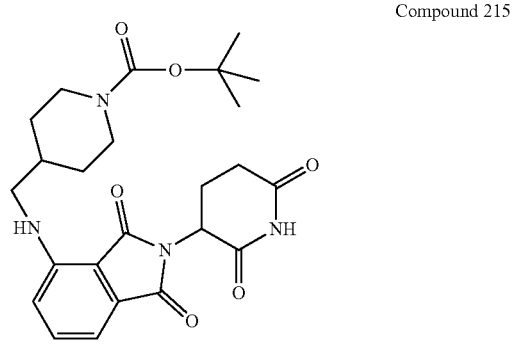 [SMILES: CC(C)(C)OC(=O)N1CCC(CNc2cccc3c2C(=O)N(C2CCC(=O)NC2=O)C3=O)CC1]

Compound 215

Yield: 17.03%

$^1$H NMR (400 MHz, DMSO-d6) δ 11.09 (s, 1H), 7.57 (t, J=7.9 Hz, 1H), 7.15 (d, J=8.6 Hz, 1H), 7.02 (d, J=7.0 Hz, 1H), 6.65-6.61 (m, 1H), 5.05 (dd, J=12.8, 5.4 Hz, 1H), 3.94 (d, J=12.3 Hz, 2H), 3.22 (t, J=6.6 Hz, 2H), 2.91-2.84 (m, 1H), 2.80-2.50 (m, 4H), 2.03-2.00 (m, 1H), 1.76 (brs, 1H), 1.69-1.64 (m, 2H), 1.39 (s, 9H), 1.10-1.05 (m, 2H); LC MS: ES+ 469.4.

Compound 216

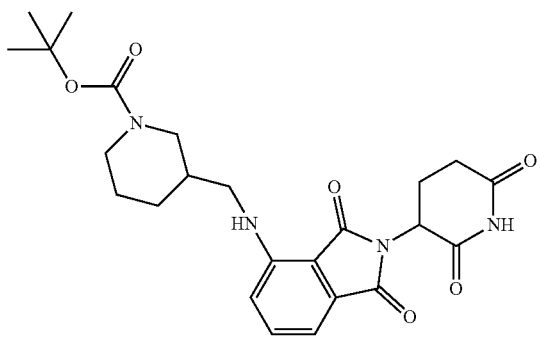

Yield: 9.8%

¹H NMR (400 MHz, DMSO-d6): δ 11.09 (s, 1H), 7.58 (t, J=7.8 Hz, 1H), 7.13 (d, J=8.5 Hz, 1H), 7.03 (d, J=7.0 Hz, 1H), 6.66 (s, 1H), 5.07-5.04 (m, 1H), 3.85 (brs, 1H), 3.71-3.69 (m, 2H), 3.21 (s, 2H), 2.91-2.76 (m, 2H), 2.61-2.50 (m, 2H), 2.02 (brs, 1H), 1.80-1.60 (m, 3H), 1.32-1.23 (m, 11H); LC MS: ES+ 471.42.

Compound 217

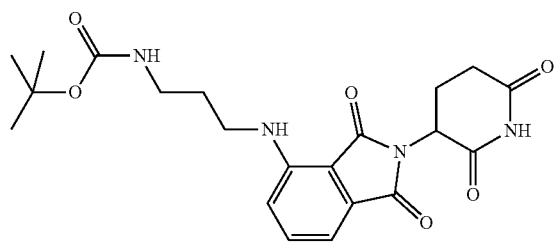

Yield: 15%

¹H NMR (400 MHz, DMSO-d₆): δ 11.09 (s, 1H), 7.57 (t, J=7.81 Hz, 1H), 7.08 (d, J=8.6 Hz, 1H), 7.01 (d, J=7.0 Hz, 1H), 6.92 (brs, 1H), 6.65 (brs, 1H), 5.05 (dd, J=12.9, 5.4 Hz, 1H), 3.29-3.20 (m, 2H), 3.02-2.97 (m, 2H), 2.89-2.83 (m, 1H), 2.63-2.52 (m, 2H), 2.03-7-2.01 (m, 1H), 1.69-1.62 (m, 2H), 1.38 (s, 9H); LC MS: ES– 429.4.

Compound 218

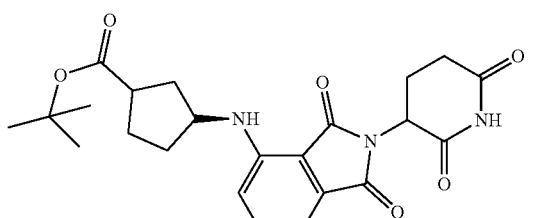

Yield: 17.7%

¹H NMR (400 MHz, DMSO-d₆) δ 11.09 (s, 1H), 7.62 (t, J=7.8 Hz, 1H), 7.22 (d, J=8.6 Hz, 1H), 7.10 (d, J=7.1 Hz, 1H), 6.37 (d, J=7.3 Hz, 1H), 5.06 (dd, J=12.7, 5.4 Hz, 1H), 4.31 (brs, 1H), 3.64 (brs, 1H), 3.39-3.35 (m, 2H), 3.17 (dd, J=10.9, 4.9 Hz, 1H), 2.89-2.83 (m, 1H), 2.59-2.50 (m, 2H), 2.21 (brs, 1H), 2.10-1.98 (m, 1H), 1.93-1.89 (m, 1H), 1.39 (s, 9H); LC MS: ES+ 441.4.

Compound 219

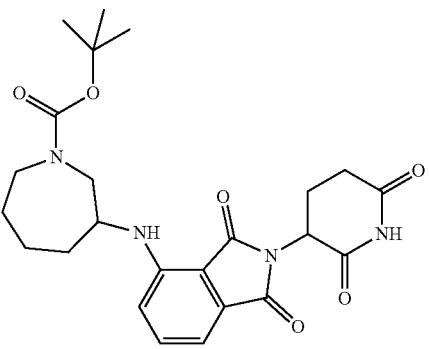

Yield: 1.8%

¹H NMR (400 MHz, DMSO-d₆, 100° C.) δ 10.69 (brs, 1H), 7.59 (t, J=7.6 Hz, 1H), 7.20 (d, J=8.16 Hz, 1H), 7.05 (d, J=7.08 Hz, 1H), 6.36 (d, J=7.8 Hz, 1H), 5.02-4.98 (m, 1H), 3.85-3.31 (m, 5H), 2.87-2.82 (m, 1H), 2.64-2.49 (m, 2H), 2.05-1.91 (m, 2H), 1.77-1.46 (m, 5H), 1.41 (s, 9H); LC MS: ES+ 471.2.

Compound 220

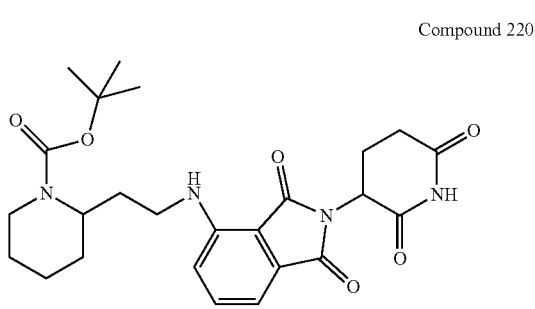 [SMILES: CC(C)(C)OC(=O)N1CCCCC1CCNc1cccc2c1C(=O)N(C1CCC(=O)NC1=O)C2=O]

Yield: 11%

¹H NMR (400 MHz, DMSO-d₆) δ 11.08 (s, 1H), 7.59 (t, J=7.8 Hz, 1H), 7.03 (t, J=7.9 Hz, 2H), 6.63 (brs, 1H), 5.05 (dd, J=12.9, 5.4 Hz, 1H), 4.24 (brs, 1H), 3.85 (d, J=13.4 Hz, 1H), 3.29-2.93 (m, 2H), 2.93-2.80 (m, 2H), 2.64-2.51 (m, 2H), 2.07-1.88 (m, 2H), 1.72-1.66 (m, 1H), 1.61-1.48 (m, 5H), 1.33 (s, 9H), 1.32-1.24 m, 1H); LC MS: ES– 483.5.

Compound 221

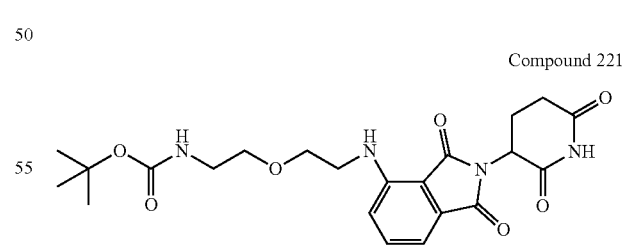

Yield: 24.8%

¹H NMR (400 MHz, DMSO-d₆) δ 11.09 (s, 1H), 7.58 (t, J=7.9 Hz, 1H), 7.15 (d, J=8.6 Hz, 1H), 7.04 (d, J=7.1 Hz, 1H), 6.76 (s, 1H), 6.61 (s, 1H), 5.06 (dd, J=12.8, 5.3 Hz, 1H), 3.58 (s, 2H), 3.49-3.38 (m, 4H), 3.08 (d, J=6.2 Hz, 2H), 2.86-281 (m, 1H), 2.59-2.49 (m, 2H), 2-011.97 (m, 1H), 1.36 (s, 9H); LC MS: ES+ 461.3.

Compound 222

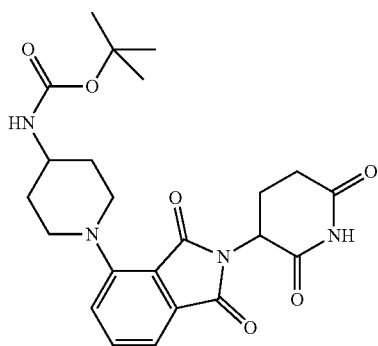

Yield: 33%
¹H NMR (400 MHz, DMSO-d6) δ 11.08 (s, 1H), 7.68 (t, J=7.8 Hz, 1H), 7.33-7.31 (m, 2H), 6.92 (d, J=7.8 Hz, 1H), 5.09 (dd, J=12.72 Hz, 5.16 Hz, 1H), 3.65-3.62 (m, 2H), 3.38 (brs, 1H), 2.95-2.84 (m, 3H), 2.63-2.52 (m, 2H), 2.06-1.96 (m, 1H), 1.85-1.79 (m, 2H), 1.64-1.56 (m, 2H), 1.40 (s, 9H); LC MS: ES+ 457.34.

Compound 223

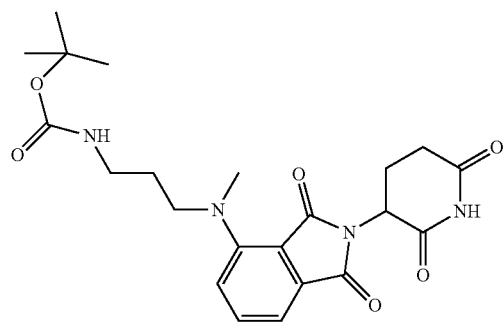

Yield: 25%
¹H NMR (400 MHz, DMSO-d6) δ 11.07 (s, 1H), 7.61 (t, J=7.78 Hz, 1H), 7.26 (d, J=8.6 Hz, 1H), 7.21 (d, J=6.9 Hz, 1H), 6.81 (s, 1H), 5.08 (dd, J=12.8, 5.4 Hz, 1H), 3.44 (t, J=7.2 Hz, 2H), 2.95-2.81 (m, 3H), 2.63-2.52 (m, 2H), 2.10-1.98 (m, 1H), 1.74-1.67 (m, 2H), 1.35 (s, 9H); LC MS: ES+ 445.32.

Compound 224

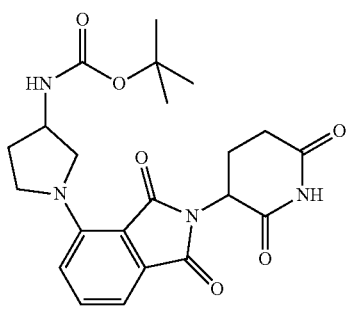

Yield: 25%
¹H NMR (400 MHz, DMSO-d6) δ 11.05 (s, 1H), 7.56 (t, J=7.8 Hz, 1H), 7.21 (brs, 1H), 7.11 (d, J=6.8 Hz, 1H), 7.08 (d, J=8.4 Hz, 1H), 5.11-5.02 (m, 1H), 4.09 (brs, 1H), 3.76 (brs, 1H), 3.63 (brs, 1H), 3.54 (brs, 1H), 3.38 (brs, 1H), 2.88-2.83 (m, 1H), 2.59-2.50 (m, 2H), 2.07-1.90 (m, 3H), 1.38 (s, 9H); LC MS: ES+ 443.2.

Compound 225

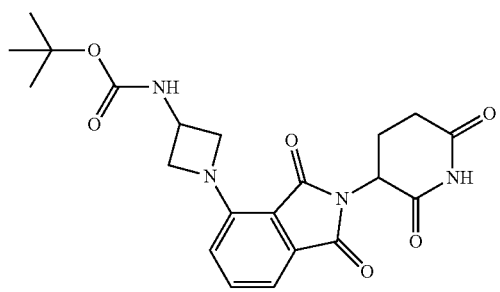

Yield: 26%
¹H NMR (400 MHz, DMSO-d6) δ 11.07 (s, 1H), 7.59-7.52 (m, 2H), 7.13 (d, J=7.0 Hz, 1H), 6.79 (d, J=8.5 Hz, 1H), 5.08-5.03 (m, 1H), 4.43-4.36 (m, 3H), 3.95 (brs, 2H), 2.90-2.83 (m, 1H), 2.59-2.50 (m, 2H), 2.00 (m, 1H), 1.39 (s, 9H); LC MS: ES+ 429.25.

Compound 226

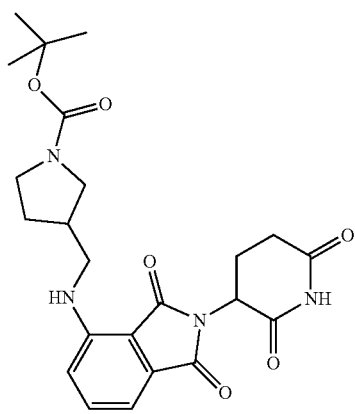

Yield: 12%
¹H NMR (400 MHz, DMSO-d6) δ 11.10 (s, 1H), 7.58 (t, J=7.7 Hz, 1H), 7.16 (d, J=8.6 Hz, 1H), 7.04 (d, J=7.1 Hz, 1H), 6.70 (brs, 1H), 5.07-5.03 (m, 1H), 3.32 (s, 3H), 3.21-3.18 (m, 1H), 3.02-2.98 (m, 1H), 2.89-2.84 (m, 1H), 2.60-2.53 (m, 1H), 2.07-2.01 (m, 1H), 1.96-1.90 (m, 1H), 1.64-1.59 (m, 1H), 1.39 (s, 9H); LC MS: ES+ 457.31.

Compound 227

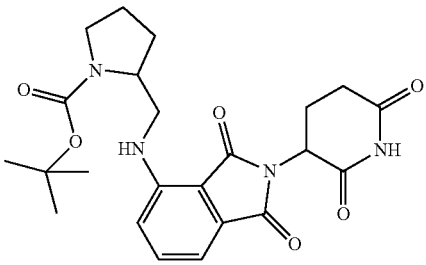

Yield: 14%

¹H NMR (400 MHz, DMSO-d6) δ 11.09 (s, 1H), 7.63-7.52 (m, 1H), 7.32-7.20 (m, 1H), 7.03 (d, J=7.0 Hz, 1H), 6.86 (s, 1H), 5.10-5.02 (m, 1H), 3.92 (brs, 1H), 3.43 (brs, 1H), 3.24 (s, 2H), 2.91-2.85 (m, 1H), 2.66-2.56 (m, 1H), 2.07-2.03 (m, 1H), 1.90-1.77 (m, 4H), 1.41 (s, 9H); LC MS: ES+457.37.

Compound 228

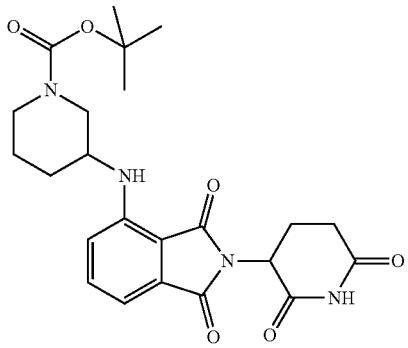

Compound 228

Yield: 12%

¹H NMR (400 MHz, DMSO-d6) δ 11.09 (s, 1H), 7.63 (t, J=7.8 Hz, 1H), 7.17 (d, J=8.5 Hz, 1H), 7.09 (d, J=7.1 Hz, 1H), 6.36 (s, 1H), 5.05 (dd, J=13.1, 5.2 Hz, 1H), 3.70 (s, 1H), 3.59-3.49 (m, 2H), 2.88-2.84 (m, 1H), 2.60-2.45 (m, 2H), 2.00-192 (m, 2H), 1.61-1.23 (m, 12H); LC MS: ES-455.4.

Compound 229

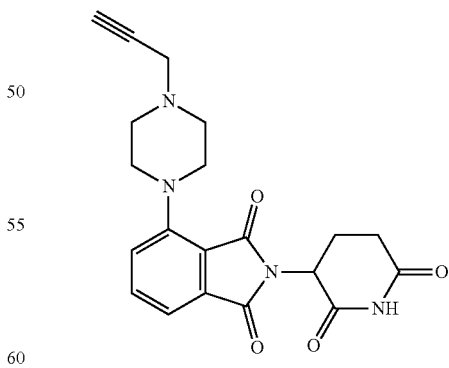

1H NMR (500 MHz, DMSO-d6): δ 11.11 (s, 1H), 7.65 (t, J=8.0 Hz, 1H), 7.16 (d, J=9.0 Hz, 2H), 7.11 (d, J=7.0 Hz, 1H), 6.94 (t, J=6.0 Hz, 1H), 5.07 (dd, J=5.5, 7.0 Hz, 1H), 4.17 (d, J=3.5 Hz, 2H), 2.90-2.86 (m, 1H), 2.61-2.53 (m, 2H), 2.05-2.03 (m, 1H). LC/MS (ES+): m/z 312.1 [M+H]⁺.

Compound 230

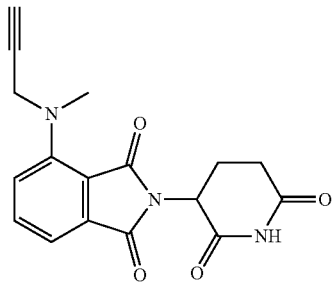

¹H NMR (400 MHz, DMSO-d₆) δ 11.08 (s, 1H), 7.75-7.69 (m, 1H), 7.37 (d, J=7.8 Hz, 2H), 5.10 (dd, J=12.9, 5.4 Hz, 1H), 4.32 (d, J=2.3 Hz, 2H), 3.23-3.20 (m, 1H), 3.01 (s, 3H), 2.88 (ddd, J=17.3, 13.9, 5.3 Hz, 1H), 2.64-2.59 (m, 1H), 2.58-2.52 (m, 1H), 2.10-1.99 (m, 1H).

Compound 231

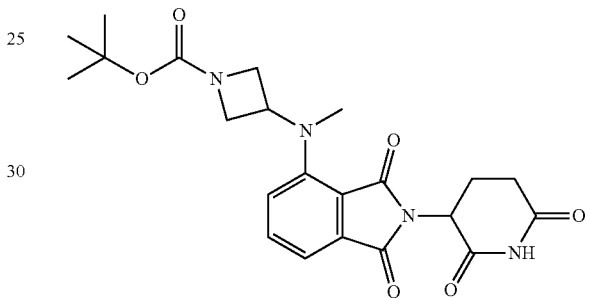

¹H NMR (400 MHz, DMSO-d₆) δ 11.09 (s, 1H), 7.59 (dd, J=8.5, 7.1 Hz, 1H), 7.12 (d, J=7.1 Hz, 1H), 6.94 (d, J=8.5 Hz, 1H), 6.87 (d, J=6.6 Hz, 1H), 5.06 (dd, J=12.7, 5.4 Hz, 1H), 4.44 (q, J=6.4 Hz, 1H), 4.26-4.16 (m, 2H), 3.89-3.73 (m, 2H), 2.99 (s, 3H), 2.88 (ddd, J=16.8, 13.7, 5.3 Hz, 1H), 2.73-2.52 (m, 2H), 2.14-1.93 (m, 1H), 1.38 (s, 8H).

LC/MS (ES−): m/z 443.3 [M+H]⁺.

Compound 232

Yield: 45.5%. ¹H NMR (400 MHz, DMSO-d₆) δ 11.07 (s, 1H), 7.74 (t, J=7.8 Hz, 1H), 7.42 (dd, J=17.3, 7.8 Hz, 2H), 5.09 (dd, J=12.7, 5.4 Hz, 1H), 4.33-3.96 (m, 2H), 3.96-3.59 (m, 2H), 3.58-3.03 (m, 4H), 2.94-2.78 (m, 1H), 2.69-2.51 (m, 2H), 2.08-1.92 (m, 2H). LCMS Rt=0.92 min. m/z[M+H]=381.7.

Compound 233

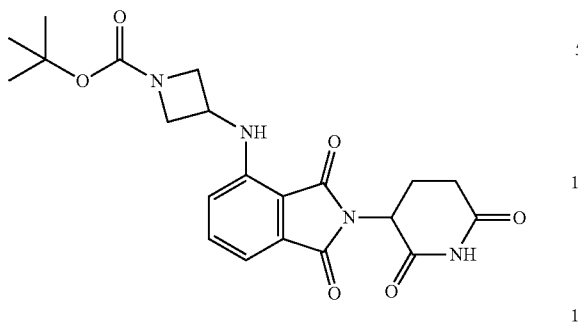

¹H NMR (400 MHz, DMSO-d₆) δ 11.09 (s, 1H), 7.59 (dd, J=8.5, 7.1 Hz, 1H), 7.12 (d, J=7.1 Hz, 1H), 6.94 (d, J=8.5 Hz, 1H), 6.87 (d, J=6.6 Hz, 1H), 5.06 (dd, J=12.7, 5.4 Hz, 1H), 4.44 (q, J=6.4 Hz, 1H), 4.26-4.16 (m, 2H), 3.89-3.73 (m, 2H), 2.88 (ddd, J=16.8, 13.7, 5.3 Hz, 1H), 2.73-2.52 (m, 2H), 2.14-1.93 (m, 1H), 1.38 (s, 8H).

LC/MS (ES−): m/z 427.3 [M−H]−.

Scheme 2
Illustrative Preparation of
4-amino-substitued 2-(2,6-dioxo-piperidin-3-yl)-isoindole-1,3-dione hydrochloride (de-Boc):

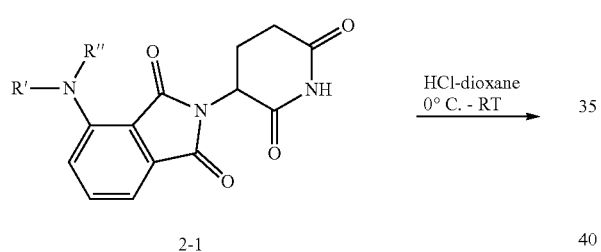

General Procedure:

A solution of Boc-substituted-4-amino-substituted 2-(2,6-dioxo-piperidin-3-yl)-isoindole-1,3-dione in dioxane at 0° C. was treated with 4M HCl in dioxane and resulting mixture allowed stir at room temperature. After complete consumption of starting material as evident from TLC & LCMS, the volatiles were stripped off, residue triturated with pentane/ether, dried and finally lyophilized to afford the target hydrochloride as a solid.

The Following Compounds were Made According the Procedure of Scheme 2:

Compound 234

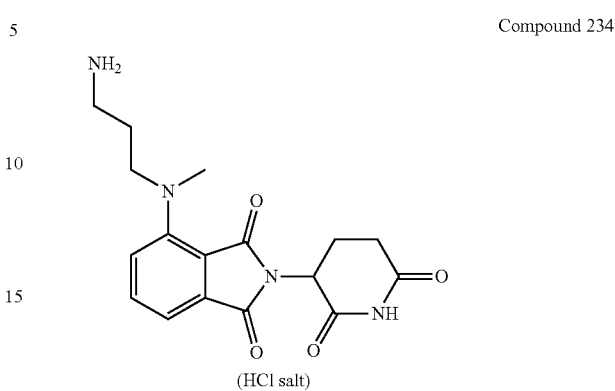

(HCl salt)

Yield: 88%
¹H NMR (400 MHz, DMSO-d6): δ 11.08 (s, 1H), 7.80 (brs, 3H), 7.66 (t, J=7.8 Hz, 1H), 7.31 (dd, J=21.6, 7.7 Hz, 2H), 5.08 (dd, J=13.0, 5.3 Hz, 1H), 3.48 (brs, 2H), 2.99 (s, 3H), 2.92-2.84 (m, 1H), 2.79 (brs, 2H), 2.61-2.49 (m, 2H), 2.06-2.00 (m, 1H), 1.94-1.88 (m, 2H); LC MS: ES+345.32.

Compound 235

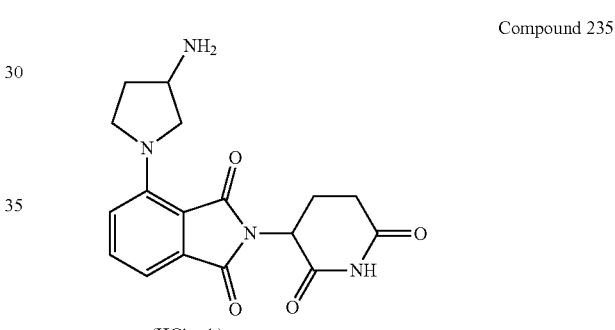

(HCl salt)

Yield: 73%
¹H NMR (400 MHz, DMSO-d6) δ 11.08 (s, 1H), 8.03 (brs, 3H), 7.65-7.61 (m, 1H), 7.22 (d, J=6.9 Hz, 1H), 7.15 (d, J=8.6 Hz, 1H), 5.10-5.04 (m, 1H), 3.92 (brs, 2H), 3.75-3.66 (brs, 2H), 3.57 (brs, 1H), 2.89-2.84 (m, 1H), 2.66-2.56 (m, 1H), 2.32-2.24 (m, 1H), 2.06-1.98 (m, 3H); LC MS: ES+ 343.29.

Compound 236

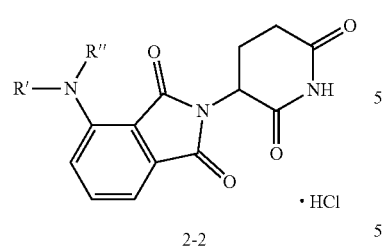

(HCl salt)

Yield: 93%
¹H NMR (400 MHz, DMSO-d6): δ 11.10 (s, 1H), 7.96 (s, 3H), 7.70 (d, J=7.8 Hz, 1H), 7.36 (t, J=7.1 Hz, 2H), 5.09 (d, J=12.6 Hz, 1H), 3.72 (d, J=12.7 Hz, 2H), 3.32-3.25 (m, 1H), 2.99-2.89 (m, 4H), 2.61-2.57 (m, 1H), 2.02-1.98 (m, 3H), 1.77-1.71 (m, 2H); LC MS: ES+ 357.34.

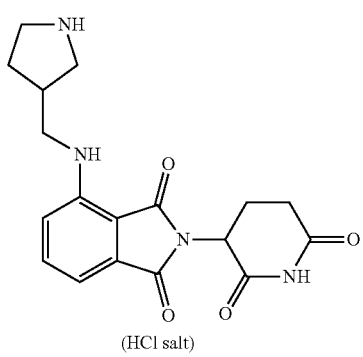

Compound 237

(HCl salt)

Yield: 75%

¹H NMR (400 MHz, DMSO-d6) δ 11.10 (s, 1H), 8.76 (brs, 2H), 7.60 (t, J=7.8 Hz, 1H), 7.20 (d, J=8.5 Hz, 1H), 7.06 (d, J=7.1 Hz, 1H), 6.81 (brs, 1H), 5.06 (d, J=10.7 Hz, 1H), 3.38-3.36 (m, 2H), 3.30-3.26 (s, 2H), 3.14 (brs, 1H), 2.92-2.85 (m, 2H), 2.65-2.49 (m, 3H), 2.04 (brs, 2H), 1.67 (brs, 1H); LC MS: ES+ 357.34.

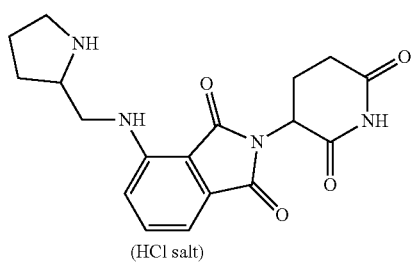

Compound 238

(HCl salt)

Yield: 82%

¹H NMR (400 MHz, DMSO-d6): δ 11.11 (s, 1H), 8.97 (brs, 1H), 8.58 (brs, 1H), 7.63 (t, J=7.84 Hz, 1H), 7.25 (d, J=8.6 Hz, 1H), 7.12 (d, J=7.1 Hz, 1H), 6.95-6.89 (m, 1H), 5.08 (dd, J=12.8, 5.3 Hz, 1H), 3.73-3.65 (m, 2H), 3.56-3.53 (m, 1H), 3.18-3.13 (m, 2H), 2.93-2.86 (m, 1H), 2.67-2.54 (m, 2H), 2.13-2.04 (m, 2H), 1.99-1.90 (m, 2H), 1.71-1.60 (m, 1H); LC MS: ES+ 357.3.

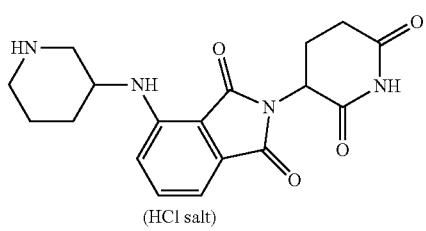

Compound 239

(HCl salt)

Yield: 37%

¹H NMR (400 MHz, DMSO-d6) δ 11.11 (s, 1H), 8.83 (brs, 1H), 8.60 (brs, 1H) 7.66 (t, J=7.9 Hz, 1H), 7.18 (d, J=8.6 Hz, 1H), 7.13 (d, J=7.0 Hz, 1H), 6.38 (d, J=8.4 Hz, 1H), 5.09-5.05 (m, 1H), 3.92 (brs, 1H, 3.39-3.21 (m, 2H), 2.96-2.82 (m, 3H), 2.66-2.56 (m, 2H), 2.03 (brs, 2H), 1.91-1.87 (m, 1H), 1.77-1.64 (m, 2H); LC MS: ES+ 357.3.

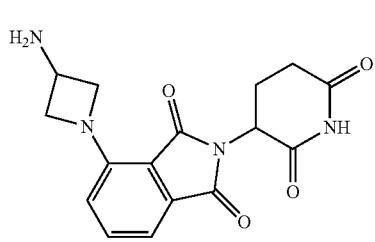

Compound 240

Yield: 19%

¹H NMR (400 MHz, DMSO-d6) δ 11.07 (s, 1H), 7.55 (t, J=7.8 Hz, 1H), 7.09 (d, J=7.1 Hz, 1H), 6.77 (d, J=8.6 Hz, 1H), 5.05 (dd, J=13.1, 5.4 Hz, 1H), 4.40 (brs, 2H), 3.73 (brs, 2H), 2.91-2.85 (m, 1H), 2.58-2.49 (m, 2H), 2.00 (brs, 1H); LC MS: ES+ 329.2.

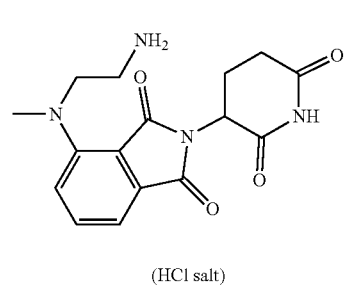

Compound 241

(HCl salt)

Yield: 46.45%

¹H NMR (400 MHz, DMSO-d6) δ 11.10 (s, 1H), 7.87 (brs, 3H), 7.69 (t, J=7.8 Hz, 1H), 7.37 (d, J=8.24 Hz, 1H), 7.33 (d, J=6.88 Hz, 1H), 5.15-5.06 (m, 1H), 3.74-3.54 (m, 4H), 3.48 (dd, J=12.0, 4.8 Hz, 1H), 3.13 (brs, 2H), 3.01 (s, 3H), 2.64-2.82 (m, 1H), 2.62-2.52 (m, 2H), 2.04-1.99 (m, 1H); LC MS: ES+ 331.2.

Compound 242

(HCl salt)

Yield: 83.3%

¹H NMR (400 MHz, DMSO-d6) δ 11.10 (s, 1H), 7.74 (brs, 3H), 7.60 (t, J=7.8 Hz, 1H), 7.15 (d, J=8.7 Hz, 1H), 7.05 (d, J=7.0 Hz, 1H), 6.76 (s, 1H), 5.11-5.02 (m, 1H), 3.41 (d, J=6.8 Hz, 2H), 2.86 (brs, 4H), 2.64-2.54 (m, 1H), 2.03 (brs, 1H), 1.87-1.79 (m, 2H); LC MS: ES+ 331.2.

Compound 243

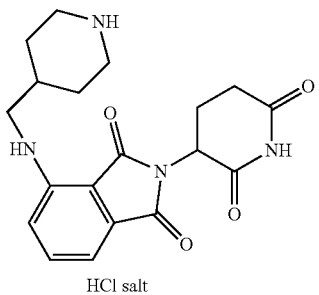

HCl salt

Yield: 88.9%
$^1$H NMR (400 MHz, DMSO-d6) δ 11.10 (s, 1H), 8.43 (brs, 2H), 7.63-7.54 (t, J=7.84 Hz, 1H), 7.16 (d, J=8.6 Hz, 1H), 7.04 (d, J=7.0 Hz, 1H), 6.74 (t, J=6.3 Hz, 1H), 5.05 (dd, J=12.6, 5.4 Hz, 1H), 3.31-3.23 (m, 4H), 2.96-2.77 (m, 3H), 2.59-2.49 (m, 2H), 2.07-1.99 (m, 1H), 1.90-1.83 (m, 3H), 1.40-1.31 (m, 2H); LC MS: ES+ 371.3.

Compound 244

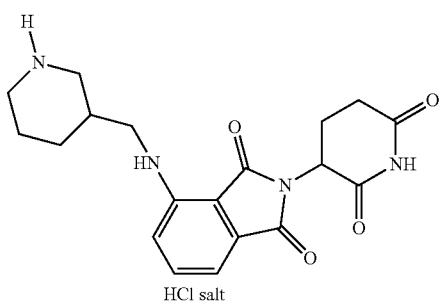

HCl salt

Yield: 47.28%
$^1$H NMR (400 MHz, DMSO-d6) δ 11.10 (s, 1H), 8.39 (brs, 2H), 7.60 (t, J=7.8 Hz, 1H), 7.16 (d, J=8.7 Hz, 1H), 7.05 (d, J=7.1 Hz, 1H), 6.79 (t, J=6.34 Hz, 1H), 5.06 (dd, J=12.5, 5.2 Hz, 1H), 3.26-3.18 (m, 4H), 2.92-2.82 (m, 1H), 2.79-2.73 (m, 1H), 2.67-2.50 (m, 3H), 2.04-2.01 (m, 2H), 1.83-1.77 (s, 2H), 1.59-1.56 (m, 1H), 1.224-1.20 (m, 1H); LC MS: ES+ 371.2.

Compound 245

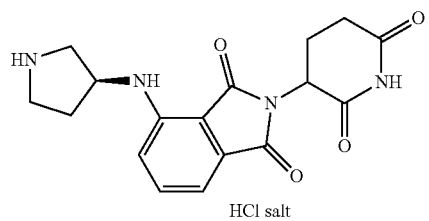

HCl salt

Yield: 83.5%
$^1$H NMR (400 MHz, DMSO-d6) δ 11.11 (s, 1H), 9.05 (brs, 2H), 7.70-7.61 (t, J=7.8 Hz, 1H), 7.16 (dd, J=11.8, 7.8 Hz, 2H), 6.59 (d, J=7.4 Hz, 1H), 5.07 (dd, J=12.7, 5.4 Hz, 1H), 4.47-4.42 (m, 1H), 3.51-3.45 (m, 1H), 3.37-3.32 (m, 2H), 3.28-3.15 (m, 2H), 2.90-2.84 (m, 1H), 2.64-2.51 (m, 1H), 2.42-2.28 (m, 1H), 2.07-1.99 (m, 1H), 1.98-1.91 (m, 1H); LC MS: ES+ 343.3.

Compound 246

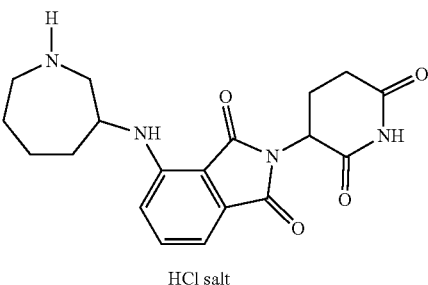

HCl salt

Yield: 69%
$^1$H NMR (400 MHz, DMSO-d6) δ 11.11 (s, 1H), 8.97 (s, 1H), 8.87 (s, 1H), 7.66 (t, J=7.8 Hz, 1H), 7.23 (d, J=8.7 Hz, 1H), 7.12 (d, J=7.0 Hz, 1H), 6.45 (d, J=8.6 Hz, 1H), 5.07 (dd, J=12.7, 5.3 Hz, 1H), 4.15 (brs, 1H), 3.69 (d, J=8.5 Hz, 1H), 3.48 (d, J=13.1 Hz, 1H), 3.24-3.13 (m, 4H), 2.92-2.83 (m, 1H), 2.59 (d, J=18.6 Hz, 2H), 2.05 (brs, 2H), 1.90-1.74 (m, 3H), 1.62-158 (m, 1H); LC MS: ES+ 371.3.

Compound 247

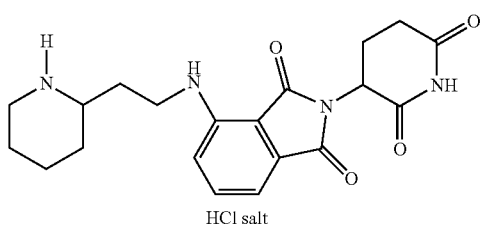

HCl salt

Yield: 74%
$^1$H NMR (400 MHz, DMSO-d6) δ 11.10 (s, 1H), 8.57 (brs, 1H), 8.42 (brs, 1H), 7.66-7.57 (t, J=7.86 Hz, 1H), 7.13 (d, J=8.6 Hz, 1H), 7.06 (d, J=7.0 Hz, 1H), 6.77 (t, J=6.2 Hz, 1H), 5.06 (dd, J=12.8, 5.4 Hz, 1H), 3.44 (q, J=6.7 Hz, 2H), 3.32-3.21 (m, 1H), 3.10 (brs, 1H), 2.88-2.84 (m, 2H), 2.64-2.52 (m, 2H), 2.07-1.84 (m, 3H), 1.79-1.74 (m, 3H), 1.60-1.57 (m, 1H), 1.42-1.39 (m, 2H); LC MS: ES+ 385.3.

Compound 248

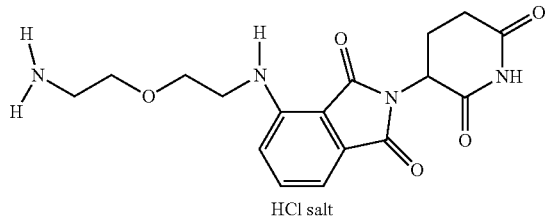

HCl salt

Yield: 62%
$^1$H NMR (400 MHz, DMSO-d6) δ 11.11 (s, 1H), 7.83 (brs, 2H), 7.60 (t, J=7.8 Hz, 1H), 7.17 (d, J=8.6 Hz, 1H), 7.06 (d, J=7.1 Hz, 1H), 6.64 (t, J=5.9 Hz, 1H), 5.06 (dd, J=12.7, 5.3 Hz, 1H), 3.68-3.61 (m, 4H), 3.52-3.49 (m, 2H), 3.03-2.82 (m, 3H), 2.64-2.51 (m, 2H), 2.03-2.01 (m, 1H); LC MS: ES+ 361.3.

Compound 249

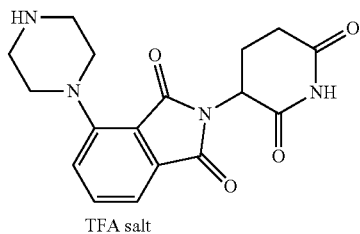

TFA salt

¹H NMR (400 MHz, DMSO-d₆) δ 11.07 (s, 1H), 8.80 (br, 2H), 7.74 (t, J=7.8 Hz, 1H), 7.42 (dd, J=15.9, 7.8 Hz, 2H), 5.09 (dd, J=12.7, 5.4 Hz, 1H), 3.47 (t, J=4.9 Hz, 4H), 3.29 (br, 4H), 2.87 (ddd, J=18.0, 13.7, 5.3 Hz, 1H), 2.73-2.51 (m, 2H), 2.01 (ddd, J=10.7, 5.9, 3.6 Hz, 1H).
LC/MS (ES+): m/z 343.3 [M+H]⁺.

Compound 250

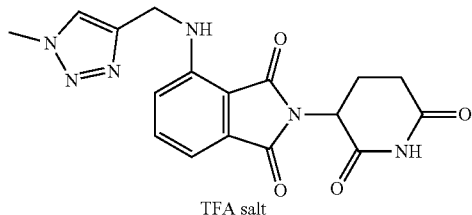

TFA salt

¹H NMR (400 MHz, DMSO-d₆) δ 11.10 (s, 1H), 7.95 (s, 1H), 7.56 (dd, J=8.5, 7.1 Hz, 1H), 7.16 (d, J=8.6 Hz, 1H), 7.04 (d, J=7.1 Hz, 1H), 5.05 (dd, J=12.9, 5.4 Hz, 1H), 4.58 (s, 2H), 3.98 (s, 3H), 2.87 (ddd, J=17.2, 14.0, 5.4 Hz, 1H), 2.68-2.53 (m, 1H), 2.13-1.92 (m, 1H).
LC/MS (ES+): m/z 369.7 [M+H]⁺.

Compound 251

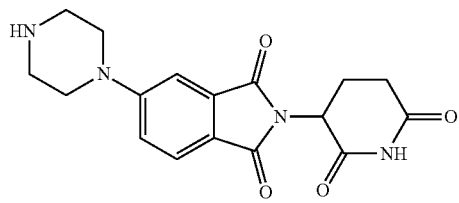

Scheme 3
Synthesis of (2-(2,6-dioxo-piperidin-3-yl)-1,3-dioxoisoindolin-4-yl)alanine (Compound 252)

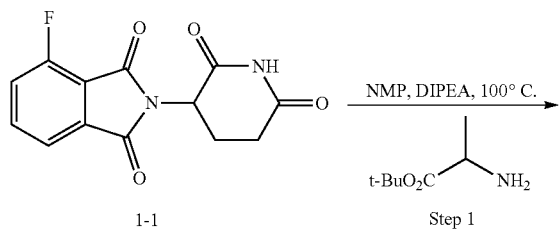

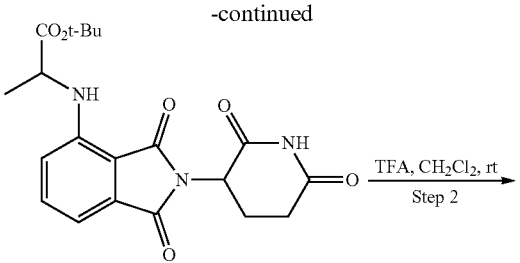

3-1

Compound 252

Step 1: An oven dried pressure tube was charged with 2-(2,6-dioxopiperidin-3-yl)-4-fluoroisoindoline-1,3-dione 1-1 (3 g, 10.68 mmol), DL-Alanine tert-butyl ester hydrochloride (2.95 g, 16.30 mmol), diisopropylethylamine (9.25 mL, 54.34 mmol), NMP (30 mL) and the reaction mixture was heated at 100° C. for 16 h. The reaction mixture was cooled to room temperature and diluted with water. The resulting solid compound which was precipitated out was fileted and washed with water, petroleum ether, dried under vacuum to yield tert-butyl (2-(2,6-dioxopiperidin-3-yl)-1,3-dioxoisoindolin-4-yl)alaninate 3-1 (2.8 g) as yellow gummy solid.

Step 2

Compound 252

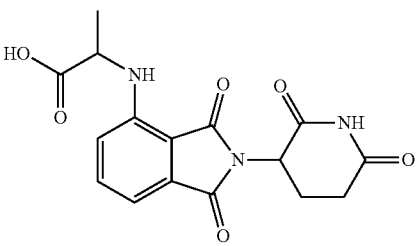

To a solution of tert-butyl (2-(2,6-dioxopiperidin-3-yl)-1,3-dioxoisoindolin-4-yl)alaninate (2.8 g, 6.98 mmol) in dichloromethane (20 mL) was added TFA (20 mL) at 0° C. and the reaction mixture was stirred at room temperature for 1 h. The reaction mixture was concentrated under reduced pressure and the crude was purified by prep. HPLC purification to yield (2-(2,6-dioxopiperidin-3-yl)-1,3-dioxoisoindolin-4-yl)alanine Compound 252 (700 mg) as pale yellow solid. ¹H NMR (DMSOd₆, 400 MHz): δ 13.16 (s, 1H), 11.13 (s, 1H), 7.79 (s, 1H), 7.63-7.60 (m, 1H), 7.12-7.07 (m, 2H), 6.73-6.70 (m, 1H), 5.08 (dd, J=5.6, 13.0 Hz, 1H), 4.45 (t, J=7.2 Hz, 1H), 2.94-2.85 (m, 1H), 2.68-2.51 (m, 2H), 2.06-2.03 (m, 1H), 1.46 (d, J=6.8 Hz, 3H). MM-ESI+APCI calc'd. [M+H]⁺ 346.0, found 346.1.

Example 2: Illustrative Preparation of Click Library

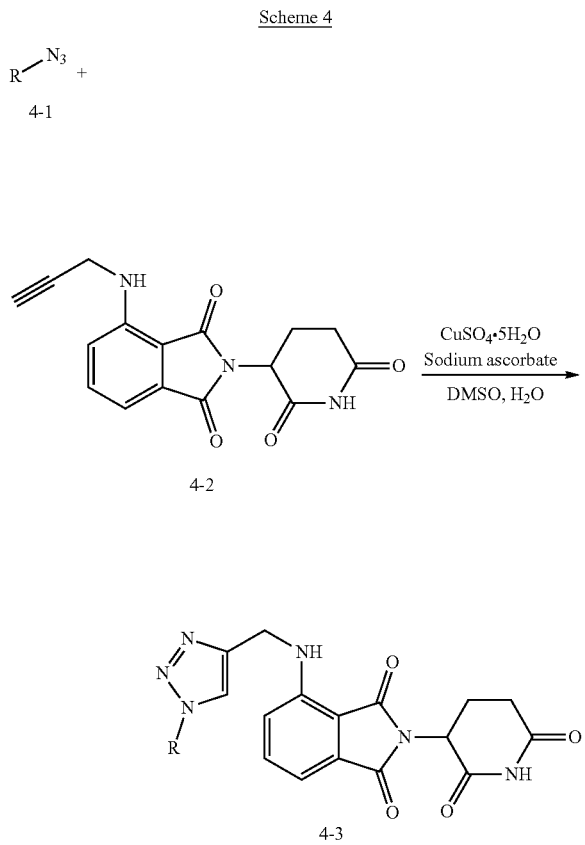

Scheme 4

General Procedure:

A solution of alkyne 4-1 (0.0555 mmol) and azide 4-2 (0.0500 mmol) in 500 uL DMSO was treated with $CuSO_4 \cdot 5H_2O$ (0.0111 mmol) in water and sodium (R)-2-((S)-1,2-dihydroxyethyl)-4-hydroxy-5-oxo-2,5 dihydrofuran-3-olate (0.0333 mmol). The vial was put under and atmosphere of N2 and stirred at rt. The reaction was filtered and purified by preparative HPLC.

General Methods for Preparatory HPLC Purification:

Method-1

Preparative HPLC was conducted on a Waters auto purification instrument equipped with a Waters X Select CSH C18 (5 µm, 19×50 mm) column operating at 25° C. and a flow rate of 25 mL/min. Mobile phase: A=0.1% Trifluoroacetic Acid in Water, B=Acetonitrile; Gradient Profile: Mobile phase initial composition of 4% B for 3 minutes, then from 5% B to 15% B in 13 minutes, 15% to 95% B in 0.5 minutes, and holding at 95% B for 2 minutes and returned to initial condition.

Method-2

Preparative HPLC was conducted on a Waters auto purification instrument equipped with a Waters X Select CSH C18 (5 µm, 19×50 mm) column operating at 25° C. and a flow rate of 25 mL/min. Mobile phase: A=0.1% Trifluoroacetic Acid in Water, B=Acetonitrile; Gradient Profile: Mobile phase initial composition of 4% B for 3 minutes, then from 5% B to 20% B in 13 minutes, 20% to 95% B in 0.5 minutes, and holding at 95% B for 2 minutes and returned to initial condition.

Method-3

Preparative HPLC was conducted on a Waters auto purification instrument equipped with a Waters X Select CSH C18 (5 µm, 19×50 mm) column operating at 25° C. and a flow rate of 25 mL/min. Mobile phase: A=0.1% Trifluoroacetic Acid in Water, B=Acetonitrile; Gradient Profile: Mobile phase initial composition of 4% B for 3 minutes, then from 10% B to 25% B in 13 minutes, 25% to 95% B in 0.5 minutes, and holding at 95% B for 2 minutes and returned to initial condition.

Method-4

Preparative HPLC was conducted on a Waters auto purification instrument equipped with a Waters X Select CSH C18 (5 µm, 19×50 mm) column operating at 25° C. and a flow rate of 25 mL/min. Mobile phase: A=0.1% Trifluoroacetic Acid in Water, B=Acetonitrile; Gradient Profile: Mobile phase initial composition of 4% B for 3 minutes, then from 15% B to 30% B in 13 minutes, 30% to 95% B in 0.5 minutes, and holding at 95% B for 2 minutes and returned to initial condition.

Method-5

Preparative HPLC was conducted on a Waters auto purification instrument equipped with a Waters X Select CSH C18 (5 µm, 19×50 mm) column operating at 25° C. and a flow rate of 25 mL/min. Mobile phase: A=0.1% Trifluoroacetic Acid in Water, B=Acetonitrile; Gradient Profile: Mobile phase initial composition of 4% B for 3 minutes, then from 20% B to 35% B in 13 minutes, 35% to 95% B in 0.5 minutes, and holding at 95% B for 2 minutes and returned to initial condition.

Method-6

Preparative HPLC was conducted on a Waters auto purification instrument equipped with a Waters X Select CSH C18 (5 µm, 19×50 mm) column operating at 25° C. and a flow rate of 25 mL/min. Mobile phase: A=0.1% Trifluoroacetic Acid in Water, B=Acetonitrile; Gradient Profile: Mobile phase initial composition of 4% B for 3 minutes, then from 25% B to 40% B in 13 minutes, 40% to 95% B in 0.5 minutes, and holding at 95% B for 2 minutes and returned to initial condition.

Method-7

Preparative HPLC was conducted on a Waters auto purification instrument equipped with a Waters X Select CSH C18 (5 µm, 19×50 mm) column operating at 25° C. and a flow rate of 25 mL/min. Mobile phase: A=0.1% Trifluoroacetic Acid in Water, B=Acetonitrile; Gradient Profile: Mobile phase initial composition of 4% B for 3 minutes, then from 30% B to 45% B in 13 minutes, 45% to 95% B in 0.5 minutes, and holding at 95% B for 2 minutes and returned to initial condition.

Method-8

Preparative HPLC was conducted on a Waters auto purification instrument equipped with a Waters X Bridge Prep C18 (5 µm, 19×100 mm) column operating at 25° C. and a flow rate of 25 mL/min. Mobile phase: A=0.1% Trifluoroacetic Acid in Water, B=Acetonitrile; Gradient Profile: Mobile phase initial composition of 4% B for 3 minutes, then from 5% B to 25% B in 13 minutes, 25% to 95% B in 0.5 minutes, and holding at 95% B for 2 minutes and returned to initial condition.

The following compounds were made according to the general procedure in Scheme 4:

2-(2,6-Dioxopiperidin-3-yl)-4-(((1-(2-(pyridin-2-yl)propyl)-1H-1,2,3-triazol-4-yl)methyl)amino)isoindoline-1,3-dione (Compound 253)

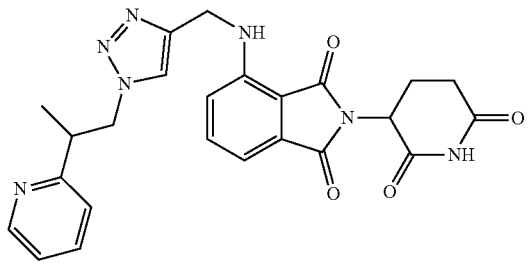 [SMILES: CC(Cn1cc(CNc2cccc3c2C(=O)N(C2CCC(=O)NC2=O)C3=O)nn1)c1ccccn1]

Purified by Method 2. $^1$H NMR (300 MHz, DMSO-d$_6$) δ 11.10 (s, 1H), 8.52 (s, 1H), 7.79 (s, 1H), 7.73 (t, J=7.8 Hz, 1H), 7.55 (t, J=7.9 Hz, 1H), 7.35-7.22 (m, 2H), 7.10-6.97 (m, 3H), 5.13-5.00 (m, 1H), 4.75-4.56 (m, 2H), 4.52 (s, 2H), 3.61-3.45 (m, 1H), 2.98-2.78 (m, 1H), 2.67-2.54 (m, 2H), 2.15-1.88 (m, 1H), 1.19 (d, J=7.8 Hz, 3H). LC/MS (ES+): m/z 476.6 (M+H)$^+$.

2-(2,6-Dioxopiperidin-3-yl)-4-(((1-(2-methoxyethyl)-1H-1,2,3-triazol-4-yl)methyl)amino)isoindoline-1,3-dione (Compound 254)

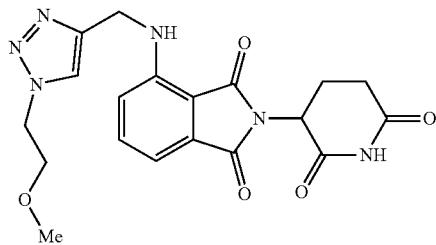 [SMILES: COCCn1cc(CNc2cccc3c2C(=O)N(C2CCC(=O)NC2=O)C3=O)nn1]

Purified by Method 3. $^1$H NMR (300 MHz, DMSO-d$_6$) δ 11.10 (s, 1H), 7.99 (s, 1H), 7.58 (t, J=7.9 Hz, 1H), 7.19 (d, J=8.7 Hz, 1H), 7.12-7.02 (m, 2H), 5.12-5.00 (m, 1H), 4.60 (d, J=4.4 Hz, 2H), 4.49 (t, J=4.8 Hz, 2H), 3.69 (t, J=5.4 Hz, 2H), 3.21 (s, 3H), 2.98-2.79 (m, 1H), 2.68-2.48 (m, 2H), 2.08-1.90 (m, 1H). LC/MS (ES+): m/z 412.8 (M+H)$^+$.

2-(2,6-Dioxopiperidin-3-yl)-4-(((1-(2-(6-methylpyrazin-2-yl)ethyl)-1H-1,2,3-triazol-4-yl)methyl)amino)isoindoline-1,3-dione (Compound 255)

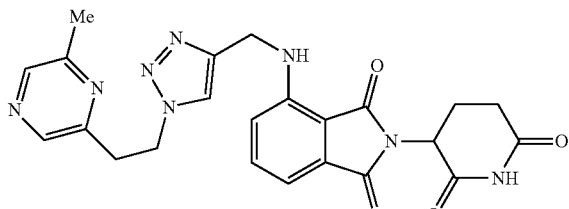

Purified by Method 3. $^1$H NMR (300 MHz, DMSO-d$_6$) δ 11.10 (s, 1H), 8.35 (s, 1H), 8.23 (s, 1H), 7.96 (s, 1H), 7.60-7.49 (m, 1H), 7.16-7.01 (m, 3H), 5.06 (dd, J=11.7, 4.6 Hz, 1H), 4.72 (t, J=7.1 Hz, 2H), 4.55 (s, 2H), 3.29 (t, J=7.2 Hz, 2H), 2.96-2.81 (m, 1H), 2.68-2.53 (m, 2H), 2.42 (s, 3H), 2.09-1.96 (m, 1H). LC/MS (ES+): m/z 475.9 (M+H)$^+$.

4-(((1-(2-(2,2-Dichlorocyclopropyl)ethyl)-1H-1,2,3-triazol-4-yl)methyl)amino)-2-(2,6-dioxopiperidin-3-yl)isoindoline-1,3-dione (Compound 256)

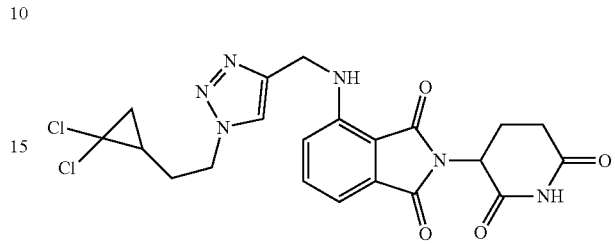

Purified by Method 5. $^1$H NMR (300 MHz, DMSO-d$_6$) δ 11.10 (s, 1H), 8.07 (s, 1H), 7.57 (t, J=7.7 Hz, 1H), 7.16 (d, J=8.6 Hz, 1H), 7.13-7.01 (m, 2H), 5.06 (dd, J=12.6, 4.6 Hz, 1H), 4.61 (d, J=5.6 Hz, 2H), 4.49 (t, J=6.7 Hz, 2H), 2.99-2.79 (m, 1H), 2.65-2.53 (m, 2H), 2.18-1.82 (m, 3H), 1.67-1.54 (m, 2H), 1.19-1.11 (m, 1H). LC/MS (ES+): m/z 491.0 (M+H)$^+$.

3-(4-(((2-(2,6-Dioxopiperidin-3-yl)-1,3-dioxoisoindolin-4-yl)amino)methyl)-1H-1,2,3-triazol-1-yl)-N-methylpropanamide (Compound 257)

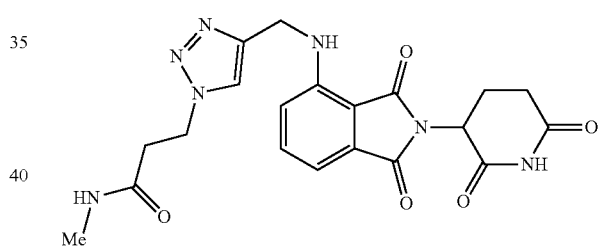

Purified by Method 2. $^1$H NMR (300 MHz, DMSO-d$_6$) δ 11.10 (s, 1H), 7.93 (d, J=2.0 Hz, 1H), 7.89-7.82 (m, 1H), 7.57 (t, J=7.8 Hz, 1H), 7.17 (d, J=8.2 Hz, 1H), 7.10-7.02 (m, 2H), 5.06 (dd, J=14.5, 4.3 Hz, 1H), 4.57 (s, 2H), 4.52 (t, J=7.6 Hz, 2H), 2.99-2.79 (m, 1H), 2.71-2.59 (m, 2H), 2.10-1.94 (m, 1H). CH$_3$ and CH$_2$ under solvent. LC/MS (ES+): m/z 439.9 (M+H)$^+$.

2-(2,6-Dioxopiperidin-3-yl)-4-(((1-(isoxazol-5-ylmethyl)-1H-1,2,3-triazol-4-yl)methyl)amino)isoindoline-1,3-dione (Compound 258)

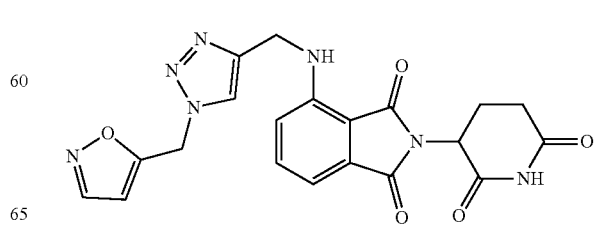

Purified by Method 3. ¹H NMR (300 MHz, DMSO-d₆) δ 11.10 (s, 1H), 8.57 (s, 1H), 8.13 (s, 1H), 7.58 (t, J=7.9 Hz, 1H), 7.21-7.15 (m, 1H), 7.14-7.02 (m, 2H), 6.51 (s, 1H), 5.87 (s, 2H), 5.12-4.99 (m, 1H), 4.62 (d, J=6.0 Hz, 2H), 2.98-2.80 (m, 1H), 2.66-2.53 (m, 2H), 2.13-1.94 (m, 1H). LC/MS (ES+): m/z 435.9 (M+H)⁺.

2-(2,6-Dioxopiperidin-3-yl)-4-(((1-((tetrahydrofuran-3-yl)methyl)-1H-1,2,3-triazol-4-yl)methyl) amino)isoindoline-1,3-dione (Compound 259)

Purified by Method 3. 1H NMR (300 MHz, DMSO-d6) δ 11.10 (s, 1H), 8.06 (d, J=2.3 Hz, 1H), 7.58 (t, J=7.6 Hz, 1H), 7.20-7.12 (m, 1H), 7.11-7.03 (m, 2H), 5.06 (dd, J=14.2, 3.1 Hz, 1H), 4.60 (d, J=5.8 Hz, 2H), 4.33 (d, J=7.6 Hz, 2H), 3.73 (q, J=7.0 Hz, 1H), 3.67-3.55 (m, 2H), 3.48-3.38 (m, 1H), 3.01-2.80 (m, 2H), 2.78-2.59 (m, 2H), 2.12-1.96 (m, 1H), 1.96-1.80 (m, 1H), 1.56 (m, 1H). LC/MS (ES+): m/z 438.9 (M+H)⁺.

4-(((1-(2-Bromoethyl)-1H-1,2,3-triazol-4-yl)methyl) amino)-2-(2,6-dioxopiperidin-3-yl)isoindoline-1,3-dione (Compound 260)

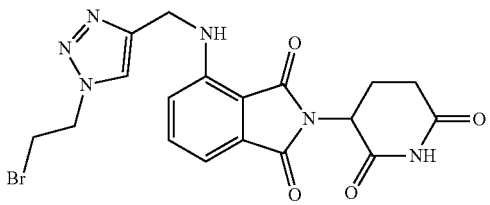 [SMILES: O=C1CCC(N2C(=O)c3cccc(NCc4cn(CCBr)nn4)c3C2=O)C(=O)N1]

Purified by Method 4. ¹H NMR (300 MHz, DMSO-d₆) δ 11.10 (s, 1H), 8.09 (s, 1H), 7.58 (t, J=8.0 Hz, 1H), 7.17 (d, J=8.8 Hz, 1H), 7.14-7.04 (m, 2H), 5.07 (dd, 1H), 4.76 (t, J=5.9 Hz, 2H), 4.62 (d, J=6.0 Hz, 2H), 3.91 (t, J=5.9 Hz, 2H), 2.97-2.78 (m, 1H), 2.66-2.54 (m, 2H), 2.09-1.92 (m, 1H). LC/MS (ES+): m/z 460.9 (M+H)⁺.

2-(2,6-Dioxopiperidin-3-yl)-4-(((1-(pyridin-3-yl)-1H-1,2,3-triazol-4-yl)methyl)amino)isoindoline-1,3-dione (Compound 261)

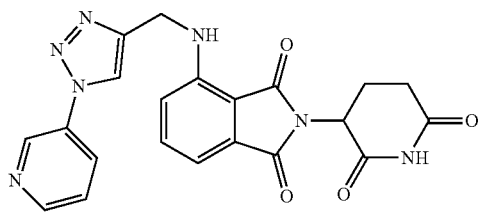 [SMILES: O=C1CCC(N2C(=O)c3cccc(NCc4cn(-c5cccnc5)nn4)c3C2=O)C(=O)N1]

Purified by Method 4. ¹H NMR (300 MHz, DMSO-d₆) δ 11.10 (s, 1H), 9.13 (s, 1H), 8.83 (s, 1H), 8.71-8.64 (m, 1H), 8.36-8.28 (m, 1H), 7.69-7.53 (m, 2H), 7.27-7.13 (m, 2H), 7.11-7.03 (m, 1H), 5.07 (dd, J=12.6, 4.6 Hz, 1H), 4.73 (d, J=5.9 Hz, 2H), 2.98-2.80 (m, 1H), 2.66-2.54 (m, 2H), 2.10-1.97 (m, 1H). LC/MS (ES+): m/z 432.0 (M+H)⁺.

2-(2,6-Dioxopiperidin-3-yl)-4-(((1-(1-methyl-1H-pyrazol-3-yl)-1H-1,2,3-triazol-4-yl)methyl)amino) isoindoline-1,3-dione (Compound 262)

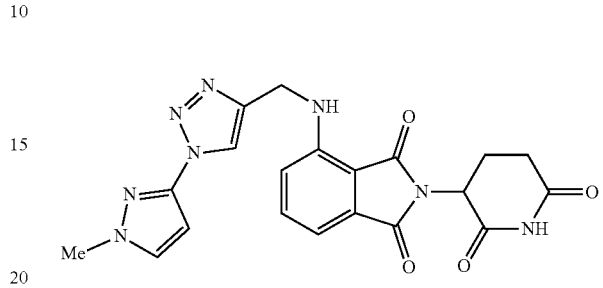

Purified by Method 4. ¹H NMR (300 MHz, DMSO-d₆) δ 11.10 (s, 1H), 8.43 (s, 1H), 7.88 (s, 1H), 7.59 (t, J=7.9 Hz, 1H), 7.22 (d, J=8.8 Hz, 1H), 7.19-7.10 (m, 1H), 7.06 (d, J=7.0 Hz, 1H), 6.67-6.58 (m, 1H), 5.07 (dd, J=13.4, 4.9 Hz, 1H), 4.68 (s, 2H), 3.88 (s, 3H), 2.99-2.76 (m, 1H), 2.65-2.54 (m, 1H), 2.12-1.90 (m, 2H). LC/MS (ES+): m/z 435.0 (M+H)⁺.

4-(((1-((R)-5-Chloro-2,3-dihydro-1H-inden-1-yl)-1H-1,2,3-triazol-4-yl)methyl)amino)-2-(2,6-dioxopiperidin-3-yl)isoindoline-1,3-dione (Compound 263)

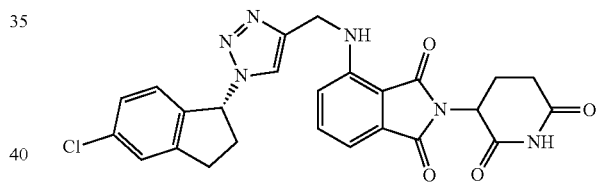

Purified by Method 7. ¹H NMR (300 MHz, DMSO-d₆) δ 11.10 (s, 1H), 8.03 (s, 1H), 7.58 (t, J=7.8 Hz, 1H), 7.45 (s, 1H), 7.29-7.21 (m, 1H), 7.20-7.14 (m, 1H), 7.11-7.01 (m, 3H), 6.18 (t, J=7.0 Hz, 1H), 5.06 (dd, J=12.3, 5.2 Hz, 1H), 4.58 (d, J=4.2 Hz, 2H), 3.23-3.09 (m, 1H), 3.05-2.80 (m, 2H), 2.71 (m, 1H), 2.63-2.59 (m, 2H), 2.49-2.34 (m, 1H), 2.07-1.90 (m, 1H). LC/MS (ES+): m/z 505.0 (M+H)⁺.

Tert-Butyl 4-(4-(((2-(2,6-Dioxopiperidin-3-yl)-1,3-dioxoisoindolin-4-yl)amino)methyl)-1H-1,2,3-triazol-1-yl)piperidine-1-carboxylate (Compound 264)

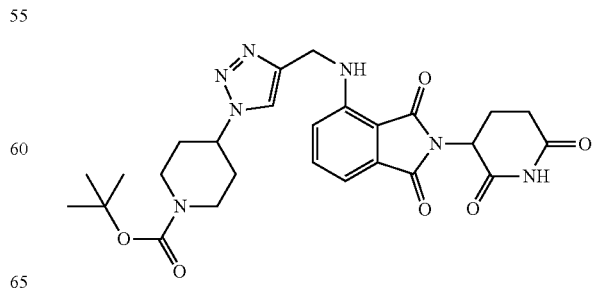

Purified by Method 6. LC/MS (ES+): m/z 538.2 (M+H)⁺.

535

Tert-Butyl 4-((4-(((2-(2,6-Dioxopiperidin-3-yl)-1,3-dioxoisoindolin-4-yl)amino)methyl)-1H-1,2,3-triazol-1-yl)methyl)piperidine-1-carboxylate (Compound 265)

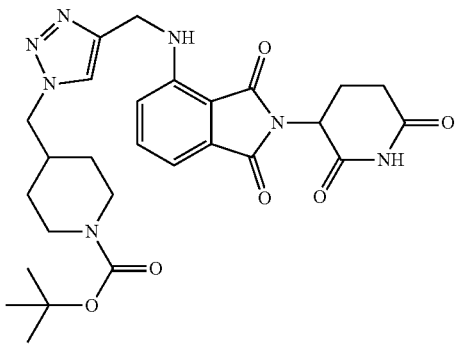 [SMILES: CC(C)(C)OC(=O)N1CCC(Cn2cc(CNc3cccc4c3C(=O)N(C3CCC(=O)NC3=O)C4=O)nn2)CC1]

Purified by Method 7. $^1$H NMR (300 MHz, DMSO-$d_6$) δ 11.10 (s, 1H), 7.99 (s, 1H), 7.57 (t, J=7.8 Hz, 1H), 7.15 (d, J=8.7 Hz, 1H), 7.10-7.00 (m, 2H), 5.06 (dd, J=12.0, 5.1 Hz, 1H), 4.60 (s, 2H), 4.24 (d, J=6.8 Hz, 2H), 3.89 (app d, J=12.8 Hz, 2H), 2.98-2.76 (m, 1H), 2.69-2.54 (m, 3H), 2.11-1.88 (d, J=19.1 Hz, 2H), 1.44 (s, 1H), 1.40-1.30 (m, 9H), 1.03 (d, J=10.8 Hz, 2H). LC/MS (ES+): m/z 552.1 (M+H)$^+$.

2-(2,6-Dioxopiperidin-3-yl)-4-(((1-(4-fluorobenzyl)-1H-1,2,3-triazol-4-yl)methyl)amino)isoindoline-1,3-dione (Compound 266)

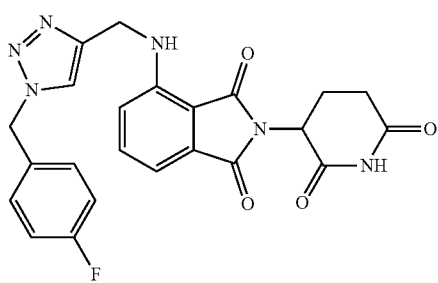 [SMILES: O=C1CCC(N2C(=O)c3cccc(NCc4cn(Cc5ccc(F)cc5)nn4)c3C2=O)C(=O)N1]

Purified by Method 6. $^1$H NMR (300 MHz, DMSO-$d_6$) δ 11.09 (s, 1H), 8.07 (d, J=1.9 Hz, 1H), 7.57 (t, J=7.8 Hz, 1H), 7.36 (t, J=7.0 Hz, 2H), 7.25-7.13 (m, 3H), 7.11-7.02 (m, 2H), 5.55 (s, 2H), 5.05 (dd, J=12.9, 4.7 Hz, 1H), 4.59 (d, J=5.3 Hz, 2H), 2.86 (d, J=16.0 Hz, 1H), 2.64-2.59 (s, 2H), 2.03 (s, 1H). LC/MS (ES+): m/z 463.0 (M+H)$^+$.

536

2-(2,6-Dioxopiperidin-3-yl)-4-(((1-(2-morpholinoethyl)-1H-1,2,3-triazol-4-yl)methyl)amino)isoindoline-1,3-dione (Compound 267)

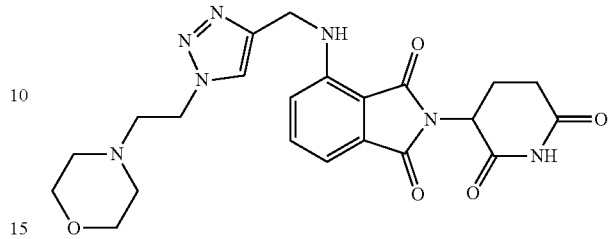

Purified by Method 1. LC/MS (ES+): m/z 468.2 (M+H)$^+$.

Tert-Butyl (2S)-2-((4-(((2-(2,6-dioxopiperidin-3-yl)-1,3-dioxoisoindolin-4-yl)amino)methyl)-1H-1,2,3-triazol-1-yl)methyl)pyrrolidine-1-carboxylate (Compound 268)

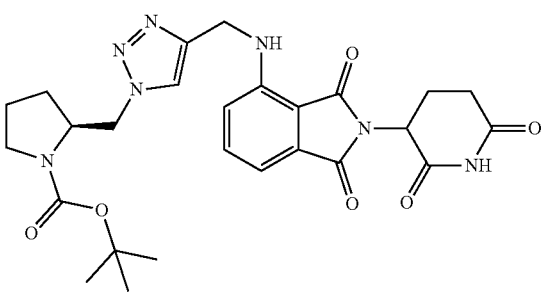 [SMILES: CC(C)(C)OC(=O)N1CCC[C@H]1Cn1cc(CNc2cccc3c2C(=O)N(C2CCC(=O)NC2=O)C3=O)nn1]

Purified by Method 6. $^1$H NMR (300 MHz, DMSO-$d_6$) δ 11.09 (s, 1H), 7.90 (s, 0.5H), 7.77 (s, 0.5H), 7.56 (t, J=7.9 Hz, 1H), 7.26-7.00 (m, 3H), 5.06 (dd, J=12.8, 6.5 Hz, 1H), 4.60 (d, J=4.7 Hz, 2H), 4.43 (d, J=18.1 Hz, 2H), 4.02 (app s, 1H), 3.25-2.99 (m, 2H), 2.98-2.79 (m, 2H), 2.69-2.51 (m, 2H), 2.11-1.95 (m, 1H), 1.90-1.76 (m, 1H), 1.73-1.51 (m, 2H), 1.35 (s, 9H). LC/MS (ES+): m/z 538.1 (M+H)$^+$.

Tert-Butyl 3-((4-(((2-(2,6-Dioxopiperidin-3-yl)-1,3-dioxoisoindolin-4-yl)amino)methyl)-1H-1,2,3-triazol-1-yl)methyl)piperidine-1-carboxylate (Compound 269)

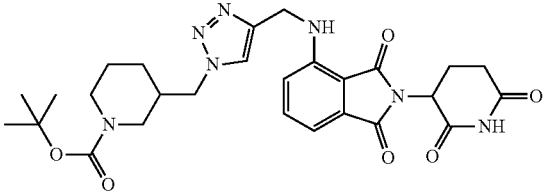 [SMILES: CC(C)(C)OC(=O)N1CCCC(Cn2cc(CNc3cccc4c3C(=O)N(C3CCC(=O)NC3=O)C4=O)nn2)C1]

Purified by Method 7. $^1$H NMR (300 MHz, DMSO-$d_6$) δ 11.10 (s, 1H), 8.08-7.98 (m, 1H), 7.57 (t, J=8.0 Hz, 1H), 7.17 (d, J=8.4 Hz, 1H), 7.12-7.00 (m, 2H), 5.06 (dd, J=11.7, 3.8 Hz, 1H), 4.60 (s, 2H), 4.24 (d, J=7.2 Hz, 2H), 2.98-2.71 (m, 2H), 2.65-2.52 (m, 2H), 2.10-1.96 (m, 1H), 1.97-1.84 (m, 1H), 1.60 (d, J=11.4 Hz, 2H), 1.27 (s, 9H), 1.11 (s, 5H). LC/MS (ES+): m/z 552.1 (M+H)+.

4-(((1-(2-(3,5-Dimethylisoxazol-4-yl)ethyl)-1H-1,2,3-triazol-4-yl)methyl)amino)-2-(2,6-dioxopiperidin-3-yl)isoindoline-1,3-dione (Compound 270)

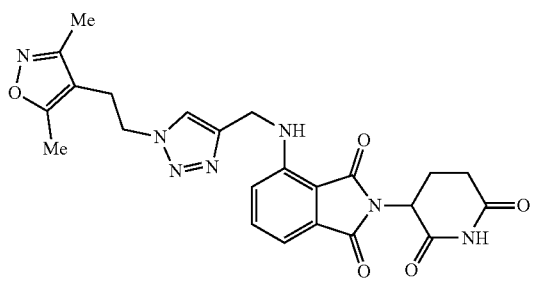 [SMILES: Cc1noc(C)c1CCn1cc(CNc2cccc3c2C(=O)N(C2CCC(=O)NC2=O)C3=O)nn1]

Purified by Method 4. $^1$H NMR (300 MHz, DMSO-d$_6$) δ 11.10 (s, 1H), 7.91 (s, 1H), 7.56 (t, J=7.9 Hz, 1H), 7.12 (s, 1H), 7.11-7.03 (m, 2H), 5.06 (app d, J=12.2 Hz, 1H), 4.57 (s, 2H), 4.43 (t, J=7.1 Hz, 3H), 2.89 (m, 1H), 2.81 (t, J=6.0 Hz, 2H), 2.58 (m, 2H), 2.04 (m, 1H), 1.99 (s, 3H), 1.95 (s, 3H). LC/MS (ES+): m/z 478.1 (M+H)+.

4-(((1-(Azetidin-3-ylmethyl)-1H-1,2,3-triazol-4-yl)methyl)amino)-2-(2,6-dioxopiperidin-3-yl)isoindoline-1,3-dione (Compound 271)

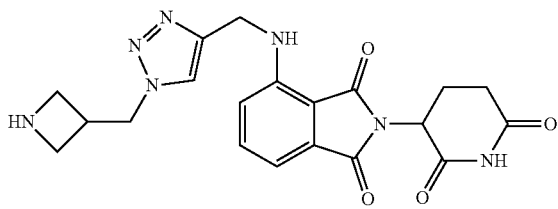 [SMILES: O=C1CCC(N2C(=O)c3cccc(NCc4cn(CC5CNC5)nn4)c3C2=O)C(=O)N1]

Purified by Method 1, then Method 8. LC/MS (ES+): m/z 424.1 (M+H)+.

4-(((1-(2-Aminoethyl)-1H-1,2,3-triazol-4-yl)methyl)amino)-2-(2,6-dioxopiperidin-3-yl)isoindoline-1,3-dione

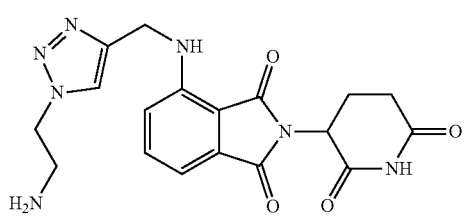

Purified by Method 1. LC/MS (ES+): m/z 397.9 (M+H)+.

Scheme 5
Illustrative Preparation of Click Library from N-Methyl

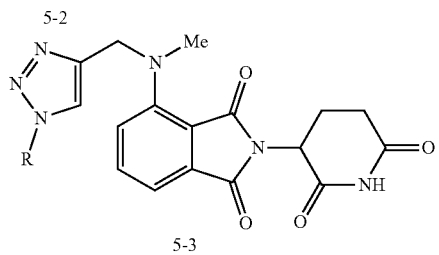

General Procedure:

A solution of alkyne 5-2 (0.0500 mmol) and azide 5-1 (0.0500 mmol) in 500 uL DMSO was treated with CuSO$_4$*5H$_2$O (0.0100 mmol) in water and sodium (R)-2-((S)-1,2-dihydroxyethyl)-4-hydroxy-5-oxo-2,5-dihydrofuran-3-olate (0.0300 mmol). The vial was put under and atmosphere of N2 and stirred at rt. The reaction was filtered to remove copper salts, and purified by prep HPLC.

The following compounds were made according to the general procedure in Scheme 5:

2-(2,6-Dioxopiperidin-3-yl)-4-(methyl((1-(2-(pyridin-2-yl)propyl)-1H-1,2,3-triazol-4-yl)methyl)amino)isoindoline-1,3-dione (Compound 273)

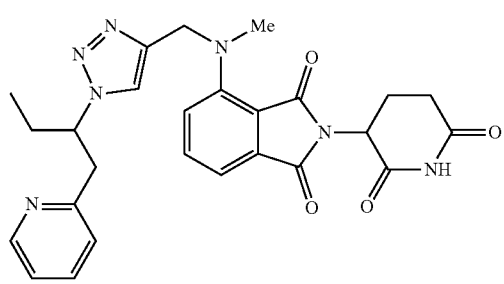 [SMILES: CCC(Cc1ccccn1)n1cc(CN(C)c2cccc3c2C(=O)N(C2CCC(=O)NC2=O)C3=O)nn1]

Purified by Method 2. $^1$H NMR (300 MHz, DMSO-d$_6$) δ 11.10 (s, 1H), 8.54 (s, 1H), 7.83-7.70 (m, 2H), 7.63 (s, 1H), 7.35-7.19 (m, 4H), 5.17-5.06 (m, 1H), 4.68 (s, 2H), 4.64-4.52 (m, 2H), 3.56-3.44 (m, 1H), 2.87 (s, 3H), 2.74-2.55 (m, 2H), 2.33-2.22 (m, 1H), 2.10-1.94 (m, 2H), 1.18 (d, J=7.0 Hz, 3H). LC/MS (ES+): m/z 488.2 (M+H)+.

2-(2,6-Dioxopiperidin-3-yl)-4-(methyl((1-(pyridin-3-yl)-1H-1,2,3-triazol-4-yl)methyl)amino)isoindoline-1,3-dione (Compound 274)

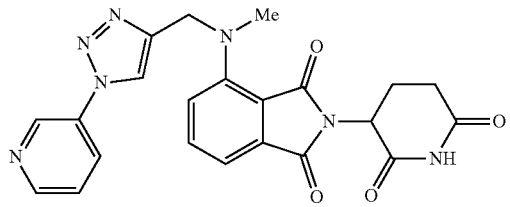 [SMILES: CN(Cc1cn(-c2cccnc2)nn1)c1cccc2c1C(=O)N(C1CCC(=O)NC1=O)C2=O]

Purified by Method 4. ¹H NMR (300 MHz, DMSO-d₆) δ 11.09 (s, 1H), 9.12 (s, 1H), 8.78 (s, 1H), 8.71-8.64 (m, 1H), 8.31 (d, J=8.0 Hz, 1H), 7.70-7.59 (m, 2H), 7.37 (d, J=8.8 Hz, 1H), 7.31 (d, J=7.1 Hz, 1H), 5.18-5.07 (m, 1H), 4.90 (s, 2H), 3.06 (s, 3H), 2.98-2.78 (m, 1H), 2.65-2.53 (m, 2H), 2.11-1.95 (m, 1H). LC/MS (ES+): m/z 446.1 (M+H)⁺.

2-(2,6-Dioxopiperidin-3-yl)-4-(methyl((1-(1-methyl-1H-pyrazol-3-yl)-1H-1,2,3-triazol-4-yl)methyl)amino)isoindoline-1,3-dione (Compound 275)

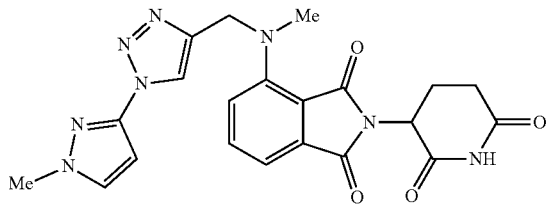 [SMILES: CN(Cc1cn(-c2ccn(C)n2)nn1)c1cccc2c1C(=O)N(C1CCC(=O)NC1=O)C2=O]

Purified by Method 4. ¹H NMR (300 MHz, DMSO-d₆) δ 11.09 (s, 1H), 8.40 (s, 1H), 7.89 (s, 1H), 7.66 (t, J=7.8 Hz, 1H), 7.41-7.27 (m, 2H), 6.67-6.61 (m, 1H), 5.19-5.08 (m, 1H), 4.83 (s, 2H), 3.88 (s, 3H), 3.00 (s, 3H), 2.96-2.80 (m, 1H), 2.66-2.54 (m, 2H), 2.11-1.99 (m, 1H). LC/MS (ES+): m/z 449.1 (M+H)⁺.

4-(((1-((R)-5-Chloro-2,3-dihydro-1H-inden-1-yl)-1H-1,2,3-triazol-4-yl)methyl)(methyl)amino)-2-(2,6-dioxopiperidin-3-yl)isoindoline-1,3-dione (Compound 276)

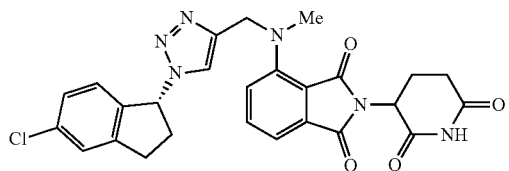 [SMILES: CN(Cc1cn([C@@H]2CCc3cc(Cl)ccc32)nn1)c1cccc2c1C(=O)N(C1CCC(=O)NC1=O)C2=O]

Purified by Method 7. ¹H NMR (300 MHz, DMSO-d₆) δ 11.09 (s, 1H), 7.97 (s, 1H), 7.63 (t, J=7.9 Hz, 1H), 7.44 (s, 1H), 7.36-7.18 (m, 3H), 7.04-6.93 (m, 1H), 6.20-6.12 (m, 1H), 5.15-5.03 (m, 1H), 4.74 (s, 2H), 3.21-3.05 (m, 1H), 3.04-2.80 (m, 6H), 2.77-2.66 (m, 1H), 2.65-2.52 (m, 2H), 2.43-2.34 (m, 1H), 2.11-1.90 (m, 1H). LC/MS (ES+): m/z 519.1 (M+H)⁺.

2-(2,6-Dioxopiperidin-3-yl)-4-(methyl((1-(piperidin-4-yl)-1H-1,2,3-triazol-4-yl)methyl)amino)isoindoline-1,3-dione (Compound 277)

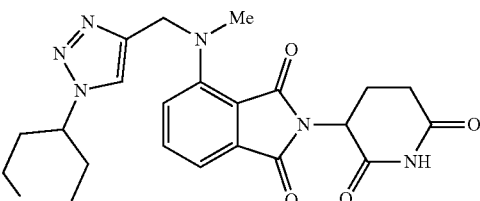

Purified by Method 7. ¹H NMR (300 MHz, DMSO-d₆) δ 11.09 (s, 1H), 8.67 (bs, 1H), 8.40 (bs, 1H), 8.05 (s, 1H), 7.65 (t, J=8.1 Hz, 1H), 7.38-7.25 (m, 2H), 5.18-5.05 (m, 1H), 4.75 (app s, 3H), 3.46-3.35 (m, 2H), 3.18-3.01 (m, 2H), 2.97 (s, 3H), 2.91-2.78 (m, 1H), 2.65-2.54 (m, 2H), 2.32-2.21 (m, 2H), 2.18-1.96 (m, 3H), 1.40 (s, 1H) (TFA salt). LC/MS (ES+): m/z 452.1 (M+H)⁺.

2-(2,6-Dioxopiperidin-3-yl)-4-(methyl((1-(piperidin-4-ylmethyl)-1H-1,2,3-triazol-4-yl)methyl)amino)isoindoline-1,3-dione (Compound 278)

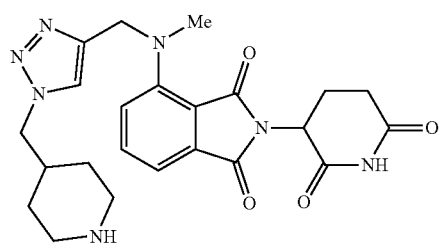 [SMILES: CN(Cc1cn(CC2CCNCC2)nn1)c1cccc2c1C(=O)N(C1CCC(=O)NC1=O)C2=O]

Purified by Method 7. ¹H NMR (300 MHz, DMSO-d₆) δ 11.10 (s, 1H), 8.48 (bs, 1H), 8.16 (bs, 1H), 7.96 (s, 1H), 7.65 (t, J=7.9 Hz, 1H), 7.36-7.24 (m, 2H), 5.17-5.06 (m, 1H), 4.76 (s, 2H), 4.29 (d, J=6.8 Hz, 2H), 3.30-3.17 (m, 2H), 2.97 (s, 3H), 2.93-2.72 (m, 3H), 2.66-2.53 (m, 2H), 2.13-1.99 (m, 2H), 1.62-1.49 (m, 2H), 1.41-1.20 (m, 4H) (TFA salt). LC/MS (ES+): m/z 466.2 (M+H)⁺.

2-(2,6-Dioxopiperidin-3-yl)-4-(((1-(4-fluorobenzyl)-1H-1,2,3-triazol-4-yl)methyl)(methyl)amino)isoindoline-1,3-dione (Compound 279)

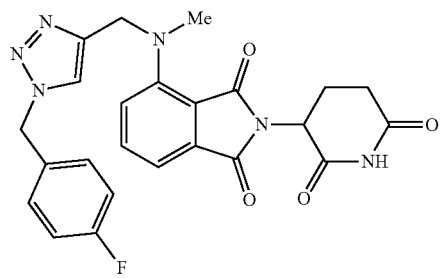 [SMILES: CN(Cc1cn(Cc2ccc(F)cc2)nn1)c1cccc2c1C(=O)N(C1CCC(=O)NC1=O)C2=O]

Purified by Method 6. ¹H NMR (300 MHz, DMSO-d₆) δ 11.09 (s, 1H), 8.03 (s, 1H), 7.63 (t, J=8.0 Hz, 1H), 7.34-7.25

(m, 4H), 7.22-7.13 (m, 2H), 5.55 (s, 2H), 5.16-5.05 (m, 1H), 4.75 (d, J=2.5 Hz, 2H), 2.95 (s, 3H), 2.91-2.80 (m, 1H), 2.64-2.53 (m, 2H), 2.10-1.92 (m, 1H). LC/MS (ES+): m/z 477.1 (M+H)+.

2-(2,6-Dioxopiperidin-3-yl)-4-(methyl((1-(2-morpholinoethyl)-1H-1,2,3-triazol-4-yl)methyl)amino)isoindoline-1,3-dione (Compound 280)

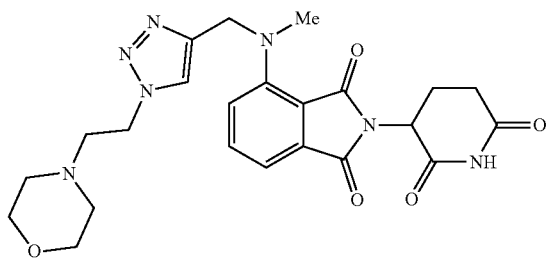

Purified by Method 1. LC/MS (ES+): m/z 482.1 (M+H)+.

2-(2,6-Dioxopiperidin-3-yl)-4-(methyl((1-(((S)-pyrrolidin-2-yl)methyl)-1H-1,2,3-triazol-4-yl)methyl)amino)isoindoline-1,3-dione (Compound 281)

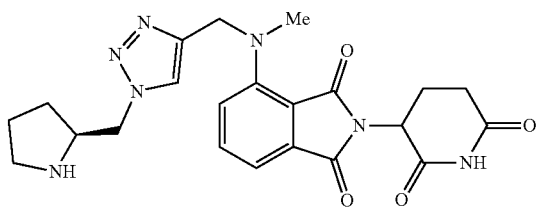

Purified by Method 7. LC/MS (ES+): m/z 452.1 (M+H)+.

2-(2,6-Dioxopiperidin-3-yl)-4-(methyl((1-(piperidin-3-ylmethyl)-1H-1,2,3-triazol-4-yl)methyl)amino)isoindoline-1,3-dione (Compound 282)

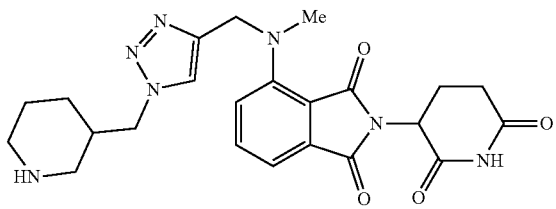

Purified by Method 7. ¹H NMR (300 MHz, DMSO-d$_6$) δ 11.10 (s, 1H), 8.55 (bs, 1H), 8.26 (bs, 1H), 7.98 (s, 1H), 7.65 (t, J=7.6 Hz, 1H), 7.35-7.26 (m, 2H), 5.20-5.01 (m, 1H), 4.75 (s, 2H), 4.31 (d, J=6.7 Hz, 2H), 3.27-3.15 (m, 1H), 3.11-3.01 (m, 1H), 2.96 (s, 3H), 2.92-2.81 (m, 1H), 2.76-2.54 (m, 3H), 2.24-2.11 (m, 1H), 2.09-1.95 (m, 1H), 1.82-1.69 (m, 1H), 1.61-1.47 (m, 2H), 1.33 (s, 1H), 1.17-1.05 (m, 1H) (TFA salt). LC/MS (ES+): m/z 466.2 (M+H)+.

4-(((1-(2-(3,5-Dimethylisoxazol-4-yl)ethyl)-1H-1,2,3-triazol-4-yl)methyl)(methyl)amino)-2-(2,6-dioxopiperidin-3-yl)isoindoline-1,3-dione (Compound 283)

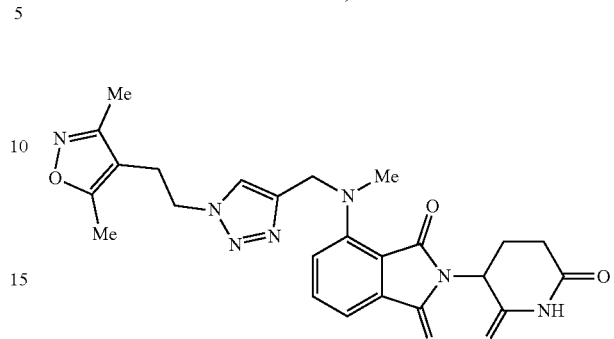

Purified by Method 4. LC/MS (ES+): m/z 492.2 (M+H)+.

2-(2,6-Dioxopiperidin-3-yl)-4-(((1-(2-methoxyethyl)-1H-1,2,3-triazol-4-yl)methyl)(methyl)amino)isoindoline-1,3-dione (Compound 284)

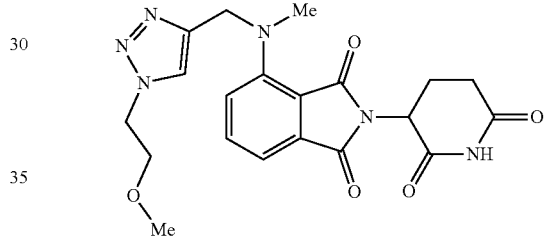

Purified by Method 3. ¹H NMR (300 MHz, DMSO-d$_6$) δ 11.09 (s, 1H), 7.95 (s, 1H), 7.64 (t, J=8.2 Hz, 1H), 7.31 (t, J=9.9 Hz, 2H), 5.11 (d, J=11.8 Hz, 1H), 4.75 (s, 2H), 4.53-4.44 (m, 2H), 3.72-3.63 (m, 2H), 3.18 (s, 3H), 2.97 (s, 3H), 2.92-2.79 (m, 1H), 2.65-2.52 (m, 2H), 2.10-1.98 (m, 1H). LC/MS (ES+): m/z 427.1 (M+H)+.

2-(2,6-Dioxopiperidin-3-yl)-4-(methyl((1-(2-(6-methylpyrazin-2-yl)ethyl)-1H-1,2,3-triazol-4-yl)methyl)amino)isoindoline-1,3-dione (Compound 285)

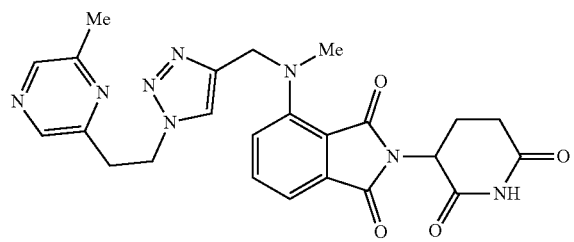 [SMILES: Cc1cncc(CCn2cc(CN(C)c3cccc4c3C(=O)N(C3CCC(=O)NC3=O)C4=O)nn2)n1]

Purified by Method 3. LC/MS (ES+): m/z 489.2 (M+H)+.

543

4-(((1-(2-(2,2-Dichlorocyclopropyl)ethyl)-1H-1,2,3-triazol-4-yl)methyl)(methyl)amino)-2-(2,6-dioxopiperidin-3-yl)isoindoline-1,3-dione (Compound 286)

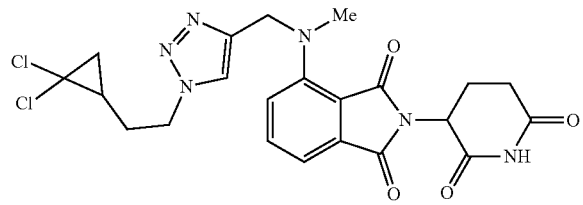 [SMILES: CN(Cc1cn(CCC2CC2(Cl)Cl)nn1)c1cccc2c1C(=O)N(C1CCC(=O)NC1=O)C2=O]

Purified by Method 6. LC/MS (ES+): m/z 505.0 (M+H)$^+$.

3-(4-(((2-(2,6-Dioxopiperidin-3-yl)-1,3-dioxoisoindolin-4-yl)(methyl)amino)methyl)-1H-1,2,3-triazol-1-yl)-N-methylpropanamide (Compound 287)

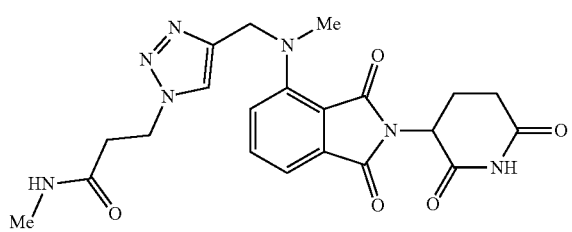 [SMILES: CNC(=O)CCn1cc(CN(C)c2cccc3c2C(=O)N(C2CCC(=O)NC2=O)C3=O)nn1]

Purified by Method 2. LC/MS (ES+): m/z 454.2 (M+H)$^+$.

2-(2,6-Dioxopiperidin-3-yl)-4-(((1-(isoxazol-5-ylmethyl)-1H-1,2,3-triazol-4-yl)methyl)(methyl)amino)isoindoline-1,3-dione (Compound 288)

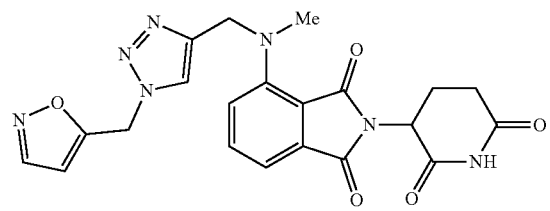

Purified by Method 3. $^1$H NMR (300 MHz, DMSO-d$_6$) δ 11.09 (s, 1H), 8.57 (s, 1H), 8.12 (s, 1H), 7.71-7.51 (m, 1H), 7.31 (t, J=8.6 Hz, 2H), 6.46 (s, 1H), 5.88 (s, 2H), 5.18-5.05 (m, 1H), 4.76 (s, 2H), 2.95 (s, 3H), 2.92-2.79 (m, 1H), 2.65-2.54 (m, 2H), 2.10-1.97 (m, 1H). LC/MS (ES+): m/z 450.1 (M+H)$^+$.

544

2-(2,6-Dioxopiperidin-3-yl)-4-(methyl((1-((tetrahydrofuran-3-yl)methyl)-1H-1,2,3-triazol-4-yl)methyl)amino)isoindoline-1,3-dione (Compound 289)

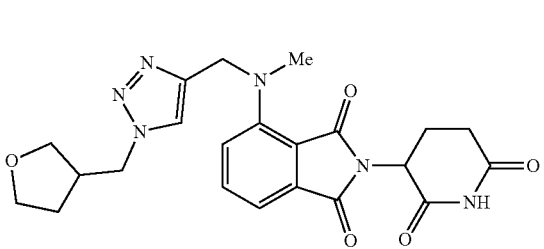

Purified by Method 3. LC/MS (ES+): m/z 453.2 (M+H)$^+$.

4-(((1-(2-Bromoethyl)-1H-1,2,3-triazol-4-yl)methyl)(methyl)amino)-2-(2,6-dioxopiperidin-3-yl)isoindoline-1,3-dione (Compound 290)

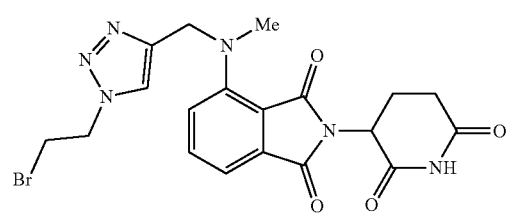

Purified by Method 4. LC/MS (ES+): m/z 475.3 (M+H)$^+$.

Example 3: Illustrative Preparation of Tert-Butyl 3-(4-(2-(tert-butoxy)-2-oxoethoxy)-6-methoxy-1,3-dioxoisoindolin-2-yl)-2,6-dioxopiperidine-1-carboxylate & [2-(2,6-Dioxo-piperidin-3-yl)-6-methoxy-1,3-dioxo-2,3-dihydro-1H-isoindol-4-yloxy]-acetic Acid

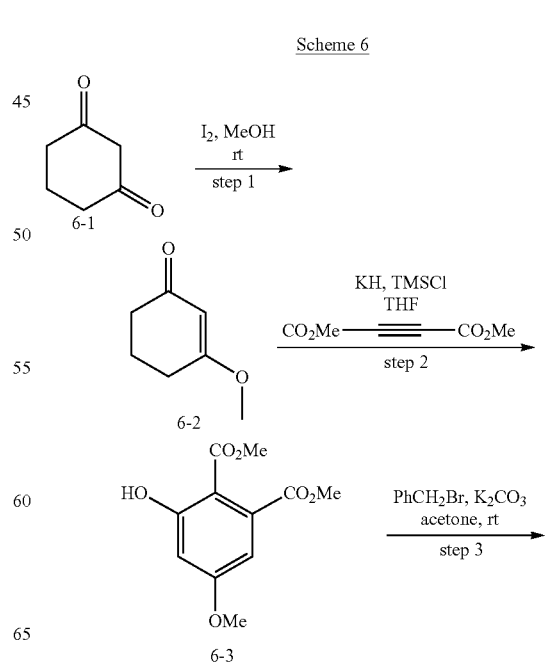

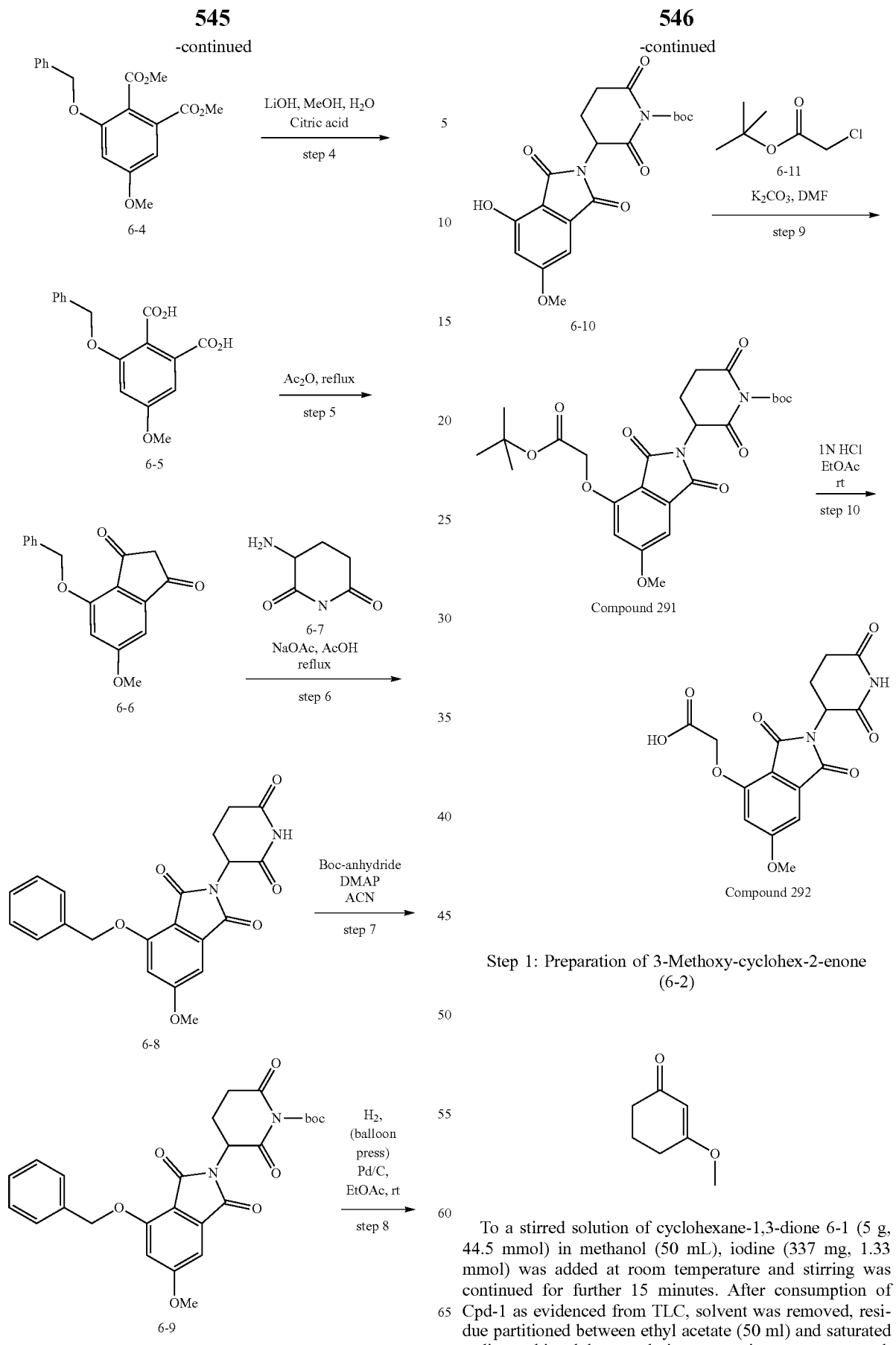

Step 1: Preparation of 3-Methoxy-cyclohex-2-enone (6-2)

To a stirred solution of cyclohexane-1,3-dione 6-1 (5 g, 44.5 mmol) in methanol (50 mL), iodine (337 mg, 1.33 mmol) was added at room temperature and stirring was continued for further 15 minutes. After consumption of Cpd-1 as evidenced from TLC, solvent was removed, residue partitioned between ethyl acetate (50 ml) and saturated sodium thiosulphate solution, organic part separated, washed with water, brine, dried over sodium sulphate and evaporated to afford a crude residue which was purified over neutral alumina (elution with DCM) to afford 3-methoxy-cyclohex-2-enone 6-2 (3.00 g, 23.7 mmol, 53%) as a yellow liquid. LCMS: ES+ 126.8.

Step 2: Preparation of Dimethyl 3-hydroxy-5-methoxyphthalate (6-3)

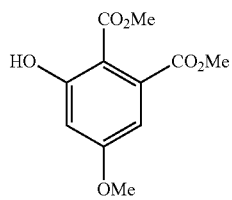 [SMILES: COC(=O)c1cc(OC)cc(O)c1C(=O)OC]

To a stirred suspension of potassium hydride (2.11 g, 15.8 mmol) in dry THF (10 mL) at 0° C. under an inert atmosphere was added a solution of 3-methoxycyclohex-2-enone 6-2 (2 g, 15.8 mmol) in dry THF (10 mL) followed by warming up to room temperature and stirring for further 15 h. The reaction mixture was cooled down to 0° C., treated with freshly distilled chlorotrimethylsilane (1.71 g, 15.8 mmol) in one portion followed by vigorous stirring for 15 minutes. The pale yellow mixture was cooled down to −78° C., dimethyl but-2-ynedioate (2.24 g, 15.8 mmol) was added dropwise, warmed up to 50° C. over a period of 1 h. After an additional hour, the orange colored reaction mixture was diluted with xylene (10 mL), THF was distilled off and the temperature gradually raised to 120° C. After stirring at the same temperature for 12 hrs, the reaction mixture was cooled, extracted with ether (2×50 mL), combined organic extracts washed with water, concentrated to afford a crude residue, which was purified by flash chromatography (elution with 10% ethyl-acetate in hexane) to obtain the desired product, dimethyl 3-hydroxy-5-methoxyphthalate 6-3 (750 mg, 3.12 mmol, 19.7%) as a light yellow solid. GCMS: m/z 240.0.

Step 3: Preparation of 3-Benzyloxy-5-methoxy-phthalic Acid Dimethyl Ester (6-4)

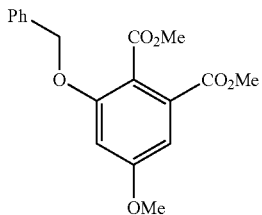 [SMILES: COC(=O)c1cc(OC)cc(OCc2ccccc2)c1C(=O)OC]

A stirred solution of dimethyl 3-hydroxy-5-methoxyphthalate 6-3 (650 mg, 2.70 mmol) in dry DMF (2 mL) was treated with benzyl bromide (554 mg, 3.24 mmol) and the mixture was heated at 80° C. for 30 minutes in presence of potassium carbonate (1.11 g, 8.10 mmol). After consumption of Cpd-3 as evident from TLC, the reaction mixture was partitioned between ethylacetate (2×20 mL) and ice cold water. The combined organic extracts were concentrated, residual crude purified by flash chromatography to obtain dimethyl 3-(benzyloxy)-5-methoxyphthalate 6-4 (650 mg, 1.96 mmol, 72.9%) as a sticky yellow solid. LCMS: ES+ 331.1.

Step 4: Preparation of 3-Benzyloxy-5-methoxy-phthalic Acid (6-5)

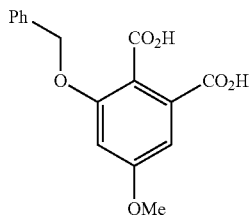 [SMILES: COc1cc(OCc2ccccc2)c(C(=O)O)c(C(=O)O)c1]

A stirred solution of dimethyl 3-(benzyloxy)-5-methoxyphthalate 6-4 (650 mg, 1.96 mmol) in mixture of MeOH-Water (3:1, v/v, 9 mL) at RT was hydrolysed with lithium hydroxide (213 mg, 5.09 mmol). After completion consumption of Cpd-4 as ensured by LCMS, the volatiles were stripped off and the residue acidified with saturated citric acid solution, extracted with ethyl acetate, organic extracts dried over sodium sulphate and evaporated to obtain 3-(benzyloxy)-5-methoxyphthalic acid 6-5 (350 mg, 1.15 mmol, 59.1%) as a white solid which was used in next step without further purification. LCMS: ES+ 301.1.

Step 5: Preparation of 4-Benzyloxy-6-methoxy-isobenzofuran-1,3-dione (6-6)

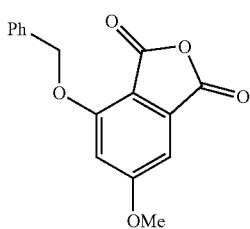 [SMILES: COc1cc(OCc2ccccc2)c2c(c1)C(=O)OC2=O]

A mixture of 3-(benzyloxy)-5-methoxyphthalic acid 6-5 (200 mg, 661 µmol) and acetic anhydride (2 mL) was heated at 80° C. for 1 h. The volatiles were stripped off to afford 4-(benzyloxy)-6-methoxyisobenzofuran-1,3-dione 6-6 (140 mg, 492 µmol, 74.8%) as a white solid, which was used in the next step without further purification. $^1$H NMR (400 MHz, DMSO-$d_6$) δ 7.50 (d, J=6.8 Hz, 2H), 7.43 (t, J=7 Hz, 2H), 7.38-7.36 (m, 1H), 7.17 (br s, 1H), 7.14 (br s, 1H), 5.38 (s, 2H), 3.95 (s, 3H).

Step 6: Preparation of 4-Benzyloxy-2-(2,6-dioxo-piperidin-3-yl)-6-methoxy-isoindole-1,3-dione (6-8)

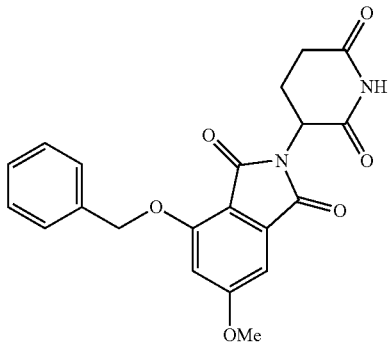 [SMILES: COc1cc(OCc2ccccc2)c2c(c1)C(=O)N(C1CCC(=O)NC1=O)C2=O]

To a stirred solution of 4-(benzyloxy)-6-methoxyisobenzofuran-1,3-dione 6-6 (300 mg, 1.05 mmol) in acetic acid (3 mL), sodium acetate (52.2 mg, 1.26 mmol) was added followed by the addition of 3-aminopiperidine-2,6-dione 6-7 (161 mg, 1.26 mmol). The reaction mixture was warmed at 100° C. for 40 minutes. After consumption of Cpd-6 as evident from TLC, the reaction mass was partitioned between ethyl acetate (3×10 mL) and saturated sodium bicarbonate, combined organic extracts dried over sodium sulfate, concentrated to afford a crude residue which was purified by column chromatography to afford 4-(benzyloxy)-2-(2,6-dioxopiperidin-3-yl)-6-methoxyisoindoline-1,3-dione 6-8 (270 mg, 684 μmol, 65.2%) as a pale yellow sticky solid. LCMS: ES+ 395.1.

Step 7: Preparation of 3-(4-Benzyloxy-6-methoxy-1,3-dioxo-1,3-dihydro-isoindol-2-yl)-2,6-dioxo-piperidine-1-carboxylic Acid Tert-Butyl Ester (6-9)

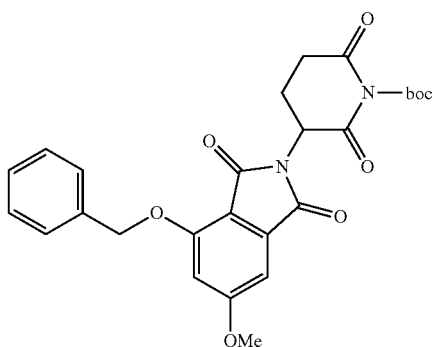

A stirred solution 4-(benzyloxy)-2-(2,6-dioxopiperidin-3-yl)-6-methoxyisoindoline-1,3-dione 6-8 (260 mg, 659 μmol) in acetonitrile (8 mL) at 0° C. was treated with Boc anhydride (157 mg, 724 μmol) in presence of catalytic amount of DMAP. The reaction mixture was warmed to room temperature and stirred for further 30 minutes. After consumption of Cpd-8 as evidenced from TLC, the solvent was evaporated, the crude reaction mass was partitioned between ethyl acetate and water, combined organic extracts dried over sodium sulfate and concentrated to afford a crude residue which was purified by column chromatography (elution with 20% ethyl acetate in hexane) to afford tert-butyl 3-(4-(benzyloxy)-6-methoxy-1,3-dioxoisoindolin-2-yl)-2,6-dioxopiperidine-1-carboxylate 6-9 (250 mg, 505 μmol, 76.9%) as a yellow solid. LCMS: calculated for [M+H−boc]+ 395.3; found 395.1.

Step 8: Preparation of 3-(4-Hydroxy-6-methoxy-1, 3-dioxo-1, 3-dihydro-isoindol-2-yl)-2, 6-dioxo-piperidine-1-carboxylic Acid Tert-Butyl Ester (6-10)

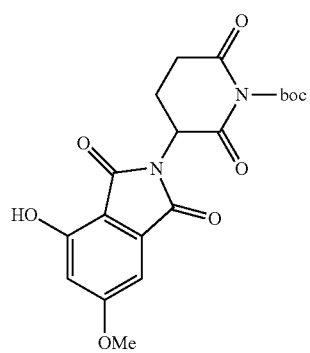

A solution of tert-butyl 3-(4-(benzyloxy)-6-methoxy-1,3-dioxoisoindolin-2-yl)-2,6-dioxopiperidine-1-carboxylate 6-9 (250 mg, 505 μmol) in ethyl acetate (8 mL) was hydrogenated under 1 atm in presence of palladium-carbon (17.1 mg, 161 μmol, 0.5 mol %). After consumption of Cpd-8 as evidenced from TLC, the reaction mixture was filtered over a Celite bed, filtrate concentrated to afford tert-butyl-3-(4-hydroxy-6-methoxy-1,3-dioxoisoindolin-2-yl)-2,6-dioxopiperidine-1-carboxylate 6-10 (150 mg, 370 μmol, 73.5%) as a white solid. LCMS: ES+403.9.

Step 9: Preparation of Tert-Butyl 3-(4-(2-(tert-butoxy)-2-oxoethoxy)-6-methoxy-1,3-dioxoisoindolin-2-yl)-2,6-dioxopiperidine-1-carboxylate (Compound 291)

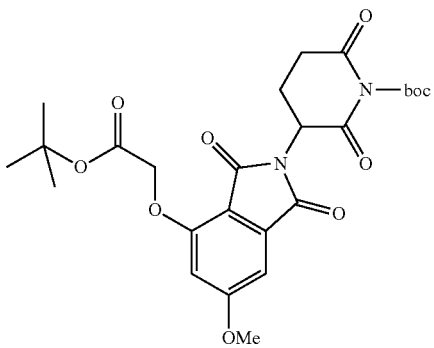

To the stirred solution of dimethyl 3-hydroxy-5-methoxyphthalate 6-10 (650 mg, 2.70 mmol) in dry DMF (2 mL) was treated with tertiary butyl chloroacetate (61.2 mg, 407 μmol) in presence of K$_2$CO$_3$ (152 mg, 1.10 mmol) followed by stirring at room temperature for 2 hr. After completion of reaction as evidenced from TLC, the reaction mixture was partitioned between ethyl acetate (2×20 mL) and ice cold water, combined organic extracts concentrated and the resulting crude was purified by column chromatography to afford tert-butyl 3-(4-(2-(tert-butoxy)-2-oxoethoxy)-6-methoxy-1,3-dioxoisoindolin-2-yl)-2,6-dioxopiperidine-1-carboxylate Compound 291 (100 mg, 192 μmol, 52.3%) as a white solid. $^1$H NMR (400 MHz, DMSO-d$_6$) δ 7.07 (s, 1H), 6.83 (s, 1H), 5.34 (d, J=10.5 Hz, 1H), 4.97-4.95 (m, 2H), 3.92-3.90 (m, 3H), 3.09-3.07 (m, 1H), 2.79-2.57 (m, 2H), 2.08-2.01 (m, 1H), 1.48 (s, 8H), 1.43 (s, 10H); LCMS: calculated for [M+H−boc]$^+$ 419.4; found 419.1.

Step 10: Preparation of 2-((2-(2, 6-dioxopiperidin-3-yl)-6-methoxy-1, 3-dioxoisoindolin-4-yl)oxy)acetic Acid (Compound 292)

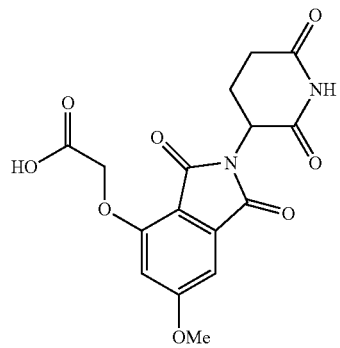 [SMILES: COc1cc(OCC(=O)O)c2c(c1)C(=O)N(C1CCC(=O)NC1=O)C2=O]

A solution of tert-butyl 3-(4-(2-(tert-butoxy)-2-oxoethoxy)-6-methoxy-1,3-dioxoisoindolin-2-yl)-2,6-dioxopiperidine-1-carboxylate Compound 291 (80 mg, 154 μmol) in ethyl acetate was treated with 1N HCl (1:1 v/v, 10 mL) and the mixture stirred at room temperature for 16 hrs. After consumption of Cpd-12 as evidenced from TLC and LCMS, reaction mass was concentrated the crude was purified by prep HPLC to afford 2-((2-(2,6-dioxopiperidin-3-yl)-6-methoxy-1,3-dioxoisoindolin-4-yl)oxy)acetic acid Compound 292 (25.0 mg, 69.0 μmol, 44.8%) as a white solid. $^1$H NMR (400 MHz, DMSO-d$_6$) δ 13.41 (brs, 1H), 11.09 (s, 1H), 7.05 (s, 1H), 6.82 (s, 1H), 5.07 (d, J=8.9 Hz, 1H), 4.95 (s, 2H), 3.91 (s, 3H), 2.89-2.85 (m, 1H), 2.60-2.55 (m, 1H), 2.03-2.00 (m, 2H). LCMS: calculated for [M+H]$^+$ 363.3; found 363.2; calculated for [M+Na]$^+$ 385.2; found 385.2.

Example 4: Illustrative Preparation of Thalidomide Analogs

Compound 293

Compound 294

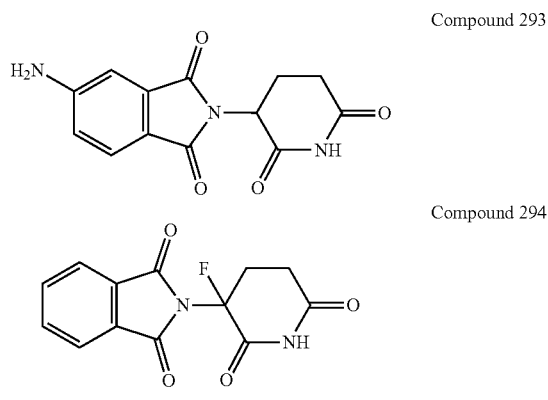

Scheme 7
N-Methylation of Imide

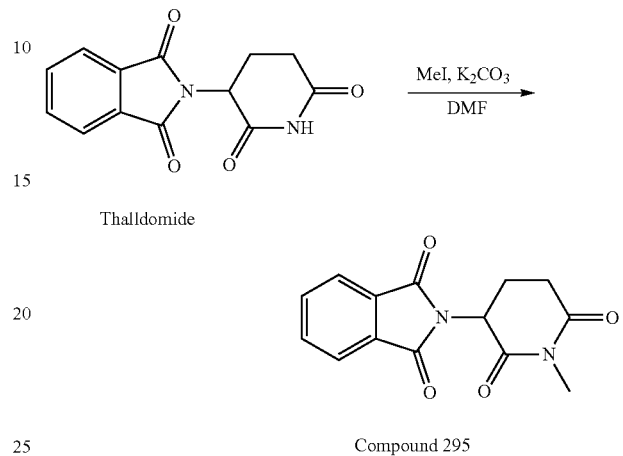

A 20 mL scintillation flask under N$_2$ was charged with 2-(2,6-dioxopiperidin-3-yl)isoindoline-1,3-dione (500 mg, 1.93 mmol) and the reaction mixture was diluted with N,N-dimethylformamide (5 mL 1.93 mmol) The solution was cooled to 0° C., iodomethane (143 μL, 2.31 mmol) and Potassium Carbonate (533 mg, 3.86 mmol) was added sequentially and the reaction was stirred to rt for 12 h. The reaction was filtered, concentrated; residue was purified via Isco 0-5% MeOH/DCM (40 g column, 16 CV) to provide 2-(1-methyl-2,6-dioxopiperidin-3-yl)isoindoline-1,3-dione Compound 295 (380 mg, 1.39 mmol, 72.3%). $^{13}$C NMR (400 MHz, DMSO-d$_6$) δ 171.55, 169.41, 166.99, 134.76, 131.12, 123.29, 49.49, 30.98, 26.47, 21.08. LCMS: m/z 273.2 [M+H]$^+$.

Example 5: Illustrative Preparation of Lenolidomide Analogs

Scheme 8
Preparation of 3-(4-Bromo-1-oxoisoindolin-2-yl)piperidine-2,6-dione (Compound 296)

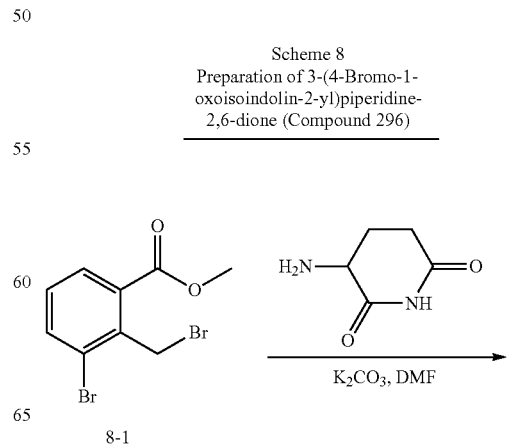

8-1

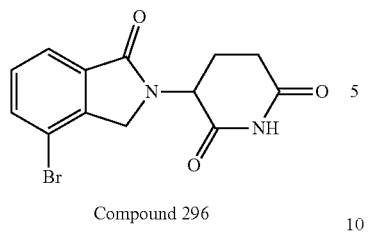

Compound 296

To a mixture of methyl 3-bromo-2-(bromomethyl)benzoate 8-1 (500 mg, 1.62 mmol) 3-aminopiperidine-2,6-dione (248 mg, 1.94 mmol) and potassium carbonate (279 mg, 2.02 mmol) in DMF (2.5 mL) being heated to 45° C. The mixture was left standing overnight. LCMS showed the reaction. The reaction mixture was stirred for 2 hours at 45° C. and cooled to 20° C. to 25° C. De-ionized water (2.5 ml) was added to the reaction mixture at 20° C. to 25° C. and stirred for 15 minutes to 20 minutes. The solid obtained was filtered, washed with de-ionized water (2×5 ml) and dried under vacuum at 40° C. to 45° C. for 20 hours to obtain Compound 296 3-(4-bromo-1-oxoisoindolin-2-yl)piperidine-2,6-dione (2.80 g, 8.66 mmol) as white solid. 1H NMR (500 MHz, DMSO-d6): δ 11.02 (s, 1H), 7.88 (d, J=8 Hz, 1H), 7.78 (d, J=7.5 Hz, 1H), 7.53 (t, J=7.5 Hz, 1H), 5.17-5.13 (m, 1H), 4.44 (d, J=18 Hz, 1H), 4.28 (d, J=18, 1H), 2.95-2.88 (m, 1H), 2.62 (d, J=1.5, 1H), 2.51-2.46 (m, 1H), 2.04-2.01 (m, 1H). ES-MS (m/z): 322.91 (M+H+).

Scheme 9
Preparation of Compounds 297 and 298.

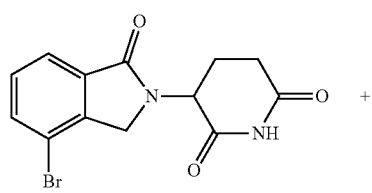

Compound 296

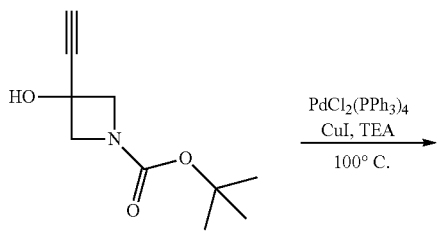

9-1

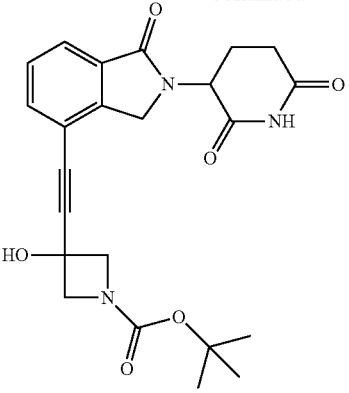

Compound 297

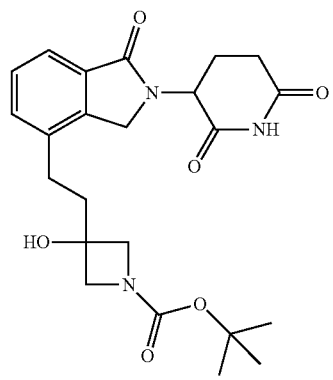

Compound 298

Step 1: Compound 297

Brought tert-butyl 3-ethynyl-3-hydroxy-azetidine-1-carboxylate (274.66 mg, 1.39 mmol), 3-(4-bromo-1-oxo-isoindolin-2-yl)piperidine-2,6-dione Compound 296 (0.15 g, 464.19 umol) Copper (I) iodide (8.84 mg, 46.42 umol, 1.57 uL) and Bis(Triphenylphosphine)palladium (II) chloride (16.29 mg, 23.21 umol) up in TEA (4.64 mL) which was freshly purged with Ar for 120 minutes. The MW vial was then sealed and heated in the MW reactor for 4 hours at 100° C. The reaction was then concentrated and purified by reversed phase isco 10-100% ACN/Water w 0.1% TFA to give tert-butyl 3-[2-[2-(2,6-dioxo-3-piperidyl)-1-oxo-isoindolin-4-yl]ethynyl]-3-hydroxy-azetidine-1-carboxylate Compound 297 (15 mg, 34.13 umol, 7.35% yield). LC/MS (ES−): m/z 438.3 [M−H]−.

Step 2: Compound 298 tert-Butyl 3-((2-(2,6-dioxopiperidin-3-yl)-1-oxoisoindolin-4-yl)ethynyl)-3-hydroxyazetidine-1-carboxylate (Compound 297) (5.0 mg, 0.01137 mmol) was brought up in EtOH (2 mL), added wet 5% Pd/C (10.0 mg) and then put reaction under a hydrogen balloon. Stirred at r.t. overnight. Filtered over celite and concentrated. Purified by reversed phase isco 10-100% ACN/water w 0.1% TFA. Isolated tert-butyl 3-(2-(2-(2,6-dioxopiperidin-3-yl)-1-oxoisoindolin-4-yl) ethyl)-3-hydroxyazetidine-1-carboxylate (Compound 298) (1.40 mg, 0.003156 mmol, 27.7%) as a white solid. LC/MS (ES−): m/z 442.2 [M−H]−.

Scheme 10: Preparation of Compounds 299 and 300.

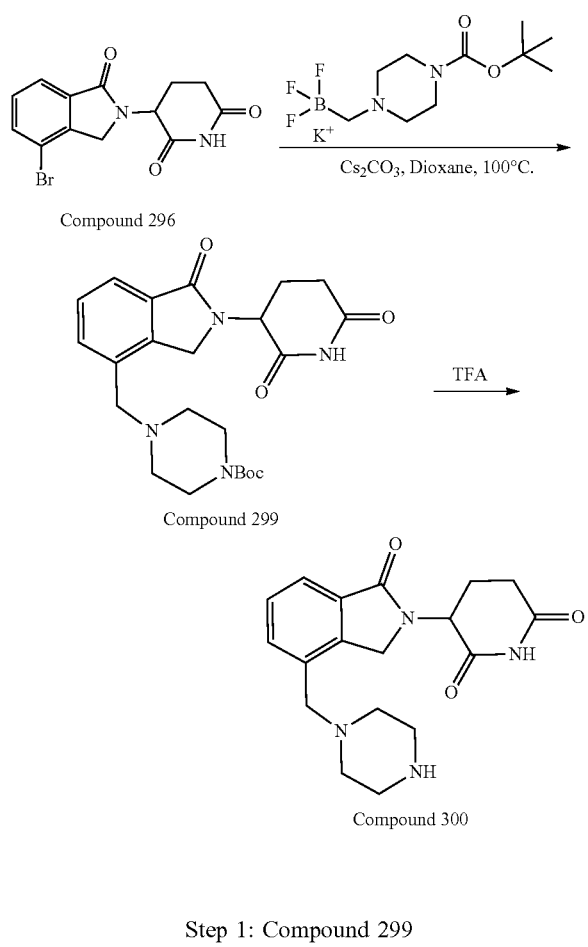

Step 1: Compound 299

To a solution of 3-(4-bromo-1-oxoisoindolin-2-yl)piperidine-2,6-dione Compound 296 (0.500 g, 1.54 mmol), potassium ((4-(tert-butoxycarbonyl)piperazin-1-yl)methyl)trifluoroborate (563 mg, 1.84 mmol) and Cesium carbonate (1.50 g, 4.62 mmol) were taken up in Dioxane (8 mL) and water (2 mL) The reaction mixture was bubbled with argon through solvents for 10 minutes. n-butyl diadamantyl phosphine (110 mg, 308 µmol) and palladium acetate (34.5 mg, 154 µmol) were added and the vial was purged with Ar and sealed. The reaction was stirred at 100° C. for 16 h, The reaction progress was monitored by TLC and LCMS.er TLC showed consumption of SM, the reaction mixture was cooled to room temperature and quenched by adding water (25 mL). The mixture was extracted with Ethyl Acetate (50 mL×3). The organic layer was dried over anhydrous sodium sulfate, filtered and concentrated. The crude product was purified by flash column chromatography using 12.0 g redisef and eluted with Methanol in DCM (3%-5%) to obtain tert-butyl 4-((2-(2,6-dioxopiperidin-3-yl)-1-oxoisoindolin-4-yl)methyl)piperazine-1-carboxylate Compound 299 (400 mg, 903 µmol, 58.7%) as a grey solid. $^1$H NMR (400 MHz, DMSO-d6) δ 1.38 (s, 9H), 1.99-2.04 (m, 1H), 2.27-2.38 (m, 4H), 2.57-2.64 (m, 2H), 2.80-2.88 (m, 1H), 2.91-3.33 (m, 4H), 3.58 (s, 2H), 4.36 (d, J=17.2 Hz, 1H), 4.53 (d, J=16.8 Hz, 1H) 5.14 (dd, J=13.2 Hz & 4.8 Hz, 1H), 7.48 (t, J=8.0 Hz, 1H), 7.53 (d, J=8.0 Hz, 1H), 7.63 (d, J=8.0 Hz, 1H), 10.99 (s, 1H). ES-MS (m/z): 443.05 (M+H$^+$).

Step 2: Compound 300

To a RB flask tert-butyl 4-((2-(2,6-dioxopiperidin-3-yl)-1-oxoisoindolin-4-yl)methyl)piperazine-1-carboxylate Compound 299 (0.350 g, 0.7909 mmol) in DCM (6 mL) was added under nitrogen atmosphere at RT. To the reaction mixture 25% TFA in DCM (5 mL) was added dropwise at 0° C. and stirred the reaction mixture for 2 hours at RT. After completion of the starting material the reaction mixture was concentrated by using rota vapour. The residue was triturated by diethyl ether (15 mL) to get Compound 300 TFA salt (0.30 g, 0.8771 mmol, 100.0%) as an off white solid. To a RB flask the TFA salt (0.030 g, 87.7 µmol) was added in DCM (5 mL). potassium carbonate (60.4 mg, 438 µmol) was added to the reaction mixture. Stirred the reaction mixture for 1 hour at RT. Filtered the reaction mixture by using sintered to get 3-(1-oxo-4-(piperazin-1-ylmethyl)isoindolin-2-yl)piperidine-2,6-dione Compound 300 (15.0 mg, 43.8 µmol, 50.0%) as a desired product. $^1$H NMR (400 MHz, DMSO-d6) δ 1.99-2.04 (m, 1H), 2.18-2.26 (m, 4H), 2.38-2.43 (m, 1H), 2.55-2.62 (m, 1H), 2.61-2.68 (m, 4H), 2.80-2.92 (m, 1H), 3.50 (s, 2H), 4.37 (d, J=17.6 Hz, 1H), 4.47 (d, J=18 Hz, 1H), 5.12 (dd, J=12.8 Hz & 4.8 Hz, 1H), 7.44 (t, J=6.8 Hz, 1H), 7.50 (d, J=8.0 Hz, 1H), 7.60 (d, J=8.0 Hz, 1H). ES-MS (m/z): 343.24 (M+H$^+$).

Scheme 11

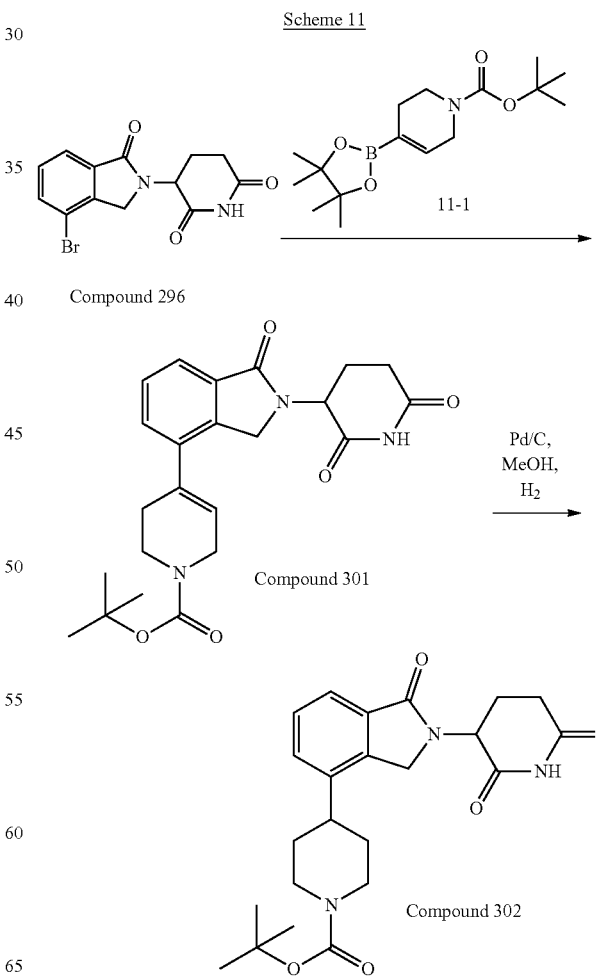

Step 1: Compound 301

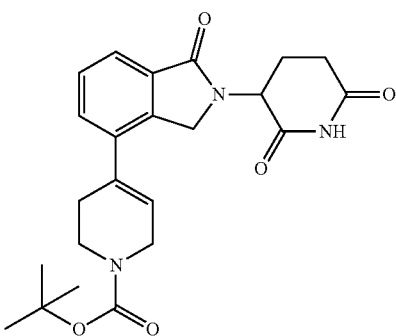 [SMILES: CC(C)(C)OC(=O)N1CC=C(c2cccc3c2CN(C2CCC(=O)NC2=O)C3=O)CC1]

To a solution of 3-(4-bromo-1-oxoisoindolin-2-yl)piperidine-2,6-dione Compound 296 (1 g, 3.09 mmol), tert-butyl 4-(4,4,5,5-tetramethyl-1,3,2-dioxaborolan-2-yl)-5,6-dihydropyridine-1(2H)-carboxylate 11-1 (1.14 g, 3.70 mmol), cesium carbonate (3.01 g, 9.27 mmol) and Dioxane (8 mL) and WATER (2 mL) in (4:1), purged nitrogen for 10 min. Then added Pd(OAc)$_2$ (69.3 mg, 309 µmol) n-butyl diadamantyl phosphine (221 mg, 618 µmol) and sealed the cap. stirred the reaction at 100° C. for 1 h. The reaction progress was monitored by TLC. After completion of reaction quenched the reaction with water (20 mL) and extracted with ethyl acetate (10 mL×3). Combined the organic layers and dried over anhydrous sodium sulfate, filtered and distilled, washing with pentane (10 mL×3) was given to obtain tert-butyl 4-(2-(2,6-dioxopiperidin-3-yl)-1-oxoisoindolin-4-yl)-5,6-dihydropyridine-1(2H)-carboxylate (Compound 301) (500 mg, 1.17 mmol, 38.1%) as off white solid. $^1$H NMR (400 MHz, DMSO-d6) δ 1.43 (s, 9H), 1.89-1.99 (m, 2H), 2.36-2.45 (m, 1H), 2.49-2.68 (m, 2H), 2.87-2.95 (m, 1H), 3.53-3.56 (m, 2H), 4.00 (bs, 2H), 4.37 (d, J=17.2 Hz, 1H), 4.55 (d, J=17.6 Hz, 1H), 5.15 (dd, J=13.2 Hz & 5.2 Hz, 1H), 6.02 (bs, 1H), 7.50-7.57 (m, 2H), 7.65 (d, J=7.2 Hz, 1H), 11.00 (s, 1H). LC/MS (ES+): m/z 426.16 [M+H]$^+$.

Step 2: Compound 302

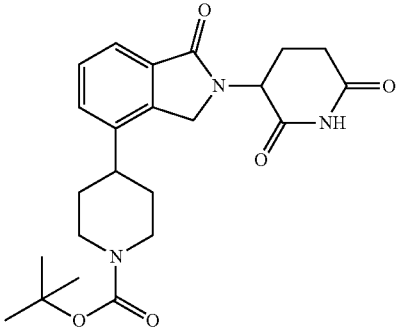 [SMILES: CC(C)(C)OC(=O)N1CCC(c2cccc3c2CN(C2CCC(=O)NC2=O)C3=O)CC1]

To a solution of tert-butyl 4-(2-(2,6-dioxopiperidin-3-yl)-1-oxoisoindolin-4-yl)-5,6-dihydropyridine-1(2H)-carboxylate (Compound 301) (50 mg, 117 µmol) in METHANOL (2.5 mL), DMF (0.5 mL) added 10% Pd/C (0 µg, 0 µmol) and hydrogenated the reaction using balloon pressure for 1 h. The reaction was monitored by TLC, filtered the RM via celite bed and distilled the filterate, washing from diethyl ether (5 mL×3) was given to obtain tert-butyl 4-(2-(2,6-dioxopiperidin-3-yl)-1-oxoisoindolin-4-yl)piperidine-1-carboxylate Compound 302 (15.0 mg, 35.0 µmol, 30.0%) as white solid. $^1$H NMR (400 MHz, DMSO-d6) δ 1.42 (s, 9H), 1.48-1.62 (m, 2H), 1.72-1.78 (m, 2H), 1.95-2.05 (m, 1H), 2.35-2.48 (m, 2H), 2.57-2.68 (m, 1H), 2.77-2.82 (m, 2H), 2.89-2.97 (m, 1H), 4.05-4.15 (m, 2H), 4.36 (d, J=17.2 Hz, 1H), 4.53 (d, J=16.8 Hz, 1H), 5.14 (dd, J=13.2 Hz & 4.8 Hz, 1H), 7.47 (t, J=8.0 Hz, 1H), 7.53 (d, J=8.0 Hz, 1H), 7.58 (d, J=8.0 Hz, 1H), 11.01 (s, 1H). LC/MS (ES+): m/z 428.12 [M+H]$^+$.

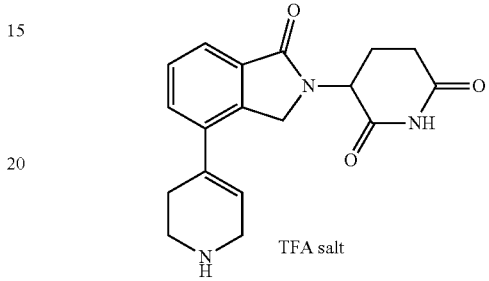
TFA salt

Compound 303 was prepared by following procedure in scheme 10. Yield 86.9% as light brown solid. $^1$H NMR (400 MHz, DMSO-d6) δ 2.01-2.04 (m, 1H), 2.33-2.40 (m, 1H), 2.42-2.66 (m, 3H), 2.90-2.98 (m, 1H), 3.35 (bs, 2H), 3.77 (bs, 2H) 4.37(d, J=17.2 Hz, H), 4.56 (d, J=17.2 Hz, 1H), 5.18 (dd, J=13.2 Hz & 5.2 Hz, 1H), 6.04 (bs, 1H), 7.55-7.62 (m, 2H), 7.71 (d, J=6.8 Hz, 1H), 11.05 (s, 1H). ES-MS (m/z): 326.22 (M+H$^+$-TFA).

Scheme 12

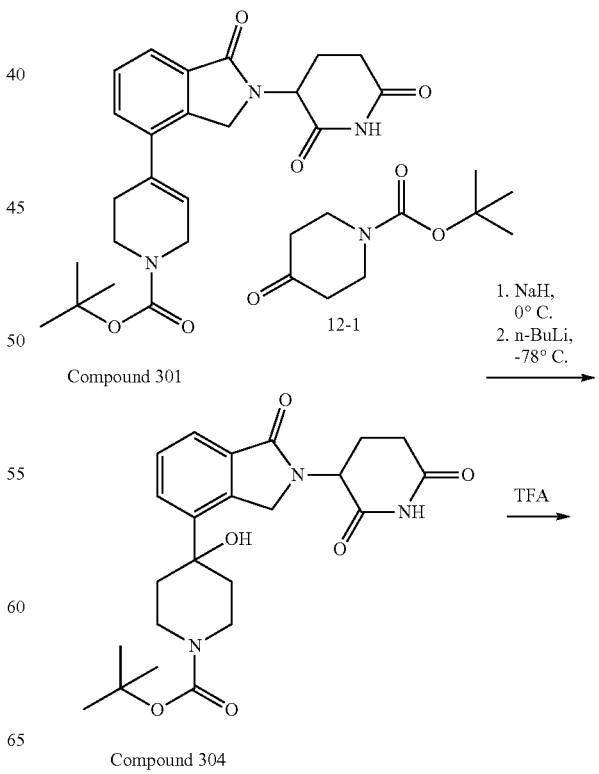

559
-continued

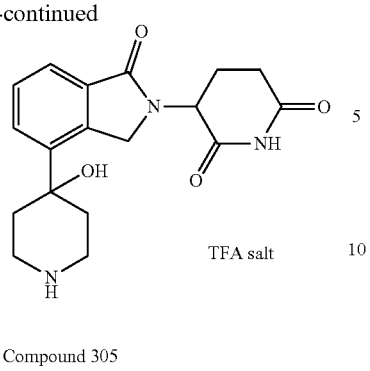

Compound 305

Step 1: Compound 304

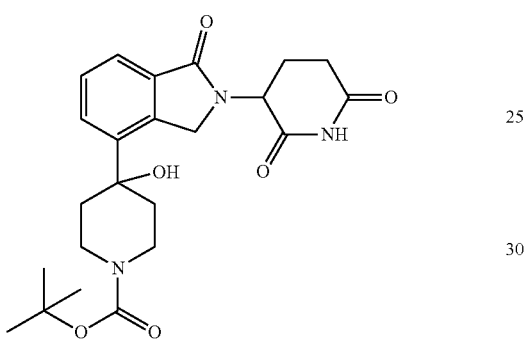

To solution of 3-(4-bromo-1-oxoisoindolin-2-yl)piperidine-2,6-dione Compound 301(1.0 g, 3.09 mmol), tert-butyl 4-oxopiperidine-1-carboxylate (1.53 g, 7.72 mmol) in dry Tetrahydrofuran (20 mL), Sodium hydride (123 mg, 3.09 mmol) was added at 0° C. and the reaction mixture was stirred at same temperature for 1 h. Then the reaction mixture was evacuated and back filled with nitrogen to remove hydrogen gas. Then n-Butyl Lithium (6.16 mL, 15.4 mmol) was added at −78° C. and stirred for another 16 h at rt. The reaction progress was monitored by TLC and LCMS. TLC and LCMS showed product formation along with starting material and debrominated product. The reaction mixture was quenched saturated aqueous ammonium chloride solution (20 mL) and extracted with ethylacetate (100.0 mL×3). The organic layers were dried over anhydrous sodium sulfate, filtered and concentrated to afford crude product. The crude product was purified by flash column chromatography on combi-flash instrument (using 12.0 g Redisef) and eluted with 4% to 5% methanol in DCM to get tert-butyl 4-(2-(2,6-dioxopiperidin-3-yl)-1-oxoisoindolin-4-yl)-4-hydroxypiperidine-1-carboxylate Compound 304 (190 mg, 428 μmol, 13.8%) as brown solid. $^1$H NMR (400 MHz, DMSO-d6) δ 1.38 (s, 9H), 1.69-1.79 (m, 3H), 1.90-2.01 (m, 2H), 2.42-2.50 (m, 2H), 2.50-2.66 (m, 2H), 2.87-2.90 (m, 1H), 3.12-3.33 (m, 2H), 3.87(bs, 2H) 4.59 (d, J=18.0 Hz, 1H), 4.70 (d, J=18.0 Hz, 1H), 5.13 (dd, J=13.2 Hz & 4.8 Hz, 1H), 5.32 (s, 1H), 7.47 (t, J=8.0 Hz, 1H), 7.53 (d, J=8.0 Hz, 1H), 7.58 (d, J=8.0 Hz, 1H), 11.01(s, 1H). ES-MS (m/z): 444.27 (M+H$^+$).

Step 2: Compound 305

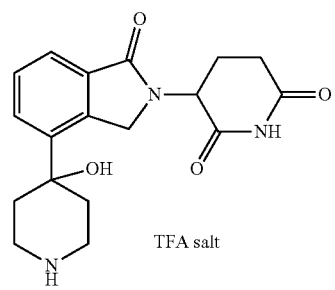 [SMILES: O=C1CCC(N2Cc3c(cccc3C3(O)CCNCC3)C2=O)C(=O)N1]

Compound 305 was prepared by following procedure in scheme 10. Yield 87.8% as light brown solid. $^1$H NMR (400 MHz, DMSO-d6) δ 1.87-1.99 (m, 1H), 2.01-2.04 (m, 2H), 2.32-2.37 (m, 1H), 2.41-2.42 (m, 2H), 2.49-2.58 (m, 3H), 2.92-2.99 (m, 1H), 3.24-3.37 (m, 1H), 4.59 (d, J=18.0 Hz, 1H), 4.70 (d, J=18.0 Hz, 1H), 5.16 (dd, J=13.2 Hz & 4.8 Hz, 1H), 5.69 (s, 1H), 7.52-7.58 (m, 2H), 7.64-7.67 (m, 1H), 11.01 (s, 1H). ES-MS (m/z): 344.21 (M+H$^+$-TFA).

Scheme 13

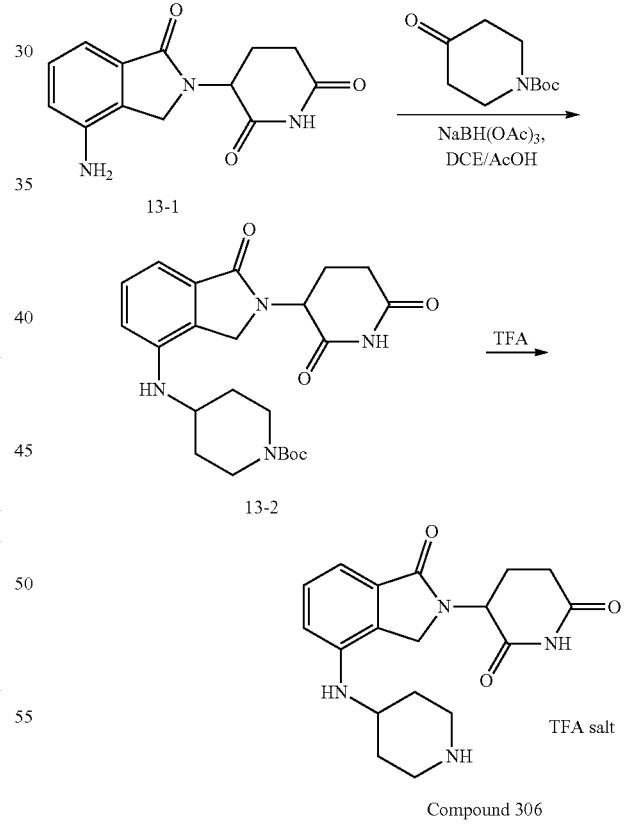

Step 1: 13-2

Brought tert-butyl 4-oxopiperidine-1-carboxylate (76.8 mg, 0.3856 mmol) and 3-(4-amino-1-oxoisoindolin-2-yl)piperidine-2,6-dione 13-1 (50 mg, 0.1928 mmol) up in DCE (1.92 mL)/acetic acid (200 μL, 3.31 mmol) and added 4A MS (small scoop, activated) and stirred at r.t. for 4 hours. Added sodium triacetoxyborohydride (40.8 mg, 0.1928 mmol) and stirred O/N at r.t. In AM quenched with sat sodium bicarb solution and extracted into dcm×2. Dried combined organic layers over sodium sulfate and concentrated. Purified by isco 12 g column 0-10% MeOH/DCM to give tert-butyl 4-((2-(2,6-dioxopiperidin-3-yl)-1-oxoisoindolin-4-yl)amino)piperidine-1-carboxylate 13-2 (80.0 mg, 0.1807 mmol, 93.7%) as an oil.

Step 2: Compound 306

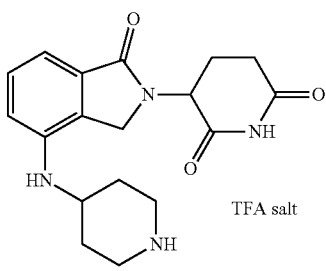 [SMILES: O=C1CCC(N2Cc3c(NC4CCNCC4)cccc3C2=O)C(=O)N1]

TFA salt

Compound 306 was prepared by following procedure in Scheme 10. $^1$H NMR (400 MHz, DMSO-d$_6$) δ 10.99 (s, 1H), 7.28 (t, J=7.7 Hz, 1H), 6.95 (d, J=7.4 Hz, 1H), 6.86 (d, J=8.1 Hz, 1H), 5.19-5.05 (m, 1H), 4.30-4.06 (m, 2H), 3.80-3.60 (m, 2H), 3.33 (d, J=12.5 Hz, 2H), 3.10-2.84 (m, 4H), 2.66-2.58 (m, 1H), 2.36-2.20 (m, 1H), 2.12-1.98 (m, 2H), 1.90-1.75 (m, 1H), 1.68-1.44 (m, 2H). LC/MS (ES+): m/z 343.3 [M+H]$^+$.

Scheme 14

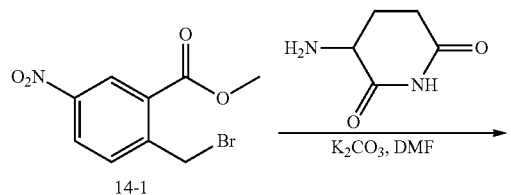

14-1

Step 1: 14-2 was prepared according to procedure in Scheme 8.

Step 2: Compound 307

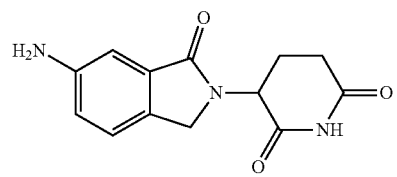 [SMILES: Nc1ccc2c(c1)C(=O)N(C1CCC(=O)NC1=O)C2]

To a solution of 3-(6-nitro-1-oxoisoindolin-2-yl)piperidine-2,6-dione (2.0 g, 6.91 mmol) in 10% DMF in THF (30 ml), 10% Pd/C (50% Moisture) (2 g) was added. The reaction mixture was stirred at rt for 1 hour under Hydrogen atmosphere. The reaction mixture was monitored by TLC and LCMS. After completion the reaction mixture was filtered through celite bed and washed with methanol (300.0 mL). The filtrate was concentrated to get 3-(6-amino-1-oxoisoindolin-2-yl)piperidine-2,6-dione Compound 307 (1.50 g, 5.78 mmol, 83.7%) as dark gray solid. $^1$H NMR (400 MHz, DMSO-d6) δ 1.94-1.98 (m, 1H), 2.30-2.40 (m, 2H), 2.84-2.93 (m, 1H), 4.12 (d, J=16.0 Hz, 1H), 4.24 (d, J=16.0 Hz, 1H), 5.04 (dd, J=13.6 Hz & 4.8 Hz, 1H), 5.34 (s, 2H), 6.81 (d, J=8.0 Hz, 1H), 6.85 (s, 1H), 7.20 (d, J=8.0 Hz, 1H), 10.95 (s, 1H). ES-MS (m/z): 260.20 (M+H$^+$).

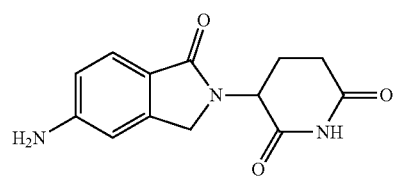

Compound 308 was prepared by literature procedures (Muller, George W. et al. From U.S., 7629360, 8 Dec. 2009) 1H NMR (500 MHz, DMSO-d6): δ 10.91 (s, 1H), 7.35 (d, J=8.5 Hz 1H), 6.62-6.61 (m, 2H), 5.80 (s, 2H), 5.02-4.98 (m, 1H), 4.25 (d, J=16.5 Hz, 1H), 4.10 (d, J=17 Hz, 1H), 2.92-2.85 (m, 1H), 2.58-2.55 (m, 1H), 2.38-2.30 (m, 1H), 1.95-1.91 (m, 1H). LC/MS (ES+): m/z 260.1 [M+H]$^+$.

Scheme 15

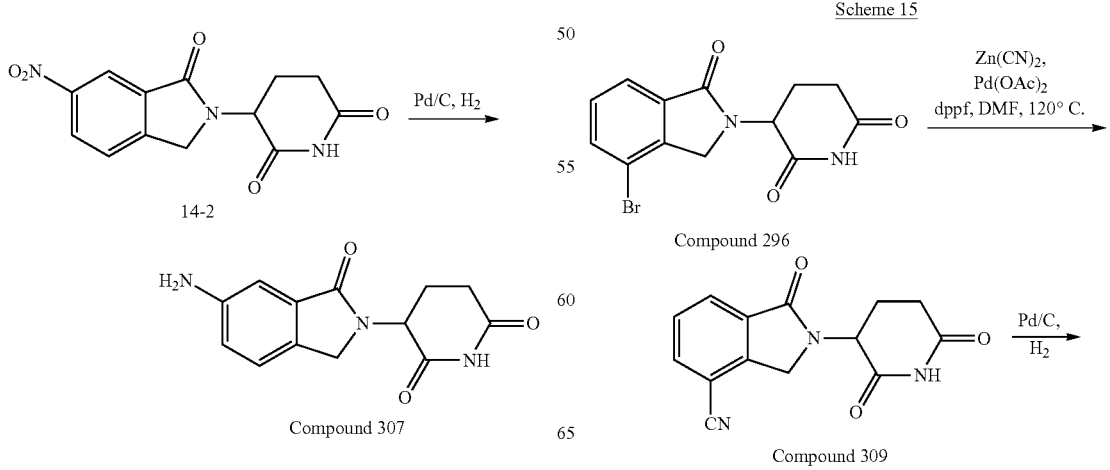

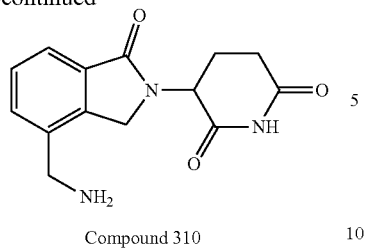

Compound 310

Step 1: Compound 309

A mixture of 3-(4-bromo-1-oxoisoindolin-2-yl)piperidine-2,6-dione (Compound 296) (1.8 g, 5.57 mmol), ZINC CYANIDE (654 mg, 5.57 mmol), Tris(dibenzylideneacetone)dipalladium (222 μmol), 1,1'-BIS(DIPHENYLPHOSPHINO)FERROCENE (473 μmol) in DMF (35 mL) was heated to 120° C. under N2 for 12 hours. The mixture was cooled to room temperature and poured into EtOAc (100 mL) and sat. NaHCO$_3$(40 mL). The EtOAc solution was washed with water (2×40 mL), brine (40 mL), and dried (MgSO4). Solvent was removed and the residue was purified by reverse phase flash to get 2-(2,6-dioxopiperidin-3-yl)-1-oxoisoindoline-4-carbonitrile Compound 309 (950 mg, 3.52 mmol, 63.7%) as white solid. 1H NMR (500 MHz, DMSO-d6): δ 11.02 (s, 1H), 8.14-8.06 (m, 2H), 7.76 (t, J=7.5 Hz, 1H), 5.17-5.13 (m, 1H), 4.70 (d, J=18 Hz, 1H), 4.52 (d, J=18 Hz, 1H), 2.94-2.81 (m, 1H), 2.62-2.61 (m, 1H), 2.51-2.43 (m, 1H), 2.03-1.99 (m, 1H). ES-MS (m/z): 343.24 [M+H]$^+$ 270.0.

Step 2: Compound 310

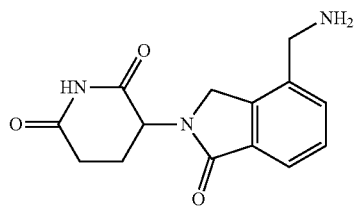 [SMILES: NCc1cccc2c1CN(C1CCC(=O)NC1=O)C2=O]

Compound 310 was prepared according to scheme 14. 1H NMR (500 MHz, DMSO-d6): δ 11.06 (s, 1H), 8.65 (s, 2H), 7.81 (d, J=8.0 Hz, 1H), 7.75 (d, J=7.5 Hz, 1H), 7.60 (t, J=8.0 Hz, 1H), 5.17 (dd, J=5.0 Hz, 8.0 Hz, 1H), 4.74 (d, J=17.5 Hz, 1H), 4.50 (d, J=17.5 Hz, 1H), 4.08 (s, 2H), 2.97-2.91 (m, 1H), 2.64-2.61 (m, 1H), 2.40-2.33 (m, 1H), 2.02-2.00 (m, 1H).

Scheme 16: Preparation of Compound 311

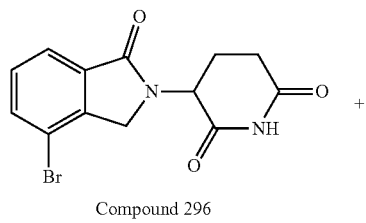

Compound 296

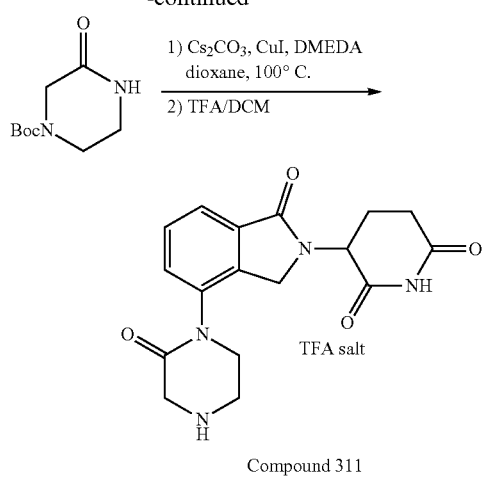

Compound 311

To a solution of 3-(4-bromo-1-oxoisoindolin-2-yl)piperidine-2,6-dione (compound 296) (1 g, 3.09 mmol), tert-butyl 3-oxopiperazine-1-carboxylate (1.23 g, 6.18 mmol) and Cesium carbonate (3.01 g, 9.27 mmol) were added in Dioxane (15 mL). Purged the reaction mixture for 15 minutes. DMEDA (272 mg, 3.09 mmol) and CuI (292 mg, 1.54 mmol) were added and purged the reaction mixture for 5 minutes through argon. Stirred the RM at 100° C. for about 16 hours. Progress of the reaction was monitored by TLC and LCMS·TLC showed consumption of SM, the reaction mixture was cooled to room temperature and quenched by adding water (50*4 mL). The mixture was extracted with Ethyl Acetate (50*6 mL). The organic layer was dried over anhydrous sodium sulfate, filtered and dried. The crude product was purified by flash column chromatography using 12.0 g redisef and eluted with Methanol in DCM (2%-5%) to obtain tert-butyl 4-(2-(2,6-dioxopiperidin-3-yl)-1-oxoisoindolin-4-yl)-3-oxopiperazine-1-carboxylate (170 mg, 384 μmol, 12.5%) as an off-white solid. LC/MS (ES+): m/z 443[M+H]$^+$.

To a round bottom flask tert-butyl 4-(2-(2,6-dioxopiperidin-3-yl)-1-oxoisoindolin-4-yl)-3-oxopiperazine-1-carboxylate (0.050 g, 113 μmol) in DCM (1.5 mL) was added under nitrogen atmosphere at RT. 25% TFA IN DCM (1 mL) was added dropwise at 0° C. Stirred the reaction mixture for 2 hours at RT. After completion of the starting material the reaction mixture was concentrated. The residue was triturated by diethyl ether (4 mL) to get 3-(1-oxo-4-(2-oxopiperazin-1-yl)isoindolin-2-yl)piperidine-2,6-dione with TFA salt (compound 311) (12.0 mg, 35.0 μmol, 31.0%) as a off white solid. $^1$H NMR (400 MHz, DMSO-d6) δ 2.02-2.05 (m, 1H), 2.25-2.32 (m, 1H), 2.50-2.63 (m, 1H), 2.89-2.98 (m, 1H), 3.54 (bs, 2H), 3.87 (bs, 2H), 3.91 (bs, 2H), 4.22 (d, J=17.6 Hz, 1H), 4.33 (d, J=17.6 Hz, 1H), 5.16 (dd, J=13.2 Hz & 5.2 Hz, 1H), 7.59 (d, J=7.6 Hz, 1H), 7.65 (t, J=8.0 Hz, 1H), 7.75 (d, J=8.0 Hz, 1H), 11.04(s, 1H). ES-MS (m/z): 343.24 (M+H$^+$-TFA).

Scheme 17

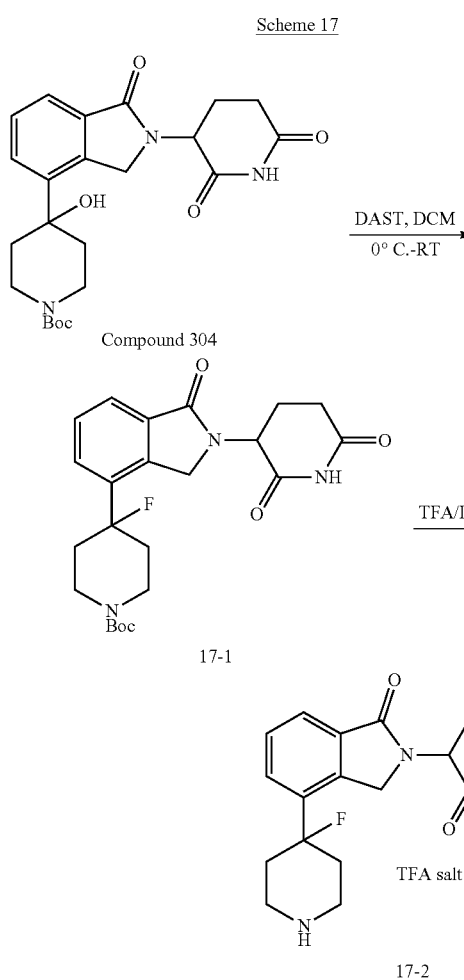

Compound 304

17-1

TFA salt 17-2

To a solution of tert-butyl 4-(2-(2,6-dioxopiperidin-3-yl)-1-oxoisoindolin-4-yl)-4-hydroxypiperidine-1-carboxylate (compound 304) (1.3 g, 2.93 mmol) in DCM (26 mL), Diethylaminosulfur trifluoride (DAST) (573 µL, 4.39 mmol) was added at 0° C. The reaction was stirred at rt for 1 h. Reaction progress was monitored by TLC and LCMS analysis. The reaction mixture was quenched with water (20.0 mL) and extracted with DCM (25.0 mL×2). The organic layers were dried over sodium sulfate, filtered and concentrated to afford crude. The product was purified by silica gel flash chromatography (12 g Isco gold, DCM/MeOH 0-10%) to give tert-butyl 4-(2-(2,6-dioxopiperidin-3-yl)-1-oxoisoindolin-4-yl)-4-fluoropiperidine-1-carboxylate (450 mg, 1.01 mmol, crude) with contamination of tert-butyl 4-(2-(2,6-dioxopiperidin-3-yl)-1-oxoisoindolin-4-yl)-3,6-dihydropyridine-1(2H)-carboxylate. The crude product 17-1 (58.51% by LCMS) as such taken for the next step without further purification. [M+H]+ 446.

To a solution of tert-butyl 4-(2-(2,6-dioxopiperidin-3-yl)-1-oxoisoindolin-4-yl)-4-fluoropiperidine-1-carboxylate 17-1 (300 mg, 673 µmol) in DCM (3.0 mL), 25% TFA in DCM (3.0 mL) was added at 0° C. The reaction mixture was stirred at rt for 2 h. The reaction progress was monitored by TLC and LCMS analysis. After consumption of starting material the solvent was evaporated to dryness and triturated with diethylether (20.0 mL) to afford 3-(4-(4-fluoropiperidin-4-yl)-1-oxoisoindolin-2-yl)piperidine-2,6-dione with TFA salt (250 mg, 544 µmol, crude) with contamination of 3-(1-oxo-4-(1,2,3,6-tetrahydropyridin-4-yl)isoindolin-2-yl)piperidine-2,6-dione with TFA salt 17-2. This compound as such taken for the next step without further purification. M+H+ 346.

Example 6: Illustrative Preparation of Heterocyclic Lenalidomide Related Compounds Scheme 18: Preparation Compound 312

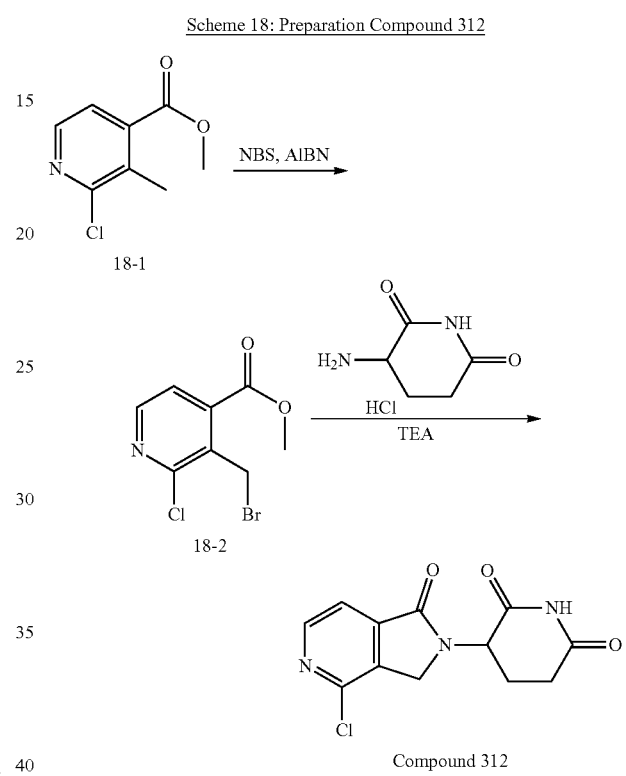

Compound 312

Step 1: 18-2

Methyl 2-chloro-3-methylisonicotinate 18-1 (4.73 g, 26.9 mmol), NBS (6.21, 34.9 mmol), and AIBN (397 mg, 2.42 mmol) in CCl4 (50 mL) were stirred at Ti=78C for 8 h. RXN is done. Dilute with MTBE, wash with NaHCO3×2, water× 2. Concentrate. TLC looks clean. The crude solid 15-2 was used directly without further purification.

Step 2: Compound 312

Methyl 3-(bromomethyl)-2-chloroisonicotinate 18-2 (7.11 g, 26.9 mmol), 3-aminopiperidine-2,6-dione (4.42 g, 26.9 mmol) in DMF (50 mL) was stirred at RT. Et3N (2.2 eq.) was added over 3 h. Stir for over the weekend. Dilute with DCM, wash with NaHCO3×2, brine×2, dry (Na2SO4), concentrate. Slurry MTBE. filter, wash with MTBE Result: isolate product 1.597 g as white solid. Yield 21% over 2 steps. $^1$H NMR (400 MHz, DMSO-$d_6$) δ 11.02 (s, 1H), 8.61 (d, J=5.0 Hz, 1H), 7.78 (d, J=5.0 Hz, 1H), 5.16 (dd, J=13.3, 5.1 Hz, 1H), 4.58 (d, J=18.2 Hz, 1H), 4.42 (d, J=18.2 Hz, 1H), 3.29 (s, 1H), 2.97-2.83 (m, 1H), 2.64-2.54 (m, 1H), 2.42 (dd, J=13.3, 4.5 Hz, 1H), 2.01 (ddd, J=12.5, 5.7, 3.0 Hz, 1H). LC/MS (ES+): m/z 260.1 [M+H]$^+$.

Scheme 19

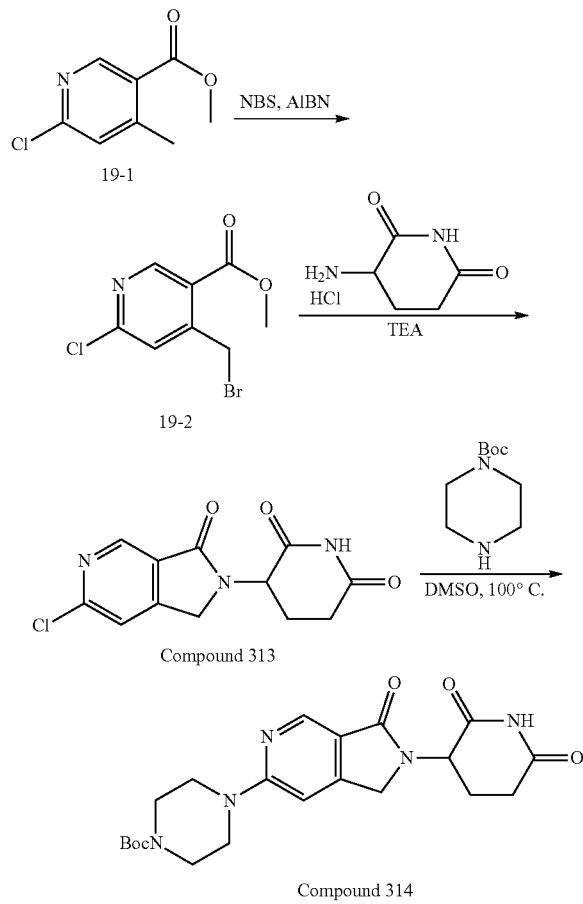

Compound 313

Compound 314

Step 1: Preparation of Methyl 4-(bromomethyl)-6-chloronicotinate 19-2

To a solution of methyl 6-chloro-4-methylnicotinate (0.5 g, 2.69 mmol) in carbontetrachloride (10 mL) at 0° C. under nitrogen atmosphere was added NBS (525 mg, 2.95 mmol). After 5 minutes AIBN (44.1 mg, 269 μmol) was added and the stirred reaction mixture was heated at 90° C. for 5 h. After complete consumption of methyl 6-chloro-4-methylnicotinate, the reaction was cooled to ambient temperature and diluted with water. The crude reaction mixture was extracted with DCM (3×50 mL) and the organic layer was washed with Brine, the phases separated, and the organic layer dried over anhydrous sodium sulfate. The solution was filtered, concentrated and the crude residue was purified by silica gel column chromatography using 50% EtOAc/Hexane as eluent. The pure fractions were combined and concentrated under reduced pressure to provide methyl 4-(bromomethyl)-6-chloronicotinate (135 mg, 510 μmol, 18.9%) as a cream colored solid. ES-MS (m/z): 264.04 (M+H$^+$).

Step 2: Preparation of 3-(6-Chloro-3-oxo-1,3-dihydro-2H-pyrrolo[3,4-c]pyridin-2-yl)piperidine-2,6-dione (Compound 313)

To a solution of methyl 4-(bromomethyl)-6-chloronicotinate 19-2 (0.3 g, 1.13 mmol) in acetonitrile (3 mL) was added DIPEA (981 μL, 5.64 mmol) at 0° C. under nitrogen atmosphere. The reaction mixture was stirred for 5 minutes then 3-aminopiperidine-2,6-dione (222 mg, 1.35 mmol) was added. The reaction was then heated at 90° C. for 32 hours. Upon completion of the reaction, the solution was concentrated to provide a crude residue which was purified by silica gel column chromatography using 25% MeOH/DCM as eluent. The pure fractions were pooled, and concentrated under reduced pressure to provide 3-(6-chloro-3-oxo-1,3-dihydro-2H-pyrrolo[3,4-c]pyridin-2-yl)piperidine-2,6-dione (compound 313) (63.7 mg, 227 μmol, 20.1%) as an off-white solid. $^1$H NMR (400 MHz, DMSO-d6) δ 1.96-2.05 (m, 1H), 2.32-2.46 (m, 1H), 2.55-2.68 (m, 1H), 2.83-2.94 (m, 1H), 4.43 (d, J=18.4 Hz, 1H), 4.56 (d, J=18.4 Hz, 1H), 5.13 (dd, J=13.2 Hz, 5.2 Hz, 1H), 7.87 (s, 1H), 8.77 (s, 1H), 11.03 (s, 1H). ES-MS (m/z): 280.12 (M+H$^+$).

Step 3: Compound 314

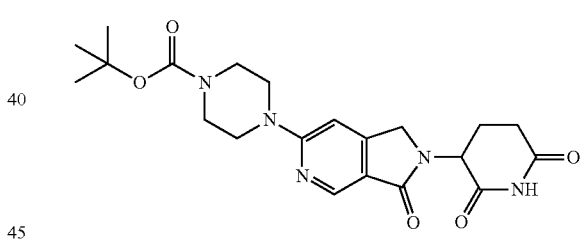

To a solution of 3-(6-chloro-3-oxo-1,3-dihydro-2H-pyrrolo[3,4-c]pyridin-2-yl)piperidine-2,6-dione (compound 313) (0.3 g, 1.07 mmol) in DMSO (6 mL) under an atmosphere of nitrogen, was added DIPEA (745 μL, 4.28 mmol) and tert-butyl piperazine-1-carboxylate (298 mg, 1.60 mmol). The reaction mixture was at 110° C. for 32 hours. The reaction was cooled and quenched with water. The aqueous solution was extracted with DCM (3×100 ml) and the combined organic layer was washed with brine solution, then dried over anhydrous sodium sulfate. The solution was filtered, concentrated and the crude solid was triturated with pentane and diethyl ether to provide tert-butyl 4-(2-(2,6-dioxopiperidin-3-yl)-3-oxo-2,3-dihydro-1H-pyrrolo[3,4-c]pyridin-6-yl)piperazine-1-carboxylate (compound 314) (134 mg, 313 μmol, 29.1%) as a cream colored solid. $^1$H NMR (400 MHz, DMSO-d6) δ 1.39 (s, 9H), 1.93-1.96 (m, 1H), 2.34-2.38 (m, 1H), 2.50-2.59 (m, 1H), 2.82-2.93 (m, 1H), 3.43 (bs, 4H), 3.64 (bs, 4H), 4.23 (d, J=17.6 Hz, 1H), 4.37 (d, J=17.6 Hz, 1H), 5.06 (dd, J=13.6 Hz, 4.8, 1H), 6.98 (s, 1H), 8.46 (s, 1H), 10.96 (s, 1H). ES-MS (m/z): 430.38 (M+H$^+$).

Scheme 20: Preparation of Compound 315

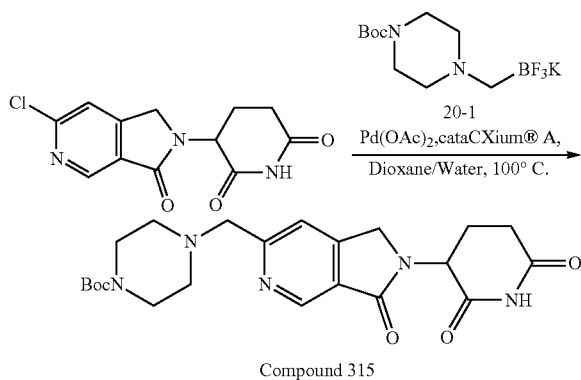

Compound 315

To a solution of 3-(6-chloro-3-oxo-1,3-dihydro-2H-pyrrolo[3,4-c]pyridin-2-yl)piperidine-2,6-dione (350 mg, 1.25 mmol) and 20-1 in dioxane (4 mL) and water (1 mL), was added cesium carbonate (1.21 g, 3.75 mmol). The solution was purged with nitrogen gas for 15 minutes, then palladium (II) acetate (28.0 mg, 125 µmol), and cataCXium® A (89.6 mg, 250 µmol) were added.

The reaction was purged again nitrogen for 5 minutes then heated at 100° C. for 1 hour. The reaction was quenched with water (20 mL) and the solution extracted with ethyl acetate (3×20 mL). The combined organic layers were dried over anhydrous sodium sulfate, filtered and concentrated. The crude residue was purified by silica gel flash chromatography using a DCM/MeOH gradient (0-10% MeOH) to provide tert-butyl 4-((2-(2,6-dioxopiperidin-3-yl)-3-oxo-2,3-dihydro-1H-pyrrolo[3,4-c]pyridin-6-yl)methyl)piperazine-1-carboxylate (compound 315) (250 mg, 563 µmol, 45.1%) as off-white solid. $^1$H NMR (400 MHz, DMSO-d6) δ 1.39 (s, 9H), 1.99-2.02 (m, 1H), 2.37-2.41 (m, 5H), 2.50-2.62 (m, 1H), 2.86-2.96 (m, 1H), 3.32-3.34 (bs, 4H), 3.74 (s, 2H), 4.40 (d, J=18.8 Hz, 1H), 4.54 (d, J=18.4 Hz, 1H), 5.13 (dd, J=13.6 Hz & 5.2 Hz, 1H), 7.74 (s, 1H), 8.86 (s, 1H), 11.02 (s, 1H). ES-MS (m/z): 444.31 (M+H).

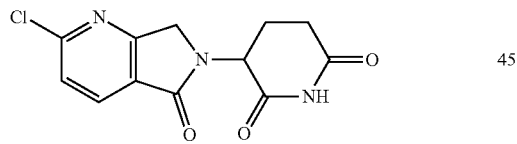

Compound 316 was synthesized following representative general procedure scheme 19, step 1 to provide desired product (384 mg) 61% yield. $^1$H NMR (400 MHz, DMSO-d6) δ 1.95-2.08 (m, 1H), 2.35-2.46 (m, 1H), 2.52-2.68 (m, 1H), 2.83-2.98 (m, 1H), 4.38 (d, J=18.4 Hz, 1H), 4.55 (d, J=18.4 Hz, 1H), 5.17 (dd, J=13.2 Hz, 5.2 Hz, 1H), 7.68 (d, J=8.0 Hz, 1H), 8.20 (d, J=8.0 Hz, 1H), 11.03 (s, 1H). ES-MS (m/z): 280.00 (M+H$^+$).

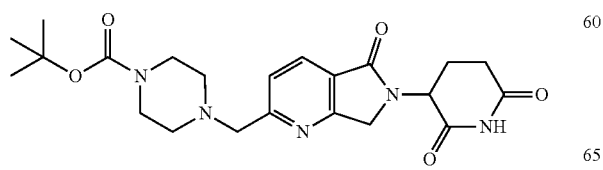

Compound 317 was synthesized following representative general procedure in scheme 20 to provide the desired product (300 mg) 38% yield.

$^1$H NMR (400 MHz, DMSO-d6) δ 1.38 (s, 9H), 1.99-2.01 (m, 1H), 2.17-2.24 (m, 1H), 2.38-2.43 (m, 4H), 2.44-2.49 (m, 1H), 2.50-2.62 (m, 4H), 2.88-2.92 (m, 1H), 3.73 (s, 2H), 4.33 (d, J=18.0 Hz, 1H), 4.49 (d, J=18.0 Hz, 1H), 5.16 (dd, J=13.2 Hz & 5.2 Hz, 1H), 7.61 (d, J=7.6 Hz, 1H), 8.12 (d, J=8.0 Hz, 1H), 11.01(s, 1H). ES-MS (m/z): 444.28 (M+H$^+$).

Scheme 21

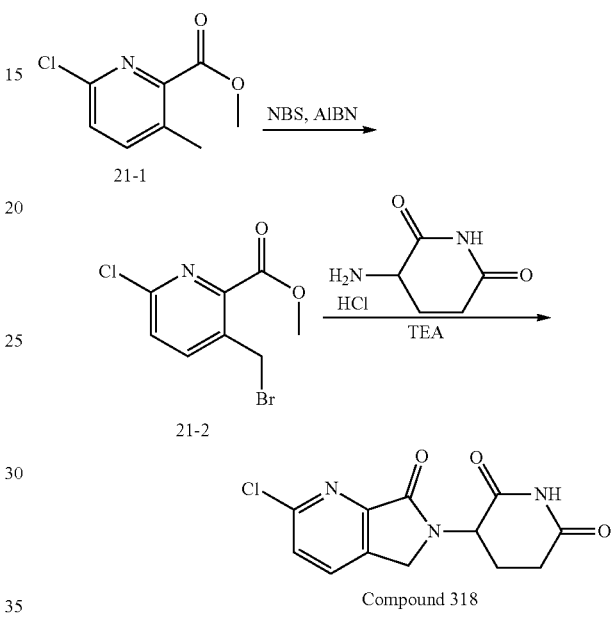

Compound 318

Step 1

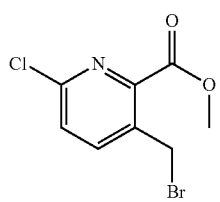

Methyl 3-(bromomethyl)-6-chloropicolinate 21-2 was synthesized following representative general procedure Scheme 19, step 1 to provide desired product (2.4 g) 85% yield. ES-MS (m/z): 264.08 (M+H$^+$).

Step 2

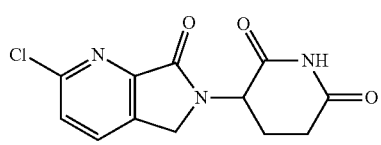

Compound 318 was synthesized following representative general procedure scheme 19, step 2 to provide desired product (1 g) 40% yield. $^1$H NMR (400 MHz, DMSO-d6) δ 1.95-2.08 (m, 1H), 2.35-2.48 (m, 1H), 2.52-2.68 (m, 1H), 2.83-2.98 (m, 1H), 4.39 (d, J=18.0 Hz, 1H), 4.51 (d, J=18.0 Hz, 1H), 5.16 (dd, J=13.2 Hz, 4.8 Hz, 1H), 7.75 (d, J=8.0 Hz, 1H), 8.17 (d, J=8.0 Hz, 1H), 11.04 (s, 1H). ES-MS (m/z): 279.99 (M+H$^+$).

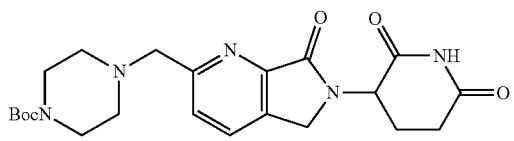 [SMILES: CC(C)(C)OC(=O)N1CCN(Cc2ccc3c(n2)C(=O)N(C2CCC(=O)NC2=O)C3)CC1]

Compound 319 was synthesized following representative general procedure in scheme 20 to provide desired product (250 mg) 45% yield. $^1$H NMR (400 MHz, DMSO-d6) δ 1.39 (s, 9H), 1.97-2.06 (m, 1H), 2.35-2.45 (m, 5H), 2.52-2.68 (m, 4H), 2.86-2.97 (m, 1H), 3.71 (s, 2H), 4.34 (d, J=17.6 Hz, 1H), 4.47 (d, J=17.6 Hz, 1H), 5.16 (dd, J=13.2 Hz, 5.2 Hz, 1H), 7.66 (d, J=7.6 Hz, 1H), 8.05 (d, J=8.0 Hz, 1H), 11.02 (s, 1H). ES-MS (m/z): 444.24 (M+H$^+$).

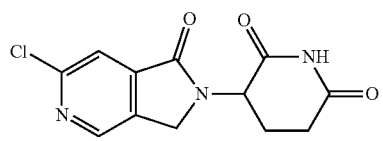 [SMILES: O=C1CCC(N2Cc3cnc(Cl)cc3C2=O)C(=O)N1]

3-(6-Chloro-1-oxo-1,3-dihydro-2H-pyrrolo[3,4-c]pyridin-2-yl)piperidine-2,6-dione (compound 320) was synthesized following representative general procedure scheme 19, step 2 to provide desired product (1.4 g) 66% yield. $^1$H NMR (400 MHz, DMSO-d6) δ 2.01-2.04 (m, 1H), 2.32-2.40 (m, 1H), 2.37-2.45 (m, 1H), 2.92-2.97 (m, 1H), 4.46 (d, J=18.0 Hz, 1H), 4.57 (d, J=18.0 Hz, 1H) 5.17 (dd, J=12.8 Hz, 5.2 Hz, 1H), 7.84 (s, 1H), 8.76 (s, 1H), 11.05 (s, 1H). ES-MS (m/z): 280.06 (M+H$^+$).

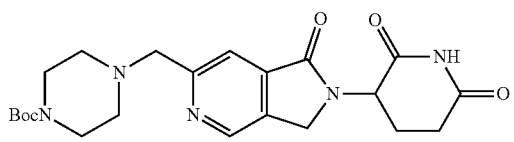 [SMILES: CC(C)(C)OC(=O)N1CCN(Cc2cc3c(cn2)CN(C2CCC(=O)NC2=O)C3=O)CC1]

Compound 321 was synthesized following representative general procedure in scheme 20 to provide desired product (300 mg) 38% yield. $^1$H NMR (400 MHz, DMSO-d6) δ 1.38 (s, 9H), 1.99-2.04 (m, 1H), 2.39 (bs, 5H), 2.56-2.63 (m, 1H), 2.87-2.94 (m, 1H), 3.31 (bs, 4), 3.74 (s, 2H), 4.43 (d, J=17.6 Hz, 1H), 4.56 (d, J=17.6 Hz, 1H), 5.14 (dd, J=13.2 Hz, 4.8 Hz, 1H), 7.73 (s, 1H), 8.83 (s, 1H), 11.03 (s, 1H). ES-MS (m/z): 444.21 (M+H$^+$).

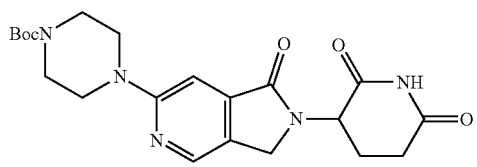 [SMILES: CC(C)(C)OC(=O)N1CCN(c2cc3c(cn2)CN(C2CCC(=O)NC2=O)C3=O)CC1]

Compound 322 was synthesized following representative general procedure scheme 19, step 3 to provide desired product (10 mg) 3% yield. $^1$H NMR (400 MHz, DMSO-d6) δ 1.42 (s, 9H), 1.95-2.05 (m, 1H), 2.32-2.45 (m, 1H), 2.55-2.65 (m, 1H), 2.85-2.95 (m, 1H), 3.34 (bs, 4H), 3.55 (bs, 4H), 4.29 (d, J=16.8 Hz, 1H), 4.41 (d, J=16.4 Hz, 1H), 5.12 (dd, J=12.8 Hz, 5.2 Hz, 1H), 7.09 (s, 1H), 8.42 (s, 1H), 11.00 (s, 1H). ES-MS (m/z): 430.22 (M+H).

Scheme 22

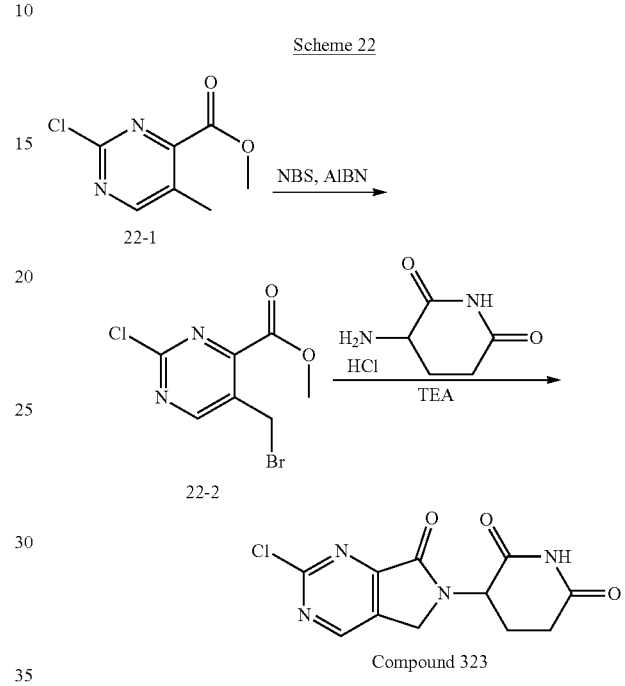

Step 1: 22-2

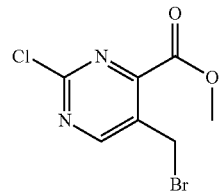

Methyl 5-(bromomethyl)-2-chloropyrimidine-4-carboxylate 22-2 was synthesized following representative general procedure in scheme 21, step 1 to provide desired product (1 g) 59% yield. ES-MS (m/z): 264.89 (M+H$^+$).

Step 2: Compound 323

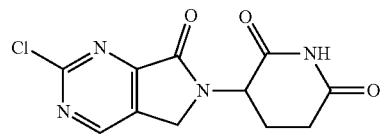 [SMILES: O=C1CCC(N2Cc3cnc(Cl)nc3C2=O)C(=O)N1]

Compound 323 was synthesized from 22-2 following representative general procedure in scheme 21, step 2 to provide desired product (620 mg). ¹H NMR (400 MHz, DMSO-d6) δ 1.98-2.10 (m, 1H), 2.35-2.46 (m, 1H), 2.55-2.70 (m, 1H), 2.85-2.95 (m, 1H), 4.55 (q, J=18.0 Hz, 2H), 5.20 (dd, J=13.2 Hz, 5.2 Hz, 1H), 7.17 (s, 1H), 11.07 (s, 1H). ES-MS (m/z): 281.05 (M+H⁺).

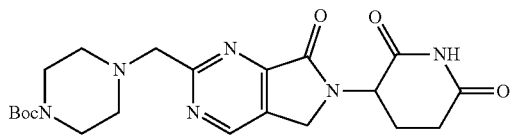

Compound 324 was synthesized following representative general procedure in scheme 20 to provide desired product (25 mg) 3% yield. ¹H NMR (400 MHz, DMSO-d6) δ 1.38 (s, 9H), 1.95-2.05 (m, 1H), 2.50-2.75 (m, 2H), 2.81-2.89 (m, 1H), 3.30 (bs, 8H), 3.86 (s, 2H), 4.45 (d, J=18.0 Hz, 1H), 4.57 (d, J=18.0 Hz, 1H), 5.12 (dd, J=13.2 Hz, 4.8 Hz, 1H), 9.17 (s, 1H), 11.06 (s, 1H). ES-MS (m/z): 445.28 (M+H⁺).

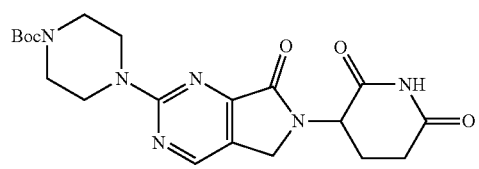 [SMILES: CC(C)(C)OC(=O)N1CCN(c2ncc3c(n2)C(=O)N(C2CCC(=O)NC2=O)C3)CC1]

Compound 325 was synthesized following representative general procedure scheme 19, step 3 to provide desired product (30 mg) 15% yield. ¹H NMR (400 MHz, DMSO-d6) δ 1.42 (s, 9H), 1.98-2.01 (m, 1H), 2.32-2.42 (m, 1H), 2.50-2.61 (m, 1H), 2.82-2.93 (m, 1H), 3.42 (bs, 4H), 3.79 (bs, 4H), 4.26 (d, J=16.8 Hz, 1H), 4.37 (d, J=17.6 Hz, 1H), 5.14 (dd, J=13.2 Hz, 4.8 Hz, 1H), 8.74 (s, 1H), 11.02 (s, 1H). ES-MS (m/z): 431.29 (M+H⁺).

Example 7: Illustrative Preparation of 5-member Glutarimide

Scheme 23

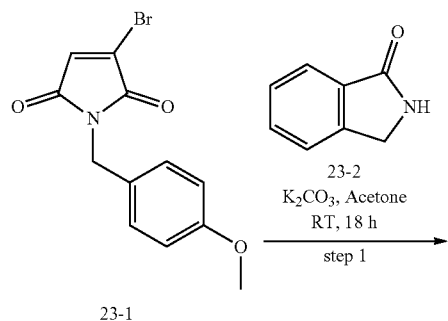

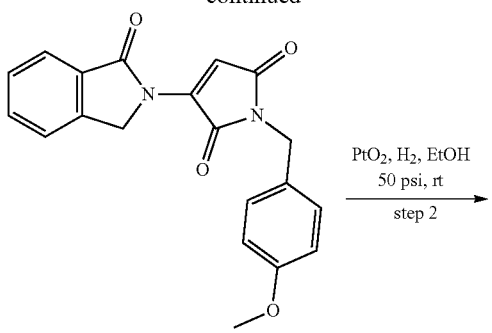

Step-1

To a stirred solution of 23-2 (448 mg, 3.37 mmol) and 23-1 (1000 mg, 3.37 mmol) and Potassium carbonate (931 mg, 6.74 mmol) in Acetone (20.0 mL). It was stirred at room temperature for 16 hours. It was diluted with water and extracted with ethyl acetate. Organic part was dried over sodium sulfate, concentrated under reduced pressure and purified by column chromatography using (silica, gradient, 0%-30% ethyl acetate in hexane to afford 3 as off white solid. Yield-20%; LC MS: ES+ 349.3.

Step-2

Compound 23-3 (100 mg, 287 μmol) was taken in Ethanol (10 mL) in a parr-shaker vessel. It was degassed with argon for 10 minutes. Platinum dioxide (6.51 mg, 28.7 μmol) was added to the reaction mixture. It was shacked in the presence of hydrogen at 50 psi for 16 h. It was filtered through celite and concentrated under reduced pressure and was purified by column chromatography using (silica, gradient, 0%-25% Ethyl acetate in hexane) to provide 23-4 as white solid. Yield-40%; LC MS: ES+ 351.1.

Step-3

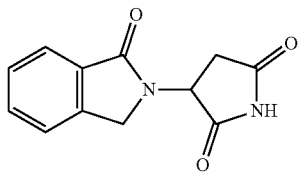

Compound 326

To a stirred solution of 23-4 (32 mg, 91.3 μmol) in Acetonitrile (0.5 mL) and Water (2 mL). Ceric ammonium nitrate (99.7 mg, 182 μmol) was added to the reaction mixture and was stirred at room temperature for 2 hours. It was diluted with water and was extracted with ethyl acetate, dried over sodium sulfate and concentrated under reduced pressure. It was purified by preparative TLC (40% ethyl acetate in hexane) to provide Compound 326 as off white solid. Yield-19%; 1H NMR (400 MHz, DMSO-d6) δ 11.51 (s, 1H), 7.71 (d, J=7.36 Hz, 1H), 7.64-7.61 (m, 2H), 7.52 (d, J=7.52 Hz, 1H), 5.23 (t, J=7.42 Hz, 1H), 4.62 (d, J=17.24 Hz, 1H), 4.37 (d, J=17.24 Hz, 1H), 2.97-2.92 (m, 1H); LC MS: ES+ 231.3.

Example 8: Illustrative Preparation of 7-Member Glutarimide

Scheme 24

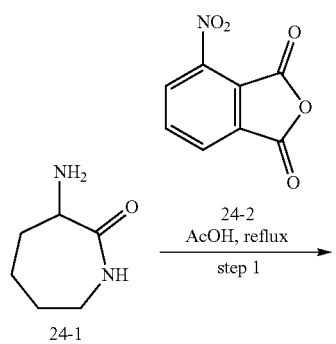

Step-1

To a mixture of 24-1 (150 mg, 780 μmol) and 24-2 (100 mg, 780 μmol) in Acetic acid (3 mL) taken was added Ammonium acetate (60.1 mg, 780 μmol) and refluxed for 2 hours. Water was then added to the reaction mixture and the compound was extracted with DCM. The organic phase was separated, dried over anhydrous sodium sulfate and evaporated in vacuo to obtain the crude which was purified by silica gel column to afford 24-3 as white solid. Yield-21%; LC MS: ES+ 304.1.

Step-2

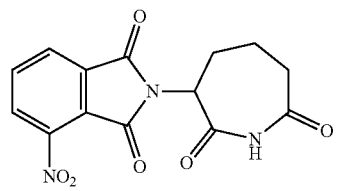 [SMILES: O=C1CCCC(N2C(=O)c3cccc([N+](=O)[O-])c3C2=O)C(=O)N1]

A mixture of periodic acid (224 mg, 984 μmol) and chromium trioxide (3.27 mg, 32.8 μmol) in Acetonitrile (3.0 mL) was stirred at room temperature for 30 min. Then acetic anhydride (92.5 μL, 984 μmol) was added. The reaction mixture was cooled to 0° C. and 24-3 (50 mg, 164 μmol) was added in one portion and the reaction mixture was further stirred for 30 min at room temperature. After completion of the reaction, ice-water (15-20 mL) was added and the mixture was extracted with ethyl acetate (3×50 mL). The combined organic layer was washed with saturated NaHCO₃ solution, saturated Na₂S₂O₃ solution, and finally with brine. The organic phase was dried over anhydrous sodium sulfate and the solvent was removed under reduced pressure. The crude product was filtered through silica gel column using ethyl acetate as eluent to obtain Compound 327 as white solid. Yield-40%; $^1$H NMR (400 MHz, DMSO-d6) δ 10.86 (s, 1H), 8.34 (d, J=7.96 Hz, 1H), 8.24 (d, J=7.36 Hz, 1H), 8.11 (t, J=7.78 Hz, 1H), 5.26 (dd, J=12, 3.08 Hz, 1H), 3.18-3.09 (m, 1H), 2.66-2.52 (m, 2H), 2.18-2.12 (m, 1H), 1.99-1.82 (m, 2H); LC MS: ES+318.2.

Example 9: Illustrative Preparation of 3,4-Substituted-2,6-Dioxopiperdine Intermediates Scheme 25

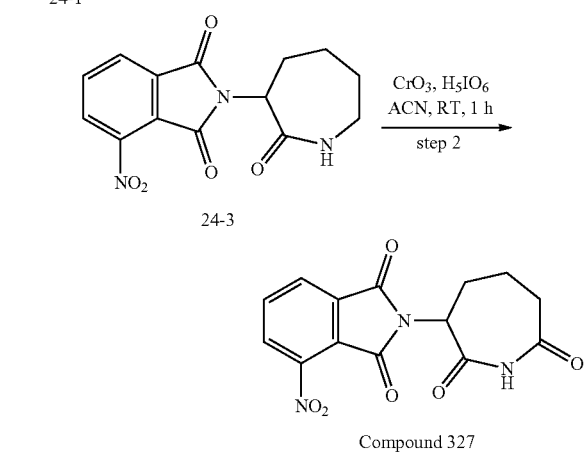

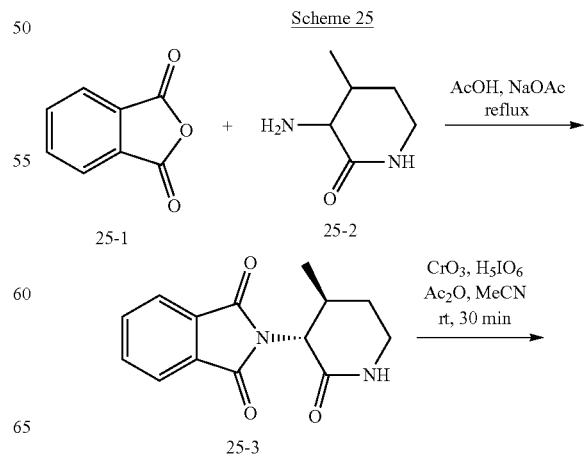

-continued

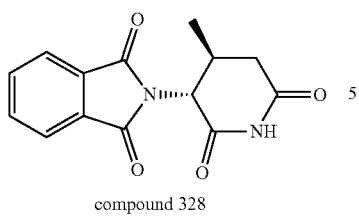

compound 328

Step 1: Preparation of 2-(4-methyl-2-oxopiperidin-3-yl)isoindoline-1,3-dione (25-3)

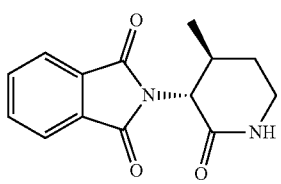 [SMILES: C[C@H]1CCNC(=O)[C@@H]1N1C(=O)c2ccccc2C1=O]

To a stirred solution of compound 25-1 (173 mg, 1170 µmol) in toluene (5.0 mL), compound 25-2 (150.0 mg, 1170 µmol) was added and the reaction mixture was heated at 120° C. in a sealed tube for 12 h. After checking TLC (Rf-0.3 in 30% EtOAc-hexane) the reaction mixture was diluted with ethyl acetate, washed with water, organic part was separated and concentrated under reduced pressure. The crude compound 25-3 (100 mg, 388 µmol, 33%) was used for the next step without any further purification. LCMS: ES+ 259.0.

Step 2: Preparation of 2-(4-methyl-2,6-dioxopiperidin-3-yl)isoindoline-1,3-dione (Compound 328)

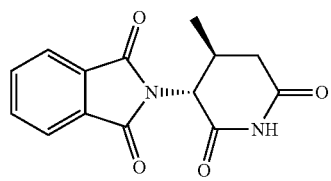 [SMILES: C[C@H]1CC(=O)NC(=O)[C@@H]1N1C(=O)c2ccccc2C1=O]

To stirred solution of $H_5IO_6$ (793 mg, 3480 µmol) and $Cr_2O_3$ (28.9 mg, 290 µmol) in acetonitrile (10.0 mL), acetic anhydride (0.1 mL) was added at room temperature. The reaction mixture was then stirred at same temperature for 30 min. To this reaction mixture compound 25-3 (150.0 mg, 580 µmol) was added at 0° C. at a time. The reaction mixture was then stirred at this temperature for 1 h. TLC showed formation of new spot (Rf-0.6 in 70% ea-hex). The reaction mixture was diluted with ethyl acetate; organic part was washed with water, aqueous $Na_2S_2O_3$ solution and dried over $Na_2SO_4$. The product was purified by preparative HPLC to give Compound 328 (40 mg, 147 µmol, 25%) as white solid. $^1$H NMR (400 MHz, DMSO-$d_6$) δ 11.18 (s, 1H), 7.93 (dtd, J=8.8, 5.7, 3.2 Hz, 3H), 4.90 (d, J=11.5 Hz, 1H), 2.80-2.61 (m, 4H), 0.92 (d, J=5.9 Hz, 3H); LC MS: ES+ 273.1.

Example 10: Degrader Example

Scheme 26

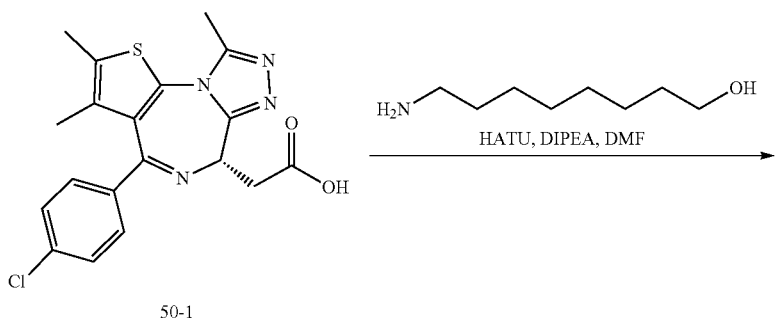

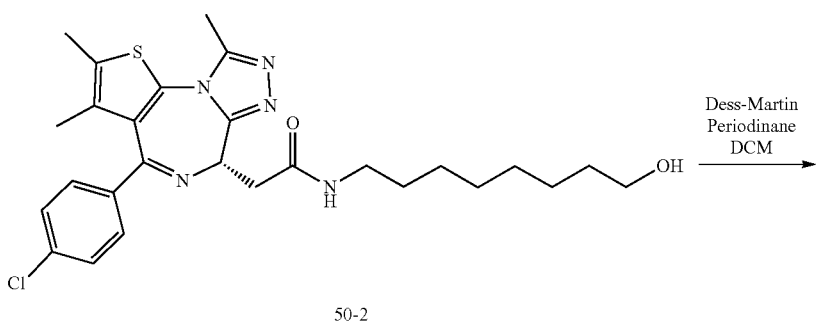

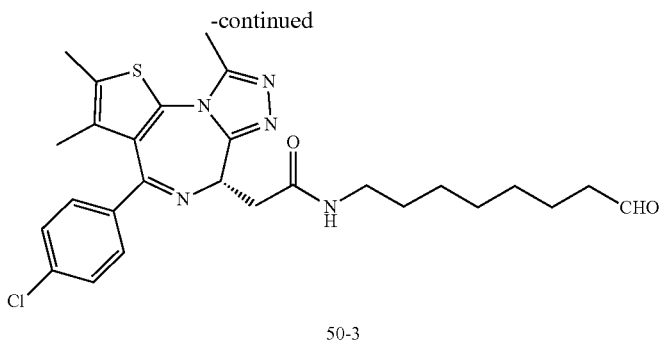

50-3

(S)-2-(4-(4-Chlorophenyl)-2,3,9-trimethyl-6H-thieno[3,2-f][1,2,4]triazolo[4,3-a][1,4]diazepin-6-yl)-N-(8-hydroxyoctyl)acetamide (50-2)

To a solution of (S)-2-(4-(4-chlorophenyl)-2,3,9-trimethyl-6H-thieno[3,2-f][1,2,4]triazolo[4,3-a][1,4]diazepin-6-yl)acetic acid 50-1(450 mg, 1.12 mmol) in DMF (2.80 mL) was added 8-aminooctan-1-ol (244 mg, 1.68 mmol), Diisopropylethylamine (389 µL, 2.24 mmol) and HATU (509 mg, 1.34 mmol), The reaction was stirred for 24 h, at which time the reaction was concentrated and purified by isco (24 g column 0-10% MeOH/DCM) to provide (S)-2-(4-(4-chlorophenyl)-2,3,9-trimethyl-6H-thieno[3,2-f][1,2,4]triazolo[4,3-a][1,4]diazepin-6-yl)-N-(3-hydroxypropyl)acetamide (400 mg, 67.6%). LCMS ES+=529.1.

Synthesis of (S)-2-(4-(4-Chlorophenyl)-2,3,9-trimethyl-6H-thieno[3,2-f][1,2,4]triazolo[4,3-a][1,4]diazepin-6-yl)-N-(8-oxooctyl)acetamide (50-3)

A 25 mL rbf was charged with (S)-2-(4-(4-chlorophenyl)-2,3,9-trimethyl-6H-thieno[3,2-f][1,2,4]triazolo[4,3-a][1,4]diazepin-6-yl)-N-(8-hydroxyoctyl)acetamide 50-2 (400 mg, 757 µmol) and dichloromethane (4 mL). Dess-Martin Periodinane (0.3 M in DCM, 3.02 mL, 908 µmol) was added and the reaction was stirred at rt for 1 h, then quenched with 0.5 mL isopropanol, sat'd sodium thiosulfate, and sat'd sodium bicarbonate. The reaction was extracted 3×DCM, organics were dried over Na₂SO₄, filtered and concentrated to provide (S)-2-(4-(4-chlorophenyl)-2,3,9-trimethyl-6H-thieno[3,2-f][1,2,4]triazolo[4,3-a][1,4]diazepin-6-yl)-N-(8-oxooctyl)acetamide (390 mg, 741 mmol, 98% yield) (50-3), which was used in subsequent reactions without further purification. LCMS ES+ 527.3.

Scheme 27:
2-((S)-4-(4-Chlorophenyl)-2,3,9-trimethyl-6H-thieno[3,2-f][1,2,4]triazolo[4,3-a][1,4]diazepin-6-yl)-N-(8-(4-(2-(2,6-dioxopiperidin-3-yl)-1,3-dioxoisoindolin-4-yl)piperazin-1-yl)octyl)acetamide
(Degronimer 4)

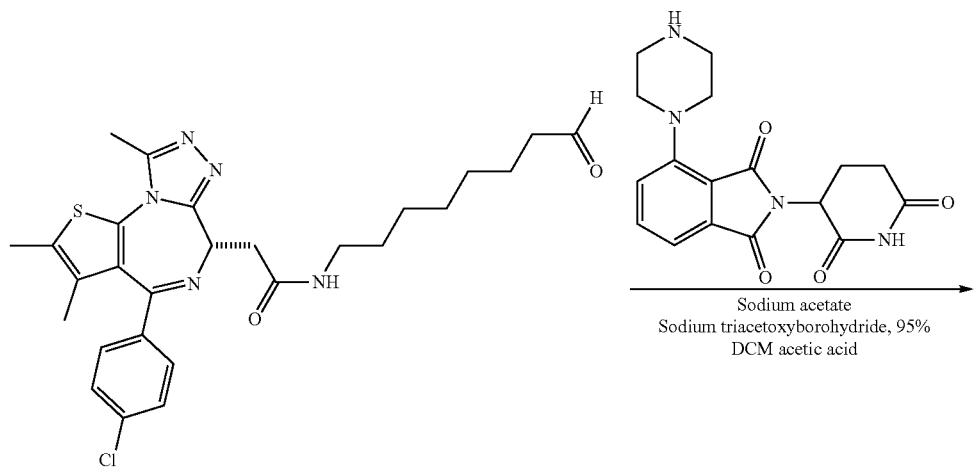

-continued

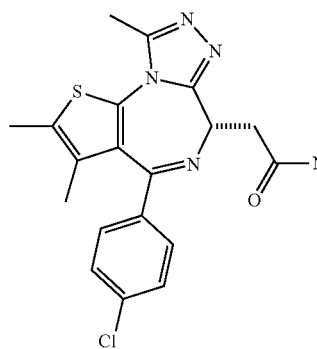

Degronimer 4

2-[4-(4-chlorophenyl)-2,3,9-trimethyl-6H-[1,2,4]triazolothieno[1,4]diazepin-6-yl]-N-(8-oxooctyl)acetamide (10 mg, 19.01 umol), 2-(2,6-dioxo-3-piperidyl)-4-piperazin-1-yl-isoindoline-1,3-dione (6.51 mg, 19.01 umol), Sodium acetate (7.80 mg, 95.04 umol, 5.10 uL) were added to a vial followed by DCM (95.04 uL). The solution was stirred at 25° C. for 30 min and acetic acid (3.42 mg, 57.02 umol, 3.26 uL) was added and stirred for an additional 30 min. The reaction was cooled to 0° C. and Sodium triacetoxyborohydride, 95% (4.03 mg, 19.01 umol) was added and the reaction was gradually warmed to RT and stirred for 12 hours. 1 ml of DMSO was added to the reaction and the DCM was evaporated under vacuum. Upon completion of the reaction as determined by LCMS, the reaction was purified directly on a reverse-phase C18 column, eluting with 10-100% MeCN in H₂O. The product containing fractions were combined, solvent removed and product extracted 3×CH₂Cl₂. The organic layers were dried over Na₂SO₄, filtered and solvent removed to give 2-((S)-4-(4-chlorophenyl)-2,3,9-trimethyl-6H-thieno[3,2-f][1,2,4]triazolo[4,3-a][1,4]diazepin-6-yl)-N-(8-(4-(2-(2,6-dioxopiperidin-3-yl)-1,3-dioxoisoindolin-4-yl)piperazin-1-yl)octyl)acetamide (13 mg, 13.73 umol, 72.21% yield) as a yellow oil. 1H NMR (400 MHz, DMSO-d6) δ 11.05 (s, 1H), 8.22 (d, J=2.5 Hz, 1H), 8.18 (t, J=5.5 Hz, 1H), 8.12 (t, J=5.6 Hz, 1H), 7.87 (dd, J=9.6, 2.5 Hz, 1H), 7.50-7.38 (m, 5H), 6.43 (d, J=9.5 Hz, 1H), 5.35 (bs, 1H), 4.52-4.42 (m, 1H), 3.28-3.01 (m, 6H), 2.62-2.54 (m, 4H), 2.39 (s, 2H), 2.22-2.12 (m, 1H), 2.10-1.99 (m, 1H), 1.61 (s, 2H), 1.50-1.38 (m, 4H), 1.26 (s, 6H), 1.22 (s, 6H), 0.92 (t, J=7.5 Hz, 1H), 0.86-0.80 (m, 1H). LC/MS (ES+): m/z 852.5 (M+H)⁺.

X. Representative Degrons of the Present Invention

TABLE 1

| Compound # | Structure | Kd |
|---|---|---|
| Compound 1 | 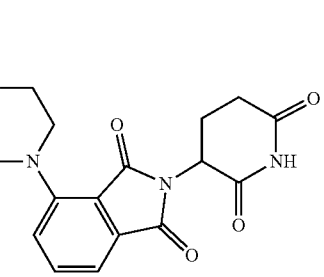 | +++ |
| Compound 2 | 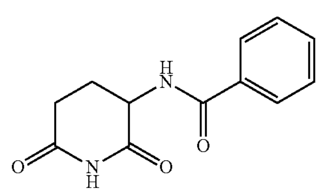 [SMILES: O=C1CCC(NC(=O)c2ccccc2)C(=O)N1] | +++ |
| Compound 3 | 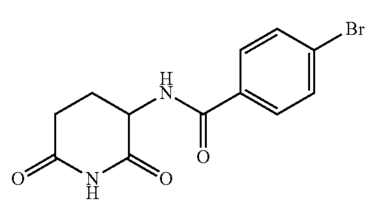 [SMILES: O=C1CCC(NC(=O)c2ccc(Br)cc2)C(=O)N1] | + |

TABLE 1-continued

| Compound # | Structure | Kd |
|---|---|---|
| Compound 4 | [structure: N-(2,6-dioxopiperidin-3-yl)-6-methoxynicotinamide] | + |
| Compound 5 | [structure: 3-cyclopropyl-N-(2,6-dioxopiperidin-3-yl)benzamide] | ++++ |
| Compound 6 | [structure: N-(2,6-dioxopiperidin-3-yl)-[1,1'-biphenyl]-3-carboxamide] | ++++ |
| Compound 7 | [structure: N-(2,6-dioxopiperidin-3-yl)-2-methoxybenzamide] | + |
| Compound 8 | [structure: N-(2,6-dioxopiperidin-3-yl)-3-methylpicolinamide] | + |
| Compound 9 | [structure: 3-(benzyloxy)-N-(2,6-dioxopiperidin-3-yl)benzamide] | |
| Compound 10 | [structure: N-(2,6-dioxopiperidin-3-yl)-3-methoxybenzamide] | +++ |
| Compound 11 | [structure: N-(2,6-dioxopiperidin-3-yl)-2-methylisonicotinamide] | + |

TABLE 1-continued

| Compound # | Structure | Kd |
|---|---|---|
| Compound 12 | 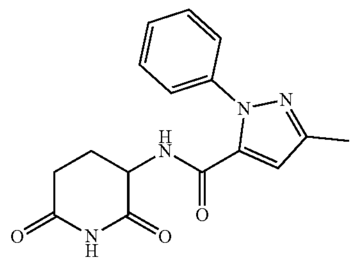 [SMILES: Cc1cc(C(=O)NC2CCC(=O)NC2=O)n(-c2ccccc2)n1] | + |
| Compound 13 | 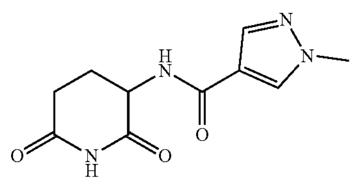 [SMILES: Cn1cc(C(=O)NC2CCC(=O)NC2=O)cn1] | +++ |
| Compound 14 | 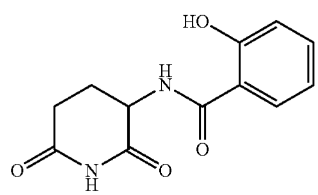 [SMILES: O=C1CCC(NC(=O)c2ccccc2O)C(=O)N1] | +++++ |
| Compound 15 | 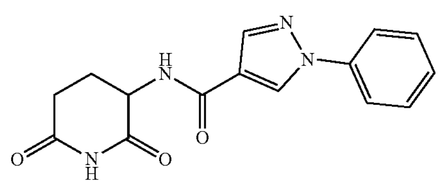 [SMILES: O=C1CCC(NC(=O)c2cnn(-c3ccccc3)c2)C(=O)N1] | +++ |
| Compound 16 | 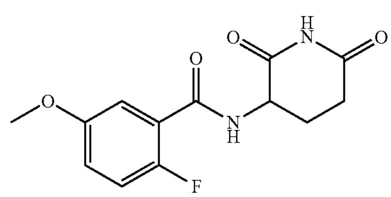 [SMILES: COc1ccc(F)c(C(=O)NC2CCC(=O)NC2=O)c1] | + |
| Compound 17 | 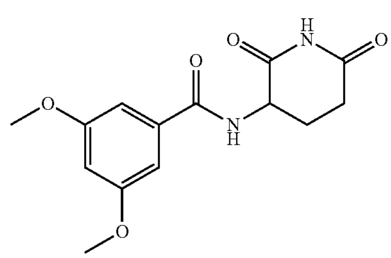 [SMILES: COc1cc(OC)cc(C(=O)NC2CCC(=O)NC2=O)c1] | +++ |
| Compound 18 | 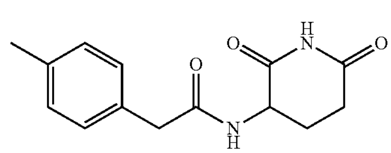 [SMILES: Cc1ccc(CC(=O)NC2CCC(=O)NC2=O)cc1] | +++ |

TABLE 1-continued

| Compound # | Structure | Kd |
|---|---|---|
| Compound 19 | 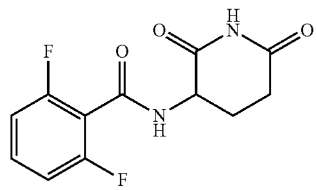 [SMILES: O=C1CCC(NC(=O)c2c(F)cccc2F)C(=O)N1] | + |
| Compound 20 | 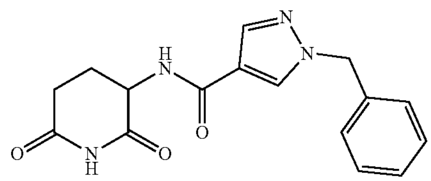 [SMILES: O=C1CCC(NC(=O)c2cnn(Cc3ccccc3)c2)C(=O)N1] | ++++ |
| Compound 21 | 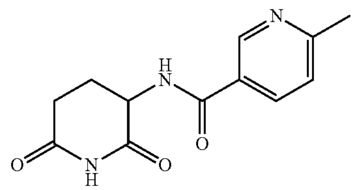 [SMILES: Cc1ccc(C(=O)NC2CCC(=O)NC2=O)cn1] | + |
| Compound 22 | 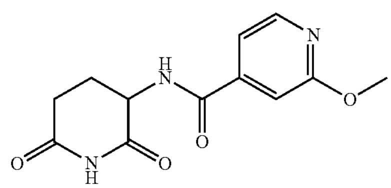 [SMILES: COc1cc(C(=O)NC2CCC(=O)NC2=O)ccn1] | + |
| Compound 23 | 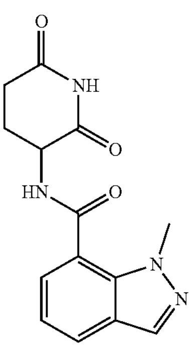 [SMILES: Cn1ncc2cccc(C(=O)NC3CCC(=O)NC3=O)c21] | ++++ |
| Compound 24 | 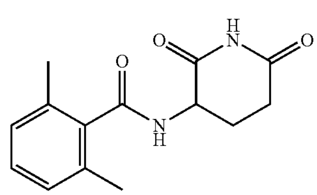 [SMILES: Cc1cccc(C)c1C(=O)NC1CCC(=O)NC1=O] | + |
| Compound 25 | 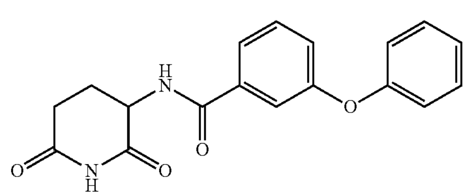 [SMILES: O=C1CCC(NC(=O)c2cccc(Oc3ccccc3)c2)C(=O)N1] | ++++ |

TABLE 1-continued

| Compound # | Structure | Kd |
|---|---|---|
| Compound 26 | (structure) | ++++ |
| Compound 27 | (structure) | +++ |
| Compound 28 | (structure) | ++++ |
| Compound 29 | (structure) | ++++ |
| Compound 30 | (structure) | ++++ |
| Compound 31 | (structure) | ++++ |
| Compound 32 | (structure) | ++++ |

TABLE 1-continued

| Compound # | Structure | Kd |
|---|---|---|
| Compound 33 | 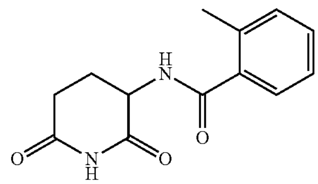 [SMILES: Cc1ccccc1C(=O)NC1CCC(=O)NC1=O] | ++++ |
| Compound 34 | 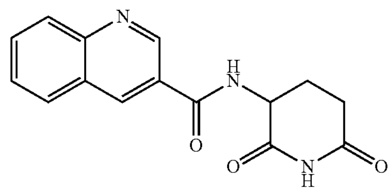 [SMILES: O=C1CCC(NC(=O)c2cnc3ccccc3c2)C(=O)N1] | ++++ |
| Compound 35 | 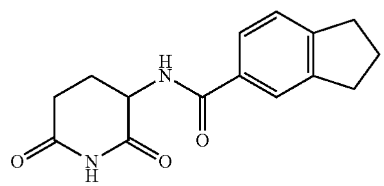 [SMILES: O=C1CCC(NC(=O)c2ccc3c(c2)CCC3)C(=O)N1] | ++++ |
| Compound 36 | 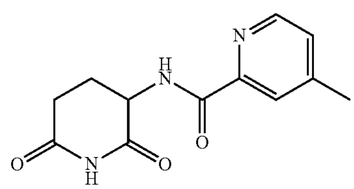 [SMILES: Cc1ccnc(C(=O)NC2CCC(=O)NC2=O)c1] | ++++ |
| Compound 37 | 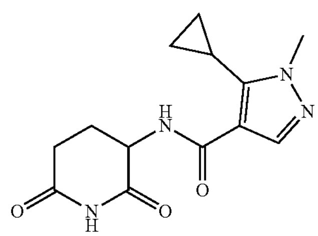 [SMILES: Cn1ncc(C(=O)NC2CCC(=O)NC2=O)c1C1CC1] | ++++ |
| Compound 38 | 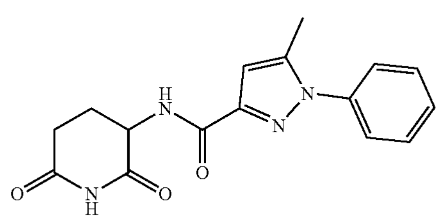 [SMILES: Cc1cc(C(=O)NC2CCC(=O)NC2=O)nn1-c1ccccc1] | ++++ |
| Compound 39 | 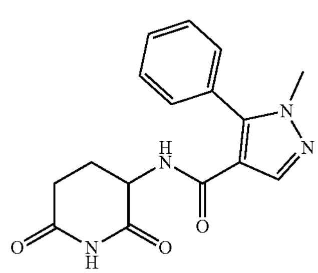 [SMILES: Cn1ncc(C(=O)NC2CCC(=O)NC2=O)c1-c1ccccc1] | ++++ |

TABLE 1-continued

| Compound # | Structure | Kd |
|---|---|---|
| Compound 40 | 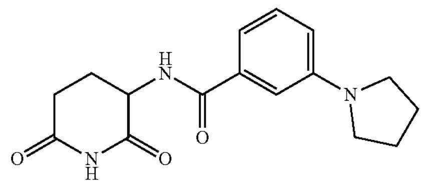 [SMILES: O=C1CCC(NC(=O)c2cccc(N3CCCC3)c2)C(=O)N1] | ++++ |
| Compound 41 | 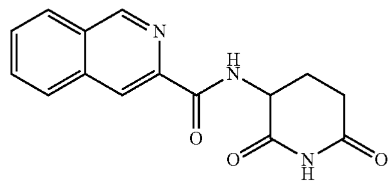 [SMILES: O=C1CCC(NC(=O)c2cc3ccccc3cn2)C(=O)N1] | ++++ |
| Compound 42 | 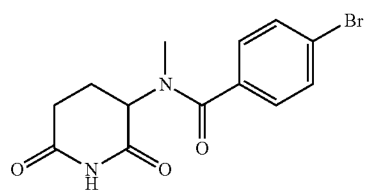 [SMILES: CN(C(=O)c1ccc(Br)cc1)C1CCC(=O)NC1=O] | ++++ |
| Compound 43 | 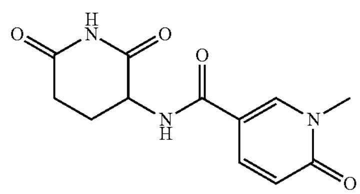 [SMILES: Cn1cc(C(=O)NC2CCC(=O)NC2=O)ccc1=O] | + |
| Compound 44 | 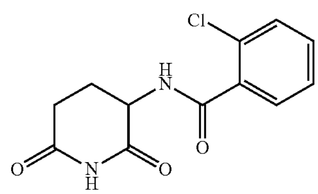 [SMILES: O=C1CCC(NC(=O)c2ccccc2Cl)C(=O)N1] | + |
| Compound 45 | 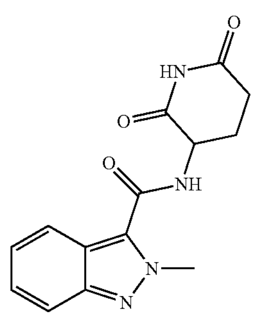 [SMILES: Cn1nc2ccccc2c1C(=O)NC1CCC(=O)NC1=O] | +++ |
| Compound 46 | 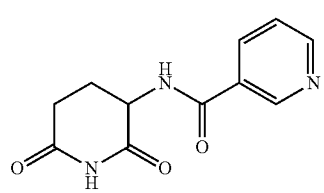 [SMILES: O=C1CCC(NC(=O)c2cccnc2)C(=O)N1] | +++ |

TABLE 1-continued

| Compound # | Structure | Kd |
|---|---|---|
| Compound 47 | (structure) | + |
| Compound 48 | (structure) | +++ |
| Compound 49 | (structure) | ++++ |
| Compound 50 | (structure) | +++ |
| Compound 51 | (structure) | ++++ |
| Compound 52 | (structure) | ++++ |
| Compound 53 | (structure) | ++++ |
| Compound 54 | (structure) | ++++ |

TABLE 1-continued

| Compound # | Structure | Kd |
|---|---|---|
| Compound 55 | 2,6-dichloro-4-cyano-N-(2,6-dioxopiperidin-3-yl)benzamide | ++++ |
| Compound 56 | N-(2,6-dioxopiperidin-3-yl)-1,5-dimethyl-1H-pyrazole-3-carboxamide | ++++ |
| Compound 57 | N-(2,6-dioxopiperidin-3-yl)-1-phenyl-1H-pyrazole-5-carboxamide | +++ |
| Compound 58 | 1-benzyl-N-(2,6-dioxopiperidin-3-yl)-N-methyl-1H-pyrazole-4-carboxamide | ++++ |
| Compound 59 | N-(2,6-dioxopiperidin-3-yl)-2-methoxy-N-methylisonicotinamide | + |
| Compound 60 | N-(2,6-dioxopiperidin-3-yl)-N,3,5-trimethylisoxazole-4-sulfonamide | |
| Compound 61 | N-(2,6-dioxopiperidin-3-yl)-N-methylpyridazine-3-carboxamide | + |

TABLE 1-continued

| Compound # | Structure | Kd |
|---|---|---|
| Compound 62 | 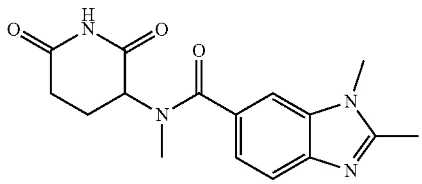 [SMILES: Cc1nc2ccc(C(=O)N(C)C3CCC(=O)NC3=O)cc2n1C] | ++++ |
| Compound 63 | 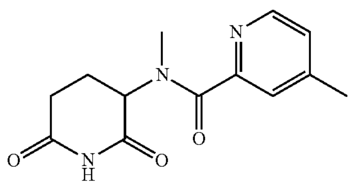 [SMILES: Cc1ccnc(C(=O)N(C)C2CCC(=O)NC2=O)c1] | ++++ |
| Compound 64 | 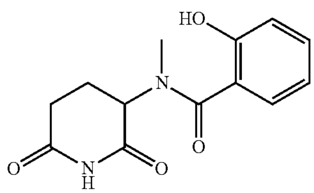 [SMILES: CN(C(=O)c1ccccc1O)C1CCC(=O)NC1=O] | +++ |
| Compound 65 | 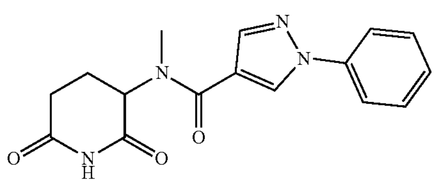 [SMILES: CN(C(=O)c1cnn(-c2ccccc2)c1)C1CCC(=O)NC1=O] | ++++ |
| Compound 66 | 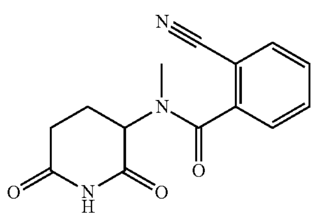 [SMILES: CN(C(=O)c1ccccc1C#N)C1CCC(=O)NC1=O] | +++ |
| Compound 67 | 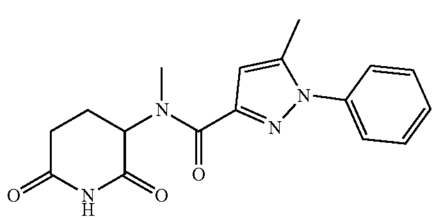 [SMILES: Cc1cc(C(=O)N(C)C2CCC(=O)NC2=O)nn1-c1ccccc1] | ++++ |
| Compound 68 | 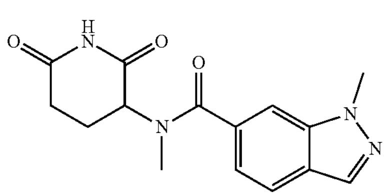 [SMILES: CN(C(=O)c1ccc2cnn(C)c2c1)C1CCC(=O)NC1=O] | |

TABLE 1-continued

| Compound # | Structure | Kd |
|---|---|---|
| Compound 69 | *N-methyl-N-(2,6-dioxopiperidin-3-yl)-1-methyl-1H-indazole-5-carboxamide* | +++ |
| Compound 70 | *N-methyl-N-(2,6-dioxopiperidin-3-yl)-3-(pyrrolidin-1-yl)benzamide* | ++++ |
| Compound 71 | *N-methyl-N-(2,6-dioxopiperidin-3-yl)-2,3-dihydro-1H-indene-5-carboxamide* | ++++ |
| Compound 72 | *N-methyl-N-(2,6-dioxopiperidin-3-yl)isoquinoline-3-carboxamide* | ++++ |
| Compound 73 | *N-methyl-N-(2,6-dioxopiperidin-3-yl)-3-cyclopropylbenzamide* | ++++ |
| Compound 74 | *N-methyl-N-(2,6-dioxopiperidin-3-yl)-3-(trifluoromethoxy)benzamide* | +++ |
| Compound 75 | *N-methyl-N-(2,6-dioxopiperidin-3-yl)-1-phenyl-1H-pyrazole-5-carboxamide* | + |
| Compound 76 | *N-methyl-N-(2,6-dioxopiperidin-3-yl)-1-methyl-1H-pyrazole-4-carboxamide* | +++ |

TABLE 1-continued

| Compound # | Structure | Kd |
|---|---|---|
| Compound 77 | N-methyl-N-(2,6-dioxopiperidin-3-yl)-2-(trifluoromethyl)isonicotinamide | + |
| Compound 78 | N-methyl-N-(2,6-dioxopiperidin-3-yl)-2-methoxybenzamide | + |
| Compound 79 | N-methyl-N-(2,6-dioxopiperidin-3-yl)-3,5-dimethoxybenzamide | ++++ |
| Compound 80 | N-methyl-N-(2,6-dioxopiperidin-3-yl)-5-(cyclopropylmethoxy)picolinamide | +++++ |
| Compound 81 | N-methyl-N-(2,6-dioxopiperidin-3-yl)-3-(benzyloxy)benzamide | ++++ |
| Compound 82 | N-methyl-N-(2,6-dioxopiperidin-3-yl)-[1,1'-biphenyl]-3-carboxamide | +++++ |
| Compound 83 | N-methyl-N-(2,6-dioxopiperidin-3-yl)-3-methoxybenzamide | +++ |

TABLE 1-continued
| Compound # | Structure | Kd |
|---|---|---|
| Compound 84 | 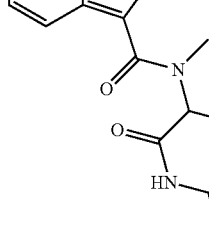 | +++ |
| Compound 85 | 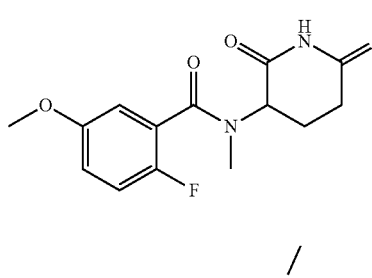 | |
| Compound 86 | 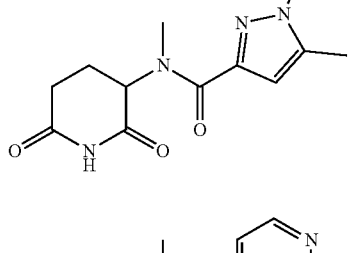 | ++++ |
| Compound 87 | 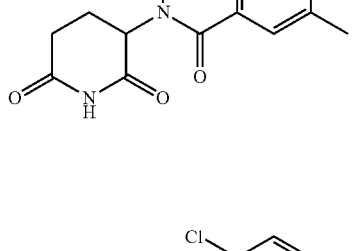 | + |
| Compound 88 | 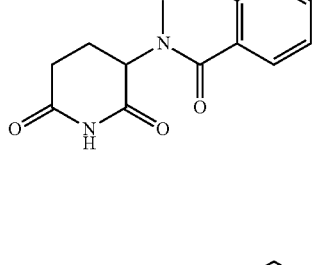 | + |
| Compound 89 | 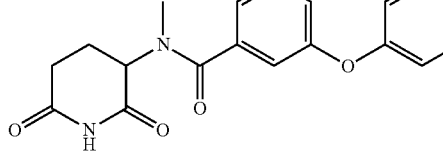 | ++++ |

TABLE 1-continued
| Compound # | Structure | Kd |
|---|---|---|
| Compound 90 | 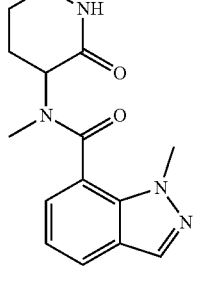 | +++ |
| Compound 91 | 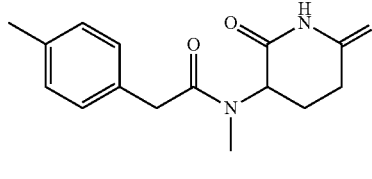 | +++ |
| Compound 92 | 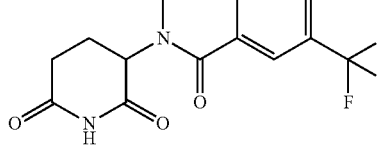 | + |
| Compound 93 | 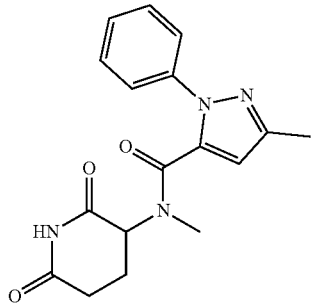 [SMILES: Cc1cc(C(=O)N(C)C2CCC(=O)NC2=O)n(-c2ccccc2)n1] | + |
| Compound 94 | 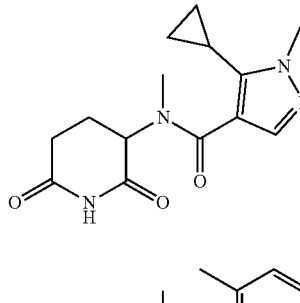 | + |
| Compound 95 | 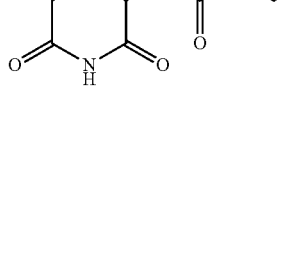 | + |

TABLE 1-continued

| Compound # | Structure | Kd |
|---|---|---|
| Compound 96 | 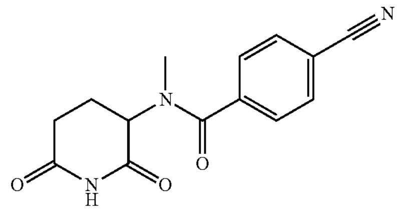 [SMILES: CN(C(=O)c1ccc(C#N)cc1)C1CCC(=O)NC1=O] | +++ |
| Compound 97 | 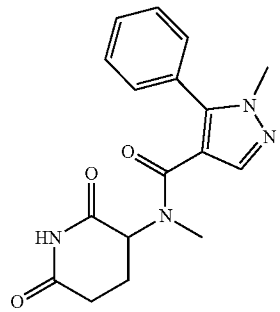 | +++ |
| Compound 98 | 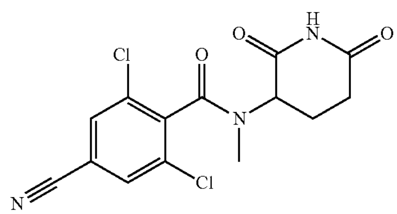 [SMILES: CN(C(=O)c1c(Cl)cc(C#N)cc1Cl)C1CCC(=O)NC1=O] | +++ |
| Compound 99 | 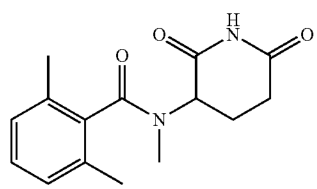 [SMILES: Cc1cccc(C)c1C(=O)N(C)C1CCC(=O)NC1=O] | + |
| Compound 100 | 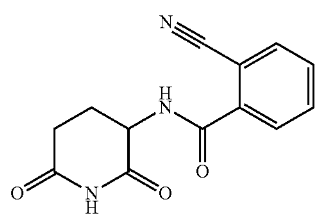 [SMILES: N#Cc1ccccc1C(=O)NC1CCC(=O)NC1=O] | +++++ |
| Compound 101 | 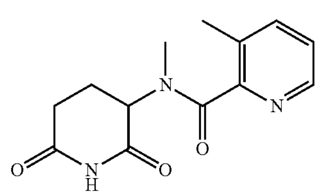 [SMILES: Cc1cccnc1C(=O)N(C)C1CCC(=O)NC1=O] | +++ |
| Compound 102 | 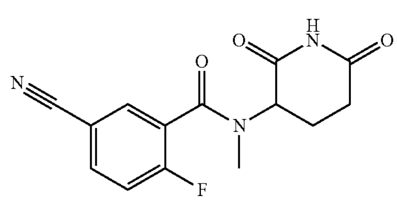 [SMILES: CN(C(=O)c1cc(C#N)ccc1F)C1CCC(=O)NC1=O] | +++ |

TABLE 1-continued

| Compound # | Structure | Kd |
|---|---|---|
| Compound 103 | [structure] | + |
| Compound 104 | [structure] | ++++ |
| Compound 105 | [structure] | + |
| Compound 106 | [structure] | +++ |
| Compound 107 | [structure] | ++++ |
| Compound 108 | [structure] | ++ |
| Compound 109 | [structure] | + |
| Compound 110 | [structure] | + |

TABLE 1-continued

| Compound # | Structure | Kd |
|---|---|---|
| Compound 111 | 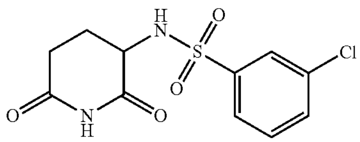 [SMILES: O=C1CCC(NS(=O)(=O)c2cccc(Cl)c2)C(=O)N1] | + |
| Compound 112 | 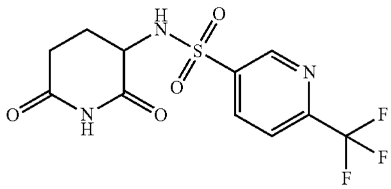 [SMILES: O=C1CCC(NS(=O)(=O)c2ccc(C(F)(F)F)nc2)C(=O)N1] | + |
| Compound 113 | 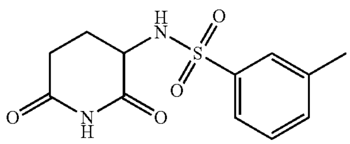 [SMILES: Cc1cccc(S(=O)(=O)NC2CCC(=O)NC2=O)c1] | + |
| Compound 114 | 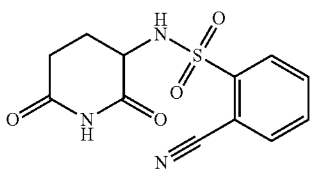 [SMILES: N#Cc1ccccc1S(=O)(=O)NC1CCC(=O)NC1=O] | +++ |
| Compound 115 | 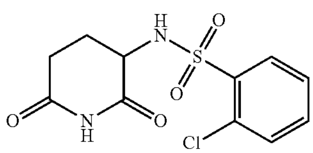 [SMILES: O=C1CCC(NS(=O)(=O)c2ccccc2Cl)C(=O)N1] | + |
| Compound 116 | 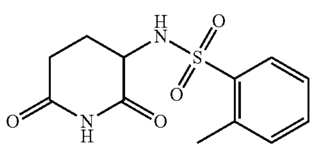 [SMILES: Cc1ccccc1S(=O)(=O)NC1CCC(=O)NC1=O] | + |
| Compound 117 | 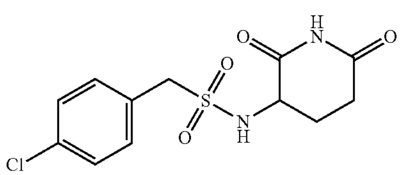 [SMILES: O=C1CCC(NS(=O)(=O)Cc2ccc(Cl)cc2)C(=O)N1] | + |
| Compound 118 | 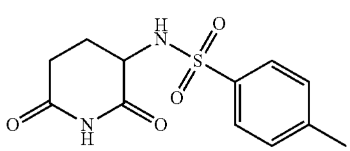 [SMILES: Cc1ccc(S(=O)(=O)NC2CCC(=O)NC2=O)cc1] | + |
| Compound 119 | 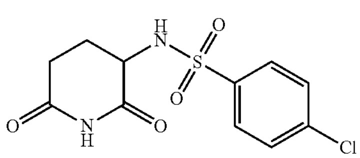 [SMILES: O=C1CCC(NS(=O)(=O)c2ccc(Cl)cc2)C(=O)N1] | + |

TABLE 1-continued

| Compound # | Structure | Kd |
|---|---|---|
| Compound 120 | 3-pyridyl sulfonamide of 3-aminoglutarimide | + |
| Compound 121 | 3,5-dimethylisoxazole-4-sulfonamide of 3-aminoglutarimide | + |
| Compound 122 | 3-cyanobenzenesulfonamide of 3-aminoglutarimide | + |
| Compound 123 | 4-cyanobenzenesulfonamide of 3-aminoglutarimide | + |
| Compound 124 | 2-fluorobenzenesulfonamide of 3-aminoglutarimide | + |
| Compound 125 | 2-pyridyl sulfonamide of 3-aminoglutarimide | + |
| Compound 126 | 3-fluorobenzenesulfonamide of 3-aminoglutarimide | + |
| Compound 127 | N-methyl benzenesulfonamide of 3-aminoglutarimide | ++++ |
| Compound 128 | quinoline-8-sulfonamide of 3-aminoglutarimide | ++++ |

TABLE 1-continued

| Compound # | Structure | Kd |
|---|---|---|
| Compound 129 | [2,6-dioxopiperidin-3-yl, N-methyl, sulfonyl, 2-fluorophenyl] | ++++ |
| Compound 130 | [2,6-dioxopiperidin-3-yl, N-methyl, sulfonyl, 4-fluorophenyl] | +++ |
| Compound 131 | [2,6-dioxopiperidin-3-yl, N-methyl, sulfonyl, 3-fluorophenyl] | +++ |
| Compound 132 | [2,6-dioxopiperidin-3-yl, N-methyl, sulfonyl, 3-chlorophenyl] | +++ |
| Compound 133 | [2,6-dioxopiperidin-3-yl, NH, sulfonyl, 1-methylimidazol-4-yl] | + |
| Compound 134 | [2,6-dioxopiperidin-3-yl, N-methyl, sulfonyl, 4-chlorophenyl] | ++++ |
| Compound 135 | [4-chlorophenyl-CH2-sulfonyl, N-methyl, 2,6-dioxopiperidin-3-yl] | ++++ |
| Compound 136 | [2,6-dioxopiperidin-3-yl, N-methyl, sulfonyl, 2-chlorophenyl] | +++ |

TABLE 1-continued

| Compound # | Structure | Kd |
|---|---|---|
| Compound 137 | 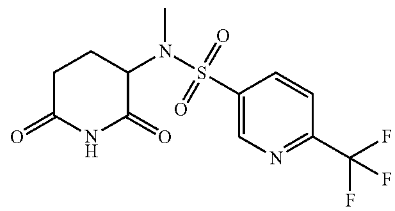 [SMILES: CN(C1CCC(=O)NC1=O)S(=O)(=O)c1ccc(C(F)(F)F)nc1] | +++ |
| Compound 138 | 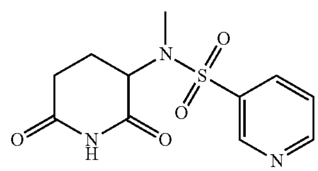 [SMILES: CN(C1CCC(=O)NC1=O)S(=O)(=O)c1cccnc1] | +++ |
| Compound 139 | 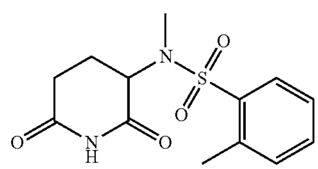 [SMILES: Cc1ccccc1S(=O)(=O)N(C)C1CCC(=O)NC1=O] | ++++ |
| Compound 140 | 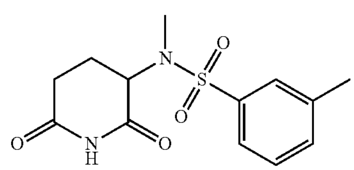 [SMILES: Cc1cccc(S(=O)(=O)N(C)C2CCC(=O)NC2=O)c1] | ++++ |
| Compound 141 | 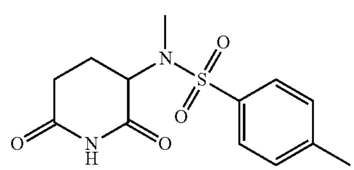 [SMILES: Cc1ccc(S(=O)(=O)N(C)C2CCC(=O)NC2=O)cc1] | ++++ |
| Compound 142 | 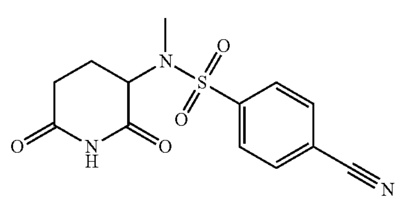 [SMILES: CN(C1CCC(=O)NC1=O)S(=O)(=O)c1ccc(C#N)cc1] | +++ |
| Compound 143 | 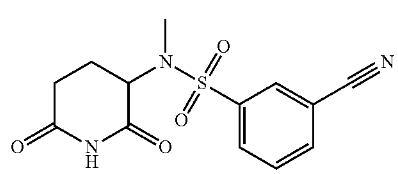 [SMILES: CN(C1CCC(=O)NC1=O)S(=O)(=O)c1cccc(C#N)c1] | ++++ |
| Compound 144 | 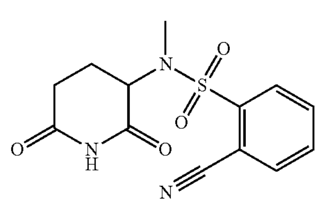 [SMILES: CN(C1CCC(=O)NC1=O)S(=O)(=O)c1ccccc1C#N] | ++++ |

TABLE 1-continued

| Compound # | Structure | Kd |
|---|---|---|
| Compound 145 | [3-(N-methyl-quinoline-8-sulfonamido)piperidine-2,6-dione] | ++++ |
| Compound 146 | [3-(N-methyl-1-methyl-1H-imidazole-5-sulfonamido)piperidine-2,6-dione] | +++++ |
| Compound 147 | [3-(N-methyl-pyridine-2-sulfonamido)piperidine-2,6-dione] | ++++ |
| Compound 148 | [3-(3-methyl-6-oxopyridazin-1(6H)-yl)piperidine-2,6-dione] | ++++ |
| Compound 149 | [3-(6-oxo-3-phenylpyridazin-1(6H)-yl)piperidine-2,6-dione] | +++++ |
| Compound 150 | [3-(3-(4-Boc-piperazin-1-yl)-6-oxopyridazin-1(6H)-yl)piperidine-2,6-dione] | +++ |
| Compound 151 | [3-(3-((2-methoxyethyl)amino)-6-oxopyridazin-1(6H)-yl)piperidine-2,6-dione] | +++ |
| Compound 152 | [3-(3-((2-hydroxyethyl)amino)-6-oxopyridazin-1(6H)-yl)piperidine-2,6-dione] | + |

TABLE 1-continued

| Compound # | Structure | Kd |
|---|---|---|
| Compound 153 | 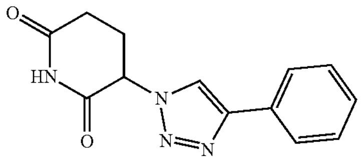 [SMILES: O=C1CCC(n2cc(-c3ccccc3)nn2)C(=O)N1] | +++++ |
| Compound 154 | 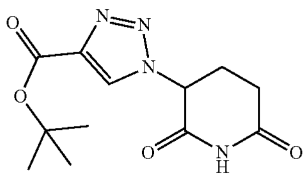 [SMILES: CC(C)(C)OC(=O)c1cn(C2CCC(=O)NC2=O)nn1] | +++++ |
| Compound 155 | 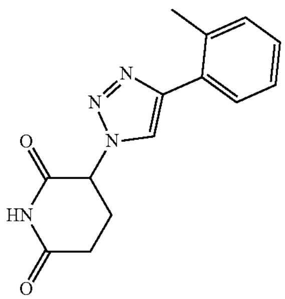 [SMILES: Cc1ccccc1-c1cn(C2CCC(=O)NC2=O)nn1] | ++++ |
| Compound 156 | 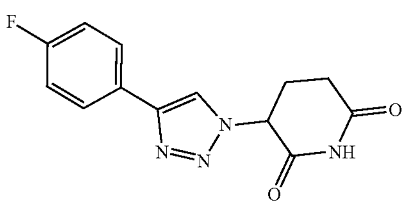 [SMILES: O=C1CCC(n2cc(-c3ccc(F)cc3)nn2)C(=O)N1] | +++++ |
| Compound 157 | 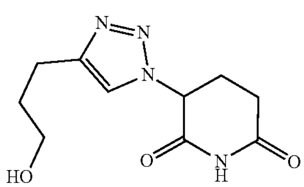 [SMILES: O=C1CCC(n2cc(CCCO)nn2)C(=O)N1] | ++++ |
| Compound 158 | 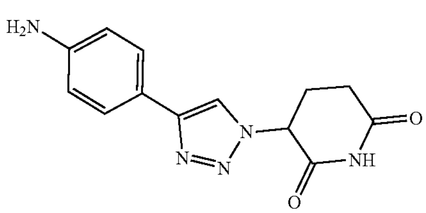 [SMILES: Nc1ccc(-c2cn(C3CCC(=O)NC3=O)nn2)cc1] | +++++ |
| Compound 159 | 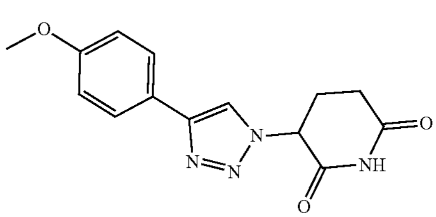 [SMILES: COc1ccc(-c2cn(C3CCC(=O)NC3=O)nn2)cc1] | +++++ |

TABLE 1-continued

| Compound # | Structure | Kd |
|---|---|---|
| Compound 160 | 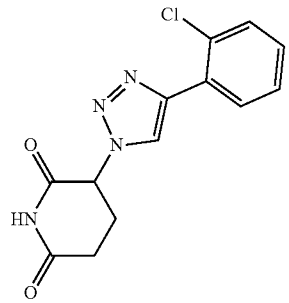 [SMILES: O=C1CCC(n2cc(-c3ccccc3Cl)nn2)C(=O)N1] | +++++ |
| Compound 161 | 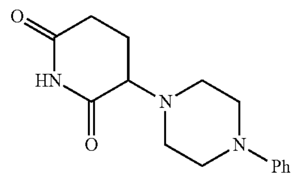 [SMILES: O=C1CCC(N2CCN(c3ccccc3)CC2)C(=O)N1] | ++++ |
| Compound 162 | 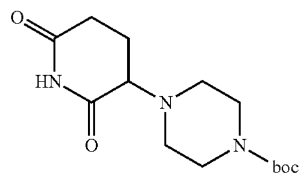 | + |
| Compound 163 | 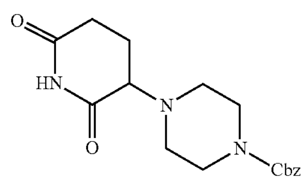 [SMILES: O=C1CCC(N2CCN(C(=O)OCc3ccccc3)CC2)C(=O)N1] | + |
| Compound 164 | 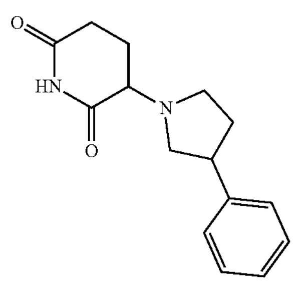 [SMILES: O=C1CCC(N2CCC(c3ccccc3)C2)C(=O)N1] | + |
| Compound 165 | 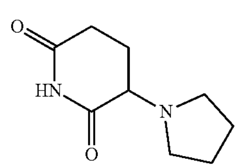 [SMILES: O=C1CCC(N2CCCC2)C(=O)N1] | + |
| Compound 166 | 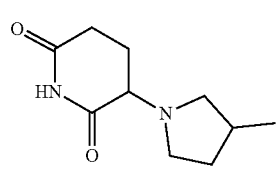 | + |

TABLE 1-continued
| Compound # | Structure | Kd |
|---|---|---|
| Compound 167 | 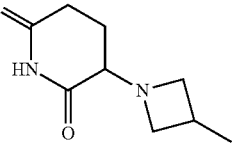 | + |
| Compound 168 | 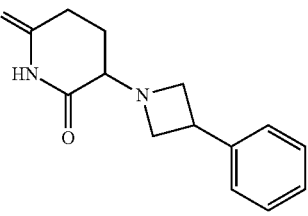 | + |
| Compound 169 | 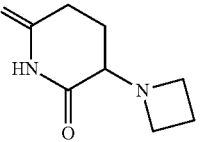 | ++++ |
| Compound 170 | 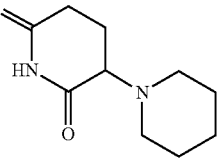 | + |
| Compound 171 | 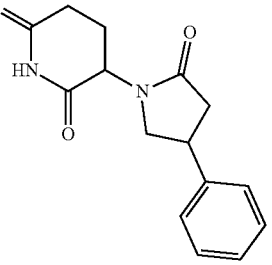 | +++++ |
| Compound 172 | 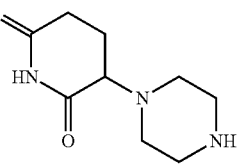 | + |
| Compound 173 | 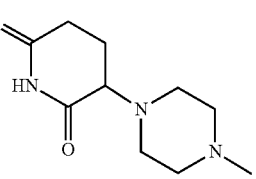 | + |
| Compound 174 | 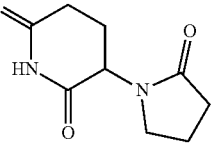 | ++++ |

TABLE 1-continued

| Compound # | Structure | Kd |
|---|---|---|
| Compound 175 | 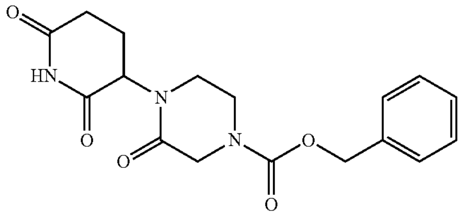 [SMILES: O=C1CCC(N2CCN(C(=O)OCc3ccccc3)CC2=O)C(=O)N1] | ++++ |
| Compound 176 | 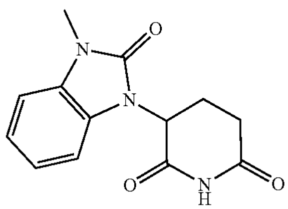 [SMILES: Cn1c(=O)n(C2CCC(=O)NC2=O)c2ccccc21] | +++++ |
| Compound 177 | 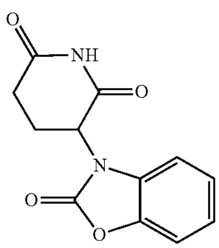 [SMILES: O=C1CCC(n2c(=O)oc3ccccc32)C(=O)N1] | +++++ |
| Compound 178 | 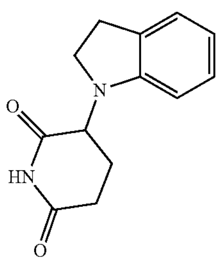 [SMILES: O=C1CCC(N2CCc3ccccc32)C(=O)N1] | +++++ |
| Compound 179 | 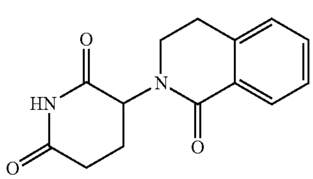 [SMILES: O=C1CCC(N2CCc3ccccc3C2=O)C(=O)N1] | +++++ |
| Compound 180 | 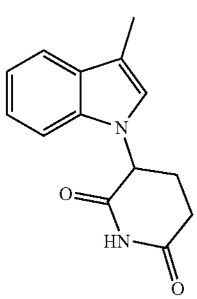 [SMILES: Cc1cn(C2CCC(=O)NC2=O)c2ccccc12] | +++++ |

TABLE 1-continued

| Compound # | Structure | Kd |
|---|---|---|
| Compound 181 | (benzyl-oxazolidinone attached to glutarimide N) | ++++ |
| Compound 182 | (isoquinolin-1(2H)-one attached to glutarimide) | +++++ |
| Compound 183 | (benzimidazol-1-yl glutarimide) | +++++ |
| Compound 184 | (3-methyl-2H-indazol-2-yl glutarimide) | +++++ |
| Compound 185 | (2H-indazol-2-yl glutarimide) | ++++ |
| Compound 186 | (pyrazolo[3,4-b]pyridin-1-yl glutarimide) | +++ |
| Compound 187 | (1H-indazol-1-yl glutarimide) | +++++ |

TABLE 1-continued

| Compound # | Structure | Kd |
|---|---|---|
| Compound 188 | indol-1-yl-glutarimide | +++++ |
| Compound 189 | 3-(3-phenyl-pyrazol-1-yl)-glutarimide | ++++ |
| Compound 190 | 3-(4-boc-3-oxopiperazin-1-yl)-glutarimide | ++++ |
| Compound 191 | 3-(3-oxopiperazin-1-yl)-glutarimide | ++++ |
| Compound 192 | 3-(4-phenyl-3-oxopiperazin-1-yl)-glutarimide | +++++ |
| Compound 193 | 3-[4-(pyridin-2-yl)-2-oxopiperazin-1-yl]-glutarimide | ++++ |
| Compound 194 | 3-(4-phenyl-pyrazol-1-yl)-glutarimide | ++++ |

TABLE 1-continued
| Compound # | Structure | Kd |
|---|---|---|
| Compound 195 | 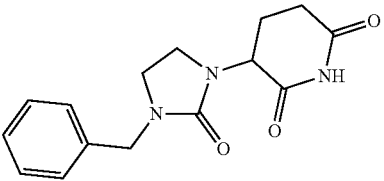 [SMILES: O=C1CCC(N2CCN(Cc3ccccc3)C2=O)C(=O)N1] | |
| Compound 196 | 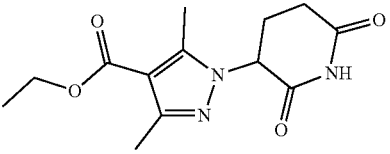 [SMILES: CCOC(=O)c1c(C)nn(C2CCC(=O)NC2=O)c1C] | |
| Compound 197 | 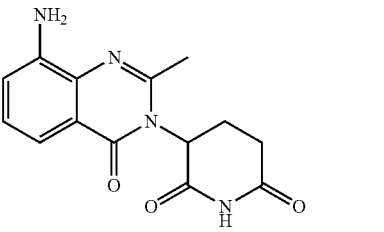 [SMILES: Cc1nc2c(N)cccc2c(=O)n1C1CCC(=O)NC1=O] | +++ |
| Compound 198 | 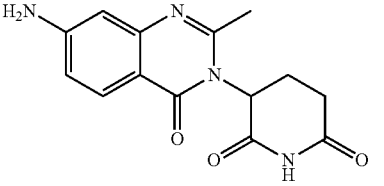 [SMILES: Cc1nc2cc(N)ccc2c(=O)n1C1CCC(=O)NC1=O] | + |
| Compound 199 | 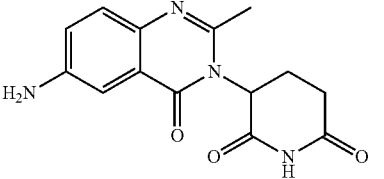 [SMILES: Cc1nc2ccc(N)cc2c(=O)n1C1CCC(=O)NC1=O] | + |
| Compound 200 | 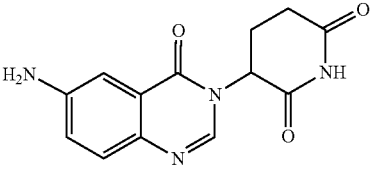 [SMILES: Nc1ccc2ncn(C3CCC(=O)NC3=O)c(=O)c2c1] | +++++ |
| Compound 201 | 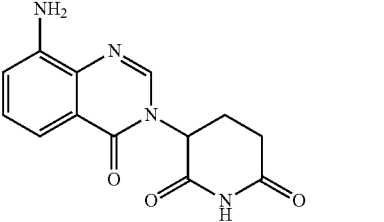 [SMILES: Nc1cccc2c(=O)n(C3CCC(=O)NC3=O)cnc12] | +++++ |

TABLE 1-continued

| Compound # | Structure | Kd |
|---|---|---|
| Compound 202 | 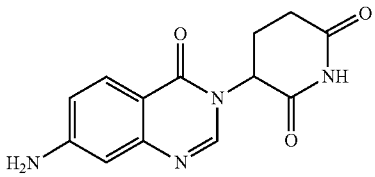 [SMILES: Nc1ccc2c(=O)n(C3CCC(=O)NC3=O)cnc2c1] | +++++ |
| Compound 203 | 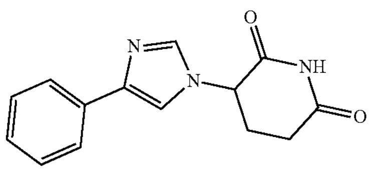 [SMILES: O=C1CCC(n2cnc(-c3ccccc3)c2)C(=O)N1] | ++++ |
| Compound 204 | 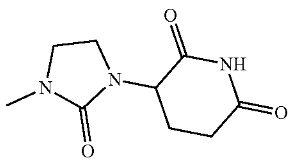 | ++++ |
| Compound 205 | 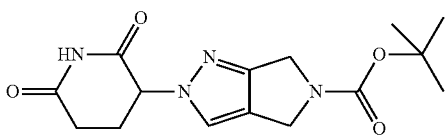 [SMILES: CC(C)(C)OC(=O)N1Cc2cn(C3CCC(=O)NC3=O)nc2C1] | +++ |
| Compound 206 | 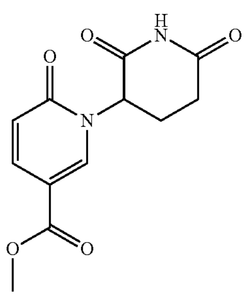 [SMILES: COC(=O)c1ccc(=O)n(C2CCC(=O)NC2=O)c1] | +++++ |
| Compound 207 | 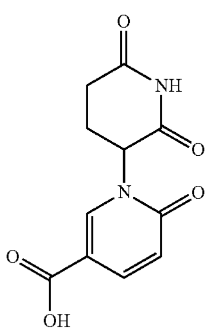 [SMILES: O=C1CCC(n2cc(C(=O)O)ccc2=O)C(=O)N1] | |
| Compound 208 | 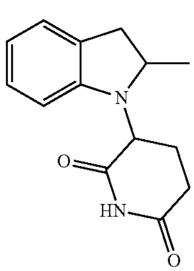 [SMILES: CC1Cc2ccccc2N1C1CCC(=O)NC1=O] | +++++ |

TABLE 1-continued

| Compound # | Structure | Kd |
|---|---|---|
| Compound 209 | (2-methylindol-1-yl piperidine-2,6-dione) | +++++ |
| Compound 210 | (7-azaindol-1-yl piperidine-2,6-dione) | ++++ |
| Compound 211 | (maleimido piperidine-2,6-dione) | ++++ |
| Compound 212 | (7-bromo-2-methylquinazolin-4(3H)-one piperidine-2,6-dione) | + |
| Compound 213 | (6-bromo-2-methylquinazolin-4(3H)-one piperidine-2,6-dione) | + |

In Table 1 above
>100 μM = +
>30 μM = ++
50-100 μM = +++
10-50 μM = ++++
<10 μM = +++++.

TABLE 2

| Compound # | Structure | Kd |
|---|---|---|
| Compound 214 | 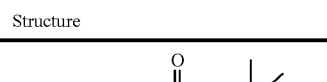 | +++++ |

TABLE 2-continued

| Compound # | Structure | Kd |
|---|---|---|
| Compound 215 | 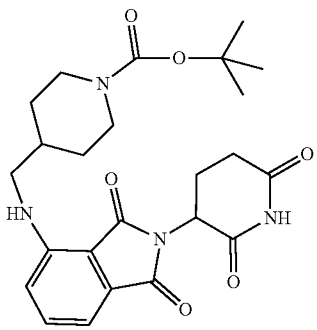 [SMILES: CC(C)(C)OC(=O)N1CCC(CNc2cccc3c2C(=O)N(C2CCC(=O)NC2=O)C3=O)CC1] | +++++ |
| Compound 216 | 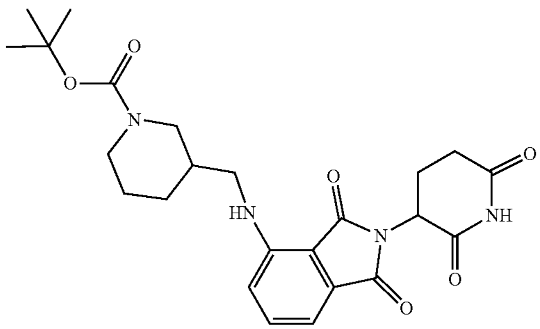 [SMILES: CC(C)(C)OC(=O)N1CCCC(CNc2cccc3c2C(=O)N(C2CCC(=O)NC2=O)C3=O)C1] | +++++ |
| Compound 217 | 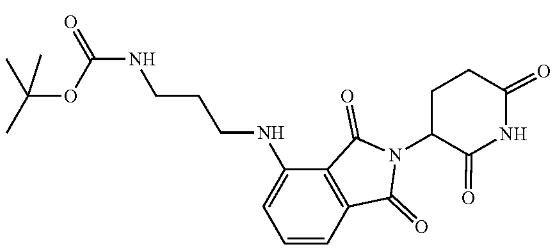 [SMILES: CC(C)(C)OC(=O)NCCCNc1cccc2c1C(=O)N(C1CCC(=O)NC1=O)C2=O] | +++++ |
| Compound 218 | 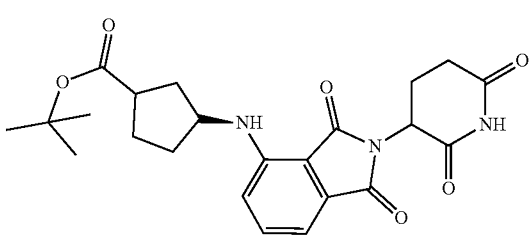 | +++++ |
| Compound 219 | 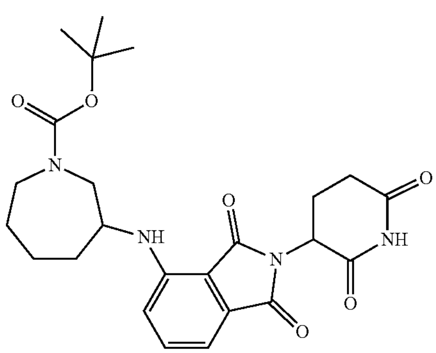 [SMILES: CC(C)(C)OC(=O)N1CCCCC(Nc2cccc3c2C(=O)N(C2CCC(=O)NC2=O)C3=O)C1] | +++++ |

TABLE 2-continued

| Compound # | Structure | Kd |
|---|---|---|
| Compound 220 | 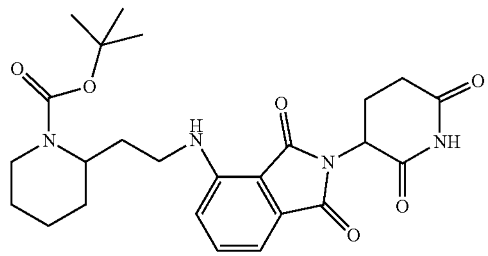 [SMILES: CC(C)(C)OC(=O)N1CCCCC1CCNc1cccc2c1C(=O)N(C1CCC(=O)NC1=O)C2=O] | +++++ |
| Compound 221 | 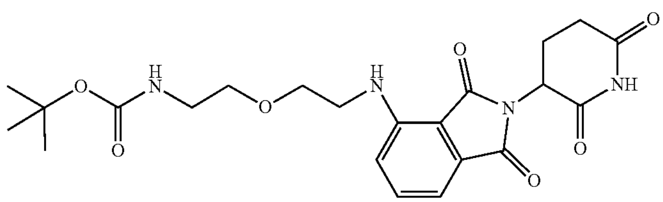 [SMILES: CC(C)(C)OC(=O)NCCOCCNc1cccc2c1C(=O)N(C1CCC(=O)NC1=O)C2=O] | 2.06 uM |
| Compound 222 | 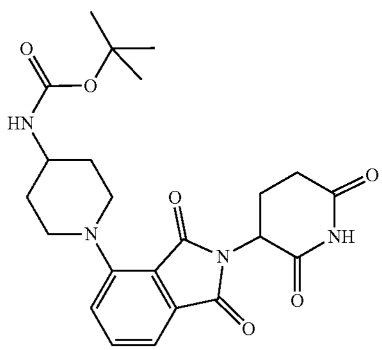 [SMILES: CC(C)(C)OC(=O)NC1CCN(c2cccc3c2C(=O)N(C2CCC(=O)NC2=O)C3=O)CC1] | +++++ |
| Compound 223 | 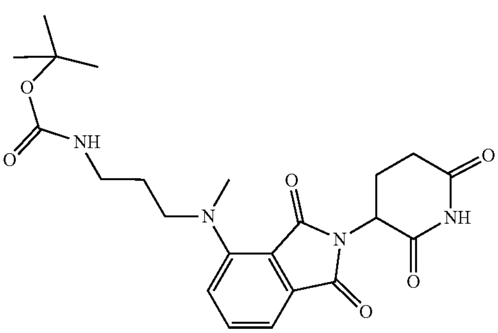 [SMILES: CN(CCCNC(=O)OC(C)(C)C)c1cccc2c1C(=O)N(C1CCC(=O)NC1=O)C2=O] | +++++ |
| Compound 224 | 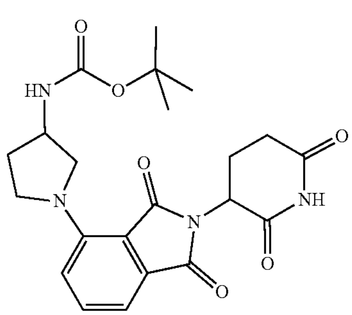 [SMILES: CC(C)(C)OC(=O)NC1CCN(c2cccc3c2C(=O)N(C2CCC(=O)NC2=O)C3=O)C1] | +++++ |

TABLE 2-continued

| Compound # | Structure | Kd |
|---|---|---|
| Compound 225 | 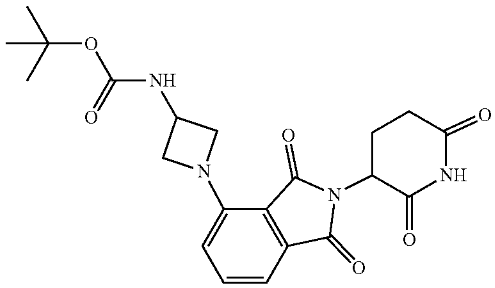 [SMILES: CC(C)(C)OC(=O)NC1CN(c2cccc3c2C(=O)N(C2CCC(=O)NC2=O)C3=O)C1] | +++++ |
| Compound 226 | 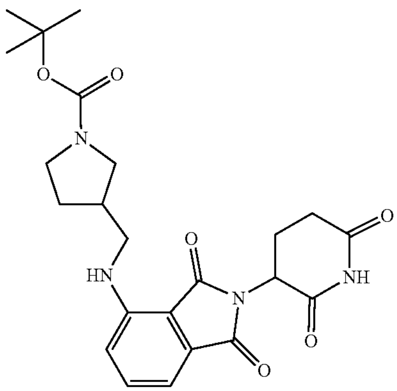 [SMILES: CC(C)(C)OC(=O)N1CCC(CNc2cccc3c2C(=O)N(C2CCC(=O)NC2=O)C3=O)C1] | +++++ |
| Compound 227 | 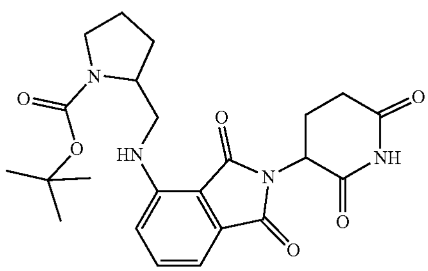 [SMILES: CC(C)(C)OC(=O)N1CCCC1CNc1cccc2c1C(=O)N(C1CCC(=O)NC1=O)C2=O] | +++++ |
| Compound 228 | 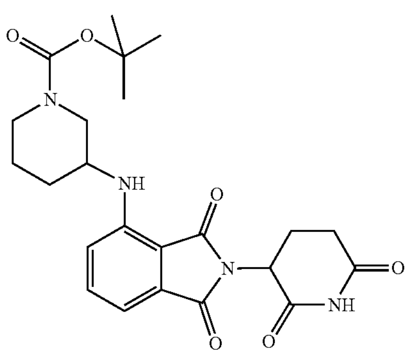 [SMILES: CC(C)(C)OC(=O)N1CCCC(Nc2cccc3c2C(=O)N(C2CCC(=O)NC2=O)C3=O)C1] | +++++ |
| Compound 229 | 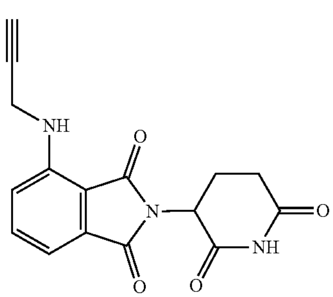 [SMILES: C#CCNc1cccc2c1C(=O)N(C1CCC(=O)NC1=O)C2=O] | +++++ |

TABLE 2-continued

| Compound # | Structure | Kd |
|---|---|---|
| Compound 230 | 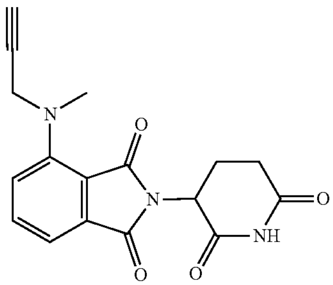 [SMILES: C#CCN(C)c1cccc2c1C(=O)N(C1CCC(=O)NC1=O)C2=O] | |
| Compound 231 | 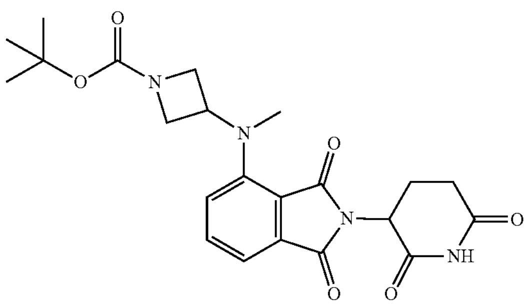 [SMILES: CN(c1cccc2c1C(=O)N(C1CCC(=O)NC1=O)C2=O)C1CN(C(=O)OC(C)(C)C)C1] | +++++ |
| Compound 232 | 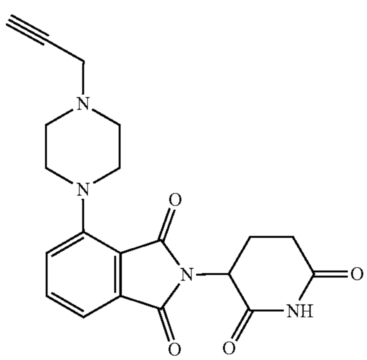 [SMILES: C#CCN1CCN(c2cccc3c2C(=O)N(C2CCC(=O)NC2=O)C3=O)CC1] | |
| Compound 233 | 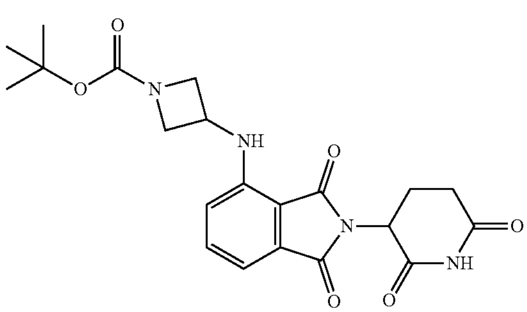 [SMILES: CC(C)(C)OC(=O)N1CC(Nc2cccc3c2C(=O)N(C2CCC(=O)NC2=O)C3=O)C1] | +++++ |

TABLE 2-continued
| Compound # | Structure | Kd |
|---|---|---|
| Compound 234 | 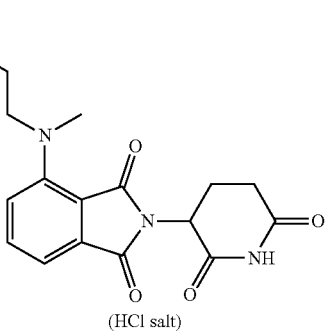 (HCl salt) | +++++ |
| Compound 235 | 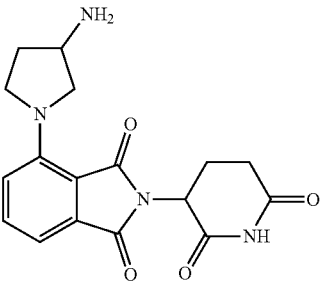 (HCl salt) | +++++ |
| Compound 236 | 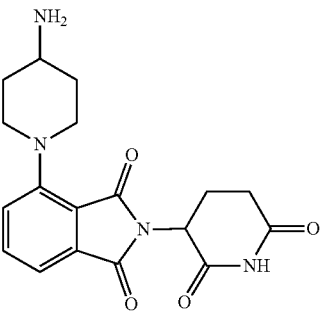 (HCl salt) | +++++ |
| Compound 237 | 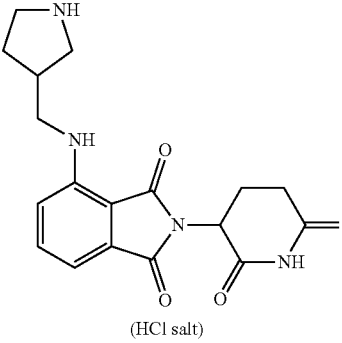 (HCl salt) | +++++ |

TABLE 2-continued
| Compound # | Structure | Kd |
|---|---|---|
| Compound 238 | 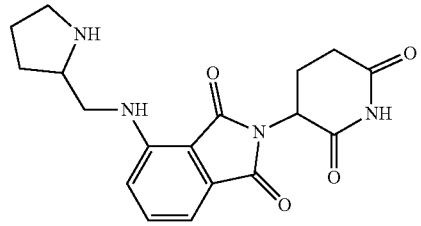 (HCl salt) | |
| Compound 239 | 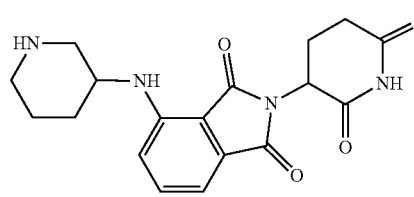 (HCl salt) | +++++ |
| Compound 240 | 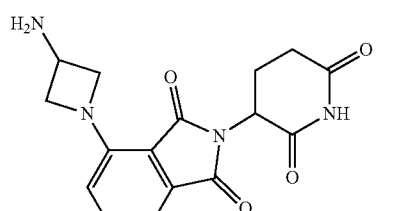 | ++++ |
| Compound 241 | 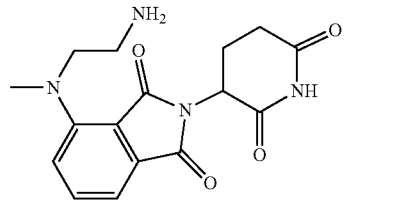 [SMILES: CN(CCN)c1cccc2c1C(=O)N(C1CCC(=O)NC1=O)C2=O] | ++++ |
| Compound 242 | 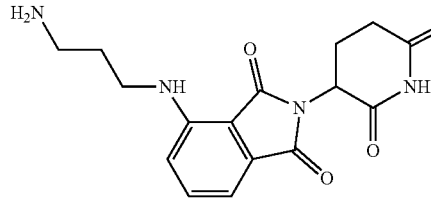 (HCl salt) | +++++ |
| Compound 243 | 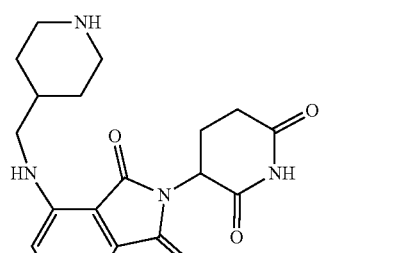 HCl salt | +++++ |

TABLE 2-continued
| Compound # | Structure | Kd |
|---|---|---|
| Compound 244 | 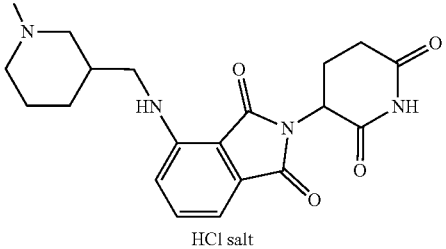<br>HCl salt | +++++ |
| Compound 245 | 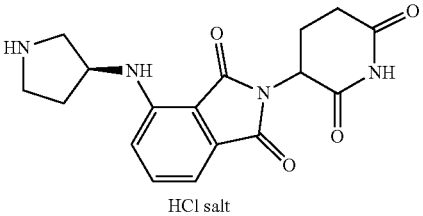 [SMILES: O=C1CCC(N2C(=O)c3cccc(N[C@H]4CCNC4)c3C2=O)C(=O)N1]<br>HCl salt | ++++ |
| Compound 246 | 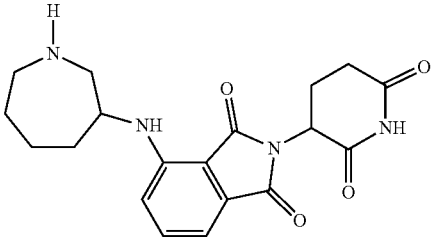<br>HCl salt | +++++ |
| Compound 247 | 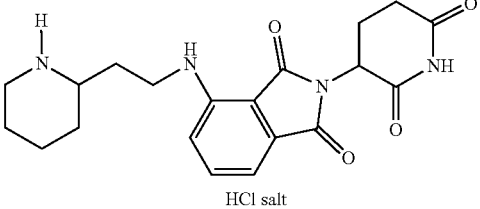<br>HCl salt | +++++ |
| Compound 248 | 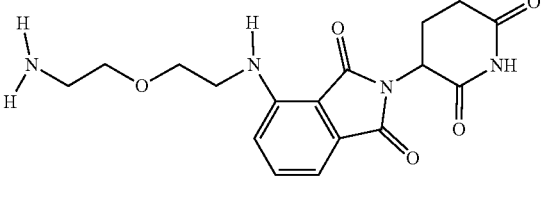<br>HCl salt | +++++ |
| Compound 249 | 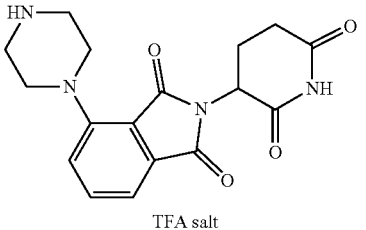 [SMILES: O=C1CCC(N2C(=O)c3cccc(N4CCNCC4)c3C2=O)C(=O)N1]<br>TFA salt | +++++ |

TABLE 2-continued

| Compound # | Structure | Kd |
|---|---|---|
| Compound 250 | (structure shown; TFA salt) | +++++ |
| Compound 251 | (structure shown) | +++++ |
| Compound 252 | (structure shown) | +++++ |
| Compound 253 | (structure shown) | +++++ |
| Compound 254 | (structure shown) | +++++ |
| Compound 255 | (structure shown) | +++++ |

TABLE 2-continued

| Compound # | Structure | Kd |
|---|---|---|
| Compound 256 | 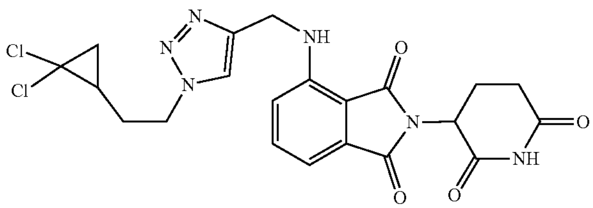 [SMILES: O=C1CCC(N2C(=O)c3cccc(NCc4cn(CCC5CC5(Cl)Cl)nn4)c3C2=O)C(=O)N1] | +++++ |
| Compound 257 | 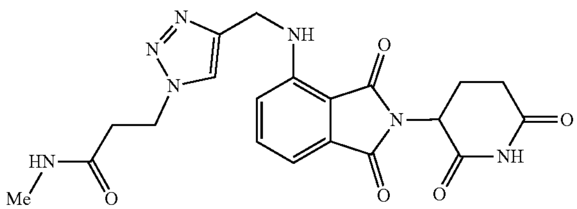 [SMILES: CNC(=O)CCn1cc(CNc2cccc3c2C(=O)N(C2CCC(=O)NC2=O)C3=O)nn1] | +++++ |
| Compound 258 | 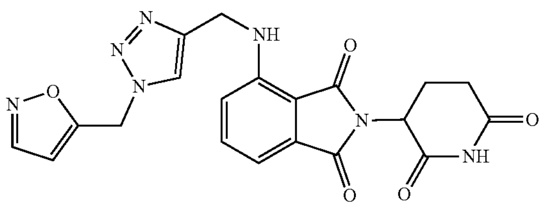 [SMILES: O=C1CCC(N2C(=O)c3cccc(NCc4cn(Cc5ccno5)nn4)c3C2=O)C(=O)N1] | +++++ |
| Compound 259 | 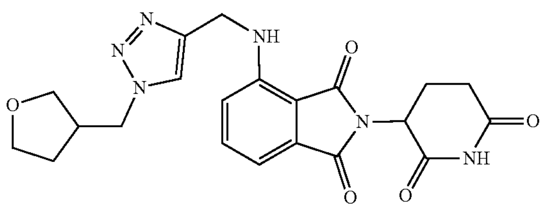 [SMILES: O=C1CCC(N2C(=O)c3cccc(NCc4cn(CC5CCOC5)nn4)c3C2=O)C(=O)N1] | +++++ |
| Compound 260 | 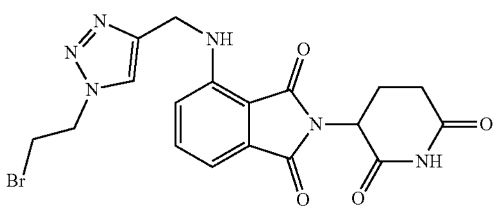 [SMILES: O=C1CCC(N2C(=O)c3cccc(NCc4cn(CCBr)nn4)c3C2=O)C(=O)N1] | +++++ |
| Compound 261 | 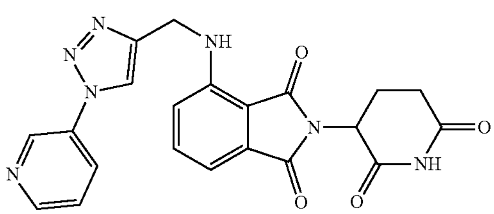 [SMILES: O=C1CCC(N2C(=O)c3cccc(NCc4cn(-c5cccnc5)nn4)c3C2=O)C(=O)N1] | +++++ |
| Compound 262 | 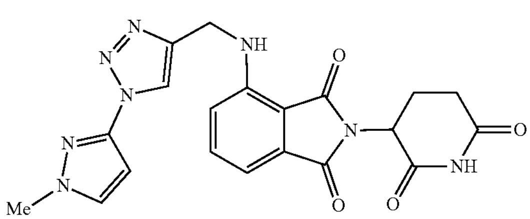 [SMILES: Cn1ccc(-n2cc(CNc3cccc4c3C(=O)N(C3CCC(=O)NC3=O)C4=O)nn2)n1] | +++++ |

TABLE 2-continued
| Compound # | Structure | Kd |
|---|---|---|
| Compound 263 | 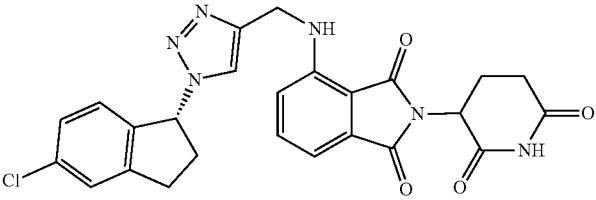 [SMILES: O=C1CCC(N2C(=O)c3cccc(NCc4cn([C@@H]5CCc6cc(Cl)ccc65)nn4)c3C2=O)C(=O)N1] | +++++ |
| Compound 264 | 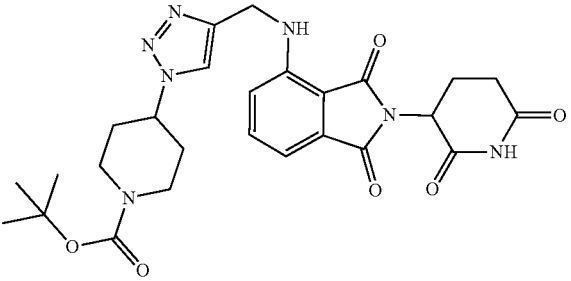 | +++++ |
| Compound 265 | 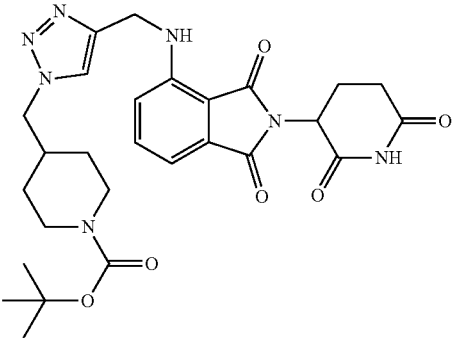 [SMILES: CC(C)(C)OC(=O)N1CCC(Cn2cc(CNc3cccc4c3C(=O)N(C3CCC(=O)NC3=O)C4=O)nn2)CC1] | +++++ |
| Compound 266 | 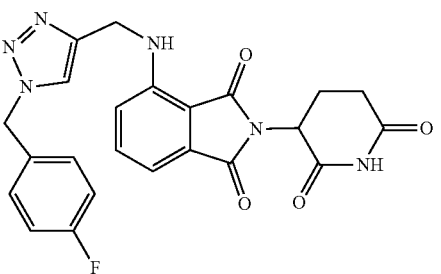 [SMILES: O=C1CCC(N2C(=O)c3cccc(NCc4cn(Cc5ccc(F)cc5)nn4)c3C2=O)C(=O)N1] | +++++ |
| Compound 267 | 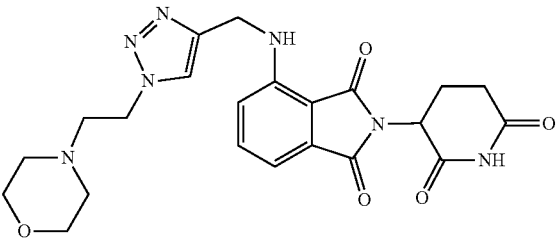 [SMILES: O=C1CCC(N2C(=O)c3cccc(NCc4cn(CCN5CCOCC5)nn4)c3C2=O)C(=O)N1] | +++++ |

TABLE 2-continued

| Compound # | Structure | Kd |
|---|---|---|
| Compound 268 | 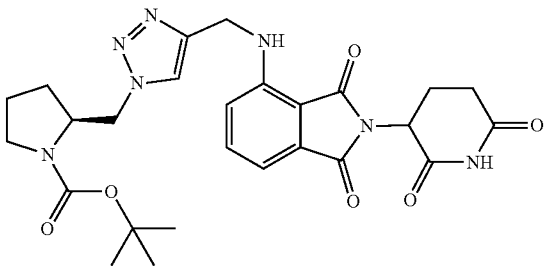 [SMILES: CC(C)(C)OC(=O)N1CCC[C@H]1Cn1cc(CNc2cccc3c2C(=O)N(C2CCC(=O)NC2=O)C3=O)nn1] | +++++ |
| Compound 269 | 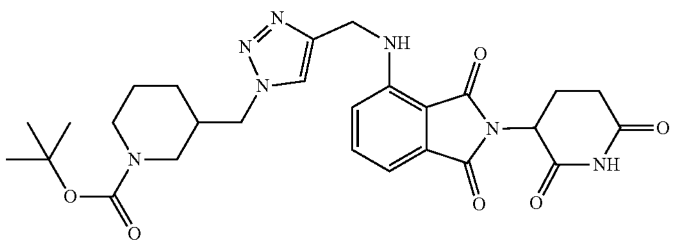 [SMILES: CC(C)(C)OC(=O)N1CCCC(Cn2cc(CNc3cccc4c3C(=O)N(C3CCC(=O)NC3=O)C4=O)nn2)C1] | +++++ |
| Compound 270 | 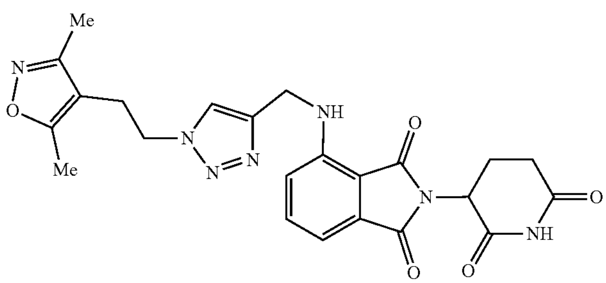 [SMILES: Cc1noc(C)c1CCn1cc(CNc2cccc3c2C(=O)N(C2CCC(=O)NC2=O)C3=O)nn1] | +++++ |
| Compound 271 | 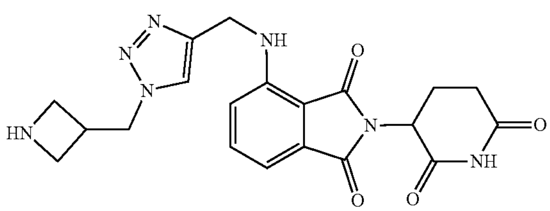 [SMILES: O=C1CCC(N2C(=O)c3cccc(NCc4cn(CC5CNC5)nn4)c3C2=O)C(=O)N1] | +++++ |
| Compound 272 | 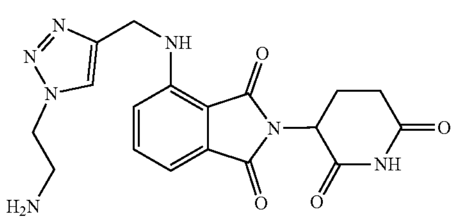 [SMILES: NCCn1cc(CNc2cccc3c2C(=O)N(C2CCC(=O)NC2=O)C3=O)nn1] | +++++ |
| Compound 273 | 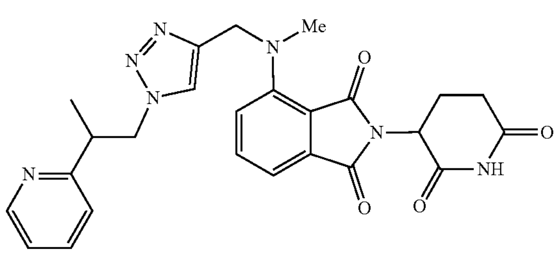 [SMILES: CC(Cn1cc(CN(C)c2cccc3c2C(=O)N(C2CCC(=O)NC2=O)C3=O)nn1)c1ccccn1] | |

TABLE 2-continued

| Compound # | Structure | Kd |
|---|---|---|
| Compound 274 | 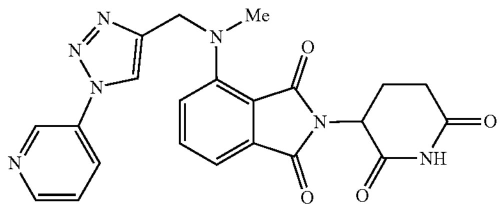 [SMILES: CN(Cc1cn(-c2cccnc2)nn1)c1cccc2c1C(=O)N(C1CCC(=O)NC1=O)C2=O] | |
| Compound 275 | 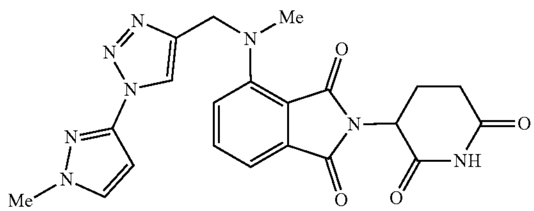 [SMILES: CN(Cc1cn(-c2ccn(C)n2)nn1)c1cccc2c1C(=O)N(C1CCC(=O)NC1=O)C2=O] | |
| Compound 276 | 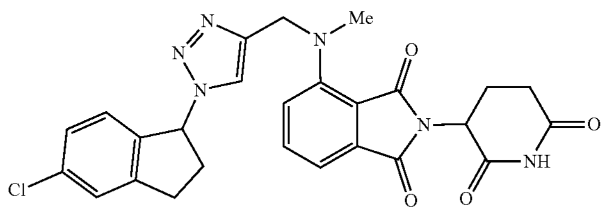 [SMILES: CN(Cc1cn(C2CCc3cc(Cl)ccc32)nn1)c1cccc2c1C(=O)N(C1CCC(=O)NC1=O)C2=O] | |
| Compound 277 | 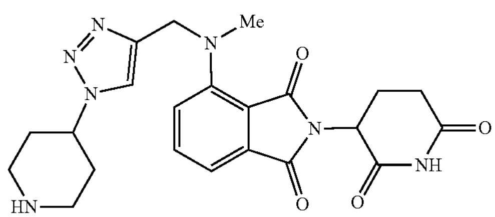 [SMILES: CN(Cc1cn(C2CCNCC2)nn1)c1cccc2c1C(=O)N(C1CCC(=O)NC1=O)C2=O] | |
| Compound 278 | 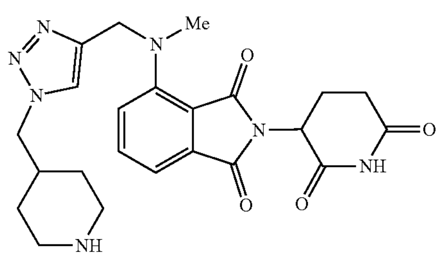 [SMILES: CN(Cc1cn(CC2CCNCC2)nn1)c1cccc2c1C(=O)N(C1CCC(=O)NC1=O)C2=O] | |
| Compound 279 | 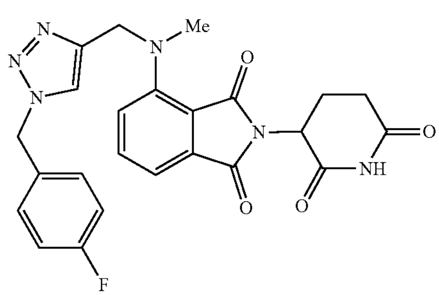 [SMILES: CN(Cc1cn(Cc2ccc(F)cc2)nn1)c1cccc2c1C(=O)N(C1CCC(=O)NC1=O)C2=O] | |

TABLE 2-continued

| Compound # | Structure | Kd |
|---|---|---|
| Compound 280 | 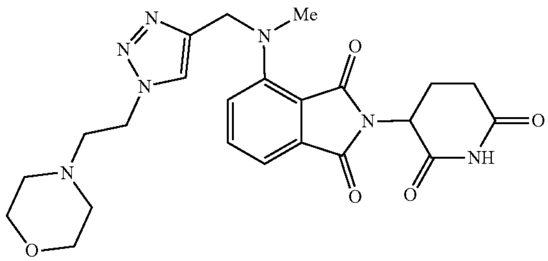 [SMILES: CN(Cc1cn(CCN2CCOCC2)nn1)c1cccc2c1C(=O)N(C1CCC(=O)NC1=O)C2=O] | |
| Compound 281 | 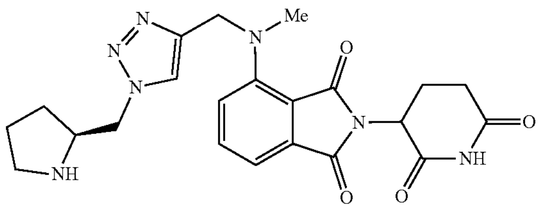 [SMILES: CN(Cc1cn(C[C@@H]2CCCN2)nn1)c1cccc2c1C(=O)N(C1CCC(=O)NC1=O)C2=O] | |
| Compound 282 | 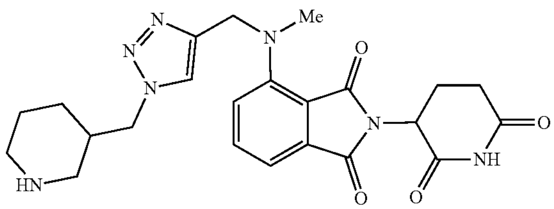 [SMILES: CN(Cc1cn(CC2CCCNC2)nn1)c1cccc2c1C(=O)N(C1CCC(=O)NC1=O)C2=O] | |
| Compound 283 | 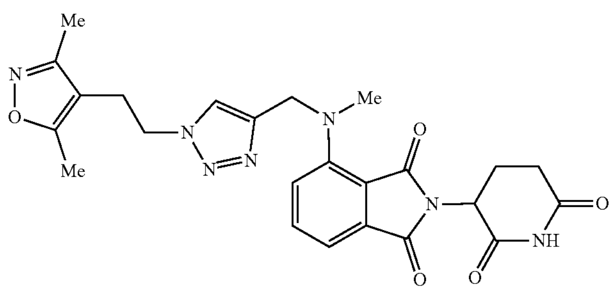 [SMILES: Cc1noc(C)c1CCn1cc(CN(C)c2cccc3c2C(=O)N(C2CCC(=O)NC2=O)C3=O)nn1] | |
| Compound 284 | 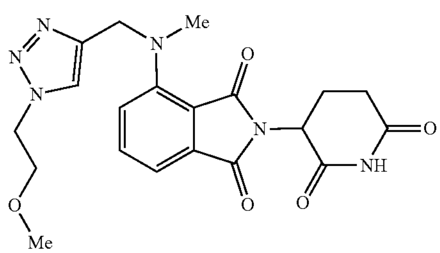 [SMILES: COCCn1cc(CN(C)c2cccc3c2C(=O)N(C2CCC(=O)NC2=O)C3=O)nn1] | |
| Compound 285 | 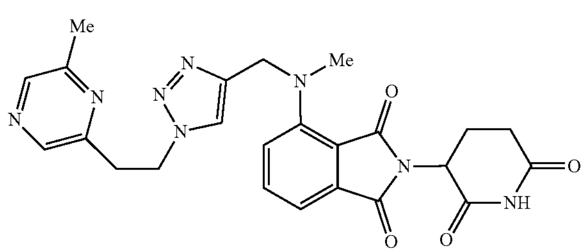 [SMILES: Cc1cncc(CCn2cc(CN(C)c3cccc4c3C(=O)N(C3CCC(=O)NC3=O)C4=O)nn2)n1] | |

TABLE 2-continued
| Compound # | Structure | Kd |
|---|---|---|
| Compound 286 | 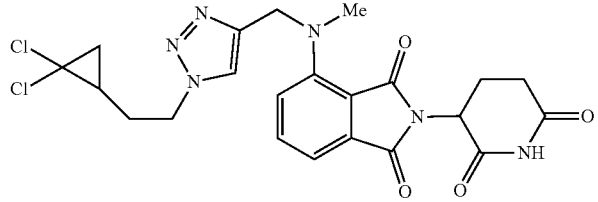 [SMILES: CN(Cc1cn(CCC2CC2(Cl)Cl)nn1)c1cccc2c1C(=O)N(C1CCC(=O)NC1=O)C2=O] | |
| Compound 287 | 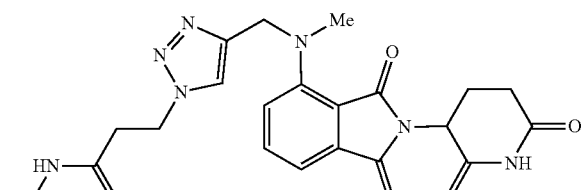 | |
| Compound 288 | 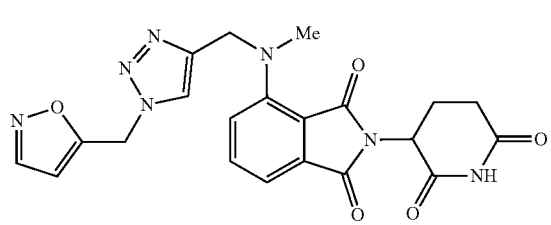 [SMILES: CN(Cc1cn(Cc2ccno2)nn1)c1cccc2c1C(=O)N(C1CCC(=O)NC1=O)C2=O] | |
| Compound 289 | 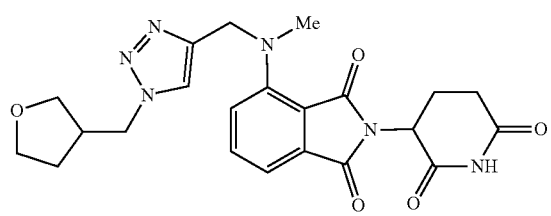 [SMILES: CN(Cc1cn(CC2CCOC2)nn1)c1cccc2c1C(=O)N(C1CCC(=O)NC1=O)C2=O] | |
| Compound 290 | 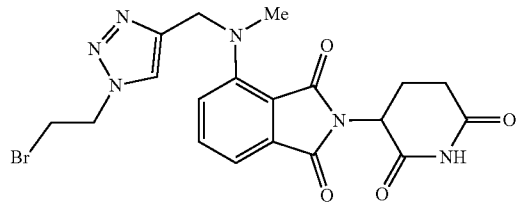 [SMILES: CN(Cc1cn(CCBr)nn1)c1cccc2c1C(=O)N(C1CCC(=O)NC1=O)C2=O] | |
| Compound 291 | 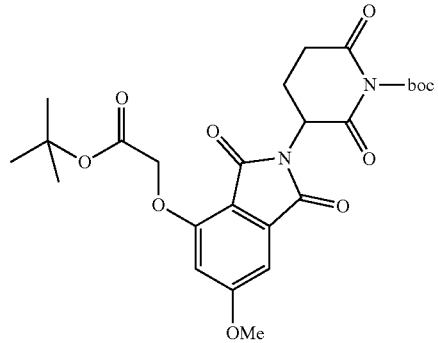 | +++++ |

TABLE 2-continued
| Compound # | Structure | Kd |
|---|---|---|
| Compound 292 | 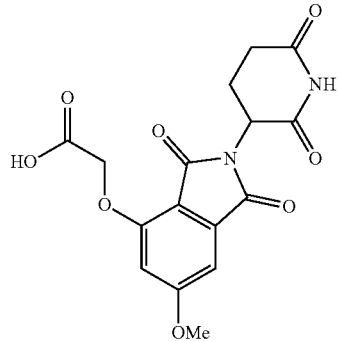 [SMILES: COc1cc(OCC(=O)O)c2c(c1)C(=O)N(C1CCC(=O)NC1=O)C2=O] | +++++ |
| Compound 293 | 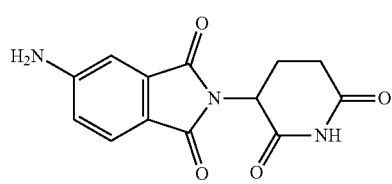 [SMILES: Nc1ccc2c(c1)C(=O)N(C1CCC(=O)NC1=O)C2=O] | +++++ |
| Compound 294 | 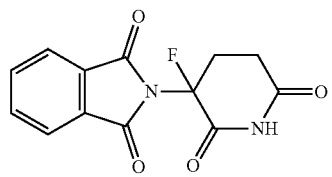 [SMILES: O=C1CCC(F)(N2C(=O)c3ccccc3C2=O)C(=O)N1] | ++++ |
| Compound 295 | 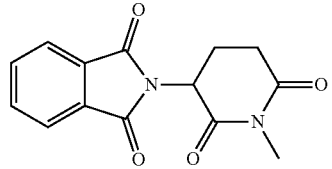 [SMILES: CN1C(=O)CCC(N2C(=O)c3ccccc3C2=O)C1=O] | + |
| Compound 296 | 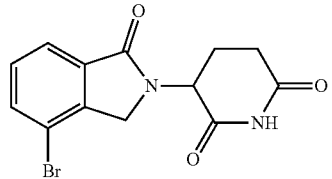 | +++++ |
| Compound 297 | 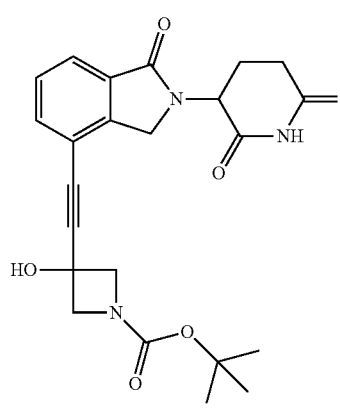 | +++++ |

TABLE 2-continued
| Compound # | Structure | Kd |
|---|---|---|
| Compound 298 | 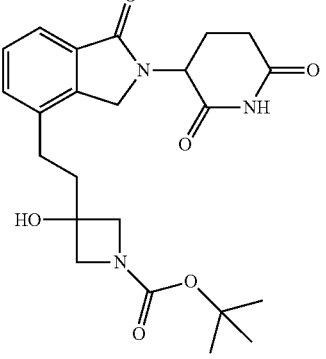 | |
| Compound 299 | 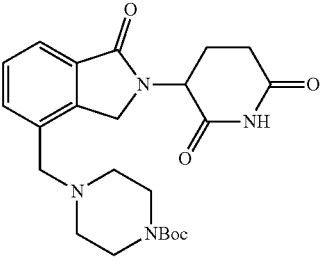 [SMILES: CC(C)(C)OC(=O)N1CCN(Cc2cccc3c2CN(C2CCC(=O)NC2=O)C3=O)CC1] | +++++ |
| Compound 300 | 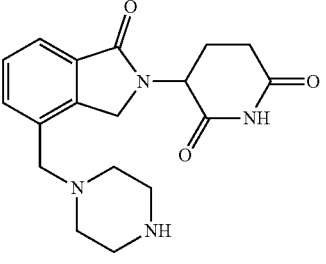 [SMILES: O=C1CCC(N2Cc3c(CN4CCNCC4)cccc3C2=O)C(=O)N1] | +++++ |
| Compound 301 | 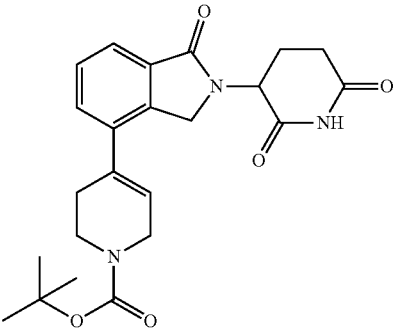 [SMILES: CC(C)(C)OC(=O)N1CC=C(c2cccc3c2CN(C2CCC(=O)NC2=O)C3=O)CC1] | +++++ |
| Compound 302 | 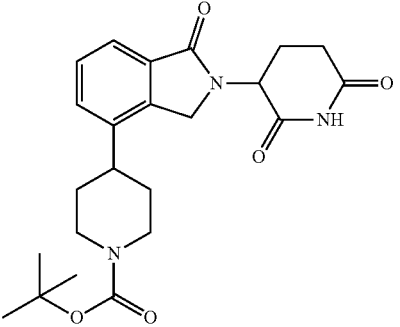 [SMILES: CC(C)(C)OC(=O)N1CCC(c2cccc3c2CN(C2CCC(=O)NC2=O)C3=O)CC1] | +++++ |

TABLE 2-continued
| Compound # | Structure | Kd |
|---|---|---|
| Compound 303 | 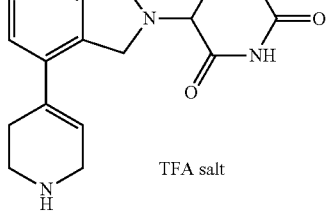 TFA salt | +++++ |
| Compound 304 | 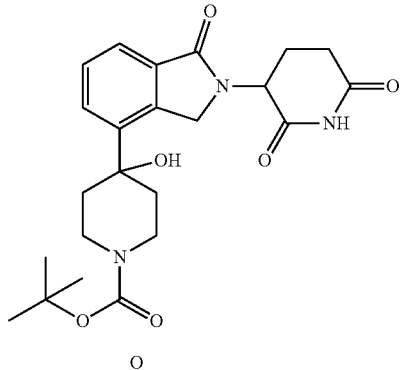 | ++++ |
| Compound 305 | 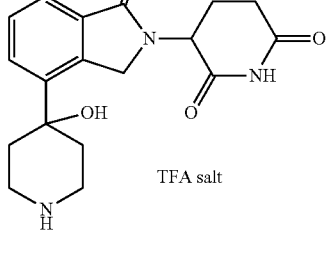 TFA salt | ++++ |
| Compound 306 | 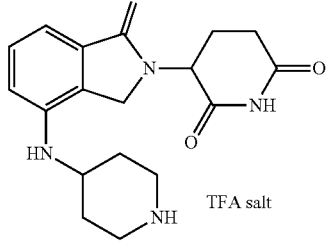 TFA salt | +++++ |
| Compound 307 | 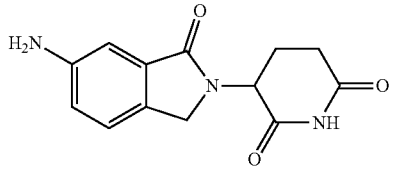 [SMILES: Nc1ccc2c(c1)C(=O)N(C1CCC(=O)NC1=O)C2] | +++++ |
| Compound 308 | 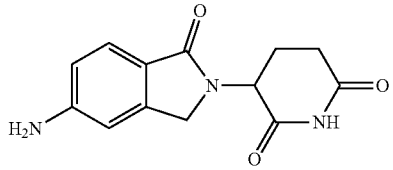 [SMILES: Nc1ccc2c(c1)CN(C1CCC(=O)NC1=O)C2=O] | +++++ |

TABLE 2-continued

| Compound # | Structure | Kd |
|---|---|---|
| Compound 309 | 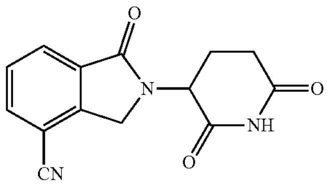 [SMILES: N#Cc1cccc2c1CN(C1CCC(=O)NC1=O)C2=O] | |
| Compound 310 | 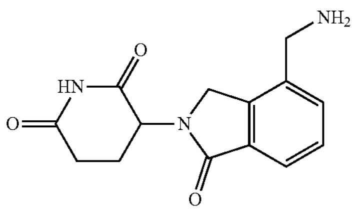 [SMILES: NCc1cccc2c1CN(C1CCC(=O)NC1=O)C2=O] | |
| Compound 311 | TFA salt | ++++ |
| Compound 312 | 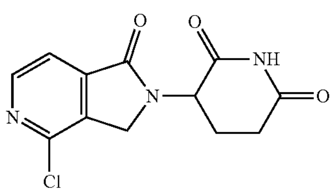 [SMILES: O=C1CCC(N2Cc3c(ccnc3Cl)C2=O)C(=O)N1] | +++++ |
| Compound 313 | 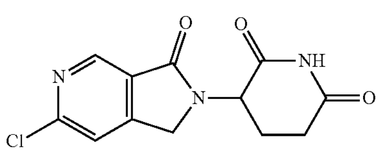 [SMILES: O=C1CCC(N2Cc3cc(Cl)ncc3C2=O)C(=O)N1] | ++++ |
| Compound 314 | 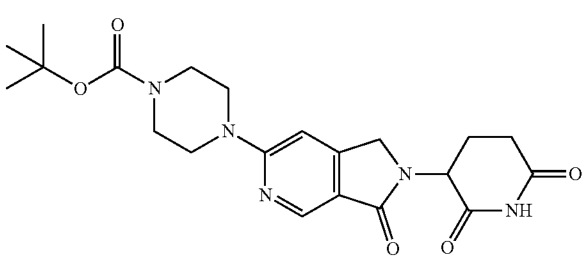 [SMILES: CC(C)(C)OC(=O)N1CCN(c2cc3c(cn2)C(=O)N(C2CCC(=O)NC2=O)C3)CC1] | |
| Compound 315 | 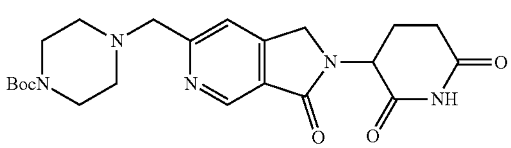 [SMILES: CC(C)(C)OC(=O)N1CCN(Cc2cc3c(cn2)C(=O)N(C2CCC(=O)NC2=O)C3)CC1] | ++++ |

TABLE 2-continued

| Compound # | Structure | Kd |
|---|---|---|
| Compound 316 | 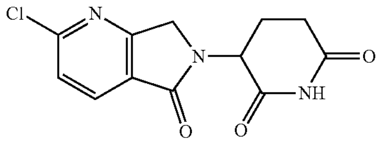 [SMILES: O=C1CCC(N2Cc3nc(Cl)ccc3C2=O)C(=O)N1] | ++++ |
| Compound 317 | 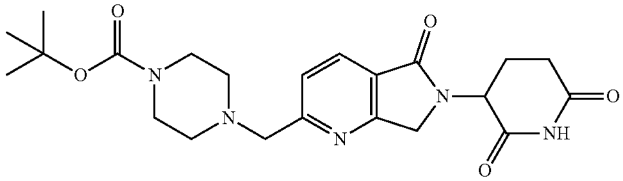 [SMILES: CC(C)(C)OC(=O)N1CCN(Cc2ccc3c(n2)CN(C2CCC(=O)NC2=O)C3=O)CC1] | ++++ |
| Compound 318 | 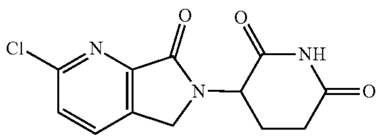 | +++++ |
| Compound 319 | 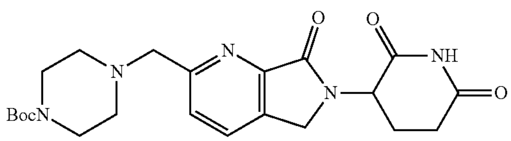 | ++++ |
| Compound 320 | 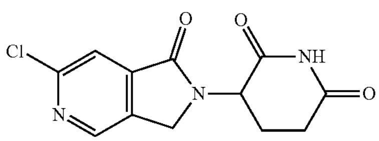 [SMILES: O=C1CCC(N2Cc3cnc(Cl)cc3C2=O)C(=O)N1] | |
| Compound 321 | 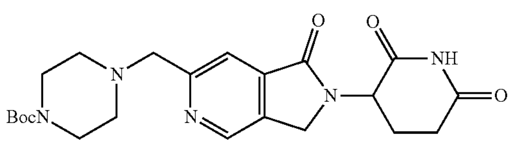 [SMILES: CC(C)(C)OC(=O)N1CCN(Cc2cc3c(cn2)CN(C2CCC(=O)NC2=O)C3=O)CC1] | |
| Compound 322 | 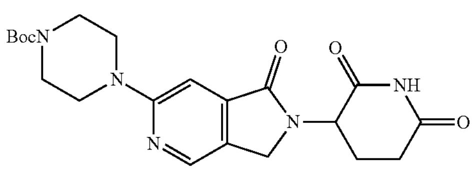 | |
| Compound 323 | 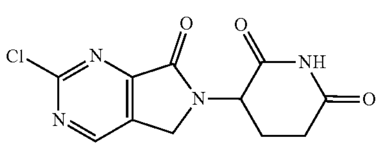 [SMILES: O=C1CCC(N2Cc3cnc(Cl)nc3C2=O)C(=O)N1] | ++++ |
| Compound 324 | 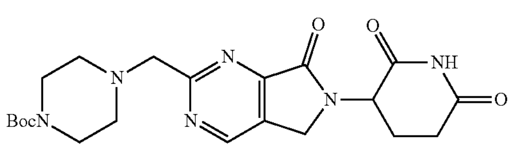 | ++++ |
| Compound 325 | 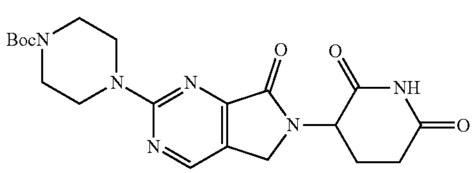 | +++ |

TABLE 2-continued

| Compound # | Structure | Kd |
|---|---|---|
| Compound 326 | (isoindolinone linked to 2,5-dioxopyrrolidine) | + |
| Compound 327 | (4-nitrophthalimide linked to 3-amino-azepane-2,7-dione) | + |
| Compound 328 | (phthalimide linked to 4-methyl-2,6-dioxopiperidin-3-yl) | +++ |

In Table 2 above
>100 μM = +
>30 μM = ++
50-100 μM = +++
10-50 μM = ++++
<10 μM = +++++.

XI. Representative Degronimer of the Present Invention

TABLE 3

| Cmpd# | Structure | Kd |
|---|---|---|
| Degronimer 1 | (thienotriazolodiazepine-CH2-C(O)NH-(CH2)7-NHC(O)-pyridinone-glutarimide) | +++++ |
| Degronimer 2 | (thienotriazolodiazepine-CH2-C(O)NH-(CH2)6-C(O)NH-benzimidazole-glutarimide) | +++++ |

TABLE 3-continued

| Cmpd# | Structure | Kd |
|---|---|---|
| Degronimer 3 | 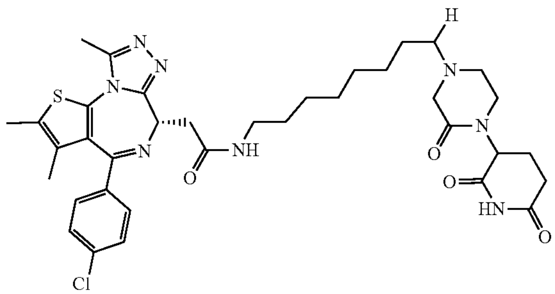 [SMILES: Cc1sc2c(c1C)C(c1ccc(Cl)cc1)=N[C@@H](CC(=O)NCCCCCCCCN1CCN(C3CCC(=O)NC3=O)C(=O)C1)c1nnc(C)n1-2] | +++++ |

In Table 3 above
>100 μM = +
>30 μM = ++
50-100 μM = +++
10-50 μM = ++++
<10 μM = +++++.

TABLE 4

| Cmpd# | Structure | Kd |
|---|---|---|
| Degronimer 4 | 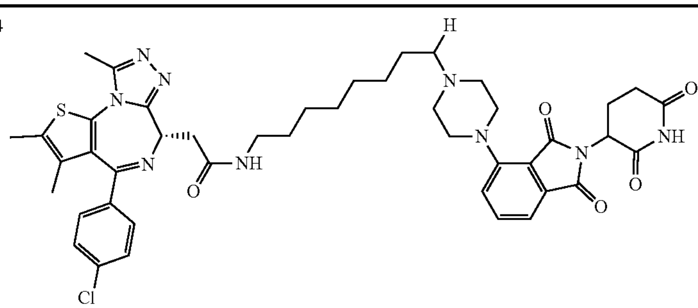 | +++++ |

In Table 4 above
>100 μM = +
>30 μM = ++
50-100 μM = +++
10-50 μM = ++++
<10 μM = +++++.

TABLE 5

| Cell Line | Sample | Time (hr) | LD50 | GI50 | Emax |
|---|---|---|---|---|---|
| MOLT4.1 | Degronimer 3 | 72 | ++ | ++ | **** |
| MOLT4.2 | Degronimer 3 | 72 | + | + | * |
| MOLT4.1 | Degronimer 4 | 72 | ++ | ++ | **** |
| MOLT4.2 | Degronimer 4 | 72 | + | + | * |

In Table 5 above for LD50 and GI50 >1 μM = + and 100 nM-1 μM = ++; for Emax >50% = * 0-50% =  −50%-0% = * and −100%-0% = ****

TABLE 6

| Modification | Cell line | Time (hr) | Sample | Emax [%] | DC50 [nM] |
|---|---|---|---|---|---|
| BRD4_BD1 | 293T.29 | 3 | Degronimer 3 | ** | ++ |
| BRD4_BD1 | 293T.29 | 3 | Degronimer 4 | ** | ++ |

In Table 6 above for DC50 >0.83 μM = + and 100 nM-830 nM = ++; for Emax >50% = * and 0-50% = **

Example 11: CRBN-DDB1 Fluorescence Polarization (FP) Assay

Measuring compound ligand binding to CRBN-DDB 1was carried out using an established sensitive and quantitative in vitro fluorescence polarization (FP) based binding assay. (See, I. J. Enyedy et al, J. Med. Chem., 44: 313-4324 [2001]). Compounds were dispensed from serially diluted DMSO stock into black 384-well compatible fluorescence polarization plates using an Echo acoustic dispenser. Compound binding to CRBN-DDB1 was measured by displacement of either a (−)-Thalidomide-Alexa Fluor® or Pomalidomide-fluorescein conjugated probe dye. A 20 μL mixture containing 400 nM CRBN-DDB1 and 5 nM probe dye in 50 mM Hepes, pH 7.4, 200 mM NaCl, 1% DMSO and 0.1% pluronic acid-127 acid was added to wells containing compound and incubated at room temperature for 60 min. Matching control wells excluding CRBN-DDB1 were used to correct for background fluorescence. Plates were read on an Envision plate reader with appropriate FP filter sets. The corrected S (perpendicular) and P (parallel) values were used to calculate fluorescence polarization (FP) with the following equation: FP=1000*(S−G*P)/(S+G*P). The fractional amount of bound probe (FB) to CRBN-DDB1 as a function of compound concentration was fitted according to Wang; FEBS Letters 360, (1995), 111-114 to obtain fits for parameter offsets and binding constant ($K_A$) of competitor compound.

Example 12: Cell Viability Analysis

RPMI 1640 medium and fetal bovine serum (FBS) were purchased from Gibco (Grand Island, NY, USA). CellTiter-Glo® 2.0 Assay was purchased from Promega (Medison, WI, USA). MOLT4.1 (WT) cell line was purchased from ATCC (Manassas, VA, USA) and MOLT4.2 (CRBN Knock Out) cell line was generated in house. Cell culture flasks and 384-well microplates were acquired from VWR (Radnor, PA, USA).

MOLT4.1 and MOLT4.2 cell viability was determined based on quantification of ATP using CellTiter-Glo® 2.0 luminescent Assay kit, which signals the presence of metabolically-active cells. Briefly, MOLT4.1 and MOLT4.2 cells were seeded into 384-well plates at a cell density of 750 cells per well, the plates were kept at 37° C. with 5% C02 overnight. On the following day, test compounds were added to the cells from a top concentration of 1 M with 10 points, half log titration in duplicates. The cells treated in the absence of the test compound were the negative control and the cells treated in the absence of CellTiter-Glo® 2.0 were the positive control. At the same day of compound treatment, CellTiter-Glo® 2.0 was added to a plate with cells treated in the absence of the test compound to establish Cytostatic control value ($C_{T0}$). Cells treated with the test compound were incubated for 72 hr. CellTiter-Glo reagent was then added to the cells and Luminescence was acquired on EnVision™ Multilabel Reader (PerkinElmer, Santa Clara, CA, USA).

Example 13: HiBit Assay

Materials: DMEM no-phenol red medium and fetal bovine serum (FBS) were purchased from Gibco (Grand Island, NY, USA). Nano-Glo® HiBiT Lytic Assay System was purchased from Promega (Medison, WI, USA). 293T.29 (HiBiT-BRD4 BD1) cell line was generated in house, ectopically expressing BRD4 BD1 domain with HiBiT fusion tag. Cell culture flasks and 384-well microplates were acquired from VWR (Radnor, PA, USA).

BRD4 BD1 Degradation Analysis: BRD4 BD1 degradation was determined based on quantification of luminescent signal using Nano-Glo® HiBiT Lytic Assay kit. Test compounds were added to the 384-well plate from a top concentration of 1 μM with 11 points, half log titration in quadruplicates. 293T.29 cells were added into 384-well plates at a cell density of 15000 cells per well. The plates were kept at 37° C. with 5% CO2 for 3 hours. The cells treated in the absence of the test compound were the negative control and the cells treated with 30 nM of a known BRD4 degrader were the positive control. After 3-hour incubation, Nano-Glo® HiBiT Lytic Assay reagents were added to the cells. Luminescence was acquired on EnVision™ Multilabel Reader (PerkinElmer, Santa Clara, CA, USA).

All publications and patent applications cited in this specification are herein incorporated by reference as if each individual publication or patent application were specifically and individually indicated to be incorporated by reference.

Although the foregoing invention has been described in some detail by way of illustration and example for purposes of clarity of understanding, it will be readily apparent to one of ordinary skill in the art in light of the teachings of this invention that certain changes and modifications may be made thereto without departing from the spirit or scope of the invention as defined in the appended claims.

We claim:

1. A method for degrading a Targeted Protein via the cereblon E3 Ligase ubiquitin proteasome pathway, wherein the method comprises contacting the Targeted Protein with a compound having an N-acyl glutarimide of the following formula:

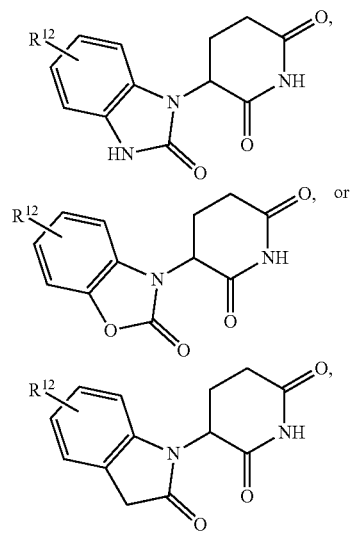

or a pharmaceutically acceptable salt thereof,
wherein:
$R^{12}$ is a Linker-Targeting Ligand;
Linker is:

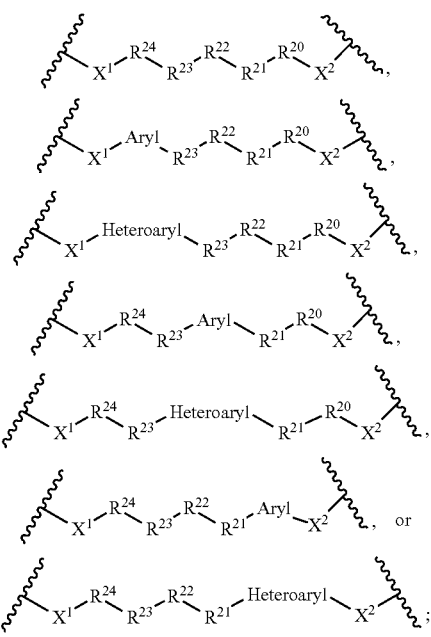

$X^1$ is a bond, —NH—, —NR$^{25}$—, —CH$_2$—, —CHR$^{25}$—, —C(R$^{25}$)$_2$—, —O—, or —S—;

$X^2$ is a bond, —NH—, —NR$^{25}$—, —CH$_2$—, —CHR$^{25}$—, —C(R$^{25}$)$_2$—, —O—, or —S—;

$R^{20}$ is a bond, —CR$^{27}$R$^{28}$—, —CH(OR$^{26}$)—, poly[CH(OH)CH(OH)], poly[CH$_2$CH(OH)CH(OH)], —CH(OH)C(O)O—, —CH$_2$CH(OH)C(O)O—, poly(lactic-co-glycolic acid), alkylene, haloalkylene, -alkylene(R$^{27}$)-alkylene(R$^{28}$)—, arylalkylene, heteroarylalkylene, —C(OR$^{26}$)alkyl-, alkenylene, alkynylene, —C(O)—, —C(O)alkylene, —C(O)O—, —C(O)Oalkylene, —C(O)NH—, —C(O)N(alkyl)-, —C(S)—, —NH—, —N(alkyl)-, —NHC(O)—, —N(alkyl)C(O)—, —NHC(O)NH—, —NHC(O)NR$^{25}$—, —NR$^{25}$C(O)NR$^{25}$—, —O—, —O-alkylene, —OC(O)—, —P(O)(OR$^{26}$)—, —P(O)(OR$^{26}$)O—, —S—, —S(O)—, —S(O)$_2$—, carbocyclylene, heterocyclylene, arylene, or heteroarylene;

$R^{21}$ is a bond, —CR$^{27}$R$^{28}$—, —CH(OR$^{26}$)—, poly[CH(OH)CH(OH)], poly[CH$_2$CH(OH)CH(OH)], —CH(OH)C(O)O—, —CH$_2$CH(OH)C(O)O—, poly(lactic-co-glycolic acid), alkylene, haloalkylene, -alkylene(R$^{27}$)-alkylene(R$^{28}$)—, arylalkylene, heteroarylalkylene, —C(OR$^{26}$)alkyl-, alkenylene, alkynylene, —C(O)—, —C(O)alkylene, —C(O)O—, —C(O)Oalkylene, —C(O)NH—, —C(O)N(alkyl)-, —C(S)—, —NH—, —N(alkyl)-, —NHC(O)—, —N(alkyl)C(O)—, —NHC(O)NH—, —NHC(O)NR$^{25}$—, —NR$^{25}$C(O)NR$^{25}$—, —O—, —O-alkylene, —OC(O)—, —P(O)(OR$^{26}$)—, —P(O)(OR$^{26}$)O—, —S—, —S(O)—, —S(O)$_2$—, carbocyclylene, heterocyclylene, arylene, or heteroarylene;

$R^{22}$ is a bond, —CR$^{27}$R$^{28}$—, —CH(OR$^{26}$)—, poly[CH(OH)CH(OH)], poly[CH$_2$CH(OH)CH(OH)], —CH(OH)C(O)O—, —CH$_2$CH(OH)C(O)O—, poly(lactic-co-glycolic acid), alkylene, haloalkylene, -alkylene(R$^{27}$)-alkylene(R$^{28}$)—, arylalkylene, heteroarylalkylene, —C(OR$^{26}$)alkyl-, alkenylene, alkynylene, —C(O)—, —C(O)alkylene, —C(O)O—, —C(O)Oalkylene, —C(O)NH—, —C(O)N(alkyl)-, —C(S)—, —NH—, —N(alkyl)-, —NHC(O)—, —N(alkyl)C(O)—, —NHC(O)NH—, —NHC(O)NR$^{25}$—, —NR$^{25}$C(O)NR$^{25}$—, —O—, —O-alkylene, —OC(O)—, —P(O)(OR$^{26}$)—, —P(O)(OR$^{26}$)O—, —S—, —S(O)—, —S(O)$_2$—, carbocyclylene, heterocyclylene, arylene, or heteroarylene;

$R^{23}$ is a bond, —CR$^{27}$R$^{28}$—, —CH(OR$^{26}$)—, poly[CH(OH)CH(OH)], poly[CH$_2$CH(OH)CH(OH)], —CH(OH)C(O)O—, —CH$_2$CH(OH)C(O)O—, poly(lactic-co-glycolic acid), alkylene, haloalkylene, -alkylene(R$^{27}$)-alkylene(R$^{28}$)—, arylalkylene, heteroarylalkylene, —C(OR$^{26}$)alkyl-, alkenylene, alkynylene, —C(O)—, —C(O)alkylene, —C(O)O—, —C(O)Oalkylene, —C(O)NH—, —C(O)N(alkyl)-, —C(S)—, —NH—, —N(alkyl)-, —NHC(O)—, —N(alkyl)C(O)—, —NHC(O)NH—, —NHC(O)NR$^{25}$—, —NR$^{25}$C(O)NR$^{25}$—, —O—, —O-alkylene, —OC(O)—, —P(O)(OR$^{26}$)—, —P(O)(OR$^{26}$)O—, —S—, —S(O)—, —S(O)$_2$—, carbocyclylene, heterocyclylene, arylene, or heteroarylene;

$R^{24}$ is a bond, —CR$^{27}$R$^{28}$—, —CH(OR$^{26}$)—, poly[CH(OH)CH(OH)], poly[CH$_2$CH(OH)CH(OH)], —CH(OH)C(O)O—, —CH$_2$CH(OH)C(O)O—, poly(lactic-co-glycolic acid), alkylene, haloalkylene, -alkylene(R$^{27}$)-alkylene(R$^{28}$)—, arylalkylene, heteroarylalkylene, —C(OR$^{26}$)alkyl-, alkenylene, alkynylene, —C(O)—, —C(O)alkylene, —C(O)O—, —C(O)Oalkylene, —C(O)NH—, —C(O)N(alkyl)-, —C(S)—, —NH—, —N(alkyl)-, —NHC(O)—, —N(alkyl)C(O)—, —NHC(O)NH—, —NHC(O)NR$^{25}$—, —NR$^{25}$C(O)NR$^{25}$—, —O—, —O-alkylene, —OC(O)—, —P(O)(OR$^{26}$)—, —P(O)(OR$^{26}$)O—, —S—, —S(O)—, —S(O)$_2$—, carbocyclylene, heterocyclylene, arylene, or heteroarylene;

each $R^{25}$ is independently alkyl, alkenyl, alkynyl, —C(O)H, —C(O)alkyl, —C(O)OH, or —C(O)Oalkyl;

each $R^{26}$ is independently hydrogen, alkyl, arylalkyl, heteroarylalkyl, alkenyl, alkynyl, aryl, heteroaryl, or heterocyclyl;

each $R^{27}$ is independently H, alkyl, or NH$_2$;

each $R^{28}$ is independently H, alkyl, or NH$_2$; or each $R^{27}$ and $R^{28}$, together with the carbon atom to which they are attached, independently forms —C(CH$_2$)—, —C(O)—, a C$_3$-C$_6$ spirocarbocyclylene, or a 4-, 5-, or 6-membered spiroheterocyclylene, wherein the 4-, 5-, or 6-membered spiroheterocyclylene contains 1 or 2 heteroatoms independently selected from the group consisting of N and O; and Targeted Protein is 4BVV, ABL1, ABL2, AKT1, AKT2, androgen receptor, AP1, AP2, ASH1L, ATAD2, ATF2, AXL, BAZ2A, BAZ2B, Bcl-2, Bcl-XL, BCR-ABL, BMX, BRPF1, cathepsin, CECR2, CSF1R, cyclin dependent kinase, DDR1, dihydrofolate reductase, DOT1L, EED, EHMT1, EHMT2, EPHA2, EPHA3, EPHA4, EPHA7, EPHB4, estrogen receptor, EZH2, factor Xa, fatty acid binding protein, FES, FKBP, FLAP, FLT3, FYN, GSG2, HBV, HCK, HCV protease, HDM2, heat shock protein, histone acetyltransferase, HIV integrase, HIV protease, HIV reverse transcriptase, IDO1, IDH1, IGF1R, INSR, ITK, kallikrein 7, KDM4, KDM5, KDM6, KIT, kringle domain V, KSR1, L3MBTL3, lactoylglutathione lyase, LCK, LSD1, LYN, lysine methyltransferase, lysine-specific histone demethylase, mast/stem cell growth factor receptor, MCL-1, MDM2, MDM4, MEK1, MEN1, MER, MERTK, MET, mPGES-1, MST1R, MTH1, NTRK, PAK1, PAK4, PB1, PDGFR receptor, PDZ, PHIP, phospholipase A2 domain, PNET, PPAR-gamma, protein S100-A7, RAML receptor, RCC receptor, ROS1 receptor, saposin-B, Sec7, SEGA receptor, SETD2, SETD7, SETD8, SETDB1, SF6D, SH2 domain, SMYD2, SMYD3, SUV4-20H1, TAF1, TAF1L, TANK1, TEC, tie 2 receptor, TNIK, mTORC1, mTORC2, TRKB, TRIM24, U09-CX-5279, VEGF receptor, or YES;

wherein the alkylene, each alkylene of -alkylene(R$^{27}$)-alkylene(R$^{28}$)—, alkyl of —C(OR$^{26}$)alkyl-, alkylene of arylalkylene, alkylene of heteroarylalkylene, alkenylene, alkynylene, —C(O)alkylene, —C(O)Oalkylene-, —C(O)N(alkyl)-, —N(alkyl)-, —N(alkyl)C(O)—, or —O-alkylene- of $R^{20}$, $R^{21}$, $R^{22}$, $R^{23}$, and $R^{24}$ is optionally and independently substituted with one substituent independently selected from the group consisting of F, Cl, Br, I, —CN, —NO$_2$, —C(O)OH, —C(O)Oalkyl, —NH$_2$, —NH(alkyl), —N(alkyl)$_2$, —OH, —O(alkyl), —O(aryl), —O(heteroaryl), heterocyclyl, aryl, and heteroaryl;

wherein the carbocyclylene, heterocyclylene, arylene, or heteroarylene of $R^{20}$, $R^{21}$, $R^{22}$, $R^{23}$, and $R^{24}$ is optionally and independently substituted with one substituent independently selected from the group consisting of F, Cl, Br, I, —CN, —NO$_2$, alkyl, haloalkyl, arylalkyl, heteroarylalkyl, alkenyl, alkynyl, —C(O)OH, —C(O)

Oalkyl, —NH₂, —NHI(alkyl), —N(alkyl)₂, OH, —O(alkyl), —O(aryl), —O(heteroaryl), heterocyclyl, aryl, and heteroaryl;

wherein the compound having an N-acyl glutarimide binds to cereblon;

wherein the compound having an N-acyl glutarimide contains a Targeting Ligand for the Targeted Protein; and wherein the Targeting Ligand is a small molecule means for binding a Targeted Protein that mediates a disease.

2. The method of claim 1, wherein the Linker is:

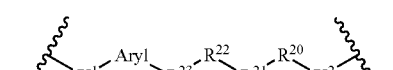

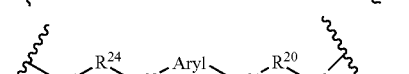, or

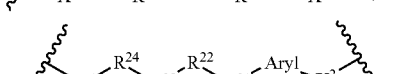.

3. The method of claim 1, wherein the Linker is:

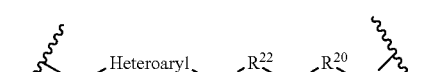,

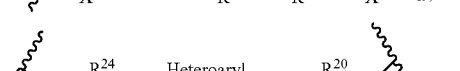, or

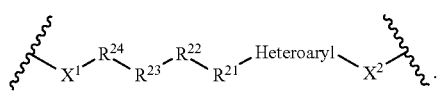.

4. The method of claim 1, wherein the Linker is:

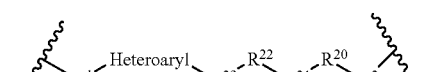,

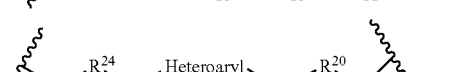, or

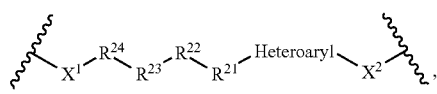, wherein:
(i) -Heteroaryl- is

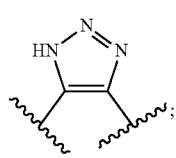 [SMILES: *c1nn[nH]c1*];

or
(ii) -Heteroaryl- is

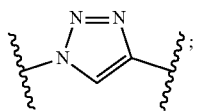;

or
(iii) -Heteroaryl- is

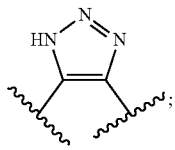 [SMILES: *c1nn[nH]c1*];

and
X² is —CH₂—; or
(iv) -Heteroaryl- is

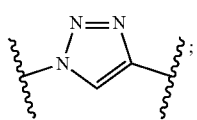;

and
X² is —CH₂—; or
(v) -Heteroaryl- is

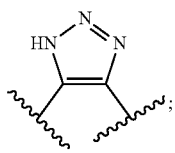 [SMILES: *c1nn[nH]c1*];

X¹ is —NH—; and
X² is —CH₂—; or
(vi) -Heteroaryl- is

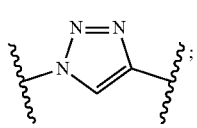;

X¹ is —NH—; and
X² is —CH₂—; or
(vii) -Heteroaryl- is

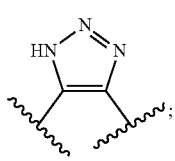 [SMILES: *c1nn[nH]c1*];

X¹ is —O—; and
X² is —CH₂—; or (viii) -Heteroaryl- is

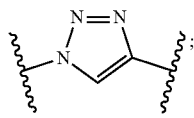 [SMILES: *c1cn(*)nn1]

$X^1$ is —O—; and
$X^2$ is —CH$_2$—.

5. The method of claim 1, wherein $X^1$ is a bond.
6. The method of claim 1, wherein $X^2$ is a bond.
7. The method of claim 1, wherein $R^{21}$ is a bond.
8. The method of claim 7, wherein $R^{22}$ is a bond.
9. The method of claim 8, wherein $R^{23}$ is a bond.
10. The method of claim 1, wherein:
(i) $R^{20}$ is heterocyclylene, arylene, or heteroarylene, wherein the heterocyclylene, arylene, or heteroarylene is optionally substituted; or
(ii) $R^{21}$ is heterocyclylene, arylene, or heteroarylene, wherein the heterocyclylene, arylene, or heteroarylene is optionally substituted; or
(iii) $R^{22}$ is heterocyclylene, arylene, or heteroarylene, wherein the heterocyclylene, arylene, or heteroarylene is optionally substituted; or
(iv) $R^{23}$ is heterocyclylene, arylene, or heteroarylene, wherein the heterocyclylene, arylene, or heteroarylene is optionally substituted; or
(v) $R^{24}$ is heterocyclylene, arylene, or heteroarylene, wherein the heterocyclylene, arylene, or heteroarylene is optionally substituted.
11. The method of claim 1, wherein:
(i) $R^{20}$ is heterocyclylene, arylene, or heteroarylene, wherein the heterocyclylene, arylene, or heteroarylene is optionally substituted; and
$R^{21}$ is heterocyclylene, arylene, or heteroarylene, wherein the heterocyclylene, arylene, or heteroarylene is optionally substituted; or
(ii) $R^{20}$ is heterocyclylene, arylene, or heteroarylene, wherein the heterocyclylene, arylene, or heteroarylene is optionally substituted; and
$R^{22}$ is heterocyclylene, arylene, or heteroarylene, wherein the heterocyclylene, arylene, or heteroarylene is optionally substituted; or
(iii) $R^{20}$ is heterocyclylene, arylene, or heteroarylene, wherein the heterocyclylene, arylene, or heteroarylene is optionally substituted; and
$R^{23}$ is heterocyclylene, arylene, or heteroarylene, wherein the heterocyclylene, arylene, or heteroarylene is optionally substituted; or
(iv) $R^{20}$ is heterocyclylene, arylene, or heteroarylene, wherein the heterocyclylene, arylene, or heteroarylene is optionally substituted; and
$R^{24}$ is heterocyclylene, arylene, or heteroarylene, wherein the heterocyclylene, arylene, or heteroarylene is optionally substituted; or
(v) $R^{21}$ is heterocyclylene, arylene, or heteroarylene, wherein the heterocyclylene, arylene, or heteroarylene is optionally substituted; and
$R^{22}$ is heterocyclylene, arylene, or heteroarylene, wherein the heterocyclylene, arylene, or heteroarylene is optionally substituted; or
(vi) $R^{21}$ is heterocyclylene, arylene, or heteroarylene, wherein the heterocyclylene, arylene, or heteroarylene is optionally substituted; and
$R^{23}$ is heterocyclylene, arylene, or heteroarylene, wherein the heterocyclylene, arylene, or heteroarylene is optionally substituted; or
(vii) $R^{21}$ is heterocyclylene, arylene, or heteroarylene, wherein the heterocyclylene, arylene, or heteroarylene is optionally substituted; and
$R^{24}$ is heterocyclylene, arylene, or heteroarylene, wherein the heterocyclylene, arylene, or heteroarylene is optionally substituted; or
(viii) $R^{22}$ is heterocyclylene, arylene, or heteroarylene, wherein the heterocyclylene, arylene, or heteroarylene is optionally substituted; and
$R^{23}$ is heterocyclylene, arylene, or heteroarylene, wherein the heterocyclylene, arylene, or heteroarylene is optionally substituted; or
(ix) $R^{22}$ is heterocyclylene, arylene, or heteroarylene, wherein the heterocyclylene, arylene, or heteroarylene is optionally substituted; and
$R^{24}$ is heterocyclylene, arylene, or heteroarylene, wherein the heterocyclylene, arylene, or heteroarylene is optionally substituted; or
(x) $R^{23}$ is heterocyclylene, arylene, or heteroarylene, wherein the heterocyclylene, arylene, or heteroarylene is optionally substituted; and
$R^{24}$ is heterocyclylene, arylene, or heteroarylene, wherein the heterocyclylene, arylene, or heteroarylene is optionally substituted.
12. The method of claim 1, wherein:
(i) $R^{20}$ is heterocyclylene, arylene, or heteroarylene, wherein the heterocyclylene, arylene, or heteroarylene is optionally substituted;
$R^{21}$ is heterocyclylene, arylene, or heteroarylene, wherein the heterocyclylene, arylene, or heteroarylene is optionally substituted; and
$R^{22}$ is heterocyclylene, arylene, or heteroarylene, wherein the heterocyclylene, arylene, or heteroarylene is optionally substituted; or
(ii) $R^{20}$ is heterocyclylene, arylene, or heteroarylene, wherein the heterocyclylene, arylene, or heteroarylene is optionally substituted;
$R^{21}$ is heterocyclylene, arylene, or heteroarylene, wherein the heterocyclylene, arylene, or heteroarylene is optionally substituted; and
$R^{23}$ is heterocyclylene, arylene, or heteroarylene, wherein the heterocyclylene, arylene, or heteroarylene is optionally substituted; or
(iii) $R^{20}$ is heterocyclylene, arylene, or heteroarylene, wherein the heterocyclylene, arylene, or heteroarylene is optionally substituted;
$R^{21}$ is heterocyclylene, arylene, or heteroarylene, wherein the heterocyclylene, arylene, or heteroarylene is optionally substituted; and
$R^{24}$ is heterocyclylene, arylene, or heteroarylene, wherein the heterocyclylene, arylene, or heteroarylene is optionally substituted; or
(iv) $R^{20}$ is heterocyclylene, arylene, or heteroarylene, wherein the heterocyclylene, arylene, or heteroarylene is optionally substituted;
$R^{22}$ is heterocyclylene, arylene, or heteroarylene, wherein the heterocyclylene, arylene, or heteroarylene is optionally substituted; and
$R^{23}$ is heterocyclylene, arylene, or heteroarylene, wherein the heterocyclylene, arylene, or heteroarylene is optionally substituted; or
(v) $R^{20}$ is heterocyclylene, arylene, or heteroarylene, wherein the heterocyclylene, arylene, or heteroarylene is optionally substituted;
$R^{22}$ is heterocyclylene, arylene, or heteroarylene, wherein the heterocyclylene, arylene, or heteroarylene is optionally substituted; and R²⁴ is heterocyclylene, arylene, or heteroarylene, wherein the heterocyclylene, arylene, or heteroarylene is optionally substituted; or
(vi) R²⁰ is heterocyclylene, arylene, or heteroarylene, wherein the heterocyclylene, arylene, or heteroarylene is optionally substituted;
R²³ is heterocyclylene, arylene, or heteroarylene, wherein the heterocyclylene, arylene, or heteroarylene is optionally substituted; and
R²⁴ is heterocyclylene, arylene, or heteroarylene, wherein the heterocyclylene, arylene, or heteroarylene is optionally substituted; or
(vii) R²¹ is heterocyclylene, arylene, or heteroarylene, wherein the heterocyclylene, arylene, or heteroarylene is optionally substituted;
R²² is heterocyclylene, arylene, or heteroarylene, wherein the heterocyclylene, arylene, or heteroarylene is optionally substituted; and
R²³ is heterocyclylene, arylene, or heteroarylene, wherein the heterocyclylene, arylene, or heteroarylene is optionally substituted; or
(viii) R²¹ is heterocyclylene, arylene, or heteroarylene, wherein the heterocyclylene, arylene, or heteroarylene is optionally substituted;
R²² is heterocyclylene, arylene, or heteroarylene, wherein the heterocyclylene, arylene, or heteroarylene is optionally substituted; and
R²⁴ is heterocyclylene, arylene, or heteroarylene, wherein the heterocyclylene, arylene, or heteroarylene is optionally substituted; or
(ix) R²¹ is heterocyclylene, arylene, or heteroarylene, wherein the heterocyclylene, arylene, or heteroarylene is optionally substituted;
R²³ is heterocyclylene, arylene, or heteroarylene, wherein the heterocyclylene, arylene, or heteroarylene is optionally substituted; and
R²⁴ is heterocyclylene, arylene, or heteroarylene, wherein the heterocyclylene, arylene, or heteroarylene is optionally substituted; or
(x) R²² is heterocyclylene, arylene, or heteroarylene, wherein the heterocyclylene, arylene, or heteroarylene is optionally substituted;
R²³ is heterocyclylene, arylene, or heteroarylene, wherein the heterocyclylene, arylene, or heteroarylene is optionally substituted; and
R²⁴ is heterocyclylene, arylene, or heteroarylene, wherein the heterocyclylene, arylene, or heteroarylene is optionally substituted.

13. The method of claim 1, wherein the Targeted Protein is the estrogen receptor or androgen receptor.

14. The method of claim 1, wherein the Targeted Protein is selected from the group consisting of ABL1, ABL2, AKT1, AKT2, AP1, AP2, ASH1L, ATAD2, ATF2, AXL, BAZ2A, BAZ2B, Bcl-2, Bcl-XL, BCR-ABL, and BMX.

15. The method of claim 1, wherein the Targeted Protein is selected from the group consisting of BRPF1, cathepsin, CECR2, CSF1R, cyclin dependent kinase, DDR1, dihydrofolate reductase, DOT1L, EED, EHMT1, EHMT2, EPHA2, EPHA3, EPHA4, EPHA7, EPHB4, and EZH2.

16. The method of claim 1, wherein the Targeted Protein is selected from the group consisting of factor Xa, fatty acid binding protein, FES, FKBP, FLAP, FLT3, FYN, GSG2, HBV, HCK, HCV protease, HDM2, heat shock protein, histone acetyltransferase, HIV integrase, HIV protease, HIV reverse transcriptase, IDO1, IDH1, IGF1R, INSR, and ITK.

17. The method of claim 1, wherein the Targeted Protein is selected from the group consisting of 4BVV, kallikrein 7, KDM4, KDM5, KDM6, KIT, kringle domain V, KSR1, L3MBTL3, lactoylglutathione lyase, LCK, LSD1, LYN, lysine methyltransferase, lysine-specific histone demethylase, mast/stem cell growth factor receptor, MCL-1, MDM2, MDM4, MEK1, MEN1, MER, MERTK, MET, mPGES-1, MST1R, MTH1, and NTRK.

18. The method of claim 1, wherein the Targeted Protein is selected from the group consisting of PAKI, PAK4, PB1, PDGFR receptor, PDZ, PHIP, phospholipase A2 domain, PNET, PPAR-gamma, protein S100-A7, RAML receptor, RCC receptor, ROS1 receptor, saposin-B, Sec7, SEGA receptor, SETD2, SETD7, SETD8, SETDB1, SH2 domain, SMYD2, SMYD3, and SUV4-20H1.

19. The method of claim 1, wherein the Targeted Protein is selected from the group consisting of SF6D, TAF1, TAF1L, TANK1, TEC, tie 2 receptor, TNIK, mTORC1, mTORC2, TRKB, TRIM24, U09-CX-5279, VEGF receptor, and YES.

20. The method of claim 1, wherein the compound having an N-acyl glutarimide is of the following formula:

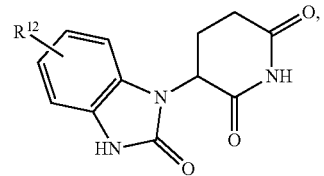

or a pharmaceutically acceptable salt thereof.

21. The method of claim 1, wherein the compound having an N-acyl glutarimide is of the following formula:

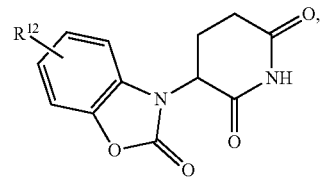

or a pharmaceutically acceptable salt thereof.

22. The method of claim 1, wherein the compound having an N-acyl glutarimide is of the following formula:

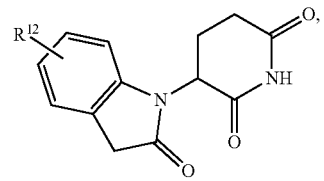

or a pharmaceutically acceptable salt thereof.

* * * * *